US012570655B2

(12) United States Patent
Chu et al.

(10) Patent No.: US 12,570,655 B2
(45) Date of Patent: Mar. 10, 2026

(54) CYSTEINE COVALENT MODIFIERS OF AKT1 AND USES THEREOF

(71) Applicant: Terremoto Biosciences, Inc., South San Francisco, CA (US)

(72) Inventors: Hang Chu, San Mateo, CA (US); Solomon H. Reisberg, Contra Costa, CA (US); Adam Zajdlik, San Francisco, CA (US); Kin S. Yang, San Mateo, CA (US); Jordan D. Carelli, San Francisco, CA (US); Peter A. Thompson, Kirkland, WA (US)

(73) Assignee: TERREMOTO BIOSCIENCES, Inc., South San Francisco, CA (US)

(*) Notice: Subject to any disclaimer, the term of this patent is extended or adjusted under 35 U.S.C. 154(b) by 0 days.

(21) Appl. No.: 19/224,601

(22) Filed: May 30, 2025

(65) Prior Publication Data

US 2025/0289819 A1 Sep. 18, 2025

Related U.S. Application Data

(63) Continuation of application No. PCT/US2024/051051, filed on Oct. 11, 2024.

(60) Provisional application No. 63/686,523, filed on Aug. 23, 2024, provisional application No. 63/562,578, filed on Mar. 7, 2024, provisional application No. 63/590,256, filed on Oct. 13, 2023.

(51) Int. Cl.

| | |
|---|---|
| ***C07D 471/04*** | (2006.01) |
| ***A61K 31/444*** | (2006.01) |
| ***A61K 31/4545*** | (2006.01) |
| ***A61K 31/4709*** | (2006.01) |
| ***A61K 31/4725*** | (2006.01) |
| ***A61K 31/496*** | (2006.01) |
| ***A61K 31/497*** | (2006.01) |
| ***A61K 31/5377*** | (2006.01) |
| ***A61K 31/5383*** | (2006.01) |
| ***A61K 31/5386*** | (2006.01) |
| ***A61K 31/553*** | (2006.01) |
| ***A61P 35/00*** | (2006.01) |
| ***C07D 519/00*** | (2006.01) |

(52) U.S. Cl.

CPC .......... *C07D 471/04* (2013.01); *A61K 31/444* (2013.01); *A61K 31/4545* (2013.01); *A61K 31/4709* (2013.01); *A61K 31/4725* (2013.01); *A61K 31/496* (2013.01); *A61K 31/497* (2013.01); *A61K 31/5377* (2013.01); *A61K 31/5383* (2013.01); *A61K 31/5386* (2013.01); *A61K 31/553* (2013.01); *A61P 35/00* (2018.01); *C07D 519/00* (2013.01)

(58) Field of Classification Search

CPC .................................................. C07D 471/04
USPC .................................................. 514/210.16
See application file for complete search history.

(56) References Cited

FOREIGN PATENT DOCUMENTS

| | | | | |
|---|---|---|---|---|
| WO | WO-2011082270 | A2 | | 7/2011 |
| WO | WO-2020081572 | A1 | | 4/2020 |
| WO | 2020159285 | | * | 8/2020 |
| WO | WO-2020159285 | A1 | | 8/2020 |
| WO | WO-2021203016 | A2 | | 10/2021 |
| WO | WO-2022166469 | A1 | | 8/2022 |
| WO | WO-2023168291 | A1 | | 9/2023 |
| WO | WO-2024178390 | A1 | | 8/2024 |
| WO | WO-2025034613 | A1 | | 2/2025 |
| WO | WO-2025081045 | A1 | | 4/2025 |

OTHER PUBLICATIONS

Ashwell, Mark A. et al. Discovery And Optimization Of A Series Of 3-(3-phenyl-3h-imidazo[4,5-b]pyridin-2-yl)pyridin-2-amines: Orally Bioavailable, Selective, And Potent ATP-independent Akt Inhibitors. Journal of Medicinal Chemistry 55(11):5291-5310 (2012).
Hinz, Nico, and Manfred Jucker. Distinct functions of AKT isoforms in breast cancer: a comprehensive review. Cell Communication and Signaling 17(1):154, 1-29 (2019).
Klein, Karen A. et al. Progression of metastatic human prostate cancer to androgen independence in immunodeficient SCID mice. Nature medicine 3(4):402-408 (1997).
Lapierre, Jean-Marc. et al. Discovery of 3-(3-(4-(1-Aminocyclobutyl) phenyl)-5-phenyl-3 H-imidazo [4, 5-b] pyridin-2-yl) pyridin-2-amine (ARQ 092): An orally bioavailable, selective, and potent allosteric AKT inhibitor. Journal of medicinal chemistry 59(13):6455-6469 (2016).
Pascual, J, and N C Turner. Targeting the PI3-kinase pathway in triple-negative breast cancer. Annals of Oncology 30(7):1051-1060 (2019).
PCT/US2024/051051 International Search Report and Written Opinion dated Mar. 21, 2025.
Song et al., AKT as a Therapeutic Target for Cancer. Cancer Research; 79(6), 1019-1031 (2019).
Vasta, James D. et al. Quantitative, Wide-Spectrum Kinase Profiling in Live Cells for Assessing the Effect of Cellular ATP on Target Engagement. Cell chemical biology 25(2):206-214_e1-e11 (2018). Published Online Nov. 22, 2017.

(Continued)

*Primary Examiner* — Niloofar Rahmani
(74) *Attorney, Agent, or Firm* — WILSON SONSINI GOODRICH & ROSATI

(57) ABSTRACT

Provided herein are covalent modifiers of AKT1 of Formula (I), (I-A), (II), (II-A), (III), (II-A), or (III-B), and pharmaceutical compositions thereof. In some embodiments, the present disclosure provides methods of modulating AKT1 using a compound or salt of Formula (I), (I-A), (II), (II-A), (III), (III-A), or (III-B), and pharmaceutical compositions thereof.

55 Claims, 4 Drawing Sheets

Specification includes a Sequence Listing.

(56) References Cited

OTHER PUBLICATIONS

Yu, Yi. et al. Targeting AKT1-E17K and the PI3K/AKT pathway with an allosteric AKT inhibitor, ARQ 092. PLoS One 10(10):e0140479, 1-26 (2015).
Co-pending U.S. Appl. No. 19/225,802, inventors Chu; Hang et al., filed Jun. 2, 2025.

* cited by examiner

CYSTEINE COVALENT MODIFIERS OF AKT1 AND USES THEREOF

CROSS REFERENCE TO RELATED APPLICATIONS

This application is a continuation application of International Patent Application No. PCT/US2024/051051, filed Oct. 11, 2024, which claims the benefit of U.S. Provisional Application No. 63/590,256 filed on Oct. 13, 2023, U.S. Provisional Application No. 63/562,578 filed on Mar. 7, 2024, and U.S. Provisional Application No. 63/686,523 filed on Aug. 23, 2024, the entirety of each is incorporated herein by reference.

SEQUENCE LISTING

The instant application contains a Sequence Listing which has been submitted electronically in XML format and is hereby incorporated by reference in its entirety. Said XML copy, created on May 30, 2025, is named 61402-712_301_SL.xml and is 5,556 bytes in size.

BACKGROUND OF THE INVENTION

The AKT or Protein Kinase B (PKB) family of serine/threonine protein kinases is comprised of 3 highly homologous members, AKT1, AKT2 and AKT3. The family of AKT proteins are involved in signal transduction pathways that regulate cellular processes including apoptosis, proliferation, differentiation, and metabolism. The AKT1 pathway is the most frequently dysregulated signaling pathways in human cancers. Enhanced activation of all the isoforms can be implicated in tumor development and progression, and has been demonstrated in breast, ovarian, pancreatic, and prostate cancers among others (Song et al., 2019). In cancer cells, AKT1 is involved in proliferation and growth, promoting tumor initiation, and suppressing apoptosis, whereas AKT2 regulates cytoskeleton dynamics, favoring local tissue invasion and metastasis. The role of AKT3 hyperactivation in cancer is hypothesized to be involved with possible stimulation of cell proliferation (Hinz et al., *Cell Commun Signal* 2019, 17 (1), 154; Pascual et al., *Ann. Oncol.* 2019, 30 (7), 1051-1060). Expression of these AKT family members is altered in many human malignant carcinomas including gastric, breast, prostate, ovarian, and pancreatic. AKT family members are rarely mutated however, the most common mutation is AKT1 E17K which has been reported in 6-8% of breast cancers, 2-6% of colorectal cancers, and in 6% of meningiomas, in humans (Yu et al., *PLOS One* 2015, 10 (10), No. e0140479). Thus, there is a need to develop new treatments for the modulation of AKT1 and mutants thereof.

SUMMARY OF THE INVENTION

In one aspect, the present disclosure provides compounds represented by the Formula (I):

(I)

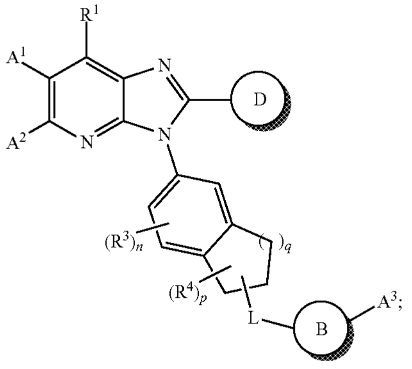

or a pharmaceutically acceptable salt thereof, wherein:

$R^1$ is selected from:

hydrogen, halogen, —$OR^{10}$, —$SR^{10}$, —$N(R^{10})_2$, —$NO_2$, and —CN;

$C_{1-6}$ alkyl optionally substituted with one or more substituents independently selected from: halogen, —$OR^{10}$, —$SR^{10}$, —$N(R^{10})_2$, —$NO_2$, and —CN; and $C_{3-8}$ carbocycle and 4- to 8-membered heterocycle, any of which is optionally substituted with one or more substituents independently selected from halogen, —$OR^{10}$, —$SR^{10}$, —$N(R^{10})_2$, —$NO_2$, —CN, $C_{1-6}$ alkyl, and $C_{1-6}$ haloalkyl;

$A^1$ and $A^2$ are each independently selected from (i), (ii), and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and 4- to 10-membered heterocycle and $C_{3-10}$ carbocycle, any of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and (iii) 4- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, —$N(R^{11})$, and —CN;

$C_{1-6}$ alkyl, $C_{2-6}$ alkenyl, and $C_{2-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, $=O$, $=S$, $=N(R^{11})$, and —CN; and $C_{3-10}$ carbocycle and 3- to 10-membered heterocycle, any of which is optionally substituted with one or more substituents independently selected from:

halogen, $—OR^{11}$, $—N(R^{11})_2$, $—C(O)R^{11}$, $—C(O)N(R^{11})_2$, $—N(R^{11})C(O)R^{11}—C(O)OR^{11}$, $—OC(O)R^{11}$, $—NO_2$, $=O$, $=S$, $=N(R^{11})$, —CN;

$C_{1-6}$ alkyl $C_{2-6}$ alkenyl, and $C_{3-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—NO_2$, $=O$, $=S$, $=N(R^{11})$, and —CN; and $C_{3-10}$ carbocycle and 4- to 10-membered heterocycle any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—NO_2$, $=O$, $=S$, $=N(R^{11})$, and —CN;

$R^3$ is independently selected at each instance from:

halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, and —CN; and $C_{1-6}$ alkyl, $C_{2-6}$ alkenyl, and $C_{2-6}$ alkynyl, any one of which is optionally substituted with one or more substituents independently selected from: halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, $=O$, $=S$, $=N(R^{13})$, and —CN;

$R^4$ is independently selected at each instance from:

halogen, $—OR^{14}$, $—SR^{14}$, $—N(R^{14})_2$, $—C(O)R^{14}$, $—C(O)N(R^{14})_2$, $—N(R^{14})C(O)R^{14}$, $—C(O)OR^{14}$, $—OC(O)R^{14}$, $—NO_2$, $=O$, $=S$, $=N(R^{14})$, and —CN; and $C_{1-6}$ alkyl, $C_{2-6}$ alkenyl, and $C_{2-6}$ alkynyl, any one of which is optionally substituted with one or more substituents independently selected from halogen, $—OR^{14}$, $—SR^{14}$, $—N(R^{14})_2$, $—C(O)R^{14}$, $—C(O)N(R^{14})_2$, $—N(R^{14})C(O)R^{14}$, $—C(O)OR^{14}$, $—OC(O)R^{14}$, $—NO_2$, $=O$, $=S$, $=N(R^{14})$, and —CN;

L is represented by $-L^1-L^2-L^3-L^4-$, wherein $L^1$, $L^2$, $L^3$, and $L^4$ are each independently selected from (a) and (b):

(a) —O—, $—N(R^{15})—$, —S—, —S(O)—, $—S(O)_2—$, $—S(O)(NR^{15})—$, $—N(R^{15})C(O)—$, $—N(R^{15})C(O)O—$, $—N(R^{15})S(O)_2—$, $—N(R^{15})S(O)_2N(R^{15})—$, $—S(O)(NR^{15})N(R^{15})—$, $—N(R^{15})N(R^{15})—$, $—(R^{15})NC(O)N(R^{15})—$, and $—(R^{15})NC(O)N(R^{15})N(R^{15})—$; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, $—OR^{15}$, $—SR^{15}$, $=O$, $=S$, and —CN;

wherein $L^1$, $L^2$, $L^3$, and $L^4$ are each optionally absent;

wherein no more than two of $L^1$, $L^2$, $L^3$, and $L^4$ are selected from (a) and the two selected are not adjacent;

Ring B selected from 3- to 10-membered heterocyclene and $C_{3-10}$ carbocyclene, any of which is optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN; and 3- to 6-membered heterocycle and $C_{3-6}$ carbocycle, each of which is optionally substituted with one or more substituents independently selected from: halogen, $C_{1-6}$ alkyl, $C_{1-6}$ haloalkyl, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN;

Ring D is selected from:

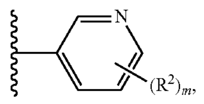
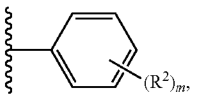
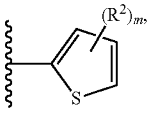
and
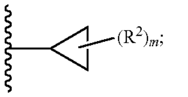

$R^2$ is independently selected at each instance from halogen, $C_{1-6}$ alkyl, $C_{1-6}$ haloalkyl, $—OR^{12}$, $—SR^{12}$, $—N(R^{12})_2$, $—NO_2$, and —CN;

$A^3$ is cysteine susceptible electrophile;

$R^{10}$, $R^{11}$, $R^{12}$, $R^{13}$, $R^{14}$, $R^{15}$, and $R^{16}$ are each independently selected at each occurrence from:

hydrogen, $C_{1-6}$ alkyl, optionally substituted with one or more substituents independently selected from halogen, —OH, $—O—C_{1-6}$ alkyl, $—O—C_{1-6}$ haloalkyl, $C_{3-6}$ carbocycle, and 3- to 6-membered heterocycle; and $C_{3-6}$ carbocycle and 3- to 6-membered heterocycle, each of which is optionally substituted with one or more substituents independently selected from halogen, —OH, $—O—C_{1-6}$ alkyl, $—O—C_{1-6}$ haloalkyl, $C_{1-6}$ alkyl, and $C_{1-6}$ haloalkyl;

m is selected from 0, 1, 2, and 3;

n is selected from 0, 1, 2, and 3;

q is selected from 1, 2, and 3; and p is selected from 0, 1, 2, 3, 4, and 5.

In another aspect, the present disclosure provides a pharmaceutical composition comprising a compound or salt of Formula (I), (I-A), (II), (II-A), (III), (III-A), or (III-B), and a pharmaceutically acceptable excipient.

In another aspect, the present disclosure provides a method of modulating activity of wild-type AKT1 comprising, administering to a subject in need thereof a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B), and a pharmaceutically acceptable excipient.

In another aspect, the present disclosure provides a method of modulating activity of mutant AKT1 comprising, administering to a subject in need thereof a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B), and a pharmaceutically acceptable excipient.

In another aspect, the present disclosure provides a method of selectively modulating activity of wild-type AKT1 over wild-type AKT2 comprising administering to a subject in need thereof a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B) and a pharmaceutically acceptable excipient.

In another aspect, the present disclosure provides a method of selectively modulating activity of a mutant AKT1 over wild-type AKT2 comprising administering to a subject in need thereof a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B) and a pharmaceutically acceptable excipient.

In another aspect, the present disclosure provides a method of treating cancer in a subject in need thereof, the method comprising administering to the subject a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B) and a pharmaceutically acceptable excipient. In some embodiments, the cancer is selected from breast cancer, colorectal cancer, and meningioma. In some embodiments, the administration modulates activity of a mutant AKT1. In some embodiments, the mutant AKT1 is AKT1 E17K. In some embodiments, the administration modulates activity of wild-type AKT1.

In another aspect, the present disclosure provides an AKT1 protein covalently bound to a compound, wherein the compound is covalently bound to a cysteine residue of the AKT1 protein. In some embodiments, the compound is an exogenous AKT1 modulator. In some embodiments, the compound is an exogenous AKT1 inhibitor. In some embodiments, the exogenous AKT1 inhibitor is a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B). In some embodiments, the AKT1 protein comprises a E17K mutation, a E40K mutation, or a E49K mutation. In some embodiments, the cysteine residue is selected from C296 and C310. In some embodiments, the cysteine residue is C296. In some embodiments, the AKT1 protein is in vivo. In some embodiments, the AKT1 protein is an in vivo engineered AKT1 protein, wherein the in vivo engineered AKT1 protein is generated by contacting the AKT1 protein in vivo with the compound. In some embodiments, the in vivo engineered AKT1 protein is a human in vivo engineered AKT1 protein. In some embodiments, the covalent bond between the compound and the cysteine residue is an irreversible covalent bond. In some embodiments, the irreversible covalent bond in the in vivo AKT1 protein is a carbon-sulfur single bond. In some embodiments, the carbon-sulfur single bond results from an irreversible reaction between the thiol functional group of C296 and a cysteine susceptible electrophile on the compound, wherein the cysteine susceptible electrophile is selected from: an acrylate group, an acrylamide group, a vinyl group, a vinylsulfone group, a vinylsulfonamide group, an ynamide, and an epoxide group. In some embodiments, the cysteine susceptible electrophile is selected from: an acrylate group, an acrylamide group, a vinylsulfone group, and a vinylsulfonamide group.

In another aspect, the present disclosure provides an in vivo engineered AKT1 protein comprising a non-naturally occurring irreversible covalent modification at a cysteine residue, the irreversible covalent modification being generated from an in vivo nucleophilic reaction between an exogenous cysteine susceptible electrophile and a cysteine residue of AKT1, wherein the exogenous cysteine susceptible electrophile undergoes a nucleophilic addition with the thiol functional group on the cysteine residue and forms a carbon-sulfur single bond between the exogenous cysteine susceptible electrophile and the thiol functional group on the cysteine residue. In some embodiments, the cysteine susceptible electrophile is selected from: an acrylate group, an acrylamide group, a vinyl group, a vinylsulfone group, a vinylsulfonamide group, an ynamide, and an epoxide group. In some embodiments, the cysteine susceptible electrophile is selected from: an acrylate group, an acrylamide group, a vinylsulfone group, and a vinylsulfonamide group. In some embodiments, the AKT1 protein comprises a E17K mutation. In some embodiments, the cysteine residue is selected from C296 and C310. In some embodiments, the cysteine residue is C296. In some embodiments, the in vivo engineered AKT1 protein is a human in vivo engineered AKT1 protein.

In another aspect, the present disclosure provides a method of covalently modifying an AKT1 protein, comprising contacting the AKT1 protein with an exogenous AKT1 modulator, wherein the AKT1 modulator comprises a cysteine susceptible electrophile thereby forming a covalent AKT1 adduct. In some embodiments, the contacting is in vitro. In some embodiments, the contacting is in vivo. In some embodiments, the AKT1 modulator is an AKT1 inhibitor. In some embodiments, the cysteine susceptible electrophile is selected from: an acrylamide group, a vinyl group, a vinylsulfone group, a vinylsulfonamide group, an ynamide, and an epoxide group. In some embodiments, the cysteine susceptible electrophile is selected from: an acrylate group, an acrylamide group, a vinylsulfone group, and a vinylsulfonamide group.

In another aspect, the present disclosure provides a method of attenuating AKT1 activity, comprising contacting AKT1 protein with an AKT1 inhibitor, wherein the AKT1 inhibitor comprises a cysteine susceptible electrophile. In some embodiments, the contacting is in vitro. In some embodiments, following the contacting, the AKT1 activity is attenuated by 50% or more relative to a control in the absence of the exogenous AKT1 inhibitor. In some embodiments, following the contacting, the AKT1 activity is attenuated by 70% or more relative to a control in the absence of the exogenous AKT1 inhibitor. In some embodiments, the cysteine susceptible electrophile is selected from: an acrylate group, an acrylamide group, a vinyl group, a vinylsulfone group, a vinylsulfonamide group, an ynamide, and an epoxide group. In some embodiments, the cysteine susceptible electrophile is selected from: an acrylate group, an acrylamide group, a vinylsulfone group, and a vinylsulfonamide group. In some embodiments, the exogenous AKT1 inhibitor is a compound or salt of Formula (I), (I-A), (II), (II-A), (III), (III-A), or (III-B), or a pharmaceutical composition comprising a compound or salt of Formula (I), (I-A), (II), (II-A), (III), (III-A), or (III-B).

INCORPORATION BY REFERENCE

All publications, patents, and patent applications mentioned in this specification are herein incorporated by reference for the specific purposes identified herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A provides a 2-D diagram from the crystal structure of Compound 13/AKT1 WT with the AKT1 WT rendered in a cartoon model and Compound 13 with the AKT1 WT cysteine residue C296 rendered in stick model. FIG. 1B provides a 2-D diagram close-up from the crystal structure of Compound 13/AKT1 WT with Compound 13 depicted by a thicker stick model and the residues of AKT1 WT depicted by a thinner stick model. FIG. 1C provides a 2-D diagram close-up from the crystal structure of Compound 13/AKT1 WT detailing the interactions between the residues of AKT1 WT and Compound 13, specifically showing the covalent bond between C296 cysteine residue of AKT1 WT and Compound 13 (contains SEQ ID NO: 4).

FIG. 2A provides a 2-D diagram from the crystal structure of Compound 13/AKT E17K with the AKT E17K rendered in a cartoon model and Compound 13 with the AKT E17K cysteine residue C296 rendered in stick model. FIG. 2B provides a 2-D diagram close-up from the crystal structure of Compound 13/AKT E17K with Compound 13 depicted by a thicker stick model and the residues of AKT E17K depicted by a thinner stick model. FIG. 2C provides a 2-D diagram close-up from the crystal structure of Compound 13/AKT E17K detailing the interactions between the residues of AKT E17K and Compound 13, specifically showing the covalent bond between C296 cysteine residue of AKT E17K and Compound 13 (contains SEQ ID NO: 4).

DETAILED DESCRIPTION OF THE INVENTION

Figure 1A:
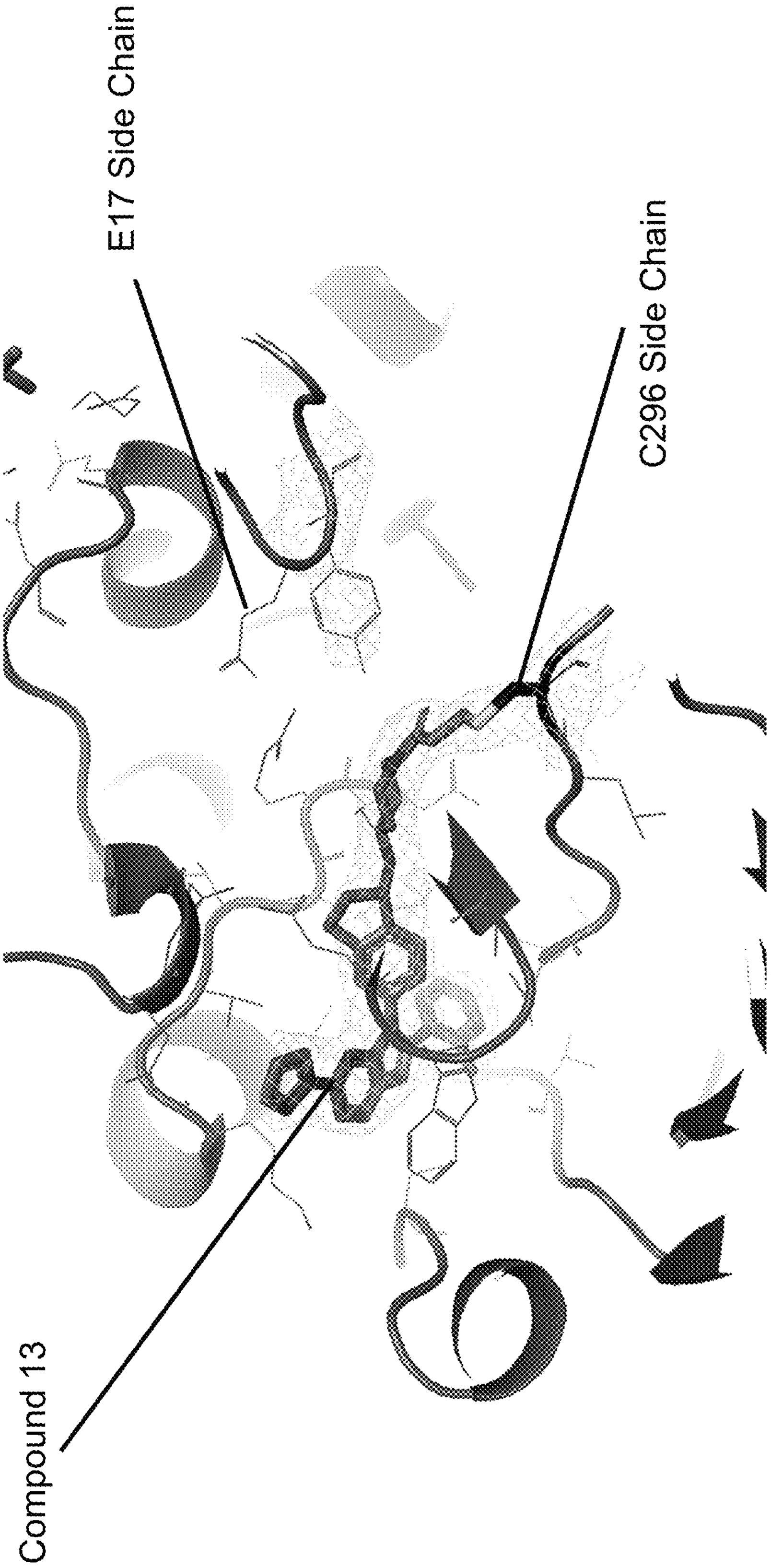
FIGS. 1A-1C provide diagrams of the crystal structure for the Compound 13/AKT1 WT co-crystallization complex.

The AKT or Protein Kinase B (PKB) family of serine/threonine protein kinases regulate a myriad of key cellular functions, including apoptosis, proliferation, differentiation, and metabolism. The AKT family is comprised of 3 highly homologous members, AKT1, AKT2 and AKT3, and each member possesses a unique tissue distribution and may perform a unique set of biological functions. Aberrant expression and/or activation of all AKT isoforms has been implicated in tumor development, including breast, ovarian, pancreatic, and prostate cancers among others.

Inhibitors of AKT proteins have been developed for the treatment of cancer, including the two major classes of small-molecule AKT inhibitors being investigated in the clinic: allosteric and ATP-competitive inhibitors. First, allosteric inhibitors (such as miransertib (ARQ 092) and MK-2206) interfere with PH-domain mediated membrane recruitment (the first step in AKT activation) and inhibit AKT kinase activation and AKT phosphorylation. Second, ATP-competitive inhibitors of AKT (such as ipatasertib and capivasertib) bind to the active kinase, in which the PH-domain has shifted from the kinase domain and exposed the ATP-binding pocket site, thus inhibiting ATP binding.

Provided herein are compounds for modulating (e.g., inhibiting) AKT1 function, as well as methods and compositions for using compounds of the present disclosure in the treatment of cancer. In some embodiments, the compounds selectively inhibit (e.g., 2×, 5×, 10×, 50×, 100×, etc.) an AKT1 protein over an AKT2 and/or AKT3 protein.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a," "an," and "the" includes plural references unless the context clearly dictates otherwise.

"Alkyl" refers to a straight or branched hydrocarbon chain monovalent radical consisting solely of carbon and hydrogen atoms, containing no unsaturation, and preferably having from one to twelve carbon atoms (i.e., $C_{1-12}$ alkyl). The alkyl is attached to the remainder of the molecule through a single bond. An alkyl chain may be optionally substituted by one or more substituents such as those substituents described herein. In certain embodiments, an alkyl comprises one to twelve carbon atoms (i.e., $C_{1-12}$ alkyl). In certain embodiments, an alkyl comprises one to eight carbon atoms (i.e., $C_{1-8}$ alkyl). In other embodiments, an alkyl comprises one to five carbon atoms (i.e., $C_{1-5}$ alkyl). In other embodiments, an alkyl comprises one to four carbon atoms (i.e., $C_{1-4}$ alkyl). In other embodiments, an alkyl comprises one to three carbon atoms (i.e., $C_{1-3}$ alkyl). In other embodiments, an alkyl comprises one to two carbon atoms (i.e., $C_{1-2}$ alkyl). In other embodiments, an alkyl comprises one carbon atom (i.e., $C_1$ alkyl). In other embodiments, an alkyl comprises five to fifteen carbon atoms (i.e., $C_{5-15}$ alkyl). In other embodiments, an alkyl comprises five to eight carbon atoms (i.e., $C_{5-8}$ alkyl). In other embodiments, an alkyl comprises two to five carbon atoms (i.e., $C_{2-5}$ alkyl). In other embodiments, an alkyl comprises three to five carbon atoms (i.e., $C_{3-5}$ alkyl). For example, the alkyl group may be attached to the rest of the molecule by a single bond, such as, methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl), and the like.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_{2-12}$ alkenyl). An alkenyl chain may be optionally substituted by one or more substituents such as those substituents described herein. In certain embodiments, an alkenyl comprises two to eight carbon atoms (i.e., $C_{2-8}$ alkenyl). In certain embodiments, an alkenyl comprises two to six carbon atoms (i.e., $C_{2-6}$ alkenyl). In other embodiments, an alkenyl comprises two to four carbon atoms (i.e., $C_{2-4}$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_{2-12}$ alkynyl). An alkylnyl chain may be optionally substituted by one or more substituents such as those substituents described herein. In certain embodiments, an alkynyl comprises two to eight carbon atoms (i.e., $C_{2-8}$ alkynyl). In other embodiments, an alkynyl comprises two to six carbon atoms (i.e., $C_{2-6}$ alkynyl). In other embodiments, an alkynyl comprises two to four carbon atoms (i.e., $C_{2-4}$ alkynyl). The alkynyl is attached to the rest of the molecule by a single bond, for example, ethynyl, propynyl, butynyl, pentynyl, hexynyl, and the like.

"Alkylene" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, (methyl)ethylene, butylene, and the like. The alkylene chain is attached to the rest of the molecule through a single bond and to the radical group through a single bond. An alkylene chain may be optionally substituted by one or more substituents such as those substituents described herein. In certain embodiments, an alkylene comprises one to ten carbon atoms (i.e., $C_{1-10}$ alkylene). In certain embodiments, an alkylene comprises one to eight carbon atoms (i.e., $C_{1-8}$ alkylene). In other embodiments, an alkylene comprises one to five carbon atoms (i.e., $C_{1-5}$ alkylene). In other embodiments, an alkylene comprises one to four carbon atoms (i.e., $C_{1-4}$ alkylene). In other embodiments, an alkylene comprises one to three carbon atoms (i.e., $C_{1-3}$ alkylene). In other embodiments, an alkylene comprises one to two carbon atoms (i.e., $C_{1-2}$ alkylene). In other embodiments, an alkylene comprises one carbon atom (i.e., $C_1$ alkylene). In other embodiments, an alkylene comprises five to eight carbon atoms (i.e., $C_{5-8}$ alkylene). In other embodiments, an alkylene comprises two to five carbon atoms (i.e., $C_{2-5}$ alkylene). In other embodiments, an alkylene comprises three to five carbon atoms (i.e., $C_{3-5}$ alkylene).

"Alkenylene" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. An alkenylene chain may be optionally substituted by one or more substituents such as those substituents described herein. In certain embodiments, an alkenylene comprises two to ten carbon atoms (i.e., $C_{2-10}$ alkenylene). In certain embodiments, an alkenylene comprises two to eight carbon atoms (i.e., $C_{2-8}$ alkenylene). In other embodiments, an alkenylene comprises two to five carbon atoms (i.e., $C_{2-5}$ alkenylene). In other embodiments, an alkenylene comprises two to four carbon atoms (i.e., $C_{2-4}$ alkenylene). In other embodiments, an alkenylene comprises two to three carbon atoms (i.e., $C_{2-3}$ alkenylene). In other embodiments, an alkenylene comprises two carbon atoms (i.e., $C_2$ alkenylene). In other embodiments, an alkenylene comprises five to eight carbon atoms (i.e., $C_{5-8}$ alkenylene). In other embodiments, an alkenylene comprises three to five carbon atoms (i.e., $C_{3-5}$ alkenylene).

"Alkynylene" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. An alkynylene chain may be optionally substituted by one or more substituents such as those substituents described herein. In certain embodiments, an alkynylene comprises two to ten carbon atoms (i.e., $C_{2-10}$ alkynylene). In certain embodiments, an alkynylene comprises two to eight carbon atoms (i.e., $C_{2-8}$ alkynylene). In other embodiments, an alkynylene comprises two to five carbon atoms (i.e., $C_{2-5}$ alkynylene). In other embodiments, an alkynylene comprises two to four carbon atoms (i.e., $C_{2-4}$ alkynylene). In other embodiments, an alkynylene comprises two to three carbon atoms (i.e., $C_{2-3}$ alkynylene). In other embodiments, an alkynylene comprises two carbon atoms (i.e., $C_2$ alkynylene). In other embodiments, an alkynylene comprises five to eight carbon atoms (i.e., $C_{5-8}$ alkynylene). In other embodiments, an alkynylene comprises three to five carbon atoms (i.e., $C_{3-5}$ alkynylene).

The term "$C_{x-y}$" when used in conjunction with a chemical moiety, such as alkyl, alkenyl, or alkynyl is meant to include groups that contain from x to y carbons in the chain. For example, the term "$C_{1-6}$ alkyl" refers to saturated hydrocarbon groups, including straight-chain alkyl and branched-chain alkyl groups that contain from 1 to 6 carbons. The term —$C_{x-y}$ alkylene-refers to an alkylene chain with from x to y carbons in the alkylene chain. For example, —$C_{1-6}$ alkylene-may be selected from methylene, ethylene, propylene, butylene, pentylene, and hexylene, any one of which may be optionally substituted.

The terms "$C_{x-y}$ alkenyl" and "$C_{x-y}$ alkynyl" refer to unsaturated aliphatic groups analogous in length and possible substitution to the alkyls described above, but that contain at least one double or triple bond, respectively. The term —$C_{x-y}$ alkenylene-refers to a alkenylene chain with from x to y carbons in the alkenylene chain. For example, —$C_{2-6}$ alkenylene- may be selected from ethenylene, propenylene, butenylene, pentenylene, and hexenylene, any one of which may be optionally substituted. An alkenylene chain may have one double bond or more than one double bond in the alkenylene chain. The term —$C_{x-y}$ alkynylene-refers to a alkynylene chain with from x to y carbons in the alkynylene chain. For example, —$C_{2-6}$ alkynylene- may be selected from ethynylene, propynylene, butynylene, pentynylene, and hexynylene, any one of which may be optionally substituted. An alkynylene chain may have one triple bond or more than one triple bond in the alkynylene chain.

The term "carbocycle" as used herein refers to a saturated, unsaturated or aromatic ring in which each atom of the ring is carbon. Carbocycle includes 3- to 10-membered monocyclic rings and polycyclic rings (e.g., 6- to 12-membered bicyclic rings). Each ring of a polycyclic carbocycle may be selected from saturated, unsaturated, and aromatic rings. Polycyclic carbocycles may be fused, bridged or spiro-ring systems. Each ring of a bicyclic carbocycle may be selected from saturated, unsaturated, and aromatic rings. Bicyclic carbocycles may be fused, bridged or spiro-ring systems. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Carbocycle may be optionally substituted by one or more substituents such as those substituents described herein.

The term "carbocyclene" as used herein refers to a divalent saturated, unsaturated or aromatic ring in which each atom of the ring is carbon. The carbocyclene is attached to the rest of the molecule through a single bond and to the radical group through a single bond. A carbocyclene may be optionally substituted by one or more substituents such as those substituents described herein. Carbocyclene includes divalent 3- to 10-membered monocyclic rings and divalent polycyclic rings (e.g., 6- to 12-membered bicyclic rings). Each ring of a polycyclic carbocyclene may be selected from saturated, unsaturated, and aromatic rings. Polycyclic carbocyclenes may be fused, bridged or spiro-ring systems. Polycyclic carbocyclenes may be fused, bridged or spiro-ring systems. The single bond connecting the carbocyclene to the rest of the molecule and the single bond connecting the carbocyclene to the radical group may be located on the same ring or different rings of a polycyclic carbocyclene. In some embodiments, the carbocycle is an arylene, for example, a phenylene. A "phenylene" as used herein refers to a divalent benzene group. The phenylene is attached to the rest of the molecule through a single bond and to the radical group through a single bond. A phenylene may be optionally substituted by one or more substituents such as those substituents described herein.

"Cycloalkyl" refers to a stable fully saturated monocyclic or polycyclic hydrocarbon radical consisting solely of carbon and hydrogen atoms, which includes fused, bridged, or spiro-ring systems, and preferably having from three to twelve carbon atoms (i.e., $C_{3-12}$ cycloalkyl). In certain embodiments, a cycloalkyl comprises three to ten carbon atoms (i.e., $C_{3-10}$ cycloalkyl). In other embodiments, a cycloalkyl comprises five to seven carbon atoms (i.e., $C_{5-7}$ cycloalkyl). The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Cycloalkyl may be optionally substituted by one or more substituents such as those substituents described herein.

"Aryl" refers to a radical derived from an aromatic monocyclic or aromatic polycyclic hydrocarbon ring system by removing a hydrogen atom from a ring carbon atom. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) p-electron system in accordance with the Hückel theory. The ring system from which aryl groups are derived include, but are not limited to, groups such as benzene, fluorene, indane, indene, tetralin and naphthalene. Aryl may be optionally substituted by one or more substituents such as those substituents described herein.

A "$C_{x-y}$ carbocycle" is meant to include groups that contain from x to y carbons in a ring. For example, the term "$C_{3-6}$ carbocycle" can be a saturated, unsaturated or aromatic ring system that contains from 3 to 6 carbon atoms—any one of which may be optionally substituted as provided herein.

The term "heterocycle" as used herein refers to a saturated, unsaturated, non-aromatic or aromatic ring comprising one or more heteroatoms. Exemplary heteroatoms include N, O, Si, P, B, and S atoms. Heterocycles include 3- to 10-membered monocyclic rings and polycyclic rings (e.g., 6- to 12-membered bicyclic rings). Polycyclic heterocycles may be fused, bridged or spiro-ring systems. Each ring of a polycyclic heterocycle may be selected from saturated, unsaturated, and aromatic rings. In some embodiments, the heterocycle comprises at least one heteroatom selected from oxygen, nitrogen, sulfur, or any combination thereof. In some embodiments, the heterocycle comprises at least one heteroatom selected from oxygen, nitrogen, or any combination thereof. In some embodiments, the heterocycle comprises at least one heteroatom selected from oxygen, sulfur, or any combination thereof. In some embodiments, the heterocycle comprises at least one heteroatom selected from nitrogen, sulfur, or any combination thereof. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, and quinolinyl. Heterocycle may be optionally substituted by one or more substituents such as those substituents described herein. Bicyclic heterocycles may be fused, bridged or spiro-ring systems. In an exemplary embodiment, a heterocycle, e.g., pyridyl, may be fused to a saturated or unsaturated ring, e.g., cyclohexane, cyclopentane, or cyclohexene. Heterocycle may be optionally substituted by one or more substituents such as those substituents described herein.

The term "heterocyclene" as used herein refers to a divalent saturated, unsaturated, non-aromatic or aromatic ring comprising one or more heteroatoms. Exemplary heteroatoms include N, O, Si, P, B, and S atoms. The heterocyclene is attached to the rest of the molecule through a single bond and to the radical group through a single bond. The single bond attaching the heterocyclene group to the rest of the molecule and the single bond attaching the heterocyclene group to the radical group may be each independently connected through any atom of the heterocyclene as valency permits, including a carbon atom in the heterocyclene ring or a heteroatom in the heterocyclene ring. A heterocyclene may be optionally substituted by one or more substituents such as those substituents described herein. Heterocyclenes include 3- to 10-membered monocyclic rings and polycyclic rings (e.g., 6- to 12-membered bicyclic rings). Each ring of a polycyclic heterocyclene may be selected from saturated, unsaturated, and aromatic rings. Polycyclic heterocyclenes may be fused, bridged or spiro-ring systems. The single bond connecting the heterocyclene to the rest of the molecule and the single bond connecting the heterocyclene to the radical group may be located on the same ring or different rings of a polycyclic heterocyclene and may be attached to the rest of the molecule or the radical group through any atom of the heterocyclene, valence permitting, such as a carbon or nitrogen atom of the heterocycle. In some embodiments, the heterocyclene comprises at least one heteroatom selected from oxygen, nitrogen, sulfur, or any combination thereof. In some embodiments, the heterocyclene comprises at least one heteroatom selected from oxygen, nitrogen, or any combination thereof. In some embodiments, the heterocyclene comprises at least one heteroatom selected from oxygen, sulfur, or any combination thereof. In some embodiments, the heterocyclene comprises at least one heteroatom selected from nitrogen, sulfur, or any combination thereof. In some embodiments, the heterocyclene is a heteroarylene. In some embodiments, the heterocyclene is a heterocycloalkylene.

"Heterocycloalkyl" refers to a stable 3 to 12 membered non-aromatic ring radical that comprises two to twelve carbon atoms and at least one heteroatom wherein each heteroatom may be selected from N, O, Si, P, B, and S atoms. In some embodiments, the heterocycloalkyl comprises at least one heteroatom selected from oxygen, nitrogen, sulfur, or any combination thereof. In some embodiments, the heterocycloalkyl comprises at least one heteroatom selected from oxygen, nitrogen, or any combination thereof. In some embodiments, the heterocycloalkyl comprises at least one heteroatom selected from oxygen, sulfur, or any combination thereof. In some embodiments, the heterocycloalkyl comprises at least one heteroatom selected from nitrogen, sulfur, or any combination thereof. The heterocycloalkyl may be selected from monocyclic or bicyclic, and fused, bridged, or spiro-ring systems. The heteroatoms in the heterocycloalkyl radical are optionally oxidized. One or more nitrogen atoms, if present, are optionally quaternized. The heterocycloalkyl radical is partially or fully saturated. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxothiomorpholinyl. Heterocycloalkyl may be optionally substituted by one or more substituents such as those substituents described herein.

The term "heteroaryl" refers to a radical derived from a 5- to 12-membered aromatic ring radical whose ring structure comprise at least one heteroatom, preferably between one to four heteroatoms. In some embodiments, the heteroaryl comprises at least one heteroatom selected from oxygen, nitrogen, sulfur, or any combination thereof. In some embodiments, the heteroaryl comprises at least one heteroatom selected from oxygen, nitrogen, or any combination thereof. In some embodiments, the heteroaryl comprises at least one heteroatom selected from oxygen, sulfur, or any combination thereof. In some embodiments, the heteroaryl comprises at least one heteroatom selected from nitrogen, sulfur, or any combination thereof. As used herein, the heteroaryl ring may be selected from monocyclic or bicyclic and fused or bridged ring systems wherein at least one of the rings in the ring system is aromatic, i.e., it contains a cyclic, delocalized (4n+2) p-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Heteroaryl includes aromatic single ring structures, preferably 5- to 6-membered rings, whose ring structures include at least one heteroatom, preferably one to four heteroatoms, more preferably one or two heteroatoms. Heteroaryl groups include, for example, pyrrole, furan, thiophene, imidazole, oxazole, thiazole, pyrazole, pyridine, pyrazine, pyridazine, and pyrimidine, and the like. Heteroaryl may be optionally substituted by one or more substituents such as those substituents described herein. Heteroaryl also includes polycyclic ring systems having two or more rings in which two or more atoms are common to two adjoining rings wherein at least one of the rings is heteroaromatic, e.g., the other rings can be aromatic or non-aromatic carbocyclic, or heterocyclic. Heteroaryl may be optionally substituted by one or more substituents such as those substituents described herein.

An "X-membered heterocycle" refers to the number of endocyclic atoms, i.e., X, in the ring. For example, a 5-membered heteroaryl ring or 5-membered aromatic heterocycle has 5 endocyclic atoms, e.g., triazole, oxazole, thiophene, etc.

"Alkoxy" refers to a radical bonded through an oxygen atom of the formula: —O-alkyl, where alkyl is an alkyl chain as defined above.

"Halo" or "halogen" refers to halogen substituents such as bromo, chloro, fluoro, and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, and I). When an alkyl group is substituted with more than one halogen radical, each halogen may be independently selected for example, 1-chloro,2-fluoroethane.

The term "substituted" refers to moieties having substituents replacing a hydrogen on one or more carbons or substitutable heteroatoms, e.g., an NH or $NH_2$ of a compound. Unless specified otherwise (e.g., by using the terms "substituted" or "optionally substituted," or by the inclusion of an "—R" group), chemical groups described herein are unsubstituted. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino, or thioxo group. As used herein, the term "substituted" is contemplated to include all permissible substituents of organic compounds. In a broad aspect, the permissible substituents include acyclic and cyclic, branched and unbranched, carbocyclic and heterocyclic, and aromatic and non-aromatic substituents of organic compounds. The permissible substituents can be one or more and the same or different for appropriate organic compounds.

In some embodiments, substituents may include any substituents described herein, for example: halogen, hydroxy, oxo (═O), thioxo (═S), cyano (—CN), nitro ($—NO_2$), imino (=N—H), oximo (=N—OH), hydrazino (=N—$NH_2$), $—R^b—OR^a$, $—R^b—OC(O)R^a$, $—R^b—OC(O)OR^a$, $—R^b—OC(O)N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)R^a$ (where t is 0, 1, or 2), $—R^b—S(O)_t OR^a$ (where t is 1 or 2), $—R^b—S(O)_t N(R^a)_2$ (where t is 1 or 2), and $—P(O)(R^a)_2$; and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any one of which may be optionally substituted by alkyl, alkenyl, alkynyl, halogen, haloalkyl, haloalkenyl, haloalkynyl, oxo (=O), thioxo (=S), cyano (—CN), nitro ($—NO_2$), imino (=N—H), oximo (=N—OH), hydrazine (=N—$NH_2$), $—R^b—OR^a$, $—R^b—OC(O)R^a$, $—R^b—OC(O)OR^a$, $—R^b—OC(O)N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)R^a$ (where t is 0, 1, or 2), $—R^b—S(O)_tOR^a$ (where t is 1 or 2), $—R^b—S(O)_tN(R^a)_2$ (where t is 1 or 2), and $—P(O)(R^a)_2$; wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro ($—NO_2$), imino (=N—H), oximo (=N—OH), hydrazine (=N—$NH_2$), $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)R^a$ (where t is 1 or 2), $—R^b—S(O)_tR^a$ (where t is 0, 1, or 2), $—R^b—S(O)_t OR^a$ (where t is 1 or 2), $—R^b—S(O)_t N(R^a)_2$ (where t is 1 or 2), and $—P(O)(R^a)_2$; and wherein each $R^b$ is independently selected from a direct bond or a straight or branched alkylene, alkenylene, or alkynylene chain, and each Reis a straight or branched alkylene, alkenylene or alkynylene chain. It will be understood by those skilled in the art that substituents can themselves be substituted, if appropriate.

The term "salt" or "pharmaceutically acceptable salt" refers to salts derived from a variety of organic and inorganic counter ions well known in the art. Pharmaceutically acceptable acid addition salts can be formed with inorganic acids and organic acids. Pharmaceutically acceptable base addition salts can be formed with inorganic and organic bases.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The terms "subject," "individual," and "patient" may be used interchangeably and refer to humans as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a compound or salt described herein.

The terms "administer," "administered," "administers," and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In certain embodiments, oral routes of administering a composition can be used. The terms "administer," "administered," "administers," and "administering" a compound should be understood to mean providing a compound or salt of the invention or a prodrug of a compound or salt of the invention to the individual in need.

As used herein, "treatment" or "treating" refers to an approach for obtaining beneficial or desired results with respect to a disease, disorder, or medical condition including, but not limited to, a therapeutic benefit and/or a prophylactic benefit. In certain embodiments, treatment or treating involves administering a compound or composition disclosed herein to a subject. A therapeutic benefit may include the eradication or amelioration of the underlying disorder being treated. Also, a therapeutic benefit may be achieved with the eradication or amelioration of one or more of the physiological symptoms associated with the underlying disorder, such as observing an improvement in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treating can be used herein to refer to a method that results in some level of treatment or amelioration of the disease or condition and can contemplate a range of results directed to that end, including but not restricted to prevention of the condition entirely.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

Compounds

A compound represented by the structure of Formula (I):

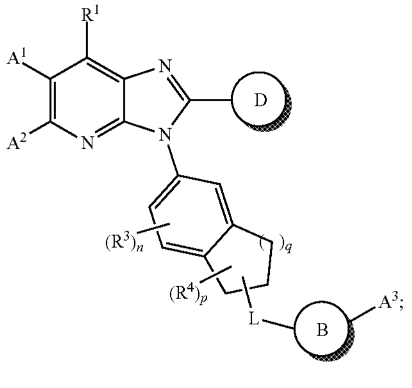

(I)

or a pharmaceutically acceptable salt thereof, wherein:

$R^1$ is selected from:

hydrogen, halogen, —$OR^{10}$, —$SR^{10}$, —$N(R^{10})_2$, —$NO_2$, and —CN;

$C_{1-6}$ alkyl optionally substituted with one or more substituents independently selected from: halogen, —$OR^{10}$, —$SR^{10}$, —$N(R^{10})_2$, —$NO_2$, and —CN; and $C_{3-8}$ carbocycle and 4- to 8-membered heterocycle, any of which is optionally substituted with one or more substituents independently selected from halogen, —$OR^{10}$, —$SR^{10}$, —$N(R^{10})_2$, —$NO_2$, —CN, $C_{1-6}$ alkyl, and $C_{1-6}$ haloalkyl;

$A^1$ and $A^2$ are each independently selected from (i), (ii), and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and 4- to 10-membered heterocycle and $C_{3-10}$ carbocycle, any of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and (iii) 4- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{2-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —CN; $C(O)OR^{11}$, —$OC(O)R^{11}$, —$NO_2$, =O, =S, =$N(R^{11})$, —CN;

$C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN; and $C_{3-10}$ carbocycle and 4- to 10-membered heterocycle any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN;

$R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl, $C_{2-6}$ alkenyl, and $C_{2-6}$ alkynyl, any one of which is optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN;

$R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; and $C_{1-6}$ alkyl, $C_{2-6}$ alkenyl, and $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN;

L is represented by -$L^1$-$L^2$-$L^3$-$L^4$-, wherein $L^1$, $L^2$, $L^3$, and $L^4$ are each independently selected from (a) and (b):

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, —$OR^{15}$, —$SR^{15}$, =O, =S, and —CN;

wherein $L^1$, $L^2$, $L^3$, and $L^4$ are each optionally absent;

wherein no more than two of $L^1$, $L^2$, $L^3$, and $L^4$ are selected from (a) and the two selected are not adjacent;

Ring B selected from 3- to 10-membered heterocyclene and $C_{3-10}$ carbocyclene, any of which is optionally substituted with one or more substituents independently selected from:

halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN; and 3- to 6-membered heterocycle and $C_{3-6}$ carbocycle, each of which is optionally substituted with one or more substituents independently selected from: halogen, $C_{1-6}$ alkyl, $C_{1-6}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

Ring D is selected from:

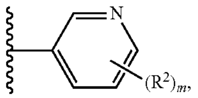 , 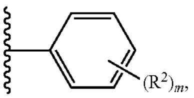 ,

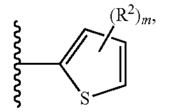 and 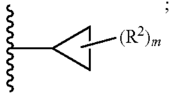 ;

$R^2$ is independently selected at each instance from halogen, $C_{1-6}$ alkyl, $C_{1-6}$ haloalkyl, —$OR^{12}$, —$SR^{12}$, —$N(R^{12})_2$, —$NO_2$, and —CN;

$A^3$ is cysteine susceptible electrophile;

$R^{10}$, $R^{11}$, $R^{12}$, $R^{13}$, $R^{14}$, $R^{15}$, and $R^{16}$ are each independently selected at each occurrence from:

hydrogen, $C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and $C_{3-6}$ carbocycle and 3- to 6-membered heterocycle, each of which is optionally substituted with one or more substituents independently selected from halogen, —OH, —O—$C_{1-6}$ alkyl, —O—$C_{1-6}$ haloalkyl, $C_{1-6}$ alkyl, and $C_{1-6}$ haloalkyl;

m is selected from 0, 1, 2, and 3;

n is selected from 0, 1, 2, and 3;

q is selected from 1, 2, and 3; and p is selected from 0, 1, 2, 3, 4, and 5.

In some embodiments, for the compound or salt of Formula (I), $A^1$ and $A^2$ are each independently selected from (i) and (ii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN; and (ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and 3- to 10-membered heterocycle and $C_{3-10}$ carbocycle, any of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN.

In some embodiments, for the compound or salt of Formula (I), $A^1$ and $A^2$ are each independently selected from (i) and (ii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN; and (ii) $C_{1-6}$ alkyl, $C_{2-6}$ alkenyl, and $C_{2-6}$ alkynyl, any of which is optionally substituted with one or more substituents independently selected from 3- to 10-membered heterocycle and $C_{3-10}$ carbocycle, any of which is optionally substituted with one or more substituents independently selected from: halogen, —$OR^{11}$, —$SR^{11}$, —$N(R^{11})_2$, —$C(O)R^{11}$, $C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN.

In some embodiments, for the compound or salt of Formula (I), $A^1$ and $A^2$ are each independently selected from (i) and (ii):

(i) hydrogen, halogen, —$OR^{11}$, —$SR^{11}$, —$N(R^{11})_2$, —$NO_2$, and —CN; and (ii) $C_{1-6}$ alkyl, $C_{2-6}$ alkenyl, and $C_{2-6}$ alkynyl, any of which is optionally substituted with one or more substituents independently selected from 3- to 10-membered heterocycle optionally substituted with one or more substituents independently selected from halogen, halogen, —$OR^{11}$, —$SR^{11}$, —$N(R^{11})_2$, —$NO_2$, and —CN.

In some embodiments, for the compound or salt of Formula (I), $A^1$ and $A^2$ are each independently selected from hydrogen, halogen, —$OR^{11}$, —$SR^{11}$, —$N(R^{11})_2$, —$NO_2$, and —CN; and $C_{1-6}$ alkyl optionally substituted with one or more substituents independently selected from halogen, —$OR^{11}$, —$SR^{11}$, —$N(R^{11})_2$, —$NO_2$, —CN, 3- to 10-membered heterocycle and $C_{3-10}$ carbocycle, the 3- to 10-membered heterocycle and $C_{3-10}$ carbocycle are each optionally substituted with one or more substituents independently selected from halogen, —$OR^{11}$, —$SR^{11}$, —$N(R^{11})_2$, —$NO_2$, —CN, $C_{1-6}$ alkyl, and $C_{1-6}$ haloalkyl. In some embodiments, $A^1$ and $A^2$ are each independently selected from hydrogen, halogen, —$OR^{11}$, —$SR^{11}$, —$N(R^{11})_2$, —$NO_2$, and —CN; and $C_{1-6}$ alkyl optionally substituted with one or more substituents independently selected from halogen, —$OR^{11}$, —$SR^{11}$, —$N(R^{11})_2$, —$NO_2$, —CN, 3- to 6-membered heterocycle and $C_{3-6}$carbocycle, the 3- to 6-membered heterocycle and $C_{3-6}$ carbocycle are each optionally substituted with one or more substituents independently selected from halogen, —$OR^{11}$, —$SR^{11}$, —$N(R^{11})_2$, —$NO_2$, —CN, $C_{1-6}$ alkyl, and $C_{1-6}$ haloalkyl. In some embodiments, $A^1$ and $A^2$ are each independently selected from hydrogen, halogen, —$OR^{11}$, —$SR^{11}$, —$N(R^{11})_2$, —$NO_2$, and —CN; and $C_{1-6}$ alkyl optionally substituted with one or more substituents independently selected from halogen, —$OR^{11}$, —$SR^{11}$, —$N(R^{11})_2$, —$NO_2$, —CN, 3- to 6-membered heterocycle optionally substituted with one or more substituents independently selected from halogen, —$OR^{11}$, —$SR^{11}$, —$N(R^{11})_2$, —$NO_2$, —CN, $C_{1-6}$ alkyl, and $C_{1-6}$ haloalkyl. In some embodiments, $A^2$ is

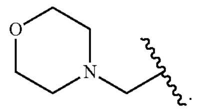 [SMILES: *CN1CCOCC1]

In some embodiments, for the compound or salt of Formula (I), $A^1$ and $A^2$ are each independently selected from (i) and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN; and (iii) 4- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{2-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN;

$C_{1-6}$ alkyl $C_{2-6}$ alkenyl, and $C_{2-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN; and $C_{3-10}$ carbocycle and 4- to 10-membered heterocycle any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), $A^1$ and $A^2$ are each independently selected from (i) and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN; and (iii) 4- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$NO_2$, =$N(R^{11})$, and —CN;

$C_{1-6}$ alkyl, $C_{2-6}$ alkenyl, and $C_{2-6}$ alkynyl, any one of which is optionally substituted with one or more substituents independently selected from: halogen, —$OR^{11}$, —$SR^{11}$, —$N(R^{11})_2$, —$C(O)R^{11}$, —$NO_2$, =$N(R^{11})$, and —CN; and $C_{3-10}$ carbocycle and 4- to 10-membered heterocycle, any of which is optionally substituted with one or more substituents independently selected from: halogen, —$OR^{11}$, —$SR^{11}$, —$N(R^{11})_2$, —$C(O)R^{11}$, —$NO_2$, =$N(R^{11})$, —CN, $C_{1-6}$ alkyl, $C_{1-6}$ haloalkyl, $C_{2-6}$ alkenyl, $C_{2-6}$ haloalkenyl, $C_{2-6}$ alkynyl, and $C_{2-6}$ haloalkynyl.

In some embodiments, for the compound or salt of Formula (I), $A^1$ and $A^2$ are each independently selected from:

hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, —CN; and 4- to 6-membered heterocycle and $C_{3-6}$ carbocycle, each of which is optionally substituted by one or substituents independently selected from: halogen, —$OR^{11}$, —$SR^{11}$, —$N(R^{11})_2$, —$C(O)R^{11}$, —$NO_2$, =$N(R^{11})$, —CN, $C_{1-6}$ alkyl, $C_{2-6}$ alkenyl, $C_{2-6}$ alkynyl, $C_{3-6}$ carbocycle and 3- to 6-membered heterocycle.

In some embodiments, for the compound or salt of Formula (I), $A^1$ and $A^2$ are each independently selected from hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, —CN, and 4- to 10-membered heterocycle and $C_{3-10}$ carbocycle, the 4- to 10-membered heterocycle and $C_{3-10}$ carbocycle are optionally substituted with one or more substituents independently selected from $C_{1-6}$ alkyl, $C_{1-6}$ haloalkyl, $C_{2-6}$ alkenyl, $C_{2-6}$ alkynyl, $C_{3-10}$ carbocycle and 4- to 10-membered heterocycle. In some embodiments, $A^1$ and $A^2$ are each independently selected from hydrogen, halogen, —$OR^{11}$, —$SR^{11}$, —$N(R^{11})_2$, —$NO_2$, —CN, and 4- to 10-membered heterocycle and $C_{3-10}$ carbocycle, the 4- to 10-membered heterocycle and $C_{3-10}$ carbocycle are optionally substituted with one or more substituents independently selected from $C_{1-6}$ alkyl, $C_{1-6}$ haloalkyl, $C_{2-6}$ alkenyl, $C_{2-6}$ alkynyl, $C_{3-10}$ carbocycle and 4- to 10-membered heterocycle. In some embodiments, $A^1$ and $A^2$ are each independently selected from hydrogen, halogen, —$OR^{11}$, —$SR^{11}$, —$N(R^{11})_2$, —$NO_2$, —CN, and 4- to 10-membered heterocycle and $C_{3-10}$ carbocycle, the 4- to 10-membered heterocycle and $C_{3-10}$ carbocycle are optionally substituted with one or more substituents independently selected from $C_{1-6}$ alkyl, $C_{1-6}$ haloalkyl, $C_{2-6}$ alkenyl, $C_{2-6}$ alkynyl, $C_{3-6}$ carbocycle and 4- to 6-membered heterocycle. In some embodiments, $A^1$ and $A^2$ are each independently selected from hydrogen, halogen, —$OR^{11}$, —$SR^{11}$, —$N(R^{11})_2$, —$NO_2$, —CN, and 4- to 6-membered heterocycle and $C_{3-6}$ carbocycle, the 4- to 6-membered heterocycle and $C_{3-6}$ carbocycle are optionally substituted with one or more substituents independently selected from $C_{1-6}$ alkyl, $C_{1-6}$ haloalkyl, $C_{2-6}$ alkenyl, $C_{2-6}$ alkynyl, $C_{3-6}$ carbocycle and 4- to 6-membered heterocycle. In some embodiments, $A^2$ is selected from

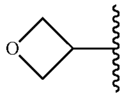 and 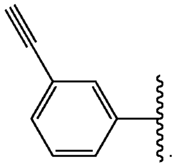.

In some embodiments, for the compound or salt of Formula (I), Ring D is selected from:

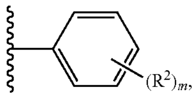 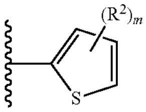 , and 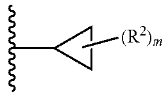 .

In some embodiments, Ring D is selected from:

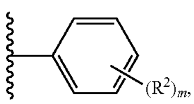 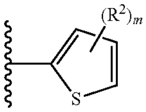 , and 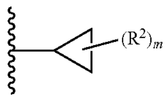 ;

and m is selected from 0, 1, and 2. In some embodiments, Ring D

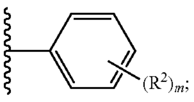

and m is selected from 0, 1, and 2. In some embodiments, embodiments, Ring D is

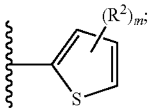

and m is selected from 0, 1, and 2. In some embodiments, Ring D is

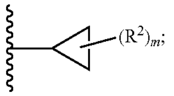

and m is selected from 0, 1, and 2.

In some embodiments, for the compound or salt of Formula (I), Ring D is selected from:

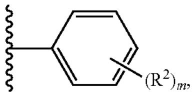 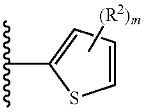 , and 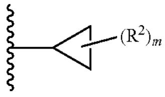 ;

m is selected from 0, 1, and 2; and each $R^2$ is selected from halogen, $C_{1-6}$ alkyl, $C_{1-6}$ haloalkyl, —$OR^{12}$, —$N(R^{12})_2$, and —CN.

In some embodiments, for the compound or salt of Formula (I), Ring D is

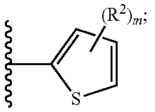

and m is selected from 0 and 1. In some embodiments, Ring D is

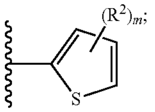

m is selected from 0 and 1; and $R^2$ is selected from halogen, $C_{1-6}$ alkyl, $C_{1-6}$ haloalkyl, —$OR^{12}$, —$N(R^{12})_2$, and —CN. In some embodiments, Ring D is

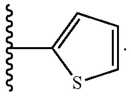

In some embodiments, for the compound or salt of Formula (I), Ring D is

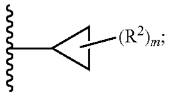

and m is selected from 0 and 1. In some embodiments, Ring D is

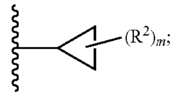

m is selected from 0 and 1; and $R^2$ is selected from halogen, $C_{1-6}$ alkyl, $C_{1-6}$ haloalkyl, —$OR^{12}$, —$N(R^{12})_2$, and —CN. In some embodiments, Ring D is

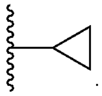

In some embodiments, for the compound or salt of Formula (I), Ring D is

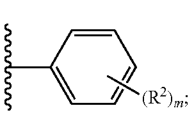

and m is selected from 0 and 1. In some embodiments, Ring D is

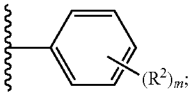

m is selected from 0 and 1; and $R^2$ is selected from halogen, $C_{1-6}$ alkyl, $C_{1-6}$ haloalkyl, —$OR^{12}$, —$N(R^{12})_2$, and —CN. In some embodiments, Ring D is selected from

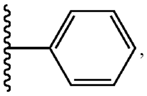, 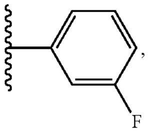, 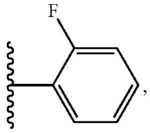,

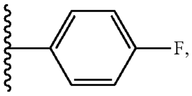, 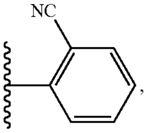, and 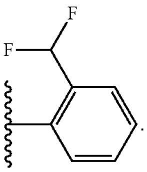.

In some embodiments, Ring D is

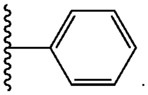

In some embodiments, Ring D is selected from

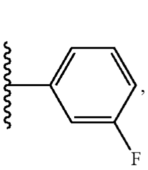, 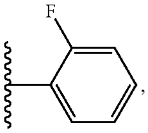, and 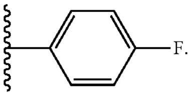

In some embodiments, Ring D is

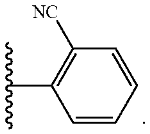 [SMILES: *c1ccccc1C#N]

In some embodiments, Ring D is

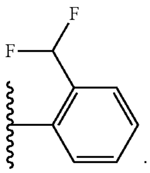

In some embodiments, for the compound or salt of Formula (I), Ring D is

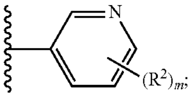

and m is selected from 1, 2, and 3. In some embodiments, Ring D is

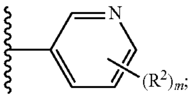

m is selected from 1, 2, and 3; and each $R^2$ is selected from halogen, $C_{1-6}$ alkyl, $C_{1-6}$ haloalkyl, —$OR^{12}$, —$N(R^{12})_2$, and —CN. In some embodiments, Ring D is represented by

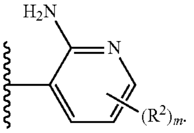

In some embodiments, for the compound or salt of Formula (I), Ring D is

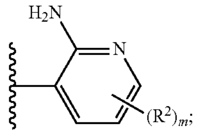

m is selected from 0, 1, 2, and 3; and each $R^2$ is selected from halogen, $C_{1-6}$ alkyl, $C_{1-6}$ haloalkyl, —$OR^{12}$, —$N(R^{12})_2$, and —CN. In some embodiments, Ring D is represented by

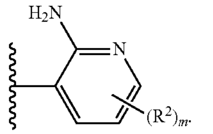

In some embodiments, for the compound or salt of Formula (I), Ring D is

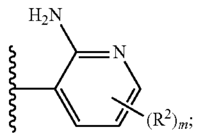

and each $R^2$ is selected from halogen, $C_{1-6}$ alkyl, $C_{1-6}$ haloalkyl, —$OR^{12}$, —$N(R^{12})_2$, and —CN. In some embodiments, Ring D is represented by

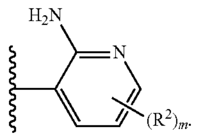

In some aspects, the structure Formula (I) is represented by the structure of Formula (II):

(II)

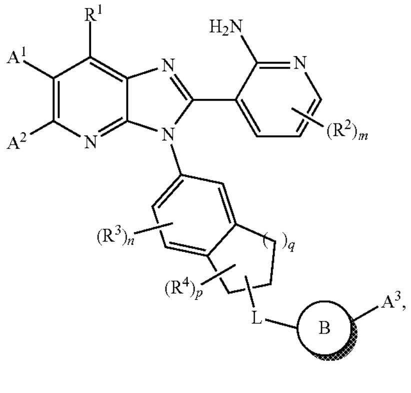

or a pharmaceutically acceptable salt thereof, wherein:

$R^1$ is selected from hydrogen, halogen, —$OR^{10}$, —$SR^{10}$, —$N(R^{10})_2$, —$NO_2$, and —CN; and $C_{1-6}$ alkyl optionally substituted with one or more substituents independently selected from: halogen, —$OR^{10}$, —$SR^{10}$, —$N(R^{10})_2$, —$NO_2$, and —CN;

$A^1$ and $A^2$ are each independently selected from (i), (ii), and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN;

$R^2$ is independently selected at each instance from halogen, $C_{1-6}$ alkyl, $C_{1-6}$ haloalkyl, —$OR^{12}$, —$SR^{12}$, —$N(R^{12})_2$, —$NO_2$, and —CN;

$R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl, $C_{2-6}$ alkenyl, and $C_{2-6}$ alkynyl, any one of which is optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN;

$R^4$ is independently selected at each instance from:
halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; and
$C_{1-6}$ alkyl, $C_{2-6}$ alkenyl, and $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN;

L is represented by -$L^1$-$L^2$-$L^3$-$L^4$-, wherein $L^1$, $L^2$, $L^3$, and $L^4$ are each independently selected from (a) and (b):
(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and
(b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, —$OR^{15}$, —$SR^{15}$, =O, =S, and —CN;
wherein $L^2$, $L^3$, and $L^4$ are each optionally absent;
wherein no more than two of $L^1$, $L^2$, $L^3$, and $L^4$ are selected from (a) and the two selected are not adjacent;

Ring B selected from 3- to 10-membered heterocyclene and $C_{3-10}$ carbocyclene, any of which is optionally substituted with one or more substituents independently selected from:
halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;
$C_{1-6}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN; and
3- to 6-membered heterocycle and $C_{3-6}$ carbocycle, each of which is optionally substituted with one or more substituents independently selected from: halogen, $C_{1-6}$ alkyl, $C_{1-6}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

$A^3$ is cysteine susceptible electrophile;

$R^{10}$, $R^{11}$, $R^{12}$, $R^{13}$, $R^{14}$, $R^{15}$, and $R^{16}$ are each independently selected at each occurrence from:
hydrogen,
$C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and
$C_{3-6}$ carbocycle and 3- to 6-membered heterocycle, each of which is optionally substituted with one or more substituents independently selected from halogen, —OH, —O—$C_{1-6}$ alkyl, —O—$C_{1-6}$ haloalkyl, $C_{1-6}$ alkyl, and $C_{1-6}$ haloalkyl;

m is selected from 0, 1, 2, and 3;
n is selected from 0, 1, 2, and 3;
q is selected from 1, 2, and 3; and
p is selected from 0, 1, 2, 3, 4, and 5.

In some embodiments, for the compound or salt of Formula (I) or (II), the cysteine susceptible electrophile is selected from a haloacetamide, a haloalkyl ketone, a halo amidine, a halo benzylphosphonate, an acyloxyalkyl ketone, a sulfonyl oxirane, an epoxide, a diazoalkyl ketone, a halotriazine, an acrylamide, a cyano acrylamide, a vinyl sulfone, a vinyl sulfonamide, an acrylate, a fumarate, a carbonyl acrylate, a maleimide, a ketoamide, a nitrile, an alkene, an alkyne, a keto heterocycle, and an ynamide. In some embodiments, the cysteine susceptible electrophile is selected from a haloacetamide, a haloalkyl ketone, and a halo amidine. In some embodiments, the cysteine susceptible electrophile is selected from an acrylate group, an acrylamide group, a vinyl group, a vinylsulfone group, a vinylsulfonamide group, an ynamide, an alkene, an alkyne, and an epoxide group. In some embodiments, the cysteine susceptible electrophile is selected from an acrylate group, an acrylamide group, a vinylsulfone group, a vinylsulfonamide group, an alkene, and an alkyne. In some embodiments, the cysteine susceptible electrophile is selected from an acrylate group, an acrylamide group, an alkene, and an alkyne.

In some embodiments, for the compound or salt of Formula (I) or (II), the cysteine susceptible electrophile is an alpha-beta unsaturated carbonyl, an alpha-beta unsaturated sulfone, an alpha-beta unsaturated amide, and an alpha-beta unsaturated sulfonamide. In some embodiments, the cysteine susceptible electrophile is selected from an alpha-beta unsaturated carbonyl and an alpha-beta unsaturated amide. In some embodiments, the cysteine susceptible electrophile is an alpha-beta unsaturated carbonyl.

In some embodiments, for the compound or salt of Formula (I) or (II), $R^{10}$, $R^{11}$, $R^{12}$, $R^{13}$, $R^{14}$, $R^{15}$, and $R^{16}$ are each independently selected at each occurrence from
hydrogen,
$C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and
$C_{3-6}$ carbocycle and 3- to 6-membered heterocycle, each of which is optionally substituted with one or more substituents independently selected from halogen, —OH, $C_{1-6}$ alkyl, and $C_{1-6}$ haloalkyl.

In some embodiments, for the compound or salt of Formula (I) or (II), $R^{10}$, $R^{11}$, $R^{12}$, $R^{13}$, $R^{14}$, $R^{15}$, and $R^{16}$ are each independently selected at each occurrence from
hydrogen,
$C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and
$C_{3-6}$ carbocycle and 3- to 6-membered heterocycle.

In some embodiments, for the compound or salt of Formula (I) or (II), $R^{15}$ is selected at each occurrence from
hydrogen,
$C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and
$C_{3-6}$ carbocycle and 3- to 6-membered heterocycle, each of which is optionally substituted with one or more substituents independently selected from halogen, —OH, $C_{1-6}$ alkyl, and $C_{1-6}$ haloalkyl.

In some embodiments, for the compound or salt of Formula (I), (I-A), (II), (II-A), (III), or (III-A), $R^{15}$ is selected at each occurrence from:

hydrogen, $C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and $C_{3-6}$ carbocycle and 3- to 6-membered heterocycle.

In some embodiments, for the compound or salt of Formula (I) or (II), $R^{15}$ is selected at each occurrence from hydrogen and $C_{1-6}$ alkyl optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle. In some embodiments, $R^{15}$ is $C_{1-6}$ alkyl optionally substituted with one or more substituents independently selected from halogen, —O—$C_{1-6}$ alkyl, —O—$C_{1-6}$ haloalkyl, $C_{3-6}$ carbocycle, and 3- to 6-membered heterocycle. In some embodiments, $R^{15}$ is $C_{1-6}$ alkyl optionally substituted with one or more substituents independently selected from halogen, —O—$C_{1-6}$ alkyl, and 3- to 6-membered heterocycle. In some embodiments, $R^{15}$ is $C_{1-6}$ alkyl optionally substituted with one or more substituents independently selected from —O—$C_{1-6}$ alkyl and 3- to 6-membered heterocycle. In some embodiments, $R^{15}$ is $C_{1-6}$ alkyl optionally substituted with one or more substituents independently selected from —O—$C_{1-3}$ alkyl and 4- to 5-membered heterocycle. In some embodiments, $R^{15}$ is $C_{1-6}$ alkyl optionally substituted with —$OCH_3$ or oxetanyl.

In some embodiments, for the compound or salt of Formula (I) or (II), $L^1$ is —N($R^{15}$)—; and $R^{15}$ is selected at each occurrence from $C_{1-6}$ alkyl optionally substituted with one or more substituents independently selected from —O—$C_{1-6}$ alkyl and 3- to 6-membered heterocycle. In some embodiments, $L^1$ is —N($R^{15}$)—; and $R^{15}$ is selected at each occurrence from $C_{1-3}$ alkyl optionally substituted with one or more substituents independently selected from —O—$C_{1-3}$ alkyl and 4- to 5-membered heterocycle. In some embodiments, $L^1$ is —N($R^{15}$)—; and $R^{15}$ is selected at each occurrence from $C_{1-3}$ alkyl optionally substituted with one or more substituents independently selected from —$OCH_3$ and oxetanyl.

In some embodiments, for the compound or salt of Formula (I) or (II), L is selected from

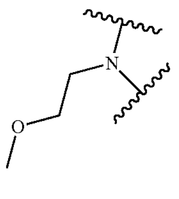

and

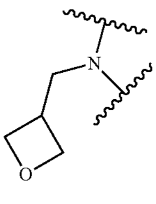

.

In some embodiments, L is

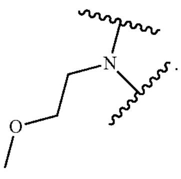 [SMILES: *N(*)CCOC]

.

In some embodiments, L is

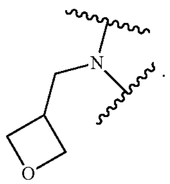 [SMILES: *N(*)CC1COC1]

.

In some aspects, the structure Formula (I) or (II) is represented by the structure of Formula (II-A):

(II-A)

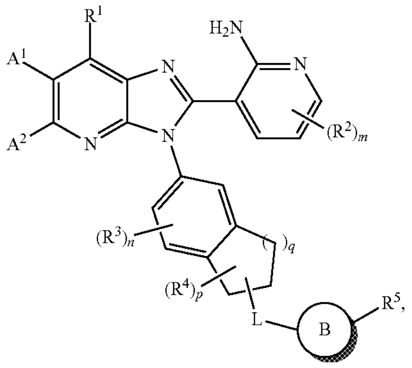

or a pharmaceutically acceptable salt thereof, wherein:

the cysteine susceptible electrophile is $R^5$;

$R^5$ is selected from:

—C(O)$R^{17}$, —$S(O)_2R^{17}$, —N($R^{19}$)C(O)($R^{17}$), —C(O)N($R^{17}$)($R^{19}$), —N($R^{19}$)$S(O)_2R^{17}$, —$S(O)_2N(R^{17})$($R^{19}$), and —CN;

$C_{1-6}$ alkyl substituted with one or more substituents independently selected from —C(O)$R^{17}$, —$S(O)_2R^{17}$, —N($R^{19}$)C(O)($R^{17}$), —C(O)N($R^{17}$)($R^{19}$), and —N($R^{19}$)$S(O)_2R^{17}$, —$S(O)_2N(R^{17})(R^{19})$, and —CN;

$C_{2-6}$ alkenyl and $C_{2-6}$ alkynyl, each of which is optionally substituted with one or more substituents independently selected from —C(O)$R^{19}$, —$S(O)_2R^{19}$, —N($R^{19}$)C(O)($R^{19}$), —C(O)N$(R^{19})_2$, —N($R^{19}$)$S(O)_2R^{19}$, —$S(O)_2N(R^{19})(R^{19})$, and —CN; and $C_{3-6}$ carbocycle and 3- to 6-membered heterocycle, each of which is substituted with one or more substituents independently selected from ═O, $C_{2-6}$ alkenyl, $C_{2-6}$ alkynyl, —C(O)$R^{17}$, —$S(O)_2R^{17}$, —N($R^{19}$)C(O)($R^{17}$), —C(O)N($R^{17}$)($R^{19}$), —N($R^{19}$)$S(O)_2R^{17}$, —$S(O)_2N(R^{17})(R^{19})$, and —CN;

$R^{17}$ is independently selected at each occurrence from:

$C_{1-6}$ alkyl, $C_{2-6}$ alkenyl, and $C_{2-6}$ alkynyl each of which is optionally substituted with one or more substituents independently selected from halogen, —$OR^{18}$, —$SR^{18}$, —N$(R^{18})_2$, —C(O)N$(R^{18})_2$, —C(O)$OR^{18}$, —OC(O)$R^{18}$, —N($R^{18}$)C(O)$R^{18}$, —N($R^{18}$)$S(O)_2R^{18}$, —$S(O)_2N(R^{18})_2$, —N($R^{18}$)C(O)N$(R^{18})_2$, —N($R^{18}$)C(O)$OR^{18}$, —OC(O)N$(R^{18})_2$, —S(O)$R^{18}$, —$S(O)_2R^{18}$, —$NO_2$, and —CN; and $C_{3-6}$ carbocyclenyl. 3- to 6-membered heterocyclenyl, and 3- to 6-membered heterocyclyl, each of which is optionally substituted with one or more substituents independently selected from halogen, $C_{1-6}$ alkyl, $C_{1-6}$ haloalkyl, halogen, —$OR^{18}$, —$SR^{18}$, —N($R^{18}$)$_2$, —C(O)N($R^{18}$)$_2$, —C(O)OR$^{18}$, —OC(O)R$^{18}$, —N($R^{18}$)C(O)R$^{18}$, —N($R^{18}$)S(O)$_2$R$^{18}$, —S(O)$_2$N($R^{18}$)$_2$, —N($R^{18}$)C(O)N($R^{18}$)$_2$, —N($R^{18}$)C(O)OR$^{18}$, —OC(O)N($R^{18}$)$_2$, —S(O)R$^{18}$, —S(O)$_2$R$^{18}$, —$NO_2$, and —CN; and $R^{18}$ and $R^{19}$ are each independently selected at each occurrence from: hydrogen, $C_{1-6}$ alkyl, $C_{1-6}$ haloalkyl, $C_{3-6}$ carbocycle, and 3- to 6-membered heterocycle.

In some embodiments, for the compound or salt of Formula (I), (II) or (II-A), $R^5$ is selected from —C(O)R$^{17}$, —S(O)$_2$R$^{17}$, —N($R^{19}$)C(O)($R^{17}$), —C(O)N($R^{17}$)($R^{19}$), —N($R^{19}$)S(O)$_2$R$^{17}$, —S(O)$_2$N($R^{17}$)($R^{19}$), and —CN. In some embodiments, $R^5$ is selected from —C(O)R$^{17}$—, N($R^{19}$)C(O)($R^{17}$), —C(O)N($R^{17}$)($R^{19}$), —S(O)$_2$R$^{17}$ and —CN. In some embodiments, $R^5$ is selected from —C(O)R$^{17}$—, N($R^{19}$)C(O)($R^{17}$), —C(O)N($R^{17}$)($R^{19}$), —S(O)$_2$R$^{17}$ and —CN, wherein each $R^{19}$ is independently selected at each occurrence from hydrogen, $C_{1-3}$ alkyl, and $C_{1-3}$ haloalkyl. In some embodiments, $R^5$ is selected from —C(O)R$^{17}$—, N($R^{19}$)C(O)($R^{17}$), —C(O)N($R^{17}$)($R^{19}$), —S(O)$_2$R$^{17}$ and —CN, wherein each $R^{19}$ is independently selected at each occurrence from hydrogen and methyl. In some embodiments, $R^5$ is selected from —CN,

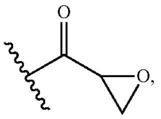
,
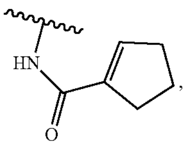
,
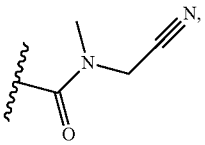
and
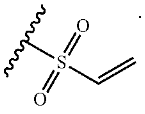
.

In some embodiments, $R^5$ is selected from

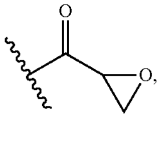
and
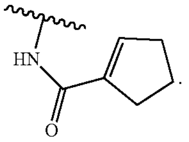
.

In some embodiments, $R^5$ is selected from

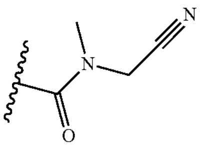
and
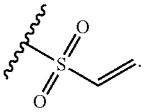
.

In some embodiments, $R^5$ is —CN.

In some embodiments, for the compound or salt of Formula (I), (II), or (II-A), $R^5$ is $C_{1-6}$ alkyl substituted with one or more substituents independently selected from —C(O)R$^{17}$, —S(O)$_2$R$^{17}$, —N($R^{19}$)C(O)($R^{17}$), —C(O)N($R^{17}$)($R^{19}$), and —N($R^{19}$)S(O)$_2$R$^{17}$, —S(O)$_2$N($R^{17}$)($R^{19}$), and —CN. In some embodiments, $R^5$ is $C_{1-6}$ alkyl substituted with one or more substituents independently selected from —N($R^{19}$)C(O)($R^{17}$) and —C(O)N($R^{17}$)($R^{19}$). In some embodiments, $R^5$ is $C_{1-6}$ alkyl substituted with one or more —N($R^{19}$)C(O)($R^{17}$). In some embodiments, $R^5$ is $C_{1-6}$ alkyl substituted with one or more —N(H)C(O)($R^{17}$). In some embodiments, $R^5$ is

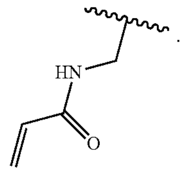 [SMILES: *CNC(=O)C=C]
.

In some embodiments, $R^5$ is selected from

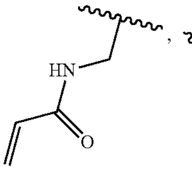
,
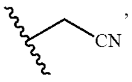
,
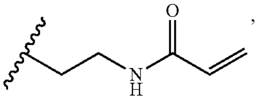
,
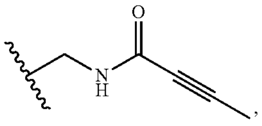
,
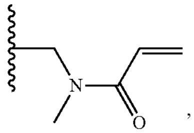
, and
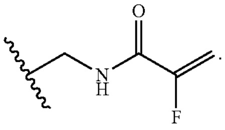
.

In some embodiments, for the compound or salt of Formula (I), (II), or (II-A), $R^5$ is selected from $C_{2-6}$ alkenyl and $C_{2-6}$ alkynyl, each of which is optionally substituted with one or more substituents independently selected from —C(O)R$^{19}$, —S(O)$_2$R$^{19}$, —N($R^{19}$)C(O)($R^{19}$), —C(O)N($R^{19}$)$_2$, —N($R^{19}$)S(O)$_2$R$^{19}$, —S(O)$_2$N($R^{17}$)($R^{19}$), and —CN. In some embodiments, $R^5$ is $C_{2-6}$ alkenyl substituted with one or more substituents independently selected from —C(O)R$^{19}$, —S(O)$_2$R$^{19}$, —N($R^{19}$)C(O)($R^{19}$), —C(O)N($R^{19}$)$_2$, —N($R^{19}$)S(O)$_2$R$^{19}$, —S(O)$_2$N($R^{17}$)($R^{19}$), and —CN. In some embodiments, $R^5$ is $C_{2-6}$ alkenyl substituted with one or more substituents independently selected from —N($R^{19}$)C(O)($R^{19}$) and —C(O)N($R^{19}$)$_2$. In some embodiments, $R^5$ is $C_{2-3}$ alkenyl substituted with one or more —C(O)N($R^{19}$)$_2$. In some embodiments $R^5$ is

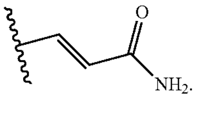 [SMILES: */C=C/C(N)=O]

In some embodiments, for the compound or salt of Formula (I), (II), or (II-A), $R^5$ is selected from $C_{3-6}$ carbocycle and 3- to 6-membered heterocycle, each of which is substituted with one or more substituents independently selected from =O, $C_{2-6}$ alkenyl, $C_{2-6}$ alkynyl, —C(O)R$^{17}$, —S(O)$_2$R$^{17}$, —N($R^{19}$)C(O)($R^{17}$), —C(O)N($R^{17}$)($R^{19}$), —N($R^{19}$)S(O)$_2$R$^{17}$, —S(O)$_2$N($R^{17}$)($R^{19}$), —S(O)$_2$R$^{17}$, and —CN. In some embodiments, $R^5$ is 3- to 6-membered heterocycle substituted with one or more substituents independently selected from =O, $C_{2-6}$ alkenyl, $C_{2-6}$ alkynyl, —C(O)R$^{17}$, —S(O)$_2$R$^{17}$, —N($R^{19}$)C(O)($R^{17}$), —C(O)N $(R^{17})(R^{19})$, —$N(R^{19})S(O)_2R^{17}$, —$S(O)_2N(R^{17})(R^{19})$, —$S(O)_2R^{17}$, and —CN. In some embodiments, $R^5$ is 3- to 6-membered heterocycle substituted with one or more substituents independently selected from =O, $C_{2-6}$ alkenyl, $C_{2-6}$ alkynyl, —$C(O)R^{17}$, and —CN.

In some embodiments, for the compound or salt of Formula (I), (II), or (II-A), $R^5$ is selected from azetidinyl and pyrrolidinyl each of which is substituted with one or more substituents independently selected from =O, $C_{2-6}$ alkenyl, $C_{2-6}$ alkynyl, —$C(O)R^{17}$, —$S(O)_2R^{17}$, —$N(R^{19})C(O)(R^{17})$, —$C(O)N(R^{17})(R^{19})$, —$N(R^{19})S(O)_2R^{17}$, —$S(O)_2N(R^{17})(R^{19})$, —$S(O)_2R^{17}$, and —CN. In some embodiments, $R^5$ is selected from azetidinyl and pyrrolidinyl each of which is substituted with one or more substituents independently selected from =O, $C_{2-6}$ alkenyl, $C_{2-6}$ alkynyl, —$C(O)R^{17}$, —$S(O)_2R^{17}$, —$N(R^{19})C(O)(R^{17})$, —$C(O)N(R^{17})(R^{19})$, —$N(R^{19})S(O)_2R^{17}$, —$S(O)_2N(R^{17})(R^{19})$, —$S(O)_2R^{17}$, and —CN. In some embodiments, $R^5$ is selected from azetidinyl and pyrrolidinyl each of which is substituted with one or more substituents independently selected from =O, $C_{2-6}$ alkenyl, $C_{2-6}$ alkynyl, —$C(O)R^{17}$, and —CN. In some embodiments, $R^5$ is selected from

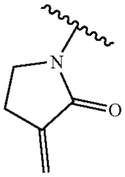 and 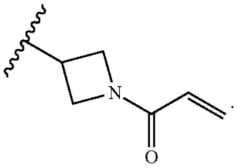.

In some embodiments, $R^5$ is

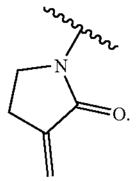 [SMILES: *N1CCC(=C)C1=O].

In some embodiments, $R^5$ is

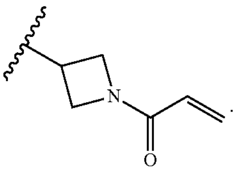.

In some embodiments, for the compound or salt of Formula (I), (II), or (II-A), $R^{17}$ is independently selected at each occurrence from:

$C_{1-6}$ alkyl substituted with halogen, —$OR^{18}$, —$SR^{18}$, —$N(R^{18})_2$, —$C(O)N(R^{18})_2$, —$C(O)OR^{18}$, —$OC(O)R^{18}$, —$N(R^{18})Cd(O)R^{18}$, —$N(R^{18})S(O)_2R^{18}$, —$S(O)_2N(R^{18})_2$, —$N(R^{18})C(O)N(R^{18})_2$, —$N(R^{18})C(O)OR^{18}$, —$OC(O)N(R^{18})_2$, —$S(O)R^{18}$, —$S(O)_2R^{18}$, —$NO_2$, and —CN;

$C_{2-6}$ alkenyl and $C_{2-6}$ alkynyl, each of which is optionally substituted with one or more substituents independently selected from halogen, —$OR^{18}$, —$SR^{18}$, —$N(R^{18})_2$, —$C(O)N(R^{18})_2$, —$C(O)OR^{18}$, —$OC(O)R^{18}$, —$N(R^{18})C(O)R^{18}$, —$N(R^{18})S(O)_2R^{18}$, —$S(O)_2N(R^{18})_2$, —$N(R^{18})C(O)N(R^{18})_2$, —$N(R^{18})C(O)OR^{18}$, —$OC(O)N(R^{18})_2$, —$S(O)R^{18}$, —$S(O)_2R^{18}$, —$NO_2$, and —CN; and $C_{3-6}$ carbocyclenyl. 3- to 6-membered heterocyclenyl, and 3- to 6-membered heterocyclyl, each of which is optionally substituted with one or more substituents independently selected from halogen, $C_{1-6}$ alkyl, $C_{1-6}$ haloalkyl, halogen, —$OR^{18}$, —$SR^{18}$, —$N(R^{18})_2$, —$C(O)N(R^{18})_2$, —$C(O)OR^{18}$, —$OC(O)R^{18}$, —$N(R^{18})C(O)R^{18}$, —$N(R^{18})S(O)_2R^{18}$, —$S(O)_2N(R^{18})_2$, —$N(R^{18})C(O)N(R^{18})_2$, —$N(R^{18})C(O)OR^{18}$, —$OC(O)N(R^{18})_2$, —$S(O)R^{18}$, —$S(O)_2R^{18}$, —$NO_2$, and —CN.

In some embodiments, for the compound or salt of Formula (I), (II), or (II-A), $R^{17}$ is $C_{1-6}$ alkyl substituted with halogen, —$OR^{18}$, —$SR^{18}$, —$N(R^{18})_2$, —$C(O)N(R^{18})_2$, —$C(O)OR^{18}$, —$OC(O)R^{18}$, —$N(R^{18})C(O)R^{18}$, —$N(R^{18})S(O)_2R^{18}$, —$S(O)_2N(R^{18})_2$, —$N(R^{18})C(O)N(R^{18})_2$, —$N(R^{18})C(O)OR^{18}$, —$OC(O)N(R^{18})_2$, —$S(O)R^{18}$, —$S(O)_2R^{18}$, —$NO_2$, and —CN. In some embodiments, $R^{17}$ is $C_{1-6}$ alkyl substituted with halogen, —$OR^{18}$, —$N(R^{18})_2$, —$C(O)N(R^{18})_2$, —$NO_2$, and —CN.

In some embodiments, for the compound or salt of Formula (II) or (II-A), $R^{17}$ is independently selected at each occurrence from $C_{3-6}$ carbocyclenyl. 3- to 6-membered heterocyclenyl, and 3- to 6-membered heterocyclyl, each of which is optionally substituted with one or more substituents independently selected from halogen, $C_{1-6}$ alkyl, $C_{1-6}$ haloalkyl, halogen, —$OR^{18}$, —$SR^{18}$, —$N(R^{18})_2$, —$C(O)N(R^{18})_2$, —$C(O)OR^{18}$, —$OC(O)R^{18}$, —$N(R^{18})C(O)R^{18}$, —$N(R^{18})S(O)_2R^{18}$, —$S(O)_2N(R^{18})_2$, —$N(R^{18})C(O)N(R^{18})_2$, —$N(R^{18})C(O)OR^{18}$, —$OC(O)N(R^{18})_2$, —$S(O)R^{18}$, —$S(O)_2R^{18}$, —$NO_2$, and —CN. In some embodiments, $R^{17}$ is independently selected at each occurrence from $C_{3-6}$ carbocyclenyl. 3- to 6-membered heterocyclenyl, and 3- to 6-membered heterocyclyl, each of which is optionally substituted with substituents independently selected from halogen, $C_{1-6}$ alkyl, $C_{1-6}$ haloalkyl, halogen, —$OR^{18}$, —$N(R^{18})_2$, —$NO_2$, and —CN.

In some embodiments, for the compound or salt of Formula (I), (II), or (II-A), $R^5$ is selected from —CN.

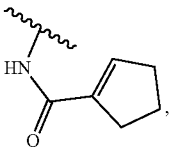, 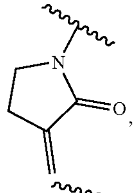, 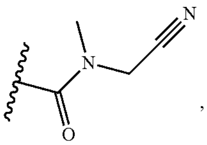, 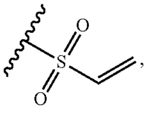, 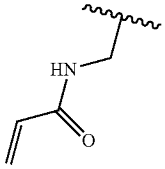, 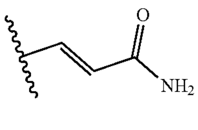, 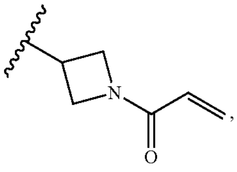 [SMILES: *C1CN(C(=O)C=C)C1], and 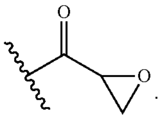.

In some embodiments, for the compound or salt of Formula (I), (II), or (II-A), $R^5$ is selected from —CN,

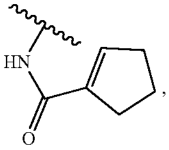,
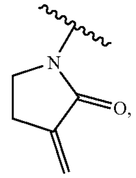,
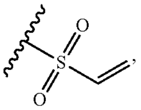,
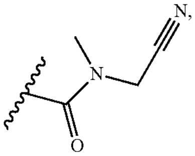,
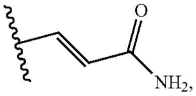,
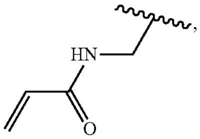,
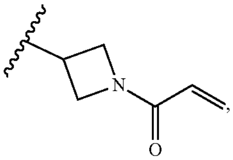,
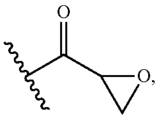,
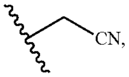,
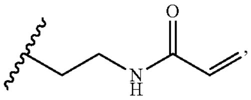,
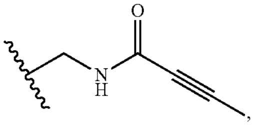,
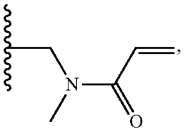, and
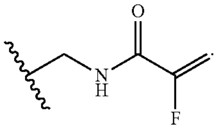.
In some embodiments, for the compound or salt of Formula (I), (II), or (II-A),
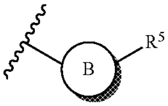
is selected from:
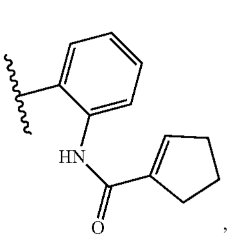,
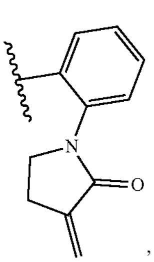,
-continued
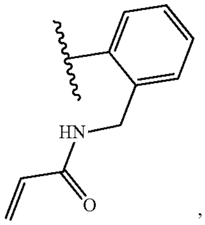,
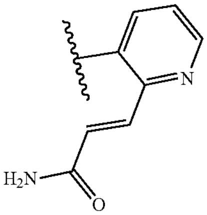,
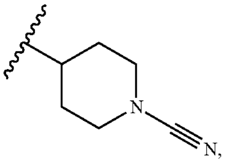,
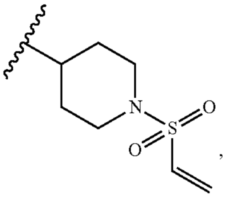,
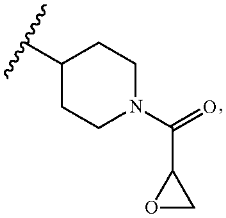,
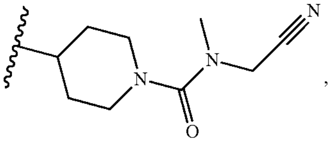, and
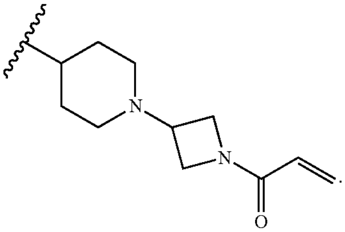.
In some embodiments, for the compound or salt of Formula (I), (II), or (II-A),
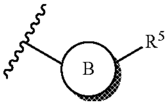
is selected from:
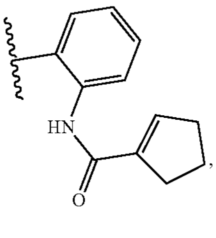,
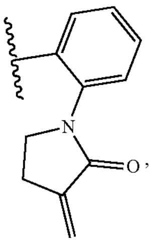, -continued

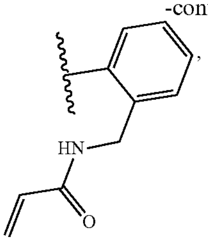

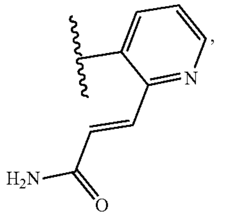

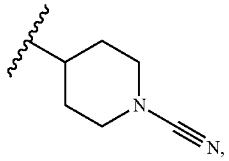

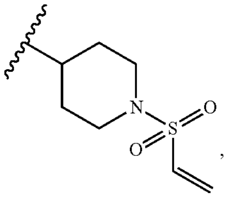

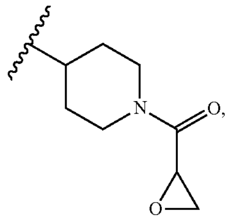

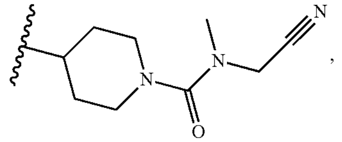

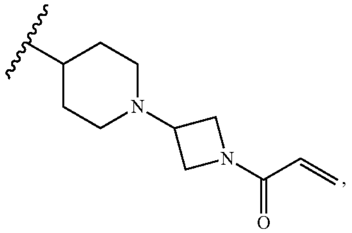

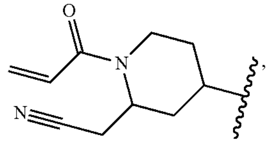

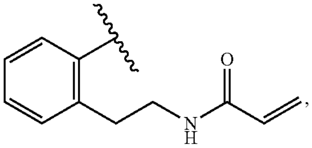

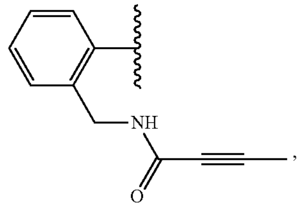

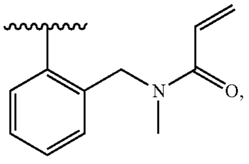

and

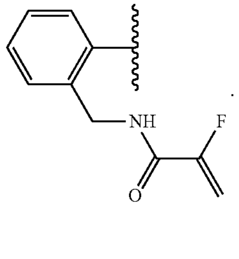

In some embodiments, for the compound or salt of Formula (I), (II), or (II-A), $R^{18}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{18}$ is independently selected at each occurrence from: hydrogen, $C_{1-6}$ alkyl, and $C_{1-6}$ haloalkyl. In some embodiments, $R^{18}$ is independently selected at each occurrence from: hydrogen, $C_{1-3}$ alkyl, and $C_{1-3}$ haloalkyl. In some embodiments, $R^{18}$ is independently selected at each occurrence from: hydrogen and $C_{1-3}$ alkyl. In some embodiments, $R^{18}$ is independently selected at each occurrence from: hydrogen and methyl. In some embodiments, $R^{18}$ is methyl.

In some embodiments, for the compound or salt of Formula (I), (II), or (II-A), $R^{19}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{19}$ is independently selected at each occurrence from: hydrogen, $C_{1-6}$ alkyl, and $C_{1-6}$ haloalkyl. In some embodiments, $R^{19}$ is independently selected at each occurrence from: hydrogen, $C_{1-3}$ alkyl, and $C_{1-3}$ haloalkyl. In some embodiments, $R^{19}$ is independently selected at each occurrence from: hydrogen and $C_{1-3}$ alkyl. In some embodiments, $R^{19}$ is independently selected at each occurrence from: hydrogen and methyl.

In some aspects, the structure of Formula (I), (II), or (II-A), is represented by the structure of Formula (III):

(III)

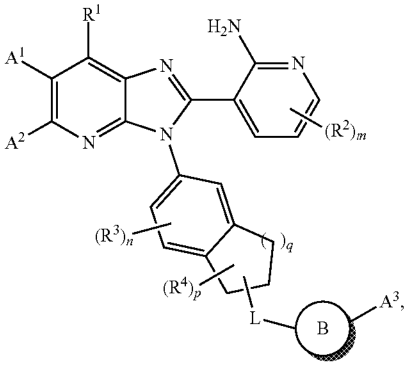

or a pharmaceutically acceptable salt thereof, wherein:

$R^1$ is selected from hydrogen, halogen, $—OR^{10}$, $—SR^{10}$, $—N(R^{10})_2$, $—NO_2$, and —CN; and $C_{1-6}$ alkyl optionally substituted with one or more substituents independently selected from: halogen, $—OR^{10}$, $—SR^{10}$, $—N(R^{10})_2$, $—NO_2$, and —CN;

$A^1$ and $A^2$ are each independently selected from (i), (ii), and (iii):

(i) hydrogen, halogen, $—OR^{11}$, $—SR^{11}$, $—N(R^{11})_2$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, $—OR^{11}$, $—SR^{11}$, $—N(R^{11})_2$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, =O, =S, $=N(R^{11})$, and —CN; and (iii) 5- to 10-membered heterocycle and $C_{3-10}$ carbocycle, any of which is optionally substituted with one or more substituents independently selected from:

halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—S(O)_2N(R^{11})_2$, $—NO_2$, $=O$, $=S$, $=N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, $=O$, $=S$, $=N(R^{11})$, and —CN; and $C_{3-10}$ carbocycle and 3- to 10-membered heterocycle, any of which is optionally substituted with one or more substituents independently selected from:

halogen, $—OR^{11}$, $—N(R^{11})_2$, $—C(O)R^{11}$, $—C(O)N(R^{11})_2$, $—N(R^{11})C(O)R^{11}—C(O)OR^{11}$, $—OC(O)R^{11}$, $—NO_2$, $=O$, $=S$, $=N(R^{11})$, —CN; and $C_{1-6}$ alkyl $C_{2-6}$ alkenyl, and $C_{3-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—NO_2$, $=O$, $=S$, $=N(R^{11})$, and —CN;

$R^2$ is independently selected at each instance from halogen, $C_{1-6}$ alkyl, $C_{1-6}$ haloalkyl, $—OR^{12}$, $—SR^{12}$, $—N(R^{12})_2$, $—NO_2$, and —CN;

$R^3$ is independently selected at each instance from:

halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, and —CN; and $C_{1-6}$ alkyl, $C_{2-6}$ alkenyl, and $C_{2-6}$ alkynyl, any one of which is optionally substituted with one or more substituents independently selected from: halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, $=O$, $=S$, $—N(R^{13})$, and —CN;

$R^4$ is independently selected at each instance from:

halogen, $—OR^{14}$, $—SR^{14}$, $—N(R^{14})_2$, $—C(O)R^{14}$, $—C(O)N(R^{14})_2$, $—N(R^{14})C(O)R^{14}$, $—C(O)OR^{14}$, $—OC(O)R^{14}$, $—NO_2$, $=O$, $=S$, $=N(R^{14})$, and —CN; and $C_{1-6}$ alkyl, $C_{2-6}$ alkenyl, and $C_{2-6}$ alkynyl, any one of which is optionally substituted with one or more substituents independently selected from halogen, $—OR^{14}$, $—SR^{14}$, $—N(R^{14})_2$, $—C(O)R^{14}$, $—C(O)N(R^{14})_2$, $—N(R^{14})C(O)R^{14}$, $—C(O)OR^{14}$, $—OC(O)R^{14}$, $—NO_2$, $=O$, $=S$, $=N(R^{14})$, and —CN;

L is represented by $-L^1-L^2-L^3-L^4-$, wherein $L^1$, $L^2$, $L^3$, and $L^4$ are each independently selected from (a) and (b):

(a) —O—, $—N(R^{15})—$, —S—, —S(O)—, $—S(O)_2—$, $—S(O)(NR^{15})—$, $—N(R^{15})C(O)—$, $—N(R^{15})C(O)O—$, $—N(R^{15})S(O)_2—$, $—N(R^{15})S(O)_2N(R^{15})—$, $—S(O)(NR^{15})N(R^{15})—$, $—N(R^{15})N(R^{15})—$, $—(R^{15})NC(O)N(R^{15})—$, and $—(R^{15})NC(O)N(R^{15})N(R^{15})—$; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, $—OR^{15}$, $—SR^{15}$, $=O$, $=S$, and —CN;

wherein $L^2$, $L^3$, and $L^4$ are each optionally absent;

wherein no more than two of $L^1$, $L^2$, $L^3$, and $L^4$ are selected from (a) and the two selected are not adjacent;

Ring B selected from 3- to 10-membered heterocyclene and $C_{3-10}$ carbocyclene, any of which is optionally substituted with one or more substituents independently selected from:

halogen, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, $—OR^{16}$, —SR 16, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN; and 3- to 6-membered heterocycle and $C_{3-6}$ carbocycle, each of which is optionally substituted with one or more substituents independently selected from: halogen, $C_{1-6}$ alkyl, $C_{1-6}$ haloalkyl, $—OR^{16}$, $—SR^{16}$, $—N(R^{16})_2$, $—C(O)N(R^{16})_2$, $—C(O)OR^{16}$, $—OC(O)R^{16}$, $—N(R^{16})C(O)R^{16}$, $—N(R^{16})S(O)_2R^{16}$, $—S(O)_2N(R^{16})_2$, $—N(R^{16})C(O)N(R^{16})_2$, $—N(R^{16})C(O)OR^{16}$, $—OC(O)N(R^{16})_2$, $—S(O)R^{16}$, $—S(O)_2R^{16}$, $—NO_2$, $=O$, $=S$, $=N(R^{16})$, and —CN;

$A^3$ is cysteine susceptible electrophile;

$R^{10}$, $R^{11}$, $R^{12}$, $R^{13}$, $R^{14}$, $R^{15}$, and $R^{16}$ are each independently selected at each occurrence from:

hydrogen, $C_{1-6}$ alkyl, $C_{1-6}$ haloalkyl, $C_{3-6}$ carbocycle, and 3- to 6-membered heterocycle;

m is selected from 0, 1, 2, and 3;

n is selected from 0, 1, 2, and 3;

q is selected from 1, 2, and 3; and p is selected from 0, 1, 2, 3, 4, and 5.

In some embodiments, for the compound or salt of Formula (I), (II), (II-A), or (III), the cysteine susceptible electrophile is selected from an acrylate group, an acrylamide group, a vinyl group, a vinylsulfone group, a vinylsulfonamide group, an ynamide, and an epoxide group. In some embodiments, the cysteine susceptible electrophile is selected from an acrylate group, an acrylamide group, a vinylsulfone group, and a vinylsulfonamide group. In some embodiments, the cysteine susceptible electrophile is selected from an acrylate group, acrylamide group, a vinyl group, a vinylsulfonamide group, and an ynamide group. In some embodiments, the cysteine susceptible electrophile is selected from an acrylamide group, a vinyl group, a vinylsulfonamide group, and an ynamide. In some embodiments, the cysteine susceptible electrophile is an acrylamide group.

In some embodiments, for the compound or salt of Formula (I), (II), (II-A), or (III), the cysteine susceptible electrophile of $A^3$ is $R^5$, wherein $R^5$ is selected from $—C(O)R^{17}$, $—S(O)_2R^{17}$, $—N(R^{19})C(O)(R^{17})$, $—C(O)N(R^{17})(R^{19})$, and $—N(R^{19})S(O)_2R^{17}$, and $—S(O)_2N(R^{17})(R^{19})$;

$R^{17}$ is independently selected at each occurrence from $C_{2-6}$ alkenyl and $C_{2-6}$ alkynyl each of which is optionally substituted with one or more substituents independently selected from halogen, $—OR^{18}$, $—SR^{18}$, $—N(R^{18})_2$, $—C(O)N(R^{18})_2$, $—C(O)OR^{18}$, $—OC(O)R^{18}$, $—N(R^{18})C(O)R^{18}$, $—N(R^{18})S(O)_2R^{18}$, $—S(O)_2N(R^{18})_2$, $—N(R^{18})C(O)N(R^{18})_2$, $—N(R^{18})C(O)OR^{18}$, $—OC(O)N(R^{18})_2$, $—S(O)R^{18}$, $—S(O)_2R^{18}$, $—NO_2$, and —CN; and $R^{18}$ and $R^{19}$ are each independently selected at each occurrence from: hydrogen, $C_{1-6}$ alkyl, $C_{1-6}$ haloalkyl, $C_{3-6}$ carbocycle, and 3- to 6-membered heterocycle.

In some embodiments, for the compound or salt of Formula (I), (II), (II-A), or (III), the cysteine susceptible electrophile is $R^5$, wherein $R^5$ is selected from $—C(O)R^{17}$, $—S(O)_2R^{17}$, $—N(R^{19})C(O)(R^{17})$, $—C(O)N(R^{17})(R^{19})$, and $—N(R^{19})S(O)_2R^{17}$, and $—S(O)_2N(R^{17})(R^{19})$;

$R^{17}$ is independently selected at each occurrence from $C_{2-6}$ alkenyl and $C_{2-6}$ alkynyl each of which is optionally substituted with one or more substituents independently selected from halogen, $—OR^{18}$, $—SR^{18}$, $—N(R^{18})_2$, $—C(O)N(R^{18})_2$, $—C(O)OR^{18}$, $—OC(O)R^{18}$, $—N(R^{18})C(O)R^{18}$, $—N(R^{18})S(O)_2R^{18}$, $—S(O)_2N(R^{18})_2$, $—N(R^{18})C(O)N(R^{18})_2$, $—N(R^{18})C(O)OR^{18}$, $—OC(O)N(R^{18})_2$, $—S(O)R^{18}$, $—S(O)_2R^{18}$, $—NO_2$, and —CN; and $R^{18}$ and $R^{19}$ are each independently selected at each occurrence from: hydrogen, $C_{1-6}$ alkyl, $C_{1-6}$ haloalkyl, $C_{3-6}$ carbocycle, and 3- to 6-membered heterocycle.

In some embodiments, for the compound or salt of Formula (I), (II), (II-A), or (III), the cysteine susceptible electrophile is $R^5$, wherein $R^5$ is selected from $—C(O)R^{17}$, $—S(O)_2R^{17}$, $—N(R^{19})C(O)(R^{17})$, $—C(O)N(R^{17})(R^{19})$, and $—N(R^{19})S(O)_2R^{17}$, and $—S(O)_2N(R^{17})(R^{19})$;

$R^{17}$ is independently selected at each occurrence from $C_{2-6}$ alkenyl and $C_{2-6}$ alkynyl each of which is optionally substituted with one or more substituents independently selected from halogen, $—OR^{18}$, $—SR^{18}$, $—N(R^{18})_2$, $—C(O)N(R^{18})_2$, $—C(O)OR^{18}$, $—OC(O)R^{18}$, $—N(R^{18})C(O)R^{18}$, $—N(R^{18})S(O)_2R^{18}$, $—S(O)_2N(R^{18})_2$, $—N(R^{18})C(O)N(R^{18})_2$, $—N(R^{18})C(O)OR^{18}$, $—OC(O)N(R^{18})_2$, $—S(O)R^{18}$, $—S(O)_2R^{18}$, $—NO_2$, and —CN; and $R^{18}$ and $R^{19}$ are each independently selected at each occurrence from: hydrogen, $C_{1-6}$ alkyl, $C_{1-6}$ haloalkyl, $C_{3-6}$ carbocycle, and 3- to 6-membered heterocycle.

In some embodiments, for the compound or salt of Formula (I), (II), (II-A), or (III), the cysteine susceptible electrophile is $R^5$, wherein $R^5$ is selected from an acrylate group, an acrylamide group, a vinyl group, a vinylsulfone group, a vinylsulfonamide group, an ynamide, and an epoxide group. In some embodiments, the cysteine susceptible electrophile is selected from an acrylate group, an acrylamide group, a vinylsulfone group, and a vinylsulfonamide group.

In some aspects, the structure of Formula (I), (II), (II-A), or (III), is represented by the structure of Formula (III-A):

(III-A)

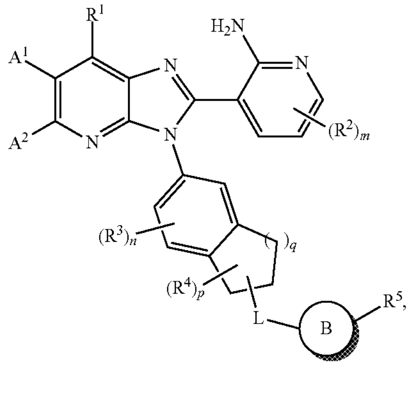

or a pharmaceutically acceptable salt thereof, wherein:

the cysteine susceptible electrophile is $R^5$;

$R^5$ is selected from $—C(O)R^{17}$, $—S(O)_2R^{17}$, $—N(R^{19})C(O)(R^{17})$, $—C(O)N(R^{17})(R^{19})$, and $—N(R^{19})S(O)_2R^{17}$, and $—S(O)_2N(R^{17})(R^{19})$;

$R^{17}$ is independently selected at each occurrence from $C_{2-6}$ alkenyl and $C_{2-6}$ alkynyl each of which is optionally substituted with one or more substituents independently selected from halogen, $—OR^{18}$, $—SR^{18}$, $—N(R^{18})_2$, $—C(O)N(R^{18})_2$, $—C(O)OR^{18}$, $—OC(O)R^{18}$, $—N(R^{18})C(O)R^{18}$, $—N(R^{18})S(O)_2R^{18}$, $—S(O)_2N(R^{18})_2$, $—N(R^{18})C(O)N(R^{18})_2$, $—N(R^{18})C(O)OR^{18}$, $—OC(O)N(R^{18})_2$, $—S(O)R^{18}$, $—S(O)_2R^{18}$, $—NO_2$, and —CN; and $R^{18}$ and $R^{19}$ are each independently selected at each occurrence from: hydrogen, $C_{1-6}$ alkyl, $C_{1-6}$ haloalkyl, $C_{3-6}$ carbocycle, and 3- to 6-membered heterocycle.

In some embodiments, for the compound or salt of Formula (I), (II), (II-A), (III), or (III-A), q is selected from 1, 2, and 3. In some embodiments, q is selected from 1 and 2. In some embodiments, q is 1.

In some embodiments, for the compound or salt of Formula (I), (I), (II), (II-A), (III), or (III-A). m is selected from 0, 1, 2, and 3. In some embodiments, m is selected from 0, 1, and 2. In some embodiments, m is selected from 0 and 1. In some embodiments, m is 0.

In some embodiments, for the compound or salt of Formula (I), (II), (II-A), (III), or (III-A), n is selected from 0, 1, 2, and 3. In some embodiments, n is selected from 0, 1, and 2. In some embodiments n is selected from 0 and 1. In some embodiments, n is 0.

In some embodiments, for the compound or salt of Formula (I), (II), (II-A), (III), or (III-A), p is selected from 0, 1, 2, 3, 4, and 5. In some embodiments, p is selected from 0, 1, 2, 3, and 4. In some embodiments, p is selected from 0, 1, 2, and 3. In some embodiments, p is selected from 0, 1, and 2. In some embodiments, p is selected from 0 and 1. In some embodiments, p is 0.

In some embodiments, for the compound or salt of Formula (I), (II), (II-A), (III), or (III-A), $R^1$ is selected from hydrogen, halogen, $—OR^{10}$, $—SR^{10}$, $—N(R^{10})_2$, $—NO_2$, —CN; and $C_{1-6}$ alkyl optionally substituted with one or more substituents independently selected from: halogen, $—OR^{10}$, $—SR^{10}$, $—N(R^{10})_2$, $—NO_2$, and —CN.

In some embodiments, for the compound or salt of Formula (I), (II), (II-A), (III), or (III-A), $R^1$ is selected from hydrogen, halogen, $—OR^{10}$, $—SR^{10}$, $—N(R^{10})_2$, $—NO_2$, —CN; and $C_{1-6}$ alkyl optionally substituted with one or more substituents independently selected from: halogen, $—OR^{10}$, $—SR^{10}$, $—N(R^{10})_2$, $—NO_2$, and —CN; and $R^{10}$ is independently selected at each occurrence from: hydrogen, $C_{1-6}$ alkyl, $C_{1-6}$ haloalkyl, $C_{3-6}$ carbocycle, and 3- to 6-membered heterocycle.

In some embodiments, for the compound or salt of Formula (I), (II), (II-A), (III), or (III-A), $R^1$ is selected from hydrogen, halogen, $—OR^{10}$, $—N(R^{10})_2$, $—NO_2$, —CN; and $C_{1-6}$ alkyl optionally substituted with one or more substituents independently selected from halogen, $—OR^{10}$, and $—N(R^{10})_2$. In some embodiments, $R^1$ is selected from hydrogen, $—OR^{10}$, and —CN; and $C_{1-6}$ alkyl optionally substituted with one or more $—OR^{10}$.

In some embodiments, for the compound or salt of Formula (I), (II), (II-A), (III), or (III-A), $R^1$ is selected from hydrogen, $—OR^{10}$, and —CN; and $C_{1-6}$ alkyl optionally substituted with one or more $—OR^{10}$; and $R^{10}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^1$ is selected from hydrogen, —$OR^{10}$, and —CN; and $C_{1-6}$ alkyl optionally substituted with one or more —$OR^{10}$; and $R^{10}$ is independently selected at each occurrence from: hydrogen, $C_{1-3}$ alkyl, and $C_{1-3}$ haloalkyl.

In some embodiments, for the compound or salt of Formula (I), (II), (II-A), (III), or (III-A), $R^1$ is selected from hydrogen, methoxy, —CN, methyl, ethyl, and (methoxy) methyl. In some embodiments, $R^1$ is selected from hydrogen, methoxy, and methyl. In some embodiments, $R^1$ is hydrogen.

In some embodiments, for the compound or salt of Formula (I), (II), (II-A), (III), or (III-A), $R^2$ is independently selected at each instance from halogen, $C_{1-6}$ alkyl, $C_{1-6}$ haloalkyl, —$OR^{12}$, —$SR^{12}$, —$N(R^{12})_2$, —$NO_2$, and —CN. In some embodiments, $R^2$ is independently selected at each instance from halogen, $C_{1-6}$ alkyl, $C_{1-6}$ haloalkyl, —$OR^{12}$, —$N(R^{12})_2$, and —CN. In some embodiments, $R^2$ is independently selected at each instance from halogen, $C_{1-6}$ alkyl, and $C_{1-6}$ haloalkyl. In some embodiments, $R^2$ is independently selected at each instance from halogen, $C_{1-4}$ alkyl, and $C_{1-4}$ haloalkyl.

In some embodiments, for the compound or salt of Formula (I), (II), (II-A), (III), or (III-A), $R^{12}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{12}$ is independently selected at each occurrence from: hydrogen, $C_{1-6}$ alkyl, and $C_{1-6}$ haloalkyl. In some embodiments, $R^{12}$ is independently selected at each occurrence from: hydrogen, $C_{1-3}$ alkyl, and $C_{1-3}$ haloalkyl. In some embodiments, $R^{12}$ is independently selected at each occurrence from: hydrogen and $C_{1-3}$ alkyl.

In some embodiments, for the compound or salt of Formula (I), (II), (II-A), (III), or (III-A), $R^3$ is independently selected at each instance from:

halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, and —CN; and $C_{1-6}$ alkyl, $C_{2-6}$ alkenyl, and $C_{2-6}$ alkynyl, any one of which is optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, =O, =S, =$N(R^{13})$, and —CN.

In some embodiments, for the compound or salt of Formula (I), (II), (II-A), (III), or (III-A), $R^3$ is independently selected at each instance from halogen, —$OR^{13}$, —$N(R^{13})_2$, —CN, $C_{1-6}$ alkyl, and $C_{1-6}$ haloalkyl. In some embodiments, $R^3$ is independently selected at each instance from halogen, $C_{1-6}$ alkyl, and $C_{1-6}$ haloalkyl. In some embodiments, $R^3$ is independently selected at each instance from halogen, $C_{1-3}$ alkyl, and $C_{1-3}$ haloalkyl.

In some embodiments, for the compound or salt of Formula (I), (II), (II-A), (III), or (III-A), $R^{13}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{13}$ is independently selected at each occurrence from: hydrogen, $C_{1-6}$ alkyl, and $C_{1-6}$ haloalkyl. In some embodiments, $R^{13}$ is independently selected at each occurrence from: hydrogen, $C_{1-3}$ alkyl, and $C_{1-3}$ haloalkyl. In some embodiments, $R^{13}$ is independently selected at each occurrence from: hydrogen and $C_{1-3}$ alkyl.

In some embodiments, for the compound or salt of Formula (I), (II), (II-A), (III), or (III-A), $R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN; and $C_{1-6}$ alkyl, $C_{2-6}$ alkenyl, and $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, =$N(R^{14})$, and —CN.

In some embodiments, for the compound or salt of Formula (I), (II), (II-A), (III), or (III-A), $R^4$ is independently selected at each instance from halogen, —$OR^{14}$, —$N(R^{14})_2$, —$NO_2$, =O, —CN, $C_{1-6}$ alkyl and $C_{1-6}$ haloalkyl. In some embodiments, $R^4$ is independently selected at each instance from halogen, —$OR^{14}$, —$N(R^{14})_2$, =O, —CN, $C_{1-6}$ alkyl and $C_{1-6}$ haloalkyl. In some embodiments, $R^4$ is independently selected at each instance from halogen, $C_{1-6}$ alkyl and $C_{1-6}$ haloalkyl. In some embodiments, $R^4$ is independently selected at each instance from halogen, $C_{1-3}$ alkyl and $C_{1-3}$ haloalkyl.

In some embodiments, for the compound or salt of Formula (I), (II), (II-A), (III), or (III-A), $R^4$ is selected from hydrogen, halogen, —$OR^{14}$, —$N(R^{14})_2$, —$NO_2$, —CN; and $C_{1-6}$ alkyl optionally substituted with one or more substituents independently selected from halogen, —$OR^{14}$, and —$N(R^{14})_2$. In some embodiments, $R^4$ is selected from halogen, —$OR^{14}$, $C_{1-6}$ alkyl, and $C_{1-6}$ haloalkyl. In some embodiments, $R^4$ is selected from fluoro, —OH, and —$OCH_3$.

In some embodiments, for the compound or salt of Formula (I), (II), (II-A), (III), or (III-A), $R^{14}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{14}$ is independently selected at each occurrence from: hydrogen, $C_{1-6}$ alkyl, and $C_{1-6}$ haloalkyl. In some embodiments, $R^{14}$ is independently selected at each occurrence from: hydrogen, $C_{1-3}$ alkyl, and $C_{1-3}$ haloalkyl. In some embodiments, $R^{14}$ is independently selected at each occurrence from: hydrogen and $C_{1-3}$ alkyl.

In some embodiments, for the compound or salt of Formula (I), (II), (II-A), (III), or (III-A), $A^1$ and $A^2$ are each independently selected from (i), (ii), and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, ═O, ═S, ═$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, ═O, ═S, ═$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$ —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, ═O, ═S, ═$N(R^{11})$, and —CN.

In some embodiments, for the compound or salt of Formula (I), (II), (II-A), (III), or (III-A), $A^1$ and $A^2$ are each independently selected from (i), (ii), and (iii):

(i) hydrogen, halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$S(O)_2R^{11}$, —$S(O)_2N(R^{11})_2$, —$NO_2$, ═O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$S(O)_2R^{11}$, —$S(O)_2N(R^{11})_2$, —$NO_2$, ═O, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, —O, and —CN; and $C_{3-10}$ carbocycle and 3- to 10-membered heterocycle, any of which is optionally substituted with one or more substituents independently selected from: halogen, $C_{1-6}$ alkyl, $C_{1-6}$ haloalkyl, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, ═O, and —CN.

In some embodiments, for the compound or salt of Formula (I), (II), (II-A), (III), or (III-A), $A^1$ and $A^2$ are each independently selected from (i), (ii), and (iii):

(i) hydrogen, halogen, —$OR^{11}$, —$N(R^{11})_2$, —$C(O)R^{11}$, —$C(O)N(R^{11})_2$, —$N(R^{11})C(O)R^{11}$, and —CN (ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, halogen, —$OR^{11}$, —$N(R^{11})_2$, —$C(O)R^{11}$, —$C(O)N(R^{11})_2$, —$N(R^{11})C(O)R^{11}$, ═O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, ═O, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, ═O, and —CN; and $C_{3-10}$ carbocycle and 3- to 10-membered heterocycle, any of which is optionally substituted with one or more substituents independently selected from: halogen, $C_{1-6}$ alkyl, $C_{1-6}$ haloalkyl, —$OR^{11}$, —$N(R^{11})_2$, —$C(O)R^{11}$, —$C(O)N(R^{11})_2$, —$N(R^{11})C(O)R^{11}$, ═O, and —CN.

In some embodiments, for the compound or salt of Formula (I), (II), (II-A), (III), or (III-A), $A^1$ and $A^2$ are each independently selected from (i), (ii), and (iii):

(i) hydrogen, halogen, —$OR^{11}$, —$N(R^{11})_2$, and —CN (ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, halogen, —$OR^{11}$, —$N(R^{11})_2$, ═O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, ═O, and —CN; and $C_{1-6}$ alkyl optionally substituted with one or more substituents independently selected from: halogen, —$OR^{11}$, —$N(R^{11})_2$, ═O, and —CN; and $C_{3-10}$ carbocycle and 3- to 10-membered heterocycle, any of which is optionally substituted with one or more substituents independently selected from: halogen, $C_{1-6}$ alkyl, $C_{1-6}$ haloalkyl, —$OR^{11}$, —$N(R^{11})_2$, ═O, and —CN.

In some embodiments, for the compound or salt of Formula (I), (II), (II-A), (III), or (III-A), $A^1$ and $A^2$ are each independently selected:

hydrogen, halogen, —$OR^{11}$, —$N(R^{11})_2$, ═O, $C_{1-6}$ alkyl, and $C_{1-6}$ haloalkyl; and 5- to 10-membered heterocycle and $C_{3-10}$ carbocycle, any of which is optionally substituted with one or more substituents independently selected from halogen, —$OR^{11}$, $C_{1-6}$ alkyl, $C_{1-6}$ haloalkyl, $C_{3-10}$ carbocycle and 3- to 10-membered heterocycle, wherein each of the $C_{1-6}$ alkyl, $C_{1-6}$ haloalkyl, $C_{3-10}$ carbocycle and 3- to 10-membered heterocycle are optionally substituted with one or more substituents independently selected from: halogen, $C_{1-6}$ alkyl, $C_{1-6}$ haloalkyl, —$OR^{11}$, —$N(R^{11})_2$, and ═O.

In some embodiments, for the compound or salt of Formula (I), (II), (II-A), (III), or (III-A), $A^1$ and $A^2$ are each independently selected from hydrogen, halogen, —$OR^{11}$, —$N(R^{11})_2$. ═O, $C_{1-6}$ alkyl, $C_{1-6}$ haloalkyl, 5- to 10-membered heterocycle and $C_{3-10}$ carbocycle. In some embodiments, $A^1$ and $A^2$ are each independently selected from hydrogen, halogen, $C_{1-4}$ alkyl, $C_{1-4}$ haloalkyl, —$OR^{11}$, —$N(R^{11})_2$, and —CN. In some embodiments, $A^1$ and $A^2$ are each independently selected from hydrogen, halogen, $C_{1-4}$ alkyl, and $C_{1-4}$ haloalkyl. In some embodiments, $A^1$ and $A^2$ are each independently selected from hydrogen, halogen, $C_{1-6}$ alkyl, $C_{1-6}$ haloalkyl, 5- to 10-membered heterocycle and $C_{3-10}$ carbocycle. In some embodiments, $A^1$ and $A^2$ are each independently selected from hydrogen, 5- to 10-membered heterocycle and $C_{3-10}$ carbocycle. In some embodiments, $A^1$ and $A^2$ are each independently selected from hydrogen, 5- to 6-membered heterocycle and $C_{3-6}$ carbocycle. In some embodiments, $A^1$ and $A^2$ are each independently selected from hydrogen, 5- to 6-membered heteroaryl and $C_{3-6}$ saturated carbocycle. In some embodiments, $A^1$ and $A^2$ are each independently selected from hydrogen, 5-membered heteroaryl and $C_{3-6}$ cycloalkyl. In some embodiments, $A^1$ and $A^2$ are each independently selected from hydrogen, pyrazole, triazole, and cyclopropyl.

In some embodiments, for the compound or salt of Formula (I), (II), (II-A), (III), or (III-A), $A^1$ is selected from (i), (ii), and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), or (III-A), $A^1$ is selected from: hydrogen, halogen, —$OR^{11}$, —$N(R^{11})_2$, —CN, $C_{1-6}$ alkyl, $C_{1-6}$ haloalkyl, 5- to 6-membered heterocycle, and $C_{3-6}$ carbocycle. In some embodiments, $A^1$ is selected from: hydrogen, halogen, $C_{1-6}$ alkyl, $C_{1-6}$ haloalkyl, —$OR^{11}$, —$N(R^{11})_2$, and —CN. In some embodiments, $A^1$ is selected from hydrogen, halogen, $C_{1-4}$ alkyl, $C_{1-4}$ haloalkyl, —$OR^{11}$, —$N(R^{11})_2$, and —CN. In some embodiments, $A^1$ is selected from hydrogen, halogen, $C_{1-4}$ alkyl, and $C_{1-4}$ haloalkyl. In some embodiments, $A^1$ is selected from hydrogen, fluoro, and methyl. In some embodiments, $A^1$ is hydrogen.

In some embodiments, for the compound or salt of Formula (I), (II), (II-A), (III), or (III-A), $A^1$ is selected from hydrogen, halogen, $C_{1-4}$ alkyl, $C_{1-4}$ haloalkyl, —$OR^{11}$, —$N(R^{11})_2$, —CN, 5- to 10-membered heterocycle and $C_{3-10}$ carbocycle. In some embodiments, $A^1$ is selected from hydrogen, halogen, and $C_{1-3}$ alkyl, $C_{1-3}$ haloalkyl, 3- to 6-membered heterocycle, and $C_{3-6}$ carbocycle. In some embodiments, $A^1$ is selected from hydrogen, fluoro, methyl,

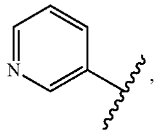, 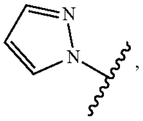, and 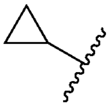.

In some aspects, the structure of Formula (I), (II), (II-A), (III), or (III-A), is represented by the structure of Formula (III-B):

(III-B)

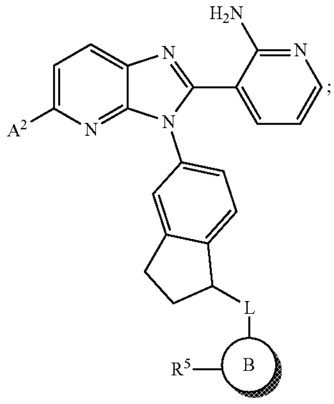;

or a pharmaceutically acceptable salt thereof.

In some embodiments, for the compound or salt of Formula (I), (II), (II-A), (III), (III-A), or (III-B), $A^2$ is selected from (i), (ii), and (iii).

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN;

(ii) $C_{1-6}$ alkyl, $C_{2-6}$ alkenyl, and $C_{2-6}$ alkynyl, any of which is optionally substituted with one or more substituents independently selected from halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, $OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, —$N(R^{11})$, and —CN; and (iii) 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), (III-A), or (III-B), $A^2$ is selected from (i), (ii), and (iii).

(i) hydrogen, halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;

(ii) $C_{1-6}$ alkyl, $C_{2-6}$ alkenyl, and $C_{2-6}$ alkynyl, any of which is optionally substituted with one or more substituents independently selected from —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), or (III-B), $A^2$ is selected from (i), (ii), and (iii).

(i) hydrogen, halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;

(ii) $C_{1-6}$ alkyl optionally substituted with one or more substituents independently selected from —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and (iii) 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), or (III-B), $A^2$ is selected from (i), (ii), and (iii).

(i) hydrogen, halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, and =O;

(ii) $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, and =O; and (iii) 5- to 10-membered heterocycle and $C_{3-10}$ carbocycle, any of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O.

In some embodiments, for the compound or salt of Formula (I), (II), (II-A), (III), (III-A), or (III-B), $A^2$ is selected from (i), (ii), and (iii):

(i) hydrogen, halogen, —$OR^{11}$, —$N(R^{11})_2$, and =O;

(ii) $C_{1-6}$ alkyl optionally substituted with one or more substituents independently selected from halogen, —$OR^{11}$, —$N(R^{11})_2$, and =O; and (iii) 5- to 10-membered heterocycle and $C_{3-10}$ carbocycle, any of which is optionally substituted with one or more substituents independently selected from: halogen, —$OR^{11}$, —$N(R^{11})_2$, and =O; and $C_{1-6}$ alkyl optionally substituted with one or more substituents independently selected from halogen, —$OR^{11}$, —$N(R^{11})_2$, and =O.

In some embodiments, for the compound or salt of Formula (I), (II), (II-A), (III), (III-A), or (III-B), $A^2$ is selected from: hydrogen, halogen, —$OR^{11}$, —$N(R^{11})_2$, $C_{1-6}$ alky, and $C_{1-6}$ haloalkyl; and 5- to 10-membered heterocycle and $C_{3-10}$ carbocycle, any of which is optionally substituted with one or more substituents independently selected from: halogen, —$OR^{11}$, —$N(R^{11})_2$, $C_{1-6}$ alkyl, and $C_{1-6}$ haloalkyl.

In some embodiments, for the compound or salt of Formula (I), (II), (II-A), (III), (III-A), or (III-B), $A^2$ is selected from: hydrogen, halogen, $C_{1-6}$ alky, and $C_{1-6}$ haloalkyl; and 5- to 10-membered heterocycle and $C_{3-10}$ carbocycle. In some embodiments, $A^2$ is selected from hydrogen, halogen, $C_{1-6}$ alkyl, and $C_{1-6}$ haloalkyl. In some embodiments, $A^2$ is selected from hydrogen, halogen, $C_{1-4}$ alkyl, and $C_{1-4}$ haloalkyl. In some embodiments, $A^2$ is selected from 5- to 10-membered heterocycle and $C_{3-10}$ carbocycle. In some embodiments, $A^2$ is selected from 5- to 6-membered heterocycle and $C_{3-6}$ carbocycle.

In some embodiments, for the compound or salt of Formula (I), (II), (II-A), (III), (III-A), or (III-B), $A^2$ is selected from hydrogen, halogen, —$OR^{11}$, —$N(R^{11})_2$, CN, and =O; and $C_{1-6}$ alkyl optionally substituted with one or more substituents independently selected from halogen, —$OR^{11}$, —$N(R^{11})_2$, and =O. In some embodiments, $A^2$ is selected from hydrogen, halogen, —$OR^{11}$, —$N(R^{11})_2$, CN, and =O; and $C_{1-6}$ alkyl optionally substituted with one or more substituents independently selected from halogen and —$OR^{11}$. In some embodiments, $A^2$ is selected from $A^2$ is selected from hydrogen, halogen, $C_{1-4}$ alkyl, $C_{1-4}$ haloalkyl, —$OR^{11}$, —$N(R^{11})_2$, and —CN. In some embodiments, $A^2$ is selected from hydrogen, halogen, $C_{1-4}$ alkyl, and $C_{1-4}$ haloalkyl. In some embodiments, $A^2$ is $C_{1-4}$ alkyl. In some embodiments, $A^2$ is selected from hydrogen and methyl. In some embodiments, $A^2$ is methyl.

In some embodiments, for the compound or salt of Formula (I), (II), (II-A), (III), (III-A), or (III-B), $A^2$ is selected from 5- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), (III-A), or (III-B), $A^2$ is selected from 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;

$C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), or (III-B), $A^2$ is selected from 5- to 10-membered heterocycle and $C_{3-10}$ carbocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, =O, and —CN;

$C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =O; and $C_{3-10}$ carbocycle and 3- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$. =O, and —CN; and $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =O.

In some embodiments, for the compound or salt of Formula (I), (II), (II-A), (III), (III-A), or (III-B), $A^2$ is selected from 5- to 10-membered heterocycle and $C_{3-10}$ carbocycle, any of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is selected from 5- to 10-membered heterocycle and $C_{3-10}$ carbocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, and —$N(R^{11})_2$.

In some embodiments, for the compound or salt of Formula (I), (II), (II-A), (III), (III-A), or (III-B), $A^2$ is selected from 5- to 6-membered heteroaryl and $C_{3-6}$ saturated carbocycle, any of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is selected from 5- to 6-membered heteroaryl and $C_{3-6}$ saturated carbocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, and —$N(R^{11})_2$.

In some embodiments, for the compound or salt of Formula (I), (II), (II-A), (III), (III-A), or (III-B), $A^2$ is selected from pyrazolyl, triazolyl, and cyclopropyl, any of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is selected from pyrazolyl, triazolyl, and cyclopropyl, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, and —$N(R^{11})_2$. In some embodiments, $A^2$ is selected from pyrazolyl, triazolyl, and cyclopropyl, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, and —$N(R^{11})_2$; and $R^{11}$ is independently selected at each occurrence from hydrogen, $C_{1-3}$ alkyl, and $C_{1-3}$ haloalkyl. In some embodiments, $A^2$ is selected from pyrazolyl, triazolyl, and cyclopropyl, any of which is optionally substituted with one or more substituents independently selected from halogen, —$OR^{11}$, —$N(R^{11})_2$, —CN, $C_{1-6}$ alkyl, and $C_{1-6}$ haloalkyl.

In some embodiments, for the compound or salt of Formula (I), (II), (II-A), (III), (III-A), or (III-B), $A^2$ is 5- to 10-membered heterocycle optionally substituted with one or more substituents independently selected from:

- halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and
- $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and
- $C_{3-10}$ carbocycle and 3- to 10-membered heterocycle, any of which is optionally substituted with one or more substituents independently selected from:
  - halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN; and
  - $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), (III-A), or (III-B), $A^2$ is 5- to 10-membered heterocycle optionally substituted with one or more substituents independently selected from:

- halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;
- $C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN; and
- $C_{3-10}$ carbocycle and 3- to 10-membered heterocycle, any of which is optionally substituted with one or more substituents independently selected from:
  - halogen, —$OR^{11}$, —$N(R^{11})_2$, —$C(O)R^{11}$, —$C(O)N(R^{11})_2$, —$N(R^{11})C(O)R^{11}$—O, and —CN; and
  - $C_{1-6}$ alkyl, $C_{2-6}$ alkenyl, and $C_{2-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), or (III-B), $A^2$ is 5- to 10-membered heterocycle optionally substituted with one or more substituents independently selected from:

- halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN;
- $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN; and
- $C_{3-10}$ carbocycle and 3- to 10-membered heterocycle, any of which is optionally substituted with one or more substituents independently selected from:
  - halogen, —$OR^{11}$, —$N(R^{11})_2$, —$C(O)R^{11}$, —$C(O)N(R^{11})_2$, —$N(R^{11})C(O)R^{11}$—O, and —CN; and
  - $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, =O, and —CN.

In some embodiments, for the compound or salt of Formula (I), (II), (II-A), (III), (III-A), or (III-B), $A^2$ is 5- to 10-membered heterocycle optionally substituted with one or more substituents independently selected from:

- halogen, —$OR^{11}$, —$N(R^{11})_2$, —$C(O)R^{11}$, —$C(O)N(R^{11})_2$, —$N(R^{11})C(O)R^{11}$, =O, and —CN;
- $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =O; and
- $C_{3-10}$ carbocycle and 3- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$. =O, and —CN; and $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =O.

In some embodiments, for the compound or salt of Formula (I), (II), (II-A), (III), (III-A), or (III-B), $A^2$ is 5- to 10-membered heterocycle optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O.

In some embodiments, for the compound or salt of Formula (I), (II), (II-A), (III), (III-A), or (III-B), $A^2$ is 5- to 10-membered heterocycle optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from: halogen, —$OR^{11}$, and —$N(R^{11})_2$. In some embodiments, $A^2$ is selected from 5- to 10-membered heterocycle, each of which is optionally substituted with one or more substituents independently selected from halogen, —$OR^{11}$, —$N(R^{11})_2$, $C_{1-6}$ alkyl, $C_{1-6}$ haloalkyl. In some embodiments, $A^2$ is selected from 5- to 10-membered heterocycle.

In some embodiments, for the compound or salt of Formula (I), (II), (II-A), (III), (III-A), or (III-B), $A^2$ is selected from pyrazolyl, triazolyl, oxazolyl, thiazolyl, morpholinyl, pyridinyl, pyrazinyl, and 6,7-dihydro-4H-pyrazolo[5,1-c][1,4]oxazinyl, each of which is substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is selected from pyrazolyl, triazolyl, oxazolyl, thiazolyl, morpholinyl, pyridinyl, pyrazinyl, and 6,7-dihydro-4H-pyrazolo[5,1-c][1,4]oxazinyl, each of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from: halogen, —$OR^{11}$, and —$N(R^{11})_2$. In some embodiments, $A^2$ is selected from pyrazolyl, triazolyl, oxazolyl, thiazolyl, morpholinyl, pyridinyl, pyrazinyl, and 6,7-dihydro-4H-pyrazolo[5,1-c][1,4]oxazinyl, each of which is optionally substituted with one or more substituents independently selected from halogen, —$OR^{11}$, —$N(R^{11})_2$, and —CN; and $C_{1-6}$ alkyl optionally substituted with one or more substituents independently selected from: halogen, —$OR^{11}$, and —$N(R^{11})_2$.

In some embodiments, for the compound or salt of Formula (I), (II), (II-A), (III), (III-A), or (III-B), $A^2$ is selected from pyrazolyl, triazolyl, oxazolyl, thiazolyl, morpholinyl, pyridinyl, pyrazinyl, and 6,7-dihydro-4H-pyrazolo[5,1-c][1,4]oxazinyl, each of which is optionally substituted with one or more substituents independently selected from halogen, —$OR^{11}$, —$N(R^{11})_2$, —CN, $C_{1-6}$ alkyl, and $C_{1-6}$ haloalkyl. In some embodiments, $A^2$ is selected from pyrazolyl, triazolyl, oxazolyl, thiazolyl, morpholinyl, pyridinyl, pyrazinyl, and 6,7-dihydro-4H-pyrazolo[5,1-c][1,4]oxazinyl, each of which is optionally substituted with one or more substituents independently selected from halogen, $C_{1-6}$ alkyl and $C_{1-6}$ haloalkyl. In some embodiments, $A^2$ is selected from pyrazolyl, triazolyl, oxazolyl, thiazolyl, morpholinyl, pyridinyl, pyrazinyl, and 6,7-dihydro-4H-pyrazolo[5,1-c][1,4]oxazinyl, each of which is optionally substituted with one or more substituents independently selected from fluoro, methyl, and —$CHF_2$. In some embodiments, $A^2$ is selected from

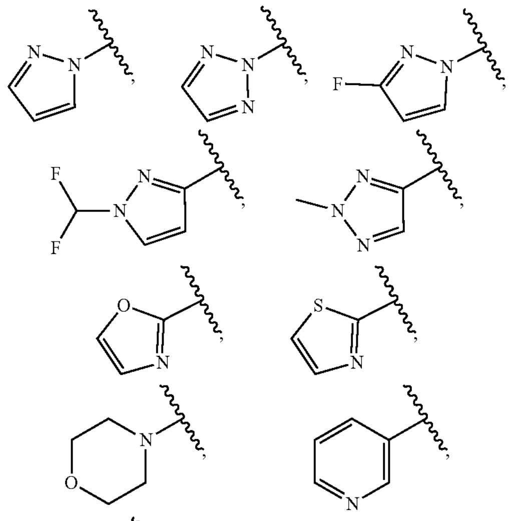

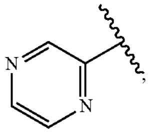

and

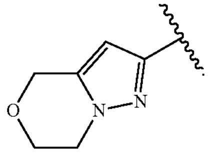

In some embodiments, $A^2$ is

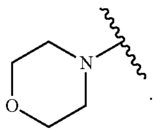 [SMILES: *N1CCOCC1]

In some embodiments, $A^2$ is selected from

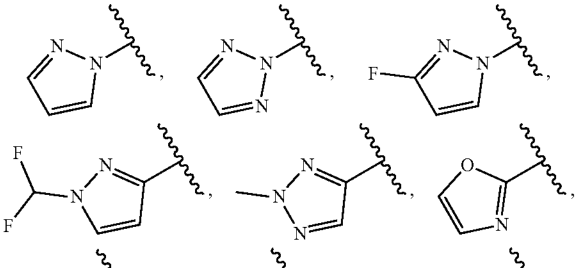

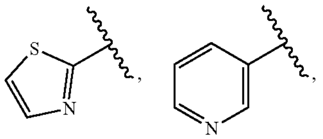

and

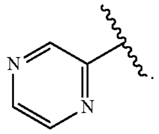

In some embodiments, $A^2$ is

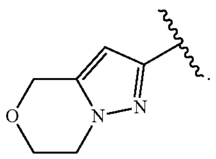 [SMILES: *c1cc2n(n1)CCOC2]

In some embodiments, for the compound or salt of Formula (I), (II), (II-A), (III), (III-A), or (III-B), $A^2$ is 5- to 6-membered heteroaryl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —O, and —CN; and $C_{1-6}$ alkyl optionally substituted with one or more substituents independently selected from: halogen, —$OR^{11}$, and —$N(R^{11})_2$. In some embodiments, $A^2$ is selected from 5- to 6-membered heteroaryl, each of which is optionally substituted with one or more substituents independently selected from halogen, —$OR^{11}$, —$N(R^{11})_2$, $C_{1-6}$ alkyl, $C_{1-6}$ haloalkyl. In some embodiments, $A^2$ is selected from 5- to 6-membered heteroaryl. In some embodiments, $A^2$ is 5-membered heteroaryl.

In some embodiments, for the compound or salt of Formula (I), (II), (II-A), (III), (III-A), or (III-B), $A^2$ is selected from pyrazolyl and triazolyl, each of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, ═O, and —CN; and $C_{1-6}$ alkyl optionally substituted with one or more substituents independently selected from: halogen, —$OR^{11}$, and —$N(R^{11})_2$. In some embodiments, $A^2$ is selected from pyrazolyl and triazolyl, each of which is optionally substituted with one or more substituents independently selected from halogen, —$OR^{11}$, —$N(R^{11})_2$, $C_{1-6}$ alkyl, $C_{1-6}$ haloalkyl. In some embodiments, $A^2$ is selected from pyrazolyl and triazolyl. In some embodiments, $A^2$ is pyrazolyl.

In some embodiments, for the compound or salt of Formula (I), (II), (II-A), (III), (III-A), or (III-B), $A^2$ is selected from

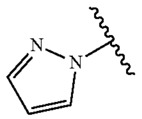
and
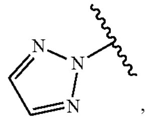
, each of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, ═O, and —CN; and $C_{1-6}$ alkyl optionally substituted with one or more substituents independently selected from: halogen, —$OR^{11}$, and —$N(R^{11})_2$. In some embodiments, $A^2$ is selected from

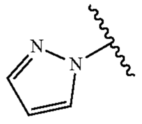
and
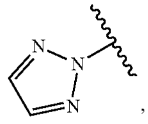
, each of which is optionally substituted with one or more substituents independently selected from halogen, —$OR^{11}$, —$N(R^{11})_2$, $C_{1-6}$ alkyl, $C_{1-6}$ haloalkyl. In some embodiments, $A^2$ is selected from

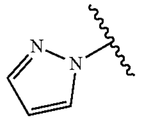
and
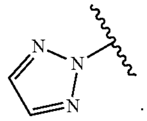
.

In some embodiments, $A^2$ is

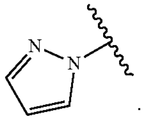 [SMILES: *n1cccn1]
.

In some embodiments, for the compound or salt of Formula (I), (II), (II-A), (III), (III-A), or (III-B), $A^2$ is 5- to 10-membered heterocycle optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN. In some embodiments, $A^2$ is 5- to 10-membered saturated heterocycle optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN. In some embodiments, $A^2$ is 5- to 10-membered heteroaryl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN In some embodiments, for the compound or salt of Formula (I), (II), (II-A), (III), (III-A), or (III-B), $A^2$ is 5- to 8-membered heterocycle optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN. In some embodiments, 5- to 8-membered saturated heterocycle optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, ═O, and —CN. In some embodiments, $A^2$ is selected from

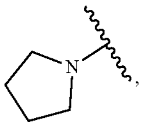
,
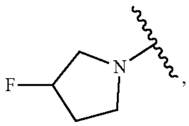
,
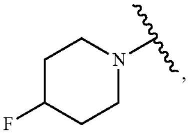
,
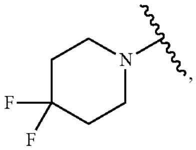
,
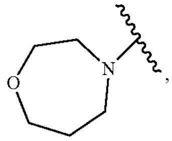
,
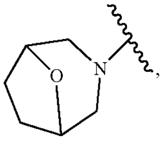
, and
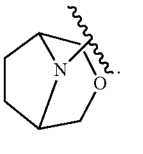
.

In some embodiments, $A^2$ is selected from

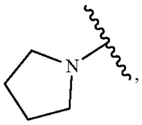
,
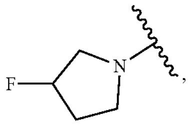
,
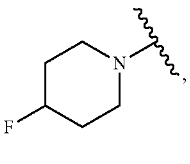
,

-continued

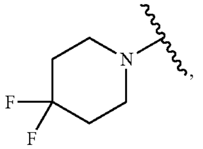, 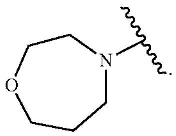.

In some embodiments, $A^2$ is selected from

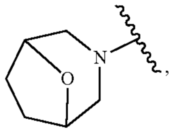, and 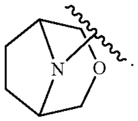.

In some embodiments, for the compound or salt of Formula (I), (II), (II-A), (III), (III-A), or (III-B), $A^2$ is 5- to 6-membered heteroaryl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, and —CN. In some embodiments, $A^2$ is 5- to 6-membered heteroaryl optionally substituted with one or more substituents independently selected from halogen, —$OR^{11}$, —$N(R^{11})_2$, and —CN. In some embodiments, $A^2$ is 5- to 6-membered heteroaryl optionally substituted with one or more substituents independently selected from halogen, —$OR^{11}$, —$N(R^{11})_2$, and —CN; and $R^{11}$ is selected from halogen, $C_{1-6}$ alkyl, $C_{1-6}$ haloalkyl, $C_{3-6}$ carbocycle, and 3- to 6-membered heterocycle. In some embodiments, $A^2$ is selected from

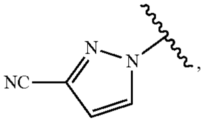, 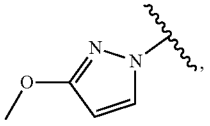, 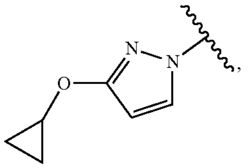, 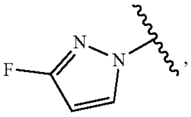, and 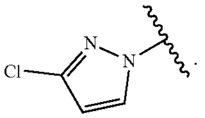.

In some embodiments, for the compound or salt of Formula (I), (II), (II-A), (III), (III-A), or (III-B), $A^2$ is 5- to 10-membered heterocycle optionally substituted with one or more $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN. In some embodiments, $A^2$ is 5- to 8-membered heterocycle optionally substituted with one or more $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, =O, and —CN. In some embodiments, $A^2$ is 5- to 8-membered saturated heterocycle optionally substituted with one or more $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$NO_2$, =O, and —CN. In some embodiments, $A^2$ is

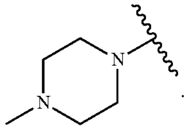 [SMILES: *N1CCN(C)CC1].

In some embodiments, for the compound or salt of Formula (I), (II), (II-A), (III), (III-A), or (III-B), $A^2$ is 5- to 6-membered heteroaryl optionally substituted with one or more $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$NO_2$, and —CN. In some embodiments, $A^2$ is 5- to 6-membered heteroaryl optionally substituted with one or more $C_{1-3}$ alkyl optionally substituted with one or more substituents independently selected from: halogen, —$OR^{11}$, —$N(R^{11})_2$, —$NO_2$, and —CN. In some embodiments, $A^2$ is selected from

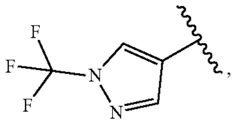, 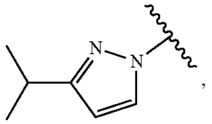, 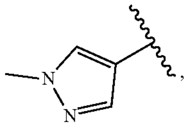, 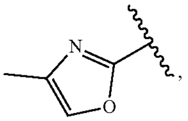, 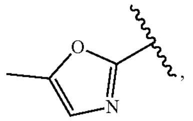, 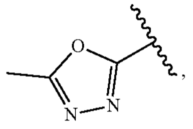, 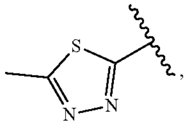, 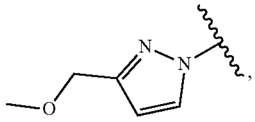, and 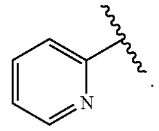 [SMILES: *c1ccccn1].

In some embodiments, $A^2$ is 5-membered heteroaryl optionally substituted with one or more $C_{1-3}$ alkyl optionally substituted with one or more substituents independently selected from: halogen, —$OR^{11}$, —$N(R^{11})_2$, —$NO_2$, and —CN. In some embodiments, $A^2$ is selected from

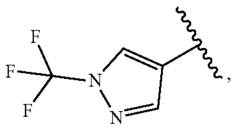, 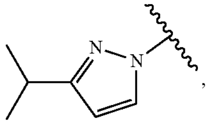, 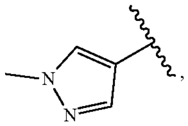, 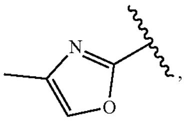, 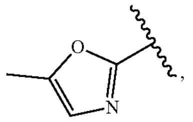,

-continued

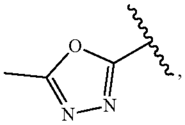, 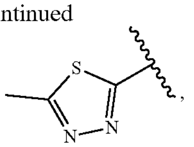, and

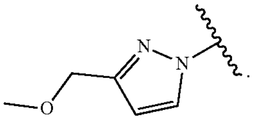.

In some embodiments, $A^2$ is 6-membered heteroaryl optionally substituted with one or more $C_{1-3}$ alkyl optionally substituted with one or more substituents independently selected from: halogen, —$OR^{11}$, —$N(R^{11})_2$, —$NO_2$, and —CN. In some embodiments, $A^2$ is

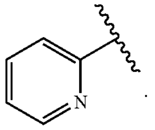.

In some embodiments, for the compound or salt of Formula (I), (II), (II-A), (III), (III-A), or (III-B), $A^2$ is 5- to 10-membered heterocycle optionally substituted with one or more $C_{3-10}$ carbocycle and 3- to 10-membered heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, —CN, $C_{1-6}$ alkyl and $C_{1-6}$ haloalkyl. In some embodiments, $A^2$ is 5- to 10-membered heterocycle optionally substituted with one or more $C_{3-6}$ saturated carbocycle and 3- to 6-membered saturated heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, —CN, $C_{1-6}$ alkyl and $C_{1-6}$ haloalkyl. In some embodiments, $A^2$ is 5- to 6-membered heterocycle optionally substituted with one or more $C_{3-6}$ saturated carbocycle and 3- to 6-membered saturated heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, —CN, $C_{1-6}$ alkyl and $C_{1-6}$ haloalkyl. In some embodiments, $A^2$ is 5- to 6-membered heteroaryl optionally substituted with one or more $C_{3-6}$ saturated carbocycle and 3- to 6-membered saturated heterocycle, any of which is optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, =O, —CN, $C_{1-6}$ alkyl and $C_{1-6}$ haloalkyl. In some embodiments, $A^2$ is selected from

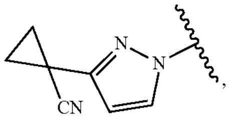, 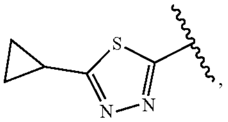,

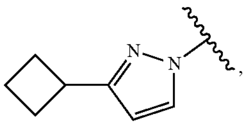, 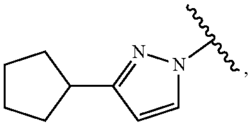, and

-continued

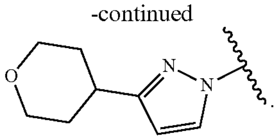.

In some embodiments, $A^2$ is selected from

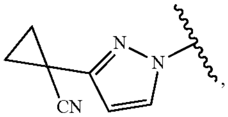, 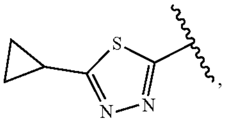,

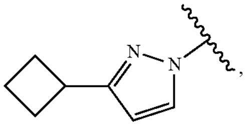, and 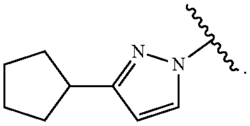.

In some embodiments, $A^2$ is

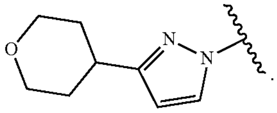 [SMILES: *n1ccc(C2CCOCC2)n1].

In some embodiments, for the compound or salt of Formula (I), (II), (II-A), (III), (III-A), or (III-B), $A^2$ is $C_{3-10}$ carbocycle optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$—$C(O)OR^{11}$, —$OC(O)R^{11}$, —$NO_2$, =O, =S, =$N(R^{11})$, —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

In some embodiments, for the compound or salt of Formula (I), (II), (II-A), (III), (III-A), or (III-B), $A^2$ is $C_{3-10}$ carbocycle optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl, $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl $C_{2-6}$ alkenyl, and $C_{3-6}$ alkynyl, any one of which is optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN.

In some embodiments, for the compound or salt of Formula (I), (II), (II-A), (III), (III-A), or (III-B), $A^2$ is $C_{3-10}$ carbocycle optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, =O, and —CN;

$C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =0; and $C_{3-10}$ carbocycle and 3- to 10-membered heterocycle; wherein the $C_{3-10}$ carbocycle and 3- to 10-membered heterocycle are each optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$. =O, and —CN; and $C_{1-6}$ alkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and =O.

In some embodiments, for the compound or salt of Formula (I), (II), (II-A), (III), (III-A), or (III-B), $A^2$ is $C_{3-10}$ carbocycle optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, =O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O.

In some embodiments, for the compound or salt of Formula (I), (II), (II-A), (III), (III-A), or (III-B), $A^2$ is $C_{3-6}$ saturated carbocycle optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is $C_{3-6}$ saturated carbocycle optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is $C_{3-6}$ saturated carbocycle optionally substituted with one or more substituents independently selected from: halogen, —$OR^{11}$, —$N(R^{11})_2$, $C_{1-6}$ alkyl, and $C_{1-6}$ haloalkyl. In some embodiments, $A^2$ is $C_{3-6}$ saturated carbocycle.

In some embodiments, for the compound or salt of Formula (I), (II), (II-A), (III), (III-A), or (III-B), $A^2$ is $C_{3-6}$ cycloalkyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is $C_{3-6}$ cycloalkyl optionally substituted with one or more substituents independently selected from: halogen, —$OR^{11}$, —$N(R^{11})_2$, $C_{1-6}$ alkyl, and $C_{1-6}$ haloalkyl. In some embodiments, $A^2$ is $C_{3-6}$ cycloalkyl optionally substituted with one or more substituents independently selected from: halogen, $C_{1-6}$ alkyl, and $C_{1-6}$ haloalkyl. In some embodiments, $A^2$ is $C_{3-6}$ cycloalkyl.

In some embodiments, for the compound or salt of Formula (I), (II), (II-A), (III), (III-A), or (III-B), $A^2$ is cyclopropyl optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is cyclopropyl optionally substituted with one or more substituents independently selected from: halogen, —$OR^{11}$, —$N(R^{11})_2$, $C_{1-6}$ alkyl, and $C_{1-6}$ haloalkyl. In some embodiments, $A^2$ is cyclopropyl optionally substituted with one or more substituents independently selected from: halogen, $C_{1-6}$ alkyl, and $C_{1-6}$ haloalkyl. In some embodiments, $A^2$ is cyclopropyl.

In some embodiments, for the compound or salt of Formula (I), (II), (II-A), (III), (III-A), or (III-B), $A^2$ is

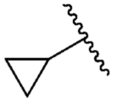 [SMILES: *C1CC1]

optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and =O. In some embodiments, $A^2$ is

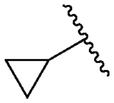 [SMILES: *C1CC1]

optionally substituted with one or more substituents independently selected from: halogen, —$OR^{11}$, —$N(R^{11})_2$, $C_{1-6}$ alkyl, and $C_{1-6}$ haloalkyl. In some embodiments, $A^2$ is

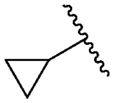 [SMILES: *C1CC1]

substituted with one or more substituents independently selected from: halogen, $C_{1-6}$ alkyl, and $C_{1-6}$ haloalkyl. In some embodiments, $A^2$ is

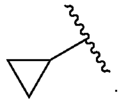 [SMILES: *C1CC1]

In some embodiments, for the compound or salt of Formula (I), (II), (II-A), (III), (III-A), or (III-B), $A^2$ is $C_{3-6}$ carbocycle optionally substituted with one or more substituents independently selected from: halogen, —$OR^{11}$, —$N(R^{11})_2$, —$C(O)R^{11}$, —$C(O)N(R^{11})_2$, —$N(R^{11})C(O)R^{11}$, ═O, and —CN; and $C_{1-6}$ alkyl optionally substituted with one or more substituents independently selected from halogen, —$OR^{11}$, —$N(R^{11})_2$, —$C(O)R^{11}$, —$C(O)N(R^{11})_2$, —$N(R^{11})C(O)R^{11}$, and ═O. In some embodiments, $A^2$ is $C_{3-6}$ carbocycle optionally substituted with one or more substituents independently selected from: halogen, —$OR^{11}$, —$N(R^{11})_2$, —CN, $C_{1-6}$ alkyl. In some embodiments, $A^2$ is selected from

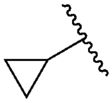
,
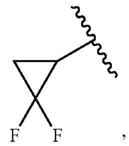
,
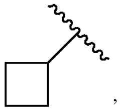
,
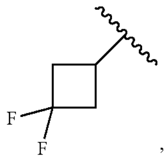
, and
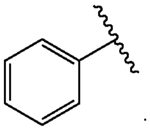

In some embodiments, for the compound or salt of Formula (I), (II), (II-A), (III), (III-A), or (III-B), $R^{11}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{11}$ is independently selected at each occurrence from: hydrogen, $C_{1-6}$ alkyl, and $C_{1-6}$ haloalkyl. In some embodiments, $R^{11}$ is independently selected at each occurrence from: hydrogen, $C_{1-4}$ alkyl, and $C_{1-4}$ haloalkyl. In some embodiments, $R^{11}$ is independently selected at each occurrence from: hydrogen, $C_{1-3}$ alkyl, and $C_{1-3}$ haloalkyl. In some embodiments, $R^{11}$ is independently selected at each occurrence from: hydrogen and $C_{1-3}$ alkyl. In some embodiments, $R^{11}$ is independently selected at each occurrence from: hydrogen and methyl.

In some embodiments, for the compound or salt of Formula (I), (II), (II-A), (III), (III-A), or (III-B), L is represented by -$L^1$-$L^2$-$L^3$-$L^4$-, wherein $L^1$, $L^2$, $L^3$, and $L^4$ are each independently selected from (a) and (b):

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, —$OR^{15}$, —$SR^{15}$, ═O, ═S, and —CN;

wherein $L^2$, $L^3$, and $L^4$ are each optionally absent;

wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), or (III-B), $L^1$, $L^2$, $L^3$, and $L^4$ are each independently selected from (a) and (b):

(a) —O—, —$N(R^{15})$—, —S—, —$N(R^{15})C(O)$—, —$N(R^{15})C(O)O$—, —$N(R^{15})S(O)_2$—$N(R^{15})N(R^{15})$—, and $(R^{15})NC(O)N(R^{15})$—; and (b) $C_{1-6}$ alkylene, $C_{2-6}$ alkenylene, $C_{2-6}$ alkynylene, $C_{3-6}$ carbocyclene, and 3- to 6-membered heterocyclene, any of which is optionally substituted with one or more substituents independently selected from halogen, —$OR^{15}$, ═O, and —CN;

wherein $L^2$, $L^3$, and $L^4$ are each optionally absent;

wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), or (III-B), $L^1$, $L^2$, $L^3$, and $L^4$ are each independently selected from (a) and (b):

(a) —O—, —$N(R^{15})$—, and —$N(R^{15})C(O)$—;

(b) $C_{1-6}$ alkylene;

wherein $L^2$, $L^3$, and $L^4$ are each optionally absent;

wherein no more than two of $L^1$, $L^2$, $L^3$, and $L^4$ are selected from (a) and the two selected are not adjacent; and $R^{15}$ is selected from hydrogen and $C_{1-4}$ alkyl.

In some embodiments, for the compound or salt of Formula (I), (II), (II-A), (III), (III-A), or (III-B), $L^1$, $L^2$, $L^3$, and $L^4$ are each independently selected from (a) and (b):

(a) —O—, —N(H)—, and —N(H)C(O)—;

(b) $C_{1-6}$ alkylene;

wherein $L^2$, $L^3$, and $L^4$ are each optionally absent;

wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), or (III-B), $L^1$, $L^2$, $L^3$, and $L^4$ are each independently selected from (a) and (b):

(a) —N(H)—, and —N(H)C(O)—;

(b) methylene;

wherein $L^2$, $L^3$, and $L^4$ are each optionally absent;

wherein no more than two of $L^1$, $L^2$, $L^3$, and $L^4$ are selected from (a) and the two selected are not adjacent.

In some embodiments, for the compound or salt of Formula (I), (II), (II-A), (III), (III-A), or (III-B), $L^2$, $L^3$, and $L^4$ are each optionally absent. In some embodiments, $L^3$ and $L^4$ are each optionally absent. In some embodiments, $L^4$ is absent. In some embodiments, $L^3$ is absent.

In some embodiments, for the compound or salt of Formula (II), (II-A), (III), (III-A), or (III-B), $L^2$ is absent or selected from:

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, —$OR^{15}$, —$SR^{15}$, ═O, ═S, and —CN.

In some embodiments, for the compound or salt of Formula (I), (II), (II-A), (III), (III-A), or (III-B), $L^2$ is absent or selected from:

(a) —O—, —$N(R^{15})$—, —S—, —$N(R^{15})C(O)$—, —$N(R^{15})C(O)O$—, —$N(R^{15})S(O)_2$—$N(R^{15})N(R^{15})$—, and $(R^{15})NC(O)N(R^{15})$—; and (b) $C_{1-6}$ alkylene, $C_{2-6}$ alkenylene, $C_{2-6}$ alkynylene, $C_{3-6}$ carbocyclene, and 3- to 6-membered heterocyclene, any of which is optionally substituted with one or more substituents independently selected from halogen, —$OR^{15}$, =O, and —CN.

In some embodiments, for the compound or salt of Formula (I), (II), (II-A), (III), (III-A), or (III-B), $L^2$ is absent or selected from —O—, —$N(R^{15})$—, and —$N(R^{15})C(O)$—, and $C_{1-6}$ alkylene.

In some embodiments, for the compound or salt of Formula (I), (II), (II-A), (III), (III-A), or (III-B), $L^2$ is absent or selected from —$N(R^{15})$— and —$N(R^{15})C(O)$—, and $C_{1-3}$ alkyl; and $R^{15}$ is selected at each occurrence from hydrogen and methyl. In some embodiments, $L^2$ is absent or selected from —N(H)—, —N(H)C(O)—, and methylene. In some embodiments, $L^2$ is absent or methylene. In some embodiments, $L^2$ is absent.

In some embodiments, for the compound or salt of Formula (I), (II), (II-A), (III), (III-A), or (III-B), $L^1$ is selected from:

(a) —O—, —$N(R^{15})$—, —S—, —S(O)—, —$S(O)_2$—, —$S(O)(NR^{15})$—, —$N(R^{15})C(O)$—, —$N(R^{15})C(O)O$—, —$N(R^{15})S(O)_2$—, —$N(R^{15})S(O)_2N(R^{15})$—, —$S(O)(NR^{15})N(R^{15})$—, —$N(R^{15})N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, —$OR^{15}$, —$SR^{15}$, =O, =S, and —CN.

In some embodiments, for the compound or salt of Formula (I), (II), (II-A), (III), (III-A), or (III-B), $L^1$ is selected from:

(a) —O—, —$N(R^{15})$—, —S—, —$N(R^{15})C(O)$—, —$N(R^{15})C(O)O$—, —$N(R^{15})S(O)_2$—$N(R^{15})N(R^{15})$—, and $(R^{15})NC(O)N(R^{15})$—; and (b) $C_{1-6}$ alkylene, $C_{2-6}$ alkenylene, $C_{2-6}$ alkynylene, $C_{3-6}$ carbocyclene, and 3- to 6-membered heterocyclene, any of which is optionally substituted with one or more substituents independently selected from halogen, —$OR^{15}$, =O, and —CN.

In some embodiments, for the compound or salt of Formula (I), (II), (II-A), (III), (III-A), or (III-B), $L^1$ is selected from —O—, —$N(R^{15})$—, and —$N(R^{15})C(O)$—, and $C_{1-6}$ alkylene. In some embodiments, $L^1$ is selected from —O—, —$N(R^{15})$—, and —$N(R^{15})C(O)$—, and $C_{1-6}$ alkylene, and $R^{15}$ is selected at each occurrence from hydrogen and $C_{1-4}$ alkyl.

In some embodiments, for the compound or salt of Formula (I), (II), (II-A), (III), (III-A), or (III-B), $L^1$ is selected from —$N(R^{15})$— and —$N(R^{15})C(O)$—; and $R^{15}$ is selected at each occurrence from hydrogen and methyl. In some embodiments, $L^1$ is selected from —N(H)— and —N(H)C(O)—. In some embodiments, $L^1$ is —N(H)C(O)—.

In some embodiments, for the compound or salt of Formula (I), (II), (II-A), (III), (III-A), or (III-B), L is selected from —O—, —$N(R^{15})$—, —$N(R^{15})$—$C_{1-3}$ alkyl-, and —$N(R^{15})C(O)$—; and $R^{15}$ is selected from hydrogen and $C_{1-4}$ alkyl. In some embodiments, L is selected from —O—, —$N(R^{15})$—, —$N(R^{15})$—$C_{1-3}$ alkyl-, and —$N(R^{15})C(O)$—; and $R^{15}$ is independently selected from hydrogen and methyl. In some embodiments, L is selected from —O—, —NH—,

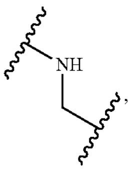
, and
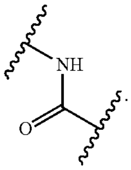
.

In some embodiments, L is selected from —NH— and

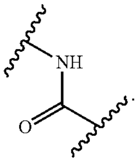 [SMILES: *NC(*)=O]
.

In some embodiments, for the compound or salt of Formula (I), (II), (II-A), (III), (III-A), or (III-B), L is selected from —O—, —NH—, —$N(CH_3)$—,

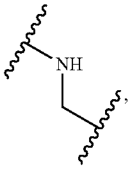
, and
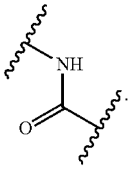
.

In some embodiments, for the compound or salt of Formula (I), (II), (II-A), (III), (III-A), or (III-B), $L^1$ is selected from —O—, —$N(R^{15})$—, —$N(R^{15})C(O)$—, $C_{1-6}$ alkylene, and 3- to 6-membered heterocyclene. In some embodiments, L is selected from —O—, —NH—, —$CH_2$—, —$N(CH_3)$—,

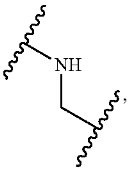
,
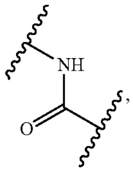
, and
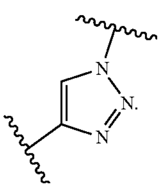
.

In some embodiments, L is selected from —O—, —NH—, —$CH_2$—, and —$N(CH_3)$—. In some embodiments, L is selected from

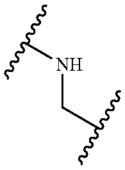
and
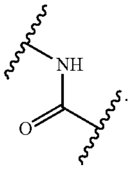
.

In some embodiments, L is

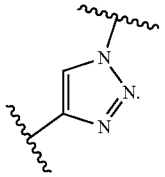 [SMILES: *c1cn(*)nn1]

In some embodiments, for the compound or salt of Formula (I), (II), (II-A), (III), (III-A), or (III-B), $R^{15}$ is independently selected at each occurrence from hydrogen, $C_{1-6}$ alkyl, $C_{1-6}$ haloalkyl, $C_{3-6}$ carbocycle, and 3- to 6-membered heterocycle. In some embodiments, $R^{15}$ is independently selected at each occurrence from: hydrogen, $C_{1-6}$ alkyl, and $C_{1-6}$ haloalkyl. In some embodiments, $R^{15}$ is independently selected at each occurrence from: hydrogen, $C_{1-4}$ alkyl, and $C_{1-4}$ haloalkyl. In some embodiments, $R^{15}$ is independently selected at each occurrence from: hydrogen and $C_{1-4}$ alkyl. In some embodiments, $R^{15}$ is independently selected at each occurrence from: hydrogen, $C_{1-3}$ alkyl, and $C_{1-3}$ haloalkyl. In some embodiments, $R^{15}$ is independently selected at each occurrence from: hydrogen and $C_{1-3}$ alkyl. In some embodiments, $R^{15}$ is independently selected at each occurrence from: hydrogen and methyl. In some embodiments, $R^{15}$ hydrogen.

In some embodiments, for the compound or salt of Formula (I), (II), (II-A), (III), (III-A), or (III-B), Ring B selected from 3- to 10-membered heterocyclene and $C_{3-10}$ carbocyclene, any of which is optionally substituted with one or more substituents independently selected from:

halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN; and 3- to 6-membered heterocycle and $C_{3-6}$ carbocycle, each of which is optionally substituted with one or more substituents independently selected from: halogen, $C_{1-6}$ alkyl, $C_{1-6}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN.

In some embodiments, for the compound or salt of Formula (I), (II), (II-A), (III), (III-A), or (III-B), Ring B selected from 3- to 10-membered heterocyclene and $C_{3-10}$ carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-6}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$NO_2$, and —CN; and 3- to 6-membered heterocycle and $C_{3-6}$ carbocycle, each of which is optionally substituted with one or more substituents independently selected from: halogen, $C_{1-6}$ alkyl, $C_{1-6}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from 3- to 10-membered heterocyclene and $C_{3-10}$ carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$NO_2$, and —CN; and 4- to 6-membered heterocycle and $C_{3-6}$ carbocycle, each of which is optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from 3- to 10-membered heterocyclene and $C_{3-10}$ carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from 3- to 10-membered heterocyclene and $C_{3-10}$ carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from 5- to 10-membered heterocyclene and $C_{3-6}$ carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from 5- to 10-membered heterocyclene and $C_{3-6}$ carbocyclene, any of which is optionally substituted with one or more substituents independently selected from halogen, —$OR^{16}$, and $C_{1-3}$ alkyl. In some embodiments, Ring B is selected from 5- to 10-membered heterocyclene and $C_{3-6}$ carbocyclene, any of which is optionally substituted with one or more substituents independently selected from halogen, —$OR^{16}$, and $C_{1-3}$ alkyl; and $R^{16}$ is selected from hydrogen, $C_{1-3}$ alkyl, and $C_{1-3}$ haloalkyl. In some embodiments, Ring B is selected from 5- to 10-membered heterocyclene and $C_{3-6}$ carbocyclene, any of which is optionally substituted with one or more substituents independently selected from halogen and $C_{1-3}$ alkyl. In some embodiments, Ring B is selected from 5- to 10-membered heterocyclene and $C_{3-6}$ carbocyclene, any of which is optionally substituted with one or more substituents independently selected from fluoro and methyl.

In some embodiments, for the compound or salt of Formula (I), (II), (II-A), (III), (III-A), or (III-B), Ring B is selected from 5- to 10-membered saturated heterocyclene, 5- to 10-membered unsaturated heterocyclene, and $C_{3-6}$ unsaturated carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from azetidinylene, pyrrolidinylene, piperidinylene, phenylene, pyridinylene, indolinylene, 3-azabicyclo[3.2.1]octanylene, cyclobutylene, cyclohexylene, pyrazolylene, 1,2,3,4-tetrahydroquinolinylene, azaspiro[3.5]nonanylene, azaspiro[3.3]heptanylene, azaspiro[3.4], octanylene, 1,4 oxazepanylene, 3-azabicyclo[3.1.1]heptanylene, 3-oxa-6-azabicyclo[3.2.2]nonanylene, piperazinylene, azepanylene, 2-azabicyclo[2.2.2]octanylene, 2-azabicyclo[2.2.1]heptanylene each of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, —O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from azetidinylene, pyrrolidinylene, piperidinylene, phenylene, pyridinylene, indolinylene, isoindolinylene, tetrahydroisoquinolinyl, 3-azabicyclo[3.2.1]octanylene, cyclobutylene, cyclohexylene, pyrazolylene, 1,2,3,4-tetrahydroquinolinylene, azaspiro[3.5]nonanylene, azaspiro[3.3]heptanylene, azaspiro[3.4], octanylene, 1,4 oxazepanylene, 3-azabicyclo[3.1.0]heptanylene, 3-azabicyclo[3.1.1]heptanylene, 3-oxa-6-azabicyclo[3.2.2]nonanylene, 3-oxa-7-azabicyclo[3.3.1]nonanylene, 3-azabicyclo[3.3.1]nonanylene, piperazinylene, azepanylene, 2-azabicyclo[2.2.2]octanylene, 2-azabicyclo[2.2.1]heptanylene, 2-azabicyclo[3.2.1]octanylene, each of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from azetidinylene, pyrrolidinylene, piperidinylene, phenylene, pyridinylene, indolinylene, and 3-azabicyclo[3.2.1]octanylene, each of which is optionally substituted one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

In some embodiments, for the compound or salt of Formula (I), (II), (II-A), (III), (III-A), or (III-B), Ring B is selected from azetidinylene, pyrrolidinylene, piperidinylene, phenylene, pyridinylene, indolinylene, and 3-azabicyclo[3.2.1]octanylene, each of which is optionally substituted with one or more substituents independently selected from: halogen, —$OR^{16}$, —CN, and $C_{1-3}$ alkyl, wherein the $C_{1-3}$ alkyl is optionally substituted with halogen and —$OR^{16}$; and $R^{16}$ is selected from hydrogen, $C_{1-3}$ alkyl, and $C_{1-3}$ haloalkyl. In some embodiments, Ring B is selected from azetidinylene, pyrrolidinylene, piperidinylene, phenylene, pyridinylene, indolinylene, and 3-azabicyclo[3.2.1]octanylene, each of which is optionally substituted one or more substituents independently selected from: halogen, —$OR^{16}$, and $C_{1-3}$ alkyl; and $R^{16}$ is selected from hydrogen, $C_{1-3}$ alkyl, and $C_{1-3}$ haloalkyl.

In some embodiments, for the compound or salt of Formula (I), (II), (II-A), (III), (III-A), or (III-B), $R^{16}$ is independently selected at each occurrence from: hydrogen, $C_{1-6}$ alkyl, $C_{1-6}$ haloalkyl, $C_{3-6}$ carbocycle, and 3- to 6-membered heterocycle. In some embodiments, $R^{16}$ is independently selected at each occurrence from: hydrogen, $C_{1-6}$ alkyl, and $C_{1-6}$ haloalkyl. In some embodiments, $R^{16}$ is independently selected at each occurrence from: hydrogen, $C_{1-4}$ alkyl, and $C_{1-4}$ haloalkyl. In some embodiments, $R^{16}$ is independently selected at each occurrence from: hydrogen, $C_{1-3}$ alkyl, and $C_{1-3}$ haloalkyl. In some embodiments, $R^{16}$ is independently selected at each occurrence from: hydrogen, $C_{1-3}$ alkyl, and $C_{1-3}$ haloalkyl. In some embodiments, $R^{16}$ is hydrogen.

In some embodiments, for the compound or salt of Formula (I), (II), (II-A), (III), (III-A), or (III-B), $R^5$ is selected from —C(O)$R^{17}$, —S(O)$_2R^{17}$, —N($R^{19}$)C(O)($R^{17}$), —C(O)N($R^{17}$)($R^{19}$), and —N($R^{19}$)S(O)$_2R^{17}$, and —S(O)$_2$N($R^{17}$)($R^{19}$); and $R^{17}$ is independently selected at each occurrence from $C_{2-6}$ alkenyl and $C_{2-6}$ alkynyl each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —NO$_2$, and —CN.

In some embodiments, for the compound or salt of Formula (I), (II), (II-A), (III), (III-A), or (III-B), $R^5$ is selected from —C(O)$R^{17}$, —N($R^{19}$)C(O)($R^{17}$), and —N($R^{19}$)S(O)$_2R^{17}$; and $R^{17}$ is selected from $C_{2-6}$ alkenyl and $C_{2-6}$ alkynyl, each of which is optionally substituted with one or more substituents independently selected from: halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —NO$_2$, and —CN.

In some embodiments, for the compound or salt of Formula (I), (II), (II-A), (III), (III-A), or (III-B), $R^5$ is selected from —C(O)$R^{17}$, —N($R^{19}$)C(O)($R^{17}$), and —N($R^{19}$)S(O)$_2R^{17}$; and $R^{17}$ is selected from $C_{2-6}$ alkenyl and $C_{2-6}$ alkynyl, each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —NO$_2$, and —CN.

In some embodiments, for the compound or salt of Formula (I), (II), (II-A), (III), (III-A), or (III-B), $R^5$ is selected from —C(O)$R^{17}$, —N($R^{19}$)C(O)($R^{17}$), and —N($R^{19}$)S(O)$_2R^{17}$; and $R^{17}$ is selected from $C_{2-4}$ alkenyl and $C_{2-4}$ alkynyl, each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —NO$_2$, and —CN.

In some embodiments, for the compound or salt of Formula (I), (II), (II-A), (III), (III-A), or (III-B), $R^5$ is selected from —C(O)$R^{17}$, —N($R^{19}$)C(O)($R^{17}$), and —N($R^{19}$)S(O)$_2R^{17}$; and $R^{17}$ is selected from $C_{2-4}$ alkenyl and $C_{2-4}$ alkynyl, each of which is optionally substituted with one or more substituents independently selected from: halogen, —O$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —NO$_2$, and —CN.

In some embodiments, for the compound or salt of Formula (I), (II), (II-A), (III), (III-A), or (III-B), $R^5$ is selected from —C(O)$R^{17}$, —N($R^{19}$)C(O)($R^{17}$), and —N($R^{19}$)S(O)$_2R^{17}$; and $R^{17}$ is selected from $C_{2-4}$ alkenyl and $C_{2-4}$ alkynyl, each of which is optionally substituted with one or more substituents independently selected from: halogen, —O$R^{18}$, —N($R^{18}$)$_2$, —NO$_2$, and —CN.

In some embodiments, for the compound or salt of Formula (I), (II), (II-A), (III), (III-A), or (III-B), $R^5$ is —C(O)$R^{17}$; and $R^{17}$ is selected from $C_{2-4}$ alkenyl and $C_{2-4}$ alkynyl, each of which is optionally substituted with one or more substituents independently selected from: halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —NO$_2$, and —CN.

In some embodiments, for the compound or salt of Formula (I), (II), (II-A), (III), (III-A), or (III-B), $R^5$ is —C(O)$R^{17}$; and $R^{17}$ is selected from $C_{2-6}$ alkenyl and $C_{2-6}$ alkynyl, each of which is optionally substituted with one or more substituents independently selected from: halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —NO$_2$, and —CN. In some embodiments, $R^5$ is —C(O)$R^{17}$; and $R^{17}$ is selected from $C_{2-6}$ alkenyl and $C_{2-6}$ alkynyl, each of which is optionally substituted with one or more substituents independently selected from: halogen, —O$R^{18}$, —N($R^{18}$)$_2$, —NO$_2$, and —CN. In some embodiments, $R^5$ is —C(O)$R^{17}$; $R^{17}$ is selected from $C_{2-6}$ alkenyl and $C_{2-6}$ alkynyl, each of which is optionally substituted with one or more substituents independently selected from: halogen, —O$R^{18}$, —N($R^{18}$)$_2$, —NO$_2$, and —CN; and $R^{18}$ is selected from hydrogen, $C_{1-3}$ alkyl, and $C_{1-3}$ haloalkyl.

In some embodiments, for the compound or salt of Formula (I), (II), (II-A), (III), (III-A), or (III-B), $R^5$ is —C(O)$R^{17}$; and $R^{17}$ is selected from $C_{2-4}$ alkenyl and $C_{2-4}$ alkynyl, each of which is optionally substituted with one or more substituents independently selected from:

halogen, —O$R^{18}$, —N($R^{18}$)$_2$, —NO$_2$, and —CN.

In some embodiments, for the compound or salt of Formula (I), (II), (II-A), (III), (III-A), or (III-B), $R^5$ is —C(O)$R^{17}$;

$R^{17}$ is selected from $C_{2-4}$ alkenyl and $C_{2-4}$ alkynyl, each of which is optionally substituted with one or more substituents independently selected from:

halogen, —O$R^{18}$, —N($R^{18}$)$_2$, —NO$_2$, and —CN; and $R^{18}$ is selected from hydrogen, $C_{1-3}$ alkyl, and $C_{1-3}$ haloalkyl.

In some embodiments, for the compound or salt of Formula (I), (II), (II-A), (III), (III-A), or (III-B), $R^5$ is —C(O)$R^{17}$; and $R^{17}$ is selected from $C_{2-4}$ alkenyl and $C_{2-4}$ alkynyl, each of which is optionally substituted with one or more substituents independently selected from:

halogen and —N($R^{18}$)$_2$.

In some embodiments, for the compound or salt of Formula (I), (II), (II-A), (III), (III-A), or (III-B), $R^5$ is —C(O)$R^{17}$;

$R^{17}$ is selected from $C_{2-4}$ alkenyl and $C_{2-4}$ alkynyl, each of which is optionally substituted with one or more substituents independently selected from:

halogen and —N($R^{18}$)$_2$; and $R^{18}$ is selected from hydrogen methyl.

In some embodiments, for the compound or salt of Formula (I), (II), (II-A), (III), (III-A), or (III-B), $R^5$ is —C(O)$R^{17}$;

$R^{17}$ is selected from $C_{2-4}$ alkenyl and $C_{2-4}$ alkynyl, each of which is optionally substituted with one or more substituents independently selected from:

fluoro and —N($CH_3$)$_2$.

In some embodiments, for the compound or salt of Formula (I), (II), (II-A), (III), (III-A), or (III-B), $R^5$ is —N($R^{19}$)C(O)($R^{17}$); and $R^{17}$ is selected from $C_{2-6}$ alkenyl and $C_{2-6}$ alkynyl, each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —$NO_2$, and —CN.

In some embodiments, for the compound or salt of Formula (I), (II), (II-A), (III), (III-A), or (III-B), $R^5$ is —N($R^{19}$)C(O)($R^{17}$); and $R^{17}$ is selected from $C_{2-4}$ alkenyl and $C_{2-4}$ alkynyl, each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —$NO_2$, and —CN.

In some embodiments, for the compound or salt of Formula (I), (II), (II-A), (III), (III-A), or (III-B), $R^5$ is —N($R^{19}$)C(O)($R^{17}$); and $R^{17}$ is selected from $C_{2-4}$ alkenyl and $C_{2-4}$ alkynyl, each of which is optionally substituted with one or more substituents independently selected from:

halogen, —O$R^{18}$, —N($R^{18}$)$_2$, —$NO_2$, and —CN.

In some embodiments, for the compound or salt of Formula (I), (II), (II-A), (III), (III-A), or (III-B), $R^5$ is —N($R^{19}$)C(O)($R^{17}$);

$R^{17}$ is selected from $C_{2-4}$ alkenyl and $C_{2-4}$ alkynyl, each of which is optionally substituted with one or more substituents independently selected from:

halogen, —O$R^{18}$, —N($R^{18}$)$_2$, —$NO_2$, and —CN; and each of $R^{18}$ and $R^{19}$ are independently selected from hydrogen, $C_{1-3}$ alkyl, and $C_{1-3}$ haloalkyl.

In some embodiments, for the compound or salt of Formula (I), (II), (II-A), (III), (III-A), or (III-B), $R^5$ is —N($R^{19}$)C(O)($R^{17}$);

$R^{17}$ is selected from $C_{2-4}$ alkenyl and $C_{2-4}$ alkynyl, each of which is optionally substituted with one or more halogen.

In some embodiments, for the compound or salt of Formula (I), (II), (II-A), (III), (III-A), or (III-B), $R^5$ is —N($R^{19}$)C(O)($R^{17}$);

$R^{17}$ is selected from $C_{2-4}$ alkenyl and $C_{2-4}$ alkynyl, each of which is optionally substituted with one or more halogen; and $R^{19}$ is independently selected from hydrogen and methyl.

In some embodiments, for the compound or salt of Formula (I), (II), (II-A), (III), (III-A), or (III-B), $R^5$ is —N($R^{19}$)C(O)($R^{17}$);

$R^{17}$ is selected from $C_{2-4}$ alkenyl and $C_{2-4}$ alkynyl, each of which is optionally substituted with one or more fluoro; and $R^{19}$ is independently selected from hydrogen and methyl.

In some embodiments, for the compound or salt of Formula (I), (II), (II-A), (III), (III-A), or (III-B), $R^5$ is —N($R^{19}$)S(O)$_2R^{17}$, and $R^{17}$ is selected from $C_{2-6}$ alkenyl and $C_{2-6}$ alkynyl, each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —$NO_2$, and —CN.

In some embodiments, for the compound or salt of Formula (I), (II), (II-A), (III), (III-A), or (III-B), $R^5$ is —N($R^{19}$)S(O)$_2R^{17}$; and $R^{17}$ is selected from $C_{2-4}$ alkenyl and $C_{2-4}$ alkynyl, each of which is optionally substituted with one or more substituents independently selected from:

halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —$NO_2$, and —CN.

In some embodiments, for the compound or salt of Formula (I), (II), (II-A), (III), (III-A), or (III-B), $R^5$ is —N($R^{19}$)S(O)$_2R^{17}$, and $R^{17}$ is selected from $C_{2-4}$ alkenyl and $C_{2-4}$ alkynyl, each of which is optionally substituted with one or more substituents independently selected from:

halogen, —O$R^{18}$, —N($R^{18}$)$_2$, —$NO_2$, and —CN.

In some embodiments, for the compound or salt of Formula (I), (II), (II-A), (III), (III-A), or (III-B), $R^5$ is —N($R^{19}$)S(O)$_2R^{17}$;

$R^{17}$ is selected from $C_{2-4}$ alkenyl and $C_{2-4}$ alkynyl, each of which is optionally substituted with one or more substituents independently selected from:

halogen, —O$R^{18}$, —N($R^{18}$)$_2$, —$NO_2$, and —CN; and each of $R^{18}$ and $R^{19}$ are independently selected from hydrogen, $C_{1-3}$ alkyl, and $C_{1-3}$ haloalkyl.

In some embodiments, for the compound or salt of Formula (I), (II), (II-A), (III), (III-A), or (III-B), $R^5$ is —N($R^{19}$)S(O)$_2R^{17}$; and $R^{17}$ is $C_{2-4}$ alkenyl.

In some embodiments, for the compound or salt of Formula (I), (II), (II-A), (III), (III-A), or (III-B), $R^5$ is —N($R^{19}$)S(O)$_2R^{17}$; $R^{17}$ is $C_{2-4}$ alkenyl; and $R^{19}$ is hydrogen.

In some embodiments, for the compound or salt of Formula (I), (II), (II-A), (III), (III-A), or (III-B), $R^5$ is selected from: wherein $R^5$ is selected from:

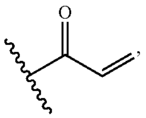

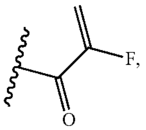

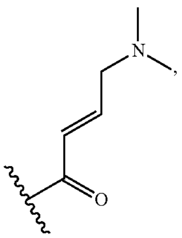

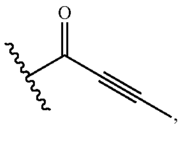

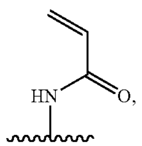

-continued

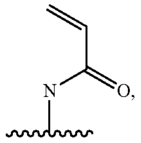

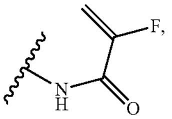

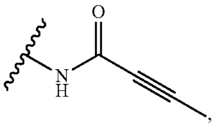

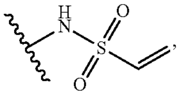

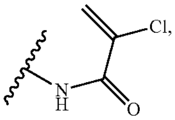

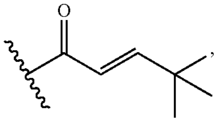

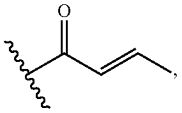

and

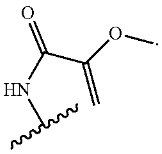

In some embodiments, for the compound or salt of Formula (I), (II), (II-A), (III), (III-A), or (III-B), $R^5$ is selected from:

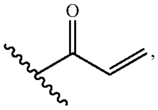

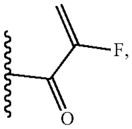

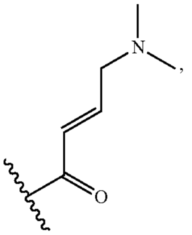

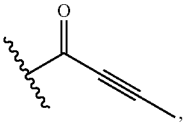

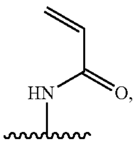

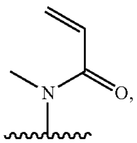

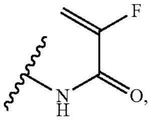

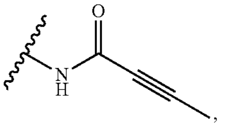

and

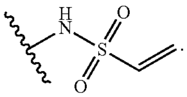

In some embodiments, for the compound or salt of Formula (I), (II), (II-A), (III), (III-A), or (III-B), $A^3$ is $R^5$, wherein $R^5$ is defined as in Formula (II-A). In some embodiments, $A^3$ is selected from —$C(O)R^{17}$, —$S(O)_2R^{17}$, —$N(R^{19})C(O)(R^{17})$, —$C(O)N(R^{17})(R^{19})$, and —$N(R^{19})S(O)_2R^{17}$, and —$S(O)_2N(R^{17})(R^{19})$, wherein $R^{17}$ and $R^{19}$ are defined as in Formula (II-A). In some embodiments, $A^3$ is selected from:

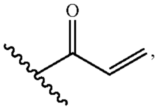

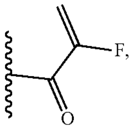

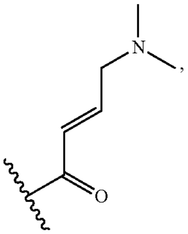

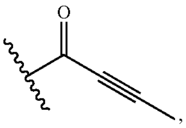

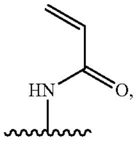

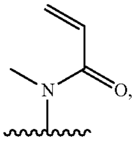

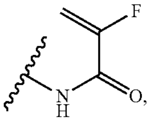

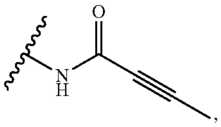

and

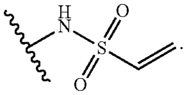

In some embodiments, for the compound or salt of Formula (I), (II), (II-A), (III), (III-A), or (III-B),

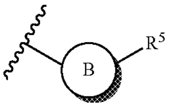

is selected from:

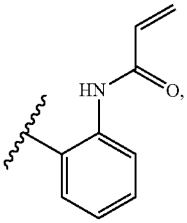

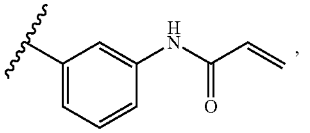

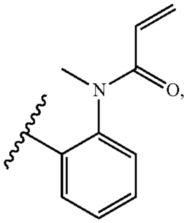

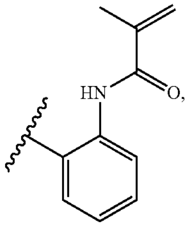

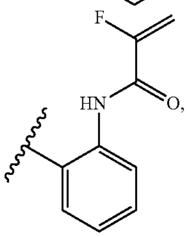

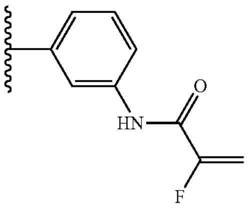

,

-continued
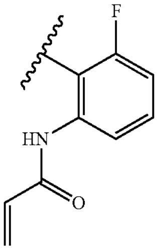,
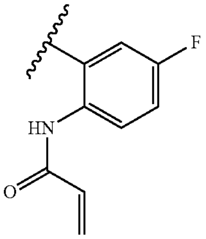,
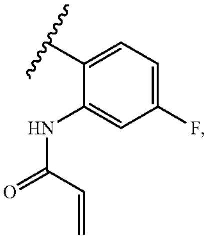
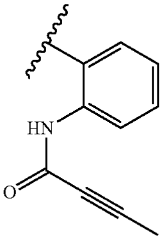,
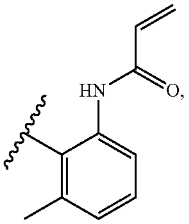
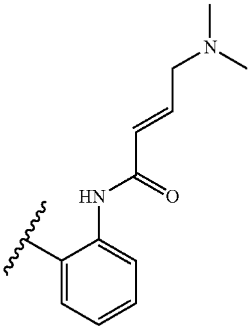,
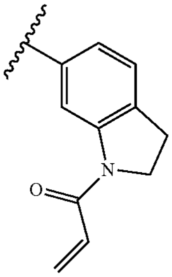,
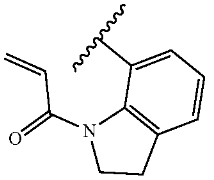,
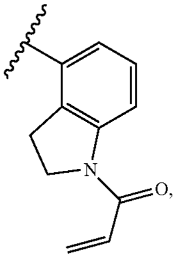
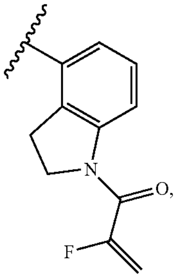
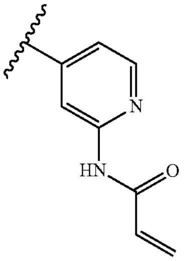,
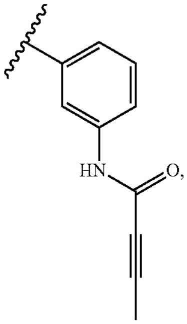
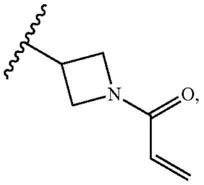
-continued
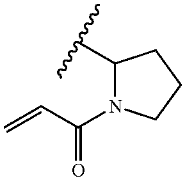,
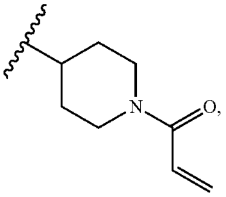
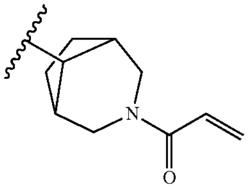,
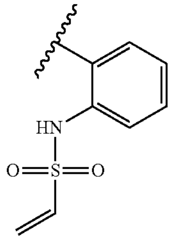,
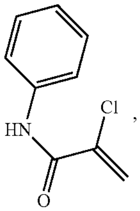,
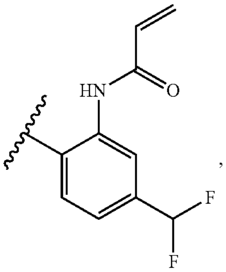,
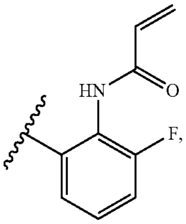
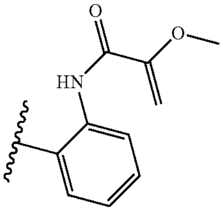,
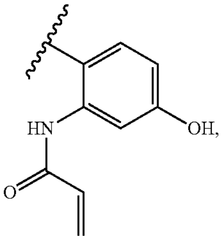
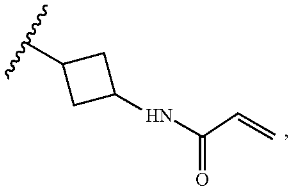
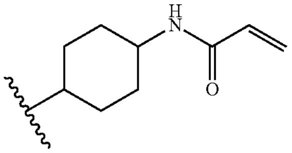,
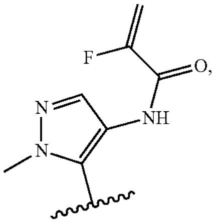
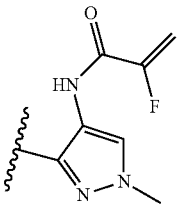,
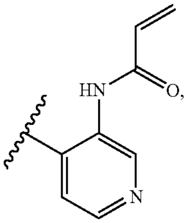

-continued
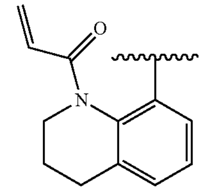,
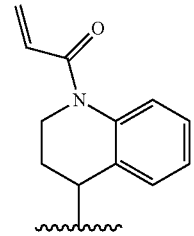,
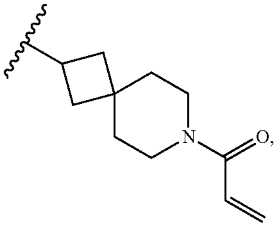,
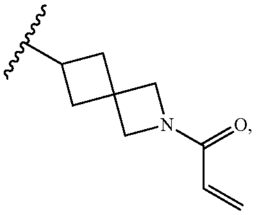,
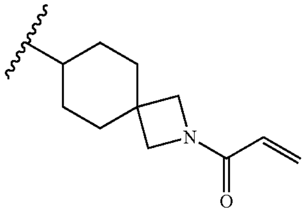,
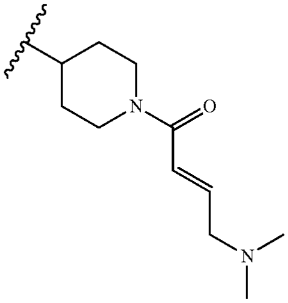,
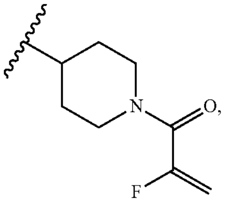,
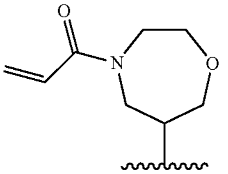,
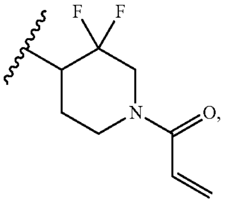,
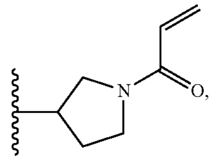,
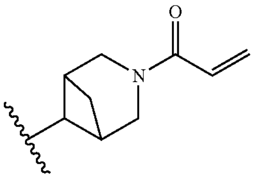,
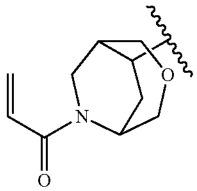,
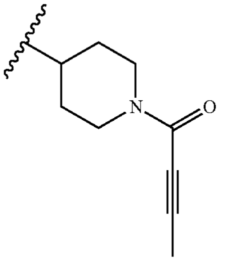,
-continued
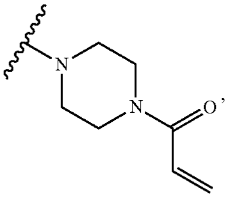,
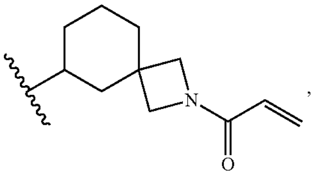,
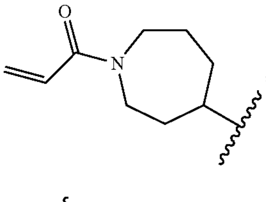,
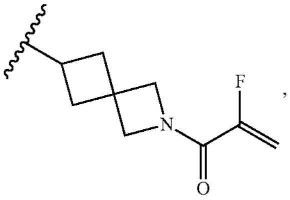,
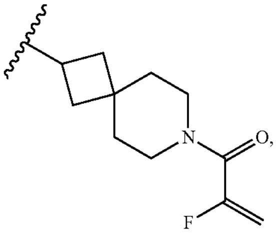,
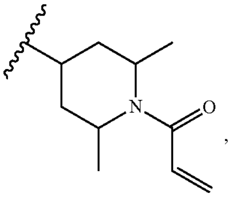,
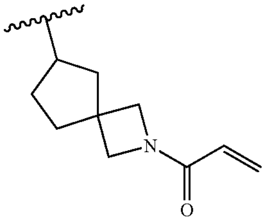,
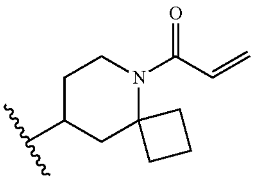,
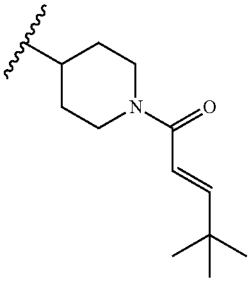,
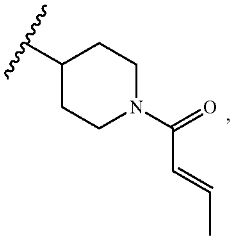,
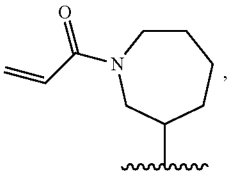,
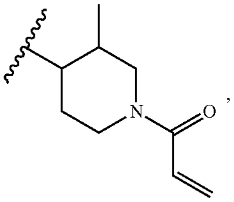,
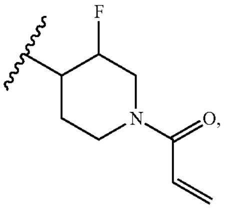,
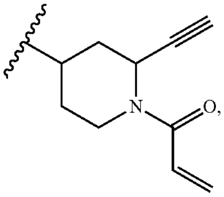, -continued
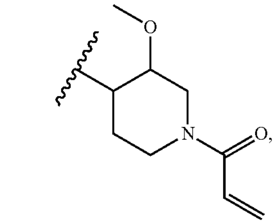,
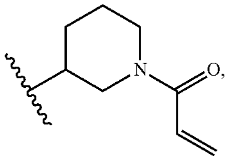,
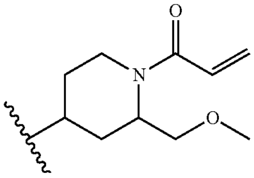,
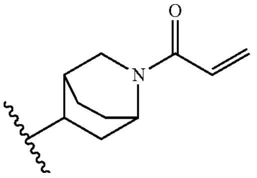,
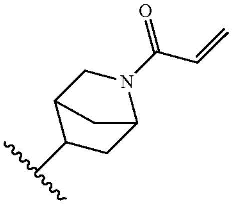,
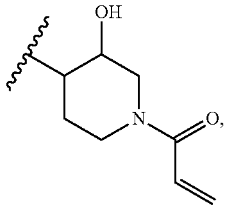,
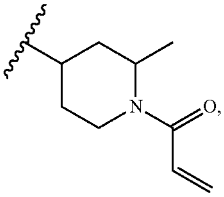,
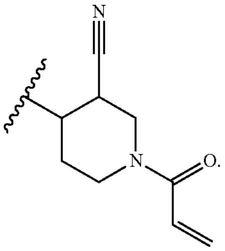.
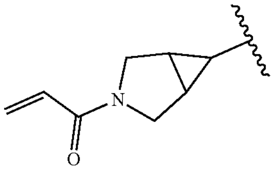,
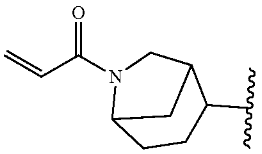,
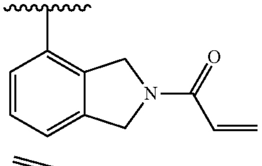,
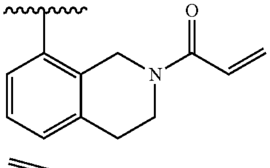,
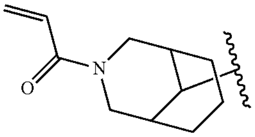,
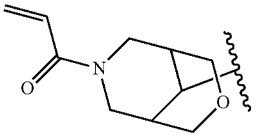,
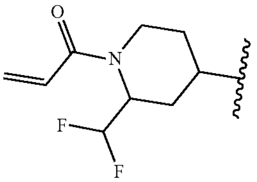,
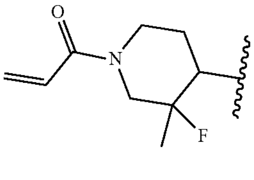,
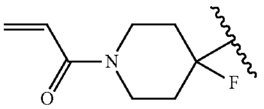,
-continued
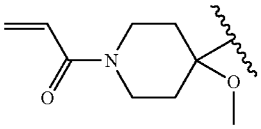, and
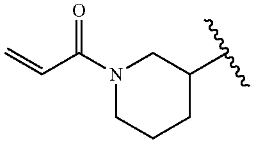.
In some embodiments, for the compound or salt of Formula (I), (II), (II-A), (III), (III-A), or (III-B),
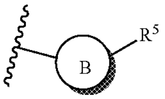
is selected from:
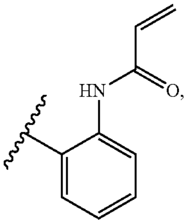,
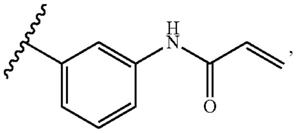,
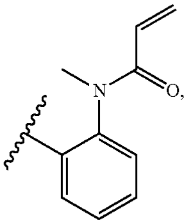,
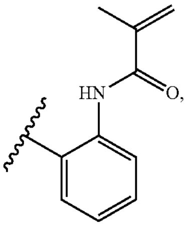,
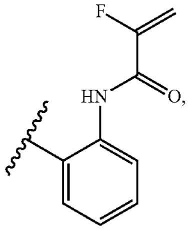,
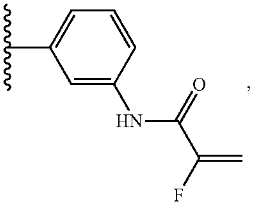,
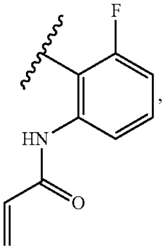,
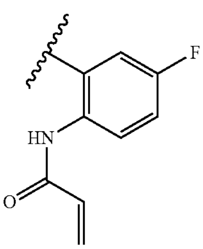, -continued
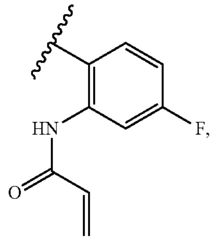 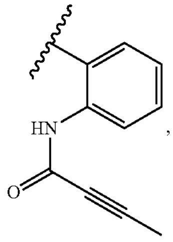,
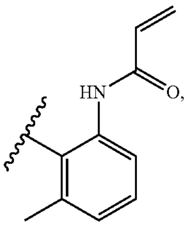 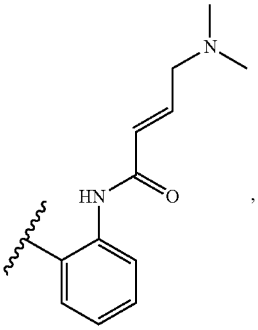,
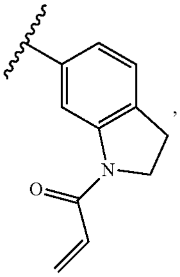, 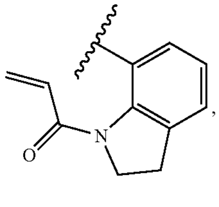,
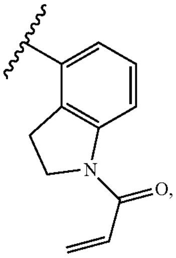 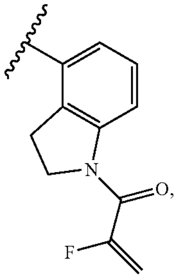 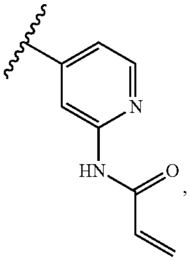,
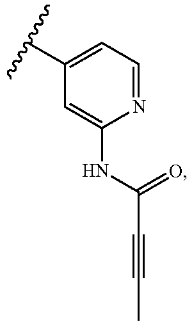 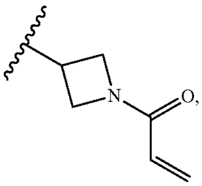
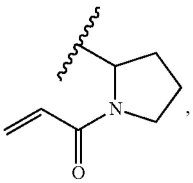, 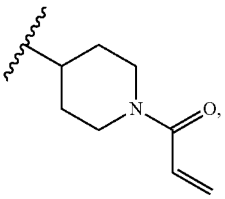
-continued
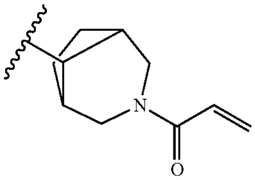, 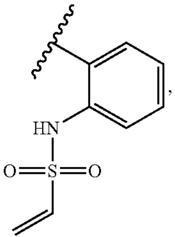,
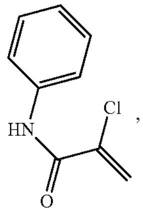, 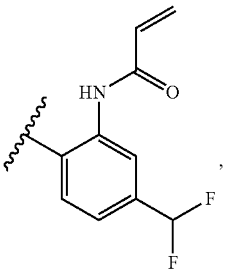, 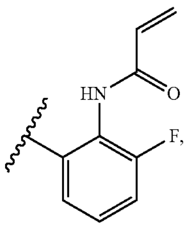
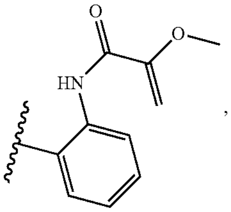, 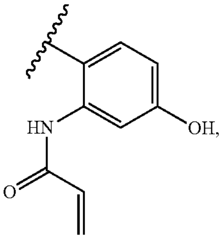
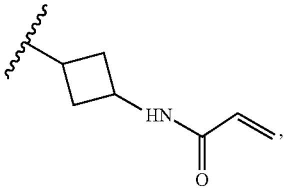
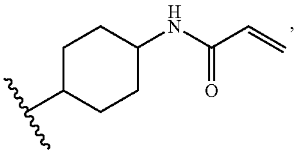, 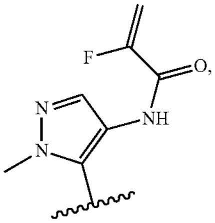
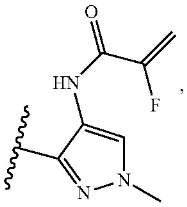, 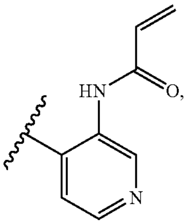
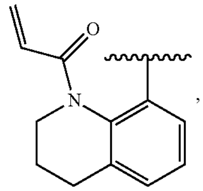, 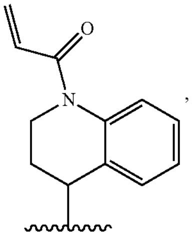, -continued
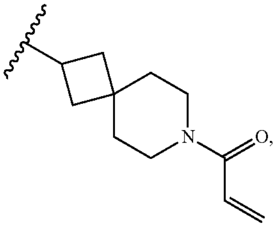
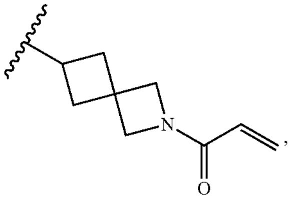
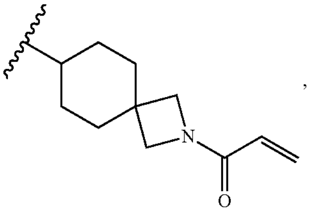
,
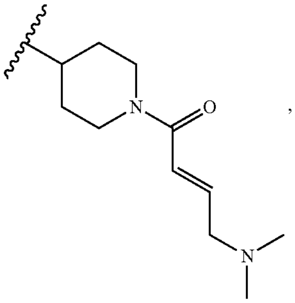
,
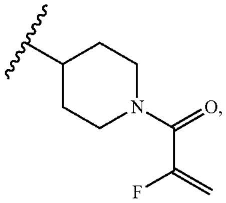
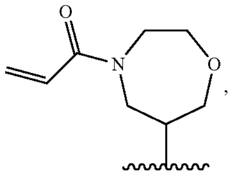
,
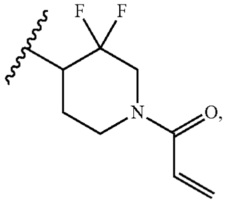
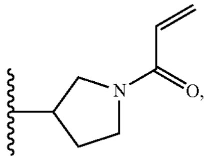
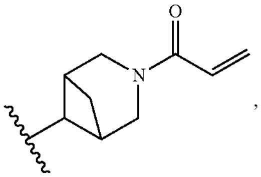
,
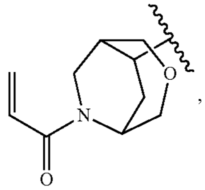
,
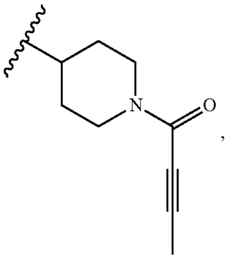
,
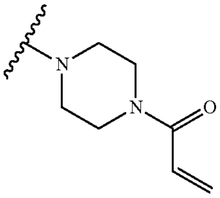
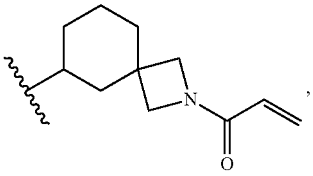
,
-continued
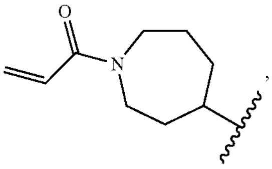
,
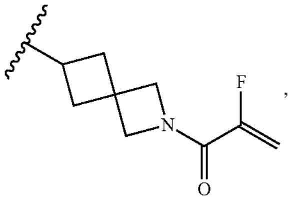
,
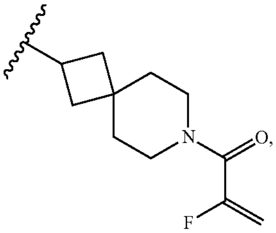
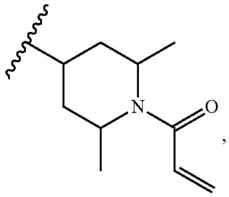
,
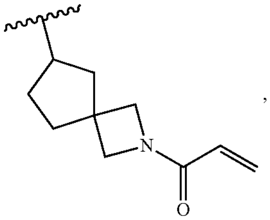
,
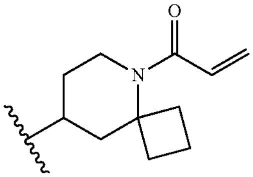
,
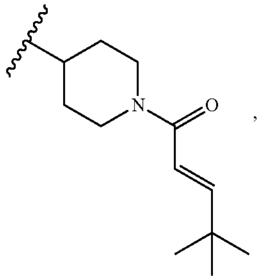
,
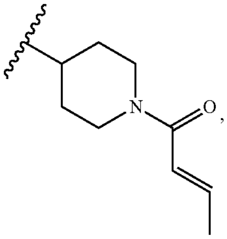
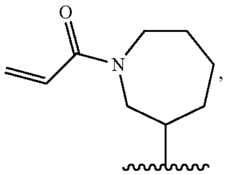
,
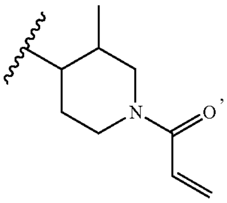
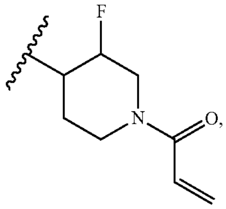
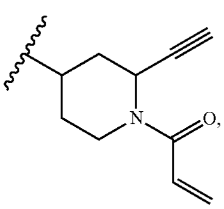
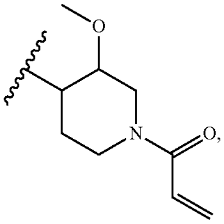
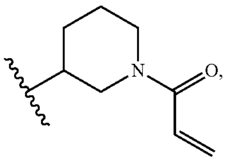

-continued
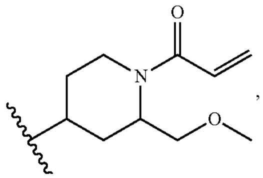,
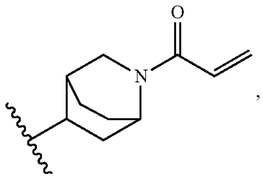,
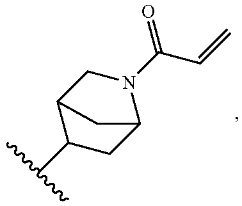,
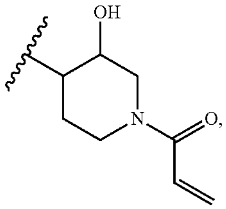
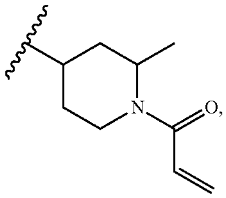 and
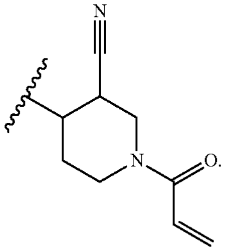
In some embodiments, for the compound or salt of Formula (I), (II), (II-A), (III), (III-A), or (III-B),
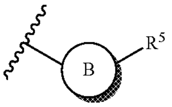
is selected from:
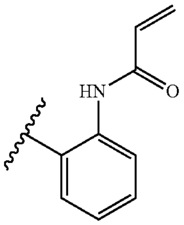,
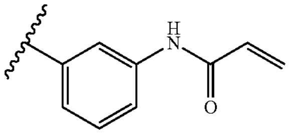,
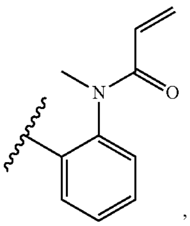,
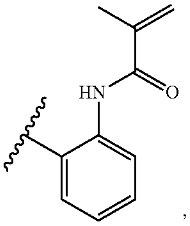,
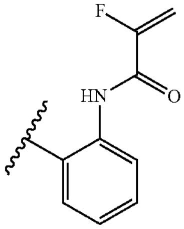,
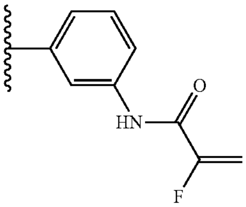,
-continued
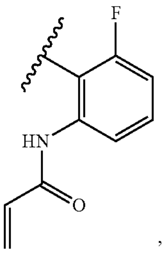,
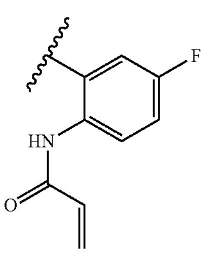,
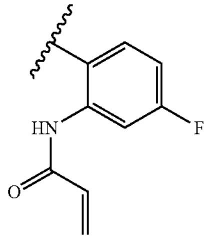,
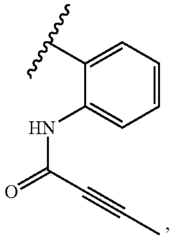,
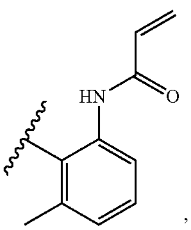,
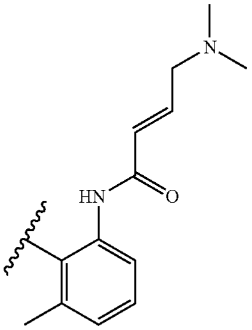,
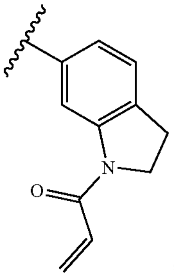,
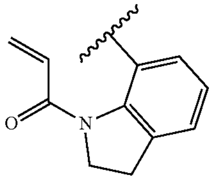,
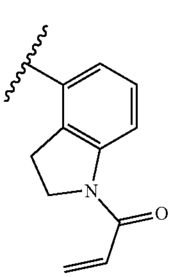,
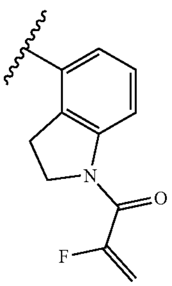,
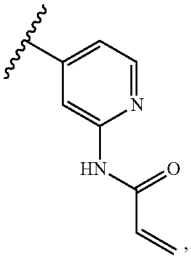,
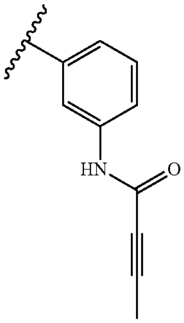, -continued

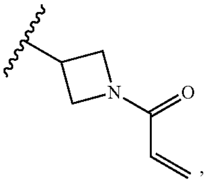

,

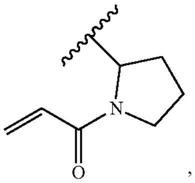

,

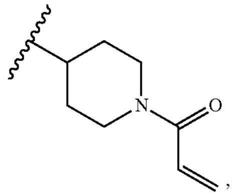

,

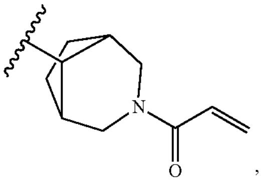

, and

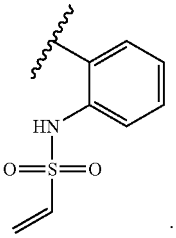

.

In some aspects, for the compound or salt of Formula (I), q is 2; and the structure of Formula (I) is represented by

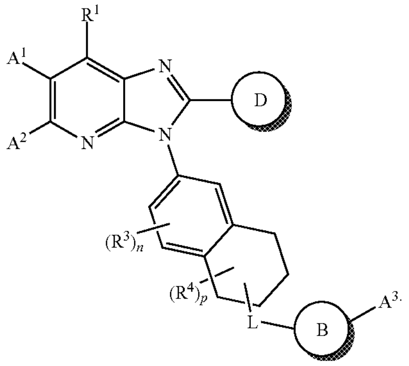

In some embodiments, for the compound or salt of Formula (I), (II), (II-A), (III), (III-A), or (III-B), the cysteine susceptible electrophile is selected from a haloacetamide, a haloalkyl ketone, a halo amidine, a halo benzylphosphonate, an acyloxyalkyl ketone, a sulfonyl oxirane, an epoxide, a diazoalkyl ketone, a halotriazine, an acrylamide, a cyano acrylamide, a vinyl sulfone, a vinyl sulfonamide, an acrylate, a fumarate, a carbonyl acrylate, a maleimide, a keto-amide, a nitrile, an alkene, an alkyne, a keto heterocycle, and an ynamide. In some embodiments, the cysteine susceptible electrophile is selected from an acrylate group, an acrylamide group, a vinyl group, a vinylsulfone group, a vinylsulfonamide group, an ynamide, an alkene, an alkyne, and an epoxide group. In some embodiments, the cysteine susceptible electrophile is selected from an acrylate group, an acrylamide group, a vinylsulfone group, a vinylsulfonamide group, an alkene, and an alkyne. In some embodiments, the cysteine susceptible electrophile is selected from an acrylate group, an acrylamide group, an alkene, and an alkyne.

In some embodiments, for the compound or salt of Formula (I), (II), (II-A), (III), (III-A), or (III-B), the cysteine susceptible electrophile is an alpha-beta unsaturated carbonyl, an alpha-beta unsaturated sulfone, an alpha-beta unsaturated amide, and an alpha-beta unsaturated sulfonamide. In some embodiments, the cysteine susceptible electrophile is selected from an alpha-beta unsaturated carbonyl and an alpha-beta unsaturated amide. In some embodiments, the cysteine susceptible electrophile is an alpha-beta unsaturated carbonyl.

In certain aspects, the disclosure provides a compound or salt represented the structure of Formula (I) wherein:

$R^1$ is selected from hydrogen, halogen, $-OR^{10}$, $-SR^{10}$, $-N(R^{10})_2$, $-NO_2$, $-CN$, and $C_{1-6}$ alkyl optionally substituted with one or more substituents independently selected from: halogen, $-OR^{10}$, $-SR^{10}$, $-N(R^{10})_2$, $-NO_2$, and $-CN$, for example $R^1$ is hydrogen;

$A^1$ is selected from hydrogen, halogen, $-OR^{11}$, $-SR^{11}$, $-N(R^{11})_2$, $-C(O)N(R^{11})_2$, $-N(R^{11})C(O)R^{11}$, $-C(O)OR^{11}$, $-OC(O)R^{11}$, $-N(R^{11})C(O)OR^{11}$, $-OC(O)N(R^{11})_2$, $-N(R^{11})C(O)N(R^{11})_2$, $-S(O)R^{11}$, $-S(O)_2R^{11}$, $-N(R^{11})S(O)_2R^{11}$, $-S(O)_2N(R^{11})_2$, $-NO_2$, $-CN$, $C_{1-6}$ alkyl, and $C_{1-6}$ haloalkyl, for example $A^1$ is hydrogen;

$A^2$ is selected from:

$C_{1-6}$ alkyl optionally substituted with one or more substituents independently selected from halogen, $-OR^{11}$, $-SR^{11}$, $-N(R^{11})_2$, $-C(O)N(R^{11})_2$, $-N(R^{11})C(O)R^{11}$, $-C(O)OR^{11}$, $-OC(O)R^{11}$, $-N(R^{11})C(O)OR^{11}$, $-OC(O)N(R^{11})_2$, $-N(R^{11})C(O)N(R^{11})_2$, $-S(O)R^{11}$, $-S(O)_2R^{11}$, $-N(R^{11})S(O)_2R^{11}$, $-S(O)_2N(R^{11})_2$, $-NO_2$, $=O$, $=S$, $=N(R^{11})$, and $-CN$; and 4- to 8-membered heterocycle and $C_{3-8}$ carbocycle, each of which is optionally substituted with one or more substituents independently selected from halogen, $-OR^{11}$, $-SR^{11}$, $-N(R^{11})_2$, $-C(O)N(R^{11})_2$, $-N(R^{11})C(O)R^{11}$, $-C(O)OR^{11}$, $-OC(O)R^{11}$, $-N(R^{11})C(O)OR^{11}$, $-OC(O)N(R^{11})_2$, $-N(R^{11})C(O)N(R^{11})_2$, $-S(O)R^{11}$, $-S(O)_2R^{11}$, $-N(R^{11})S(O)_2R^{11}$, $-S(O)_2N(R^{11})_2$, $-NO_2$, $=O$, $=S$, $=N(R^{11})$, $-CN$, $C_{1-6}$ alkyl, and $C_{1-6}$ haloalkyl, for example $A^2$ is pyrazolyl;

n is 0 or 1, for example n is 0;

p is 0 or 1, for example p is 0;

q is 1;

L is represented by $-L^1-L^2-$, wherein $L^1$ and $L^2$ are each independently selected from (a) and (b):

(a) $-O-$, $-N(R^{15})-$, $-S-$, $-S(O)-$, $-S(O)_2-$, $-S(O)(NR^{15})-$, $-N(R^{15})C(O)-$, $-N(R^{15})C(O)O-$, $-N(R^{15})S(O)_2-$, $-N(R^{15})S(O)_2N(R^{15})-$, $-S(O)(NR^{15})N(R^{15})-$, $-N(R^{15})N(R^{15})-$, $-(R^{15})NC(O)N(R^{15})-$, $-(R^{15})NC(O)N(R^{15})N(R^{15})-$; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, $-OR^{15}$, $-SR^{15}$, $=O$, $=S$, and $-CN$;

wherein $L^2$ is optionally absent;

wherein when both $L^1$ and $L^2$ are present, either: $L^1$ is selected from (a) and $L^2$ is selected from (b); or $L^1$ is selected from (b) and $L^2$ is selected from (a);

Ring B is selected from 3- to 8-membered heterocyclene and $C_{3-8}$ carbocyclene, each of which is optionally substituted halogen, $-OR^{16}$, $-SR^{16}$, $-N(R^{16})_2$, $-C(O)N(R^{16})_2$, $-C(O)OR^{16}$, $-OC(O)R^{16}$, $-N(R^{16})C(O)R^{16}$, $-N(R^{16})S(O)_2R^{16}$, $-S(O)_2N(R^{16})_2$, $-N(R^{16})C(O)N(R^{16})_2$, $-N(R^{16})C(O)OR^{16}$, $-OC(O)$ $N(R^{16})_2$, —$S(O)R^{16}$, —$S(O)_2R^{16}$, —$NO_2$, =O, =S, =$N(R^{16})$, —CN, $C_{1-6}$ alkyl, and $C_{1-6}$ haloalkyl; for example Ring B is piperidinylene;

Ring D is selected from:

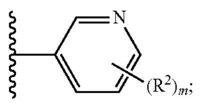

$R^2$ is independently selected at each instance from halogen, $C_{1-6}$ alkyl, $C_{1-6}$ haloalkyl, —$OR^{12}$, —$SR^{12}$, —$N(R^{12})_2$, —$NO_2$, and —CN, for example $R^2$ is —$N(R^{12})_2$;

$A^3$ is selected from a haloacetamide, a haloalkyl ketone, a halo amidine, a halo benzylphosphonate, an acyloxyalkyl ketone, a sulfonyl oxirane, an epoxide, a diazoalkyl ketone, a halotriazine, an acrylamide, a cyano acrylamide, a vinyl sulfone, a vinyl sulfonamide, an acrylate, a fumarate, a carbonyl acrylate, a maleimide, a ketoamide, a nitrile, an alkene, an alkyne, a keto heterocycle, and an ynamide, for example $A^3$ is an acrylate; and $R^{10}$, $R^{11}$, $R^{12}$, $R^{15}$, and $R^{16}$ are each independently selected at each occurrence from: hydrogen, $C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and $C_{3-6}$ carbocycle and 3- to 6-membered heterocycle, each of which is optionally substituted with one or more substituents independently selected from halogen, —OH, —O—$C_{1-6}$ alkyl, —O—$C_{1-6}$ haloalkyl, $C_{1-6}$ alkyl, and $C_{1-6}$ haloalkyl.

In some embodiments, the compound or salt of Formula (I), (I-A), (II), (II-A), (III), (III-A), or (III-B) is a compound of Table 1. * Denotes a stereocenter with an undetermined absolute stereochemistry of a single isomer.

TABLE 1

Chemical structures of selected compounds.

| Comp. No. | Structure |
|---|---|
| 1 | 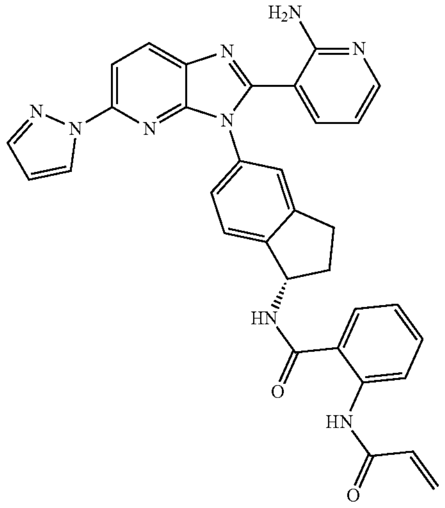 |
| 2 | 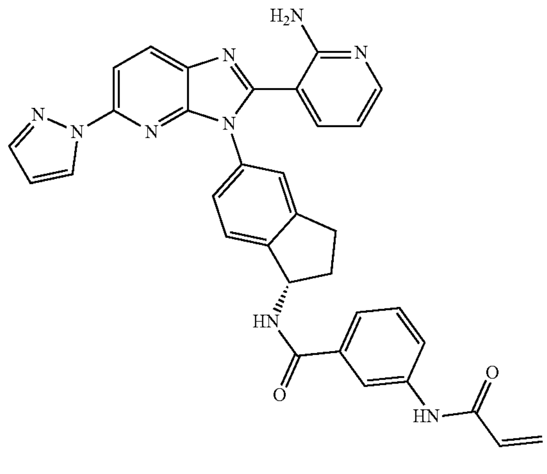 [SMILES: C=CC(=O)Nc1cccc(C(=O)N[C@H]2CCc3cc(-n4c(-c5cccnc5N)nc5ccc(-n6cccn6)nc54)ccc32)c1] |

TABLE 1-continued
| Chemical structures of selected compounds. | |
|---|---|
| Comp. No. | Structure |
| 3 | 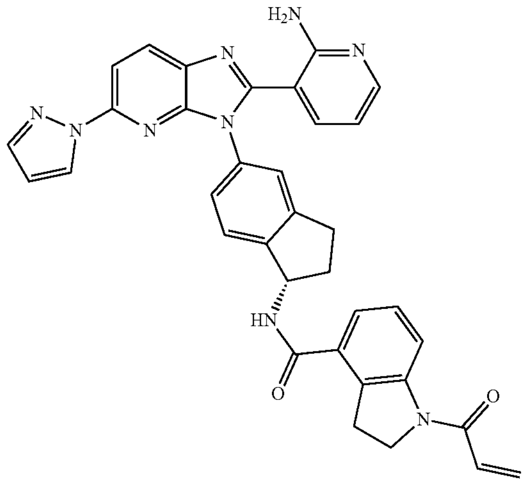 [SMILES: C=CC(=O)N1CCc2c(C(=O)N[C@H]3CCc4cc(-n5c(-c6cccnc6N)nc6ccc(-n7cccn7)nc65)ccc43)cccc21] |
| 4 | 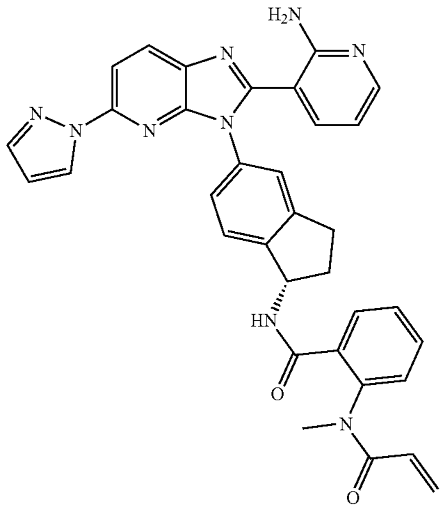 [SMILES: C=CC(=O)N(C)c1ccccc1C(=O)N[C@H]1CCc2cc(-n3c(-c4cccnc4N)nc4ccc(-n5cccn5)nc43)ccc21] |
| 5 | 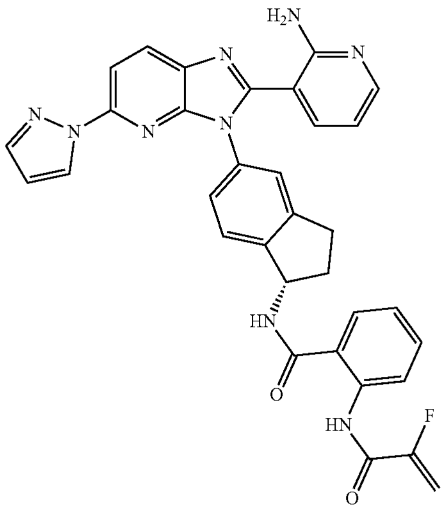 [SMILES: C=C(F)C(=O)Nc1ccccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 6 | 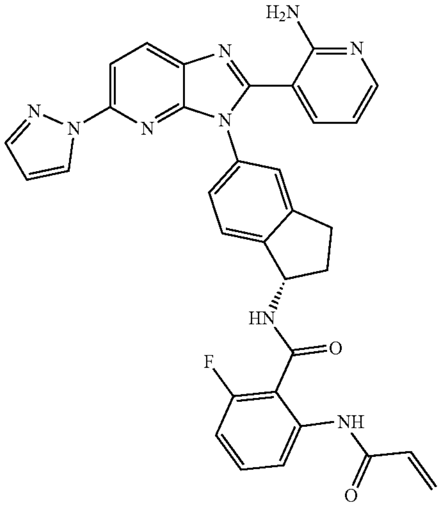 [SMILES: C=CC(=O)Nc1cccc(F)c1C(=O)N[C@H]1CCc2cc(-n3c(-c4cccnc4N)nc4ccc(-n5cccn5)nc43)ccc21] |
| 7 | 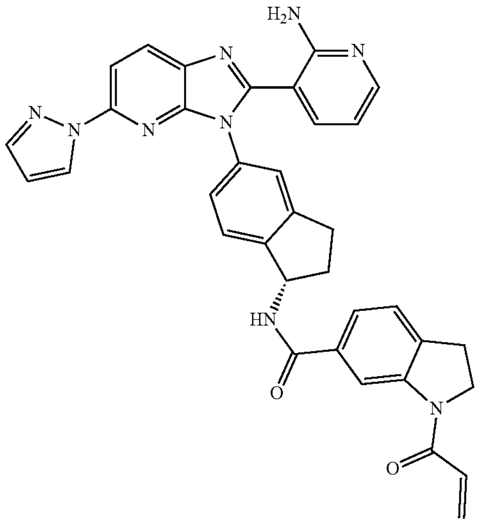 [SMILES: C=CC(=O)N1CCc2ccc(C(=O)N[C@H]3CCc4cc(-n5c(-c6cccnc6N)nc6ccc(-n7cccn7)nc65)ccc43)cc21] |
| 8 | 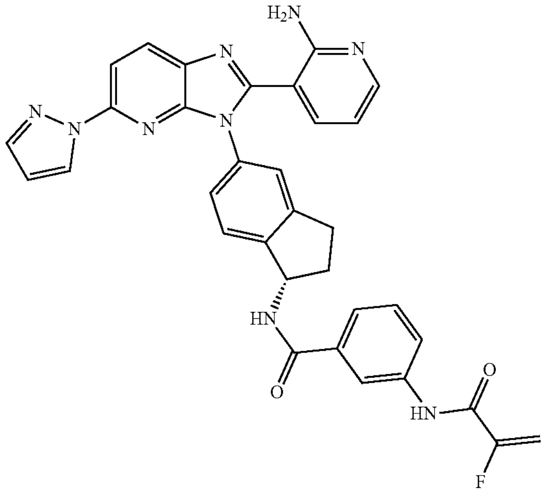 [SMILES: C=C(F)C(=O)Nc1cccc(C(=O)N[C@H]2CCc3cc(-n4c(-c5cccnc5N)nc5ccc(-n6cccn6)nc54)ccc32)c1] |

TABLE 1-continued
| Chemical structures of selected compounds. | |
|---|---|
| Comp. No. | Structure |
| 9 | 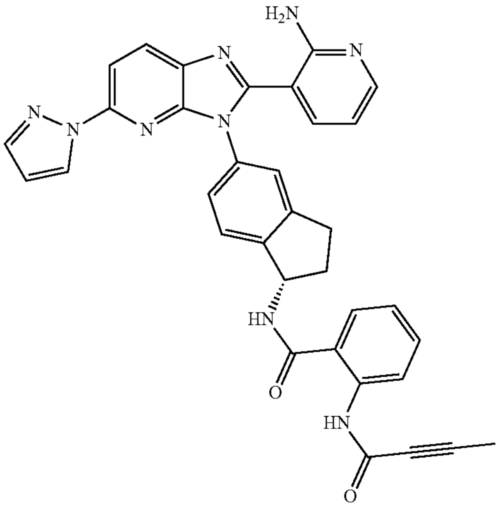 [SMILES: CC#CC(=O)Nc1ccccc1C(=O)N[C@H]1CCc2cc(-n3c(-c4cccnc4N)nc4ccc(-n5cccn5)nc43)ccc21] |
| 10 | 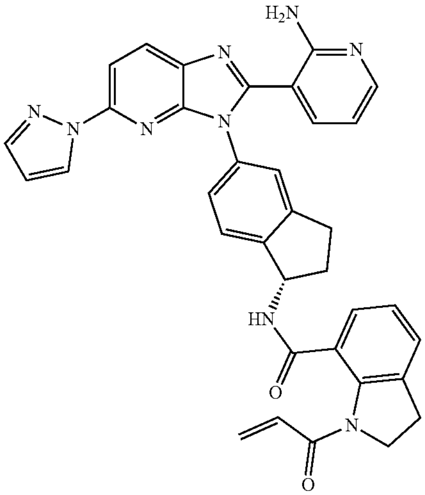 [SMILES: C=CC(=O)N1CCc2cccc(C(=O)N[C@H]3CCc4cc(-n5c(-c6cccnc6N)nc6ccc(-n7cccn7)nc65)ccc43)c21] |
| 11 | 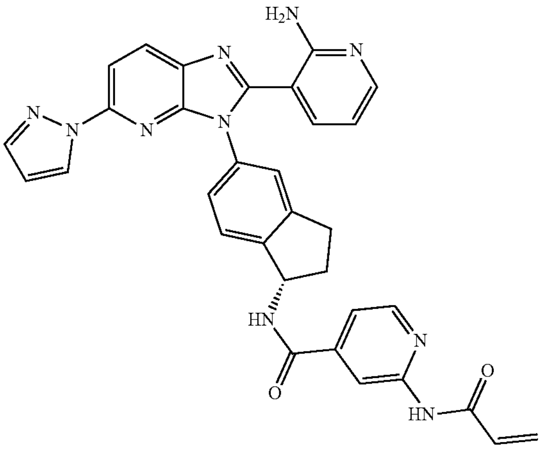 [SMILES: C=CC(=O)Nc1cc(C(=O)N[C@H]2CCc3cc(-n4c(-c5cccnc5N)nc5ccc(-n6cccn6)nc54)ccc32)ccn1] |

TABLE 1-continued
| Chemical structures of selected compounds. | |
|---|---|
| Comp. No. | Structure |
| 12 | 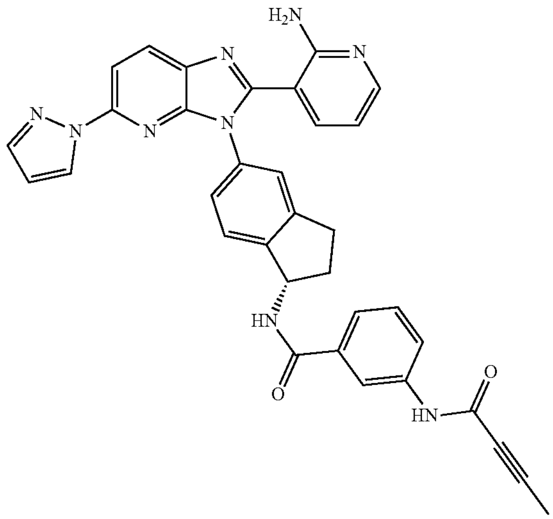 [SMILES: CC#CC(=O)Nc1cccc(C(=O)N[C@H]2CCc3cc(-n4c(-c5cccnc5N)nc5ccc(-n6cccn6)nc54)ccc32)c1] |
| 13 | 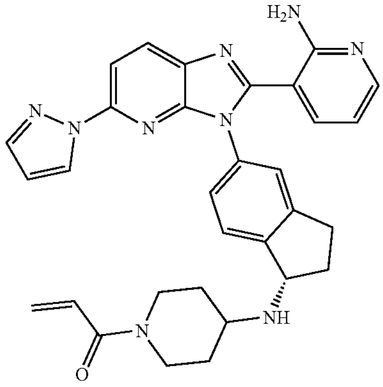 [SMILES: C=CC(=O)N1CCC(N[C@H]2CCc3cc(-n4c(-c5cccnc5N)nc5ccc(-n6cccn6)nc54)ccc32)CC1] |
| 14 | 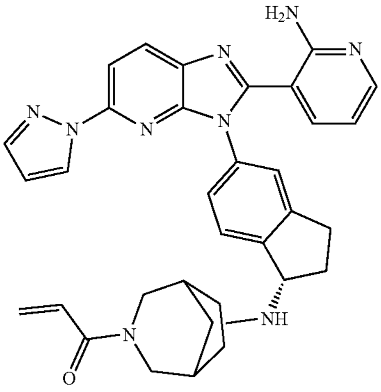 |

TABLE 1-continued
| Comp. No. | Structure |
| --- | --- |
| 15 | 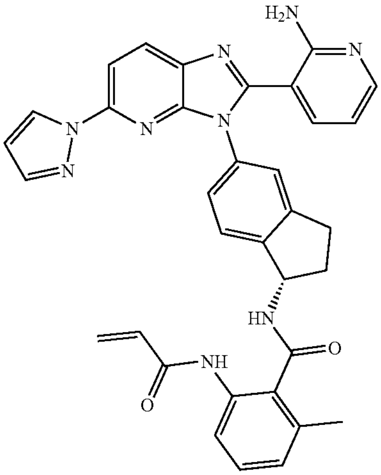 [SMILES: C=CC(=O)Nc1cccc(C)c1C(=O)N[C@H]1CCc2cc(-n3c(-c4cccnc4N)nc4ccc(-n5cccn5)nc43)ccc21] |
| 16 | 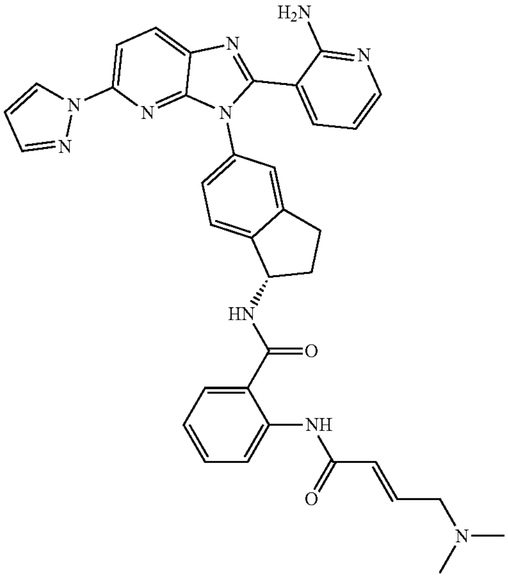 [SMILES: CN(C)C/C=C/C(=O)Nc1ccccc1C(=O)N[C@H]1CCc2cc(-n3c(-c4cccnc4N)nc4ccc(-n5cccn5)nc43)ccc21] |
| 17 | 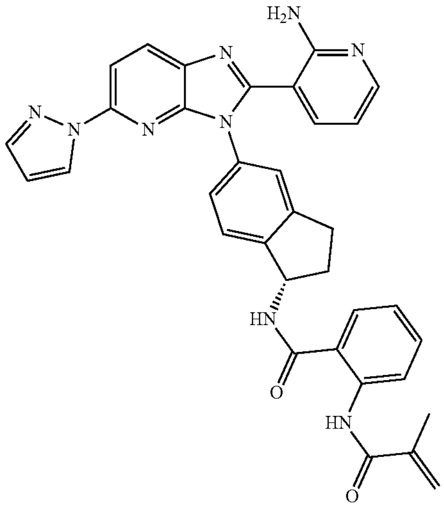 [SMILES: C=C(C)C(=O)Nc1ccccc1C(=O)N[C@H]1CCc2cc(-n3c(-c4cccnc4N)nc4ccc(-n5cccn5)nc43)ccc21] |
Chemical structures of selected compounds.

TABLE 1-continued
| Chemical structures of selected compounds. | |
|---|---|
| Comp. No. | Structure |
| 18 | 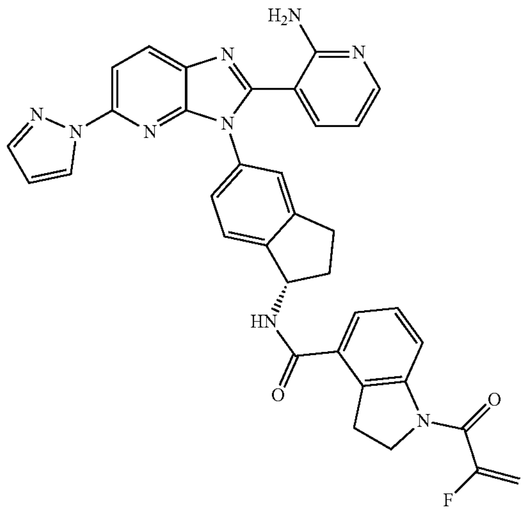 [SMILES: C=C(F)C(=O)N1CCc2c(C(=O)N[C@H]3CCc4cc(-n5c(-c6cccnc6N)nc6ccc(-n7cccn7)nc65)ccc43)cccc21] |
| 19 | 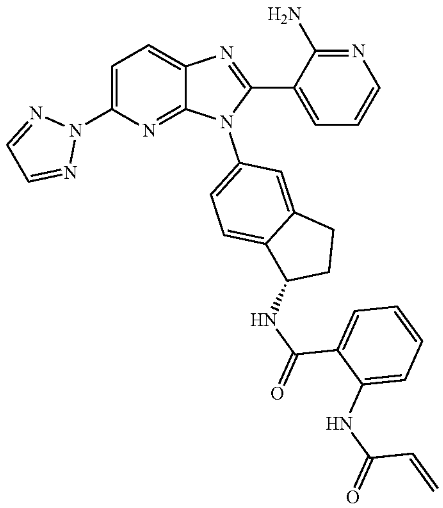 [SMILES: C=CC(=O)Nc1ccccc1C(=O)N[C@H]1CCc2cc(-n3c(-c4cccnc4N)nc4ccc(-n5nccn5)nc43)ccc21] |
| 20 | 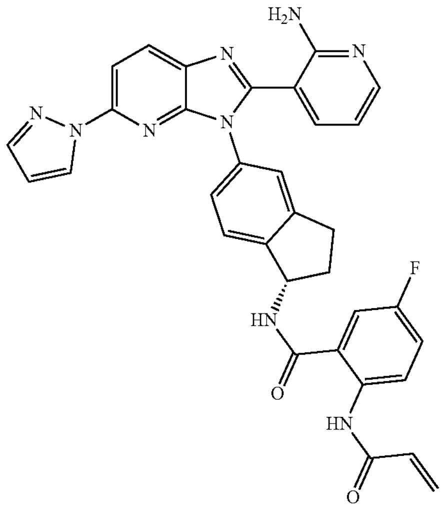 [SMILES: C=CC(=O)Nc1ccc(F)cc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 21 | 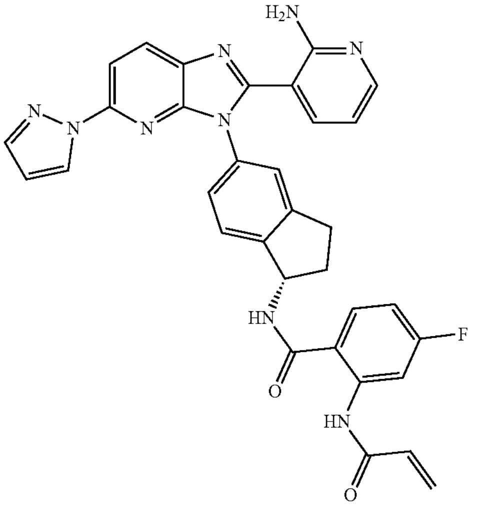 [SMILES: C=CC(=O)Nc1cc(F)ccc1C(=O)N[C@H]1CCc2cc(-n3c(-c4cccnc4N)nc4ccc(-n5cccn5)nc43)ccc21] |
| 22 | 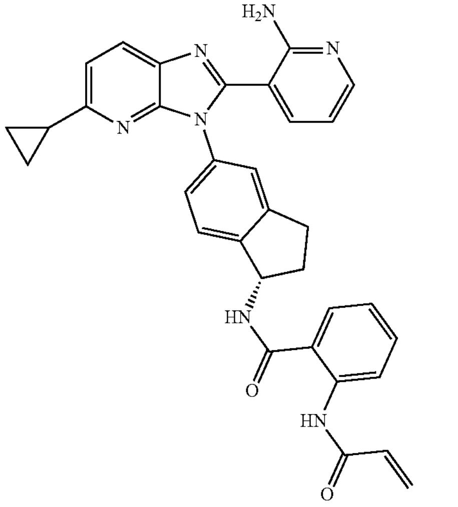 [SMILES: C=CC(=O)Nc1ccccc1C(=O)N[C@H]1CCc2cc(-n3c(-c4cccnc4N)nc4ccc(C5CC5)nc43)ccc21] |
| 23 | 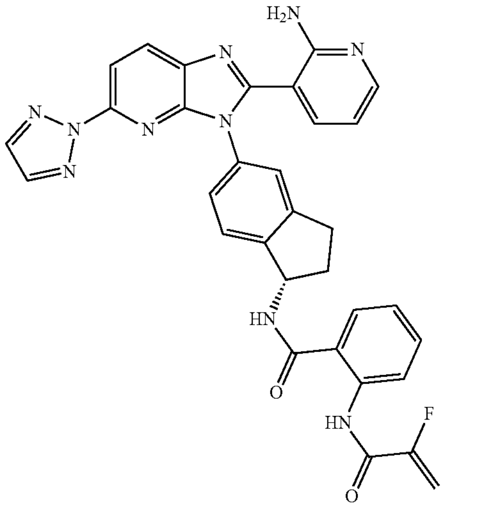 [SMILES: C=C(F)C(=O)Nc1ccccc1C(=O)N[C@H]1CCc2cc(-n3c(-c4cccnc4N)nc4ccc(-n5nccn5)nc43)ccc21] |

TABLE 1-continued
| Chemical structures of selected compounds. | |
|---|---|
| Comp. No. | Structure |
| 24 | 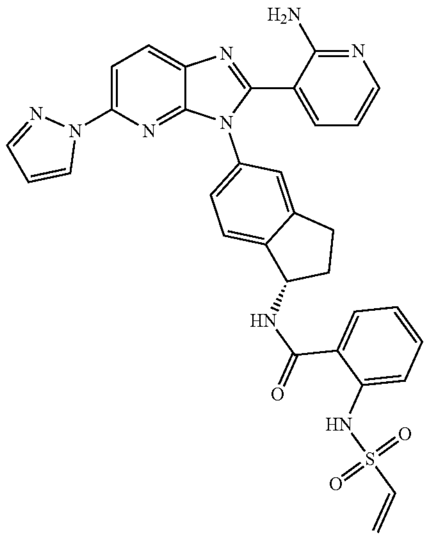 [SMILES: C=CS(=O)(=O)Nc1ccccc1C(=O)N[C@H]1CCc2cc(-n3c(-c4cccnc4N)nc4ccc(-n5cccn5)nc43)ccc21] |
| 25 | 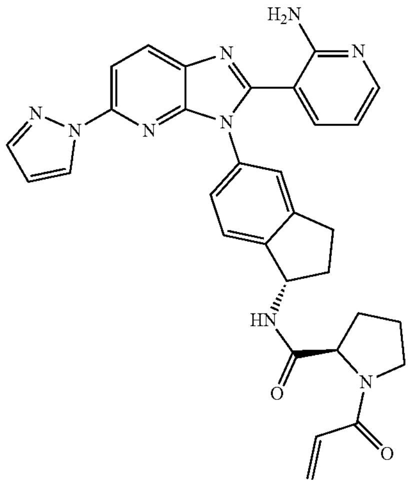 [SMILES: C=CC(=O)N1CCC[C@@H]1C(=O)N[C@H]1CCc2cc(-n3c(-c4cccnc4N)nc4ccc(-n5cccn5)nc43)ccc21] |
| 26 | 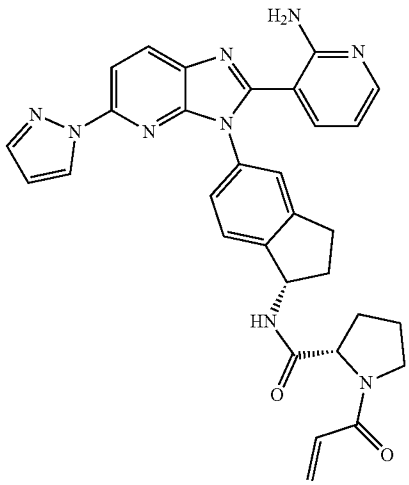 [SMILES: C=CC(=O)N1CCC[C@H]1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 27 | 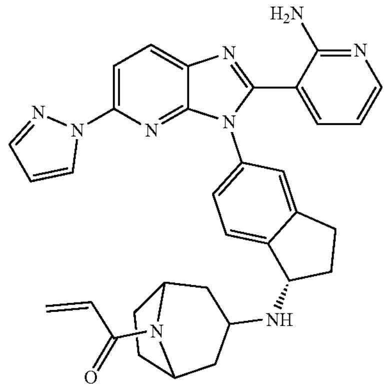 [SMILES: C=CC(=O)N1C2CCC1CC(N[C@H]1CCc3cc(-n4c(-c5cccnc5N)nc5ccc(-n6cccn6)nc54)ccc31)C2] |
| 28 | 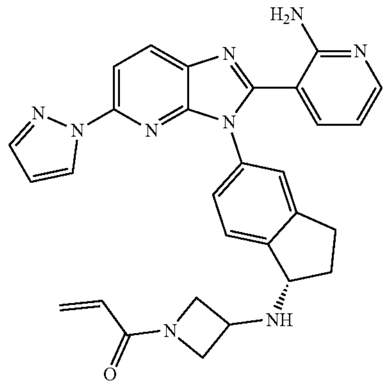 [SMILES: C=CC(=O)N1CC(N[C@H]2CCc3cc(-n4c(-c5cccnc5N)nc5ccc(-n6cccn6)nc54)ccc32)C1] |
| 29 | 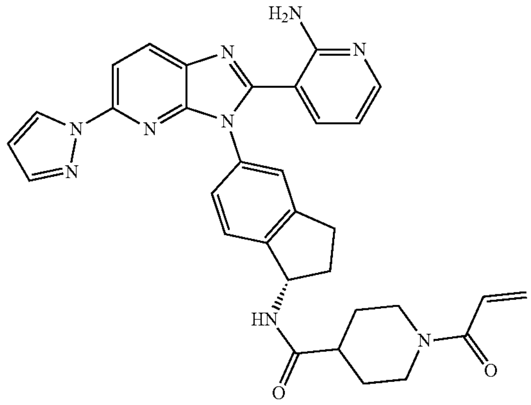 [SMILES: C=CC(=O)N1CCC(C(=O)N[C@H]2CCc3cc(-n4c(-c5cccnc5N)nc5ccc(-n6cccn6)nc54)ccc32)CC1] |

TABLE 1-continued
Chemical structures of selected compounds.
| Comp. No. | Structure |
|---|---|
| 30 | 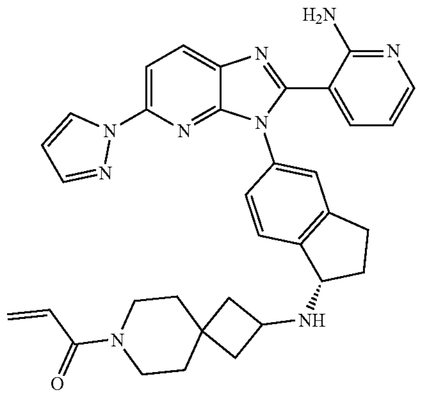 [SMILES: C=CC(=O)N1CCC2(CC1)CC(N[C@H]1CCc3cc(-n4c(-c5cccnc5N)nc5ccc(-n6cccn6)nc54)ccc31)C2] |
| 31 | 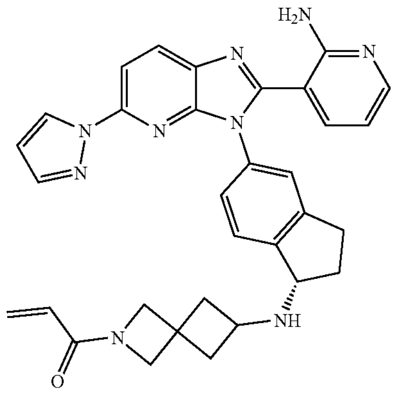 [SMILES: C=CC(=O)N1CC2(CC(N[C@H]3CCc4cc(-n5c(-c6cccnc6N)nc6ccc(-n7cccn7)nc65)ccc43)C2)C1] |
| 32 | 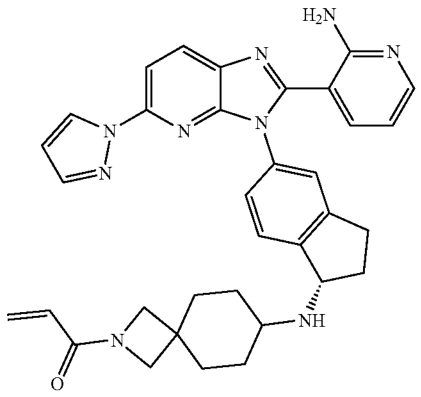 [SMILES: C=CC(=O)N1CC2(CCC(N[C@H]3CCc4cc(-n5c(-c6cccnc6N)nc6ccc(-n7cccn7)nc65)ccc43)CC2)C1] |

TABLE 1-continued
| Chemical structures of selected compounds. | |
|---|---|
| Comp. No. | Structure |
| 33 | 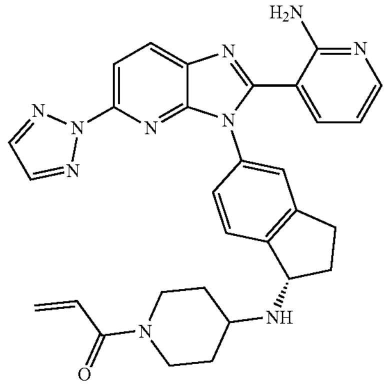 [SMILES: C=CC(=O)N1CCC(N[C@H]2CCc3cc(-n4c(-c5cccnc5N)nc5ccc(-n6nccn6)nc54)ccc32)CC1] |
| 34 | 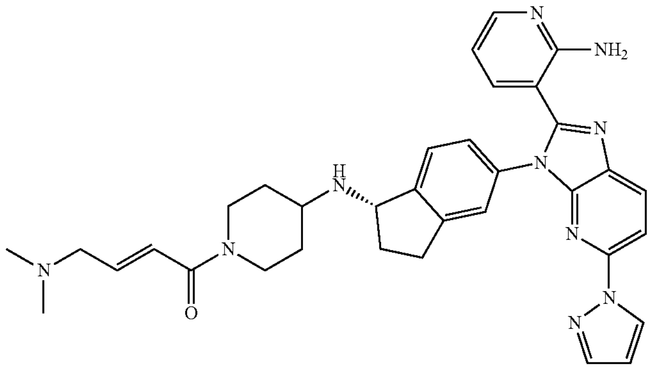 [SMILES: CN(C)C/C=C/C(=O)N1CCC(N[C@H]2CCc3cc(-n4c(-c5cccnc5N)nc5ccc(-n6cccn6)nc54)ccc32)CC1] |
| 35 | 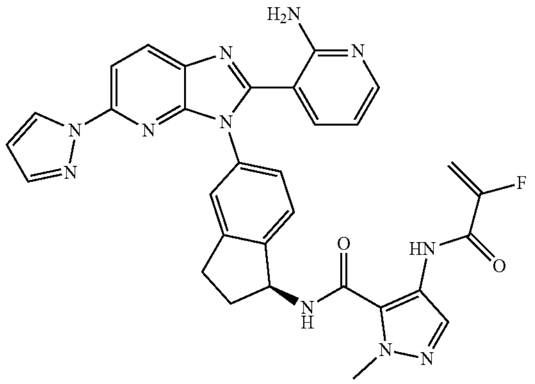 [SMILES: C=C(F)C(=O)Nc1cnn(C)c1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 36 | 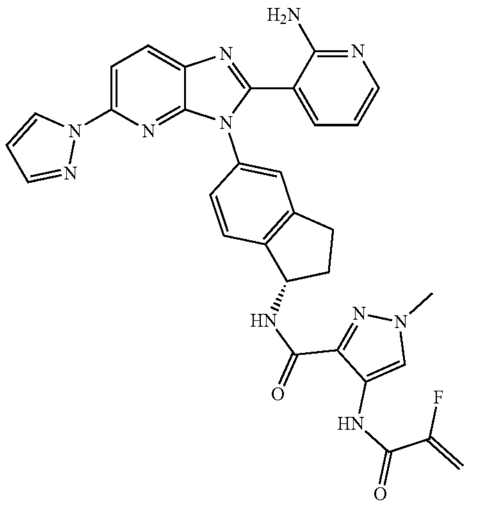 [SMILES: C=C(F)C(=O)Nc1cn(C)nc1C(=O)N[C@H]1CCc2cc(-n3c(-c4cccnc4N)nc4ccc(-n5cccn5)nc43)ccc21] |
| 37 | 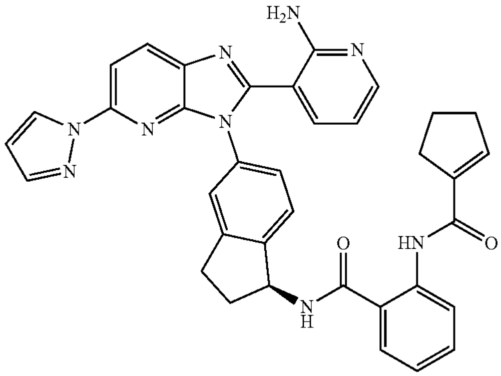 [SMILES: Nc1ncccc1-c1nc2ccc(-n3cccn3)nc2n1-c1ccc2c(c1)CC[C@@H]2NC(=O)c1ccccc1NC(=O)C1=CCCC1] |
| 38 | 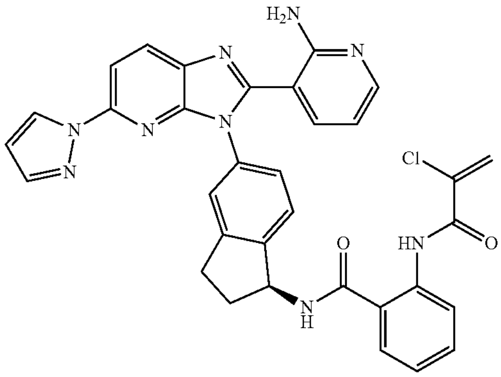 [SMILES: C=C(Cl)C(=O)Nc1ccccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 39 | 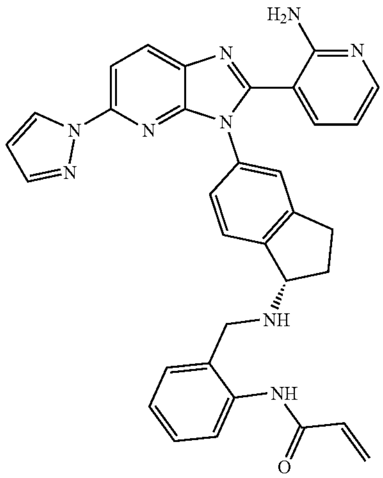 [SMILES: C=CC(=O)Nc1ccccc1CN[C@H]1CCc2cc(-n3c(-c4cccnc4N)nc4ccc(-n5cccn5)nc43)ccc21] |
| 40 | 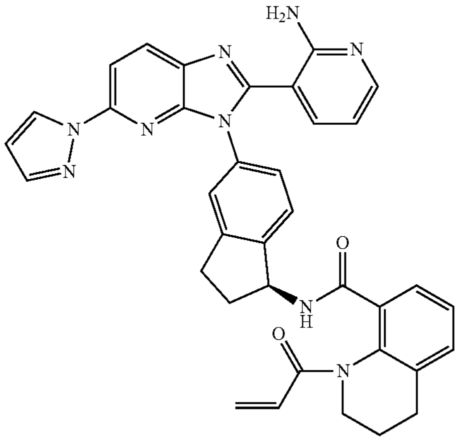 [SMILES: C=CC(=O)N1CCCc2cccc(C(=O)N[C@H]3CCc4cc(-n5c(-c6cccnc6N)nc6ccc(-n7cccn7)nc65)ccc43)c21] |
| 41 | 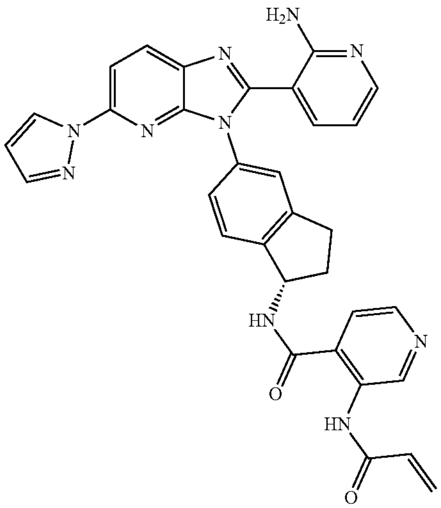 [SMILES: C=CC(=O)Nc1cnccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 42 | 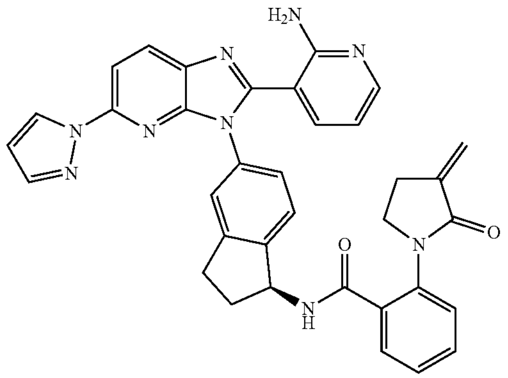 [SMILES: C=C1CCN(c2ccccc2C(=O)N[C@H]2CCc3cc(-n4c(-c5cccnc5N)nc5ccc(-n6cccn6)nc54)ccc32)C1=O] |
| 43 | 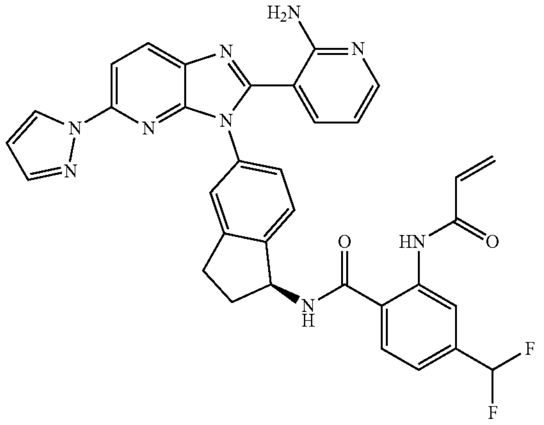 [SMILES: C=CC(=O)Nc1cc(C(F)F)ccc1C(=O)N[C@H]1CCc2cc(-n3c(-c4cccnc4N)nc4ccc(-n5cccn5)nc43)ccc21] |
| 44 | 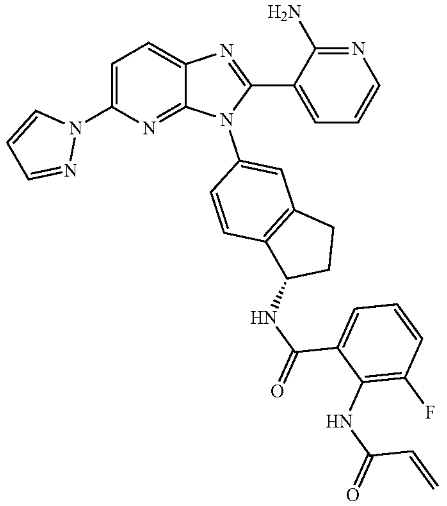 [SMILES: C=CC(=O)Nc1c(F)cccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 45 | 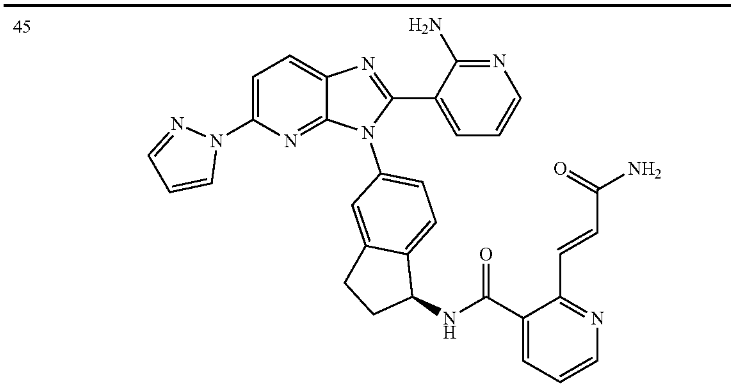 |
| 46 | 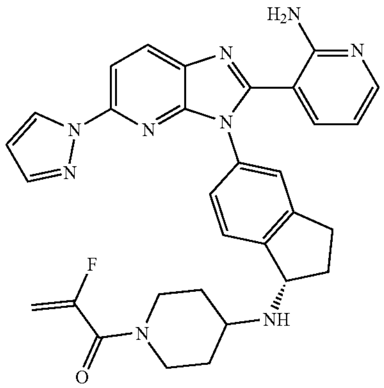 [SMILES: C=C(F)C(=O)N1CCC(N[C@H]2CCc3cc(-n4c(-c5cccnc5N)nc5ccc(-n6cccn6)nc54)ccc32)CC1] |
| 47 | 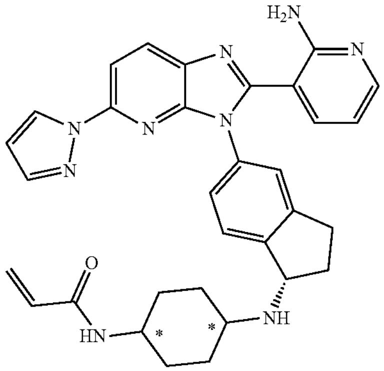 [SMILES: C=CC(=O)NC1CCC(N[C@H]2CCc3cc(-n4c(-c5cccnc5N)nc5ccc(-n6cccn6)nc54)ccc32)CC1] |
| 48 | 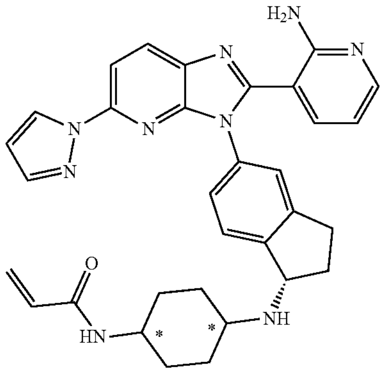 [SMILES: C=CC(=O)NC1CCC(N[C@H]2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 49 | 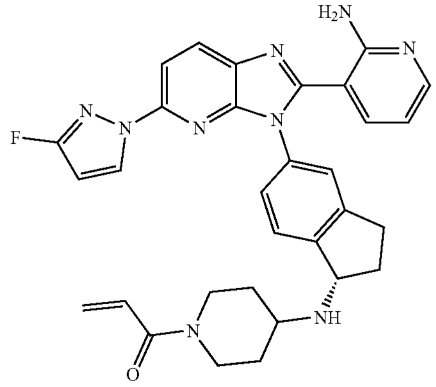 [SMILES: C=CC(=O)N1CCC(N[C@H]2CCc3cc(-n4c(-c5cccnc5N)nc5ccc(-n6ccc(F)n6)nc54)ccc32)CC1] |
| 50 | 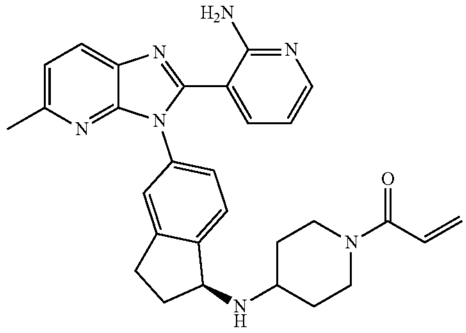 [SMILES: C=CC(=O)N1CCC(N[C@H]2CCc3cc(-n4c(-c5cccnc5N)nc5ccc(C)nc54)ccc32)CC1] |
| 51 | 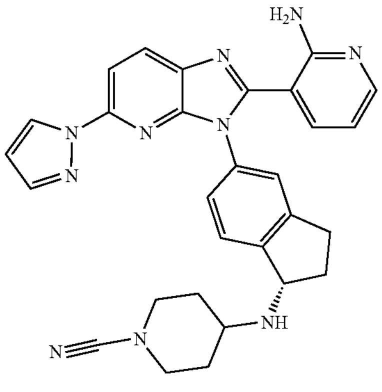 [SMILES: N#CN1CCC(N[C@H]2CCc3cc(-n4c(-c5cccnc5N)nc5ccc(-n6cccn6)nc54)ccc32)CC1] |
| 52 | 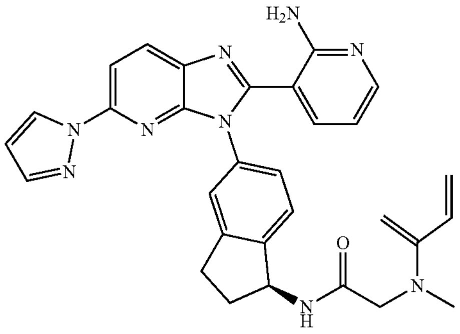 [SMILES: C=CC(=C)N(C)CC(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 53 | 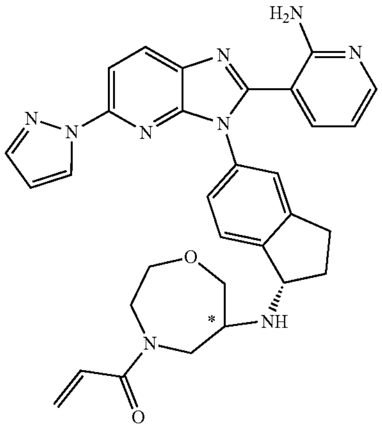 [SMILES: C=CC(=O)N1CCOCC(N[C@H]2CCc3cc(-n4c(-c5cccnc5N)nc5ccc(-n6cccn6)nc54)ccc32)C1] |
| 54 | 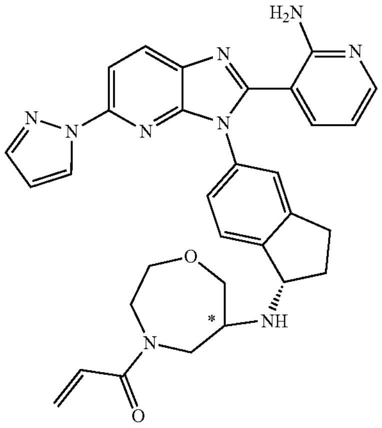 [SMILES: C=CC(=O)N1CCOCC(N[C@H]2CCc3cc(-n4c(-c5cccnc5N)nc5ccc(-n6cccn6)nc54)ccc32)C1] |
| 55 | 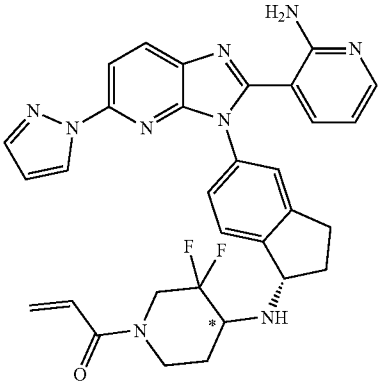 [SMILES: C=CC(=O)N1CCC(N[C@H]2CCc3cc(-n4c(-c5cccnc5N)nc5ccc(-n6cccn6)nc54)ccc32)C(F)(F)C1] |

TABLE 1-continued
| Comp. No. | Structure |
| --- | --- |
| 56 | 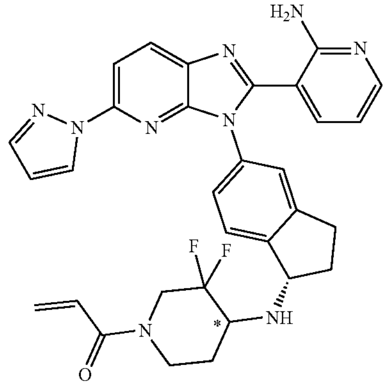 [SMILES: C=CC(=O)N1CCC(N[C@H]2CCc3cc(-n4c(-c5cccnc5N)nc5ccc(-n6cccn6)nc54)ccc32)C(F)(F)C1] |
| 57 | 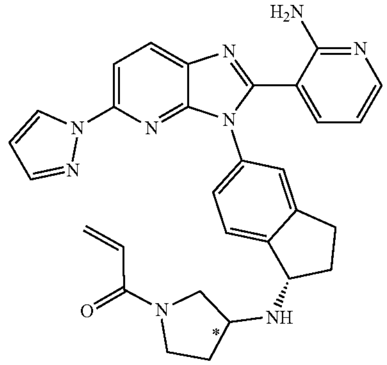 [SMILES: C=CC(=O)N1CCC(N[C@H]2CCc3cc(-n4c(-c5cccnc5N)nc5ccc(-n6cccn6)nc54)ccc32)C1] |
| 58 | 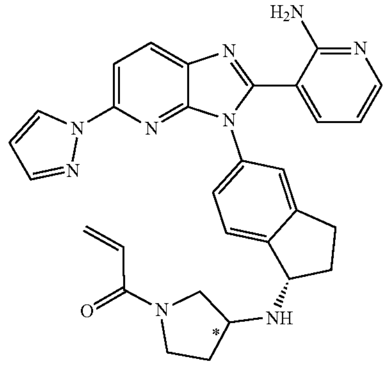 [SMILES: C=CC(=O)N1CCC(N[C@H]2CCc3cc(-n4c(-c5cccnc5N)nc5ccc(-n6cccn6)nc54)ccc32)C1] |
| 59 | 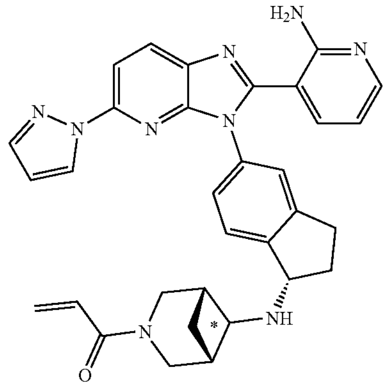 [SMILES: C=CC(=O)N1C[C@H]2C[C@@H](C1)C2N[C@H]1CCc2cc(-n3c(-c4cccnc4N)nc4ccc(-n5cccn5)nc43)ccc21] |
Chemical structures of selected compounds.

TABLE 1-continued
Chemical structures of selected compounds.
| Comp. No. | Structure |
| --- | --- |
| 60 | 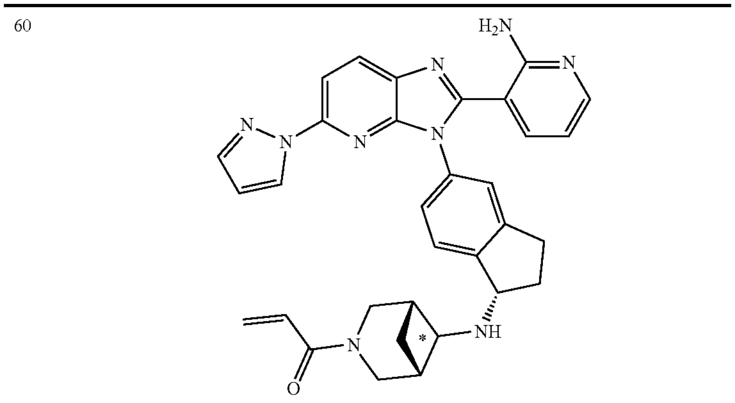 |
| 61 | 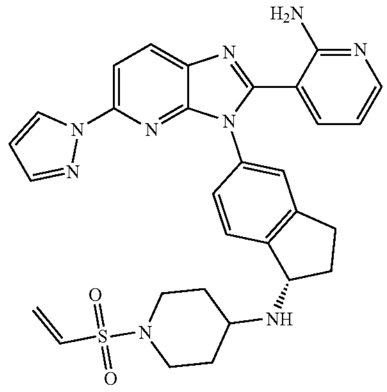 [SMILES: C=CS(=O)(=O)N1CCC(N[C@H]2CCc3cc(-n4c(-c5cccnc5N)nc5ccc(-n6cccn6)nc54)ccc32)CC1] |
| 62 | 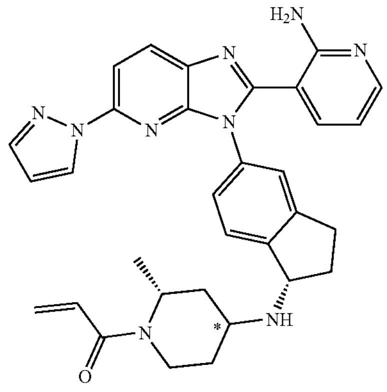 [SMILES: C=CC(=O)N1CCC(N[C@H]2CCc3cc(-n4c(-c5cccnc5N)nc5ccc(-n6cccn6)nc54)ccc32)C[C@H]1C] |
| 63 | 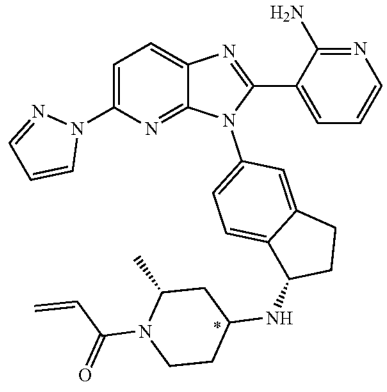 [SMILES: C=CC(=O)N1CCC(N[C@H]2CCc3cc(-n4c(-c5cccnc5N)nc5ccc(-n6cccn6)nc54)ccc32)C[C@H]1C] |

TABLE 1-continued
| Chemical structures of selected compounds. | |
|---|---|
| Comp. No. | Structure |
| 64 | 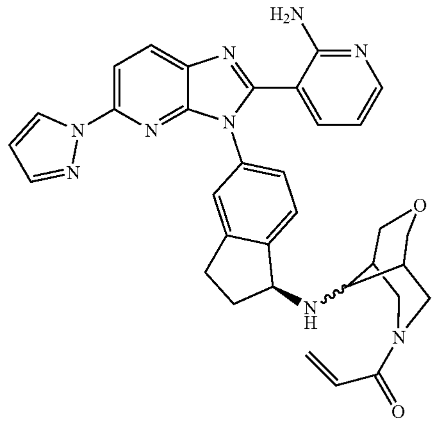 [SMILES: C=CC(=O)N1CC2COCC(C1)C2N[C@H]1CCc2cc(-n3c(-c4cccnc4N)nc4ccc(-n5cccn5)nc43)ccc21] |
| 65 | 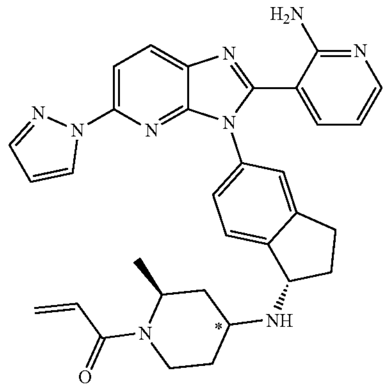 [SMILES: C=CC(=O)N1CCC(N[C@H]2CCc3cc(-n4c(-c5cccnc5N)nc5ccc(-n6cccn6)nc54)ccc32)C[C@@H]1C] |
| 66 | 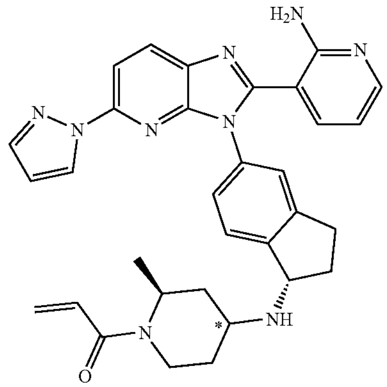 [SMILES: C=CC(=O)N1CCC(N[C@H]2CCc3cc(-n4c(-c5cccnc5N)nc5ccc(-n6cccn6)nc54)ccc32)C[C@@H]1C] |

TABLE 1-continued
| Comp. No. | Structure |
| --- | --- |
| 67 | 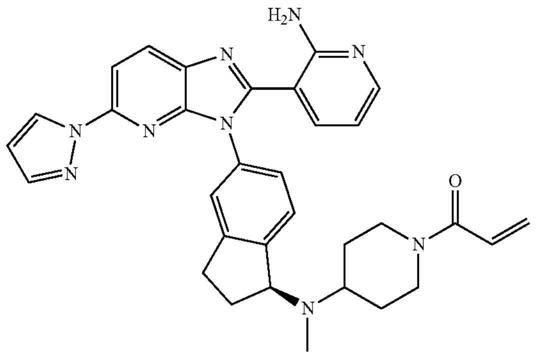 [SMILES: C=CC(=O)N1CCC(N(C)[C@H]2CCc3cc(-n4c(-c5cccnc5N)nc5ccc(-n6cccn6)nc54)ccc32)CC1] |
| 68 | 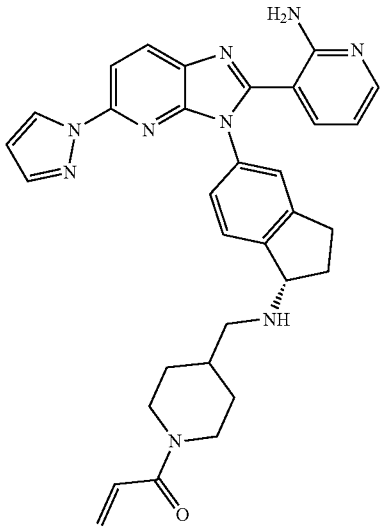 [SMILES: C=CC(=O)N1CCC(CN[C@H]2CCc3cc(-n4c(-c5cccnc5N)nc5ccc(-n6cccn6)nc54)ccc32)CC1] |
| 69 | 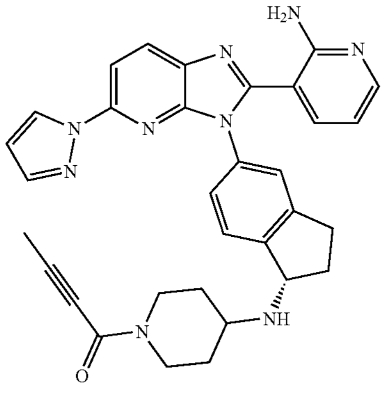 [SMILES: CC#CC(=O)N1CCC(N[C@H]2CCc3cc(-n4c(-c5cccnc5N)nc5ccc(-n6cccn6)nc54)ccc32)CC1] |
Chemical structures of selected compounds.

TABLE 1-continued
| Chemical structures of selected compounds. | |
|---|---|
| Comp. No. | Structure |
| 70 | 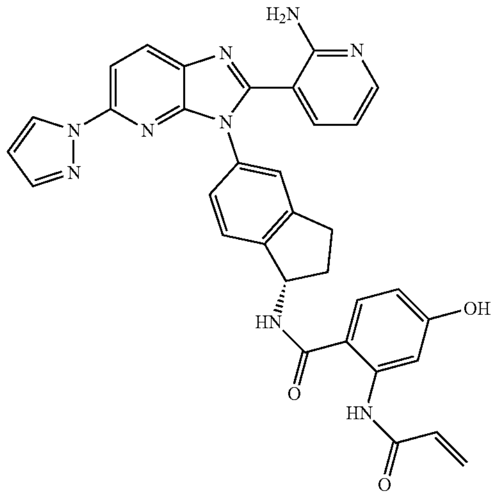 [SMILES: C=CC(=O)Nc1cc(O)ccc1C(=O)N[C@H]1CCc2cc(-n3c(-c4cccnc4N)nc4ccc(-n5cccn5)nc43)ccc21] |
| 71 | 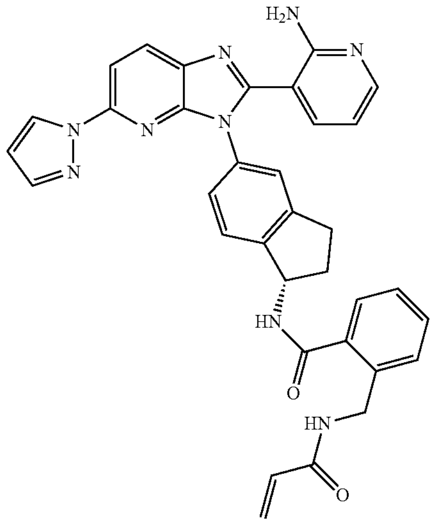 [SMILES: C=CC(=O)NCc1ccccc1C(=O)N[C@H]1CCc2cc(-n3c(-c4cccnc4N)nc4ccc(-n5cccn5)nc43)ccc21] |
| 72 | 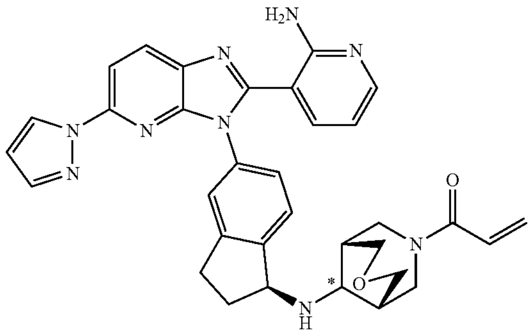 [SMILES: C=CC(=O)N1C[C@H]2COC[C@@H](C1)C2N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 73 | 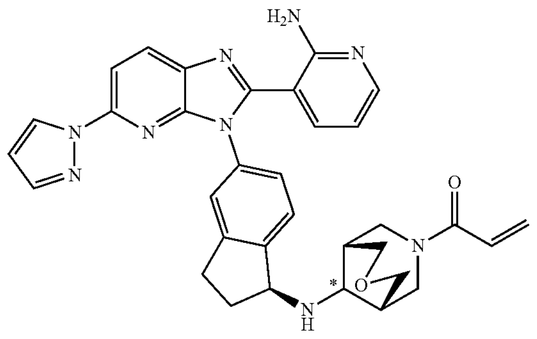 [SMILES: C=CC(=O)N1C[C@H]2COC[C@@H](C1)C2N[C@H]1CCc2cc(-n3c(-c4cccnc4N)nc4ccc(-n5cccn5)nc43)ccc21] |
| 74 | 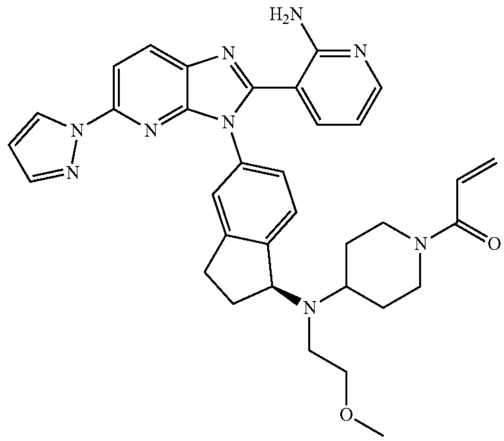 [SMILES: C=CC(=O)N1CCC(N(CCOC)[C@H]2CCc3cc(-n4c(-c5cccnc5N)nc5ccc(-n6cccn6)nc54)ccc32)CC1] |
| 75 | 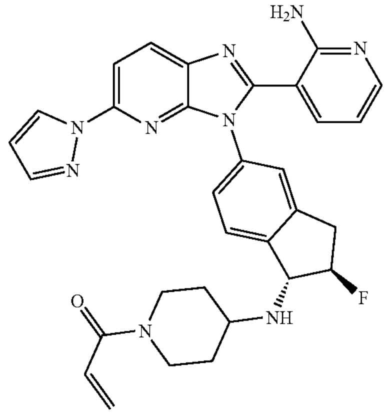 [SMILES: C=CC(=O)N1CCC(N[C@@H]2c3ccc(-n4c(-c5cccnc5N)nc5ccc(-n6cccn6)nc54)cc3C[C@H]2F)CC1] |

TABLE 1-continued
| Chemical structures of selected compounds. | |
|---|---|
| Comp. No. | Structure |
| 76 | 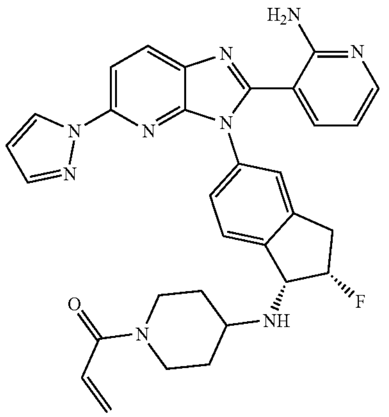 [SMILES: C=CC(=O)N1CCC(N[C@@H]2c3ccc(-n4c(-c5cccnc5N)nc5ccc(-n6cccn6)nc54)cc3C[C@@H]2F)CC1] |
| 77 | 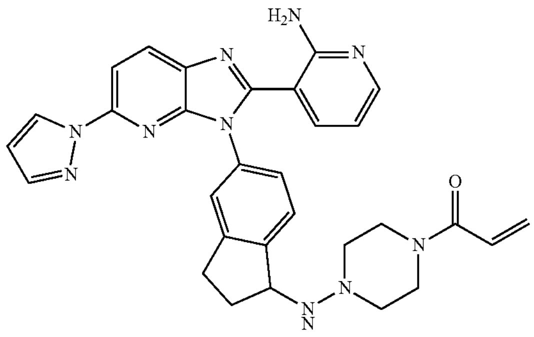 |
| 78 | 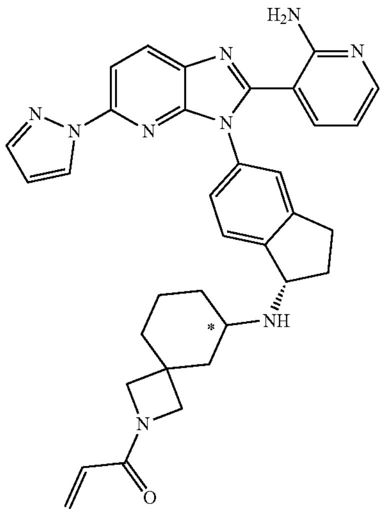 [SMILES: C=CC(=O)N1CC2(CCCC(N[C@H]3CCc4cc(-n5c(-c6cccnc6N)nc6ccc(-n7cccn7)nc65)ccc43)C2)C1] |

TABLE 1-continued
| Chemical structures of selected compounds. | |
|---|---|
| Comp. No. | Structure |
| 79 | 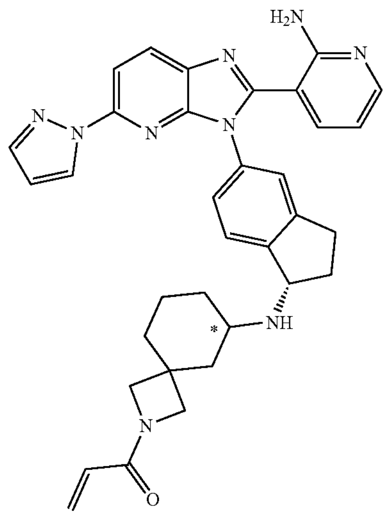 [SMILES: C=CC(=O)N1CC2(CCCC(N[C@H]3CCc4cc(-n5c(-c6cccnc6N)nc6ccc(-n7cccn7)nc65)ccc43)C2)C1] |
| 80 | 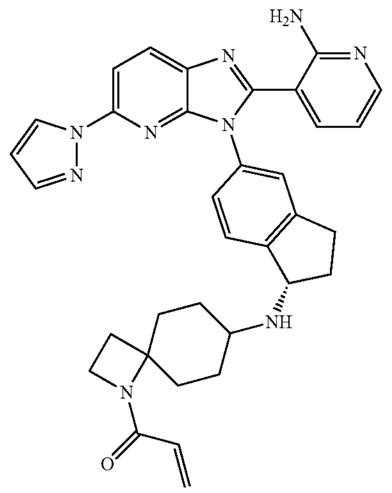 [SMILES: C=CC(=O)N1CCC12CCC(N[C@H]1CCc3cc(-n4c(-c5cccnc5N)nc5ccc(-n6cccn6)nc54)ccc31)CC2] |
| 81 | 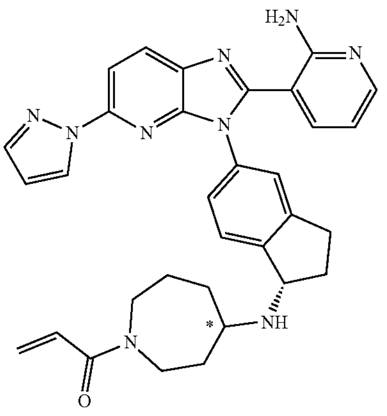 [SMILES: C=CC(=O)N1CCCC(N[C@H]2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 82 | 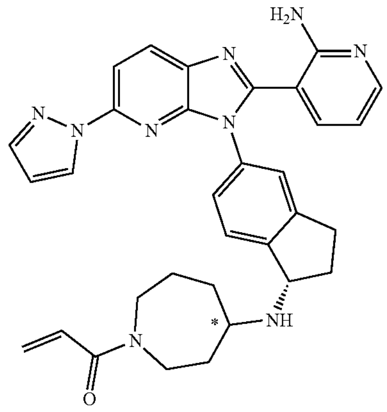 [SMILES: C=CC(=O)N1CCCC(N[C@H]2CCc3cc(-n4c(-c5cccnc5N)nc5ccc(-n6cccn6)nc54)ccc32)CC1] |
| 83 | 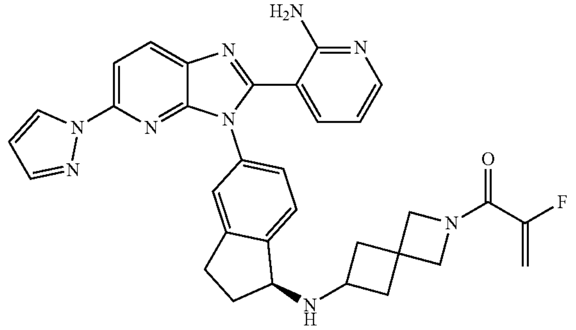 [SMILES: C=C(F)C(=O)N1CC2(CC(N[C@H]3CCc4cc(-n5c(-c6cccnc6N)nc6ccc(-n7cccn7)nc65)ccc43)C2)C1] |
| 84 | 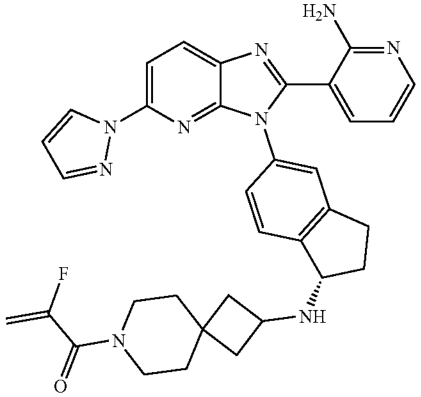 [SMILES: C=C(F)C(=O)N1CCC2(CC1)CC(N[C@H]1CCc3cc(-n4c(-c5cccnc5N)nc5ccc(-n6cccn6)nc54)ccc31)C2] |
| 85 | 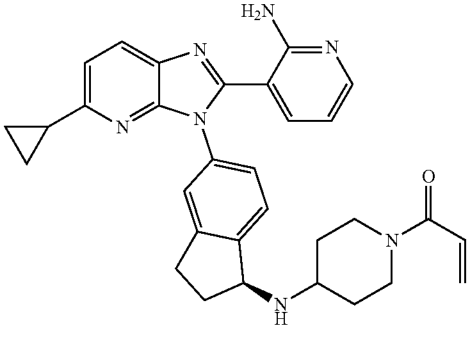 [SMILES: C=CC(=O)N1CCC(N[C@H]2CCc3cc(-n4c(-c5cccnc5N)nc5ccc(C6CC6)nc54)ccc32)CC1] |

TABLE 1-continued
| Chemical structures of selected compounds. | |
|---|---|
| Comp. No. | Structure |
| 86 | 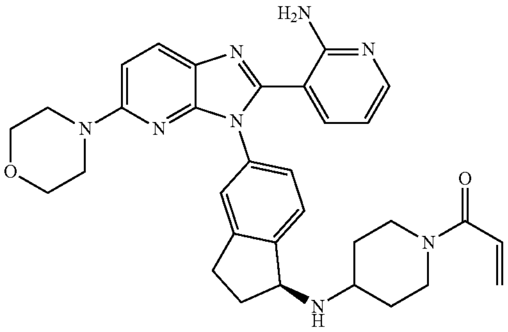 [SMILES: C=CC(=O)N1CCC(N[C@H]2CCc3cc(-n4c(-c5cccnc5N)nc5ccc(N6CCOCC6)nc54)ccc32)CC1] |
| 87 | 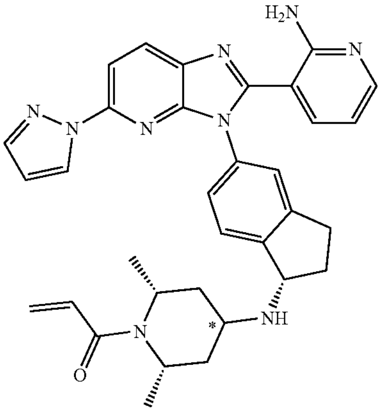 [SMILES: C=CC(=O)N1[C@H](C)CC(N[C@H]2CCc3cc(-n4c(-c5cccnc5N)nc5ccc(-n6cccn6)nc54)ccc32)C[C@@H]1C] |
| 88 | 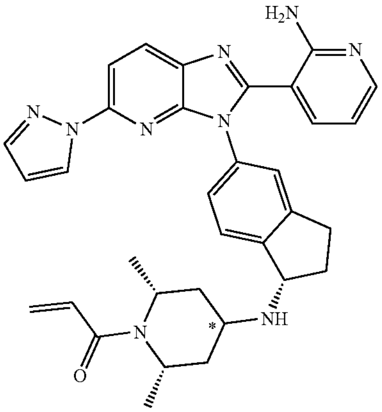 [SMILES: C=CC(=O)N1[C@H](C)CC(N[C@H]2CCc3cc(-n4c(-c5cccnc5N)nc5ccc(-n6cccn6)nc54)ccc32)C[C@@H]1C] |

TABLE 1-continued
| Chemical structures of selected compounds. | |
|---|---|
| Comp. No. | Structure |
| 89 | 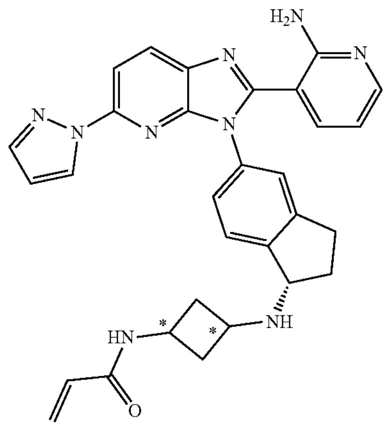 [SMILES: C=CC(=O)NC1CC(N[C@H]2CCc3cc(-n4c(-c5cccnc5N)nc5ccc(-n6cccn6)nc54)ccc32)C1] |
| 90 | 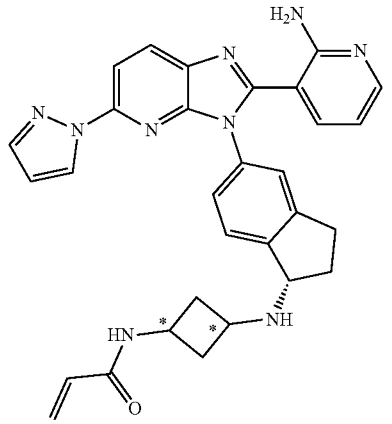 [SMILES: C=CC(=O)NC1CC(N[C@H]2CCc3cc(-n4c(-c5cccnc5N)nc5ccc(-n6cccn6)nc54)ccc32)C1] |
| 91 | 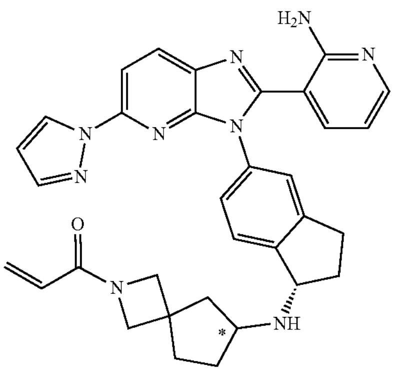 [SMILES: C=CC(=O)N1CC2(CCC(N[C@H]3CCc4cc(-n5c(-c6cccnc6N)nc6ccc(-n7cccn7)nc65)ccc43)C2)C1] |

TABLE 1-continued
| Chemical structures of selected compounds. | |
|---|---|
| Comp. No. | Structure |
| 92 | 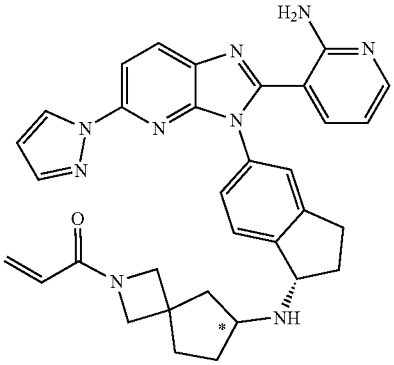 [SMILES: C=CC(=O)N1CC2(CCC(N[C@H]3CCc4cc(-n5c(-c6cccnc6N)nc6ccc(-n7cccn7)nc65)ccc43)C2)C1] |
| 93 | 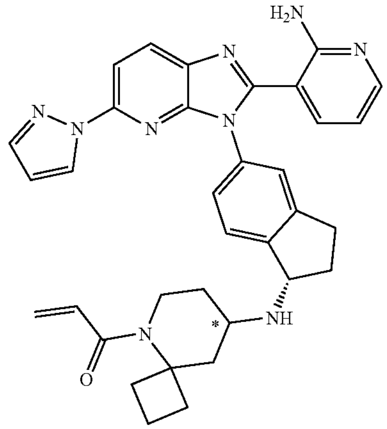 [SMILES: C=CC(=O)N1CCC(N[C@H]2CCc3cc(-n4c(-c5cccnc5N)nc5ccc(-n6cccn6)nc54)ccc32)CC12CCC2] |
| 94 | 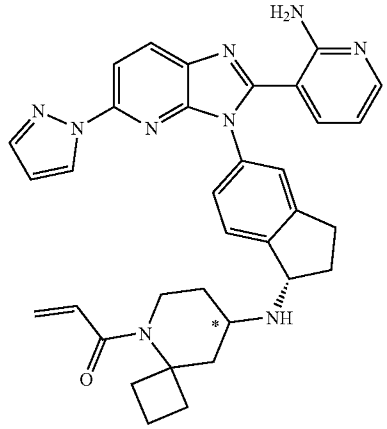 [SMILES: C=CC(=O)N1CCC(N[C@H]2CCc3cc(-n4c(-c5cccnc5N)nc5ccc(-n6cccn6)nc54)ccc32)CC12CCC2] |

TABLE 1-continued
| Chemical structures of selected compounds. | |
|---|---|
| Comp. No. | Structure |
| 95 | 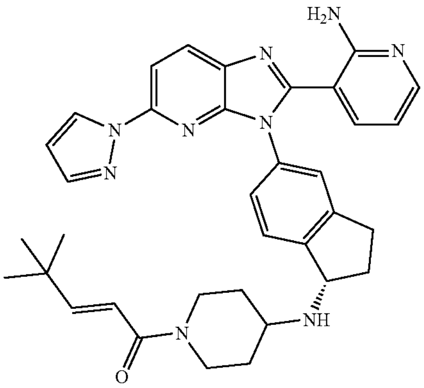 [SMILES: CC(C)(C)/C=C/C(=O)N1CCC(N[C@H]2CCc3cc(-n4c(-c5cccnc5N)nc5ccc(-n6cccn6)nc54)ccc32)CC1] |
| 96 | 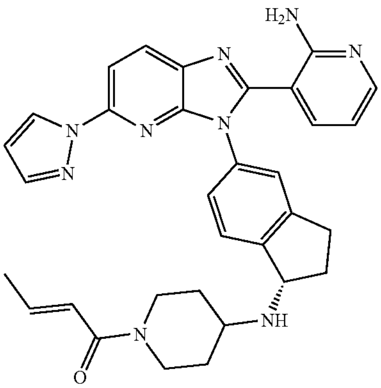 [SMILES: C/C=C/C(=O)N1CCC(N[C@H]2CCc3cc(-n4c(-c5cccnc5N)nc5ccc(-n6cccn6)nc54)ccc32)CC1] |
| 97 | 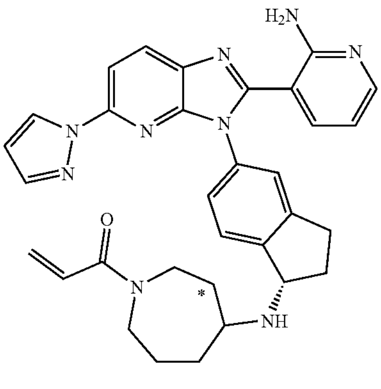 [SMILES: C=CC(=O)N1CCCC(N[C@H]2CCc3cc(-n4c(-c5cccnc5N)nc5ccc(-n6cccn6)nc54)ccc32)CC1] |
| 98 | 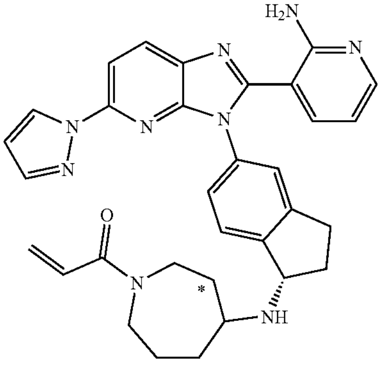 [SMILES: C=CC(=O)N1CCCC(N[C@H]2CCc3cc(-n4c(-c5cccnc5N)nc5ccc(-n6cccn6)nc54)ccc32)CC1] |

TABLE 1-continued
| Comp. No. | Chemical structures of selected compounds. Structure |
|---|---|
| 99 | 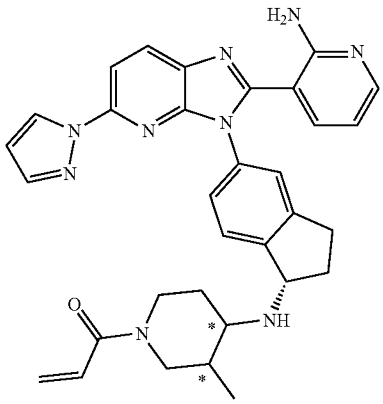 [SMILES: C=CC(=O)N1CCC(N[C@H]2CCc3cc(-n4c(-c5cccnc5N)nc5ccc(-n6cccn6)nc54)ccc32)C(C)C1] |
| 100 | 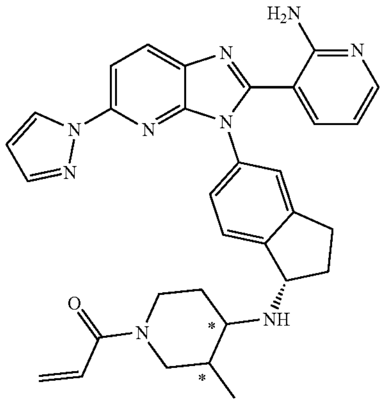 [SMILES: C=CC(=O)N1CCC(N[C@H]2CCc3cc(-n4c(-c5cccnc5N)nc5ccc(-n6cccn6)nc54)ccc32)C(C)C1] |
| 101 | 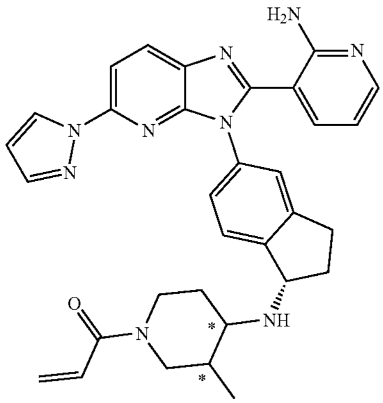 [SMILES: C=CC(=O)N1CCC(N[C@H]2CCc3cc(-n4c(-c5cccnc5N)nc5ccc(-n6cccn6)nc54)ccc32)C(C)C1] |

TABLE 1-continued
| Chemical structures of selected compounds. | |
| --- | --- |
| Comp. No. | Structure |
| 102 | 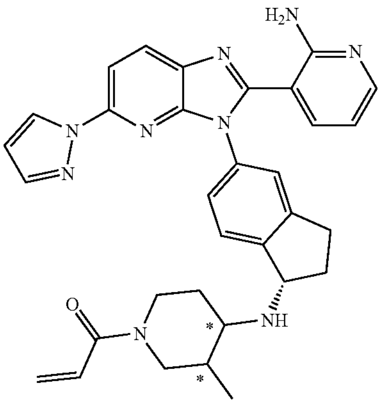 [SMILES: C=CC(=O)N1CCC(N[C@H]2CCc3cc(-n4c(-c5cccnc5N)nc5ccc(-n6cccn6)nc54)ccc32)C(C)C1] |
| 103 | 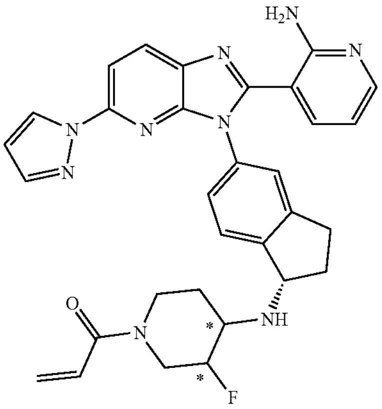 [SMILES: C=CC(=O)N1CCC(N[C@H]2CCc3cc(-n4c(-c5cccnc5N)nc5ccc(-n6cccn6)nc54)ccc32)C(F)C1] |
| 104 | 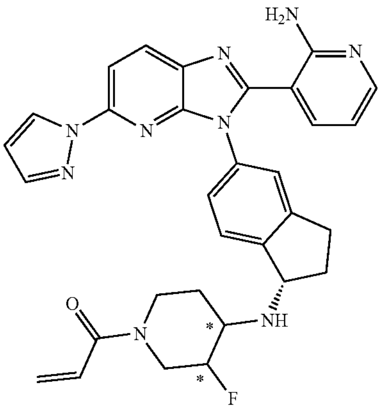 [SMILES: C=CC(=O)N1CCC(N[C@H]2CCc3cc(-n4c(-c5cccnc5N)nc5ccc(-n6cccn6)nc54)ccc32)C(F)C1] |

TABLE 1-continued
| Chemical structures of selected compounds. | |
|---|---|
| Comp. No. | Structure |
| 105 | 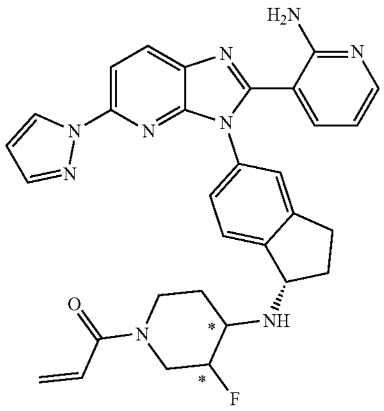 [SMILES: C=CC(=O)N1CCC(N[C@H]2CCc3cc(-n4c(-c5cccnc5N)nc5ccc(-n6cccn6)nc54)ccc32)C(F)C1] |
| 106 | 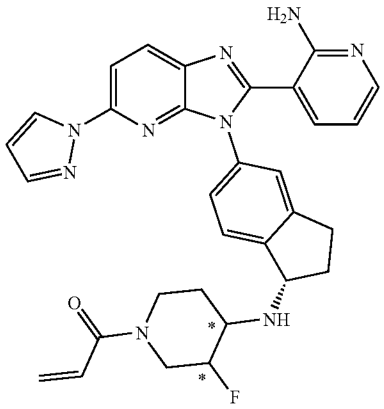 [SMILES: C=CC(=O)N1CCC(N[C@H]2CCc3cc(-n4c(-c5cccnc5N)nc5ccc(-n6cccn6)nc54)ccc32)C(F)C1] |
| 107 | 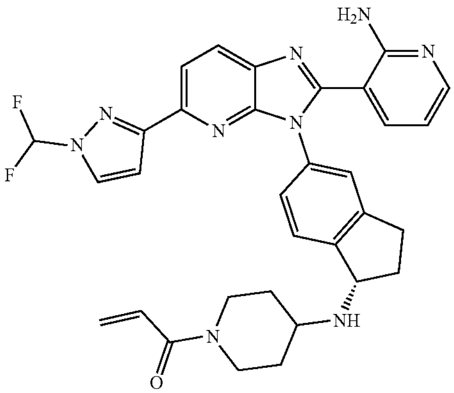 [SMILES: C=CC(=O)N1CCC(N[C@H]2CCc3cc(-n4c(-c5cccnc5N)nc5ccc(-c6ccn(C(F)F)n6)nc54)ccc32)CC1] |

TABLE 1-continued
| Chemical structures of selected compounds. | |
|---|---|
| Comp. No. | Structure |
| 108 | 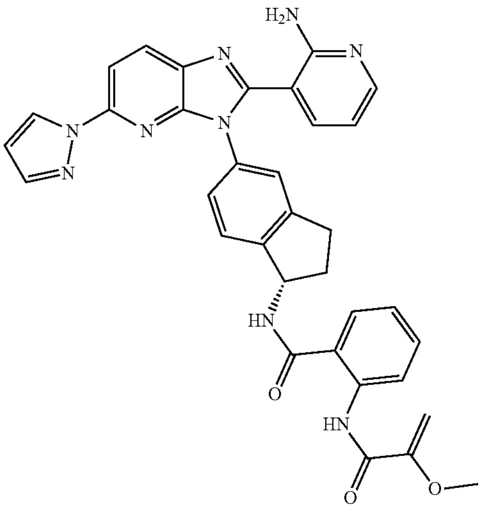 [SMILES: C=C(OC)C(=O)Nc1ccccc1C(=O)N[C@H]1CCc2cc(-n3c(-c4cccnc4N)nc4ccc(-n5cccn5)nc43)ccc21] |
| 109 | 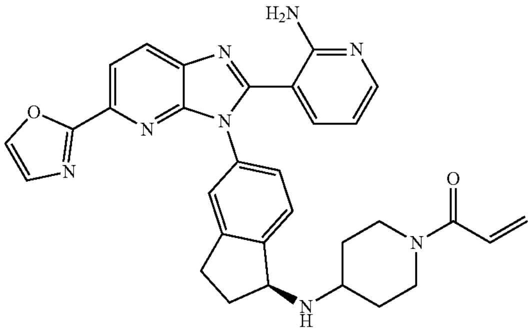 [SMILES: C=CC(=O)N1CCC(N[C@H]2CCc3cc(-n4c(-c5cccnc5N)nc5ccc(-c6ncco6)nc54)ccc32)CC1] |
| 110 | 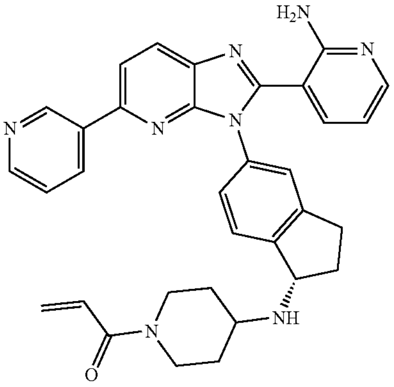 [SMILES: C=CC(=O)N1CCC(N[C@H]2CCc3cc(-n4c(-c5cccnc5N)nc5ccc(-c6cccnc6)nc54)ccc32)CC1] |

TABLE 1-continued
Chemical structures of selected compounds.
| Comp. No. | Structure |
| --- | --- |
| 111 | 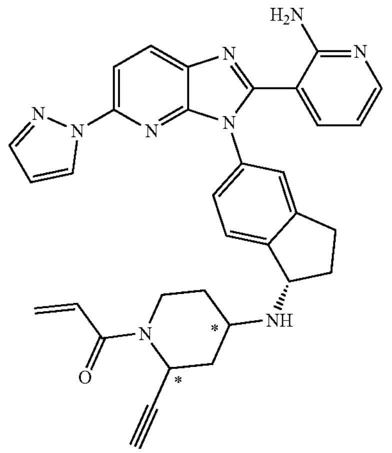 [SMILES: C#CC1CC(N[C@H]2CCc3cc(-n4c(-c5cccnc5N)nc5ccc(-n6cccn6)nc54)ccc32)CCN1C(=O)C=C] |
| 112 | 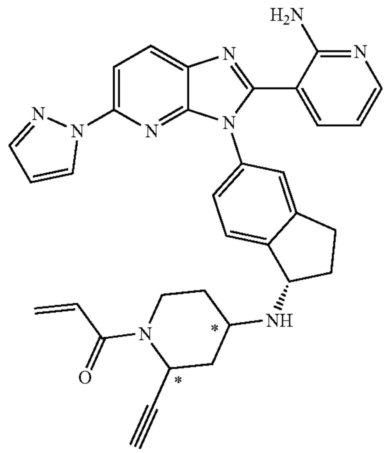 [SMILES: C#CC1CC(N[C@H]2CCc3cc(-n4c(-c5cccnc5N)nc5ccc(-n6cccn6)nc54)ccc32)CCN1C(=O)C=C] |
| 113 | 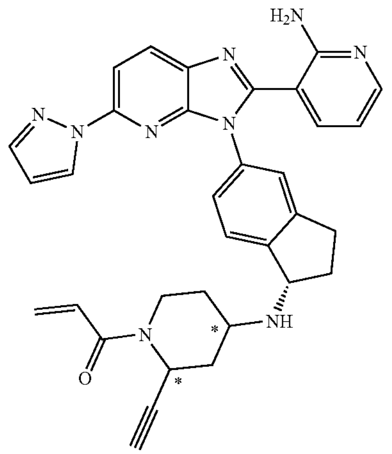 [SMILES: C#CC1CC(N[C@H]2CCc3cc(-n4c(-c5cccnc5N)nc5ccc(-n6cccn6)nc54)ccc32)CCN1C(=O)C=C] |

TABLE 1-continued
| Chemical structures of selected compounds. | |
|---|---|
| Comp. No. | Structure |
| 114 | 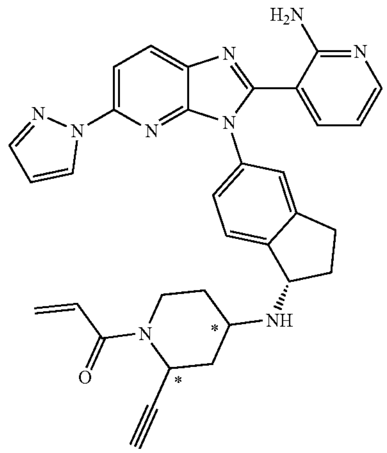 [SMILES: C#CC1CC(N[C@H]2CCc3cc(-n4c(-c5cccnc5N)nc5ccc(-n6cccn6)nc54)ccc32)CCN1C(=O)C=C] |
| 115 | 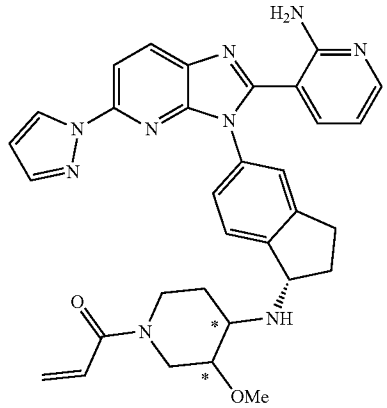 [SMILES: C=CC(=O)N1CCC(N[C@H]2CCc3cc(-n4c(-c5cccnc5N)nc5ccc(-n6cccn6)nc54)ccc32)C(OC)C1] |
| 116 | 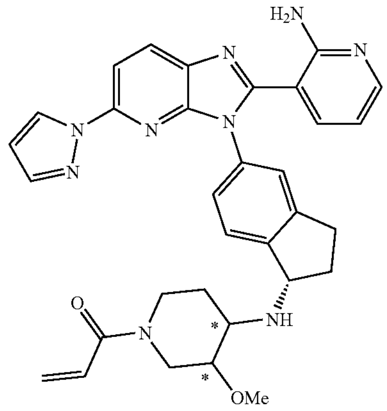 [SMILES: C=CC(=O)N1CCC(N[C@H]2CCc3cc(-n4c(-c5cccnc5N)nc5ccc(-n6cccn6)nc54)ccc32)C(OC)C1] |

TABLE 1-continued
| Chemical structures of selected compounds. | |
|---|---|
| Comp. No. | Structure |
| 117 | 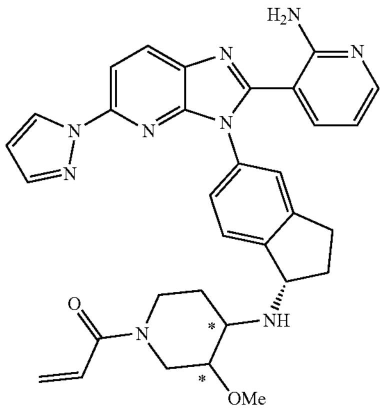 [SMILES: C=CC(=O)N1CCC(N[C@H]2CCc3cc(-n4c(-c5cccnc5N)nc5ccc(-n6cccn6)nc54)ccc32)C(OC)C1] |
| 118 | 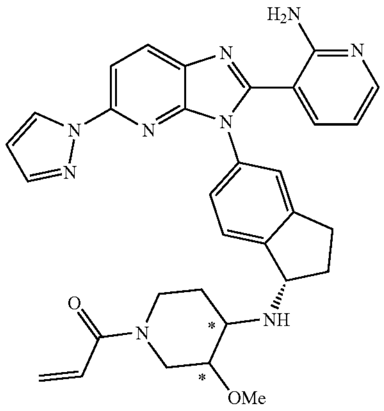 [SMILES: C=CC(=O)N1CCC(N[C@H]2CCc3cc(-n4c(-c5cccnc5N)nc5ccc(-n6cccn6)nc54)ccc32)C(OC)C1] |
| 119 | 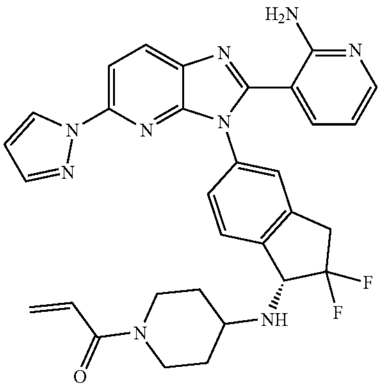 [SMILES: C=CC(=O)N1CCC(N[C@@H]2c3ccc(-n4c(-c5cccnc5N)nc5ccc(-n6cccn6)nc54)cc3CC2(F)F)CC1] |

TABLE 1-continued
| Chemical structures of selected compounds. | |
|---|---|
| Comp. No. | Structure |
| 120 | 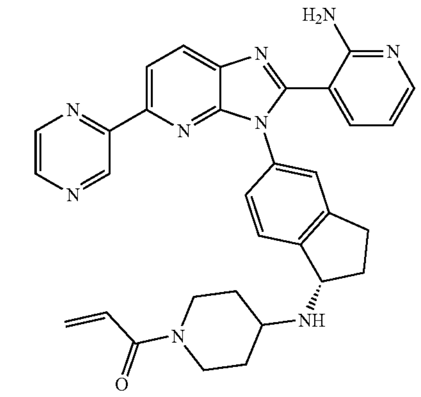 [SMILES: C=CC(=O)N1CCC(N[C@H]2CCc3cc(-n4c(-c5cccnc5N)nc5ccc(-c6cnccn6)nc54)ccc32)CC1] |
| 121 | 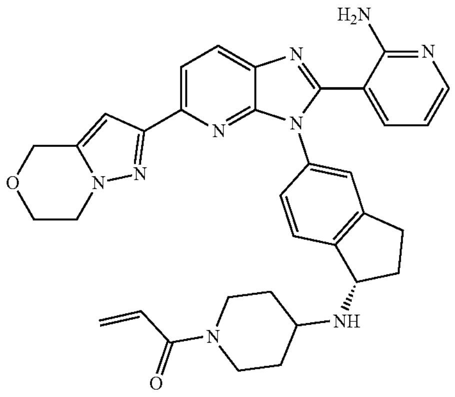 [SMILES: C=CC(=O)N1CCC(N[C@H]2CCc3cc(-n4c(-c5cccnc5N)nc5ccc(-c6cc7n(n6)CCOC7)nc54)ccc32)CC1] |
| 122 | 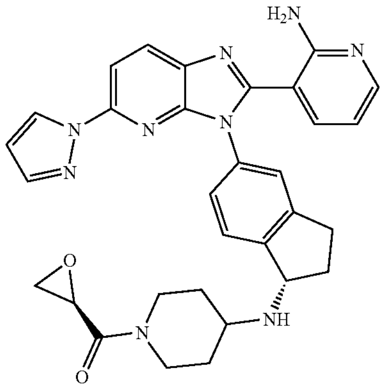 [SMILES: Nc1ncccc1-c1nc2ccc(-n3cccn3)nc2n1-c1ccc2c(c1)CC[C@@H]2NC1CCN(C(=O)[C@H]2CO2)CC1] |

TABLE 1-continued
| Chemical structures of selected compounds. | |
| --- | --- |
| Comp. No. | Structure |
| 123 | 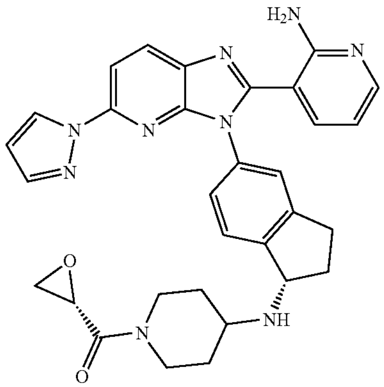 [SMILES: Nc1ncccc1-c1nc2ccc(-n3cccn3)nc2n1-c1ccc2c(c1)CC[C@@H]2NC1CCN(C(=O)[C@@H]2CO2)CC1] |
| 124 | 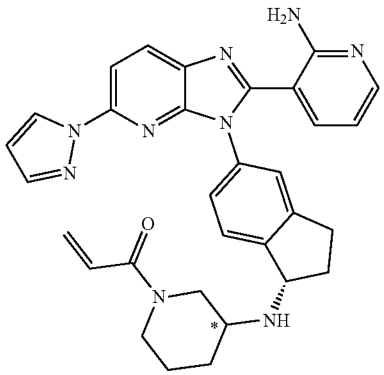 [SMILES: C=CC(=O)N1CCCC(N[C@H]2CCc3cc(-n4c(-c5cccnc5N)nc5ccc(-n6cccn6)nc54)ccc32)C1] |
| 125 | 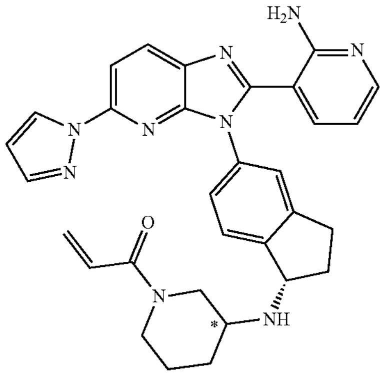 [SMILES: C=CC(=O)N1CCCC(N[C@H]2CCc3cc(-n4c(-c5cccnc5N)nc5ccc(-n6cccn6)nc54)ccc32)C1] |

TABLE 1-continued
| Chemical structures of selected compounds. | |
|---|---|
| Comp. No. | Structure |
| 126 | 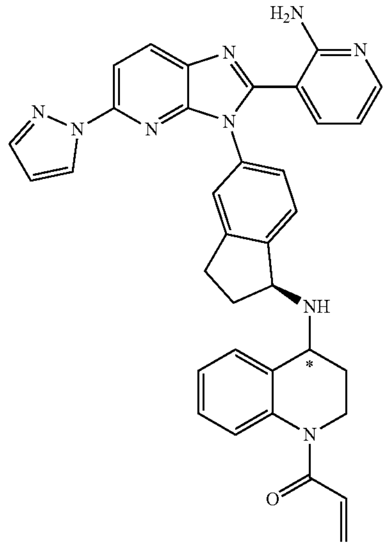 [SMILES: C=CC(=O)N1CCC(N[C@H]2CCc3cc(-n4c(-c5cccnc5N)nc5ccc(-n6cccn6)nc54)ccc32)c2ccccc21] |
| 127 | 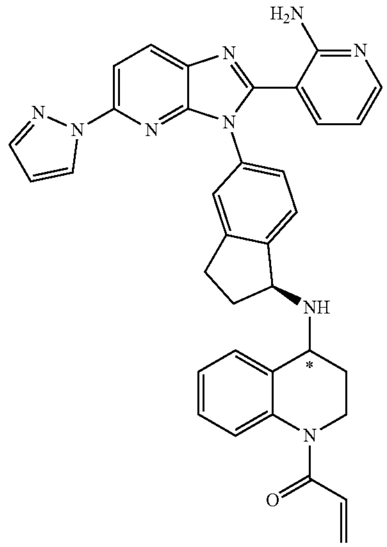 [SMILES: C=CC(=O)N1CCC(N[C@H]2CCc3cc(-n4c(-c5cccnc5N)nc5ccc(-n6cccn6)nc54)ccc32)c2ccccc21] |
| 128 | 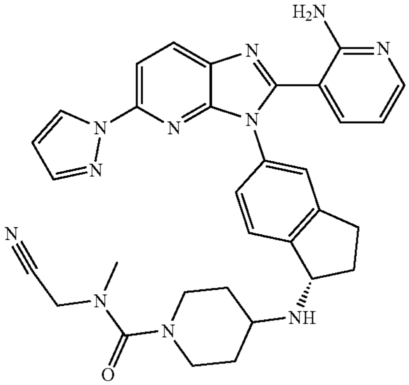 [SMILES: CN(CC#N)C(=O)N1CCC(N[C@H]2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 129 | 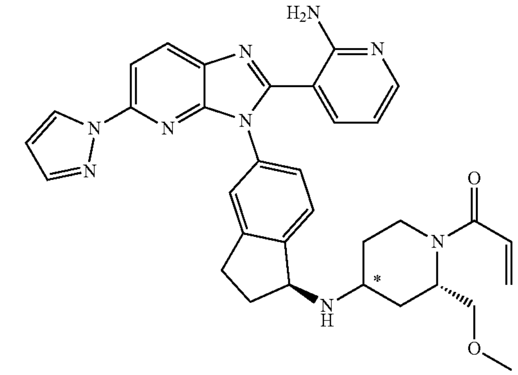 [SMILES: C=CC(=O)N1CCC(N[C@H]2CCc3cc(-n4c(-c5cccnc5N)nc5ccc(-n6cccn6)nc54)ccc32)C[C@H]1COC] |
| 130 | 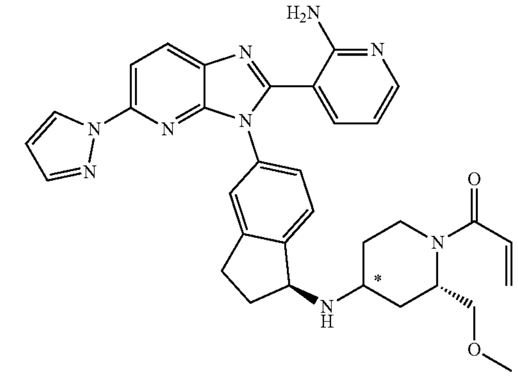 [SMILES: C=CC(=O)N1CCC(N[C@H]2CCc3cc(-n4c(-c5cccnc5N)nc5ccc(-n6cccn6)nc54)ccc32)C[C@H]1COC] |
| 131 | 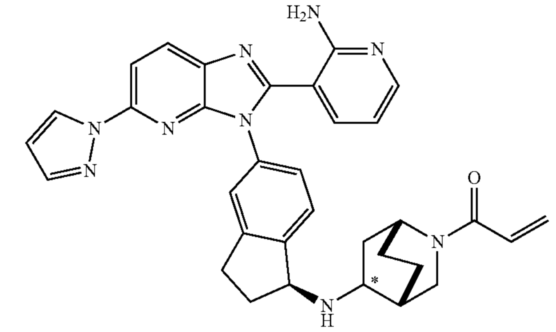 |
| 132 | 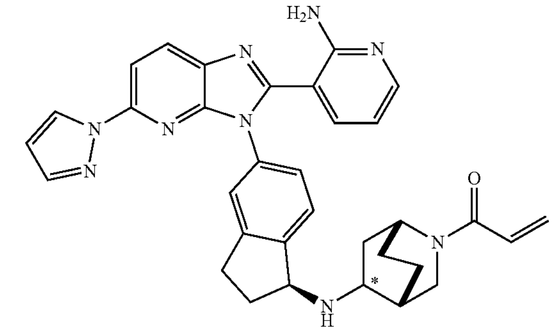 |

TABLE 1-continued
| Comp. No. | Structure |
|---|---|
| 133 | 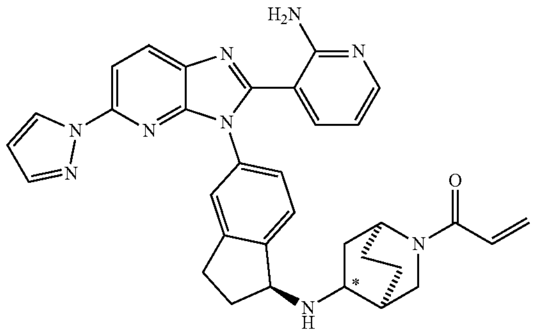 |
| 134 | 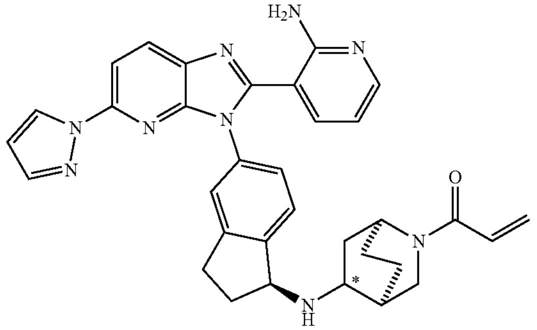 |
| 135 | 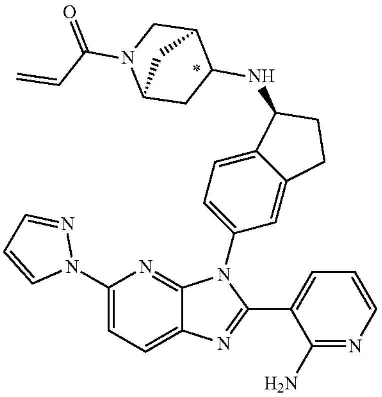 [SMILES: C=CC(=O)N1C[C@@H]2C[C@H]1CC2N[C@H]1CCc2cc(-n3c(-c4cccnc4N)nc4ccc(-n5cccn5)nc43)ccc21] |
| 136 | 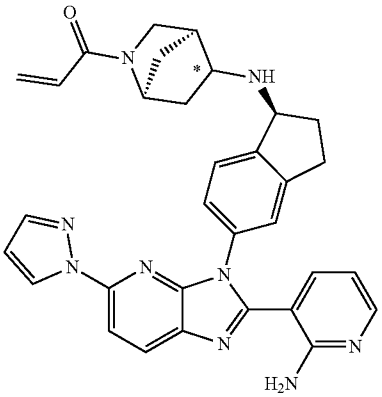 [SMILES: C=CC(=O)N1C[C@@H]2C[C@H]1CC2N[C@H]1CCc2cc(-n3c(-c4cccnc4N)nc4ccc(-n5cccn5)nc43)ccc21] |
Chemical structures of selected compounds.

TABLE 1-continued
| Chemical structures of selected compounds. | |
|---|---|
| Comp. No. | Structure |
| 137 | 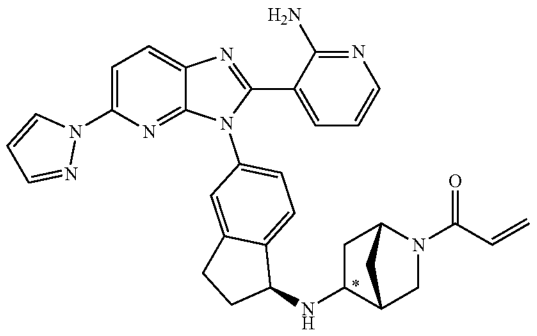 [SMILES: C=CC(=O)N1C[C@H]2C[C@@H]1CC2N[C@H]1CCc2cc(-n3c(-c4cccnc4N)nc4ccc(-n5cccn5)nc43)ccc21] |
| 138 | 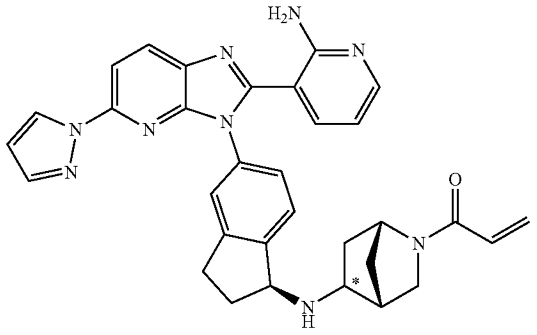 [SMILES: C=CC(=O)N1C[C@H]2C[C@@H]1CC2N[C@H]1CCc2cc(-n3c(-c4cccnc4N)nc4ccc(-n5cccn5)nc43)ccc21] |
| 139 | 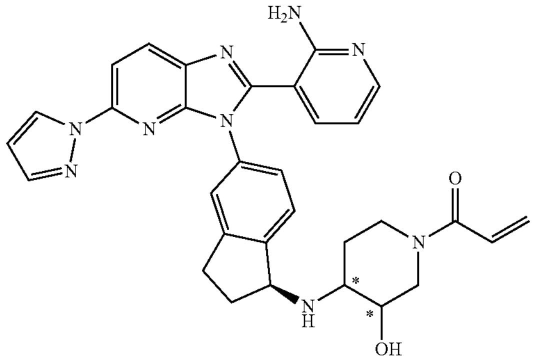 [SMILES: C=CC(=O)N1CCC(N[C@H]2CCc3cc(-n4c(-c5cccnc5N)nc5ccc(-n6cccn6)nc54)ccc32)C(O)C1] |
| 140 | 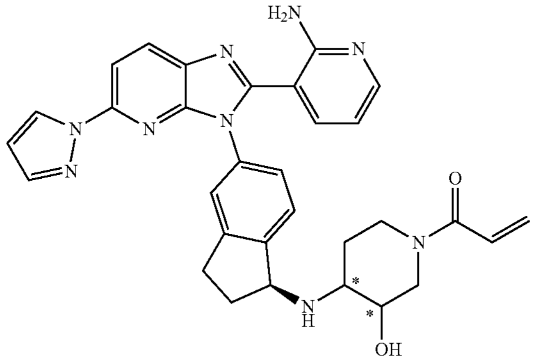 [SMILES: C=CC(=O)N1CCC(N[C@H]2CCc3cc(-n4c(-c5cccnc5N)nc5ccc(-n6cccn6)nc54)ccc32)C(O)C1] |

TABLE 1-continued
Chemical structures of selected compounds.
| Comp. No. | Structure |
|---|---|
| 141 | 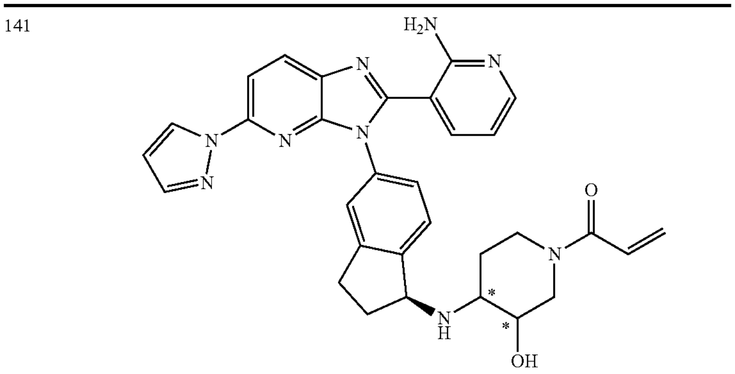 |
| 142 | 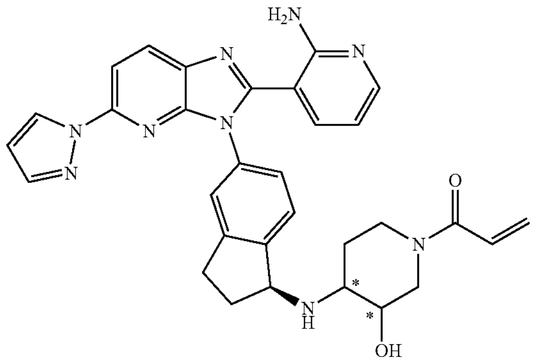 [SMILES: C=CC(=O)N1CCC(N[C@H]2CCc3cc(-n4c(-c5cccnc5N)nc5ccc(-n6cccn6)nc54)ccc32)C(O)C1] |
| 143 | 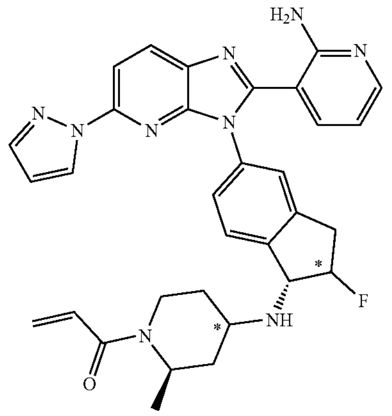 [SMILES: C=CC(=O)N1CCC(N[C@@H]2c3ccc(-n4c(-c5cccnc5N)nc5ccc(-n6cccn6)nc54)cc3CC2F)C[C@H]1C] |
| 144 | 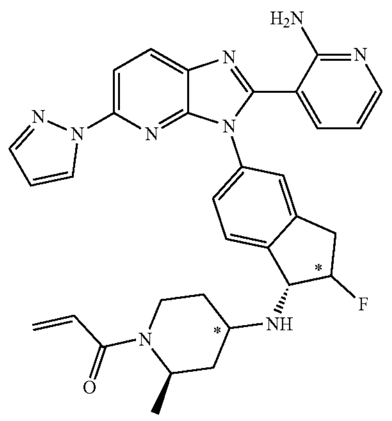 [SMILES: C=CC(=O)N1CCC(N[C@@H]2c3ccc(-n4c(-c5cccnc5N)nc5ccc(-n6cccn6)nc54)cc3CC2F)C[C@H]1C] |

TABLE 1-continued
| Chemical structures of selected compounds. | |
|---|---|
| Comp. No. | Structure |
| 145 | 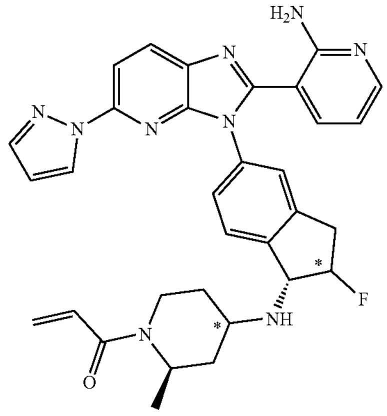 [SMILES: C=CC(=O)N1CCC(N[C@@H]2c3ccc(-n4c(-c5cccnc5N)nc5ccc(-n6cccn6)nc54)cc3CC2F)C[C@H]1C] |
| 146 | 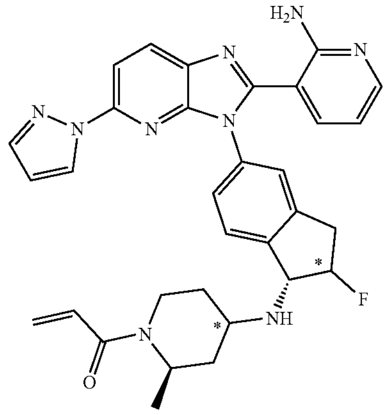 [SMILES: C=CC(=O)N1CCC(N[C@@H]2c3ccc(-n4c(-c5cccnc5N)nc5ccc(-n6cccn6)nc54)cc3CC2F)C[C@H]1C] |
| 147 | 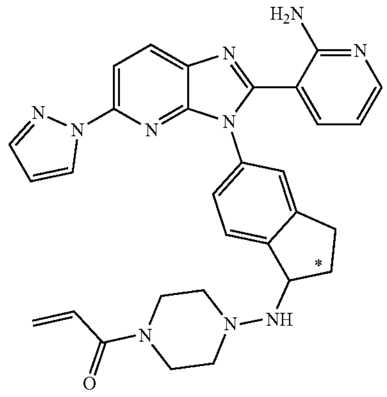 [SMILES: C=CC(=O)N1CCN(NC2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 148 | 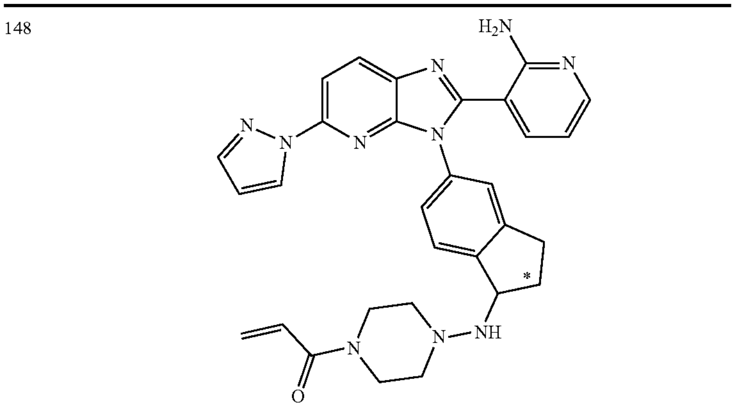 |
| 149 | 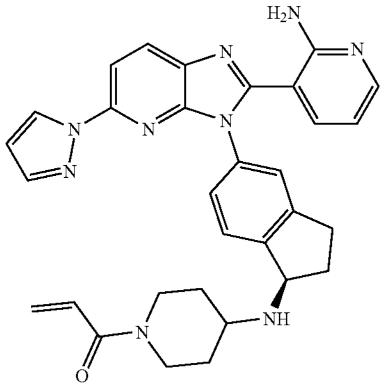 [SMILES: C=CC(=O)N1CCC(N[C@@H]2CCc3cc(-n4c(-c5cccnc5N)nc5ccc(-n6cccn6)nc54)ccc32)CC1] |
| 150 | 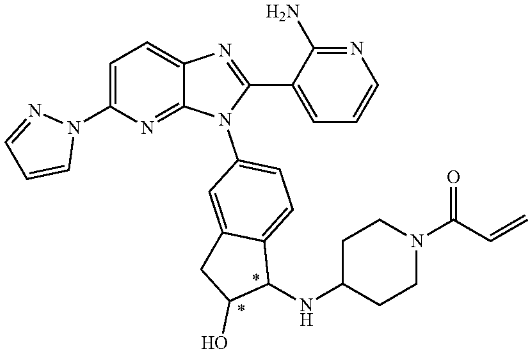 [SMILES: C=CC(=O)N1CCC(NC2c3ccc(-n4c(-c5cccnc5N)nc5ccc(-n6cccn6)nc54)cc3CC2O)CC1] |
| 151 | 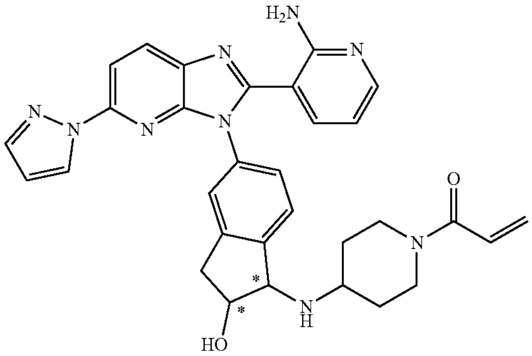 [SMILES: C=CC(=O)N1CCC(NC2c3ccc(-n4c(-c5cccnc5N)nc5ccc(-n6cccn6)nc54)cc3CC2O)CC1] |

TABLE 1-continued
| Chemical structures of selected compounds. | |
|---|---|
| Comp. No. | Structure |
| 152 | 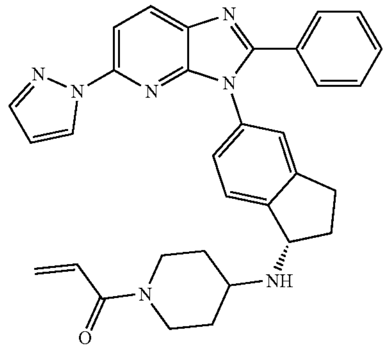 [SMILES: C=CC(=O)N1CCC(N[C@H]2CCc3cc(-n4c(-c5ccccc5)nc5ccc(-n6cccn6)nc54)ccc32)CC1] |
| 153 | 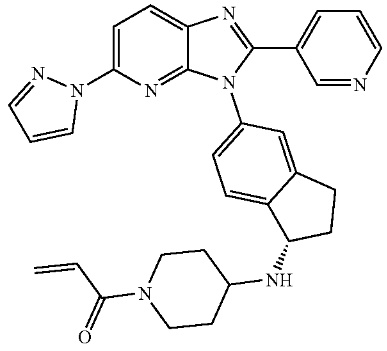 [SMILES: C=CC(=O)N1CCC(N[C@H]2CCc3cc(-n4c(-c5cccnc5)nc5ccc(-n6cccn6)nc54)ccc32)CC1] |
| 154 | 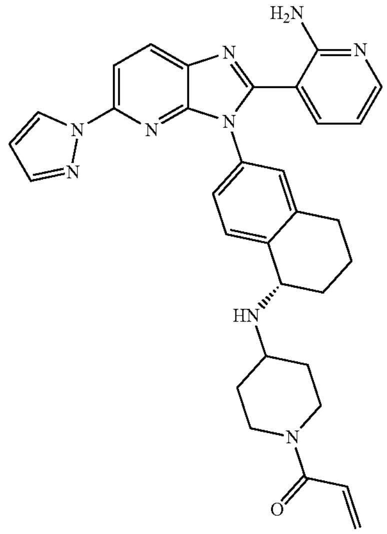 [SMILES: C=CC(=O)N1CCC(N[C@H]2CCCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 155 | 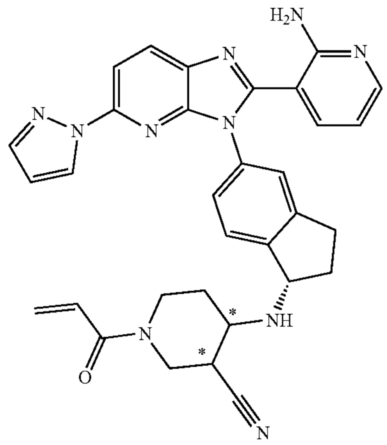 [SMILES: C=CC(=O)N1CCC(N[C@H]2CCc3cc(-n4c(-c5cccnc5N)nc5ccc(-n6cccn6)nc54)ccc32)C(C#N)C1] |
| 156 | 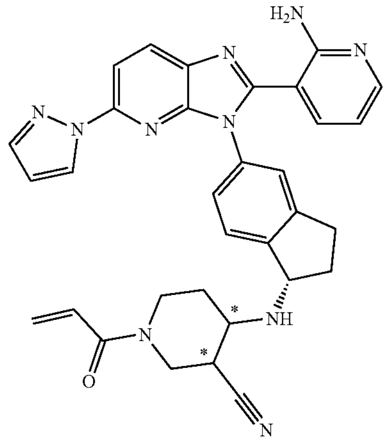 [SMILES: C=CC(=O)N1CCC(N[C@H]2CCc3cc(-n4c(-c5cccnc5N)nc5ccc(-n6cccn6)nc54)ccc32)C(C#N)C1] |
| 157 | 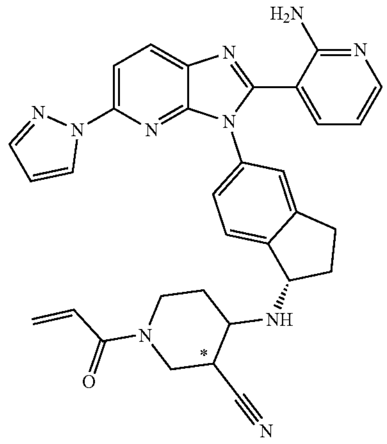 [SMILES: C=CC(=O)N1CCC(N[C@H]2CCc3cc(-n4c(-c5cccnc5N)nc5ccc(-n6cccn6)nc54)ccc32)C(C#N)C1] |

TABLE 1-continued
| Chemical structures of selected compounds. | |
|---|---|
| Comp. No. | Structure |
| 158 | 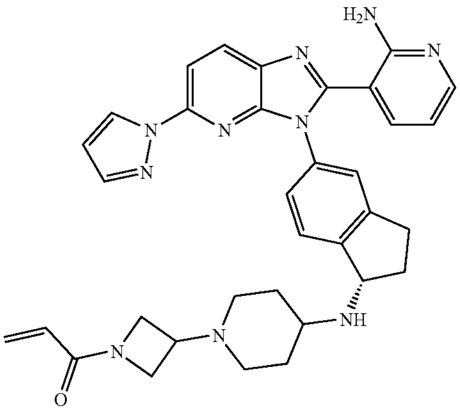 [SMILES: C=CC(=O)N1CC(N2CCC(N[C@H]3CCc4cc(-n5c(-c6cccnc6N)nc6ccc(-n7cccn7)nc65)ccc43)CC2)C1] |
| 159 | 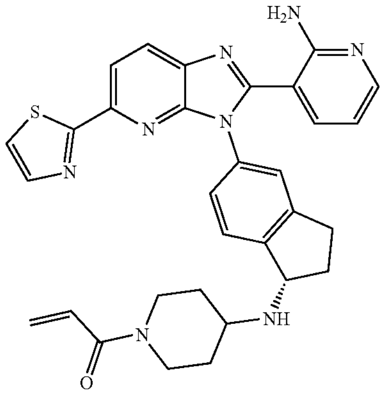 [SMILES: C=CC(=O)N1CCC(N[C@H]2CCc3cc(-n4c(-c5cccnc5N)nc5ccc(-c6nccs6)nc54)ccc32)CC1] |
| 160 | 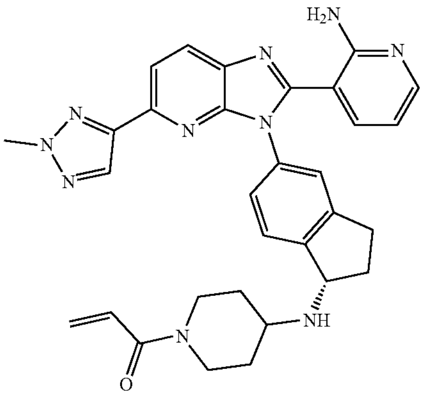 [SMILES: C=CC(=O)N1CCC(N[C@H]2CCc3cc(-n4c(-c5cccnc5N)nc5ccc(-c6cnn(C)n6)nc54)ccc32)CC1] |

TABLE 1-continued
| Comp. No. | Structure |
|---|---|
| Chemical structures of selected compounds. | |
| 161 | 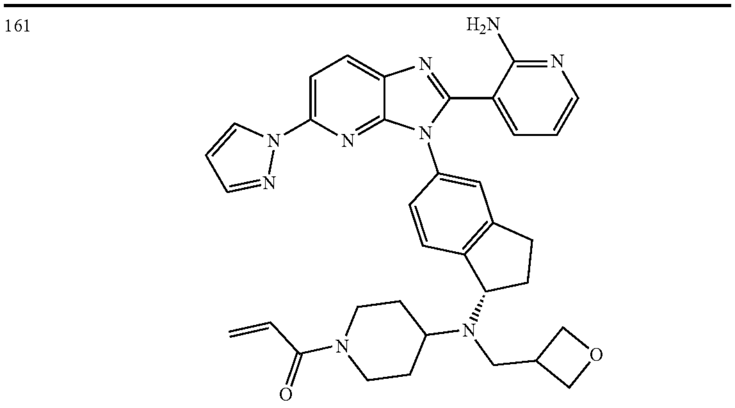 |
| 162 | 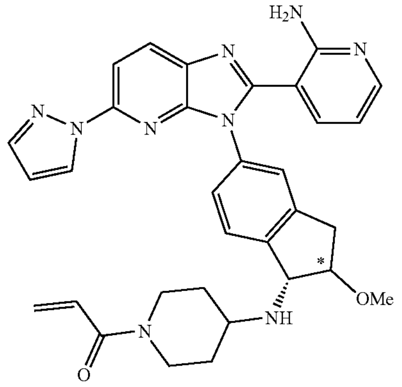 [SMILES: C=CC(=O)N1CCC(N[C@@H]2c3ccc(-n4c(-c5cccnc5N)nc5ccc(-n6cccn6)nc54)cc3CC2OC)CC1] |
| 163 | 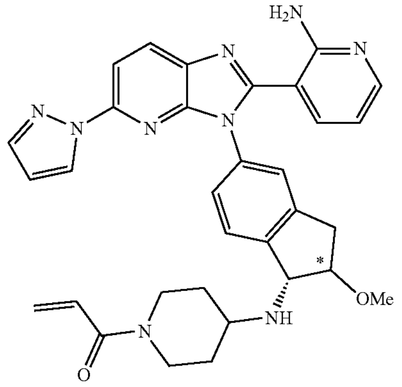 [SMILES: C=CC(=O)N1CCC(N[C@@H]2c3ccc(-n4c(-c5cccnc5N)nc5ccc(-n6cccn6)nc54)cc3CC2OC)CC1] |
| 164 | 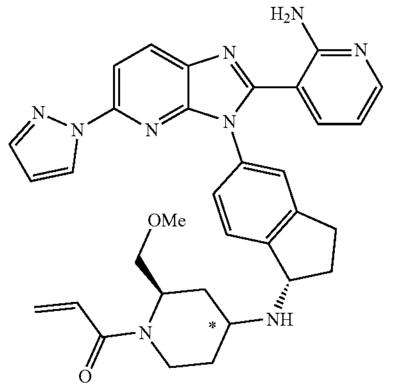 [SMILES: C=CC(=O)N1CCC(N[C@H]2CCc3cc(-n4c(-c5cccnc5N)nc5ccc(-n6cccn6)nc54)ccc32)C[C@@H]1COC] |

TABLE 1-continued
| Chemical structures of selected compounds. | |
|---|---|
| Comp. No. | Structure |
| 165 | 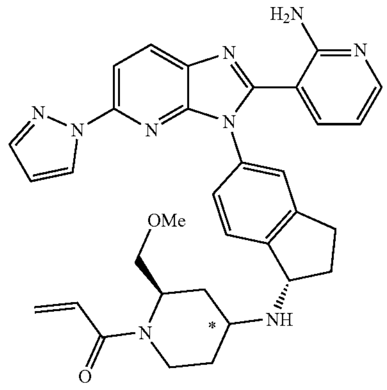 [SMILES: C=CC(=O)N1CCC(N[C@H]2CCc3cc(-n4c(-c5cccnc5N)nc5ccc(-n6cccn6)nc54)ccc32)C[C@@H]1COC] |
| 166 | 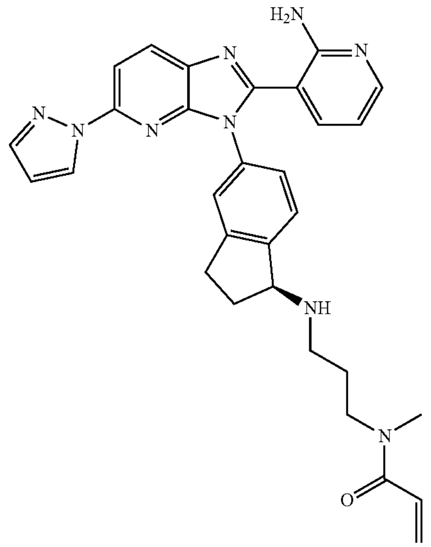 [SMILES: C=CC(=O)N(C)CCCN[C@H]1CCc2cc(-n3c(-c4cccnc4N)nc4ccc(-n5cccn5)nc43)ccc21] |
| 167 | 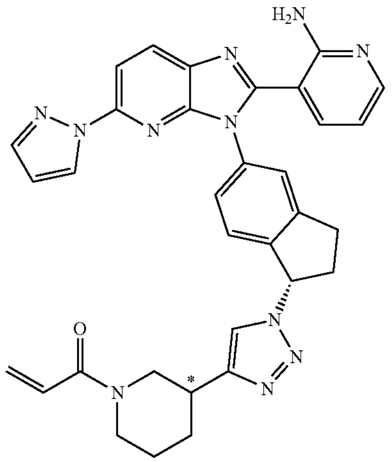 [SMILES: C=CC(=O)N1CCCC(c2cn([C@H]3CCc4cc(-n5c(-c6cccnc6N)nc6ccc(-n7cccn7)nc65)ccc43)nn2)C1] |

TABLE 1-continued
| Chemical structures of selected compounds. | |
|---|---|
| Comp. No. | Structure |
| 168 | 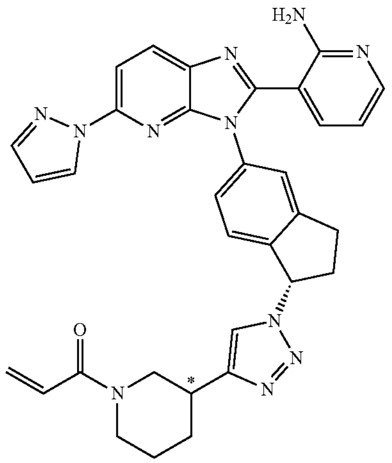 [SMILES: C=CC(=O)N1CCCC(c2cn([C@H]3CCc4cc(-n5c(-c6cccnc6N)nc6ccc(-n7cccn7)nc65)ccc43)nn2)C1] |
| 169 | 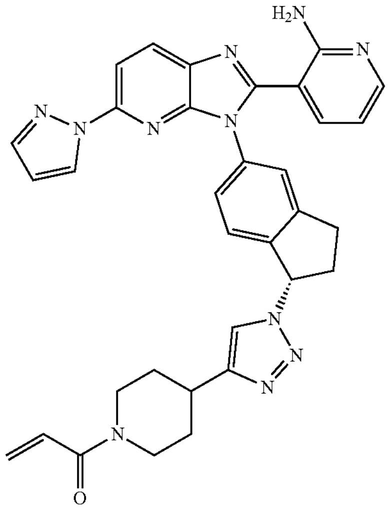 [SMILES: C=CC(=O)N1CCC(c2cn([C@H]3CCc4cc(-n5c(-c6cccnc6N)nc6ccc(-n7cccn7)nc65)ccc43)nn2)CC1] |
| 170 | 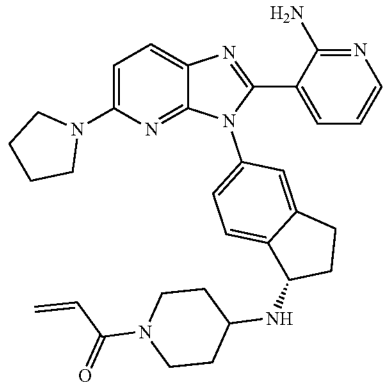 [SMILES: C=CC(=O)N1CCC(N[C@H]2CCc3cc(-n4c(-c5cccnc5N)nc5ccc(N6CCCC6)nc54)ccc32)CC1] |

TABLE 1-continued
| Chemical structures of selected compounds. | |
|---|---|
| Comp. No. | Structure |
| 171 | 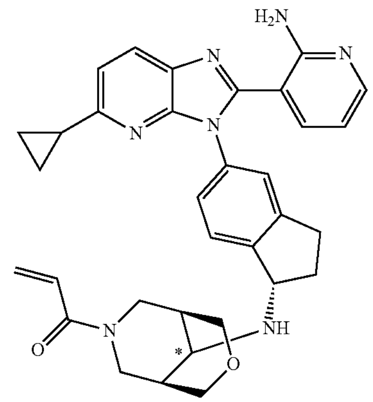 [SMILES: C=CC(=O)N1C[C@H]2COC[C@@H](C1)C2N[C@H]1CCc2cc(-n3c(-c4cccnc4N)nc4ccc(C5CC5)nc43)ccc21] |
| 172 | 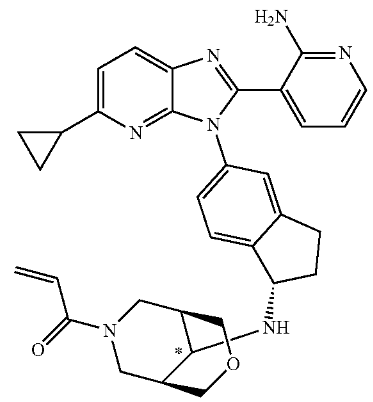 [SMILES: C=CC(=O)N1C[C@H]2COC[C@@H](C1)C2N[C@H]1CCc2cc(-n3c(-c4cccnc4N)nc4ccc(C5CC5)nc43)ccc21] |
| 173 | 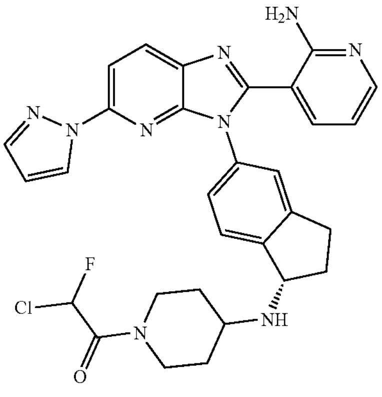 [SMILES: Nc1ncccc1-c1nc2ccc(-n3cccn3)nc2n1-c1ccc2c(c1)CC[C@@H]2NC1CCN(C(=O)C(F)Cl)CC1] |

TABLE 1-continued
| Chemical structures of selected compounds. | |
|---|---|
| Comp. No. | Structure |
| 174 | 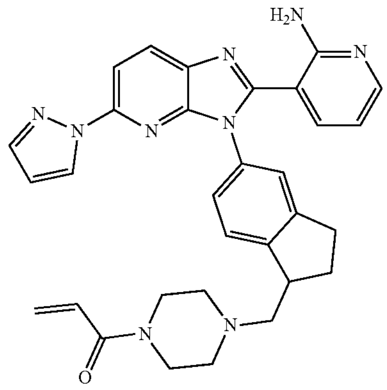 [SMILES: C=CC(=O)N1CCN(CC2CCc3cc(-n4c(-c5cccnc5N)nc5ccc(-n6cccn6)nc54)ccc32)CC1] |
| 175 | 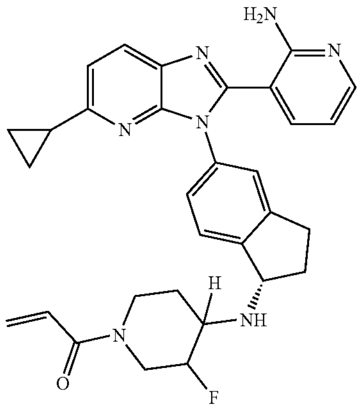 [SMILES: C=CC(=O)N1CCC(N[C@H]2CCc3cc(-n4c(-c5cccnc5N)nc5ccc(C6CC6)nc54)ccc32)C(F)C1] |
| 176 | 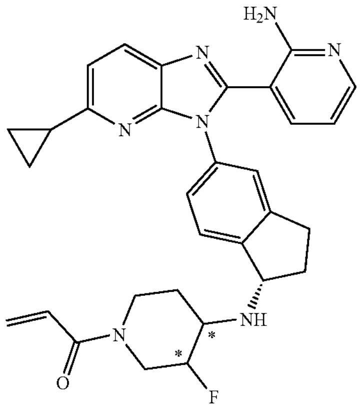 [SMILES: C=CC(=O)N1CCC(N[C@H]2CCc3cc(-n4c(-c5cccnc5N)nc5ccc(C6CC6)nc54)ccc32)C(F)C1] |

TABLE 1-continued
| Chemical structures of selected compounds. | |
|---|---|
| Comp. No. | Structure |
| 177 | 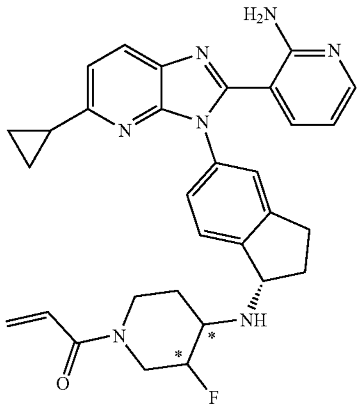 [SMILES: C=CC(=O)N1CCC(N[C@H]2CCc3cc(-n4c(-c5cccnc5N)nc5ccc(C6CC6)nc54)ccc32)C(F)C1] |
| 178 | 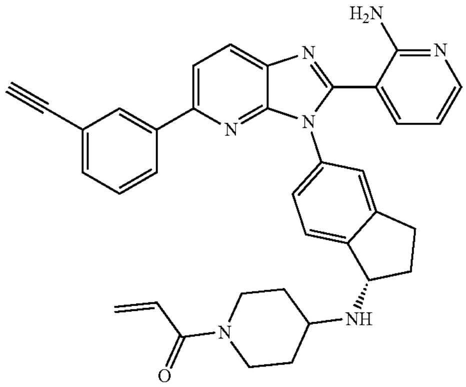 [SMILES: C#Cc1cccc(-c2ccc3nc(-c4cccnc4N)n(-c4ccc5c(c4)CC[C@@H]5NC4CCN(C(=O)C=C)CC4)c3n2)c1] |
| 179 | 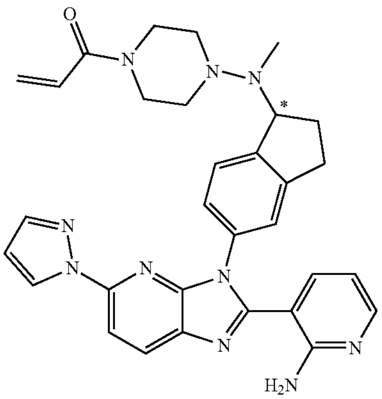 [SMILES: C=CC(=O)N1CCN(N(C)C2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 180 | 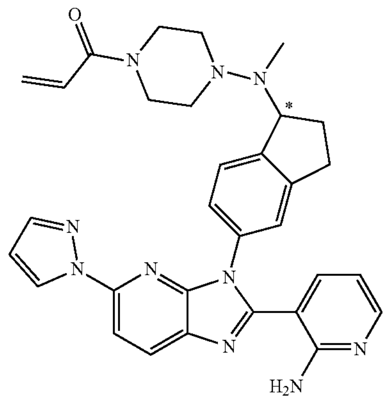 [SMILES: C=CC(=O)N1CCN(N(C)C2CCc3cc(-n4c(-c5cccnc5N)nc5ccc(-n6cccn6)nc54)ccc32)CC1] |
| 181 | 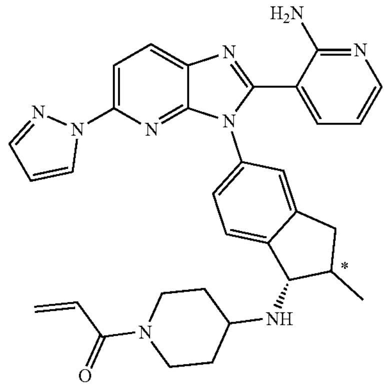 [SMILES: C=CC(=O)N1CCC(N[C@@H]2c3ccc(-n4c(-c5cccnc5N)nc5ccc(-n6cccn6)nc54)cc3CC2C)CC1] |
| 182 | 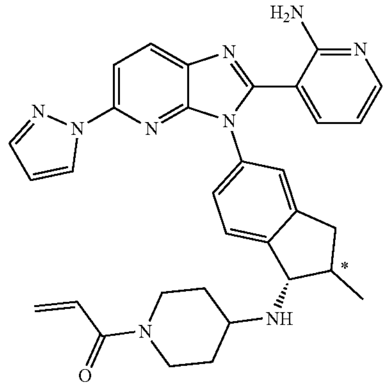 [SMILES: C=CC(=O)N1CCC(N[C@@H]2c3ccc(-n4c(-c5cccnc5N)nc5ccc(-n6cccn6)nc54)cc3CC2C)CC1] |

TABLE 1-continued
| Chemical structures of selected compounds. | |
|---|---|
| Comp. No. | Structure |
| 183 | 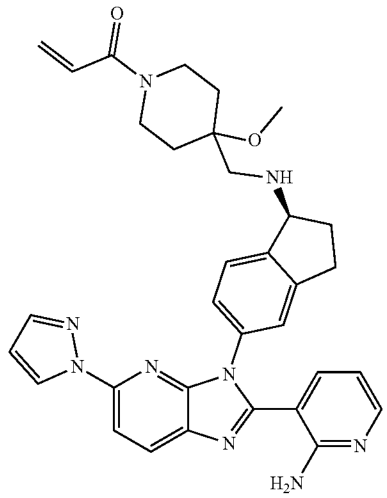 [SMILES: C=CC(=O)N1CCC(CN[C@H]2CCc3cc(-n4c(-c5cccnc5N)nc5ccc(-n6cccn6)nc54)ccc32)(OC)CC1] |
| 184 | 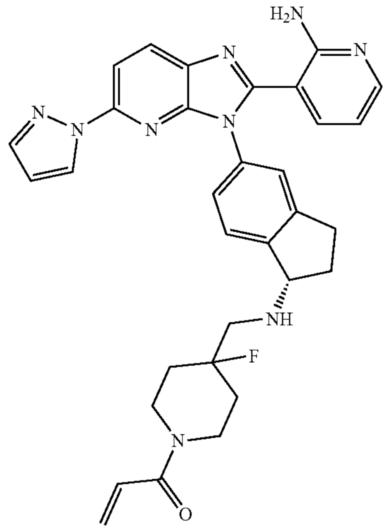 [SMILES: C=CC(=O)N1CCC(F)(CN[C@H]2CCc3cc(-n4c(-c5cccnc5N)nc5ccc(-n6cccn6)nc54)ccc32)CC1] |
| 185 | 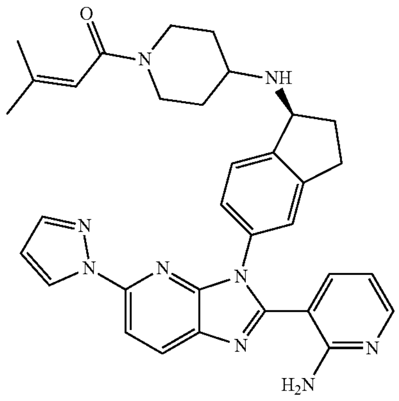 [SMILES: CC(C)=CC(=O)N1CCC(N[C@H]2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 186 | 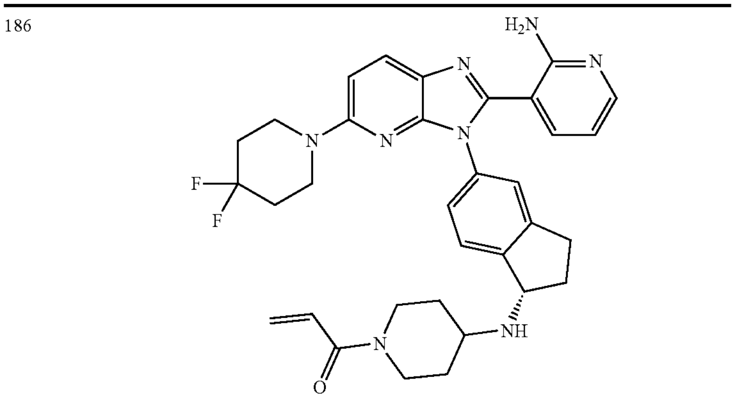 |
| 187 | 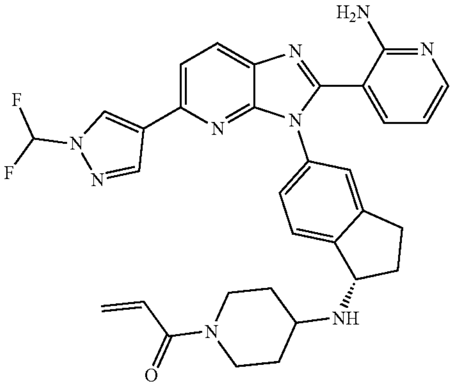 [SMILES: C=CC(=O)N1CCC(N[C@H]2CCc3cc(-n4c(-c5cccnc5N)nc5ccc(-c6cnn(C(F)F)c6)nc54)ccc32)CC1] |
| 188 | 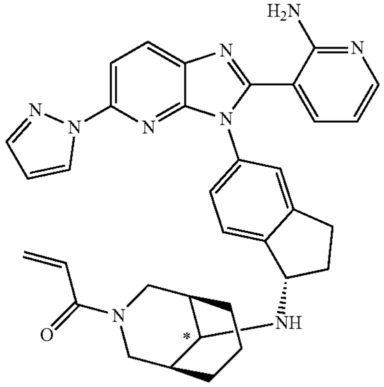 [SMILES: C=CC(=O)N1C[C@H]2CCC[C@@H](C1)C2N[C@H]1CCc2cc(-n3c(-c4cccnc4N)nc4ccc(-n5cccn5)nc43)ccc21] |
| 189 | 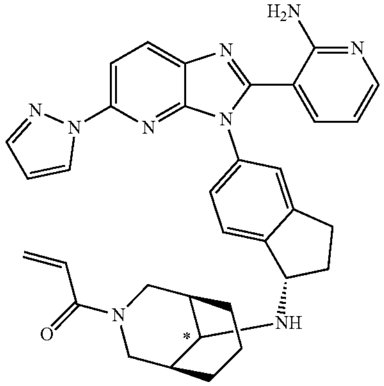 [SMILES: C=CC(=O)N1C[C@H]2CCC[C@@H](C1)C2N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 190 | 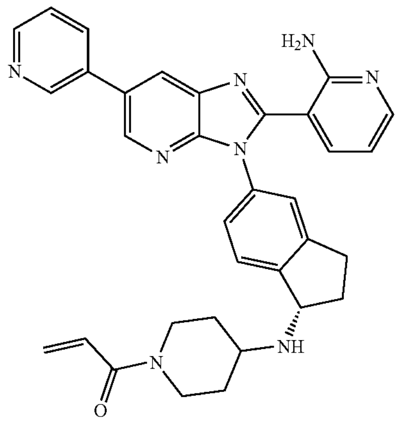 [SMILES: C=CC(=O)N1CCC(N[C@H]2CCc3cc(-n4c(-c5cccnc5N)nc5cc(-c6cccnc6)cnc54)ccc32)CC1] |
| 191 | 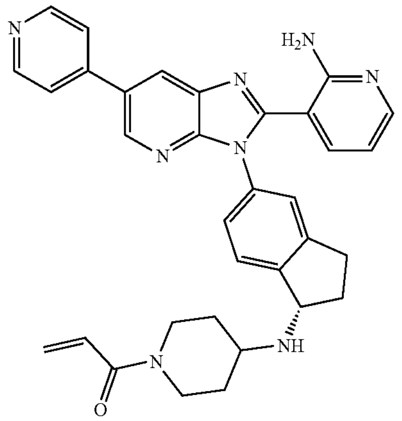 [SMILES: C=CC(=O)N1CCC(N[C@H]2CCc3cc(-n4c(-c5cccnc5N)nc5cc(-c6ccncc6)cnc54)ccc32)CC1] |
| 192 | 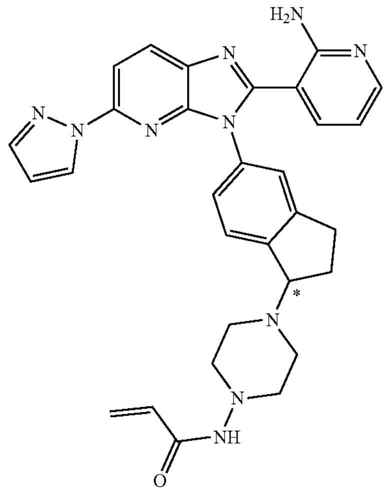 [SMILES: C=CC(=O)NN1CCN(C2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 193 | 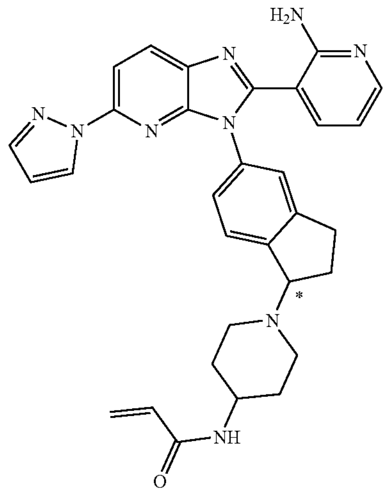 [SMILES: C=CC(=O)NC1CCN(C2CCc3cc(-n4c(-c5cccnc5N)nc5ccc(-n6cccn6)nc54)ccc32)CC1] |
| 194 | 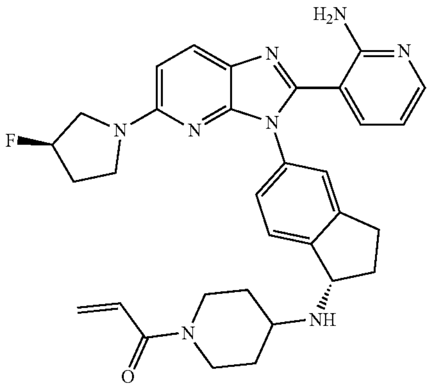 [SMILES: C=CC(=O)N1CCC(N[C@H]2CCc3cc(-n4c(-c5cccnc5N)nc5ccc(N6CC[C@@H](F)C6)nc54)ccc32)CC1] |
| 195 | 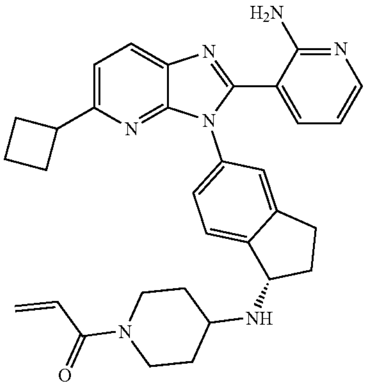 [SMILES: C=CC(=O)N1CCC(N[C@H]2CCc3cc(-n4c(-c5cccnc5N)nc5ccc(C6CCC6)nc54)ccc32)CC1] |

TABLE 1-continued
| Chemical structures of selected compounds. | |
|---|---|
| Comp. No. | Structure |
| 196 | 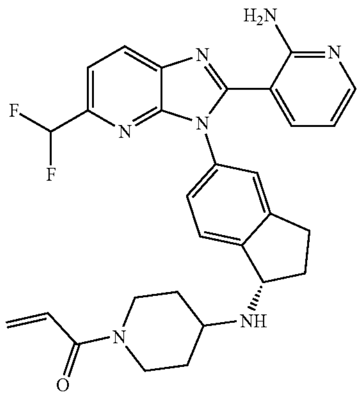 [SMILES: C=CC(=O)N1CCC(N[C@H]2CCc3cc(-n4c(-c5cccnc5N)nc5ccc(C(F)F)nc54)ccc32)CC1] |
| 197 | 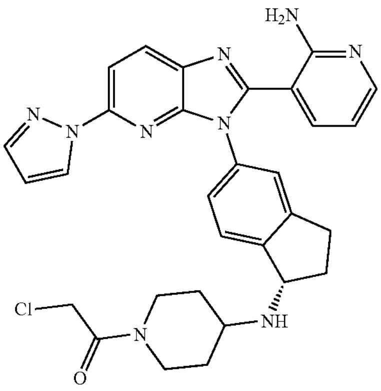 [SMILES: Nc1ncccc1-c1nc2ccc(-n3cccn3)nc2n1-c1ccc2c(c1)CC[C@@H]2NC1CCN(C(=O)CCl)CC1] |
| 198 | 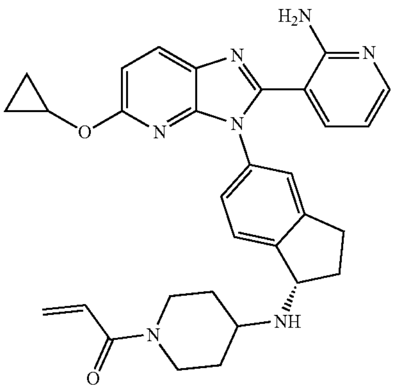 [SMILES: C=CC(=O)N1CCC(N[C@H]2CCc3cc(-n4c(-c5cccnc5N)nc5ccc(OC6CC6)nc54)ccc32)CC1] |

TABLE 1-continued
| Chemical structures of selected compounds. | |
|---|---|
| Comp. No. | Structure |
| 199 | 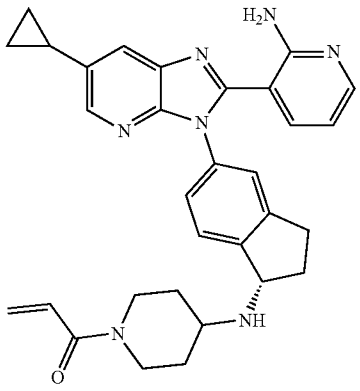 [SMILES: C=CC(=O)N1CCC(N[C@H]2CCc3cc(-n4c(-c5cccnc5N)nc5cc(C6CC6)cnc54)ccc32)CC1] |
| 200 | 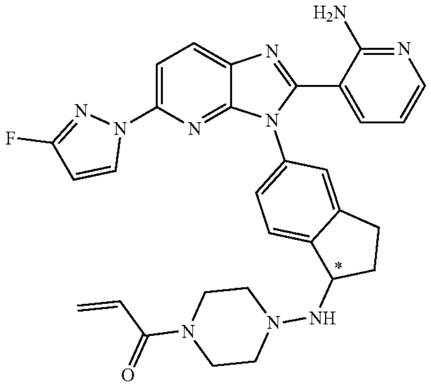 [SMILES: C=CC(=O)N1CCN(NC2CCc3cc(-n4c(-c5cccnc5N)nc5ccc(-n6ccc(F)n6)nc54)ccc32)CC1] |
| 201 | 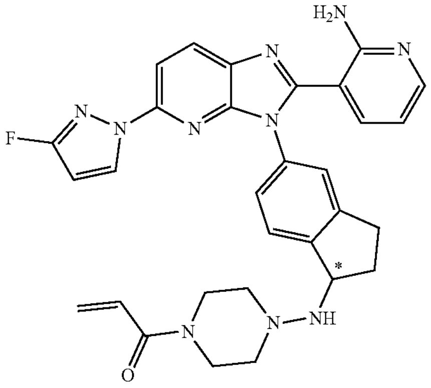 [SMILES: C=CC(=O)N1CCN(NC2CCc3cc(-n4c(-c5cccnc5N)nc5ccc(-n6ccc(F)n6)nc54)ccc32)CC1] |

TABLE 1-continued
| Chemical structures of selected compounds. | |
|---|---|
| Comp. No. | Structure |
| 202 | 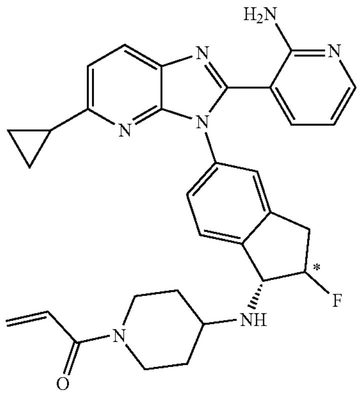 [SMILES: C=CC(=O)N1CCC(N[C@@H]2c3ccc(-n4c(-c5cccnc5N)nc5ccc(C6CC6)nc54)cc3CC2F)CC1] |
| 203 | 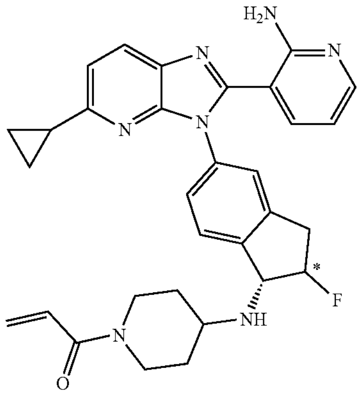 [SMILES: C=CC(=O)N1CCC(N[C@@H]2c3ccc(-n4c(-c5cccnc5N)nc5ccc(C6CC6)nc54)cc3CC2F)CC1] |
| 204 | 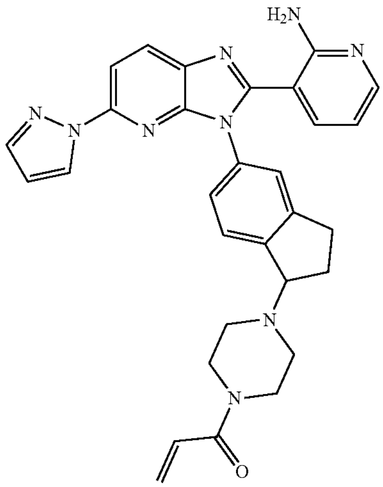 [SMILES: C=CC(=O)N1CCN(C2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 205 | 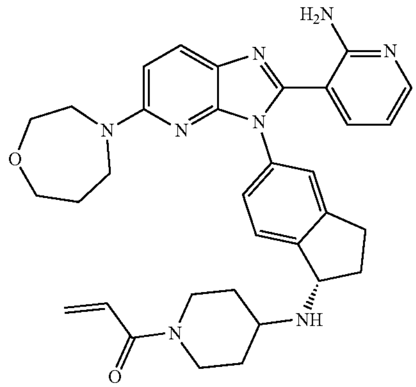 [SMILES: C=CC(=O)N1CCC(N[C@H]2CCc3cc(-n4c(-c5cccnc5N)nc5ccc(N6CCCOCC6)nc54)ccc32)CC1] |
| 206 | 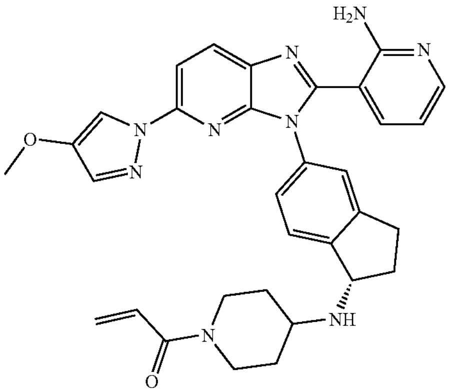 [SMILES: C=CC(=O)N1CCC(N[C@H]2CCc3cc(-n4c(-c5cccnc5N)nc5ccc(-n6cc(OC)cn6)nc54)ccc32)CC1] |
| 207 | 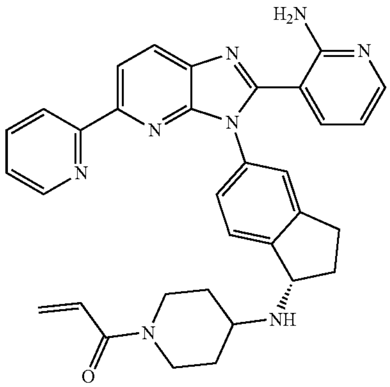 [SMILES: C=CC(=O)N1CCC(N[C@H]2CCc3cc(-n4c(-c5cccnc5N)nc5ccc(-c6ccccn6)nc54)ccc32)CC1] |

TABLE 1-continued
| Chemical structures of selected compounds. | |
|---|---|
| Comp. No. | Structure |
| 208 | 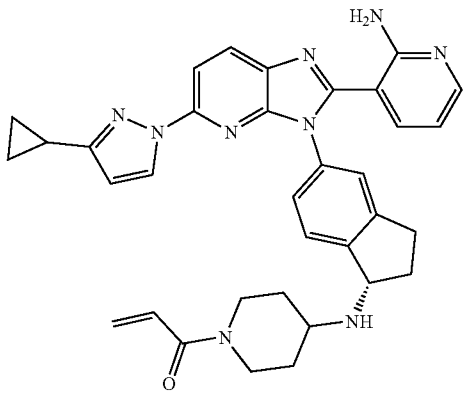 [SMILES: C=CC(=O)N1CCC(N[C@H]2CCc3cc(-n4c(-c5cccnc5N)nc5ccc(-n6ccc(C7CC7)n6)nc54)ccc32)CC1] |
| 209 | 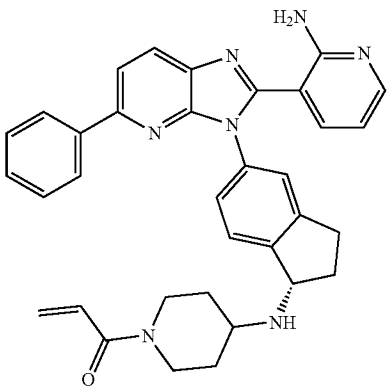 |
| 210 | 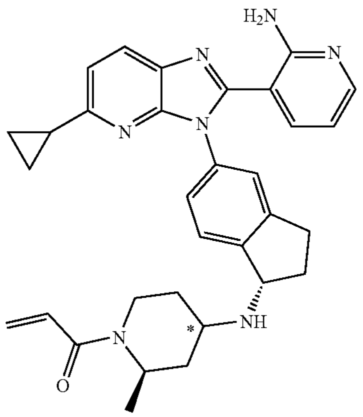 [SMILES: C=CC(=O)N1CCC(N[C@H]2CCc3cc(-n4c(-c5cccnc5N)nc5ccc(C6CC6)nc54)ccc32)C[C@H]1C] |

TABLE 1-continued
| Chemical structures of selected compounds. | |
|---|---|
| Comp. No. | Structure |
| 211 | 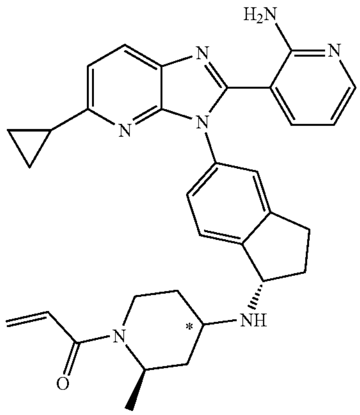 [SMILES: C=CC(=O)N1CCC(N[C@H]2CCc3cc(-n4c(-c5cccnc5N)nc5ccc(C6CC6)nc54)ccc32)C[C@H]1C] |
| 212 | 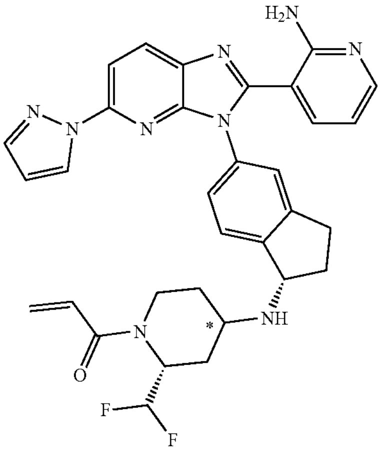 [SMILES: C=CC(=O)N1CCC(N[C@H]2CCc3cc(-n4c(-c5cccnc5N)nc5ccc(-n6cccn6)nc54)ccc32)C[C@@H]1C(F)F] |
| 213 | 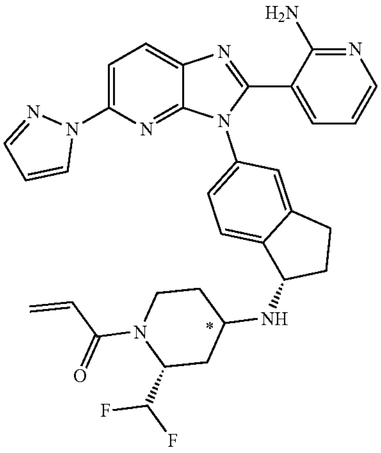 [SMILES: C=CC(=O)N1CCC(N[C@H]2CCc3cc(-n4c(-c5cccnc5N)nc5ccc(-n6cccn6)nc54)ccc32)C[C@@H]1C(F)F] |

TABLE 1-continued
Chemical structures of selected compounds.
| Comp. No. | Structure |
| --- | --- |
| 214 | 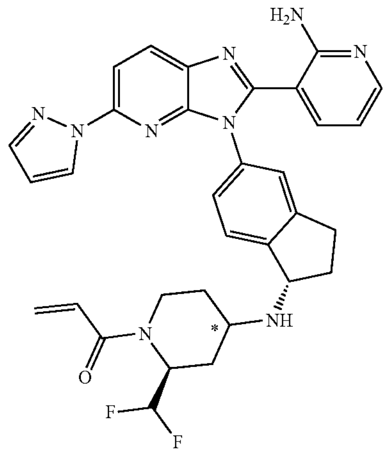 [SMILES: C=CC(=O)N1CCC(N[C@H]2CCc3cc(-n4c(-c5cccnc5N)nc5ccc(-n6cccn6)nc54)ccc32)C[C@H]1C(F)F] |
| 215 | 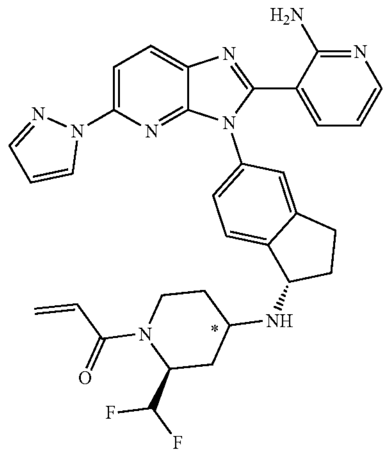 [SMILES: C=CC(=O)N1CCC(N[C@H]2CCc3cc(-n4c(-c5cccnc5N)nc5ccc(-n6cccn6)nc54)ccc32)C[C@H]1C(F)F] |
| 216 | 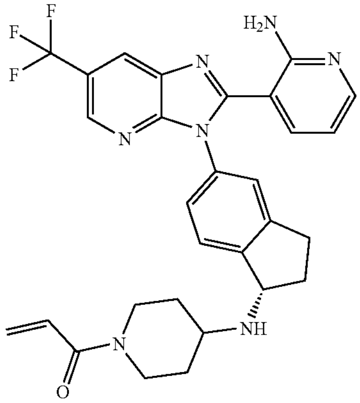 [SMILES: C=CC(=O)N1CCC(N[C@H]2CCc3cc(-n4c(-c5cccnc5N)nc5cc(C(F)(F)F)cnc54)ccc32)CC1] |

TABLE 1-continued
| Chemical structures of selected compounds. | |
|---|---|
| Comp. No. | Structure |
| 217 | 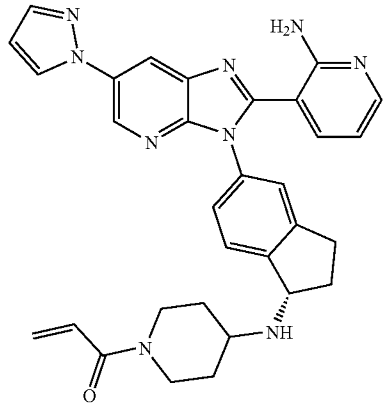 [SMILES: C=CC(=O)N1CCC(N[C@H]2CCc3cc(-n4c(-c5cccnc5N)nc5cc(-n6cccn6)cnc54)ccc32)CC1] |
| 218 | 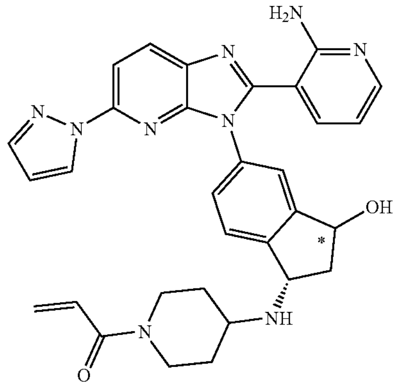 [SMILES: C=CC(=O)N1CCC(N[C@H]2CC(O)c3cc(-n4c(-c5cccnc5N)nc5ccc(-n6cccn6)nc54)ccc32)CC1] |
| 219 | 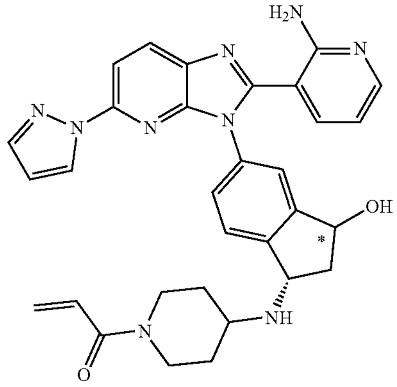 [SMILES: C=CC(=O)N1CCC(N[C@H]2CC(O)c3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 220 | 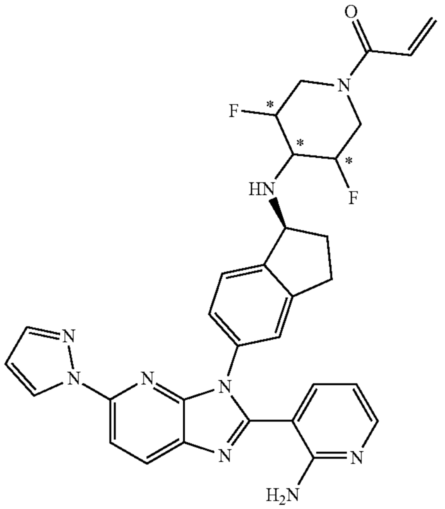 [SMILES: C=CC(=O)N1CC(F)C(N[C@H]2CCc3cc(-n4c(-c5cccnc5N)nc5ccc(-n6cccn6)nc54)ccc32)C(F)C1] |
| 221 | 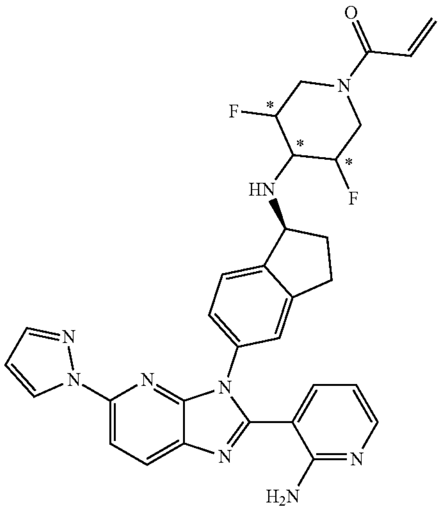 [SMILES: C=CC(=O)N1CC(F)C(N[C@H]2CCc3cc(-n4c(-c5cccnc5N)nc5ccc(-n6cccn6)nc54)ccc32)C(F)C1] |
| 222 | 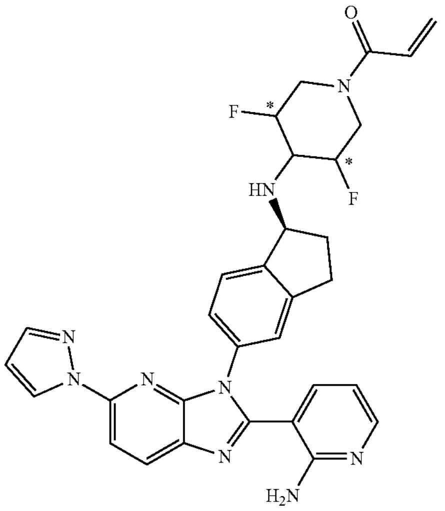 [SMILES: C=CC(=O)N1CC(F)C(N[C@H]2CCc3cc(-n4c(-c5cccnc5N)nc5ccc(-n6cccn6)nc54)ccc32)C(F)C1] |

TABLE 1-continued
| Chemical structures of selected compounds. | |
|---|---|
| Comp. No. | Structure |
| 223 | 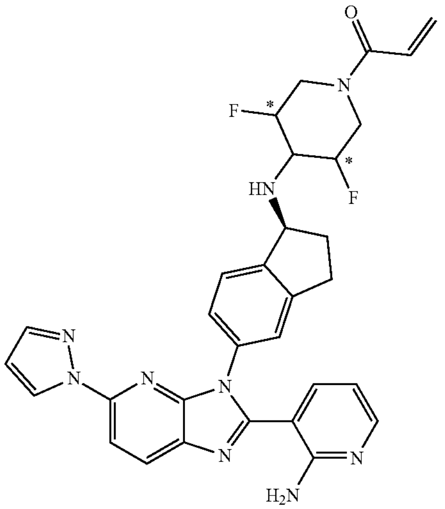 [SMILES: C=CC(=O)N1CC(F)C(N[C@H]2CCc3cc(-n4c(-c5cccnc5N)nc5ccc(-n6cccn6)nc54)ccc32)C(F)C1] |
| 224 | 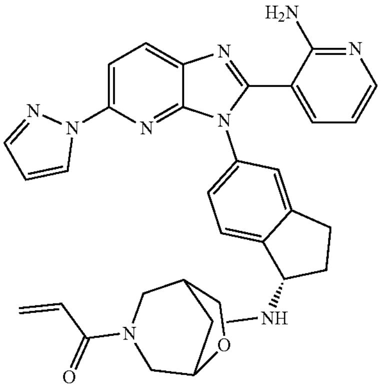 |
| 225 | 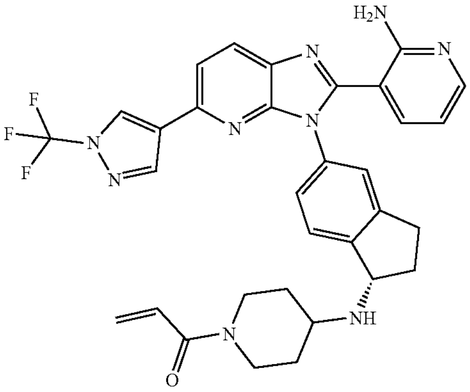 [SMILES: C=CC(=O)N1CCC(N[C@H]2CCc3cc(-n4c(-c5cccnc5N)nc5ccc(-c6cnn(C(F)(F)F)c6)nc54)ccc32)CC1] |

TABLE 1-continued
| Chemical structures of selected compounds. | |
|---|---|
| Comp. No. | Structure |
| 226 | 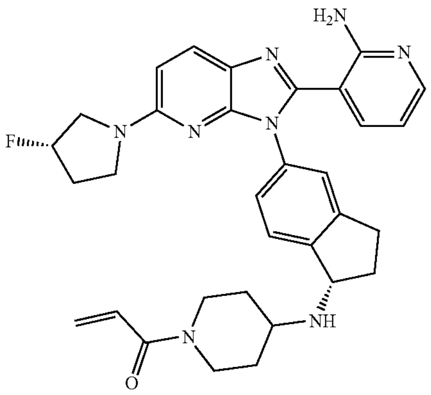 [SMILES: C=CC(=O)N1CCC(N[C@H]2CCc3cc(-n4c(-c5cccnc5N)nc5ccc(N6CC[C@H](F)C6)nc54)ccc32)CC1] |
| 227 | 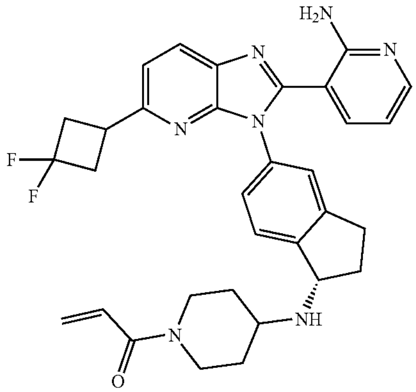 [SMILES: C=CC(=O)N1CCC(N[C@H]2CCc3cc(-n4c(-c5cccnc5N)nc5ccc(C6CC(F)(F)C6)nc54)ccc32)CC1] |
| 228 | 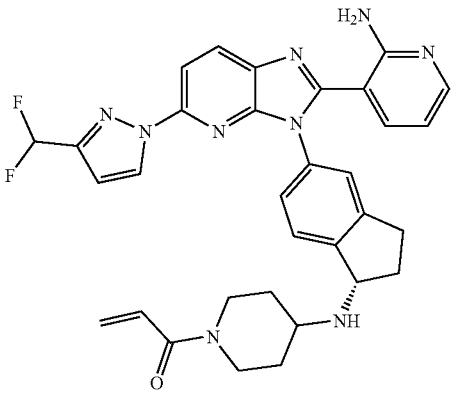 [SMILES: C=CC(=O)N1CCC(N[C@H]2CCc3cc(-n4c(-c5cccnc5N)nc5ccc(-n6ccc(C(F)F)n6)nc54)ccc32)CC1] |

TABLE 1-continued
| Chemical structures of selected compounds. | |
|---|---|
| Comp. No. | Structure |
| 229 | 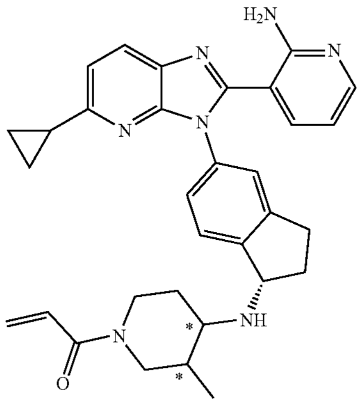 [SMILES: C=CC(=O)N1CCC(N[C@H]2CCc3cc(-n4c(-c5cccnc5N)nc5ccc(C6CC6)nc54)ccc32)C(C)C1] |
| 230 | 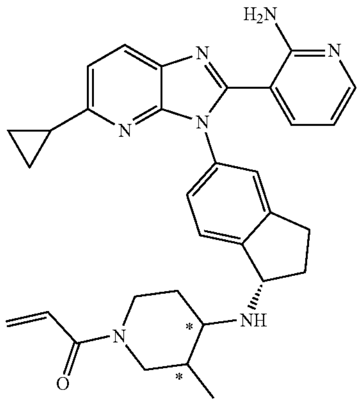 [SMILES: C=CC(=O)N1CCC(N[C@H]2CCc3cc(-n4c(-c5cccnc5N)nc5ccc(C6CC6)nc54)ccc32)C(C)C1] |
| 231 | 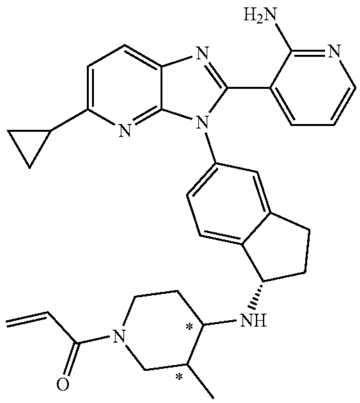 [SMILES: C=CC(=O)N1CCC(N[C@H]2CCc3cc(-n4c(-c5cccnc5N)nc5ccc(C6CC6)nc54)ccc32)C(C)C1] |

TABLE 1-continued
| Comp. No. | Structure |
|---|---|
| Chemical structures of selected compounds. | |
| 232 | 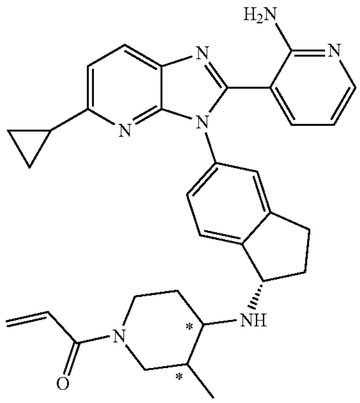 [SMILES: C=CC(=O)N1CCC(N[C@H]2CCc3cc(-n4c(-c5cccnc5N)nc5ccc(C6CC6)nc54)ccc32)C(C)C1] |
| 233 | 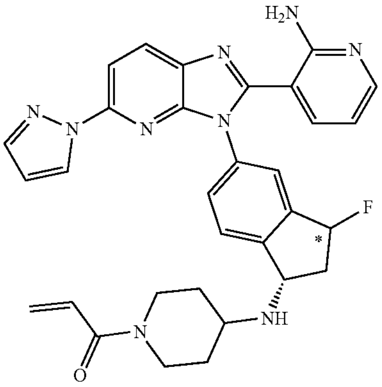 [SMILES: C=CC(=O)N1CCC(N[C@H]2CC(F)c3cc(-n4c(-c5cccnc5N)nc5ccc(-n6cccn6)nc54)ccc32)CC1] |
| 234 | 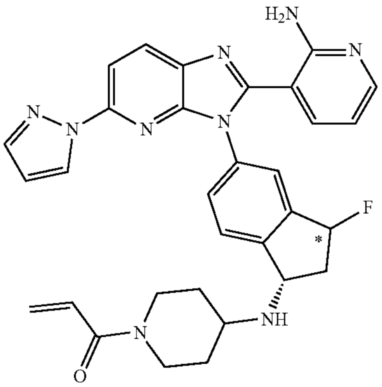 [SMILES: C=CC(=O)N1CCC(N[C@H]2CC(F)c3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 235 | 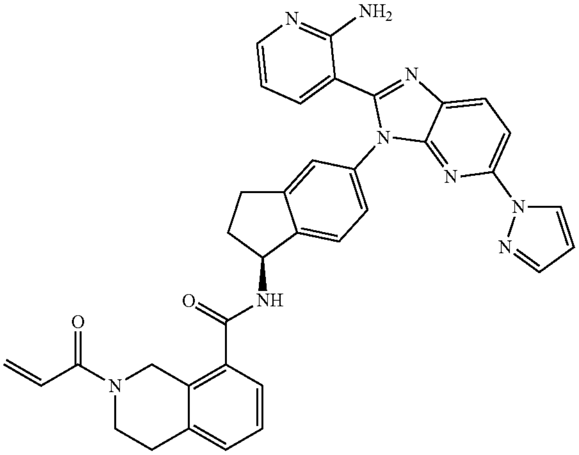 [SMILES: C=CC(=O)N1CCc2cccc(C(=O)N[C@H]3CCc4cc(-n5c(-c6cccnc6N)nc6ccc(-n7cccn7)nc65)ccc43)c2C1] |
| 236 | 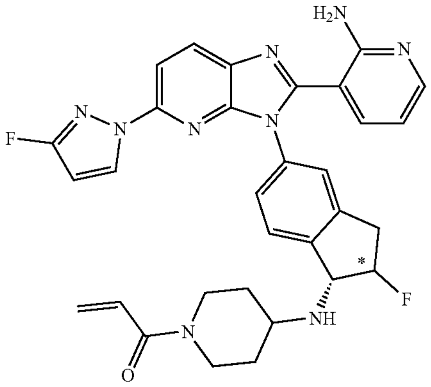 [SMILES: C=CC(=O)N1CCC(N[C@@H]2c3ccc(-n4c(-c5cccnc5N)nc5ccc(-n6ccc(F)n6)nc54)cc3CC2F)CC1] |
| 237 | 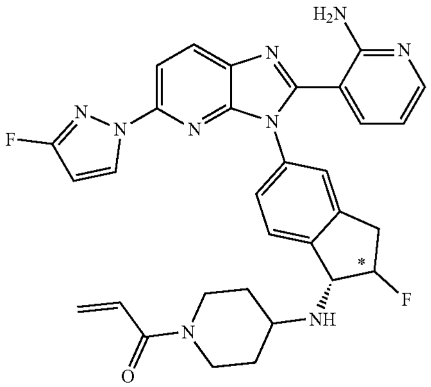 [SMILES: C=CC(=O)N1CCC(N[C@@H]2c3ccc(-n4c(-c5cccnc5N)nc5ccc(-n6ccc(F)n6)nc54)cc3CC2F)CC1] |

TABLE 1-continued
| Chemical structures of selected compounds. | |
|---|---|
| Comp. No. | Structure |
| 238 | 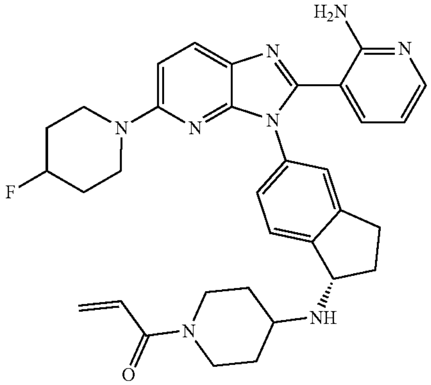 [SMILES: C=CC(=O)N1CCC(N[C@H]2CCc3cc(-n4c(-c5cccnc5N)nc5ccc(N6CCC(F)CC6)nc54)ccc32)CC1] |
| 239 | 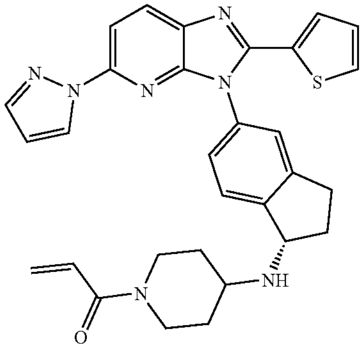 [SMILES: C=CC(=O)N1CCC(N[C@H]2CCc3cc(-n4c(-c5cccs5)nc5ccc(-n6cccn6)nc54)ccc32)CC1] |
| 240 | 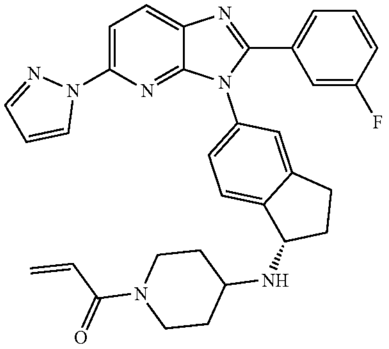 [SMILES: C=CC(=O)N1CCC(N[C@H]2CCc3cc(-n4c(-c5cccc(F)c5)nc5ccc(-n6cccn6)nc54)ccc32)CC1] |
| 241 | 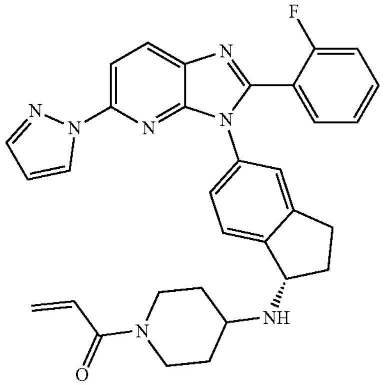 [SMILES: C=CC(=O)N1CCC(N[C@H]2CCc3cc(-n4c(-c5ccccc5F)nc5ccc(-n6cccn6)nc54)ccc32)CC1] |

TABLE 1-continued
| Chemical structures of selected compounds. | |
|---|---|
| Comp. No. | Structure |
| 242 | 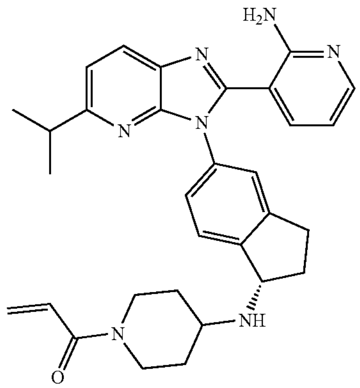 [SMILES: C=CC(=O)N1CCC(N[C@H]2CCc3cc(-n4c(-c5cccnc5N)nc5ccc(C(C)C)nc54)ccc32)CC1] |
| 243 | 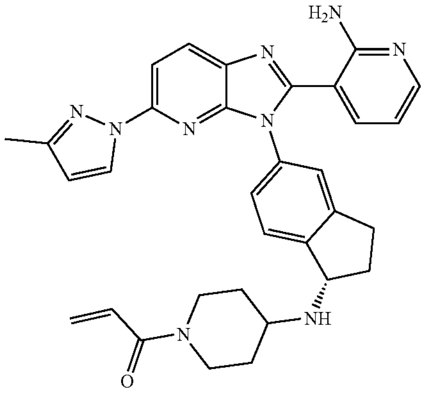 [SMILES: C=CC(=O)N1CCC(N[C@H]2CCc3cc(-n4c(-c5cccnc5N)nc5ccc(-n6ccc(C)n6)nc54)ccc32)CC1] |
| 244 | 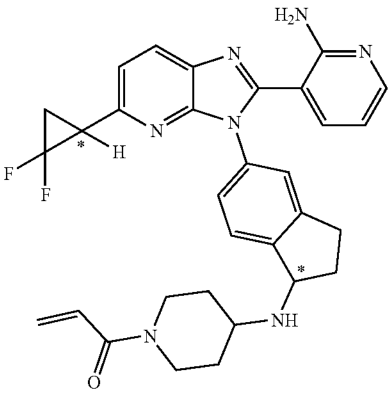 [SMILES: C=CC(=O)N1CCC(NC2CCc3cc(-n4c(-c5cccnc5N)nc5ccc(C6CC6(F)F)nc54)ccc32)CC1] |

TABLE 1-continued
Chemical structures of selected compounds.
| Comp. No. | Structure |
|---|---|
| 245 | 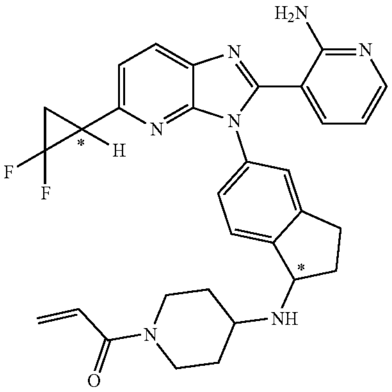 [SMILES: C=CC(=O)N1CCC(NC2CCc3cc(-n4c(-c5cccnc5N)nc5ccc(C6CC6(F)F)nc54)ccc32)CC1] |
| 246 | 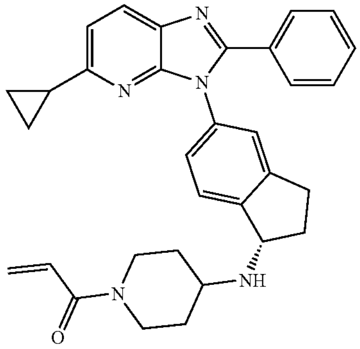 [SMILES: C=CC(=O)N1CCC(N[C@H]2CCc3cc(-n4c(-c5ccccc5)nc5ccc(C6CC6)nc54)ccc32)CC1] |
| 247 | 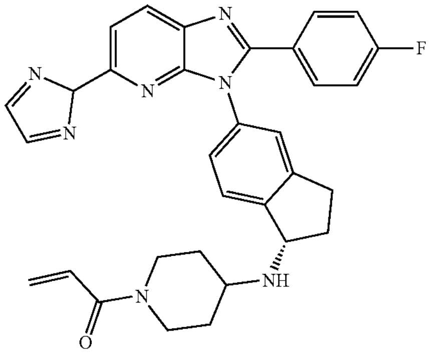 [SMILES: C=CC(=O)N1CCC(N[C@H]2CCc3cc(-n4c(-c5ccc(F)cc5)nc5ccc(C6N=CC=N6)nc54)ccc32)CC1] |
| 248 | 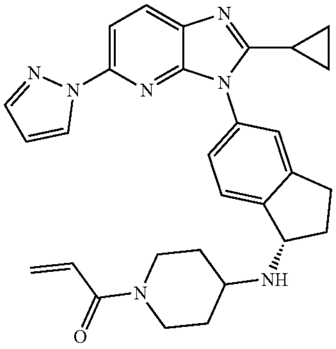 [SMILES: C=CC(=O)N1CCC(N[C@H]2CCc3cc(-n4c(C5CC5)nc5ccc(-n6cccn6)nc54)ccc32)CC1] |

TABLE 1-continued
| Chemical structures of selected compounds. | |
|---|---|
| Comp. No. | Structure |
| 249 | 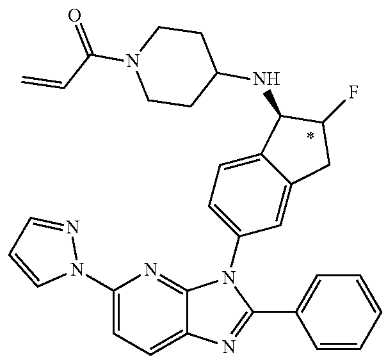 [SMILES: C=CC(=O)N1CCC(N[C@@H]2c3ccc(-n4c(-c5ccccc5)nc5ccc(-n6cccn6)nc54)cc3CC2F)CC1] |
| 250 | 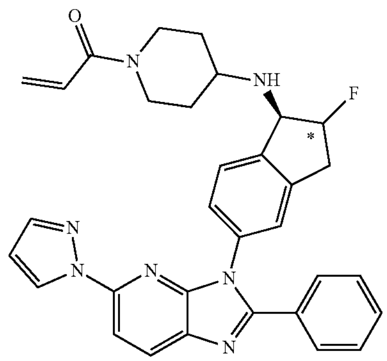 [SMILES: C=CC(=O)N1CCC(N[C@@H]2c3ccc(-n4c(-c5ccccc5)nc5ccc(-n6cccn6)nc54)cc3CC2F)CC1] |
| 251 | 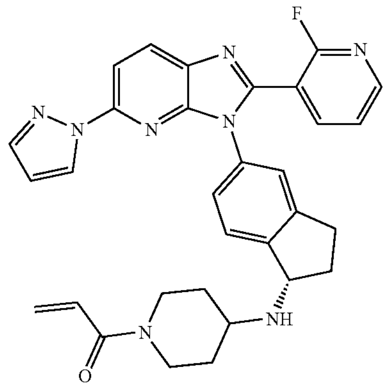 [SMILES: C=CC(=O)N1CCC(N[C@H]2CCc3cc(-n4c(-c5cccnc5F)nc5ccc(-n6cccn6)nc54)ccc32)CC1] |
| 252 | 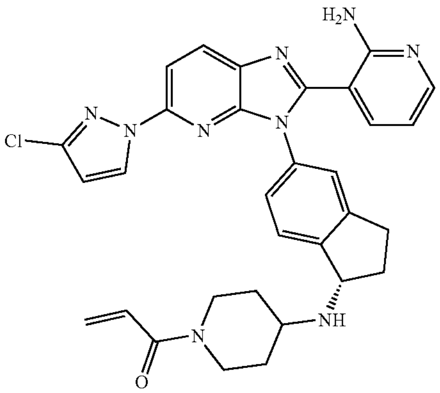 [SMILES: C=CC(=O)N1CCC(N[C@H]2CCc3cc(-n4c(-c5cccnc5N)nc5ccc(-n6ccc(Cl)n6)nc54)ccc32)CC1] |

TABLE 1-continued
| Chemical structures of selected compounds. | |
|---|---|
| Comp. No. | Structure |
| 253 | 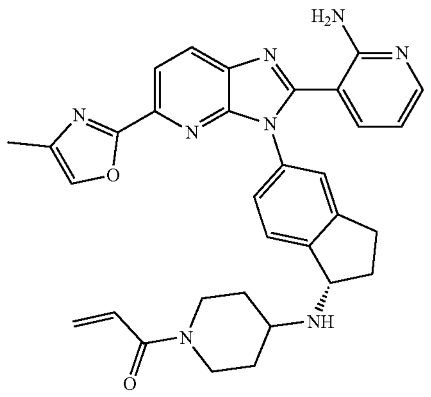 [SMILES: C=CC(=O)N1CCC(N[C@H]2CCc3cc(-n4c(-c5cccnc5N)nc5ccc(-c6nc(C)co6)nc54)ccc32)CC1] |
| 254 | 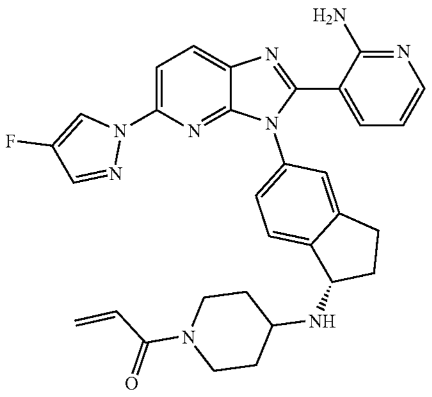 [SMILES: C=CC(=O)N1CCC(N[C@H]2CCc3cc(-n4c(-c5cccnc5N)nc5ccc(-n6cc(F)cn6)nc54)ccc32)CC1] |
| 255 | 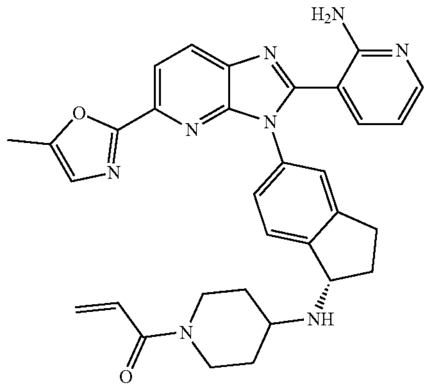 [SMILES: C=CC(=O)N1CCC(N[C@H]2CCc3cc(-n4c(-c5cccnc5N)nc5ccc(-c6ncc(C)o6)nc54)ccc32)CC1] |

TABLE 1-continued
| Comp. No. | Structure |
|---|---|
| 256 | 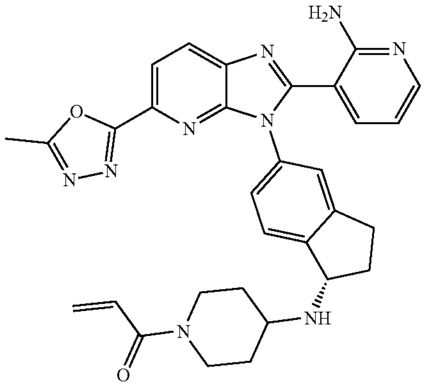 |
| 257 | 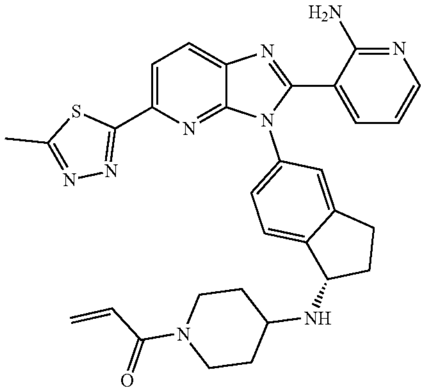 [SMILES: C=CC(=O)N1CCC(N[C@H]2CCc3cc(-n4c(-c5cccnc5N)nc5ccc(-c6nnc(C)s6)nc54)ccc32)CC1] |
| 258 | 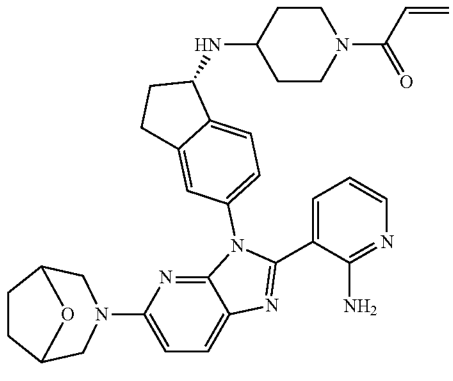 [SMILES: C=CC(=O)N1CCC(N[C@H]2CCc3cc(-n4c(-c5cccnc5N)nc5ccc(N6CC7CCC(C6)O7)nc54)ccc32)CC1] |
| 259 | 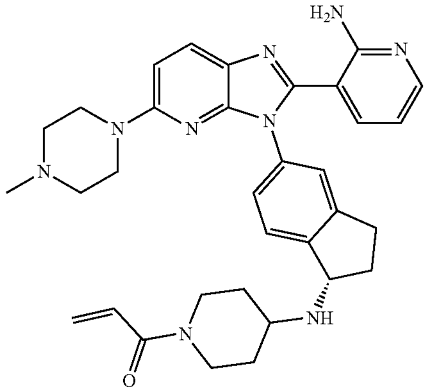 [SMILES: C=CC(=O)N1CCC(N[C@H]2CCc3cc(-n4c(-c5cccnc5N)nc5ccc(N6CCN(C)CC6)nc54)ccc32)CC1] |
Chemical structures of selected compounds.

TABLE 1-continued
| Chemical structures of selected compounds. | |
|---|---|
| Comp. No. | Structure |
| 260 | 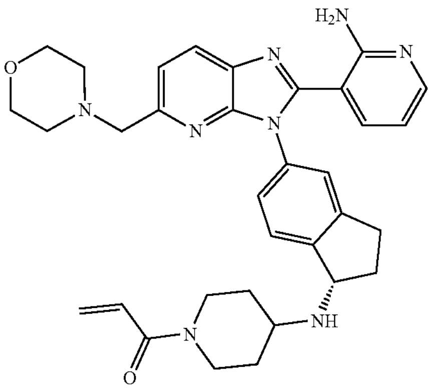 [SMILES: C=CC(=O)N1CCC(N[C@H]2CCc3cc(-n4c(-c5cccnc5N)nc5ccc(CN6CCOCC6)nc54)ccc32)CC1] |
| 261 | 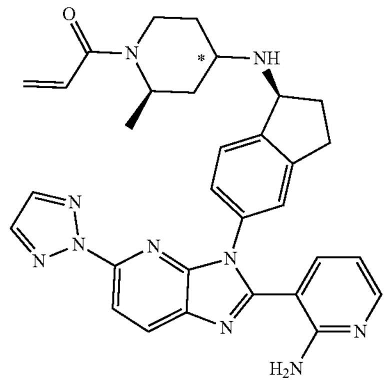 [SMILES: C=CC(=O)N1CCC(N[C@H]2CCc3cc(-n4c(-c5cccnc5N)nc5ccc(-n6nccn6)nc54)ccc32)C[C@H]1C] |
| 262 | 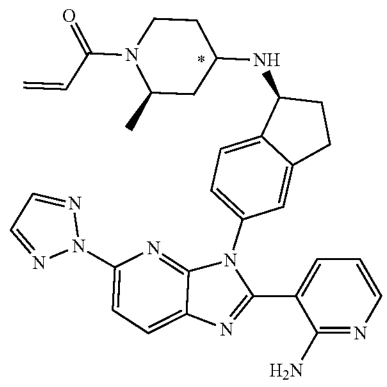 [SMILES: C=CC(=O)N1CCC(N[C@H]2CCc3cc(-n4c(-c5cccnc5N)nc5ccc(-n6nccn6)nc54)ccc32)C[C@H]1C] |

TABLE 1-continued
| Chemical structures of selected compounds. | |
|---|---|
| Comp. No. | Structure |
| 263 | 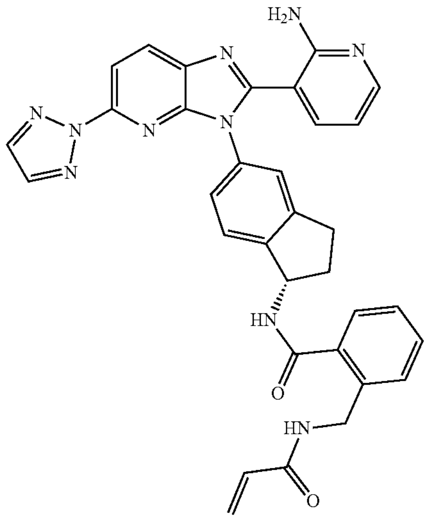 [SMILES: C=CC(=O)NCc1ccccc1C(=O)N[C@H]1CCc2cc(-n3c(-c4cccnc4N)nc4ccc(-n5nccn5)nc43)ccc21] |
| 264 | 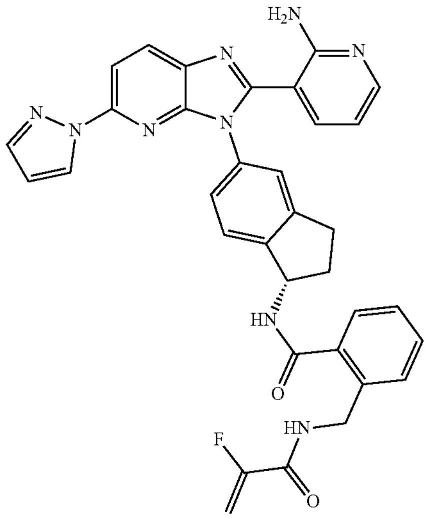 [SMILES: C=C(F)C(=O)NCc1ccccc1C(=O)N[C@H]1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 265 | 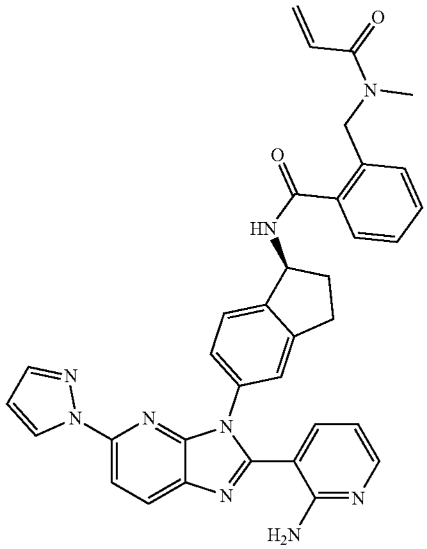 [SMILES: C=CC(=O)N(C)Cc1ccccc1C(=O)N[C@H]1CCc2cc(-n3c(-c4cccnc4N)nc4ccc(-n5cccn5)nc43)ccc21] |
| 266 | 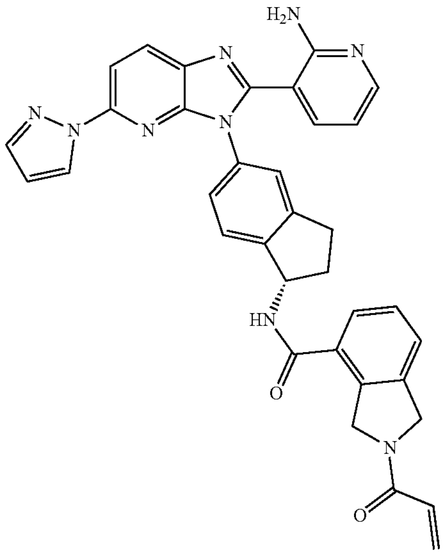 [SMILES: C=CC(=O)N1Cc2cccc(C(=O)N[C@H]3CCc4cc(-n5c(-c6cccnc6N)nc6ccc(-n7cccn7)nc65)ccc43)c2C1] |

TABLE 1-continued
| Chemical structures of selected compounds. | |
|---|---|
| Comp. No. | Structure |
| 267 | 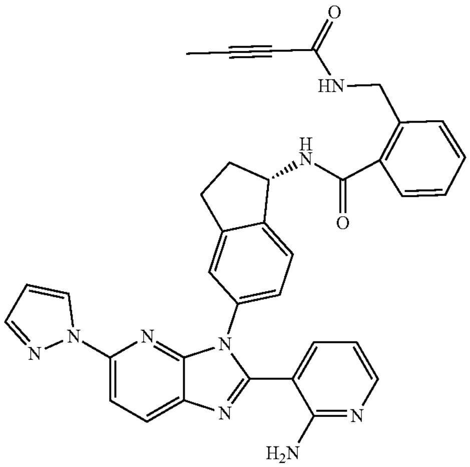 [SMILES: CC#CC(=O)NCc1ccccc1C(=O)N[C@H]1CCc2cc(-n3c(-c4cccnc4N)nc4ccc(-n5cccn5)nc43)ccc21] |
| 268 | 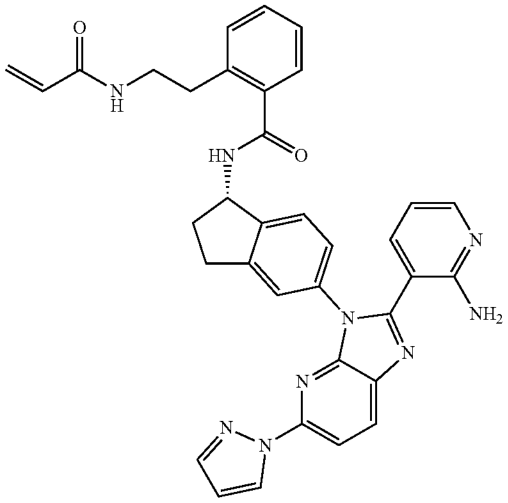 [SMILES: C=CC(=O)NCCc1ccccc1C(=O)N[C@H]1CCc2cc(-n3c(-c4cccnc4N)nc4ccc(-n5cccn5)nc43)ccc21] |
| 269 | 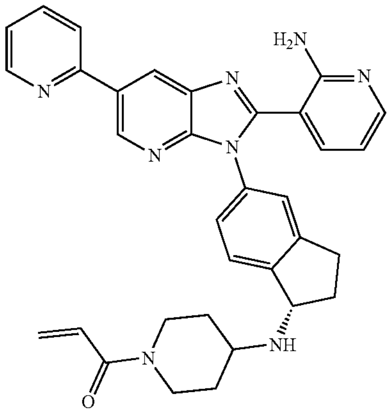 [SMILES: C=CC(=O)N1CCC(N[C@H]2CCc3cc(-n4c(-c5cccnc5N)nc5cc(-c6ccccn6)cnc54)ccc32)CC1] |

TABLE 1-continued
| Chemical structures of selected compounds. | |
|---|---|
| Comp. No. | Structure |
| 270 | 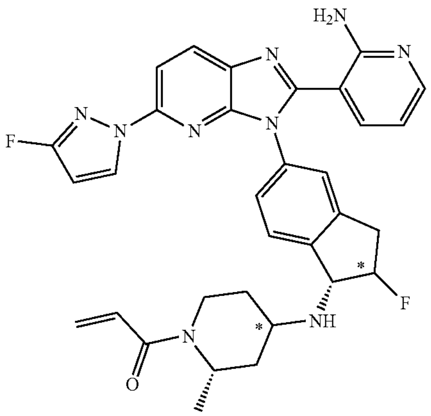 [SMILES: C=CC(=O)N1CCC(N[C@@H]2c3ccc(-n4c(-c5cccnc5N)nc5ccc(-n6ccc(F)n6)nc54)cc3CC2F)C[C@@H]1C] |
| 271 | 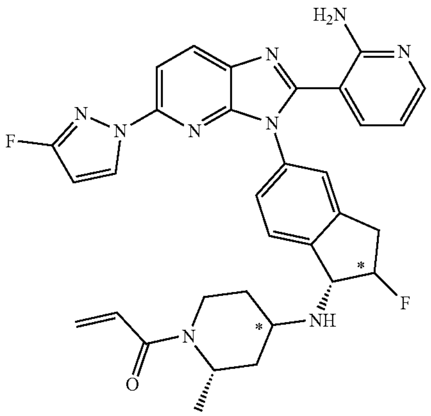 [SMILES: C=CC(=O)N1CCC(N[C@@H]2c3ccc(-n4c(-c5cccnc5N)nc5ccc(-n6ccc(F)n6)nc54)cc3CC2F)C[C@@H]1C] |
| 272 | 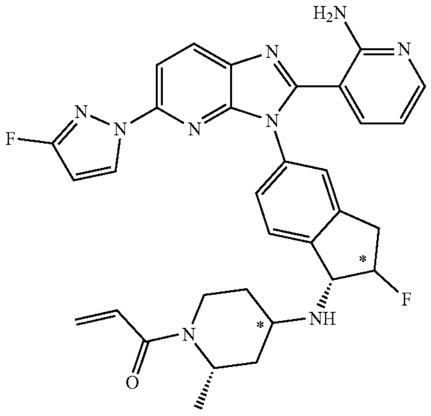 [SMILES: C=CC(=O)N1CCC(N[C@@H]2c3ccc(-n4c(-c5cccnc5N)nc5ccc(-n6ccc(F)n6)nc54)cc3CC2F)C[C@@H]1C] |

TABLE 1-continued
| Chemical structures of selected compounds. | |
|---|---|
| Comp. No. | Structure |
| 273 | 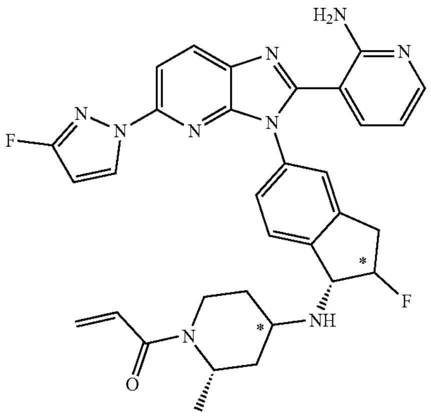 [SMILES: C=CC(=O)N1CCC(N[C@@H]2c3ccc(-n4c(-c5cccnc5N)nc5ccc(-n6ccc(F)n6)nc54)cc3CC2F)C[C@@H]1C] |
| 274 | 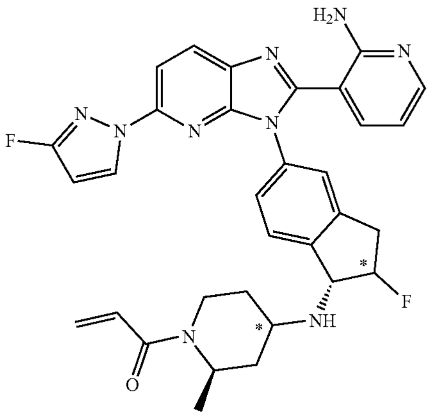 |
| 275 | 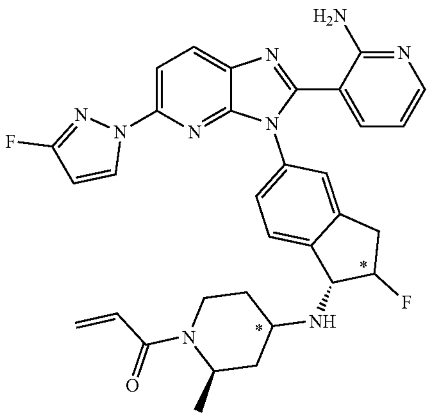 |

TABLE 1-continued
| Chemical structures of selected compounds. | |
|---|---|
| Comp. No. | Structure |
| 276 | 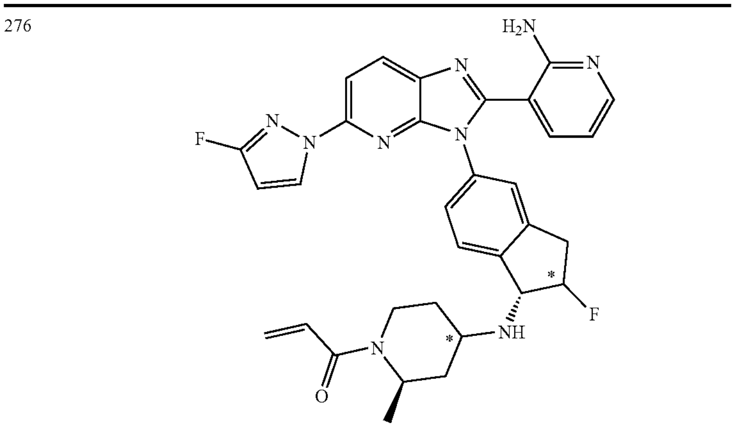 |
| 277 | 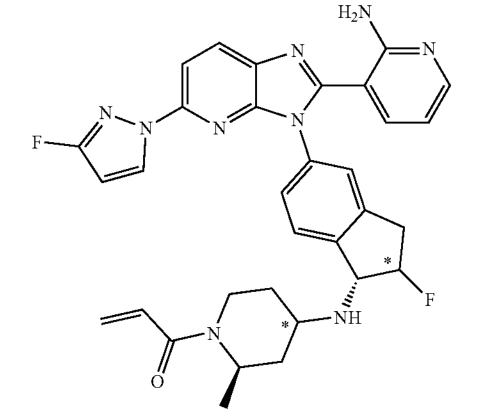 |
| 278 | 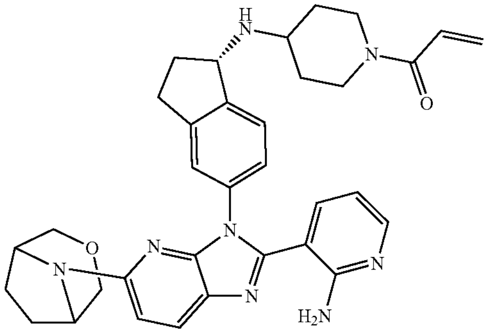 [SMILES: C=CC(=O)N1CCC(N[C@H]2CCc3cc(-n4c(-c5cccnc5N)nc5ccc(N6C7CCC6COC7)nc54)ccc32)CC1] |
| 279 | 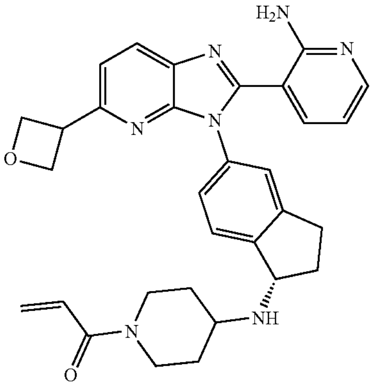 [SMILES: C=CC(=O)N1CCC(N[C@H]2CCc3cc(-n4c(-c5cccnc5N)nc5ccc(C6COC6)nc54)ccc32)CC1] |

TABLE 1-continued
Chemical structures of selected compounds.
| Comp. No. | Structure |
| --- | --- |
| 280 | 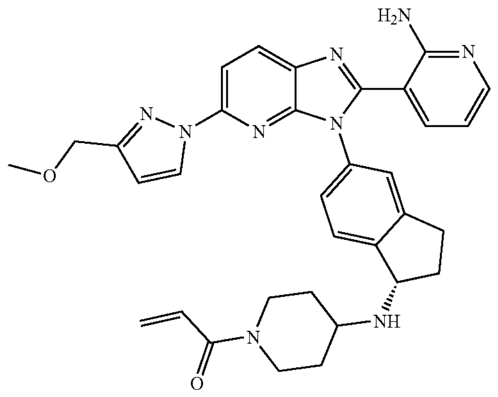 [SMILES: C=CC(=O)N1CCC(N[C@H]2CCc3cc(-n4c(-c5cccnc5N)nc5ccc(-n6ccc(COC)n6)nc54)ccc32)CC1] |
| 281 | 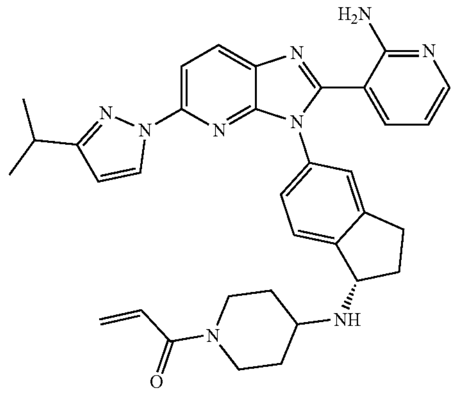 [SMILES: C=CC(=O)N1CCC(N[C@H]2CCc3cc(-n4c(-c5cccnc5N)nc5ccc(-n6ccc(C(C)C)n6)nc54)ccc32)CC1] |
| 282 | 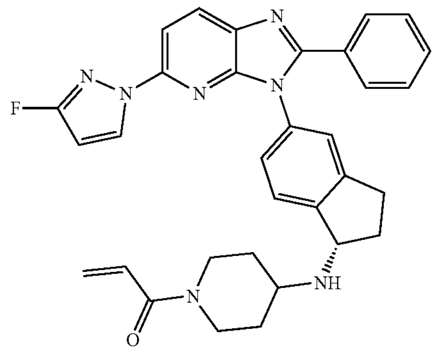 [SMILES: C=CC(=O)N1CCC(N[C@H]2CCc3cc(-n4c(-c5ccccc5)nc5ccc(-n6ccc(F)n6)nc54)ccc32)CC1] |
| 283 | 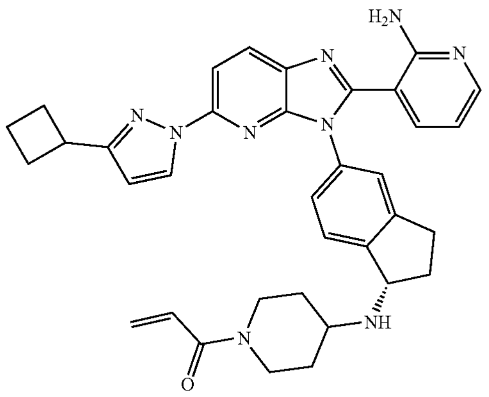 [SMILES: C=CC(=O)N1CCC(N[C@H]2CCc3cc(-n4c(-c5cccnc5N)nc5ccc(-n6ccc(C7CCC7)n6)nc54)ccc32)CC1] |

TABLE 1-continued
| Chemical structures of selected compounds. | |
|---|---|
| Comp. No. | Structure |
| 284 | 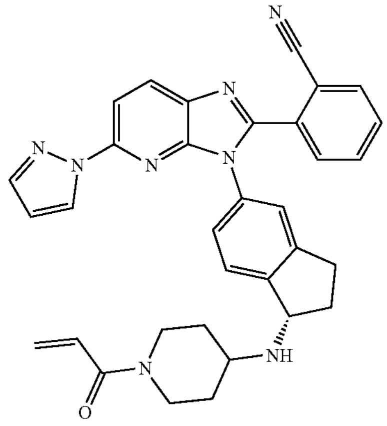 [SMILES: C=CC(=O)N1CCC(N[C@H]2CCc3cc(-n4c(-c5ccccc5C#N)nc5ccc(-n6cccn6)nc54)ccc32)CC1] |
| 285 | 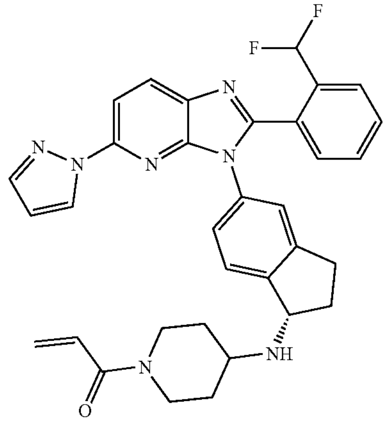 [SMILES: C=CC(=O)N1CCC(N[C@H]2CCc3cc(-n4c(-c5ccccc5C(F)F)nc5ccc(-n6cccn6)nc54)ccc32)CC1] |
| 286 | 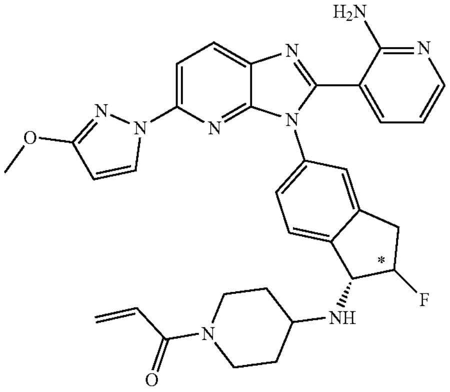 [SMILES: C=CC(=O)N1CCC(N[C@@H]2c3ccc(-n4c(-c5cccnc5N)nc5ccc(-n6ccc(OC)n6)nc54)cc3CC2F)CC1] |

TABLE 1-continued
| Chemical structures of selected compounds. | |
|---|---|
| Comp. No. | Structure |
| 287 | 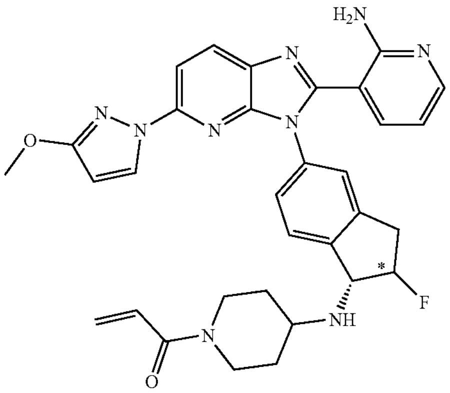 [SMILES: C=CC(=O)N1CCC(N[C@@H]2c3ccc(-n4c(-c5cccnc5N)nc5ccc(-n6ccc(OC)n6)nc54)cc3CC2F)CC1] |
| 288 | 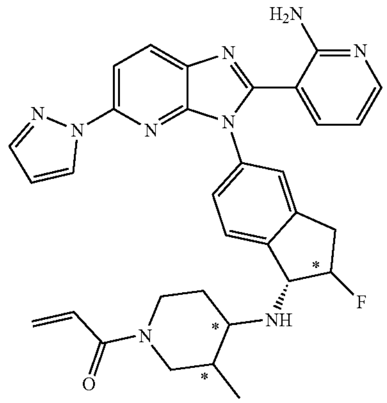 [SMILES: C=CC(=O)N1CCC(N[C@@H]2c3ccc(-n4c(-c5cccnc5N)nc5ccc(-n6cccn6)nc54)cc3CC2F)C(C)C1] |
| 289 | 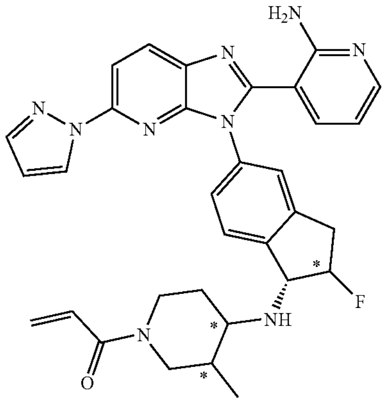 [SMILES: C=CC(=O)N1CCC(N[C@@H]2c3ccc(-n4c(-c5cccnc5N)nc5ccc(-n6cccn6)nc54)cc3CC2F)C(C)C1] |

TABLE 1-continued
| Chemical structures of selected compounds. | |
|---|---|
| Comp. No. | Structure |
| 290 | 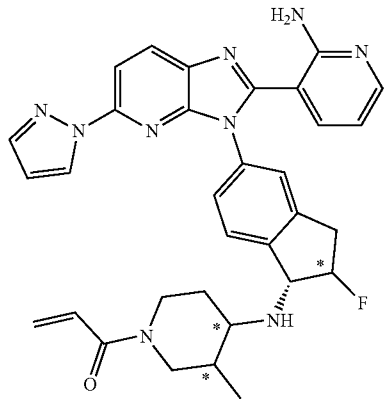 [SMILES: C=CC(=O)N1CCC(N[C@@H]2c3ccc(-n4c(-c5cccnc5N)nc5ccc(-n6cccn6)nc54)cc3CC2F)C(C)C1] |
| 291 | 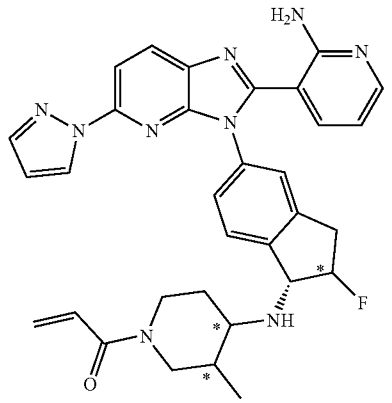 [SMILES: C=CC(=O)N1CCC(N[C@@H]2c3ccc(-n4c(-c5cccnc5N)nc5ccc(-n6cccn6)nc54)cc3CC2F)C(C)C1] |
| 292 | 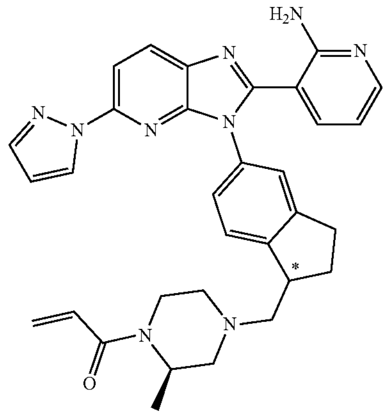 [SMILES: C=CC(=O)N1CCN(CC2CCc3cc(-n4c(-c5cccnc5N)nc5ccc(-n6cccn6)nc54)ccc32)C[C@H]1C] |

TABLE 1-continued
| Chemical structures of selected compounds. | |
|---|---|
| Comp. No. | Structure |
| 293 | 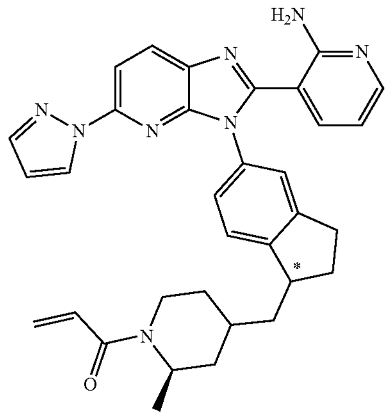 [SMILES: C=CC(=O)N1CCC(CC2CCc3cc(-n4c(-c5cccnc5N)nc5ccc(-n6cccn6)nc54)ccc32)C[C@H]1C] |
| 294 | 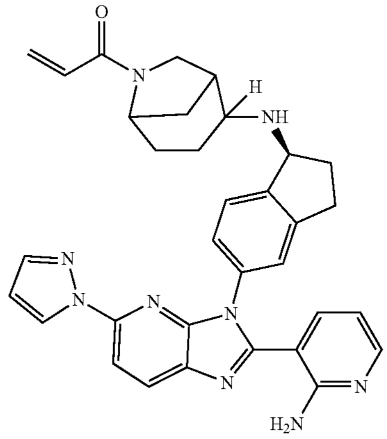 [SMILES: C=CC(=O)N1CC2CC1CCC2N[C@H]1CCc2cc(-n3c(-c4cccnc4N)nc4ccc(-n5cccn5)nc43)ccc21] |
| 295 | 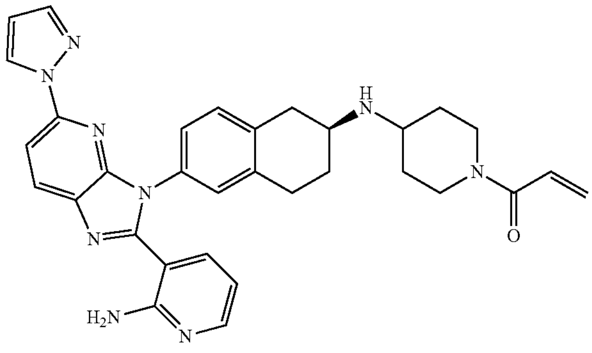 [SMILES: C=CC(=O)N1CCC(N[C@H]2CCc3cc(-n4c(-c5cccnc5N)nc5ccc(-n6cccn6)nc54)ccc3C2)CC1] |

TABLE 1-continued
| Chemical structures of selected compounds. | |
|---|---|
| Comp. No. | Structure |
| 296 | 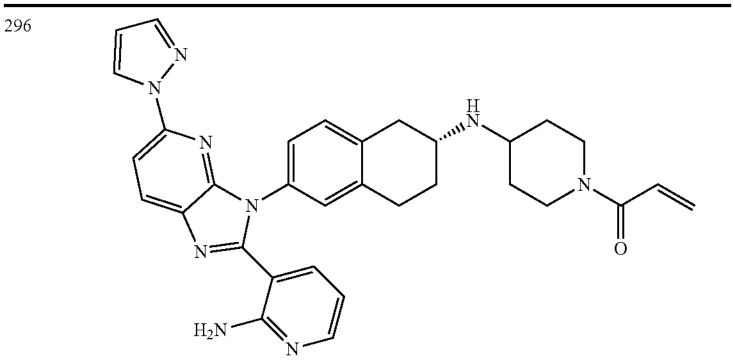 |
| 297 | 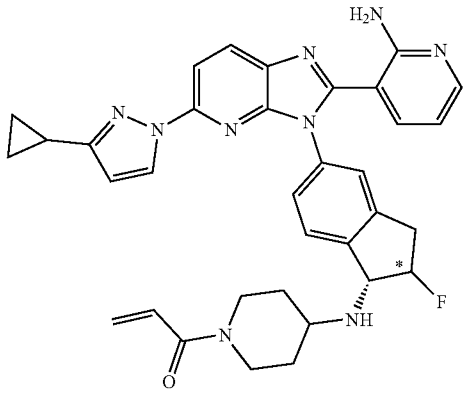 [SMILES: C=CC(=O)N1CCC(N[C@@H]2c3ccc(-n4c(-c5cccnc5N)nc5ccc(-n6ccc(C7CC7)n6)nc54)cc3CC2F)CC1] |
| 298 | 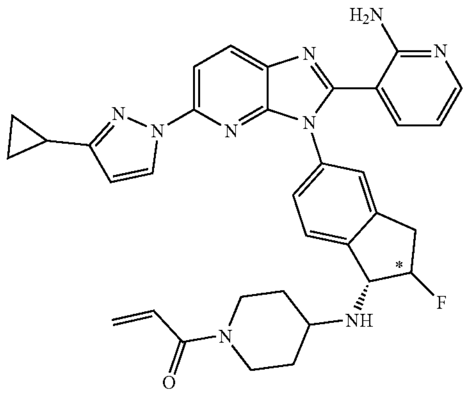 [SMILES: C=CC(=O)N1CCC(N[C@@H]2c3ccc(-n4c(-c5cccnc5N)nc5ccc(-n6ccc(C7CC7)n6)nc54)cc3CC2F)CC1] |
| 299 | 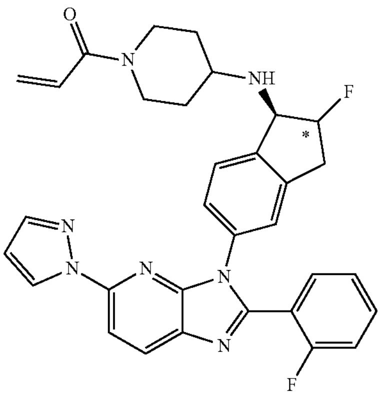 [SMILES: C=CC(=O)N1CCC(N[C@@H]2c3ccc(-n4c(-c5ccccc5F)nc5ccc(-n6cccn6)nc54)cc3CC2F)CC1] |

TABLE 1-continued
| Chemical structures of selected compounds. | |
|---|---|
| Comp. No. | Structure |
| 300 | 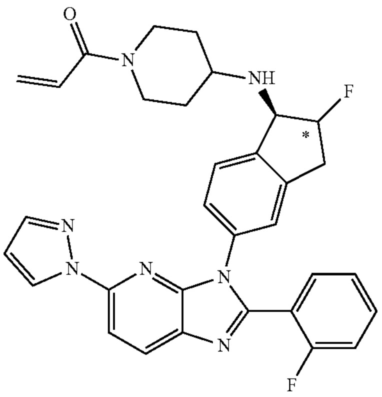 [SMILES: C=CC(=O)N1CCC(N[C@@H]2c3ccc(-n4c(-c5ccccc5F)nc5ccc(-n6cccn6)nc54)cc3CC2F)CC1] |
| 301 | 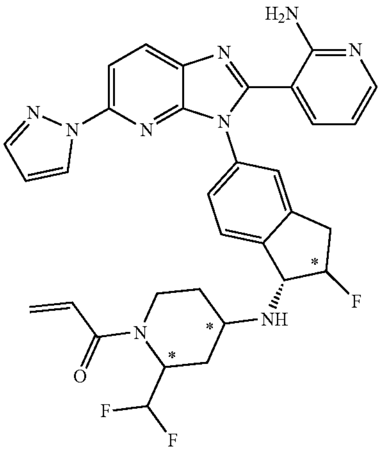 [SMILES: C=CC(=O)N1CCC(N[C@@H]2c3ccc(-n4c(-c5cccnc5N)nc5ccc(-n6cccn6)nc54)cc3CC2F)CC1C(F)F] |
| 302 | 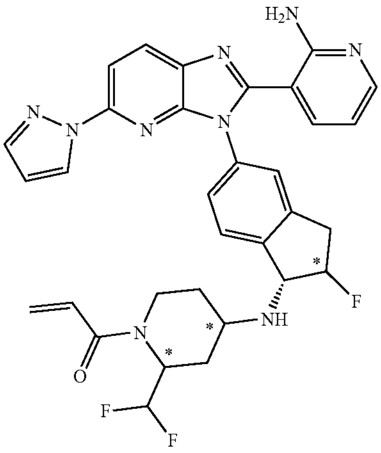 [SMILES: C=CC(=O)N1CCC(N[C@@H]2c3ccc(-n4c(-c5cccnc5N)nc5ccc(-n6cccn6)nc54)cc3CC2F)CC1C(F)F] |

TABLE 1-continued
| Chemical structures of selected compounds. | |
|---|---|
| Comp. No. | Structure |
| 303 | 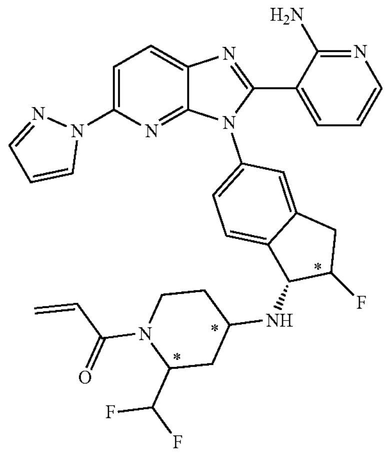 [SMILES: C=CC(=O)N1CCC(N[C@@H]2c3ccc(-n4c(-c5cccnc5N)nc5ccc(-n6cccn6)nc54)cc3CC2F)CC1C(F)F] |
| 304 | 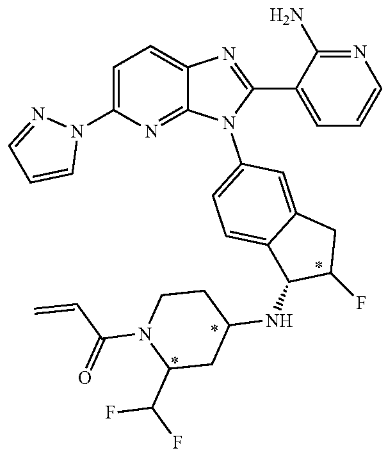 [SMILES: C=CC(=O)N1CCC(N[C@@H]2c3ccc(-n4c(-c5cccnc5N)nc5ccc(-n6cccn6)nc54)cc3CC2F)CC1C(F)F] |
| 305 | 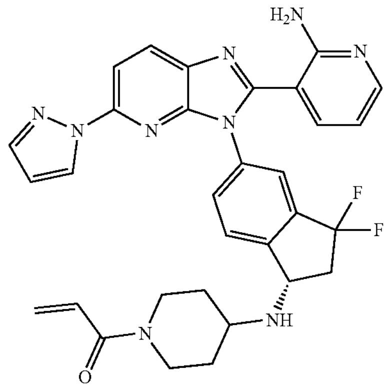 [SMILES: C=CC(=O)N1CCC(N[C@H]2CC(F)(F)c3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 306 | 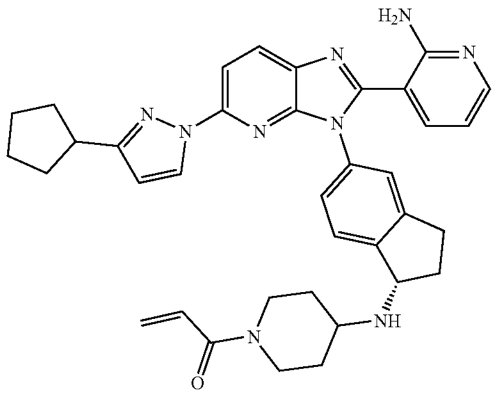 [SMILES: C=CC(=O)N1CCC(N[C@H]2CCc3cc(-n4c(-c5cccnc5N)nc5ccc(-n6ccc(C7CCCC7)n6)nc54)ccc32)CC1] |
| 307 | 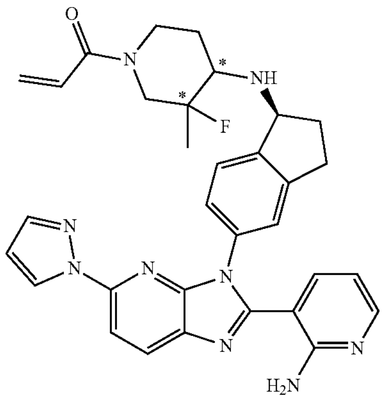 [SMILES: C=CC(=O)N1CCC(N[C@H]2CCc3cc(-n4c(-c5cccnc5N)nc5ccc(-n6cccn6)nc54)ccc32)C(C)(F)C1] |
| 308 | 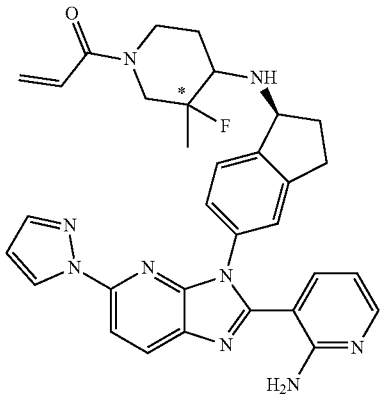 [SMILES: C=CC(=O)N1CCC(N[C@H]2CCc3cc(-n4c(-c5cccnc5N)nc5ccc(-n6cccn6)nc54)ccc32)C(C)(F)C1] |

TABLE 1-continued
| Comp. No. | Structure |
| --- | --- |
| 309 | 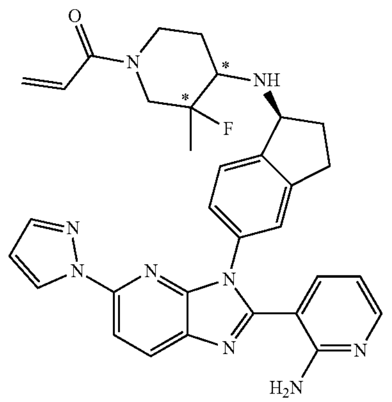 [SMILES: C=CC(=O)N1CCC(N[C@H]2CCc3cc(-n4c(-c5cccnc5N)nc5ccc(-n6cccn6)nc54)ccc32)C(C)(F)C1] |
| 310 | 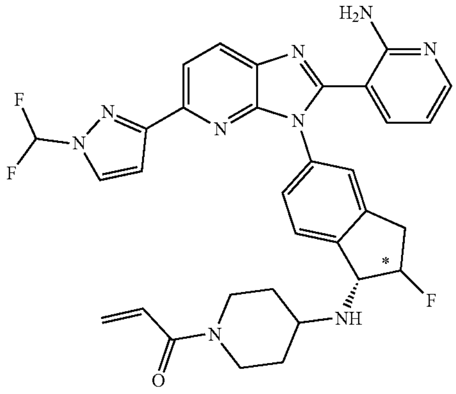 [SMILES: C=CC(=O)N1CCC(N[C@@H]2c3ccc(-n4c(-c5cccnc5N)nc5ccc(-c6ccn(C(F)F)n6)nc54)cc3CC2F)CC1] |
| 311 | 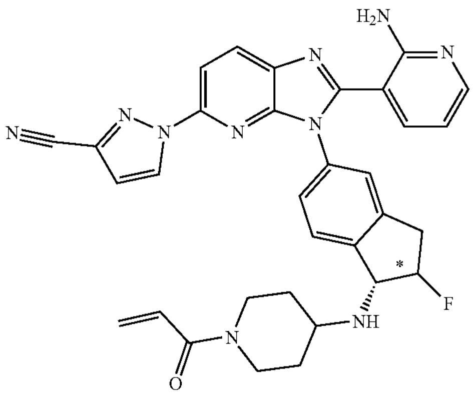 [SMILES: C=CC(=O)N1CCC(N[C@@H]2c3ccc(-n4c(-c5cccnc5N)nc5ccc(-n6ccc(C#N)n6)nc54)cc3CC2F)CC1] |
Chemical structures of selected compounds.

TABLE 1-continued
Chemical structures of selected compounds.
| Comp. No. | Structure |
| --- | --- |
| 312 | 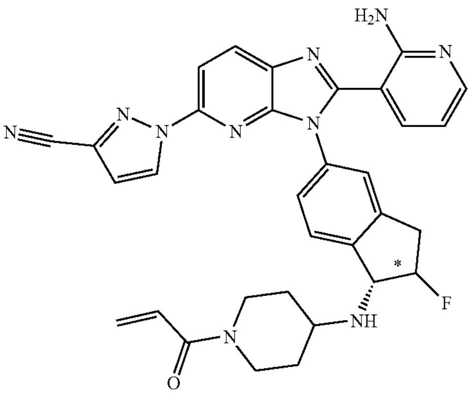 [SMILES: C=CC(=O)N1CCC(N[C@@H]2c3ccc(-n4c(-c5cccnc5N)nc5ccc(-n6ccc(C#N)n6)nc54)cc3CC2F)CC1] |
| 313 | 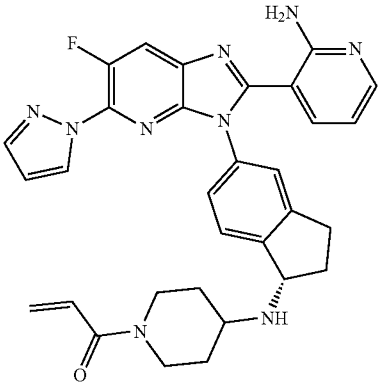 [SMILES: C=CC(=O)N1CCC(N[C@H]2CCc3cc(-n4c(-c5cccnc5N)nc5cc(F)c(-n6cccn6)nc54)ccc32)CC1] |
| 314 | 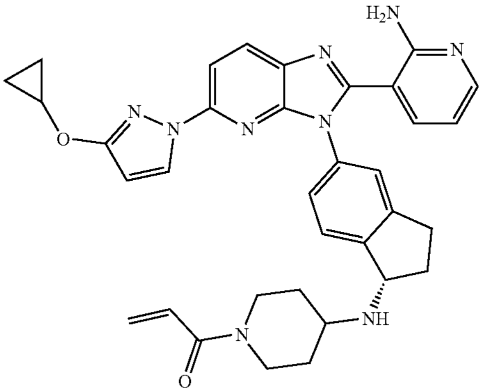 [SMILES: C=CC(=O)N1CCC(N[C@H]2CCc3cc(-n4c(-c5cccnc5N)nc5ccc(-n6ccc(OC7CC7)n6)nc54)ccc32)CC1] |

TABLE 1-continued
Chemical structures of selected compounds.
| Comp. No. | Structure |
| --- | --- |
| 315 | 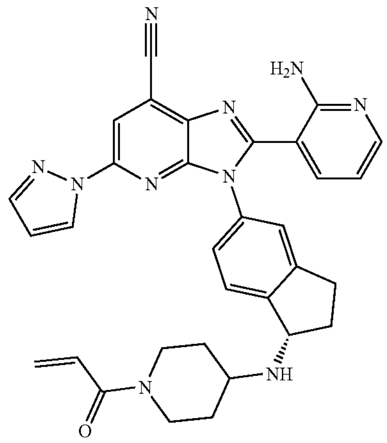 [SMILES: C=CC(=O)N1CCC(N[C@H]2CCc3cc(-n4c(-c5cccnc5N)nc5c(C#N)cc(-n6cccn6)nc54)ccc32)CC1] |
| 316 | 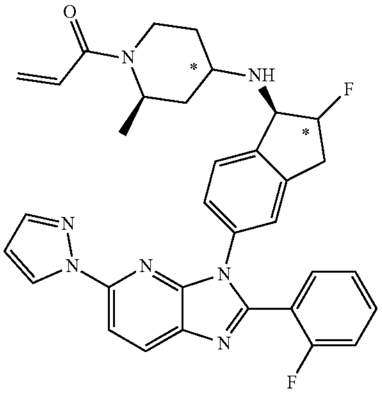 [SMILES: C=CC(=O)N1CCC(N[C@@H]2c3ccc(-n4c(-c5ccccc5F)nc5ccc(-n6cccn6)nc54)cc3CC2F)C[C@H]1C] |
| 317 | 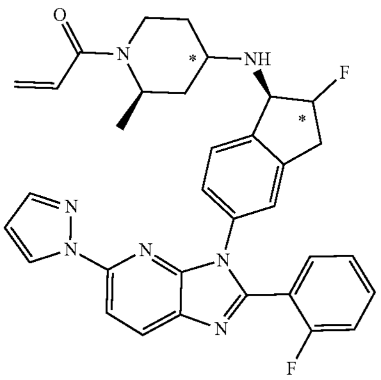 [SMILES: C=CC(=O)N1CCC(N[C@@H]2c3ccc(-n4c(-c5ccccc5F)nc5ccc(-n6cccn6)nc54)cc3CC2F)C[C@H]1C] |

TABLE 1-continued
Chemical structures of selected compounds.
| Comp. No. | Structure |
| --- | --- |
| 318 | 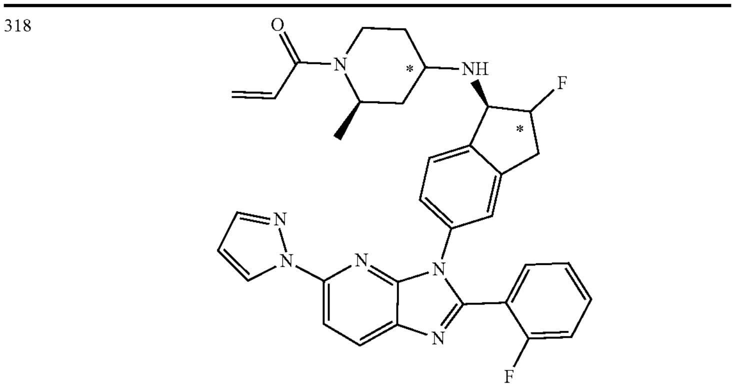 |
| 319 | 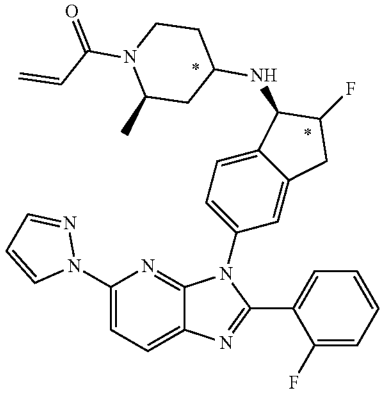 [SMILES: C=CC(=O)N1CCC(N[C@@H]2c3ccc(-n4c(-c5ccccc5F)nc5ccc(-n6cccn6)nc54)cc3CC2F)C[C@H]1C] |
| 320 | 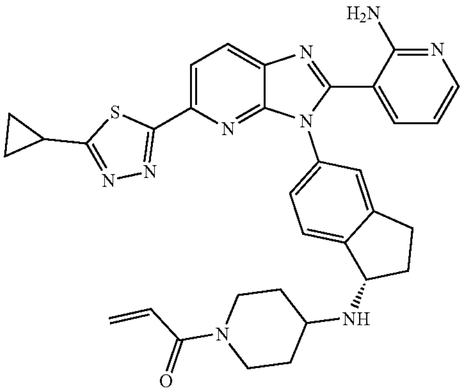 [SMILES: C=CC(=O)N1CCC(N[C@H]2CCc3cc(-n4c(-c5cccnc5N)nc5ccc(-c6nnc(C7CC7)s6)nc54)ccc32)CC1] |
| 321 | 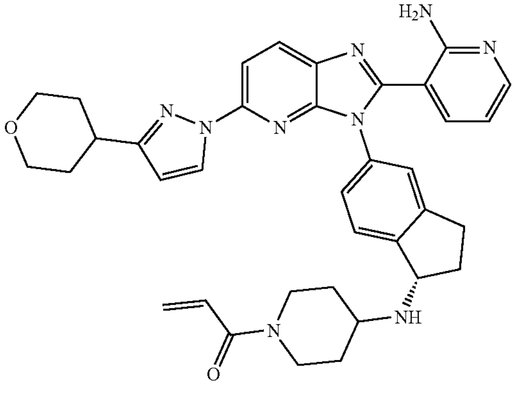 [SMILES: C=CC(=O)N1CCC(N[C@H]2CCc3cc(-n4c(-c5cccnc5N)nc5ccc(-n6ccc(C7CCOCC7)n6)nc54)ccc32)CC1] |

TABLE 1-continued
Chemical structures of selected compounds.
| Comp. No. | Structure |
| --- | --- |
| 322 | 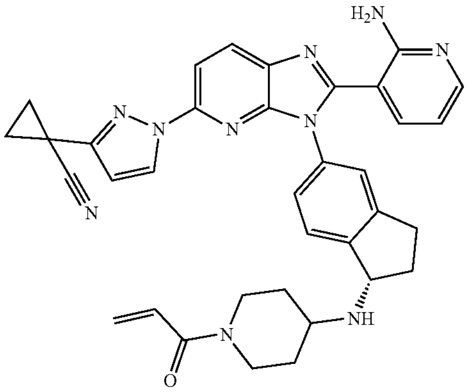 [SMILES: C=CC(=O)N1CCC(N[C@H]2CCc3cc(-n4c(-c5cccnc5N)nc5ccc(-n6ccc(C7(C#N)CC7)n6)nc54)ccc32)CC1] |
| 323 | 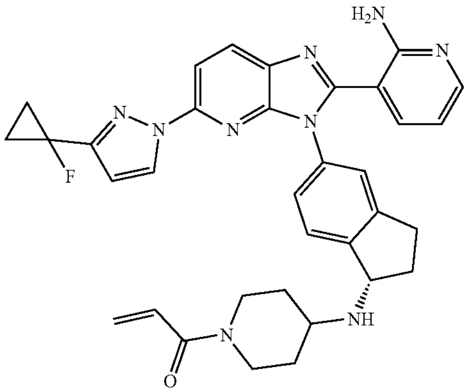 [SMILES: C=CC(=O)N1CCC(N[C@H]2CCc3cc(-n4c(-c5cccnc5N)nc5ccc(-n6ccc(C7(F)CC7)n6)nc54)ccc32)CC1] |
| 324 | 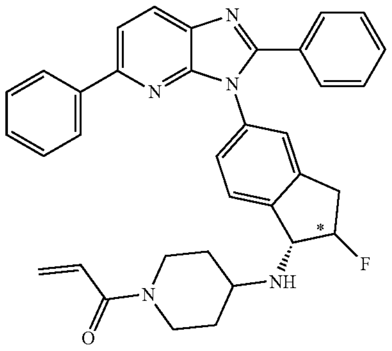 [SMILES: C=CC(=O)N1CCC(N[C@@H]2c3ccc(-n4c(-c5ccccc5)nc5ccc(-c6ccccc6)nc54)cc3CC2F)CC1] |
| 325 | 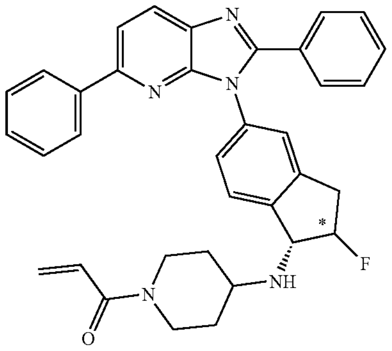 [SMILES: C=CC(=O)N1CCC(N[C@@H]2c3ccc(-n4c(-c5ccccc5)nc5ccc(-c6ccccc6)nc54)cc3CC2F)CC1] |

TABLE 1-continued
| Chemical structures of selected compounds. | |
|---|---|
| Comp. No. | Structure |
| 326 | 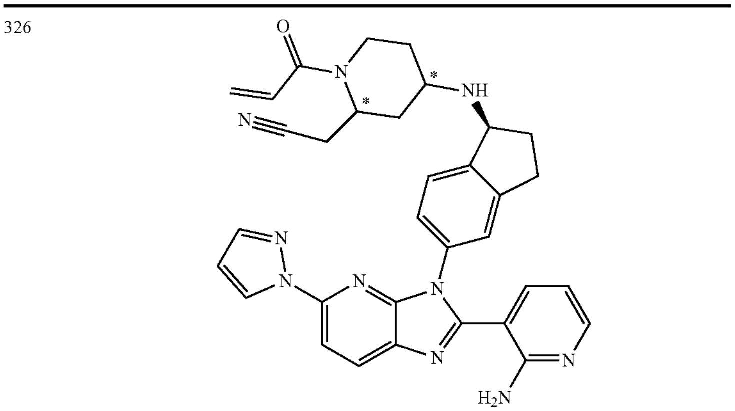 |
| 327 | 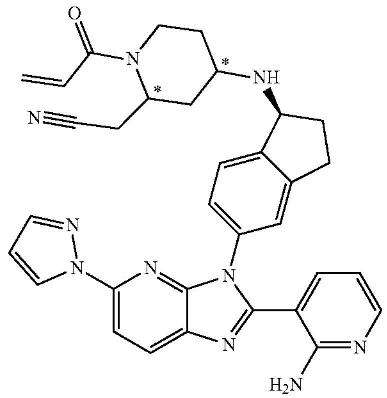 [SMILES: C=CC(=O)N1CCC(N[C@H]2CCc3cc(-n4c(-c5cccnc5N)nc5ccc(-n6cccn6)nc54)ccc32)CC1CC#N] |
| 328 | 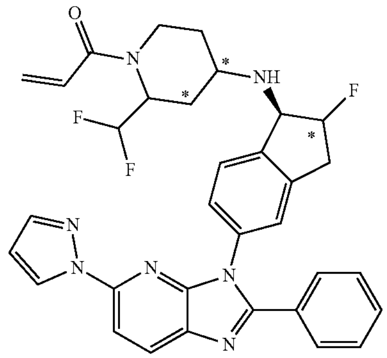 [SMILES: C=CC(=O)N1CCC(N[C@@H]2c3ccc(-n4c(-c5ccccc5)nc5ccc(-n6cccn6)nc54)cc3CC2F)CC1C(F)F] |
| 329 | 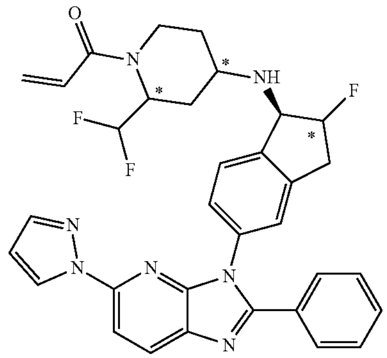 [SMILES: C=CC(=O)N1CCC(N[C@@H]2c3ccc(-n4c(-c5ccccc5)nc5ccc(-n6cccn6)nc54)cc3CC2F)CC1C(F)F] |

TABLE 1-continued
| Chemical structures of selected compounds. | |
|---|---|
| Comp. No. | Structure |
| 330 | 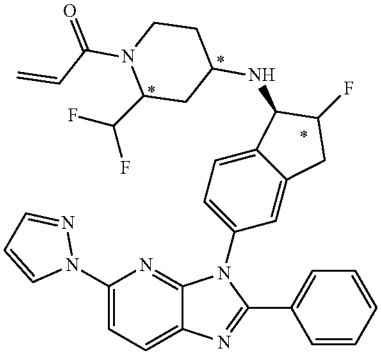 [SMILES: C=CC(=O)N1CCC(N[C@@H]2c3ccc(-n4c(-c5ccccc5)nc5ccc(-n6cccn6)nc54)cc3CC2F)CC1C(F)F] |
| 331 | 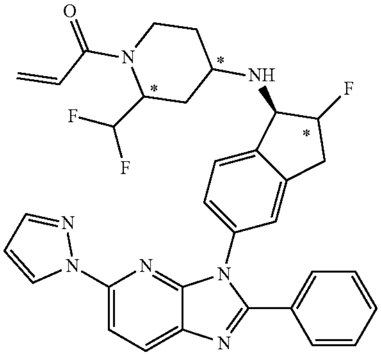 [SMILES: C=CC(=O)N1CCC(N[C@@H]2c3ccc(-n4c(-c5ccccc5)nc5ccc(-n6cccn6)nc54)cc3CC2F)CC1C(F)F] |
| 332 | 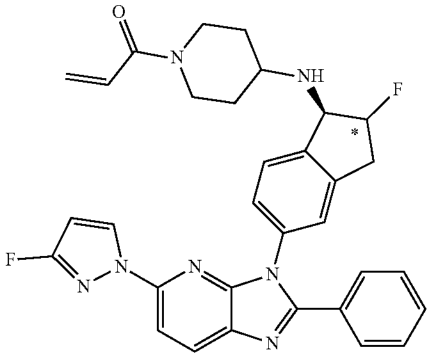 [SMILES: C=CC(=O)N1CCC(N[C@@H]2c3ccc(-n4c(-c5ccccc5)nc5ccc(-n6ccc(F)n6)nc54)cc3CC2F)CC1] |
| 333 | 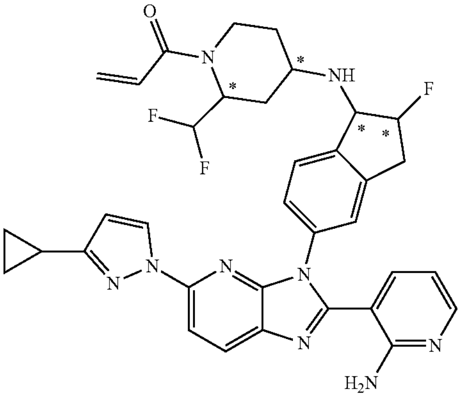 [SMILES: C=CC(=O)N1CCC(NC2c3ccc(-n4c(-c5cccnc5N)nc5ccc(-n6ccc(C7CC7)n6)nc54)cc3CC2F)CC1C(F)F] |

TABLE 1-continued
| Chemical structures of selected compounds. | |
|---|---|
| Comp. No. | Structure |
| 334 | 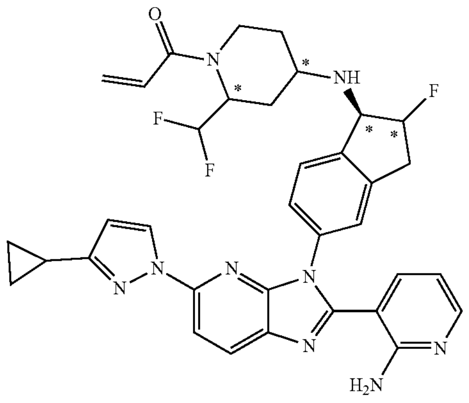 [SMILES: C=CC(=O)N1CCC(N[C@@H]2c3ccc(-n4c(-c5cccnc5N)nc5ccc(-n6ccc(C7CC7)n6)nc54)cc3CC2F)CC1C(F)F] |
| 335 | 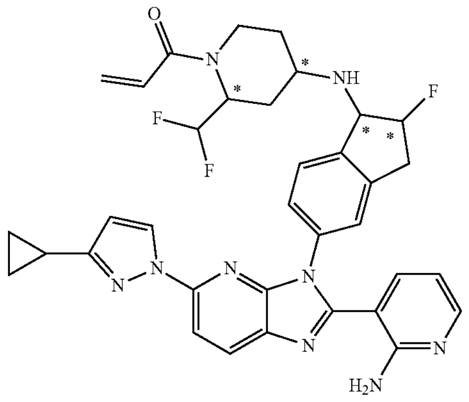 [SMILES: C=CC(=O)N1CCC(NC2c3ccc(-n4c(-c5cccnc5N)nc5ccc(-n6ccc(C7CC7)n6)nc54)cc3CC2F)CC1C(F)F] |
| 336 | 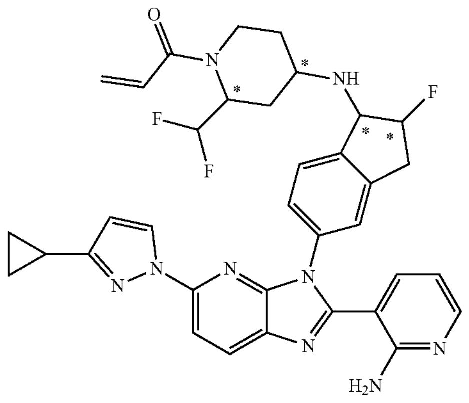 [SMILES: C=CC(=O)N1CCC(NC2c3ccc(-n4c(-c5cccnc5N)nc5ccc(-n6ccc(C7CC7)n6)nc54)cc3CC2F)CC1C(F)F] |

TABLE 1-continued
| Chemical structures of selected compounds. | |
|---|---|
| Comp. No. | Structure |
| 337 | 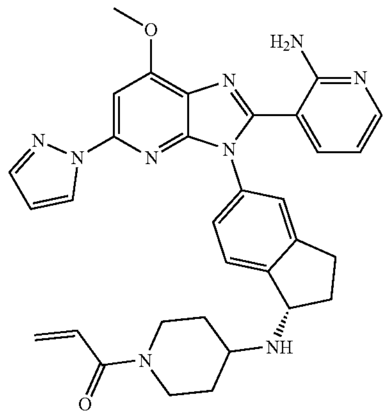 [SMILES: C=CC(=O)N1CCC(N[C@H]2CCc3cc(-n4c(-c5cccnc5N)nc5c(OC)cc(-n6cccn6)nc54)ccc32)CC1] |
| 338 | 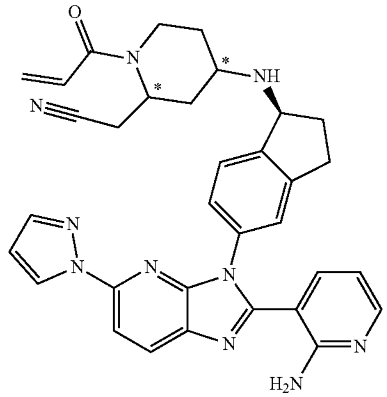 [SMILES: C=CC(=O)N1CCC(N[C@H]2CCc3cc(-n4c(-c5cccnc5N)nc5ccc(-n6cccn6)nc54)ccc32)CC1CC#N] |
| 339 | 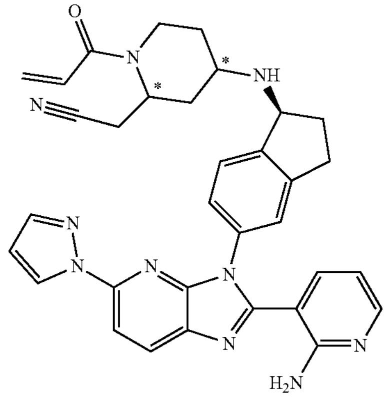 [SMILES: C=CC(=O)N1CCC(N[C@H]2CCc3cc(-n4c(-c5cccnc5N)nc5ccc(-n6cccn6)nc54)ccc32)CC1CC#N] |

TABLE 1-continued
| Chemical structures of selected compounds. | |
|---|---|
| Comp. No. | Structure |
| 340 | 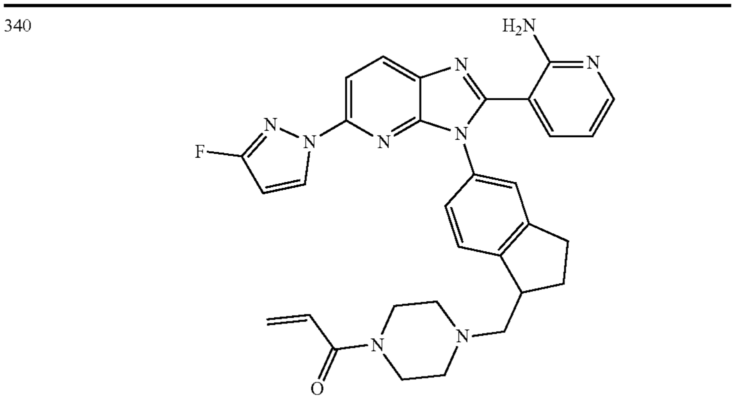 |
| 341 | 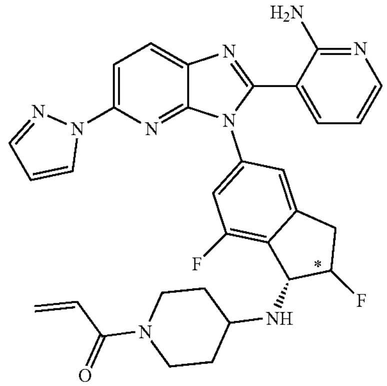 [SMILES: C=CC(=O)N1CCC(N[C@@H]2c3c(F)cc(-n4c(-c5cccnc5N)nc5ccc(-n6cccn6)nc54)cc3CC2F)CC1] |
| 342 | 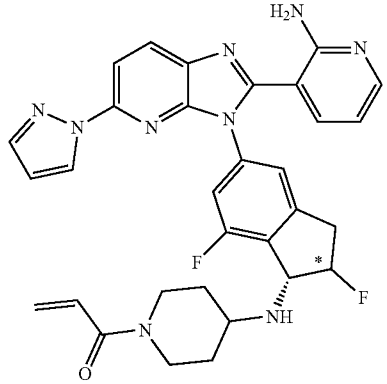 [SMILES: C=CC(=O)N1CCC(N[C@@H]2c3c(F)cc(-n4c(-c5cccnc5N)nc5ccc(-n6cccn6)nc54)cc3CC2F)CC1] |
| 343 | 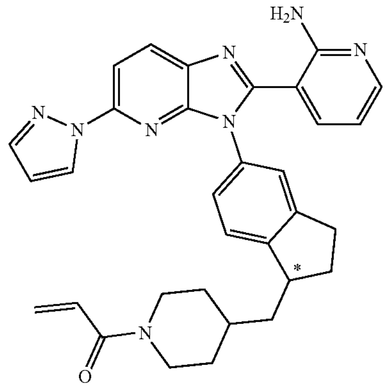 [SMILES: C=CC(=O)N1CCC(CC2CCc3cc(-n4c(-c5cccnc5N)nc5ccc(-n6cccn6)nc54)ccc32)CC1] |

TABLE 1-continued
| Chemical structures of selected compounds. | |
|---|---|
| Comp. No. | Structure |
| 344 | 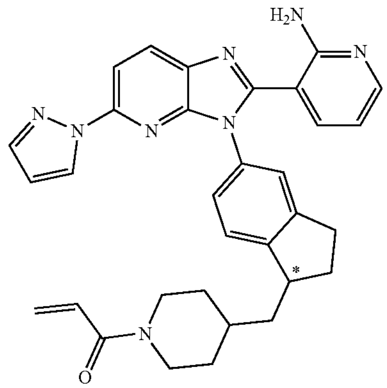 |
| 345 | 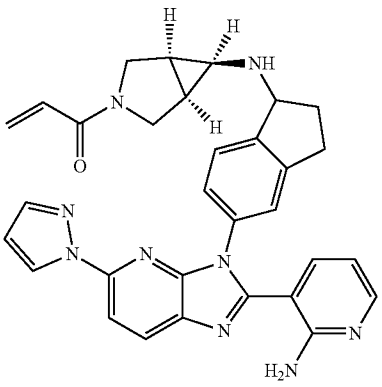 [SMILES: C=CC(=O)N1C[C@@H]2[C@H](C1)[C@@H]2NC1CCc2cc(-n3c(-c4cccnc4N)nc4ccc(-n5cccn5)nc43)ccc21] |
| 346 | 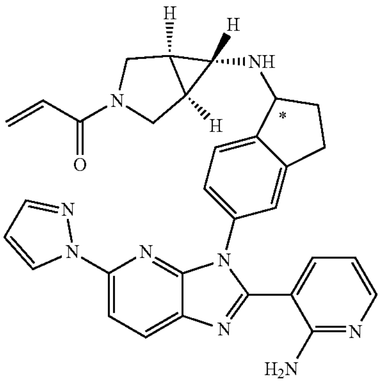 [SMILES: C=CC(=O)N1C[C@@H]2[C@H](C1)[C@H]2NC1CCc2cc(-n3c(-c4cccnc4N)nc4ccc(-n5cccn5)nc43)ccc21] |

TABLE 1-continued
| Chemical structures of selected compounds. | |
|---|---|
| Comp. No. | Structure |
| 347 | 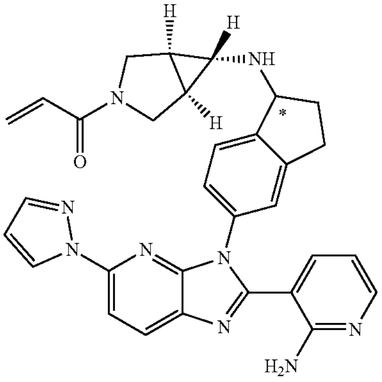 [SMILES: C=CC(=O)N1C[C@@H]2[C@H](C1)[C@H]2NC1CCc2cc(-n3c(-c4cccnc4N)nc4ccc(-n5cccn5)nc43)ccc21] |
| 348 | 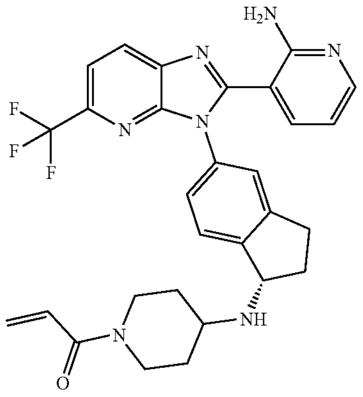 [SMILES: C=CC(=O)N1CCC(N[C@H]2CCc3cc(-n4c(-c5cccnc5N)nc5ccc(C(F)(F)F)nc54)ccc32)CC1] |
| 349 | 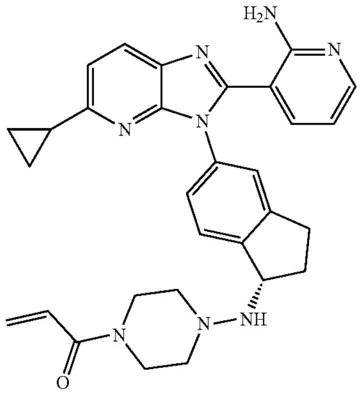 [SMILES: C=CC(=O)N1CCN(N[C@H]2CCc3cc(-n4c(-c5cccnc5N)nc5ccc(C6CC6)nc54)ccc32)CC1] |

TABLE 1-continued

| Chemical structures of selected compounds. | |
|---|---|
| Comp. No. | Structure |
| 350 | 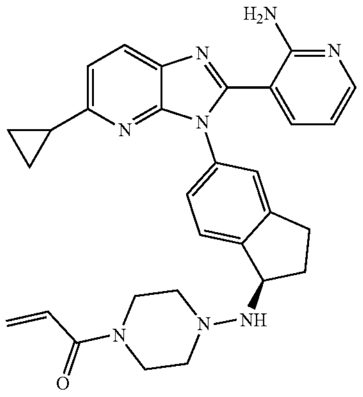 [SMILES: C=CC(=O)N1CCN(N[C@@H]2CCc3cc(-n4c(-c5cccnc5N)nc5ccc(C6CC6)nc54)ccc32)CC1] |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds or salts of Formula (I), (I-A), (II), (II-A), (III), (III-A), or (III-B), are intended to include all Z-, E- and tautomeric forms as well.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(+)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. The present chemical entities, pharmaceutical compositions and methods are meant to include all such possible stereoisomers, including racemic mixtures, optically pure forms, mixtures of diastereomers and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

The compounds or salts for Formula (I), (I-A), (II), (II-A), (III), (III-A), or (III-B), herein may in some cases exist as diastereomers, enantiomers, or other stereoisomeric forms. The compounds presented herein include all diastereomeric, enantiomeric, and epimeric forms as well as the racemates, mixtures of diastereomers, and other mixtures thereof, to the extent they can be made by one of ordinary skill in the art by routine experimentation. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions," John Wiley And Sons, Inc., 1981, herein incorporated by reference for this disclosure). Stereoisomers may also be obtained by stereoselective synthesis. Furthermore, a mixture of two enantiomers enriched in one of the two can be purified to provide further optically enriched form of the major enantiomer by recrystallization and/or trituration.

In certain embodiments, compounds or salts for Formula (I), (I-A), (II), (II-A), (III), (III-A), or (III-B), may comprise two or more enantiomers or diastereomers of a compound wherein a single enantiomer or diastereomer accounts for at least about 70% by weight, at least about 80% by weight, at least about 90% by weight, at least about 98% by weight, or at least about 99% by weight or more of the total weight of all stereoisomers. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller (1975) *J. Chromatogr.,* 113 (3): 283-302). Racemic mixtures of chiral compounds can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

A "tautomer" refers to a molecule wherein a proton shift from one atom of a molecule to another atom of the same molecule is possible. In certain embodiments, the compounds or salts for Formula (I), (I-A), (II), (II-A), (III), (III-A), or (III-B), exist as tautomers. In circumstances where tautomerization is possible, a chemical equilibrium of the tautomers may exist. The exact ratio of the tautomers depends on several factors, including physical state, temperature, solvent, and pH. Some non-limiting examples of tautomeric equilibrium include:

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6 (10)] 2000, 110 pp; George W.; Varma, Rajender S. The Synthesis of Radiolabeled Compounds via Organometallic Intermediates, Tetrahedron, 1989, 45 (21), 6601-21; and Evans, E. Anthony. Synthesis of radiolabeled compounds, J. Radioanal. Chem., 1981, 64 (1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Unless otherwise stated, compounds described herein are intended to include compounds which differ only in the presence of one or more isotopically enriched atoms. For example, compounds having the present structures except for the replacement of a hydrogen by a deuterium or tritium,

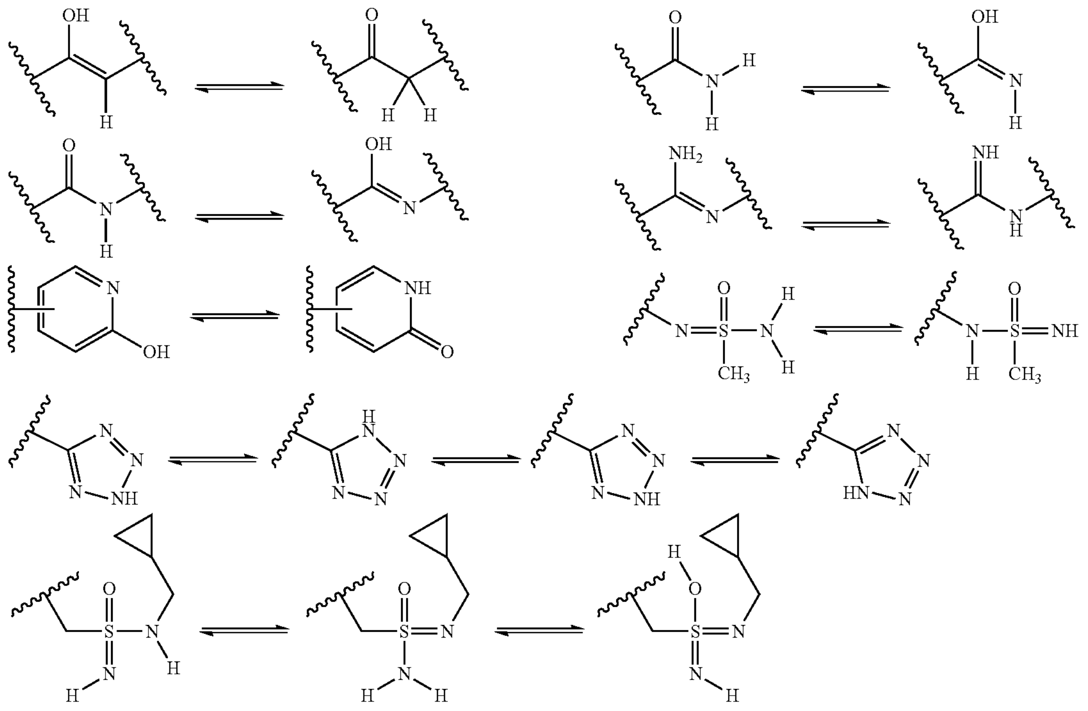

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound may be deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

Included in the present disclosure are salts, particularly pharmaceutically acceptable salts, of the compounds of Formula (I), (I-A), (II), (II-A), (III), (III-A), or (III-B). The compounds of the present disclosure may possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The methods and compositions of Formula (I), (I-A), (II), (II-A), (III), (III-A), or (III-B), include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of Formula (I), (I-A), (II), (II-A), (III), (III-A), or (III-B), also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of compounds represented by Formula (I), (I-A), (II), (II-A), (III), (III-A), or (III-B). The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

In certain embodiments, compounds or salts of Formula (I), (I-A), (II), (II-A), (III), (III-A), or (III-B), may be prodrugs, e.g., wherein a hydroxyl in the parent compound is presented as an ester or a carbonate, or carboxylic acid present in the parent compound is presented as an ester. The term “prodrug” is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Pharmaceutical Formulations

In some aspects, the present disclosure provides a pharmaceutical composition comprising a compound or salt of Formula (I), (I-A), (II), (II-A), (III), (III-A), or (III-B), and at least one pharmaceutically acceptable excipient. In some embodiments, the pharmaceutical composition comprises a compound or salt of Formula (I), (I-A), (II), (II-A), (III), (III-A), or (III-B), and a pharmaceutically acceptable excipient.

Pharmaceutical compositions can be formulated using one or more physiologically-acceptable carriers comprising excipients and auxiliaries. Formulation can be modified depending upon the route of administration chosen. Pharmaceutical compositions comprising a compound, salt or conjugate can be manufactured, for example, by lyophilizing the compound, salt or conjugate, mixing, dissolving, emulsifying, encapsulating or entrapping the conjugate. The pharmaceutical compositions can also include the compounds, salts or conjugates in a free-base form or pharmaceutically-acceptable salt form.

A compound or salt of Formula (I), (I-A), (II), (II-A), (III), (III-A), or (III-B), may be formulated in any suitable pharmaceutical formulation. A pharmaceutical formulation of the present disclosure typically contains an active ingredient (e.g., compound or salt of any one of Formula (I), (I-A), (II), (II-A), (III), (III-A), or (III-B), and one or more pharmaceutically acceptable excipients or carriers, including but not limited to: inert solid diluents and fillers, diluents, sterile aqueous solution and various organic solvents, permeation enhancers, antioxidents, solubilizers, and adjuvants.

Methods of Treatment

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient’s health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a “prophylactically effective amount or dose.” In this use, the precise amounts also depend on the patient’s state of health, weight, and the like. When used in a patient, effective amounts for this use will depend on the severity and course of the disease, disorder or condition, previous therapy, the patient’s health status and response to the drugs, and the judgment of the treating physician.

In some aspects, the present disclosure provides a method for treatment, comprising administering to a subject in need thereof an effective amount of a compound or salt of Formula (I), (I-A), (II), (II-A), (III), (III-A), or (III-B). In some aspects, the present disclosure provides a method for treating cancer in a patient in need thereof, comprising administering to the subject an effective amount of a compound or salt of Formula (I), (I-A), (II), (II-A), (III), (III-A), or (III-B). In some embodiments, the cancer is selected from breast cancer, colorectal cancer, and meningioma. In some embodiments, the cancer is breast cancer. In some embodiments, the cancer is colorectal cancer. In some embodiments, the cancer is meningioma. In some embodiments, the administration modulates the activity of wild-type AKT1. In some embodiments, the administration modulates the activity of a mutant AKT1. In some embodiments, the mutant AKT1 is AKT1 E17K.

In certain aspects, the present disclosure can be used as a method of inhibiting an AKT1 protein in a subject in need thereof, comprising administering to the subject a compound or salt of Formula (I), (I-A), (II), (II-A), (III), (III-A), or (III-B), or a pharmaceutical composition of Formula (I), (I-A), (II), (II-A), (III), (III-A), or (III-B). In some embodiments, the AKT protein is wild-type AKT1. In some embodiments, the AKT protein is a mutant AKT1 protein. In some embodiments, the mutant AKT1 protein comprises an E17K mutant. In some embodiments, the administrating modulates the activity of mutant AKT1. In some embodiments, the administrating modulates the activity of wild-type AKT1. In some aspects, the present disclosure provides a method of modulating activity of mutant AKT1. In some embodiments, the administering selectively modulates the activity of wild-type AKT1 over wild-type AKT2. In some embodiments, the administering selectively modulates the activity of mutant AKT1 over wild-type AKT2.

AKT1 Protein

In some aspects, the present disclosure provides an AKT1 protein covalently bound to a compound, wherein the compound is covalently bound to a cysteine residue of the AKT1 protein. In some embodiments, the compound is exogenous. In some embodiments, the exogenous compound is selected from an exogenous AKT1 inhibitor and an exogenous AKT1 activator. In some embodiments, the exogenous compound is an exogenous AKT1 modulator. In some embodiments, the exogenous compound is an exogenous AKT1 inhibitor.

In some embodiments, the AKT1 protein is selected from a wild-type AKT1 protein and a mutated AKT1 protein. In some embodiments, the AKT1 protein is a mutated AKT1 protein. In some embodiments, the mutated AKT1 protein comprises a mutation selected from a E17K mutation, a E40K mutation, and a E49K mutation. In some embodiments, the mutated AKT1 protein comprises a E17K mutation. In some embodiments, the mutated AKT1 protein comprises a E40K mutation. In some embodiments, the mutated AKT1 protein comprises a E49K mutation.

In some embodiments, the exogenous compound is in contact a cysteine residue of the AKT1 protein as described herein. In some embodiments, the contact is between the cysteine reside of the AKT1 protein and the exogenous compound is a covalent bond. In some embodiments, the cysteine reside is selected from C296 and C310. In some embodiments, the cysteine residue is C296. In some embodiments, the cysteine residue is C310.

In some embodiments, the covalent bond between the exogenous compound and the cysteine residue is an irreversible covalent bond. In some embodiments, the irreversible covalent bond is a single bond. In some embodiments, the irreversible covalent bond is a single bond between a carbon atom on the exogenous compound and the sulfur atom on the sidechain of the cysteine residue.

In some embodiments, the covalent bond between the exogenous compound and the cysteine residue is an irreversible covalent bond, wherein the cysteine residue is selected from C296 and C310. In some embodiments, the covalent bond between the exogenous compound and the cysteine residue is an irreversible single covalent bond, wherein the cysteine residue is selected from C296 and C310. In some embodiments, the covalent bond between the exogenous compound and the cysteine residue is an irreversible covalent bond, wherein the cysteine residue is C296. In some embodiments, the covalent bond between the exogenous compound and the cysteine residue is an irreversible covalent single bond, wherein the cysteine residue is C296. In some embodiments, the covalent bond between the exogenous compound and the cysteine residue is an irreversible covalent bond, wherein the cysteine residue is C310. In some embodiments, the covalent bond between the exogenous compound and the cysteine residue is an irreversible covalent single bond, wherein the cysteine residue is C310.

In some embodiments, the irreversible covalent bond in the in vivo AKT1 protein comprises a carbon-sulfur interaction. In some embodiments, the carbon-sulfur interaction is a carbon-sulfur single bond.

In some embodiments, the AKT1 protein is covalently bound with the exogenous compound, wherein the exogenous compound is bound at only one residue of the AKT1 protein. In some embodiments, the AKT1 protein is covalently bond with the exogenous compound via one covalent bond. In some embodiments, the AKT1 protein is covalently bound with the exogenous compound, wherein the exogenous compound is bound at one cysteine residue. In some embodiments, the AKT1 protein has a single covalent bond between a cysteine residue and the exogenous compound. In some embodiments, the AKT1 protein has a single covalent bond between C296 and the exogenous compound. In some embodiments, the AKT1 protein has a single covalent bond between C310 and the exogenous compound.

In some embodiments, the exogenous compound has reduced engagement at other cysteine residues when covalently bound at a cysteine residue selected from C296 and C310. In some embodiments, the exogenous compound is in contact with one cysteine residue selected from C296 and C310, and has reduced engagement at the remaining cysteine residues. In some embodiments, the exogenous compound is in contact with C296, and has reduced engagement at C310. In some embodiments, the exogenous compound is in contact with C310, and has reduced engagement at C296.

In some embodiments, the AKT1 protein has a single cysteine residue covalently bound with the exogenous compound. In some embodiments, the AKT1 protein has a single cysteine residue covalently bound with the exogenous compound, wherein the single cysteine residue is selected from C296 and C310. In some embodiments, the AKT1 protein has a single cysteine residue covalently bound with the exogenous compound, wherein the single cysteine residue is C296. In some embodiments, the AKT1 protein has a single cysteine residue covalently bound with the exogenous compound, wherein the single cysteine residue is C310.

In some embodiments, the AKT1 protein is in vivo. In some embodiments, the AKT1 protein is in vitro. In some embodiments, the AKT1 protein is ex vivo. In some embodiments, the AKT1 protein is an in vivo engineered protein.

In some embodiments, the AKT1 protein is an in vivo engineered AKT1 protein, wherein the in vivo engineered AKT1 protein is generated by contacting the AKT1 protein in vivo with the exogenous compound. In some embodiments, the AKT1 protein is a mammalian in vivo engineered AKT1 protein, wherein the in vivo engineered AKT1 protein is generated by contacting the AKT1 protein in vivo with the exogenous compound. In some embodiments, the AKT1 protein is a human in vivo engineered AKT1 protein, wherein the in vivo engineered AKT1 protein is generated by contacting the AKT1 protein in vivo with the exogenous compound.

In some embodiments, the irreversible covalent bond in the in vivo AKT1 protein is between a carbon atom and a sulfur atom. In some embodiments, the irreversible covalent bond in the in vivo AKT1 protein is between a carbon atom of the exogenous compound and a sulfur atom of the cysteine residue. In some embodiments, the irreversible covalent bond in the in vivo AKT1 protein is between a carbon atom of the exogenous compound and a sulfur atom of the cysteine residue selected from C296 and C310. In some embodiments, the irreversible covalent bond in the in vivo AKT1 protein is between a carbon atom of the exogenous compound and a sulfur atom of the C296 cysteine residue. In some embodiments, the irreversible covalent bond in the in vivo AKT1 protein is between a carbon atom of the exogenous compound and a sulfur atom of the C310 cysteine residue.

In some embodiments, the irreversible covalent bond in the in vivo AKT1 protein is a carbon-sulfur single bond. In some embodiments, the irreversible covalent bond in the in vivo AKT1 protein is a carbon-sulfur single bond between the exogenous compound and the cysteine residue. In some embodiments, the carbon-sulfur single bond is between the exogenous compound and the cysteine residue, wherein the cysteine residue is selected from C296 and C310. In some embodiments, the carbon-sulfur single bond is between the exogenous compound and the C296 cysteine residue. In some embodiments, the carbon-sulfur single bond is between the exogenous compound and the C310 cysteine residue.

In some embodiments, the exogenous compound comprises a cysteine susceptible electrophile. In some embodiments, the cysteine susceptible electrophile is selected from: an acrylate group, an acrylamide group, a vinyl group, a vinylsulfone group, a vinylsulfonamide group, an ynamide, and an epoxide group. In some embodiments, the cysteine susceptible electrophile is selected from: an acrylate group, an acrylamide group, a vinylsulfone group, and a vinylsulfonamide group. In some embodiments, the cysteine susceptible electrophile is selected from an acrylate group and an acrylamide group. In some embodiments, the cysteine susceptible electrophile is an acrylamide group. In some embodiments, the exogenous compound comprises an acrylate group, an acrylamide group, a vinyl group, a vinylsulfone group, a vinylsulfonamide group, an ynamide, and an epoxide group. In some embodiments, the exogenous compound comprises an acrylate group, an acrylamide group, a vinylsulfone group, and a vinylsulfonamide group. In some embodiments, the exogenous compound comprises an acrylate group and an acrylamide group. In some embodiments, the exogenous compound comprises an acrylamide group.

In some embodiments, the irreversible covalent bond is between the cysteine susceptible electrophile and the cysteine residue. In some embodiments, the irreversible covalent bond is between the cysteine susceptible electrophile and the cysteine residue selected from C296 and C310. In some embodiments, the irreversible covalent bond is between the cysteine susceptible electrophile and the C296 cysteine residue. In some embodiments, the irreversible covalent bond is between the cysteine susceptible electrophile and the C310 cysteine residue.

In some embodiments, the carbon-sulfur bond is an irreversible bond that results from an irreversible reaction. In some embodiments, the carbon-sulfur bond is an irreversible bond that results from an irreversible reaction between the exogenous compound and a cysteine residue. In some embodiments, the carbon-sulfur bond is an irreversible bond that results from an irreversible reaction between the exogenous compound and a cysteine residue selected from C296 and C310. In some embodiments, the carbon-sulfur bond is an irreversible bond that results from an irreversible reaction between the exogenous compound and the C296 cysteine residue. In some embodiments, the carbon-sulfur bond is an irreversible bond that results from an irreversible reaction between the exogenous compound and the C310 cysteine residue.

In some embodiments, the carbon-sulfur single bond results from an irreversible reaction between the thiol functional group of a cysteine residue and a cysteine susceptible electrophile on the exogenous compound. In some embodiments, the carbon-sulfur single bond results from an irreversible reaction between the thiol functional group of a cysteine residue and the cysteine susceptible electrophile on the exogenous compound, wherein the cysteine residue is selected from C296 and C310. In some embodiments, the carbon-sulfur single bond results from an irreversible reaction between the thiol functional group of C296 and a cysteine susceptible electrophile on the exogenous compound. In some embodiments, the carbon-sulfur single bond results from an irreversible reaction between the thiol functional group of C310 and a cysteine susceptible electrophile on the exogenous compound.

In some embodiments, the cysteine susceptible electrophile of the exogenous compound is selected from: an acrylamide group, a vinyl group, a vinylsulfone group, a vinylsulfonamide group, an ynamide, and an epoxide group. In some embodiments, the cysteine susceptible electrophile of the exogenous compound is selected from: an acrylate group, an acrylamide group, a vinylsulfone group, and a vinylsulfonamide group. In some embodiments, the cysteine susceptible electrophile of the exogenous compound is selected from: an acrylate group and an acrylamide group. In some embodiments, the cysteine susceptible electrophile of the exogenous compound is an acrylamide group.

In some embodiments, the carbon-sulfur single bond results from an irreversible reaction between the thiol functional group of a cysteine residue and the acrylate group on the exogenous compound. In some embodiments, the carbon-sulfur single bond results from an irreversible reaction between the thiol functional group of a cysteine residue and the acrylate group on the exogenous compound, wherein the cysteine residue is selected from C296 and C310. In some embodiments, the carbon-sulfur single bond results from an irreversible reaction between the thiol functional group of C296 and the acrylate group on the exogenous compound. In some embodiments, the carbon-sulfur single bond results from an irreversible reaction between the thiol functional group of C310 and the acrylate group on the exogenous compound.

In some embodiments, the carbon-sulfur single bond results from an irreversible reaction between the thiol functional group of a cysteine residue and the acrylamide group on the exogenous compound. In some embodiments, the carbon-sulfur single bond results from an irreversible reaction between the thiol functional group of a cysteine residue and the acrylamide group on the exogenous compound, wherein the cysteine residue is selected from C296 and C310. In some embodiments, the carbon-sulfur single bond results from an irreversible reaction between the thiol functional group of C296 and the acrylamide group on the exogenous compound. In some embodiments, the carbon-sulfur single bond results from an irreversible reaction between the thiol functional group of C310 and the acrylamide group on the exogenous compound.

In some embodiments, the carbon-sulfur single bond results from an irreversible reaction between the thiol functional group of a cysteine residue and the vinyl group on the exogenous compound. In some embodiments, the carbon-sulfur single bond results from an irreversible reaction between the thiol functional group of a cysteine residue and the vinyl group on the exogenous compound, wherein the cysteine residue is selected from C296 and C310. In some embodiments, the carbon-sulfur single bond results from an irreversible reaction between the thiol functional group of C296 and the vinyl group on the exogenous compound. In some embodiments, the carbon-sulfur single bond results from an irreversible reaction between the thiol functional group of C310 and the vinyl group on the exogenous compound.

In some embodiments, the carbon-sulfur single bond results from an irreversible reaction between the thiol functional group of a cysteine residue and the vinylsulfone group on the exogenous compound. In some embodiments, the carbon-sulfur single bond results from an irreversible reaction between the thiol functional group of a cysteine residue and the vinylsulfone group on the exogenous compound, wherein the cysteine residue is selected from C296 and C310. In some embodiments, the carbon-sulfur single bond results from an irreversible reaction between the thiol functional group of C296 and the vinylsulfone group on the exogenous compound. In some embodiments, the carbon-sulfur single bond results from an irreversible reaction between the thiol functional group of C310 and the vinylsulfone group on the exogenous compound.

In some embodiments, the carbon-sulfur single bond results from an irreversible reaction between the thiol functional group of a cysteine residue and the vinylsulfonamide group on the exogenous compound. In some embodiments, the carbon-sulfur single bond results from an irreversible reaction between the thiol functional group of a cysteine residue and the vinylsulfonamide group on the exogenous compound, wherein the cysteine residue is selected from C296 and C310. In some embodiments, the carbon-sulfur single bond results from an irreversible reaction between the thiol functional group of C296 and the vinylsulfonamide group on the exogenous compound. In some embodiments, the carbon-sulfur single bond results from an irreversible reaction between the thiol functional group of C310 and the vinylsulfonamide group on the exogenous compound.

In some embodiments, the carbon-sulfur single bond results from an irreversible reaction between the thiol functional group of a cysteine residue and the ynamide group on the exogenous compound. In some embodiments, the carbon-sulfur single bond results from an irreversible reaction between the thiol functional group of a cysteine residue and the ynamide group on the exogenous compound, wherein the cysteine residue is selected from C296 and C310. In some embodiments, the carbon-sulfur single bond results from an irreversible reaction between the thiol functional group of C296 and the ynamide group on the exogenous compound. In some embodiments, the carbon-sulfur single bond results from an irreversible reaction between the thiol functional group of C310 and the ynamide group on the exogenous compound.

In some embodiments, the carbon-sulfur single bond results from an irreversible reaction between the thiol functional group of a cysteine residue and the epoxide group on the exogenous compound. In some embodiments, the carbon-sulfur single bond results from an irreversible reaction between the thiol functional group of a cysteine residue and the epoxide group on the exogenous compound, wherein the cysteine residue is selected from C296 and C310. In some embodiments, the carbon-sulfur single bond results from an irreversible reaction between the thiol functional group of C296 and the epoxide group on the exogenous compound. In some embodiments, the carbon-sulfur single bond results from an irreversible reaction between the thiol functional group of C310 and the epoxide group on the exogenous compound.

In some embodiments, the exogenous compound is a compound or salt as disclosed herein. In some embodiments, the exogenous compound is selected from a compound or salt of Formula (II), Formula (II-A), or Formula (III). In some embodiments, the exogenous compound is selected from a compound or salt in Table 1.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous cysteine susceptible electrophile and the cysteine residue of AKT1, wherein the cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous acrylate group and the cysteine residue of AKT1, wherein the acrylate group undergoes a nucleophilic addition with the thiol functional group on the cysteine residue and forming a carbon-sulfur single bond between the exogenous acrylate group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous acrylamide group and the cysteine residue of AKT1, wherein the acrylamide group undergoes a nucleophilic addition with the thiol functional group on the cysteine residue and forming a carbon-sulfur single bond between the exogenous acrylamide group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous vinyl group and the cysteine residue of AKT1, wherein the vinyl group undergoes a nucleophilic addition with the thiol functional group on the cysteine residue and forming a carbon-sulfur single bond between the exogenous vinyl group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous vinylsulfone group and the cysteine residue of AKT1, wherein the vinylsulfone group undergoes a nucleophilic addition with the thiol functional group on the cysteine residue and forming a carbon-sulfur single bond between the exogenous vinylsulfone group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous vinylsulfonamide group and the cysteine residue of AKT1, wherein the vinylsulfonamide group undergoes a nucleophilic addition with the thiol functional group on the cysteine residue and forming a carbon-sulfur single bond between the exogenous vinylsulfonamide group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous ynamide group and the cysteine residue of AKT1, wherein the ynamide group undergoes a nucleophilic addition with the thiol functional group on the cysteine residue and forming a carbon-sulfur single bond between the exogenous ynamide group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprising a non-naturally occurring irreversible covalent modification at a cysteine residue, the irreversible covalent modification being generated from an in vivo nucleophilic reaction between an exogenous epoxide group and the cysteine residue of AKT1, wherein the epoxide group undergoes a nucleophilic addition with the thiol functional group on the cysteine residue and forming a carbon-sulfur single bond between the exogenous epoxide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous acrylate group and the cysteine residue of AKT1, wherein the exogenous acrylate group undergoes a nucleophilic addition with the thiol functional group on the cysteine residue and forming a carbon-sulfur single bond between the exogenous acrylate group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous acrylamide group and the cysteine residue of AKT1, wherein the exogenous acrylamide group undergoes a nucleophilic addition with the thiol functional group on the cysteine residue and forming a carbon-sulfur single bond between the exogenous acrylamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous vinyl group and the cysteine residue of AKT1, wherein the exogenous vinyl group undergoes a nucleophilic addition with the thiol functional group on the cysteine residue and forming a carbon-sulfur single bond between the exogenous vinyl group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous vinylsulfone group and the cysteine residue of AKT1, wherein the exogenous vinylsulfone group undergoes a nucleophilic addition with the thiol functional group on the cysteine residue and forming a carbon-sulfur single bond between the exogenous vinylsulfone group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous vinylsulfonamide group and the cysteine residue of AKT1, wherein the exogenous vinylsulfonamide group undergoes a nucleophilic addition with the thiol functional group on the cysteine residue and forming a carbon-sulfur single bond between the exogenous vinylsulfonamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous ynamide group and the cysteine residue of AKT1, wherein the exogenous ynamide group undergoes a nucleophilic addition with the thiol functional group on the cysteine residue and forming a carbon-sulfur single bond between the exogenous ynamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue selected from C296 and C310, the irreversible covalent modification being generated from an in vivo nucleophilic reaction between an exogenous epoxide group and the cysteine residue of AKT1, wherein the exogenous epoxide group undergoes a nucleophilic addition with the thiol functional group on the cysteine residue and forming a carbon-sulfur single bond between the exogenous epoxide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous acrylate group and the cysteine residue of AKT1, wherein the exogenous acrylate group undergoes a nucleophilic addition with the thiol functional group on the cysteine residue and forming a carbon-sulfur single bond between the exogenous acrylate group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous acrylamide group and the cysteine residue of AKT1, wherein the exogenous acrylamide group undergoes a nucleophilic addition with the thiol functional group on the cysteine residue and forming a carbon-sulfur single bond between the exogenous acrylamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous vinyl group and the cysteine residue of AKT1, wherein the exogenous vinyl group undergoes a nucleophilic addition with the thiol functional group on the cysteine residue and forming a carbon-sulfur single bond between the exogenous vinyl group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous vinylsulfone group and the cysteine residue of AKT1, wherein the exogenous vinylsulfone group undergoes a nucleophilic addition with the thiol functional group on the cysteine residue and forming a carbon-sulfur single bond between the exogenous vinylsulfone group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous vinylsulfonamide group and the cysteine residue of AKT1, wherein the exogenous vinylsulfonamide group undergoes a nucleophilic addition with the thiol functional group on the cysteine residue and forming a carbon-sulfur single bond between the exogenous vinylsulfonamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous ynamide group and the cysteine residue of AKT1, wherein the exogenous ynamide group undergoes a nucleophilic addition with the thiol functional group on the cysteine residue and forming a carbon-sulfur single bond between the exogenous ynamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C296, the irreversible covalent modification being generated from an in vivo nucleophilic reaction between an exogenous epoxide group and the cysteine residue of AKT1, wherein the exogenous epoxide group undergoes a nucleophilic addition with the thiol functional group on the cysteine residue and forming a carbon-sulfur single bond between the exogenous epoxide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous acrylate group and the cysteine residue of AKT1, wherein the exogenous acrylate group undergoes a nucleophilic addition with the thiol functional group on the cysteine residue and forming a carbon-sulfur single bond between the exogenous acrylate group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous acrylamide group and the cysteine residue of AKT1, wherein the exogenous acrylamide group undergoes a nucleophilic addition with the thiol functional group on the cysteine residue and forming a carbon-sulfur single bond between the exogenous acrylamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous vinyl group and the cysteine residue of AKT1, wherein the exogenous vinyl group undergoes a nucleophilic addition with the thiol functional group on the cysteine residue and forming a carbon-sulfur single bond between the exogenous vinyl group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous vinylsulfone group and the cysteine residue of AKT1, wherein the exogenous vinylsulfone group undergoes a nucleophilic addition with the thiol functional group on the cysteine residue and forming a carbon-sulfur single bond between the exogenous vinylsulfone group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous vinylsulfonamide group and the cysteine residue of AKT1, wherein the exogenous vinylsulfonamide group undergoes a nucleophilic addition with the thiol functional group on the cysteine residue and forming a carbon-sulfur single bond between the exogenous vinylsulfonamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous ynamide group and the cysteine residue of AKT1, wherein the exogenous ynamide group undergoes a nucleophilic addition with the thiol functional group on the cysteine residue and forming a carbon-sulfur single bond between the exogenous ynamide group and the thiol functional group on the cysteine residue. In some embodiments, the in vivo engineered AKT1 protein is a human in vivo engineered AKT1 protein.

In another aspect, the present disclosure provides an in vivo engineered AKT1 protein comprising a non-naturally occurring irreversible covalent modification at a cysteine residue C310, the irreversible covalent modification being generated from an in vivo nucleophilic reaction between an exogenous epoxide group and the cysteine residue of AKT1, wherein the exogenous epoxide group undergoes a nucleophilic addition with the thiol functional group on the cysteine residue and forming a carbon-sulfur single bond between the exogenous epoxide group and the thiol functional group on the cysteine residue. In some embodiments, the in vivo engineered AKT1 protein is a human in vivo engineered AKT1 protein.

In certain aspects the present disclosure provides an in vivo engineered AKT1 protein comprises a mutation selected from E17K, E40K, and E49K, a non-naturally occurring irreversible covalent modification at a cysteine residue, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue.

In certain aspects the present disclosure provides an in vivo engineered AKT1 protein comprising a E17K mutation, a non-naturally occurring irreversible covalent modification at a cysteine residue, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the cysteine susceptible electrophile is selected from: an acrylate group, an acrylamide group, a vinyl group, a vinylsulfone group, a vinylsulfonamide group, an ynamide group, and an epoxide group. In some embodiments, the cysteine susceptible electrophile is selected from: an acrylate group, an acrylamide group, a vinylsulfone group, and a vinylsulfonamide group. In some embodiments, the cysteine susceptible electrophile is selected from: an acrylate group and an acrylamide group. In some embodiments, the cysteine susceptible electrophile is an acrylamide group.

In another aspect, the present disclosure provides an in vivo engineered AKT1 protein comprising a E17K mutation, a non-naturally occurring irreversible covalent modification at a cysteine residue selected from C296 and C310, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the in vivo engineered AKT1 protein is a human in vivo engineered AKT1 protein.

In certain aspects the present disclosure provides a human in vivo engineered AKT1 protein comprising a E17K mutation, a non-naturally occurring irreversible covalent modification at a cysteine residue, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the cysteine susceptible electrophile is selected from: an acrylate group, an acrylamide group, a vinyl group, a vinylsulfone group, a vinylsulfonamide group, an ynamide group, and an epoxide group. In some embodiments, the cysteine susceptible electrophile is selected from: an acrylate group, an acrylamide group, a vinylsulfone group, and a vinylsulfonamide group. In some embodiments, the cysteine susceptible electrophile is selected from: an acrylate group and an acrylamide group. In some embodiments, the cysteine susceptible electrophile is an acrylamide group.

In another aspect, the present disclosure provides a human in vivo engineered AKT1 protein comprising a E17K mutation, a non-naturally occurring irreversible covalent modification at a cysteine residue, the irreversible covalent modification being generated from an in vivo nucleophilic reaction between an exogenous cysteine susceptible electrophile and the cysteine residue of AKT1, wherein the exogenous cysteine susceptible electrophile undergoes a nucleophilic addition with the thiol functional group on the cysteine residue and forming a carbon-sulfur single bond between the exogenous cysteine susceptible electrophile and the thiol functional group on the cysteine residue. In some embodiments, the cysteine susceptible electrophile is selected from: an acrylate group, an acrylamide group, a vinyl group, a vinylsulfone group, a vinylsulfonamide group, an ynamide group, and an epoxide group. In some embodiments, the cysteine susceptible electrophile is selected from: an acrylate group, an acrylamide group, a vinylsulfone group, and a vinylsulfonamide group. In some embodiments, the cysteine susceptible electrophile is selected from: an acrylate group and an acrylamide group. In some embodiments, the cysteine susceptible electrophile is an acrylamide group.

Method of Modifying AKT1 Proteins

In some aspects the present disclosure provides a method of modifying an AKT1 protein as disclosed herein. In some embodiments, the method of covalently modifying an AKT1 protein, comprises contacting the AKT1 protein with an exogenous compound, wherein the exogenous compound comprises an irreversible electrophilic moiety thereby forming an irreversible covalent AKT1 adduct. In some embodiments, the contacting is in vitro or in vivo. In some embodiments, the contacting is in vitro. In some embodiments, the contacting is in vivo. In some embodiments, the AKT1 protein is wild type AKT1 or a mutated AKT1. In some embodiments, the mutated AKT1 is E17K AKT1. In some embodiments, the wild type AKT1 protein is wild type. In some embodiments, the AKT1 protein is E17K AKT1. In some embodiments, the exogenous compound is an AKT1 inhibitor. In some embodiments, the irreversible covalent moiety on the AKT1 inhibitor is a cysteine susceptible electrophile. In some embodiments, the irreversible covalent AKT1 adduct is formed between the irreversible covalent moiety and a cysteine reside of the AKT1 protein. In some embodiments, the irreversible covalent AKT1 adduct is formed between the cysteine susceptible electrophile and the cysteine residue of the AKT1 protein. In some embodiments, irreversible covalent AKT1 adduct is formed between the irreversible covalent moiety and a cysteine residue of the AKT1 protein selected from C296 and C310. In some embodiments, irreversible covalent AKT1 adduct is formed between the cysteine susceptible electrophile and a cysteine residue of the AKT1 protein selected from C296 and C310. In some embodiments, irreversible covalent AKT1 adduct is formed between the cysteine susceptible electrophile and the C296 cysteine residue of the AKT1 protein. In some embodiments, irreversible covalent AKT1 adduct is formed between the cysteine susceptible electrophile and the C310 cysteine residue of the AKT1 protein. In some embodiments, the cysteine susceptible electrophile is selected from: an acrylate group, an acrylamide group, a vinyl group, a vinylsulfone group, a vinylsulfonamide group, an ynamide group, and an epoxide group. In some embodiments, the cysteine susceptible electrophile is selected from: an acrylate group, an acrylamide group, a vinylsulfone group, and a vinylsulfonamide group. In some embodiments, the cysteine susceptible electrophile is selected from: an acrylate group and an acrylamide group. In some embodiments, the cysteine susceptible electrophile is an acrylamide group.

In another aspect, the method of covalently modifying an AKT1 protein, comprises contacting the AKT1 protein with an exogenous AKT1 modulator, wherein the AKT1 modulator comprises an irreversible electrophilic moiety thereby forming an irreversible covalent AKT1 adduct. In some embodiments, the contacting is in vitro or in vivo. In some embodiments, the contacting is in vitro. In some embodiments, the contacting is in vivo. In some embodiments, the AKT1 protein is wild type AKT1 or a mutated AKT1. In some embodiments, the mutated AKT1 is selected from E17K AKT1, E40K AKT1, and E49K AKT1. In some embodiments, the mutated AKT1 is E17K AKT1. In some embodiments, the wild type AKT1 protein is wild type. In some embodiments, the AKT1 protein is E17K AKT1. In some embodiments, the irreversible covalent moiety on the AKT1 modulator is a cysteine susceptible electrophile. In some embodiments, the irreversible covalent AKT1 adduct is formed between the irreversible covalent moiety and a cysteine reside of the AKT1 protein. In some embodiments, the irreversible covalent AKT1 adduct is formed between the cysteine susceptible electrophile and the cysteine residue of the AKT1 protein. In some embodiments, irreversible covalent AKT1 adduct is formed between the irreversible covalent moiety and a cysteine residue of the AKT1 protein selected from C296 and C310. In some embodiments, irreversible covalent AKT1 adduct is formed between the cysteine susceptible electrophile and a cysteine residue of the AKT1 protein selected from C296 and C310. In some embodiments, irreversible covalent AKT1 adduct is formed between the cysteine susceptible electrophile and the C296 cysteine residue of the AKT1 protein. In some embodiments, irreversible covalent AKT1 adduct is formed between the cysteine susceptible electrophile and the C310 cysteine residue of the AKT1 protein. In some embodiments, the exogenous AKT1 modulator is an AKT1 inhibitor. In some embodiments, the cysteine susceptible electrophile is selected from: an acrylate group, an acrylamide group, a vinyl group, a vinylsulfone group, a vinylsulfonamide group, an ynamide group, and an epoxide group. In some embodiments, the cysteine susceptible electrophile is selected from: an acrylate group, an acrylamide group, a vinylsulfone group, and a vinylsulfonamide group. In some embodiments, the cysteine susceptible electrophile is selected from: an acrylate group and an acrylamide group. In some embodiments, the cysteine susceptible electrophile is an acrylamide group.

In certain aspects the present disclosure provides a method of attenuating AKT1 activity. In some embodiments, the method of covalently modifying an AKT1 protein, comprises contacting the AKT1 protein with an exogenous AKT1 inhibitor, wherein the AKT1 modulator comprises an irreversible electrophilic moiety thereby forming an irreversible covalent AKT1 adduct. In some embodiments, the contacting is in vitro or in vivo. In some embodiments, the contacting is in vitro. In some embodiments, the contacting is in vivo. In some embodiments, the AKT1 protein is wild type AKT1 or a mutated AKT1. In some embodiments, the mutated AKT1 is selected from E17K AKT1, E40K AKT1, and E49K AKT1. In some embodiments, the mutated AKT1 is E17K AKT1. In some embodiments, the wild type AKT1 protein is wild type. In some embodiments, the AKT1 protein is E17K AKT1. In some embodiments, the irreversible covalent moiety on the AKT1 inhibitor is a cysteine susceptible electrophile. In some embodiments, the irreversible covalent AKT1 adduct is formed between the irreversible covalent moiety and a cysteine reside of the AKT1 protein. In some embodiments, the irreversible covalent AKT1 adduct is formed between the cysteine susceptible electrophile and the cysteine residue of the AKT1 protein. In some embodiments, irreversible covalent AKT1 adduct is formed between the irreversible covalent moiety and a cysteine residue of the AKT1 protein selected from C296 and C310. In some embodiments, irreversible covalent AKT1 adduct is formed between the cysteine susceptible electrophile and a cysteine residue of the AKT1 protein selected from C296 and C310. In some embodiments, irreversible covalent AKT1 adduct is formed between the cysteine susceptible electrophile and the C296 cysteine residue of the AKT1 protein. In some embodiments, irreversible covalent AKT1 adduct is formed between the cysteine susceptible electrophile and the C310 cysteine residue of the AKT1 protein.

In some aspects, the method of attenuating AKT1 activity, comprises contacting AKT1 protein with an exogenous compound, wherein the exogenous compound comprises an irreversible electrophilic moiety. In some embodiments, the AKT1 protein is wild type AKT1 or a mutated AKT1. In some embodiments, the mutated AKT1 is selected from E17K AKT1, E40K AKT1, and E49K AKT1. In some embodiments, the mutated AKT1 is E17K AKT1. In some embodiments, the wild type AKT1 protein is wild type. In some embodiments, the contacting is in vitro or in vivo. In some embodiments, the contacting is in vitro.

In some embodiments, following the contacting, the AKT1 activity is attenuated by 50% to 95% relative to a control in the absence of the exogenous compound. In some embodiments, following the contacting, the AKT1 activity is attenuated by 75% to 95% relative to a control in the absence of the exogenous compound. In some embodiments, following the contacting, the AKT1 activity is attenuated by 50%, 55%, 60%, 65%, 70%, 75%, 80%, 85%, 90%, 95%, or more relative to a control in the absence of the exogenous compound. In some embodiments, following the contacting, the AKT1 activity is attenuated by 50% or more relative to a control in the absence of the exogenous compound. In some embodiments, following the contacting, the AKT1 activity is attenuated by 70% or more relative to a control in the absence of the exogenous compound.

In some embodiments, following the contacting, the AKT1 activity is attenuated by about 50% to about 95% relative to a control in the absence of the exogenous compound. In some embodiments, following the contacting, the AKT1 activity is attenuated by about 75% to about 95% relative to a control in the absence of the exogenous compound. In some embodiments, following the contacting, the AKT1 activity is attenuated by about 50%, about 55%, about 60%, about 65%, about 70%, about 75%, about 80%, about 85%, about 90%, about 95%, or more relative to a control in the absence of the exogenous compound. In some embodiments, following the contacting, the AKT1 activity is attenuated by about 50% or more relative to a control in the absence of the exogenous compound. In some embodiments, following the contacting, the AKT1 activity is attenuated by about 70% or more relative to a control in the absence of the exogenous compound.

In some embodiments, following the contacting, the AKT1 activity is attenuated by at least 50% to at least 95% relative to a control in the absence of the exogenous compound. In some embodiments, following the contacting, the AKT1 activity is attenuated by at least 75% to at least 95% relative to a control in the absence of the exogenous compound. In some embodiments, following the contacting, the AKT1 activity is attenuated by at least 50%, at least 55%, at least 60%, at least 65%, at least 70%, at least 75%, at least 80%, at least 85%, at least 90%, or at least 95% relative to a control in the absence of the exogenous compound. In some embodiments, following the contacting, the AKT1 activity is attenuated by at least 50% relative to a control in the absence of the exogenous compound. In some embodiments, following the contacting, the AKT1 activity is attenuated by at least 70% relative to a control in the absence of the exogenous compound.

In some embodiments, following the contacting, the AKT1 activity is attenuated by at most 50% to at most 95% relative to a control in the absence of the exogenous compound. In some embodiments, following the contacting, the AKT1 activity is attenuated by at most 75% to at most 95% relative to a control in the absence of the exogenous compound. In some embodiments, following the contacting, the AKT1 activity is attenuated by at most 50% relative to a control in the absence of the exogenous compound. In some embodiments, following the contacting, the AKT1 activity is attenuated by at most 70% relative to a control in the absence of the exogenous compound. In some embodiments, following the contacting, the AKT1 activity is attenuated by at most 50%, at most 55%, at most 60%, at most 65%, at most 70%, at most 75%, at most 80%, at most 85%, at most 90%, or at most 95% relative to a control in the absence of the exogenous compound.

In some embodiments, the exogenous compound is more selective toward mutated AKT1 than wild-type AKT1. In some embodiments, the mutated AKT1 is E17K AKT1. In some embodiments, the exogenous compound is 2-fold to 100-fold more selective for E17K AKT1 over wild-type AKT1. In some embodiments, the exogenous compound is 2-fold to 10-fold more selective for E17K AKT1 over wild-type AKT1. In some embodiments, the exogenous compound is 2-fold to 5-fold more selective for E17K AKT1 over wild-type AKT1. In some embodiments, the exogenous compound is 2-fold more selective for E17K AKT1 over wild-type AKT1. In some embodiments, the exogenous compound is 3-fold more selective for E17K AKT1 over wild-type AKT1. In some embodiments, the exogenous compound is 4-fold more selective for E17K AKT1 over wild-type AKT1. In some embodiments, the exogenous compound is 5-fold more selective for E17K AKT1 over wild-type AKT1. In some embodiments, the exogenous compound is 10-fold more selective for E17K AKT1 over wild-type AKT1. In some embodiments, the exogenous compound is 2-fold, 3-fold, 4-fold, 5-fold, 6-fold, 7-fold, 8-fold, 9-fold, 10-fold, 15-fold, 20-fold, 25-fold, 50-fold, 75-fold, or 100-fold more selective for E17K AKT1 over wild-type AKT1.

In some embodiments, the exogenous compound is at least 2-fold more selective for E17K AKT1 over wild-type AKT1. In some embodiments, the exogenous compound is at least 3-fold more selective for E17K AKT1 over wild-type AKT1. In some embodiments, the exogenous compound is at least 4-fold more selective for E17K AKT1 over wild-type AKT1. In some embodiments, the exogenous compound is at least 5-fold more selective for E17K AKT1 over wild-type AKT1. In some embodiments, the exogenous compound is at least 10-fold more selective for E17K AKT1 over wild-type AKT1. In some embodiments, the exogenous compound is at least 2-fold more selective for E17K AKT1 over wild-type AKT1. In some embodiments, the exogenous compound is at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, at least 75-fold, or at least 100-fold more selective for E17K AKT1 over wild-type AKT1.

In some embodiments, the exogenous compound is about 2-fold more selective for E17K AKT1 over wild-type AKT1. In some embodiments, the exogenous compound is about 3-fold more selective for E17K AKT1 over wild-type AKT1. In some embodiments, the exogenous compound is about 4-fold more selective for E17K AKT1 over wild-type AKT1. In some embodiments, the exogenous compound is about 5-fold more selective for E17K AKT1 over wild-type AKT1. In some embodiments, the exogenous compound is about 10-fold more selective for E17K AKT1 over wild-type AKT1. In some embodiments, the exogenous compound is about 2-fold, about 3-fold, about 4-fold, about 5-fold, about 6-fold, about 7-fold, about 8-fold, about 9-fold, about 10-fold, about 15-fold, about 20-fold, about 25-fold, about 50-fold, about 75-fold, or about 100-fold more selective for E17K AKT1 over wild-type AKT1.

In some embodiments, the exogenous compound is at most 2-fold more selective for E17K AKT1 over wild-type AKT1. In some embodiments, the exogenous compound is at most 3-fold more selective for E17K AKT1 over wild-type AKT1. In some embodiments, the exogenous compound is at most 4-fold more selective for E17K AKT1 over wild-type AKT1. In some embodiments, the exogenous compound is at most 5-fold more selective for E17K AKT1 over wild-type AKT1. In some embodiments, the exogenous compound is at most 10-fold more selective for E17K AKT1 over wild-type AKT1. In some embodiments, the exogenous compound is at most 2-fold more selective for E17K AKT1 over wild-type AKT1. In some embodiments, the exogenous compound is at most 2-fold, at most 3-fold, at most 4-fold, at most 5-fold, at most 6-fold, at most 7-fold, at most 8-fold at most 9-fold, at most 10-fold, at most 15-fold, at most 20-fold, at most 25-fold, at most 50-fold at most 75-fold, or at most 100-fold more selective for E17K AKT1 over wild-type AKT1.

In another aspect, the present disclosure provides a method of attenuating AKT1 activity, comprising contacting AKT1 protein with an AKT1 inhibitor, wherein the AKT1 inhibitor comprises an irreversible electrophilic moiety. In some embodiments, the AKT1 protein is wild type AKT1 or a mutated AKT1. In some embodiments, the mutated AKT1 is selected from E17K AKT1, E40K AKT1, and E49K AKT1. In some embodiments, the mutated AKT1 is E17K AKT1. In some embodiments, the wild type AKT1 protein is wild type. In some embodiments, the contacting is in vitro or in vivo. In some embodiments, the contacting is in vitro.

In some embodiments, following the contacting, the AKT1 activity is attenuated by 50% to 95% relative to a control in the absence of the exogenous AKT1 inhibitor. In some embodiments, following the contacting, the AKT1 activity is attenuated by 75% to 95% relative to a control in the absence of the exogenous AKT1 inhibitor. In some embodiments, following the contacting, the AKT1 activity is attenuated by 50%, 55%, 60%, 65%, 70%, 75%, 80%, 85%, 90%, 95%, or more relative to a control in the absence of the exogenous AKT1 inhibitor. In some embodiments, following the contacting, the AKT1 activity is attenuated by 50% or more relative to a control in the absence of the exogenous AKT1 inhibitor. In some embodiments, following the contacting, the AKT1 activity is attenuated by 70% or more relative to a control in the absence of the exogenous AKT1 inhibitor.

In some embodiments, following the contacting, the AKT1 activity is attenuated by about 50% to about 95% relative to a control in the absence of the exogenous AKT1 inhibitor. In some embodiments, following the contacting, the AKT1 activity is attenuated by about 75% to about 95% relative to a control in the absence of the exogenous AKT1 inhibitor. In some embodiments, following the contacting, the AKT1 activity is attenuated by about 50%, about 55%, about 60%, about 65%, about 70%, about 75%, about 80%, about 85%, about 90%, about 95%, or more relative to a control in the absence of the exogenous AKT1 inhibitor. In some embodiments, following the contacting, the AKT1 activity is attenuated by about 50% or more relative to a control in the absence of the exogenous AKT1 inhibitor. In some embodiments, following the contacting, the AKT1 activity is attenuated by about 70% or more relative to a control in the absence of the exogenous AKT1 inhibitor.

In some embodiments, following the contacting, the AKT1 activity is attenuated by at least 50% to at least 95% relative to a control in the absence of the exogenous AKT1 inhibitor. In some embodiments, following the contacting, the AKT1 activity is attenuated by at least 75% to at least 95% relative to a control in the absence of the exogenous AKT1 inhibitor. In some embodiments, following the contacting, the AKT1 activity is attenuated by at least 50%, at least 55%, at least 60%, at least 65%, at least 70%, at least 75%, at least 80%, at least 85%, at least 90%, or at least 95% relative to a control in the absence of the exogenous AKT1 inhibitor. In some embodiments, following the contacting, the AKT1 activity is attenuated by at least 50% relative to a control in the absence of the exogenous AKT1 inhibitor. In some embodiments, following the contacting, the AKT1 activity is attenuated by at least 70% relative to a control in the absence of the exogenous AKT1 inhibitor.

In some embodiments, following the contacting, the AKT1 activity is attenuated by at most 50% to at most 95% relative to a control in the absence of the exogenous AKT1 inhibitor. In some embodiments, following the contacting, the AKT1 activity is attenuated by at most 75% to at most 95% relative to a control in the absence of the exogenous AKT1 inhibitor. In some embodiments, following the contacting, the AKT1 activity is attenuated by at most 50% relative to a control in the absence of the exogenous AKT1 inhibitor. In some embodiments, following the contacting, the AKT1 activity is attenuated by at most 70% relative to a control in the absence of the exogenous AKT1 inhibitor. In some embodiments, following the contacting, the AKT1 activity is attenuated by at most 50%, at most 55%, at most 60%, at most 65%, at most 70%, at most 75%, at most 80%, at most 85%, at most 90%, or at most 95% relative to a control in the absence of the exogenous AKT1 inhibitor.

In some aspects, the exogenous compound is a compound or salt of Formula (I), (I-A), (II), (II-A), (III), (III-A), or (III-B). In some embodiments, the exogenous AKT1 inhibitor is a compound or salt of Formula (I), (I-A), (II), (II-A), (III), (III-A), or (III-B). In some embodiments, the AKT1 inhibitor is a compound or salt of Formula (I), (I-A), (II), (II-A), (III), (III-A), or (III-B).

EXAMPLES

The invention now being generally described, it will be more readily understood by reference to the following examples which are included merely for purposes of illustration of certain aspects and embodiments of the present invention, and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Example 1: (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide Example 1

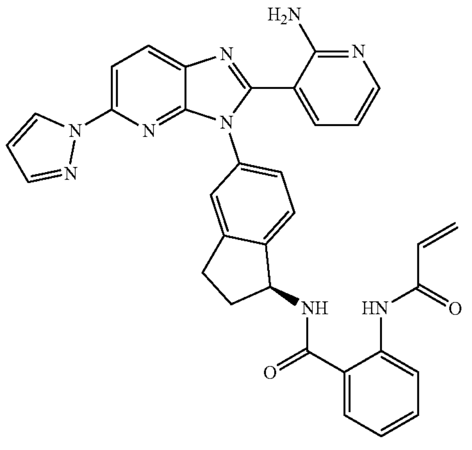

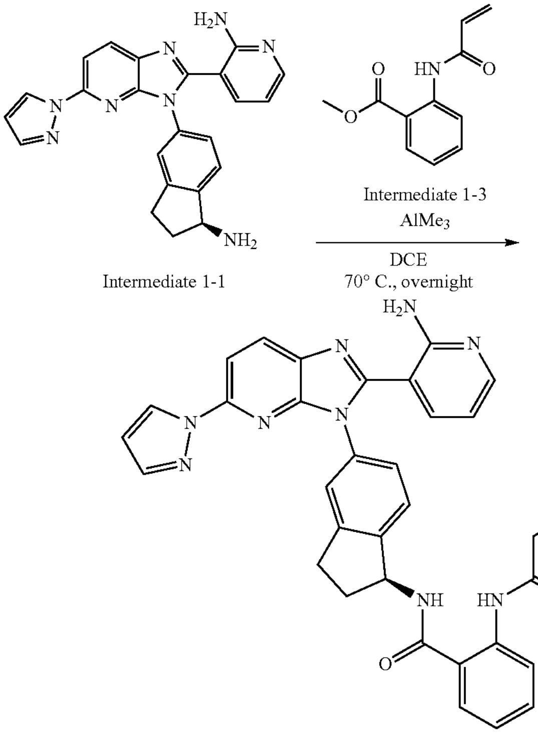

Intermediate 1-1

Example 1

Step 1: Synthesis of (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Example 1)

(S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) was dissolved in water and the pH was brought to 9-10 with saturated aqueous sodium bicarbonate. The mixture was extracted twice with dichloromethane. The organic layers were combined, dried over anhydrous sodium sulfate, filtered, and concentrated in vacuo to obtain the free base. To a cooled (0° C.) solution of free base (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (100 mg, 0.245 mmol, 1 equiv) and methyl 2-acrylamidobenzoate (Intermediate 1-3) (100 mg, 0.490 mmol, 2 equiv) in DCE (3 mL) was added trimethylaluminium (0.1 mL, 0.980 mmol, 1 M in toluene, 4 equiv). The resulting mixture was stirred overnight at 70° C. After cooling to room temperature, the reaction mixture was quenched by the addition of water and the resulting mixture was extracted 3 times with ethyl acetate. The organic phases were combined, dried over anhydrous $Na_2SO_4$, filtered, and concentrated under vacuum. The crude product was purified by preparative HPLC on a XBridge Prep OBD C18 Column using a gradient of acetonitrile in water (+10 mmol/L $NH_4HCO_3$) to afford (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Example 1) (39.6 mg, 20%). MS (ESI) calcd. for $C_{33}H_{27}O_2N_9$: 581.23 m/z, found 582.30 $[M+H]^+$. $^1H$ NMR (500 MHz, DMSO-$d_6$) δ (ppm): 8.32-8.38 (m, 2H), 8.27-8.32 (m, 1H), 7.98-8.02 (m, 1H), 7.91-7.96 (m, 1H), 7.83-7.75 (m, 2H), 7.49-7.56

(m, 1H), 7.40-7.45 (m, 1H), 7.36 (s, 1H), 7.23-7.30 (m, 2H), 7.16-7.23 (m, 1H), 6.51-6.56 (m, 1H), 6.42-6.49 (m, 1H), 6.34-6.41 (m, 1H), 6.21-6.28 (m, 1H), 5.78-5.84 (m, 1H), 5.57-5.64 (m, 1H), 2.98-3.07 (m, 1H), 2.84-2.94 (m 1H), 2.53-2.58 (m, 1H), 2.03-2.14 (m, 1H).

Intermediate 1-1: (S)-3-(3-(1-amino-2,3-dihydro-1H-inden-5-yl)-5-(1H-pyrazol-1-yl)-3H-imidazo[4,5-b]pyridin-2-yl)pyridin-2-amine Intermediate 1-1

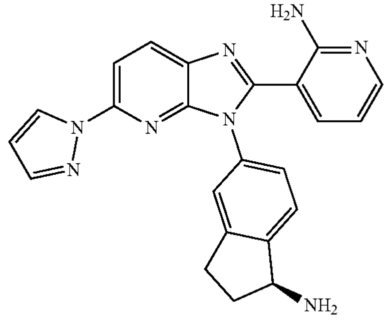

Synthetic Route:

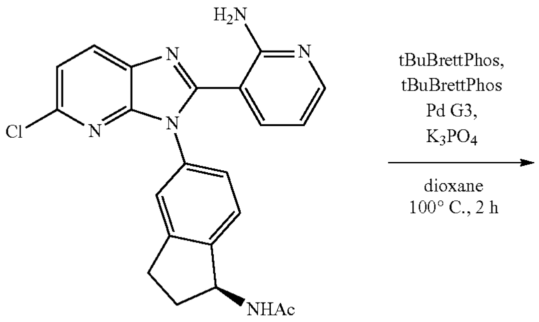

Intermediate 1-2

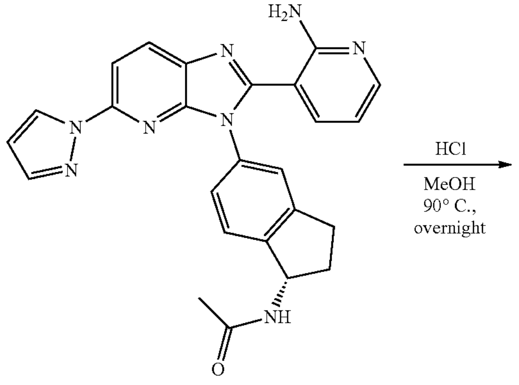

-continued

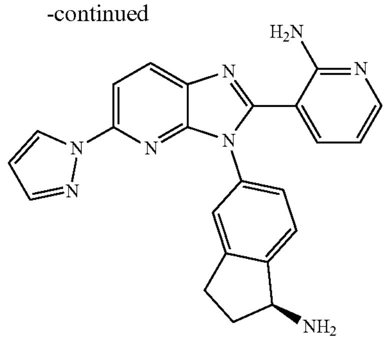

Intermediate 1-1

Step 1: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide To a mixture of (S)-N-(5-(2-(2-aminopyridin-3-yl)-5-chloro-3H-imidazo[4,5-b]pyridin-3-yl)-2,3-dihydro-1H-inden-1-yl)acetamide (Intermediate 1-2) (200 mg, 0.477 mmol, 1 equiv), pyrazole (39 mg, 0.57 mmol, 1.5 equiv), t-BuBrettPhos Pd G3 (41 mg, 0.048 mmol, 0.1 equiv), t-BuBrettPhos (23 mg, 0.048 mmol, 0.1 equiv) and $K_3PO_4$ (304 mg, 1.43 mmol, 3 equiv) was added 1,4-dioxane (5 mL) under $N_2$ at room temperature. The resulting mixture was stirred at 100° C. for 2 h under nitrogen atmosphere. Brine was added and the mixture was extracted with ethyl acetate. The combined organic layers were dried over anhydrous sodium sulfate, filtered, and concentrated under reduced pressure. The resulting residue was purified by silica gel column chromatography using a gradient of methanol in ethyl acetate to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide (84 mg, 39%) as a white solid. MS (ESI) calcd. for $C_{25}H_{22}N_8O$: 450.19 m/z, found 451.15 $[M+H]^+$.

Step 2: Synthesis of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1

To a stirred suspension of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)acetamide (1.00 g, 2.22 mmol, 1 equiv) in methanol (5 mL) was added HCl (5 mL, concentrated) and the resulting solution was stirred at 90° C. overnight under nitrogen atmosphere. The solution was cooled to room temperature and diluted with dichloromethane. The solution was concentrated to dryness under reduced pressure. The crude solid was taken up into DMSO and pyrrolidine (395 mg, 5.55 mmol, 2.5 equiv) was added. The solution was stirred for 2 min followed by addition of TFA (959 mg, 6.66 mmol, 3 equiv). The solution was purified by preparative HPLC on a Phenomenex Gemini C18 Column using a gradient of acetonitrile in water (+0.05% TFA) to afford (S)-3-(3-(1-amino-2,3-dihydro-1H-inden-5-yl)-5-(1H-pyrazol-1-yl)-3H-imidazo[4,5-b]pyridin-2-yl)pyridin-2-amine (TFA salt) (Intermediate 1-1) (869 mg, 75%) as a yellow solid. MS (ESI) calcd. for $C_{23}H_{20}N_8$: 408.08 m/z, found 409.15 $[M+H]^+$.

Intermediate 1-2: (S)-N-(5-(2-(2-aminopyridin-3-yl)-5-chloro-3H-imidazo[4,5-b]pyridin-3-yl)-2,3-dihydro-1H-inden-1-yl)acetamide Intermediate 1-2

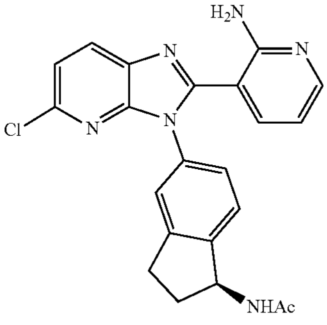

Synthetic Route:

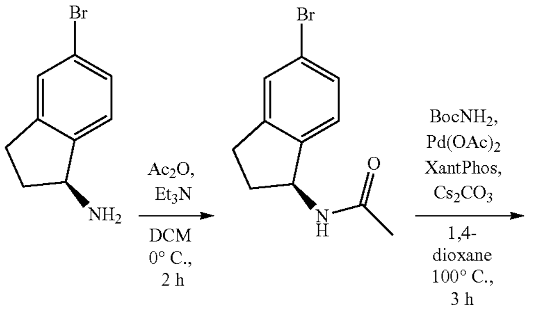

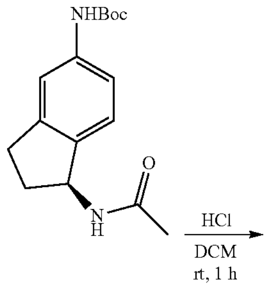

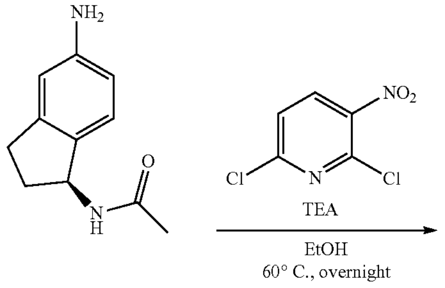

-continued

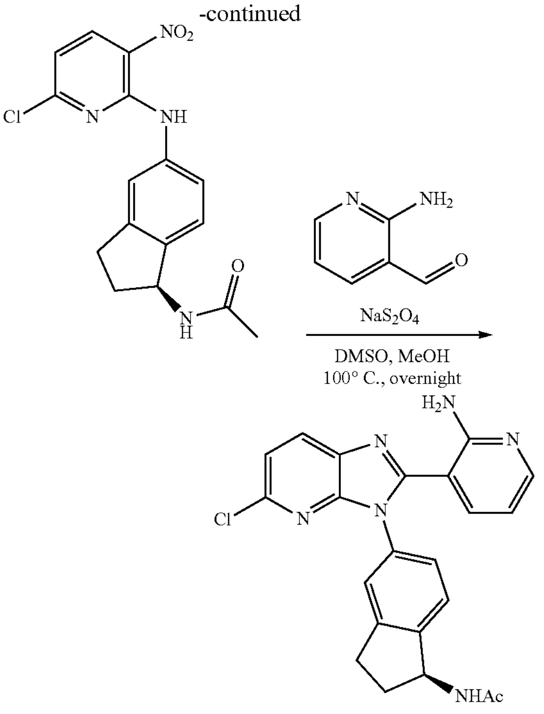

Intermediate 1-2

Step 1: Synthesis of (S)-N-(5-bromo-2,3-dihydro-1H-inden-1-yl)acetamide

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water and extracted 3 times with ethyl acetate. The combined organic layers were dried over anhydrous sodium sulfate and concentrated under reduced pressure. The crude product was re-crystallized from petroleum ether to afford (S)-N-(5-bromo-2,3-dihydro-1H-inden-1-yl)acetamide (90 g, 83% yield) as a white solid. MS (ESI) calculated for $C_{11}H_{12}BrNO$: 253.01, found 254.00 $[M+H]^+$, 256.00 $[M+H+2]^+$.

Step 2: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (40 g, 157 mmol, 1 equiv), tert-butyl carbamate (27.66 g, 236 mmol, 1.5 equiv), XantPhos (9.11 g, 15.7 mmol, 10 mol %), palladium (III) acetate (3.54 g, 15.7 mmol, 10 mol %), and cesium carbonate (154 g, 472 mmol, 10 mol %) was added 1,4-dioxane (300 mL) under nitrogen atmosphere. The resulting mixture was stirred for 3 h at 100° C. The reaction mixture was quenched by addition of water and extracted 3 times with ethyl acetate. The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48%). MS (ESI) calculated for $C_{16}H_{22}N_2O_3$: 290.16 m/z, found 289.05 $[M-H]^-$.

Step 3: Synthesis of (S)-N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N hydrochloric acid in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H-inden-1-yl]acetamide (hydrochloride salt) (23 g, 81%) as a white solid. MS (ESI) calculated for $C_{11}H_{14}N_2O$: 190.11 m/z, found 191.15 $[M+H]^+$.

Step 4: Synthesis of N-[(1S)-5-[(6-chloro-3-nitropyridin-2-yl)amino]-2,3-dihydro-1H-inden-1-yl]acetamide To a solution of N-[(1S)-5-amino-2,3-dihydro-1H-inden-1-yl]acetamide (100 g, 526 mmol, 1 equiv) in ethanol (2 L) was added triethylamine (160 g, 1.58 mol, 3 equiv) and 2,6-dichloro-3-nitropyridine (122 g, 631 mmol, 1.2 equiv). The resulting mixture was stirred at 60° C. overnight. The mixture was then cooled to room temperature and quenched with water. The resulting precipitate was collected by filtration and rinsed with ethanol/water to afford N-[(1S)-5-[(6-chloro-3-nitropyridin-2-yl)amino]-2,3-dihydro-1H-inden-1-yl]acetamide (100 g, 49%) as a red solid. MS (ESI) calculated for $C_{16}H_{15}ClN_4O_3$: 346.08 m/z, found 345.00 $[M-H]^-$.

Step 5: Synthesis of N-[(1S)-5-[2-(2-aminopyridin-3-yl)-5-chloroimidazo[4,5-b]pyridin-3-yl]-2,3-dihydro-1H-inden-1-yl]acetamide (Intermediate 1-2

To a solution of N-[(1S)-5-[(6-chloro-3-nitropyridin-2-yl)amino]-2,3-dihydro-1H-inden-1-yl]acetamide (100 g, 288 mmol, 1 equiv) in dimethyl sulfoxide (1.8 L) and methanol (300 mL) was added 2-aminopyridine-3-carbaldehyde (38.74 g, 317.2 mmol, 1.1 equiv) and sodium dithionite (110 g, 634 mmol, 2.2 equiv). The resulting mixture was stirred at 100° C. overnight. Water was added and the precipitated solids were collected by filtration, rinsing with water. The solid collected was purified by silica gel column chromatography eluting with dichloromethane/methanol (10:1) to afford N-[(1S)-5-[2-(2-aminopyridin-3-yl)-5-chloroimidazo[4,5-b]pyridin-3-yl]-2,3-dihydro-1H-inden-1-yl]acetamide (Intermediate 1-2) (43.2 g, 31%) as a yellow solid. MS (ESI) calculated for $C_{22}H_{19}ClN_6O$: 418.13 m/z, found 419.10 $[M+H]^+$.

Intermediate 1-3: methyl 2-acrylamidobenzoate

Intermediate 1-3

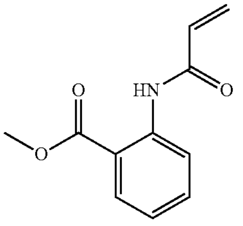

Synthetic Route:

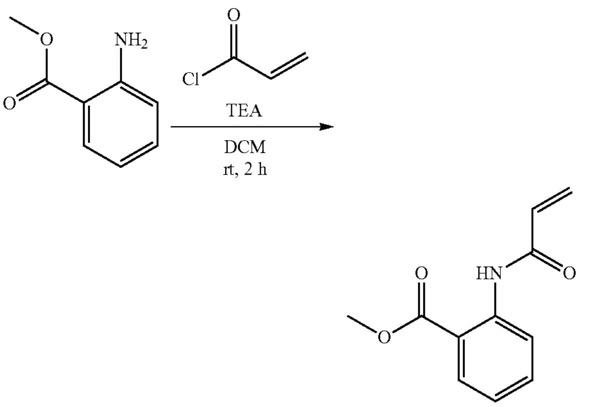

Intermediate 1-3

Step 1: Synthesis of methyl 2-acrylamidobenzoate (Intermediate 1-3

To a cooled (0° C.) solution of methyl 2-aminobenzoate (500 mg, 3.31 mmol, 1 equiv) and triethylamine (1.004 g, 9.924 mmol, 3 equiv) in DCM (10 mL) was added acryloyl chloride (898 mg, 9.92 mmol, 3 equiv). The resulting mixture was stirred for 2 h at room temperature. The reaction was then quenched by the addition water and extracted with DCM 3 times. The organic phases were combined, dried over anhydrous $Na_2SO_4$ and concentrated in vacuum. The resulting residue was purified by flash column chromatography on silica gel using a gradient of ethyl acetate in petroleum ether to afford methyl 2-acrylamidobenzoate (Intermediate 1-3) (500 mg, 74%) as a colorless oil. MS (ESI) calcd. for $C_{11}H_{11}O_3N$: 205.07 m/z, found 206.00 $[M+H]^+$.

Example 2: (S)-3-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide Example 2

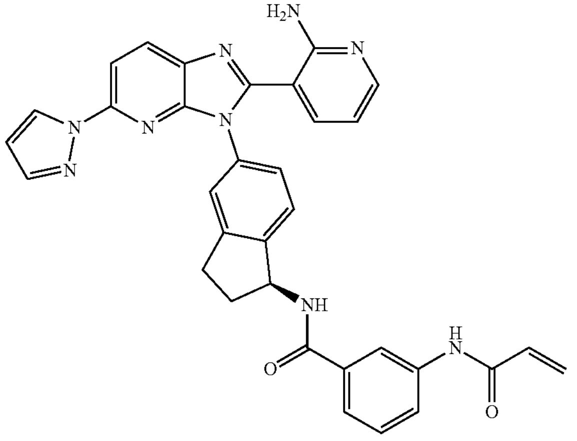

Synthetic Route:

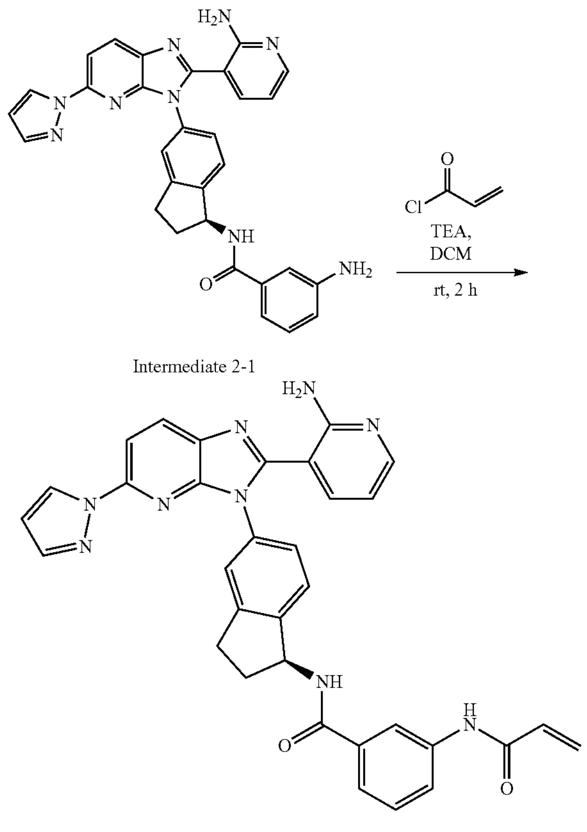

Intermediate 2-1

Example 2

Step 1: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-3-(prop-2-enamido)benzamide (Example 2)

To a stirred mixture of (S)-3-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Intermediate 2-1) (180 mg, 0.341 mmol, 1 equiv) and triethylamine (69 mg, 0.68 mmol, 2 equiv) in DCM (15 mL) was added acryloyl chloride (124 mg, 1.36 mmol, 4 equiv) in portions at room temperature. The reaction mixture was stirred for 2 h. The resulting mixture was washed with water and the aqueous phase was extracted with dichloromethane 2 times. The combined organic layers were washed with brine, dried over anhydrous $Na_2SO_4$. After filtration, the filtrate was concentrated under reduced pressure. The crude product was then purified by preparative HPLC on a XBridge Prep OBD C18 Column using a gradient of acetonitrile in water (+10 mmol/L ammonium bicarbonate) to afford (S)-3-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Example 2) (35 mg, 18%) as an off-white solid. MS (ESI) calcd. for $C_{33}H_{27}N_9O_2$: 581.23 m/z, found 582.35 $[M+H]^+$. $^1$H-NMR (400 MHz, DMSO-$d_6$) δ (ppm): 8.36-8.38 (m, 2H), 8.19-8.21 (m, 1H), 8.14-8.15 (m, 1H), 8.02-8.04 (m, 1H), 7.94-7.96 (m, 1H), 7.80-7.88 (m, 1H), 7.62-7.64 (m, 1H), 7.42-7.45 (m, 3H), 7.31-7.38 (m, 2H), 6.54-6.56 (m, 1H), 6.46-6.48 (m, 2H), 6.26-6.30 (m, 1H), 5.77-5.80 (m, 1H), 5.62-5.64 (m, 1H), 3.00-3.02 (m, 1H), 2.94-3.00 (m, 1H), 2.51-2.52 (m, 1H), 2.10-2.30 (m, 1H).

Intermediate 2-1: (S)-3-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide Intermediate 2-1

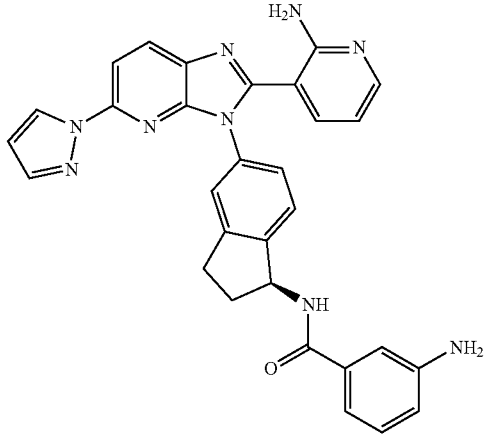

Synthetic Route:

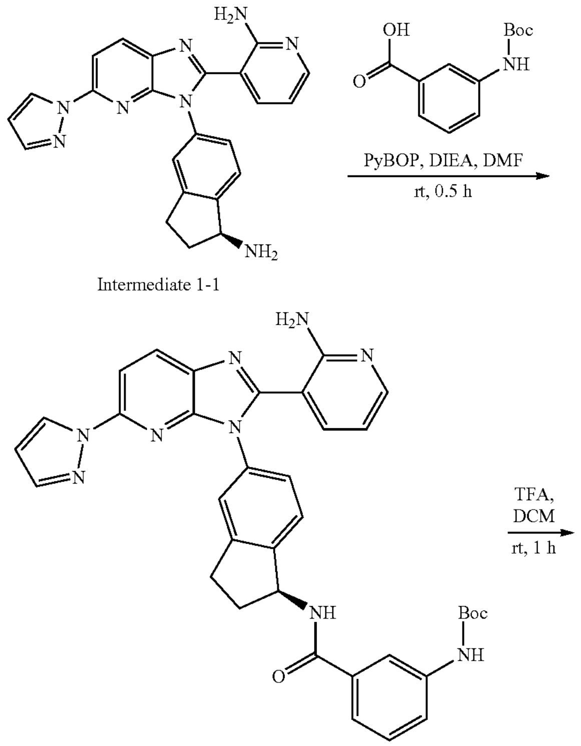

Intermediate 1-1

-continued

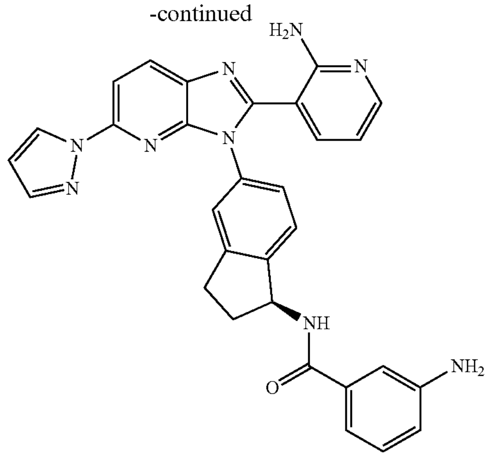

Intermediate 2-1

Step 1: Synthesis of tert-butyl (S)-(3-((5-(2-(2-aminopyridin-3-yl)-5-(1H-pyrazol-1-yl)-3H-imidazo[4,5-b]pyridin-3-yl)-2,3-dihydro-1H-inden-1-yl)carbamoyl)phenyl)carbamate A solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (200 mg, 0.490 mmol), 3-((tert-butoxycarbonyl)amino)benzoic acid (128 mg, 0.539 mmol), PyBOP (255 mg, 0.490 mmol) and N,N-diisopropylethylamine (190 mg, 1.470 mmol) in DMF (3 mL) was stirred for 0.5 h at room temperature. The reaction mixture was purified by reverse-phase flash column chromatography on C18 silica gel using a gradient of acetonitrile in water (+0.05% $NH_4HCO_3$) to afford tert-butyl (S)-(3-((5-(2-(2-aminopyridin-3-yl)-5-(1H-pyrazol-1-yl)-3H-imidazo[4,5-b]pyridin-3-yl)-2,3-dihydro-1H-inden-1-yl)carbamoyl)phenyl)carbamate (170 mg, 49%) as a yellow solid. MS (ESI) calcd. for $C_{35}H_{33}N_9O_3$: 627.27 m/z, found 628.20 $[M+H]^+$.

Step 2: Synthesis of (S)-3-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Intermediate 2-1

A solution of tert-butyl (S)-(3-((5-(2-(2-aminopyridin-3-yl)-5-(1H-pyrazol-1-yl)-3H-imidazo[4,5-b]pyridin-3-yl)-2,3-dihydro-1H-inden-1-yl)carbamoyl)phenyl)carbamate (160 mg, 0.255 mmol) in TFA (1.5 mL) and DCM (4.5 mL) was stirred for 1 h at room temperature. The resulting mixture was concentrated under reduced pressure to afford (S)-3-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Intermediate 2-1) (130 mg, 97%) as a yellow solid. MS (ESI) calcd. for $C_{30}H_{25}N_9O$: 527.22 m/z, found 528.20 $[M+H]^+$.

Example 3: N-[(1S)-5-[2-(2-aminopyridin-3-yl)-5-(pyrazol-1-yl)imidazo[4,5-b]pyridin-3-yl]-2,3-dihydro-1H-inden-1-yl]-1-(prop-2-enoyl)-2,3-dihydroindole-4-carboxamide Example 3

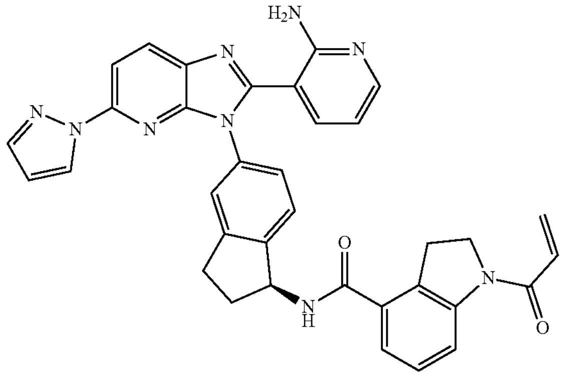

Synthetic Route:

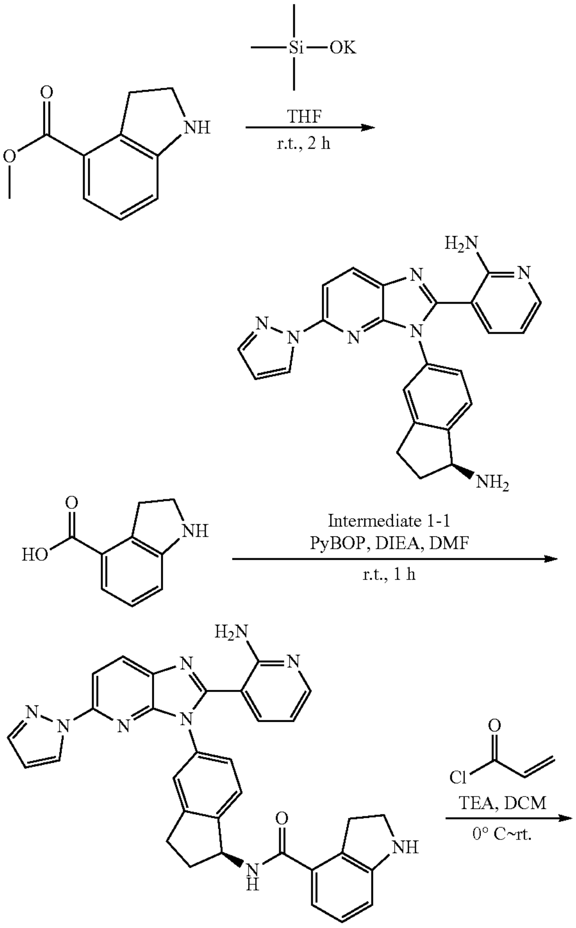

-continued

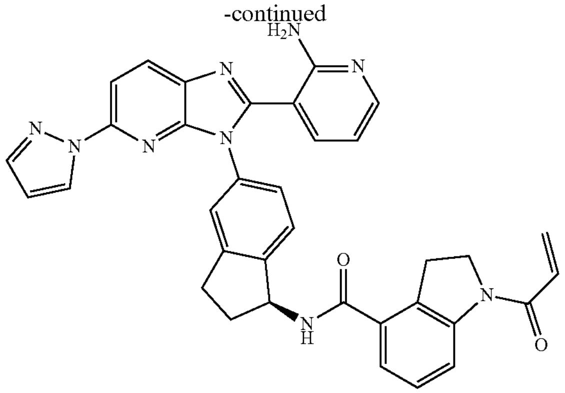

Example 3

Step 1: Synthesis of 2,3-dihydro-1H-indole-4-carboxylic acid

To a solution of methyl 2,3-dihydro-1H-indole-4-carboxylate (500 mg, 2.82 mmol) in THF (20 mL) was added potassium trimethylsilanolate (1.81 g, 14.1 mmol) and the obtained solution was stirred at room temperature for 2 h. The mixture was adjusted to pH-6 with 1M HCl and purified by reverse phase flash column chromatography on C18 silica gel using a gradient of acetonitrile in water (+0.05% ammonium bicarbonate) to afford 2,3-dihydro-1H-indole-4-carboxylic acid (300 mg, 65%). MS (ESI) calcd. for $C_9H_9NO_2$: 163.06 m/z, found 164.10 $[M+H]^+$.

Step 2: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2,3-dihydro-1H-indole-4-carboxamide To a solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (200 mg, 0.490 mmol) in DMF (5 mL) were added DIEA (190 mg, 1.47 mmol), PyBOP (306 mg, 0.588 mmol) and 2,3-dihydro-1H-indole-4-carboxylic acid (96 mg, 0.59 mmol). The reaction mixture was stirred at room temperature for 30 min. The resulting mixture was purified by reverse-phase flash column chromatography on C18 silica gel using a gradient of acetonitrile in water (+0.05% $NH_4HCO_3$) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2,3-dihydro-1H-indole-4-carboxamide (150 mg, 55%) as a yellow solid. MS (ESI) calcd. for $C_{32}H_{27}N_9O$: 553.23 m/z, found 554.30 $[M+H]^+$.

Step 3: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-1-(prop-2-enoyl)-2,3-dihydroindole-4-carboxamide (Example 3)

To a cooled (0° C.) solution of N-[(1S)-5-[2-(2-aminopyridin-3-yl)-5-(pyrazol-1-yl)imidazo[4,5-b]pyridin-3-yl]-2,3-dihydro-1H-inden-1-yl]-2,3-dihydro-1H-indole-4-carboxamide (100 mg, 0.181 mmol) in DCM (5 mL) were added triethylamine (27.4 mg, 0.271 mmol) and acryloyl chloride (16.4 mg, 0.181 mmol). The mixture was stirred at room temperature for 1 h. The resulting mixture was concentrated under reduced pressure and the crude product was purified by Prep-HPLC on a XSelect CSH Fluoro Phenyl column using a gradient of acetonitrile in water (+0.05% TFA) to N-[(1S)-5-[2-(2-aminopyridin-3-yl)-5-(pyrazol-1-yl)imidazo[4,5-b]pyridin-3-yl]-2,3-dihydro-1H-inden-1-yl]-1-(prop-2-enoyl)-2,3-dihydroindole-4-carboxamide (Example 3) (14.2 mg, 13%) as a yellow solid (TFA salt). MS (ESI) calcd. for $C_{35}H_{29}N_9O_2$: 607.24 m/z, found 608.15 $[M+H]^+$. $^1H$ NMR (400 MHz, DMSO-$d_6$) δ (ppm): 8.41-8.43 (m, 2H), 8.37-8.38 (m, 1H), 8.05-8.07 (m, 1H), 7.99-8.01 (m, 1H), 7.82-7.83 (m, 1H), 7.69-7.70 (m, 1H), 7.29-7.45 (m, 5H), 6.74-6.77 (m, 2H), 6.56-6.57 (m, 1H), 6.33-6.34 (m, 1H), 5.83-5.86 (m, 1H), 5.59-5.60 (m, 1H), 4.23-4.24 (m, 2H), 3.42-3.44 (m, 2H), 3.09-3.10 (m, 1H), 2.91-2.93 (m, 1H), 2.50-2.51 (m, 1H), 2.05-2.15 (m, 1H).

Example 4: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(N-methylacrylamido)benzamide Example 4

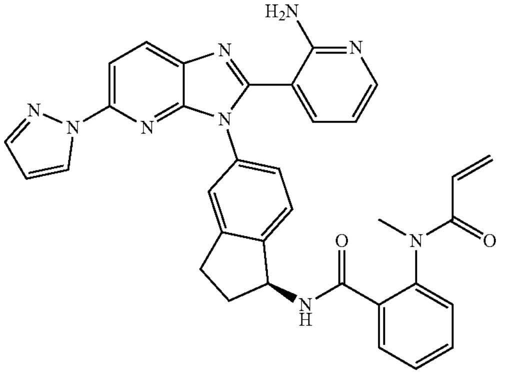

Synthetic Route:

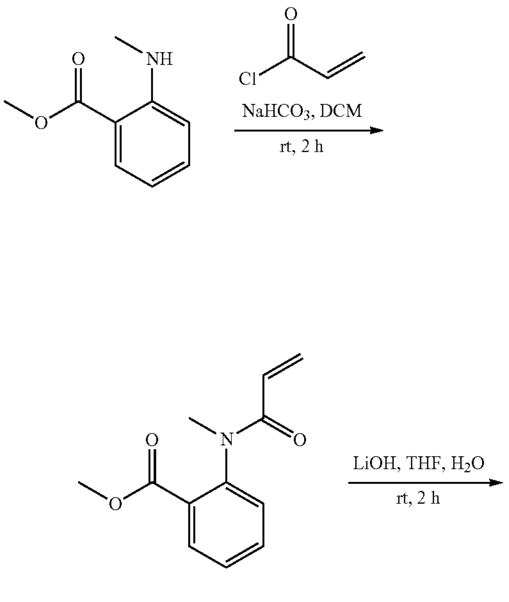

-continued

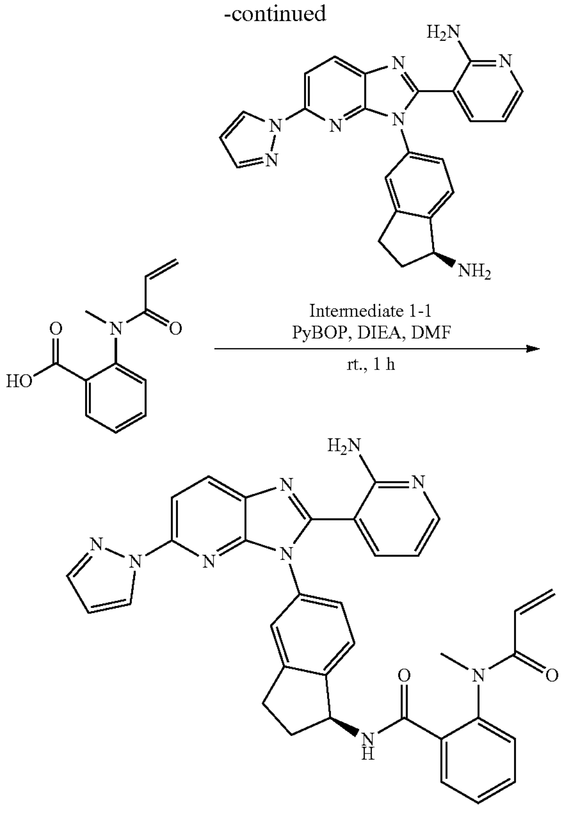

Example 4

Step 1: Synthesis of methyl 2-(N-methylprop-2-enamido)benzoate

To a solution of methyl 2-(methylamino)benzoate (1.000 g, 6.054 mmol) in DCM (20 mL) was added $NaHCO_3$ (1.02 g, 12.1 mmol) and acryloyl chloride (0.55 g, 6.1 mmol). The resulting mixture was stirred at room temperature for 2 h. The solvent was removed by distillation under vacuum. The reaction was quenched with water. The resulting mixture was extracted with ethyl acetate 3 times. The organic layers were combined, dried over $Na_2SO_4$, filtered, and concentrated to afford methyl 2-(N-methylprop-2-enamido)benzoate (1.4 g) as a yellow oil, which was used directly in the next step without further purification. MS (ESI) calcd. for $C_{12}H_{13}NO_3$: 219.09 m/z, found 220.10 $[M+H]^+$.

Step 2: Synthesis of 2-(N-methylprop-2-enamido)benzoic acid

To a solution of methyl 2-(N-methylprop-2-enamido) benzoate (220 mg, 1.00 mmol) in THF (10 mL) was added LiOH (4.01 mL, 8.02 mmol, 2M in $H_2O$). The resulting mixture was stirred at room temperature for 3 h. The mixture was acidified to pH 6 with HCl (2M). The solvent was removed by distillation under vacuum to afford 2-(N-methylprop-2-enamido)benzoic acid (190 mg) (crude) as a light-yellow solid. MS (ESI) calcd. for $C_{11}H_{11}NO_3$: 205.07 m/z, found 206.05 $[M+H]^+$.

Step 3: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-(N-methylprop-2-enamido)benzamide (Example 4

To a solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (170 mg, 0.416 mmol) in DMF (3 mL) were added DIEA (161 mg, 1.25 mmol), PyBOP (217 mg, 0.416 mmol) and 2-(N-methylprop-2-enamido)benzoic acid (102 mg, 0.499 mmol). The resulting mixture was stirred at room temperature for 1 h. The resulting mixture was purified by reverse-phase flash column chromatography on C18 silica gel using a gradient of acetonitrile in water (+0.05% $NH_4HCO_3$). The product was further purified by Prep-HPLC on a XSelect CSH F-Phenyl OBD column using a gradient of acetonitrile in water (+0.05% TFA) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-(N-methylprop-2-enamido)benzamide (35 mg, 14%) as a yellow solid (TFA salt). MS (ESI) calcd. for $C_{34}H_{29}N_9O_2$: 595.24 m/z, found 596.35 $[M+H]^+$. $^1H$ NMR (400 MHz, DMSO-$d_6$) δ (ppm): 8.37-8.42 (m, 2H), 7.99-8.02 (m, 2H), 7.79-7.81 (m, 2H), 7.47-7.58 (m, 3H), 7.24-7.41 (m, 4H), 6.81-6.84 (m, 1H), 6.12 (s, 1H), 5.85-6.12 (m, 2H), 5.37-5.52 (m, 2H), 3.14-3.22 (m, 3H), 2.81-2.97 (m, 2H), 2.42-2.51 (m, 1H), 1.88-2.02 (m, 1H).

Example 5: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(2-fluoroacrylamido) benzamide Example 5

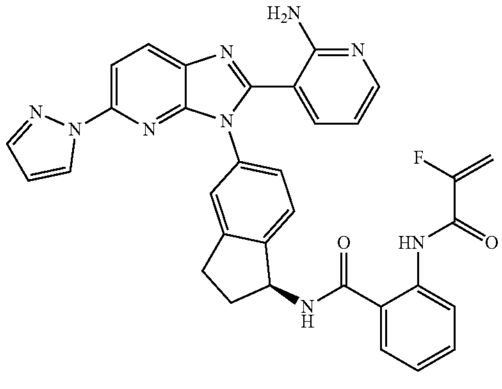

Example 5 was prepared in a manner analogous to Example 4 (final step only) using Intermediate 5-1 in place of Intermediate 1-1 and 2-fluoroacrylic acid in place of 2-(N-methylprop-2-enamido)benzoic acid. MS (ESI) calcd. for $C_{33}H_{26}FN_9O_2$: 599.22 m/z, found 600.15 $[M+H]^+$. $^1H$ NMR (300 MHz, DMSO-$d_6$) δ (ppm): 8.48-8.50 (m, 11H), 8.35-8.38 (m, 2H), 7.89-8.03 (m, 3H), 8.81-8.12 (m, 1H), 7.57-7.60 (m, 1H), 7.39-7.43 (m, 2H), 7.26-7.29 (m, 3H), 6.55-6.56 (m, 1H), 6.45-6.49 (m, 1H), 5.66-5.83 (m, 2H), 5.46-5.52 (m, 1H), 2.85-3.15 (m, 2H), 2.51-2.53 (m, 1H), 2.07-2.18 (m, 1H). $^{19}F$ NMR (282 MHz, DMSO-$d_6$) δ (ppm): −119.54. (formic acid salt)

Intermediate 5-1: (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide Intermediate 5-1

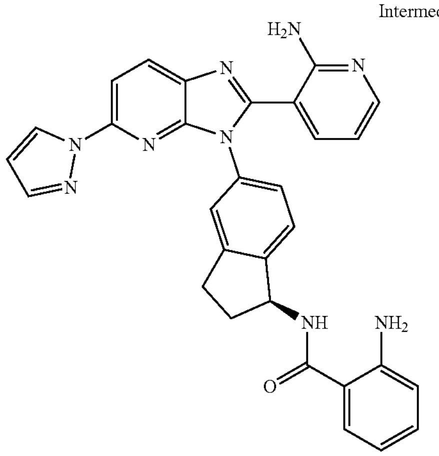

Intermediate 5-1 was prepared in a manner analogous to Intermediate 2-1 using 2-((tert-butoxycarbonyl)amino)benzoic acid in place of 3-((tert-butoxycarbonyl)amino)benzoic acid. MS (ESI) calcd. for $C_{30}H_{25}N_9O$, 527.22 m/z, found 528.30 $[M+H]^+$.

Example 6: N-[(1S)-5-[2-(2-aminopyridin-3-yl)-5-(pyrazol-1-yl)imidazo[4,5-b]pyridin-3-yl]-2,3-dihydro-1H-inden-1-yl]-2-fluoro-6-(prop-2-enamido) benzamide Example 6

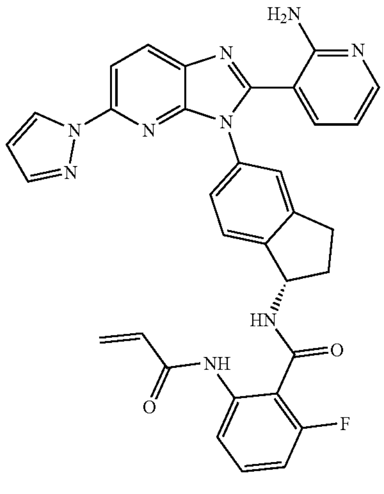

Example 6 was prepared in a manner analogous to Example 1 (via Intermediate 1-3) starting from methyl 2-amino-6-fluorobenzoate instead of methyl 2-aminobenzoate. MS (ESI) calcd. for $C_{33}H_{26}FN_9O_2$: 599.22 m/z, found 600.20 [M+H]. $^1H$ NMR (400 MHz, DMSO-$d_6$) δ (ppm): 8.39-8.45 (m, 1H), 8.30-8.39 (m, 1H), 8.00-8.10 (m, 2H), 7.80-7.89 (m, 1H), 7.75-7.80 (m, 1H), 7.58-7.75 (m, 1H), 7.45-7.58 (m, 3H), 7.30-7.40 (m, 1H), 7.10-7.20 (m, 1H), 6.85-6.90 (m, 1H), 6.55-6.65 (m, 1H), 6.40-6.55 (m, 1H), 6.10-6.30 (m, 1H), 5.75-5.95 (m, 1H), 5.45-5.75 (m, 1H), 2.85-3.10 (m, 2H), 2.40-2.50 (m, 1H), 1.85-2.05 (m, 1H). (TFA salt)

Example 7: (S)-1-acryloyl-N-(5-(2-(2-aminopyridin-3-yl)-5-(1H-pyrazol-1-yl)-3H-imidazo[4,5-b]pyridin-3-yl)-2,3-dihydro-1H-inden-1-yl)indoline-6-carboxamide Example 7

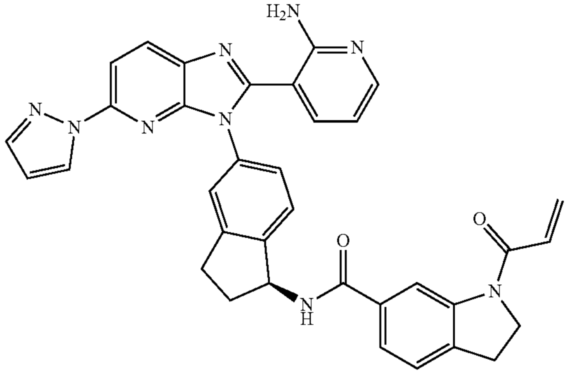

Synthetic Route:

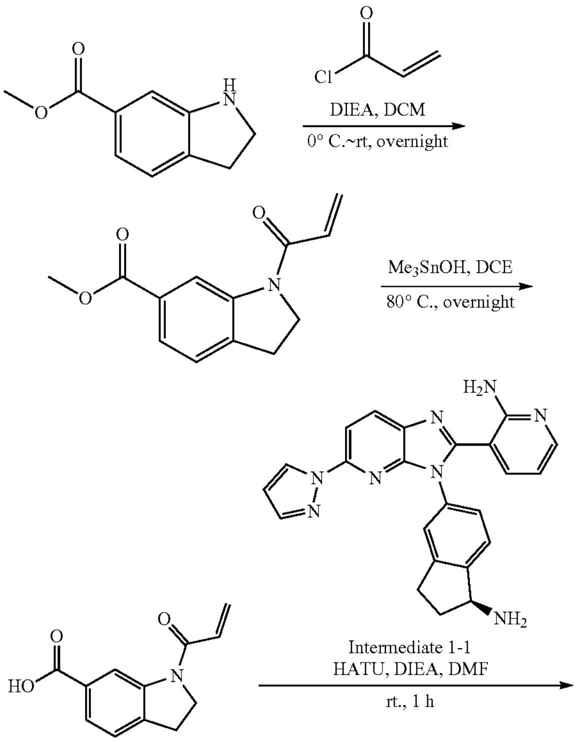

-continued

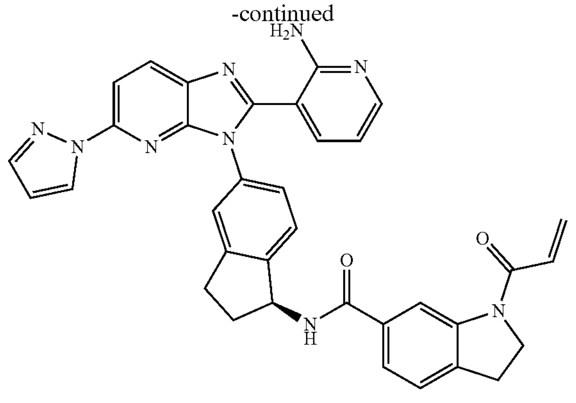

Example 7

Step 1: Synthesis of methyl 1-acryloylindoline-6-carboxylate

Acryloyl chloride (1.02 g, 11.3 mmol) was added to a solution of methyl 2,3-dihydro-1H-indole-6-carboxylate (1.00 g, 5.64 mmol) and N,N-diisopropylethylamine (1.46 g, 11.3 mmol) in dichloromethane (10 mL) at 0° C. The reaction was stirred at 25° C. overnight. The reaction was quenched with saturated aqueous ammonium chloride and the mixture was extracted 3 times with ethyl acetate. The combined organic layers were washed with brine and dried over anhydrous $Na_2SO_4$. After filtration, the filtrate was concentrated under reduced pressure. The residue was purified by silica gel column chromatography using a gradient of ethyl acetate in petroleum ether to afford methyl 1-acryloylindoline-6-carboxylate (1.0 g, 70%) as a yellow solid. MS (ESI) calcd. for $C_{13}H_3NO_3$: 231.09 m/z, found 232.15 $[M-H]^+$.

Step 2: Synthesis of 1-acryloylindoline-6-carboxylic acid

To a cooled (0° C.) solution of methyl 1-acryloylindoline-6-carboxylate (200 mg, 0.865 mmol) in DCE (5 mL) was added trimethylstannanol (938 mg, 5.19 mmol). The resulting solution was then stirred overnight at 80° C. The reaction mixture was concentrated under reduced pressure to afford 1-acryloylindoline-6-carboxylic acid (130 mg, 69%) as a white solid which was used in the next step directly without further purification. MS (ESI) calcd. for $C_{12}H_{11}NO_3$: 217.07 m/z, found 218.05 $[M+H]^+$.

Step 3: Synthesis of (S)-1-acryloyl-N-(5-(2-(2-aminopyridin-3-yl)-5-(1H-pyrazol-1-yl)-3H-imidazo[4,5-b]pyridin-3-yl)-2,3-dihydro-1H-inden-1-yl)indoline-6-carboxamide (Example 7

To a solution of 1-acryloylindoline-6-carboxylic acid (53.18 mg, 0.245 mmol) in DMF (3 mL) were added (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (100 mg, 0.245 mmol), N,N-diisopropylethylamine (127 mg, 0.980 mmol) and HATU (112 mg, 0.294 mmol) in sequence. The resulting solution was stirred at 25° C. for 1 h. The reaction was quenched with saturated aqueous ammonium chloride and extracted 3 times with ethyl acetate. The combined organic layers were washed with brine, dried over anhydrous $Na_2SO_4$. After filtration, the filtrate was concentrated under reduced pressure. The obtained residue was purified by Prep-HPLC on a XSelect CSH Fluoro Phenyl column using a gradient of acetonitrile in water (+0.1% formic acid) to afford (S)-1-acryloyl-N-(5-(2-(2-aminopyridin-3-yl)-5-(1H-pyrazol-1-yl)-3H-imidazo[4,5-b]pyridin-3-yl)-2,3-dihydro-1H-inden-1-yl)indoline-6-carboxamide (Example 7) (20.6 mg, 14%) as a white solid. MS (ESI) calcd. for $C_{35}H_{29}N_9O_2$: 607.24 m/z, found 608.35 $[M+H]^+$. $^1H$ NMR (400 MHz, DMSO-$d_6$) δ (ppm): 8.64-8.65 (m, 1H), 8.35-8.37 (m, 2H), 8.01-8.02 (m, 1H), 7.94-7.97 (m, 1H), 7.80-7.81 (m, 1H), 7.58-7.60 (m, 1H), 7.28-7.37 (m, 5H), 6.75-6.77 (m, 1H), 6.55-6.56 (m, 1H), 6.48-6.51 (m, 1H), 6.36-6.37 (m, 1H), 5.86-5.89 (m, 1H), 5.62-5.64 (m, 1H), 4.25-4.27 (m, 2H), 3.20-3.24 (m, 2H), 3.01-3.03 (m, 1H), 2.91-2.93 (m, 1H), 2.45-2.50 (m, 1H), 2.09-2.14 (m, 1H).

Example 8: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-3-(2-fluoroacrylamido)benzamide Example 8

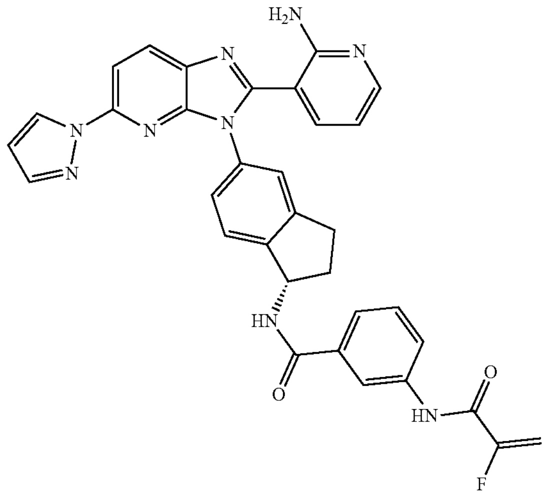

Example 8 was prepared in a manner analogous to Example 4 (final step only) using Intermediate 2-1 in place of Intermediate 1-1 and 2-fluoroacrylic acid in place of 2-(N-methylprop-2-enamido)benzoic acid. MS (ESI) calcd. for $C_{33}H_{26}FN_9O_2$: 599.22 m/z, found 600.30 $[M+H]^+$. $^1H$ NMR (400 MHz, DMSO-$d_6$) δ (ppm): 8.30-8.45 (m, 2H), 8.15-8.30 (m, 1H), 8.00-8.05 (m, 1H), 7.90-8.00 (m, 1H), 7.80-7.90 (m, 1H), 7.70-7.80 (m, 1H), 7.60-7.70 (m, 1H), 7.40-7.50 (m, 1H), 7.30-7.40 (m, 2H), 7.20-7.30 (m, 2H), 6.50-6.60 (m, 1H), 6.35-6.50 (m, 1H), 5.60-5.90 (m, 2H), 5.30-5.50 (m, 1H), 2.85-3.15 (m, 2H), 2.50-2.60 (m, 1H), 2.00-2.20 (m, 1H). $^{19}F$ NMR (376 MHz, DMSO-$d_6$) δ (ppm): −116.82. (TFA salt)

Example 9: N-[(1S)-5-[2-(2-aminopyridin-3-yl)-5-(pyrazol-1-yl)imidazo[4,5-b]pyridin-3-yl]-2,3-dihydro-1H-inden-1-yl]-2-(but-2-ynamido)benzamide Example 9

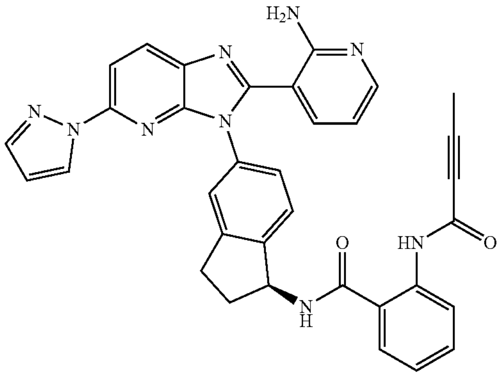

Example 9 was prepared in a manner analogous to Example 1 using Intermediate 9-1 in place of Intermediate 1-3 and a reaction time of 2 h instead of overnight. MS (ESI) calcd. for $C_{34}H_{27}N_9O_2$: 593.23 m/z, found 594.15 $[M+H]^+$. $^1H$ NMR (300 MHz, DMSO-$d_6$) δ (ppm): 8.32-8.34 (m, 2H), 8.23-8.29 (m, 1H), 8.01-8.05 (m, 1H), 7.92-8.00 (m, 1H), 7.74-7.78 (m, 2H), 7.45-7.55 (m, 1H), 7.34-7.40 (m, 2H), 7.25-7.28 (m, 2H), 7.20-7.25 (m, 1H), 6.52-6.55 (m, 1H), 6.44-6.47 (m, 1H), 5.55-5.61 (m, 1H), 2.99-3.10 (m, 1H), 2.87-2.98 (m, 1H), 2.51-2.55 (m, 1H), 2.01-2.15 (m, 1H), 1.95-2.01 (m, 3H). (formic acid salt)

Intermediate 9-1: methyl 2-(but-2-ynamido)benzoate

Intermediate 9-1

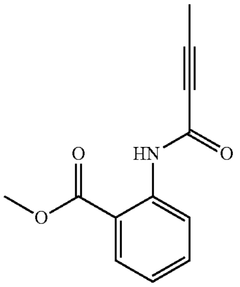

Synthetic Route:

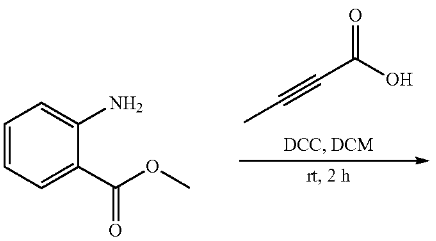

-continued

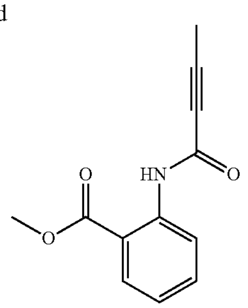

Intermediate 9-1

Step 1: Synthesis of methyl 2-(but-2-ynamido)benzoate (Intermediate 9-1

To a solution of 2-butynoic acid (1.67 g, 19.8 mmol) and DCC (2.05 g, 9.92 mmol) in DCM (30 mL) was added methyl anthranilate (1.00 g, 6.62 mmol). The mixture was stirred at room temperature for 2 h. The reaction was quenched with water and extracted with ethyl acetate 3 times. The combined organic layers were washed with brine and dried over anhydrous $Na_2SO_4$. After filtration, the filtrate was concentrated under reduced pressure. The obtained residue was purified by silica gel column chromatography using a gradient of ethyl acetate in petroleum ether to afford methyl 2-(but-2-ynamido)benzoate (Intermediate 9-1) (1.4 g, 97%) as an off-white solid. MS (ESI) calcd. for $C_{12}H_1NO_3$: 217.07 (m/z), found 218.05 $[M+H]^+$.

Example 10: N-[(1S)-5-[2-(2-aminopyridin-3-yl)-5-(pyrazol-1-yl)imidazo[4,5-b]pyridin-3-yl]-2,3-dihydro-1H-inden-1-yl]1-(prop-2-enoyl)-2,3-dihydroindole-7-carboxamide Example 10

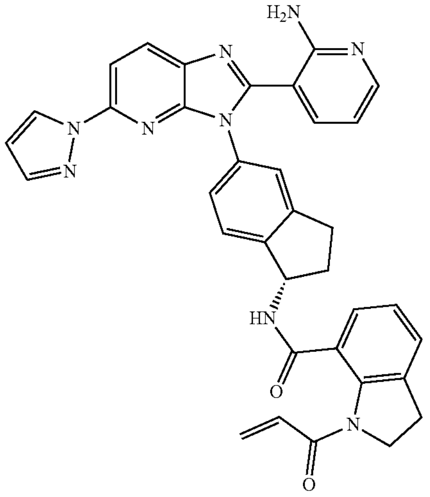

Example 10 was prepared in a manner analogous to Example 3 using methyl 2,3-dihydro-1H-indole-7-carboxylate in place of methyl 2,3-dihydro-1H-indole-4-carboxylate. MS (ESI) calcd. for $C_{35}H_{29}N_9O_2$: 607.24 m/z, found 608.20 $[M+H]^+$. $^1H$ NMR (400 MHz, DMSO-$d_6$) δ (ppm): 8.42-8.44 (m, 1H), 8.35-8.36 (m, 1H), 8.06-8.08 (m, 1H), 7.99-8.02 (m, 1H), 7.82-7.83 (m, 1H), 7.72-7.73 (m, 1H), 7.62-7.70 (m, 1H), 7.29-7.40 (m, 4H), 7.11-7.15 (m, 1H), 6.79-6.80 (m, 1H), 6.56-6.57 (m, 2H), 6.27-6.28 (m, 1H), 5.78-5.81 (m, 1H), 5.41-5.50 (m, 1H), 4.17-4.19 (m, 2H), 3.08-3.10 (m, 2H), 2.91-3.00 (m, 1H), 2.85-2.90 (m, 1H), 2.45-2.50 (m, 1H), 2.05-2.15 (m, 1H). (TFA salt)

Example 11: (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)isonicotinamide Example 11

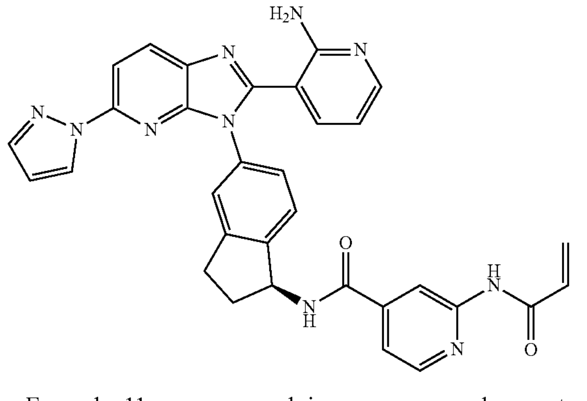

Example 11 was prepared in a manner analogous to Example 7 using methyl 2-aminoisonicotinate in place of methyl 2,3-dihydro-1H-indole-6-carboxylate and reaction times of 2 h for the first two steps. MS (ESI) calcd. for $C_{32}H_{26}N_{10}O_2$: 582.22 m/z, found 583.10 $[M+H]^+$. $^1$HNMR (400 MHz, DMSO-$d_6$) δ (ppm): 8.60-8.75 (m, 1H), 8.45-8.60 (m, 1H), 8.25-8.45 (m, 2H), 8.00-8.20 (m, 1H), 7.90-8.00 (m, 1H), 7.65-7.90 (m, 1H), 7.55-7.65 (m, 1H), 7.40-7.55 (m, 2H), 7.20-7.40 (m, 2H), 6.50-6.79 (m, 3H), 6.25-6.50 (m, 1H), 5.75-6.00 (m, 1H), 5.55-5.75 (m, 1H), 3.00-3.25 (m, 1H), 2.80-3.00 (m, 1H), 2.55-2.65 (m, 1H), 2.00-2.30 (m, 1H). (formic acid salt)

Example 12: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-3-(but-2-ynamido)benzamide Example 12

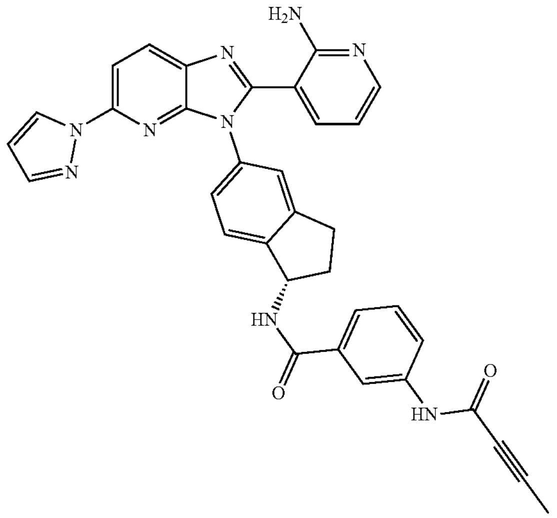

Example 12 was prepared in a manner analogous to Example 7 (starting from Step 2) using Intermediate 12-1 in place of the methyl ester staring material. MS (ESI) calcd. for $C_{34}H_{27}N_9O_2$: 593.23 m/z, found 594.30 $[M+H]^+$. $^1$H NMR (400 MHz, DMSO-$d_6$) δ (ppm): 8.38-8.40 (m, 2H), 8.06-8.07 (m, 1H), 7.97-8.02 (m, 2H), 7.82-7.83 (m, 1H), 7.67-7.69 (m, 1H), 7.58-7.63 (m, 2H), 7.46-7.48 (m, 1H), 7.37-7.44 (m, 2H), 7.30-7.32 (m, 1H), 6.69-6.71 (m, 1H), 6.58-6.60 (m, 1H), 5.58-5.62 (m, 1H), 3.04-3.06 (m, 1H), 2.92-2.94 (m, 1H), 2.45-2.50 (m, 1H), 2.11-2.14 (m, 1H), 2.02-2.04 (m, 3H). (formic acid salt)

Intermediate 12-1: methyl 3-(but-2-ynamido)benzoate

Intermediate 12-1

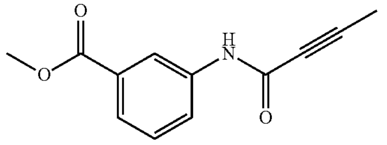

Intermediate 12-1 was prepared in a manner analogous to Intermediate 9-1 using 3-aminobenzoate in place of methyl anthranilate. MS (ESI) calcd. for $C_{12}H_{11}NO_3$: 217.07 m/z, found 218.00 $[M+H]^+$.

Example 13: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)prop-2-en-1-one Example 13

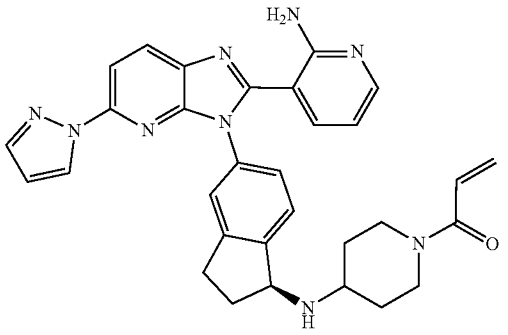

Synthetic Route

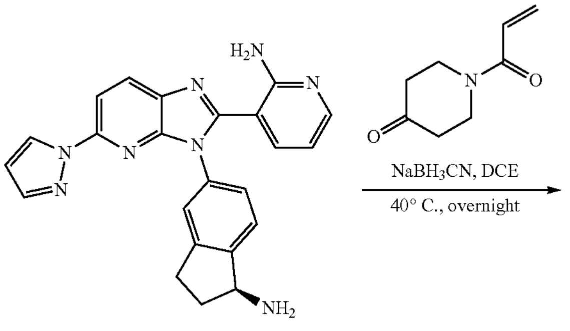

Intermediate 1-1

-continued

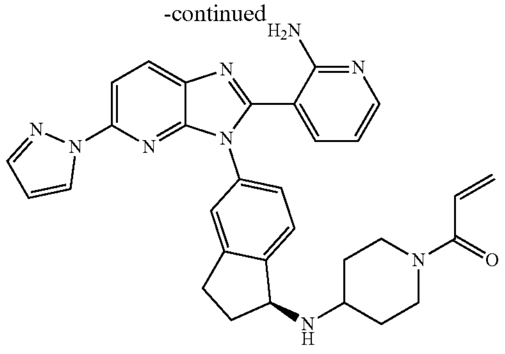

Example 13

Step 1: Synthesis of 1-(4-{1[(1S)-5-[2-(2-amino-pyridin-3-yl)-5-(pyrazol-1-yl)imidazo[4,5-b]pyridin-3-yl]-2,3-dihydro-1H-inden-1-yl]amino}piperidin-1-yl)prop-2-en-1-one (Example 13)

To a solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (200 mg, 0.490 mmol) in DCE (10 mL) was added 1-(prop-2-enoyl)piperidin-4-one (75 mg, 0.490 mmol). The resulting mixture was stirred at 40° C. overnight. $NaBH_3CN$ (123 mg, 1.960 mmol) was added and the mixture was stirred at 40° C. for 1 h. The reaction was quenched with $H_2O$. The resulting mixture was extracted with dichloromethane 3 times. The organic layers were combined, dried over $Na_2SO_4$, filtered and concentrated. The resulting mixture was purified by reverse phase flash column chromatography on C18 silica gel using a gradient of acetonitrile in water (+0.05% $NH_4HCO_3$). The material obtained was further purified by Prep-HPLC on a XSelect CSH Fluoro Phenyl column using a gradient of acetonitrile in water (+0.1% formic acid) to afford 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)prop-2-en-1-one (Example 13, formic acid salt) (41.6 mg, 15%) as an off-white solid. MS (ESI) calcd. for $C_{31}H_{31}N_9O$: 545.27 m/z, found 546.15 $[M+H]^+$. $^1H$ NMR (400 MHz, DMSO-$d_6$) δ (ppm): 8.33-8.35 (m, 2H), 7.98-7.99 (m, 1H), 7.93-7.95 (m, 1H), 7.79-7.80 (m, 1H), 7.60-7.62 (m, 1H), 7.42-7.43 (m, 1H), 7.28-7.30 (m, 2H), 6.76-6.83 (m, 1H), 6.54-6.55 (m, 1H), 6.44-6.47 (m, 1H), 6.08-6.13 (m, 1H), 5.70-5.73 (m, 1H), 4.70-4.75 (m, 1H), 4.38-4.48 (m, 1H), 4.05-4.15 (m, 1H), 3.28-3.33 (m, 1H), 3.04-3.18 (m, 2H), 2.88-2.90 (m, 1H), 2.69-2.75 (m, 1H), 2.50-2.51 (m, 1H), 1.98-2.15 (m, 3H), 1.33-1.46 (m, 2H).

Example 14: 1-(8-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3-azabicyclo[3.2.1]octan-3-yl)prop-2-en-1-one Example 14

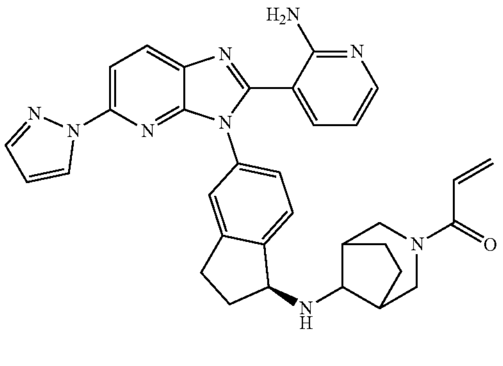

Example 14 was prepared in a manner analogous to Example 13 using Intermediate 14-1 in place of 1-(prop-2-enoyl)piperidin-4-one. MS (ESI) calcd. for $C_{33}H_{33}N_9O$: 571.28 m/z, found 572.40 $[M+H]^+$. $^1H$ NMR (300 MHz, DMSO-$d_6$) δ (ppm): 8.43-8.45 (m, 1H), 8.33-8.36 (m, 1H), 8.05-8.12 (m, 1H), 8.01-8.04 (m, 1H), 7.80-7.88 (m, 3H), 7.59-7.60 (m, 1H), 7.44-7.46 (m, 1H), 6.75-6.88 (m, 2H), 6.55-6.60 (m, 1H), 6.10-6.14 (m, 1H), 5.70-5.73 (m, 1H), 5.05-5.07 (m, 1H), 4.00-4.10 (m, 1H), 3.80-3.93 (m, 1H), 3.43-3.55 (m, 1H), 3.40-3.43 (m, 1H), 3.18-3.29 (m, 1H), 3.05-3.13 (m, 1H), 2.95-3.01 (m, 1H), 2.55-2.70 (m, 1H), 2.45-2.52 (m, 1H), 2.32-2.42 (m, 1H), 2.10-2.20 (m, 1H), 1.65-1.85 (m, 2H), 1.35-1.58 (m, 2H). (TFA salt)

Intermediate 14-1: 3-acryloyl-3-azabicyclo[3.2.1]octan-8-one

Intermediate 14-1

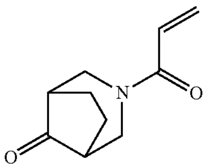

Synthetic Route:

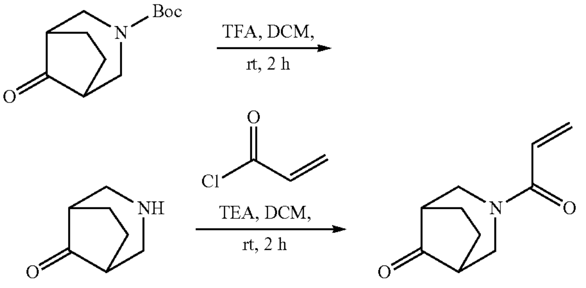

Intermediate 14-1

Step 1: Synthesis of 3-azabicyclo[3.2.1]octan-8-one

To a solution of tert-butyl 8-oxo-3-azabicyclo[3.2.1]octane-3-carboxylate (300 mg, 1.33 mmol) in DCM (10 mL) was added TFA (10 mL) and the resulting mixture was stirred at room temperature for 2 h. The solvent was removed by distillation under vacuum to afford 3-azabicyclo[3.2.1]octan-8-one (166 mg, crude quant) as a brown oil, which was used in the next step without purification. MS (ESI) calcd. for $C_7H_{11}NO$: 125.08 m/z, found 126.05 $[M+H]^+$.

Step 2: Synthesis of 3-(prop-2-enoyl)-3-azabicyclo[3.2.1]octan-8-one

To a cooled (0° C.) solution of 3-azabicyclo[3.2.1]octan-8-one (166 mg, 1.33 mmol) and triethylamine (671 mg, 6.63 mmol) in DCM (10 mL) was added acryloyl chloride (180 mg, 1.99 mmol) and the residue mixture was stirred at room temperature for 2 h. The reaction was quenched with $H_2O$ and extracted with dichloromethane 3 times. The organic layers were combined, dried over $Na_2SO_4$, filtered and concentrated. The residue was purified by silica gel column chromatography using a gradient of ethyl acetate in petroleum ether to afford 3-(prop-2-enoyl)-3-azabicyclo[3.2.1]octan-8-one (Intermediate 14-1) (150 mg, 63%) as a yellow oil. MS (ESI) calcd. for $C_{10}H_{13}NO_2$: 179.09 m/z, found: 198.10 $[M+H_2O+H]^+$.

Example 15: (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)-6-methylbenzamide Example 15

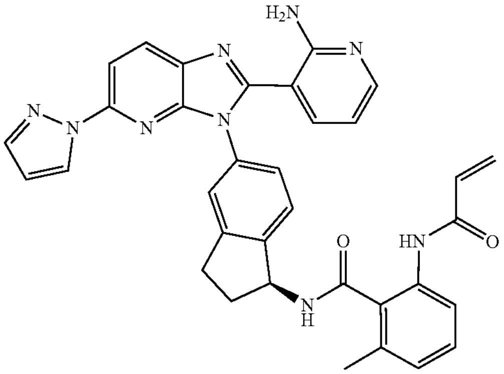

Example 15 was prepared in a manner analogous to Example 3 (starting from Step 2) using 2-amino-6-methylbenzoic acid in place of 2,3-dihydro-1H-indole-4-carboxylic acid and N,N-diisopropylethylamine/acetonitrile in place of triethylamine/dichloromethane. MS (ESI) calcd. for $C_{34}H_{29}N_9O_2$: 595.24 m/z, found 596.20 $[M+H]^+$. $^1H$ NMR (400 MHz, DMSO-$d_6$) δ (ppm): 8.32-8.36 (m, 2H), 7.98-8.00 (m, 1H), 7.94-7.95 (m, 1H), 7.79-7.80 (m, 1H), 7.42-7.43 (m, 2H), 7.31-7.34 (m, 1H), 7.27-7.29 (m, 1H), 7.21-7.23 (m, 2H), 7.09-7.11 (m, 1H), 6.50-6.55 (m, 2H), 6.41-6.44 (m, 1H), 6.16-6.19 (m, 1H), 5.67-5.69 (m, 1H), 5.54-5.58 (m, 1H), 2.85-2.87 (m, 1H), 2.50-2.51 (m, 1H), 2.46-2.47 (m, 1H), 2.31 (s, 3H), 1.96-1.99 (m, 1H). (formic acid salt)

Example 16: (S,E)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(4-(dimethylamino)but-2-enamido)benzamide Example 16

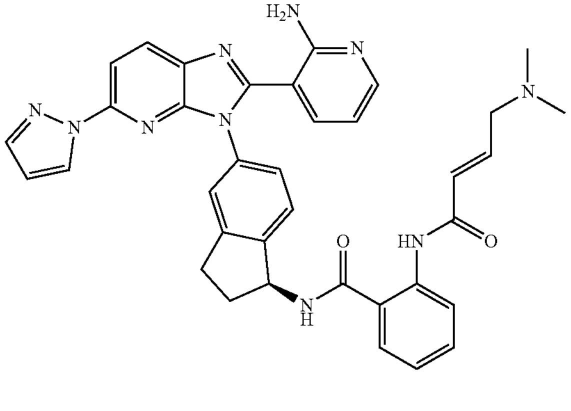

Synthetic Route:

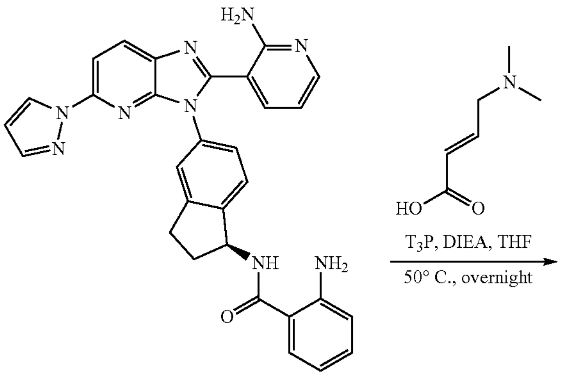

Intermediate 5-1

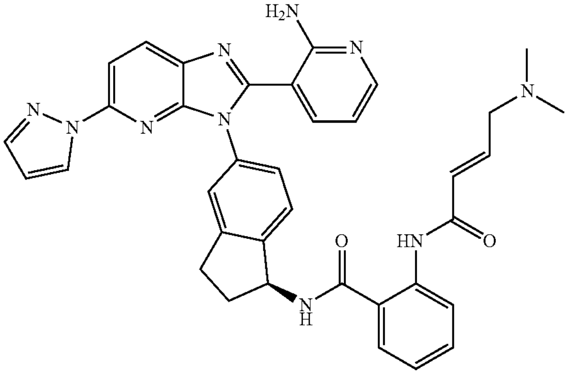

Example 16

Step 1: Synthesis of (S,E)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(4-(dimethylamino)but-2-enamido)benzamide (Example 16)

To a solution of (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Intermediate 5-1) (150 mg, 0.284 mmol) and (E)-4-(dimethylamino)but-2-enoic acid (55 mg, 0.43 mmol) in THE (5 mL) were added $T_3P$ (360 mg, 0.568 mmol, 50% in THF) and N,N-diisopropylethylamine (110 mg, 0.852 mmol). The resulting mixture was stirred overnight at 50° C. The reaction mixture was purified by reverse phase flash column chromatography on C18 silica gel using a gradient of acetonitrile in water (+0.05% $NH_4HCO_3$). The material obtained was further purified by Prep-HPLC on a XSelect CSH Prep C18 OBD Column using a gradient of acetonitrile in water (+0.1% TFA) to afford (S,E)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(4-(dimethylamino)but-2-enamido)benzamide (Example 16, TFA salt) (29.6 mg, 13.6%) as an off-white solid. MS (ESI) calcd. for $C_{36}H_{34}N_{10}O_2$: 638.29 m/z, found 639.20 $[M+H]^+$. $^1H$ NMR (300 MHz, DMSO-$d_6$) δ (ppm): 8.33-8.37 (m, 3H), 7.94-8.03 (m, 2H), 7.75-7.85 (m, 2H), 7.54-7.56 (m, 1H), 7.50-7.51 (m, 2H), 7.15-7.29 (m, 3H), 6.70-6.80 (m, 1H), 6.60-6.65 (m, 1H), 6.45-6.55 (m, 1H), 6.25-6.30 (m, 1H), 5.55-5.63 (m, 1H), 3.17-3.18 (m, 2H), 2.85-3.15 (m, 2H), 2.51-2.53 (m, 1H), 2.07-2.22 (m, 7H).

Example 17: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-methacrylamidobenzamide Example 17

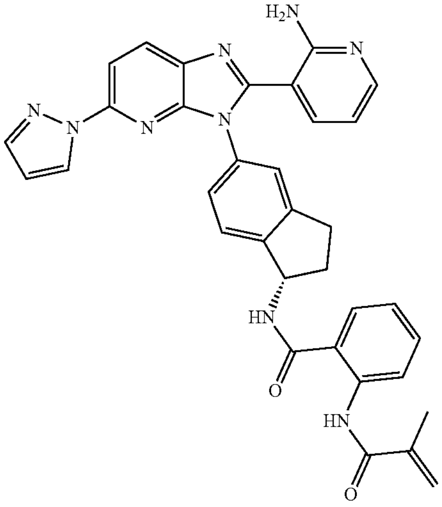

Example 17 was prepared in a manner analogous to Example 4 (Step 3 only) using Intermediate 5-1 in place of Intermediate 1-1 and methacrylic acid in place of 2-(N-methylprop-2-enamido)benzoic acid. MS (ESI) calcd. for $C_{34}H_{29}N_9O_2$: 595.24 m/z, found 596.15 $[M+H]^+$. $^1H$ NMR (300 MHz, DMSO-$d_6$) δ (ppm): 8.38-8.49 (m, 3H), 8.01-8.07 (m, 2H), 7.72-7.95 (m, 3H), 7.15-7.59 (m, 5H), 6.75-6.85 (m, 1H), 6.83-6.85 (m, 1H), 5.91 (s, 1H), 5.55-5.65 (m, 2H), 2.85-3.12 (m, 2H), 2.51-2.52 (m, 1H), 2.01-2.25 (m, 4H). (TFA salt) Example 18: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-(2-fluoroacryloyl)indoline-4-carboxamide Example 18

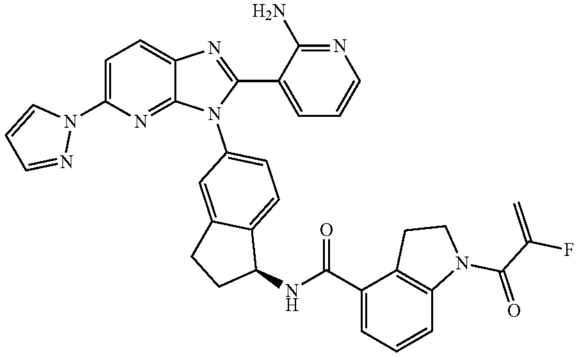

Synthetic Route:

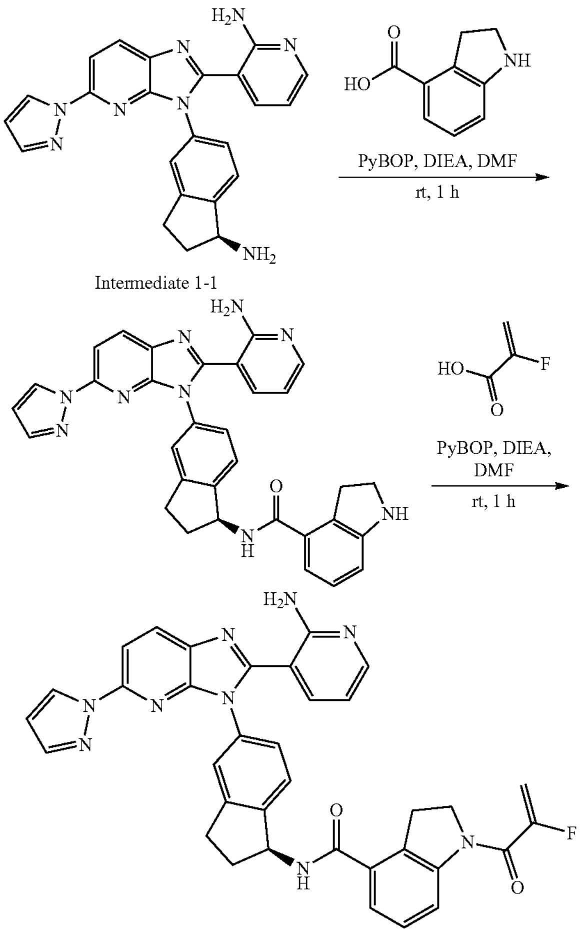

Example 18

Step 1: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)indoline-4-carboxamide A solution of indoline-4-carboxylic acid (300 mg, 1.84 mmol), (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (826 mg, 2.02 mmol), PyBOP (1148 mg, 2.207 mmol) and N,N-diisopropylethylamine (594 mg, 4.60 mmol) in DMF (3 mL) was stirred for 1 h at room temperature. The resulting mixture was purified by reverse-phase flash chromatography on C18 silica gel using a gradient of acetonitrile in water (+0.05% ammonium bicarbonate) to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)indoline-4-carboxamide (130 mg, 13% yield) as a white solid. MS (ESI) calcd. for $C_{32}H_{27}N_9O$: 553.23 m/z, found 554.30 $[M+H]^+$.

Step 2: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-(2-fluoroacryloyl)indoline-4-carboxamide (Example 18)

A solution of (S)-N-(5-(2-(2-aminopyridin-3-yl)-5-(1H-pyrazol-1-yl)-3H-imidazo[4,5-b]pyridin-3-yl)-2,3-dihydro- 1H-inden-1-yl)indoline-4-carboxamide (130 mg, 0.235 mmol), 2-fluoroacrylic acid (25.4 mg, 0.282 mmol), PyBOP (122 mg, 0.235 mmol) and N,N-diisopropylethylamine (61 mg, 0.47 mmol) in DMF (2 mL) was stirred for 1 h at room temperature. The resulting mixture was purified by Prep-HPLC on a XBridge Prep OBD C18 Column using a gradient of acetonitrile in water (+10 mmol/L ammonium bicarbonate) to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-(2-fluoroacryloyl)indoline-4-carboxamide (16.7 mg, 11% yield) as a white solid. MS (ESI) calcd. for $C_{35}H_{28}FN_9O_2$: 625.23 m/z, found 626.15 $[M+H]^+$. $^1H$ NMR (300 MHz, DMSO-$d_6$) δ (ppm): 8.36-8.37 (m, 2H), 8.02-8.07 (m, 3H), 7.94-7.97 (m, 1H), 7.26-7.39 (m, 6H), 6.51-6.56 (m, 1H), 6.42-6.49 (m, 1H), 5.42-5.62 (m, 3H), 4.23-4.27 (m, 2H), 3.38-3.43 (m, 2H), 3.00-3.02 (m, 2H), 2.74-2.85 (m, 1H), 2.05-2.08 (m, 1H). $^{19}F$ NMR (282 MHz, DMSO-$d_6$) δ (ppm): −109.06.

Example 19: (S)-2-acrylamido-N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)benzamide Example 19

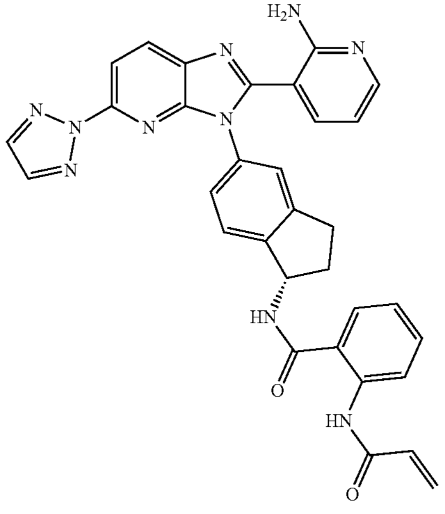

Example 19 was prepared in a manner analogous to Example 2 using Intermediate 19-2 in place of Intermediate 2-1. MS (ESI) calcd. for $C_{32}H_{26}N_{10}O_2$: 582.22 m/z, found 583.15 $[M+H]^+$. $^1H$ NMR (300 MHz, DMSO-$d_6$) δ (ppm): 11.47-11.55 (m, 1H), 9.13-9.21 (m, 1H), 8.37-8.49 (m, 2H), 8.10-8.19 (m, 2H), 7.94-8.06 (m, 2H), 7.79-7.88 (m, 1H), 7.52-7.59 (m, 1H), 7.39-7.51 (m, 2H), 7.24-7.36 (m, 2H), 7.12-7.22 (m, 1H), 6.89-6.97 (m, 2H), 6.34-6.58 (m, 2H), 6.19-6.28 (m, 1H), 5.77-5.85 (m, 1H), 5.62-5.71 (m, 1H), 2.84-3.08 (m, 2H), 2.51-2.60 (m, 1H), 2.06-2.19 (m, 1H). (formic acid salt)

Intermediate 19-2: (S)-2-amino-N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)benzamide Intermediate 19-2

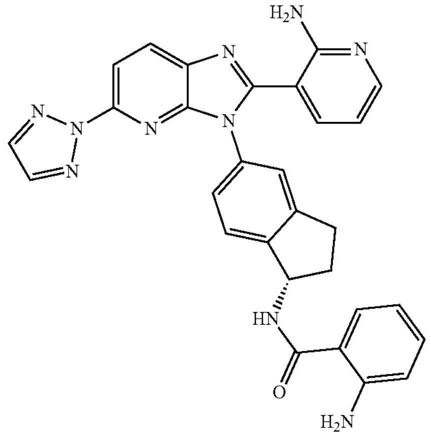

Intermediate 19-2 was prepared in a manner analogous to Intermediate 2-1 using 2-((tert-butoxycarbonyl)amino)benzoic acid in place of 3-((tert-butoxycarbonyl)amino)benzoic acid, Intermediate 19-1 in place of Intermediate 1-1 and 4N HCl in dioxane in place of TFA. MS (ESI) calcd. for $C_{29}H_{24}N_{10}O$: 528.21 m/z, found 529.25 $[M+H]^+$.

Intermediate 19-1: (S)-3-(3-(1-amino-2,3-dihydro-1H-inden-5-yl)-5-(2H-1,2,3-triazol-2-yl)-3H-imidazo[4,5-b]pyridin-2-yl)pyridin-2-amine Intermediate 19-1

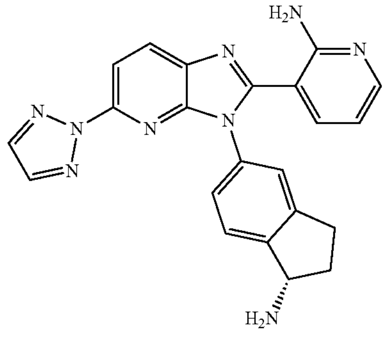

Synthetic Route:

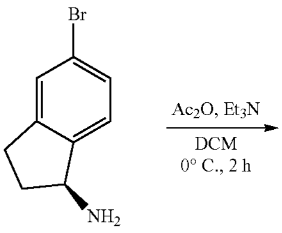

-continued

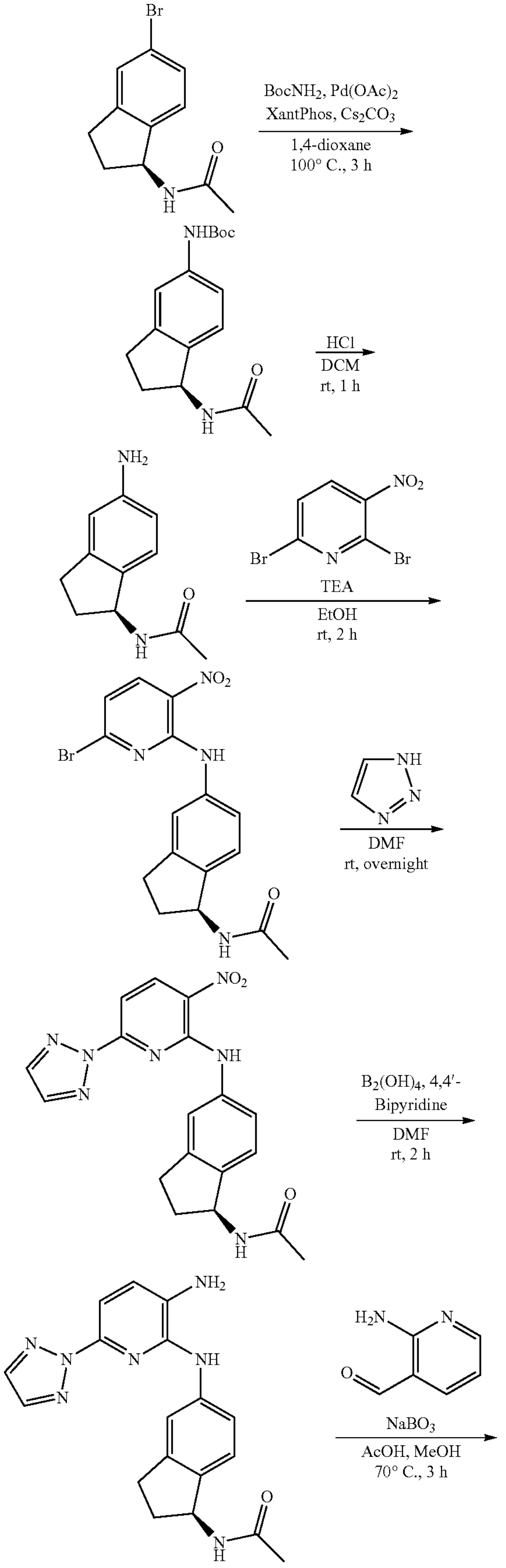

-continued

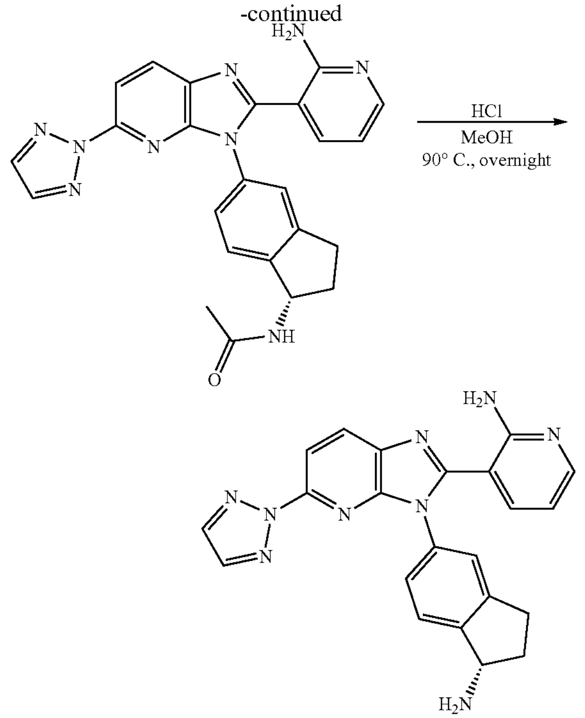

Intermediate 19-1

Step 1: Synthesis of (S)-N-(5-bromo-2,3-dihydro-1H-inden-1-yl)acetamide

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water and extracted 3 times with ethyl acetate. The combined organic layers were dried over anhydrous sodium sulfate and concentrated under reduced pressure. The crude product was re-crystallized from petroleum ether to afford (S)-N-(5-bromo-2,3-dihydro-1H-inden-1-yl)acetamide (90 g, 83% yield) as a white solid. MS (ESI) calculated for $C_{11}H_{12}BrNO$: 253.01, found 254.00 $[M+H]^+$, 256.00 $[M+H+2]^+$.

Step 2: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (40 g, 157 mmol, 1 equiv), tert-butyl carbamate (27.66 g, 236 mmol, 1.5 equiv), XantPhos (9.11 g, 15.7 mmol, 10 mol %), palladium (III) acetate (3.54 g, 15.7 mmol, 10 mol %), and cesium carbonate (154 g, 472 mmol, 10 mol %) was added 1,4-dioxane (300 mL) under nitrogen atmosphere. The resulting mixture was stirred for 3 h at 100° C. The reaction mixture was quenched by addition of water and extracted 3 times with ethyl acetate. The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48%). MS (ESI) calculated for $C_{16}H_{22}N_2O_3$: 290.16 m/z, found 289.05 [M−H]$^-$.

Step 3: Synthesis of (S)-N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N hydrochloric acid in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H-inden-1-yl]acetamide (hydrochloride salt) (23 g, 81%) as a white solid. MS (ESI) calculated for $C_{11}H_{14}N_2O$: 190.11 m/z, found 191.15 [M+H]$^+$.

Step 4: Synthesis of (S)-N-(5-((6-bromo-3-nitropyridin-2-yl)amino)-2,3-dihydro-1H-inden-1-yl)acetamide A solution of (S)-N-(5-amino-2,3-dihydro-1H-inden-1-yl)acetamide (17 g, 89 mmol), 2,6-dibromo-3-nitropyridine (25.19 g, 89.36 mmol) and triethylamine (45.21 g, 446.8 mmol) in EtOH (200 mL) was stirred at room temperature for 2 h. The reaction was quenched with water and the precipitated solids were collected by filtration, washing with EtOH/$H_2O$=1:1 to afford (S)-N-(5-((6-bromo-3-nitropyridin-2-yl)amino)-2,3-dihydro-1H-inden-1-yl)acetamide (26 g, 74.37% yield) as an orange solid. MS (ESI) calcd. for $C_{16}H_{15}BrN_4O_3$: 390.03, found 413.00 [M+Na]$^+$, 415.00 [M+Na+2]$^+$.

Step 5: Synthesis of (S)-N-(5-((3-nitro-6-(2H-1,2,3-triazol-2-yl)pyridin-2-yl)amino)-2,3-dihydro-1H-inden-1-yl)acetamide To a solution of (S)-N-(5-((6-bromo-3-nitropyridin-2-yl)amino)-2,3-dihydro-1H-inden-1-yl)acetamide (50.0 g, 128 mmol) in DMF (1.5 L) was added $K_2CO_3$ (52.99 g, 383.4 mmol) and 1H-1,2,3-triazole (17.65 g, 255.6 mmol). The resulting mixture was stirred at room temperature overnight. The product was precipitated by the addition of $H_2O$. The precipitated solids were collected by filtration and washed with water. The crude product was re-crystallized from petroleum ether to afford (S)-N-(5-((3-nitro-6-(2H-1,2,3-triazol-2-yl)pyridin-2-yl)amino)-2,3-dihydro-1H-inden-1-yl)acetamide (45 g, 93%) as a yellow solid. MS (ESI) calculated for $C18H_{17}N_7O_3$: 379.14 m/z, found 380.15 [M+H]$^+$. $^1$H NMR (400 MHz, DMSO-$d_6$) δ (ppm): 7.98 (s, 2H), 7.79 (d, J=2.1 Hz, 1H), 7.68 (dd, J=8.3, 2.1 Hz, 1H), 7.17 (d, J=8.1 Hz, 1H), 7.13-7.04 (m, 2H), 5.18 (t, J=7.4 Hz, 1H), 2.93-2.85 (m, 1H), 2.80-2.70 (m, 1H), 2.43-2.31 (m, 1H), 1.87 (s, 3H), 1.82-1.71 (m, 1H).

Step 6: Synthesis of (S)-N-(5-((3-amino-6-(2H-1,2,3-triazol-2-yl)pyridin-2-yl)amino)-2,3-dihydro-1H-inden-1-yl)acetamide To a cooled (0° C.) solution of (S)-N-(5-((3-nitro-6-(2H-1,2,3-triazol-2-yl)pyridin-2-yl)amino)-2,3-dihydro-1H-inden-1-yl)acetamide (1.3 g, 3.4 mmol) and 4,4-bipyridine (27 mg, 0.17 mmol) in DMF (25 mL) was added $B_2(OH)_4$ (0.92 g, 10 mmol). The resulting mixture was stirred at room temperature for 2 h. The reaction was quenched with $H_2O$. The resulting mixture was extracted with ethyl acetate 3 times. The organic layers were combined, dried over $Na_2SO_4$, filtered and concentrated. The residue obtained was purified by silica gel column chromatography using a gradient of ethyl acetate in petroleum ether to afford (S)-N-(5-((3-amino-6-(2H-1,2,3-triazol-2-yl)pyridin-2-yl)amino)-2,3-dihydro-1H-inden-1-yl)acetamide (800 mg, 67%) as a yellow solid. MS (ESI) calcd. for $C18H_{19}N_7O$: 349.17 m/z, found 350.15 [M+H]$^+$.

Step 7: Synthesis of (S)-N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)acetamide To a solution of (S)-N-(5-((3-amino-6-(2H-1,2,3-triazol-2-yl)pyridin-2-yl)amino)-2,3-dihydro-1H-inden-1-yl)acetamide (700 mg, 2.00 mmol) in AcOH (10 mL) and MeOH (2 mL) was added 2-aminonicotinaldehyde (269 mg, 2.20 mmol) and sodium perborate (328 mg, 4.00 mmol). The resulting mixture was stirred at 70° C. for 3 h. The solvent was removed by distillation under vacuum. The resulting mixture was purified by reverse-phase flash column chromatography on C18 silica gel using a gradient of acetonitrile in water (+0.05% ammonium bicarbonate) to afford (S)-N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)acetamide (520 mg, 57%) as a reddish brown solid. MS (ESI) calcd. for $C_{24}H_{21}N_9O$: 451.19 m/z, found 452.20 [M+H]$^+$.

Step 8: Synthesis of (S)-3-(3-(1-amino-2,3-dihydro-1H-inden-5-yl)-5-(2H-1,2,3-triazol-2-yl)-3H-imidazo[4,5-b]pyridin-2-yl)pyridin-2-amine (Intermediate 19-1

A solution of (S)-N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)acetamide (520 mg, 1.152 mmol) in HCl (20 mL, concentrated) and MeOH (20 mL) was stirred at 90° C. overnight. The solvent was removed by distillation under vacuum to afford (S)-3-(3-(1-amino-2,3-dihydro-1H-inden-5-yl)-5-(2H-1,2,3-triazol-2-yl)-3H-imidazo[4,5-b]pyridin-2-yl)pyridin-2-amine (Intermediate 19-1) (400 mg, 85%) crude as a yellow solid. MS (ESI) calcd. for $C_{22}H_{19}N_9$: 409.18 m/z, found 410.20 [M+H]$^+$.

Example 20: N-[(1S)-5-[2-(2-aminopyridin-3-yl)-5-(pyrazol-1-yl)imidazo[4,5-b]pyridin-3-yl]-2,3-dihydro-1H-inden-1-yl]-5-fluoro-2-(prop-2-enamido)benzamide Example 20

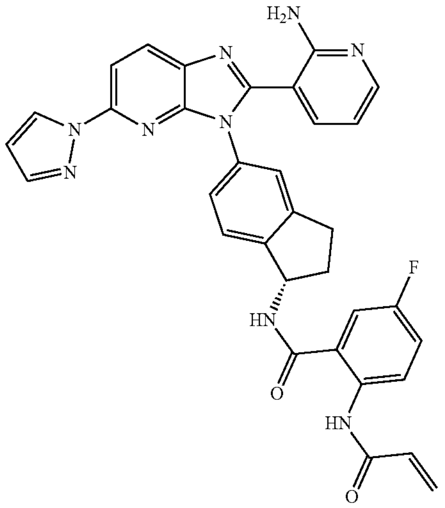

Example 20 was prepared in a manner analogous to Example 3 (steps 2 and 3 only) using 2-amino-5-fluorobenzoic acid in place of 2,3-dihydro-1H-indole-4-carboxylic acid. MS (ESI) calcd. for $C_{33}H_{26}FN_9O_2$: 599.22 m/z, found 600.10 $[M+H]^+$. $^1H$ NMR (400 MHz, DMSO-$d_6$) δ (ppm): 8.35-8.36 (m, 2H), 8.27-8.31 (m, 1H), 8.01-8.02 (m, 1H), 7.94-7.97 (m, 1H), 7.81-7.82 (m, 1H), 7.63-7.66 (m, 1H), 7.46-7.48 (m, 1H), 7.38-7.41 (m, 2H), 7.26-7.31 (m, 2H), 6.55-6.57 (m, 1H), 6.45-6.47 (m, 2H), 6.23-6.28 (m, 1H), 5.80-5.83 (m, 1H), 5.61-5.82 (m, 1H), 2.98-3.05 (m, 1H), 2.91-2.93 (m, 1H), 2.51-2.55 (m, 1H), 2.05-2.10 (m, 1H). $^{19}F$ NMR (376 MHz, DMSO-$d_6$) δ (ppm): −118.14. (formic acid salt)

Example 21: (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-fluorobenzamide Example 21

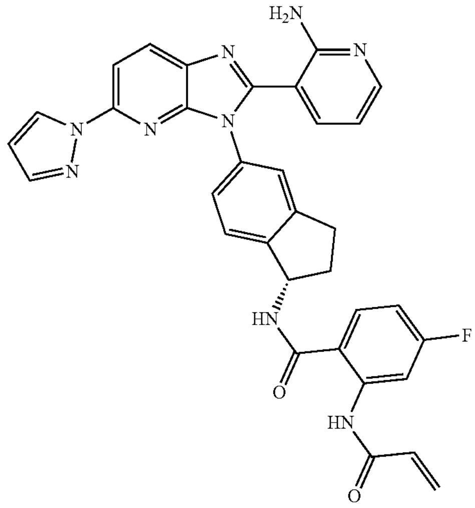

Example 21 was prepared in a manner analogous to Example 3 (steps 2 and 3 only) using 2-amino-4-fluorobenzoic acid in place of 2,3-dihydro-1H-indole-4-carboxylic acid. MS (ESI) calcd. for $C_{33}H_{26}FN_9O_2$: 599.22 m/z, found 600.10 $[M+H]^+$. 1H NMR (400 MHz, DMSO-$d_6$) δ (ppm): 8.41-8.56 (m, 1H), 8.36-8.41 (m, 1H), 8.19-8.36 (m, 1H), 8.08-8.19 (m, 1H), 7.99-8.08 (m, 1H), 7.99-7.88 (m, 1H), 7.81-7.88 (m, 1H), 7.65-7.81 (m, 1H), 7.41-7.59 (m, 2H), 7.21-7.41 (m, 1H), 6.93-7.20 (m, 1H), 6.68-6.93 (m, 1H), 6.51-6.68 (m, 1H), 6.33-6.51 (m, 1H), 6.15-6.33 (m, 1H), 5.75-6.01 (m, 1H), 5.48-5.75 (m, 1H), 3.02-3.21 (m, 1H), 2.75-3.02 (m, 1H), 2.58-2.61 (m, 1H), 1.98-2.25 (m, 1H). (formic acid salt)

Example 22: N-[(1S)-5-[2-(2-aminopyridin-3-yl)-5-cyclopropylimidazo[4,5-b]pyridin-3-yl]-2,3-dihydro-1H-inden-1-yl]-2-(prop-2-enamido)benzamide Example 22

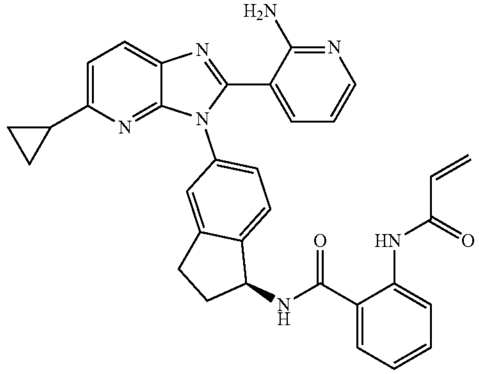

Example 22 was prepared in a manner analogous to Example 1 using Intermediate 22-2 in place of Intermediate 1-1. MS (ESI) calcd. for $C_{33}H_{29}N_7O_2$: 555.24 m/z, found: 556.25 $[M+H]^+$. $^1H$ NMR (400 MHz, DMSO-$d_6$) δ (ppm): 8.20-8.30 (m, 1H), 8.02-8.05 (m, 1H), 7.95-8.00 (m, 1H), 7.69-7.80 (m, 1H), 7.55-7.60 (m, 1H), 7.95-7.54 (m, 1H), 7.35-7.43 (m, 1H), 7.28-7.34 (m, 1H), 7.22-7.34 (m, 1H), 7.15-7.21 (m, 2H), 6.65-6.75 (m, 1H), 6.31-6.41 (m, 1H), 6.18-6.30 (m, 1H), 5.78-5.85 (m, 1H), 5.51-5.61 (m, 1H), 2.93-3.05 (m, 1H), 2.79-2.92 (m, 1H), 2.02-2.20 (m, 2H), 1.11-1.30 (m, 1H), 0.85-1.01 (m, 2H), 0.71-0.84 (m, 2H). (TFA salt)

Intermediate 22-2: 3-{3-[(1S)-1-amino-2,3-dihydro-1H-inden-5-yl]-5-cyclopropylimidazo[4,5-b]pyridin-2-yl}pyridin-2-amine Intermediate 22-2

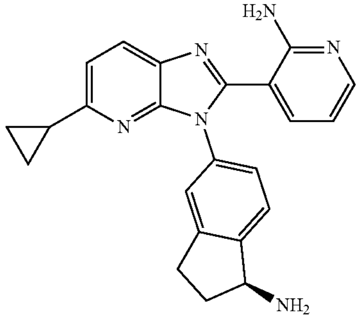

Synthetic Route:

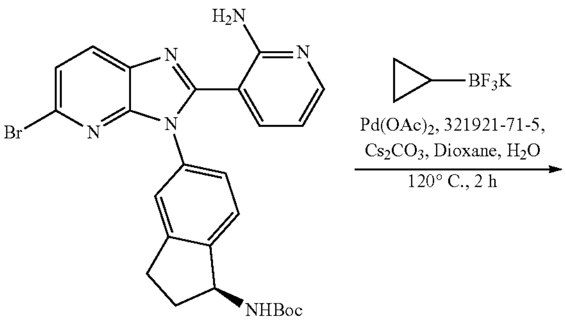

Intermediate 22-1

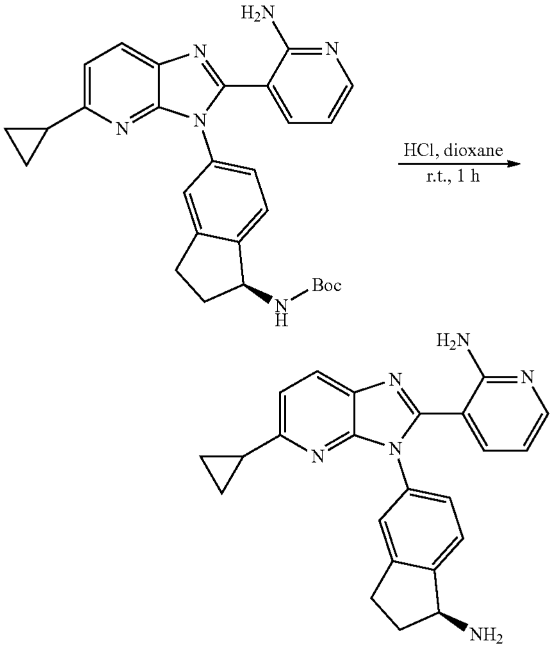

Intermediate 22-2

Step 1: Synthesis of tert-butyl N-[(1S)-5-[2-(2-aminopyridin-3-yl)-5-cyclopropylimidazo[4,5-b]pyridin-3-yl]-2,3-dihydro-1H-inden-1-yl]carbamate A mixture of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 22-1) (300 mg, 0.575 mmol), potassium cyclopropyltrifluoroboranuide (75 mg, 0.69 mmol), $Pd(OAc)_2$ (12.9 mg, 0.057 mmol), Butyldi-1-adamantylphosphine (20.4 mg, 0.057 mmol) and $Cs_2CO_3$ (562 mg, 1.73 mmol) were suspended in dioxane (4 mL) and $H_2O$ (1 mL) at 25° C. under nitrogen atmosphere. The resulting mixture was stirred for 2 h at 120° C. under nitrogen atmosphere. After cooling to the room temperature, the reaction mixture was quenched by addition of water. The resulting mixture was extracted with ethyl acetate 3 times. The combined organic layers were dried over anhydrous $Na_2SO_4$. After filtration, the filtrate was concentrated under reduced pressure. The residue was purified by reverse phase flash chromatography on C18 silica gel using a gradient of acetonitrile in water (+0.05% $NH_4HCO_3$) to afford tert-butyl N-[(1S)-5-[2-(2-aminopyridin-3-yl)-5-cyclopropylimidazo[4,5-b]pyridin-3-yl]-2,3-dihydro-1H-inden-1-yl]carbamate (210 mg, 76% yield) as a yellow solid. MS (ESI) calcd. for $C_{28}H_{30}N_6O_2$: 482.24 m/z, found: 483.25 $[M+H]^+$.

Step 2: Synthesis of 3-{3-[(1S)-1-amino-2,3-dihydro-1H-inden-5-yl]-5-cyclopropylimidazo[4,5-b]pyridin-2-yl}pyridin-2-amine (Intermediate 22-2

A mixture of tert-butyl N-[(1S)-5-[2-(2-aminopyridin-3-yl)-5-cyclopropylimidazo[4,5-b]pyridin-3-yl]-2,3-dihydro-1H-inden-1-yl]carbamate (210 mg, 0.435 mmol) in HCl (10 mL, 4M in 1,4-dioxane) was stirred at room temperature for 1 h. The reaction mixture was concentrated to afford 3-{3-[(1S)-1-amino-2,3-dihydro-1H-inden-5-yl]-5-cyclopropylimidazo[4,5-b]pyridin-2-yl}pyridin-2-amine (Intermediate 22-2) (110 mg, 66% yield) as a yellow solid. MS (ESI) calcd. for $C_{23}H_{22}N_6$: 382.19 m/z, found: 383.20 $[M+H]^+$.

Intermediate 22-1: tert-butyl (S)-(5-(2-(2-aminopyridin-3-yl)-5-bromo-3H-imidazo[4,5-b]pyridin-3-yl)-2,3-dihydro-1H-inden-1-yl)carbamate Intermediate 22-1

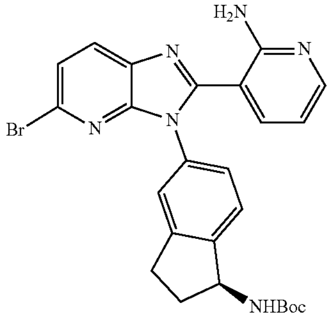

Synthetic Route:

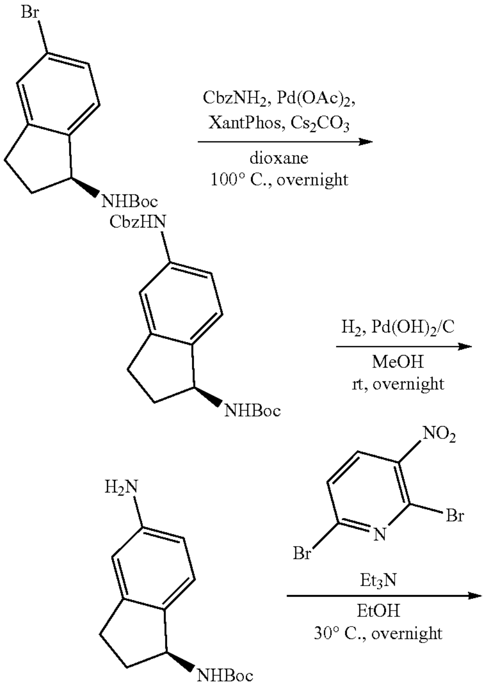

-continued

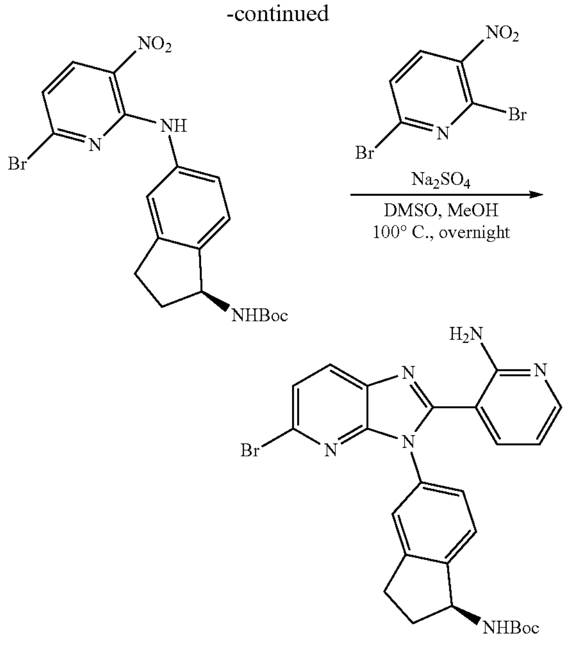

Intermediate 22-1

Step 1: Synthesis of benzyl N-[(1S)-1-[(tert-butoxycarbonyl)amino]-2,3-dihydro-1H-inden-5-yl]carbamate To a solution of tert-butyl N-[(1S)-5-bromo-2,3-dihydro-1H-inden-1-yl]carbamate (60.00 g, 192.18 mmol, 1 equiv), benzyl acetate (34.63 g, 230.6 mmol, 1.2 equiv) and Xant-Phos (22.24 g, 38.44 mmol, 0.2 equiv) in 1,4-dioxane (1200 mL) were added $Cs_2CO_3$ (125.23 g, 384.36 mmol, 2 equiv) and $Pd(OAc)_2$ (4.31 g, 19.2 mmol, 0.1 equiv). The resulting mixture was stirred overnight at 100° C. under a nitrogen atmosphere. The mixture was cooled to room temperature and the product was precipitated by the addition of $H_2O$. The precipitated solids were collected by filtration and washed with water 3 times. The residue taken up into ethyl acetate the solids were removed by filtration, rinsing 3 times with ethyl acetate. The filtrate was concentrated under reduced pressure to afford benzyl N-[(1S)-1-[(tert-butoxycarbonyl)amino]-2,3-dihydro-1H-inden-5-yl]carbamate (50 g, 46%) as a grey solid. MS (ESI) calcd. for $C_{22}H_{26}N_2O_4$: 382.19 m/z, found: 381.10 $[M-H]^-$.

Step 2: Synthesis of tert-butyl N-[(1S)-5-amino-2,3-dihydro-1H-inden-1-yl]carbamate To a solution of benzyl N-[(1S)-1-[(tert-butoxycarbonyl)amino]-2,3-dihydro-1H-inden-5-yl]carbamate (50 g, 131 mmol, 1 equiv) in 500 mL $CH_3OH$ was added $Pd(OH)_2/C$ (5 g, 35.605 mmol, 0.27 equiv) (10%, 5 g) in a pressure tank. The mixture was hydrogenated at room temperature under 30 psi of hydrogen overnight. The resulting mixture was filtered through a Celite pad and concentrated under reduced pressure to afford tert-butyl N-[(1S)-5-amino-2,3-dihydro-1H-inden-1-yl]carbamate (40 g, 73%) as a brown solid. MS (ESI) calcd. for $C_{14}H_{20}N_2O_2$, 248.15 m/z, found: 249.15 $[M+H]^+$.

Step 3: Synthesis of tert-butyl N-[(1S)-5-[(6-bromo-3-nitropyridin-2-yl)amino]-2,3-dihydro-1H-inden-1-yl]carbamate tert-Butyl N-[(1S)-5-amino-2,3-dihydro-1H-inden-1-yl]carbamate (40 g, 161 mmol, 1 equiv) was suspended in EtOH (800 mL) followed by addition of triethylamine (48.90 g, 483.2 mmol, 3 equiv). Once dissolved, 2,6-dibromo-3-nitropyridine (54.49 g, 193.3 mmol, 1.2 equiv) was added and the mixture was stirred at 30° C. overnight. The mixture was allowed to cool to rt. The precipitated solids were collected by filtration and washed with EtOH 3 times to afford tert-butyl N-[(1S)-5-[(6-bromo-3-nitropyridin-2-yl)amino]-2,3-dihydro-1H-inden-1-yl]carbamate (30 g, 27%) as a red solid. MS (ESI) calcd. for $C_{19}H_{21}BrN_4O_4$: 448.07 m/z, found 447.00 $[M-H]^-$.

Step 4: Synthesis of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 22-1 tert-Butyl N-[(1S)-5-[(6-bromo-3-nitropyridin-2-yl)amino]-2,3-dihydro-1H-inden-1-yl]carbamate (30 g, 67 mmol, 1 equiv) was dissolved in DMSO (600 mL) and MeOH (100 mL), followed by addition of 2-aminopyridine-3-carbaldehyde (8.97 g, 73.4 mmol, 1.1 equiv) and $Na_2S_2O_4$ (25.57 g, 146.9 mmol, 2.2 equiv). The resulting mixture was stirred at 100° C. overnight. The product was precipitated by the addition of $H_2O$. The precipitated solids were collected by filtration and washed with $H_2O$ 3 times. The residue was purified by silica gel column chromatography eluting with $CH_2Cl_2$/MeOH (10:1) to afford tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 22-1) (15 g, 36%) as a yellow solid. MS (ESI) calcd. for $C_{25}H_{25}BrN_6O_2$: 520.12 m/z, found: 521.20 $[M+H]^+$.

Example 23: (S)-N-(5-(2-(2-aminopyridin-3-yl)-5-(2H-1,2,3-triazol-2-yl)-3H-imidazo[4,5-b]pyridin-3-yl)-2,3-dihydro-1H-inden-1-yl)-2-(2-fluoroacrylamido)benzamide Example 23

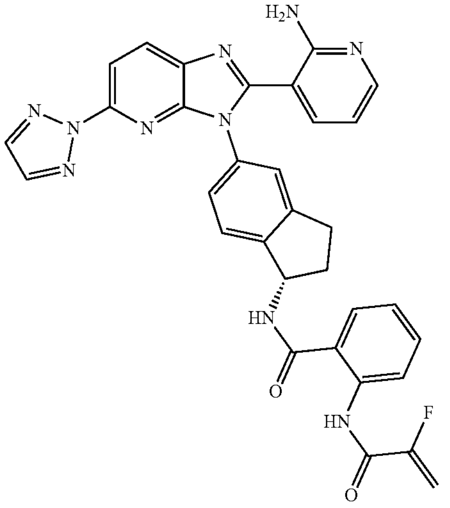

Example 23 was prepared in a manner analogous to Example 18 (last step only) using Intermediate 19-2 in place of the amine starting material. MS (ESI) calcd. for $C_{32}H_{25}FN_{10}O_2$: 600.21 m/z, found 601.15 $[M+H]^+$. $^1H$ NMR (300 MHz, DMSO-$d_6$) δ (ppm): 8.43-8.52 (m, 2H), 8.11-8.14 (m, 3H), 8.03-8.05 (m, 1H), 7.80-7.89 (m, 2H), 7.55-7.65 (m, 1H), 7.39-7.45 (m, 2H), 7.32-7.38 (m, 1H), 7.22-7.28 (m, 1H), 6.75-6.85 (m, 1H), 5.60-5.80 (m, 2H), 5.42-5.55 (m, 1H), 3.05-3.12 (m, 1H), 2.85-3.00 (m, 1H), 2.51-2.52 (m, 1H), 2.05-2.20 (m, 1H). $^{19}F$ NMR (300 MHz, DMSO-$d_6$) δ (ppm): −119.76. (TFA salt)

Example 24: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(vinylsulfonamido)benzamide Example 24

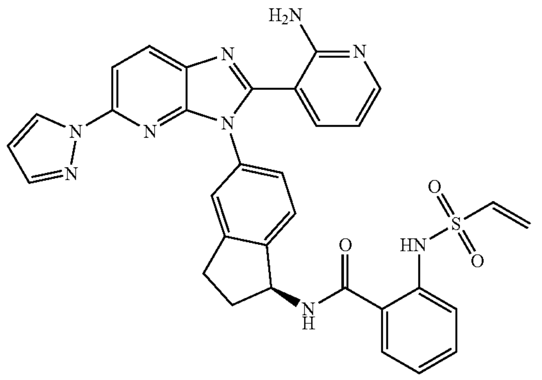

Synthetic Route:

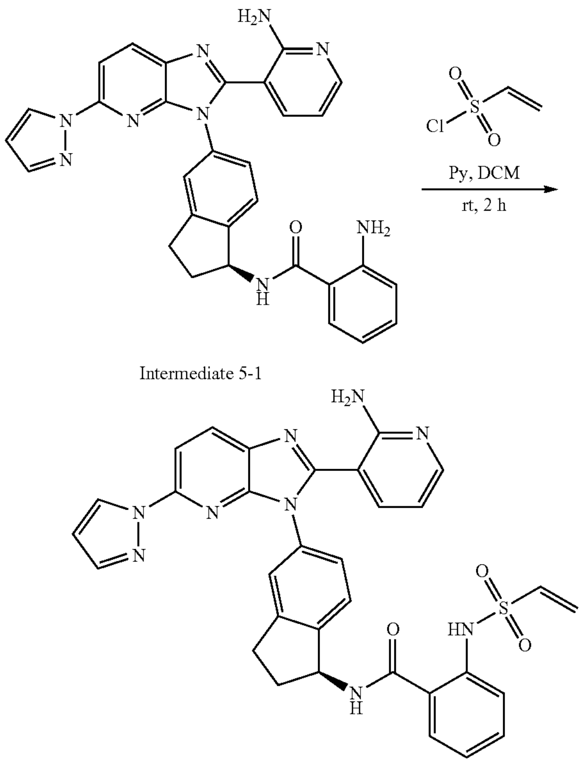

Step 1: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(vinylsulfonamido)benzamide (Example 24)

A solution of (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Intermediate 5-1) (60 mg, 0.11 mmol) and pyridine (18 mg, 0.23 mmol) in DCM (2 ml) was treated with vinylsulfonyl chloride (20 mg, 0.16 mmol) at 0° C. The resulting mixture was stirred for 2 h at room temperature. The resulting mixture was diluted with water and extracted with ethyl acetate 3 times. The combined organic layers were dried over anhydrous $Na_2SO_4$. After filtration, the filtrate was concentrated under reduced pressure. The residue was purified by Prep-HPLC on a XBridge Prep OBD C18 Column using a gradient of acetonitrile in water (+10 mmol/L $NH_4HCO_3$) to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(vinylsulfonamido)benzamide (14.3 mg, 20% yield) as an off-white solid. MS (ESI) calcd. for $C_{32}H_{27}N_9O_3S$: 617.20 m/z, found 618.10 $[M+H]^+$. $^1H$ NMR (400 MHz, DMSO-$d_6$) δ (ppm): 8.32-8.46 (m, 2H), 8.02-8.10 (m, 1H), 7.96-8.01 (m, 1H), 7.84-7.92 (m, 1H), 7.79-7.83 (m, 1H), 7.51-7.58 (m, 1H), 7.39-7.50 (m, 3H), 7.26-7.34 (m, 2H), 7.15-7.24 (m, 1H), 6.79-6.90 (m, 1H), 6.56-6.62 (m, 1H), 6.48-6.54 (m, 1H), 6.18-6.30 (m, 1H), 6.07-6.16 (m, 1H), 5.57-5.66 (m, 1H), 3.01-3.13 (m, 1H), 2.89-2.99 (m, 1H), 2.58-2.62 (m, 1H), 2.09-2.21 (m, 1H).

Example 25: (2S)—N-[(1S)-5-[2-(2-aminopyridin-3-yl)-5-(pyrazol-1-yl)imidazo[4,5-b]pyridin-3-yl]-2,3-dihydro-1H-inden-1-yl]-1-(prop-2-enoyl)pyrrolidine-2-carboxamide Example 25

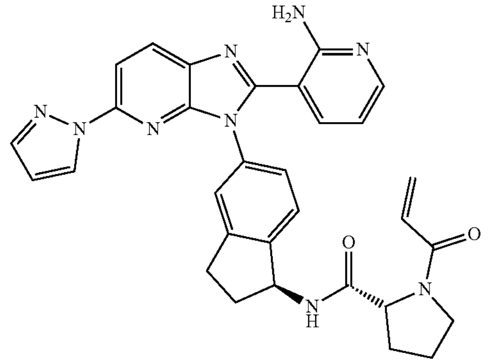

Example 25 was prepared in a manner analogous to Example 4 (final step only) using acryloyl-D-proline in place of 2-(N-methylprop-2-enamido)benzoic acid. MS (ESI) calcd. for $C_{31}H_{29}N_9O_2$: 559.24, m/z, found 560.30 $[M+H]^+$. $^1H$ NMR (400 MHz, DMSO-$d_6$) δ (ppm): 8.31-8.38 (m, 2H), 7.96-8.02 (m, 1H), 7.91-7.94 (m, 1H), 7.78-7.82 (m, 1H), 7.25-7.37 (m, 4H), 6.34-6.66 (m, 3H), 6.15-6.22 (m, 1H), 5.64-5.77 (m, 1H), 5.33-5.42 (m, 1H), 4.38-4.55 (m, 1H), 3.43-3.73 (m, 2H), 2.85-2.96 (m, 2H), 2.41-2.47 (m, 1H), 2.13-2.35 (m, 1H), 1.87-2.01 (m, 4H).

Example 26: (S)-1-acryloyl-N—((S)-5-(2-(2-aminopyridin-3-yl)-5-(1H-pyrazol-1-yl)-3H-imidazo[4,5-b]pyridin-3-yl)-2,3-dihydro-1H-inden-1-yl)pyrrolidine-2-carboxamide Example 26

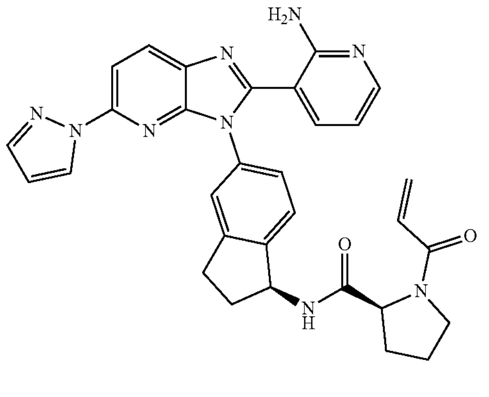

Example 26 was prepared in a manner analogous to Example 4 (final step only) using acryloyl-L-proline in place of 2-(N-methylprop-2-enamido)benzoic acid. MS (ESI) calcd. for $C_{31}H_{29}N_9O_2$, 559.24: (m/z), found 560.30[M+H]$^+$. $^1$H NMR (400 MHz, DMSO-$d_6$) δ (ppm): 8.31-8.40 (m, 2H), 7.99-8.04 (m, 1H), 7.91-7.96 (m, 1H), 7.78-7.82 (m, 1H), 7.25-7.34 (m, 4H), 6.34-6.61 (m, 3H), 6.15-6.22 (m, 1H), 5.74-5.77 (m, 1H), 5.33-5.42 (m, 1H), 4.39-4.55 (m, 1H), 3.43-3.73 (m, 2H), 2.85-2.96 (m, 2H), 2.41-2.47 (m, 1H), 2.13-2.35 (m, 1H), 1.87-2.00 (m, 4H).

Example 27: 1-(3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-8-azabicyclo[3.2.1]octan-8-yl)prop-2-en-1-one Example 27

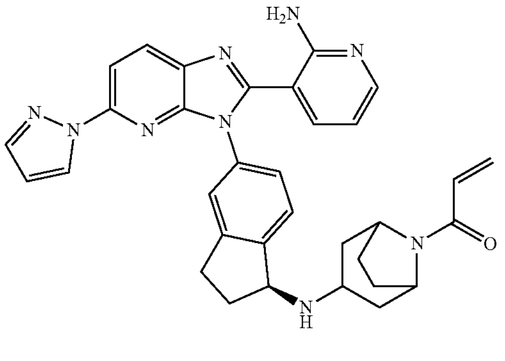

Example 27 was prepared in a manner analogous to Example 13 using Intermediate 27-1 in place of 1-(prop-2-enoyl)piperidin-4-one. MS (ESI) calcd. for $C_{33}H_{33}N_9O$: 571.28 m/z, found: 572.40 [M+H]$^+$. $^1$H NMR (300 MHz, DMSO-$d_6$) δ (ppm): 8.40-8.45 (m, 1H), 8.36-8.39 (m, 1H), 8.07-8.12 (m, 1H), 7.99-8.04 (m, 1H), 7.80-7.85 (m, 1H), 7.64-7.75 (m, 2H), 7.55-7.59 (m, 1H), 7.40-7.48 (m, 1H), 6.65-6.81 (m, 2H), 6.57-6.60 (m, 1H), 6.13-6.21 (m, 1H), 5.68-5.78 (m, 1H), 4.85-4.92 (m, 1H), 4.52-4.65 (m, 2H), 3.09-3.20 (m, 1H), 2.89-3.02 (m, 2H), 2.52-2.68 (m, 2H), 2.41-2.45 (m, 1H), 1.85-2.19 (m, 3H), 1.53-1.84 (m, 4H).

Intermediate 27-1: 8-acryloyl-8-azabicyclo[3.2.1]octan-3-one

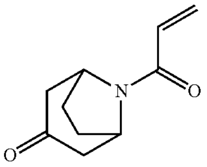

Intermediate 27-1 was prepared in a manner analogous to Intermediate 14-1 using tert-butyl 3-oxo-8-azabicyclo[3.2.1]octane-8-carboxylate in place of tert-butyl 8-oxo-3-azabicyclo[3.2.1]octane-3-carboxylate. MS (ESI) calcd. for $C_{10}H_{13}NO_2$: 179.09 m/z, found: 180.10 [M+H]$^+$.

Example 28: (S)-1-(3-((5-(2-(2-aminopyridin-3-yl)-5-(1H-pyrazol-1-yl)-3H-imidazo[4,5-b]pyridin-3-yl)-2,3-dihydro-1H-inden-1-yl)amino)azetidin-1-yl)prop-2-en-1-one Example 28

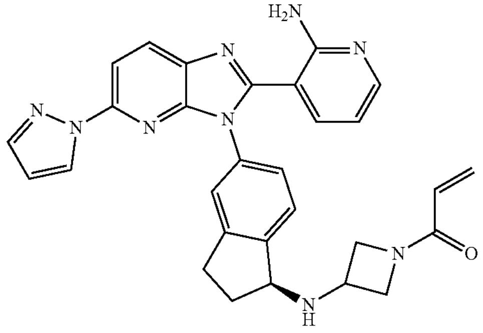

Example 28 was prepared in a manner analogous to Example 13 using Intermediate 28-1 in place of 1-(prop-2-enoyl)piperidin-4-one. MS (ESI) calcd. for $C_{29}H_{27}N_9O$: 517.23 m/z, found: 518.30 [M+H]$^+$. $^1$H NMR (400 MHz, DMSO-$d_6$) δ (ppm): 8.34-8.52 (m, 2H), 7.98-8.15 (m, 2H), 7.80-7.90 (m, 1H), 7.56-7.79 (m, 3H), 7.40-7.55 (m, 1H), 6.71-6.90 (m, 1H), 6.55-6.70 (m, 1H), 6.25-6.40 (m, 1H), 6.15-6.24 (m, 1H), 5.69-5.85 (m, 1H), 4.84-5.00 (m, 1H), 4.50-4.64 (m, 1H), 4.26-4.41 (m, 2H), 4.14-4.25 (m, 1H), 3.87-4.01 (m, 1H), 3.12-3.30 (m, 1H), 2.95-3.10 (m, 1H), 2.41-2.61 (m, 1H), 2.18-2.30 (m, 1H).

Intermediate 28-1: 1-acryloylazetidin-3-one

Intermediate 28-1

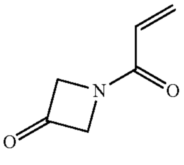

Intermediate 28-1 was prepared in a manner analogous to Intermediate 14-1 using tert-butyl 3-oxoazetidine-1-carboxylate in place of tert-butyl 8-oxo-3-azabicyclo[3.2.1]octane-3-carboxylate. MS (ESI) calcd. for $C_6H_7NO_2$: 125.05 m/z, found: 126.10 $[M+H]^+$.

Example 29: N-[(1S)-5-[2-(2-aminopyridin-3-yl)-5-(pyrazol-1-yl)imidazo[4,5-b]pyridin-3-yl]-2,3-dihydro-1H-inden-1-yl]-1-(prop-2-enoyl)piperidine-4-carboxamide Example 29

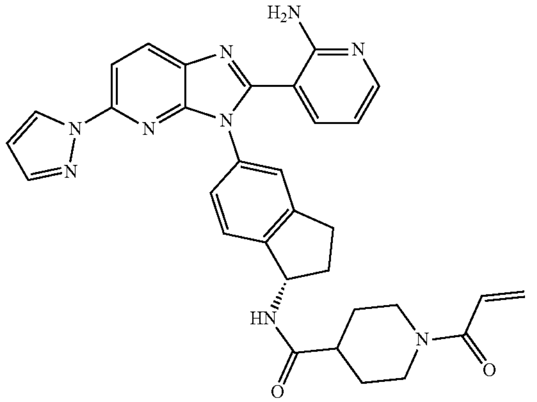

Example 29 was prepared in a manner analogous to Example 2 (via Intermediate 2-1) using 1-(tert-butoxycarbonyl)piperidine-4-carboxylic acid in place of 3-((tert-butoxycarbonyl)amino)benzoic acid and 4N HCl in dioxane in place of TFA/DCM. MS (ESI) calcd. for $C_{32}H_{31}N_9O_2$: 573.26 m/z, found: 574.15 $[M+H]^+$. $^1H$ NMR (300 MHz, DMSO-$d_6$) δ (ppm): 8.32-8.39 (m, 3H), 8.00-8.04 (m, 1H), 7.93-7.98 (m, 1H), 7.79-7.84 (m, 1H), 7.35-7.41 (m, 1H), 7.21-7.31 (m, 3H), 6.88-6.94 (m, 2H), 6.79-6.86 (m, 1H), 6.54-6.59 (m, 1H), 6.42-6.47 (m, 1H), 6.15-6.22 (m, 1H), 5.62-5.69 (m, 1H), 5.31-5.38 (m, 1H), 4.35-4.45 (m, 1H), 4.03-4.12 (m, 1H), 3.01-3.13 (m, 1H), 2.91-3.00 (m, 1H), 2.81-2.90 (m, 1H), 2.62-2.78 (m, 1H), 2.39-2.52 (m, 1H), 1.42-1.95 (m, 6H). (formic acid salt).

Example 30: 1-(2-{[(1S)-5-[2-(2-aminopyridin-3-yl)-5-(pyrazol-1-yl)imidazo[4,5-b]pyridin-3-yl]-2,3-dihydro-1H-inden-1-yl]amino}-7-azaspiro[3.5]nonan-7-yl)prop-2-en-1-one Example 30

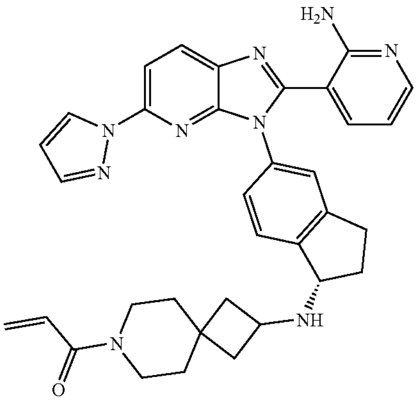

Example 30 was prepared in a manner analogous to Example 14 (via Intermediate 14-1) using tert-butyl 2-oxo-7-azaspiro[3.5]nonane-7-carboxylate in place of tert-butyl 8-oxo-3-azabicyclo[3.2.1]octane-3-carboxylate. MS (ESI) calcd. for $C_{34}H_{35}N_9O$: 585.30 m/z, found: 586.25 [M+H]. $^1H$ NMR (400 MHz, DMSO-$d_6$) δ (ppm): 8.40-8.48 (m, 1H), 8.35-8.39 (m, 1H), 8.01-8.05 (m, 2H), 7.81-7.90 (m, 1H), 7.72-7.80 (m, 2H), 7.57-7.62 (m, 1H), 7.41-7.48 (m, 1H), 6.75-6.90 (m, 2H), 6.55-6.62 (m, 1H), 6.08-6.15 (m, 1H), 5.68-5.76 (m, 1H), 4.72-4.81 (m, 1H), 3.35-3.59 (m, 4H), 3.12-3.25 (m, 1H), 2.95-3.05 (m, 1H), 2.48-2.60 (m, 2H), 2.13-2.35 (m, 3H), 1.91-2.05 (m, 2H), 1.49-1.70 (m, 4H). (TFA salt).

Example 31: 1-(6-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azaspiro[3.3]heptan-2-yl)prop-2-en-1-one Example 31

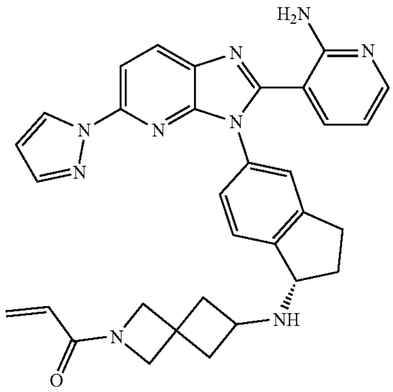

Example 31 was prepared in a manner analogous to Example 14 (via Intermediate 14-1) using tert-butyl 6-oxo-2-azaspiro[3.3]heptane-2-carboxylate in place of tert-butyl 8-oxo-3-azabicyclo[3.2.1]octane-3-carboxylate. MS (ESI) calcd. for $C_{32}H_{31}N_9O$: 557.27 m/z, found: 558.20 $[M+H]^+$. $^1H$ NMR (400 MHz, DMSO-$d_6$) δ (ppm): 8.34-8.38 (m, 2H), 8.27 (s, 1H), 7.95-8.00 (m, 2H), 7.81-7.82 (m, 1H), 7.57-7.60 (m, 1H), 7.41 (s, 1H), 7.26-7.31 (m, 2H), 6.54-6.55 (m, 1H), 6.42-6.45 (m, 1H), 6.25-6.32 (m, 1H), 6.08-6.13 (m, 1H), 5.68-5.70 (m, 1H), 4.42-4.43 (m, 1H), 4.25 (s, 1H), 4.15 (s, 1H), 3.98 (s, 1H), 3.87 (s, 1H), 3.47-3.71 (m, 1H), 3.02-3.04 (m, 1H), 2.85-2.87 (m, 1H), 2.37-2.53 (m, 2H), 2.10-2.18 (m, 2H), 1.96-2.00 (m, 1H). (formic acid salt).

Example 32: 1-(7-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azaspiro[3.5]nonan-2-yl)prop-2-en-1-one Example 32

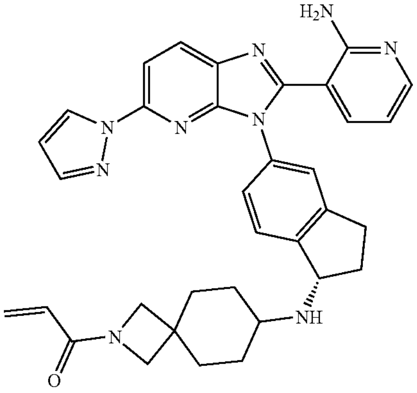

Example 32 was prepared in a manner analogous to Example 14 (via Intermediate 14-1) using tert-butyl 7-oxo-2-azaspiro[3.5]nonane-2-carboxylate in place of tert-butyl 8-oxo-3-azabicyclo[3.2.1]octane-3-carboxylate. MS (ESI) calcd. for $C_{34}H_{35}N_9O$, 585.30 m/z, found 586.20 $[M+H]^+$. $^1$H NMR (400 MHz, DMSO-$d_6$) δ (ppm): 8.22-8.59 (m, 2H), 7.95-8.17 (m, 2H), 7.76-7.95 (m, 2H), 7.65-7.76 (m, 1H), 7.53-7.65 (m, 1H), 7.32-7.53 (m, 1H), 6.72-6.95 (m, 1H), 6.48-6.72 (m, 1H), 6.21-6.48 (m, 1H), 6.05-6.21 (m, 1H), 5.61-5.86 (m, 1H), 4.87-5.11 (m, 1H), 3.87-3.95 (m, 1H), 3.69-3.74 (m, 1H), 3.52-3.69 (m, 1H), 3.09-3.41 (m, 2H), 2.81-3.09 (m, 1H), 2.56-2.67 (m, 2H), 2.09-2.35 (m, 2H), 1.81-2.09 (m, 3H), 1.52-1.81 (m, 2H), 1.39-1.52 (m, 2H). (formic acid salt).

Example 33: 1-(4-{[(1S)-5-[2-(2-aminopyridin-3-yl)-5-(1,2,3-triazol-2-yl)imidazo[4,5-b]pyridin-3-yl]-2,3-dihydro-1H-inden-1-yl]amino}piperidin-1-yl)prop-2-en-1-one Example 33

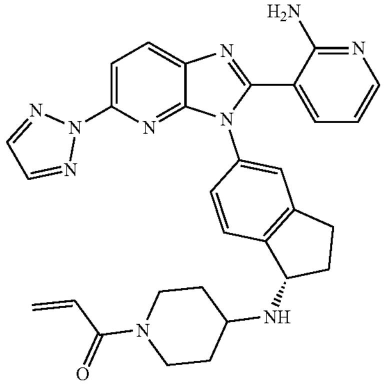

Example 33 was prepared in a manner analogous to Example 13 using Intermediate 19-1 in place of Intermediate 1-1. MS (ESI) calcd. for $C_{30}H_{30}N_{10}O$, 546.26 m/z, found 547.10 $[M+H]^+$. $^1$H NMR (400 MHz, DMSO-$d_6$) δ (ppm): 8.39-8.56 (m, 1H), 8.21-8.39 (m, 1H), 8.07-8.21 (m, 2H), 8.01-8.07 (m, 1H), 7.88-8.01 (m, 1H), 7.51-7.72 (m, 1H), 7.36-7.51 (m, 1H), 7.18-7.36 (m, 2H), 6.64-6.95 (m, 1H), 6.38-6.61 (m, 1H), 5.95-6.28 (m, 1H), 5.56-5.86 (m, 1H), 4.52-4.78 (m, 1H), 4.28-4.52 (m, 1H), 3.91-4.22 (m, 1H), 2.95-3.38 (m, 3H), 2.72-2.95 (m, 2H), 2.03-2.23 (m, 1H), 1.82-2.03 (m, 2H), 1.56-1.21 (m, 2H). (formic acid salt).

Example 34: (2E)-1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-4-(dimethylamino)but-2-en-1-one Example 34

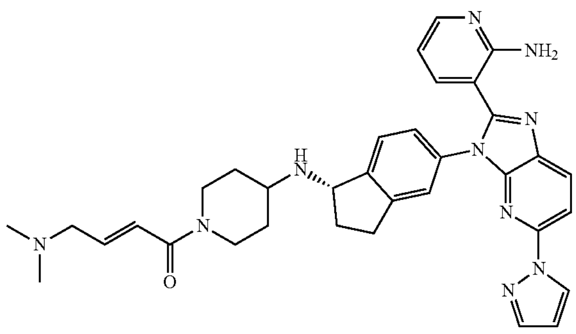

Synthetic Route:

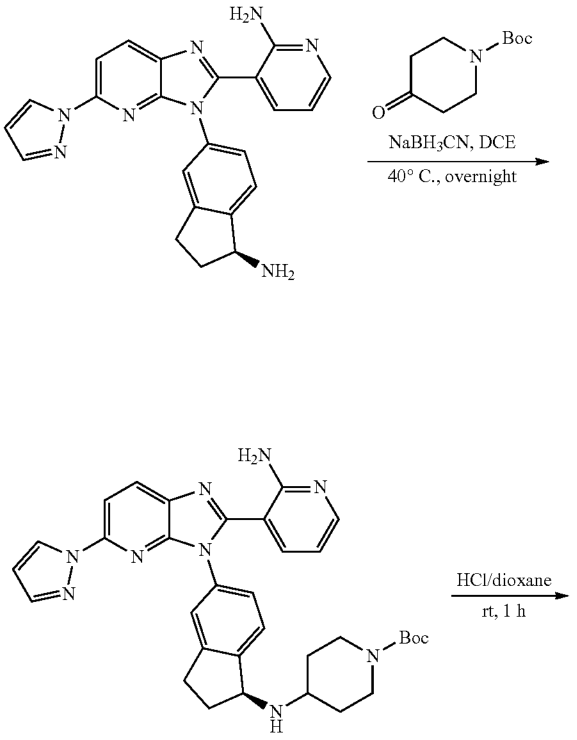

-continued

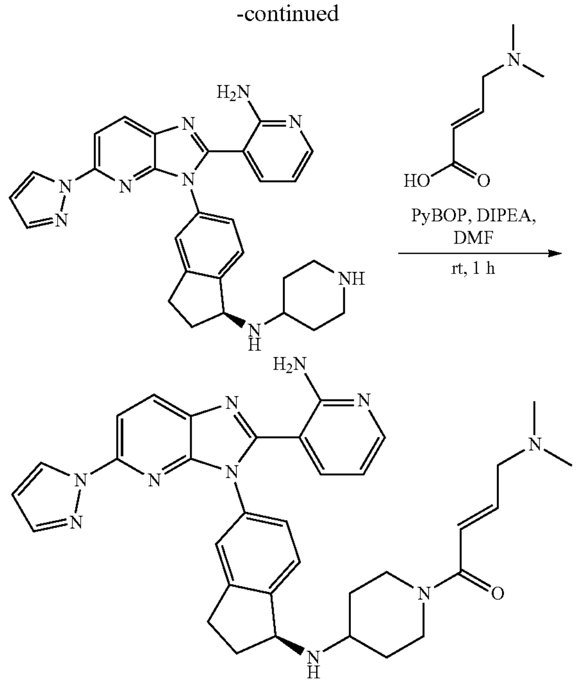

Example 34

Step 1: Synthesis of tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carboxylate To a solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (410 mg, 1.00 mmol) in DCE (10 mL) was added tert-butyl 4-oxopiperidine-1-carboxylate (200 mg, 1.00 mmol). The resulting mixture was stirred at 40° C. for 1 h. To the above mixture was added $NaBH_3CN$ (252 mg, 4.02 mmol). The resulting mixture was stirred overnight at 40° C. The mixture was filtered and the filter cake was washed with acetonitrile (3×5 mL). The filtrate was concentrated under reduced pressure. The resulting mixture was purified by reverse-phase flash column chromatography on C18 silica gel using a gradient of acetonitrile in water (+0.05% ammonium bicarbonate) to afford tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carboxylate (260 mg, 44% yield) as a yellow solid. MS (ESI) calcd. for $C_{33}H_{37}N_9O_2$: 591.31 m/z, found: 592.40 $[M+H]^+$.

Step 2: Synthesis of 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine A solution of tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carboxylate (260 mg, 0.439 mmol) in 4N HCl in 1,4-dioxane (10 mL) was stirred at room temperature for 1 h. The solvent was removed by distillation under vacuum to afford 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine HCl (220 mg) as a yellow solid, which was used directly in the next step without further purification. MS (ESI) calcd. for $C_{28}H_{29}N_9$: 491.25 m/z, found: 492.25 $[M+H]^+$.

Step 3: Synthesis of (2E)-1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-4-(dimethylamino)but-2-en-1-one (Example 34)

To a solution of 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine (100 mg, 0.203 mmol) in DMF (2 mL) was added N,N-diisopropylethylamine (78.87 mg, 0.609 mmol), PyBOP (105.86 mg, 0.203 mmol), (2E)-4-(dimethylamino)but-2-enoic acid (39.4 mg, 0.304 mmol). The resulting mixture was stirred at room temperature for 1 h. The resulting mixture was purified by reverse-phase flash column chromatography on C18 silica gel using a gradient of acetonitrile in water (+0.05% $NH_4HCO_3$) to afford (2E)-1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-4-(dimethylamino)but-2-en-1-one (80 mg) as a yellow solid. The product was then further purified by Prep-HPLC on a XSelect CSH Prep C18 OBD Column using a gradient of acetonitrile in water (+0.05% TFA) to afford (2E)-1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-4-(dimethylamino)but-2-en-1-one (Example 34, TFA salt) (51.7 mg, 41.91% yield) as a light yellow solid. MS (ESI) calcd. for $C_{34}H_{38}N_{10}O$: 602.32 m/z, found: 603.25 $[M+H]^+$. $^1H$-NMR (400 MHz, DMSO-$d_6$) (ppm): 8.42-8.44 (m, 1H), 8.35-8.36 (m, 1H), 8.05-8.06 (m, 1H), 8.00-8.02 (m, 1H), 7.82-7.83 (m, 1H), 7.69-7.72 (m, 2H), 7.57-7.58 (m, 1H), 7.42-7.44 (m, 1H), 6.94-6.97 (m, 1H), 6.72-6.75 (m, 1H), 6.55-6.63 (m, 2H), 4.97-4.99 (m, 1H), 4.51-3.58 (m, 1H), 4.13-4.17 (m, 1H), 3.86-3.88 (m, 2H), 3.55-3.61 (m, 1H), 3.18-3.21 (m, 2H), 2.95-2.99 (m, 1H), 2.73-2.77 (m, 7H), 2.56-2.61 (m, 1H), 2.12-2.27 (m, 3H), 1.49-1.56 (m, 2H).

Example 35: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(2-fluoroacrylamido)-1-methyl-1H-pyrazole-5-carboxamide Example 35

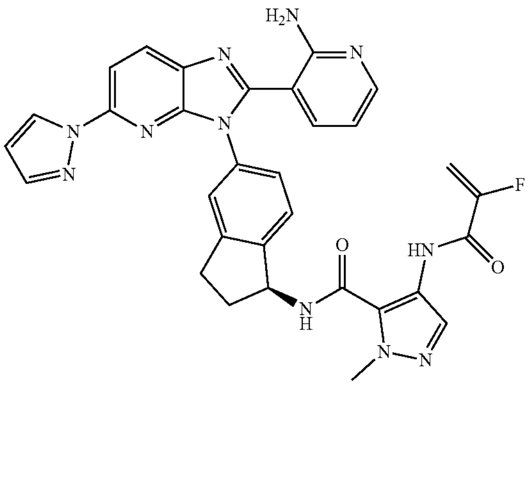

Synthetic Route:

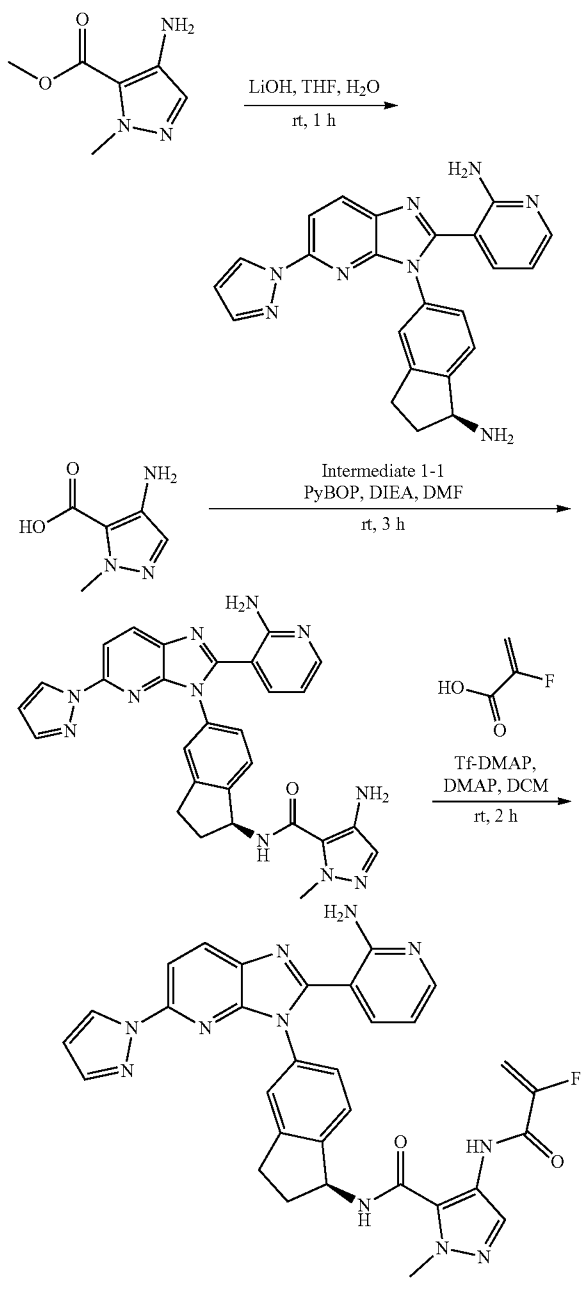

Example 35

Step 1: Synthesis of 4-amino-1-methyl-1H-pyrazole-5-carboxylic acid

Methyl 4-amino-1-methyl-1H-pyrazole-5-carboxylate (300 mg, 1.93 mmol) was dissolved in THE (8 mL). A solution of LiOH (185.2 mg, 7.736 mmol) in $H_2O$ (2 mL) was added and the mixture was stirred for 1 h at room temperature. The resulting mixture was concentrated under reduced pressure to afford 4-amino-1-methyl-1H-pyrazole-5-carboxylic acid (300 mg, crude) as a white solid. MS (ESI) calcd. for $C_5H_7N_3O_2$, 141.05 m/z, found 142.05 $[M+H]^+$.

Step 2: Synthesis of (S)-4-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1H-pyrazole-5-carboxamide To a solution of 4-amino-1-methyl-1H-pyrazole-5-carboxylic acid (300 mg, 2.13 mmol) and (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (200 mg, 0.490 mmol) in DMF (5 mL) were added PyBOP (306 mg, 0.588 mmol) and N,N-diisopropylethylamine (190 mg, 1.47 mmol). The mixture was stirred at room temperature for 3 h. The reaction mixture was quenched with water (80 mL). The resulting mixture was extracted with ethyl acetate (3×80 mL) and dried over anhydrous $Na_2SO_4$. After filtration, the filtrate was concentrated under reduced pressure. The residue was purified by silica gel column chromatography using a gradient of dichloromethane in methanol to afford (S)-4-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1H-pyrazole-5-carboxamide (180 mg, 69% yield) as a yellow oil. MS (ESI) calcd. for $C_{28}H_{25}N_{11}O$, 531.22 m/z, found 532.20. $[M+H]^+$.

Step 3: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(2-fluoroacrylamido)-1-methyl-1H-pyrazole-5-carboxamide (Example 35)

To a solution of (S)-4-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1-methyl-1H-pyrazole-5-carboxamide (120 mg, 0.226 mmol) and 2-fluoroacrylic acid (40.7 mg, 0.452 mmol) in DCM (3 mL) was added 4-(dimethylamino)-1-trifluoromethanesulfonylpyridin-1-ium triflate (119 mg, 0.294 mmol) and DMAP (41.4 mg, 0.339 mmol). The resulting reaction mixture was stirred at room temperature for 2 h. The reaction mixture was quenched with water (80 mL). The resulting mixture was extracted with ethyl acetate (3×80 mL). The organic phases were combined, dried by $Na_2SO_4$ and concentrated under vacuum. The residue was purified by silica gel column chromatography using a gradient of methanol in dichloromethane to afford the crude product as a yellow solid. The crude product was purified by Prep-HPLC on a XBridge Prep OBD C18 Column using a gradient of acetonitrile in water (+0.5% TFA) to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(2-fluoroacrylamido)-1-methyl-1H-pyrazole-5-carboxamide (Example 35, TFA salt) (17.0 mg, 10% yield) as a white solid. MS (ESI) calcd. for $C_{31}H_{26}FN_{11}O_2$, 603.23 m/z, found 604.15 $[M+H]^+$. $^1H$ NMR (300 MHz, DMSO-$d_6$) δ (ppm): 8.31-8.40 (m, 2H), 7.90-8.04 (m, 2H), 7.80 (s, 1H), 7.63 (s, 1H), 7.41-7.49 (m, 1H), 7.37 (s, 1H), 7.21-7.32 (m, 2H), 6.52-7.61 (m, 1H), 6.40-6.48 (m, 1H), 5.53-5.76 (m, 2H), 5.20-5.40 (m, 1H), 3.97 (s, 3H), 2.83-3.03 (m, 2H), 2.56-2.63 (m, 1H), 1.93-2.04 (m, 1H). $^{19}F$ NMR (282 MHz, DMSO-$d_6$) δ (ppm): −118.21.

Example 36: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(2-fluoroacrylamido)-1-methyl-1H-pyrazole-3-carboxamide Example 36

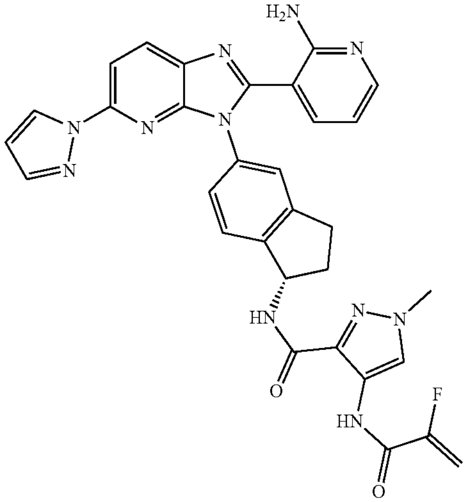

Example 36 was prepared in a manner analogous to Example 35 using methyl 4-amino-1-methyl-1H-pyrazole-3-carboxylate in place of 4-amino-1-methyl-1H-pyrazole-5-carboxylate, and for the final step: N,N-dimethylformamide in place of dichloromethane, PyBOP in place of Tf-DMAP and N,N-diisopropylethylamine in place of 4-dimethylaminopyridine. MS (ESI) calcd. for $C_{31}H_{26}FN_{11}O_2$, 603.23 m/z, found 604.10 $[M+H]^+$. $^1H$ NMR (400 MHz, DMSO-$d_6$) δ (ppm): 8.46-8.36 (m, 2H), 8.29-8.31 (m, 1H), 8.02-8.06 (m, 1H), 7.99-8.01 (m, 1H), 7.81-7.83 (m, 1H), 7.71-7.73 (m, 1H), 7.44 (s, 1H), 7.28-7.39 (m, 2H), 6.71-6.84 (m, 1H), 6.51-6.56 (m, 1H), 5.71-5.79 (m, 1H), 5.57-5.70 (m, 1H), 5.31-5.51 (m, 1H), 3.92 (s, 3H), 3.00-3.11 (m, 1H), 2.81-2.99 (m, 1H), 2.39-2.42 (m, 1H), 2.19-2.23 (m, 1H). $^{19}F$ NMR (376 MHz, DMSO-$d_6$) δ (ppm): −121.08. (TFA salt).

Example 37: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(cyclopent-1-ene-1-carboxamido)benzamide Example 37

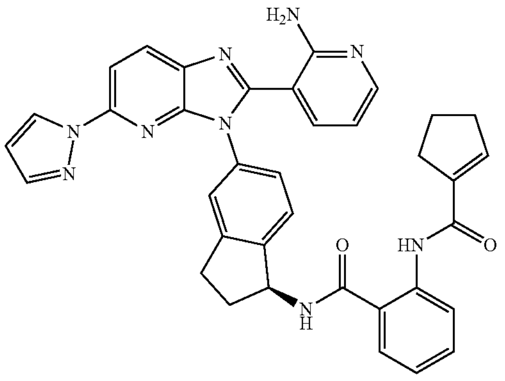

Synthetic Route:

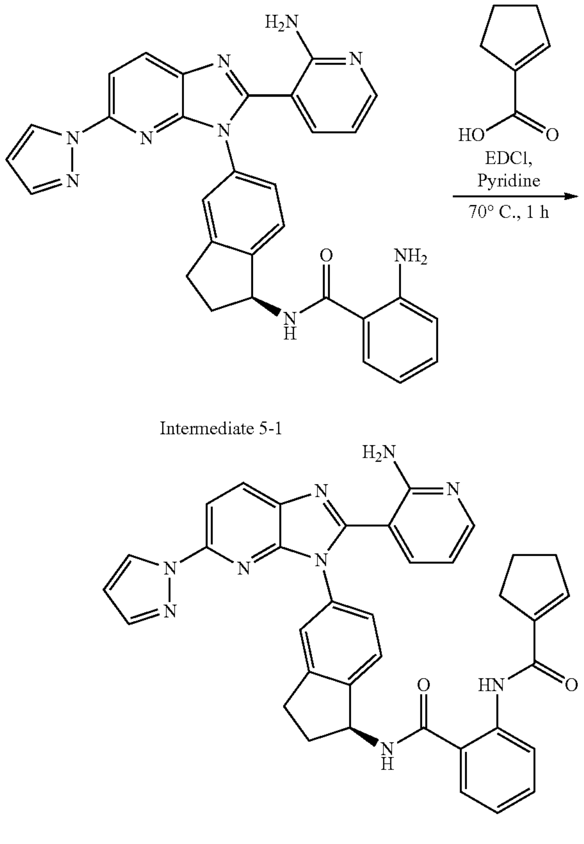

Intermediate 5-1

Example 37

Step 1: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(cyclopent-1-ene-1-carboxamido)benzamide (Example 37)

To a stirred solution of 2-amino-N-[(1S)-5-[2-(2-aminopyridin-3-yl)-5-(pyrazol-1-yl)imidazo[4,5-b]pyridin-3-yl]-2,3-dihydro-1H-inden-1-yl]benzamide (Intermediate 5-1) (100 mg, 0.190 mmol) in pyridine (1 mL) was added cyclopent-1-ene-1-carboxylic acid (31.9 mg, 0.284 mmol) and EDCI (43.6 mg, 0.227 mmol). The resulting mixture was stirred at 70° C. for 1 h. The crude reaction mixture was purified by Prep-HPLC on a XSelect CSH Prep C18 OBD Column using a gradient of acetonitrile in water (+0.05% TFA) to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(cyclopent-1-ene-1-carboxamido)benzamide (TFA salt) (56.6 mg, 48% yield) as a yellow solid. MS (ESI) calcd. for $C_{36}H_{31}N_9O_2$, 621.26 m/z, found 622.15 $[M+H]^+$. $^1H$ NMR (400 MHz, DMSO-$d_6$) δ (ppm): 8.44-8.52 (m, 1H), 8.38-8.40 (m, 1H), 8.37-8.38 (m, 1H), 8.07-8.08 (m, 1H), 8.01-8.03 (m, 1H), 7.85-7.87 (m, 2H), 7.83-7.84 (m, 1H), 7.75-7.77 (m, 1H), 7.51-7.56 (m, 2H), 7.34-7.47 (m, 1H), 7.14-7.18 (m, 1H), 6.81-6.82 (m, 1H), 6.79-6.80 (m, 1H), 6.68-6.78 (m, 1H), 5.56-5.57 (m, 1H), 3.52-3.53 (m, 2H), 2.92-3.10 (m, 2H), 2.60-2.64 (m, 3H), 2.13-2.16 (m, 1H), 1.97-1.98 (m, 2H).

Example 38: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(2-chloroacrylamido)benzamide Example 38

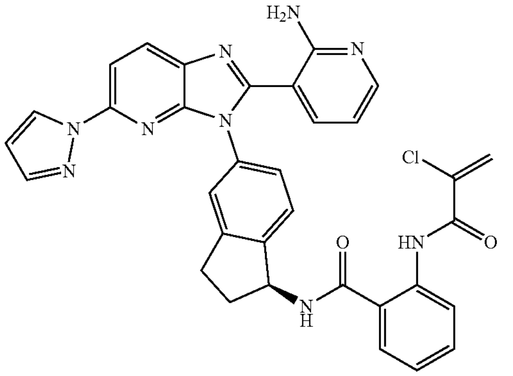

Synthetic Route:

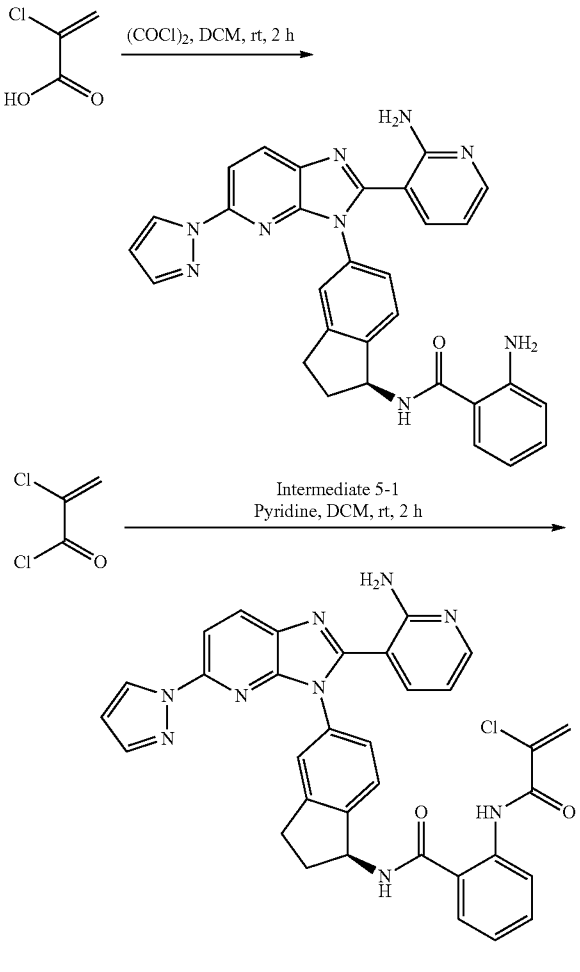

Example 38

Step 1: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(2-chloroacrylamido)benzamide (Example 38)

A solution of 2-chloroacrylic acid (300 mg, 2.82 mmol) in DCM (5 mL) was treated with $(COCl)_2$ (286 mg, 2.25 mmol) at 0° C. under nitrogen atmosphere. The resulting mixture was stirred for 2 h at room temperature under nitrogen atmosphere. The reaction mixture was added to a solution of (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide (Intermediate 5-1) (100 mg, 0.190 mmol) and pyridine (30.0 mg, 0.380 mmol) in DCM (1 ml). The mixture was stirred for 2 h at room temperature. The resulting mixture was diluted with $H_2O$ (50 mL). The resulting mixture was extracted with ethyl acetate (3×50 mL) and dried over anhydrous $Na_2SO_4$. After filtration, the filtrate was concentrated under reduced pressure. The residue was purified by silica gel column chromatography using a gradient of dichloromethane in methanol then by Prep-HPLC on a XBridge Prep Shield RP OBD C18 Column using a gradient of acetonitrile in water (+10 mmol/L ammonium bicarbonate) to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(2-chloroacrylamido)benzamide (Example 38) (27.2 mg, 23% yield) as a white solid. MS (ESI) calcd. for $C_{33}H_{26}ClN_9O_2$, 615.19 m/z, found 616.10 $[M+H]^+$. $^1H$ NMR (300 MHz, DMSO-$d_6$) δ (ppm): 8.46-8.54 (m, 1H), 8.31-8.42 (m, 2H), 7.78-8.02 (m, 4H), 7.53-7.61 (m, 1H), 7.38-7.46 (m, 2H), 7.22-7.34 (m, 3H), 6.41-6.66 (m, 3H), 6.09-6.17 (m, 1H), 5.60-5.71 (m, 1H), 2.90-3.14 (m, 2H), 2.53-2.62 (m, 1H), 2.04-2.19 (m, 1H).

Example 39: N-[2-({[(1S)-5-[2-(2-aminopyridin-3-yl)-5-(pyrazol-1-yl)imidazo[4,5-b]pyridin-3-yl]-2,3-dihydro-1H-inden-1-yl]amino}methyl)phenyl]prop-2-enamide Example 39

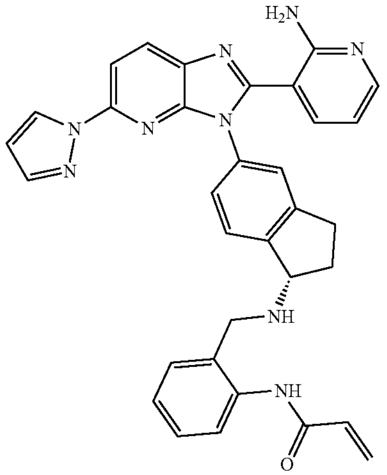

Example 39 was prepared in a manner analogous to Example 13 using Intermediate 39-1 in place of the ketone and a reaction temperature of room temperature instead of 40° C. MS (ESI) calcd. for $C_{33}H_{29}N_9O$: 567.25 m/z, found: 568.15 $[M+H]^+$. $^1H$ NMR (300 MHz, DMSO-$d_6$) δ (ppm):

8.40-8.43 (m, 1H), 8.36-8.39 (m, 1H), 8.01-8.09 (m, 2H), 7.82-7.86 (m, 1H), 7.71-7.78 (m, 1H), 7.60-7.66 (m, 2H), 7.55-7.59 (m, 1H), 7.44-7.49 (m, 1H), 7.36-7.42 (m, 3H), 6.69-6.74 (m, 1H), 6.53-6.57 (m, 1H), 6.41-6.50 (m, 1H), 6.25-6.31 (m, 1H), 5.77-5.82 (m, 1H), 4.88-4.93 (m, 1H), 4.10-4.20 (m, 2H), 3.12-3.22 (m, 1H), 2.92-3.01 (m, 1H), 2.51-2.65 (m, 1H), 2.30-2.39 (m, 1H). (TFA salt)

Intermediate 39-1: N-(2-formylphenyl)acrylamide

Intermediate 39-1

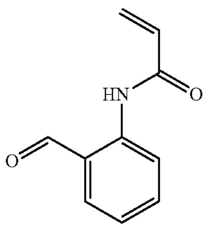

Intermediate 39-1 was prepared in a manner analogous to Intermediate 14-1 (step 2 only) using 2-aminobenzaldehyde in place of the ketone. MS (ESI) calcd. for $C_{10}H_9NO_2$: 175.06 m/z, found: 176.00 $[M+H]^+$.

Example 40: N-[(1S)-5-[2-(2-aminopyridin-3-yl)-5-(pyrazol-1-yl)imidazo[4,5-b]pyridin-3-yl]-2,3-dihydro-1H-inden-1-yl]-1-(prop-2-enoyl)-3,4-dihydro-2H-quinoline-8-carboxamide Example 40

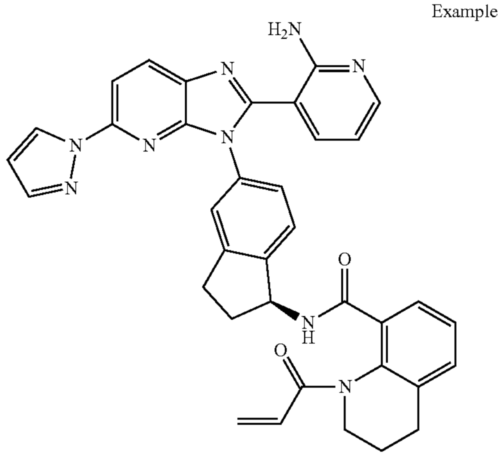

Example 40 was prepared in a manner analogous to Example 3 (steps 2 and 3 only) using 1,2,3,4-tetrahydroquinoline-8-carboxylic acid in place of 2,3-dihydro-1H-indole-4-carboxylic acid and sodium bicarbonate in place of triethylamine. MS (ESI) calcd. for $C_{36}H_{31}N_9O_2$: 621.26 m/z, found: 622.25 $[M+H]^+$. $^1$HNMR (400 MHz, DMSO-$d_6$) δ (ppm): 8.35-8.42 (m, 211), 7.98-8.03 (m, 2H), 7.78-7.80 (m, 2H), 7.41-7.78 (m, 3H), 7.27-7.40 (m, 2H), 6.78-6.82 (m, 1H), 6.54-6.55 (m, 1H), 6.08-6.17 (m, 2H), 5.28-5.75 (m 2H), 4.25-4.32 (m, 1H), 3.17-3.25 (m, 1H), 2.74-3.00 (m, 3H), 2.33-2.46 (m, 3H), 1.55-2.17 (m, 3H). (TFA salt).

Example 41: N-[(1S)-5-[2-(2-aminopyridin-3-yl)-5-(pyrazol-1-yl)imidazo[4,5-b]pyridin-3-yl]-2,3-dihydro-1H-inden-1-yl]-3-(prop-2-enamido)pyridine-4-carboxamide Example 41

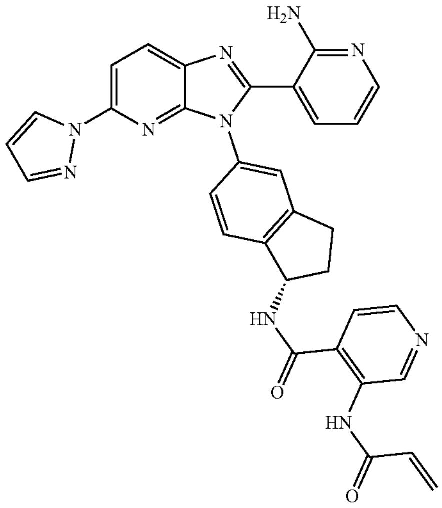

Example 41 was prepared in a manner analogous to Example 3 (steps 2 and 3 only) using 3-aminoisonicotinic acid in place of 2,3-dihydro-1H-indole-4-carboxylic acid and acetonitrile in place of dichloromethane. The final product reaction mixture was purified directly by reverse phase column chromatography first on C18 silica gel then on an XSelect CSH Prep C18 OBD Column using a gradient of acetonitrile in water (+0.05% formic acid) to afford Example 41 as the formic acid salt. MS (ESI) calcd. for $C_{32}H_{26}N_{10}O_2$: 582.22 m/z, found 605.10 $[M+Na]^+$. $^1$H NMR (400 MHz, DMSO-$d_6$) δ (ppm): 8.93-8.94 (m, 111), 8.58-8.60 (m, 111), 8.37-8.40 (m, 3H), 8.35-8.36 (m, 1H), 7.97-8.01 (m, 1H), 7.95-7.96 (m, 1H), 7.81-7.82 (m, 1H), 7.40-7.48 (m, 1H), 7.40-7.41 (m, 1H), 7.29-7.30 (m, 2H), 6.57-6.58 (m, 1H), 6.42-6.48 (m, 2H), 6.35-6.36 (m, 1H), 5.92-5.95 (m, 1H), 5.61-5.70 (m, 1H), 3.00-3.10 (m, 1H), 2.88-2.90 (m, 1H), 2.53-2.55 (m, 1H), 2.00-2.10 (m, 1H).

Example 42: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(3-methylene-2-oxopyrrolidin-1-yl)benzamide Example 42

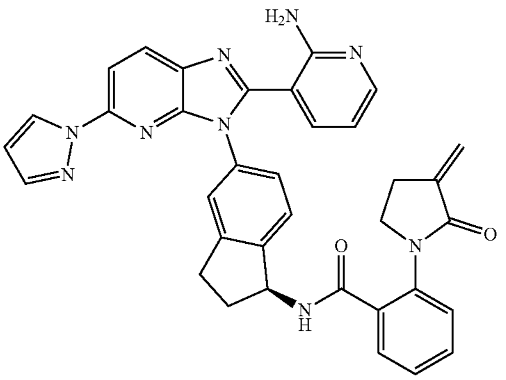

Synthetic Route:

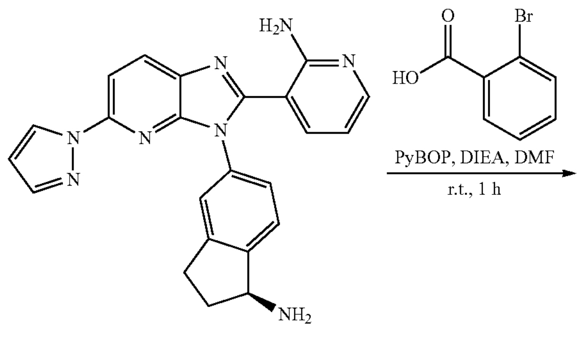

Intermediate 1-1

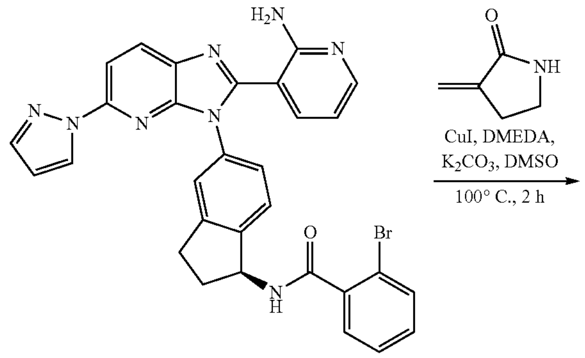

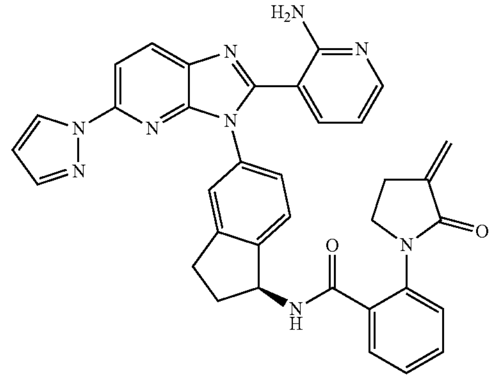

Example 42

Step 1: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-bromobenzamide To a suspension of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (203. mg, 0.497 mmol) in DMF (4 mL) was added 2-bromobenzoic acid (100 mg, 0.497 mmol), PyBOP (259 mg, 0.497 mmol) and N,N-diisopropylethylamine (193 mg, 1.49 mmol). The reaction mixture was stirred at room temperature for 1 h. The mixture was purified directly by reverse-phase flash chromatography on C18 silica gel using a gradient of acetonitrile in water (+0.05% $NH_4HCO_3$) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-bromobenzamide (200 mg, 68% yield) as a light yellow solid. MS (ESI) calcd. for $C_{30}H_{23}BrN_8O$, 590.12 m/z, found 591.15 $[M+H]^+$.

Step 2: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-(3-methylidene-2-oxopyrrolidin-1-yl)benzamide (Example 42

To a solution of N-[(1S)-5-[2-(2-aminopyridin-3-yl)-5-(pyrazol-1-yl)imidazo[4,5-b]pyridin-3-yl]-2,3-dihydro-1H-inden-1-yl]-2-bromobenzamide (200.98 mg, 0.340 mmol) in DMSO (4 mL) was added 3-methylidenepyrrolidin-2-one (66 mg, 0.68 mmol), (1R,2R)-N1,N2-dimethylcyclohexane-1,2-diamine (4.83 mg, 0.034 mmol), CuI (12.9 mg, 0.068 mmol) and $K_2CO_3$ (117 mg, 0.850 mmol). The reaction mixture was stirred at 100° C. for 1 h under a nitrogen atmosphere. The mixture was purified directly by Prep-HPLC on YMC Triart C18 ExRs column using a gradient of acetonitrile in water (+10 mmol/L $NH_4HCO_3$) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-(3-methylidene-2-oxopyrrolidin-1-yl)benzamide (19.5 mg, 9% yield) as a light yellow solid. MS (ESI) calcd. for $C_{35}H_{29}N_9O_2$, 607.24, m/z, found 608.15 $[M+H]^+$. $^1H$ NMR (400 MHz, DMSO-$d_6$) δ (ppm): 8.39-8.43 (m, 2H), 8.00-8.03 (m, 2H), 7.73-7.84 (m, 2H), 7.58-7.62 (m, 2H), 7.37-7.52 (m, 4H), 7.19-7.30 (m, 1H), 6.81-6.85 (m, 1H), 6.52-6.59 (m, 1H), 5.84-5.85 (m, 1H), 5.43-5.46 (m, 2H), 3.83-3.89 (m, 2H), 2.99-3.06 (m, 3H), 2.87-2.90 (m, 1H), 2.49-2.50 (m, 1H), 1.99-2.05 (m, 1H).

Example 43: (S)-2-acrylamido-N-(5-(2-(2-amino-pyridin-3-yl)-5-(1H-pyrazol-1-yl)-3H-imidazo[4,5-b]pyridin-3-yl)-2,3-dihydro-1H-inden-1-yl)-4-(difluoromethyl)benzamide Example 43

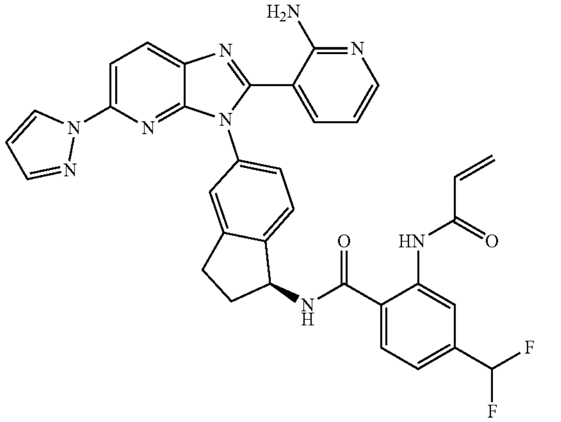

Synthetic Route:

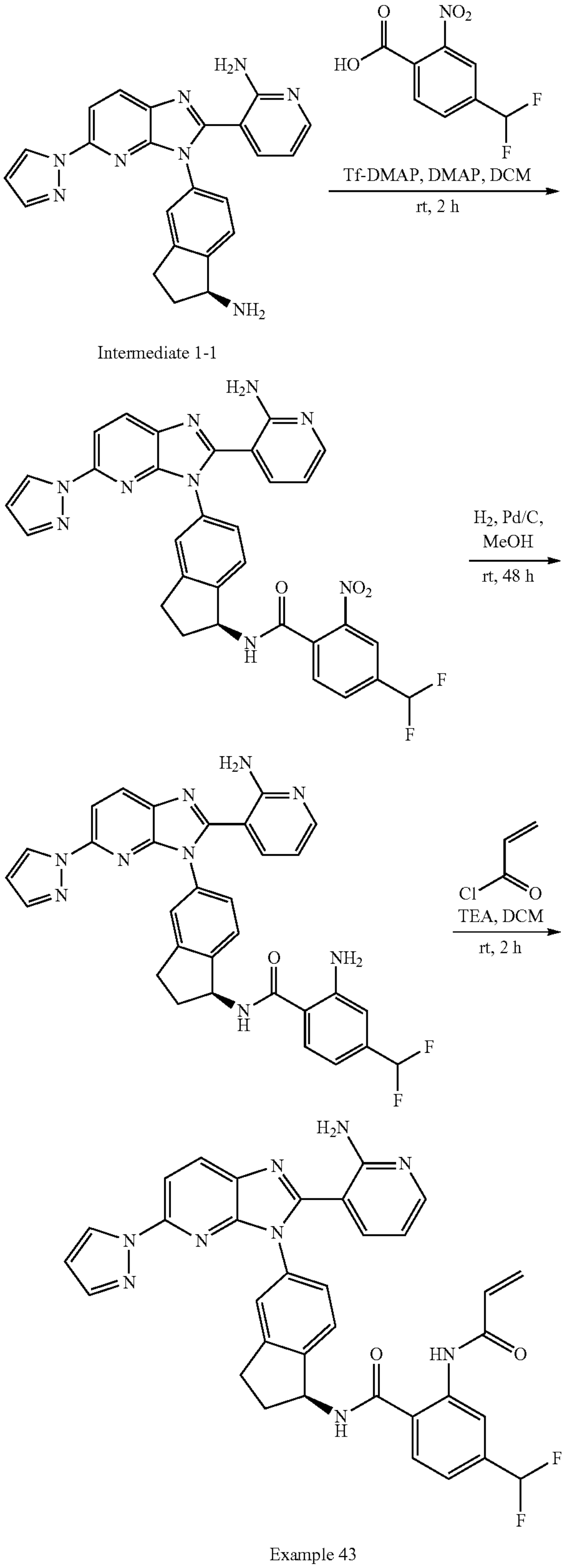

Intermediate 1-1

Example 43

Step 1: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)-2-nitrobenzamide A solution of 4-(difluoromethyl)-2-nitrobenzoic acid (150 mg, 0.691 mmol) in DCM (2 mL) was treated with (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (339 mg, 0.829 mmol), 4-(dimethylamino)-1-trifluoromethanesulfonylpyridin-1-ium triflate (334 mg, 0.829 mmol) and DMAP (101 mg, 0.829 mmol). The resulting mixture was stirred for 2 h at room temperature. The mixture was diluted with water (50 mL) and extracted with ethyl acetate (3×50 mL) then dried over anhydrous $Na_2SO_4$. After filtration, the filtrate was concentrated under reduced pressure. The residue was purified by silica gel column chromatography using a gradient of methanol in dichloromethane to afford (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)-2-nitrobenzamide (200 mg, 48% yield) as an off-white solid. MS (ESI) calcd. for $C_{31}H_{23}F_2N_9O_3$, 607.19 m/z, found 608.10 $[M+H]^+$.

Step 2: Synthesis of (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)benzamide A solution of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)-2-nitrobenzamide (120 mg, 0.198 mmol) in MeOH (50 mL) was treated with Pd/C (180 mg, 1.69 mmol) at room temperature. The resulting mixture was stirred for 24 h at room temperature under hydrogen atmosphere. The resulting mixture was filtered and concentrated under reduced pressure. The residue was purified by silica gel column chromatography using a gradient of dichloromethane in methanol to afford (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)benzamide (70 mg, 61% yield) as an off-white solid. MS (ESI) calcd. for $C_{31}H_{25}F_2N_9O$, 577.22 m/z, found 578.30 $[M+H]^+$.

Step 3: Synthesis of (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)benzamide (Example 43)

A solution of (S)-2-amino-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)benzamide (20 mg, 0.035 mmol) and triethylamine (10.5 mg, 0.105 mmol) in DCM (1 ml) was treated with acryloyl chloride (3.1 mg, 0.035 mmol) and the mixture was stirred for 2 h at room temperature. The resulting mixture was diluted with water (10 mL), extracted with ethyl acetate (3×30 mL) and dried over anhydrous $Na_2SO_4$. After filtration, the filtrate was concentrated under reduced pressure. The residue was purified by reverse-phase flash chromatography on C18 silica gel using a gradient of acetonitrile in water (0.1% TFA) to afford (S)-2-acrylamido-N-(5-(2-(2-aminopyridin-3-yl)-5-(1H-pyrazol-1-yl)-3H-imidazo[4,5-b]pyridin-3-yl)-2,3-dihydro-1H-inden-1-yl)-4-(difluoromethyl)benzamide (Example 43, TFA salt) (3.6 mg, 14% yield) as a yellow solid.

MS (ESI) calcd. for $C_{34}H_{27}F_2N_9O_2$, 631.23 m/z, found 632.15 $[M+H]^+$. $^1H$ NMR (400 MHz, DMSO-$d_6$) δ (ppm): 8.51-8.60 (m, 1H), 8.37-8.48 (m, 2H), 7.99-8.14 (m, 2H), 7.91-7.98 (m, 1H), 7.82-7.90 (m, 1H), 7.77-7.81 (m, 1H), 7.38-7.54 (m, 2H), 7.19-7.27 (m, 1H), 7.01-7.12 (m, 1H), 6.89-6.98 (m, 1H), 6.76-6.85 (m, 1H), 6.56-6.62 (m, 1H), 6.37-6.48 (m, 1H), 6.26-6.33 (m, 1H), 5.85-5.93 (m, 1H), 5.66-5.75 (m, 1H), 2.87-3.15 (m, 2H), 2.47-2.52 (m, 1H), 2.02-2.23 (m, 1H). $^{19}F$ NMR (376 MHz, DMSO-$d_6$) δ (ppm): −111.15.

Example 44: N-[(1S)-5-[2-(2-aminopyridin-3-yl)-5-(pyrazol-1-yl)imidazo[4,5-b]pyridin-3-yl]-2,3-dihydro-1H-inden-1-yl]-3-fluoro-2-(prop-2-enamido) benzamide Example 44

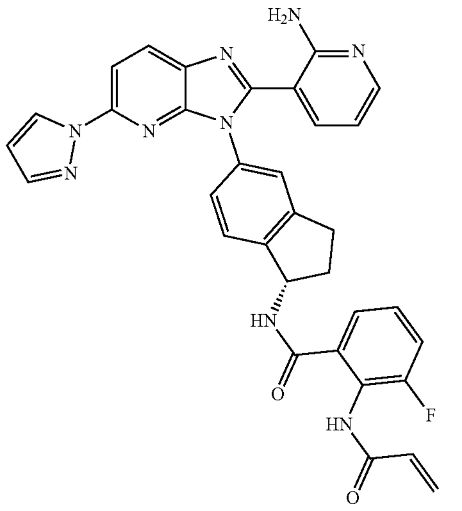

Example 44 was prepared in a manner analogous to Example 3 (steps 2 and 3 only) using 2-amino-3-fluorobenzoic acid in place of 2,3-dihydro-1H-indole-4-carboxylic acid, potassium carbonate in place of triethylamine and acetonitrile in place of dichloromethane. MS (ESI) calcd. for $C_{33}H_{26}FN_9O_2$, 599.30, m/z, found 600.15 $[M+H]^+$. $^1H$ NMR (400 MHz, DMSO-$d_6$) δ (ppm): 8.39-8.44 (m, 2H), 8.01-8.03 (m, 2H), 7.68-7.84 (m, 2H), 7.38-7.50 (m, 5H), 7.25-7.31 (m, 1H), 6.81-6.90 (m, 1H), 6.58-6.62 (m, 1H), 6.49-6.54 (m, 1H), 6.16-6.27 (m, 1H), 5.76-5.79 (m, 1H), 5.43-5.53 (m, 1H), 2.99-3.06 (m, 1H), 2.73-2.94 (m, 1H), 2.49-2.50 (m, 1H), 1.99-2.05 (m, 1H). $^{19}F$ NMR (376 MHz, DMSO-$d_6$) δ (ppm): −119.9. (TFA salt)

Example 45: N-[(1S)-5-[2-(2-aminopyridin-3-yl)-5-(pyrazol-1-yl)imidazo[4,5-b]pyridin-3-yl]-2,3-dihydro-1H-inden-1-yl]-2-[(1E)-2-carbamoyleth-1-en-1-yl]pyridine-3-carboxamide Example 45

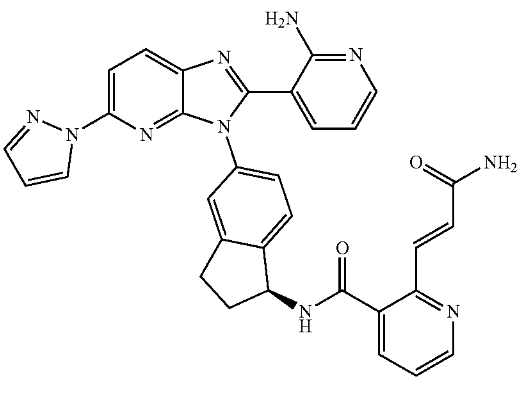

Synthetic Route:

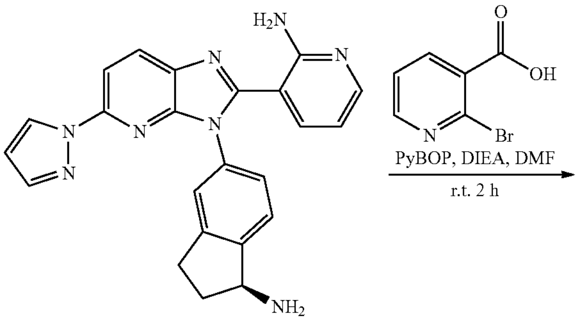

Intermediate 1-1

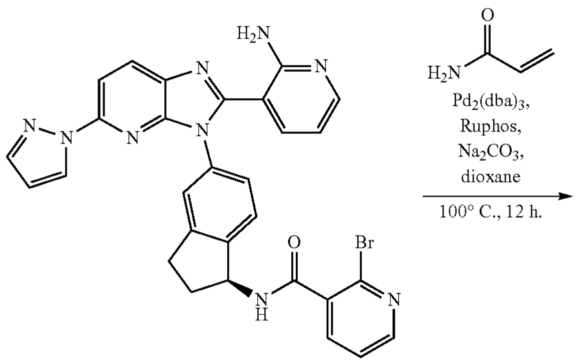

-continued

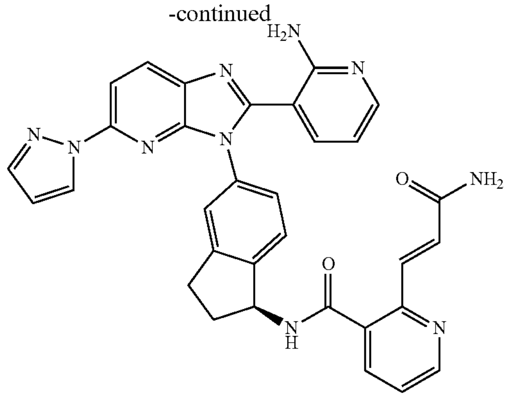

Example 45

Step 1: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-bromopyridine-3-carboxamide To a solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (300 mg, 0.734 mmol) in DMF (5 mL) were added N,N-diisopropylethylamine (474.63 mg, 3.670 mmol), PyBOP (458.65 mg, 0.881 mmol) and 2-bromopyridine-3-carboxylic acid (178 mg, 0.881 mmol). The resulting mixture was stirred at room temperature for 1 h then purified by reverse-phase flash chromatography on C18 silica gel using a gradient of acetonitrile in water (+0.05% $NH_4HCO_3$) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-bromopyridine-3-carboxamide (500 mg, 90% yield) as a yellow solid. MS (ESI) calcd. for $C_{29}H_{22}BrN_9O$: 591.11 m/z, found: 592.10 $[M+H]^+$.

Step 2: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-2-[(1E)-2-carbamoyleth-1-en-1-yl]pyridine-3-carboxamide (Example 45)

To a solution of N-[(1S)-5-[2-(2-aminopyridin-3-yl)-5-(pyrazol-1-yl)imidazo[4,5-b]pyridin-3-yl]-2,3-dihydro-1H-inden-1-yl]-2-bromopyridine-3-carboxamide (200 mg, 0.338 mmol) and polyacrylamide (240 mg, 3.38 mmol) in 1,4-dioxane (10 mL) were added $Pd_2(dba)_3$ (61.8 mg, 0.068 mmol), RuPhos (31.5 mg, 0.068 mmol) and $Na_2CO_3$ (178.9 mg, 1.690 mmol). The resulting mixture was stirred at 100° C. for 6 h under $N_2$ atmosphere. The resulting mixture was diluted with water (10 mL), extracted with ethyl acetate (3×30 mL) and dried over anhydrous $Na_2SO_4$. After filtration, the filtrate was concentrated under reduced pressure. The residue was then purified by Prep-HPLC on a XSelect CSH Fluoro Phenyl column using a gradient of acetonitrile in water (+0.05% TFA) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-[(1E)-2-carbamoyleth-1-en-1-yl]pyridine-3-carboxamide (Example 45) (14.5 mg, 7% yield) as a yellow solid. MS (ESI) calcd. for $C_{32}H_{26}N_{10}O_2$: 582.22 m/z, found: 583.15 $[M+H]^+$. $^1H$ NMR (400 MHz, DMSO-$d_6$) δ (ppm): 8.68-8.70 (m, 111), 8.39-8.45 (m, 2H), 8.01-8.04 (m, 2H), 7.90-7.92 (m, 1H), 7.80-7.83 (m, 1H), 7.76-7.79 (m, 2H), 7.51-7.59 (m, 1H), 7.48-7.50 (m, 1H), 7.45 (s, 1H), 7.36-7.42 (m, 1H), 7.16-7.19 (m, 1H), 6.80-6.82 (m, 1H), 6.57-6.59 (m, 1H), 5.61-5.62 (m, 1H), 3.03-3.09 (m, 1H), 2.92-2.98 (m, 1H), 2.46-2.56 (m, 1H), 2.02-2.07 (m, 1H). (TFA salt)

Example 46: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-2-fluoroprop-2-en-1-one Example 46

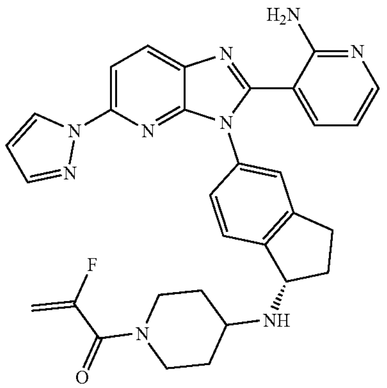

Example 46 was prepared in a manner analogous to Example 13 using Intermediate 46-1 in place of 1-(prop-2-enoyl)piperidin-4-one. MS (ESI) calcd. for $C_{31}H_{30}FN_9O$: 563.26 m/z, found: 564.20 $[M+H]^+$. $^1H$ NMR (400 MHz, DMSO-$d_6$) δ (ppm): 8.41-8.43 (m, 1H), 8.35-8.36 (m, 1H), 7.99-8.04 (m, 2H), 7.81-7.82 (m, 1H), 7.69-7.73 (m, 2H), 7.55-7.56 (m, 1H), 7.41-7.43 (m, 1H), 6.73-6.77 (m, 1H), 6.57-6.58 (m, 1H), 5.11-5.34 (m, 2H), 4.96-4.99 (m, 1H), 4.35-4.39 (m, 1H), 3.97-4.05 (m, 1H), 3.58-3.60 (m, 1H), 3.14-3.27 (m, 2H), 2.82-2.98 (m, 2H), 2.56-2.59 (m, 1H), 2.13-2.28 (m, 3H), 2.52-2.59 (m, 2H). $^{19}F$ NMR (400 MHz, DMSO-$d_6$) δ (ppm): −105.08. (TFA salt).

Intermediate 46-1: 1-(2-fluoroacryloyl)piperidin-4-one

Intermediate 46-1

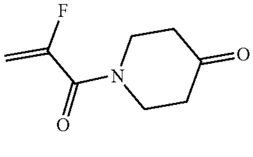

Synthetic Route:

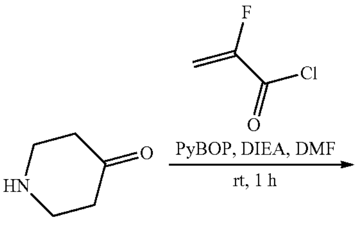

-continued

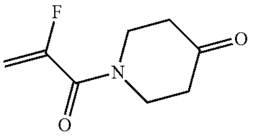

Intermediate 46-1

Step 1: Synthesis of 1-(2-fluoroprop-2-enoyl)piperidin-4-one (Intermediate 46-1

To a solution of piperidin-4-one hydrochloride (200 mg, 2.02 mmol) in DMF (5 mL) was added N,N-diisopropylethylamine (782.3 mg, 6.051 mmol), PyBOP (1049.9 mg, 2.017 mmol) and 2-fluoroprop-2-enoic acid (181.7 mg, 2.017 mmol). The resulting mixture was stirred at room temperature for 1 h. The reaction was quenched with $H_2O$ (20 mL). The resulting mixture was extracted with ethyl acetate (3×20 mL). The organic layers were combined, dried over $Na_2SO_4$, filtered and concentrated to afford 1-(2-fluoroprop-2-enoyl)piperidin-4-one (Intermediate 46-1) (200 mg, 57.91% yield) as a yellow oil. MS (ESI) calcd. for $C_8H_{10}FNO_2$: 171.07 m/z, found 172.20 $[M+H]^+$.

Example 47: N-((1*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)cyclohexyl)acrylamide and Example 48: N-((1*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)cyclohexyl)acrylamide Example 47

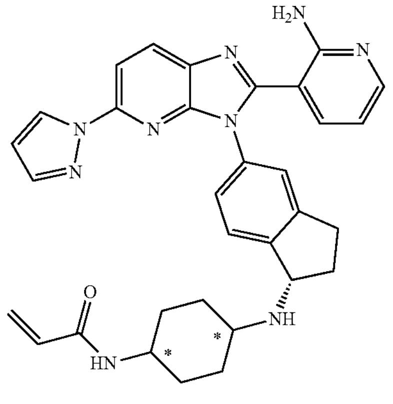

-continued

Example 48

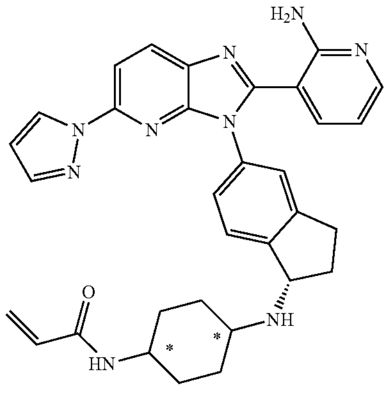

Examples 47 and 48 were prepared in a manner analogous to Example 13 using Intermediate 47-1 in place of the ketone. * Denotes a stereocenter with undetermined absolute stereochemistry of a single diastereomer.

Example 47: MS (ESI) calcd. for $C_{32}H_{33}N_9O$, 559.28 m/z, found 560.20 $[M+H]^+$. $^1H$ NMR (400 MHz, DMSO-$d_6$) δ (ppm): 8.16-8.49 (m, 2H), 7.97-8.12 (m, 1H), 7.89-7.97 (m, 1H), 7.69-7.89 (m, 1H), 7.39-7.61 (m, 1H), 7.31-7.39 (m, 1H), 7.08-7.31 (m, 2H), 6.51-6.68 (m, 1H), 6.39-6.51 (m, 1H), 6.27-6.39 (m, 1H), 5.94-6.27 (m, 1H), 5.48-5.76 (m, 1H), 4.18-4.42 (m, 1H), 3.81-3.85 (m, 2H), 2.95-3.06 (m, 1H), 2.72-2.95 (m, 2H), 2.36-2.49 (m, 1H), 1.51-1.85 (m, 8H).

Example 48: MS (ESI) calcd. for $C_{32}H_{33}N_9O$, 559.28 m/z, found 560.15 $[M+H]^+$. $^1H$ NMR (400 MHz, DMSO-$d_6$) δ (ppm): 8.32-8.41 (m, 2H), 7.97-8.09 (m, 1H), 7.91-7.97 (m, 1H), 7.69-7.89 (m, 1H), 7.41-7.63 (m, 1H), 7.28-7.41 (m, 1H), 7.11-7.28 (m, 2H), 6.51-6.68 (m, 1H), 6.32-6.51 (m, 1H), 6.14-6.32 (m, 1H), 5.94-6.14 (m, 1H), 5.48-5.69 (m, 1H), 4.18-4.42 (m, 1H), 3.39-3.68 (m, 1H), 2.85-3.12 (m, 1H), 2.68-2.85 (m, 1H), 2.55-2.66 (m, 1H), 2.39-2.50 (m, 1H), 1.99-2.15 (m, 1H), 1.88-1.99 (m, 1H), 1.74-1.88 (m, 3H), 1.32-1.05 (m, 4H).

Intermediate 47-1: N-(4-oxocyclohexyl)acrylamide

Intermediate 14-1

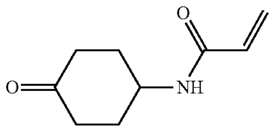

Intermediate 47-1 was prepared in a manner analogous to Intermediate 14-1 using tert-butyl (4-oxocyclohexyl)carbamate in place of tert-butyl 8-oxo-3-azabicyclo[3.2.1]octane-3-carboxylate. MS (ESI) calcd. for $C_9H_{13}NO_2$, 167.20 m/z, found 168.15 $[M+H]^+$.

Example 49: (S)-1-(4-((5-(2-(2-aminopyridin-3-yl)-5-(3-fluoro-1H-pyrazol-1-yl)-3H-imidazo[4,5-b]pyridin-3-yl)-2,3-dihydro-1H-inden-1-yl)amino)piperidin-1-yl)prop-2-en-1-one Example 49

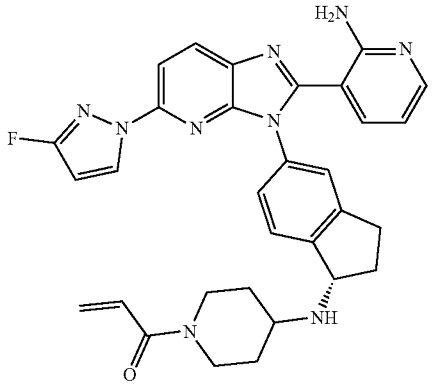

Example 49 was prepared in a manner analogous to Example 13 using Intermediate 49-1 in place of Intermediate 1-1, 1,2-dichloroethane/methanol (1:1) in place of 1,2-dichloroethane and a reaction time and temperature of 2 h at 50° C. instead of 40° C. overnight. MS (ESI) calcd. for $C_{31}H_{30}FN_9O$, 563.26 m/z, found 564.15 $[M+H]^+$. $^1H$ NMR (400 MHz, DMSO-$d_6$) δ (ppm): 8.38-8.52 (m, 1H), 8.22-8.33 (m, 1H), 8.01-8.12 (m, 1H), 7.78-7.88 (m, 1H), 7.62-7.77 (m, 2H), 7.51-7.61 (m, 1H), 7.36-7.47 (m, 1H), 6.66-6.92 (m, 2H), 6.28-6.45 (m, 1H), 6.05-6.20 (m, 1H), 5.61-5.78 (m, 1H), 4.88-5.07 (m, 1H), 4.53 (s, 1H), 4.19 (s, 1H), 3.06-3.25 (m, 2H), 2.85-3.04 (m, 1H), 2.63-2.80 (m, 1H), 2.53-2.62 (m, 1H), 2.42-2.48 (m, 1H), 2.15-2.28 (m, 2H), 2.02-2.14 (m, 1H), 1.38-1.65 (m, 2H). $^{19}F$-NMR (400 MHz, DMSO-$d_6$) δ (ppm): −126.86. (TFA salt).

Intermediate 49-1: (S)-3-(3-(1-amino-2,3-dihydro-1H-inden-5-yl)-5-(3-fluoro-1H-pyrazol-1-yl)-3H-imidazo[4,5-b]pyridin-2-yl)pyridin-2-amine Intermediate 49-1

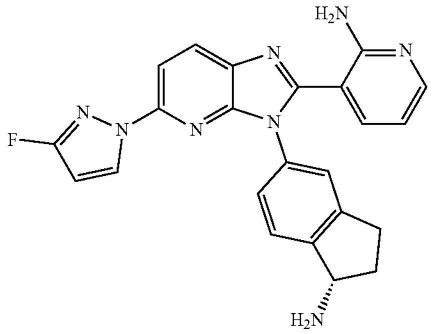

Intermediate 49-1 was prepared in a manner analogous to Intermediate 1-1 using 3-fluoro-1H-pyrazole in place of pyrazole. MS (ESI) calculated for $C_{23}H_{19}FN_8$: 426.17 m/z, found 427.10 $[M+H]^+$.

Example 50: (S)-1-(4-((5-(2-(2-aminopyridin-3-yl)-5-methyl-3H-imidazo[4,5-b]pyridin-3-yl)-2,3-dihydro-1H-inden-1-yl)amino)piperidin-1-yl)prop-2-en-1-one Example 50

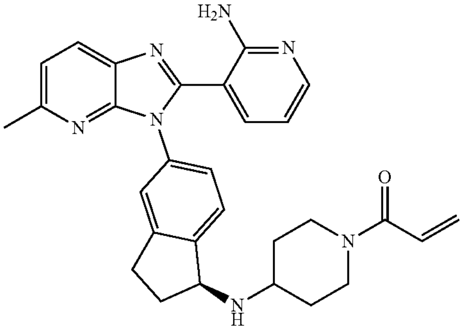

Example 50 was prepared in a manner analogous to Example 13 using Intermediate 50-1 in place of Intermediate 1-1, 1,2-dichloroethane/methanol (10:1) in place of 1,2-dichloroethane and a reaction time and temperature of 8 h at room temperature instead of 40° C. overnight. MS (ESI) calcd. for $C_{29}H_{31}N_7O$: 493.26 m/z, found: 494.05 $[M+H]^+$. $^1H$ NMR (300 MHz, DMSO-$d_6$) δ (ppm): 8.29 (s, 1H), 8.03-8.09 (m, 1H), 7.95-7.98 (m, 1H), 7.52-7.58 (m, 1H), 7.22-7.33 (m, 1H), 7.15-7.21 (m, 3H), 6.75-6.85 (m, 1H), 6.48-6.53 (m, 1H), 6.05-6.15 (m, 1H), 5.65-5.73 (m, 1H), 4.31-4.59 (m, 2H), 4.00-4.10 (m, 1H), 3.08-3.17 (m, 2H), 2.95-3.02 (m, 1H), 2.73-2.86 (m, 2H), 2.45-2.51 (m, 4H), 1.85-2.11 (m, 3H), 1.23-1.40 (m, 2H). (formic acid salt).

Intermediate 50-1: (S)-3-(3-(1-amino-2,3-dihydro-1H-inden-5-yl)-5-methyl-3H-imidazo[4,5-b]pyridin-2-yl)pyridin-2-amine Intermediate 50-1

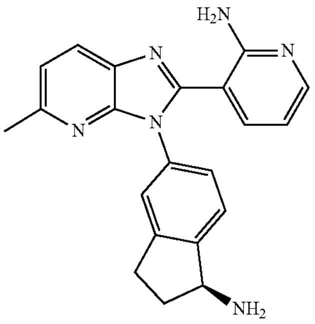

Synthetic Route:

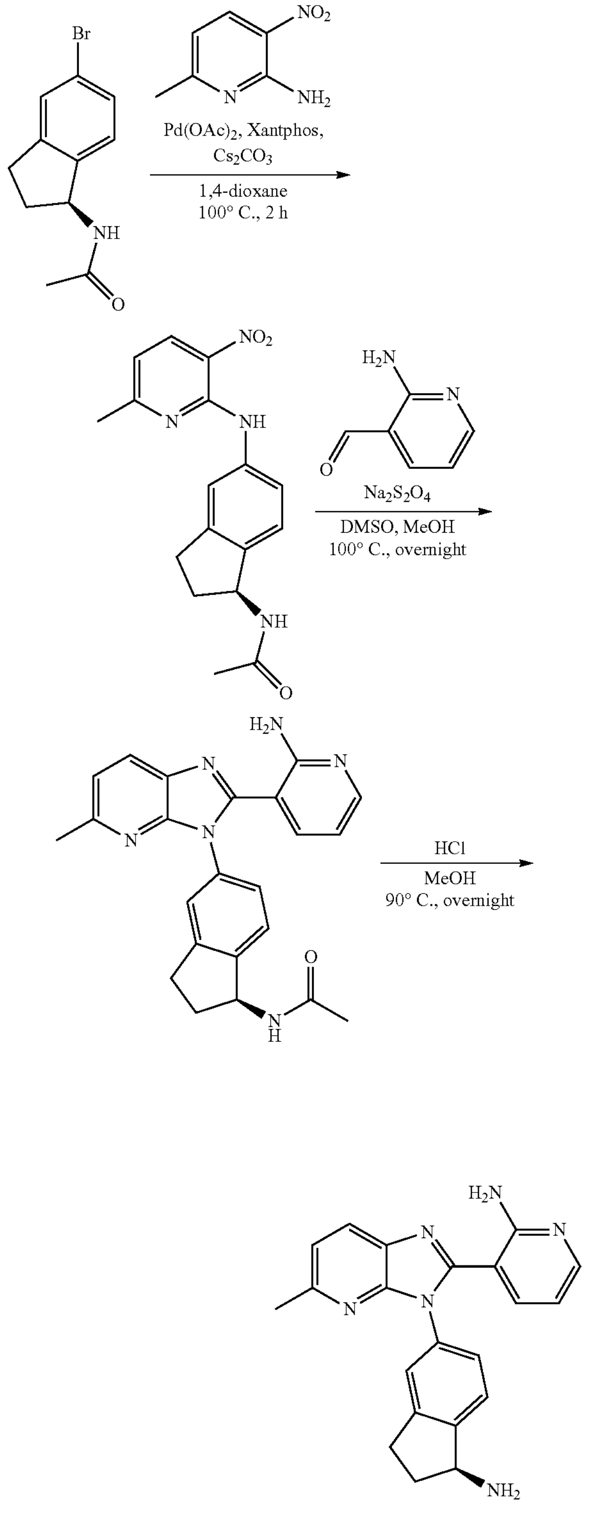

Intermediate 50-1

Step 1: Synthesis of N-[(1S)-5-[(6-methyl-3-nitropyridin-yl)amino]-2,3-dihydro-1H-inden-1-yl]acetamide To a solution of N-[(1S)-5-bromo-2,3-dihydro-1H-inden-1-yl]acetamide (600 mg, 2.36 mmol, 1 equiv), 6-methyl-3-nitropyridin-2-amine (434 mg, 2.8 mmol, 1.2 equiv) and XantPhos (273 mg, 0.47 mmol, 0.2 equiv) in 1,4-dioxane (10 mL) were added cesium carbonate (2.3 g 7.1 mmol, 3 equiv) and $Pd(OAc)_2$ (53 mg, 0.24 mmol, 0.1 equiv). The resulting mixture was stirred at 100° C. for 2 h under nitrogen atmosphere. The resulting mixture was concentrated under reduced pressure. The resulting residue was purified by reverse-phase flash chromatography on C18 silica gel using a 10 to 50% gradient of acetonitrile in water (+0.05% ammonium bicarbonate) to afford N-[(1S)-5-[(6-methyl-3-nitropyridin-2-yl)amino]-2,3-dihydro-1H-inden-1-yl]acetamide (200 mg, 26%) as a brown solid. MS (ESI) calculated for $C_{17}H_{18}N_4O_3$: 326.14 m/z, found 327.05 $[M+H]^+$.

Step 2: Synthesis of N-[(1S)-5-[2-(2-aminopyridin-3-yl)-5-methylimidazo[4,5-b]pyridin-3-yl]-2,3-dihydro-1H-inden-1-yl]acetamide To a solution of N-[(1S)-5-[(6-methyl-3-nitropyridin-2-yl)amino]-2,3-dihydro-1H-inden-1-yl]formamide (190 mg, 0.61 mmol, 1 equiv) in DMSO (5 mL) and methanol (1 mL) were added 2-aminopyridine-3-carbaldehyde (78 mg, 0.64 mmol, 1.1 equiv) and sodium dithionite (223 mg, 1.3 mmol, 2.2 equiv). The resulting mixture was stirred overnight at 100° C. under a nitrogen atmosphere. The resulting mixture was concentrated under reduced pressure and the residue purified by reverse-phase flash chromatography on C18 silica gel using a 10 to 50% gradient of acetonitrile in water (+0.05% ammonium bicarbonate) to afford N-[(1S)-5-[2-(2-aminopyridin-3-yl)-5-methylimidazo[4,5-b]pyridin-3-yl]-2,3-dihydro-1H-inden-1-yl]acetamide (135 mg, 46%) as a yellow solid. MS (ESI) calculated for $C_{23}H_{22}N_6O$: 398.19 m/z, found 399.25 $[M+H]^+$.

Step 3: Synthesis of 3-{3-[(1S)-1-amino-2,3-dihydro-1H-inden-5-yl]-5-methylimidazo[4,5-b]pyridin-2-yl}pyridin-2-amine (Intermediate 50-1

N-[(1S)-5-[2-(2-aminopyridin-3-yl)-5-methylimidazo[4,5-b]pyridin-3-yl]-2,3-dihydro-1H-inden-1-yl]acetamide (135 mg, 0.34 mmol, 1 equiv) was dissolved methanol (10 mL). HCl (10 mL, concentrated) was added, and the resulting mixture was stirred at 90° C. overnight. The resulting mixture was cooled to room temperature and concentrated under reduced pressure to afford 3-{3-[(1S)-1-amino-2,3-dihydro-1H-inden-5-yl]-5-methylimidazo[4,5-b]pyridin-2-yl}pyridin-2-amine (Intermediate 50-1) (100 mg, 75%) as a yellow solid. MS (ESI) calculated for $C_{21}H_{20}N_6$: 356.17 m/z, found 357.15 $[M+H]^+$.

Example 51: 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidine-1-carbonitrile Example 51

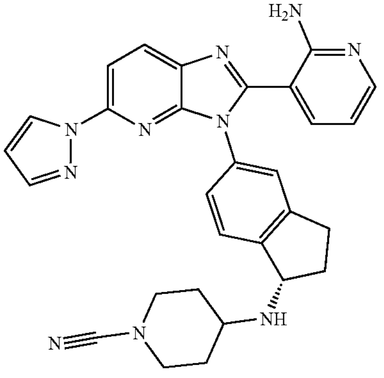

Example 51 was prepared in a manner analogous to Example 13 using 1,2-dichloroethane/methanol (5:1) in place of 1,2-dichloroethane. MS (ESI) calcd. for $C_{29}H_{28}N_{10}$: 516.25 m/z, found: 517.25 $[M+H]^+$. $^1H$-NMR (400 MHz, DMSO-$d_6$) δ (ppm): 8.39-8.48 (m, 1H), 8.32-8.39 (m, 1H), 7.99-8.15 (m, 2H), 7.78-7.85 (m, 2H), 7.68-7.76 (m, 1H), 7.55-7.61 (m, 1H), 7.40-7.48 (m, 1H), 6.76-6.85 (m, 1H), 6.53-6.60 (m, 1H), 4.94-5.05 (m, 1H), 3.40-3.59 (m, 3H), 3.10-3.22 (m, 3H), 2.91-3.05 (m, 1H), 2.55-2.62 (m, 1H), 2.16-2.28 (m, 2H), 2.05-2.15 (m, 1H), 1.68-1.85 (m, 2H). (TFA salt).

Example 52: (S)-N-(2-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-oxoethyl)-N-methylacrylamide Example 52

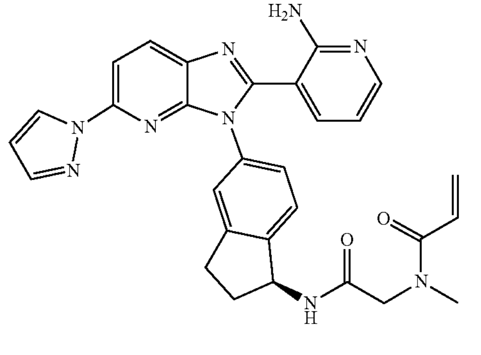

Synthetic Route:

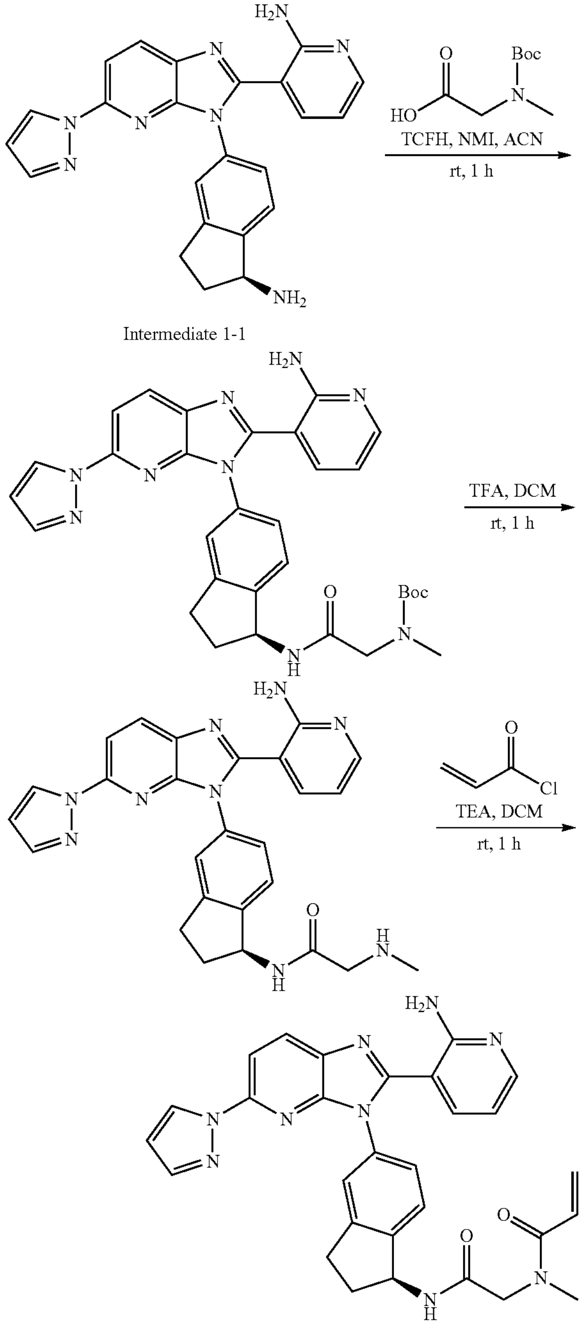

Intermediate 1-1

Example 52

Step 1: Synthesis of tert-butyl (S)-(2-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-oxoethyl)(methyl)carbamate A solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (150 mg, 0.367 mmol), N-(tert-butoxycarbonyl)-N-methylglycine (83.4 mg, 0.440 mmol), TCFH (103 mg, 0.367 mmol) and NMI (120.6 mg, 1.468 mmol) in acetonitrile (3 mL) was stirred for 1 h at room temperature. The crude product was purified by reverse-phase flash column chromatography on C18 silica gel using a gradient of acetonitrile in water (+0.05% $NH_4HCO_3$) to afford tert-butyl (S)-(2-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-oxoethyl)(methyl) carbamate (160 mg, 70% yield) as a yellow solid. MS (ESI) calcd. for $C_{31}H_{33}N_9O_3$, 579.27 m/z, found 580.25 $[M+H]^+$.

Step 2: Synthesis of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(methylamino) acetamide A solution of tert-butyl (S)-(2-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-oxoethyl)(methyl)carbamate (150 mg, 0.259 mmol) in TFA (1.5 mL) and DCM (7.5 mL) was stirred for 1 h at room temperature. The reaction mixture was concentrated to afford (S)-N-(5-(2-(2-aminopyridin-3-yl)-5-(1H-pyrazol-1-yl)-3H-imidazo[4,5-b] pyridin-3-yl)-2,3-dihydro-1H-inden-1-yl)-2-(methylamino) acetamide (120 mg, 85% yield) as a yellow solid. MS (ESI) calcd. for $C_{26}H_{25}N_9O$, 479.22 m/z, found 480.25 $[M+H]^+$.

Step 3: Synthesis of (S)-N-(2-((5-(2-(2-aminopyridin-3-yl)-5-(1H-pyrazol-1-yl)-3H-imidazo[4,5-b] pyridin-3-yl)-2,3-dihydro-1H-inden-1-yl)amino)-2-oxoethyl)-N-methylacrylamide (Example 52

To a stirred solution of (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(methylamino)acetamide (100 mg, 0.209 mmol) and triethylamine (42.2 mg, 0.418 mmol) in DCM (10 mL) was added acryloyl chloride (18.9 mg, 0.209 mmol) dropwise at 0° C. The resulting mixture was stirred for 1 h at room temperature. The reaction was quenched with $H_2O$ (100 mL). The resulting mixture was extracted with DCM (3x200 mL). The combined organic layers were washed with $H_2O$ (200 mL) and dried over anhydrous $Na_2SO_4$. After filtration, the filtrate was concentrated under reduced pressure. The crude product was then purified by Prep-HPLC on a XBridge Prep OBD C18 Column using a gradient of acetonitrile in water (+10 mmol/L $NH_4HCO_3$) to afford (S)-N-(2-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-oxoethyl)-N-methylacrylamide (Example 52) (35.14 mg, 31% yield) as a light yellow solid. MS (ESI) calcd. for $C_{29}H_{27}N_9O_2$, 533.23 m/z, found 534.25 $[M+H]^+$. $^1$H-NMR (400 MHz, DMSO-$d_6$) δ (ppm): 8.26-8.42 (m, 2H), 7.99-8.08 (m, 1H), 7.88-7.98 (m, 1H), 7.81 (s, 1H), 7.18-7.42 (m, 4H), 6.60-6.89 (m, 1H), 6.49-6.59 (m, 1H), 6.38-6.48 (m, 1H), 6.03-6.25 (m, 1H), 5.55-5.78 (m, 1H), 5.28-5.43 (m, 1H), 3.98-4.23 (m, 2H), 3.13 (s, 2H), 2.78-3.03 (m, 3H), 2.35-2.48 (m, 1H), 1.88-2.01 (m, 1H).

Example 53: 1-((*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-1,4-oxazepan-4-yl)prop-2-en-1-one and Example 54: 1-((*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-1,4-oxazepan-4-yl)prop-2-en-1-one Example 53

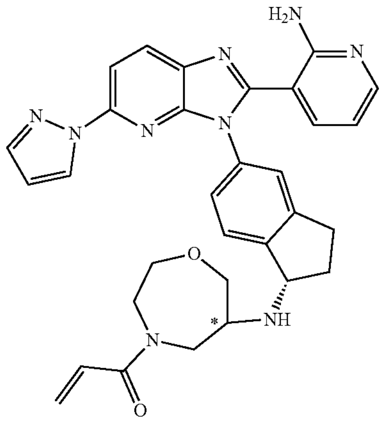

Example 54

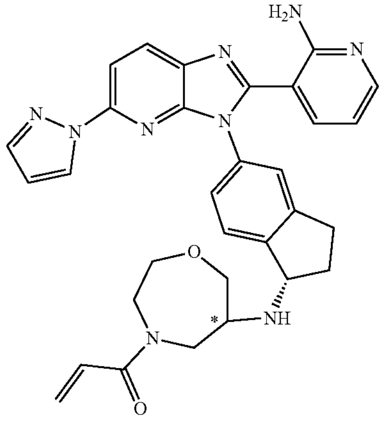

Examples 53 and 54 were prepared in a manner analogous to Example 13 using Intermediate 53-1 in place of the ketone. * Denotes a stereocenter with undetermined absolute stereochemistry of a single diastereomer. The diastereomers were separated by chiral Prep HPLC on CHIRALPAKID-3 column using a mixture of ethanol and [3:1 Hexanes/dichloromethane+0.1% diethylamine].

Example 53: MS (ESI) calcd. for $C_{31}H_{31}N_9O_2$: 561.26 m/z, found: 562.30 $[M+H]^+$. $^1$H-NMR (400 MHz, DMSO-$d_6$) δ (ppm): 8.34-8.38 (m, 2H), 8.01-8.02 (m, 1H), 7.94-8.00 (m, 1H), 7.81 (s, 1H), 7.48-7.50 (m, 1H), 7.33-7.35 (m, 1H), 7.21-7.21 (m, 2H), 6.96-6.97 (m, 2H), 6.77-6.88 (m, 1H), 6.54-6.56 (m, 1H), 6.40-6.43 (m, 1H), 6.14-6.19 (m, 1H), 5.69-5.71 (m, 1H), 4.30-4.32 (m, 1H), 4.12-4.16 (m, 1H), 3.85-3.95 (m, 2H), 3.53-3.74 (m, 6H), 3.05-3.12 (m, 1H), 2.95-3.00 (m, 1H), 2.78-2.82 (m, 1H), 2.45-2.50 (m, 1H), 1.78-1.82 (m, 1H).

Example 54: MS (ESI) calcd. for $C_{31}H_{31}N_9O_2$: 561.26 m/z, found: 562.30 $[M+H]^+$. $^1$H-NMR (400 MHz, DMSO-$d_6$) δ (ppm): 8.36-8.38 (m, 2H), 7.94-8.01 (m, 2H), 7.81 (s, 1H), 7.45-7.48 (m, 1H), 7.34-7.36 (m, 1H), 7.22-7.28 (m, 2H), 6.79-6.97 (m, 3H), 6.54-6.56 (m, 1H), 6.42-6.45 (m, 1H), 6.15-6.20 (m, 1H), 5.69-5.72 (m, 1H), 4.37-4.40 (m, 1H), 3.88-3.98 (m, 1H), 3.65-3.77 (m, 6H), 3.53-3.56 (m, 2H), 3.06-3.07 (m, 1H), 2.95-3.00 (m, 1H), 2.75-2.81 (m, 1H), 2.45-2.50 (m, 1H), 1.76-1.79 (m, 1H).

Intermediate 53-1: 4-acryloyl-1,4-oxazepan-6-one

Intermediate 53-1

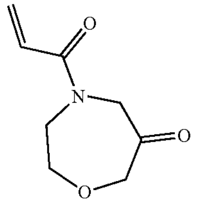

Intermediate 53-1 was prepared in a manner analogous to Intermediate 14-1 using tert-butyl 6-oxo-1,4-oxazepane-4-carboxylate in place of tert-butyl 8-oxo-3-azabicyclo[3.2.1]octane-3-carboxylate and 4N HCl in dioxane in place of TFA/dichloromethane. MS (ESI) calcd. for $C_8H_{11}NO_3$: 169.07 m/z, found: 170.15 $[M+H]^+$.

Example 55: 1-((*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,3-difluoropiperidin-1-yl)prop-2-en-1-one and Example 56: 1-((*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,3-difluoropiperidin-1-yl)prop-2-en-1-one Example 55

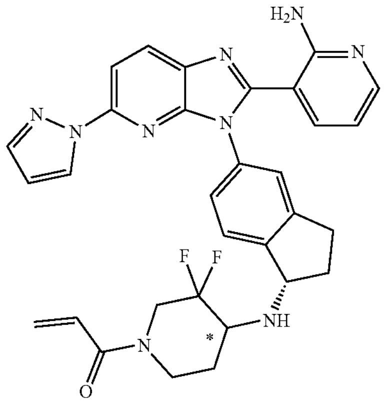

-continued

Example 56

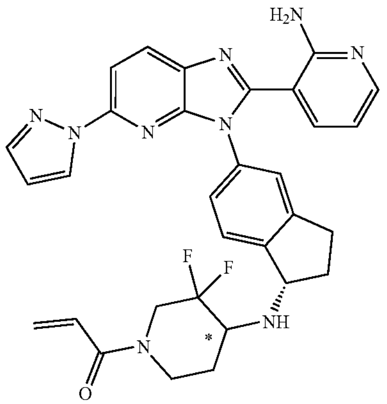

Examples 55 and 56 were prepared in a manner analogous to Example 13 using Intermediate 55-1 in place of the ketone, 1,2-dichloroethane/AcOH (100:1) in place of 1,2-dichloroethane and a reaction time and temperature of room temperature and 8 h instead of 40° C. overnight. * Denotes a stereocenter with undetermined absolute stereochemistry of a single diastereomer. The diastereomers were separated by chiral Prep HPLC on CHIRALPAK IC column using mixture of MTBE in 1:1 ethanol/dichloromethane.

Example 55: MS (ESI) calcd. for $C_{31}H_{29}F_2N_9O$: 581.25 m/z, found: 582.05 $[M+H]^+$. $^1H$ NMR (300 MHz, DMSO-$d_6$) δ (ppm): 8.31-8.38 (m, 2H), 7.99-8.04 (m, 1H), 7.94-7.96 (m, 1H), 7.82-7.86 (m, 1H), 7.51-7.58 (m, 1H), 7.32-7.40 (m, 1H), 7.20-7.29 (m, 2H), 6.95 (s, 2H), 6.82-6.92 (m, 1H), 6.52-6.56 (m, 1H), 6.41-6.47 (m, 1H), 6.10-6.19 (m, 1H), 5.68-5.76 (m, 1H), 4.19-4.31 (m, 2H), 3.89-4.11 (m, 1H), 3.60-3.75 (m, 1H), 3.45-3.56 (m, 1H), 3.12-3.21 (m, 1H), 2.89-2.99 (m, 1H), 2.71-2.82 (m, 1H), 2.34-2.42 (m, 1H), 2.23-2.30 (m, 1H), 1.89-2.01 (m, 1H), 1.73-1.85 (m, 1H), 1.49-1.69 (m, 1H). $^{19}F$-NMR (400 MHz, DMSO-$d_6$) δ (ppm): −107.95, −117.76.

Example 56: MS (ESI) calcd. for $C_{31}H_{29}F_2N_9O$: 581.25 m/z, found: 582.05 $[M+H]^+$. $^1H$ NMR (300 MHz, DMSO-$d_6$) δ (ppm): 8.31-8.38 (m, 2H), 7.99-8.04 (m, 1H), 7.94-7.96 (m, 1H), 7.82-7.86 (m, 1H), 7.51-7.58 (m, 1H), 7.32-7.34 (m, 1H), 7.20-7.29 (m, 2H), 6.95 (s, 2H), 6.82-6.92 (m, 1H), 6.52-6.56 (m, 1H), 6.41-6.47 (m, 1H), 6.10-6.19 (m, 1H), 5.68-5.76 (m, 1H), 4.31-4.41 (m, 1H), 4.19-4.30 (m, 1H), 3.82-3.99 (m, 1H), 3.50-3.76 (m, 1H), 3.41-3.49 (m, 1H), 3.19-3.25 (m, 1H), 2.89-2.97 (m, 1H), 2.72-2.82 (m, 1H), 2.41-2.50 (m, 1H), 2.37-2.42 (m, 1H), 1.78-1.95 (m, 2H), 1.45-1.67 (m, 1H). $^{19}F$-NMR (400 MHz, DMSO-$d_6$) δ (ppm): −107.74, −117.03.

Intermediate 55-1: 1-acryloyl-3,3-difluoropiperidin-4-one

Intermediate 55-1

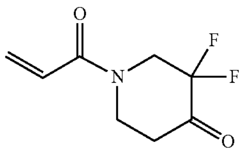

Intermediate 55-1 was prepared in a manner analogous to Intermediate 14-1 using tert-butyl 3,3-difluoro-4-oxopiperidine-1-carboxylate in place of tert-butyl 8-oxo-3-azabicyclo [3.2.1]octane-3-carboxylate and 4N HCl in dioxane in place of TFA/dichloromethane. MS (ESI) calcd. for $C_8H_9F_2NO_2$: 189.06 m/z, found: 190.10 $[M+H]^+$.

Example 57: 1-((*)-3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)pyrrolidin-1-yl)prop-2-en-1-one and Example 58: 1-((*)-3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)pyrrolidin-1-yl)prop-2-en-1-one Example 57

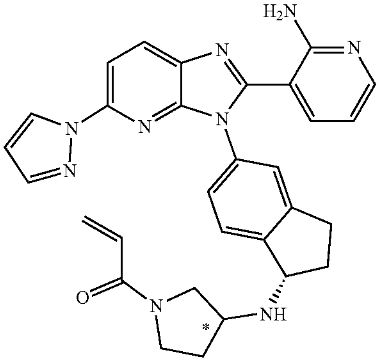

Example 58

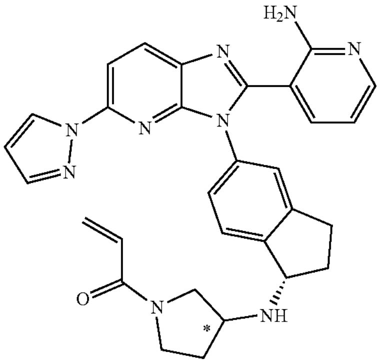

Examples 57 and 58 were prepared in a manner analogous to Example 13 using 1-acryloylpyrrolidin-3-one in place of the ketone and 1,2-dichloroethane/methanol (10:1) in place of 1,2-dichloroethane. * Denotes a stereocenter with undetermined absolute stereochemistry of a single diastereomer. The diastereomers were separated by chiral Prep HPLC on a CHIRAL Cellulose SB column using a mix of tetrahydrofuran and [hexanes+0.1% diethylamine].

Example 57: MS (ESI) calcd. for $C_{30}H_{29}N_9O$: 531.25 m/z, found: 532.30 $[M+H]^+$. $^1H$ NMR (400 MHz, DMSO-$d_6$) δ (ppm): 8.30-8.42 (m, 2H), 8.03-8.10 (m, 1H), 7.91-7.99 (m, 1H), 7.78-7.85 (m, 1H), 7.46-7.55 (m, 1H), 7.29-7.35 (m, 1H), 7.19-7.28 (m, 2H), 6.51-6.68 (m, 2H), 6.43-6.50 (m, 1H), 6.13-6.25 (m, 1H), 5.68-5.79 (m, 1H), 4.20-4.31 (m, 1H), 3.80-3.90 (m, 1H), 3.21-3.79 (m, 4H), 2.91-3.05 (m, 1H), 2.73-2.89 (m, 1H), 2.40-2.53 (m, 1H), 2.05-2.20 (m, 1H), 1.70-1.90 (m, 2H).

Example 58: MS (ESI) calcd. for $C_{30}H_{29}N_9O$: 531.25 m/z, found: 532.25 $[M+H]^+$. $^1H$ NMR (400 MHz, DMSO-$d_6$) δ (ppm): 8.29-8.37 (m, 2H), 7.98-8.02 (m, 1H), 7.88-7.97 (m, 1H), 7.75-7.82 (m, 1H), 7.43-7.50 (m, 1H), 7.26-7.32 (m, 1H), 7.18-7.25 (m, 2H), 6.48-6.63 (m, 2H), 6.38-6.47 (m, 1H), 6.08-6.16 (m, 1H), 5.61-5.71 (m, 1H), 4.20-4.29 (m, 1H), 3.48-3.62 (m, 2H), 3.40-3.47 (m, 1H), 3.25-3.39 (m, 1H), 3.13-3.22 (m, 1H), 2.90-3.00 (m, 1H), 2.70-2.81 (m, 1H), 2.35-2.48 (m, 1H), 1.99-2.18 (m, 1H), 1.70-1.91 (m, 2H).

Example 59: 1-((1R,5S,6*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-azabicyclo[3.1.1]heptan-3-yl)prop-2-en-1-one and Example 60: 1-((1R,5S,6*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-azabicyclo[3.1.1]heptan-3-yl)prop-2-en-1-one Example 59

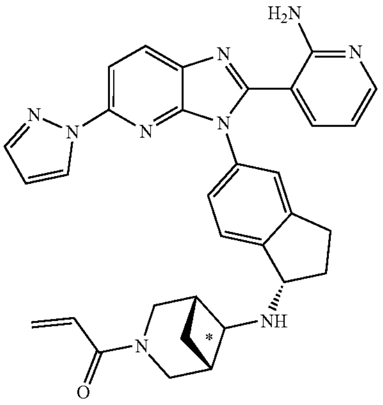

Example 60

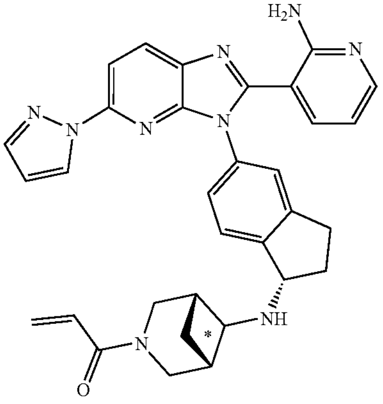

Examples 59 and 60 were prepared in a manner analogous to Example 13 using Intermediate 59-1 in place of the ketone and a reaction time and temperature of 1 h at room temperature instead of overnight at 40° C. * Denotes a stereocenter with undetermined absolute stereochemistry of a single diastereomer.

Example 59: MS (ESI) calcd. for $C_{32}H_{31}N_9O$: 557.27 m/z, found: 558.20 $[M+H]^+$. $^1H$ NMR (300 MHz, DMSO-$d_6$) δ (ppm): 8.28-8.29 (m, 2H), 7.90-7.94 (m, 2H), 7.88-7.89 (m, 1H), 7.41-7.42 (m, 1H), 7.22-7.23 (m, 3H), 6.62-6.69 (m, 1H), 6.50-6.51 (m, 1H), 6.42-6.43 (m, 1H), 6.09-6.13 (m, 1H), 5.66-5.68 (m, 1H), 4.41-4.46 (m, 1H), 4.19-4.20 (m, 1H), 3.67-3.71 (m, 2H), 3.48-3.50 (m, 2H), 3.15-3.16 (m, 1H), 2.89-2.90 (m, 1H), 2.73-2.74 (m, 1H), 2.46-2.51 (m, 1H), 2.30-2.31 (m, 2H), 1.72-1.73 (m, 2H), 1.17-1.19 (m, 1H).

Example 60: MS (ESI) calcd. for $C_{32}H_{31}N_9O$: 557.27 m/z, found: 558.20 $[M+H]^+$. $^1H$ NMR (400 MHz, DMSO-$d_6$) δ (ppm): 8.31-8.33 (m, 2H), 7.95-7.96 (m, 1H), 7.93-7.94 (m, 1H), 7.77-7.78 (m, 1H), 7.53-7.55 (m, 1H), 7.36-7.37 (m, 1H), 7.23-7.24 (m, 2H), 6.66-6.67 (m, 1H), 6.53-6.54 (m, 1H), 6.42-6.45 (m, 1H) 6.13-6.18 (m, 1H), 5.71-5.74 (m, 1H), 4.48-4.49 (m, 1H), 3.98-4.00 (m, 1H), 3.86-3.67 (m, 1H), 3.77-3.79 (m, 1H), 3.48-3.68 (m, 1H), 3.00-3.05 (m, 2H), 2.79-2.83 (m, 1H), 2.63-2.68 (m, 1H), 2.50-2.51 (m, 3H), 1.99-2.08 (m, 1H), 1.30-1.31 (m, 1H).

Intermediate 59-1: 3-acryloyl-3-azabicyclo[3.1.1]heptan-6-one

Intermediate 59-1

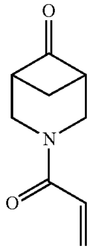

Intermediate 59-1 was prepared in a manner analogous to Intermediate 14-1 using tert-butyl 6-oxo-3-azabicyclo[3.1.1]heptane-3-carboxylate in place of tert-butyl 8-oxo-3-azabicyclo[3.2.1]octane-3-carboxylate. MS (ESI) calcd. for $C_9H_{11}NO_2$: 165.08 m/z, found 166.10 $[M+H]^+$.

Example 61: 3-{3-[(1S)-1-{[1-(ethenesulfonyl)piperidin-4-yl]amino}-2,3-dihydro-1H-inden-5-yl]-5-(pyrazol-1-yl)imidazo[4,5-b]pyridin-2-yl}pyridin-2-amine Example 61

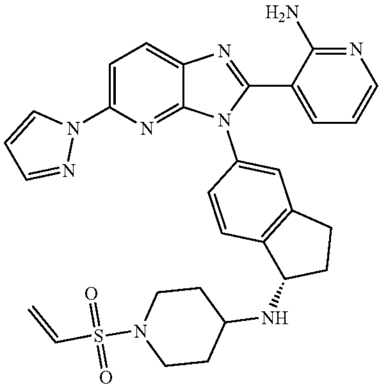

Example 61 was prepared in a manner analogous to Example 13 using Intermediate 61-1 in place of the ketone. MS (ESI) calcd. for $C_{30}H_{31}N_9O_2S$: 581.23 m/z, found: 582.20 $[M+H]^+$. $^1H$ NMR (400 MHz, DMSO-$d_6$) δ (ppm): 8.42-8.49 (m, 1H), 8.35-8.41 (m, 1H), 8.01-8.12 (m, 2H), 7.82-7.89 (m, 1H), 7.71-7.80 (m, 2H), 7.58-7.63 (m, 1H), 7.45-7.50 (m, 1H), 6.75-6.85 (m, 2H), 6.58-6.65 (m, 1H), 6.13-6.25 (m, 2H), 4.95-5.05 (m, 1H), 3.65-3.72 (m, 2H), 3.40-3.51 (m, 1H), 3.15-3.25 (m, 1H), 2.95-3.05 (m, 1H), 2.75-2.85 (m, 2H), 2.51-2.65 (m, 1H), 2.15-2.35 (m, 3H), 1.65-1.80 (m, 2H).

Intermediate 61-1: 1-(vinylsulfonyl)piperidin-4-one

Intermediate 61-1

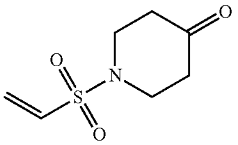

Intermediate 61-1 was prepared in a manner analogous to Intermediate 14-1 (starting from step 2) using 4-piperidinone in place of the ketone and ethenesulfonyl chloride in place of acryloyl chloride. MS (ESI) calcd. for $C_7H_{11}NO_3S$: 189.05 m/z, found: 190.10 $[M+H]^+$.

Example 62: 1-((2R,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one and Example 63: 1-((2R,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one Example 62

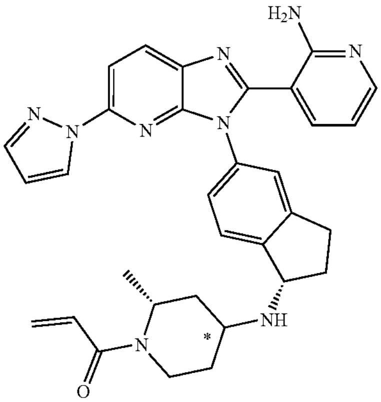

Example 63

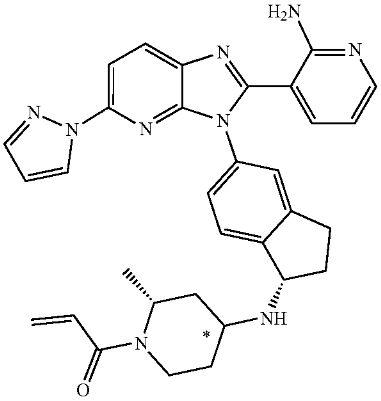

Examples 62 and 63 were prepared in a manner analogous to Example 13 using Intermediate 62-1 in place of the ketone. * Denotes a stereocenter with undetermined absolute stereochemistry of a single diastereomer.

Example 62: MS (ESI) calcd. for $C_{32}H_{33}N_9O$, 559.28 m/z, found 560.15 $[M+H]^+$. $^1$H NMR (400 MHz, DMSO-$d_6$) δ (ppm): 8.34-8.36 (m, 2H), 8.00-8.01 (m, 1H), 7.98-7.99 (m, 1H), 7.80-7.81 (m, 1H), 7.45-7.47 (m, 1H), 7.23-7.24 (m, 1H), 7.21-7.22 (m, 2H), 6.79-6.82 (m, 1H), 6.54-6.55 (m, 1H), 6.43-6.44 (m, 1H), 6.04-6.08 (m, 1H), 5.64-5.67 (m, 1H), 4.33-4.35 (m, 2H), 3.90-4.10 (m, 1H), 3.30-3.40 (m, 1H), 3.08-3.15 (m, 1H), 2.89-2.98 (m, 1H), 2.72-2.81 (m, 1H), 2.41-2.49 (m, 1H), 2.71-2.81 (m, 4H), 2.58-2.63 (m, 1H), 1.35-1.45 (m, 3H).

Example 63: MS (ESI) calcd. for $C_{32}H_{33}N_9O$, 559.28 m/z, found 560.20 $[M+H]^+$. $^1$H NMR (400 MHz, DMSO-$d_6$) δ (ppm): 8.34-8.36 (m, 2H), 8.00-8.01 (m, 1H), 7.98-7.99 (m, 1H), 7.80-7.81 (m, 1H), 7.45-7.47 (m, 1H), 7.23-7.24 (m, 1H), 7.21-7.22 (m, 2H), 6.79-6.82 (m, 1H), 6.54-6.55 (m, 1H), 6.43-6.44 (m, 1H), 6.04-6.08 (m, 1H), 5.64-5.67 (m, 1H), 3.90-4.90 (m, 3H), 2.70-3.12 (m, 4H), 2.50-2.51 (m, 1H), 2.04-2.07 (m, 1H), 1.80-1.82 (m, 2H), 1.32-1.42 (m, 1H), 1.10-1.21 (m, 4H).

Intermediate 62-1: (R)-1-acryloyl-2-methylpiperidin-4-one

Intermediate 62-1

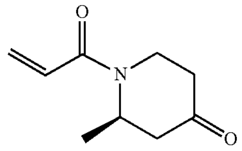

Intermediate 62-1 was prepared in a manner analogous to Intermediate 14-1 using tert-butyl (R)-2-methyl-4-oxopiperidine-1-carboxylate in place of tert-butyl 8-oxo-3-azabicyclo[3.2.1]octane-3-carboxylate. MS (ESI) calcd. for $C_9H_{13}NO_2$, 167.09 m/z, found 168.15 $[M+H]^+$.

Example 64: 1-(9-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-oxa-7-azabicyclo[3.3.1]nonan-7-yl)prop-2-en-1-one (mix of diastereomers Example 64

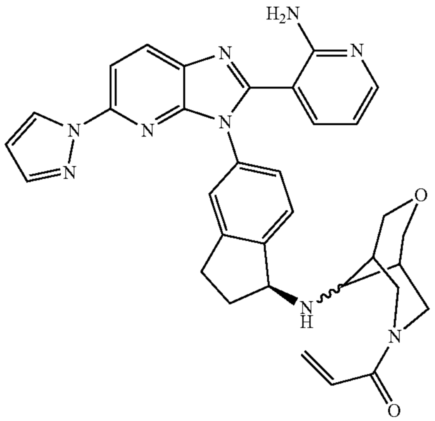

Example 64 was prepared in a manner analogous to Example 14 (via Intermediate 14-1) starting from tert-butyl 9-oxo-3-oxa-7-azabicyclo[3.3.1]nonane-7-carboxylate instead of tert-butyl 8-oxo-3-azabicyclo[3.2.1]octane-3-carboxylate. MS (ESI) calcd. for $C_{33}H_{33}N_9O_2$: 587.28 m/z, found: 588.20 $[M+H]^+$. $^1$H NMR (400 MHz, DMSO-$d_6$) δ (ppm): 8.35-8.39 (m, 2H), 8.02-8.04 (m, 1H), 7.95-8.01 (m, 1H), 7.83-7.85 (m, 1H), 7.66-7.80 (m, 1H), 7.41-7.56 (s, 1H), 7.29-7.38 (m, 2H), 6.80-6.89 (m, 1H), 6.51-6.61 (m, 1H), 6.43-6.50 (m, 1H), 6.03-6.09 (m, 1H), 5.64-5.68 (m, 1H), 4.67-4.81 (m, 1H), 4.28-4.46 (m, 1H), 3.56-4.20 (m, 5H), 3.42-3.49 (m, 1H), 3.25-3.40 (m, 1H), 2.92-3.10 (m, 3H), 2.54-2.65 (m, 1H) 1.78-2.29 (m, 3H). (formic acid salt).

Example 65: 1-((2S,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one and Example 66: 1-((2S,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one Example 65

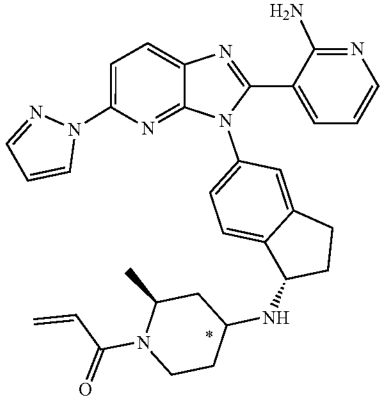

Example 66

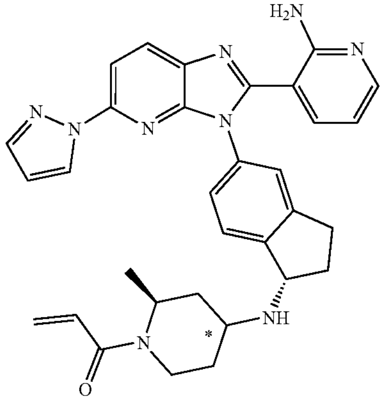

Examples 65 and 66 were prepared in a manner analogous to Example 14 (via Intermediate 14-1) starting from tert-butyl (S)-2-methyl-4-oxopiperidine-1-carboxylate instead of tert-butyl 8-oxo-3-azabicyclo[3.2.1]octane-3-carboxylate and using 1,2-dichloroethane/methanol (10:1) for 2 h at 50° C. instead of 1,2-dichloroethane overnight at 40° C. * Denotes a stereocenter with undetermined absolute stereochemistry of a single diastereomer.

Example 65: MS (ESI) calcd. for $C_{32}H_{33}N_9O$, 559.28 m/z, found 560.30[M+H]$^+$. $^1$H NMR (400 MHz, DMSO-$d_6$) δ (ppm): 8.34-8.35 (m, 2H), 8.01-8.02 (m, 1H), 7.93-7.95 (m, 1H), 7.85-7.87 (m, 1H), 7.51-7.53 (m, 1H), 7.07-7.30 (m, 3H), 6.54-6.56 (m, 1H), 6.44-6.47 (m, 1H), 6.30-6.40 (m, 1H), 6.00-6.29 (m, 1H), 5.67-5.69 (m, 1H), 4.00-5.00 (m, 3H), 3.10-3.40 (m, 2H), 3.00-3.02 (m, 1H), 2.94-3.00 (m, 1H), 2.50-2.52 (m, 1H), 2.10-2.20 (m, 1H), 1.80-2.00 (m, 3H), 1.50-1.60 (m, 1H), 1.00-1.30 (m, 4H).

Example 66: MS (ESI) calcd. for $C_{32}H_{33}N_9O$, 559.28 m/z, found 560.25 [M+H]$^+$. $^1$H NMR (400 MHz, DMSO-$d_6$) δ (ppm): 8.34-8.35 (m, 2H), 7.90-8.10 (m, 2H), 7.85-7.87 (m, 1H), 7.40-7.50 (m, 1H), 7.10-7.30 (m, 3H), 6.70-6.90 (m, 1H), 6.44-6.47 (m, 1H), 6.30-6.40 (m, 1H), 6.00-6.29 (m, 1H), 5.67-5.69 (m, 1H), 4.20-4.50 (m, 2H), 3.80-4.10 (m, 1H), 3.30-3.40 (m, 1H), 3.08-3.20 (m, 1H), 2.90-3.00 (m, 1H), 2.70-2.80 (m, 1H), 2.50-2.52 (m, 1H), 1.80-1.90 (m, 1H), 1.60-1.78 (m, 4H), 1.40-1.50 (m, 3H).

-continued

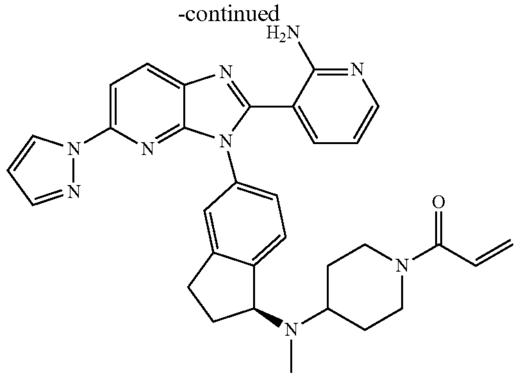

Example 67

Example 67: (S)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)(methyl)amino)piperidin-1-yl)prop-2-en-1-one Example 67

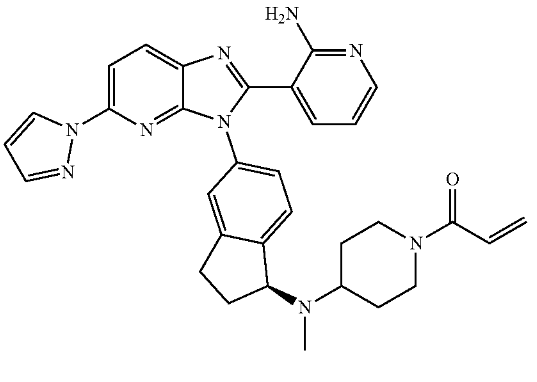

Synthetic Route:

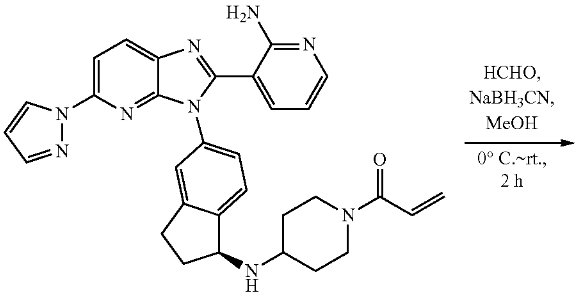

Example 13

Step 1: Synthesis of (S)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)(methyl)amino)piperidin-1-yl)prop-2-en-1-one (Example 67)

To a cooled (0° C.) solution of 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)prop-2-en-1-one (Example 13) (100 mg, 0.183 mmol) in MeOH (5.0 mL) was added HCHO (36.0 mg, 1.20 mmol) and $NaBH_3CN$ (34.6 mg, 0.549 mmol). The mixture was stirred at room temperature for 2 h. The reaction mixture was purified by reverse-phase flash column chromatography on C18 silica gel using a gradient of acetonitrile in water (+0.1% formic acid) to afford (S)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)(methyl)amino)piperidin-1-yl)prop-2-en-1-one (Example 67, formic acid salt) as an off-white solid (69.0 mg, 67% yield). MS (ESI) calcd. for $C_{32}H_{33}N_9O$, 559.28 m/z, found: 560.20 [M+H]$^+$. $^1$H NMR (400 MHz, DMSO-$d_6$) δ (ppm): 8.34-8.37 (m, 2H), 8.14-8.17 (m, 1H), 7.99-8.01 (m, 1H), 7.94-7.99 (m, 1H), 7.81-7.82 (m, 1H), 7.36-7.37 (m, 2H), 7.26-7.26 (m, 1H), 7.16-7.18 (m, 1H), 7.03 (s, 2H), 6.80-6.82 (m, 1H), 6.53-6.54 (m, 1H), 6.36-6.39 (m, 1H), 6.07-6.12 (m, 1H), 5.65-5.69 (m, 1H), 4.60-4.64 (m, 1H), 4.43-4.44 (m, 1H), 4.08-4.10 (m, 1H), 3.09-3.16 (m, 1H), 2.80-2.90 (m, 3H), 2.70-2.80 (m, 1H), 2.09-2.11 (m, 4H), 1.93-1.96 (m, 1H), 1.79-1.82 (m, 1H), 1.36-1.65 (m, 2H). (formic acid salt).

Example 68: 1-[4-({[(1S)-5-[2-(2-aminopyridin-3-yl)-5-(pyrazol-1-yl)imidazo[4,5-b]pyridin-3-yl]-2,3-dihydro-1H-inden-1-yl]amino}methyl)piperidin-1-yl]prop-2-en-1-one Example 68

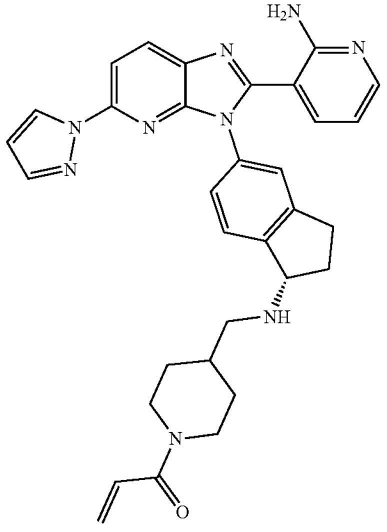

Example 68 was prepared in a manner analogous to Example 14 (via Intermediate 14-1) starting from tert-butyl 4-formylpiperidine-1-carboxylate instead of tert-butyl 8-oxo-3-azabicyclo[3.2.1]octane-3-carboxylate and using 4N HCl in dioxane instead of TFA in dichloromethane. MS (ESI) calcd. for $C_{32}H_{33}N_9O$, 559.28 m/z, found 560.15 $[M+H]^+$. $^1H$ NMR (400 MHz, DMSO-$d_6$) δ ppm: 8.39-8.56 (m, 1H), 8.26-8.39 (m, 1H), 7.98-8.07 (m, 2H), 7.78-7.82 (m, 1H), 7.69-7.75 (m, 2H), 7.50-7.52 (m, 1H), 7.40-7.42 (m, 1H), 6.69-6.82 (m, 2H), 6.64-6.95 (m, 1H), 6.02-6.16 (m, 1H), 5.62-5.75 (m, 1H), 4.85-4.96 (m, 1H), 4.31-4.49 (m, 1H), 4.01-4.12 (m, 1H), 2.85-3.21 (m, 5H), 2.60-2.70 (m, 1H), 2.51-2.60 (m, 1H), 2.16-2.29 (m, 1H), 1.89-2.03 (m, 1H), 1.72-1.89 (m, 2H), 1.06-1.21 (m, 2H). (TFA salt).

Example 69: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)but-2-yn-1-one Example 69

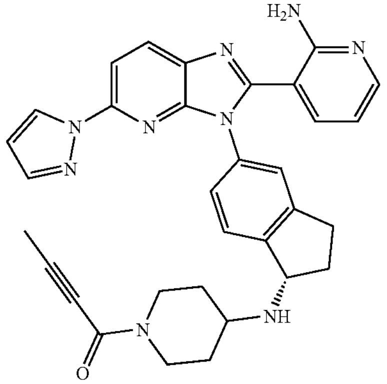

Example 69 was prepared in a manner analogous to Example 14 (via Intermediate 14-1) starting from 4-piperidinone (at step 2 of Intermediate 14-1) in place of 3-azabicyclo[3.2.1]octan-8-one and using but-2-ynoyl chloride instead of acryloyl chloride. MS (ESI) calcd. for $C_{32}H_{31}N_9O$: 557.27 m/z, found 558.20 $[M+H]^+$. $^1H$ NMR (400 MHz, DMSO-$d_6$) δ (ppm): 8.42-8.44 (m, 1H), 8.36-8.37 (m, 1H), 8.07-8.09 (m, 1H), 8.00-8.01 (m, 1H), 7.72-7.74 (m, 1H), 7.63-7.65 (m, 1H), 7.59-7.61 (m, 2H), 7.43-7.45 (m, 1H), 6.68-6.69 (m, 1H), 6.58-6.59 (m, 1H), 5.00-5.05 (m, 1H), 4.35-4.44 (m, 2H), 3.22-3.26 (m, 2H), 2.93-3.01 (m, 1H), 2.74-2.80 (m, 1H), 2.60-2.67 (m, 1H), 2.50-2.55 (m, 1H), 2.22-2.29 (m, 3H), 2.00-2.10 (m, 3H), 1.30-1.60 (m, 2H). (TFA salt).

Example 70: N-[(1S)-5-[2-(2-aminopyridin-3-yl)-5-(pyrazol-1-yl)imidazo[4,5-b]pyridin-3-yl]-2,3-dihydro-1H-inden-1-yl]-4-hydroxy-2-(prop-2-enamido)benzamide Example 70

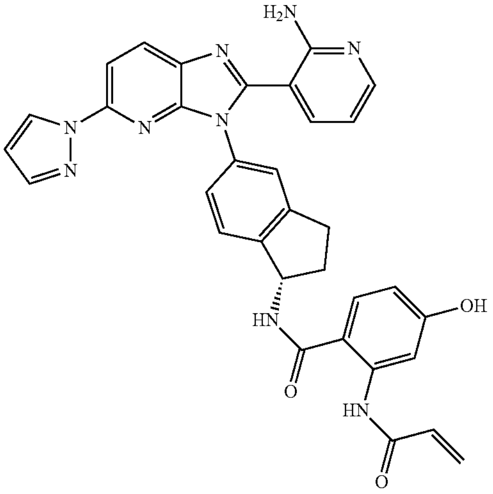

Example 70 was prepared in a manner analogous to Example 3 (starting from Step 2) using 2-amino-4-hydroxybenzoic acid in place of 2,3-dihydro-1H-indole-4-carboxylic acid. MS (ESI) calcd. for $C_{33}H_{27}N_9O_3$: 597.22 m/z, found: 598.20 $[M+H]^+$. $^1H$ NMR (400 MHz, DMSO-$d_6$) δ (ppm): 8.41-8.43 (m, 1H), 8.36-8.37 (m, 1H), 8.05-8.07 (m, 2H), 8.01-8.04 (m, 1H), 7.72-7.82 (m, 3H), 7.42-7.44 (m, 1H), 7.39-7.41 (m, 1H), 7.31-7.34 (m, 1H), 6.76-6.79 (m, 1H), 6.53-6.57 (m, 2H), 6.22-6.27 (m, 2H), 5.82-5.85 (m, 1H), 5.59-5.63 (m, 1H), 3.03-3.08 (m, 1H), 2.86-2.92 (m, 1H), 2.50-2.52 (m, 1H), 2.05-2.13 (m, 1H).

Example 71: N-[(1S)-5-[2-(2-aminopyridin-3-yl)-5-(pyrazol-1-yl)imidazo[4,5-b]pyridin-3-yl]-2,3-dihydro-1H-inden-1-yl]-2-(prop-2-enamidomethyl) benzamide Example 71

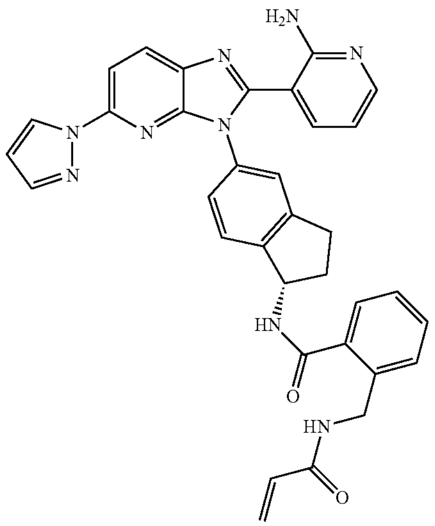

Example 71 was prepare in a manner analogous to Example 2 (via Intermediate 2-1) using 2-{[(tert-butoxycarbonyl) amino]methyl}benzoic acid in place of 3-((tert-butoxycarbonyl)amino)benzoic acid, 4N HCl in dioxane in place of TFA in dichloromethane and acetonitrile instead of dichloromethane for the final step. MS (ESI) calcd. for $C_{34}H_{29}N_9O_2$: 595.24 m/z, found: 596.10 $[M+H]^+$. $^1$H NMR (300 MHz, DMSO-$d_6$) δ (ppm): 8.95-9.01 (m, 111), 8.57-8.61 (m, 1H), 8.30-8.39 (m, 2H), 7.92-8.07 (m, 2H), 7.80 (s, 1H), 7.41-7.55 (m, 2H), 7.30-7.40 (m, 2H), 7.23-7.29 (m, 2H), 6.54 (s, 1H), 6.40-6.48 (m, 1H), 6.27-6.38 (m, 1H), 6.08-6.18 (m, 1H), 5.52-5.65 (m, 2H), 4.42-4.59 (m, 2H), 3.91-4.07 (m, 2H), 2.83-3.07 (m, 2H), 2.57-2.63 (m, 1H), 1.98-2.11 (m, 1H). (formic acid salt).

Example 72: 1-((1R,5S,9*)-9-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-oxa-7-azabicyclo[3.3.1]nonan-7-yl)prop-2-en-1-one and Example 73: 1-((1R,5S,9*)-9-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-oxa-7-azabicyclo[3.3.1]nonan-7-yl)prop-2-en-1-one Example 72

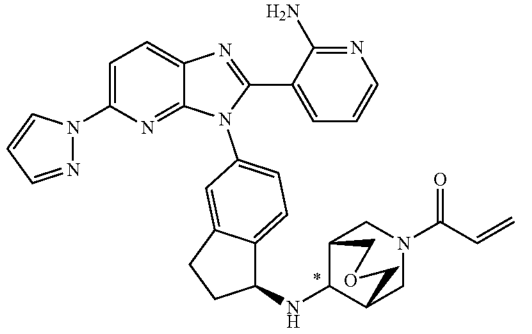

-continued

Example 73

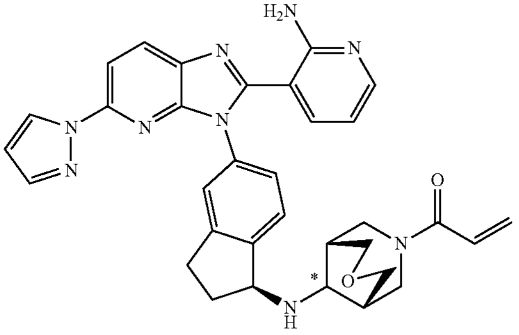

The diastereomers of Example 64 were separated by chiral Prep-HPLC on a CHIRALPAK-SB column using a mixture of [3:1 hexanes/dichloromethane (+0.5% 2M ammonia in methanol)] and ethanol to afford Examples 72 and 73. * Denotes a stereocenter with undetermined absolute stereochemistry of a single diastereomer.

Example 72: MS (ESI) calcd. for $C_{33}H_{33}N_9O_2$, 587.28 m/z, found 588.15 $[M+H]^+$. $^1$H NMR (400 MHz, DMSO-$d_6$) δ ppm: 8.22-8.49 (m, 2H), 7.96-8.15 (m, 1H), 7.89-7.96 (m, 1H), 7.70-7.89 (m, 1H), 7.45-7.69 (m, 1H), 7.33-7.45 (m, 1H), 7.14-7.33 (m, 2H), 6.65-6.97 (m, 1H), 6.55-6.65 (m, 1H), 6.35-6.55 (m, 1H), 5.98-6.18 (m, 1H), 5.56-5.80 (m, 1H), 4.52-4.82 (m, 1H), 4.22-4.42 (m, 2H), 4.08-4.42 (m, 2H), 3.47-3.75 (m, 2H), 3.29-3.47 (m, 1H), 3.09-3.29 (m, 1H), 2.88-3.09 (m, 2H), 2.68-2.88 (m, 1H), 2.42-2.52 (m, 1H), 1.72-1.95 (m, 2H), 1.62-1.72 (m, 1H).

Example 73: MS (ESI) calcd. for $C_{33}H_{33}N_9O_2$, 587.28 m/z, found 588.20 $[M+H]^+$. $^1$H NMR (400 MHz, DMSO-$d_6$) δ ppm: 8.22-8.49 (m, 2H), 7.96-8.15 (m, 1H), 7.89-7.96 (m, 1H), 7.70-7.89 (m, 1H), 7.41-7.65 (m, 1H), 7.31-7.41 (m, 1H), 7.12-7.31 (m, 2H), 6.65-6.97 (m, 1H), 6.51-6.65 (m, 1H), 6.35-6.51 (m, 1H), 5.98-6.18 (m, 1H), 5.56-5.80 (m, 1H), 4.18-4.42 (m, 2H), 3.96-4.08 (m, 1H), 3.75-4.02 (m, 3H), 3.41-3.71 (m, 2H), 3.24-3.41 (m, 1H), 3.09-3.24 (m, 1H), 2.88-3.09 (m, 1H), 2.68-2.88 (m, 1H), 2.38-2.52 (m, 1H), 1.93-2.06 (m, 1H), 1.62-1.93 (m, 2H).

Example 74: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl](2-methoxyethyl) amino}piperidin-1-yl)prop-2-en-1-one Example 74

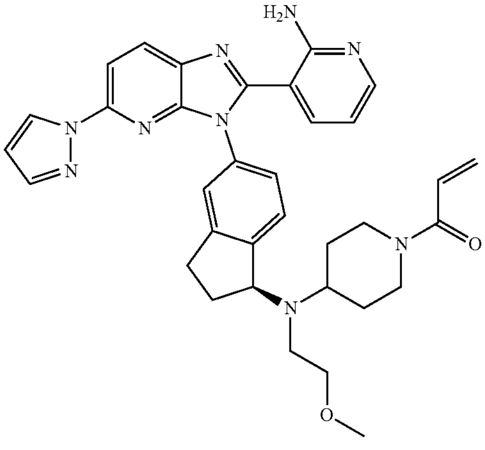

Synthetic Route:

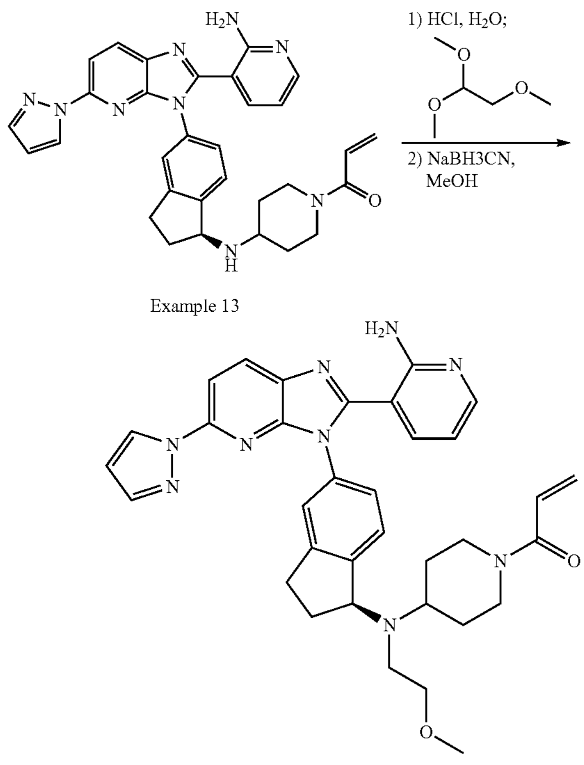

Example 13

Example 74

Step 1: Synthesis of 1-(4-{[(1S)-5-[2-(2-aminopyridin-3-yl)-5-(pyrazol-1-yl)imidazo[4,5-b]pyridin-3-yl]-2,3-dihydro-1H-inden-1-yl](2-methoxyethyl)amino}piperidin-1-yl)prop-2-en-1-one (Example 74)

A stirred solution of 1,1,2-trimethoxyethane (2.00 g, 16.6 mmol) in 1N aqueous HCl was heated to 55° C. for 4 hours. The reaction mixture was cooled to room temperature and saturated with NaCl. The reaction was extracted with DCM (5×30 mL). The combined organic layers were dried over sodium sulfate, filtered, and evaporated under vacuum at below 25° C. to afford crude methoxy-acetaldehyde as a light yellow oil. The aldehyde (135.76 mg, 1.835 mmol) was added to a cooled (0° C.) solution of 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)prop-2-en-1-one (Example 13) (200 mg, 0.367 mmol) in MeOH (5 mL) followed by $NaBH_3CN$ (46.1 mg, 0.734 mmol). The resulting mixture was stirred overnight at room temperature then the reaction was quenched with 5 mL water. The mixture was concentrated in vacuo and the residue was purified directly by Prep-HPLC on a XSelect CSH Fluoro Phenyl column using a gradient of acetonitrile in water (+10 mmol/L ammonium bicarbonate) to afford 1-(4-{[(1S)-5-[2-(2-aminopyridin-3-yl)-5-(pyrazol-1-yl)imidazo[4,5-b]pyridin-3-yl]-2,3-dihydro-1H-inden-1-yl](2-methoxyethyl)amino}piperidin-1-yl)prop-2-en-1-one (Example 74) (35.2 mg, 15.4 yield) as a white solid. MS (ESI) calcd. for $C_{34}H_{37}N_9O_2$: 603.31 m/z, found 604.35 $[M+H]^+$. $^1$H NMR (400 MHz, DMSO-$d_6$) δ (ppm): 8.23-8.35 (m, 2H), 7.91-8.02 (m, 2H), 7.79 (s, 1H), 7.80 (s, 1H), 7.13-7.38 (m, 4H), 6.75-6.80 (m, 1H), 6.51-6.52 (m, 1H), 6.38-6.42 (m, 1H), 6.10-6.17 (m, 1H), 5.71-5.77 (m, 1H), 4.42-4.55 (m, 1H), 4.04-4.15 (m, 2H), 4.24-4.26 (m, 1H), 3.13-3.15 (m, 1H), 3.10 (s, 3H), 3.01-3.05 (m, 1H), 2.76-2.88 (m, 3H), 2.60-2.62 (m, 1H), 2.41-2.45 (m, 1H), 2.07-2.13 (m, 1H), 1.88-1.97 (m, 2H), 1.67-1.73 (m, 1H), 1.40-1.55 (m, 1H), 1.21-1.33 (m, 1H).

Example 75: 1-(4-(((1R,2R)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one and Example 76: 1-(4-(((1R,2S)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one Example 75

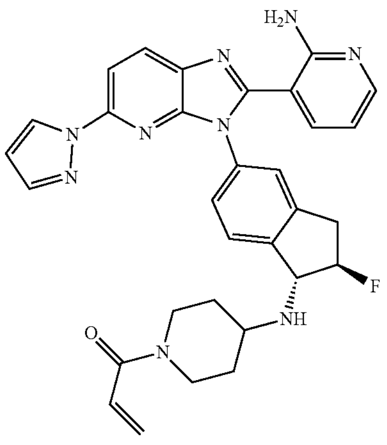

Example 76

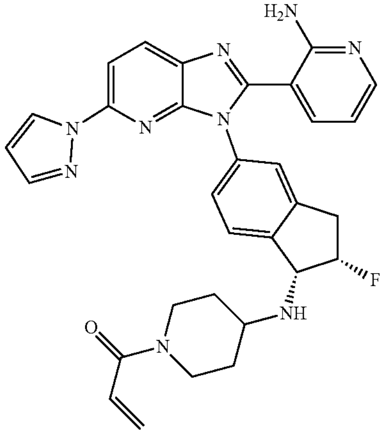

Examples 75 and 76 were prepared in a manner analogous to Example 13 using Intermediate 75-1 and 76-1 in place of Intermediate 1-1 (for Examples 75 and 76, respectively) and a reaction temperature and time of 2 h and 60° C. instead of overnight at 40° C. Absolute stereochemistry of Examples 75 and 76 was confirmed by X-ray crystallography.

Example 75: MS (ESI) calcd. for $C_{31}H_{30}FN_9O$, 563.26 m/z, found 564.15 $[M+H]^+$. $^1$H-NMR (400 MHz, DMSO-$d_6$) δ (ppm): 8.22-8.49 (m, 2H), 7.96-8.15 (m, 1H), 7.89-7.96 (m, 1H), 7.70-7.89 (m, 1H), 7.45-7.69 (m, 1H), 7.33-7.45 (m, 1H), 7.14-7.33 (m, 2H), 6.65-6.97 (m, 1H), 6.55-6.65 (m, 1H), 6.35-6.55 (m, 1H), 5.98-6.18 (m, 1H), 5.56-

5.80 (m, 1H), 4.52-4.82 (m, 1H), 4.22-4.42 (m, 2H), 4.08-4.42 (m, 2H), 3.47-3.75 (m, 2H), 3.29-3.47 (m, 1H), 3.09-3.29 (m, 1H), 2.88-3.09 (m, 2H), 2.68-2.88 (m, 1H), 2.42-2.52 (m, 1H), 1.72-1.95 (m, 2H), 1.62-1.72 (m, 1H). (formic acid salt).

Example 76: MS (ESI) calcd. for $C_{31}H_{30}FN_9O$, 563.26 m/z, found 564.15 $[M+H]^+$. $^1H$-NMR (400 MHz, DMSO-d6) δ (ppm): 8.32-8.49 (m, 2H), 7.96-8.15 (m, 1H), 7.89-7.96 (m, 1H), 7.69-7.89 (m, 1H), 7.48-7.69 (m, 1H), 7.35-7.48 (m, 1H), 7.15-7.35 (m, 2H), 6.68-6.95 (m, 1H), 6.55-6.68 (m, 1H), 6.37-6.55 (m, 1H), 5.98-6.25 (m, 1H), 5.66-5.88 (m, 1H), 5.18-5.62 (m, 1H), 4.41-4.65 (m, 1H), 4.21-4.41 (m, 1H), 4.08-4.11 (m, 1H), 3.15-3.36 (m, 2H), 3.02-3.15 (m, 2H), 2.75-3.02 (m, 1H), 2.04-2.25 (m, 1H), 1.76-2.04 (m, 1H), 1.19-1.53 (m, 2H). (formic acid salt).

Intermediate 75-1: 3-(3-((1R,2S*)-1-amino-2-fluoro-2,3-dihydro-1H-inden-5-yl)-5-(1H-pyrazol-1-yl)-3H-imidazo[4,5-b]pyridin-2-yl)pyridin-2-amine and Intermediate 76-1: 3-(3-((1R,2R*)-1-amino-2-fluoro-2,3-dihydro-1H-inden-5-yl)-5-(1H-pyrazol-1-yl)-3H-imidazo[4,5-b]pyridin-2-yl)pyridin-2-amine Intermediate 75-1

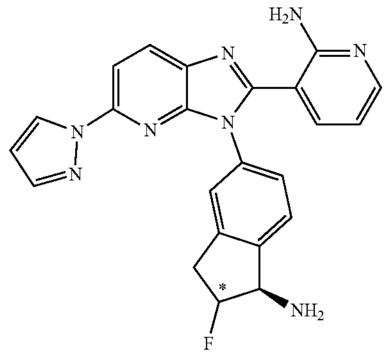

Intermediate 76-1

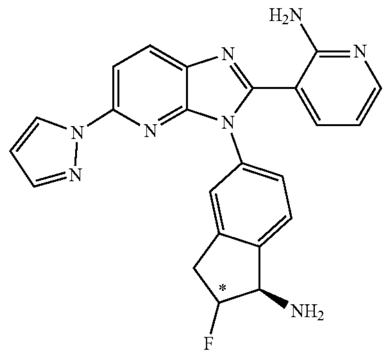

Synthetic Route:

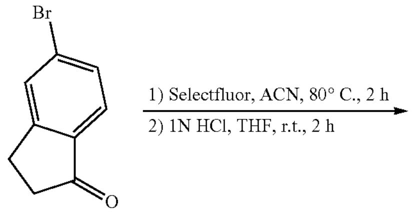

-continued

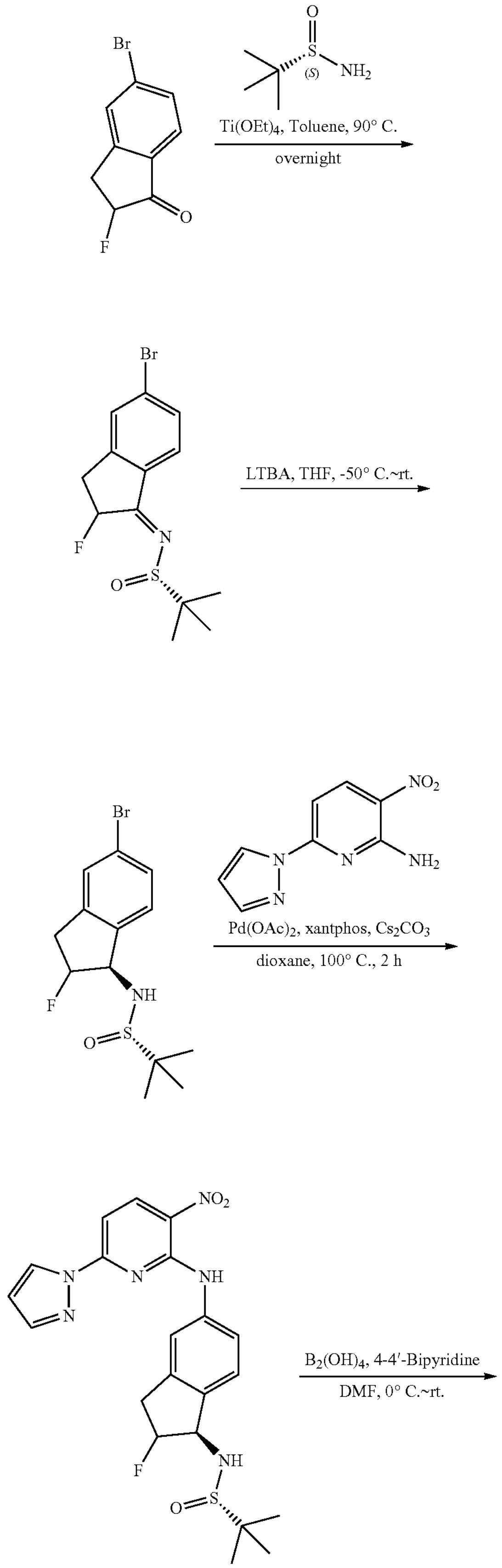

-continued

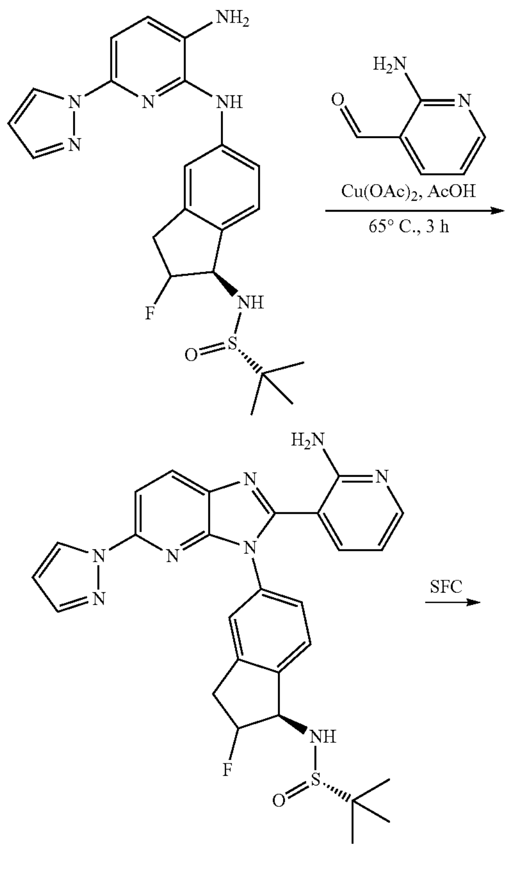

-continued

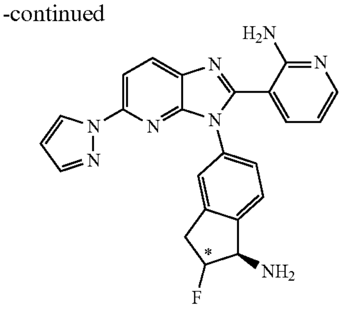

Intermediate 75-1

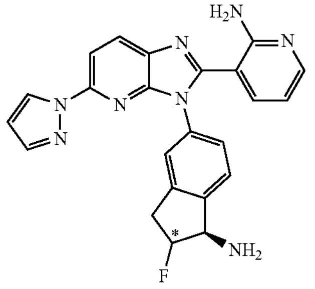

Intermediate 76-1

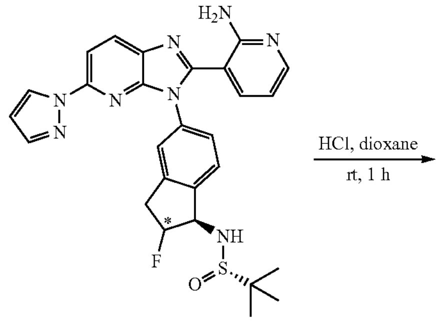

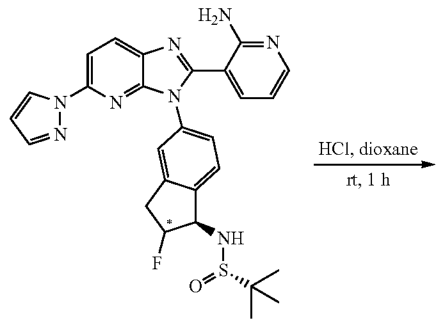

Step 1: Synthesis of 5-bromo-2-fluoro-2,3-dihydro-1H-inden-1-one

To a solution of 5-bromo-1-indanone (5.00 g, 23.8 mmol) in methanol (50 mL) was added SelectFluor (10.0 g, 28.2 mmol) and the resulting mixture was stirred under reflux for 2 hours. The reaction mixture was filtered through Celite, and the filtrate was concentrated under reduced pressure. The resulting residue was dissolved in tetrahydrofuran (50 mL), and 1 N hydrochloric acid (50 mL) was added followed by stirring at room temperature for 3 hours. To the reaction mixture, a 2 N aqueous sodium hydroxide solution (50 mL) was added, and the mixture was diluted with a saturated aqueous sodium bicarbonate solution. The mixture was extracted with ethyl acetate. The organic layer was washed with brine, dried over anhydrous magnesium sulfate, and then concentrated under reduced pressure to afford 5-bromo-2-fluoro-2,3-dihydroinden-1-one (4.0 g, 74% yield) as a white solid. MS (ESI) calcd. for $C_9H_6BrFO$, 227.96 m/z, found: 229.00 $[M+H]^+$.

Step 2: Synthesis of (S)-N-((Z)-5-bromo-2-fluoro-2,3-dihydro-1H-inden-1-ylidene)-2-methylpropane-2-sulfinamide To a solution of 5-bromo-2-fluoro-2,3-dihydroinden-1-one (3.0 g, 13 mmol) in toluene (5 mL) was added (S)-2-methylpropane-2-sulfinamide (1.90 g, 15.7 mmol) and $Ti(OEt)_4$ (5.08 g, 22.2 mmol). The mixture was stirred at 90° C. for 2 h. After cooling to room temperature, the reaction was quenched by the addition of 2M Rochelle's salt (30 mL). The resulting mixture was diluted with brine (50 mL) and extracted with ethyl acetate (3×50 mL). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)-N-(5-bromo-2-fluoro-2,3-dihydro-1H-inden-1-ylidene)-2-methylpropane-2-sulfinamide (3.0 g, 69% yield) as a yellow solid. MS (ESI) calcd. for $C_{13}H_{15}BrFNOS$: 331.00 m/z, found: 332.10 $[M+H]^+$. Note that the (S)- applies to the sulfur stereocenter and not the C—F bond for this and all instances vide infra.

Step 3: Synthesis of (S)-N-((1R)-5-bromo-2-fluoro-2,3-dihydro-1H-inden-1-yl)-2-methylpropane-2-sulfinamide To a cooled (−50° C.) solution of (S)-N-((Z)-5-bromo-2-fluoro-2,3-dihydro-1H-inden-1-ylidene)-2-methylpropane-2-sulfinamide (3.0 g, 9.0 mmol) was added LTBA (3.90 g, 15.4 mmol) and the resulting mixture was stirred at room temperature for 2 h. The reaction was quenched by the addition of 2M Rochelle's salt (30 mL). The mixture was diluted with brine (50 mL) and extracted with ethyl acetate (3×50 mL). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)-N-((1R)-5-bromo-2-fluoro-2,3-dihydro-1H-inden-1-yl)-2-methylpropane-2-sulfinamide (2.0 g, 66% yield) as a yellow solid. MS (ESI) calcd. for $C_{13}H_{17}BrFNOS$: 333.02 m/z, found: 334.10 $[M+H]^+$.

Step 4: Synthesis of (S)-N-((1R)-2-fluoro-5-((3-nitro-6-(1H-pyrazol-1-yl)pyridin-2-yl)amino)-2,3-dihydro-1H-inden-1-yl)-2-methylpropane-2-sulfinamide A mixture of (S)-N-((1R)-5-bromo-2-fluoro-2,3-dihydro-1H-inden-1-yl)-2-methylpropane-2-sulfinamide (2.0 g, 6.0 mmol), 3-nitro-6-(pyrazol-1-yl)pyridin-2-amine (1.35 g, 6.58 mmol), $Pd(OAc)_2$ (0.13 g, 0.60 mmol), $Cs_2CO_3$ (5.86 g, 18.0 mmol) and XantPhos (0.35 g, 0.60 mmol) in dioxane (4.0 mL) was stirred at 100° C. for 2 h under nitrogen atmosphere. The reaction was quenched with water (100 mL) and the mixture was extracted with ethyl acetate (3×100 mL). The combined organic extracts were washed with brine (100 mL) and dried over anhydrous $Na_2SO_4$. After filtration, the filtrate was concentrated under reduced pressure. The crude product was purified by silica gel column chromatography using a gradient of methanol in dichloromethane to afford (S)-N-((1R)-2-fluoro-5-((3-nitro-6-(1H-pyrazol-1-yl)pyridin-2-yl)amino)-2,3-dihydro-1H-inden-1-yl)-2-methylpropane-2-sulfinamide (2.5 g, 91% yield) as a yellow solid. MS (ESI) calcd. for $C_{21}H_{23}FN_6O_3S$, 458.15 m/z, found: 459.10 $[M+H]^+$.

Step 5: Synthesis of (S)-N-((1R)-5-((3-amino-6-(1H-pyrazol-1-yl)pyridin-2-yl)amino)-2-fluoro-2,3-dihydro-1H-inden-1-yl)-2-methylpropane-2-sulfinamide To a solution of (S)-N-[(1R)-2-fluoro-5-{[3-nitro-6-(pyrazol-1-yl)pyridin-2-yl]amino}-2,3-dihydro-1H-inden-1-yl]-2-methylpropane-2-sulfinamide (2.5 g, 5.5 mmol) in DMF (30 mL) was added $B_2(OH)_4$ (1.47 g, 16.4 mmol) and 4-(pyridin-4-yl)pyridine (25.0 mg, 0.163 mmol). The resulting mixture was stirred at room temperature for 1 h. The reaction was quenched by the addition of water (200 mL) and then the mixture was extracted with ethyl acetate (3×100 mL). The combined organic extracts were washed with brine (100 mL) and dried over anhydrous $Na_2SO_4$. After filtration, the filtrate was concentrated under reduced pressure to afford (S)-N-((1R)-5-((3-amino-6-(1H-pyrazol-1-yl)pyridin-2-yl)amino)-2-fluoro-2,3-dihydro-1H-inden-1-yl)-2-methylpropane-2-sulfinamide (2.0 g, 86% yield) as a yellow solid. MS (ESI) calcd. for $C_{21}H_{25}FN_6OS$: 428.17 m/z. found: 429.15 $[M+H]^+$.

Step 6: Synthesis of (S)-N-((1R)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)-2-methylpropane-2-sulfinamide To a solution of (S)-N-[(1R)-5-{[3-amino-6-(pyrazol-1-yl)pyridin-2-yl]amino}-2-fluoro-2,3-dihydro-1H-inden-1-yl]-2-methylpropane-2-sulfinamide (2.0 g, 4.7 mmol) and 2-aminopyridine-3-carbaldehyde (0.68 g, 5.6 mmol) in AcOH (60 mL) was added $Cu(OAc)_2$ (171 mg, 0.94 mmol). The mixture was stirred at 65° C. for 1.0 h. After cooling to room temperature, the mixture was concentrated and the residue obtained was purified by reverse phase flash column chromatography on C18 silica gel using a gradient of acetonitrile in water (+0.05 mmol/L $NH_4HCO_3$) to afford (S)-N-((1R)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)-2-methylpropane-2-sulfinamide (1.47 g, 59% yield). MS (ESI) calcd. for $C_{27}H_{27}FN_8OS$, 530.20 m/z, found: 531.25 $[M+H]^+$. The two diastereomers were separated by chiral SFC on a (S,S)-Whelk-O 1 5 μm Kromasil column using a mix of $CO_2$ and [acetonitrile/methanol 4:1]. The first eluting peak was carried through step 7 below to afford Intermediate 75-1 and the second eluting peak was converted to Intermediate 76-1.

Step 7: Synthesis of 3-(3-((1R)-1-amino-2-fluoro-2,3-dihydro-1H-inden-5-yl)-5-(1H-pyrazol-1-yl)-3H-imidazo[4,5-b]pyridin-2-yl)pyridin-2-amine (Intermediates 75-1 and 76-1

The two diastereomers of (S)-N-((1R)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)-2-methylpropane-2-sulfinamide (500 mg, 0.754 mmol) were dissolved separately in 4N HCl in dioxane (8 mL) and the resulting mixtures were stirred at room temperature for 1 h under nitrogen atmosphere. The solvent was removed under vacuum to afford 3-(3-((1R)-1-amino-2-fluoro-2,3-dihydro-1H-inden-5-yl)-5-(1H-pyrazol-1-yl)-3H-imidazo[4,5-b]pyridin-2-yl)pyridin-2-amine (400 mg, crude) as a light yellow solid. MS (ESI) calcd. For $C_{23}H_{19}FN_8$: 426.17 m/z, found: 427.30 $[M+H]^+$.

Example 77: 1-[4-({5-[2-(2-aminopyridin-3-yl)-5-(pyrazol-1-yl)imidazo[4,5-b]pyridin-3-yl]-2,3-dihydro-1H-inden-1-yl}amino)piperazin-1-yl]prop-2-en-1-one Example 77

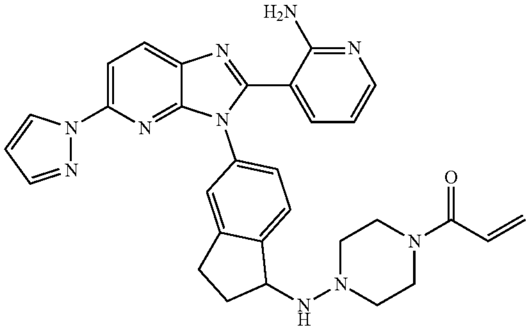

Synthetic Route:

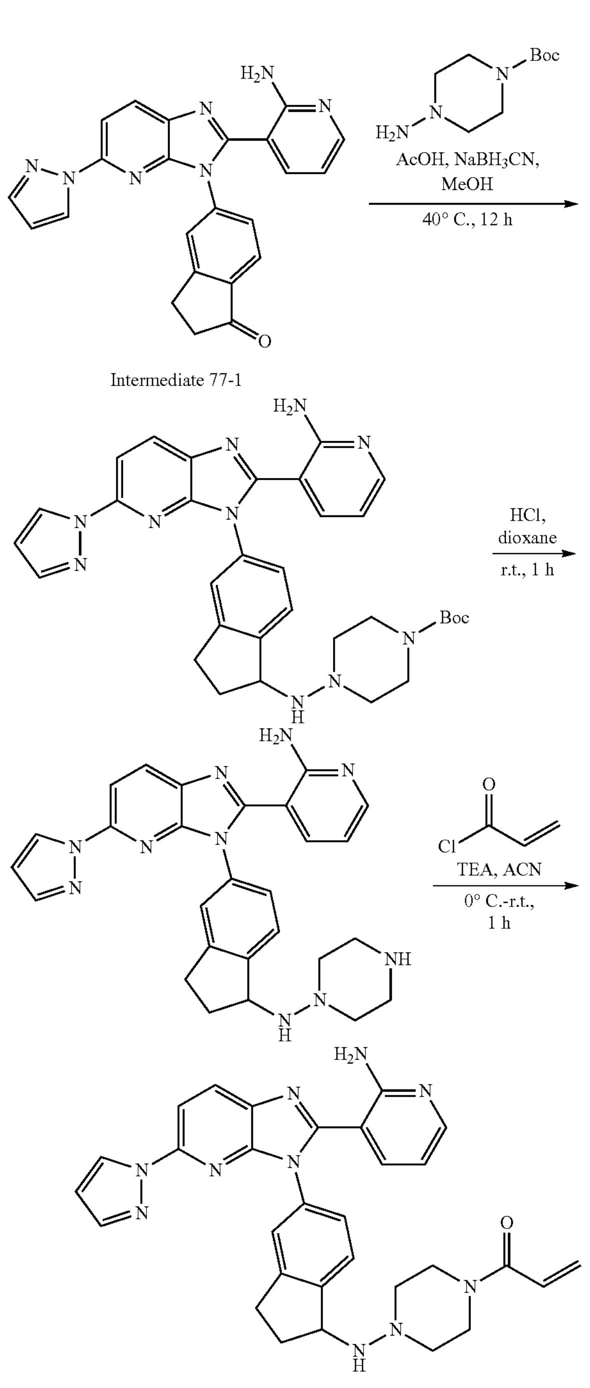

Intermediate 77-1

Example 77

Step 1: Synthesis of tert-butyl 4-({5-[2-(2-amino-pyridin-3-yl)-5-(pyrazol-1-yl)imidazo[4,5-b]pyridin-3-yl]-2,3-dihydro-1H-inden-1-yl}amino)piperazine-1-carboxylate To a solution of 5-[2-(2-aminopyridin-3-yl)-5-(pyrazol-1-yl)imidazo[4,5-b]pyridin-3-yl]-2,3-dihydroinden-1-one (Intermediate 77-1) (300 mg, 0.736 mmol) in MeOH (10 mL) and AcOH (0.5 mL) was added tert-butyl 4-aminopiperazine-1-carboxylate (222.3 mg, 1.104 mmol). The resulting mixture was stirred for 12 h at 40° C. $NaBH_3CN$ (185.1 mg, 2.944 mmol) was added and the reaction mixture was stirred at 40° C. for another 1 hour. The resulting mixture was purified by reverse-phase flash column chromatography on C18 silica gel using a gradient of acetonitrile in water (+0.05% $NH_4HCO_3$) to afford tert-butyl 4-({5-[2-(2-amino-pyridin-3-yl)-5-(pyrazol-1-yl)imidazo[4,5-b]pyridin-3-yl]-2,3-dihydro-1H-inden-1-yl}amino)piperazine-1-carboxylate (100 mg, 17% yield) as a yellow solid. MS (ESI) calcd. for $C_{32}H_{36}N_{10}O_2$: 592.30 m/z, found: 593.20 $[M+H]^+$.

Step 2: Synthesis of N-{5-[2-(2-aminopyridin-3-yl)-5-(pyrazol-1-yl)imidazo[4,5-b]pyridin-3-yl]-2,3-dihydro-1H-inden-1-yl}piperazin-1-amine A solution of tert-butyl 4-({5-[2-(2-aminopyridin-3-yl)-5-(pyrazol-1-yl)imidazo[4,5-b]pyridin-3-yl]-2,3-dihydro-1H-inden-1-yl}amino)piperazine-1-carboxylate (100 mg, 0.169 mmol) in 4N HCl in 1,4-dioxane (4.2 mL) was stirred for 1 h at room temperature. The resulting mixture was concentrated under reduced pressure to afford N-{5-[2-(2-aminopyridin-3-yl)-5-(pyrazol-1-yl)imidazo[4,5-b]pyridin-3-yl]-2,3-dihydro-1H-inden-1-yl}piperazin-1-amine (120 mg, 85% yield) as a white solid. MS (ESI) calcd. for $C_{27}H_{28}N_{10}$: 492.25 m/z, found: 493.30 $[M+H]^+$.

Step 3: Synthesis of 1-[4-({5-[2-(2-aminopyridin-3-yl)-5-(pyrazol-1-yl)imidazo[4,5-b]pyridin-3-yl]-2,3-dihydro-1H-inden-1-yl}amino)piperazin-1-yl]prop-2-en-1-one To a cooled (0° C.) solution of N-{5-[2-(2-aminopyridin-3-yl)-5-(pyrazol-1-yl)imidazo[4,5-b]pyridin-3-yl]-2,3-dihydro-1H-inden-1-yl}piperazin-1-amine (100 mg, 0.203 mmol) in ACN (5 mL) were added triethylamine (102.7 mg, 1.015 mmol) and acryloyl chloride (3.67 mg, 0.041 mmol). The mixture was stirred at 0° C. for 10 min and then at ambient temperature for 1 hour. The resulting mixture was concentrated under reduced pressure and the residue was purified by reverse-phase flash column chromatography on C18 silica gel using a gradient of acetonitrile in water (+0.05% $NH_4HCO_3$). The material obtained was further purified by Prep-HPLC on XSelect CSH Fluoro Phenyl column using a gradient of acetonitrile in water (+0.05% TFA) to afford 1-[4-({5-[2-(2-aminopyridin-3-yl)-5-(pyrazol-1-yl)imidazo[4,5-b]pyridin-3-yl]-2,3-dihydro-1H-inden-1-yl}amino)piperazin-1-yl]prop-2-en-1-one (8.9 mg, 8% yield) as a yellow solid. MS (ESI) calcd. for $C_{30}H_{30}N_{10}O$: 546.26 m/z, found: 547.30 $[M+H]^+$. $^1H$ NMR (400 MHz, DMSO-$d_6$) δ (ppm): 8.40-8.43 (m, 1H), 8.34-8.36 (m, 1H), 7.98-8.02 (m, 2H), 7.80-7.81 (m, 1H), 7.71-7.75 (m, 2H), 7.54-7.55 (m, 1H), 7.37-7.39 (m, 1H), 6.73-6.80 (m, 2H), 6.56-6.57 (m, 1H), 6.12-6.17 (m, 1H), 5.75-5.78 (m, 1H), 5.12-5.17 (m, 1H), 3.62-3.79 (m, 4H), 3.11-3.23 (m, 1H), 3.02-3.09 (m, 4H), 2.92-3.01 (m, 1H), 2.54-2.61 (m, 1H), 2.14-2.24 (m, 1H). (TFA salt).

Intermediate 77-1: 5-(2-(2-aminopyridin-3-yl)-5-(1H-pyrazol-1-yl)-3H-imidazo[4,5-b]pyridin-3-yl)-2,3-dihydro-1H-inden-1-one Intermediate 77-1

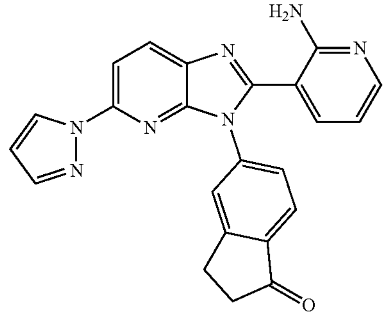

Synthetic Route:

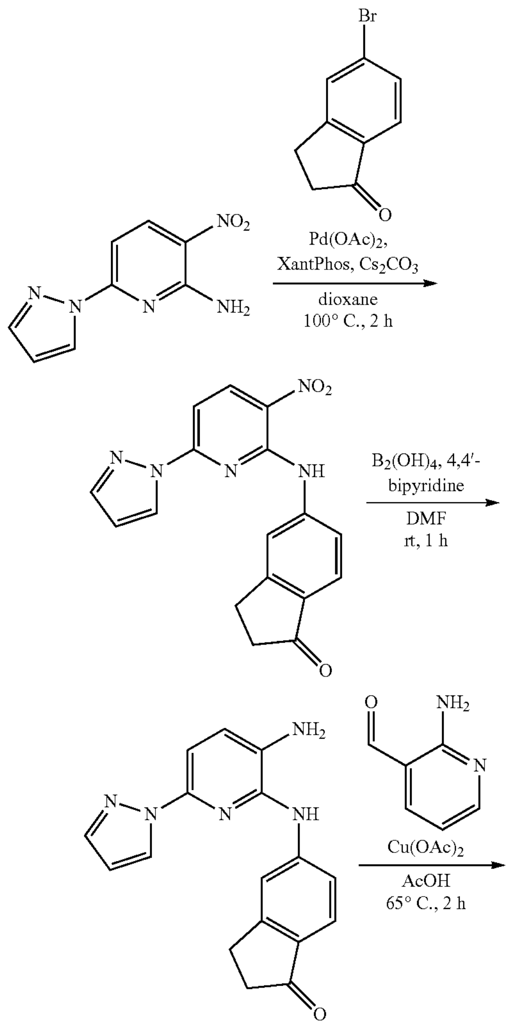

-continued

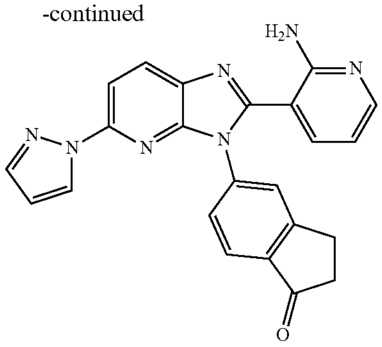

Intermediate 77-1

Step 1: Synthesis of 5-((3-nitro-6-(1H-pyrazol-1-yl)pyridin-2-yl)amino)-2,3-dihydro-1H-inden-1-one To a solution of 3-nitro-6-(pyrazol-1-yl)pyridin-2-amine (15.0 g, 73.1 mmol, 1 equiv) and 5-bromo-2,3-dihydroinden-1-one (15.43 g, 73.11 mmol, 1 equiv) in 1,4-dioxane (400 mL) were added $Pd(OAc)_2$ (1.64 g, 7.31 mmol, 0.1 equiv), XantPhos (4.23 g, 7.31 mmol, 0.1 equiv) and $Cs_2CO_3$ (71.46 g, 219.3 mmol, 3 equiv). The resulting mixture was maintained under nitrogen and stirred for 1 h at 100° C. The mixture was allowed to cool to room temperature. Water was added and the precipitated solids were collected by filtration to afford 5-((3-nitro-6-(1H-pyrazol-1-yl)pyridin-2-yl)amino)-2,3-dihydro-1H-inden-1-one (37 g, 91%) as a black solid. MS (ESI) calcd. for $C_{17}H_{13}N_5O_3$: 335.10 m/z, found: 336.00 $[M+H]^+$.

Step 2: Synthesis of 5-((3-amino-6-(1H-pyrazol-1-yl)pyridin-2-yl)amino)-2,3-dihydro-1H-inden-1-one To a cooled (0° C.) solution of 5-((3-nitro-6-(1H-pyrazol-1-yl)pyridin-2-yl)amino)-2,3-dihydro-1H-inden-1-one (10.00 g, 29.82 mmol, 1 equiv) in DMF (100 mL) were added $B_2(OH)_4$ (8.02 g, 89.5 mmol, 3 equiv) and 4-(pyridin-4-yl)pyridine (232.9 mg, 1.491 mmol, 0.05 equiv). The resulting mixture was stirred for 1 h at room temperature. Water was added and the precipitated solids were collected by filtration to afford 5-((3-amino-6-(1H-pyrazol-1-yl)pyridin-2-yl)amino)-2,3-dihydro-1H-inden-1-one (8.5 g, 50%) as a black solid. MS (ESI) calcd. for $C_{17}H_{15}N_5O$: 305.13 m/z, found: 306.15 $[M+H]^+$.

Step 3: Synthesis of 5-[2-(2-aminopyridin-3-yl)-5-(pyrazol-1-yl)imidazo[4,5-b]pyridin-3-yl]-2,3-dihydroinden-1-one (Intermediate 77-1

To a solution of 5-((3-amino-6-(1H-pyrazol-1-yl)pyridin-2-yl)amino)-2,3-dihydro-1H-inden-1-one (8.5 g, 28 mmol, 1 equiv) in AcOH (400 mL) were added 2-aminopyridine-3-carbaldehyde (4.05 g, 33.2 mmol, 1.2 equiv) and $Cu(OAc)_2$ (1.00 g, 5.53 mmol, 0.2 equiv). The resulting mixture was stirred for 12 h at 65° C. The resulting mixture was concentrated under reduced pressure. The residue was purified by silica gel column chromatography, eluting with MeOH/DCM (0-10%) to afford 5-[2-(2-aminopyridin-3-yl)-5-(pyrazol-1-yl)imidazo[4,5-b]pyridin-3-yl]-2,3-dihydroinden-1-one (Intermediate 77-1) (2.5 g, 16%) as a black solid. MS (ESI) calcd. for $C_{23}H_{17}N_7O$: 407.15 m/z, found: 408.15 $[M+H]^+$.

Example 78: 1-((*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-azaspiro[3.5]nonan-2-yl)prop-2-en-1-one and Example 79: 1-((*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-azaspiro[3.5]nonan-2-yl)prop-2-en-1-one Example 78

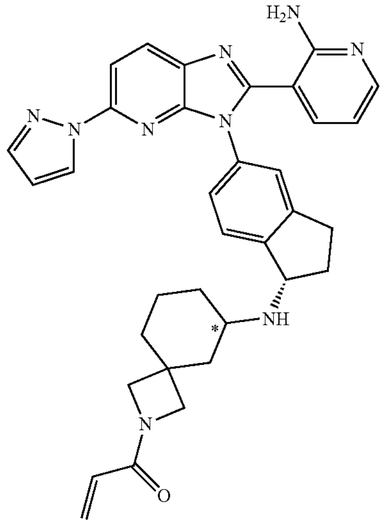

Example 79

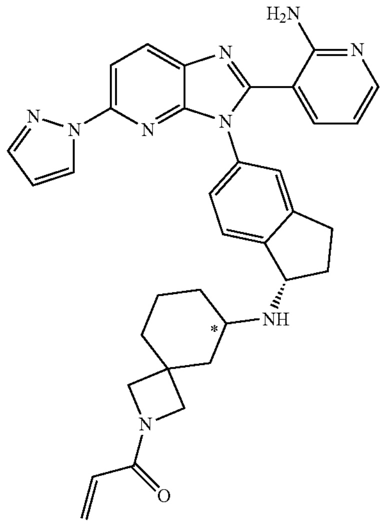

Examples 78 and 79 were prepared in a manner analogous to Example 14 (via Intermediate 14-1) starting from tert-butyl 6-oxo-2-azaspiro[3.5]nonane-2-carboxylate in place of tert-butyl 8-oxo-3-azabicyclo[3.2.1]octane-3-carboxylate and using a reaction time of 2 h instead of overnight for the final step. The two diastereomers were separated by chiral Prep-HPLC on a CHIRALPAK IA column using a mixture of [MTBE+0.5% 2M $NH_3$ in MeOH] and [1:1 ethanol/dichloromethane]. * Denotes a stereocenter with undetermined absolute stereochemistry of a single diastereomer.

Example 78: MS (ESI) calcd. for $C_{34}H_{35}N_9O$, 585.30 m/z, found 586.20 $[M+H]^+$. $^1H$ NMR (300 MHz, DMSO-$d_6$) δ (ppm): 8.32-8.34 (m, 2H), 7.97-7.98 (m, 2H), 7.78-7.79 (m, 1H), 7.44-7.47 (m, 1H), 7.30-7.31 (m, 1H), 7.19-7.22 (m, 2H), 6.52-6.53 (m, 1H), 6.41-6.42 (m, 1H), 6.09-6.10 (m, 1H), 6.03-6.04 (m, 1H), 5.61-5.65 (m, 1H), 4.32-4.33 (m, 1H), 3.87-3.90 (m, 2H), 3.54-3.59 (m, 2H), 2.90-2.91 (m, 1H), 2.74-2.77 (m, 1H), 2.48-2.49 (m, 1H), 2.02-2.06 (m, 1H), 2.02-2.06 (m, 2H), 1.80-1.88 (m, 3H), 1.31-1.35 (m, 3H), 1.03-1.05 (m, 1H).

Example 79: MS (ESI) calcd. for $C_{34}H_{35}N_9O$, 585.30 m/z, found 586.20 $[M+H]^+$. $^1H$ NMR (300 MHz, DMSO-$d_6$) δ (ppm): 8.31-8.34 (m, 2H), 7.97-7.98 (m, 2H), 7.78-7.79 (m, 1H), 7.44-7.47 (m, 1H), 7.30-7.31 (m, 1H), 7.19-7.21 (m, 2H), 6.53-6.54 (m, 1H), 6.40-6.41 (m, 2H), 6.09-6.10 (m, 1H), 5.61-5.65 (m, 1H), 4.35-4.36 (m, 1H), 3.88-3.90 (m, 2H), 3.58-3.59 (m, 2H), 2.60-3.01 (m, 3H), 2.48-2.49 (m, 1H), 2.19-2.20 (m, 1H), 1.63-1.75 (m, 4H), 1.32-1.52 (m, 3H), 1.01-1.09 (m, 1H).

Example 80: 1-(7-{[(1S)-5-[2-(2-aminopyridin-3-yl)-5-(pyrazol-1-yl)imidazo[4,5-b]pyridin-3-yl]-2,3-dihydro-1H-inden-1-yl]amino}-1-azaspiro[3.5]nonan-1-yl)prop-2-en-1-one Example 80

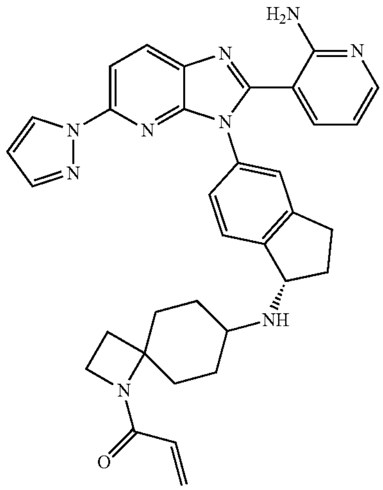

Example 80 was prepared in a manner analogous to Example 14 (via Intermediate 14-1) starting from tert-butyl 7-oxo-1-azaspiro[3.5]nonane-1-carboxylate instead of tert-butyl 8-oxo-3-azabicyclo[3.2.1]octane-3-carboxylate, using 4N HCl in dioxane instead of TFA in dichloromethane, and a reaction time of 2 h instead of overnight for the final step. The final product is a mix of diastereomers. MS (ESI) calcd. for $C_{34}H_{35}N_9O$: 585.30 m/z, found: 586.30 $[M+H]^+$. $^1H$ NMR (400 MHz, DMSO-$d_6$) δ (ppm): 8.42-8.44 (m, 1H), 8.36-8.37 (m, 1H), 8.00-8.06 (m, 2H), 7.83 (s, 1H), 7.63-7.71 (m, 2H), 7.56-7.58 (m, 1H), 7.33-7.43 (m, 1H), 6.71-6.76 (m, 1H), 6.50-6.59 (m, 2H), 6.10-6.15 (m, 1H), 5.66-5.69 (m, 1H), 4.91-4.93 (m, 1H), 4.06-4.10 (m, 1H), 3.64-3.68 (m, 1H), 3.45-3.60 (m, 2H), 3.12-3.20 (m, 2H), 2.85-2.98 (m, 2H), 2.15-2.26 (m, 2H), 2.01-2.04 (m, 1H), 1.78-1.85 (m, 3H), 1.68-1.71 (m, 1H), 1.50-1.60 (m, 1H), 1.35-1.42 (m, 1H). (TFA salt).

Example 81: 1-((*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)azepan-1-yl)prop-2-en-1-one and Example 82: 1-((*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)azepan-1-yl)prop-2-en-1-one Example 81

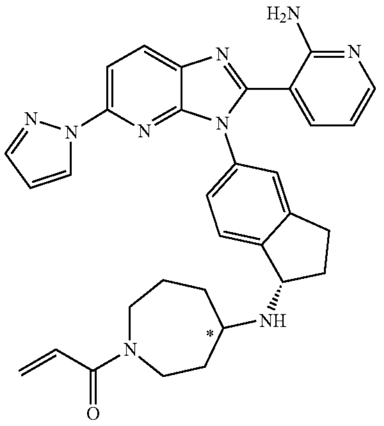

Example 82

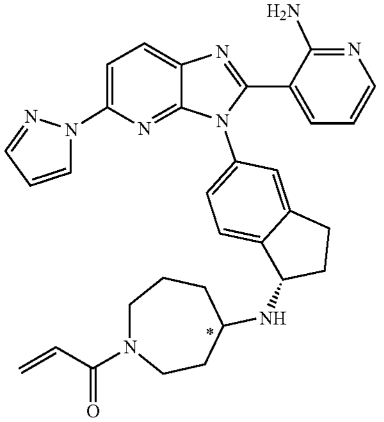

Examples 81 and 82 were prepared in a manner analogous to Example 14 (via Intermediate 14-1) starting from tert-butyl 4-oxoazepane-1-carboxylate instead of tert-butyl 8-oxo-3-azabicyclo[3.2.1]octane-3-carboxylate, 4N HCl in dioxane instead of TFA in dichloromethane, and a reaction time of 2 h instead of overnight for the final step. The diastereomers were separated by chiral Prep-HPLC on a CHIRALPAK IK column using a mixture of [MTBE+0.5% 2N $NH_3$ in methanol] and tetrahydrofuran. * Denotes a stereocenter with undetermined absolute stereochemistry of a single diastereomer.

Example 81: MS (ESI) calcd. for $C_{32}H_{33}N_9O$, 559.28 m/z, found 560.20 $[M+H]^+$. $^1H$ NMR (400 MHz, DMSO-$d_6$) δ ppm: 8.26-8.61 (m, 2H), 7.95-8.21 (m, 2H), 7.76-7.95 (m, 2H), 7.62-7.76 (m, 1H), 7.52-7.62 (m, 1H), 7.31-7.52 (m, 1H), 6.68-6.96 (m, 2H), 6.48-6.68 (m, 1H), 6.05-6.36 (m, 1H), 5.64-5.92 (m, 1H), 4.85-5.14 (m, 1H), 3.78-3.92 (m, 1H), 3.43-3.78 (m, 3H), 3.25-3.43 (m, 2H), 3.11-3.25 (m, 1H), 2.86-3.11 (m, 1H), 2.28-2.38 (m, 1H), 2.14-2.28 (m, 2H), 1.90-2.11 (m, 1H), 1.48-1.84 (m, 3H).

Example 82: MS (ESI) calcd. for $C_{32}H_{33}N_9O$, 559.28 m/z, found 560.15 $[M+H]^+$. $^1H$ NMR (400 MHz, DMSO-$d_6$) δ ppm: 8.28-8.61 (m, 2H), 7.95-8.21 (m, 2H), 7.76-7.95 (m, 2H), 7.65-7.76 (m, 1H), 7.52-7.65 (m, 1H), 7.32-7.52 (m, 1H), 6.68-6.97 (m, 2H), 6.48-6.68 (m, 1H), 6.05-6.36 (m, 1H), 5.64-5.95 (m, 1H), 4.85-5.14 (m, 1H), 3.84-3.92 (m, 1H), 3.54-3.72 (m, 2H), 3.41-3.54 (m, 1H), 3.26-3.41 (m, 2H), 3.12-3.26 (m, 1H), 2.94-3.12 (m, 1H), 2.38-2.48 (m, 1H), 2.18-2.31 (m, 1H), 2.06-2.19 (m, 1H), 1.91-2.06 (m, 1H), 3.54-3.72 (m, 3H).

Example 83: (S)-1-(6-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-azaspiro[3.3]heptan-2-yl)-2-fluoroprop-2-en-1-one Example 83

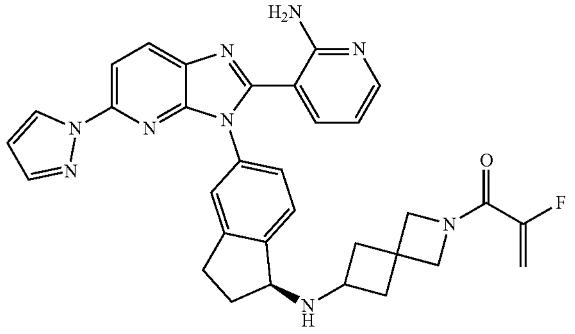

Synthetic Route:

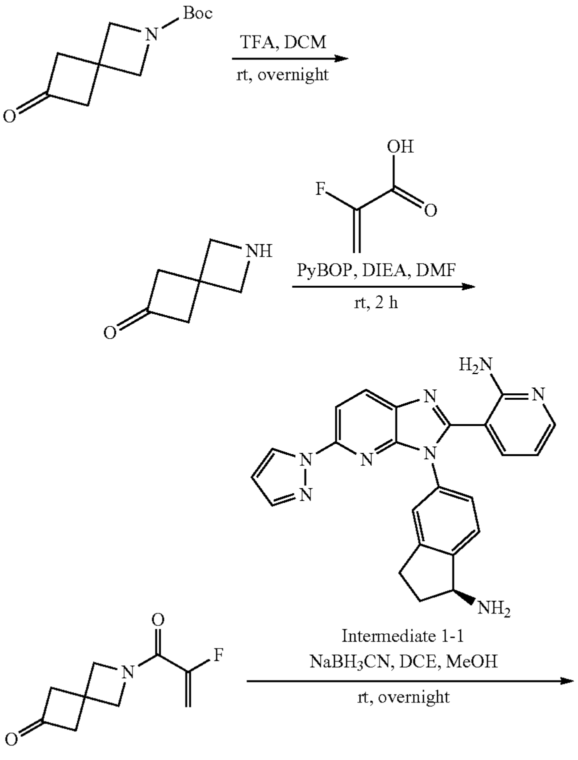

-continued

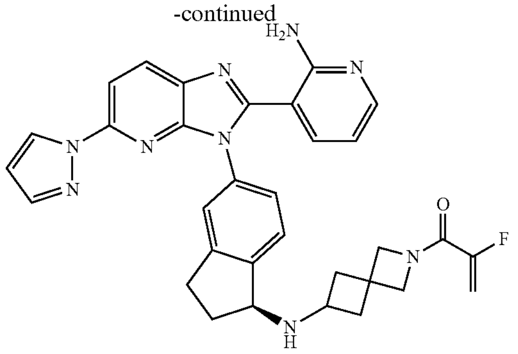

Example 83

Step 1: Synthesis of 2-azaspiro[3.3]heptan-6-one

To a stirred solution of tert-butyl 6-oxo-2-azaspiro[3.3]heptane-2-carboxylate (500 mg, 2.37 mmol) in DCM (3 mL) was added TFA (1 mL) at 0° C. The resulting mixture was stirred at room temperature overnight. The resulting mixture was concentrated under vacuum to afford 2-azaspiro[3.3]heptan-6-one (400 mg, crude) as a yellow oil. MS (ESI) calcd. for $C_6H_9NO$: 111.07 m/z, found 112.10 $[M+H]^+$.

Step 2: Synthesis of 2-(2-fluoroacryloyl)-2-azaspiro[3.3]heptan-6-one

To a stirred solution of 2-azaspiro[3.3]heptan-6-one (300 mg, 2.70 mmol), 2-fluoroacrylic acid (291.7 mg, 3.239 mmol) and N,N-diisopropylethylamine (1.047 mg, 8.097 mmol) in DMF (4 mL) was added PyBOP (1.405 mg, 2.699 mmol). The reaction mixture was stirred for 2 h at room temperature. The mixture was quenched with water (80 mL). The resulting mixture was extracted with ethyl acetate (3×80 mL). The organic layers were combined, dried over anhydrous sodium sulfate, filtered and concentrated. The crude product was purified by silica gel flash column chromatography using a gradient of ethyl acetate in petroleum ether to afford 2-(2-fluoroacryloyl)-2-azaspiro[3.3]heptan-6-one (300 mg, 61% yield) as a yellow solid. MS (ESI) calcd. for $C_9H_{10}NFO_2$: 183.07 m/z, found 184.15 $[M+H]^+$.

Step 3: Synthesis of (S)-1-(6-((5-(2-(2-aminopyridin-3-yl)-5-(1H-pyrazol-1-yl)-3H-imidazo[4,5-b]pyridin-3-yl)-2,3-dihydro-1H-inden-1-yl) amino)-2-azaspiro[3.3]heptan-2-yl)-2-fluoroprop-2-en-1-one (Example 83)

A solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (200 mg, 0.490 mmol) and 2-(2-fluoroacryloyl)-2-azaspiro[3.3]heptan-6-one (89.7 mg, 0.490 mmol) in DCE (5 mL) and MeOH (0.5 mL) was stirred for additional 3 h at room temperature. To the mixture was added $NaBH_3CN$ (92.3 mg, 1.470 mmol) and the resulting mixture was stirred overnight at room temperature. The reaction was quenched with $H_2O$ (50 mL). The resulting mixture was extracted with ethyl acetate (3×50 mL). The combined organic layers were washed with brine (50 mL) and dried over anhydrous $Na_2SO_4$. After filtration, the filtrate was concentrated under reduced pressure. The crude product was purified by Prep-HPLC on a XSelect CSH Fluoro Phenyl column using a gradient of acetonitrile in water (+0.1% formic acid) to afford (S)-1-(6-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-azaspiro[3.3]heptan-2-yl)-2-fluoroprop-2-en-1-one (Example 83, formic acid salt) (20.4 mg, 7% yield) as a white solid. MS (ESI) calcd. for $C_{32}H_{30}FN_9O$: 575.26 m/z, found 576.25 $[M+H]^+$. $^1H$ NMR (400 MHz, DMSO-$d_6$) δ (ppm): 8.28-8.30 (m, 2H), 7.96-8.01 (m, 2H), 7.80 (s, 1H), 7.53-7.56 (m, 1H), 7.36 (s, 1H), 7.25-7.28 (m, 2H), 6.52 (s, 1H), 6.35-6.45 (m, 1H), 5.49-5.56 (m, 1H), 5.37-5.44 (m, 1H), 4.12-4.41 (m, 3H), 3.81-4.08 (m, 2H), 3.29-3.43 (m, 1H), 2.99-3.12 (m, 1H), 2.81-2.84 (m, 1H), 2.36-2.38 (m, 1H), 2.30-2.36 (m, 2H), 2.02-2.14 (m, 2H), 1.81-1.96 (m, 1H). $^{19}F$ NMR (386 MHz, DMSO-$d_6$) δ (ppm): −114.01.

Example 84: (S)-1-(2-((5-(2-(2-aminopyridin-3-yl)-5-(1H-pyrazol-1-yl)-3H-imidazo[4,5-b]pyridin-3-yl)-2,3-dihydro-1H-inden-1-yl)amino)-7-azaspiro[3.5]nonan-7-yl)-2-fluoroprop-2-en-1-one Example 84

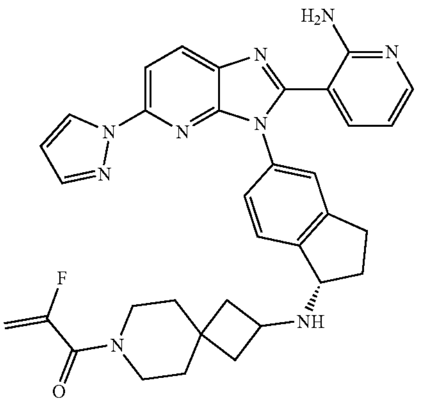

Example 84 was prepared in a manner analogous to Example 83 starting from tert-butyl 2-oxo-7-azaspiro[3.5]nonane-7-carboxylate instead of tert-butyl 6-oxo-2-azaspiro[3.3]heptane-2-carboxylate. MS (ESI) calcd. for $C_{34}H_{34}FN_9O$: 603.29 m/z, found: 604.20 $[M+H]^+$. $^1H$ NMR (400 MHz, DMSO-$d_6$) δ (ppm): 8.45-8.47 (m, 111), 8.42-8.44 (m, 111), 7.98-8.13 (m, 2H), 7.63-7.89 (m, 3H), 7.55-7.62 (m, 1H), 7.41-7.49 (m, 1H), 6.68-6.75 (m, 1H), 6.54-6.59 (m, 1H), 5.02-5.32 (m, 2H), 4.72-4.85 (m, 1H), 3.89-4.02 (m, 1H), 3.43-3.45 (m, 1H), 3.31-3.42 (m, 2H), 3.11-3.24 (m, 1H), 2.90-3.03 (m, 1H), 2.43-2.48 (m, 2H), 2.10-2.31 (m, 3H), 1.94-2.09 (m, 2H), 1.45-1.75 (m, 4H). $^{19}F$-NMR (376 MHz, DMSO-$d_6$) δ (ppm): −104.39. (TFA salt).

Example 85: (S)-1-(4-((5-(2-(2-aminopyridin-3-yl)-5-cyclopropyl-3H-imidazo[4,5-b]pyridin-3-yl)-2,3-dihydro-1H-inden-1-yl)amino)piperidin-1-yl)prop-2-en-1-one Example 85

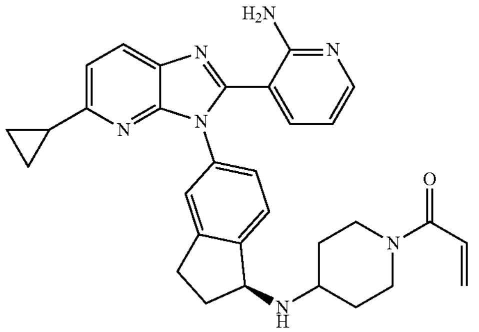

Example 85 was prepared in a manner analogous to Example 13 using Intermediate 85-2 in place of Intermediate 1-1, 1,2-dichloroethane/methanol (10:1) in place of 1,2-dichloroethane and a reaction temperature of 70° C. instead of 40° C. MS (ESI) calcd. for $C_{31}H_{33}N_7O$, 519.27 m/z, found 520.25 $[M+H]^+$. $^1H$ NMR (400 MHz, DMSO-$d_6$) δ (ppm): 8.02-8.03 (m, 111), 7.97-7.99 (m, 1H), 7.44-7.51 (m, 1H), 7.18-7.25 (m, 2H), 7.13-7.19 (m, 2H), 6.81-6.88 (m, 1H), 6.39-6.43 (m, 1H), 6.08-6.10 (m, 1H), 5.67-5.72 (m, 1H), 4.21-4.33 (m, 2H), 3.95-4.06 (m, 1H), 3.10-3.15 (m, 1H), 2.86-2.97 (m, 3H), 2.80-2.85 (m, 1H), 2.71-2.74 (m, 1H), 2.41-2.43 (m, 1H), 2.15-2.17 (m, 1H), 1.96-1.99 (m, 1H), 1.86-1.92 (m, 1H), 1.22-1.28 (m, 2H), 0.86-0.99 (m, 2H), 0.80-0.85 (m, 2H).

Intermediate 85-2: (S)-3-(3-(1-amino-2,3-dihydro-1H-inden-5-yl)-5-cyclopropyl-3H-imidazo[4,5-b]pyridin-2-yl)pyridin-2-amine Intermediate 85-2

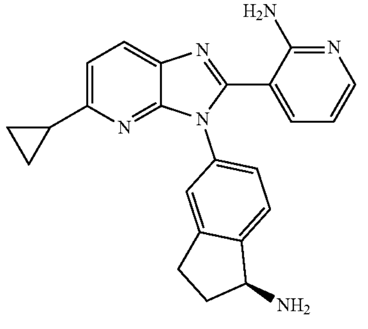

Synthetic Route:

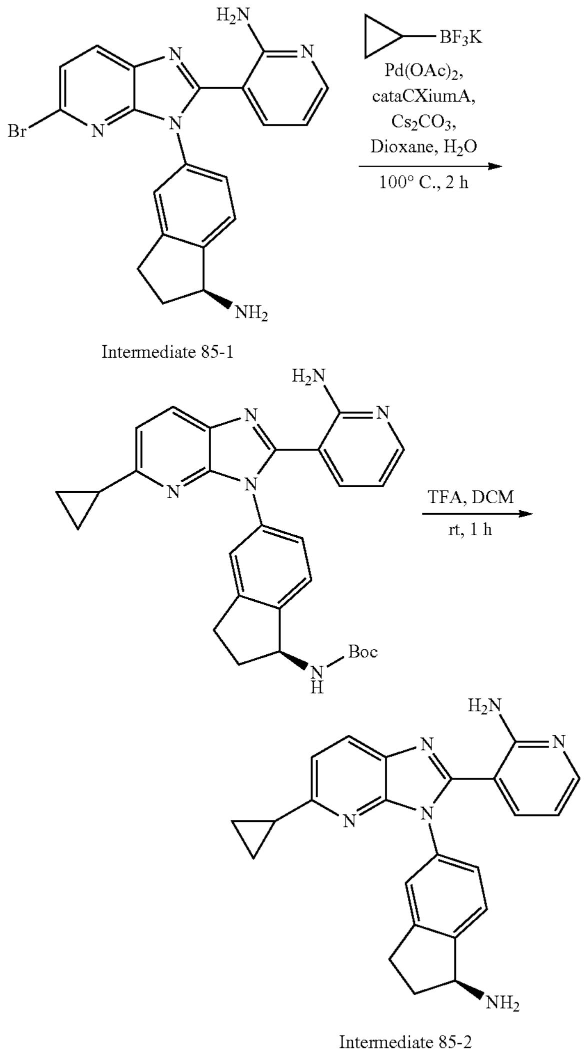

Step 1: Synthesis of tert-butyl (S)-(5-(2-(2-amino-pyridin-3-yl)-5-cyclopropyl-3H-imidazo[4,5-b]pyridin-3-yl)-2,3-dihydro-1H-inden-1-yl) carbamate A mixture of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 85-1) (1.00 g, 1.92 mmol), potassium cyclopropyltrifluoroborate (0.57 g, 3.8 mmol), $Pd(OAc)_2$ (0.04 g, 0.192 mmol), $Cs_2CO_3$ (1.25 g, 3.85 mmol) and bis(adamantan-1-yl)(butyl)phosphane (0.07 g, 0.2 mmol) in water (4 mL) and dioxane (16 mL) was stirred for 2 h at 100° C. under $N_2$ atmosphere. The reaction was quenched with water (20 mL) at room temperature. The resulting mixture was extracted with ethyl acetate (3×20 mL). The combined organic layers were washed with brine (3×50 mL) and dried over anhydrous $Na_2SO_4$. After filtration, the filtrate was concentrated under reduced pressure. The residue was purified by silica gel column chromatography using a gradient of methanol in dichloromethane to afford tert-butyl N-[(1S)-5-[2-(2-aminopyridin-3-yl)-5-cyclopropylimidazo[4,5-b]pyridin-3-yl]-2,3-dihydro-1H-inden-1-yl]carbamate (0.6 g, 65% yield) as a yellow oil. MS (ESI) calcd. for $C_{28}H_{30}N_6O_2$, 482.24 m/z, found 483.20 $[M+H]^+$.

Step 2: Synthesis of (S)-3-(3-(1-amino-2,3-dihydro-1H-inden-5-yl)-5-cyclopropyl-3H-imidazo[4,5-b]pyridin-2-yl) pyridin-2-amine (Intermediate 85-2

A solution of tert-butyl N-[(1S)-5-[2-(2-aminopyridin-3-yl)-5-cyclopropylimidazo[4,5-b]pyridin-3-yl]-2,3-dihydro-1H-inden-1-yl]carbamate (700 mg, 1.45 mmol) in TFA (3 mL) and DCM (15 mL) was stirred for 1 h at room temperature. The resulting mixture was concentrated under reduced pressure to afford 3-{3-[(1S)-1-amino-2,3-dihydro-1H-inden-5-yl]-5-cyclopropylimidazo[4,5-b]pyridin-2-yl}pyridin-2-amine (Intermediate 85-2) (485 mg, 87% yield) as brown oil. MS (ESI) calcd. for $C_{23}H_{22}N_6$, 382.19 m/z, found 383.25 $[M+H]^+$.

Intermediate 85-1: tert-butyl (S)-(5-(2-(2-amino-pyridin-3-yl)-5-bromo-3H-imidazo[4,5-b]pyridin-3-yl)-2,3-dihydro-1H-inden-1-yl)carbamate Intermediate 85-1

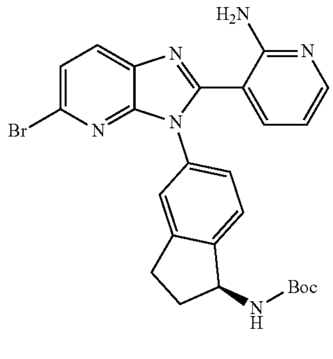

Synthetic Route:

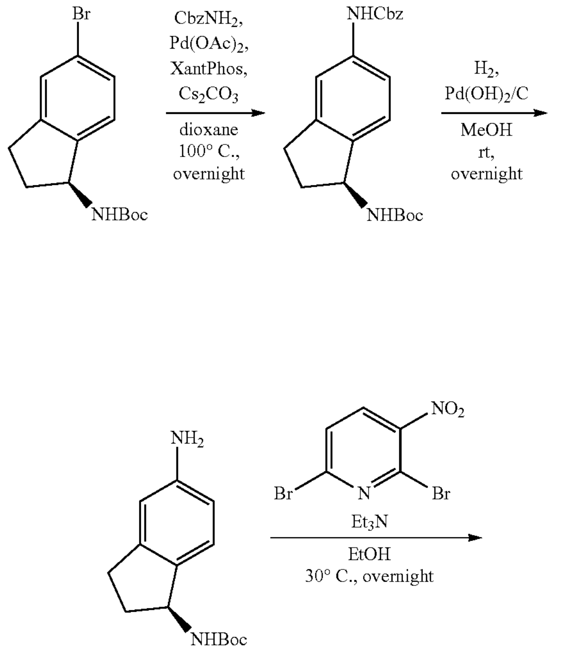

-continued

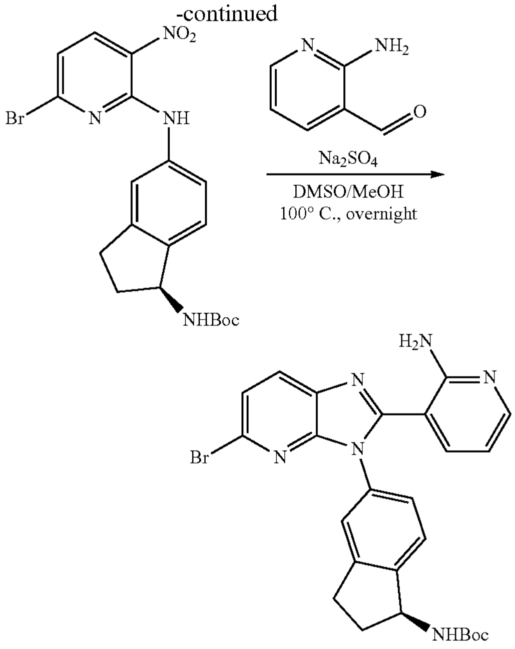

Intermediate 85-1

Step 1: Synthesis of benzyl N-[(1S)-1-[(tert-butoxy-carbonyl)amino]-2,3-dihydro-1H-inden-5-yl]carbamate To a solution of tert-butyl N-[(1S)-5-bromo-2,3-dihydro-1H-inden-1-yl]carbamate (60.00 g, 192.2 mmol, 1 equiv), benzyl carbamate (34.63 g, 230.6 mmol, 1.2 equiv) and XantPhos (22.24 g, 38.44 mmol, 0.2 equiv) in 1,4-dioxane (1.2 L) were added $Cs_2CO_3$ (125.23 g, 384.36 mmol, 2 equiv) and $Pd(OAc)_2$ (4.31 g, 19.2 mmol, 0.1 equiv). After stirring overnight at 100° C. under nitrogen atmosphere the mixture was cooled to room temperature and the product was precipitated by the addition of $H_2O$. The precipitated solids were collected by filtration and washed with $H_2O$ (3×400 ml). The suspended in ethyl acetate and filtered, washing with ethyl acetate. The filtrate was concentrated under reduced pressure to afford benzyl N-[(1S)-1-[(tert-butoxycarbonyl)amino]-2,3-dihydro-1H-inden-5-yl]carbamate (50 g, 46%) as a grey solid. MS (ESI) calcd. for $C_{22}H_{26}N_2O_4$, 382.19 m/z, found: 381.10 $[M-H]^-$.

Step 2: Synthesis of tert-butyl N-[(1S)-5-amino-2,3-dihydro-1H-inden-1-yl]carbamate To a solution of benzyl N-[(1S)-1-[(tert-butoxycarbonyl)amino]-2,3-dihydro-1H-inden-5-yl]carbamate (50.00 g, 130.7 mmol, 1 equiv) in 500 mL $CH_3OH$ was added 10% $Pd(OH)_2/C$ (5.00 g, 35.6 mmol, 0.27 equiv) in a pressure tank. The mixture was hydrogenated at room temperature under 30 psi of hydrogen overnight then filtered through a Celite pad and concentrated under reduced pressure to afford tert-butyl N-[(1S)-5-amino-2,3-dihydro-1H-inden-1-yl]carbamate (40 g, 73%) as a brown solid. MS (ESI) calcd. for $C_{14}H_{20}N_2O_2$, 248.15 m/z, found: 249.15 $[M+H]^+$.

Step 3: Synthesis of tert-butyl N-[(1S)-5-[(6-bromo-3-nitropyridin-2-yl)amino]-2,3-dihydro-1H-inden-1-yl]carbamate A mixture of tert-butyl N-[(1S)-5-amino-2,3-dihydro-1H-inden-1-yl]carbamate (40.0 g, 161 mmol, 1 equiv) and triethylamine (48.90 g, 483.2 mmol, 3 equiv) in EtOH (800 mL) was stirred at room temperature until dissolved. 2,6-dibromo-3-nitropyridine (54.49 g, 193.3 mmol, 1.2 equiv) was added and the mixture was stirred at 30° C. overnight. The mixture was allowed to cool to room temperature and the precipitated solids were collected by filtration and washed with EtOH (3×100 mL) to afford tert-butyl N-[(1S)-5-[(6-bromo-3-nitropyridin-2-yl)amino]-2,3-dihydro-1H-inden-1-yl]carbamate (30 g, 27.30%) as a red solid. MS (ESI) calcd. for $C_{19}H_{21}BrN_4O_4$, 448.07 m/z, found: 447.00 $[M-H]^-$.

Step 4: Synthesis of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 85-1

To a solution of tert-butyl N-[(1S)-5-[(6-bromo-3-nitropyridin-2-yl)amino]-2,3-dihydro-1H-inden-1-yl]carbamate (30.0 g, 66.8 mmol, 1 equiv) in DMSO (600 mL) and MeOH (100 mL) was added 2-aminopyridine-3-carbaldehyde (8.97 g, 73.4 mmol, 1.1 equiv) and the mixture was stirred until the solids were dissolved. $Na_2S_2O_4$ (25.57 g, 146.9 mmol, 2.2 equiv) was added and the mixture was stirred at 100° C. overnight. The product was precipitated by the addition of $H_2O$. The precipitated solids were collected by filtration and washed with $H_2O$ (3×500 ml). The residue was purified by silica gel column chromatography eluting with $CH_2Cl_2$/MeOH (10:1) to afford tert-butyl N-[(1S)-5-[2-(2-amino-pyridin-3-yl)-5-bromoimidazo[4,5-b]pyridin-3-yl]-2,3-dihydro-1H-inden-1-yl]carbamate (Intermediate 85-1) (15 g, 36%) as a yellow solid. MS (ESI) calcd. for $C_{25}H_{25}BrN_6O2$, 520.12 m/z, found: 521.20 $[M+H]^+$.

Example 86: (S)-1-(4-((5-(2-(2-aminopyridin-3-yl)-5-morpholino-3H-imidazo[4,5-b]pyridin-3-yl)-2,3-dihydro-1H-inden-1-yl)amino)piperidin-1-yl)prop-2-en-1-one Example 86

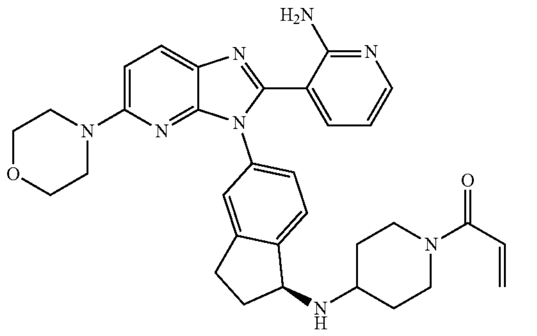

Example 86 was prepared in a manner analogous to Example 13 using Intermediate 86-2 in place of Intermediate 1-1, 1,2-dichloroethane/methanol (10:1) in place of 1,2-dichloroethane and a reaction time and temperature of 5 h at 70° C. instead of overnight at 40° C. MS (ESI) calcd. for $C_{32}H_{36}N_8O_2$, 564.30 m/z, found 565.25 $[M+H]^+$. $^1H$ NMR (300 MHz, DMSO-$d_6$) δ (ppm): 8.00-8.07 (m, 2H), 7.69-7.72 (m, 1H), 7.60-7.63 (m, 1H), 7.40-7.47 (m, 1H), 7.36-7.39 (m, 1H), 6.97-7.00 (m, 1H), 6.70-6.89 (m, 2H), 6.10-6.20 (m, 1H), 5.74-5.78 (m, 1H), 4.97-5.01 (m, 1H), 4.45-4.55 (m, 1H), 4.15-4.25 (m, 1H), 3.60-3.70 (m, 4H), 3.50-3.59 (m, 1H), 3.40-3.49 (m, 4H), 3.05-3.15 (m, 2H), 2.86-2.98 (m, 1H), 2.70-2.84 (m, 1H), 2.53-2.55 (m, 1H), 2.05-2.31 (m, 3H), 1.55-1.75 (m, 2H). (TFA salt).

Intermediate 86-2: (S)-3-(3-(1-amino-2,3-dihydro-1H-inden-5-yl)-5-morpholino-3H-imidazo[4,5-b]pyridin-2-yl)pyridin-2-amine Example 86-2

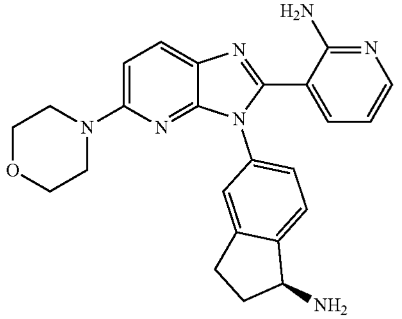

Synthetic Route:

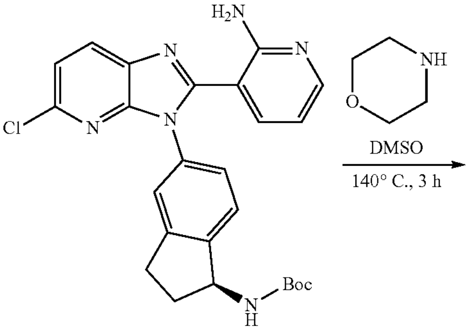

Intermediate 86-1

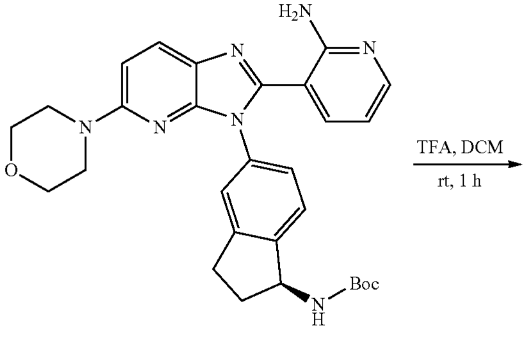

-continued

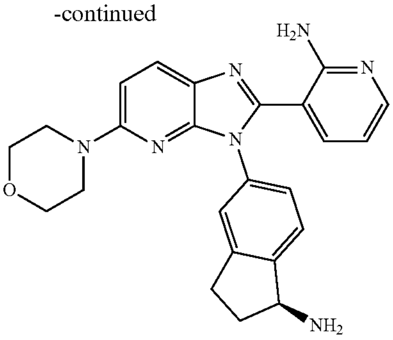

Intermediate 86-2

Step 1: Synthesis of tert-butyl (S)-(5-(2-(2-aminopyridin-3-yl)-5-morpholino-3H-imidazo[4,5-b]pyridin-3-yl)-2,3-dihydro-1H-inden-1-yl)carbamate tert-Butyl (S)-(5-(2-(2-aminopyridin-3-yl)-5-chloro-3H-imidazo[4,5-b]pyridin-3-yl)-2,3-dihydro-1H-inden-1-yl) carbamate (Intermediate 86-1) (2.00 g, 4.19 mmol) was dissolved in DMSO (30 mL). Then morpholine (1.46 g, 16.8 mmol) was added and the mixture was stirred for 3 h at 140° C. The residue was purified by reverse-phase flash chromatography on C18 silica gel using a gradient of acetonitrile in water (+0.05 mmol/L ammonium bicarbonate) to afford tert-butyl (S)-(5-(2-(2-aminopyridin-3-yl)-5-morpholino-3H-imidazo[4,5-b]pyridin-3-yl)-2,3-dihydro-1H-inden-1-yl)carbamate (1 g, 41% yield) as a brown solid. MS (ESI) calcd. for $C_{29}H_{33}N_7O_3$, 527.26 m/z, found 528.30 $[M+H]^+$.

Step 2: Synthesis of (S)-3-(3-(1-amino-2,3-dihydro-1H-inden-5-yl)-5-morpholino-3H-imidazo[4,5-b]pyridin-2-yl)pyridin-2-amine (Intermediate 86-2 tert-Butyl (S)-(5-(2-(2-aminopyridin-3-yl)-5-morpholino-3H-imidazo[4,5-b]pyridin-3-yl)-2,3-dihydro-1H-inden-1-yl)carbamate (500 mg, 1.05 mmol) was dissolved in DCM (15 mL). TFA (3 mL) was added and the mixture was stirred for 1 h at room temperature. The resulting mixture was concentrated under reduced pressure to afford (S)-3-(3-(1-amino-2,3-dihydro-1H-inden-5-yl)-5-morpholino-3H-imidazo[4,5-b]pyridin-2-yl)pyridin-2-amine (Intermediate 86-2) (400 mg, 99% yield) as a brown oil. MS (ESI) calcd. for $C_{24}H_{25}N_7O$, 427.21 m/z, found 428.25 $[M+H]^+$.

Intermediate 86-1: tert-butyl (S)-(5-(2-(2-aminopyridin-3-yl)-5-chloro-3H-imidazo[4,5-b]pyridin-3-yl)-2,3-dihydro-1H-inden-1-yl)carbamate Intermediate 86-1

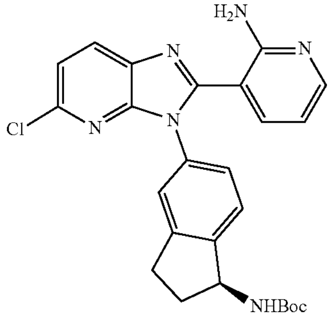

Synthetic Route:

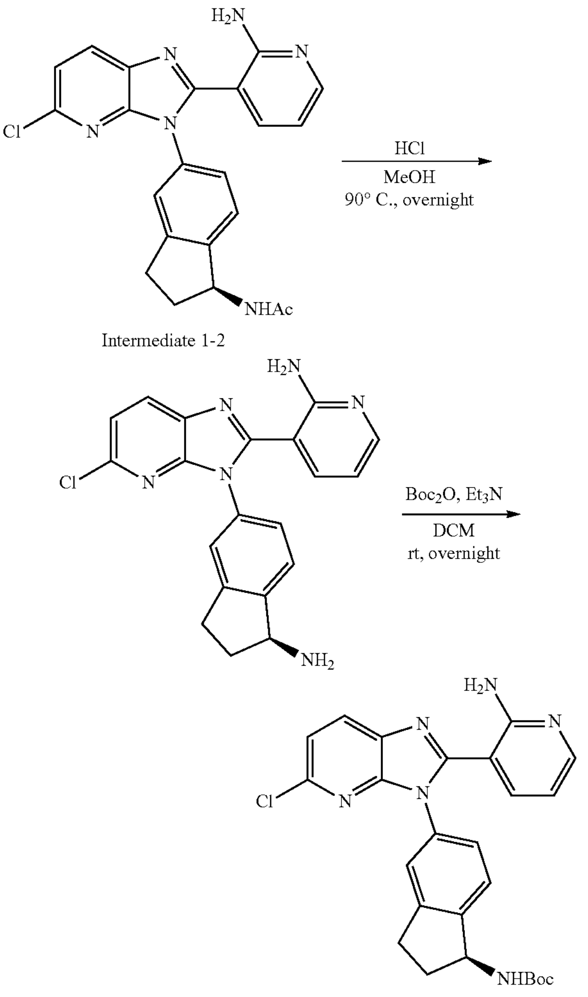

Intermediate 1-2

Intermediate 86-1

Step 1: Synthesis of (S)-3-(3-(1-amino-2,3-dihydro-1H-inden-5-yl)-5-chloro-3H-imidazo[4,5-b]pyridin-2-yl)pyridin-2-amine (S)-N-(5-(2-(2-aminopyridin-3-yl)-5-chloro-3H-imidazo[4,5-b]pyridin-3-yl)-2,3-dihydro-1H-inden-1-yl)acetamide (Intermediate 1-2) (200 mg, 0.478 mmol, 1 equiv) was dissolved in methanol (10 mL) and hydrochloric acid (10 mL, conc.) was added. The resulting mixture was stirred overnight at 90° C. The mixture was then cooled to room temperature and concentrated in vacuo to afford crude (S)-3-(3-(1-amino-2,3-dihydro-1H-inden-5-yl)-5-chloro-3H-imidazo[4,5-b]pyridin-2-yl)pyridin-2-amine as a yellow solid, which was used directly in the next step without further purification. MS (ESI) calculated for $C_{20}H_{17}ClN_6$: 376.12 m/z, found 377.15 $[M+H]^+$.

Step 2: Synthesis of tert-butyl (S)-(5-(2-(2-aminopyridin-3-yl)-5-chloro-3H-imidazo[4,5-b]pyridin-3-yl)-2,3-dihydro-1H-inden-1-yl)carbamate (Intermediate 86-1

Crude (S)-3-(3-(1-amino-2,3-dihydro-1H-inden-5-yl)-5-chloro-3H-imidazo[4,5-b]pyridin-2-yl)pyridin-2-amine was dissolved in dichloromethane (10 mL). di-tert-Butyl dicarbonate (148 mg, 0.678 mmol, 1.5 equiv) was added followed by triethylamine (137 mg, 1.36 mmol, 3 equiv) and the resulting mixture was stirred at room temperature for 2 h. The reaction was quenched by the addition of water (10 mL). The resulting mixture was extracted with ethyl acetate (3×20 mL). The organic layers were combined, dried over anhydrous sodium sulfate, filtered, and concentrated in vacuo. The residue obtained was purified by silica gel column chromatography eluting with dichloromethane/methanol (10:1) to afford tert-butyl (S)-(5-(2-(2-aminopyridin-3-yl)-5-chloro-3H-imidazo[4,5-b]pyridin-3-yl)-2,3-dihydro-1H-inden-1-yl)carbamate (Intermediate 86-1) (180 mg, 80% over two steps) as a yellow solid. MS (ESI) calculated for $C_{25}H_{25}ClN_6O_2$: 476.17 m/z, found 477.20 $[M+H]^+$.

Example 87: 1-((2S,4*,6R)-4-(((R)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2,6-dimethylpiperidin-1-yl)prop-2-en-1-one and Example 88: 1-((2S,4*,6R)-4-(((R)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2,6-dimethylpiperidin-1-yl)prop-2-en-1-one Example 87

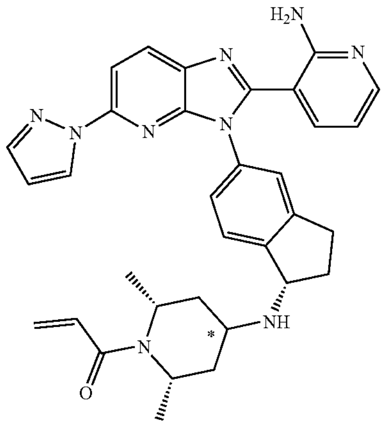

Example 88

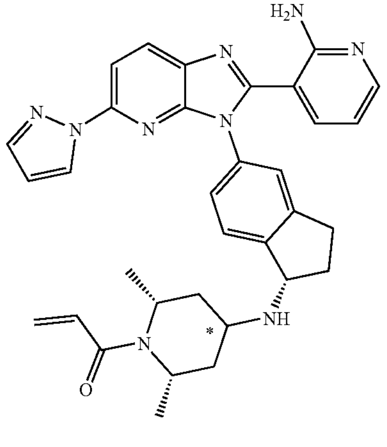

Examples 87 and 88 were prepared in a manner analogous to Example 14 (via Intermediate 14-1) starting from tert-butyl (2R,6S)-2,6-dimethyl-4-oxopiperidine-1-carboxylate in place of tert-butyl 8-oxo-3-azabicyclo[3.2.1]octane-3-carboxylate, using 10:1 1,2-dichloroethane/methanol in place of 1,2-dichloroethane and a reaction time of 4 h for the final step. The diastereomers were separated by chiral Prep-HPLC on a CHIRALPAK IC3 column using a mixture of [MTBE (+0.1% diethylamine)] and [methanol/dichloromethane (1:1)]. * Denotes a stereocenter with undetermined absolute stereochemistry of a single diastereomer.

Example 87: MS (ESI) calcd. for $C_{33}H_{35}N_9O$: 573.30 m/z, found: 574.35 $[M+H]^+$. H-NMR (400 MHz, DMSO-$d_6$) δ (ppm): 8.25-8.33 (m, 2H), 7.85-7.99 (m, 2H), 7.72-7.80 (m, 1H), 7.39-7.45 (m, 1H), 7.12-7.29 (m, 3H), 6.62-6.75 (m, 1H), 6.45-6.55 (m, 1H), 6.38-6.44 (m, 1H), 6.01-6.12 (m, 1H), 5.60-5.70 (m, 1H), 4.20-4.40 (m, 3H), 2.85-2.98 (m, 1H), 2.62-2.82 (m, 2H), 2.30-2.42 (m, 1H), 2.05-2.25 (m, 2H), 1.65-1.75 (m, 1H), 1.32-1.45 (m, 2H), 1.20-1.30 (m, 6H).

Example 88: MS (ESI) calcd. for $C_{33}H_{35}N_9O$: 573.30 m/z, found: 574.25 $[M+H]^+$. H-NMR (400 MHz, DMSO-$d_6$) δ (ppm): 8.28-8.38 (m, 2H), 7.96-8.05 (m, 1H), 7.89-7.95 (m, 1H), 7.75-7.82 (m, 1H), 7.42-7.51 (m, 1H), 7.28-7.35 (m, 1H), 7.18-7.27 (m, 2H), 6.70-6.82 (m, 1H), 6.49-6.58 (m, 1H), 6.40-6.48 (m, 1H), 6.02-6.15 (m, 1H), 5.62-5.72 (m, 1H), 4.60-4.75 (m, 1H), 4.28-4.42 (m, 2H), 3.95-4.09 (m, 1H), 3.15-3.25 (m, 1H), 2.92-3.05 (m, 1H), 2.70-2.85 (m, 1H), 2.38-2.45 (m, 1H), 1.78-1.90 (m, 2H), 1.30-1.50 (m, 2H), 1.10-1.29 (m, 6H).

Example 89: N-((1*,3*)-3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)cyclobutyl)acrylamide and Example 90: N-((1*,3*)-3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)cyclobutyl)acrylamide Example 89

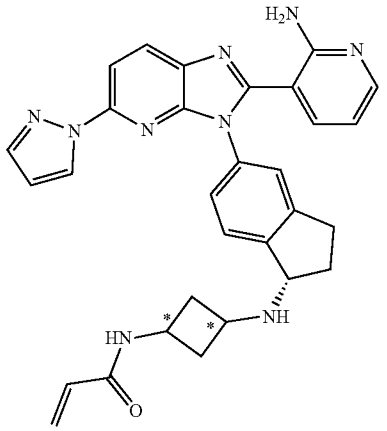

-continued

Example 90

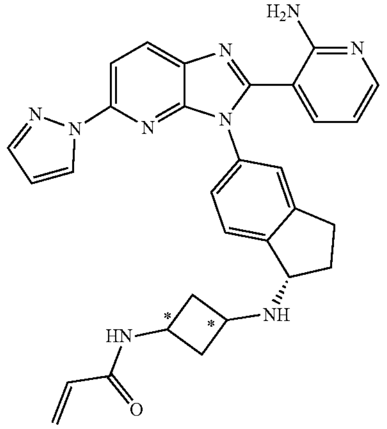

Examples 89 and 90 were prepared in a manner analogous to Example 14 (via Intermediate 14-1, starting from the second step) using 3-aminocyclobutan-1-one in place 3-azabicyclo[3.2.1]octan-8-one, using 10:1 1,2-dichloroethane/methanol in place of 1,2-dichloroethane and a reaction time and temperature of 7 h at room temperature. The diastereomers were separated by chiral Prep-HPLC on a CHIRALPAK IF column using a mixture of MTBE and [methanol/dichloromethane (1:1)]. * Denotes a stereocenter with undetermined absolute stereochemistry of a single diastereomer.

Example 89: MS (ESI) calcd. for $C_{30}H_{29}N_9O$: 531.25 m/z, found: 532.15 $[M+H]^+$. $^1H$ NMR (300 MHz, DMSO-$d_6$) δ (ppm): 8.25-8.38 (m, 3H), 7.92-8.01 (m, 2H), 7.80-7.84 (m, 1H), 7.42-7.48 (m, 1H), 7.30-7.37 (m, 1H), 7.21-7.29 (m, 2H), 6.93-7.01 (m, 2H), 6.51-6.55 (m, 1H), 6.38-6.43 (m, 1H), 6.12-6.21 (m, 1H), 6.02-6.09 (m, 1H), 5.53-5.59 (m, 1H), 4.18-4.22 (m, 1H), 3.81-3.91 (m, 1H), 3.51-3.63 (m, 2H), 2.99-3.10 (m, 1H), 2.90-2.98 (m, 1H), 2.72-2.81 (m, 1H), 2.51-2.58 (m, 1H), 2.29-2.38 (m, 1H), 1.73-1.82 (m, 1H), 1.60-1.70 (m, 2H).

Example 90: MS (ESI) calcd. for $C_{30}H_{29}N_9O$: 531.25 m/z, found: 532.15 $[M+H]^+$. $^1H$ NMR (300 MHz, DMSO-$d_6$) δ (ppm): 8.31-8.45 (m, 3H), 7.94-8.01 (m, 2H), 7.81-7.84 (m, 1H), 7.45-7.49 (m, 1H), 7.31-7.34 (m, 1H), 7.19-7.28 (m, 2H), 6.93-6.99 (m, 2H), 6.52-6.54 (m, 1H), 6.38-6.43 (m, 1H), 6.17-6.27 (m, 1H), 6.02-6.09 (m, 1H), 5.51-5.57 (m, 1H), 4.21-4.28 (m, 1H), 4.12-4.18 (m, 1H), 3.51-3.61 (m, 2H), 2.89-2.99 (m, 1H), 2.71-2.82 (m, 1H), 2.29-2.38 (m, 1H), 2.03-2.17 (m, 4H), 1.72-1.82 (m, 1H).

Example 91: 1-((*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-azaspiro[3.4]octan-2-yl)prop-2-en-1-one and Example 92: 1-((*)-6-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-azaspiro[3.4]octan-2-yl)prop-2-en-1-one Example 91

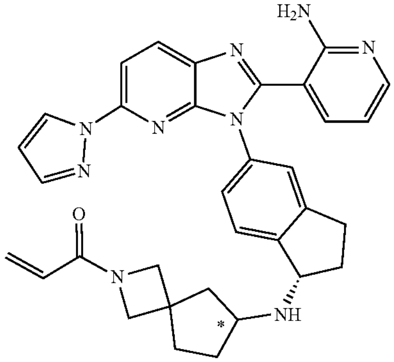

Example 92

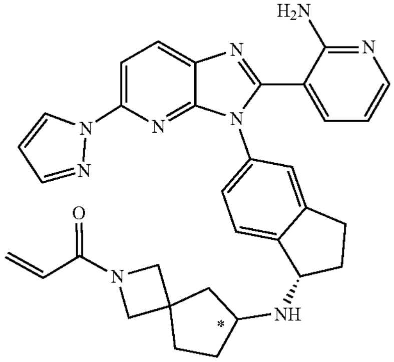

Examples 91 and 92 were prepared in a manner analogous to Example 14 (via Intermediate 14-1) using tert-butyl 6-oxo-2-azaspiro[3.4]octane-2-carboxylate in place tert-butyl 8-oxo-3-azabicyclo[3.2.1]octane-3-carboxylate. The diastereomers were separated by chiral Prep-HPLC on a CHIRALPAK AD column using a mixture of [hexanes+0.5% 2M $NH_3$-methanol] and [methanol/ethanol (1:1)]. * Denotes a stereocenter with undetermined absolute stereochemistry of a single diastereomer.

Example 91: MS (ESI) calcd. for $C_{33}H_{33}N_9O$, 571.28 m/z, found 572.35 $[M+H]^+$. $^1H$ NMR (400 MHz, DMSO-$d_6$) δ (ppm): 8.30-8.35 (m, 2H), 7.96-8.02 (m, 1H), 7.90-7.93 (m, 1H), 7.80 (s, 1H), 7.48-7.52 (m, 1H), 7.24-7.30 (m, 2H), 7.16-7.19 (m, 1H), 6.46-6.54 (m, 2H), 6.25-6.30 (m, 1H), 6.12-6.16 (m, 1H), 5.72-5.75 (m, 1H), 4.14-4.21 (m, 2H), 4.04-4.06 (m, 1H), 3.85-3.90 (m, 1H), 3.80-3.81 (m, 1H), 3.21-3.35 (m, 1H), 2.90-3.04 (m, 1H), 2.72-2.80 (m, 1H), 2.33-2.41 (m, 1H), 2.10-2.15 (m, 1H), 1.73-2.01 (m, 4H), 1.61-1.69 (m, 1H), 1.40-1.53 (m, 1H).

Example 92: MS (ESI) calcd. for $C_{33}H_{33}N_9O$, 571.28 m/z, found 572.35 $[M+H]^+$. $^1H$ NMR (400 MHz, DMSO-$d_6$) δ (ppm): 8.33-8.38 (m, 2H), 7.92-8.02 (m, 2H), 7.81 (s, 1H), 7.50-7.54 (m, 1H), 7.27-7.31 (m, 2H), 7.18-7.21 (m, 1H), 6.48-6.56 (m, 2H), 6.26-6.32 (m, 1H), 6.11-6.16 (m, 1H), 5.72-5.76 (m, 1H), 4.14-4.21 (m, 2H), 4.04-4.06 (m, 1H), 3.80-3.90 (m, 2H), 3.21-3.45 (m, 1H), 2.90-3.03 (m, 1H), 2.72-2.81 (m, 1H), 2.33-2.42 (m, 1H), 2.11-2.15 (m, 1H), 1.93-1.95 (m, 2H), 1.79-1.84 (m, 2H), 1.61-1.69 (m, 1H), 1.40-1.53 (m, 1H).

Example 93: 1-((*)-8-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-5-azaspiro[3.5]nonan-5-yl)prop-2-en-1-one and Example 94: 1-((*)-8-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-5-azaspiro[3.5]nonan-5-yl)prop-2-en-1-one Example 93

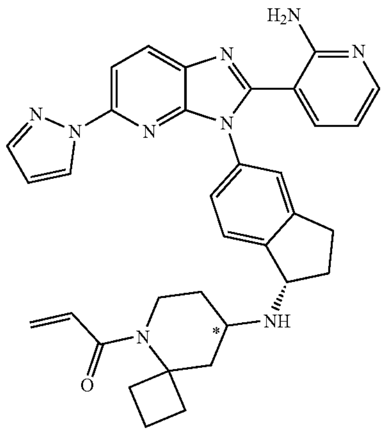

Example 94

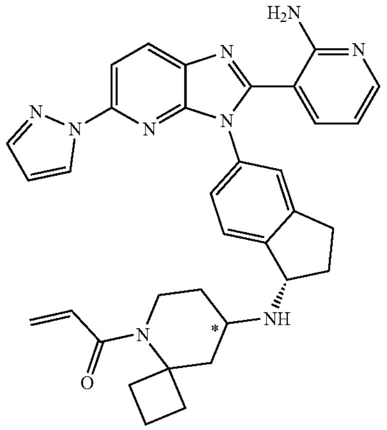

Examples 93 and 94 were prepared in a manner analogous to Example 14 (via Intermediate 14-1) using tert-butyl 8-oxo-5-azaspiro[3.5]nonane-5-carboxylate in place tert-butyl 8-oxo-3-azabicyclo[3.2.1]octane-3-carboxylate and 1,2-dichloroethane/methanol (10:1) as the solvent for the final step. The diastereomers were separated by chiral Prep-HPLC on a CHIRALPAK SC column using a mixture of [MTBE+0.5% 2M $NH_3$-MeOH] and [methanol/ethanol (1:1)]. * Denotes a stereocenter with undetermined absolute stereochemistry of a single diastereomer.

Example 93: MS (ESI) calcd. for $C_{34}H_{35}N_9O$: 585.30 m/z, found: 586.35 $[M+H]^+$. $^1$H-NMR (400 MHz, DMSO-$d_6$) δ (ppm): 8.29-8.39 (m, 2H), 7.98-8.02 (m, 1H), 7.91-7.97 (m, 1H), 7.76-7.85 (m, 1H), 7.42-7.50 (m, 1H), 7.28-7.35 (m, 1H), 7.17-7.27 (m, 2H), 6.51-6.70 (m, 2H), 6.36-6.45 (m, 1H), 5.98-6.01 (m, 1H), 5.58-5.65 (m, 1H), 4.28-4.38 (m, 1H), 2.65-3.05 (m, 4H), 2.35-2.54 (m, 3H), 2.01-2.22 (m, 3H), 1.81-2.00 (m, 2H), 1.55-1.80 (m, 3H), 1.38-1.50 (m, 1H), 1.85-1.00 (m, 1H).

Example 94: MS (ESI) calcd. for $C_{34}H_{35}N_9O$: 585.30 m/z, found: 586.35 $[M+H]^+$. $^1$H-NMR (400 MHz, DMSO-$d_6$) δ (ppm): 8.29-8.38 (m, 2H), 7.96-8.01 (m, 1H), 7.89-7.95 (m, 1H), 7.76-7.82 (m, 1H), 7.44-7.52 (m, 1H), 7.26-7.34 (m, 1H), 7.18-7.25 (m, 2H), 6.56-6.70 (m, 1H), 6.51-6.55 (m, 1H), 6.38-6.45 (m, 1H), 5.98-6.05 (m, 1H), 5.58-5.68 (m, 1H), 4.28-4.38 (m, 1H), 2.68-3.09 (m, 4H), 2.35-2.52 (m, 3H), 2.19-2.34 (m, 1H), 2.01-2.18 (m, 2H), 1.58-1.95 (m, 5H), 1.33-1.45 (m, 1H), 0.85-1.01 (m, 1H).

Example 95: (S,E)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidin-1-yl)-4,4-dimethylpent-2-en-1-one Example 95

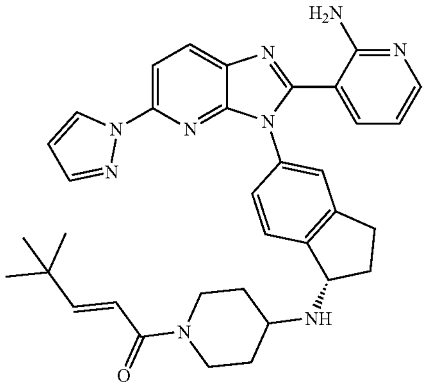

Example 95 was prepared in a manner analogous to Example 83 (starting at Step 2) using piperidin-4-one in place of 2-azaspiro[3.3]heptan-6-one, TCFH/NMI in place of PyBOP/DIPEA, (E)-4,4-dimethylpent-2-enoic acid in place of 2-fluoroacrylic acid, 1,2-dichloroethane/methanol (1:1) in place of 1,2-dichloroethane and a reaction time and temperature of 50° C. and 2 h for the final step. MS (ESI) calcd. for $C_{35}H_{39}N_9O_3$, 601.33 m/z, found: 602.35 $[M+H]^+$. $^1$H-NMR (400 MHz, DMSO-$d_6$) δ (ppm): 8.43-8.45 (m, 1H), 8.36-8.37 (m, 1H), 8.08-8.09 (m, 1H), 8.01-8.03 (m, 1H), 7.84-7.85 (m, 1H), 7.72-7.74 (m, 2H), 7.68-7.70 (m, 1H), 7.44-7.46 (m, 1H), 6.71-6.75 (m, 2H), 6.58-6.71 (m, 1H), 6.31-6.35 (m, 1H), 4.99-5.03 (m, 1H), 4.44-4.64 (m, 1H), 4.12-4.32 (m, 1H), 3.51-3.56 (m, 1H), 3.17-3.21 (m, 2H), 2.98-3.02 (m, 1H), 2.68-2.70 (m, 1H), 2.60-2.61 (m, 1H), 2.54-2.58 (m, 2H), 2.00-2.10 (m, 1H), 1.50-1.60 (m, 2H), 1.07 (s, 9H). (TFA salt).

Example 96: (S,E)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidin-1-yl)but-2-en-1-one Example 96

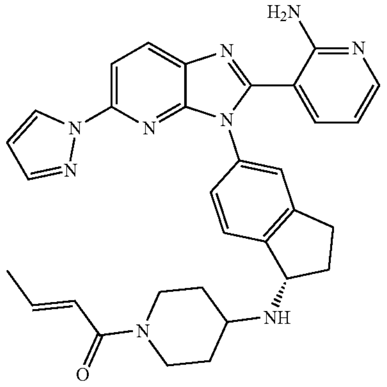

Example 96 was prepared in a manner analogous to Example 14 (via Intermediate 14-1, starting from Step 2) using piperidin-4-one in place of 3-azabicyclo[3.2.1]octan-8-one, 1,2-dichloroethane/methanol (10:1) instead of 1,2-dichloroethane and a reaction time and temperature of 3 h at room temperature for the final step. MS (ESI) calcd. for $C_{32}H_{33}N_9O$, 559.28 m/z, found 560.25 $[M+H]^+$. $^1H$ NMR (400 MHz, DMSO-$d_6$) δ (ppm): 8.31-8.37 (m, 2H), 7.97-7.99 (m, 1H), 7.92-7.94 (m, 1H), 7.76-7.79 (m, 1H), 7.45-7.78 (m, 1H), 7.30-7.32 (m, 1H), 7.22-7.24 (m, 2H), 6.59-6.72 (m, 1H), 6.46-6.54 (m, 2H), 6.43 (m, 1H), 4.32-4.52 (m, 2H), 3.99-4.12 (m, 1H), 3.08-3.17 (m, 1H), 2.73-3.01 (m, 4H), 2.72-2.75 (m, 1H), 1.65-2.15 (m, 6H), 1.01-1.35 (m, 2H).

Example 97: 1-((*)-3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)azepan-1-yl)prop-2-en-1-one and Example 98: 1-((*)-3-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)azepan-1-yl)prop-2-en-1-one Example 97

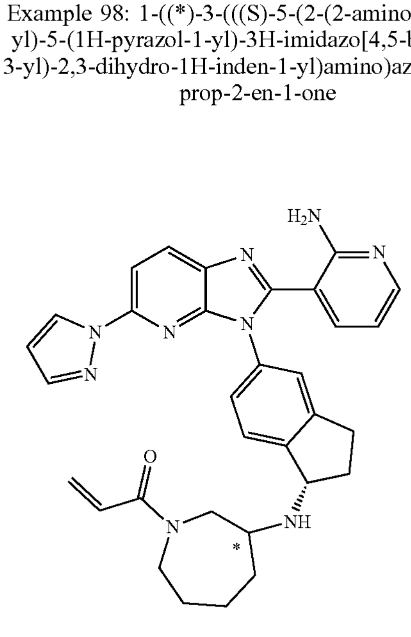

-continued

Example 98

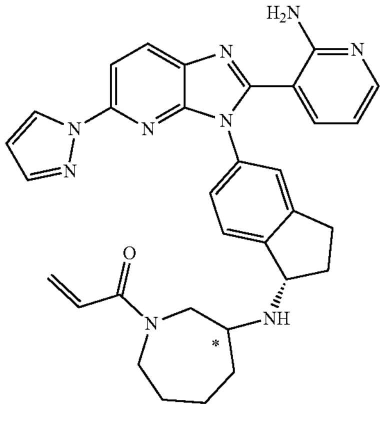

Examples 97 and 98 were prepared in a manner analogous to Example 14 (via Intermediate 14-1) using tert-butyl 3-oxoazepane-1-carboxylate in place tert-butyl 8-oxo-3-azabicyclo[3.2.1]octane-3-carboxylate. The diastereomers were separated by chiral Prep-HPLC on a CHIRALPAK SB column using a mixture of [MTBE+0.5% 2M $NH_3$-MeOH] and [dichloromethane/ethanol (1:1)]. * Denotes a stereocenter with undetermined absolute stereochemistry of a single diastereomer.

Example 97: MS (ESI) calcd. for $C_{32}H_{33}N_9O$, 559.28 m/z, found 560.15 $[M+H]^+$. $^1H$ NMR (400 MHz, DMSO-d6) δ ppm: 8.20-8.49 (m, 2H), 7.84-8.12 (m, 2H), 7.66-7.84 (m, 1H), 7.40-7.62 (m, 1H), 7.08-7.40 (m, 3H), 6.66-6.89 (m, 1H), 6.51-6.64 (m, 1H), 6.36-6.51 (m, 1H), 6.02-6.31 (m, 1H), 5.56-5.86 (m, 1H), 4.23-4.51 (m, 1H), 3.95-4.12 (m, 1H), 3.38-3.55 (m, 1H), 3.18-3.38 (m, 1H), 2.81-3.16 (m, 2H), 2.72-2.81 (m, 1H), 2.42-2.51 (m, 1H), 1.68-1.90 (m, 4H), 1.51-1.68 (m, 1H), 1.31-1.51 (m, 1H), 1.06-1.31 (m, 2H).

Example 98: MS (ESI) calcd. for $C_{32}H_{33}N_9O$, 559.28 m/z, found 560.15 $[M+H]^+$. $^1H$ NMR (400 MHz, DMSO-d6) δ ppm: 8.20-8.49 (m, 2H), 7.97-8.12 (m, 1H), 7.84-7.97 (m, 1H), 7.66-7.84 (m, 1H), 7.38-7.66 (m, 1H), 7.29-7.39 (m, 1H) 7.08-7.29 (m, 2H), 6.64-6.94 (m, 1H), 6.51-6.64 (m, 1H), 6.32-6.51 (m, 1H), 6.02-6.32 (m, 1H), 5.56-5.86 (m, 1H), 4.21-4.47 (m, 1H), 3.95-4.21 (m, 1H), 3.58-3.80 (m, 1H), 3.09-3.21 (m, 1H), 2.85-3.01 (m, 2H), 2.67-2.85 (m, 1H), 2.34-2.49 (m, 1H), 1.68-1.97 (m, 4H), 1.38-1.68 (m, 2H), 1.10-1.38 (m, 2H).

Example 99: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methylpiperidin-1-yl)prop-2-en-1-one Example 100: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methylpiperidin-1-yl)prop-2-en-1-one Example 101: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methylpiperidin-1-yl)prop-2-en-1-one and Example 102: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methylpiperidin-1-yl)prop-2-en-1-one Example 99

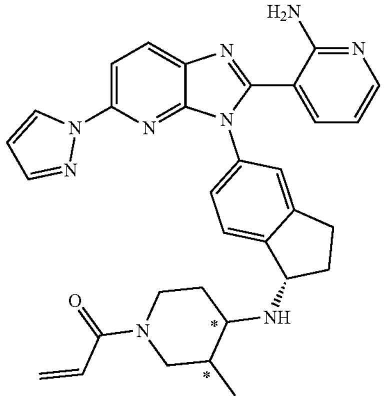

Example 100

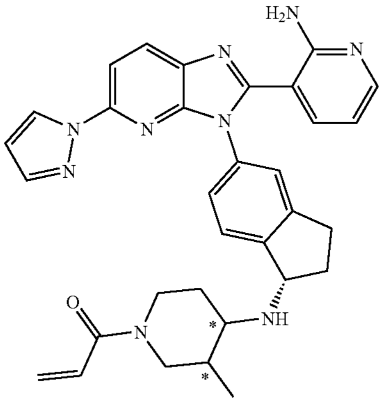

-continued

Example 101

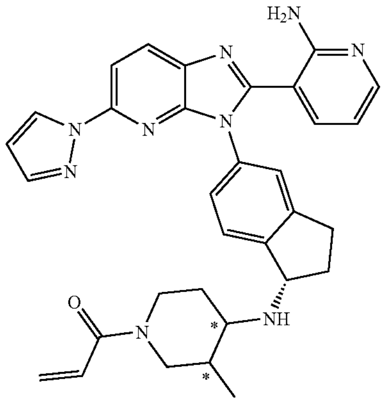

Example 102

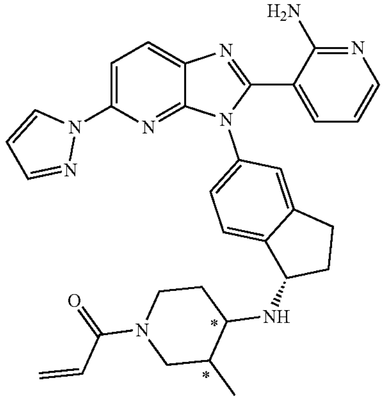

Examples 99, 100, 101, and 102 were prepared in a manner analogous to Example 14 (via Intermediate 14-1) using (R)-3-methyl-4-oxopiperidine-1-carboxylate in place tert-butyl 8-oxo-3-azabicyclo[3.2.1]octane-3-carboxylate. Note that the methyl stereocenter epimerized under the reaction conditions giving four stereoisomeric products. The diastereomers partially separated during reverse phase Prep-HPLC on a XBridge Prep OBD C18 column using a gradient of acetonitrile in water (+10 mM formic acid). Examples 99 and 101 required further separation by chiral Prep-HPLC on a CHIRALPAK IF column using a mixture of [MTBE+0.5% 2M $NH_3$-MeOH] and [dichloromethane/methanol (1:1)]. Examples 100 and 102 required further separation by chiral Prep-HPLC on a CHIRALPAK IA column using a mixture of [hexanes/dichloromethane (3:1)+0.5% 2M $NH_3$-MeOH] and ethanol. * Denotes a stereocenter with undetermined absolute stereochemistry of a single diastereomer.

Example 99: MS (ESI) calcd. for $C_{32}H_{33}N_9O$: 559.28 m/z, found: 560.15 $[M+H]^+$. $^1H$ NMR (400 MHz, DMSO-$d_6$) δ (ppm): 8.33-8.39 (m, 2H), 8.00-8.03 (m, 1H), 7.94-7.98 (m, 1H), 7.81 (s, 1H), 7.49-7.54 (m, 1H), 7.33 (s, 1H), 7.22-7.29 (m, 2H), 6.76-6.88 (m, 1H), 6.54-6.59 (m, 1H), 6.42-6.48 (m, 1H), 6.05-6.15 (m, 1H), 5.65-5.72 (m, 1H), 3.79-4.38 (m, 3H), 3.24-3.36 (m, 1H), 2.87-3.23 (m, 3H), 2.72-2.86 (m, 1H), 2.39-2.49 (m, 1H), 1.93-2.09 (m, 1H), 1.72-1.89 (m, 1H), 1.41-1.70 (m, 2H), 0.80-0.91 (m, 3H).

Example 100: MS (ESI) calcd. for $C_{32}H_{33}N_9O$: 559.28 m/z, found: 560.15 $[M+H]^+$. $^1H$ NMR (400 MHz, DMSO-$d_6$) δ (ppm): 8.34-8.36 (m, 2H), 8.00-8.06 (m, 1H), 7.93-7.99 (m, 1H), 7.81 (s, 1H), 7.46-7.48 (m, 1H), 7.32 (s, 1H), 7.23-7.25 (m, 2H), 6.76-6.83 (m, 1H), 6.54-6.55 (m, 1H), 6.42-6.45 (m, 1H), 6.07-6.12 (m, 1H), 5.66-5.69 (m, 1H), 4.33-4.36 (m, 1H), 4.25-4.30 (m, 1H), 3.90-4.05 (m, 1H), 2.77-3.15 (m, 4H), 2.41-2.45 (m, 1H), 2.06-2.12 (m, 1H), 1.73-1.74 (m, 1H), 1.39-1.42 (m, 1H), 1.20-1.26 (m, 2H), 0.93-0.98 (m, 3H).

Example 101: MS (ESI) calcd. for $C_{32}H_{33}N_9O$: 559.28 m/z, found: 560.20 $[M+H]^+$. $^1H$ NMR (400 MHz, DMSO-$d_6$) δ (ppm): 8.29-8.42 (m, 2H), 7.98-8.03 (m, 1H), 7.91-7.97 (m, 1H), 7.78-7.83 (m, 1H), 7.44-7.54 (m, 1H), 7.32 (s, 1H), 7.21-7.29 (m, 2H), 6.76-6.92 (m, 1H), 6.52-6.58 (m, 1H), 6.38-6.47 (m, 1H), 6.04-6.16 (m, 1H), 5.64-5.71 (m, 1H), 3.97-4.35 (m, 2H), 3.73-3.96 (m, 1H), 3.14-3.34 (m, 1H), 2.71-3.09 (m, 4H), 2.36-2.48 (m, 1H), 2.03-2.15 (m, 1H), 1.71-1.89 (m, 1H), 1.33-1.68 (m, 2H), 0.77-0.96 (m, 3H).

Example 102: MS (ESI) calcd. for $C_{32}H_{33}N_9O$: 559.28 m/z, found: 560.15 $[M+H]^+$. $^1H$ NMR (400 MHz, DMSO-$d_6$) δ (ppm): 8.29-8.38 (m, 2H), 7.97-8.02 (m, 1H), 7.91-7.96 (m, 1H), 7.78-7.83 (m, 1H), 7.45-7.55 (m, 1H), 7.31 (s, 1H), 7.19-7.27 (m, 2H), 6.76-6.87 (m, 1H), 6.51-6.56 (m, 1H), 6.38-6.45 (m, 1H), 6.04-6.12 (m, 1H), 5.63-5.71 (m, 1H), 4.12-4.29 (m, 2H), 3.87-4.03 (m, 1H), 2.61-3.19 (m, 4H), 2.41-2.50 (m, 1H), 1.92-2.11 (m, 1H), 1.68-1.85 (m, 1H), 1.29-1.49 (m, 1H), 1.07-1.28 (m, 2H), 0.91-0.99 (m, 3H).

Example 103: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoropiperidin-1-yl)prop-2-en-1-one Example 104: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoropiperidin-1-yl)prop-2-en-1-one Example 105: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoropiperidin-1-yl)prop-2-en-1-one and Example 106: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoropiperidin-1-yl)prop-2-en-1-one Example 103

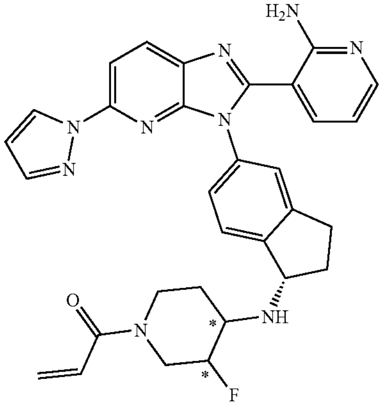

-continued

Example 104

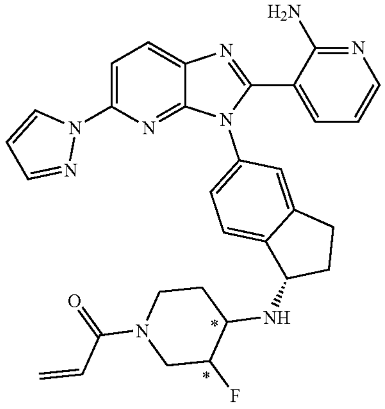

Example 105

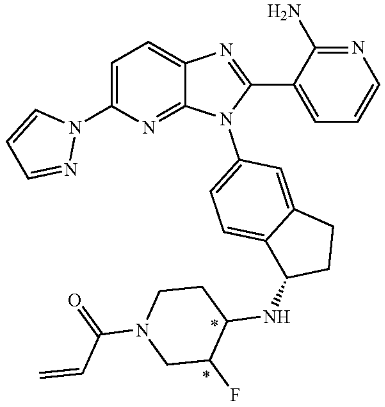

Example 106

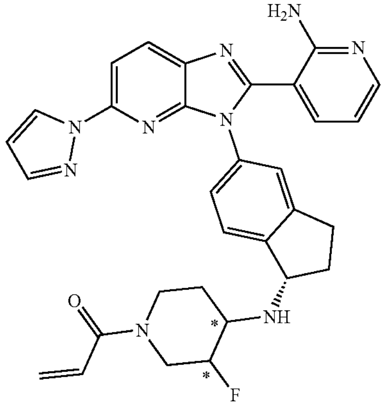

Examples 103, 104, 105, and 106 were prepared in a manner analogous to Example 14 (via Intermediate 14-1) using (3S)-3-fluoro-4-oxopiperidine-1-carboxylate in place tert-butyl 8-oxo-3-azabicyclo[3.2.1]octane-3-carboxylate. Note that the fluoro stereocenter epimerized under the reaction conditions giving four stereoisomeric products. The diastereomers partially separated during reverse phase Prep- HPLC on a XSelect CSH Fluoro Phenyl column using a gradient of acetonitrile in water (+10 mM formic acid). Examples 103 and 104 required further separation by chiral Prep-HPLC on a CHIRALPAK IC3 column using a mixture of [MTBE+0.1% diethylamine] and [dichloromethane/methanol (1:1)]. Examples 105 and 106 required further separation by chiral Prep-HPLC on a CHIRALPAK IA column using a mixture of [hexanes/dichloromethane (3:1)+0.5% 2M $NH_3$-MeOH] and ethanol. * Denotes a stereocenter with undetermined absolute stereochemistry of a single diastereomer.

Example 103: MS (ESI) calcd. for $C_{31}H_{30}FN_9O$: 563.26 m/z, found: 564.30 $[M+H]^+$. $^1$H-NMR (400 MHz, DMSO-d6) δ (ppm): 8.36-8.38 (m, 2H), 8.00-8.01 (m, 1H), 7.94-7.97 (m, 1H), 7.81 (s, 1H), 7.48-7.50 (m, 1H), 7.35 (s, 1H), 7.22-7.28 (m, 2H), 6.96 (s, 2H), 6.77-6.86 (m, 1H), 6.55 (s, 1H), 6.42-6.45 (m, 1H), 6.08-6.13 (m, 1H), 5.67-5.70 (m, 1H), 4.86-5.02 (m, 1H), 4.05-4.72 (m, 3H), 3.16-3.25 (m, 1H), 2.95-3.05 (m, 2H), 2.74-2.83 (m, 1H), 2.43-2.48 (m, 1H), 2.18 (s, 1H), 1.77-1.83 (m, 2H), 1.48-1.62 (m, 1H), 1.38-1.40 (m, 1H). $^{19}$F-NMR (400 MHz, DMSO-d6) δ (ppm): −203.65.

Example 104: MS (ESI) calcd. for $C_{31}H_{30}FN_9O$: 563.26 m/z, found: 564.30 $[M+H]^+$. $^1$H-NMR (400 MHz, DMSO-d6) δ (ppm): 8.36-8.38 (m, 2H), 8.00-8.02 (m, 1H), 7.94-7.97 (m, 1H), 7.81-7.82 (m, 1H), 7.51-7.53 (m, 1H), 7.35 (s, 1H), 7.22-7.27 (m, 2H), 6.96 (s, 2H), 6.76-6.83 (m, 1H), 6.54-6.55 (m, 1H), 6.42-6.45 (m, 1H), 6.08-6.13 (m, 1H), 5.67-5.70 (m, 1H), 4.77-4.93 (m, 1H), 4.41-4.77 (m, 1H), 4.05-4.39 (m, 2H), 2.93-3.21 (m, 3H), 2.75-2.83 (m, 1H), 2.43-2.50 (m, 1H), 2.08-2.18 (m, 1H), 1.76-1.88 (m, 2H), 1.38-1.61 (m, 2H). $^{19}$F-NMR (400 MHz, DMSO-d6) δ (ppm): −202.95.

Example 105: MS (ESI) calcd. for $C_{31}H_{30}FN_9O$: 563.26 m/z, found: 564.30 $[M+H]^+$. $^1$H-NMR (400 MHz, DMSO-d6) δ (ppm): 8.35-8.38 (m, 2H), 8.00-8.02 (m, 1H), 7.94-7.97 (m, 1H), 7.81-7.82 (m, 1H), 7.49-7.52 (m, 1H), 7.35 (s, 1H), 7.23-7.29 (m, 2H), 6.96 (s, 2H), 6.83-6.90 (m, 1H), 6.55-6.56 (m, 1H), 6.42-6.46 (m, 1H), 6.10-6.14 (m, 1H), 5.68-5.71 (m, 1H), 4.38-4.48 (m, 2H), 3.89-4.01 (m, 1H), 3.43-3.83 (m, 3H), 3.10-3.15 (m, 1H), 2.94-2.96 (m, 1H), 2.77-2.81 (m, 1H), 2.32-2.34 (m, 2H), 1.88-2.02 (m, 1H), 1.75-1.80 (m, 1H), 1.52-1.58 (m, 1H). $^{19}$F-NMR (400 MHz, DMSO-d6) δ (ppm): −185.50.

Example 106: MS (ESI) calcd. for $C_{31}H_{30}FN_9O$: 563.26 m/z, found: 564.25 $[M+H]^+$. $^1$H-NMR (400 MHz, DMSO-d6) δ (ppm): 8.35-8.38 (m, 2H), 8.00-8.02 (m, 1H), 7.94-7.96 (m, 1H), 7.81-7.82 (m, 1H), 7.50-7.52 (m, 1H), 7.35 (s, 1H), 7.23-7.29 (m, 2H), 6.95 (s, 2H), 6.81-6.88 (m, 1H), 6.55-6.56 (m, 1H), 6.41-6.44 (m, 1H), 6.10-6.14 (m, 1H), 5.68-5.71 (m, 1H), 4.45-4.65 (m, 1H), 4.36-4.41 (m, 1H), 3.93-4.01 (m, 1H), 3.62-3.80 (m, 2H), 3.45-3.55 (m, 2H), 3.09-3.12 (m, 1H), 2.95-2.99 (m, 1H), 2.76-2.82 (m, 1H), 2.39-2.43 (m, 1H), 1.80-1.98 (m, 2H), 1.47-1.52 (m, 1H). $^{19}$F-NMR (400 MHz, DMSO-d6) δ (ppm): −185.14.

Example 107: 1-(4-{[(1S)-5-[2-(2-aminopyridin-3-yl)-5-[1-(difluoromethyl) pyrazol-3-yl]imidazo[4,5-b]pyridin-3-yl]-2,3-dihydro-1H-inden-1-yl] amino}piperidin-1-yl)prop-2-en-1-one Example 107

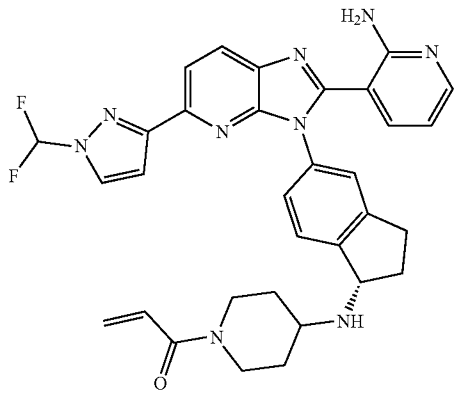

Example 107 was prepared in a manner analogous to Example 13 using 1-(prop-2-enoyl)piperidin-4-one in place of the ketone and Intermediate 107-1 in place of Intermediate 1-1. MS (ESI) calcd. For $C_{32}H_{31}F_2N_9O$, 595.26 m/z, found 596.15 $[M+H]^+$. $^1$H NMR (400 MHz, DMSO-$d_6$) δ ppm: 8.15-8.31 (m, 2H), 7.95-8.12 (m, 2H), 7.66-7.95 (m, 1H), 7.46-7.66 (m, 1H), 7.32-7.46 (m, 1H) 7.08-7.32 (m, 2H), 6.89-7.04 (m, 1H), 6.65-6.89 (m, 1H), 6.31-6.59 (m, 1H), 5.95-6.28 (m, 1H), 5.56-5.86 (m, 1H), 4.46-4.52 (m, 1H), 4.28-4.46 (m, 1H), 3.97-4.28 (m, 1H), 2.95-3.31 (m, 3H), 2.75-2.95 (m, 2H), 2.41-2.55 (m, 1H), 1.96-2.22 (m, 1H), 1.71-1.96 (m, 2H), 1.09-1.52 (m, 2H). (formic acid salt).

Intermediate 107-1: (S)-3-(3-(1-amino-2,3-dihydro-1H-inden-5-yl)-5-(1-(difluoromethyl)-1H-pyrazol-3-yl)-3H-imidazo[4,5-b]pyridin-2-yl)pyridin-2-amine Intermediate 170-1

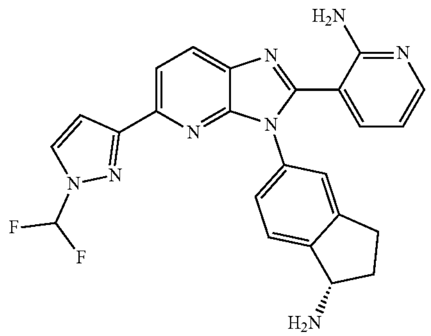

Synthetic Route:

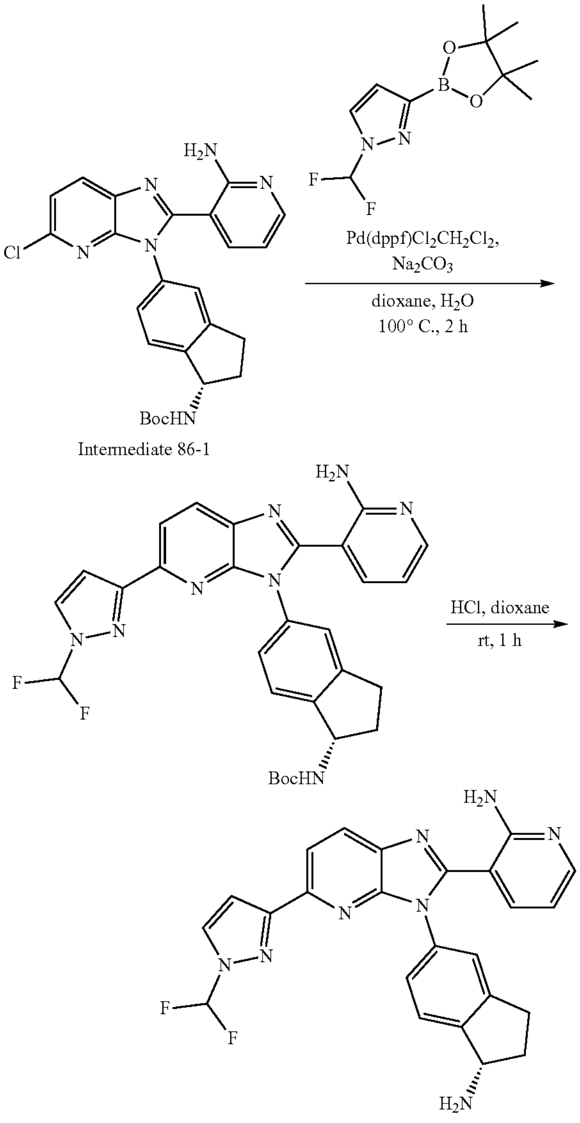

Intermediate 107-1

Step 1: Synthesis of tert-butyl N-[(1S)-5-[2-(2-aminopyridin-3-yl)-5-[1-(difluoromethyl)pyrazol-3-yl]imidazo[4,5-b]pyridin-3-yl]-2,3-dihydro-1H-inden-1-yl]carbamate To a solution of tert-butyl N-[(1S)-5-[2-(2-aminopyridin-3-yl)-5-chloroimidazo[4,5-b]pyridin-3-yl]-2,3-dihydro-1H-inden-1-yl]carbamate (Intermediate 86-1) (2.00 g, 4.19 mmol) in 1,4-dioxane (24 mL) and $H_2O$ (6 mL) were added 1-(difluoromethyl)-3-(4,4,5,5-tetramethyl-1,3,2-dioxaborolan-2-yl)pyrazole (1.23 g, 5.03 mmol), Pd(dppf)$Cl_2CH_2Cl_2$ (0.34 g, 0.42 mmol) and $Cs_2CO_3$ (4.10 g, 12.6 mmol). The resulting mixture was stirred at 100° C. for 2 h under $N_2$. The reaction was quenched by the addition of water (100 mL) at 0° C. The resulting mixture was extracted with ethyl acetate (3×100 mL). The combined organic layers were washed with water (100 mL) and dried over anhydrous $Na_2SO_4$. After filtration, the filtrate was concentrated under vacuum. The residue was purified by silica gel column chromatography using a gradient of ethyl acetate in petroleum ether to afford tert-butyl N-[(1S)-5-[2-(2-aminopyridin-3-yl)-5-[1-(difluoromethyl)pyrazol-3-yl]imidazo[4,5-b]pyridin-3-yl]-2,3-dihydro-1H-inden-1-yl]carbamate (1.5 g, 64%) as a yellow solid. MS (ESI) calcd. for $C_{29}H_{28}F_2N_8O_2$: 558.23 m/z, found: 559.30 $[M+H]^+$.

Step 2: Synthesis of 3-{3-[(1S)-1-amino-2,3-dihydro-1H-inden-5-yl]-5-[1-(difluoromethyl)pyrazol-3-yl]imidazo[4,5-b]pyridin-2-yl}pyridin-2-amine (Intermediate 107-1

A solution of tert-butyl N-[(1S)-5-[2-(2-aminopyridin-3-yl)-5-[1-(difluoromethyl)pyrazol-3-yl]imidazo[4,5-b]pyridin-3-yl]-2,3-dihydro-1H-inden-1-yl]carbamate (1.5 g, 2.7 mmol) in HCl (15 mL, 4 M in 1,4-dioxane) was stirred for 1 h at room temperature. The residue was diluted with water (100 mL), then adjusted to pH 6-7 with sodium bicarbonate. The resulting mixture was extracted with ethyl acetate (3×100 mL). The combined organic layers were washed with water (100 mL) and dried over anhydrous $Na_2SO_4$. After filtration, the filtrate was concentrated under vacuum to afford 3-{3-[(1S)-1-amino-2,3-dihydro-1H-inden-5-yl]-5-[1-(difluoromethyl)pyrazol-3-yl]imidazo[4,5-b]pyridin-2-yl}pyridin-2-amine (Intermediate 107-1) (1 g, 81%) as a yellow solid. MS (ESI) calcd. for $C_{24}H_{20}F_2N_8$, 458.18 m/z, found 459.15 $[M+H]^+$.

Example 108: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-(2-methoxyacrylamido)benzamide Example 108

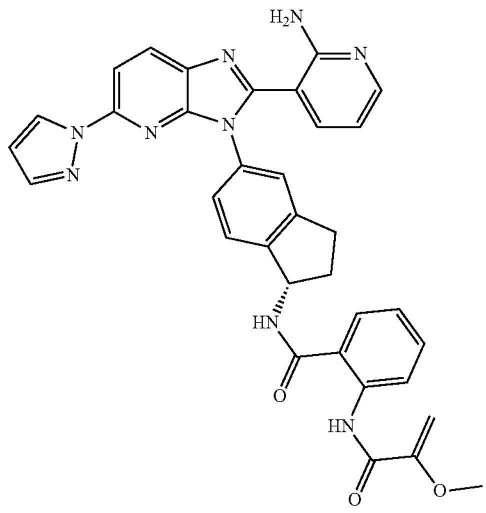

Example 108 was prepared in a manner analogous to Example 1 using Intermediate 5-1 in place of Intermediate 1-1, 2-methoxyacrylate in place of Intermediate 1-3 and 80° C. for 1 h in dichloromethane instead of 70° C. overnight in toluene. MS (ESI) calcd. for $C_{34}H_{29}N_9O_3$, 611.24 m/z, found 612.25 $[M+H]^+$. $^1H$ NMR (300 MHz, DMSO-$d_6$) δ (ppm): 8.44-8.53 (m, 2H), 8.39-8.43 (m, 1H), 8.04-8.12 (m, 1H), 7.99-8.03 (m, 1H), 7.87-7.91 (m, 1H), 7.79-7.86 (m, 2H), 7.58-7.67 (m, 1H), 7.43-7.52 (m, 2H), 7.32-7.41 (m, 1H), 7.23-7.31 (m, 1H), 6.81-6.90 (m, 1H), 6.58-6.64 (m, 1H), 5.59-5.71 (m, 1H), 5.32-5.41 (m, 1H), 4.73-4.82 (m, 1H), 3.73 (s, 3H), 2.89-3.15 (m, 2H), 2.63-2.71 (m, 1H), 2.03-2.19 (m, 1H).

Example 109: (S)-1-(4-((5-(2-(2-aminopyridin-3-yl)-5-(oxazol-2-yl)-3H-imidazo[4,5-b]pyridin-3-yl)-2,3-dihydro-1H-inden-1-yl)amino)piperidin-1-yl)prop-2-en-1-one Example 109

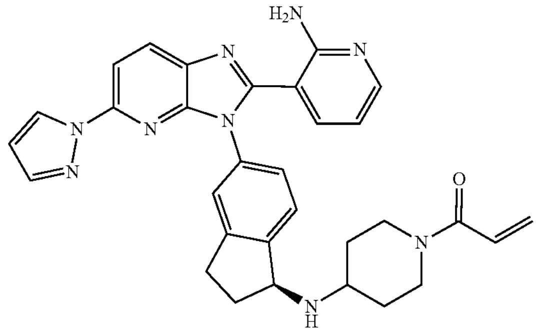

Example 109 was prepared in a manner analogous to Example 13 using Intermediate 109-2 in place of Intermediate 1-1, and methanol+5 eq AcOH instead of 1,2-dichloroethane. MS (ESI) calcd. for $C_{31}H_{30}N_8O_2$, 546.25 m/z, found 547.20 $[M+H]^+$. $^1$H-NMR (400 MHz, DMSO) S (ppm): 8.39-8.46 (m, 1H), 8.18-8.30 (m, 2H), 8.04-8.15 (m, 1H), 7.70-7.84 (m, 2H), 7.53-7.61 (m, 1H), 7.40-7.52 (m, 2H), 6.70-6.90 (m, 2H), 6.10-6.20 (m, 1H), 5.69-5.80 (m, 1H), 4.96-5.10 (m, 1H), 4.48-4.60 (m, 1H), 4.12-4.28 (m, 1H), 3.50-3.61 (m, 1H), 3.08-3.25 (m, 2H), 2.90-3.05 (m, 1H), 2.65-2.80 (m, 1H), 2.55-2.64 (m, 1H), 2.18-2.30 (m, 2H), 2.06-2.17 (m, 1H), 1.43-1.65 (m, 2H).

Intermediate 109-2: 3-{3-[(1S)-1-amino-2,3-dihydro-1H-inden-5-yl]-5-(1,3-oxazol-2-yl)imidazo[4,5-b]pyridin-2-yl}pyridin-2-amine Intermediate 109-2

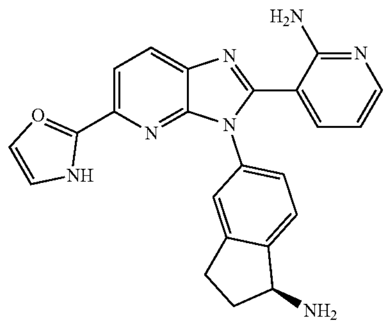

Synthetic Route:

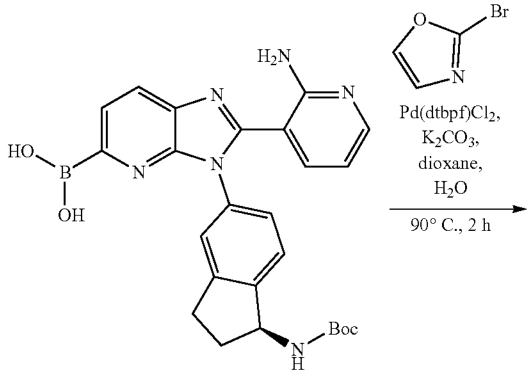

Intermediate 109-1

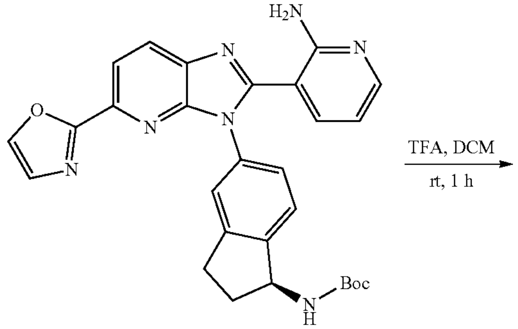

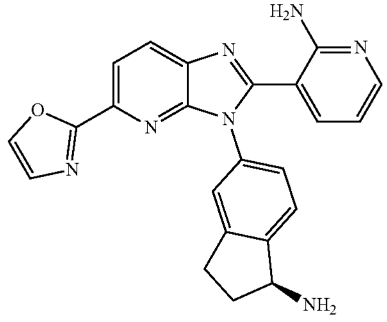

Intermediate 109-2

Step 1: Synthesis of tert-butyl N-[(1S)-5-[2-(2-aminopyridin-3-yl)-5-(1,3-oxazol-2-yl)imidazo[4,5-b]pyridin-3-yl]-2,3-dihydro-1H-inden-1-yl]carbamate To a stirred mixture of 2-(2-aminopyridin-3-yl)-3-[(1S)-1-[(tert-butoxycarbonyl)amino]-2,3-dihydro-1H-inden-5-yl]imidazo[4,5-b]pyridin-5-ylboronic acid (Intermediate 109-1) (300 mg, 0.617 mmol, 1 equiv) in dioxane (6 mL) was added 2-bromo-1,3-oxazole (109.5 mg, 0.740 mmol, 1.2 equiv), $Pd(dtbpf)Cl_2$ (40 mg, 0.062 mmol, 0.1 equiv), $K_2CO_3$ (170.5 mg, 1.234 mmol, 2 equiv) and $H_2O$ (1.5 mL). The resulting mixture was stirred at 90° C. for 2 h under a nitrogen atmosphere. The mixture was purified by reverse phase flash chromatography on C18 silica gel using a gradient of acetonitrile in water (+0.05% $NH_4HCO_3$) to afford tert-butyl N-[(1S)-5-[2-(2-aminopyridin-3-yl)-5-(1,3-oxazol-2-yl)imidazo[4,5-b]pyridin-3-yl]-2,3-dihydro-1H-inden-1-yl]carbamate (230 mg, 73%) as a yellow solid. MS (ESI) calcd. for $C_{28}H_{27}N_7O_3$: 509.22 m/z, found: 510.20 $[M+H]^+$.

Step 2: Synthesis of 3-{3-[(1S)-1-amino-2,3-dihydro-1H-inden-5-yl]-5-(1,3-oxazol-2-yl)imidazo[4,5-b]pyridin-2-yl}pyridin-2-amine (Intermediate 109-2

To a solution of tert-butyl N-[(1S)-5-[2-(2-aminopyridin-3-yl)-5-(1,3-oxazol-2-yl)imidazo[4,5-b]pyridin-3-yl]-2,3-dihydro-1H-inden-1-yl]carbamate (220 mg, 0.432 mmol, 1 equiv) in DCM (6 mL) was added TFA (2 mL) and the resulting mixture was stirred at r.t for 1 h. The mixture was basified to pH 8 with aq. NaOH (2 mol/L). The resulting mixture was extracted with ethyl acetate (2×20 ml). The combined organic layers were concentrated under reduced pressure to afford 3-{3-[(1S)-1-amino-2,3-dihydro-1H-inden-5-yl]-5-(1,3-oxazol-2-yl)imidazo[4,5-b]pyridin-2-yl}pyridin-2-amine (Intermediate 109-2) (200 mg, crude) as a yellow solid. MS (ESI) calcd. for $C_{23}H_{19}N_7O$: 409.17 m/z, found: 410.20 $[M+H]^+$.

Intermediate 109-1: (S)-(2-(2-aminopyridin-3-yl)-3-(1-((tert-butoxycarbonyl)amino)-2,3-dihydro-1H-inden-5-yl)-3H-imidazo[4,5-b]pyridin-5-yl)boronic acid Intermediate 109-1

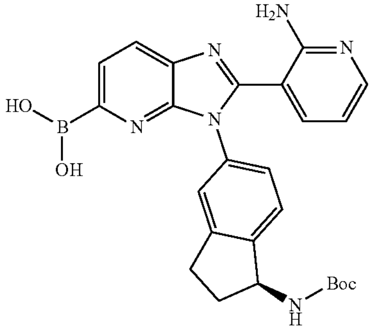

Synthetic Route:

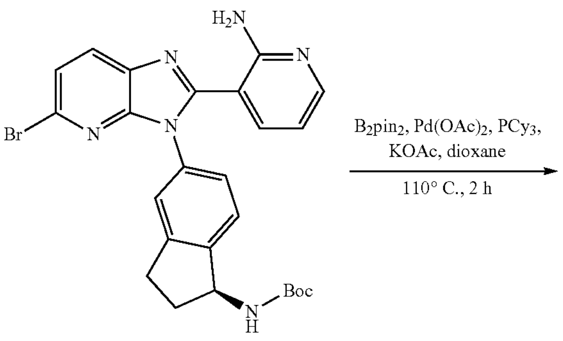

Intermediate 85-1

-continued

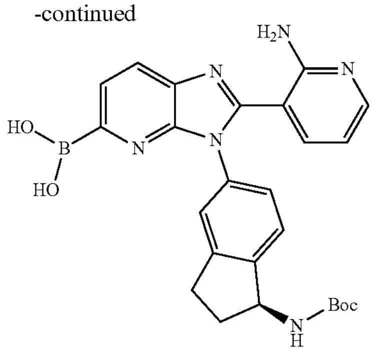

Intermediate 109-1

Step 1: Synthesis of (S)-(2-(2-aminopyridin-3-yl)-3-(1-((tert-butoxycarbonyl)amino)-2,3-dihydro-1H-inden-5-yl)-3H-imidazo[4,5-b]pyridin-5-yl)boronic acid (Intermediate 109-1

To a solution of tert-butyl (S)-(5-(2-(2-aminopyridin-3-yl)-5-bromo-3H-imidazo[4,5-b]pyridin-3-yl)-2,3-dihydro-1H-inden-1-yl)carbamate (Intermediate 85-1) (3 g, 5.8 mmol) and 4,4,5,5-tetramethyl-2-(4,4,5,5-tetramethyl-1,3,2-dioxaborolan-2-yl)-1,3,2-dioxaborolane (1.753 g, 6.905 mmol) in dioxane (30 mL) were added $Pd(OAc)_2$ (77.5 mg, 0.345 mmol), $PCy_3$ (193.6 mg, 0.690 mmol) and KOAc (1.412 g, 14.39 mmol) and the mixture was stirred for 2 h at 110° C. under a nitrogen atmosphere. After cooling to room temperature, the mixture was quenched with water (200 mL). The resulting mixture was extracted with ethyl acetate (3×200 mL). The organic layers were combined, dried over anhydrous sodium sulfate, filtered and concentrated. The crude product was purified by silica gel flash column chromatography (0-15%, MeOH/DCM) to afford (S)-(2-(2-aminopyridin-3-yl)-3-(1-((tert-butoxycarbonyl)amino)-2,3-dihydro-1H-inden-5-yl)-3H-imidazo[4,5-b]pyridin-5-yl) boronic acid (Intermediate 109-1) (1.7 g, 61% yield) as a white solid. MS (ESI) calcd. for $C_{25}H_{27}N_6BO_4$: 486.21 m/z, found 487.25 $[M+H]^+$.

Example 110: (S)-1-(4-((5-(2-(2-aminopyridin-3-yl)-5-(pyridin-3-yl)-3H-imidazo[4,5-b]pyridin-3-yl)-2,3-dihydro-1H-inden-1-yl)amino)piperidin-1-yl)prop-2-en-1-one Example 110

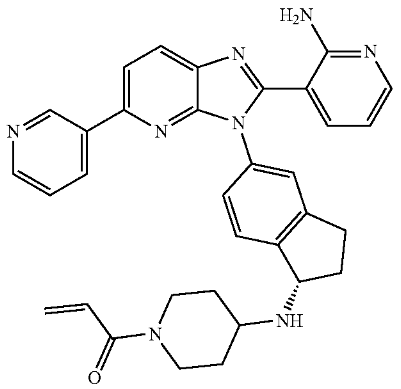

Example 110 was prepared in a manner analogous to Example 109 (via Intermediate 109-2) using 3-bromopyridine in place of 2-bromo-1,3-oxazole. MS (ESI) calcd. for $C_{33}H_{32}N_8O$, 556.27 m/z, found 557.25 $[M+H]^+$. $^1$H-NMR (400 MHz, DMSO) S (ppm): 9.25-9.35 (m, 1H), 8.65-8.75 (m, 1H), 8.60-8.64 (m, 1H), 8.40-8.50 (m, 1H), 8.05-8.22 (m, 2H), 7.66-7.85 (m, 3H), 7.56-7.65 (m, 1H), 7.45-7.55 (m, 1H), 6.75-6.90 (m, 2H), 6.08-6.20 (m, 1H), 5.68-5.78 (m, 1H), 4.88-5.08 (m, 1H), 4.40-4.60 (m, 1H), 4.12-4.25 (m, 1H), 3.50-3.60 (m, 1H), 3.06-3.25 (m, 2H), 2.90-3.05 (m, 1H), 2.67-2.80 (m, 1H), 2.54-2.65 (m, 1H), 2.18-2.30 (m, 2H), 2.05-2.17 (m, 1H), 1.42-1.62 (m, 2H).

Example 111: 1-((2*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-ethynylpiperidin-1-yl)prop-2-en-1-one and Example 112: 1-((2*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-ethynylpiperidin-1-yl)prop-2-en-1-one Example 111

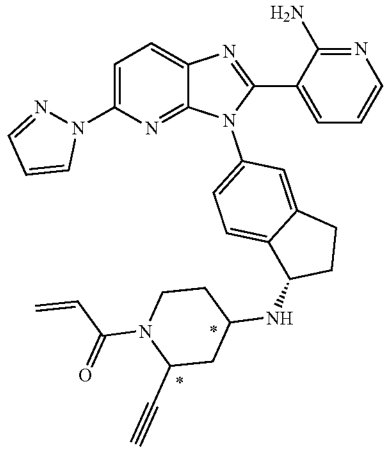

Example 112

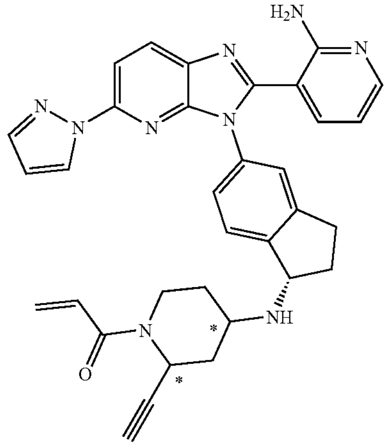

Examples and 112 were prepare in a manner analogous to Example 14 using Intermediate 111-1 in place of Intermediate 14-1. The diastereomers separated during Prep-HPLC on a Kinetex EVO C18 column using a gradient of acetonitrile in water (+10 mmol/L $NH_4HCO_3$). * Denotes a stereocenter with undetermined absolute stereochemistry of a single diastereomer.

Example 111: MS (ESI) calcd. for $C_{33}H_{31}N_9O$, 569.27 m/z, found 570.25 $[M+H]^+$. $^1$H NMR (400 MHz, DMSO-$d_6$) δ (ppm): 8.35-8.37 (m, 2H), 7.93-8.02 (m, 2H), 7.80 (s, 1H), 7.21-7.29 (m, 2H), 7.32-7.53 (m, 2H), 6.79-6.94 (m, 3H), 6.54-6.56 (m, 1H), 6.42-6.45 (m, 1H), 6.12-6.17 (m, 1H), 5.70-5.74 (m, 1H), 5.21-5.56 (m, 1H), 4.34-4.42 (m, 1H), 3.92-4.07 (m, 1H), 3.39-3.40 (m, 1H), 3.28-3.30 (m, 1H), 3.11-3.22 (m, 1H), 2.93-3.01 (m, 1H), 2.75-2.82 (m, 1H), 2.42-2.49 (m, 1H), 1.99-2.28 (m, 3H), 1.71-1.83 (m, 1H), 1.32-1.53 (m, 1H), 1.07-1.23 (m, 1H).

Example 112: MS (ESI) calcd. for $C_{33}H_{31}N_9O$, 569.27 m/z, found 570.25 $[M+H]^+$. $^1$H NMR (400 MHz, DMSO-$d_6$) δ (ppm): 8.35-8.37 (m, 2H), 7.99-8.02 (m, 1H), 7.94-7.96 (m, 1H), 7.80 (s, 1H), 7.21-7.53 (m, 4H), 6.94 (s, 2H), 6.79-6.86 (m, 1H), 6.54-6.56 (m, 1H), 6.42-6.45 (m, 1H), 6.12-6.17 (m, 1H), 5.70-5.74 (m, 1H), 5.21-5.35 (m, 1H), 4.39-4.45 (m, 1H), 3.82-4.13 (m, 1H), 3.43-3.59 (m, 1H), 3.39-3.40 (m, 1H), 3.17-3.21 (m, 1H), 2.91-2.99 (m, 1H), 2.73-2.88 (m, 1H), 2.42-2.49 (m, 1H), 2.13-2.27 (m, 2H), 1.55-1.83 (m, 4H).

Intermediate 111-1: tert-butyl (*)-2-ethynyl-4-oxopiperidine-1-carboxylate and

Intermediate 111-2: tert-butyl (*)-2-ethynyl-4-oxopiperidine-1-carboxylate

Intermediate 111-1

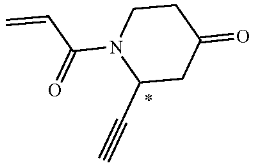

Intermediate 111-2

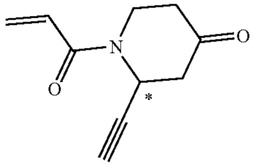

Intermediates 111-1 and 111-2 were prepared in a manner analogous to Intermediate 14-1 using tert-butyl 2-ethynyl-4-oxopiperidine-1-carboxylate in place of tert-butyl 8-oxo-3-azabicyclo[3.2.1]octane-3-carboxylate. The enantiomers were separated by chiral HPLC on a CHIRALPAK IF column eluting using a mixture of [Hex (+0.5% 2M $NH_3$-MeOH)] and ethanol to afford tert-butyl (S*)-2-ethynyl-4-oxopiperidine-1-carboxylate (Intermediate 111-1) as the second eluting peak and tert-butyl (R*)-2-ethynyl-4-oxopiperidine-1-carboxylate (Intermediate 111-2) as the first eluting peak. * Denotes a stereocenter with undetermined absolute stereochemistry of a single enantiomer. MS (ESI) calcd. for $C_{10}H_{11}NO_2$, 117.08 m/z, found 118.15 $[M+H]^+$.

Example 113: 1-((2*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-ethynylpiperidin-1-yl)prop-2-en-1-one and Example 114: 1-((2*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-ethynylpiperidin-1-yl)prop-2-en-1-one Example 113

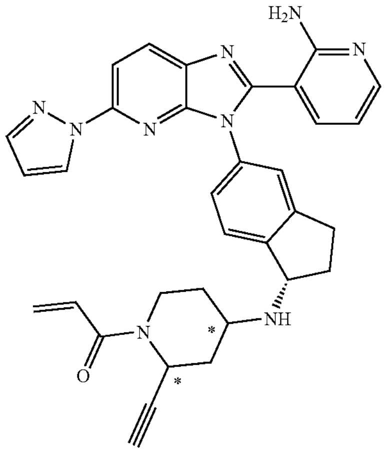

Example 114

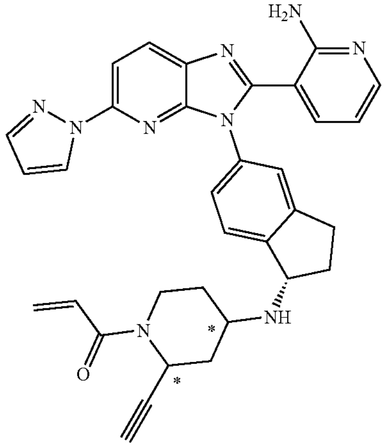

Examples 113 and 114 were prepared in a manner analogous to Example 14 using Intermediate 111-2 in place of Intermediate 14-1. The diastereomers separated during Prep-HPLC on a XSelect CSH Fluoro Phenyl column using a gradient of acetonitrile in water (+0.1% formic acid). * Denotes a stereocenter with undetermined absolute stereochemistry of a single diastereomer.

Example 113: MS (ESI) calcd. for $C_{33}H_{31}N_9O$, 569.27 m/z, found 570.25 $[M+H]^+$. $^1H$ NMR (400 MHz, DMSO-$d_6$) δ (ppm): 8.35-8.37 (m, 2H), 7.96-8.08 (m, 2H), 7.80 (s, 1H), 7.41-7.46 (m, 1H), 7.17-7.36 (m, 3H), 6.94 (s, 2H), 6.79-6.85 (m, 1H), 6.53-6.55 (m, 1H), 6.42-6.45 (m, 1H), 6.12-6.17 (m, 1H), 5.69-5.74 (m, 1H), 5.21-5.56 (m, 1H), 4.31-4.42 (m, 1H), 3.92-4.07 (m, 1H), 3.43-3.60 (m, 1H), 3.39-3.41 (m, 1H), 3.08-3.12 (m, 1H), 2.88-3.01 (m, 1H), 2.75-2.82 (m, 1H), 2.35-2.49 (m, 1H), 2.04-2.28 (m, 2H), 1.98-2.01 (m, 1H), 1.63-1.83 (m, 1H), 1.11-1.42 (m, 2H). (formic acid salt).

Example 114: MS (ESI) calcd. for $C_{33}H_{31}N_9O$, 569.27 m/z, found 570.25 $[M+H]^+$. $^1H$ NMR (400 MHz, DMSO-$d_6$) δ (ppm): 8.35-8.37 (m, 2H), 7.99-8.02 (m, 1H), 7.94-7.96 (m, 1H), 7.80 (s, 1H), 7.41-7.46 (m, 1H), 7.29-7.32 (m, 1H), 7.18-7.26 (m, 2H), 6.94 (s, 2H), 6.79-6.85 (m, 1H), 6.53-6.55 (m, 1H), 6.42-6.45 (m, 1H), 6.12-6.17 (m, 1H), 5.69-5.74 (m, 1H), 5.17-5.26 (m, 1H), 4.23-4.39 (m, 1H), 3.89-4.01 (m, 1H), 3.49-3.62 (m, 1H), 3.09-3.11 (m, 1H), 2.88-3.02 (m, 1H), 2.72-2.81 (m, 1H), 2.39-2.41 (m, 1H), 2.07-2.29 (m, 2H), 1.97-2.03 (m, 2H), 1.88-1.91 (m, 1H), 1.78-1.85 (m, 1H), 1.53-1.70 (m, 1H). (formic acid salt).

Example 115: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methoxypiperidin-1-yl)prop-2-en-1-one Example 116: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methoxypiperidin-1-yl)prop-2-en-1-one Example 117: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methoxypiperidin-1-yl)prop-2-en-1-one and Example 118: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-methoxypiperidin-1-yl)prop-2-en-1-one Rxample 115

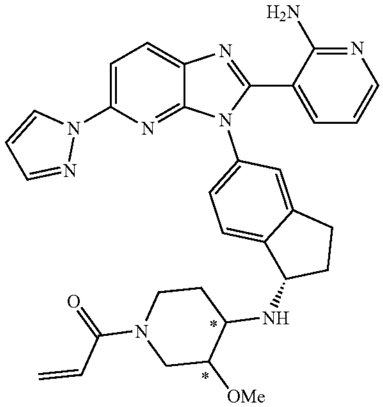

Example 116

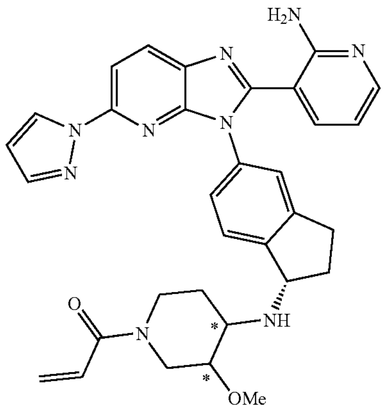

-continued

Example 117

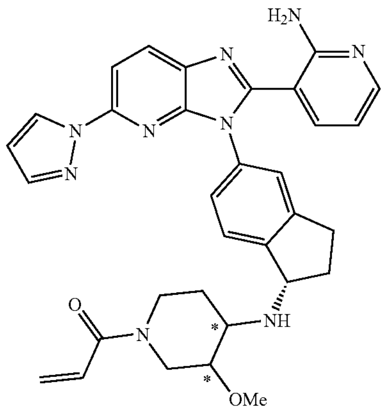

Example 118

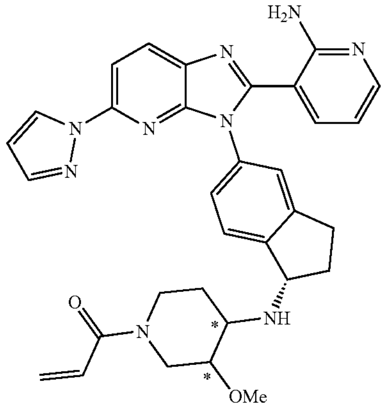

Examples 115, 116, 117 and 118 were prepared in a manner analogous to Example 14 (via Intermediate 14-1) using tert-butyl 3-methoxy-4-oxopiperidine-1-carboxylate in place tert-butyl 8-oxo-3-azabicyclo[3.2.1]octane-3-carboxylate. The diastereomers separated partially during reverse phase Prep-HPLC on a XSelect CSH Fluoro column using a gradient of acetonitrile in water (+10 mM TFA). Examples 117 and 118 required further separation by chiral Prep-HPLC on a CHIRALPAK IG column eluting using a mixture of [3:1 Hexanes/dichloromethane (+0.5% 2M $NH_3$-MeOH)] and ethanol * Denotes a stereocenter with undetermined absolute stereochemistry of a single diastereomer.

Example 115: MS (ESI) calcd. for $C_{32}H_{33}N_9O_2$: 575.28 m/z, found: 576.20 $[M+H]^+$. $^1H$-NMR (400 MHz, DMSO) δ (ppm): 8.30-8.42 (m, 2H), 7.92-8.05 (m, 2H), 7.78-7.88 (m, 1H), 7.40-7.51 (m, 1H), 7.20-7.38 (m, 3H), 6.73-6.85 (m, 1H), 6.52-6.60 (m, 1H), 6.42-6.51 (m, 1H), 6.05-6.19 (m, 1H), 5.68-5.75 (m, 1H), 4.15-4.60 (m, 3H), 3.91-4.00 (m, 1H), 3.54-3.68 (m, 1H), 3.28-3.41 (m, 3H), 3.12-3.25 (m, 1H), 2.95-3.05 (m, 2H), 2.75-2.85 (m, 1H), 2.35-2.45 (m, 1H), 1.80-1.91 (m, 1H), 1.41-1.71 (m, 2H).

Example 116: MS (ESI) calcd. for $C_{32}H_{33}N_9O_2$: 575.28 m/z, found: 576.25 $[M+H]^+$. $^1H$-NMR (400 MHz, DMSO) δ (ppm): 8.30-8.40 (m, 2H), 7.92-8.05 (m, 2H), 7.79-7.85 (m, 1H), 7.21-7.52 (m, 4H), 6.75-6.85 (m, 1H), 6.42-6.58 (m, 2H), 6.08-6.18 (m, 1H), 5.68-5.78 (m, 1H), 4.18-4.40 (m, 2H), 3.89-4.17 (m, 1H), 3.41-3.50 (m, 1H), 3.29-3.35 (m, 3H), 3.21-3.28 (m, 1H), 2.90-3.18 (m, 3H), 2.72-2.88 (m, 1H), 2.40-2.51 (m, 1H), 1.48-1.82 (m, 3H).

Example 117: MS (ESI) calcd. for $C_{32}H_{33}N_9O_2$: 575.28 m/z, found: 576.15 $[M+H]^+$. $^1H$-NMR (400 MHz, DMSO) δ (ppm): 8.32-8.40 (m, 2H), 7.93-8.05 (m, 2H), 7.78-7.84 (m, 1H), 7.48-7.55 (m, 1H), 7.22-7.35 (m, 3H), 6.72-6.89 (m, 1H), 6.52-6.59 (m, 1H), 6.42-6.50 (m, 1H), 6.08-6.18 (m, 1H), 5.68-5.75 (m, 1H), 4.32-4.39 (m, 1H), 3.89-4.20 (m, 1H), 3.62-3.71 (m, 1H), 3.40-3.50 (m, 1H), 3.20-3.39 (m, 4H), 3.05-3.19 (m, 1H), 2.85-3.00 (m, 2H), 2.70-2.84 (m, 1H), 2.42-2.51 (m, 1H), 1.78-2.01 (m, 2H), 1.31-1.45 (m, 1H). (TFA salt).

Example 118: MS (ESI) calcd. for $C_{32}H_{33}N_9O_2$: 575.28 m/z, found: 576.15 $[M+H]^+$. $^1H$-NMR (400 MHz, DMSO) δ (ppm): 8.30-8.40 (m, 2H), 7.92-8.05 (m, 2H), 7.76-7.83 (m, 1H), 7.45-7.55 (m, 1H), 7.20-7.35 (m, 3H), 6.72-6.90 (m, 1H), 6.52-6.59 (m, 1H), 6.42-6.50 (m, 1H), 6.09-6.19 (m, 1H), 5.67-5.78 (m, 1H), 4.30-4.40 (m, 1H), 3.89-4.20 (m, 1H), 3.62-3.71 (m, 1H), 3.39-3.50 (m, 1H), 3.20-3.39 (m, 4H), 3.09-3.20 (m, 1H), 2.85-3.05 (m, 2H), 2.70-2.85 (m, 1H), 2.40-2.51 (m, 1H), 1.75-2.01 (m, 2H), 1.31-1.42 (m, 1H). (TFA salt).

Example 119: 1-(4-{[(1R)-5-[2-(2-aminopyridin-3-yl)-5-(pyrazol-1-yl)imidazo[4,5-b]pyridin-3-yl]-2,2-difluoro-1,3-dihydroinden-1-yl]amino}piperidin-1-yl)prop-2-en-1-one Example 119

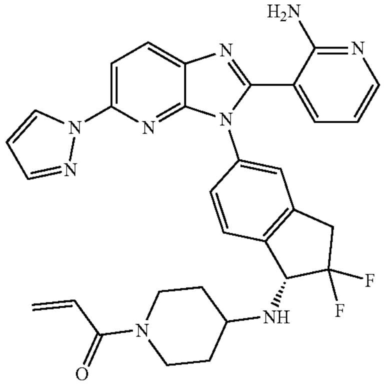

Example 119 was prepared in a manner analogous to Example 13 using Intermediate 119-2 in place of Intermediate 1-1 and a reaction time and temp of 2 h at 60° C. MS (ESI) calcd. for $C_{31}H_{29}F_2N_9O$, 581.25 m/z, found 582.15 $[M+H]^+$. $^1H$-NMR (400 MHz, DMSO-d6) δ (ppm): 8.22-8.49 (m, 2H), 7.89-8.15 (m, 2H), 7.69-7.89 (m, 1H), 7.42-7.64 (m, 1H), 7.31-7.42 (m, 2H), 7.13-7.31 (m, 1H), 6.65-6.96 (m, 1H), 6.52-6.65 (m, 1H), 6.36-6.52 (m, 1H), 5.98-6.25 (m, 1H), 5.61-5.85 (m, 1H), 4.49-4.76 (m, 1H), 4.11-4.39 (m, 1H), 3.32-3.61 (m, 2H), 3.02-3.32 (m, 2H), 2.77-3.02 (m, 1H), 2.51-2.56 (m, 1H), 1.98-2.19 (m, 1H), 1.78-1.98 (m, 1H), 1.15-1.49 (m, 2H). (formic acid salt).

Intermediate 119-2: (R)-3-(3-(1-amino-2,2-difluoro-2,3-dihydro-1H-inden-5-yl)-5-(1H-pyrazol-1-yl)-3H-imidazo[4,5-b]pyridin-2-yl)pyridin-2-amine Intermediate 119-2

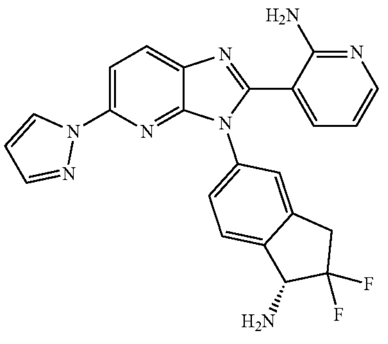

Intermediate 119-2 was prepared in a manner analogous to Intermediate 75-1 (starting from Step 2) using Intermediate 119-1 in place of 5-bromo-2-fluoro-2,3-dihydroinden-1-one and omitting the chiral separation by SFC. MS (ESI) calcd. for $C_{23}H_{18}F_2N_8$, 444.16 m/z, found: 445.15 $[M+H]^+$.

Intermediate 119-1: 5-bromo-2,2-difluoro-2,3-dihydro-1H-inden-1-one

Intermediate 119-1

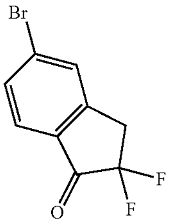

Synthetic Route:

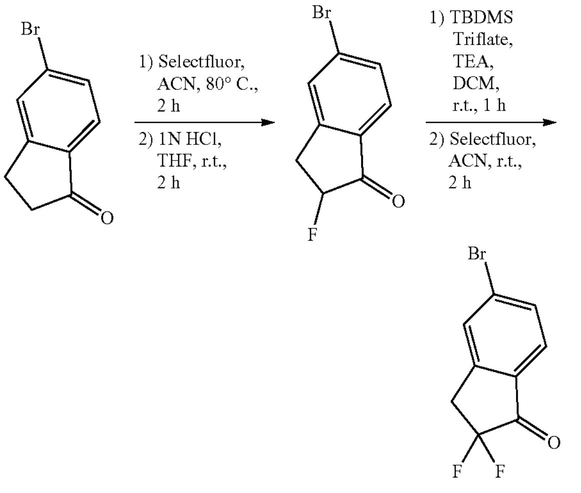

Intermediate 119-1

Step 1: Synthesis of 5-bromo-2-fluoro-2,3-dihydro-1-inden-1-one

To a solution of 5-bromo-1-indanone (5.00 g, 23.8 mmol) in methanol (50 mL) was added SelectFluor (10.0 g, 28.2 mmol) and the resulting mixture was stirred under reflux for 2 hours. The reaction mixture was filtered through Celite, and the filtrate was concentrated under reduced pressure. The resulting residue was dissolved in tetrahydrofuran (50 mL), and 1 N hydrochloric acid (50 mL) was added followed by stirring at room temperature for 3 hours. To the reaction mixture, a 2 N aqueous sodium hydroxide solution (50 mL) was added, and the mixture was diluted with a saturated aqueous sodium bicarbonate solution. The mixture was extracted with ethyl acetate. The organic layer was washed with brine, dried over anhydrous magnesium sulfate, and then concentrated under reduced pressure to afford 5-bromo-2-fluoro-2,3-dihydroinden-1-one (4.0 g, 74% yield) as a white solid. MS (ESI) calcd. for $C_9H_6BrFO$, 227.96 m/z, found: 229.00 $[M+H]^+$.

Step 2: 5-bromo-2,2-difluoro-2,3-dihydro-1H-inden-1-one (Intermediate 119-1

To a solution of 5-bromo-2-fluoro-2,3-dihydro-1H-inden-1-one (3.0 g, 13 mmol, 1 equiv) in DCM (30 mL) was added tert-butyldimethylsilyl trifluoromethanesulfonate (5.16 mL, 988 mmol, 70 equiv) and triethylamine (9.1 mL, 65.5 mmol, 5.0 equiv) and the resulting mixture was stirred at room temperature for 1 hour. The reaction mixture was diluted with saturated aqueous sodium bicarbonate and extracted with ethyl acetate. The organic layer was dried over anhydrous sodium sulfate and concentrated under reduced pressure. The resulting residue was dissolved in acetonitrile (30 mL) and Selectfluor (5.57 g, 15.7 mmol, 1.2 equiv) was added. The resulting mixture was stirred at room temperature for 2 hours. The reaction mixture was diluted with saturated aqueous sodium bicarbonate and extracted with ethyl acetate. The organic layer was washed with brine, dried over anhydrous magnesium sulfate, filtered and concentrated under reduced pressure. To the resulting residue, hexane was added, and the precipitate was collected by filtration to afford 5-bromo-2,2-difluoro-2,3-dihydro-1H-inden-1-one (Intermediate 119-1) (2.3 g, 71%). MS (ESI) calcd. for $C_9H_5BrF_2O$, 245.95 m/z, found: 247.00 $[M+H]^+$.

Example 120: (S)-1-(4-((5-(2-(2-aminopyridin-3-yl)-5-(pyrazin-2-yl)-3H-imidazo[4,5-b]pyridin-3-yl)-2,3-dihydro-1H-inden-1-yl)amino)piperidin-1-yl)prop-2-en-1-one Example 120

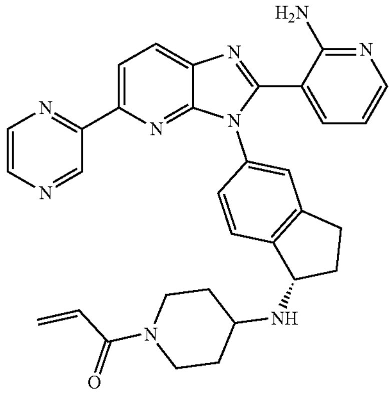

Example 120 was prepared in a manner analogous to Example 13 using Intermediate 120-1 in place of Intermediate 1-1. MS (ESI) calcd. for $C_{32}H_{31}N_9O$: 557.27 m/z, found 558.20 $[M+H]^+$. $^1H$ NMR (400 MHz, DMSO-$d_6$) δ (ppm): 9.33 (s, 1H), 8.70-8.80 (m, 2H), 8.40-8.50 (m, 2H), 8.05-8.10 (m, 1H), 7.70-7.80 (m, 2H), 7.55-7.60 (m, 1H), 7.35-7.40 (m, 1H), 6.76-6.90 (m, 2H), 6.05-6.20 (m, 1H), 5.80-5.90 (m, 1H), 5.00 (s, 1H), 4.50-4.60 (m, 1H), 4.18-4.27 (m, 1H), 3.58-3.67 (m, 1H), 3.16-3.25 (m, 2H), 2.90-3.04 (m, 1H), 2.73-2.80 (m, 1H), 2.53-2.60 (m, 1H), 2.25-2.38 (m, 2H), 2.10-2.20 (m, 1H), 1.38-1.65 (m, 2H). (TFA salt).

Intermediate 120-1: (S)-3-(3-(1-amino-2,3-dihydro-1H-inden-5-yl)-5-(pyrazin-2-yl)-3H-imidazo[4,5-b]pyridin-2-yl)pyridin-7-amine Intermediate 120-1

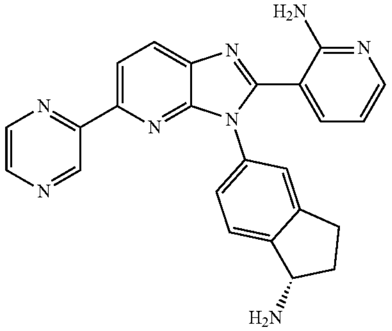

Intermediate 120-1 was prepared in a manner analogous to Intermediate 109-2 using [1,1'-bis(diphenylphosphino)ferrocene]dichloropalladium(III) in place of bis(di-tert-butylphosphino)ferrocene]dichloropalladium(III) and 2-bromopyrazine in place of 2-bromo-1,3-oxazole. MS (ESI) calcd. for $C_{24}H_{20}N_8$: 420.18 m/z, found 421.15 $[M+H]^+$.

Example 121: (S)-1-(4-((5-(2-(2-aminopyridin-3-yl)-5-(6,7-dihydro-4H-pyrazolo[5,1-c][1,4]oxazin-2-yl)-3H-imidazo[4,5-b]pyridin-3-yl)-2,3-dihydro-1H-inden-1-yl)amino)piperidin-1-yl)prop-2-en-1-one Example 121

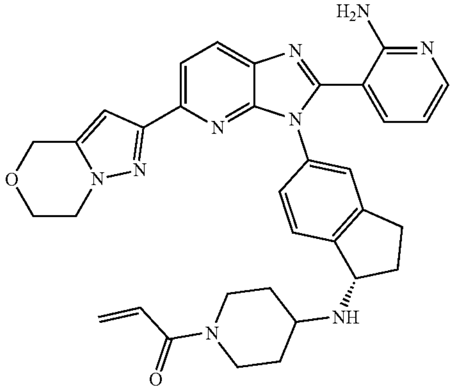

Example 121 was prepared in a manner analogous to Example 120 (via Intermediate 120-1) using 2-bromo-6,7-dihydro-4H-pyrazolo[5,1-c][1,4]oxazine in place of 2-bromopyrazine. MS (ESI) calcd. for $C_{34}H_{35}N_9O_2$: 601.29 m/z, found 602.20 $[M+H]^+$. $^1H$ NMR (400 MHz, DMSO-$d_6$) δ (ppm): 8.22-8.23 (m, 1H), 7.90-8.00 (m, 2H), 7.55-7.60 (m, 1H), 7.35-7.40 (m, 1H), 7.20-7.25 (m, 2H), 6.76-6.80 (m, 1H), 6.48-6.50 (m, 2H), 6.05-6.20 (m, 1H), 5.58-5.70 (m, 1H), 4.80 (s, 2H), 4.50-4.60 (m, 2H), 4.18-4.27 (m, 2H), 4.10-4.15 (m, 2H), 3.88-4.07 (m, 1H), 3.06-3.25 (m, 1H), 2.80-3.04 (m, 4H), 2.53-2.62 (m, 1H), 2.05-2.18 (m, 1H), 1.72-1.94 (m, 2H), 1.38-1.65 (m, 2H).

Example 122: 3-{3-[(1S)-1-({1-[(2R)-oxirane-2-carbonyl]piperidin-4-yl}amino)-2,3-dihydro-1H-inden-5-yl]-5-(pyrazol-1-yl)imidazo[4,5-b]pyridin-2-yl}pyridin-2-amine Example 122

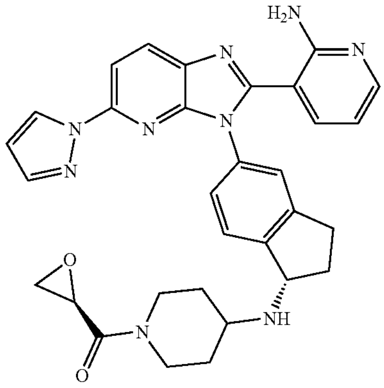

Example 122 was prepared in a manner analogous to Example 4 (last step only) using 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine (precursor to Example 34) in place of Intermediate 1-1 and (2R)-oxirane-2-carboxylic acid in place of the carboxylic acid. MS (ESI) calcd. for $C_{31}H_{31}N_9O_2$: 561.26 m/z, found: 562.15 $[M+H]^+$. $^1H$-NMR (400 MHz, DMSO-d6) δ (ppm): 8.34-8.39 (m, 2H), 7.94-8.01 (m, 2H), 8.80-8.81 (m, 1H), 7.46-7.49 (m, 1H), 7.33-7.35 (m, 1H), 7.22-7.26 (m, 2H), 6.93-6.94 (m, 2H), 6.53-6.54 (m, 1H), 6.41-6.44 (m, 1H), 4.32-4.34 (m, 1H), 4.05-4.19 (m, 2H), 3.86-3.87 (m, 1H), 3.24-3.32 (m, 1H), 2.87-2.97 (m, 4H), 2.74-2.80 (m, 2H), 2.49-2.51 (m, 1H), 2.09-2.11 (m, 1H), 1.77-2.01 (m, 3H), 1.21-1.41 (m, 2H).

Example 123: 3-{3-[(1S)-1-({1-[(2S)-oxirane-2-carbonyl]piperidin-4-yl}amino)-2,3-dihydro-1H-inden-5-yl]-5-(pyrazol-1-yl)imidazo[4,5-b]pyridin-2-yl}pyridin-2-amine Example 123

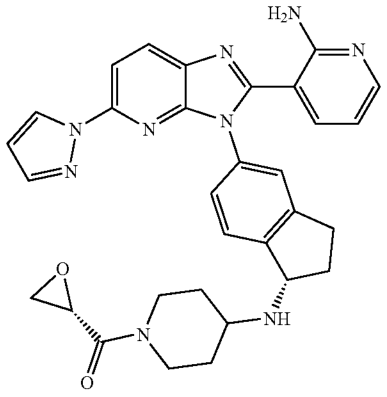

Example 123 was prepared in a manner analogous to Example 4 (last step only) using 3-{3-[(1S)-1-(piperidin-4-ylamino)-2,3-dihydro-1H-inden-5-yl]-5-(pyrazol-1-yl)imidazo[4,5-b]pyridin-2-yl}pyridin-2-amine (precursor to Example 34) in place of Intermediate 1-1 and (2S)-oxirane-2-carboxylic acid in place of the carboxylic acid. MS (ESI) calcd. for $C_{31}H_{31}N_9O_2$: 561.26 m/z, found: 562.20 $[M+H]^+$. $^1$H-NMR (400 MHz, DMSO-d6) δ (ppm): 8.34-8.38 (m, 2H), 7.94-8.01 (m, 2H), 7.80-7.81 (m, 1H), 7.22-7.49 (m, 4H), 6.93-6.94 (m, 2H), 6.53-6.54 (m, 1H), 6.41-6.44 (m, 1H), 4.32-4.34 (m, 1H), 4.05-4.19 (m, 2H), 3.84-3.88 (m, 1H), 3.21-3.32 (m, 1H), 2.74-2.95 (m, 6H), 2.44-2.51 (m, 1H), 2.09-2.11 (m, 1H), 1.77-2.01 (m, 3H), 1.21-1.41 (m, 2H).

Example 124: 1-[(3*)-3-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl]prop-2-en-1-one (assumed) and Example 125: 1-[(3*)-3-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl]prop-2-en-1-one (assumed Example 124

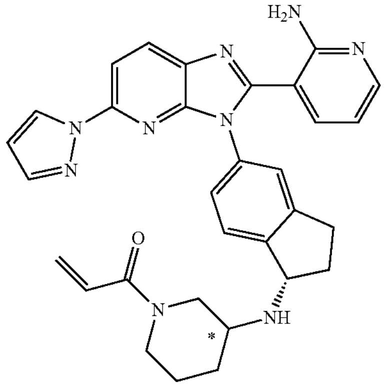

-continued

Example 125

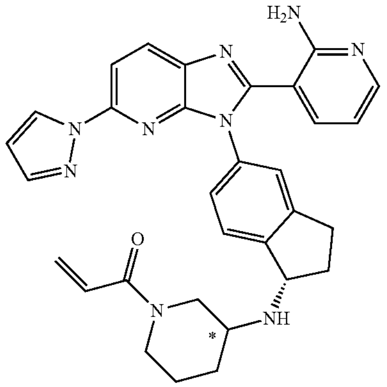

Examples 124 and 125 were prepared in a manner analogous to Example 14 (via Intermediate 14-1) using tert-butyl 3-oxopiperidine-1-carboxylate in place of tert-butyl 8-oxo-3-azabicyclo[3.2.1]octane-3-carboxylate, 4N HCl in dioxane in place of TFA in DCM, and 0° C. to room temperature for 2 h in methanol for the final step. The diastereomers were separated by chiral HPLC on a CHIRAL ART Cellulose-SB column using a mixture of [hexanes/MTBE (1:1) (+0.5% 2M $NH_3$-MeOH)] and tetrahydrofuran. * Denotes a stereocenter with undetermined absolute stereochemistry of a single diastereomer.

Example 124: MS (ESI) calcd. for $C_{31}H_{31}N_9O$: 545.27 m/z, found: 546.20 $[M+H]^+$. $^1$H NMR (400 MHz, DMSO-$d_6$) δ (ppm): 8.35-8.37 (m, 2H), 7.94-8.01 (m, 2H), 7.81 (s, 1H), 7.48-7.50 (m, 1H), 7.35-7.37 (m, 1H), 7.22-7.27 (m, 2H), 6.83-6.87 (m, 1H), 6.55 (s, 1H), 6.43-6.44 (m, 1H), 6.09-6.13 (m, 1H), 5.67-5.69 (m, 1H), 4.42-4.48 (m, 1H), 3.87-3.99 (m, 1H), 2.99-3.20 (m, 3H), 2.92-2.95 (m, 2H), 2.18-2.34 (m, 2H), 1.62-2.01 (m, 4H), 1.35-1.55 (m, 1H).

Example 125: MS (ESI) calcd. for $C_{31}H_{31}N_9O$: 545.27 m/z, found: 546.25 $[M+H]^+$. $^1$H NMR (400 MHz, DMSO-$d_6$) δ (ppm): 8.33-8.35 (m, 2H), 7.92-7.99 (m, 2H), 7.79 (s, 1H), 7.62-7.64 (m, 1H), 7.43-7.56 (m, 1H), 7.24-7.39 (m, 2H), 6.75-6.86 (m, 1H), 6.54 (s, 1H), 6.42-6.45 (m, 1H), 6.06-6.13 (m, 1H), 5.69-5.72 (m, 1H), 4.57-4.73 (m, 1H), 3.92-4.11 (m, 1H), 2.91-3.07 (m, 3H), 2.75-2.89 (m, 2H), 1.97-2.16 (m, 2H), 1.41-1.52 (m, 1H), 1.32-1.36 (m, 4H).

Example 126: 1-[(4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3,4-dihydro-2H-quinolin-1-yl]prop-2-en-1-one and Example 127: 1-[(4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3,4-dihydro-2H-quinolin-1-yl]prop-2-en-1-one Example 126

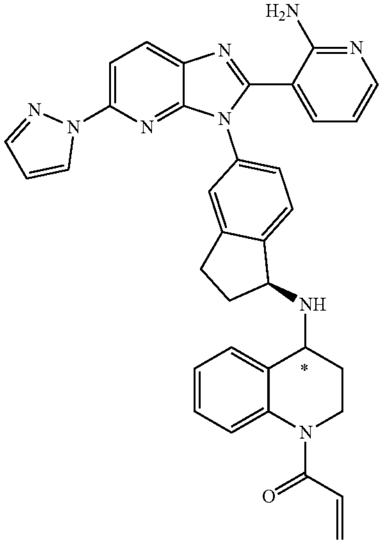

Example 127

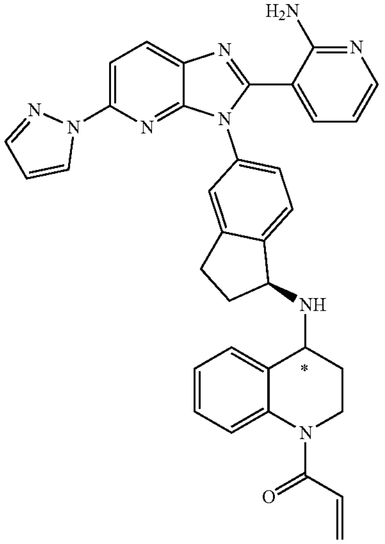

Synthetic Route:

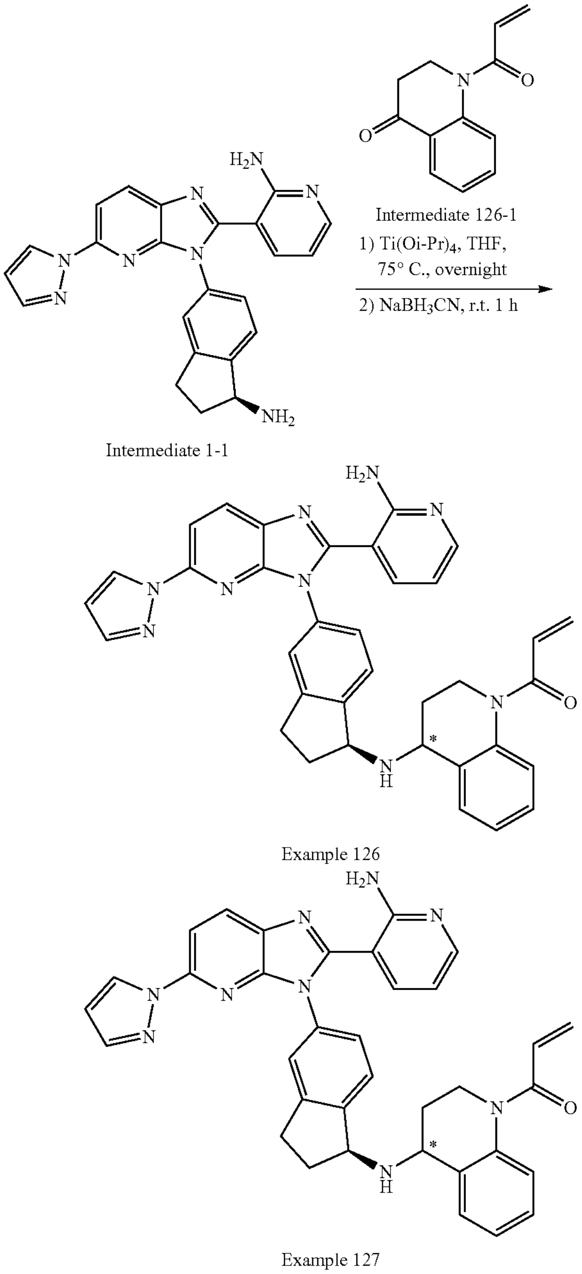

Step 1: Synthesis of 1-[(4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3,4-dihydro-2H-quinolin-1-yl]prop-2-en-1-one (Example 126) and 1-[(4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3,4-dihydro-2H-quinolin-1-yl]prop-2-en-1-one (Example 127)

To a solution of 1-(prop-2-enoyl)-2,3-dihydroquinolin-4-one (Intermediate 126-1) (100 mg, 0.497 mmol) in THF (5 mL) were added 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (203 mg, 0.497 mmol) and titanium tetraisopropoxide (28.3 mg, 0.497 mmol). The reaction mixture was stirred at 75° C. overnight. The mixture was cooled to room temperature and $NaBH_3CN$ (37.5 mg, 0.596 mmol) was added. Stirring was continue at room temperature for 1 h. The reaction was quenched with $H_2O$ (10 mL). The resulting mixture was extracted with ethyl acetate (2×50 mL). The combined organic layers were washed with brine (10 mL), dried over anhydrous sodium sulfate, filtered and concentrated in vacuo. The residue was purified by Prep-HPLC on a XBridge Prep OBD C18 Column using a gradient of acetonitrile in water (+0.05% TFA). The diastereomers were separated by chiral Prep-HPLC on a CHIRALPAK IG column using a mix of [hexanes/DCM (3:1) (+0.5% 2M $NH_3$-MeOH)] and isopropanol to afford 1-((*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,4-dihydroquinolin-1(2H)-yl)prop-2-en-1-one (Example 126) (5.3 mg, 2%) as white solid and 1-((*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,4-dihydroquinolin-1(2H)-yl)prop-2-en-1-one (19.4 mg, 8%) as yellow solid. * Denotes a stereocenter with undetermined absolute stereochemistry of a single diastereomer.

Example 126: MS (ESI) calcd. for $C_{35}H_{31}N_9O$: 593.27 m/z, found: 594.30 $[M+H]^+$. 1H NMR (300 MHz, DMSO-d6) δ (ppm): 8.32-8.36 (m, 2H), 7.95-8.00 (m, 2H), 7.80-7.93 (m, 1H), 7.48-7.49 (m, 1H), 7.15-7.49 (m, 7H), 6.49-6.54 (m, 3H), 6.22-6.27 (m, 1H), 5.69-5.72 (m, 1H), 4.17-4.18 (m, 1H), 388-3.95 (m, 2H), 3.69-3.72 (m, 1H), 2.92-2.94 (m, 1H), 2.72-2.78 (m, 1H), 2.52-2.53 (m, 1H), 2.06-2.07 (m, 1H), 2.00-2.02 (m, 1H), 1.88-1.90 (m, 1H).

Example 127: MS (ESI) calcd. for $C_{35}H_{31}N_9O$: 593.27 m/z, found: 594.30 $[M+H]^+$. $^1H$ NMR (400 MHz, DMSO-d6) δ ppm: 8.34-8.35 (m, 2H), 7.94-8.00 (m, 2H), 7.80-7.82 (m, 1H), 7.50-7.52 (m, 2H), 7.17-7.32 (m, 6H), 6.52-6.56 (m, 2H), 6.42-6.45 (m, 1H), 6.22-6.27 (m, 1H), 5.72-5.75 (m, 1H), 4.40-4.42 (m, 1H), 4.00-4.02 (m, 1H), 3.97-3.99 (m, 2H), 2.94-2.95 (m, 1H), 2.77-2.79 (m, 1H), 2.40-2.52 (m, 1H), 2.08-2.09 (m, 1H), 2.00-2.03 (m, 1H), 1.78-1.79 (m, 1H).

Intermediate 126-1: 1-acryloyl-2,3-dihydroquinolin-4(1H)-one

Intermediate 126-1

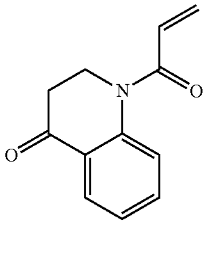

Intermediate 126-1 was prepared in a manner analogous to Intermediate 14-1 using 2,3-dihydroquinolin-4(1H)-one in place of tert-butyl 8-oxo-3-azabicyclo[3.2.1]octane-3-carboxylate. MS (ESI) calcd. for $C_{12}H_{11}NO_2$, 201.08 m/z, found 202.10 $[M+H]^+$.

Example 128: 4-{[(1S)-5-[2-(2-aminopyridin-3-yl)-5-(pyrazol-1-yl)imidazo[4,5-b]pyridin-3-yl]-2,3-dihydro-1H-inden-1-yl]amino-N}-(cyanomethyl)-N-methylpiperidine-1-carboxamide Example 128

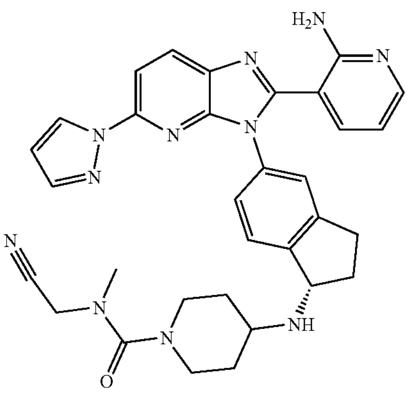

Example 128 was prepared in a manner analogous to Example 13 using Intermediate 128-1 in place of the ketone. MS (ESI) calcd. for $C_{32}H_{33}N_{11}O$: 587.29 m/z, found: 588.25 $[M+H]^+$. $^1H$-NMR (400 MHz, DMSO-d6) δ (ppm): 9.03-9.17 (m, 2H), 8.36-8.44 (m, 2H), 8.08-8.09 (m, 1H), 7.99-8.01 (m, 1H), 7.83-7.84 (m, 1H), 7.75-7.77 (m, 1H), 7.58-7.61 (m, 2H), 7.44-7.46 (m, 1H), 6.65-6.68 (m, 1H), 6.57-6.59 (m, 1H), 5.01-5.02 (m, 1H), 4.13 (s, 2H), 3.72-4.78 (m, 2H), 3.49-3.51 (m, 1H), 3.15-3.21 (m, 1H), 2.94-3.00 (m, 2H), 2.87-2.93 (m, 3H), 2.56-2.60 (m, 1H), 2.50-2.55 (m, 2H), 2.16-2.26 (m, 2H), 2.04-2.07 (m, 1H), 1.58-1.66 (m, 2H). (TFA salt).

Intermediate 128-1: N-(cyanomethyl)-N-methyl-4-oxopiperidine-1-carboxamide

Intermediate 128-1

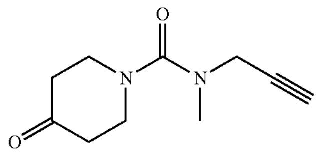

Synthetic Route:

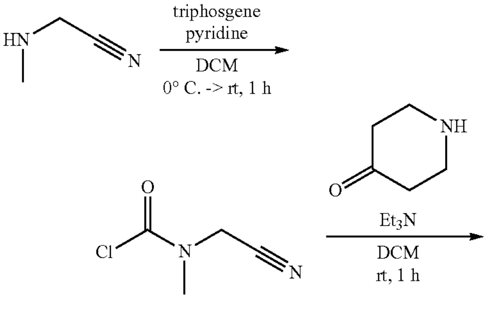

-continued

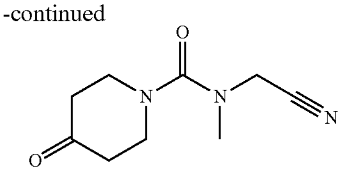

Intermediate 128-1

Step 1: Synthesis of N-(cyanomethyl)-N-methylcarbamoyl chloride

To a cooled (0° C.) solution of 2-(methylamino)acetonitrile (1 g, 14.3 mmol) in DCM (10 mL) was added pyridine (5.64 g, 71.3 mmol) and the resulting mixture was stirred at 0° C. for 20 min. Then a solution of triphosgene (4.23 g, 14.3 mmol) in DCM (10 mL) was added dropwise and the mixture was stirred at room temperature for 1 h. The reaction was quenched with $H_2O$ (50 mL). The resulting mixture was extracted with DCM (3×50 mL). The organic layers were combined, dried over $Na_2SO_4$, filtered and concentrated to afford N-(cyanomethyl)-N-methylcarbamoyl chloride (1.27 g crude) as a brown oil. MS (ESI) calcd. for $C_4H_5ClN_2O$: 132.01 m/z, found: 131.05 $[M-H]^-$.

Step 2: Synthesis of N-(cyanomethyl)-N-methyl-4-oxopiperidine-1-carboxamide (Intermediate 128-1

To a solution of 4-piperidinone (299.2 mg, 3.018 mmol) in DCM (10 mL) was added triethylamine (916.1 mg, 9.054 mmol) and N-(cyanomethyl)-N-methylcarbamoyl chloride (400 mg, 3.02 mmol). The resulting mixture was stirred at room temperature for 1 h. The solvent was removed by distillation under vacuum to afford N-(cyanomethyl)-N-methyl-4-oxopiperidine-1-carboxamide (Intermediate 128-1) (500 mg crude) as a yellow oil. MS (ESI) calcd. for $C_9H_{13}N_3O_2$: 195.10 m/z, found: 196.15 $[M+H]^+$.

Example 129: 1-[(2S,4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-(methoxymethyl)piperidin-1-yl]prop-2-en-1-one and Example 130: 1-[(2S,4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-(methoxymethyl)piperidin-1-yl]prop-2-en-1-one Example 129

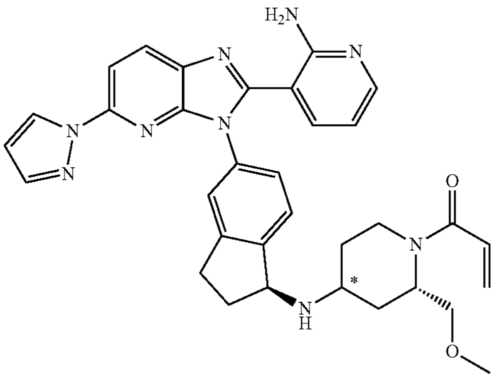

-continued

Example 130

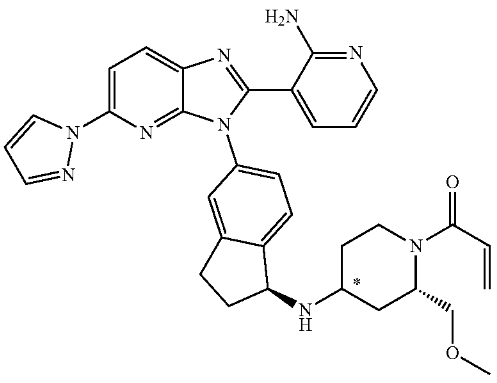

Examples 129 and 130 were prepared in a manner analogous to Example 13 (via Intermediate 14-1) using Intermediate 129-1 in place of tert-butyl 8-oxo-3-azabicyclo[3.2.1]octane-3-carboxylate and TFA/acetonitrile at 80° C. overnight (under air) instead of TFA/DCM at room temperature for 2 h. * Denotes a stereocenter with undetermined absolute stereochemistry of a single diastereomer. The diastereomers were separated by chiral Prep-HPLC on a CHIRAL ART Cellulose-SC column using an mixture of [MTBE (+0.5% 2M $NH_3$-MeOH)] and [methanol/DCM (1:1)].

Example 129: MS (ESI) calcd. for $C_{33}H_{35}N_9O_2$: 589.29 m/z, found: 590.35 $[M+H]^+$. $^1H$ NMR (400 MHz, DMSO-d6) δ (ppm): 8.41-8.28 (m, 2H), 7.98 (dd, J=23.3, 6.7 Hz, 2H), 7.81 (s, 1H), 7.50 (d, J=7.9 Hz, 1H), 7.36 (s, 1H), 7.27 (dd, J=17.9, 7.8 Hz, 2H), 6.92 (s, 2H), 6.79 (dd, J=16.7, 10.4 Hz, 1H), 6.56 (s, 1H), 6.49-6.37 (m, 1H), 6.07 (d, J=16.8 Hz, 1H), 5.63 (d, J=10.5 Hz, 1H), 4.34 (s, 1H), 4.20-3.82 (m, 1H), 3.78-3.44 (m, 2H), 3.24 (s, 3H), 3.16-3.06 (m, 2H), 3.06-2.87 (m, 2H), 2.87-2.62 (m, 2H), 1.96 (d, J=14.3 Hz, 1H), 1.71 (d, J=29.8 Hz, 4H), 1.23 (s, 1H).

Example 130: MS (ESI) calcd. for $C_{33}H_{35}N_9O_2$: 589.29 m/z, found: 590.35 $[M+H]^+$. $^1H$ NMR (300 MHz, DMSO-d6) δ 9.23 (s, 2H), 8.71-8.32 (m, 3H), 8.12-7.94 (m, 2H), 7.91-7.69 (m, 2H), 7.61-7.32 (m, 3H), 7.11 (d, J=51.0 Hz, 1H), 6.84 (td, J=17.1, 10.5 Hz, 1H), 6.62-6.54 (m, 1H), 6.12 (ddd, J=16.7, 5.8, 2.4 Hz, 1H), 5.82-5.63 (m, 1H), 4.99 (d, J=17.2 Hz, 1H), 4.52 (d, J=13.3 Hz, 1H), 3.27 (d, J=1.9 Hz, 3H), 3.15-2.77 (m, 3H), 2.43-2.14 (m, 3H), 1.90-1.39 (m, 3H), 1.17 (t, J=7.3 Hz, 4H).

Intermediate 129-1: tert-butyl (S)-7-(methoxymethyl)-1,4-dioxa-8-azaspiro[4.5]decane-8-carboxylate Intermediate 129-1

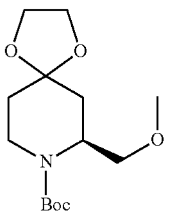

Synthetic Route:

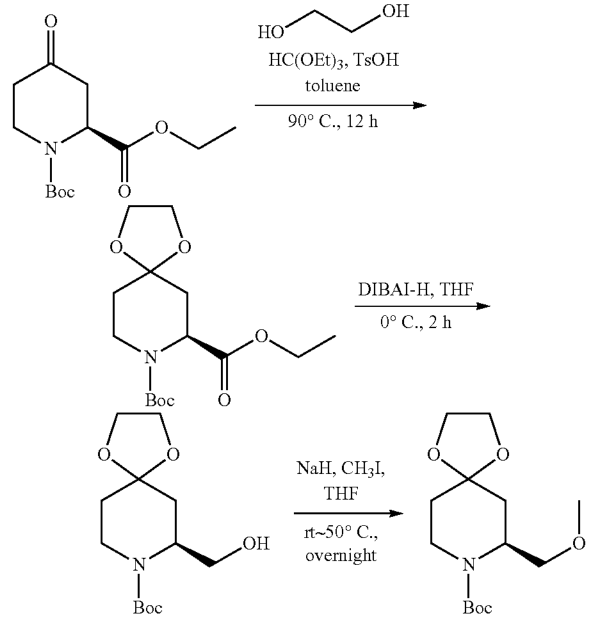

Intermediate 129-1

Step 1: Synthesis of 8-(tert-butyl) 7-ethyl (S)-1,4-dioxa-8-azaspiro[4.5]decane-7,8-dicarboxylate A solution of 1-tert-butyl 2-ethyl (2S)-4-oxopiperidine-1,2-dicarboxylate (2 g, 7.4 mmol, 1 equiv), ethylene glycol (2.29 g, 36.9 mmol, 5 equiv) and triethyl orthoformate (3.28 g, 22.1 mmol, 3 equiv) in toluene (20 mL) was treated with p-toluenesulfonic acid (0.06 g, 0.37 mmol, 0.05 equiv) at room temperature. The resulting mixture was stirred overnight at 90° C. The mixture was allowed to cool to room temperature. The reaction was quenched with water (50 mL) then extracted with ethyl acetate (3x30 mL). The combined organic layers were dried over anhydrous $Na_2SO_4$. After filtration, the filtrate was concentrated under reduced pressure. The crude product 8-(tert-butyl) 7-ethyl (S)-1,4-dioxa-8-azaspiro[4.5]decane-7,8-dicarboxylate (2 g, 69%) was obtained as a light yellow oil. MS (ESI) calcd. for $C_{15}H_{25}NO_6$: 315.17 m/z, found: 316.20 $[M+H]^+$.

Step 2: Synthesis of tert-butyl (7S)-7-(hydroxymethyl)-1,4-dioxa-8-azaspiro[4.5]decane-8-carboxylate A cooled (0° C.) solution of 8-(tert-butyl) 7-ethyl (S)-1,4-dioxa-8-azaspiro[4.5]decane-7,8-dicarboxylate (2 g, 6.3 mmol, 1 equiv) in THE (20 mL) was treated with DIBAl—H (2.25 g, 15.9 mmol, 2.5 equiv) over 5 min under nitrogen atmosphere. The resulting mixture was stirred for 2 h at 0° C. under nitrogen atmosphere. The reaction was quenched with water (50 mL) then extracted with ethyl acetate (3x30 mL). The combined organic layers were washed with potassium sodium tartrate (3x30 mL) and dried over anhydrous $Na_2SO_4$. After filtration, the filtrate was concentrated under reduced pressure. The residue was purified by silica gel column chromatography using (1:1) ethyl acetate in petroleum ether to afford tert-butyl (7S)-7-(hydroxymethyl)-1,4-dioxa-8-azaspiro[4.5]decane-8-carboxylate (1 g, 46%) as a yellow oil. MS (ESI) calcd. for $C_{13}H_{23}NO_5$: 273.16 m/z, found: 274.15 $[M+H]^+$.

Step 3: Synthesis of tert-butyl (7S)-7-(methoxymethyl)-1,4-dioxa-8-azaspiro[4.5]decane-8-carboxylate (Intermediate 129-1

A solution of tert-butyl (7S)-7-(hydroxymethyl)-1,4-dioxa-8-azaspiro[4.5]decane-8-carboxylate (804 mg, 2.94 mmol, 1 equiv) in THE (6 mL) was treated with NaH (141 mg, 5.88 mmol, 2 equiv) portion wise over 10 min at room temperature. The resulting mixture was stirred for 30 min at room temperature. To the above mixture was added methyl iodide (501 mg, 3.53 mmol, 1.2 equiv) dropwise over 2 min. The resulting mixture was stirred overnight at 50° C. The mixture was allowed to cool to room temperature. The reaction was quenched by the addition of water (50 mL) at 0° C. The resulting mixture was extracted with ethyl acetate (3x30 mL). The combined organic layers were dried over anhydrous $Na_2SO_4$. After filtration, the filtrate was concentrated under reduced pressure to afford tert-butyl (7S)-7-(methoxymethyl)-1,4-dioxa-8-azaspiro[4.5]decane-8-carboxylate (Intermediate 129-1) (540 mg, 51%) as a brown/yellow oil. MS (ESI) calcd. for $C_{14}H_{25}NO_5$: 287.17 m/z, found: 288.20 $[M+H]^+$.

Example 131: 1-[(1R,4R,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.2]octan-2-yl]prop-2-en-1-one Example 132: 1-[(1R,4R,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.2]octan-2-yl]prop-2-en-1-one Example 133: 1-[(1S,4S,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.2]octan-2-yl]prop-2-en-1-one and Example 134: 1-[(1S,4S,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.2]octan-2-yl]prop-2-en-1-one Example 131

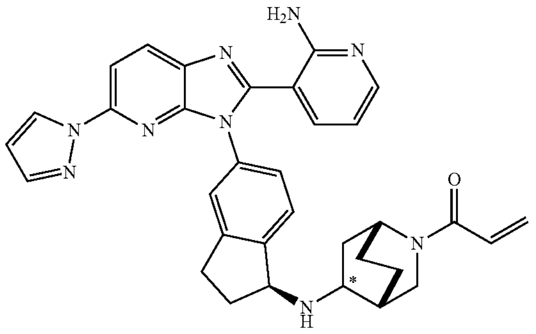

-continued

Example 132

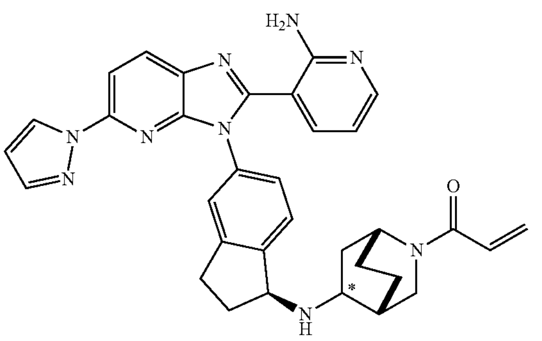

Example 133

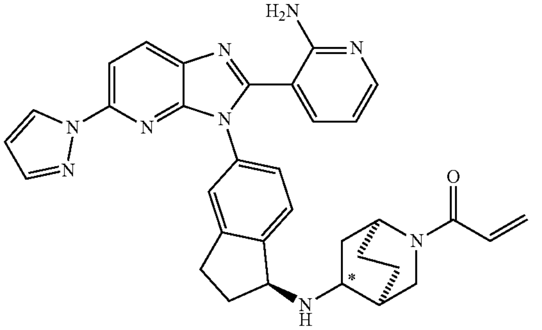

Example 134

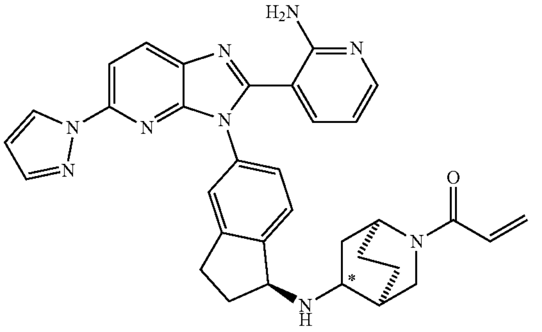

Examples 131, 132, 133 and 134 were prepared in a manner analogous to Example 14 (via Intermediate 14-1) starting from tert-butyl 5-oxo-2-azabicyclo[2.2.2]octane-2-carboxylate instead of tert-butyl 8-oxo-3-azabicyclo[3.2.1]octane-3-carboxylate, using 4N HCl in dioxane in place of TFA in DCM, and methanol instead of 1,2-dichloroethane for the final step. Example 131 was separated from the other three diastereomers by chiral Prep HPLC on a CHIRALPAK IA3 column using a mixture of [MTBE (+0.1% diethylamine)] and [EtOH/DCM (1:1)]. Example 132 was separated from the remaining two diastereomers by chiral Prep HPLC on a CHIRALPAK OD column using a mix of [hexanes (+0.5% 2M $NH_3$-MeOH)] and ethanol. Examples 133 and 134 were separated by chiral Prep-HPLC on a CHIRALPAK IA column using a mix of [MTBE (+0.5% 2M $NH_3$-MeOH)] and [ethanol/DCM (1:1)]. * Denotes a stereocenter with undetermined absolute stereochemistry of a single diastereomer.

Example 131: MS (ESI) calcd. for $C_{33}H_{33}N_9O$: 571.28 m/z, found: 572.20 $[M+H]^+$. $^1$H-NMR (400 MHz, DMSO-$d_6$) δ (ppm): 8.37-8.40 (m, 2H), 8.00-8.05 (m, 2H), 7.78-7.83 (m, 2H), 7.51-7.58 (m, 1H), 7.41-7.49 (m, 1H), 7.38-7.40 (m, 1H), 6.58-6.70 (m, 3H), 6.12-6.24 (m, 1H), 5.68-5.69 (m, 1H), 4.96-4.97 (m, 1H), 4.20-4.49 (m, 1H), 3.80-3.88 (m, 1H), 3.73-3.79 (m, 2H), 3.38-3.42 (m, 1H), 3.18-3.19 (m, 1H), 3.00-3.01 (m, 1H), 2.52-2.53 (m, 1H), 2.43-2.44 (m, 1H), 2.23-2.28 (m, 2H), 1.67-1.79 (m, 4H).

Example 132: MS (ESI) calcd. for $C_{33}H_{33}N_9O$: 571.28 m/z, found: 572.20 $[M+H]^+$. $^1$H-NMR (400 MHz, DMSO-$d_6$) δ (ppm): 8.34-8.36 (m, 2H), 7.95-8.00 (m, 1H), 7.93-7.95 (m, 1H), 7.80-7.81 (m, 1H), 7.49-7.51 (m, 1H), 7.26-7.32 (m, 1H), 7.21-7.24 (m, 2H), 6.66-6.70 (m, 1H), 6.54-6.55 (m, 1H), 6.42-6.43 (m, 1H), 6.06-6.17 (m, 1H), 5.60-5.71 (m, 1H), 4.23-4.33 (m, 2H), 4.03-4.05 (m, 1H), 3.42-3.50 (m, 1H), 3.08-3.10 (m, 1H), 2.94-2.98 (m, 1H), 2.76-2.78 (m, 1H), 2.10-2.11 (m, 4H), 1.77-1.80 (m, 2H), 1.60-1.70 (m, 1H), 1.56-1.60 (m, 1H), 1.30-1.35 (m, 1H).

Example 133: MS (ESI) calcd. for $C_{33}H_{33}N_9O$: 571.28 m/z, found: 572.20 $[M+H]^+$. $^1$H-NMR (400 MHz, DMSO-$d_6$) δ (ppm): 8.32-8.34 (m, 2H), 7.97-7.99 (m, 1H), 7.92-7.94 (m, 1H), 7.78-7.79 (m, 1H), 7.43-7.45 (m, 1H), 7.23-7.29 (m, 1H), 7.20-7.21 (m, 2H), 6.65-6.68 (m, 1H), 6.52-6.53 (m, 1H), 6.40-6.43 (m, 1H), 6.09-6.16 (m, 1H), 5.60-5.70 (m, 1H), 4.19-4.34 (m, 2H), 3.99-4.00 (m, 1H), 3.36-3.39 (m, 1H), 3.00-3.10 (m, 1H), 2.90-2.93 (m, 1H), 2.70-2.80 (m, 1H), 2.30-2.45 (m, 1H), 2.04-2.06 (m, 1H), 1.80-1.85 (m, 1H), 1.71-1.79 (m, 1H), 1.50-2.51 (m, 4H), 1.35-1.40 (m, 1H).

Example 134: MS (ESI) calcd. for $C_{33}H_{33}N_9O$: 571.28 m/z, found: 572.20 $[M+H]^+$. $^1$H-NMR (400 MHz, DMSO-$d_6$) δ (ppm): 8.33-8.36 (m, 2H), 7.93-8.00 (m, 2H), 7.78-7.83 (m, 1H), 7.49-7.51 (m, 1H), 7.25-7.32 (m, 1H), 7.21-7.24 (m, 2H), 6.66-6.69 (m, 1H), 6.53-6.54 (m, 1H), 6.40-6.43 (m, 1H), 6.05-6.17 (m, 1H), 5.59-5.60 (m, 1H), 4.00-4.35 (m, 2H), 3.50-3.59 (m, 1H), 3.29-3.35 (m, 1H), 2.90-3.00 (m, 1H), 2.82-2.93 (m, 1H), 2.76-2.78 (m, 1H), 2.40-2.51 (m, 1H), 1.97-2.09 (m, 3H), 1.75-1.82 (m, 2H), 1.60-1.70 (m, 1H), 1.22-1.39 (m, 2H).

Example 135: 1-[(1S,4S,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.1]heptan-2-yl]prop-2-en-1-one and Example 136: 1-[(1S,4S,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.1]heptan-2-yl]prop-2-en-1-one Example 135

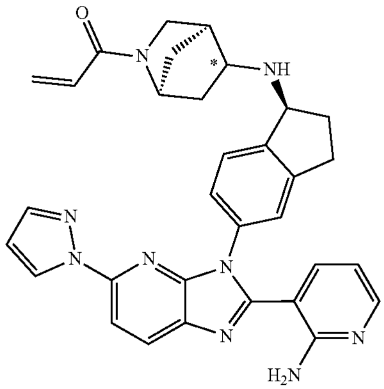

-continued

Example 136

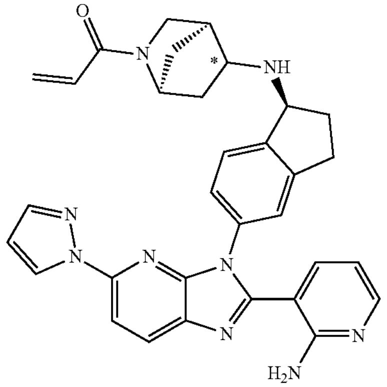

Examples 135 and 136 were prepared in a manner analogous to Example 14 (via Intermediate 14-1) starting from tert-butyl (1S,4S)-5-oxo-2-azabicyclo[2.2.1]heptane-2-carboxylate instead of tert-butyl 8-oxo-3-azabicyclo[3.2.1]octane-3-carboxylate and methanol (+5 eq AcOH) in place of 1,2-dichloroethane for the final step. * Denotes a stereocenter with undetermined absolute stereochemistry of a single diastereomer. The diastereomers were separated by chiral Prep-HPLC on a CHIRALPAK OD column using a mix of [hexanes (+0.5% 2M $NH_3$-MeOH)] and ethanol.

Example 135: MS (ESI) calcd. for $C_{32}H_{31}N_9O$: 557.27 m/z, found: 558.20 $[M+H]^+$. $^1$H-NMR (400 MHz, DMSO) δ (ppm): 8.28-8.35 (m, 2H), 7.98-8.05 (m, 1H), 7.90-7.97 (m, 1H), 7.75-7.85 (m, 1H), 7.42-7.50 (m, 1H), 7.18-7.30 (m, 3H), 6.48-6.65 (m, 2H), 6.38-6.46 (m, 1H), 6.06-6.20 (m, 1H), 5.58-5.70 (m, 1H), 4.32-4.40 (m, 1H), 4.08-4.15 (m, 1H), 3.73-3.95 (m, 1H), 3.08-3.40 (m, 2H), 2.85-2.98 (m, 1H), 2.65-2.80 (m, 2H), 2.35-2.48 (m, 1H), 1.90-2.10 (m, 1H), 1.53-1.80 (m, 3H), 1.00-1.25 (m, 1H).

Example 136: MS (ESI) calcd. for $C_{32}H_{31}N_9O$: 557.27 m/z, found: 558.20 $[M+H]^+$. $^1$H-NMR (400 MHz, DMSO) δ (ppm): 8.26-8.40 (m, 2H), 7.90-8.05 (m, 2H), 7.75-7.82 (m, 1H), 7.43-7.52 (m, 1H), 7.26-7.35 (m, 1H), 7.15-7.25 (m, 2H), 6.35-6.65 (m, 3H), 6.05-6.18 (m, 1H), 5.60-5.70 (m, 1H), 4.40-4.50 (m, 1H), 4.12-4.20 (m, 1H), 3.38-3.50 (m, 1H), 3.10-3.28 (m, 1H), 2.90-3.08 (m, 3H), 2.66-2.80 (m, 1H), 2.35-2.45 (m, 1H), 1.72-1.95 (m, 3H), 1.30-1.55 (m, 2H).

Example 137: 1-[(1R,4R,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.1]heptan-2-yl]prop-2-en-1-one and Example 138: 1-[(1R,4R,5*)-5-{[(1S)-5-[2-(2-aminopyridin-3-yl)-5-(pyrazol-1-yl)imidazo[4,5-b]pyridin-3-yl]-2,3-dihydro-1H-inden-1-yl]amino}-2-azabicyclo[2.2.1]heptan-2-yl]prop-2-en-1-one Example 137

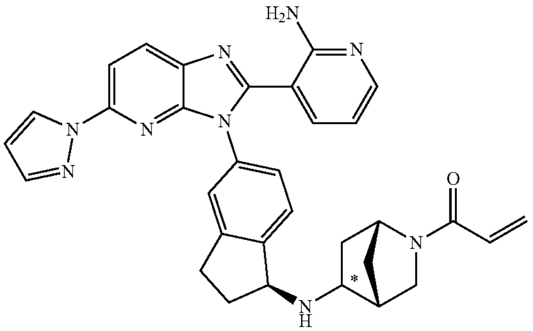

Example 138

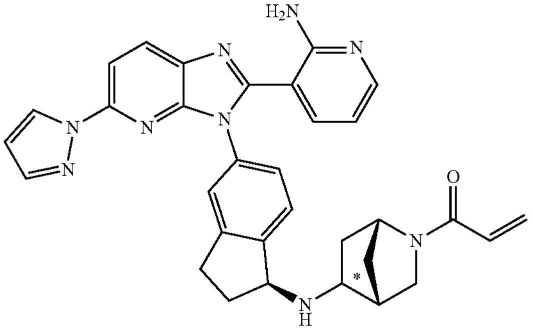

Examples 137 and 138 were prepared in a manner analogous to Example 14 (via Intermediate 14-1) starting from tert-butyl (1R,4R)-5-oxo-2-azabicyclo[2.2.1]heptane-2-carboxylate instead of tert-butyl 8-oxo-3-azabicyclo[3.2.1]octane-3-carboxylate and methanol (+5 eq AcOH) in place of 1,2-dichloroethane for the final step. * Denotes a stereocenter with undetermined absolute stereochemistry of a single diastereomer. The diastereomers were separated by chiral Prep-HPLC on a CHIRALPAK OD column using a mix of [hexanes (+0.5% 2M $NH_3$-MeOH)] and ethanol.

Example 137: MS (ESI) calcd. for $C_{32}H_{31}N_9O$: 557.27 m/z, found: 558.20 $[M+H]^+$. $^1$H-NMR (400 MHz, DMSO) S (ppm): 8.30-8.40 (m, 2H), 7.96-8.05 (m, 1H), 7.90-7.95 (m, 1H), 7.75-7.82 (m, 1H), 7.45-7.52 (m, 1H), 7.28-7.35 (m, 1H), 7.19-7.25 (m, 2H), 6.45-6.65 (m, 2H), 6.38-6.44 (m, 1H), 6.05-6.18 (m, 1H), 5.60-5.70 (m, 1H), 4.32-4.40 (m, 1H), 4.10-4.20 (m, 1H), 3.82-3.90 (m, 1H), 3.05-3.40 (m, 2H), 2.88-3.00 (m, 1H), 2.65-2.80 (m, 1H), 2.53-2.60 (m, 1H), 2.30-2.42 (m, 1H), 1.95-2.12 (m, 1H), 1.73-1.85 (m, 1H), 1.55-1.70 (m, 2H), 1.01-1.12 (m, 1H).

Example 138: MS (ESI) calcd. for $C_{32}H_{31}N_9O$: 557.27 m/z, found: 558.20 $[M+H]^+$. $^1$H-NMR (400 MHz, DMSO) δ (ppm): 8.28-8.40 (m, 2H), 7.90-8.05 (m, 2H), 7.75-7.85 (m, 1H), 7.42-7.52 (m, 1H), 7.28-7.38 (m, 1H), 7.15-7.26 (m, 2H), 6.35-6.65 (m, 3H), 6.05-6.20 (m, 1H), 5.60-5.70

(m, 1H), 4.38-4.50 (m, 1H), 4.20-4.30 (m, 1H), 3.38-3.50 (m, 1H), 3.08-3.25 (m, 1H), 2.85-3.05 (m, 2H), 2.65-2.80 (m, 1H), 2.32-2.45 (m, 1H), 1.71-1.95 (m, 3H), 1.20-1.55 (m, 3H).

Example 139: 1-[(3*,4*)-4-{[(1S)-5-[2-(2-amino-pyridin-3-yl)-5-(pyrazol-1-yl)imidazo[4,5-b]pyridin-3-yl]-2,3-dihydro-1H-inden-1-yl]amino}-3-hydroxypiperidin-1-yl]prop-2-en-1-one Example 140: 1-[(3*,4*)-4-{[(1S)-5-[2-(2-amino-pyridin-3-yl)-5-(pyrazol-1-yl)imidazo[4,5-b]pyridin-3-yl]-2,3-dihydro-1H-inden-1-yl]amino}-3-hydroxypiperidin-1-yl]prop-2-en-1-one Example 141: 1-[(3*,4*)-4-{[(1S)-5-[2-(2-amino-pyridin-3-yl)-5-(pyrazol-1-yl)imidazo[4,5-b]pyridin-3-yl]-2,3-dihydro-1H-inden-1-yl]amino}-3-hydroxypiperidin-1-yl]prop-2-en-1-one and Example 142: 1-[(3*,4*)-4-{[(1S)-5-[2-(2-amino-pyridin-3-yl)-5-(pyrazol-1-yl)imidazo[4,5-b]pyridin-3-yl]-2,3-dihydro-1H-inden-1-yl]amino}-3-hydroxypiperidin-1-yl]prop-2-en-1-one Example 139

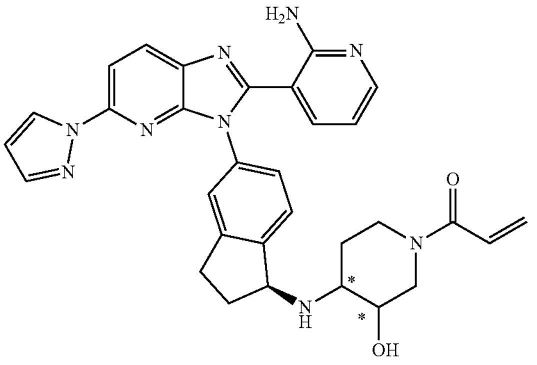

Example 140

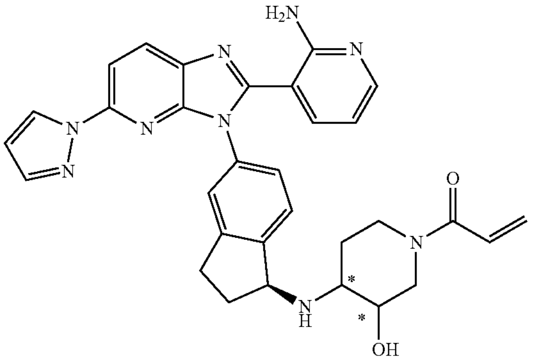

-continued

Example 141

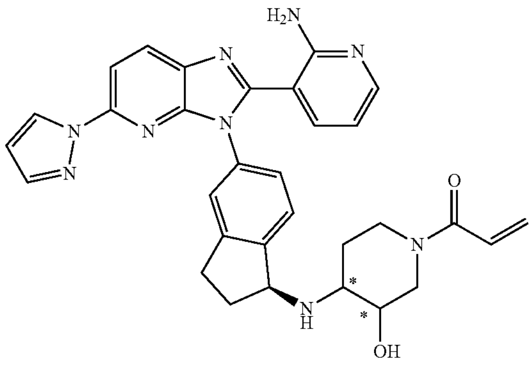

Example 142

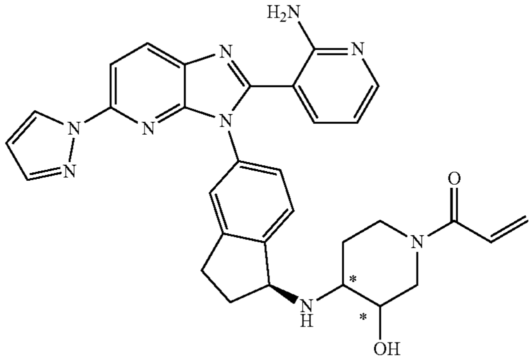

Synthetic Route:

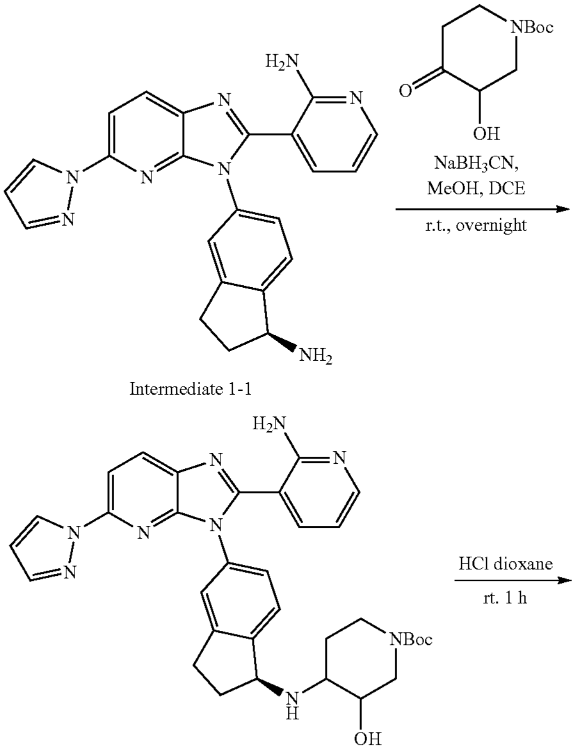

Intermediate 1-1

-continued

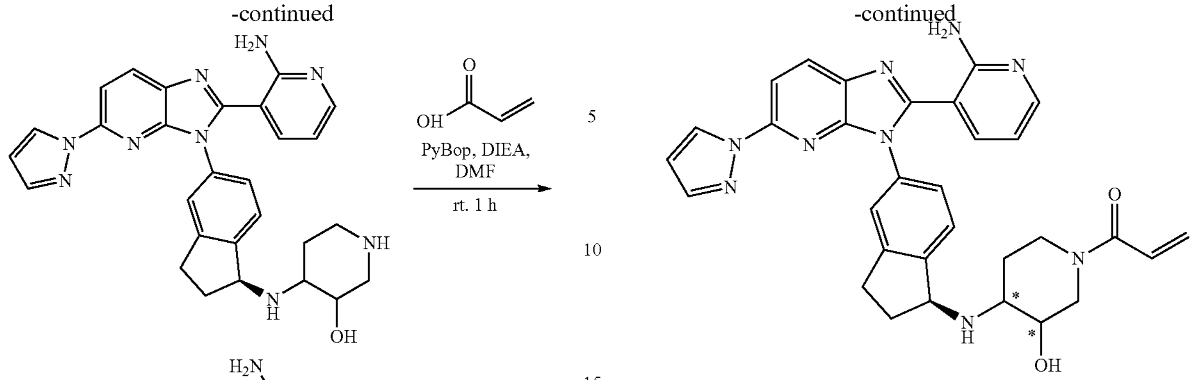

Example 141

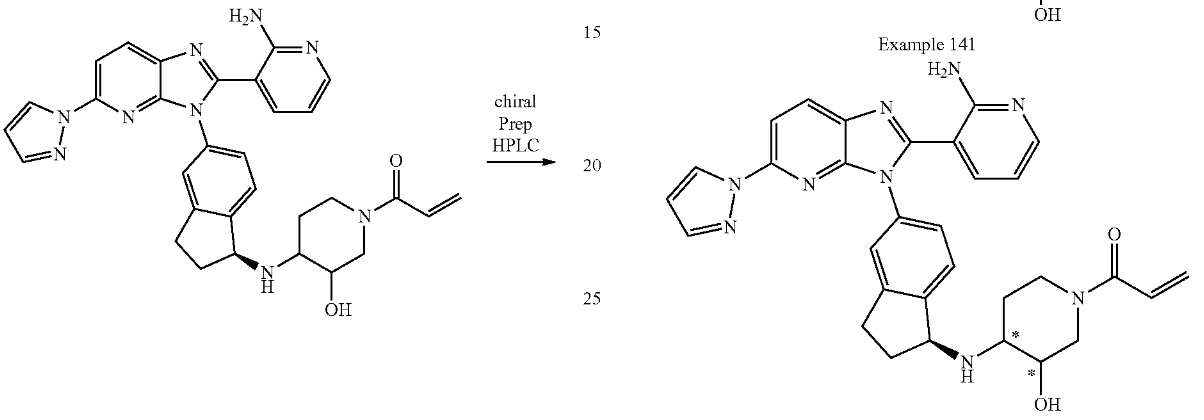

Example 142

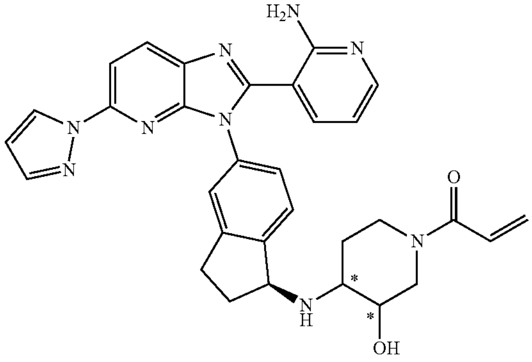

Example 139

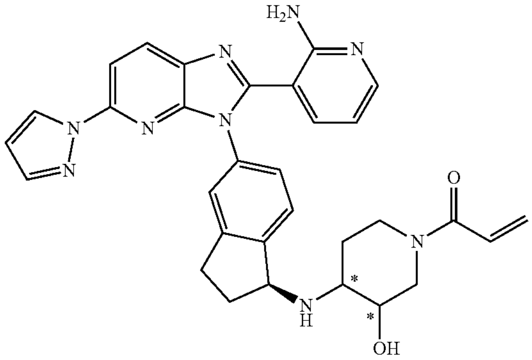

Example 140

Step 1: Synthesis of tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3-hydroxypiperidine-1-carboxylate A solution of 3-{3-[(1S)-1-amino-2,3-dihydro-1H-inden-5-yl]-5-(pyrazol-1-yl) imidazo[4,5-b]pyridin-2-yl}pyridin-2-amine (Intermediate 1-1) (1 g, 2.4 mmol) and tert-butyl (3R)-3-hydroxy-4-oxopiperidine-1-carboxylate (0.74 g, 3.427 mmol) in MeOH (3 mL) and DCE (30 mL) was stirred at room temperature overnight. $NaCNBH_3$ (0.19 g, 4.9 mmol) was added and the resulting mixture was stirred at room temperature for 1 h. The reaction was quenched with water (2 mL) and the mixture was concentrated and purified by Prep-HPLC on a XSelect CSH Fluoro Phenyl column using a gradient of acetonitrile in water (+0.1% $NH_3HCO_3$) to afford tert-butyl 4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3-hydroxypiperidine-1-carboxylate (900 mg, 60% yield) as a yellow solid. MS (ESI) calcd. for $C_{33}H_{37}N_9O_3$: 607.30 m/z, found: 608.30 $[M+H]^+$.

Step 2: Synthesis of 4-{1[(1S)-5-[2-(2-aminopyridin-3-yl)-5-(pyrazol-1-yl) imidazo[4,5-b]pyridin-3-yl]-2,3-dihydro-1H-inden-1-yl]amino}piperidin-3-ol A solution of tert-butyl 4-{[(1S)-5-[2-(2-aminopyridin-3-yl)-5-(pyrazol-1-yl) imidazo[4,5-b]pyridin-3-yl]-2,3-dihydro-1H-inden-1-yl]amino}-3-hydroxypiperidine-1-carboxylate (450 mg, 0.740 mmol) in 0.4N HCl in dioxane (10 mL) was stirred at room temperature for 1 h. The mixture was concentrated to afford 4-{[(1S)-5-[2-(2-aminopyridin-3-yl)-5-(pyrazol-1-yl) imidazo[4,5-b]pyridin-3-yl]-2,3-dihydro-1H-inden-1-yl]amino}piperidin-3-ol (375 mg, crude quant) as an off-white solid. MS (ESI) calcd. for $C_{28}H_{29}N_9O$: 507.25 m/z, found: 508.25 $[M+H]^+$.

Step 3: Synthesis of 1-(4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-hydroxypiperidin-1-yl)prop-2-en-1-one (4 diastereomers, Examples 139-142

To a solution of (3R)-4-{[(1S)-5-[2-(2-aminopyridin-3-yl)-5-(pyrazol-1-yl) imidazo[4,5-b]pyridin-3-yl]-2,3-dihydro-1H-inden-1-yl]amino}piperidin-3-ol (370 mg, 0.729 mmol) in DMF (4 mL) was added N,N-diisopropylethylamine (282.6 mg, 2.187 mmol), PyBOP (417.3 mg, 0.802 mmol) and acrylic acid (52.5 mg, 0.729 mmol). The resulting mixture was stirred at room temperature for 1 h. The mixture was purified by Prep-HPLC on a XSelect CSH Prep Fluoro-Phenyl Column using a gradient of acetonitrile in water (+10 mmol/L $NH_4HCO_3$) to give a mixture of all 4 isomers. Examples 139 and 142 each separated from Examples 140 and 141 by chiral Prep HPLC on CHIRALPAK IG column using a mixture of [hexanes/DCM (3:1) (+0.5% 2M $NH_3$-MeOH)] and isopropanol. Examples 140 and 141 required further separation by chiral Prep-HPLC on a CHIRALPAK SS column using an mixture of [hexanes/DCM (1:1) (+0.5% 2M $NH_3$-methanol] and ethanol. * Denotes a stereocenter with undetermined absolute stereochemistry of a single diastereomer.

Example 139: MS (ESI) calcd. for $C_{31}H_{31}N_9O_2$: 561.26 m/z, found: 562.25 $[M+H]^+$. $^1H$ NMR (300 MHz, DMSO-$d_6$) δ (ppm): 8.31-8.38 (m, 2H), 7.93-8.02 (m, 2H), 7.79-7.83 (m, 1H), 7.40-7.48 (m, 1H), 7.32-7.38 (m, 1H), 7.19-7.30 (m, 2H), 6.79-6.99 (m, 3H), 6.52-6.56 (m, 1H), 6.38-6.43 (m, 1H), 6.08-6.13 (m, 1H), 5.61-5.71 (m, 1H), 4.97-5.07 (m, 1H), 4.32-4.45 (m, 1H), 4.01-4.09 (m, 1H), 3.88-3.95 (m, 1H), 3.38-3.50 (m, 2H), 3.18-3.28 (m, 1H), 2.90-3.06 (m, 2H), 2.73-2.86 (m, 2H), 2.55-2.59 (m, 1H), 1.84-1.95 (m, 1H), 1.65-1.78 (m, 1H), 1.22-1.40 (m, 1H).

Example 140: MS (ESI) calcd. for $C_{31}H_{31}N_9O_2$: 561.26 m/z, found: 562.25 $[M+H]^+$. $^1H$ NMR (300 MHz, DMSO-$d_6$) δ (ppm): 8.19-8.38 (m, 3H), 7.94-8.03 (m, 2H), 7.82-7.85 (m, 1H), 7.55-7.65 (m, 1H), 7.36-7.45 (m, 1H), 7.21-7.32 (m, 2H), 6.90-6.98 (m, 2H), 6.73-6.88 (m, 1H), 6.50-6.58 (m, 1H), 6.38-6.46 (m, 1H), 6.09-6.18 (m, 1H), 5.65-5.70 (m, 1H), 4.15-4.30 (m, 1H), 3.90-4.09 (m, 2H), 3.52-3.56 (m, 1H), 2.99-3.19 (m, 2H), 2.90-2.97 (m, 2H), 2.82-2.89 (m, 2H), 2.61-2.65 (m, 1H), 2.05-2.19 (m, 1H), 1.90-2.01 (m, 1H), 1.31-1.41 (m, 1H).

Example 141: MS (ESI) calcd. for $C_{31}H_{31}N_9O_2$: 561.26 m/z, found: 562.30 $[M+H]^+$. $^1H$ NMR (300 MHz, DMSO-$d_6$) δ (ppm): 8.19-8.39 (m, 3H), 8.01-8.06 (m, 1H), 7.92-8.01 (m, 1H), 7.89-7.95 (m, 1H), 7.59-7.75 (m, 1H), 7.39-7.43 (m, 1H), 7.28-7.34 (m, 1H), 7.21-7.27 (m, 1H), 6.91-6.98 (m, 2H), 6.70-6.89 (m, 1H), 6.51-6.57 (m, 1H), 6.38-6.42 (m, 1H), 6.02-6.15 (m, 1H), 5.65-5.72 (m, 1H), 4.02-4.18 (m, 1H), 3.75-3.99 (m, 2H), 3.50-3.53 (m, 1H), 3.25-3.31 (m, 2H), 2.99-3.13 (m, 2H), 2.80-2.98 (m, 2H), 2.75-2.80 (m, 1H), 1.70-1.99 (m, 2H), 1.58-1.69 (m, 1H).

Example 142: MS (ESI) calcd. for $C_{31}H_{31}N_9O_2$: 561.26 m/z, found: 562.30 $[M+H]^+$. $^1H$ NMR (300 MHz, DMSO-$d_6$) δ (ppm): 8.29-8.36 (m, 2H), 7.93-8.02 (m, 2H), 7.73-7.83 (m, 1H), 7.50-7.58 (m, 1H), 7.20-7.39 (m, 3H), 6.89-7.01 (m, 2H), 6.72-6.86 (m, 1H), 6.50-6.55 (m, 1H), 6.40-6.46 (m, 1H), 6.03-6.11 (m, 1H), 5.63-5.70 (m, 1H), 5.10-5.23 (m, 1H), 4.30-4.42 (m, 1H), 3.89-4.01 (m, 1H), 3.44-3.55 (m, 2H), 3.02-3.13 (m, 2H), 2.90-3.01 (m, 1H), 2.70-2.82 (m, 2H), 2.60-2.69 (m, 2H), 1.91-2.02 (m, 1H), 1.78-1.89 (m, 1H), 1.28-1.39 (m, 1H).

Example 143: 1-((2R,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one and Example 144: 1-((2R,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one Example 143

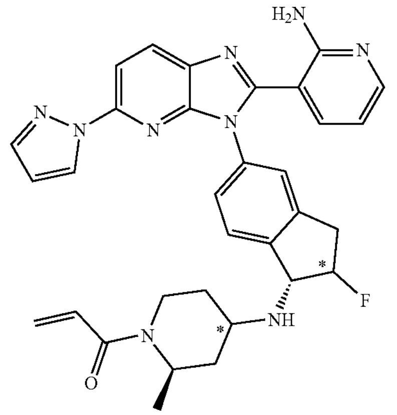

Example 144

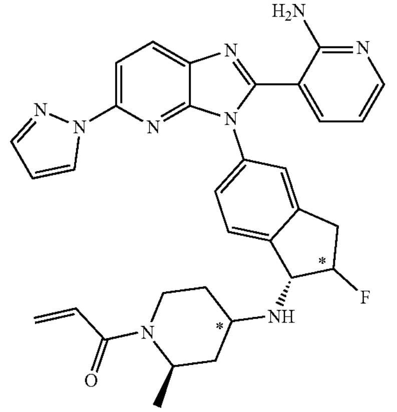

Examples 143 and 144 were prepared in a manner analogous to Example 14 (via Intermediate 14-1) starting from tert-butyl (2R)-2-methyl-4-oxopiperidine-1-carboxylate instead of tert-butyl 8-oxo-3-azabicyclo[3.2.1]octane-3-carboxylate, using 4N HCl in dioxane instead of TFA in DCM, Intermediate 76-1 in place of Intermediate 1-1 and methanol at room temperature overnight for the final step instead of 1,2-dichloroethane at 40° C. * Denotes a stereocenter with undetermined absolute stereochemistry of a single diastereomer.

Example 143: MS (ESI) calcd. for $C_{32}H_{32}FN_9O$: 577.27 m/z, found: 578.20 $[M+H]^+$. $^1H$ NMR (400 MHz, DMSO-$d_6$) δ (ppm): 8.31-8.33 (m, 2H), 7.98-8.00 (m, 1H), 7.91-7.93 (m, 1H), 7.77-7.78 (m, 1H), 7.48-7.50 (m, 1H), 7.31-7.34 (m, 2H), 7.22-7.24 (m, 1H), 6.71-6.78 (m, 1H), 6.51-6.52 (m, 1H), 6.40-6.43 (m, 1H), 6.05-6.10 (m, 1H), 5.54-5.64 (m, 1H), 5.40-5.41 (m, 1H), 4.41-4.49 (m, 2H), 3.90-

4.00 (m, 1H), 3.35-3.40 (m, 1H), 3.08-3.22 (m, 3H), 1.88-1.92 (m, 1H), 1.71-1.74 (m, 3H), 1.37-1.43 (m, 3H). $^{19}$F NMR (376 MHz, DMSO-$d_6$) δ (ppm): −197.958.

Example 144: MS (ESI) calcd. for $C_{32}H_{32}FN_9O$: 577.27 m/z, found: 578.20 $[M+H]^+$. $^1$H NMR (400 MHz, DMSO-$d_6$) δ (ppm): 8.29-8.31 (m, 2H), 7.91-7.97 (m, 2H), 7.76-7.89 (m, 1H), 7.47-7.49 (m, 1H), 7.22-7.30 (m, 3H), 6.70-6.77 (m, 1H), 6.53-6.54 (m, 1H), 6.41-6.45 (m, 1H), 6.00-6.08 (m, 1H), 5.65-5.68 (m, 1H), 5.40-5.55 (m, 1H), 4.80-4.81 (m, 1H), 4.35-4.38 (m, 2H), 3.17-3.20 (m, 2H), 3.06-3.12 (m, 1H), 2.77-2.80 (m, 1H), 2.10-2.13 (m, 1H), 1.75-1.78 (m, 1H), 1.39-1.47 (m, 1H), 1.11-1.20 (m, 4H). $^{19}$F NMR (376 MHz, DMSO-$d_6$) δ (ppm): −197.128.

Example 145: 1-((2R,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one and Example 146: 1-((2R,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one Example 145

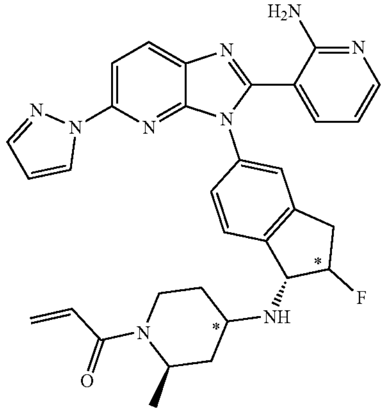

Example 146

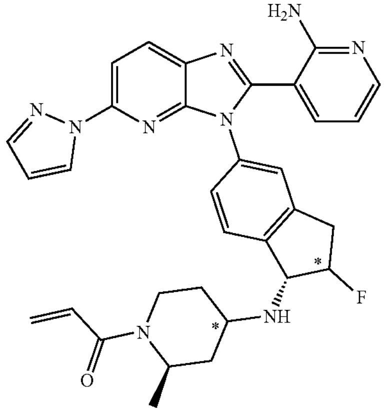

Examples 145 and 146 were prepared in a manner analogous to Example 14 (via Intermediate 14-1) starting from tert-butyl (2R)-2-methyl-4-oxopiperidine-1-carboxylate instead of tert-butyl 8-oxo-3-azabicyclo[3.2.1]octane-3-carboxylate, using 4N HCl in dioxane instead of TFA in DCM, using Intermediate 75-1 in place of Intermediate 1-1 and methanol at room temperature overnight for the final step instead of 1,2-dichloroethane at 40° C. * Denotes a stereocenter with undetermined absolute stereochemistry of a single diastereomer.

Example 145: MS (ESI) calcd. for $C_{32}H_{32}FN_9O$: 577.27 m/z, found: 578.20 $[M+H]^+$. $^1$H NMR (400 MHz, DMSO-$d_6$) δ (ppm): 8.32-8.34 (m, 2H), 7.98-8.00 (m, 1H), 7.92-7.94 (m, 1H), 7.78-7.79 (m, 1H), 7.47-7.49 (m, 1H), 7.30-7.36 (m, 1H), 7.22-7.28 (m, 2H), 6.70-6.77 (m, 1H), 6.53-6.54 (m, 1H), 6.42-6.45 (m, 1H), 6.04-6.09 (m, 1H), 5.64-5.67 (m, 1H), 5.15-5.33 (m, 1H), 4.34-4.40 (m, 2H), 3.98-4.01 (m, 1H), 3.45-3.50 (m, 1H), 3.25-3.30 (m, 1H), 3.16-3.18 (m, 1H), 2.99-3.00 (m, 1H), 1.76-1.80 (m, 2H), 1.59-1.62 (m, 1H), 1.13-1.36 (m, 4H). $^{19}$F NMR (376 MHz, DMSO-$d_6$) δ (ppm): −175.263.

Example 146: MS (ESI) calcd. for $C_{32}H_{32}FN_9O$: 577.27 m/z, found: 578.20 $[M+H]^+$. $^1$H NMR (400 MHz, DMSO-$d_6$) δ (ppm): 8.34-8.36 (m, 2H), 7.99-8.00 (m, 1H), 7.93-7.95 (m, 1H), 7.79-7.80 (m, 1H), 7.48-7.50 (m, 1H), 7.39-7.48 (m, 1H), 7.30-7.31 (m, 1H), 7.21-7.28 (m, 1H), 6.74-6.81 (m, 1H), 6.53-6.54 (m, 1H), 6.41-6.45 (m, 1H), 6.00-6.08 (m, 1H), 5.64-5.67 (m, 1H), 5.17-5.31 (m, 1H), 4.70-4.85 (m, 0.5H), 4.36-4.42 (m, 2H), 3.95-4.00 (m, 0.5H), 3.45-3.50 (m, 1H), 2.99-3.15 (m, 3H), 2.04-2.09 (m, 1H), 1.84-1.90 (m, 1H), 1.21-1.40 (m, 1H), 1.12-1.19 (m, 4H). $^{19}$F NMR (376 MHz, DMSO-$d_6$) δ (ppm): −175.292 d.

Example 147: (*)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)amino)piperazin-1-yl)prop-2-en-1-one and Example 148: (*)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)amino)piperazin-1-yl)prop-2-en-1-one Example 147

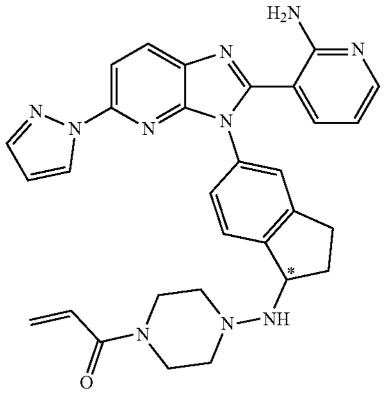

-continued

Example 148

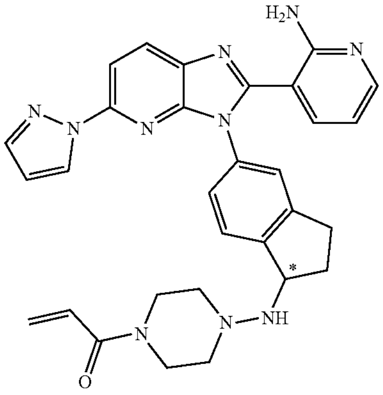

The enantiomers of racemic Example 77 were separated by chiral Prep-HPLC on a CHIRALPAK IA column using a mixture of [MTBE (+0.5% 2M $NH_3$-MeOH)] and [EtOH/DCM 1:1] to afford Example 147 as the first eluting peak and Example 148 as the second eluting peak. * Denotes a stereocenter with undetermined absolute stereochemistry of a single enantiomer.

Example 147: MS (ESI) calcd. for $C_{30}H_{30}N_{10}O$: 546.26 m/z, found: 547.15 $[M+H]^+$. $^1H$ NMR (400 MHz, DMSO-$d_6$) δ (ppm): 8.33-8.38 (m, 2H), 7.99-8.01 (m, 1H), 7.93-7.97 (m, 1H), 7.73-7.79 (m, 1H), 7.61-7.64 (m, 1H), 7.40 (s, 1H), 7.25-7.31 (m, 2H), 6.75-6.82 (m, 1H), 6.53-6.54 (m, 1H), 6.44-6.49 (m, 1H), 6.10-6.15 (m, 1H), 5.70-5.73 (m, 1H), 4.72-4.73 (m, 1H), 3.63-3.70 (m, 4H), 3.01-3.07 (m, 1H), 2.81-2.90 (m, 5H), 2.34-2.38 (m, 1H), 2.03-2.09 (m, 1H).

Example 148: MS (ESI) calcd. for $C_{30}H_{30}N_{10}O$: 546.26 m/z, found: 547.15 $[M+H]^+$. $^1H$ NMR (400 MHz, DMSO-$d_6$) δ (ppm): 8.33-8.35 (m, 2H), 7.92-7.99 (m, 2H), 7.78-7.79 (m, 1H), 7.59-7.61 (m, 1H), 7.38 (s, 1H), 7.22-7.28 (m, 2H), 6.73-6.81 (m, 1H), 6.53-6.54 (m, 1H), 6.44-6.47 (m, 1H), 6.09-6.14 (m, 1H), 5.70-5.73 (m, 1H), 4.60-4.66 (m, 1H), 3.61-3.76 (m, 4H), 3.02-3.05 (m, 1H), 2.82-2.86 (m, 1H), 2.51-2.77 (m, 4H), 2.32-2.39 (m, 1H), 2.01-2.03 (m, 1H).

Example 149: 1-(4-{[(1R)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)prop-2-en-1-one Example 149

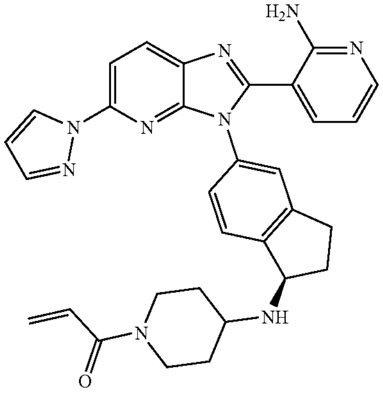

Example 149 was prepared in a manner analogous Example 13 using Intermediate 149-1 in place of Intermediate 1-1. MS (ESI) calcd. for $C_{31}H_{31}N_9O$: 545.27 m/z, found: 546.15 $[M+H]^+$. 1H NMR (300 MHz, DMSO-d6) δ 8.44-8.31 (m, 2H), 8.00 (dd, J=4.8, 1.9 Hz, 1H), 7.95 (d, J=8.6 Hz, 1H), 7.84-7.78 (m, 1H), 7.48 (d, J=7.9 Hz, 1H), 7.33 (s, 1H), 7.30-7.19 (m, 2H), 6.94 (s, 2H), 6.83 (dd, J=16.7, 10.4 Hz, 1H), 6.54 (dd, J=2.6, 1.7 Hz, 1H), 6.42 (dd, J=7.7, 4.8 Hz, 1H), 6.09 (dd, J=16.7, 2.5 Hz, 1H), 5.66 (dd, J=10.4, 2.5 Hz, 1H), 4.34 (t, J=7.3 Hz, 1H), 4.24 (s, 1H), 4.00 (s, 1H), 3.19 (d, J=13.3 Hz, 1H), 2.90 (m, 3H), 2.70-2.87 (m, 1H), 2.43 (s, 1H), 2.03-1.70 (m, 3H), 1.25 (s, 2H).

Intermediate 149-1: (R)-3-(3-(1-amino-2,3-dihydro-1H-inden-5-yl)-5-(1H-pyrazol-1-yl)-3H-imidazo[4,5-b]pyridin-2-yl)pyridin-2-amine Intermediate 149-1

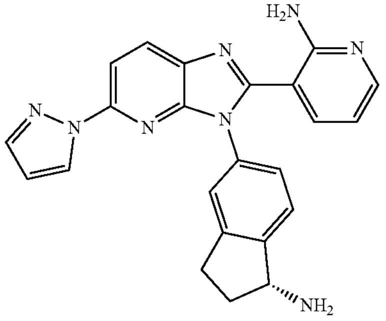

Synthetic Route:

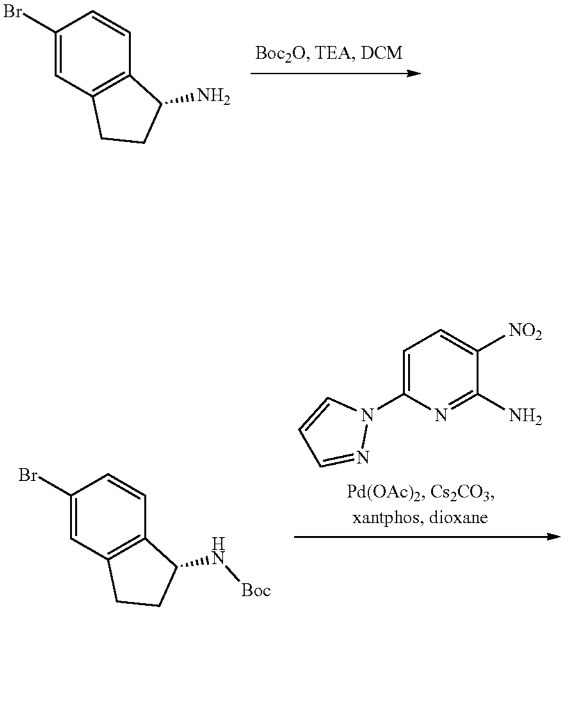

-continued

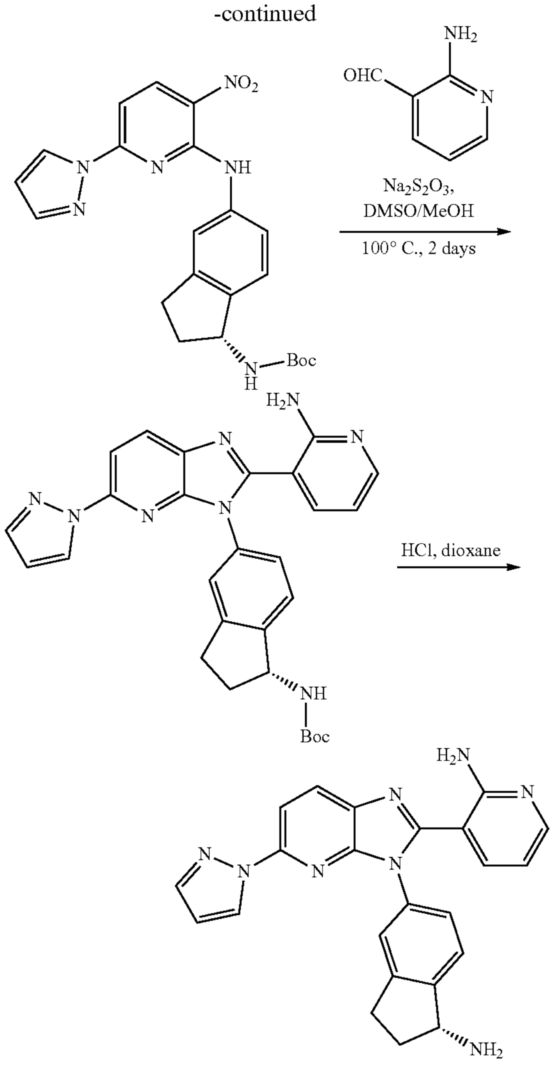

Intermediate 149-1

Step 1: Synthesis of tert-butyl N-[(1R)-5-bromo-2,3-dihydro-1H-inden-1-yl]carbamate To a stirred solution of (1R)-5-bromo-2,3-dihydro-1H-inden-1-amine (2 g, 9.4 mmol, 1 equiv) and triethylamine (2.86 g, 28.3 mmol, 3 equiv) in DCM (40 mL) was added $Boc_2O$ (2.47 g, 11.3 mmol, 1.2 equiv). The resulting mixture was stirred for 2 h at room temperature then concentrated under reduced pressure. The crude product was recrystallized from hexane (200 mL) to afford tert-butyl N-[(1R)-5-bromo-2,3-dihydro-1H-inden-1-yl]carbamate (2.7 g, 92%) as a white solid. MS (ESI) calcd. for $C_{14}H_{18}BrNO_2$: 311.05 m/z, found: 255.90 $[M-^tBu]^+$.

Step 2: Synthesis of tert-butyl N-[(1R)-5-{[3-nitro-6-(pyrazol-1-yl)pyridin-2-yl]amino}-2,3-dihydro-1H-inden-1-yl]carbamate To a stirred solution of tert-butyl N-[(1R)-5-bromo-2,3-dihydro-1H-inden-1-yl]carbamate (2.7 g, 8.6 mmol, 1 equiv) and 3-nitro-6-(pyrazol-1-yl)pyridin-2-amine (2.13 g, 10.4 mmol, 1.2 equiv) in dioxane (45 mL) were added $Pd(OAc)_2$ (0.19 g, 0.87 mmol, 0.1 equiv), XantPhos (0.50 g, 0.865 mmol, 0.1 equiv) and $Cs_2CO_3$ (8.45 g, 25.9 mmol, 3 equiv) at room temperature under nitrogen atmosphere. The resulting mixture was stirred for 5 h at 80° C. under nitrogen atmosphere. The mixture was allowed to cool to room temperature. The resulting mixture was filtered; the filter cake was washed with 1,4-dioxane (3×10 mL). The filtrate was concentrated under reduced pressure. Water was added and the resulting mixture was extracted with EA (3×50 mL). The combined organic layers were washed with brine (3×30 mL) and dried over anhydrous $Na_2SO_4$. After filtration, the filtrate was concentrated under reduced pressure to afford tert-butyl N-[(1R)-5-{[3-nitro-6-(pyrazol-1-yl)pyridin-2-yl]amino}-2,3-dihydro-1H-inden-1-yl]carbamate (3.4 g, 90%) as a yellow solid. MS (ESI) calcd. for $C_{22}H_{24}N_6O_4$: 436.19 m/z, found: 437.15 $[M+H]^+$.

Step 3: Synthesis of tert-butyl N-[(1S)-5-[2-(2-aminopyridin-3-yl)-5-(pyrazol-1-yl)imidazo[4,5-b]pyridin-3-yl]-2,3-dihydro-1H-inden-1-yl]carbamate To a stirred solution of tert-butyl N-[(1S)-5-{[3-nitro-6-(pyrazol-1-yl)pyridin-2-yl]amino}-2,3-dihydro-1H-inden-1-yl]carbamate (3.4 g, 7.8 mmol, 1 equiv) and 2-aminopyridine-3-carbaldehyde (1.43 g, 11.7 mmol, 1.5 equiv) in DMSO (75 mL) and MeOH (13 mL) was added $Na_2S_2O_4$ (2.98 g, 17.1 mmol, 2.2 equiv). The resulting mixture was stirred for 2 days at 100° C. under nitrogen atmosphere. The mixture was allowed to cool to room temperature. The reaction was quenched with saturated aqueous sodium bicarbonate and the resulting mixture was extracted with EA (3×150 mL). The combined organic layers were dried over anhydrous $Na_2SO_4$. After filtration, the filtrate was concentrated under reduced pressure to afford tert-butyl N-[(1S)-5-[2-(2-aminopyridin-3-yl)-5-(pyrazol-1-yl)imidazo[4,5-b]pyridin-3-yl]-2,3-dihydro-1H-inden-1-yl]carbamate (1.5 g, 38%) as a brown solid. MS (ESI) calcd. for $C_{28}H_{28}N_8O_2$: 508.23 m/z, found: 509.20 $[M+H]^+$.

Step 4: Synthesis of 3-{3-[(1R)-1-amino-2,3-dihydro-1H-inden-5-yl]-5-(pyrazol-1-yl)imidazo[4,5-b]pyridin-2-yl}pyridin-2-amine (Intermediate 149-1

A solution of tert-butyl (R)-(5-(2-(2-aminopyridin-3-yl)-5-(1H-pyrazol-1-yl)-3H-imidazo[4,5-b]pyridin-3-yl)-2,3-dihydro-1H-inden-1-yl)carbamate (1.5 g, 3.8 mmol, 1 equiv) in HCl (4.0 M) in 1,4-dioxane (50 mL) was stirred for 30 min at room temperature. The resulting mixture was concentrated under reduced pressure. The residue was dissolved in DCM (50 mL) and the mixture was basified to pH 10 with saturated $NaHCO_3$ (aq.). The aqueous layer was extracted with ethyl acetate (3×50 mL). The combined organic layers were dried over anhydrous $Na_2SO_4$. After filtration, the filtrate was concentrated under reduced pressure to afford 3-{3-[(1R)-1-amino-2,3-dihydro-1H-inden-5-yl]-5-(pyrazol-1-yl)imidazo[4,5-b]pyridin-2-yl}pyridin-2-amine (Intermediate 149-1) (800 mg, crude) as a brown/yellow solid. MS (ESI) calcd. for $C_{23}H_{20}N_8$: 408.18 m/z, found: 409.10 $[M+H]^+$.

Example 150: 1-(4-(((1*,2*)-5-(2-(2-aminopyridin-3-yl)-5-(1H-pyrazol-1-yl)-3H-imidazo[4,5-b]pyridin-3-yl)-2-hydroxy-2,3-dihydro-1H-inden-1-yl)amino)piperidin-1-yl)prop-2-en-1-one and Example 151: 1-(4-(((1*,2*)-5-(2-(2-aminopyridin-3-yl)-5-(1H-pyrazol-1-yl)-3H-imidazo[4,5-b]pyridin-3-yl)-2-hydroxy-2,3-dihydro-1H-inden-1-yl)amino)piperidin-1-yl)prop-2-en-1-one Example 150

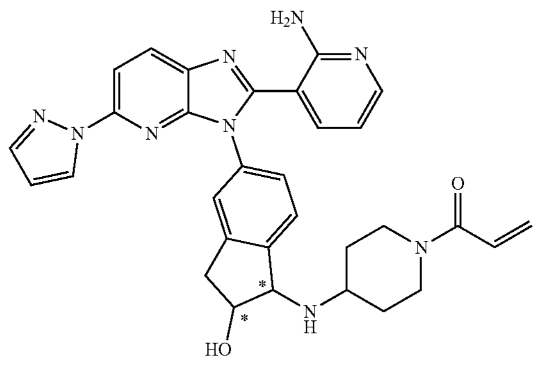

Example 151

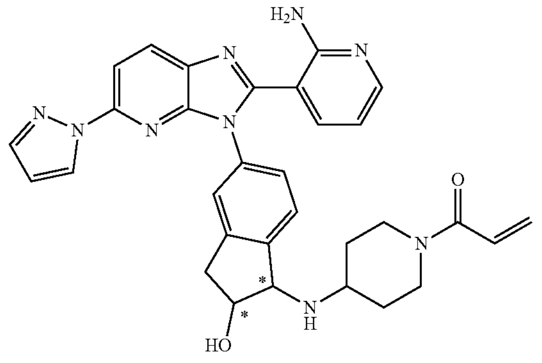

Examples 150 and 151 were prepared in a manner analogous to Example 13 using Intermediate 150-1 and 151-1 in place of Intermediate 1-1 (for Examples 150 and 151, respectively), 1,2-dichloroethane/methanol (10:1) instead of 1,2-dichloroethane and room temperature instead of 40° C. * Denotes a stereocenter with undetermined absolute stereochemistry of a single diastereomer.

Example 150: MS (ESI) calcd. for $C_{31}H_{31}N_9O_2$, 561.28 m/z, found 562.20 $[M+H]^+$. $^1H$ NMR (400 MHz, DMSO-$d_6$) δ (ppm): 8.43-8.45 (m, 2H), 8.08-8.10 (m, 1H), 8.01-8.03 (m, 1H), 7.83-7.84 (m, 1H), 7.76-7.78 (m, 1H), 7.61-7.46 (m, 1H), 7.50-7.59 (m, 2H), 6.80-6.84 (m, 1H), 6.71-6.77 (m, 1H), 6.56-6.57 (m, 1H), 6.08-6.13 (m, 1H), 5.69-5.72 (m, 1H), 4.70-4.73 (m, 2H), 4.50-4.68 (m, 1H), 4.17-4.15 (m, 1H), 3.44-3.57 (m, 2H), 2.90-3.07 (m, 2H), 2.50-2.67 (m, 1H), 2.21-2.24 (m, 1H), 2.12-2.13 (m, 1H), 1.47-1.55 (m, 2H). (TFA salt).

Example 151: MS (ESI) calcd. for $C_{31}H_{31}N_9O_2$, 561.28 m/z, found 562.20 $[M+H]^+$. $^1H$ NMR (400 MHz, DMSO-$d_6$) δ (ppm): 8.43-8.45 (m, 2H), 8.08-8.10 (m, 1H), 8.01-8.03 (m, 1H), 7.83-7.84 (m, 1H), 7.77-7.78 (m, 1H), 7.60-7.61 (m, 1H), 7.53-7.58 (m, 2H), 6.80-6.85 (m, 1H), 6.70-6.78 (m, 1H), 6.57-6.58 (m, 1H), 6.08-6.13 (m, 1H), 5.69-5.72 (m, 1H), 4.74-4.75 (m, 2H), 4.50-4.51 (m, 1H), 4.10-4.20 (m, 1H), 3.45-3.55 (m, 2H), 2.90-3.02 (m, 2H), 2.61-2.67 (m, 1H), 2.23-2.28 (m, 1H), 2.11-2.15 (m, 1H), 1.40-1.55 (m, 2H). (TFA salt).

Intermediate 150-1: (1*,2*)-1-amino-5-(2-(2-aminopyridin-3-yl)-5-(1H-pyrazol-1-yl)-3H-imidazo[4,5-b]pyridin-3-yl)-2,3-dihydro-1H-inden-2-ol and Intermediate 151-1: (1*,2*)-1-amino-5-(2-(2-aminopyridin-3-yl)-5-(1H-pyrazol-1-yl)-3H-imidazo[4,5-b]pyridin-3-yl)-2,3-dihydro-1H-inden-2-ol Intermediate 150-1

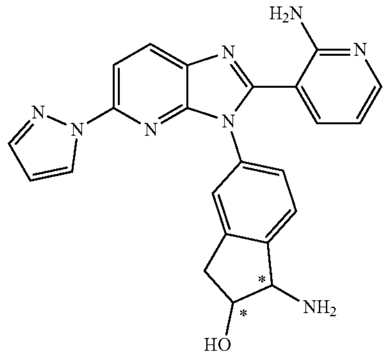

Intermediate 151-1

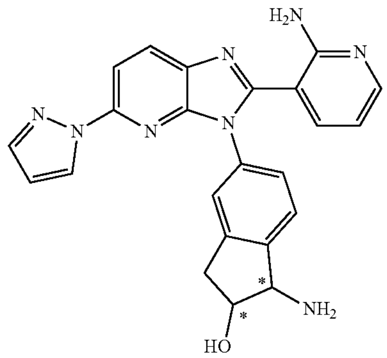

Intermediate 150-1 and Intermediate 151-1 were prepared in a manner analogous to Intermediate 75-1 and Intermediate 76-1 (starting from Step 4) using Intermediate 150-2 in place of (S)-N-((1R)-5-bromo-2-fluoro-2,3-dihydro-1H-inden-1-yl)-2-methylpropane-2-sulfinamide. The diastereomers were separated prior to the final step by chiral SFC on a CHIRAL ART Amylose-SA column using a mix of $CO_2$ and IPA. The precursor to Intermediate 150-1 eluted first. * Denotes a stereocenter with undetermined absolute stereochemistry of a single diastereomer.

Intermediate 150-2: trans-tert-butyl (-5-bromo-2-hydroxy-2,3-dihydro-1H-inden-1-yl)carbamate Intermediate 150-2

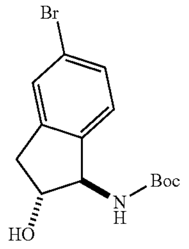

Synthetic Route:

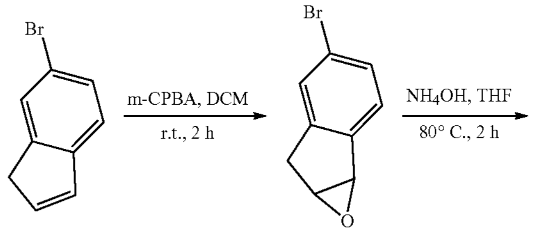

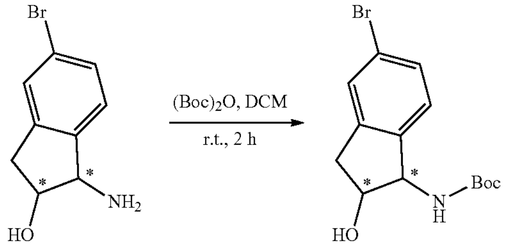

Intermediate 150-2

Step 1: Synthesis of 4-bromo-1a,6a-dihydro-6H-indeno[1,2-b]oxirene

To a solution of 5-bromo-3H-indene (2.0 g, 10 mmol, 1 equiv) in DCM (50 mL) was added m-CPBA (3.54 g, 20.5 mmol, 2 equiv) and the resulting mixture was stirred at r.t. for 2 h. The mixture was concentrated in vacuo and purified by silica gel column chromatography (0-10% ethyl acetate in petroleum ether) to afford 4-bromo-1a,6a-dihydro-6H-indeno[1,2-b]oxirene (0.9 g, 42%) as a white solid. MS (ESI) calcd. for $C_9H_7BrO$, 209.96 m/z, found: 211.10 $[M+H]^+$.

Step 2: Synthesis of trans-1-amino-5-bromo-2,3-dihydro-1H-inden-2-ol

To a solution of 4-bromo-1a,6a-dihydro-6H-indeno[1,2-b]oxirene (0.9 g, 4.3 mmol, 1 equiv) in THE (15 mL) was added $NH_4OH$ (15 mL, 385 mmol, 90 equiv) and the mixture was stirred at 80° C. for 2.0 h. After cooling to room temperature, the reaction was quenched with water (5 mL) and the mixture was extracted with ethyl acetate (3x15 mL). The combined organic extracts were washed with brine (3x10 mL), dried over anhydrous sodium sulfate, filtered and concentrated under vacuum to yield crude trans-1-amino-5-bromo-2,3-dihydro-1H-inden-2-ol (1.0 g, crude) as a light yellow solid. MS (ESI) calcd. for $C_9H_{10}BrNO$, 226.99 m/z, found 228.10 $[M+H]^+$.

Step 3: Synthesis of trans-tert-butyl (5-bromo-2-hydroxy-2,3-dihydro-1H-inden-1-yl)carbamate (Intermediate 150-2

To a solution of trans-1-amino-5-bromo-2,3-dihydro-1H-inden-2-ol (1.0 g, 4.4 mmol, 1 equiv) in DCM (30 mL) was added $(Boc)_2O$ (1.15 g, 5.26 mmol, 1.2 equiv) and the mixture was stirred at r.t. for 18 h. The reaction was quenched with water (10 mL) and the mixture was extracted with DCM (3x25 mL). The combined organic extracts were washed with brine (3x10 mL), dried over anhydrous $Na_2SO_4$, filtered and concentrated under vacuum. The crude product was purified by silica gel column chromatography (0-10% ethyl acetate in petroleum ether to afford trans-tert-butyl N-(5-bromo-2-hydroxy-2,3-dihydro-1H-inden-1-yl) carbamate (1.0 g, 69%) as a yellow solid and as a mixture of diastereomers. MS (ESI) calcd. for $C_{14}H_{18}BrNO_3$, 327.05 m/z, found: 328.10 $[M+H]^+$. * Denotes a stereocenter with undetermined absolute stereochemistry.

Example 152: (S)-1-(4-((5-(2-phenyl-5-(1H-pyrazol-1-yl)-3H-imidazo[4,5-b]pyridin-3-yl)-2,3-dihydro-1H-inden-1-yl)amino)piperidin-1-yl)prop-2-en-1-one Example 152

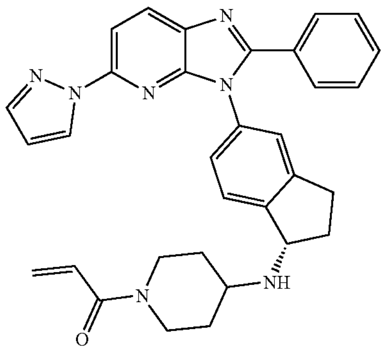

Example 152 was prepared in a manner analogous to Example 13 using Intermediate 152-1 in place of Intermediate 1-1. MS (ESI) calcd. for $C_{32}H_{31}N_7O$: 529.26 m/z, found: 530.15 $[M+H]^+$. $^1H$ NMR (300 MHz, DMSO-d6) δ 8.42-8.27 (m, 2H), 7.95 (d, J=8.6 Hz, 1H), 7.81 (dd, J=1.8, 0.7 Hz, 1H), 7.64-7.53 (m, 2H), 7.53-7.30 (m, 5H), 7.25 (dd, J=8.0, 2.0 Hz, 1H), 6.83 (dd, J=16.7, 10.4 Hz, 1H), 6.54 (dd, J=2.6, 1.7 Hz, 1H), 6.09 (dd, J=16.7, 2.5 Hz, 1H), 5.66 (dd, J=10.5, 2.5 Hz, 1H), 4.36 (t, J=7.1 Hz, 1H), 4.25 (s, 1H), 3.99 (s, 1H), 3.15 (d, J=12.7 Hz, 1H), 3.02-2.88 (m, 2H), 2.87-2.66 (m, 1H), 2.48-2.36 (m, 1H), 2.04-1.71 (m, 4H), 1.24 (s, 3H).

Intermediate 152-1: (S)-5-(2-phenyl-5-(1H-pyrazol-1-yl)-3H-imidazo[4,5-b]pyridin-3-yl)-2,3-dihydro-1H-inden-1-amine Intermediate 152-1

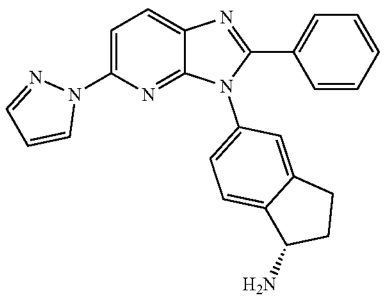

Intermediate 152-1

Intermediate 152-1 was prepared in a manner analogous to Intermediate 149-1 using (1S)-5-bromo-2,3-dihydro-1H-inden-1-amine in place of (1R)-5-bromo-2,3-dihydro-1H-inden-1-amine, benzaldehyde in place of 2-aminopyridine-3-carbaldehyde and TFA+0.05 eq methanesulfonic acid in place of 4N HCl in dioxane. MS (ESI) calcd. for $C_{24}H_{20}N_6$: 392.17 m/z, found: 393.20 $[M+H]^+$.

Example 153: (S)-1-(4-((5-(5-(1H-pyrazol-1-yl)-2-(pyridin-3-yl)-3H-imidazo[4,5-b]pyridin-3-yl)-2,3-dihydro-1H-inden-1-yl)amino)piperidin-1-yl)prop-2-en-1-one Example 153

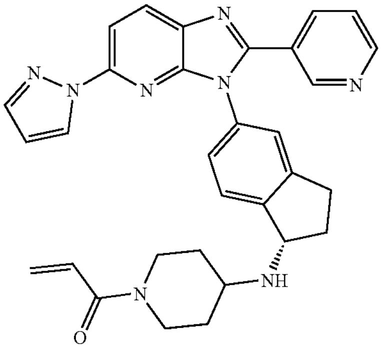

Example 153 was prepared in a manner analogous to Example 13 using Intermediate 153-1 in place of Intermediate 1-1. MS (ESI) calcd. for $C_{31}H_{30}N_8O$: 530.25 m/z, found: 531.15 $[M+H]^+$. $^1H$ NMR (400 MHz, DMSO-d6) δ 8.71 (d, J=2.2 Hz, 1H), 8.63 (dd, J=4.9, 1.7 Hz, 1H), 8.42 (d, J=8.6 Hz, 1H), 8.37 (d, J=2.5 Hz, 1H), 8.02-7.92 (m, 2H), 7.82 (d, J=1.6 Hz, 1H), 7.55-7.45 (m, 2H), 7.40 (d, J=1.9 Hz, 1H), 7.30 (dd, J=7.9, 2.0 Hz, 1H), 6.83 (dd, J=16.7, 10.5 Hz, 1H), 6.56 (t, J=2.1 Hz, 1H), 6.09 (dd, J=16.7, 2.5 Hz, 1H), 5.66 (dd, J=10.4, 2.5 Hz, 1H), 4.37 (t, J=7.2 Hz, 1H), 4.25 (s, 1H), 4.00 (s, 1H), 3.19 (t, J=12.9 Hz, 1H), 3.09-2.88 (m, 3H), 2.88-2.74 (m, 2H), 2.49-2.40 (m, 3.5 Hz, 1H), 1.97 (s, 1H), 1.86 (d, J=12.7 Hz, 1H), 1.84-1.73 (m, 1H), 1.26 (s, 2H).

Intermediate 153-1: (S)-5-(5-(1H-pyrazol-1-yl)-2-(pyridin-3-yl)-3H-imidazo[4,5-b]pyridin-3-yl)-2,3-dihydro-1H-inden-1-amine Intermediate 153-1

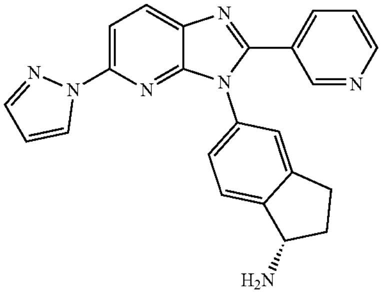

Intermediate 153-1 was prepared in a manner analogous to Intermediate 149-1 using (1S)-5-bromo-2,3-dihydro-1H-inden-1-amine in place of (1R)-5-bromo-2,3-dihydro-1H-inden-1-amine, nicotinaldehyde in place of 2-aminopyridine-3-carbaldehyde and TFA+0.05 eq methanesulfonic acid in place of 4N HCl in dioxane. MS (ESI) calcd. for $C_{23}H_{19}N_7$: 393.17 m/z, found: 394.05 $[M+H]^+$.

Example 154: (S)-1-(4-((6-(2-(2-aminopyridin-3-yl)-5-(1H-pyrazol-1-yl)-3H-imidazo[4,5-b]pyridin-3-yl)-1,2,3,4-tetrahydronaphthalen-1-yl)amino)piperidin-1-yl)prop-2-en-1-one Example 154

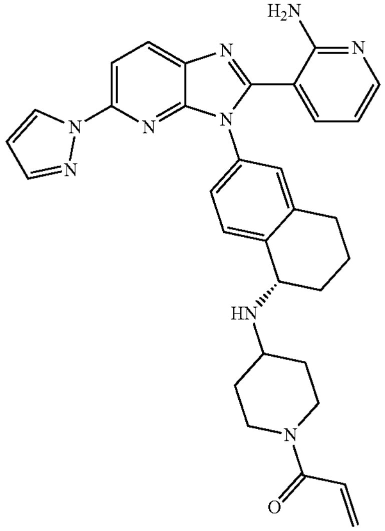

Example 154 was prepared in a manner analogous to Example 13 using Intermediate 154-1 in place of Intermediate 1-1 and 1,2-dichloroethane/methanol (1:1) in place of 1,2-dichloroethane. MS (ESI) calcd. for $C_{32}H_{33}N_9O$: 559.28 m/z, found: 560.20 $[M+H]^+$. $^1H$ NMR (400 MHz, DMSO-d6) δ 8.45-8.30 (m, 2H), 8.05-7.89 (m, 2H), 7.81 (d, J=1.6 Hz, 1H), 7.58 (d, J=8.1 Hz, 1H), 7.29-7.12 (m, 3H), 6.94 (s, 3H), 6.59-6.50 (m, 1H), 6.47-6.39 (m, 1H), 6.14-6.02 (m, 1H), 5.70-5.60 (m, 1H), 4.21 (d, J=13.5 Hz, 1H), 4.15-3.76 (m, 2H), 3.18 (s, 1H), 3.04-2.82 (m, 2H), 2.80-2.60 (m, 3H), 1.92 (d, J=7.9 Hz, 2H), 1.84-1.62 (m, 4H), 1.24 (s, 2H).

Intermediate 154-1: (S)-3-(3-(5-amino-5,6,7,8-tetrahydronaphthalen-2-yl)-5-(1H-pyrazol-1-yl)-3H-imidazo[4,5-b]pyridin-2-yl)pyridin-2-amine Intermediate 154-1

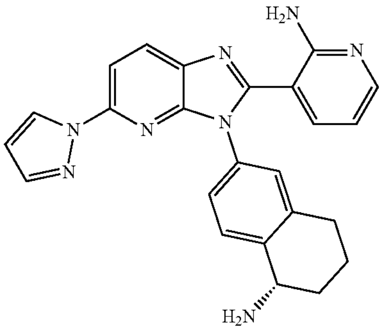

Intermediate 154-1 was prepared in a manner analogous to Intermediate 149-1 using (S)-6-bromo-1,2,3,4-tetrahydronaphthalen-1-amine in place of (1R)-5-bromo-2,3-dihydro-1H-inden-1-amine and TFA in place of 4N HCl in dioxane. MS (ESI) calcd. for $C_{24}H_{22}N_8$: 422.20 m/z, found: 423.30 $[M+H]^+$.

Example 155: (3*,4*)-1-acryloyl-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidine-3-carbonitrile Example 156: (3*,4*)-1-acryloyl-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidine-3-carbonitrile and Example 157: (3*,4*)-1-acryloyl-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidine-3-carbonitrile Example 155

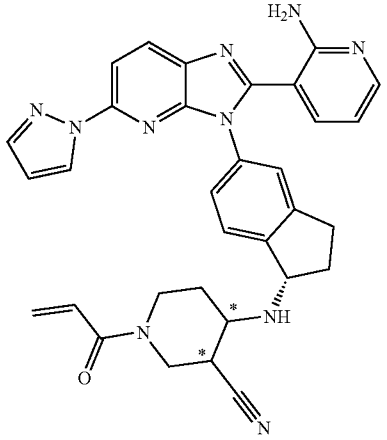

-continued

Example 156

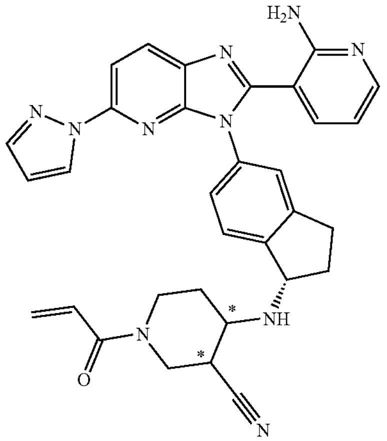

Example 157

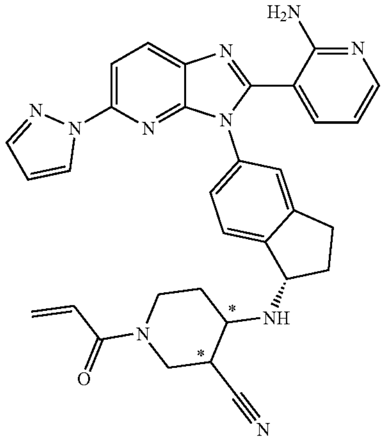

Examples 155, 156 and 157 were prepared in a manner analogous to Example 34 using tert-butyl 3-cyano-4-oxopiperidine-1-carboxylate in place of tert-butyl 4-oxopiperidine-1-carboxylate and acrylic acid in place of (2E)-4-(dimethylamino)but-2-enoic acid. The diastereomers produced in step 1 were partially separated by chiral Prep HPLC on a CHIRALPAK IE column using a mix of [Hex/DCM 3:1 (+0.5% 2M $NH_3$-MeOH)] and EtOH with the precursors to Examples 155 and 156 eluting together after the precursors to Example 157. Examples 155 and 156 were separated by chiral Prep HPLC on a CHIRALPAK IC3 column using a mix of [MTBE (+0.1% diethylamine)] and [methanol/DCM 1:1]. Example 157 is a mix of two diastereomers. * Denotes a stereocenter with undetermined absolute stereochemistry of a single diastereomer.

Example 155: MS (ESI) calcd. for $C_{32}H_{30}N_{10}O$: 570.26 m/z, found: 571.30 $[M+H]^+$. $^1H$ NMR (300 MHz, DMSO-$d_6$) δ (ppm): 8.32-8.38 (m, 2H), 7.93-8.01 (m, 2H), 7.79-8.02 (m, 1H), 7.47-7.51 (m, 1H), 7.34-7.38 (m, 1H), 7.20-7.29 (m, 2H), 6.79-6.97 (m, 3H), 6.53-6.58 (m, 1H), 6.38-6.42 (m, 1H), 6.09-6.16 (m, 1H), 5.68-5.72 (m, 1H), 4.46-4.68 (m, 1H), 4.08-4.38 (m, 2H), 3.32-3.38 (m, 1H), 3.08-3.17 (m, 2H), 2.89-2.99 (m, 2H), 2.65-2.78 (m, 2H), 2.39-2.43 (m, 2H), 1.91-1.99 (m, 1H), 1.76-1.86 (m, 1H).

Example 156: MS (ESI) calcd. for $C_{32}H_{30}N_{10}O$: 570.26 m/z, found: 571.20 $[M+H]^+$. $^1H$ NMR (300 MHz, DMSO-$d_6$) δ (ppm): 8.30-8.38 (m, 2H), 7.94-8.01 (m, 2H), 7.79-8.02 (m, 1H), 7.45-7.49 (m, 1H), 7.29-7.35 (m, 2H), 7.23-7.28 (m, 1H), 6.80-6.98 (m, 3H), 6.51-6.53 (m, 1H), 6.39-6.42 (m, 1H), 6.09-6.16 (m, 1H), 5.68-5.73 (m, 1H), 4.52-

4.68 (m, 1H), 4.08-4.38 (m, 2H), 3.50-3.56 (m, 1H), 3.31-3.36 (m, 1H), 3.07-3.16 (m, 1H), 2.89-2.99 (m, 2H), 2.67-2.79 (m, 2H), 2.51-2.56 (m, 2H), 1.70-1.86 (m, 2H).

Example 157: MS (ESI) calcd. for $C_{32}H_{30}N_{10}O$: 570.26 m/z, found: 571.25 $[M+H]^+$. $^1H$ NMR (300 MHz, DMSO-$d_6$) δ (ppm): 8.32-8.42 (m, 2H), 8.01-8.09 (m, 1H), 7.95-8.00 (m, 1H), 7.81-7.85 (m, 1H), 7.38-7.72 (m, 5H), 7.10-7.25 (m, 1H), 6.81-6.99 (m, 1H), 6.51-6.62 (m, 2H), 6.10-6.21 (m, 1H), 5.71-5.80 (m, 1H), 4.86-5.01 (m, 1H), 4.33-4.48 (m, 1H), 4.03-4.20 (m, 2H), 3.60-3.65 (m, 1H), 3.29-3.40 (m, 1H), 3.00-3.19 (m, 3H), 2.88-2.92 (m, 1H), 2.52-2.59 (m, 1H), 2.11-2.22 (m, 1H), 2.08-2.10 (m, 1H), 1.59-1.69 (m, 1H). (TFA salt).

Example 158: (S)-1-(3-(4-((5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidin-1-yl)azetidin-1-yl)prop-2-en-1-one Example 158

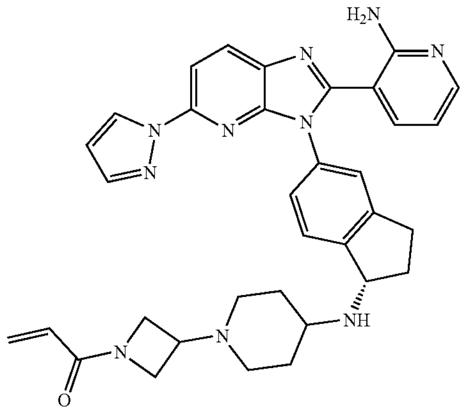

Example 158 was prepared in a manner analogous to Example 14 (via Intermediate 14-1, starting from step 2) using 1-(azetidin-3-yl)piperidin-4-one in place of 3-azabicyclo[3.2.1]octan-8-one and 1,2-dichloroethane/methanol (1:1) in place of 1,2-dichloroethane. MS (ESI) calcd. for $C_{34}H_{36}N_{10}O$, 600.31 m/z, found 601.35 $[M+H]^+$. $^1H$ NMR (300 MHz, DMSO-$d_6$) δ (ppm): 8.44-8.47 (m, 1H), 8.37-8.38 (m, 1H), 8.09-8.11 (m, 2H), 7.77-7.85 (m, 3H), 7.45-7.47 (m, 2H), 6.78-6.80 (m, 1H), 6.57-6.59 (m, 1H), 6.30-6.32 (m, 1H), 6.13-6.18 (m, 1H), 5.78-5.79 (m, 1H), 5.04-5.05 (m, 1H), 4.49-4.52 (m, 2H), 4.19-4.21 (m, 2H), 4.00-4.02 (m, 1H), 3.61-3.62 (m, 2H), 3.55-3.56 (m, 1H), 3.15-3.16 (m, 1H), 3.00-3.03 (m, 3H), 2.70-2.72 (m, 1H), 2.65-2.66 (m, 1H), 2.25-2.30 (m, 2H), 1.92-1.95 (m, 2H). (TFA salt).

Example 159: 1-(4-{[(1S)-5-[2-(2-aminopyridin-3-yl)-5-(1,3-thiazol-2-yl)imidazo[4,5-b]pyridin-3-yl]-2,3-dihydro-1H-inden-1-yl]amino}piperidin-1-yl)prop-2-en-1-one Example 159

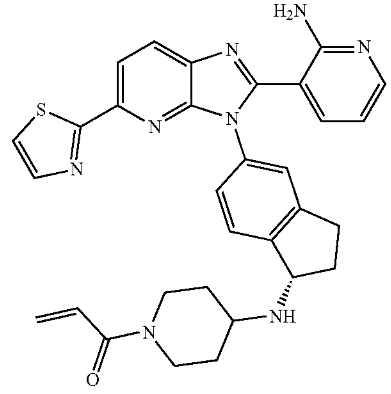

Example 159 was prepared in a manner analogous to Example 13 using Intermediate 159-1 in place of Intermediate 1-1 and 1,2-dichloroethane/methanol (10:1) in place of 1,2-dichloroethane. MS (ESI) calcd. for $C_{31}H_{30}N_8OS$: 562.22 m/z, found: 563.20 $[M+H]^+$. $^1H$ NMR (300 MHz, DMSO-$d_6$) δ (ppm): 8.30-8.35 (m, 1H), 8.20-8.26 (m, 1H), 8.01-8.05 (m, 1H), 7.94-7.98 (m, 1H), 7.78-7.81 (m, 1H), 7.54-7.59 (m, 1H), 7.38-7.41 (m, 1H), 7.25-7.34 (m, 2H), 6.80-6.90 (m, 1H), 6.41-6.48 (m, 1H), 6.08-6.14 (m, 1H), 5.68-5.72 (m, 1H), 4.51-4.58 (m, 1H), 4.30-4.41 (m, 1H), 4.00-4.12 (m, 1H), 3.09-3.19 (m, 2H), 2.98-3.05 (m, 1H), 2.80-2.92 (m, 2H), 2.47-2.52 (m, 1H), 2.01-2.11 (m, 1H), 1.85-1.98 (m, 2H), 1.25-1.41 (m, 2H). (formic acid salt).

Intermediate 159-1: (S)-3-(3-(1-amino-2,3-dihydro-1H-inden-5-yl)-5-(thiazol-2-yl)-3H-imidazo[4,5-b]pyridin-2-yl)pyridin-2-amine Example 159-1

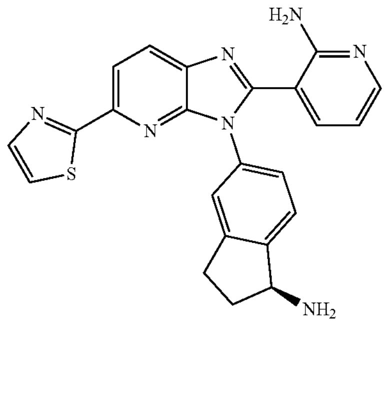

Synthetic Route:

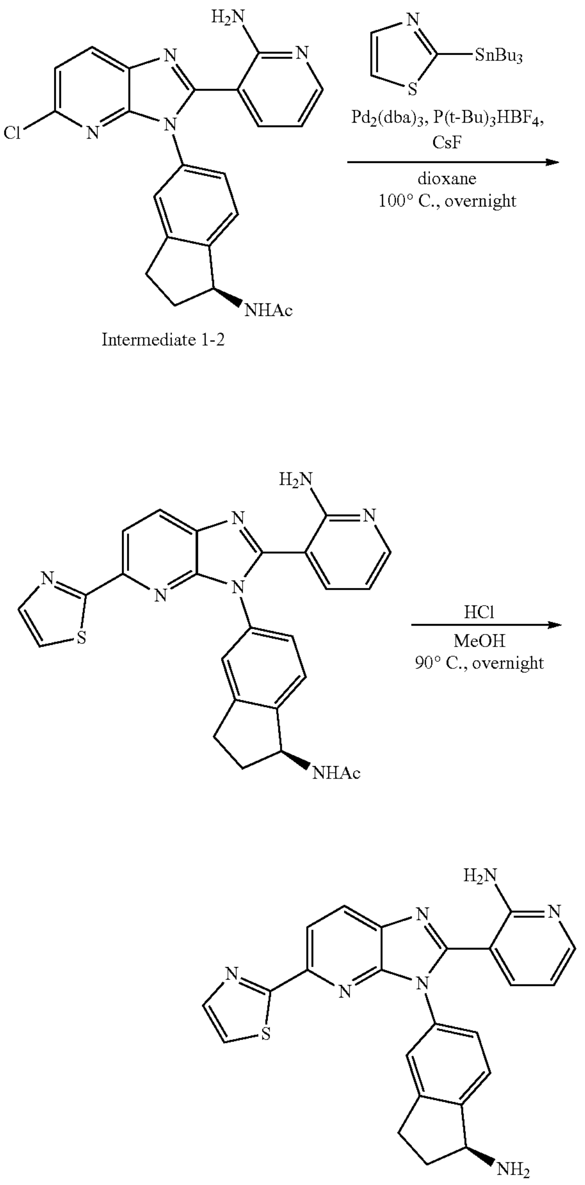

Intermediate 159-1

Step 1: Synthesis of N-[(1S)-5-[2-(2-aminopyridin-3-yl)-5-(1,3-thiazol-2-yl)imidazo[4,5-b]pyridin-3-yl]-2,3-dihydro-1H-inden-1-yl]acetamide To a solution of N-[(1S)-5-[2-(2-aminopyridin-3-yl)-5-chloroimidazo[4,5-b]pyridin-3-yl]-2,3-dihydro-1H-inden-1-yl]acetamide (Intermediate 1-2) (300 mg, 0.716 mmol, 1 equiv) and 2-(tributylstannyl)-1,3-thiazole (1.34 g, 3.58 mmol, 5 equiv) in 1,4-dioxane (5 mL) were added tris (dibenzylideneacetone)dipalladium(0) (67 mg, 0.072 mmol, 0.1 equiv), tri-tert-butylphosphonium tetrafluoroborate (21 mg, 0.072 mmol, 0.1 equiv) and cesium fluoride (272 mg, 1.79 mmol, 2.5 equiv). The resulting mixture was stirred under nitrogen atmosphere for 12 h at 100° C. The resulting mixture was concentrated under reduced pressure and residue was purified by reverse-phase flash column chromatography on C18 silica gel using a 20-95% gradient of acetonitrile in water (+0.05% ammonium bicarbonate) with a 5-minute hold at 70% acetonitrile to afford N-[(1S)-5-[2-(2-aminopyridin-3-yl)-5-(1,3-thiazol-2-yl)imidazo[4,5-b]pyridin-3-yl]-2,3-dihydro-1H-inden-1-yl]acetamide (250 mg, 67%) as a brown solid. MS (ESI) calculated for $C_{25}H_{21}N_7OS$: 467.15 m/z, found 468.15 $[M+H]^+$.

Step 2: Synthesis of 3-{3-[(1S)-1-amino-2,3-dihydro-1H-inden-5-yl]-5-(1,3-thiazol-2-yl)imidazo[4,5-b]pyridin-2-yl}pyridin-2-amine (Intermediate 159-1

To a solution of N-[(1S)-5-[2-(2-aminopyridin-3-yl)-5-(1,3-thiazol-2-yl)imidazo[4,5-b]pyridin-3-yl]-2,3-dihydro-1H-inden-1-yl]acetamide (250 mg, 0.535 mmol, 1 equiv) in methanol (20 mL) was added hydrochloric acid (20 mL, conc.). The resulting mixture was stirred at 90° C. overnight. The solvent was removed by distillation under vacuum to afford crude 3-{3-[(1S)-1-amino-2,3-dihydro-1H-inden-5-yl]-5-(1,3-thiazol-2-yl)imidazo[4,5-b]pyridin-2-yl}pyridin-2-amine (Intermediate 159-1) as a black solid, which was used in subsequent transformations without purification. MS (ESI) calculated for $C_{23}H_{19}N_7S$: 425.14 m/z, found 426.10 $[M+H]^+$.

Example 160: 1-(4-{[(1S)-5-[2-(2-aminopyridin-3-yl)-5-(2-methyl-1,2,3-triazol-4-yl)imidazo[4,5-b]pyridin-3-yl]-2,3-dihydro-1H-inden-1-yl]amino}piperidin-1-yl)prop-2-en-1-one Example 160

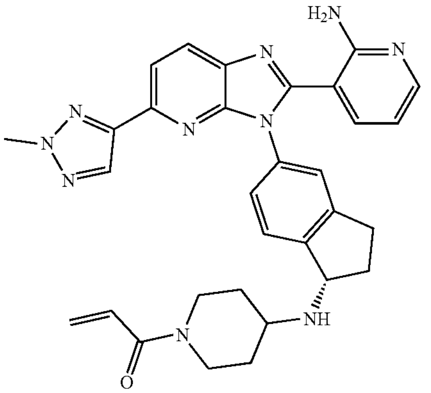

Example 160 was prepared in a manner analogous to Example 13 using Intermediate 160-1 in place of Intermediate 1-1 and methanol in place of 1,2-dichloroethane. MS (ESI) calcd. for $C_{31}H_{32}N_{10}O$, 560.28 m/z, found 561.15 $[M+H]^+$ 0.1H NMR (400 MHz, DMSO-d6) δ ppm: 8.22-8.45 (m, 1H), 8.04-8.15 (m, 1H), 7.96-8.04 (m, 1H), 7.81-7.96 (m, 1H), 7.42-7.64 (m, 1H), 7.31-7.42 (m, 1H), 7.12-7.31 (m, 2H), 6.67-6.97 (m, 1H), 6.32-6.59 (m, 1H), 5.98-6.22 (m, 1H), 5.61-5.85 (m, 1H), 4.28-4.58 (m, 2H), 4.11-4.28 (m, 3H), 3.97-4.11 (m, 1H), 3.08-3.31 (m, 1H), 2.92-3.08 (m, 2H), 2.67-2.92 (m, 2H), 2.41-2.51 (m, 1H), 1.99-2.19 (m, 1H), 1.72-1.99 (m, 2H), 1.12-1.47 (m, 2H). (formic acid salt).

Intermediate 160-1: (S)-3-(3-(1-amino-2,3-dihydro-1H-inden-5-yl)-5-(2-methyl-2H-1,2,3-triazol-4-yl)-3H-imidazo[4,5-b]pyridin-2-yl)pyridin-2-amine Example 160-1

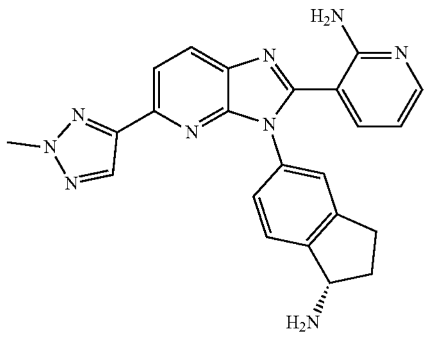

Intermediate 160-1 was prepared in a manner analogous to Intermediate 109-2 using 4-bromo-2-methyl-1,2,3-triazole in place of 2-bromo-1,3-oxazole. MS (ESI) calcd. for $C_{23}H_{21}N_9$, 423.19 m/z, found 424.25 $[M+H]^+$.

Example 161: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl](oxetan-3-ylmethyl)amino}piperidin-1-yl)prop-2-en-1-one Example 161

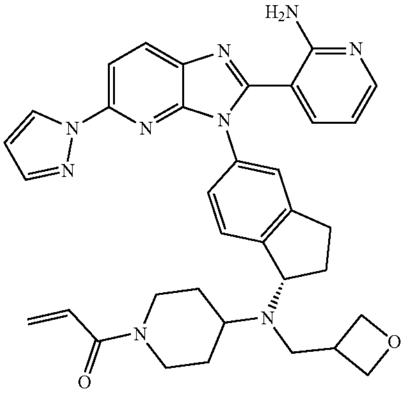

Example 161 was prepared in a manner analogous to Example 67 using oxetane-3-carbaldehyde (2 equiv) in place of formaldehyde. The amine and aldehyde were stirred together for 1 h at room temperature prior to addition of the reducing agent. MS (ESI) calcd. for $C_{35}H_{37}N_9O_2$, 615.31 m/z, found 616.25 $[M+H]^+$. $^1H$ NMR (400 MHz, DMSO-$d_6$) δ (ppm): 8.16-8.52 (m, 2H), 7.89-8.15 (m, 2H), 7.68-7.89 (m, 1H), 7.17-7.49 (m, 4H), 6.68-6.98 (m, 1H), 6.49-6.68 (m, 1H), 6.26-6.49 (m, 1H), 5.95-6.26 (m, 1H), 5.58-5.87 (m, 1H), 4.34-4.78 (m, 4H), 4.01-4.34 (m, 2H), 3.87-3.88 (m, 1H), 2.71-3.14 (m, 6H), 2.56-2.70 (m, 2H), 1.79-2.29 (m, 3H), 1.42-1.79 (m, 2H), 1.09-1.42 (m, 1H).

Example 162: 1-(4-(((1R,2*)-5-(2-(2-aminopyridin-3-yl)-5-(1H-pyrazol-1-yl)-3H-imidazo[4,5-b]pyridin-3-yl)-2-methoxy-2,3-dihydro-1H-inden-1-yl)amino)piperidin-1-yl)prop-2-en-1-one and Example 163: 1-(4-(((1R,2*)-5-(2-(2-aminopyridin-3-yl)-5-(1H-pyrazol-1-yl)-3H-imidazo[4,5-b]pyridin-3-yl)-2-methoxy-2,3-dihydro-1H-inden-1-yl)amino)piperidin-1-yl)prop-2-en-1-one Example 162

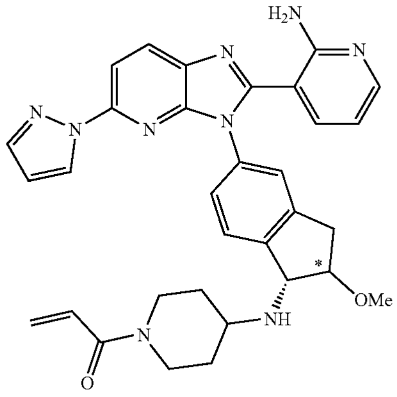

Example 163

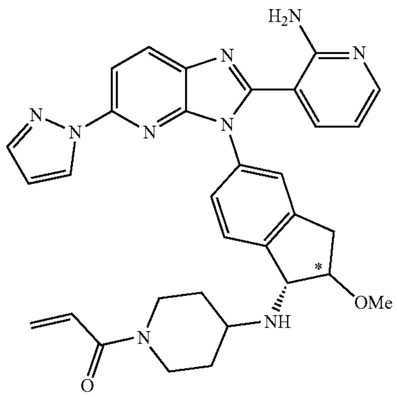

Examples 162 and 163 were prepared in a manner analogous to Example 13 using Intermediate 162-1 and 163-1 in place of Intermediate 1-1 (for Examples 162 and 163, respectively) and methanol instead of 1,2-dichloroethane. * Denotes a stereocenter with undetermined absolute stereochemistry of a single diastereomer.

Example 162: MS (ESI) calcd. for $C_{32}H_{33}N_9O_2$, 575.28 m/z, found 576.25 $[M+H]^+$. $^1H$ NMR (400 MHz, DMSO-d6) δ (ppm): 8.26-8.41 (m, 2H), 7.89-8.14 (m, 2H), 7.69-7.89 (m, 1H), 7.42-7.64 (m, 1H), 7.11-7.42 (m, 3H), 6.68-6.95 (m, 1H), 6.53-6.68 (m, 1H), 6.33-6.53 (m, 1H), 5.96-6.24 (m, 1H), 5.60-5.85 (m, 1H), 4.19-4.51 (m, 2H), 3.99-4.19 (m, 2H), 3.24-3.52 (m, 4H), 2.99-3.24 (m, 2H), 2.66-2.99 (m, 2H), 1.79-2.21 (m, 2H), 1.14-1.49 (m, 2H). (TFA salt).

Example 163: MS (ESI) calcd. for $C_{32}H_{33}N_9O_2$, 575.28 m/z, found 598.35 $[M+Na]^+$. $^1H$ NMR (400 MHz, DMSO-$d_6$) δ (ppm): 8.24-8.56 (m, 2H), 7.92-8.18 (m, 2H), 7.79-7.92 (m, 1H), 7.65-7.79 (m, 2H), 7.52-7.65 (m, 1H), 7.33-7.52 (m, 1H), 6.78-6.98 (m, 1H), 6.48-6.78 (m, 2H), 6.02-6.28 (m, 1H), 5.62-5.94 (m, 1H), 4.77-5.07 (m, 1H), 4.49-4.71 (m, 1H), 4.32-4.49 (m, 1H), 4.08-4.32 (m, 1H), 3.58-

3.72 (m, 1H), 3.51-3.58 (m, 1H), 3.36-3.51 (m, 3H), 3.06-3.27 (m, 1H), 2.89-3.06 (m, 1H), 2.65-2.89 (m, 1H), 2.22-2.34 (m, 1H), 2.14-2.22 (m, 1H), 1.42-1.66 (m, 2H). (TFA salt).

Intermediate 162-1: 3-(3-((1R,2*)-1-amino-2-methoxy-2,3-dihydro-1H-inden-5-yl)-5-(1H-pyrazol-1-yl)-3H-imidazo[4,5-b]pyridin-2-yl)pyridin-2-amine and Intermediate 163-1: 3-(3-((1R,2*)-1-amino-2-methoxy-2,3-dihydro-1H-inden-5-yl)-5-(1H-pyrazol-1-yl)-3H-imidazo[4,5-b]pyridin-2-yl)pyridin-2-amine Example 162-1

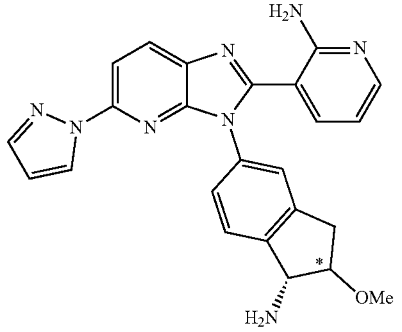

Example 163-1

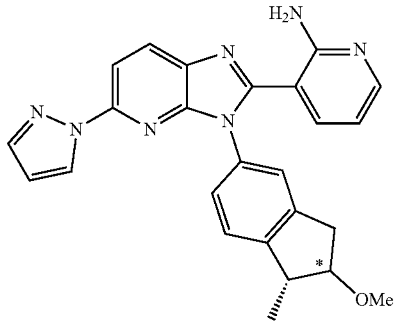

Intermediates 162-1 and Intermediate 163-1 were prepared in a manner analogous to Intermediates 75-1 and Intermediate 76-1 (starting from Step 2) using Intermediate 162-2 in place of 5-bromo-2-fluoro-2,3-dihydroinden-1-one. The diastereomers were separated prior to the last step by SFC on a (S, S)-Whelk-O 1 5 μm Kromasil column using a mixture of $CO_2$ and methanol. * Denotes a stereocenter with undetermined absolute stereochemistry of a single diastereomer.

Intermediate 162-1: MS (ESI) calcd. for $C_{24}H_{22}N_8O$: 438.19 m/z, found: 439.30 $[M+H]^+$.

Intermediate 163-1: MS (ESI) calcd. for $C_{24}H_{22}N_8O$: 438.19 m/z, found: 439.30 $[M+H]^+$.

Intermediate 162-2: 5-bromo-2-methoxy-2,3-dihydro-1H-inden-1-one

Intermediate 162-2

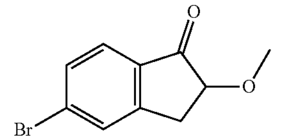

Synthetic Route:

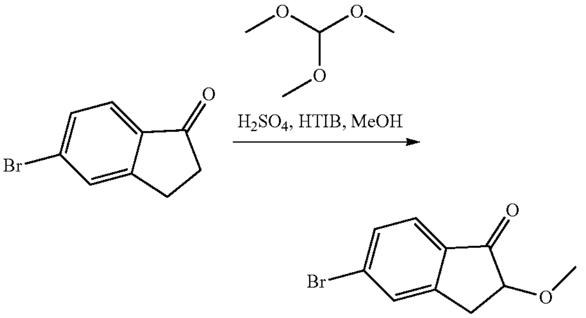

Intermediate 162-2

Step 1: Synthesis of 5-bromo-2-methoxy-2,3-dihydro-1H-inden-1-one

To a cooled (−20° C.) solution of $H_2SO_4$ (6.51 g, 66.3 mmol, 2.0 equiv) in MeOH (40.0 ml) was added 5-bromo-2,3-dihydroinden-1-one (7.0 g, 33 mmol, 1 equiv) and trimethyl orthoformate (8.80 g, 82.9 mmol, 2.5 equiv) followed by a solution of HTIB (14.31 g, 36.483 mmol, 1.1 equiv) in MeOH (40.0 ml). The mixture was stirred at room temperature for 18 h. The reaction was quenched by the addition of water (200 mL) and the mixture was filtered to afford 5-bromo-2-methoxy-2,3-dihydroinden-1-one (6.2 g, 78%) as an off-white solid. MS (ESI) calcd. for $C_{10}H_9BrO_2$ m/z, 239.98 found: 241.105 $[M+H]^+$.

Example 164: 1-((2R,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-(methoxymethyl)piperidin-1-yl)prop-2-en-1-one and Example 165: 1-((2R,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-(methoxymethyl)piperidin-1-yl)prop-2-en-1-one Example 164

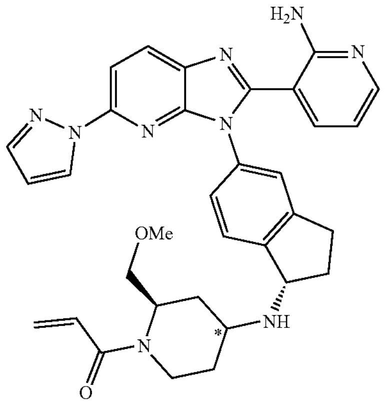

-continued

Example 165

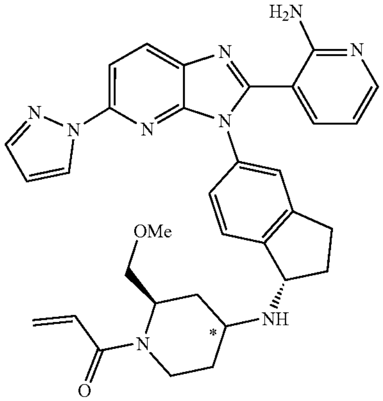

Examples 164 and 165 were prepared in a manner analogous to Example 13 (via Intermediate 14-1) using Intermediate 164-1 in place of tert-butyl 8-oxo-3-azabicyclo[3.2.1]octane-3-carboxylate, TFA/methanesulfonic acid (5:1) at 80° C. overnight (under air) instead of TFA/DCM at room temperature for 2 h and 1,2-dichloroethane/methanol (1:1) instead of 1,2-dichloroethane. * Denotes a stereocenter with undetermined absolute stereochemistry of a single diastereomer. The diastereomers were separated by chiral Prep-HPLC on a CHIRALPAK IG column using a mix of [Hex/DCM (3:1) (+0.5% 2M $NH_3$-MeOH)] and EtOH.

Example 164: MS (ESI) calcd. for $C_{33}H_{35}N_9O_2$: 589.29 m/z, found: 590.20. $^1$H NMR (300 MHz, DMSO-d6) δ 8.41-8.26 (m, 2H), 8.05-7.89 (m, 2H), 7.83-7.78 (m, 1H), 7.46 (d, J=8.0 Hz, 1H), 7.33 (s, 1H), 7.30-7.17 (m, 2H), 6.94 (s, 2H), 6.88-6.72 (m, 1H), 6.57-6.49 (m, 1H), 6.48-6.33 (m, 1H), 6.06 (d, J=16.5 Hz, 1H), 5.64 (t, J=10.8 Hz, 1H), 4.41 (s, 1H), 4.31 (s, 1H), 3.62 (t, J=9.5 Hz, 1H), 3.46 (t, J=14.9 Hz, 1H), 3.26 (s, 3H), 3.17 (s, 1H), 3.08-2.86 (m, 2H), 2.86-2.64 (m, 2H), 2.42 (d, J=11.4 Hz, 1H), 2.06 (d, J=12.2 Hz, 2H), 2.00-1.87 (m, 1H), 1.87-1.66 (m, 1H), 1.40-0.94 (m, 2H).

Example 165: MS (ESI) calcd. for $C_{33}H_{35}N_9O_2$: 589.29 m/z, found: 590.15 $[M+H]^+$. $^1$H NMR (300 MHz, DMSO-$d_6$) δ 8.35 (d, J=26.1 Hz, 2H), 8.05-7.90 (m, 2H), 7.84-7.78 (m, 1H), 7.48 (d, J=8.1 Hz, 1H), 7.41-7.20 (m, 3H), 6.92 (s, 2H), 6.87-6.70 (m, 1H), 6.59-6.49 (m, 1H), 6.49-6.34 (m, 1H), 6.15-5.95 (m, 1H), 5.68-5.53 (m, 1H), 4.29 (s, 2H), 3.97 (s, 2H), 3.49 (d, J=10.8 Hz, 1H), 3.24 (s, 3H), 3.16 (s, 1H), 2.96 (t, J=11.7 Hz, 1H), 2.87-2.65 (m, 1H), 2.46-2.37 (m, 1H) 1.96 (s, 1H), 1.81 (d, J=18.9 Hz, 4H), 1.55-1.35 (m, 2H).

Intermediate 164-1: tert-butyl (7R)-7-(methoxymethyl)-1,4-dioxa-8-azaspiro[4.5]decane-8-carboxylate Intermediate 164-1

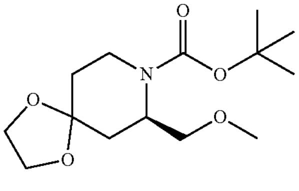

Intermediate 164-1 was prepared in a manner analogous to Intermediate 129-1 using 1-tert-butyl 2-ethyl (2R)-4-oxopiperidine-1,2-dicarboxylate instead of 1-tert-butyl 2-ethyl (2S)-4-oxopiperidine-1,2-dicarboxylate. MS (ESI) calcd. for $C_{14}H_{25}NO_5$: 287.17 m/z, found: 188.05 $[M\text{-}Boc]^+$.

Example 166: (S)-N-(3-((5-(2-(2-aminopyridin-3-yl)-5-(1H-pyrazol-1-yl)-3H-imidazo[4,5-b]pyridin-3-yl)-2,3-dihydro-1H-inden-1-yl)amino)propyl)-N-methylacrylamide Example 166

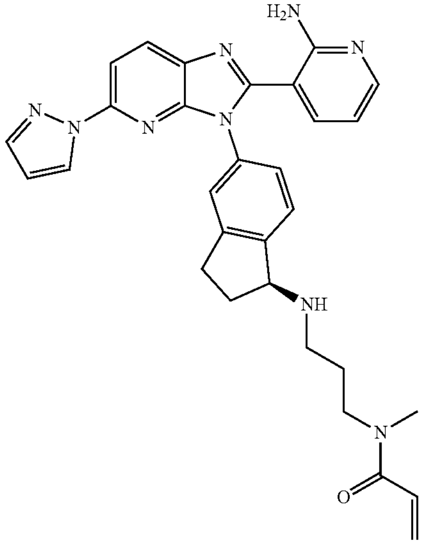

Synthetic Route:

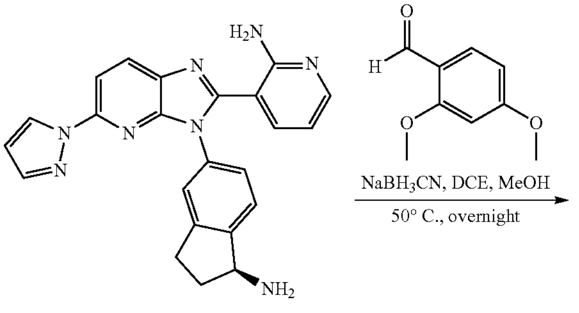

Intermediate 1-1

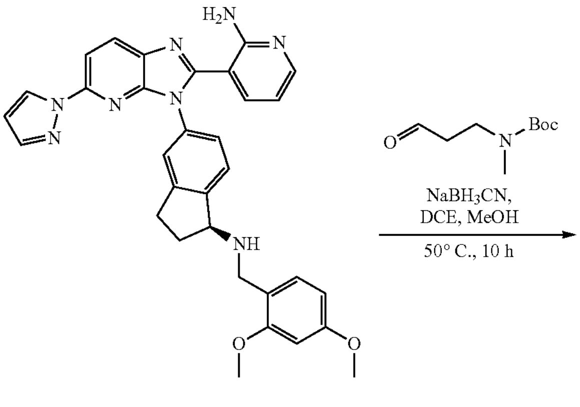

-continued

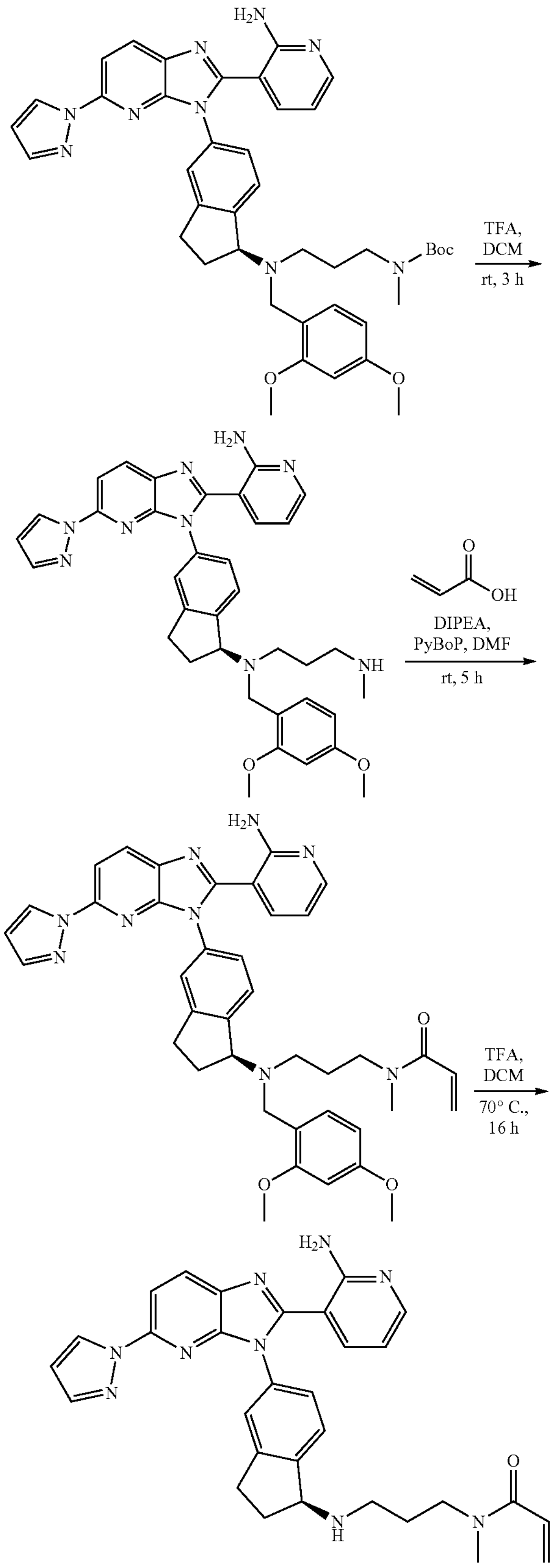

Example 166

Step 1: Synthesis of 3-{3-[(1S)-1-{[(2,4-dimethoxyphenyl) methyl]amino}-2,3-dihydro-1H-inden-5-yl]-5-(pyrazol-1-yl) imidazo[4,5-b]pyridin-2-yl}pyridin-2-amine A stirred solution of (S)-3-(3-(1-amino-2,3-dihydro-1H-inden-5-yl)-5-(1H-pyrazol-1-yl)-3H-imidazo[4,5-b]pyridin-2-yl)pyridin-2-amine (Intermediate 1-1) (500 mg, 1.22 mmol, 1 equiv) and 2,4-dimethoxybenzaldehyde (203.4 mg, 1.224 mmol, 1 equiv) in DICE (2 mL) and MeOH (8 mL) was stirred overnight at 50° C. To the mixture was added $NaBH_3CN$ (230.8 mg, 3.672 mmol, 3 equiv). The resulting mixture was stirred overnight at 50° C. The reaction was quenched with water (100 mL). The resulting mixture was extracted with ethyl acetate (3×200 mL). The combined organic layers were washed with brine (150 mL) and dried over anhydrous $Na_2SO_4$. After filtration, the filtrate was concentrated under reduced pressure. The residue was purified by silica gel column chromatography, eluting with MeOH/DCM (0-20%) to afford (S)-3-(3-(1-((2,4-dimethoxybenzyl)amino)-2,3-dihydro-1H-inden-5-yl)-5-(1H-pyrazol-1-yl)-3H-imidazo[4,5-b]pyridin-2-yl)pyridin-2-amine (300 mg, 44%) as a brown oil. MS (ESI) calcd. for $C_{32}H_{30}N_8O_2$, 558.25 m/z, found 559.30 $[M+H]^+$.

Step 2: Synthesis of tert-butyl (S)-(3-((5-(2-(2-aminopyridin-3-yl)-5-(1H-pyrazol-1-yl)-3H-imidazo[4,5-b]pyridin-3-yl)-2,3-dihydro-1H-inden-1-yl) (2,4-dimethoxybenzyl) amino) propyl)(methyl)carbamate A solution of 3-{3-[(1S)-1-{[(2,4-dimethoxyphenyl) methyl]amino}-2,3-dihydro-1H-inden-5-yl]-5-(pyrazol-1-yl) imidazo[4,5-b]pyridin-2-yl}pyridin-2-amine (300 mg, 0.537 mmol, 1 equiv) and tert-butyl N-methyl-N-(3-oxopropyl) carbamate (101 mg, 0.537 mmol, 1 equiv) in DCE (4 mL) and MeOH (2 mL) was stirred for 8 h at 50° C. To the mixture was added $NaBH_3CN$ (101 mg, 1.61 mmol, 3 equiv) and the resulting mixture was stirred for 2 h at 50° C. The reaction was quenched with $H_2O$ (10 mL). The resulting mixture was extracted with ethyl acetate (3×10 mL). After filtration, the filtrate was concentrated under reduced pressure. The residue was purified by silica gel column chromatography, eluting with MeOH/DCM (0-20%) to afford tert-butyl N-(3-{[(1S)-5-[2-(2-aminopyridin-3-yl)-5-(pyrazol-1-yl) imidazo[4,5-b]pyridin-3-yl]-2,3-dihydro-1H-inden-1-yl][(2,4-dimethoxyphenyl) methyl]amino}propyl)-N-methylcarbamate (200 mg, 51%) as a yellow solid. MS (ESI) calcd. for $C_{41}H_{47}N_9O_4$, 729.38 m/z, found 730.35 $[M+H]^+$.

Step 3: Synthesis of (S)-N1-(5-(2-(2-aminopyridin-3-yl)-5-(1H-pyrazol-1-yl)-3H-imidazo[4,5-b]pyridin-3-yl)-2,3-dihydro-1H-inden-1-yl)-N1-(2,4-dimethoxybenzyl)-N3-methylpropane-1,3-diamine A solution of tert-butyl N-(3-{[(1S)-5-[2-(2-aminopyridin-3-yl)-5-(pyrazol-1-yl) imidazo[4,5-b]pyridin-3-yl]-2,3-dihydro-1H-inden-1-yl][(2,4-dimethoxyphenyl) methyl] amino}propyl)-N-methylcarbamate (400 mg, 0.548 mmol, 1 equiv) in TFA (5 mL) and DCM (15 mL) was stirred for 3 h at r.t. The resulting mixture was concentrated under reduced pressure to afford 3-{3-[(1S)-1-{[(2,4-dimethoxyphenyl) methyl][3-(methylamino) propyl]amino}-2,3-dihydro-1H-inden-5-yl]-5-(pyrazol-1-yl) imidazo[4,5-b]pyridin-2-yl}pyridin-2-amine (280 mg, 81%) as brown oil. MS (ESI) calcd. for $C_{36}H_{39}N_9O_2$, 629.32 m/z, found 630.30 $[M+H]^+$.

Step 4: Synthesis of (S)-N-(3-((5-(2-(2-aminopyridin-3-yl)-5-(1H-pyrazol-1-yl)-3H-imidazo[4,5-b]pyridin-3-yl)-2,3-dihydro-1H-inden-1-yl) (2,4-dimethoxybenzyl) amino) propyl)-N-methylacrylamide To a stirred solution of 3-{3-[(1S)-1-{[(2,4-dimethoxyphenyl) methyl][3-(methylamino) propyl]amino}-2,3-dihydro-1H-inden-5-yl]-5-(pyrazol-1-yl) imidazo[4,5-b]pyridin-2-yl}pyridin-2-amine (200 mg, 0.318 mmol, 1 equiv), acrylic acid (22.9 mg, 0.318 mmol, 1 equiv) and DIEA (123 mg, 0.954 mmol, 3 equiv) in dimethylformamide (5 mL) was added PyBOP (165 mg, 0.318 mmol, 1 equiv) and the resulting mixture was stirred for 5 h at r.t. The mixture was purified by reverse-phase flash chromatography on C18 silica gel using a gradient of acetonitrile in water (+0.05% TFA) to afford N-(3-{[(1S)-5-[2-(2-aminopyridin-3-yl)-5-(pyrazol-1-yl) imidazo[4,5-b]pyridin-3-yl]-2,3-dihydro-1H-inden-1-yl][(2,4-dimethoxyphenyl) methyl]amino}propyl)-N-methylprop-2-enamide (100 mg, 38%) as yellow solid. MS (ESI) calcd. for $C_{39}H_{41}N_9O_3$, 683.33 m/z, found 684.35 $[M+H]^+$.

Step 5: Synthesis of (S)-N-(3-((5-(2-(2-aminopyridin-3-yl)-5-(1H-pyrazol-1-yl)-3H-imidazo[4,5-b]pyridin-3-yl)-2,3-dihydro-1H-inden-1-yl) amino) propyl)-N-methylacrylamide (Example 166

A solution of N-(3-{[(1S)-5-[2-(2-aminopyridin-3-yl)-5-(pyrazol-1-yl) imidazo[4,5-b]pyridin-3-yl]-2,3-dihydro-1H-inden-1-yl][(2,4-dimethoxyphenyl) methyl]amino}propyl)-N-methylprop-2-enamide (50 mg, 0.073 mmol, 1 equiv) in TFA (0.3 mL) and DCM (1 mL) was stirred overnight at 70° C. The resulting mixture was concentrated under reduced pressure. The crude product was purified by Prep-HPLC on a XBridge Prep Shield RP OBD C18 Column using a gradient of acetonitrile in water (+10 mmol/L $NH_4HCO_3$) to afford N-(3-{[(1S)-5-[2-(2-aminopyridin-3-yl)-5-(pyrazol-1-yl)imidazo[4,5-b]pyridin-3-yl]-2,3-dihydro-1H-inden-1-yl]amino}propyl)-N-methylprop-2-enamide (Example 166) (5.1 mg, 13%) as a yellow solid. MS (ESI) calcd. for $C_{30}H_{31}N_9O$, 533.27 m/z, found 534.25 $[M+H]^+$. $^1H$ NMR (300 MHz, DMSO-$d_6$) δ (ppm): 8.29-8.37 (m, 2H), 7.92-8.02 (m, 1H), 7.81-7.89 (m, 1H), 7.76-7.78 (m, 1H), 7.46-7.54 (m, 1H), 7.31-7.36 (m, 1H), 7.15-7.26 (m, 2H), 6.71-6.89 (m, 1H), 6.52-6.55 (m, 1H), 6.41-6.52 (m, 1H), 6.08-6.19 (m, 1H), 5.63-5.76 (m, 1H), 4.18-4.28 (m, 1H), 3.42-3.56 (m, 2H), 2.97-3.04 (m, 4H), 2.71-2.89 (m, 1H), 2.51-2.65 (m, 2H), 2.31-2.42 (m, 1H), 1.79-1.92 (m, 1H), 1.61-1.78 (m, 2H).

Example 167: 1-((*)-3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidin-1-yl)prop-2-en-1-one and Example 168: 1-((*)-3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidin-1-yl)prop-2-en-1-one Example 167

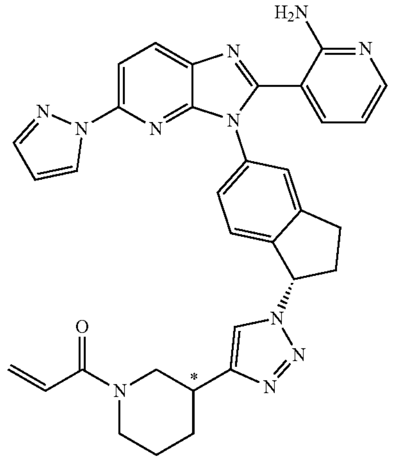

Example 168

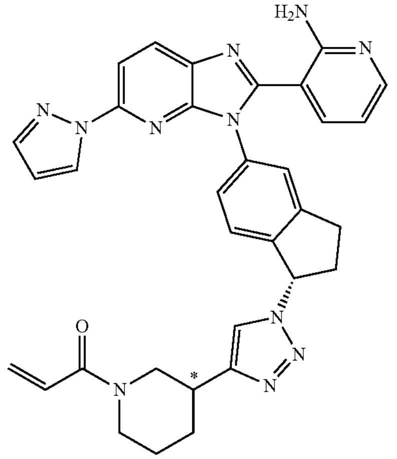

Synthetic Route:

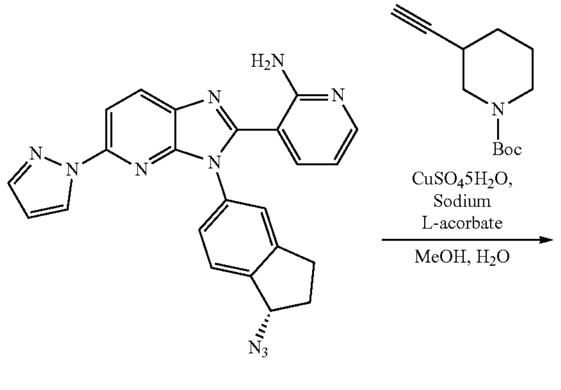

-continued

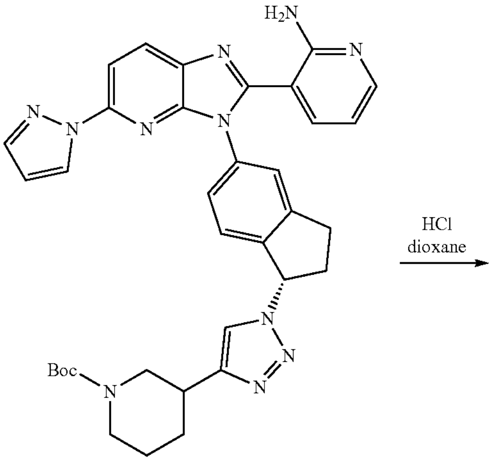

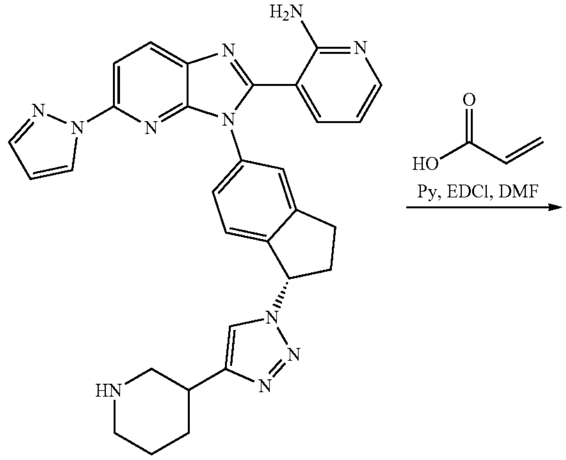

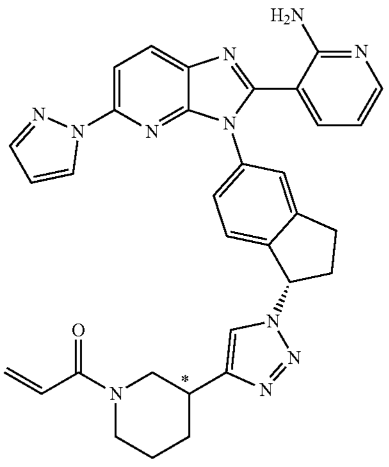

Example 167

-continued

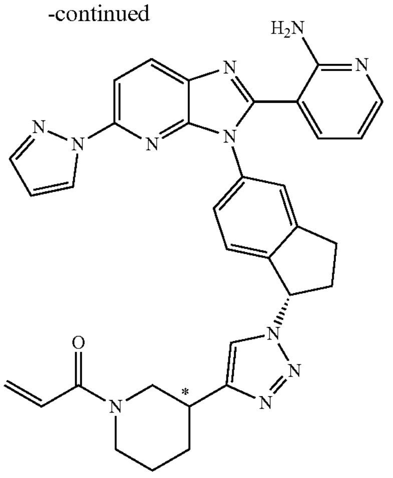

Example 168

Step 1: Synthesis of tert-butyl 3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidine-1-carboxylate A solution of 3-{3-[(1S)-1-azido-2,3-dihydro-1H-inden-5-yl]-5-(pyrazol-1-yl) imidazo[4,5-b]pyridin-2-yl}pyridin-2-amine (Intermediate 167-1) (1 g, 2.3 mmol, 1 equiv), tert-butyl 3-ethynylpiperidine-1-carboxylate (9.63 g, 46.0 mmol, 20 equiv), $CuSO_4.5H_2O$ (115 mg, 0.46 mmol, 0.2 equiv) and sodium L-ascorbate (0.18 g, 0.92 mmol, 0.4 equiv) in MeOH (50 mL) and $H_2O$ (50 mL) was stirred for 3 h at room temperature. The reaction was quenched with water. The resulting mixture was extracted with ethyl acetate (3×100 mL). The combined organic layers were dried over anhydrous $Na_2SO_4$. After filtration, the filtrate was concentrated under reduced pressure to afford tert-butyl 3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidine-1-carboxylate (960 mg, 65%) as a brown yellow solid. The crude product was used in the next step directly without further purification. MS (ESI) calcd. for $C_{35}H_{37}N_{11}O_2$: 643.31 m/z, found: 644.35 $[M+H]^+$.

Step 2: Synthesis of 3-(3-((1S)-1-(4-(piperidin-3-yl)-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine A solution of tert-butyl 3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidine-1-carboxylate (960 mg, 1.491 mmol, 1 equiv) in HCl (4M) in 1,4-dioxane (15 mL) was stirred for 3 h at room temperature. The resulting mixture was concentrated under reduced pressure. The residue was purified by trituration with DCM (20 mL). The precipitated solids were collected by filtration and washed with DCM (3×10 mL). The residue was suspended in saturated $NaHCO_3$ (aq.) (30 mL). The mixture was extracted with ethyl acetate (3×50 mL). The combined organic layers were dried over anhydrous $Na_2SO_4$. After filtration, the filtrate was concentrated under reduced pressure to afford 3-(3-((1S)-1-(4-(piperidin-3-yl)-1H-1,2,3-triazol-1-yl)-2,3-dihydro-1H-inden-5-yl)-5-(1H- pyrazol-1-yl)-3H-imidazo[4,5-b]pyridin-2-yl)pyridin-2-amine (600 mg, 74%) as a brown solid. The crude product was used in the next step directly without further purification. MS (ESI) calcd. for $C_{30}H_{29}N_{11}$: 543.26 m/z, found: 544.70 $[M+H]^+$.

Step 3: Synthesis of 1-((*)-3-(1-((S)-5-(2-(2-amino-pyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidin-1-yl)prop-2-en-1-one (Example 167) and 1-((*)-3-(1-((S)-5-(2-(2-amino-pyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidin-1-yl)prop-2-en-1-one (Example 168)

To a stirred solution of 3-(3-((1S)-1-(4-(piperidin-3-yl)-1H-1,2,3-triazol-1-yl)-2,3-dihydro-1H-inden-5-yl)-5-(1H-pyrazol-1-yl)-3H-imidazo[4,5-b]pyridin-2-yl)pyridin-2-amine (600 mg, 1.104 mmol, 1 equiv) and EDCI (423.2 mg, 2.208 mmol, 2 equiv) in pyridine (5 mL) and DMF (15 mL) was added acrylic acid (119.3 mg, 1.656 mmol, 1.5 equiv) dropwise at room temperature. The resulting mixture was stirred for 3 h at 50° C. The mixture was purified by reverse-phase flash chromatography on C18 silica gel using a gradient of acetonitrile in water (+10 mmol/L ammonium bicarbonate). The diastereomers (150 mg) were separated by Prep-HPLC on a CHIRALPAK IC column using a mixture of [MtBE (+0.5% 2M $NH_3$-MeOH)] and [MeOH:DCM 1:1] to afford 1-((*)-3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidin-1-yl)prop-2-en-1-one (Example 167) as the first eluting peak and 1-((*)-3-(1-((S)-5-(2-(2-aminopyridin-3-yl)-5-(1H-pyrazol-1-yl)-3H-imidazo[4,5-b]pyridin-3-yl)-2,3-dihydro-1H-inden-1-yl)-1H-1,2,3-triazol-4-yl)piperidin-1-yl)prop-2-en-1-one (Example 168) as the second eluting peak. * Denotes a stereocenter with undetermined absolute stereocenter of a single diastereomer.

Example 167: MS (ESI) calcd. for $C_{33}H_{31}N_{11}O$: 597.27 m/z, found: 598.20 $[M+H]^+$. $^1H$ NMR (300 MHz, DMSO-d6) δ 8.42-8.33 (m, 2H), 8.05-7.92 (m, 3H), 7.85-7.78 (m, 1H), 7.54 (s, 1H), 7.35-7.27 (m, 1H), 7.27-7.18 (m, 2H), 6.92 (s, 2H), 6.89-6.74 (m, 1H), 6.58-6.51 (m, 1H), 6.48-6.38 (m, 1H), 6.34-6.23 (m, 1H), 6.15-6.00 (m, 1H), 5.70-5.58 (m, 1H), 4.25-3.95 (m, 2H), 3.30-3.15 (m, 1H), 3.15-2.99 (m, 1H), 2.92-2.71 (m, 3H), 2.13-2.03 (m, 1H), 1.78-1.68 (m, 2H), 1.55-1.30 (m, 1H), 1.26-1.16 (m, 2H).

Example 168: MS (ESI) calcd. for $C_{33}H_{31}N_{11}O$: 597.27 m/z, found: 598.20 $[M+H]^+$. $^1H$ NMR (400 MHz, DMSO-d6) δ 8.43-8.34 (m, 2H), 8.04-7.92 (m, 3H), 7.84-7.79 (m, 1H), 7.54 (s, 1H), 7.34-7.26 (m, 1H), 7.26-7.20 (m, 2H), 6.93 (s, 2H), 6.88-6.77 (m, 1H), 6.57-6.52 (m, 1H), 6.48-6.40 (m, 1H), 6.32-6.24 (m, 1H), 6.15-6.02 (m, 1H), 5.70-5.60 (m, 1H), 4.51-3.95 (m, 2H), 3.32-3.20 (m, 2H), 3.13-2.99 (m, 2H), 2.95-2.68 (m, 3H), 2.13-2.05 (m, 1H), 1.77-1.70 (m, 2H), 1.60-1.40 (m, 1H).

Intermediate 167-1: (S)-3-(3-(1-azido-2,3-dihydro-1H-inden-5-yl)-5-(1H-pyrazol-1-yl)-3H-imidazo[4,5-b]pyridin-2-yl)pyridin-2-amine Intermediate 167-1

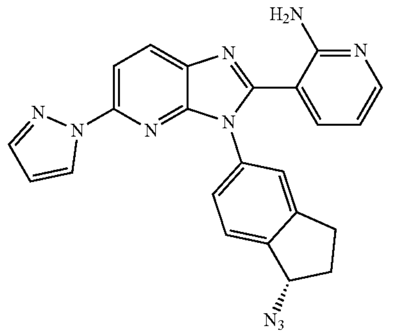

Synthetic Route:

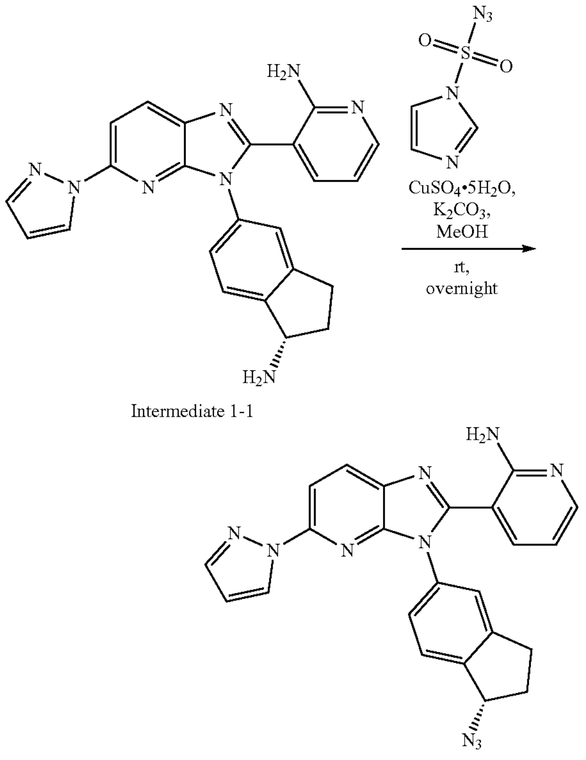

Intermediate 1-1

Intermediate 167-1

Step 1: (S)-3-(3-(1-azido-2,3-dihydro-1H-inden-5-yl)-5-(1H-pyrazol-1-yl)-3H-imidazo[4,5-b]pyridin-2-yl)pyridin-2-amine (Intermediate 167-1

A solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (300 mg, 0.734 mmol), imidazole-1-sulfonyl azide (153 mg, 0.881 mmol), potassium carbonate (409 mg, 2.94 mmol) and $CuSO_4.5H_2O$ (9.2 mg, 0.037 mmol) in MeOH (5 mL) was stirred overnight at room temperature. The resulting mixture was concentrated under reduced pressure. The residue was purified by reverse-phase flash chromatography on C18 silica gel using a gradient of acetonitrile in water (+0.05% TFA) to afford (S)-3-(3-(1-azido-2,3-dihydro-1H-inden-5-yl)-5-(1H-pyrazol-1-yl)-3H-imidazo[4,5-b]pyridin-2-yl)pyridin-2-amine (Intermediate 167-1) (200 mg, 63% yield) as a yellow solid. MS (ESI) calcd. for $C_{23}H_{18}N_{10}$, 434.17 m/z, found 435.15 $[M+H]^+$.

Example 169: 1-(4-{1-[(1S)-5-[2-(2-aminopyridin-3-yl)-5-(pyrazol-1-yl)imidazo[4,5-b]pyridin-3-yl]-2,3-dihydro-1H-inden-1-yl]-1,2,3-triazol-4-yl}piperidin-1-yl)prop-2-en-1-one Example 169

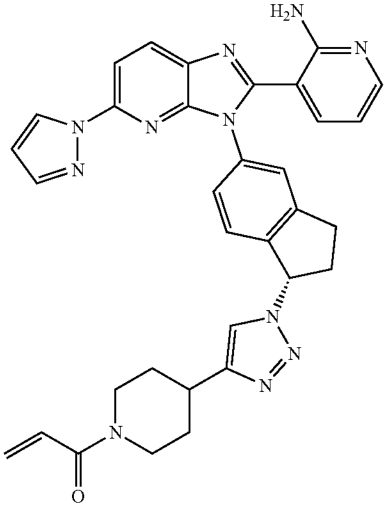

Example 169 was prepared in a manner analogous to Example 167 using tert-butyl 4-ethynylpiperidine-1-carboxylate in place of tert-butyl 3-ethynylpiperidine-1-carboxylate and omitting the chiral separation. MS (ESI) calcd. for $C_{33}H_{31}N_{11}O$: 597.27 m/z, found: 598.20 $[M+H]^+$. $^1H$ NMR (300 MHz, DMSO-d6) δ 8.41-8.33 (m, 2H), 8.05-7.91 (m, 3H), 7.85-7.78 (m, 1H), 7.54 (s, 1H), 7.35-7.17 (m, 3H), 6.92 (s, 2H), 6.90-6.76 (m, 1H), 6.59-6.51 (m, 1H), 6.46-6.36 (m, 1H), 6.31-6.20 (m, 1H), 6.15-6.03 (m, 1H), 5.71-5.61 (m, 1H), 4.46-4.36 (m, 1H), 4.13-4.02 (m, 1H), 3.32-3.16 (m, 3H), 3.12-2.94 (m, 2H), 2.86-2.72 (m, 2H), 2.03-1.87 (m, 2H), 1.50 (s, 2H).

Example 170: 1-(4-{[(1S)-5-[2-(2-aminopyridin-3-yl)-5-(pyrrolidin-1-yl)imidazo[4,5-b]pyridin-3-yl]-2,3-dihydro-1H-inden-1-yl]amino}piperidin-1-yl)prop-2-en-1-one Example 170

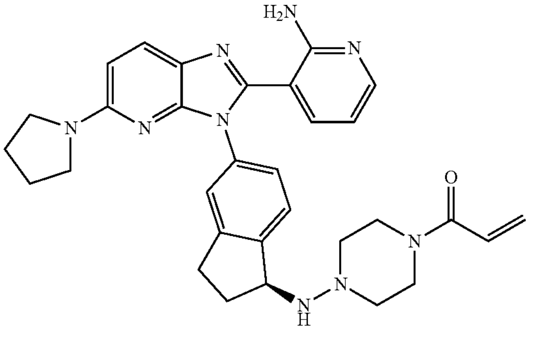

Example 170 was prepared in a manner analogous to Example 13 using 1,2-dichloroethane/methanol (1:1) in place of 1,2-dichloroethane, Intermediate 170-1 in place of Intermediate 1-1 and a reaction time of 1 h instead of overnight. MS (ESI) calcd for $C_{32}H_{36}N_8O$: 548.70, found: 549.25 $[M+H]^+$. $^1H$ NMR (300 MHz, DMSO-$d_6$) δ(ppm) 8.21 (s, 1H), 7.93-7.87 (m, 2H), 7.43-7.45 (m, 1H), 7.19-7.12 (m, 2H), 6.99-7.02 (m, 1H), 6.77-6.87 (m, 1H), 6.47-6.50 (m, 1H), 6.31-6.36 (m, 1H), 6.05-6.11 (m, 1H), 5.64-5.68 (m, 1H), 4.33-4.38 (m, 1H), 4.27 (m, 1H), 4.01 (s, 1H), 3.35-3.38 (m, 2H), 3.15 (m, 1H), 2.74-2.93 (m, 5H), 2.44 (m, 1H), 1.89-1.93 (m, 8H), 1.25 (m, 2H).

Intermediate 170-1: (S)-3-(3-(1-amino-2,3-dihydro-1H-inden-5-yl)-5-(pyrrolidin-1-yl)-3H-imidazo[4,5-b]pyridin-2-yl)pyridin-2-amine Intermediate 170-1

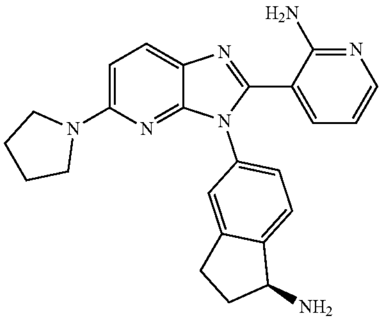

Synthetic Route:

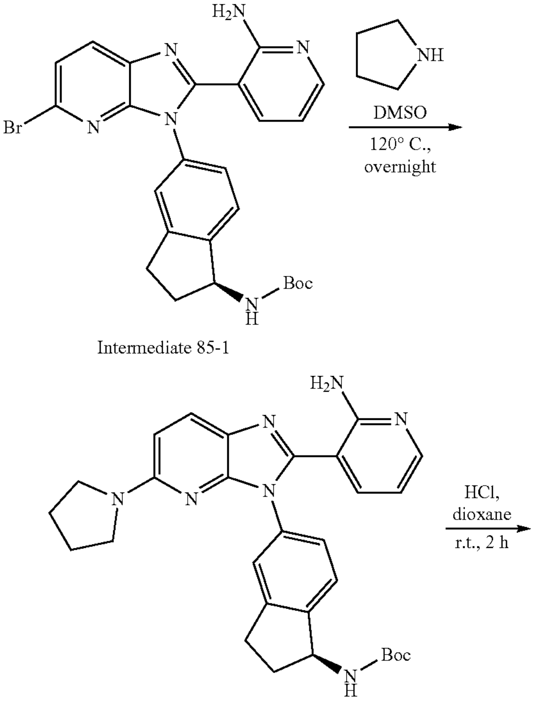

-continued

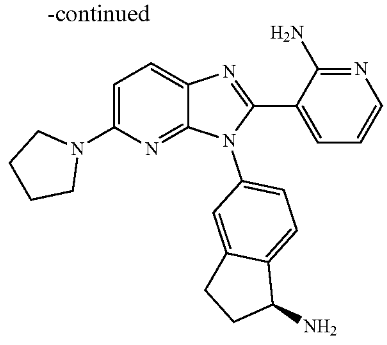

Intermediate 170-1

Step 1: Synthesis of tert-butyl (S)-(5-(2-(2-aminopyridin-3-yl)-5-(pyrrolidin-1-yl)-3H-imidazo[4,5-b]pyridin-3-yl)-2,3-dihydro-1H-inden-1-yl)carbamate To a solution of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 85-1) (200 mg, 0.384 mmol, 1 equiv) in DMSO (5 mL) was added pyrrolidine (272.8 mg, 3.840 mmol, 10 equiv). The resulting mixture was stirred at 120° C. overnight. After cooling to room temperature, the mixture was poured into water. The precipitate was collected by filtration and dried, then purified by reverse-phase flash chromatography on C18 silica gel using a gradient of acetonitrile in water (+0.05% $NH_4HCO_3$) to tert-butyl N-[(1S)-5-[2-(2-aminopyridin-3-yl)-5-(pyrrolidin-1-yl)imidazo[4,5-b]pyridin-3-yl]-2,3-dihydro-1H-inden-1-yl]carbamate (103 mg, 52%) as a yellow solid. MS (ESI) calcd. for $C_{29}H_{33}N_7O_2$: 511.27. found: 512.35 $[M+H]^+$.

Step 2: Synthesis of 3-{3-[(1S)-1-amino-2,3-dihydro-1H-inden-5-yl]-5-(pyrrolidin-1-yl)imidazo[4,5-b]pyridin-2-yl}pyridin-2-amine (Intermediate 170-1

A solution of tert-butyl N-[(1S)-5-[2-(2-aminopyridin-3-yl)-5-(pyrrolidin-1-yl)imidazo[4,5-b]pyridin-3-yl]-2,3-dihydro-1H-inden-1-yl]carbamate (103 mg, 0.201 mmol, 1 equiv) in HCl (5 mL, 4M in 1,4-dioxane) was stirred at room temperature for 3 h then concentrated under vacuum. The resulting mixture was purified by reverse-phase flash chromatography in C18 silica gel using a gradient of acetonitrile in water (+0.05% $NH_4HCO_3$) to afford 3-{3-[(1S)-1-amino-2,3-dihydro-1H-inden-5-yl]-5-(pyrrolidin-1-yl)imidazo[4,5-b]pyridin-2-yl}pyridin-2-amine (98 mg, crude) as a yellow solid. MS (ESI) calcd for $C_{24}H_{25}N_7$: 411.22; found: 412.16 $[M+H]^+$.

Example 171: 1-((1R,5S,9*)-9-(((S)-5-(2-(2-aminopyridin-3-yl)-5-cyclopropyl-3H-imidazo[4,5-b]pyridin-3-yl)-2,3-dihydro-1H-inden-1-yl)amino)-3-oxa-7-azabicyclo[3.3.1]nonan-7-yl)prop-2-en-1-one and

Example 172: 1-((1R,5S,9*)-9-(((S)-5-(2-(2-aminopyridin-3-yl)-5-cyclopropyl-3H-imidazo[4,5-b]pyridin-3-yl)-2,3-dihydro-1H-inden-1-yl)amino)-3-oxa-7-azabicyclo[3.3.1]nonan-7-yl)prop-2-en-1-one Example 171

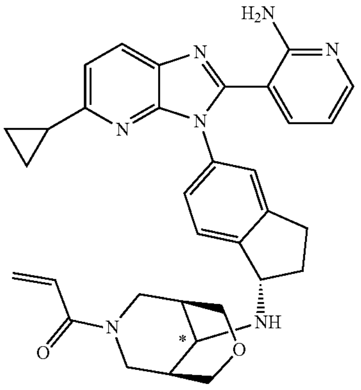

Example 172

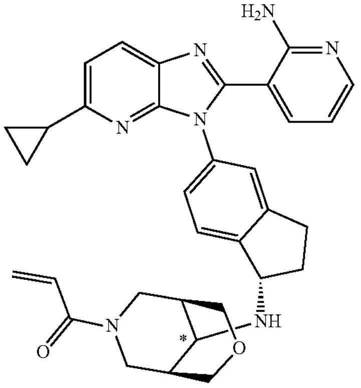

Examples 171 and 172 were prepared in a manner analogous to Example 14 (via Intermediate 14-1) starting from tert-butyl 9-oxo-3-oxa-7-azabicyclo[3.3.1]nonane-7-carboxylate instead of tert-butyl 8-oxo-3-azabicyclo[3.2.1]octane-3-carboxylate and using Intermediate 85-2 in place of Intermediate 1-1. The diastereomers were separated after the final step by chiral Prep-HPLC on a CHIRALPAK IA column using a mixture of [MtBE (+0.5% 2M $NH_3$-MeOH)] and [EtOH/DCM 1:1]. * Denotes a stereocenter with undetermined absolute stereocenter of a single diastereomer.

Example 171: MS (ESI) calcd. for $C_{33}H_{35}N_7O_2$: 561.29 m/z, found: 562.35 $[M+H]^+$. $^1H$-NMR (400 MHz, DMSO) S (ppm): 7.95-8.10 (m, 2H), 7.55-7.80 (m, 1H), 7.30-7.45 (m, 1H), 7.15-7.29 (m, 3H), 6.75-6.90 (m, 1H), 6.37-6.45 (m, 1H), 6.00-6.13 (m, 1H), 5.61-5.72 (m, 1H), 4.62-4.75 (m, 1H), 4.22-4.35 (m, 1H), 3.99-4.19 (m, 2H), 3.52-3.60 (m, 2H), 3.32-3.50 (m, 2H), 2.80-3.22 (m, 3H), 2.55-2.65 (m, 1H), 1.75-2.36 (m, 4H), 1.12-1.30 (m, 1H), 0.88-1.00 (m, 2H), 0.70-0.87 (m, 2H).

Example 172: MS (ESI) calcd. for $C_{33}H_{35}N_7O_2$: 561.29 m/z, found: 562.20 $[M+H]^+$. $^1H$-NMR (400 MHz, DMSO) δ (ppm): 7.95-8.10 (m, 2H), 7.55-7.80 (m, 1H), 7.30-7.45

(m, 1H), 7.15-7.29 (m, 3H), 6.75-6.90 (m, 1H), 6.37-6.45 (m, 1H), 6.00-6.13 (m, 1H), 5.61-5.72 (m, 1H), 4.62-4.75 (m, 1H), 4.22-4.35 (m, 1H), 3.99-4.19 (m, 2H), 3.52-3.60 (m, 2H), 3.32-3.50 (m, 2H), 2.80-3.22 (m, 3H), 2.55-2.65 (m, 1H), 1.75-2.36 (m, 4H), 1.12-1.30 (m, 1H), 0.88-1.00 (m, 2H), 0.70-0.87 (m, 2H).

Example 173: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-2-chloro-2-fluoroethanone Example 173

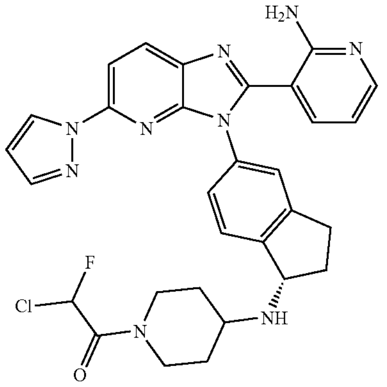

Example 173 was prepared in a manner analogous to Example 34 using chlorofluoroacetic acid in place of (2E)-4-(dimethylamino)but-2-enoic acid and HATU in place of PyBOP. MS (ESI) calcd. for $C_{30}H_{29}ClFN_9O$, 585.22 m/z, found: 586.10 $[M+H]^+$. $^1H$-NMR (400 MHz, DMSO-d6) δ (ppm): 8.22-8.51 (m, 2H), 7.88-8.13 (m, 2H), 7.71-7.88 (m, 1H), 7.41-7.62 (m, 1H), 7.05-7.41 (m, 4H), 6.52-6.67 (m, 1H), 6.32-6.52 (m, 1H), 4.28-4.46 (m, 1H), 4.08-4.28 (m, 1H), 3.65-3.91 (m, 1H), 3.05-3.32 (m, 1H), 2.85-3.05 (m, 3H), 2.65-2.85 (m, 1H), 2.28-2.52 (m, 1H), 1.96-2.16 (m, 1H), 1.86-1.96 (m, 1H), 1.65-1.86 (m, 1H), 1.08-1.54 (m, 2H).

Example 174: 1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperazin-1-yl)prop-2-en-1-one Example 174

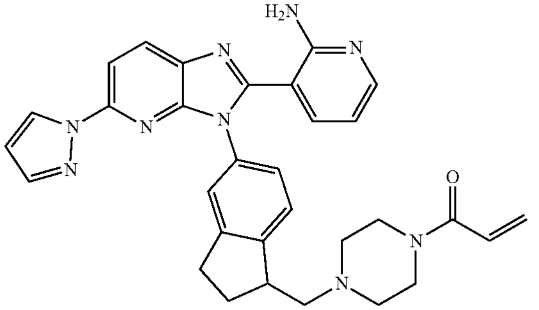

Synthetic Route:

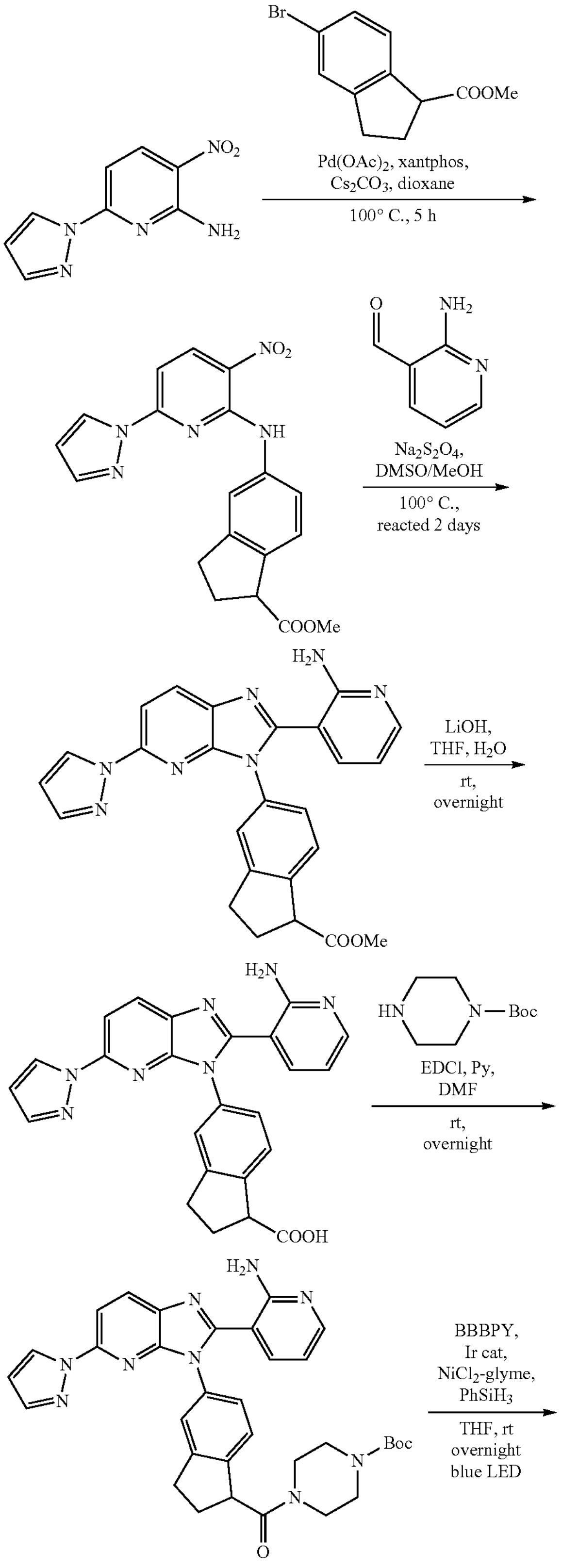

-continued

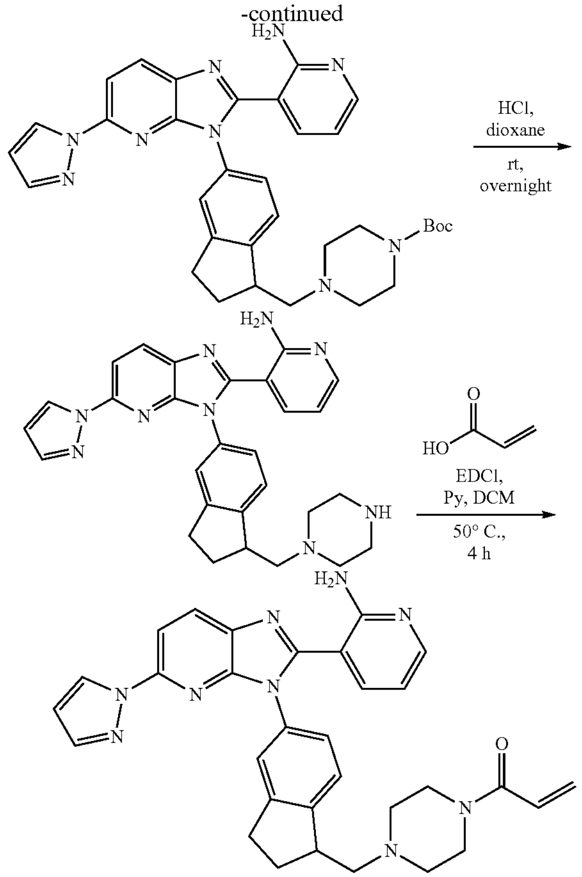

Example 174

Step 1: Synthesis of methyl 5-{[3-nitro-6-(pyrazol-1-yl)pyridin-2-yl]amino}-2,3-dihydro-1H-indene-1-carboxylate A mixture of methyl 5-bromo-2,3-dihydro-1H-indene-1-carboxylate (6 g, 23.5 mmol, 1 equiv), 3-nitro-6-(pyrazol-1-yl)pyridin-2-amine (5.79 g, 28.2 mmol, 1.2 equiv), $Pd(OAc)_2$ (528 mg, 2.35 mmol, 0.1 equiv), XantPhos (1.36 g, 2.35 mmol, 0.1 equiv) and $Cs_2CO_3$ (22.99 g, 70.56 mmol, 3.00 equiv) in dioxane (120 mL) was stirred for 5 h at 100° C. under nitrogen atmosphere. The mixture was allowed to cool to room temperature then filtered rinsing with ethyl acetate (3x30 mL). The filtrate was concentrated under reduced pressure. The residue was suspended in water (200 mL) and extracted with ethyl acetate (3x100 mL). The combined organic layers were washed with HCl (1M) (3x100 mL) and dried over anhydrous $Na_2SO_4$. After filtration, the filtrate was concentrated under reduced pressure to afford methyl 5-{[3-nitro-6-(pyrazol-1-yl)pyridin-2-yl]amino}-2,3-dihydro-1H-indene-1-carboxylate (6 g, crude) as a light brown solid. MS (ESI) calcd. for $C_{19}H_{17}N_5O_4$: 379.13 m/z, found: 380.10 $[M+H]^+$. The crude product was used in the next step directly without further purification.

Step 2: Synthesis of methyl 5-[2-(2-aminopyridin-3-yl)-5-(pyrazol-1-yl)imidazo[4,5-b]pyridin-3-yl]-2,3-dihydro-1H-indene-1-carboxylate A mixture of methyl 5-{[3-nitro-6-(pyrazol-1-yl)pyridin-2-yl]amino}-2,3-dihydro-1H-indene-1-carboxylate (6 g, 15.8 mmol, 1 equiv), 2-aminopyridine-3-carbaldehyde (2.90 g, 23.7 mmol, 1.5 equiv), and $Na_2S_2O_4$ (6.06 g, 34.8 mmol, 2.2 equiv) in DMSO (120 mL) and MeOH (20 mL) was stirred overnight at 100° C. The mixture was allowed to cool to room temperature. The reaction was quenched by the addition of water (300 mL) at room temperature. The resulting mixture was extracted with ethyl acetate (3x100 mL). The combined organic layers were washed with saturated aqueous sodium bicarbonate (3x100 mL) and dried over anhydrous $Na_2SO_4$. After filtration, the filtrate was concentrated under reduced pressure. The residue was purified by silica gel column chromatography, eluting with petroleum ether/ethyl acetate (1:1) to afford methyl 5-[2-(2-aminopyridin-3-yl)-5-(pyrazol-1-yl)imidazo[4,5-b]pyridin-3-yl]-2,3-dihydro-1H-indene-1-carboxylate (1.5 g, 21%) as a light brown solid. MS (ESI) calcd. for $C_{25}H_{21}N_7O_2$: 451.18 m/z, found: 452.20 $[M+H]^+$.

Step 3: Synthesis of 5-[2-(2-aminopyridin-3-yl)-5-(pyrazol-1-yl)imidazo[4,5-b]pyridin-3-yl]-2,3-dihydro-1H-indene-1-carboxylic acid A mixture of methyl 5-[2-(2-aminopyridin-3-yl)-5-(pyrazol-1-yl)imidazo[4,5-b]pyridin-3-yl]-2,3-dihydro-1H-indene-1-carboxylate (1.4 g, 3.1 mmol, 1 equiv) and LiOH (223 mg, 9.30 mmol, 3.00 equiv) in THF (15 mL) and $H_2O$ (15 mL) was stirred overnight at room temperature. The resulting mixture was diluted with water (30 mL). The aqueous layer was extracted with ethyl acetate (2x100 mL). The aqueous layer was acidified to pH 2 with conc. HCl. The resulting mixture was extracted with ethyl acetate (3x100 mL). The combined organic layers were washed with brine (2x100 mL) and dried over anhydrous $Na_2SO_4$. After filtration, the filtrate was concentrated under reduced pressure. The resulting mixture was concentrated under vacuum to afford 5-[2-(2-aminopyridin-3-yl)-5-(pyrazol-1-yl)imidazo[4,5-b]pyridin-3-yl]-2,3-dihydro-1H-indene-1-carboxylic acid (1.2 g, crude) as an off-white solid. The crude product was used in the next step directly without further purification. MS (ESI) calcd. for $C_{24}H_{19}N_7O_2$: 437.16 m/z, found: 438.20 $[M+H]^+$.

Step 4: Synthesis of tert-butyl 4-(5-(2-(2-aminopyridin-3-yl)-5-(1H-pyrazol-1-yl)-3H-imidazo[4,5-b]pyridin-3-yl)-2,3-dihydro-1H-indene-1-carbonyl)piperazine-1-carboxylate A solution of EDCI (310 mg, 1.62 mmol, 2 equiv) in pyridine (3 mL) and DMF (1 mL) was treated with 5-[2-(2-aminopyridin-3-yl)-5-(cyclopenta-2,4-dien-1-yl)imidazo[4,5-b]pyridin-3-yl]-2,3-dihydro-1H-indene-1-carboxylic acid (352 mg, 0.808 mmol, 1 equiv) and tert-butyl piperazine-1-carboxylate (226 mg, 1.21 mmol, 1.5 equiv) for 5 min at room temperature. The resulting mixture was stirred overnight at 50° C. under air atmosphere. The mixture was allowed to cool to room temperature. The reaction was quenched with water (20 mL) and the resulting mixture was extracted with ethyl acetate (2x10 mL). The combined organic layers were dried over anhydrous $Na_2SO_4$. After filtration, the filtrate was concentrated under reduced pressure. The residue was purified by reverse-phase flash chromatography on C18 silica gel using a gradient of acetonitrile in water (+10 mmol/L $NH_4HCO_3$) to afford tert-butyl 4-(5-(2-(2-aminopyridin-3-yl)-5-(1H-pyrazol-1-yl)-3H-imidazo[4,5-b]pyridin-3-yl)-2,3-dihydro-1H-indene-1-carbonyl)

piperazine-1-carboxylate (150 mg, 28%) as a brown yellow solid. MS (ESI) calcd. for $C_{33}H_{35}N_9O_3$: 605.29 m/z, found: 606.15 [M+H]$^+$.

Step 5: Synthesis of tert-butyl 4-((5-(2-(2-amino-pyridin-3-yl)-5-(1H-pyrazol-1-yl)-3H-imidazo[4,5-b]pyridin-3-yl)-2,3-dihydro-1H-inden-1-yl)methyl) piperazine-1-carboxylate A solution of tert-butyl 4-(5-(2-(2-aminopyridin-3-yl)-5-(1H-pyrazol-1-yl)-3H-imidazo[4,5-b]pyridin-3-yl)-2,3-dihydro-1H-indene-1-carbonyl)piperazine-1-carboxylate (405 mg, 0.669 mmol, 1 equiv) and 4,4'-di-tert-butyl-2,2'-bipyridine; bis[2-(pyridin-2-yl)phenyl]iridiumylium; hexafluoro-lambda5-phosphanuide (40 mg, 0.044 mmol, 0.07 equiv) in THF (5 mL) was treated with nickel(II) chloride ethylene glycol dimethyl ether complex (44.1 mg, 0.201 mmol, 0.3 equiv) and phenylsilane (2.89 g, 26.8 mmol, 40 equiv) at room temperature under nitrogen atmosphere. The vial was sealed with a plastic screw cap and stirred overnight at room temperature whilst being irradiated with blue LED light. The resulting mixture was concentrated under reduced pressure. The residue was purified by reverse-phase flash chromatography on C18 silica gel using a gradient of acetonitrile in water (+10 mmol/L $NH_4HCO_3$) to afford tert-butyl 4-((5-(2-(2-aminopyridin-3-yl)-5-(1H-pyrazol-1-yl)-3H-imidazo [4,5-b]pyridin-3-yl)-2,3-dihydro-1H-inden-1-yl)methyl) piperazine-1-carboxylate (140 mg, 33%) as a brown yellow solid. MS (ESI) calcd. for $C_{33}H_{37}N_9O_2$: 591.31 m/z, found: 592.20 [M+H]$^+$.

Step 6: Synthesis of 3-{3-[1-(piperazin-1-ylmethyl)-2,3-dihydro-1H-inden-5-yl]-5-(pyrazol-1-yl)imidazo [4,5-b]pyridin-2-yl}pyridin-2-amine A solution of tert-butyl 4-({5-[2-(2-aminopyridin-3-yl)-5-(pyrazol-1-yl)imidazo[4,5-b]pyridin-3-yl]-2,3-dihydro-1H-inden-1-yl}methyl)piperazine-1-carboxylate (140 mg, 0.237 mmol, 1 equiv) was treated with HCl (4 M) in 1,4-dioxane (5 mL) at room temperature. The resulting mixture was stirred overnight at room temperature under air atmosphere. The reaction was quenched with water. The mixture was basified to pH 8 with saturated $NaHCO_3$ (aq.). The resulting mixture was extracted with ethyl acetate (3x20 mL). The combined organic layers were washed with water (3x20 mL) and dried over anhydrous $Na_2SO_4$. After filtration, the filtrate was concentrated under reduced pressure to afford 3-{3-[1-(piperazin-1-ylmethyl)-2,3-dihydro-1H-inden-5-yl]-5-(pyrazol-1-yl)imidazo[4,5-b]pyridin-2-yl}pyridin-2-amine (112 mg, crude) as a brown yellow solid. MS (ESI) calcd. for $C_{28}H_{29}N_9$: 491.25 m/z, found: 492.25 [M+H]$^+$. The crude product was used in the next step directly without further purification.

Step 7: Synthesis of 1-[4-({5-[2-(2-aminopyridin-3-yl)-5-(pyrazol-1-yl)imidazo[4,5-b]pyridin-3-yl]-2,3-dihydro-1H-inden-1-yl}methyl)piperazin-1-yl]prop-2-en-1-one (Example 174)

A solution of EDCI (87 mg, 0.46 mmol, 2 equiv) in pyridine (3 mL) and DMF (1 mL) was treated with 3-{3-[1-(piperazin-1-ylmethyl)-2,3-dihydro-1H-inden-5-yl]-5-(pyrazol-1-yl)imidazo[4,5-b]pyridin-2-yl}pyridin-2-amine (112 mg, 0.228 mmol, 1 equiv) and acrylic acid (33 mg, 0.46 mmol, 2 equiv). The resulting mixture was stirred for 4 h at 50° C. The mixture was allowed to cool to room temperature. The reaction was quenched with water at room temperature. The resulting mixture was extracted with ethyl acetate (3x10 mL). The combined organic layers were washed with water (3x10 mL) and dried over anhydrous $Na_2SO_4$. After filtration, the filtrate was concentrated under reduced pressure. The residue was purified by reverse-phase flash chromatography on C18 silica gel using a gradient of acetonitrile in water (+10 mmol/L $NH_4HCO_3$). The product was further purified by Prep-HPLC on a XSelect CSH Prep Fluoro-Phenyl Column using a gradient of acetonitrile in water (+10 mmoL/L ammonium bicarbonate) to afford 1-[4-({5-[2-(2-aminopyridin-3-yl)-5-(pyrazol-1-yl)imidazo[4,5-b]pyridin-3-yl]-2,3-dihydro-1H-inden-1-yl}methyl)piperazin-1-yl]prop-2-en-1-one (Example 174) (1.3 mg, 1%) as an off-white solid. MS (ESI) calcd. for $C_{31}H_{31}N_9O$: 545.27 m/z, found: 546.15 [M+H]$^+$. $^1$H NMR (300 MHz, DMSO-$d_6$) δ (ppm): 8.43-8.26 (m, 2H), 8.06-7.88 (m, 2H), 7.81-7.60 (m, 1H), 7.58-7.44 (m, 1H), 7.35 (s, 1H), 7.27-7.13 (m, 2H), 6.94 (s, 2H), 6.89-6.74 (m, 1H), 6.59-6.50 (m, 1H), 6.47-6.35 (m, 1H), 6.18-6.05 (m, 1H), 5.71-5.63 (m, 1H), 3.71-3.43 (m, 4H), 3.03-2.73 (m, 2H), 2.73-2.58 (m, 1H), 2.49-2.38 (m, 5H), 2.37-2.16 (m, 1H), 1.92-1.72 (m, 1H), 1.44-1.09 (m, 1H).

Example 175: 1-(4-(((S)-5-(2-(2-aminopyridin-3-yl)-5-cyclopropyl-3H-imidazo[4,5-b]pyridin-3-yl)-2,3-dihydro-1H-inden-1-yl)amino)-3-fluoropiperidin-1-yl)prop-2-en-1-one Example 176: 1-((3*,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-3-fluoropiperidin-1-yl)prop-2-en-1-one and Example 177: 1-((3*,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-3-fluoropiperidin-1-yl)prop-2-en-1-one Example 175

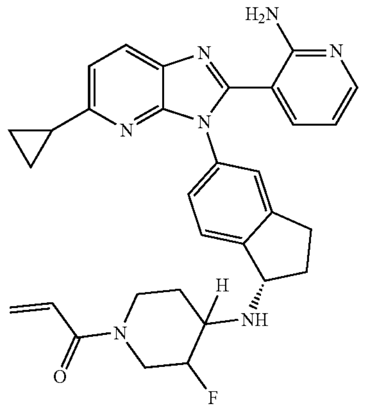

-continued

Example 176

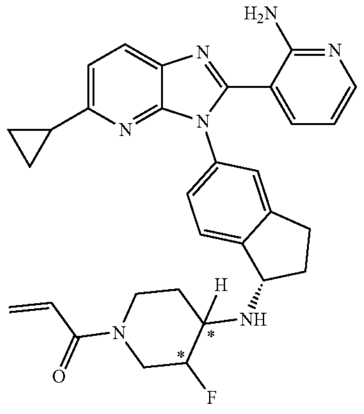

Example 177

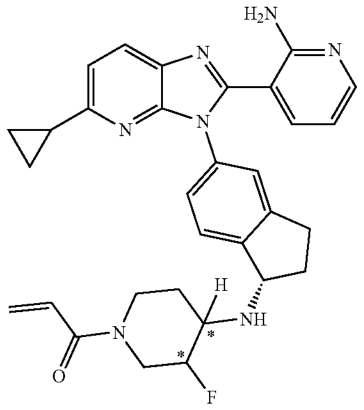

Examples 175, 176 and 177 were prepared in a manner analogous to Example 14 (via Intermediate 14-1) using (3S)-3-fluoro-4-oxopiperidine-1-carboxylate in place tert-butyl 8-oxo-3-azabicyclo[3.2.1]octane-3-carboxylate and Intermediate 85-2 in place of Intermediate 1-1. Note that the fluoro stereocenter epimerized under the reaction conditions giving four stereoisomeric products. The diastereomers partially separated during reverse phase Prep-HPLC on a XBridge Prep OBD C18 Column using a gradient of acetonitrile in water (+10 mM ammonium formate). * Denotes a stereocenter with undetermined absolute stereocenter of a single diastereomer. Note also that Example 175 is a mixture of two undetermined diastereomers.

Example 175: MS (ESI) calcd. for $C_{31}H_{32}FN_7O$: 537.27 m/z, found: 538.20 $[M+H]^+$. $^1$H-NMR (400 MHz, DMSO) δ (ppm): 7.99-8.05 (m, 1H), 7.91-7.98 (m, 1H), 7.41-7.49 (m, 1H), 7.07-7.25 (m, 4H), 6.68-6.85 (m, 1H), 6.35-6.45 (m, 1H), 6.04-6.15 (m, 1H), 5.63-5.75 (m, 1H), 4.70-4.91 (m, 1H), 4.39-4.48 (m, 1H), 4.01-4.38 (m, 2H), 3.09-3.50 (m, 1H), 2.65-3.05 (m, 4H), 2.31-2.45 (m, 1H), 2.10-2.20 (m, 1H), 1.71-1.90 (m, 2H), 1.38-1.60 (m, 1H), 0.85-1.00 (m, 2H), 0.70-0.84 (m, 2H). $^{19}$F NMR (376 MHz, DMSO-$d_6$) δ (ppm): −203.15.

Example 176: MS (ESI) calcd. for $C_{31}H_{32}FN_7O$: 537.27 m/z, found: 538.20 $[M+H]^+$. $^1$H-NMR (400 MHz, DMSO) δ (ppm): 8.28-8.39 (m, 1H), 7.96-8.05 (m, 1H), 7.90-7.95 (m, 1H), 7.40-7.48 (m, 1H), 7.08-7.25 (m, 4H), 6.70-6.82 (m, 1H), 6.38-6.45 (m, 1H), 6.05-6.15 (m, 1H), 5.66-5.75 (m, 1H), 4.28-4.52 (m, 2H), 3.56-3.85 (m, 2H), 3.32-3.55 (m, 2H), 3.01-3.15 (m, 1H), 2.82-2.98 (m, 1H), 2.65-2.80 (m, 1H), 2.35-2.48 (m, 1H), 2.05-2.20 (m, 1H), 1.82-2.04 (m, 1H), 1.66-1.80 (m, 1H), 1.40-1.55 (m, 1H), 0.88-1.00 (m, 2H), 0.72-0.87 (m, 2H). $^{19}$F NMR (376 MHz, DMSO-$d_6$) δ (ppm): −185.54.

Example 177: MS (ESI) calcd. for $C_{31}H_{32}FN_7O$: 537.27 m/z, found: 538.25 $[M+H]^+$. $^1$H-NMR (400 MHz, DMSO) δ (ppm): 7.98-8.05 (m, 1H), 7.92-7.97 (m, 1H), 7.41-7.50 (m, 1H), 7.15-7.25 (m, 2H), 7.10-7.14 (m, 2H), 6.71-6.83 (m, 1H), 6.35-6.45 (m, 1H), 6.05-6.15 (m, 1H), 5.65-5.75 (m, 1H), 4.40-4.62 (m, 1H), 4.30-4.39 (m, 1H), 3.89-4.06 (m, 1H), 3.48-3.60 (m, 2H), 3.35-3.45 (m, 1H), 3.02-3.12 (m, 1H), 2.85-2.95 (m, 1H), 2.65-2.80 (m, 1H), 2.40-2.50 (m, 1H), 2.10-2.20 (m, 1H), 1.70-2.00 (m, 2H), 1.40-1.50 (m, 1H), 0.89-1.00 (m, 2H), 0.70-0.85 (m, 2H). $^{19}$F NMR (376 MHz, DMSO-$d_6$) δ (ppm): −185.85.

Example 178: 1-(4-{[(1S)-5-[2-(2-aminopyridin-3-yl)-5-(3-ethynylphenyl)imidazo[4,5-b]pyridin-3-yl]-2,3-dihydro-1H-inden-1-yl]amino}piperidin-1-yl)prop-2-en-1-one Example 178

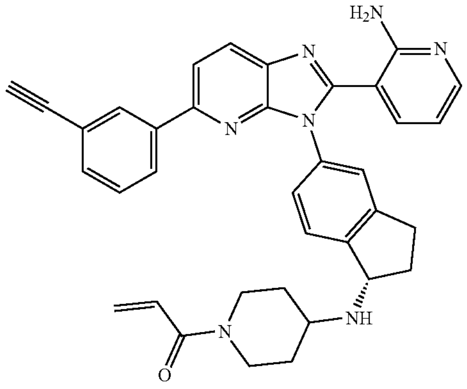

Example 178 was prepared in a manner analogous to Example 109 (via Intermediate 109-2) using Intermediate 85-1 and 3-ethynylphenylboronic acid with tribasic potassium phosphate instead of Intermediate 109-1, 2-bromo-1,3-oxazole and potassium carbonate for Step 1, HCl in dioxane instead of TFA/DCM and tetrahydrofuran as the solvent for the final step. MS (ESI) calcd. For $C_{36}H_{33}N_7O$, 579.27 m/z, found 580.20 $[M+H]^+$. 1H NMR (400 MHz, DMSO-d6) δ 8.27 (d, J=8.4 Hz, 1H), 8.16-7.94 (m, 4H), 7.56-7.43 (m, 3H), 7.36-7.25 (m, 2H), 7.22 (dd, J=7.7, 1.9 Hz, 1H), 7.00 (s, 2H), 6.83 (dd, J=16.7, 10.5 Hz, 1H), 6.42 (dd, J=7.6, 4.8 Hz, 1H), 6.09 (dd, J=16.7, 2.5 Hz, 1H), 5.66 (dd, J=10.4, 2.5 Hz, 1H), 4.36 (t, J=7.3 Hz, 1H), 4.27 (s, 2H), 3.99 (s, 1H), 3.17 (s, 1H), 3.02-2.84 (m, 3H), 2.84-2.70 (m, 1H), 2.48-2.40 (m, 1H), 2.10-2.20 (m, 1H), 1.96 (s, 1H), 1.87 (s, 1H), 1.83-1.69 (m, 1H), 1.25 (s, 2H).

Example 179: 1-(4-{[(1*)-5-[2-(2-aminopyridin-3-yl)-5-(pyrazol-1-yl)imidazo[4,5-b]pyridin-3-yl]-2,3-dihydro-1H-inden-1-yl](methyl)amino}piperazin-1-yl)prop-2-en-1-one and Example 180: 1-(4-{[(1*)-5-[2-(2-aminopyridin-3-yl)-5-(pyrazol-1-yl)imidazo[4,5-b]pyridin-3-yl]-2,3-dihydro-1H-inden-1-yl](methyl)amino}piperazin-1-yl)prop-2-en-1-one Example 179

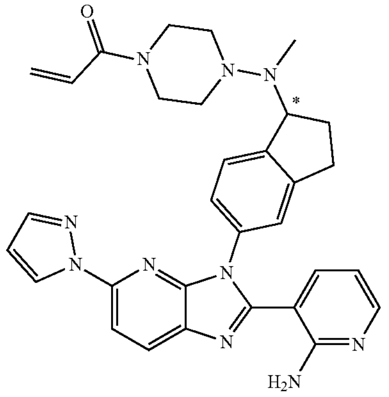

Example 180

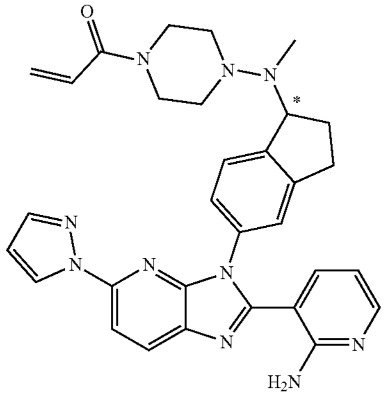

Synthetic Route:

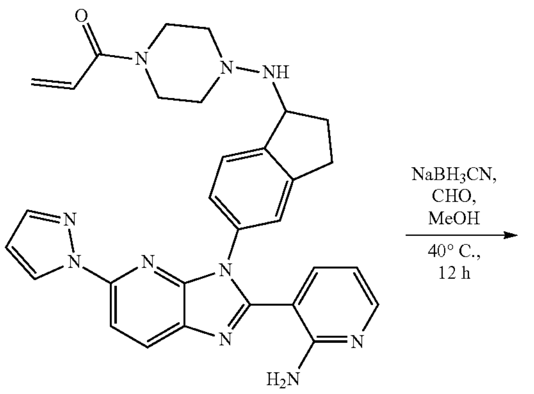

Example 77

-continued

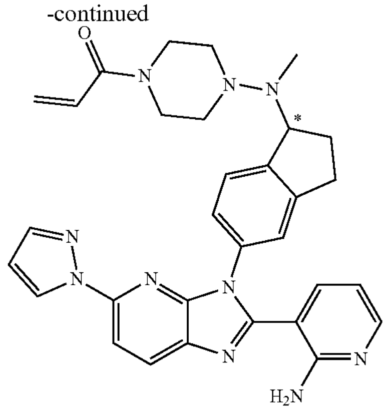

Example 179

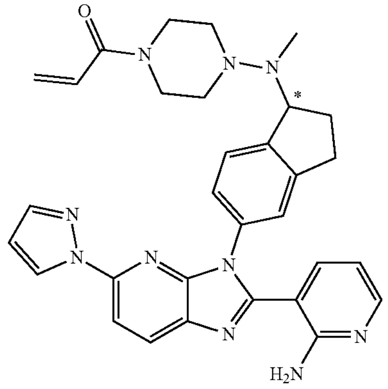

Example 180

Step 1: Synthesis of 1-(4-{[(1*)-5-[2-(2-aminopyridin-3-yl)-5-(pyrazol-1-yl)imidazo[4,5-b]pyridin-3-yl]-2,3-dihydro-1H-inden-1-yl](methyl)amino}piperazin-1-yl)prop-2-en-1-one (Example 179) and 1-(4-{[(1*)-5-[2-(2-aminopyridin-3-yl)-5-(pyrazol-1-yl)imidazo[4,5-b]pyridin-3-yl]-2,3-dihydro-1H-inden-1-yl](methyl)amino}piperazin-1-yl)prop-2-en-1-one (Example 180)

To a solution of 1-[4-({5-[2-(2-aminopyridin-3-yl)-5-(pyrazol-1-yl)imidazo[4,5-b]pyridin-3-yl]-2,3-dihydro-1H-inden-1-yl}amino)piperazin-1-yl]prop-2-en-1-one (Example 77) (500 mg, 0.915 mmol, 1 equiv) in MeOH (20 mL) was added paraformaldehyde (80.6 mg, 1.83 mmol, 2 equiv). The resulting mixture was stirred for 12 h at 40° C. $NaBH_3CN$ (172.4 mg, 2.745 mmol, 3 equiv) was added and the reaction mixture was stirred at 40° C. for another 1 hour. The mixture was purified directly by reverse-phase flash chromatography on a XBridge Prep Shield RP OBD C18 Column using a gradient of acetonitrile in water (+10 mmol/L ammonium bicarbonate). The racemic mixture was separated into enantiomers by chiral Prep-HPLC on a CHIRALPAK IF column using a mixture of [MTBE (0.5% 2M $NH_3$-MeOH)] and [EtOH/DCM (1:1)] to afford {1-(4-{[(1*)-5-[2-(2-aminopyridin-3-yl)-5-(pyrazol-1-yl)imidazo[4,5-b]pyridin-3-yl]-2,3-dihydro-1H-inden-1-yl](methyl)amino}piperazin-1-yl)prop-2-en-1-one (Example 179) (12.3 mg, 2.39%) as a white solid and the first eluting isomer and {1-(4-{[(1*)-5-[2-(2-aminopyridin-3-yl)-5-(pyrazol-1-yl)imidazo[4,5-b]pyridin-3-yl]-2,3-dihydro-1H-inden-1-yl](methyl)amino}piperazin-1-yl)prop-2-en-1-one (Example 180) (14.4 mg, 2.80%) as a white solid. * Denotes a stereocenter with undetermined absolute stereocenter of a single enantiomer.

Example 179: MS (ESI) calcd. for $C_{31}H_{32}N_{10}O$: 560.28 m/z, found: 561.20 $[M+H]^+$. $^1$H NMR (400 MHz, DMSO-$d_6$) δ (ppm): 8.33-8.35 (m, 2H), 8.00-8.01 (m, 1H), 7.95-7.99 (m, 1H), 7.81-7.82 (m, 1H), 7.54-7.56 (m, 1H), 7.31-7.32 (m, 1H), 7.22-7.25 (m, 2H), 6.73-6.80 (m, 1H), 6.54-6.55 (m, 1H), 6.41-6.44 (m, 1H), 6.09-6.13 (m, 1H), 5.69-5.73 (m, 1H), 4.31-4.33 (m, 1H), 3.49-3.55 (m, 4H), 3.04-3.07 (m, 1H), 2.70-2.78 (m, 1H), 2.63-2.69 (m, 2H), 2.39-2.52 (m, 2H), 2.33 (s, 3H), 2.16-2.21 (m, 2H).

Example 180: MS (ESI) calcd. for $C_{31}H_{32}N_{10}O$: 560.28 m/z, found: 561.20 $[M+H]^+$. $^1$H NMR (400 MHz, DMSO-$d_6$) δ (ppm): 8.33-8.35 (m, 2H), 8.00-8.01 (m, 1H), 7.95-7.99 (m, 1H), 7.81-7.82 (m, 1H), 7.54-7.56 (m, 1H), 7.32-7.33 (m, 1H), 7.22-7.25 (m, 2H), 6.73-6.80 (m, 1H), 6.54-6.55 (m, 1H), 6.41-6.44 (m, 1H), 6.08-6.13 (m, 1H), 5.69-5.72 (m, 1H), 4.31-4.33 (m, 1H), 3.52-3.72 (m, 4H), 3.02-3.07 (m, 1H), 2.72-2.84 (m, 1H), 2.62-2.63 (m, 2H), 2.49-2.54 (m, 2H), 2.33 (s, 3H), 2.18-2.22 (m, 2H).

Example 181: 1-(4-{[(1S,2*)-5-[2-(2-aminopyridin-3-yl)-5-(pyrazol-1-yl)imidazo[4,5-b]pyridin-3-yl]-2-methyl-2,3-dihydro-1H-inden-1-yl]amino}piperidin-1-yl)prop-2-en-1-one and Example 182: 1-(4-(((1S,2*)-5-(2-(2-aminopyridin-3-yl)-5-(1H-pyrazol-1-yl)-3H-imidazo[4,5-b]pyridin-3-yl)-2-methyl-2,3-dihydro-1H-inden-1-yl)amino)piperidin-1-yl)prop-2-en-1-one Example 181

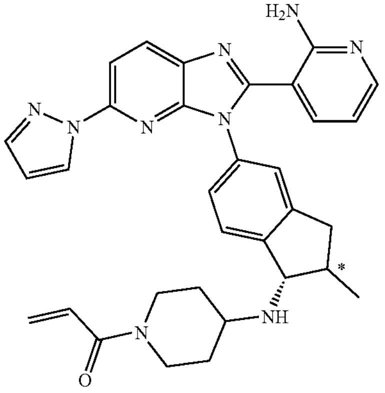

Example 182

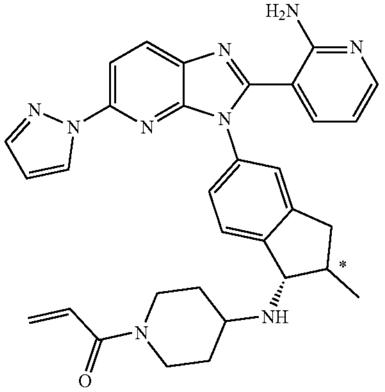

Examples 181 and 182 were prepared in a manner analogous to Example 13 using Intermediate 181-1 and 182-1 respectively instead of Intermediate 1-1 and 10:1 methanol/AcOH for 1 h at 60° C. * Denotes a stereocenter with undetermined absolute stereocenter of a single diastereomer.

Example 181: MS (ESI) calcd. for $C_{32}H_{33}N_9O$, 559.28 m/z, found 560.20 $[M+H]^+$. $^1$H-NMR (400 MHz, DMSO-d6) δ (ppm): 8.28-8.68 (m, 2H), 7.95-8.16 (m, 2H), 7.81-7.95 (m, 1H), 7.62-7.81 (m, 2H), 7.52-7.62 (m, 1H), 7.36-7.52 (m, 1H), 6.69-6.98 (m, 2H), 6.49-6.69 (m, 1H), 6.04-6.28 (m, 1H), 5.65-5.91 (m, 1H), 4.82-5.14 (m, 1H), 4.43-4.71 (m, 1H), 4.06-4.35 (m, 1H), 3.41-3.71 (m, 1H), 3.05-3.36 (m, 2H), 2.92-3.05 (m, 1H), 2.63-2.92 (m, 2H), 2.52-2.61 (m, 1H), 2.08-2.26 (m, 1H), 1.46-1.79 (m, 2H), 1.05-1.31 (m, 3H). (TFA salt)

Example 182: MS (ESI) calcd. for $C_{32}H_{33}N_9O$, 559.28 m/z, found 560.20 $[M+H]^+$. $^1$H-NMR (400 MHz, DMSO-d6) δ (ppm): 8.14-8.50 (m, 3H), 7.89-8.14 (m, 2H), 7.69-7.89 (m, 1H), 7.45-7.69 (m, 1H), 7.09-7.45 (m, 3H), 6.68-6.95 (m, 1H), 6.53-6.68 (m, 1H), 6.32-6.53 (m, 1H), 5.98-6.28 (m, 1H), 5.61-5.88 (m, 1H), 4.48-4.66 (m, 1H), 4.28-4.48 (m, 1H), 4.06-4.28 (m, 1H), 3.08-3.35 (m, 2H), 2.92-3.08 (m, 1H), 2.76-2.91 (m, 2H), 2.63-2.76 (m, 1H), 1.95-2.26 (m, 2H), 1.28-1.54 (m, 2H), 0.79-1.12 (m, 3H). (TFA salt)

Intermediate 181-1: 3-(3-((1S,2*)-1-amino-2-methyl-2,3-dihydro-1H-inden-5-yl)-5-(1H-pyrazol-1-yl)-3H-imidazo[4,5-b]pyridin-2-yl)pyridin-2-amine and Intermediate 182-1: 3-(3-((1S,2*)-1-amino-2-methyl-2,3-dihydro-1H-inden-5-yl)-5-(1H-pyrazol-1-yl)-3H-imidazo[4,5-b]pyridin-2-yl)pyridin-2-amine Example 181-1

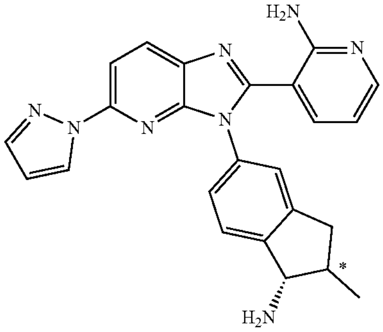

Example 182-1

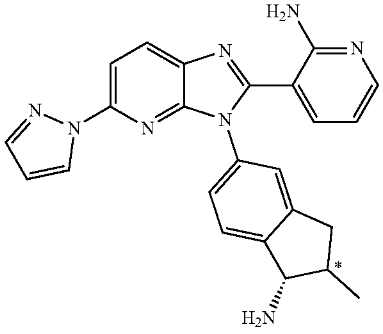

Intermediates 181-1 and 182-1 were prepared in a manner analogous to Intermediates 75-1 and 76-1 (starting from Step 2) using 5-bromo-2-methyl-2,3-dihydro-1H-inden-1-one in place of 5-bromo-2-fluoro-2,3-dihydro-1H-inden-1-one. The diastereomers were separated prior to the final step by chiral SFC on a Lux Sum Cellulose-3 column using a mixture of $CO_2$ and methanol. * Denotes a stereocenter with undetermined absolute stereocenter of a single diastereomer.

Example 183: 1-[4-({[(1S)-5-[2-(2-aminopyridin-3-yl)-5-(pyrazol-1-yl)imidazo[4,5-b]pyridin-3-yl]-2,3-dihydro-1H-inden-1-yl]amino}methyl)-4-methoxypiperidin-1-yl]prop-2-en-1-one Example 183

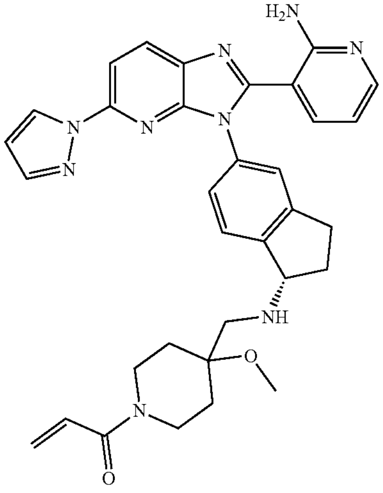

Example 183 was prepared in a manner analogous to Example 34 using tert-butyl 4-formyl-4-methoxypiperidine-1-carboxylate in place of tert-butyl 4-oxopiperidine-1-carboxylate, MeOH instead of 1,2-dichloroethane and acrylic acid instead of (2E)-4-(dimethylamino)but-2-enoic acid. MS (ESI) calcd. for $C_{33}H_{35}N_9O_2$, 589.29 m/z, found 590.20 $[M+H]^+$. $^1H$ NMR (400 MHz, DMSO-d6) δ (ppm): 9.00-9.16 (m, 1H), 8.75-8.80 (m, 1H), 8.41-8.43 (m, 111), 8.35-8.36 (m, 1H), 8.05-8.07 (m, 1H), 7.99-8.01 (m, 1H), 7.82-7.83 (m, 2H), 7.57-7.60 (m, 2H), 7.39-7.41 (m, 1H), 7.00-7.30 (m, 1H), 6.79-6.86 (m, 1H), 6.57-6.59 (m, 2H), 6.08-6.13 (m, 1H), 5.67-5.70 (m, 1H), 4.98-5.00 (m, 1H), 4.09-4.15 (m, 2H), 3.15-3.30 (m, 3H), 2.95-3.02 (m, 5H), 2.78-2.81 (m, 1H), 2.55-2.60 (m, 1H), 2.20-2.33 (m, 1H), 1.80-1.83 (m, 2H), 1.42-1.50 (m, 2H). (TFA salt)

Example 184: (S)-1-(4-(((5-(2-(2-aminopyridin-3-yl)-5-(1H-pyrazol-1-yl)-3H-imidazo[4,5-b]pyridin-3-yl)-2,3-dihydro-1H-inden-1-yl)amino)methyl)-4-fluoropiperidin-1-yl)prop-2-en-1-one Example 184

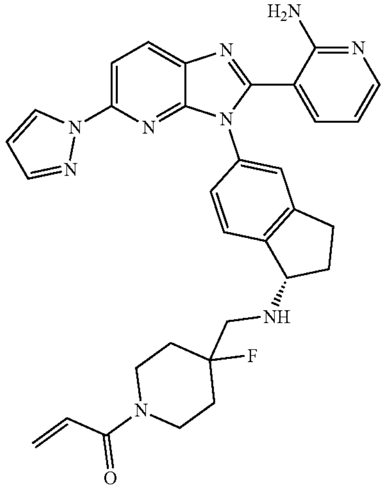

Example 184 was prepared in a manner analogous to Example 34 using 1-acryloyl-4-fluoropiperidine-4-carbaldehyde in place of tert-butyl 4-oxopiperidine-1-carboxylate, MeOH instead of 1,2-dichloroethane and acrylic acid instead of (2E)-4-(dimethylamino)but-2-enoic acid. MS (ESI) calcd. for $C_{32}H_{32}FN_9O$, 577.27 m/z, found 578.30 $[M+H]^+$. 1HNMR (400 MHz, DMSO-$d_6$) δ (ppm): 1H NMR (400 MHz, DMSO-d6) δ 9.24-9.26 (m, 2H), 8.37-8.44 (m, 2H), 7.98-8.08 (m, 2H), 7.81-7.84 (m, 2H), 7.57-7.60 (m, 2H), 7.42-7.44 (m, 1H), 7.00-7.25 (m, 1H), 6.82-6.89 (m, 1H), 6.57-6.58 (m, 2H), 6.11-6.16 (m, 1H), 5.70-5.73 (m, 1H), 4.97-5.00 (m, 1H), 4.29-4.30 (m, 1H), 4.01-4.04 (m, 1H), 3.32-3.33 (m, 2H), 3.28-3.29 (m, 2H), 2.92-2.99 (m, 2H), 2.50-2.58 (m, 1H), 2.20-2.30 (m, 1H), 1.98-2.07 (m, 2H), 1.60-1.90 (m, 2H). $^{19}F$ NMR (376 MHz, DMSO-$d_6$) δ (ppm): −73.98, −161.869. (TFA salt)

Example 185: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-3-methylbut-2-en-1-one Example 185

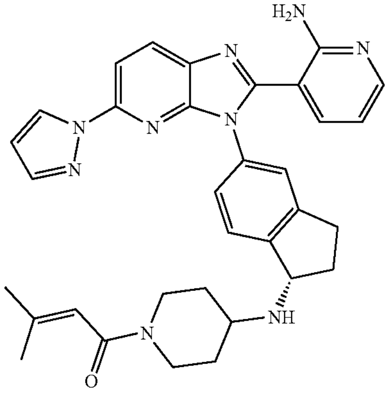

Example 185 was prepared in a manner analogous to Example 34 using 3-methylbut-2-enoic acid in place of (2E)-4-(dimethylamino)but-2-enoic acid. MS (ESI) calcd for $C_{33}H_{35}N_9O$: 573.30, found: 574.20 $[M+H]^+$. $^1H$ NMR (400 MHz, DMSO-$d_6$) δ 9.12 (m, 1H), 8.96 (m, 1H), 8.43 (m, 1H), 8.35 (m, 1H), 8.07-8.00 (m, 1H), 7.98 (m, 1H), 7.83 (s, 1H), 7.76-7.74 (m, 1H), 7.64-7.58 (m, 2H), 7.54-7.42 (m, 1H), 6.63-6.57 (m, 2H), 5.96 (s, 1H), 5.01 (m, 1H), 4.51 (m, 1H), 4.03 (m, 1H), 3.55-3.55 (m, 1H), 3.22-3.00 (m, 2H), 2.98-2.92 (m, 1H), 2.69-2.50 (m, 2H), 2.50 (s, 1H), 2.23-2.20 (m, 2H), 2.10-2.07 (m, 1H), 2.07-1.84 (m, 6H), 1.82-1.23 (m, 2H). (formic acid salt)

Example 186: 1-(4-{[(1S)-5-[2-(2-aminopyridin-3-yl)-5-(4,4-difluoropiperidin-1-yl)imidazo[4,5-b]pyridin-3-yl]-2,3-dihydro-1H-inden-1-yl]amino}piperidin-1-yl)prop-2-en-1-one Example 186

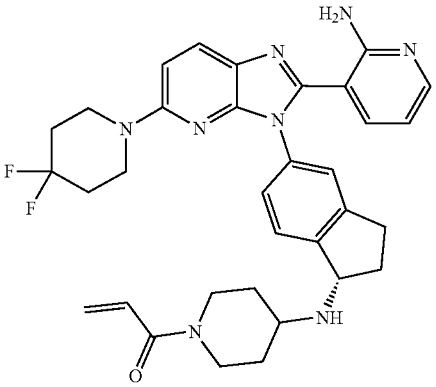

Example 186 was prepared in a manner analogous to Example 86 (via Intermediate 86-2) using 4,4-difluoropiperidine in place of morpholine. MS (ESI) calcd. for $C_{33}H_{36}F_2N_8O$: 598.30 m/z, found: 599.20 $[M+H]^+$. 1H NMR (400 MHz, DMSO-d6) δ 8.02-7.92 (m, 2H), 7.60-7.45 (m, 1H), 7.34-7.18 (m, 2H), 7.09-7.00 (m, 2H), 6.95 (s, 2H), 6.89-6.79 (m, 1H), 6.40-6.33 (m, 1H), 6.14-6.05 (m, 1H), 5.71-5.63 (m, 1H), 4.54-4.24 (m, 2H), 4.04 (s, 1H), 3.68-3.61 (m, 4H), 3.19-2.89 (m, 3H), 2.87-2.71 (m, 3H), 2.45-2.41 (m, 1H), 2.13-1.59 (m, 7H), 1.35-1.23 (m, 2H).

Example 187: 1-(4-{[(1S)-5-[2-(2-aminopyridin-3-yl)-5-[1-(difluoromethyl) pyrazol-4-yl]imidazo[4,5-b]pyridin-3-yl]-2,3-dihydro-1H-inden-1-yl]amino}piperidin-1-yl)prop-2-en-1-one Example 187

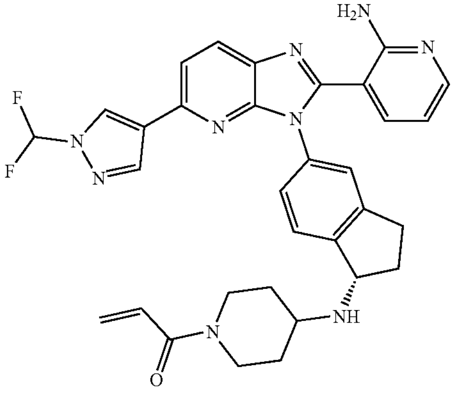

Example 187 was prepared in a manner analogous to Example 109 (via Intermediate 109-2) using 4-bromo-1-(difluoromethyl) pyrazole in place of 2-bromo-1,3-oxazole. MS (ESI) calcd. for $C_{32}H_{31}F_2N_9O$, 595.26 m/z, found 596.20 $[M+H]^+$. $^1H$ NMR (400 MHz, DMSO-d6) δ (ppm): 8.52-8.79 (m, 1H), 8.23-8.46 (m, 1H), 8.16-8.23 (m, 1H), 7.96-8.16 (m, 1H), 7.55-7.96 (m, 2H), 7.44-7.55 (m, 1H), 7.29-7.44 (m, 1H), 7.08-7.29 (m, 2H), 6.67-6.95 (m, 1H), 6.36-6.59 (m, 1H), 5.96-6.26 (m, 1H), 5.58-5.85 (m, 1H), 4.21-4.56 (m, 2H), 3.97-4.21 (m, 1H), 2.91-3.32 (m, 3H), 2.67-2.91 (m, 2H), 2.41-2.52 (m, 1H), 1.98-2.21 (m, 1H), 1.68-1.98 (m, 2H), 1.07-1.47 (m, 2H). (formic acid salt)

Example 188: 1-((1R,5S,9*)-9-(((S)-5-(2-(2-amino-pyridin-3-yl)-5-(1H-pyrazol-1-yl)-3H-imidazo[4,5-b]pyridin-3-yl)-2,3-dihydro-1H-inden-1-yl)amino)-3-azabicyclo[3.3.1]nonan-3-yl)prop-2-en-1-one and Example 189: 1-((1R,5S,9*)-9-(((S)-5-(2-(2-amino-pyridin-3-yl)-5-(1H-pyrazol-1-yl)-3H-imidazo[4,5-b]pyridin-3-yl)-2,3-dihydro-1H-inden-1-yl)amino)-3-azabicyclo[3.3.1]nonan-3-yl)prop-2-en-1-one Example 188

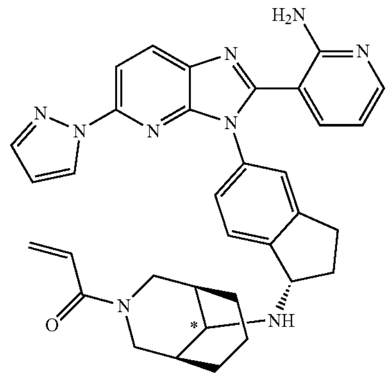

Example 189

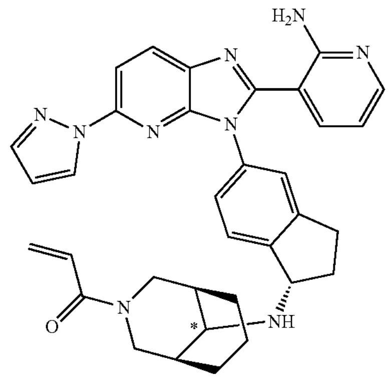

Examples 188 and 189 were prepared in a manner analogous to Example 14 (via Intermediate 14-1) using tert-butyl 9-oxo-3-azabicyclo[3.3.1]nonane-3-carboxylate in place of tert-butyl 8-oxo-3-azabicyclo[3.2.1]octane-3-carboxylate and 4N HCl in dioxane in place of TFA in DCM. The diastereomers were separated by Prep-HPLC on a XBridge Prep Phenyl Hexy OBD C18 Column using a gradient of acetonitrile in water (+10 mmol/L $NH_4HCO_3$). * Denotes a stereocenter with undetermined absolute stereocenter of a single diastereomer.

Example 188: MS (ESI) calcd. for $C_{34}H_{35}N_9O$: 585.29 m/z, found: 586.20 $[M+H]^+$. $^1H$ NMR (300 MHz, DMSO-$d_6$) δ (ppm): 8.30-8.37 (m, 2H), 7.93-8.03 (m, 2H), 7.79-7.82 (m, 1H), 7.49-7.55 (m, 1H), 7.33-7.37 (m, 1H), 7.21-7.31 (m, 2H), 6.81-6.98 (m, 3H), 6.50-6.56 (m, 1H), 6.40-6.44 (m, 1H), 6.01-6.10 (m, 1H), 5.61-5.68 (m, 1H), 4.50-4.60 (m, 1H), 4.09-4.29 (m, 2H), 3.38-3.40 (m, 1H), 2.81-3.00 (m, 3H), 2.70-2.80 (m, 1H), 2.48-2.52 (m, 1H), 2.00-2.19 (m, 3H), 1.90-1.99 (m, 1H), 1.76-1.87 (m, 2H), 1.28-1.60 (m, 4H).

Example 189: MS (ESI) calcd. for $C_{34}H_{35}N_9O$: 585.29 m/z, found: 586.20 $[M+H]^+$. 1H NMR (400 MHz, DMSO-d6) δ (ppm): 8.27-8.31 (m, 2H), 7.82-7.96 (m, 2H), 7.71-7.74 (m, 1H), 7.40-7.46 (m, 1H), 7.30-7.40 (m, 1H), 7.13-7.28 (m, 2H), 6.82-6.90 (m, 2H), 6.70-6.81 (m, 1H), 6.45-6.50 (m, 1H), 6.30-6.38 (m, 1H), 5.97-6.03 (m, 1H), 5.50-5.58 (m, 1H), 4.18-4.28 (m, 1H), 4.07-4.18 (m, 1H), 3.63-3.72 (m, 2H), 3.18-3.21 (m, 1H), 2.84-2.92 (m, 1H), 2.76-2.80 (m, 1H), 2.62-2.72 (m, 1H), 2.38-2.40 (m, 1H), 1.99-2.08 (m, 1H), 1.90-1.97 (m, 1H), 1.67-1.80 (m, 4H), 1.42-1.62 (m, 3H), 1.22-1.30 (m, 1H).

Example 190: (S)-1-(4-((5-(2-(2-aminopyridin-3-yl)-6-(pyridin-3-yl)-3H-imidazo[4,5-b]pyridin-3-yl)-2,3-dihydro-1H-inden-1-yl)amino)piperidin-1-yl)prop-2-en-1-one Example 190

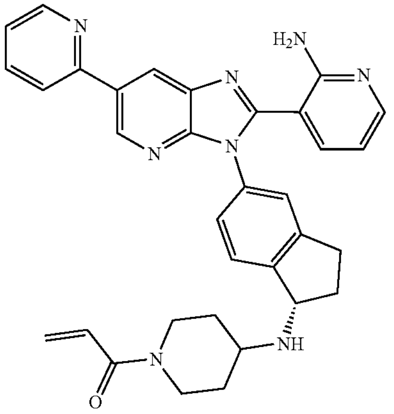

Synthetic Route:

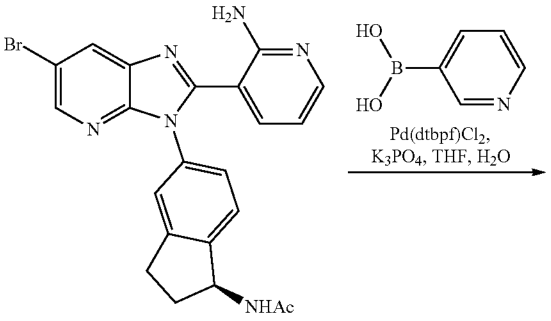

Intermediate 190-1

-continued

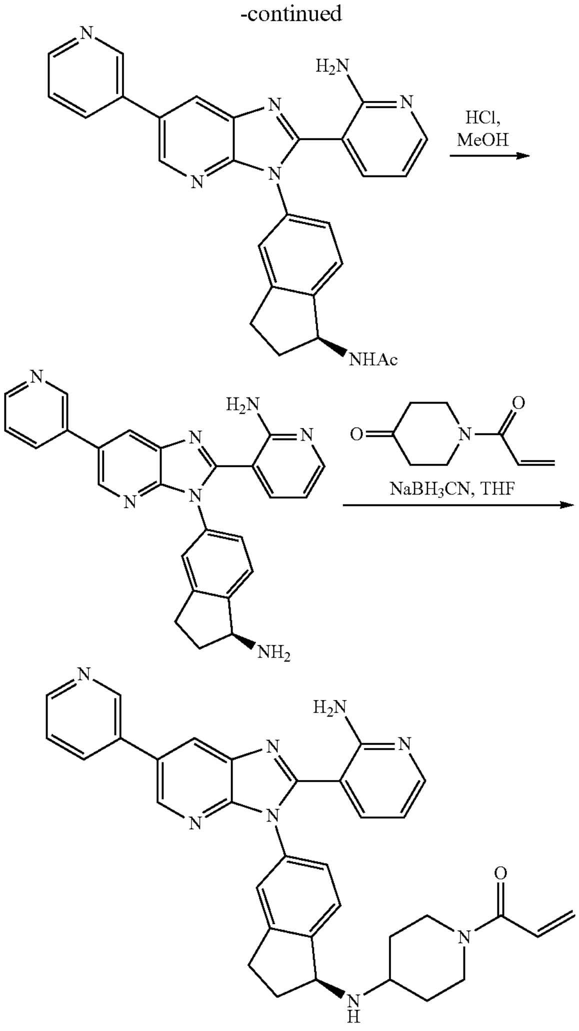

Example 190

Step 1: Synthesis of N-[(1S)-5-[2-(2-aminopyridin-3-yl)-6-(pyridin-3-yl)imidazo[4,5-b]pyridin-3-yl]-2,3-dihydro-1H-inden-1-yl]acetamide To a stirred solution of N-[(1S)-5-[2-(2-aminopyridin-3-yl)-6-bromoimidazo[4,5-b]pyridin-3-yl]-2,3-dihydro-1H-inden-1-yl]acetamide (Intermediate 190-1) (500 mg, 1.079 mmol, 1 equiv) and pyridin-3-ylboronic acid (159 mg, 1.295 mmol, 1.2 equiv) in THF (4 mL) and $H_2O$ (4 mL) was added $Pd(dtbpf)Cl_2$ (70 mg, 0.108 mmol, 0.1 equiv) and $K_3PO_4$ (687.2 mg, 3.237 mmol, 3 equiv) in portions at 50° C. under nitrogen atmosphere. The resulting mixture was stirred for 3 h at 50° C. under nitrogen then allowed to cool to room temperature. The reaction was quenched with water. The resulting mixture was extracted with $CH_2Cl_2$ (3×100 mL). The combined organic layers were dried over anhydrous $Na_2SO_4$. After filtration, the filtrate was concentrated under reduced pressure. The residue was purified by reverse-phase flash chromatography on C18 silica gel using a gradient of acetonitrile in water (+10 mmol/L $NH_4HCO_3$) afford N-[(1S)-5-[2-(2-aminopyridin-3-yl)-6-(pyridin-3-yl)imidazo[4,5-b]pyridin-3-yl]-2,3-dihydro-1H-inden-1-yl]acetamide (240 mg, 44%) as a brown yellow solid. MS (ESI) calcd. for $C_{27}H_{23}N_7O$: 461.20 m/z, found: 462.30 $[M+H]^+$.

Step 2: Synthesis of 3-{3-[(1S)-1-amino-2,3-dihydro-1H-inden-5-yl]-6-(pyridin-3-yl)imidazo[4,5-b]pyridin-2-yl}pyridin-2-amine A solution of N-[(1S)-5-[2-(2-aminopyridin-3-yl)-6-(pyridin-3-yl)imidazo[4,5-b]pyridin-3-yl]-2,3-dihydro-1H-inden-1-yl]acetamide (210 mg, 0.455 mmol, 1 equiv) in HCl (6 mL) and MeOH (6 mL) was stirred overnight at 90° C. under air atmosphere. The mixture was allowed to cool to room temperature. The reaction was quenched with water. The mixture was basified to pH 8 with saturated $NaHCO_3$ (aq.). The resulting mixture was extracted with $CH_2Cl_2$ (3x30 mL). The combined organic layers were dried over anhydrous $Na_2SO_4$. After filtration, the filtrate was concentrated under reduced pressure to afford 3-{3-[(1S)-1-amino-2,3-dihydro-1H-inden-5-yl]-6-(pyridin-3-yl) imidazo[4,5-b]pyridin-2-yl}pyridin-2-amine (150 mg, 79%) as a brown yellow solid. The crude product was used in the next step directly without further purification. MS (ESI) calcd. for $C_{25}H_{21}N_7$: 419.19 m/z, found: 420.20 $[M+H]^+$.

Step 3: Synthesis of 1-(4-{[(1S)-5-[2-(2-aminopyridin-3-yl)-6-(pyridin-3-yl)imidazo[4,5-b]pyridin-3-yl]-2,3-dihydro-1H-inden-1-yl]amino}piperidin-1-yl)prop-2-en-1-one (Example 190)

A solution of 3-{3-[(1S)-1-amino-2,3-dihydro-1H-inden-5-yl]-6-(pyridin-3-yl) imidazo[4,5-b]pyridin-2-yl}pyridin-2-amine (120 mg, 0.286 mmol, 1 equiv) and 1-(prop-2-enoyl)piperidin-4-one (175.3 mg, 1.144 mmol, 4 equiv) in THF (5 mL) was stirred for 30 min at 50° C. To the above mixture was added $NaBH_3CN$ (71.9 mg, 1.144 mmol, 4 equiv) in portions at room temperature. The resulting mixture was stirred for 4 h at 50° C. The mixture was allowed to cool to room temperature. The reaction was quenched with water. The resulting mixture was extracted with ethyl acetate (3x30 mL). The combined organic layers were dried over anhydrous $Na_2SO_4$. After filtration, the filtrate was concentrated under reduced pressure. The residue was purified by reverse-phase flash chromatography on C18 silica gel using a gradient of acetonitrile in water (+10 mmol/L $NH_4HCO_3$) to afford 1-(4-{[(1S)-5-[2-(2-aminopyridin-3-yl)-6-(pyridin-3-yl) imidazo[4,5-b]pyridin-3-yl]-2,3-dihydro-1H-inden-1-yl]amino}piperidin-1-yl)prop-2-en-1-one (Example 190) (16.0 mg, 10%) as an off-white solid. MS (ESI) calcd. for $C_{33}H_{32}N_8O$: 556.27 m/z, found: 557.20 $[M+H]^+$. $^1H$ NMR (300 MHz, DMSO-$d_6$) δ 9.05-8.98 (m, 1H), 8.71-8.59 (m, 2H), 8.59-8.54 (m, 1H), 8.26-8.16 (m, 1H), 8.06-7.98 (m, 1H), 7.60-7.49 (m, 2H), 7.42-7.36 (s, 1H), 7.34-7.26 (m, 1H), 7.26-7.17 (m, 1H), 7.12-6.96 (s, 2H), 6.91-6.76 (m, 1H), 6.48-6.38 (m, 1H), 6.15-6.03 (m, 1H), 5.72-5.61 (m, 1H), 4.47-4.41 (m, 1H), 4.33-4.27 (m, 1H), 4.04-3.98 (m, 1H), 3.26-3.08 (m, 2H), 3.02-2.96 (m, 2H), 2.89-2.73 (m, 2H), 2.44-2.31 (m, 1H), 1.99-1.93 (m, 2H), 1.92-1.86 (m, 1H), 1.33-1.27 (m, 2H).

Intermediate 190-1: (S)-N-(5-(2-(2-aminopyridin-3-yl)-6-bromo-3H-imidazo[4,5-b]pyridin-3-yl)-2,3-dihydro-1H-inden-1-yl)acetamide Intermediate 190-1

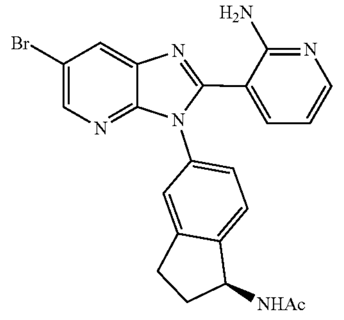

Synthetic Route:

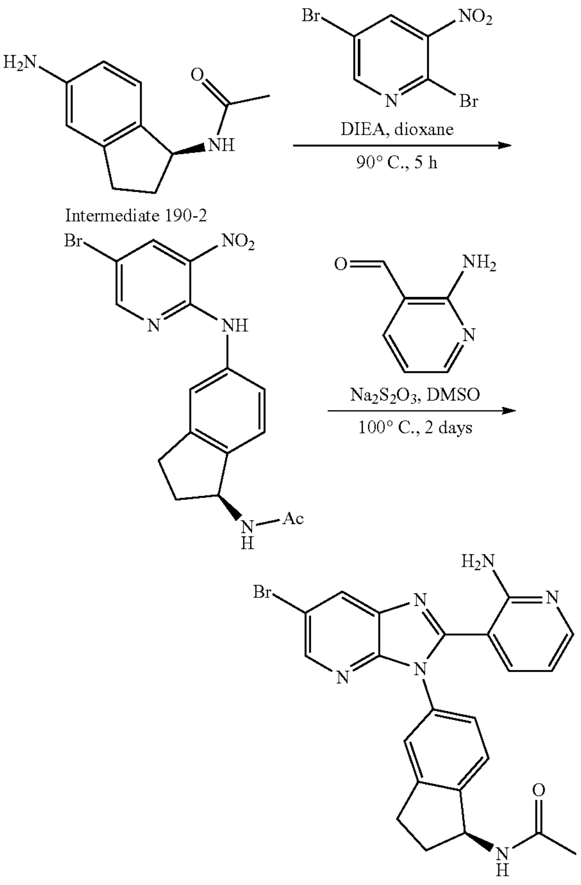

Intermediate 190-2

Intermediate 190-1

Step 1: Synthesis of N-[(1S)-5-[(5-bromo-3-nitropyridin-2-yl)amino]-2,3-dihydro-1H-inden-1-yl]acetamide A solution of 2,5-dibromo-3-nitropyridine (8 g, 28 mmol, 1.2 equiv) and N-[(1S)-5-amino-2,3-dihydro-1H-inden-1-yl]acetamide (Intermediate 190-2) (4.50 g, 23.7 mmol, 1 equiv) in 1,4-dioxane (80 mL) was treated with DIEA (16.5 mL, 94.6 mmol, 4 equiv) over 10 min at room temperature. The resulting mixture was stirred for 5 h at 90° C. The mixture was allowed to cool to room temperature. The reaction was quenched with water at room temperature. The precipitated solids were collected by filtration and washed with water (3×100 mL). The residue was purified by trituration with $Et_2O$ (200 mL) to afford N-[(1S)-5-[(5-bromo-3-nitropyridin-2-yl)amino]-2,3-dihydro-1H-inden-1-yl]acetamide (7 g, 58%) as a brown solid. MS (ESI) calcd. for $C_{16}H_{11}BrN_4O_3$: 390.03 m/z, found: 391.00 $[M+H]^+$.

Step 2: Synthesis of N-[(1S)-5-[2-(2-aminopyridin-3-yl)-6-bromoimidazo[4,5-b]pyridin-3-yl]-2,3-dihydro-1H-inden-1-yl]acetamide (Intermediate 190-1

A solution of N-[(1S)-5-[(5-bromo-3-nitropyridin-2-yl)amino]-2,3-dihydro-1H-inden-1-yl]acetamide (7 g, 18 mmol, 1 equiv) and 2-aminopyridine-3-carbaldehyde (2.6 g, 21 mmol, 1.2 equiv) in DMSO/MeOH=36 mL:6 mL was treated with $Na_2S_2O_4$ (6.85 g, 39.4 mmol, 2.2 equiv) for 10 min at room temperature under air atmosphere. The resulting mixture was stirred for 2 days at 100° C. under air atmosphere. The mixture was allowed to cool to room temperature. The reaction was quenched with water. The mixture was basified to pH 10 with NaOH. The resulting mixture was extracted with ethyl acetate (3×50 mL). The combined organic layers were dried over anhydrous $Na_2SO_4$. After filtration, the filtrate was concentrated under reduced pressure. The residue was purified by silica gel column chromatography, eluting with ethyl acetate to afford N-[(1S)-5-[2-(2-aminopyridin-3-yl)-6-bromoimidazo[4,5-b]pyridin-3-yl]-2,3-dihydro-1H-inden-1-yl]acetamide (Intermediate 190-1) (1.02 g, 11%) as a brown solid. MS (ESI) calcd. for $C_{22}H_{19}BrN_6O$: 462.08 m/z, found: 463.10 $[M+H]^+$.

Intermediate 190-2: (S)-N-(5-amino-2,3-dihydro-1H-inden-1-yl)acetamide

Intermediate 190-2

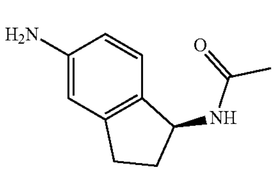

Synthetic Route:

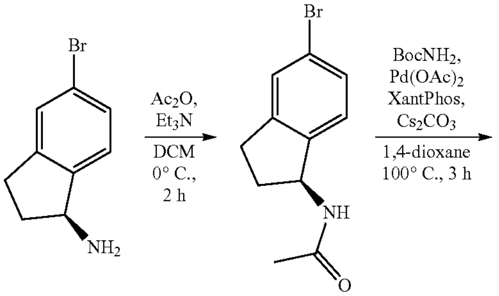

-continued

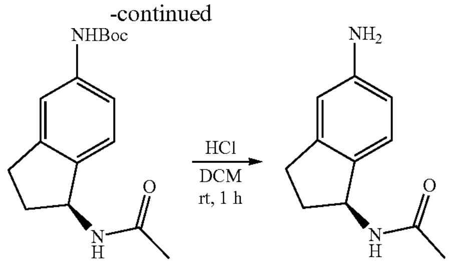

Intermediate 190-2

Step 1: Synthesis of (S)-N-(5-bromo-2,3-dihydro-1H-inden-1-yl)acetamide

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water (500 mL) and extracted with ethyl acetate (3×500 mL). The combined organic layers were dried over anhydrous sodium sulfate and concentrated under reduced pressure. The crude product was re-crystallized from petroleum ether to afford (S)-N-(5-bromo-2,3-dihydro-1H-inden-1-yl)acetamide (Intermediate 13-1) (90 g, 83% yield) as a white solid. MS (ESI) calculated for $C_{11}H_{12}BrNO$: 253.01, found 254.00 $[M+H]^+$, 256.00 $[M+H+2]^+$.

Step 2: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (Intermediate 13-1) (40 g, 157 mmol, 1 equiv), tert-butyl carbamate (27.66 g, 236 mmol, 1.5 equiv), XantPhos (CAS: 161265-03-8) (9.11 g, 15.7 mmol, 10 mol %), $Pd(OAc)_2$ (3.54 g, 15.7 mmol, 10 mol %), and cesium carbonate (154 g, 472 mmol, 3 equiv) was added 1,4-dioxane (300 mL) under nitrogen atmosphere. The resulting mixture was stirred for 3 h at 100° C. The reaction mixture was quenched by addition of water (50 mL) and extracted with ethyl acetate (3×50 mL). The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48% yield). MS (ESI) calculated for $C_{16}H_{22}N_2O_3$: 290.16, found 289.05 $[M-H]^-$.

Step 3: Synthesis of (S)-N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N HCl in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H-inden-1-yl]acetamide (hydrochloride salt) (23 g, 81% yield) as a white solid. MS (ESI) calculated for $C_{11}H_{14}N_2O$: 190.11, found 191.15 $[M+H]^+$.

Example 191: (S)-1-(4-((5-(2-(2-aminopyridin-3-yl)-6-(pyridin-4-yl)-3H-imidazo[4,5-b]pyridin-3-yl)-2,3-dihydro-1H-inden-1-yl)amino)piperidin-1-yl) prop-2-en-1-one Example 191

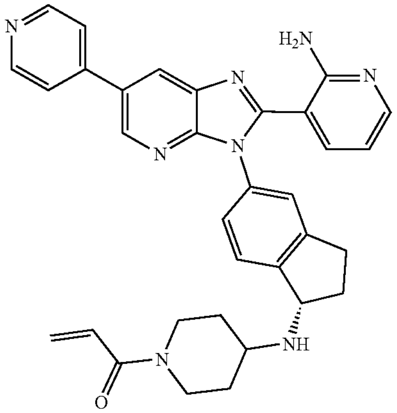

Example 191 was prepared in a manner analogous to Example 190 using pyridin-4-ylboronic acid in place of pyridin-3-ylboronic acid. MS (ESI) calcd. for $C_{33}H_{32}N_8O$: 556.27 m/z, found: 557.20[M+H]$^+$. $^1$H NMR (400 MHz, DMSO-$d_6$) δ 8.80-8.75 (m, 1H), 8.72-8.65 (m, 3H), 8.06-8.00 (m, 1H), 7.94-7.79 (m, 3H), 7.54-7.43 (m, 1H), 7.37-7.27 (m, 2H), 7.03-6.95 (s, 2H), 6.91-6.80 (m, 1H), 6.49-6.41 (m, 1H), 6.16-6.07 (m, 1H), 5.73-5.66 (m, 1H), 5.10-4.70 (m, 1H) 4.47-4.42 (m, 1H), 4.16-4.11 (m, 1H), 3.21-3.10 (m, 3H), 3.01-2.85 (m, 1H), 2.80-2.75 (m, 1H), 2.38-1.90 (m, 3H), 1.55-1.51 (m, 3H), 1.29-1.20 (m, 1H).

Example 192: N-{1-[(1*)-5-[2-(2-aminopyridin-3-yl)-5-(pyrazol-1-yl)imidazo[4,5-b]pyridin-3-yl]-2,3-dihydro-1H-inden-1-yl]piperidin-4-yl}prop-2-enamide and Example 193: N-{1-[(1*)-5-[2-(2-aminopyridin-3-yl)-5-(pyrazol-1-yl)imidazo[4,5-b]pyridin-3-yl]-2,3-dihydro-1H-inden-1-yl]piperidin-4-yl}prop-2-enamide Example 192

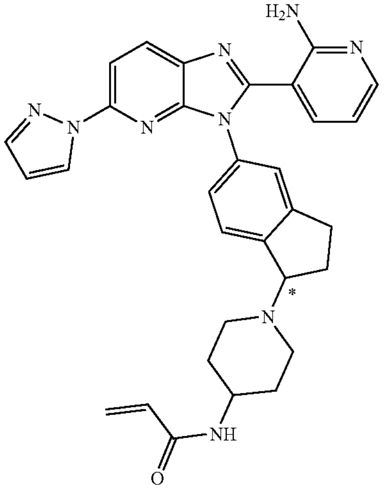

-continued

Example 193

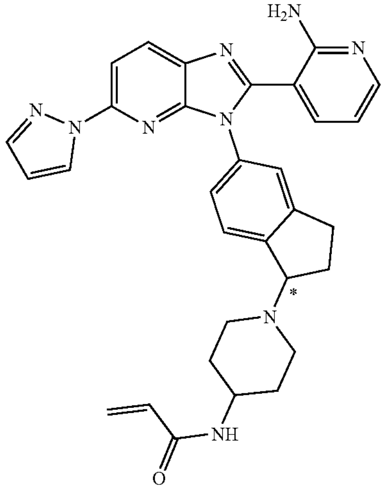

Synthetic Route:

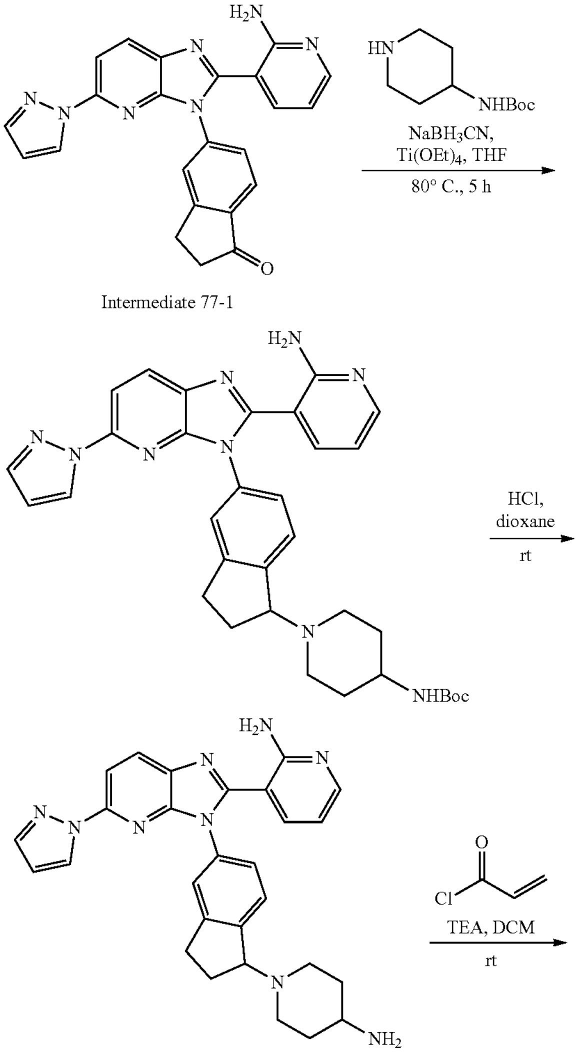

-continued

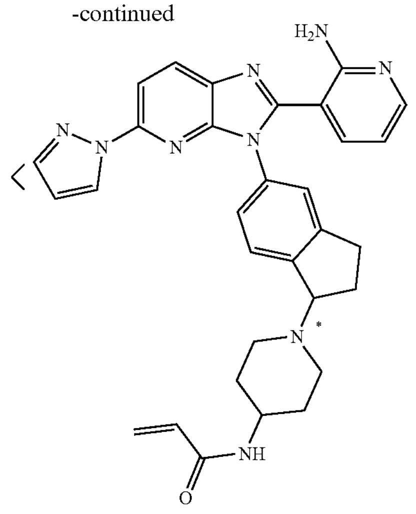

Example 192

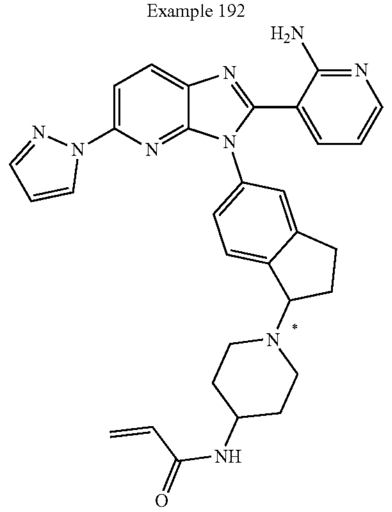

Example 193

Step 1: Synthesis of tert-butyl N-(1-{5-[2-(2-amino-pyridin-3-yl)-5-(pyrazol-1-yl)imidazo[4,5-b]pyridin-3-yl]-2,3-dihydro-1H-inden-1-yl}piperidin-4-yl) carbamate To a solution of 5-[2-(2-aminopyridin-3-yl)-5-(pyrazol-1-yl)imidazo[4,5-b]pyridin-3-yl]-2,3-dihydroinden-1-one (Intermediate 77-1) (500 mg, 1.227 mmol, 1 equiv) in THE (15 mL) were added tert-butyl N-(piperidin-4-yl)carbamate (369 mg, 1.841 mmol, 1.5 equiv) and $Ti(OEt)_4$ (559.9 mg, 2.454 mmol, 2 equiv). The resulting mixture was stirred for 4 h at 80° C. A solution of $NaBH_3CN$ (308.5 mg, 4.908 mmol, 4 equiv) was added and the reaction mixture was stirred at 80° C. for another 1 hour. The resulting mixture was purified by reverse-phase flash chromatography on C18 silica gel using a gradient of acetonitrile in water (+0.05% ammonium bicarbonate) to afford tert-butyl N-(1-{5-[2-(2-aminopyridin-3-yl)-5-(pyrazol-1-yl)imidazo[4,5-b]pyridin-3-yl]-2,3-dihydro-1H-inden-1-yl}piperidin-4-yl)carbamate (200 mg, 27%) as a black solid. MS (ESI) calcd. for $C_{33}H_{37}N_9O_2$: 591.30 m/z, found: 592.20 $[M+H]^+$.

Step 2: Synthesis of 3-{3-[1-(4-aminopiperidin-1-yl)-2,3-dihydro-1H-inden-5-yl]-5-(pyrazol-1-yl)imidazo[4,5-b]pyridin-2-yl}pyridin-2-amine To a solution of tert-butyl N-(1-{5-[2-(2-aminopyridin-3-yl)-5-(pyrazol-1-yl)imidazo[4,5-b]pyridin-3-yl]-2,3-dihydro-1H-inden-1-yl}piperidin-4-yl)carbamate (200 mg, 0.338 mmol, 1 equiv) in DCM (10 mL) was added HCl in 1,4-dioxane (10 mL). The resulting mixture was maintained under nitrogen and stirred for 1 h at room temperature. The resulting mixture was concentrated under reduced pressure to afford 3-{3-[1-(4-aminopiperidin-1-yl)-2,3-dihydro-1H-inden-5-yl]-5-(pyrazol-1-yl)imidazo[4,5-b]pyridin-2-yl}pyridin-2-amine (180 mg, crude quant) as a yellow solid. MS (ESI) calcd. for $C_{28}H_{29}N_9$: 491.25 m/z, found: 492.15 $[M+H]^+$.

Step 3: Synthesis of N-{1-[(1*)-5-[2-(2-aminopyridin-3-yl)-5-(pyrazol-1-yl)imidazo[4,5-b]pyridin-3-yl]-2,3-dihydro-1H-inden-1-yl]piperidin-4-yl}prop-2-enamide (Example 192) and N-{1-[(1*)-5-[2-(2-aminopyridin-3-yl)-5-(pyrazol-1-yl)imidazo[4,5-b] pyridin-3-yl]-2,3-dihydro-1H-inden-1-yl]piperidin-4-yl}prop-2-enamide (Example 193)

To a solution of 3-{3-[1-(4-aminopiperidin-1-yl)-2,3-dihydro-1H-inden-5-yl]-5-(pyrazol-1-yl)imidazo[4,5-b]pyridin-2-yl}pyridin-2-amine (170 mg, 0.346 mmol, 1 equiv) in ACN (5 mL) was added triethylamine (175 mg, 1.730 mmol, 5 equiv) and acryloyl chloride (31.3 mg, 0.346 mmol, 1 equiv) at 0° C. The resulting mixture was stirred for 1 h at room temperature. The mixture was purified directly by Prep-HPLC on a XSelect CSH OBD Column using a gradient of acetonitrile in water (+0.05% TFA). The enantiomers were separated by chiral Prep-HPLC on CHIRAL ART Cellulose-SB column using a mixture of [Hexanes (+0.5% 2M $NH_3$-MeOH)] and isopropanol to afford N-{1-[(1*)-5-[2-(2-aminopyridin-3-yl)-5-(pyrazol-1-yl)imidazo [4,5-b]pyridin-3-yl]-2,3-dihydro-1H-inden-1-yl]piperidin-4-yl}prop-2-enamide (Example 192) (12.2 mg, 6.43%) as a white solid and was the first eluting peak and N-{1-[(1*)-5-[2-(2-aminopyridin-3-yl)-5-(pyrazol-1-yl)imidazo[4,5-b] pyridin-3-yl]-2,3-dihydro-1H-inden-1-yl]piperidin-4-yl}prop-2-enamide (Example 193) (10.4 mg, 5%) as a white solid and was the second eluting peak. * Denotes a stereocenter with undetermined absolute stereocenter of a single enantiomer.

Example 192: MS (ESI) calcd. for $C_{31}H_{31}N_9O$: 545.27 m/z, found: 546.20 $[M+H]^+$. $^1H$ NMR (400 MHz, DMSO-$d_6$) δ (ppm): 8.36-8.37 (m, 2H), 8.00-8.01 (m, 2H), 7.95-7.97 (m, 1H), 7.81 (s, 1H), 7.29-7.39 (m, 3H), 7.15-7.17 (m, 1H), 7.02 (s, 2H), 6.54-6.55 (m, 1H), 6.36-6.38 (m, 1H), 6.21-6.25 (m, 1H), 6.06-6.18 (m, 1H), 5.58-5.59 (m, 1H), 4.39-4.45 (m, 1H), 3.50-3.62 (m, 1H), 2.65-3.09 (m, 3H), 2.26-2.33 (m, 1H), 2.11-2.22 (m, 2H), 1.91-1.96 (m, 2H), 1.50-1.79 (m, 2H), 1.21-1.38 (m, 2H).

Example 193: MS (ESI) calcd. for $C_{31}H_{31}N_9O$: 545.27 m/z, found: 546.20 $[M+H]^+$. $^1H$ NMR (400 MHz, DMSO-$d_6$) δ (ppm): 8.35-8.37 (m, 2H), 8.00-8.07 (m, 2H), 7.95-7.99 (m, 1H), 7.81 (s, 1H), 7.29-7.39 (m, 2H), 7.14-7.16 (m, 1H), 7.09-7.12 (m, 1H), 7.03 (s, 2H), 6.52-6.54 (m, 1H), 6.35-6.38 (m, 1H), 6.19-6.26 (m, 1H), 6.06-6.10 (m, 1H), 5.56-5.59 (m, 1H), 4.44-4.54 (m, 1H), 3.60-3.67 (m, 1H), 2.94-3.03 (m, 2H), 2.86-2.87 (m, 1H), 2.30-2.36 (m, 1H), 2.15-2.19 (m, 2H), 1.76-1.91 (m, 2H), 1.40-1.45 (m, 2H), 1.20-1.23 (m, 2H).

Example 194: 1-(4-{[(1S)-5-[2-(2-aminopyridin-3-yl)-5-[(3R)-3-fluoropyrrolidin-1-yl]imidazo[4,5-b]pyridin-3-yl]-2,3-dihydro-1H-inden-1-yl]amino}piperidin-1-yl)prop-2-en-1-one Example 194

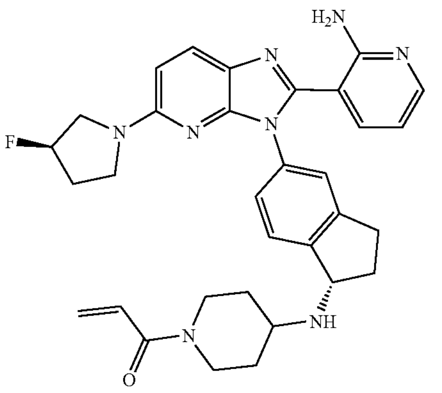

Example 194 was prepared in a manner analogous to Example 86 (via Intermediate 86-2) using (2R)-2-fluoropyrrolidine in place of morpholine and HCl in dioxane instead of TFA in DCM. MS (ESI) calcd. for $C_{32}H_{35}FN_8O$: 566.29 m/z, found: 567.15 $[M+H]^+$. $^1H$ NMR (300 MHz, DMSO-$d_6$) δ 7.98-7.89 (m, 2H), 7.45-7.40 (m, 1H), 7.33-7.11 (m, 2H), 7.08-6.94 (m, 3H), 6.89-6.76 (m, 1H), 6.58-6.50 (m, 1H), 6.36-6.31 (m, 1H), 6.13-6.04 (m, 1H), 5.69-5.63 (m, 1H), 5.53-5.29 (m, 1H), 4.39-4.16 (m, 2H), 4.05-3.91 (m, 1H), 3.77-3.54 (m, 3H), 3.53-3.41 (m, 1H), 3.33-3.11 (m, 1H), 3.00-2.82 (m, 3H), 2.80-2.67 (m, 2H), 2.34-2.14 (m, 2H), 2.14-2.02 (m, 1H), 2.00-1.90 (m, 1H), 1.90-1.70 (m, 2H), 1.34-1.13 (m, 2H).

Example 195: 1-(4-{[(1S)-5-[2-(2-aminopyridin-3-yl)-5-cyclobutylimidazo[4,5-b]pyridin-3-yl]-2,3-dihydro-1H-inden-1-yl]amino}piperidin-1-yl)prop-2-en-1-one Example 195

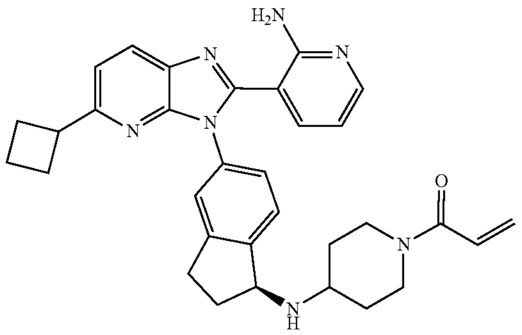

Synthetic Route:

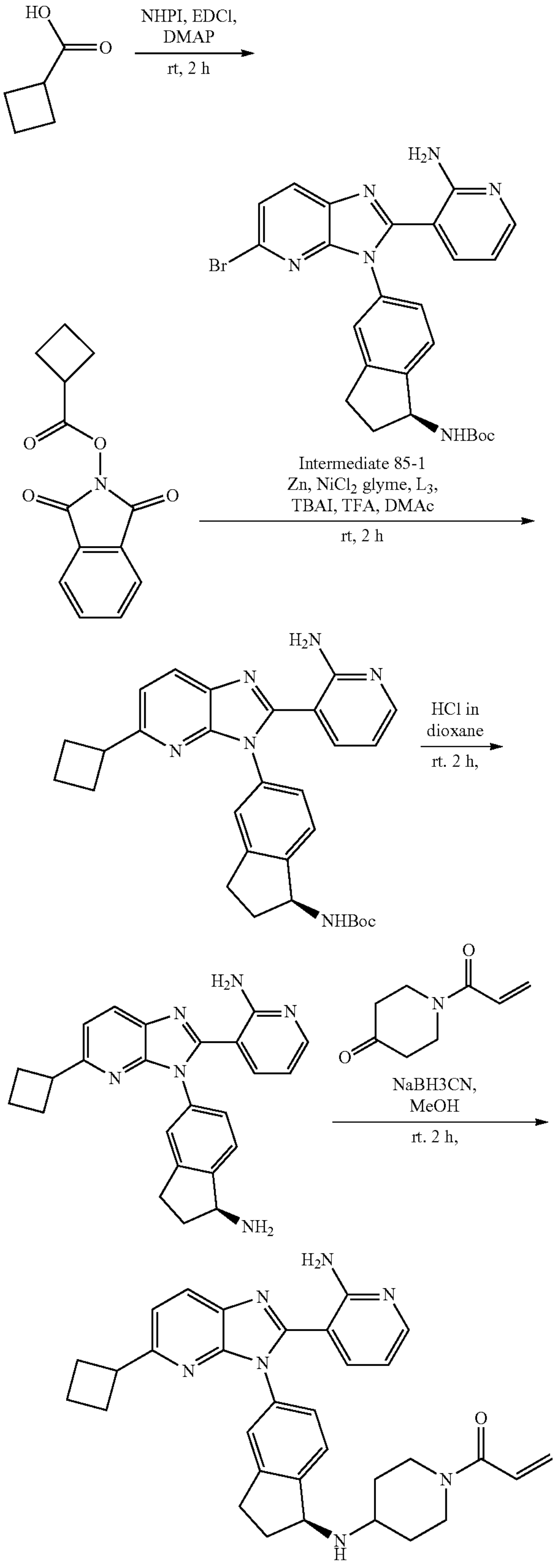

Example 195

-continued

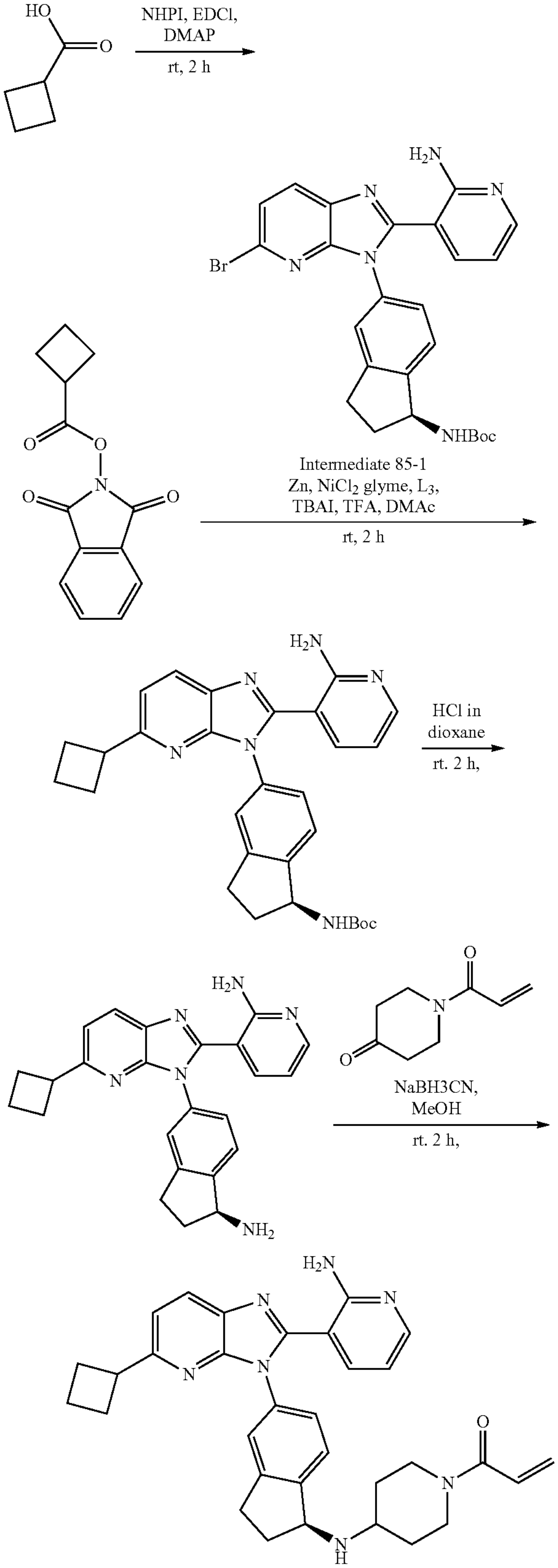

Example 195

Step 1: Synthesis of 1,3-dioxoisoindol-2-yl cyclobutanecarboxylate

To a solution of cyclobutanecarboxylic acid (1 g, 10 mmol, 1 equiv) in DCM (30 mL) was added phthalimide (1.47 g, 9.988 mmol, 1 equiv), EDCI (2.11 g, 11 mmol, 1.1 equiv) and DMAP (0.12 g, 0.999 mmol, 0.1 equiv). After stirring for 2 h at room temperature, the reaction was quenched by the addition of water (20 mL) at 0° C. The resulting mixture was extracted with DCM (30 mL×3). The combined organic layers were washed with water (10 mL×3) and dried over anhydrous $Na_2SO_4$. After filtration, the filtrate was concentrated under reduced pressure. The residue was purified by silica gel column (0-30% ethyl acetate in petroleum ether) giving 1,3-dioxoisoindol-2-yl cyclobutanecarboxylate (2.2 g, 90% yield) as a white solid. $^1H$ NMR (400 MHz, DMSO-$d_6$) δ (ppm): 7.86-7.89 (m, 2H), 7.78-7.81 (m, 2H), 3.49-3.53 (m, 1H), 2.51-2.57 (m, 2H), 2.40-2.49 (m, 2H), 2.04-2.14 (m, 2H).

Step 2: Synthesis of tert-butyl N-[(1S)-5-[2-(2-aminopyridin-3-yl)-5-cyclobutylimidazo[4,5-b]pyridin-3-yl]-2,3-dihydro-1H-inden-1-yl]carbamate To a solution of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 85-1) (1 g, 1.9 mmol, 1 equiv) in DMAc (10 mL) was added 1,3-dioxoisoindol-2-yl cyclobutanecarboxylate (0.52 g, 2.1 mmol, 1.1 equiv), 5-methoxypyridine-2-carboximidamide (0.06 g, 0.384 mmol, 0.2 equiv), Zn (1.25 g, 19.2 mmol, 10 equiv), TBAI (0.71 g, 1.9 mmol, 1 equiv), $NiCl_2$-glyme (0.08 g, 0.38 mmol, 0.2 equiv) and TFA (0.11 g, 0.96 mmol, 0.5 equiv). After stirring for 2 h at room temperature under a nitrogen atmosphere, the resulting mixture was purified by reverse-phase flash chromatography on C18 silica gel using a gradient of acetonitrile in water (+0.05% ammonium bicarbonate) to afford tert-butyl N-[(1S)-5-[2-(2-aminopyridin-3-yl)-5-cyclobutylimidazo[4,5-b]pyridin-3-yl]-2,3-dihydro-1H-inden-1-yl]carbamate (400 mg, 42% yield) as a light yellow solid. MS (ESI) calcd. for $C_{29}H_{32}N_6O_2$, 496.26 m/z, found 497.25 $[M+H]^+$.

Step 3: Synthesis of 3-{3-[(1S)-1-amino-2,3-dihydro-1H-inden-5-yl]-5-cyclobutylimidazo[4,5-b]pyridin-2-yl}pyridin-2-amine To a solution of tert-butyl N-[(1S)-5-[2-(2-aminopyridin-3-yl)-5-cyclobutylimidazo[4,5-b]pyridin-3-yl]-2,3-dihydro-1H-inden-1-yl]carbamate (200 mg, 0.403 mmol, 1 equiv) in dioxane (5 mL) was added HCl (6 mL, 4 M in dioxane). After stirring for 2 h at room temperature under a nitrogen atmosphere, the resulting mixture was purified by reverse-phase flash chromatography on C18 silica gel using a gradient of acetonitrile in water (+0.05% ammonium bicarbonate) to afford 3-{3-[(1S)-1-amino-2,3-dihydro-1H-inden-5-yl]-5-cyclobutylimidazo[4,5-b]pyridin-2-yl}pyridin-2-amine (150 mg, 94% yield) as a light yellow solid. MS (ESI) calcd. for $C_{24}H_{24}N_6$, 396.21 m/z, found 397.25 $[M+H]^+$.

Step 4: Synthesis of 1-(4-{[(1S)-5-[2-(2-aminopyridin-3-yl)-5-cyclobutylimidazo[4,5-b]pyridin-3-yl]-2,3-dihydro-1H-inden-1-yl]amino}piperidin-1-yl)prop-2-en-1-one To a yellow solution of 3-{3-[(1S)-1-amino-2,3-dihydro-1H-inden-5-yl]-5-cyclobutylimidazo[4,5-b]pyridin-2- yl}pyridin-2-amine (150 mg, 0.378 mmol, 1 equiv) in MeOH (3 mL) was added 1-(prop-2-enoyl)piperidin-4-one (86.93 mg, 0.567 mmol, 1.5 equiv) and $NaBH_3CN$ (47.55 mg, 0.756 mmol, 2 equiv) at 0° C. After being stirred overnight at rt, water (4 mL) was added to the solution and the mixture was concentrated directly. The residue was purified Prep-HPLC on a YMC Triart C18 ExRs column using a gradient of acetonitrile in water (+10 mmol/L ammonium bicarbonate) to afford 1-(4-{[(1S)-5-[2-(2-aminopyridin-3-yl)-5-cyclobutylimidazo[4,5-b]pyridin-3-yl]-2,3-dihydro-1H-inden-1-yl]amino}piperidin-1-yl)prop-2-en-1-one (Example 195) (31.0 mg, 15% yield) as a white solid. MS (ESI) calcd. for $C_{32}H_{35}N_7O$, 533.29 m/z, found 534.35 $[M+H]^+$. $^1H$ NMR (400 MHz, DMSO-$d_6$) δ (ppm): 8.03-8.05 (m, 1H), 7.92-7.94 (m, 1H), 7.43-7.45 (m, 1H), 7.27-7.30 (m, 1H), 7.10-7.19 (m, 3H), 6.72-6.78 (m, 1H), 6.37-6.40 (m, 1H), 6.04-6.08 (m, 1H), 5.65-5.69 (m, 1H), 4.26-4.30 (m, 2H), 3.93-4.01 (m, 1H), 3.60-3.65 (m, 1H), 3.05-3.17 (m, 1H), 2.83-2.92 (m, 2H), 2.65-2.69 (m, 2H), 2.32-2.42 (m, 1H), 2.09-2.23 (m, 4H), 1.67-1.99 (m, 5H), 1.05-1.28 (m, 2H).

Example 196: 1-(4-{[(1R)-5-[2-(2-aminopyridin-3-yl)-5-(difluoromethyl)imidazo[4,5-b]pyridin-3-yl]-?3-dihydro-1H-inden-1-yl]amino}piperidin-1-yl)prop-2-en-1-one Example 196

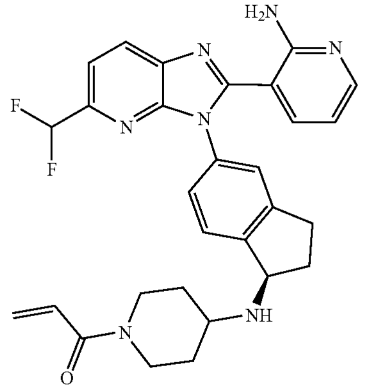

Example 196 was prepared in a manner analogous to Example 195 using Step 1 detailed below instead of Steps 1 and 2. MS (ESI) calcd. for $C_{29}H_{29}F_2N_7O$: 529.24 m/z, found: 530.15 $[M+H]^+$. $^1H$-NMR (400 MHz, DMSO-$d_6$) δ (ppm): 8.35-8.37 (m, 1H), 8.00-8.01 (m, 1H), 7.68-7.70 (m, 1H), 7.46-7.48 (m, 1H), 7.20-7.31 (m, 3H), 6.98-7.11 (m, 1H), 6.78-6.85 (m, 1H), 6.41-6.45 (m, 1H), 6.06-6.11 (m, 1H), 5.66-5.69 (m, 1H), 4.30-4.34 (m, 2H), 3.95-4.23 (m, 1H), 3.10-3.21 (m, 1H), 2.72-2.96 (m, 4H), 2.39-2.52 (m, 1H), 1.73-1.98 (m, 3H), 1.19-1.28 (m, 2H).

Synthetic Route:

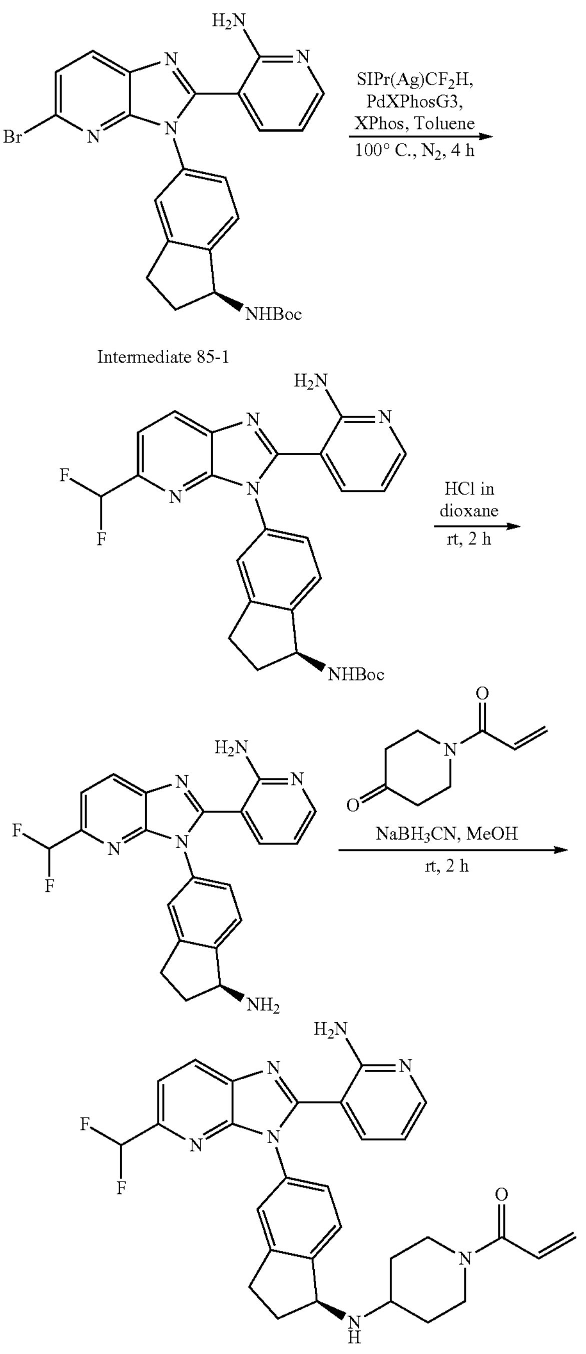

Example 196

Step 1: Synthesis of tert-butyl N-[(1R)-5-[2-(2-aminopyridin-3-yl)-5-(difluoromethyl)imidazo[4,5-b]pyridin-3-yl]-2,3-dihydro-1H-inden-1-yl]carbamate To a solution of tert-butyl N-[(1R)-5-[2-(2-aminopyridin-3-yl)-5-bromoimidazo[4,5-b]pyridin-3-yl]-2,3-dihydro-1H-inden-1-yl]carbamate (Intermediate 85-1) (150 mg, 0.288 mmol, 1 equiv), [1,3-Bis[2,6-bis(i-propyl)phenyl]-2-imidazolidinylidene]difluoromethyl silver(I) (238.0 mg, 0.432 mmol, 1.5 equiv), XPhos Pd G3 (24.35 mg, 0.029 mmol, 0.1 equiv) and XPhos (13.71 mg, 0.029 mmol, 0.1 equiv) in toluene (6 mL) was stirred for 4 h at 100° C. under nitrogen atmosphere in the dark. The resulting mixture was purified by reverse-phase flash chromatography on C18 silica gel using a gradient of acetonitrile in water (+0.05% ammonium bicarbonate) to afford tert-butyl N-[(1R)-5-[2-(2-aminopyridin-3-yl)-5-(difluoromethyl)imidazo[4,5-b]pyridin-3-yl]-2,3-dihydro-1H-inden-1-yl]carbamate (100 mg, 70.58%) as a yellow solid. MS (ESI) calcd. for $C_{26}H_{26}F_2N_6O_2$: 492.21 m/z, found: 493.25[M+H]$^+$.

Steps 2 and 3 were carried out in a manner analogous to Steps 3 and 4 from Example 195.

Example 197: 1-(4-{[(1S)-5-[2-(2-aminopyridin-3-yl)-5-(pyrazol-1-yl)imidazo[4,5-b]pyridin-3-yl]-2,3-dihydro-1H-inden-1-yl]amino}piperidin-1-yl)-2-chloroethanone Example 197

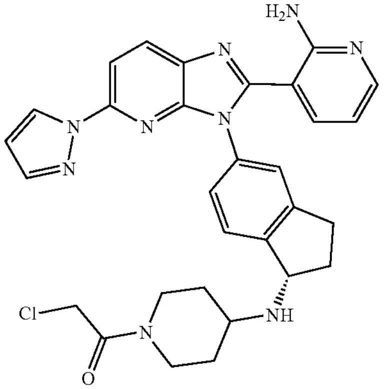

Example 197 was prepared in a manner analogous to Example 34 using chloroacetic acid in place of (2E)-4-(dimethylamino)but-2-enoic acid. MS (ESI) calcd. for $C_{30}H_{30}ClN_9O$, 567.23 m/z, found 568.30 [M+H]$^+$. $^1$H NMR (400 MHz, DMSO-$d_6$) δ(ppm) 8.35-8.33 (m, 2H), 8.29-8.23 (m, 1H), 8.00 (m, 1H), 7.92-7.99 (m, 1H), 7.79 (s, 1H), 7.59-7.61 (m, 1H), 7.40-7.30 (m, 1H), 7.28-7.24 (m, 2H), 6.54 (m, 1H), 6.42-6.46 (m, 1H), 4.66-4.63 (m, 1H), 4.40-4.30 (m, 2H) 3.86 (s, 1H), 3.71 (s, 2H), 3.21-2.81 (m, 3H), 2.77-2.46 (m, 2H), 2.07-1.99 (m, 3H), 1.50-1.36 (m, 2H). (formic acid salt)

Example 198: 1-(4-{[(1S)-5-[2-(2-aminopyridin-3-yl)-5-cyclopropoxyimidazo[4,5-b]pyridin-3-yl]-2,3-dihydro-1H-inden-1-yl]amino}piperidin-1-yl)prop-2-en-1-one Example 198

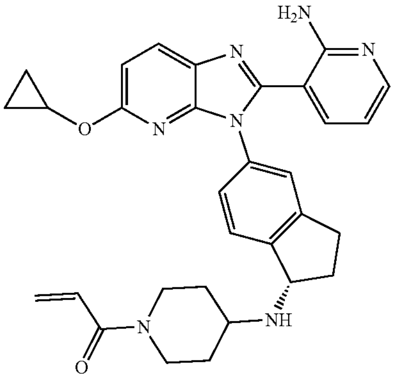

Example 198 was prepared in a manner analogous to Example 13 using Intermediate 198-1 in place of Intermediate 1-1. MS (ESI) calcd. for $C_{31}H_{33}N_7O_2$: 535.27 m/z, found: 536.20 [M+H]$^+$. $^1$H-NMR (400 MHz, DMSO) S (ppm): 8.18-8.25 (m, 1H), 8.00-8.06 (m, 1H), 7.62-7.72 (m, 2H), 7.50-7.55 (m, 1H), 7.30-7.40 (m, 1H), 7.01-7.10 (m, 1H), 6.68-6.90 (m, 2H), 6.10-6.18 (m, 1H), 5.68-5.76 (m, 1H), 4.94-5.02 (m, 1H), 4.45-4.60 (m, 1H), 4.11-4.25 (m, 1H), 4.05-4.10 (m, 1H), 3.49-3.60 (m, 1H), 3.08-3.20 (m, 2H), 2.89-3.00 (m, 1H), 2.64-2.80 (m, 1H), 2.54-2.63 (m, 1H), 2.04-2.27 (m, 3H), 1.40-1.60 (m, 2H), 0.62-0.80 (m, 4H). (TFA salt)

Intermediate 198-1: (S)-3-(3-(1-amino-2,3-dihydro-1H-inden-5-yl)-5-cyclopropoxy-3H-imidazo[4,5-b]pyridin-2-yl)pyridin-2-amine Intermediate 198-1

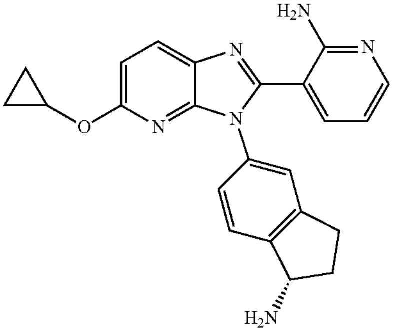

Intermediate 198-1 was prepared in a manner analogous to Intermediate 50-1 using Intermediate 198-2 in place of 6-methyl-3-nitropyridin-2-amine. MS (ESI) calcd. for $C_{23}H_{22}N_6O$: 398.19 m/z, found: 399.25 [M+H]$^+$.

Intermediate 198-2: 6-cyclopropoxy-3-nitropyridin-2-amine

Intermediate 198-2

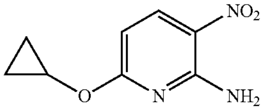

Synthetic Route:

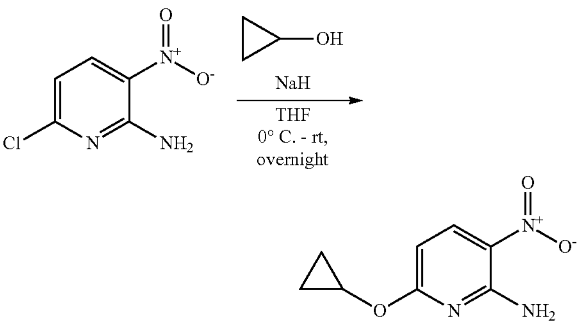

Intermediate 198-2

Step 1: Synthesis of 6-cyclopropoxy-3-nitropyridin-2-amine (Intermediate 198-2

Cyclopropanol (1.34 g, 23 mmol, 2 equiv) was dissolved in tetrahydrofuran (10 mL) and cooled to 0° C. under nitrogen atmosphere. Sodium hydride (60% dispersion in mineral oil) (0.92 g, 23 mmol, 2 equiv) was added and the resulting mixture was stirred at room temperature for 20 minutes. 6-chloro-3-nitropyridin-2-amine (2 g, 11 mmol, 1 equiv) was then added and the resulting mixture was stirred at room temperature overnight. The mixture was concentrated in vacuo and purified by flash column chromatography on silica gel column using a 0-50% gradient of ethyl acetate in petroleum ether to afford 6-cyclopropoxy-3-nitropyridin-2-amine (Intermediate 198-2) (1.5 g, 49%) as a yellow solid. MS (ESI) calculated for $C_8H_9N_3O_3$: 195.06 m/z, found 196.00 $[M+H]^+$. $^1H$ NMR (400 MHz, DMSO-$d_6$) δ 8.23-8.32 (m, 1H), 8.10-8.19 (m, 2H), 6.13-6.22 (m, 1H), 3.90 (s, 1H), 0.69-0.86 (m, 4H).

Example 199: 1-(4-{[(1S)-5-[2-(2-aminopyridin-3-yl)-6-cyclopropylimidazo[4,5-b]pyridin-3-yl]-2,3-dihydro-1H-inden-1-yl]amino}piperidin-1-yl)prop-2-en-1-one Example 199

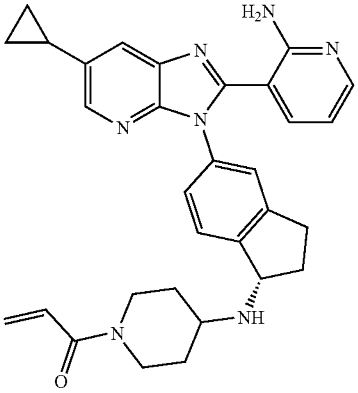

Example 199 was prepared in a manner analogous to Example 190 except that the conditions for Step 1 outlined below were used instead. MS (ESI) calcd. for $C_{31}H_{33}N_7O$: 519.27 m/z, found: 520.25 $[M+H]^+$. 1H NMR (300 MHz, DMSO-d6) δ (ppm): 8.24-8.14 (m, 1H), 8.04-7.92 (m, 1H), 7.85-7.72 (m, 1H), 7.47-7.35 (m, 1H), 7.35-7.24 (m, 1H), 7.24-7.16 (m, 1H), 7.16-7.07 (m, 1H), 7.05 (s, 2H), 6.90-6.70 (m, 1H), 6.45-6.32 (m, 1H), 6.09 (s, 1H), 5.74-5.55 (m, 1H), 4.46-4.11 (m, 2H), 4.10-3.78 (m, 1H), 3.26-3.05 (m, 1H), 3.03-2.84 (m, 3H), 2.84-2.61 (m, 1H), 2.47-2.32 (m, 1H), 2.22-2.01 (m, 2H), 2.01-1.81 (m, 2H), 1.81-1.63 (m, 1H), 1.24 (s, 2H), 1.08-0.91 (m, 2H), 0.91-0.70 (m, 2H).

Synthetic Route:

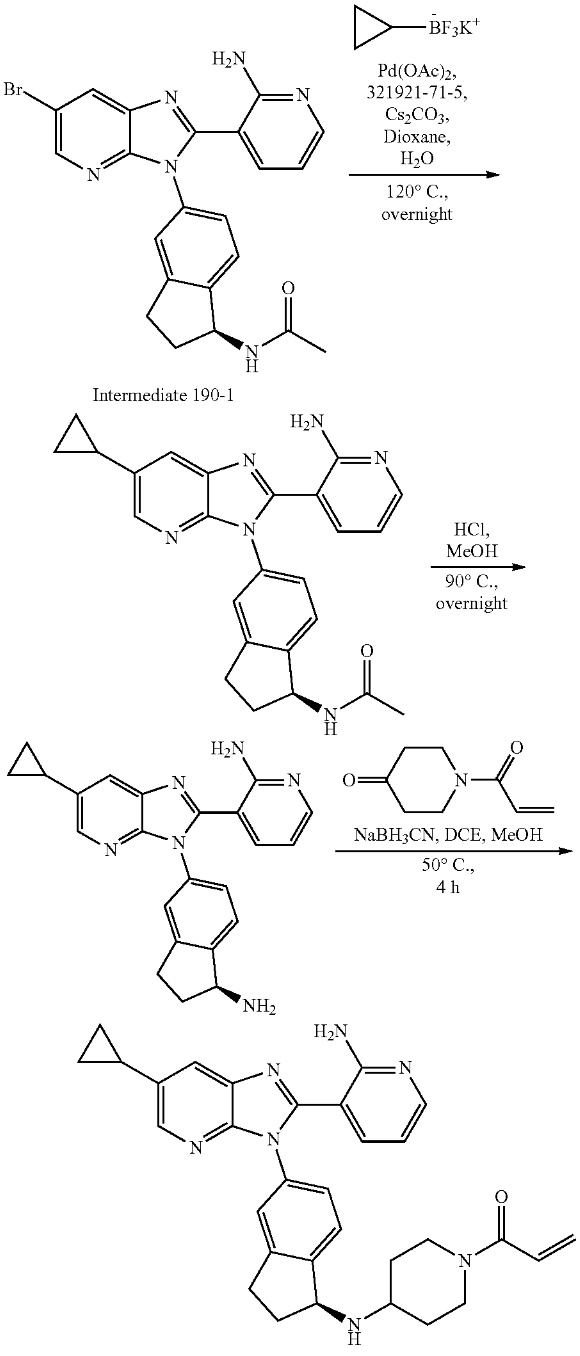

Step 1: Synthesis of N-[(1S)-5-[2-(2-aminopyridin-3-yl)-6-cyclopropylimidazo[4,5-b]pyridin-3-yl]-2,3-dihydro-1H-inden-1-yl]acetamide A mixture of N-[(1S)-5-[2-(2-aminopyridin-3-yl)-6-bromoimidazo[4,5-b]pyridin-3-yl]-2,3-dihydro-1H-inden-1-yl]acetamide (Intermediate 190-1) (500 mg, 1.079 mmol, 1 equiv), potassium cyclopropyltrifluoroborate (192 mg, 1.295 mmol, 1.2 equiv), bis(adamantan-1-yl)(butyl)phosphane (77 mg, 0.216 mmol, 0.2 equiv) and $Pd(OAc)_2$ (49 mg, 0.216 mmol, 0.2 equiv) in 1,4-dioxane/$H_2O$=8 mL: 2 mL was treated with $Cs_2CO_3$ (1.05 g, 3.237 mmol, 3 equiv) at room temperature under nitrogen atmosphere. The resulting mixture was stirred overnight at 120° C. under nitrogen atmosphere. The mixture was allowed to cool to room temperature. The reaction was quenched with water at room temperature. The precipitated solids were collected by filtration and washed with $H_2O$ (3×20 mL). The residue was dissolved in $CH_2Cl_2$ (20 mL). The resulting mixture was filtered, the filter cake was washed with $CH_2Cl_2$ (3×20 mL). The filtrate was concentrated under reduced pressure to afford N-[(1S)-5-[2-(2-aminopyridin-3-yl)-6-cyclopropylimidazo[4,5-b]pyridin-3-yl]-2,3-dihydro-1H-inden-1-yl]acetamide (393 mg, 71.64%) as a brown yellow solid. MS (ESI) calcd. for $C_{25}H_{24}N_6O$: 424.20 m/z, found: 425.20 $[M+H]^+$.

Steps 2 and 3 were carried out in a manner analogous to Example 190.

Example 200: 1-(4-{[(1*)-5-[2-(2-aminopyridin-3-yl)-5-(3-fluoropyrazol-1-yl)imidazo[4,5-b]pyridin-3-yl]-2,3-dihydro-1H-inden-1-yl]amino}piperazin-1-yl)prop-2-en-1-one and Example 201: 1-(4-{[(1*)-5-[2-(2-aminopyridin-3-yl)-5-(3-fluoropyrazol-1-yl)imidazo[4,5-b]pyridin-3-yl]-2,3-dihydro-1H-inden-1-yl]amino}piperazin-1-yl)prop-2-en-1-one Example 200

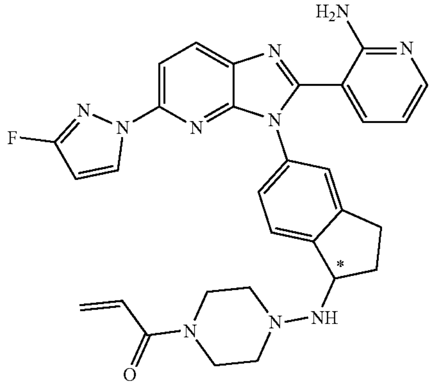

Example 201

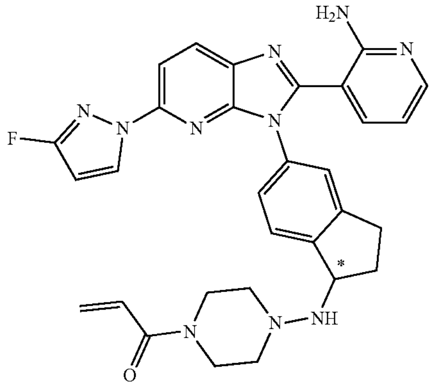

Examples 200 and 201 were prepared in a manner analogous to Example 77 using Intermediate 200-1 in place of Intermediate 77-1. The enantiomers were separated by chiral Prep-HPLC on a CHIRALPAK IA column using a mixture of [MtBE (+0.5% 2M $NH_3$-MeOH)] and [EtOH/DCM (1:1)] with Example 200 eluting first. * Denotes a stereocenter with undetermined absolute stereocenter of a single enantiomer.

Example 200: MS (ESI) calcd. for $C_{30}H_{29}FN_{10}O$: 564.25 m/z, found: 565.15 $[M+H]^+$. $^1H$ NMR (400 MHz, DMSO-$d_6$) δ (ppm): 8.28-8.38 (m, 2H), 8.00-8.03 (m, 1H), 7.73-7.80 (m, 1H), 7.53-7.60 (m, 1H), 7.30-7.34 (m, 1H), 7.19-7.23 (m, 2H), 6.93-6.99 (m, 2H), 6.78-6.86 (m, 1H), 6.34-6.42 (m, 2H), 6.08-6.15 (m, 1H), 5.68-5.73 (m, 1H), 4.93-4.95 (m, 1H), 4.40-4.46 (m, 1H), 3.54-3.62 (m, 4H), 2.93-3.02 (m, 1H), 2.73-2.88 (m, 1H), 2.61-2.72 (m, 4H), 2.22-2.30 (m, 1H), 1.88-1.96 (m, 1H). $^{19}F$-NMR (400 MHz, DMSO-$d_6$) δ (ppm): −127.35.

Example 201: MS (ESI) calcd. for $C_{30}H_{29}FN_{10}O$: 564.25 m/z, found: 565.15 $[M+H]^+$. $^1H$ NMR (400 MHz, DMSO-$d_6$) δ (ppm): 8.28-8.38 (m, 2H), 8.00-8.03 (m, 1H), 7.73-7.80 (m, 1H), 7.53-7.60 (m, 1H), 7.30-7.34 (m, 1H), 7.19-7.23 (m, 2H), 6.93-6.99 (m, 2H), 6.78-6.86 (m, 1H), 6.40-6.43 (m, 1H), 6.34-6.39 (m, 1H), 6.08-6.15 (m, 1H), 5.68-5.73 (m, 1H), 4.93-4.95 (m, 1H), 4.40-4.46 (m, 1H), 3.54-3.65 (m, 4H), 2.93-3.02 (m, 1H), 2.73-2.88 (m, 1H), 2.61-2.72 (m, 4H), 2.22-2.30 (m, 1H), 1.88-1.96 (m, 1H). $^{19}F$-NMR (400 MHz, DMSO-$d_6$) δ (ppm): −127.35.

Intermediate 200-1: 5-(2-(2-aminopyridin-3-yl)-5-(3-fluoro-1H-pyrazol-1-yl)-3H-imidazo[4,5-b]pyridin-3-yl)-2,3-dihydro-1H-inden-1-one Intermediate 200-1

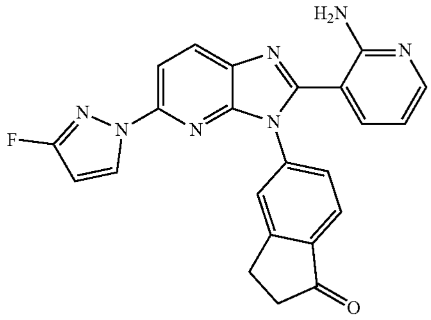

Intermediate 200-1 was prepared in a manner analogous to Intermediate 1-1 using Intermediate 200-2 in place of Intermediate 1-2 and 3-fluoro-1H-pyrazole in place of pyrazole. MS (ESI) calcd. for $C_{23}H_{16}FN_7O$: 425.14 m/z, found: 426.15 $[M+H]^+$.

Intermediate 200-2: N-(3-(5-chloro-3-(2,3-dihydrospiro[indene-1,2'-[1,3]dithiolan]-5-yl)-3H-imidazo[4,5-b]pyridin-2-yl)pyridin-2-yl)pivalamide Intermediate 200-2

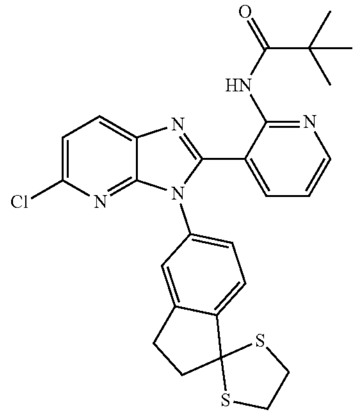

Synthetic Route:

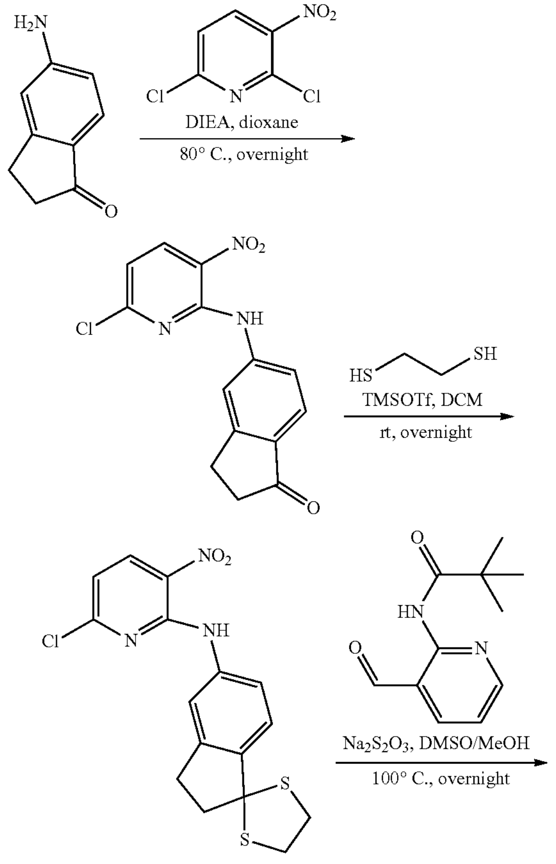

-continued

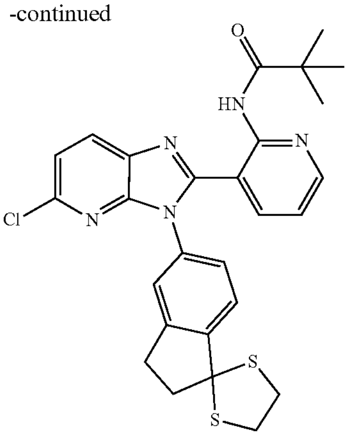

Step 1: Synthesis of 5-[(6-chloro-3-nitropyridin-2-yl)amino]-2,3-dihydroinden-1-one To a solution of 5-amino-2,3-dihydroinden-1-one (50 g, 339.7 mmol, 1 equiv) and DIEA (131.73 g, 1.019 mmol, 3 equiv) in dioxane (1000 mL) was added 2,6-dichloro-3-nitropyridine (98.34 g, 509.590 mmol, 1.5 equiv) and the resulting mixture was stirred at 80° C. overnight. The mixture was allowed to cool to rt. The resulting mixture was filtered and the filter cake was washed with EtOH (3×200 mL). The filtrate was concentrated under reduced pressure. The residue was purified by trituration with petroleum ether/ethyl acetate (10:1) (1000 mL). The residue was purified by trituration with water (1000 mL). The precipitated solids were collected by filtration and washed with water (3×200 mL). The resulting solid was dried under infrared light to afford 5-[(6-chloro-3-nitropyridin-2-yl)amino]-2,3-dihydroinden-1-one (75 g, 48%) as a brown solid. MS (ESI) calcd. for $C_{14}H_{10}ClN_3O_3$, 303.04 m/z, found: 303.95 $[M+H]^+$.

Step 2: Synthesis of 6-chloro-N-{2',3'-dihydrospiro[1,3-dithiolane-2,1'-inden]-5'-yl}-3-nitropyridin-2-amine To a solution of 5-[(6-chloro-3-nitropyridin-2-yl)amino]-2,3-dihydroinden-1-one (68 g, 223.9 mmol, 1 equiv) and 1,2-ethanedithiol (63.27 g, 671.715 mmol, 3 equiv) in DCM (1400 mL) was added TMSOTf (9.95 g, 44.8 mmol, 0.2 equiv) and the resulting mixture was stirred at rt overnight. The reaction was quenched with water at room temperature and the mixture was extracted with $CH_2Cl_2$ (3×800 mL). The combined extracts were concentrated under reduced pressure and the residue was purified by trituration with petroleum ether/ethyl acetate (10:1) (1000 mL). The resulting solid was dried under infrared light to afford 6-chloro-N-{2',3'-dihydrospiro[1,3-dithiolane-2,1'-inden]-5'-yl}-3-nitropyridin-2-amine (66 g, 43%) as a brown solid. MS (ESI) calcd. for $C_{16}H_{14}ClN_3O_2S_2$, 379.02 m/z, found: 379.95 $[M+H]^+$.

Step 3: Synthesis of N-[3-(5-chloro-3-{2',3'-dihydrospiro[1,3-dithiolane-2,1'-inden]-5'-yl}imidazo[4,5-b]pyridin-2-yl)pyridin-2-yl]-2,2-dimethylpropanamide (Intermediate 200-2

To a solution of 6-chloro-N-{2',3'-dihydrospiro[1,3-dithiolane-2,1'-inden]-5'-yl}-3-nitropyridin-2-amine (50 g, 131.621 mmol, 1 equiv) and N-(3-formylpyridin-2-yl)-2,2-dimethylpropanamide (29.86 g, 144.783 mmol, 1.1 equiv) in DMSO (900 mL) and MeOH (150 mL) was added $Na_2S_2O_4$ (50.41 g, 289.6 mmol, 2.2 equiv) and the resulting mixture was stirred at 100° C. overnight. The resulting mixture was filtered and the filter cake was washed with ethyl acetate (3×500 mL). The filtrate was concentrated under reduced pressure. The mixture/residue was brought to pH 10 with saturated $K_2CO_3$ (aq.). The mixture was extracted with ethyl acetate (3×800 mL). The combined organic layers were washed with $H_2O$ (3×200 mL) and dried over anhydrous $Na_2SO_4$. After filtration, the filtrate was concentrated under reduced pressure. The crude product was re-crystallized from petroleum ether/ethyl acetate (5:1) (1000 mL) to afford N-[3-(5-chloro-3-{2',3'-dihydrospiro[1,3-dithiolane-2,1'-inden]-5'-yl}imidazo[4,5-b]pyridin-2-yl)pyridin-2-yl]-2,2-dimethylpropanamide (Intermediate 200-2) (45 g, 45%) as a yellow solid. MS (ESI) calcd. for $C_{27}H_{26}ClN_5OS_2$, 535.13 m/z, found: 536.10 $[M+H]^+$.

Example 202: 1-(4-(((1R,2*)-5-(2-(2-aminopyridin-3-yl)-5-cyclopropyl-3H-imidazo[4,5-b]pyridin-3-yl)-2-fluoro-2,3-dihydro-1H-inden-1-yl)amino)piperidin-1-yl)prop-2-en-1-one and Example 203: 1-(4-(((1R,2*)-5-(2-(2-aminopyridin-3-yl)-5-cyclopropyl-3H-imidazo[4,5-b]pyridin-3-yl)-2-fluoro-2,3-dihydro-1H-inden-1-yl)amino)piperidin-1-yl)prop-2-en-1-one

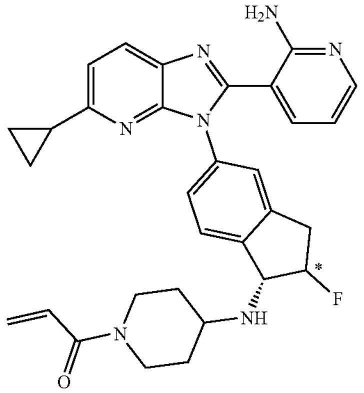

Example 202

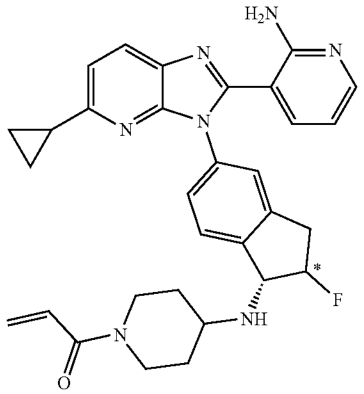

Example 203

Examples 202 and 203 were prepared in a manner analogous to Example 13 using Intermediates 202-1 and 203-1, respectively, in place of Intermediate 1-1. * Denotes a stereocenter with undetermined absolute stereocenter of a single diastereomer.

Example 202: MS (ESI) calcd. for $C_{31}H_{32}FN_7O$: 537.27 m/z, found: 538.15 $[M+H]^+$. $^1H$ NMR (400 MHz, DMSO-$d_6$) δ (ppm): 8.05-8.12 (m, 2H), 7.72-7.76 (m, 2H), 7.51-7.52 (m, 2H), 7.33-7.49 (m, 1H), 7.33-7.35 (m, 1H), 6.75-6.78 (m, 1H), 6.14-6.18 (m, 1H), 5.92-5.93 (m, 1H), 5.74-5.79 (m, 1H), 5.22-5.28 (m, 1H), 4.51-4.62 (m, 1H), 4.15-4.26 (m, 1H), 3.29-3.74 (m, 4H), 2.63-2.82 (m, 1H), 2.33-2.42 (m, 1H), 2.17-2.22 (m, 2H), 1.53-1.64 (m, 2H), 0.97-1.00 (m, 2H), 0.81-0.84 (m, 2H). $^{19}F$ NMR (376 MHz, DMSO-$d_6$) δ −196.72. (TFA salt)

Example 203: MS (ESI) calcd. for $C_{31}H_{32}FN_7O$: 537.27 m/z, found: 538.15 $[M+H]^+$. $^1H$ NMR (400 MHz, DMSO-$d_6$) δ (ppm): 8.06-8.11 (m, 2H), 7.73-7.75 (m, 1H), 7.63-7.66 (m, 1H), 7.43-7.52 (m, 2H), 7.32-7.34 (m, 1H), 6.83-6.85 (m, 1H), 6.71-6.75 (m, 1H), 6.13-6.17 (m, 1H), 5.73-5.76 (m, 2H), 5.25-5.29 (m, 1H), 4.53-4.64 (m, 1H), 4.12-4.27 (m, 1H), 3.60-3.73 (m, 2H), 3.16-3.19 (m, 2H), 2.65-2.83 (m, 1H), 2.17-2.23 (m, 3H), 1.57-1.64 (m, 2H), 0.97-1.00 (m, 2H), 0.83-0.84 (m, 2H). $^{19}F$ NMR (376 MHz, DMSO-$d_6$) 5-177.97. (TFA salt)

Intermediate 202-1: 3-(3-((1R,2*)-1-amino-2-fluoro-2,3-dihydro-1H-inden-5-yl)-5-cyclopropyl-3H-imidazo[4,5-b]pyridin-2-yl)pyridin-2-amine and Intermediate 203-1: 3-(3-((1R,2*)-1-amino-2-fluoro-2,3-dihydro-1H-inden-5-yl)-5-cyclopropyl-3H-imidazo[4,5-b]pyridin-2-yl)pyridin-2-amine

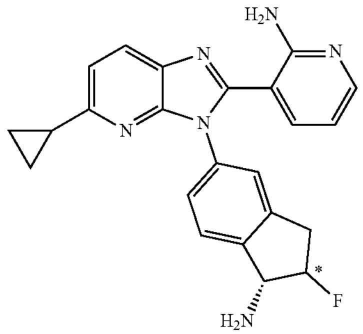

Intermediate 202-1

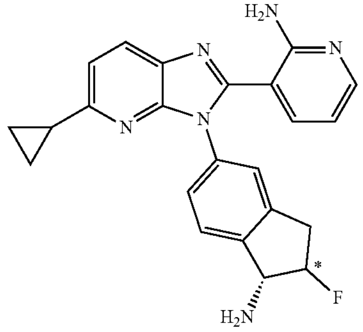

Intermediate 203-1

Intermediates 202-1 and 203-1 were prepared in a manner analogous to Intermediates 75-1 and 76-1 starting from Step 4 using 6-cyclopropyl-3-nitropyridin-2-amine in place of 3-nitro-6-(pyrazol-1-yl)pyridin-2-amine. The diastereomers were separated prior to the final step by chiral Prep-HPLC in a CHIRALPAK IG column using a mixture of [Hex/DCM (3:1) (+0.5% 2M $NH_3$-MeOH)] and ethanol with Intermediate 202-1 eluting first. * Denotes a stereocenter with undetermined absolute stereocenter of a single diastereomer.

Intermediate 202-1: MS (ESI) calcd. for $C_{23}H_{21}FN_6$: 400.18 m/z, found: 401.25 $[M+H]^+$.

Intermediate 203-1: MS (ESI) calcd. for $C_{23}H_{21}FN_6$: 400.18 m/z, found: 401.25 $[M+H]^+$.

Example 204: 1-(4-{5-[2-(2-aminopyridin-3-yl)-5-(pyrazol-1-yl)imidazo[4,5-b]pyridin-3-yl]-2,3-dihydro-1H-inden-1-yl}piperazin-1-yl)prop-2-en-1-one Example 204

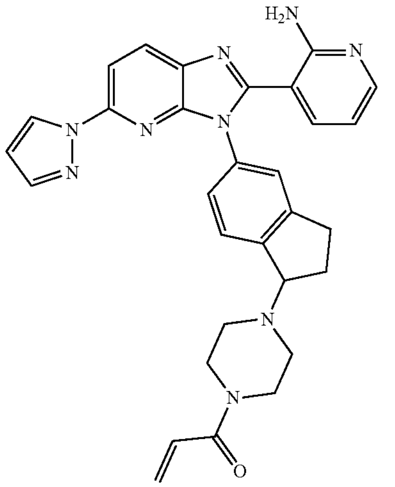

Example 204 was prepared in a manner analogous to Example 77 using tert-butyl piperazine-1-carboxylate in place of tert-butyl 4-aminopiperazine-1-carboxylate, DCE/MeOH instead of MeOH/AcOH and TFA in DCM instead of HCl in dioxane. MS (ESI) calcd. for $C_{30}H_{29}N_9O$, 531.25 m/z, found 532.20 $[M+H]^+$. $^1H$ NMR (400 MHz, DMSO-$d_6$) δ (ppm): 8.40-8.44 (m, 2H), 8.01-8.06 (m, 2H), 7.82-7.83 (m, 1H), 7.75-7.77 (m, 1H), 7.57-7.59 (m, 2H), 7.45-7.47 (m, 1H), 6.75-6.82 (m, 1H), 6.67-6.70 (m, 1H), 6.56-6.57 (m, 1H), 6.15-6.20 (m, 1H), 5.76-5.79 (m, 1H), 5.05-5.07 (m, 1H), 4.14-4.15 (m, 2H), 3.28-3.30 (m, 2H), 3.09-3.16 (m, 3H), 2.94-3.00 (m, 1H), 2.46-2.50 (m, 4H). (TFA salt)

Example 205: 1-(4-{[(1S)-5-[2-(2-aminopyridin-3-yl)-5-(1,4-oxazepan-4-yl)imidazo[4,5-b]pyridin-3-yl]-2,3-dihydro-1H-inden-1-yl]amino}piperidin-1-yl)prop-2-en-1-one Example 205

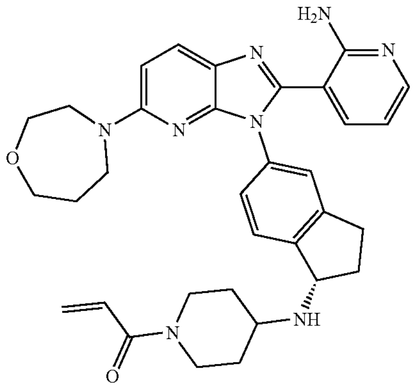

Example 205 was prepared in a manner analogous to Example 170 (via Intermediate 170-1) using 1,4-oxazepane in place of pyrrolidine. MS (ESI) calcd. for $C_{33}H_{38}N_8O_2$: 578.31 m/z, found: 579.40 $[M+H]^+$. $^1H$ NMR (300 MHz, DMSO-d6) δ (ppm): 7.99-7.85 (m, 2H), 7.60 (s, 1H), 7.28 (s, 1H), 7.21-7.13 (m, 1H), 7.11-7.02 (m, 1H), 6.94 (s, 2H), 6.91-6.78 (m, 1H), 6.78-6.72 (m, 1H), 6.41-6.31 (m, 1H), 6.16-6.04 (m, 1H), 5.73-5.62 (m, 1H), 4.57 (s, 1H), 4.36 (s, 1H), 4.07 (s, 1H), 3.80-3.63 (m, 6H), 3.63-3.51 (m, 2H), 3.15 (s, 2H), 2.97 (s, 1H), 2.90-2.69 (m, 2H), 2.46 (s, 1H), 2.15-1.79 (m, 5H), 1.41 (s, 2H), 1.24 (s, 1H).

Example 206: 1-(4-{[(1S)-5-[2-(2-aminopyridin-3-yl)-5-(3-methoxypyrazol-1-yl)imidazo[4,5-b]pyridin-3-yl]-2,3-dihydro-1H-inden-1-yl]amino}piperidin-1-yl)prop-2-en-1-one Example 206

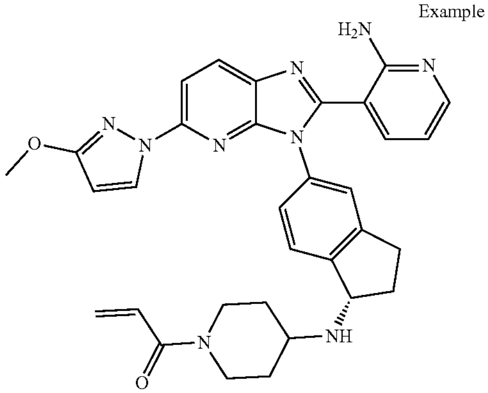

Example 206 was prepared in a manner analogous to Example 13 (via Intermediate 1-1) using Intermediate 85-1 in place of Intermediate 1-2, 3-methoxy-1H-pyrazole in place of pyrazole, EPhos/EPhos Pd G4/cesium carbonate in place of tBuBrettPhos/tBuBrettPhos Pd G3/tribasic potassium phosphate, a reaction time of overnight for step 1, 4N HCl in dioxane at room temperature for 2 h for the deprotection and tetrahydrofuran instead of DCE for the final step. MS (ESI) calcd. For $C_{32}H_{33}N_9O_2$, 575.28 m/z, found 576.40 $[M+H]^+$. $^1H$ NMR (400 MHz, DMSO-$d_6$) δ 8.34-8.27 (m, 1H), 8.22-8.15 (m, 1H), 8.03-7.97 (m, 11H), 7.81-7.74 (m, 11H), 7.54-7.47 (m, 1H), 7.33 (s, 1H), 7.28-7.18 (m, 2H), 6.94 (s, 2H), 6.89-6.78 (m, 1H), 6.46-6.38 (m, 1H), 6.15-5.96 (m, 2H), 5.71-5.63 (m, 1H), 4.47-4.17 (m, 2H), 4.01 (s, 1H), 3.92 (s, 3H), 3.35 (s, 1H), 3.17 (s, 1H), 2.92-2.73 (m, 2H), 2.54-2.48 (m, 2H), 2.45 (s, 1H), 2.10-1.74 (m, 3H), 1.29 (s, 2H).

Example 207: (S)-1-(4-((5-(2-(2-aminopyridin-3-yl)-5-(pyridin-2-yl)-3H-imidazo[4,5-b]pyridin-3-yl)-2,3-dihydro-1H-inden-1-yl)amino)piperidin-1-yl)prop-2-en-1-one Example 207

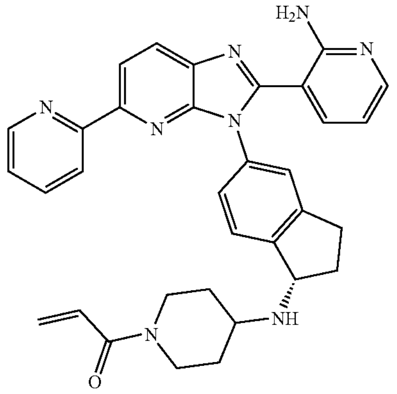

Example 207 was prepared in a manner analogous to Example 159 (via Intermediate 159-1) using 2-(tributylstannyl)pyridine in place of 2-(tributylstannyl)-1,3-thiazole, Intermediate 85-1 in place of Intermediate 1-2 and 4N HCl in dioxane at room temperature for 2 h for the deprotection. MS (ESI) mass calcd. for $C_{33}H_{32}N_8O$, 556.27 m/z, found 557.35 $[M+H]^+$. $^1H$ NMR (400 MHz, DMSO-$d_6$) δ 9.20-8.94 (m, 2H), 8.71 (dd, J=4.8, 1.7 Hz, 1H), 8.53 (d, J=8.4 Hz, 1H), 8.40 (d, J=8.4 Hz, 1H), 8.20 (d, J=7.9 Hz, 1H), 8.12 (dd, J=5.8, 1.7 Hz, 1H), 7.93 (td, J=7.7, 1.8 Hz, 1H), 7.79 (d, J=8.2 Hz, 1H), 7.73 (dd, J=7.6, 1.7 Hz, 1H), 7.62 (d, J=1.9 Hz, 1H), 7.52 (dd, J=8.1, 2.0 Hz, 1H), 7.49-7.42 (m, 1H), 6.95-6.82 (m, 1H), 6.79-6.71 (m, 1H), 6.15 (dd, J=16.7, 2.4 Hz, 1H), 5.73 (dd, J=10.4, 2.4 Hz, 1H), 5.07-5.03 (m, 1H), 4.57-4.53 (m, 1H), 4.24-4.20 (m, 1H), 3.69-3.52 (m, 1H), 3.26-3.11 (m, 2H), 3.04-2.92 (m, 1H), 2.79-2.68 (m, 1H), 2.66-2.55 (m, 2H), 2.31-2.18 (m, 2H), 2.17-2.09 (m, 1H), 1.66-1.40 (m, 2H). (TFA salt)

Example 208: (S)-1-(4-((5-(2-(2-aminopyridin-3-yl)-5-(3-cyclopropyl-1H-pyrazol-1-yl)-3H-imidazo[4,5-b]pyridin-3-yl)-2,3-dihydro-1H-inden-1-yl)amino)piperidin-1-yl)prop-2-en-1-one Example 208

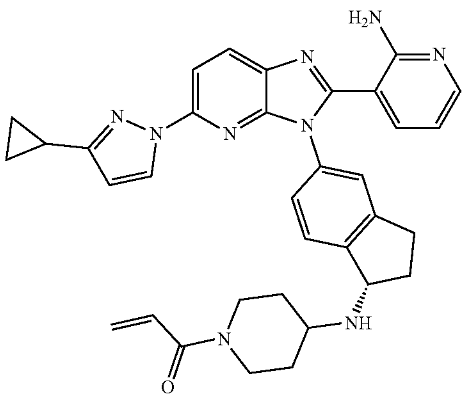

Example 208 was prepared in a manner analogous to Example 13 (via Intermediate 1-1) using Intermediate 85-1 in place of Intermediate 1-2, 3-cyclopropyl-1H-pyrazole in place of pyrazole, EPhos/EPhos Pd G4/cesium carbonate in place of tBuBrettPhos/tBuBrettPhos Pd G3/tribasic potassium phosphate, a reaction time of overnight for step 1, 4N HCl in dioxane at room temperature for 2 h for the deprotection and MeOH instead of DCE for the final step. MS (ESI) calcd. For $C_{34}H_{35}N_9O$, 585.30 m/z, found 586.20 $[M+H]^+$. $^1H$ NMR (400 MHz, DMSO-$d_6$) δ (ppm): 8.31 (d, J=8.4 MHz, 1H), 8.18-8.19 (m, 1H), 7.99-8.00 (m, 1H), 7.86 (d, J=8.8 MHz, 1H), 7.46 (d, J=8.0 MHz, 1H), 7.31-7.32 (m, 1H), 7.20-7.25 (m, 2H), 6.94 (s, 2H), 6.79-6.86 (m, 1H), 6.40-6.43 (m, 1H), 6.25-6.26 (m, 1H), 6.06-6.11 (m, 1H), 5.64-5.67 (m, 1H), 4.32-4.33 (m, 1H), 4.22-4.24 (m, 1H), 3.97-4.01 (m, 1H), 3.14-3.17 (m, 1H), 2.88-2.93 (m, 3H), 2.73-2.81 (m, 1H), 2.42-2.46 (m, 1H), 2.08-2.09 (m, 1H), 1.98-2.00 (m, 2H), 1.85-1.86 (m, 1H), 1.74-1.79 (m, 1H), 1.23-1.24 (m, 2H), 0.94-0.96 (m, 2H), 0.75-0.78 (m, 2H).

Example 209: (S)-1-(4-((5-(2-(2-aminopyridin-3-yl)-5-phenyl-3H-imidazo[4,5-b]pyridin-3-yl)-2,3-dihydro-1H-inden-1-yl)amino)piperidin-1-yl)prop-2-en-1-one Example 209

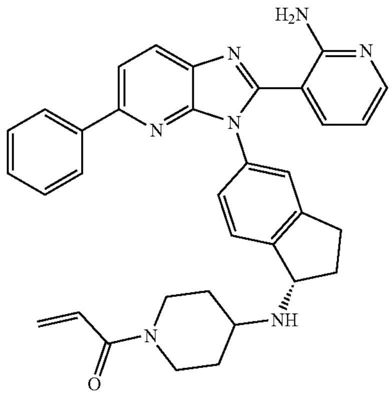

Example 209 was prepared in a manner analogous to Example 107 (via Intermediate 107-1) using phenylboronic acid instead of 1-(difluoromethyl)-3-(4,4,5,5-tetramethyl-1,3,2-dioxaborolan-2-yl)pyrazole and Intermediate 85-1 in place of Intermediate 86-1. MS (ESI) calcd. For $C_{34}H_{33}N_7O$, 555.27 m/z, found 556.35 $[M+H]^+$. $^1H$ NMR (400 MHz, DMSO-$d_6$) δ (ppm): 8.26 (d, J=8.4 Hz, 1H), 7.96-8.03 (m, 4H), 7.45-7.5 (m, 3H), 7.39-7.41 (m, 1H), 7.31-7.34 (m, 1H), 7.28-7.30 (m, 1H), 7.21-7.24 (m, 1H), 6.94 (s, 2H), 6.80-6.86 (m, 1H), 6.40-6.43 (m, 1H), 6.06-6.11 (m, 1H), 5.64-5.67 (m, 1H), 4.33-4.35 (m, 1H), 4.25-4.28 (m, 1H), 3.99-4.03 (m, 1H), 3.14-3.20 (m, 1H), 2.88-2.94 (m, 3H), 2.77-2.79 (m, 1H), 2.44-2.46 (m, 1H), 2.18-2.22 (m, 1H), 1.73-1.97 (m, 3H), 1.23-1.25 (m, 2H).

Example 210: 1-((2R,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-2-methylpiperidin-1-yl)prop-2-en-1-one and Example 211: 1-((2R,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-2-methylpiperidin-1-yl)prop-2-en-1-one Example 210

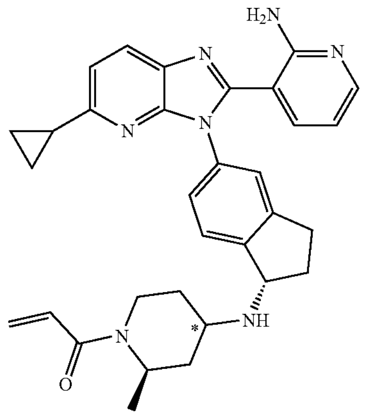

Example 211

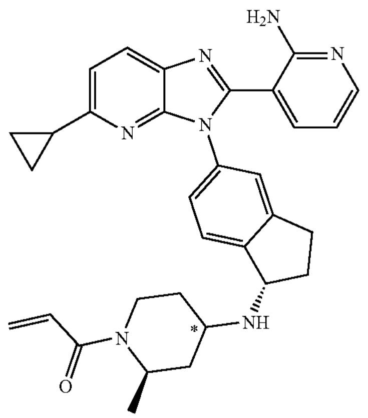

Examples 210 and 211 were prepared in a manner analogous to Example 14 (via Intermediate 14-1) using tert-butyl (R)-2-methyl-4-oxopiperidine-1-carboxylate in place of tert-butyl 8-oxo-3-azabicyclo[3.2.1]octane-3-carboxylate and Intermediate 85-2 in place of Intermediate 1-1. The diastereomers separated during purification by reverse-phase flash chromatography on C18 silica gel using a gradient of acetonitrile in water (+0.05% ammonium bicarbonate). Each were further purified separately by Prep HPLC on a XBridge Prep RP OBD C18 column using a gradient of acetonitrile in water (+0.05% ammonium bicarbonate). * Denotes a stereocenter with undetermined absolute stereocenter of a single diastereomer.

Example 210: MS (ESI) calcd. for $C_{32}H_{35}N_7O$, 533.29 m/z, found 534.30 $[M+H]^+$. $^1H$ NMR (400 MHz, DMSO-$d_6$) δ (ppm): 8.03 (d, J=8.2 Hz, 1H), 7.95-7.98 (m, 1H), 7.42 (d, J=8.0 Hz, 1H), 7.21-7.24 (m, 2H), 7.13-7.16 (m, 2H), 6.95 (s, 2H), 6.78-6.85 (m, 1H), 6.37-6.40 (m, 1H), 6.05-6.10 (m, 1H), 5.64-5.67 (m, 1H), 4.79-4.92 (m, 1H), 4.31-4.47 (m, 2H), 3.89-4.04 (m, 1H), 2.99-3.10 (m, 1H), 2.89-2.96 (m, 1H), 2.64-2.81 (m, 2H), 2.40-2.47 (m, 1H), 2.14-2.20 (m, 1H), 2.03-2.10 (m, 1H), 1.94-2.01 (m, 1H), 1.73-1.87 (m, 2H), 1.03-1.24 (m, 4H), 0.92-0.96 (m, 2H), 0.80-0.90 (m, 2H).

Example 211: MS (ESI) calcd. for $C_{32}H_{35}N_7O$, 533.29 m/z, found 534.30 $[M+H]^+$. $^1H$ NMR (400 MHz, DMSO-$d_6$) δ (ppm): 7.94-8.06 (m, 2H), 7.44 (d, J=7.9 Hz, 1H), 7.21-7.26 (m, 2H), 7.12-7.20 (m, 2H), 6.93 (s, 2H), 6.73-6.84 (m, 1H), 6.35-6.43 (m, 1H), 6.03-6.14 (m, 1H), 5.59-5.69 (m, 1H), 4.30-4.44 (m, 2H), 3.87-4.04 (m, 1H), 3.32-3.33 (m, 1H), 3.07-3.16 (m, 1H), 2.87-2.99 (m, 1H), 2.69-2.82 (m, 1H), 2.39-2.48 (m, 1H), 2.12-2.22 (m, 1H), 1.97-2.06 (m, 1H), 1.60-1.86 (m, 5H), 1.42 (d, J=6.8 Hz, 3H), 0.89-0.98 (m, 2H), 0.78-0.85 (m, 2H).

Example 212: 1-((2R,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-(difluoromethyl)piperidin-1-yl)prop-2-en-1-one Example 213: 1-((2R,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-(difluoromethyl)piperidin-1-yl)prop-2-en-1-one Example 214: 1-((2S,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-(difluoromethyl)piperidin-1-yl)prop-2-en-1-one and Example 215: 1-((2S,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-2-(difluoromethyl)piperidin-1-yl)prop-2-en-1-one Example 212

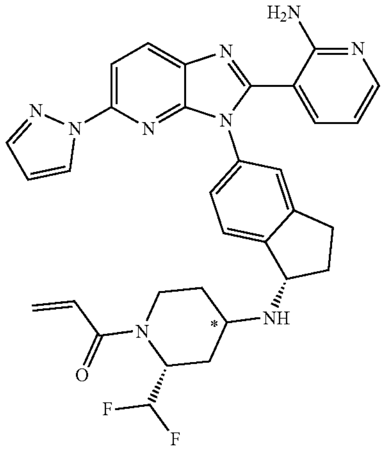

-continued

Example 213

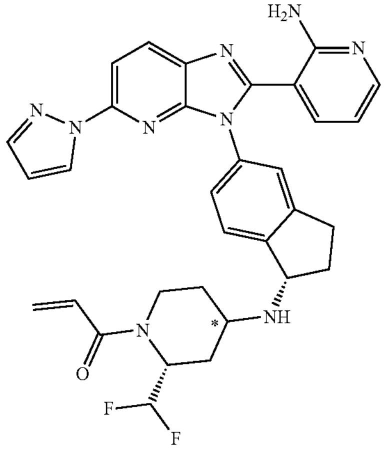

Example 214

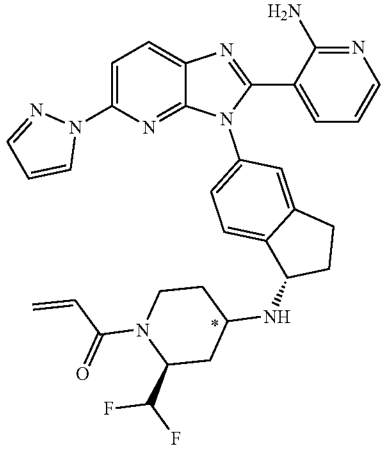

Example 215

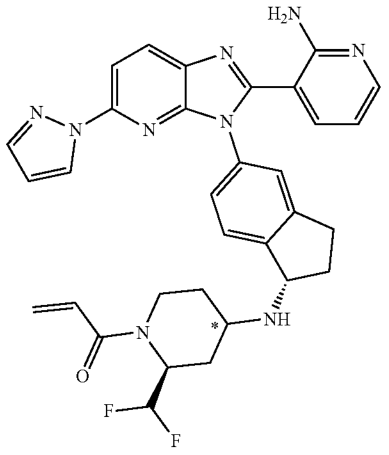

Examples 212, 213, 214 and 215 were prepared in a manner analogous to Example 14 (via Intermediate 14-1) using tert-butyl 2-(difluoromethyl)-4-oxopiperidine-1-carboxylate in place of tert-butyl 8-oxo-3-azabicyclo[3.2.1] octane-3-carboxylate. Examples 212 and 213 were separated from 214 and 215 by reverse-phase flash chromatography on C18 silica gel using a gradient of acetonitrile in water (+0.05% ammonium bicarbonate). Examples 212 and 213 were separated by chiral Prep-HPLC on a CHIRALPAK IE column using a mixture of [MtBE (+0.5% 2M $NH_3$-MeOH)] and [MeOH/DCM (1:1)]. Examples 214 and 215 were separated by chiral Prep-HPLC on a CHIRALPAK IK column using a mixture of [hexanes (+0.5% 2M $NH_3$-MeOH)] and ethanol. * Denotes a stereocenter with undetermined absolute stereocenter of a single diastereomer.

Example 212: MS (ESI) calcd. for $C_{32}H_{31}F_2N_9O$: 595.26 m/z, found: 596.15 $[M+H]^+$. $^1H$ NMR (400 MHz, DMSO-$d_6$) δ (ppm): 8.43-8.45 (m, 1H), 8.36-8.36 (m, 1H), 8.07-8.09 (m, 1H), 8.01-8.03 (m, 1H), 7.79-8.83 (m, 1H), 7.77-7.78 (m, 1H), 7.70-7.71 (m, 1H), 7.60-7.69 (m, 1H), 7.44-7.46 (m, 1H), 6.80-6.85 (m, 2H), 6.57-6.58 (m, 1H), 6.15-6.20 (m, 1H), 5.75-5.81 (m, 1H), 5.01-5.04 (m, 2H), 4.20-4.60 (m, 1H), 2.96-3.27 (m, 3H), 2.57-2.61 (m, 2H), 2.23-2.36 (m, 4H), 1.80-1.95 (m, 1H), 1.51-1.65 (m, 1H). (TFA salt)

Example 213: MS (ESI) calcd. for $C_{32}H_{31}F_2N_9O$: 595.26 m/z, found: 596.30 $[M+H]^+$. $^1H$ NMR (400 MHz, DMSO-$d_6$) δ (ppm): 8.32-8.34 (m, 2H), 7.97-7.99 (m, 1H), 7.92-7.94 (m, 1H), 7.79-7.80 (m, 1H), 7.46-7.48 (m, 1H), 7.29-7.30 (m, 1H), 7.21-7.24 (m, 2H), 6.79-6.83 (m, 1H), 6.52-6.53 (m, 1H), 6.41-6.44 (m, 1H), 6.09-6.14 (m, 1H), 5.70-5.75 (m, 1H), 4.50-5.05 (m, 1H), 4.00-4.50 (m, 2H), 3.22-3.52 (m, 1H), 2.90-3.05 (m, 2H), 2.74-2.80 (m, 2H), 2.37-2.39 (m, 1H), 2.20-2.22 (m, 1H), 1.95-1.98 (m, 1H), 1.75-1.80 (m, 1H), 1.33-1.38 (m, 1H), 1.16-1.20 (m, 1H).

Example 214: MS (ESI) calcd. for $C_{32}H_{31}F_2N_9O$: 595.26 m/z, found: 596.15 $[M+H]^+$. $^1H$ NMR (400 MHz, DMSO-$d_6$) δ (ppm): 8.33-8.34 (m, 2H), 7.98-7.99 (m, 1H), 7.92-7.94 (m, 1H), 7.79-7.80 (m, 1H), 7.46-7.48 (m, 1H), 7.26-7.27 (m, 1H), 7.23-7.25 (m, 2H), 6.81-6.85 (m, 1H), 6.53-6.54 (m, 1H), 6.42-6.45 (m, 1H), 6.09-6.14 (m, 1H), 5.70-5.73 (m, 1H), 4.40-4.80 (m, 1H), 4.26-4.30 (m, 2H), 3.14-3.22 (m, 2H), 2.91-2.97 (m, 1H), 2.75-2.81 (m, 1H), 2.08-2.11 (m, 1H), 1.69-1.76 (m, 5H), 1.28-1.30 (m, 1H). (TFA salt)

Example 215: MS (ESI) calcd. for $C_{32}H_{31}F_2N_9O$: 595.26 m/z, found: 596.20 $[M+H]^+$. $^1H$ NMR (400 MHz, DMSO-$d_6$) δ (ppm): 8.30-8.33 (m, 2H), 7.97-7.98 (m, 1H), 7.96-7.97 (m, 1H), 7.77-7.78 (m, 1H), 7.46-7.48 (m, 1H), 7.28-7.30 (m, 1H), 7.20-7.25 (m, 2H), 6.75-6.81 (m, 1H), 6.52-6.53 (m, 1H), 6.42-6.45 (m, 1H), 6.09-6.13 (m, 1H), 5.70-5.73 (m, 1H), 4.40-4.75 (m, 1H), 4.22-4.26 (m, 2H), 3.45-3.70 (m, 1H), 2.89-3.17 (m, 3H), 2.71-2.76 (m, 1H), 2.39-2.41 (m, 1H), 1.75-1.86 (m, 4H), 1.50-4.65 (m, 1H).

Example 216: 1-(4-{[(1S)-5-[2-(2-aminopyridin-3-yl)-6-(trifluoromethyl) imidazo[4,5-b]pyridin-3-yl]-2,3-dihydro-1H-inden-1-yl]amino}piperidin-1-yl) prop-2-en-1-one Example 216

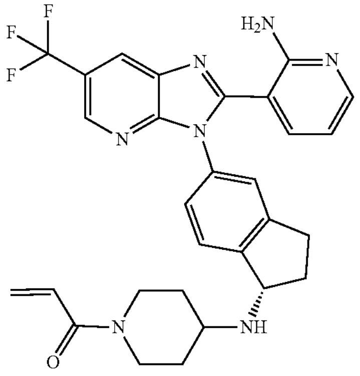

Synthetic Route:

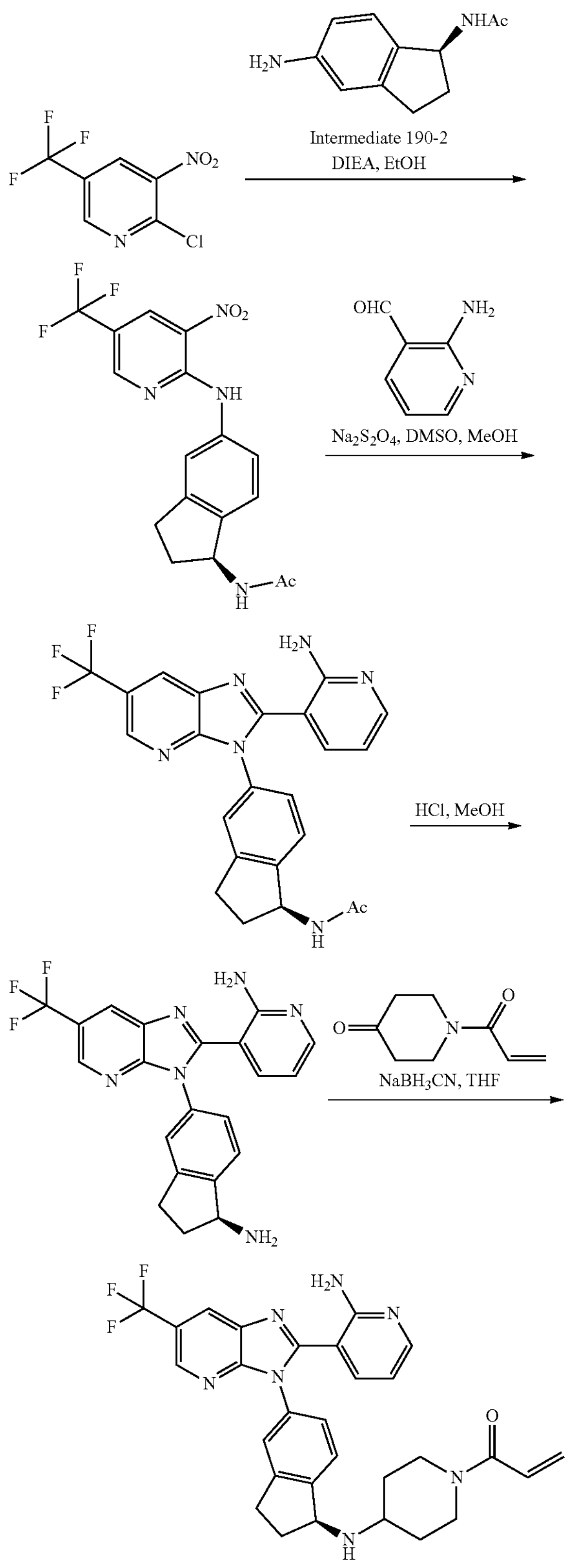

Example 216

Step 1: Synthesis of N-[(1S)-5-{[3-nitro-5-(trifluoromethyl) pyridin-2-yl]amino}-2,3-dihydro-1H-inden-1-yl]acetamide A solution of 2-chloro-3-nitro-5-(trifluoromethyl) pyridine (1 g, 4.4 mmol, 1 equiv) DIEA (1.71 g, 13.2 mmol, 3 equiv) and N-[(1S)-5-amino-2,3-dihydro-1H-inden-1-yl]acetamide (Intermediate 190-2) (0.92 g, 4.8 mmol, 1.1 equiv) in EtOH (20 mL) was stirred overnight at 80° C. The mixture was allowed to cool to room temperature. The reaction was quenched with water. The precipitated solids were collected by filtration and washed with EtOH (20 mL) to afford N-[(1S)-5-{[3-nitro-5-(trifluoromethyl) pyridin-2-yl] amino}-2,3-dihydro-1H-inden-1-yl]acetamide (850 mg, 41%) as an orange solid. The crude product was used in the next step directly without further purification. MS (ESI) calcd. for $C_{17}H_{15}F_3N_4O_3$: 380.11 m/z, found: 381.15 $[M+H]^+$.

Step 2: Synthesis of N-[(1S)-5-[2-(2-aminopyridin-3-yl)-6-(trifluoromethyl) imidazo[4,5-b]pyridin-3-yl]-2,3-dihydro-1H-inden-1-yl]acetamide A solution of N-[(1S)-5-{[3-nitro-5-(trifluoromethyl) pyridin-2-yl]amino}-2,3-dihydro-1H-inden-1-yl]acetamide (850 mg, 2.24 mmol, 1 equiv) 2-aminopyridine-3-carbaldehyde (286 mg, 2.347 mmol, 1.05 equiv) and $Na_2S_2O_4$ (856 mg, 4.917 mmol, 2.2 equiv) in DMSO (24 mL) and MeOH (4 mL, 91.858 mmol) was stirred overnight at 105° C. under air atmosphere. The mixture was allowed to cool to room temperature. The reaction was quenched with water. The precipitated solids were collected by filtration and washed with water to afford N-[(1S)-5-[2-(2-aminopyridin-3-yl)-6-(trifluoromethyl) imidazo[4,5-b]pyridin-3-yl]-2,3-dihydro-1H-inden-1-yl]acetamide (800 mg, 67%) as a brown/yellow solid. The crude product was used in the next step directly without further purification. MS (ESI) calcd. for $C_{23}H_{19}F_3N_6O$: 452.16 m/z, found: 453.20 $[M+H]^+$.

Step 3: Synthesis of 3-{3-[(1S)-1-amino-2,3-dihydro-1H-inden-5-yl]-6-(trifluoromethyl) imidazo[4,5-b]pyridin-2-yl}pyridin-2-amine A solution of N-[(1S)-5-[2-(2-aminopyridin-3-yl)-6-(trifluoromethyl) imidazo[4,5-b]pyridin-3-yl]-2,3-dihydro-1H-inden-1-yl]acetamide (800 mg, 1.768 mmol, 1 equiv) in HCl (10 mL, conc) and MeOH (10 mL) was stirred overnight at 90° C. under air atmosphere. The mixture was allowed to cool to room temperature. The resulting mixture was concentrated under reduced pressure. The mixture was basified to pH 8 with saturated $NaHCO_3$ (aq.). The resulting mixture was extracted with $CH_2Cl_2$ (3×50 mL). The combined organic layers were dried over anhydrous $Na_2SO_4$. After filtration, the filtrate was concentrated under reduced pressure to afford 3-{3-[(1S)-1-amino-2,3-dihydro-1H-inden-5-yl]-6-(trifluoromethyl) imidazo[4,5-b]pyridin-2-yl}pyridin-2-amine (440 mg, 52%) as a brown yellow solid. The crude product was used in the next step directly without further purification. MS (ESI) calcd. for $C_{21}H_{17}F_3N_6$: 410.15 m/z, found: 411.25 $[M+H]^+$.

Step 4: Synthesis of 1-(4-{[(1S)-5-[2-(2-aminopyridin-3-yl)-6-(trifluoromethyl) imidazo[4,5-b]pyridin-3-yl]-2,3-dihydro-1H-inden-1-yl]amino}piperidin-1-yl)prop-2-en-1-one (Example 216)

A solution of 3-{3-[(1S)-1-amino-2,3-dihydro-1H-inden-5-yl]-6-(trifluoromethyl) imidazo[4,5-b]pyridin-2- yl}pyridin-2-amine (440 mg, 1.07 mmol, 1 equiv) and 1-(prop-2-enoyl)piperidin-4-one (657 mg, 4.288 mmol, 4 equiv) in THF (5 mL) was stirred for 30 min at 50° C. under air atmosphere. To the above mixture was added $NaBH_3CN$ (269.49 mg, 4.288 mmol, 4 equiv) in portions at room temperature. The resulting mixture was stirred for 4 h at 50° C. The mixture was allowed to cool to room temperature. The reaction was quenched with water at room temperature. The resulting mixture was extracted with ethyl acetate (3×50 mL). The combined organic layers were dried over anhydrous $Na_2SO_4$. After filtration, the filtrate was concentrated under reduced pressure. The residue was purified by reverse-phase flash chromatography on C18 silica gel using a gradient of acetonitrile in water (+0.05% ammonium bicarbonate) to afford 1-(4-{[(1S)-5-[2-(2-aminopyridin-3-yl)-6-(trifluoromethyl) imidazo[4,5-b]pyridin-3-yl]-2,3-dihydro-1H-inden-1-yl]amino}piperidin-1-yl)prop-2-en-1-one (15.1 mg, 3%) as an off-white solid. MS (ESI) calcd. for $C_{29}H_{28}F_3N_7O$: 547.23 m/z, found: 548.20 $[M+H]^+$. $^1H$ NMR (300 MHz, DMSO-$d_6$) δ 8.73-8.61 (m, 2H), 8.06-7.98 (m, 1H), 7.49-7.40 (m, 1H), 7.39-7.27 (m, 2H), 7.24-7.16 (m, 1H), 6.94 (s, 2H), 6.90-6.75 (m, 1H), 6.49-6.39 (m, 1H), 6.14-6.02 (m, 1H), 5.70-5.60 (m, 1H), 4.35-4.29 (m, 1H), 4.25-4.19 (m, 1H), 4.05-3.91 (m, 1H), 3.20-3.14 (m, 1H), 2.93-2.87 (m, 4H), 2.47-2.36 (m, 1H), 2.11-1.99 (m, 1H), 1.97-1.73 (m, 3H), 1.27-1.21 (m, 2H). $^{19}F$ NMR (282 MHz, DMSO-$d_6$) δ −58.45.

Example 217: 1-(4-{[(1S)-5-[2-(2-aminopyridin-3-yl)-6-(pyrazol-1-yl)imidazo[4,5-b]pyridin-3-yl]-2,3-dihydro-1H-inden-1-yl]amino}piperidin-1-yl)prop-2-en-1-one Example 217

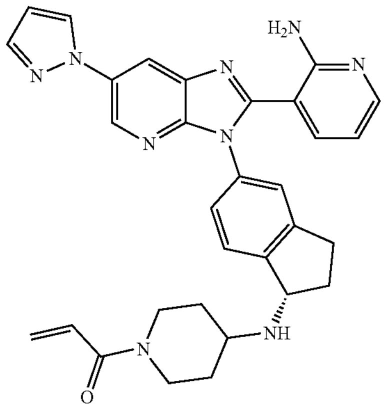

Example 217 was prepared in a manner analogous to Example 13 (via Intermediate 1-1) using Intermediate 190-1 in place of Intermediate 1-2. MS (ESI) calcd. For $C_{31}H_{31}N_9O$, 545.26 m/z, found 546.15 $[M+H]^+$. $^1H$ NMR (400 MHz, DMSO-$d_6$) δ 8.91-8.79 (m, 1H), 8.65-8.55 (m, 2H), 8.06-7.97 (m, 1H), 7.85-7.76 (m, 1H), 7.50-7.43 (m, 1H), 7.36 (s, 1H), 7.34-7.23 (m, 1H), 7.23-7.15 (m, 1H), 7.02 (s, 2H), 6.89-6.74 (m, 1H), 6.67-6.57 (m, 1H), 6.47-6.38 (m, 1H), 6.13-6.00 (m, 1H), 5.70-5.57 (m, 1H), 4.39-4.29 (m, 1H), 4.24 (s, 1H), 3.99 (s, 1H), 3.45-3.36 (m, 1H), 3.16 (s, 1H), 2.47-2.31 (m, 2H), 2.00-1.82 (m, 3H), 1.81-1.69 (m, 2H), 1.24 (s, 3H).

Example 218: 1-(4-(((1S,3*)-5-(2-(2-aminopyridin-3-yl)-5-(1H-pyrazol-1-yl)-3H-imidazo[4,5-b]pyridin-3-yl)-3-hydroxy-2,3-dihydro-1H-inden-1-yl)amino)piperidin-1-yl)prop-2-en-1-one and Example 219: 1-(4-(((1S,3*)-5-(2-(2-aminopyridin-3-yl)-5-(1H-pyrazol-1-yl)-3H-imidazo[4,5-b]pyridin-3-yl)-3-hydroxy-2,3-dihydro-1H-inden-1-yl)amino)piperidin-1-yl)prop-2-en-1-one Example 218

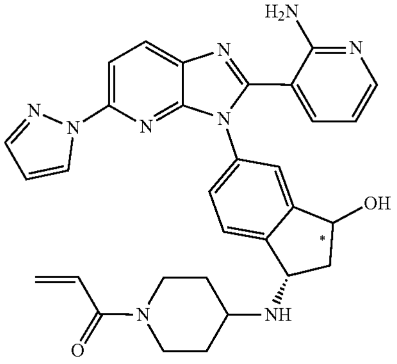

Example 219

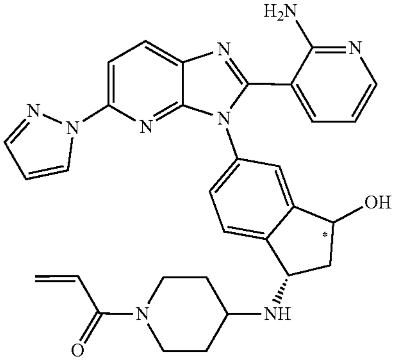

Example 218 and 219 were prepared in a manner analogous to Example 13 using Intermediate 218-1 and 219-1 in place of Intermediate 1-1. * Denotes a stereocenter with undetermined absolute stereocenter of a single diastereomer.

Example 218: MS (ESI) calcd. for $C_{31}H_{31}N_9O_2$, 561.26 m/z, found 562.15 $[M+H]^+$. $^1H$-NMR (400 MHz, DMSO-d6) δ (ppm): 8.28-8.56 (m, 2H), 7.95-8.16 (m, 2H), 7.84-7.95 (m, 1H), 7.71-7.84 (m, 2H), 7.61-7.71 (m, 1H), 7.42-7.61 (m, 1H), 6.71-6.97 (m, 2H), 6.51-6.71 (m, 1H), 6.02-6.29 (m, 1H), 5.65-5.92 (m, 1H), 5.02-5.26 (m, 1H), 4.74-4.98 (m, 1H), 4.39-4.74 (m, 1H), 4.08-4.34 (m, 1H), 3.46-3.77 (m, 1H), 3.11-3.32 (m, 1H), 2.91-3.11 (m, 1H), 2.68-2.91 (m, 1H), 2.21-2.38 (m, 1H), 2.05-2.21 (m, 1H), 1.85-2.05 (m, 1H), 1.36-1.74 (m, 2H).

Example 219: MS (ESI) calcd. for $C_{31}H_{31}N_9O_2$, 561.26 m/z, found 562.20 $[M+H]^+$. $^1H$-NMR (400 MHz, DMSO-d6) δ (ppm): 8.29-8.61 (m, 2H), 7.95-8.21 (m, 2H), 7.84-7.95 (m, 1H), 7.72-7.84 (m, 2H), 7.62-7.72 (m, 1H), 7.42-7.62 (m, 1H), 6.71-6.97 (m, 2H), 6.51-6.71 (m, 1H), 6.02-6.29 (m, 1H), 5.65-5.92 (m, 1H), 5.28-5.53 (m, 1H), 4.96-5.21 (m, 1H), 4.41-4.72 (m, 1H), 4.11-4.41 (m, 1H), 3.46-3.77 (m, 1H), 3.04-3.38 (m, 1H), 2.71-2.86 (m, 1H), 2.58-2.71 (m, 1H), 2.31-2.46 (m, 1H), 2.05-2.31 (m, 2H), 1.41-1.72 (m, 2H).

Intermediate 218-1: (1*,3S)-3-amino-6-(2-(2-aminopyridin-3-yl)-5-(1H-pyrazol-1-yl)-3H-imidazo[4,5-b]pyridin-3-yl)-2,3-dihydro-1H-inden-1-ol and Intermediate 219-1: (1*,3S)-3-amino-6-(2-(2-aminopyridin-3-yl)-5-(1H-pyrazol-1-yl)-3H-imidazo[4,5-b]pyridin-3-yl)-2,3-dihydro-1H-inden-1-ol Exmaple 218-1

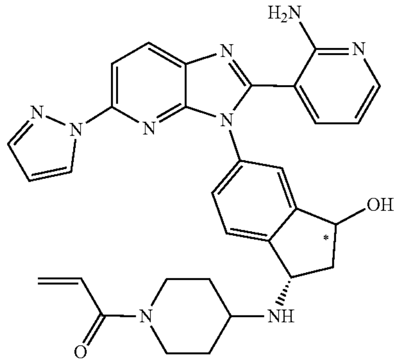

Example 219-1

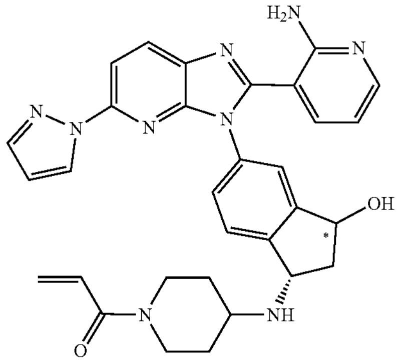

Synthetic Route:

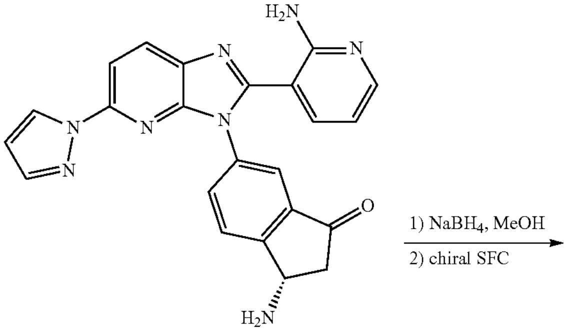

Intermediate 218-2

-continued

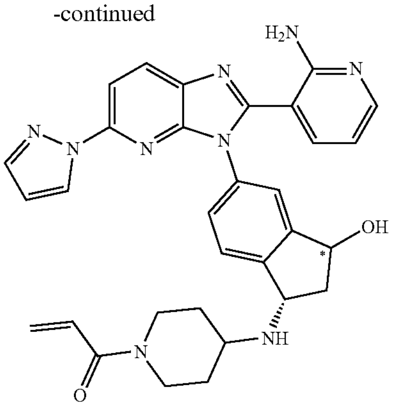

Intermediate 218-1

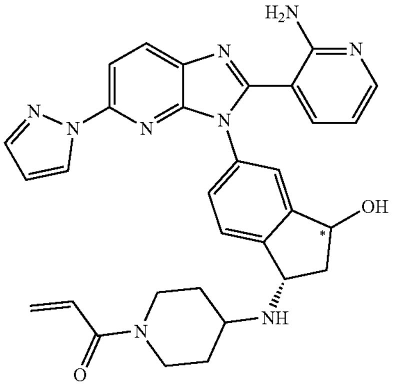

Intermediate 219-1

Step 1: Synthesis of 3-amino-6-[2-(2-aminopyridin-3-yl)-5-(pyrazol-1-yl)imidazo[4,5-b]pyridin-3-yl]-2,3-dihydro-1H-inden-1-ol To a solution of (S)-3-amino-6-(2-(2-aminopyridin-3-yl)-5-(1H-pyrazol-1-yl)-3H-imidazo[4,5-b]pyridin-3-yl)-2,3-dihydro-1H-inden-1-one (Intermediate 218-2) (230 mg, 0.544 mmol, 1 equiv) in methanol (5 mL) was added sodium borohydride (41 mg, 1.1 mmol, 2 equiv). The resulting mixture was stirred at room temperature for 1 h. The reaction mixture was concentrated in vacuo and the residue was purified by reverse-phase flash column chromatography on C18 silica gel using a 0-95% gradient of acetonitrile in water (+0.05% ammonium bicarbonate) with a 10 minute hold at 50% acetonitrile to afford (3S)-3-amino-6-(2-(2-aminopyridin-3-yl)-5-(1H-pyrazol-1-yl)-3H-imidazo[4,5-b]pyridin-3-yl)-2,3-dihydro-1H-inden-1-ol (144 mg, 62%) as a yellow solid. MS (ESI) calculated for $C_{23}H_{20}N_8O$: 424.18 m/z, found 425.55 $[M+H]^+$.

The resulting diastereomeric mixture was separated by chiral SFC on a CHIRALPAK IC-3 column eluting with a 70:30 mix of (hexanes/dichloromethane (3:1)+0.1% N,N-diisopropylethylamine):isopropanol with the first eluting peaked assigned as Intermediate 218-1 and the second eluting peak assigned as Intermediate 219-2. * Denotes a stereocenter with undetermined absolute stereocenter of a single diastereomer.

Intermediate 218-2: (S)-3-amino-6-(2-(2-aminopyridin-3-yl)-5-(1H-pyrazol-1-yl)-3H-imidazo[4,5-b]pyridin-3-yl)-2,3-dihydro-1H-inden-1-one Intermediate 218-2

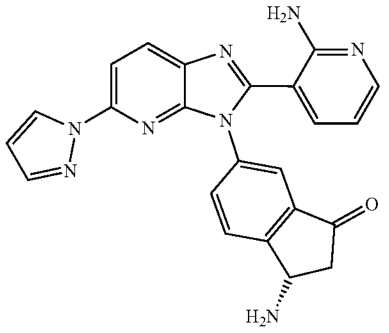

Intermediate 218-2 was prepared in a manner analogous to Intermediate 50-1 using 3-nitro-6-(pyrazol-1-yl)pyridin-2-amine in place of 6-methyl-3-nitropyridin-2-amine and Intermediate 218-3 in place of N-[(1S)-5-bromo-2,3-dihydro-1H-inden-1-yl]acetamide. MS (ESI) calcd. for $C_{23}H_{18}N_8O$, 422.16 m/z, found 423.25 $[M+H]^+$.

Intermediate 218-3: (S)-N-(5-bromo-3-oxo-2,3-dihydro-1H-inden-1-yl)acetamide

Intermediate 218-3

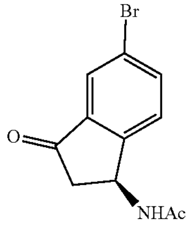

Synthetic Route:

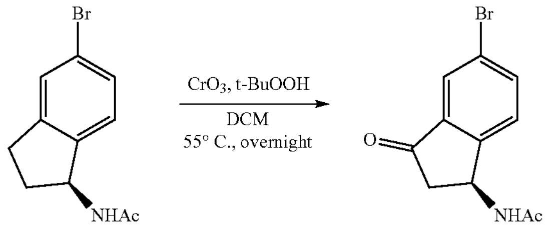

Intermediate 218-4 Intermediate 218-3

Step 1: Synthesis of N-[(1S)-5-bromo-3-oxo-1,2-dihydroinden-1-yl]acetamide (Intermediate 218-3

To a solution of N-[(1S)-5-bromo-2,3-dihydro-1H-inden-1-yl]acetamide (Intermediate 218-4) (1.00 g, 3.94 mmol, 1 equiv) in dichloromethane (20 mL) was added chromium (VI) oxide (0.200 g, 1.97 mmol, 0.5 equiv) followed by tert-butyl hydroperoxide (5.05 g (70% aqueous), 39.4 mmol, 10 equiv). The resulting mixture was stirred at 50° C. overnight then cooled to room temperature and concentrated under reduced pressure. The residue was purified by silica gel column chromatography using a 0-20% gradient of methanol in dichloromethane to afford N-[(1S)-5-bromo-3-oxo-1,2-dihydroinden-1-yl]acetamide (Intermediate 218-3) (250 mg, 23%) as a white solid. MS (ESI) calculated for $C_{11}H_{10}BrNO_2$: 266.99 m/z, found 265.95 $[M-H]^-$.

Intermediate 218-4: (S)-N-(5-bromo-2,3-dihydro-1H-inden-1-yl)acetamide

Intermediate 218-4

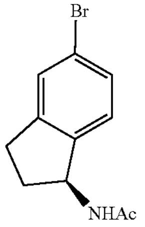

Synthetic Route:

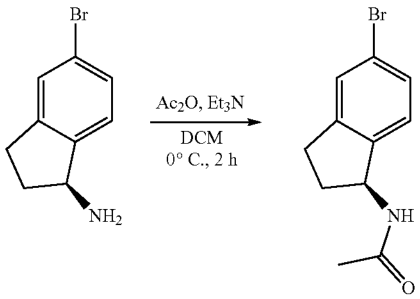

Intermediate 218-4

To a mixture of (S)-5-bromo-2,3-dihydro-1H-inden-1-amine (74 g, 350 mmol, 1 equiv) and triethylamine (106 g, 1.05 mol, 3 equiv) in dichloromethane (1.5 L) was added acetic anhydride (55.2 g, 526 mmol, 1.5 equiv) at 0° C. and the mixture was stirred at 0° C. for 2 h. The reaction mixture was quenched by addition of water (500 mL) and extracted with ethyl acetate (3×500 mL). The combined organic layers were dried over anhydrous sodium sulfate and concentrated under reduced pressure. The crude product was re-crystallized from petroleum ether to afford (S)-N-(5-bromo-2,3-dihydro-1H-inden-1-yl)acetamide (Intermediate 218-4) (90 g, 83% yield) as a white solid. MS (ESI) calculated for $C_{11}H_{12}BrNO$: 253.01, found 254.00 $[M+H]^+$, 256.00 $[M+H+2]^+$.

Example 220: 1-((3*,4*,5*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,5-difluoropiperidin-1-yl)prop-2-en-1-one Example 221: 1-((3*,4*,5*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,5-difluoropiperidin-1-yl)prop-2-en-1-one Example 222: 1-((3*,5*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,5-difluoropiperidin-1-yl)prop-2-en-1-one and Example 223: 1-((3*,5*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3,5-difluoropiperidin-1-yl)prop-2-en-1-one Example 220

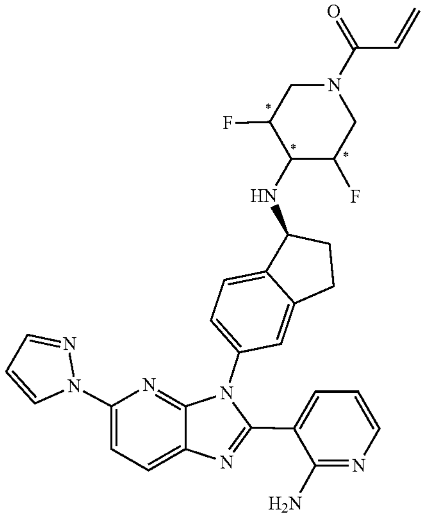

Example 221

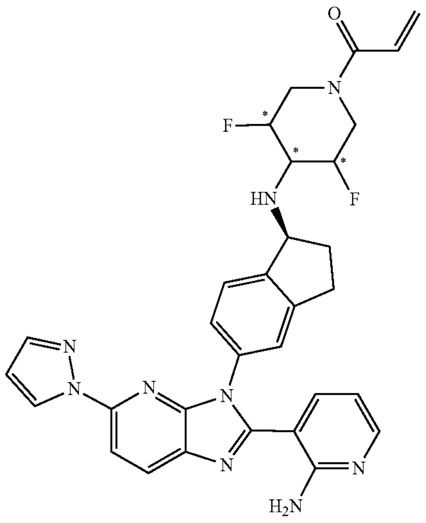

-continued

Example 222

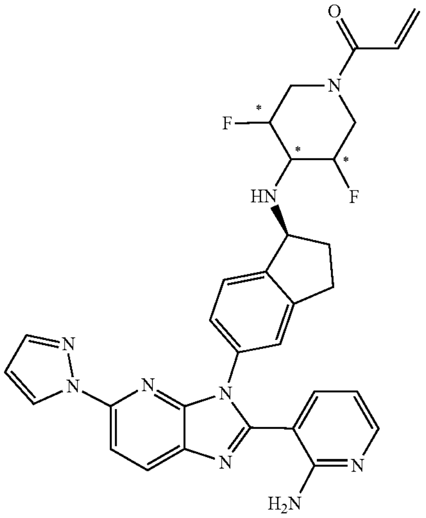

Example 223

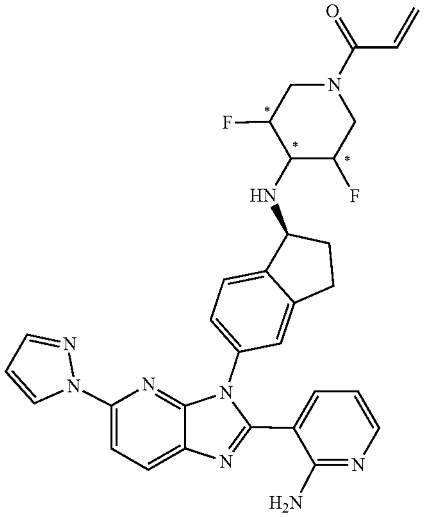

Examples 220, 221, 222 and 223 were prepared in a manner analogous to Example 13 using Intermediate 220-1 in place of the ketone. Examples 220 and 221 separated from Examples 222 and 223 during purification by Prep-HPLC on a XSelect CSH OBD Column using a gradient of acetonitrile in water (+0.05% formic acid). Examples 220 and 221 were separated by chiral Prep-HPLC on a CHIRALPAK-IK column using a mixture of [MtBE (+0.5% 2M $NH_3$-MeOH)] and [MeOH/DCM (1:1)]. Examples 222 and 223 were separated by chiral Prep-HPLC on a CHIRALPAK IE column using a mixture of [MtBE (+0.5% 2M $NH_3$-MeOH)] and MeOH. * Denotes a stereocenter with undetermined absolute stereocenter of a single diastereomer.

Example 220: MS (ESI) calcd. for $C_{31}H_{29}F_2N_9O$: 581.25 m/z, found: 582.40 $[M+H]^+$. $^1H$ NMR (300 MHz, DMSO-$d_6$) δ (ppm): 8.29-8.41 (m, 2H), 7.88-8.05 (m, 2H), 7.75-7.88 (m, 1H), 7.40-7.51 (m, 1H), 7.35 (s, 1H), 7.14-7.31 (m, 2H), 6.96 (s, 2H), 6.48-6.58 (m, 1H), 6.35-6.46 (m, 1H), 5.02-5.15 (m, 1H), 4.43-4.77 (m, 1H), 4.06-4.31 (m, 2H), 3.59-4.05 (m, 2H), 3.04-3.23 (m, 1H), 2.89-3.04 (m, 1H), 2.66-2.89 (m, 3H), 2.52-2.60 (m, 1H), 2.23-2.42 (m, 1H), 1.70-1.91 (m, 1H), 1.37-1.72 (m, 2H). $^{19}F$ NMR (282 MHz, DMSO-$d_6$) δ (ppm): −201.82, −203.52.

Example 221: MS (ESI) calcd. for $C_{31}H_{29}F_2N_9O$: 581.25 m/z, found: 582.40 $[M+H]^+$. $^1H$ NMR (300 MHz, DMSO-$d_6$) δ (ppm): 8.29-8.40 (m, 2H), 7.88-8.05 (m, 2H), 7.75-7.88 (m, 1H), 7.13-7.51 (m, 4H), 6.96 (s, 2H), 6.48-6.57 (m, 1H), 6.33-6.47 (m, 1H), 5.02-5.14 (m, 1H), 4.43-4.47 (m, 1H), 4.05-4.32 (m, 2H), 3.59-4.05 (m, 2H), 3.05-3.24 (m, 1H), 2.89-3.04 (m, 1H), 2.78-2.89 (m, 2H), 2.69-2.78 (m, 1H), 2.58-2.60 (m, 1H), 2.30-2.45 (m, 1H), 1.72-1.90 (m, 1H), 1.45-1.70 (m, 2H). $^{19}F$ NMR (282 MHz, DMSO-$d_6$) δ (ppm): −201.82, −203.52.

Example 222: MS (ESI) calcd. for $C_{31}H_{29}F_2N_9O$: 581.25 m/z, found: 582.10 $[M+H]^+$. $^1H$ NMR (300 MHz, DMSO-$d_6$) δ (ppm): 8.25-8.42 (m, 2H), 7.75-8.06 (m, 3H), 7.12-7.51 (m, 4H), 6.97 (s, 2H), 6.34-6.58 (m, 2H), 5.26-5.40 (m, 1H), 4.07-4.52 (m, 2H), 3.66-3.99 (m, 2H), 3.38-3.65 (m, 2H), 2.67-3.06 (m, 4H), 2.53-2.65 (m, 1H), 2.23-2.45 (m, 1H), 1.67-1.92 (m, 2H), 1.31-1.54 (m, 1H). $^{19}F$ NMR (282 MHz, DMSO-$d_6$) δ (ppm): −188.14, −188.65.

Example 223: MS (ESI) calcd. for $C_{31}H_{29}F_2N_9O$: 581.25 m/z, found: 582.10 $[M+H]^+$. $^1H$ NMR (300 MHz, DMSO-$d_6$) δ (ppm): 8.26-8.42 (m, 2H), 7.87-8.05 (m, 2H), 7.76-7.84 (m, 1H), 7.15-7.50 (m, 4H), 6.97 (s, 2H), 6.35-6.58 (m, 2H), 5.26-5.40 (m, 1H), 4.07-4.50 (m, 2H), 3.65-4.00 (m, 2H), 3.39-3.65 (m, 2H), 2.89-3.04 (m, 1H), 2.67-2.89 (m, 3H), 2.53-2.65 (m, 1H), 2.20-2.45 (m, 1H), 1.64-1.98 (m, 2H), 1.29-1.53 (m, 1H). $^{19}F$ NMR (282 MHz, DMSO-$d_6$) δ (ppm): −188.14, −188.65.

Example 224: 1-(8-{[(1S)-5-[2-(2-aminopyridin-3-yl)-5-(pyrazol-1-yl)imidazo[4,5-b]pyridin-3-yl]-2,3-dihydro-1H-inden-1-yl]amino}-6-oxa-3-azabicyclo[3.2.1]octan-3-yl)prop-2-en-1-one Example 224

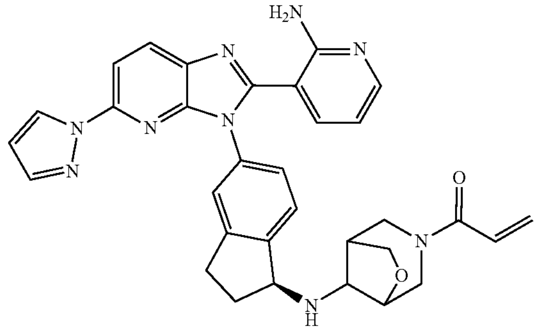

Synthetic Route:

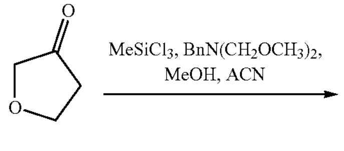

-continued

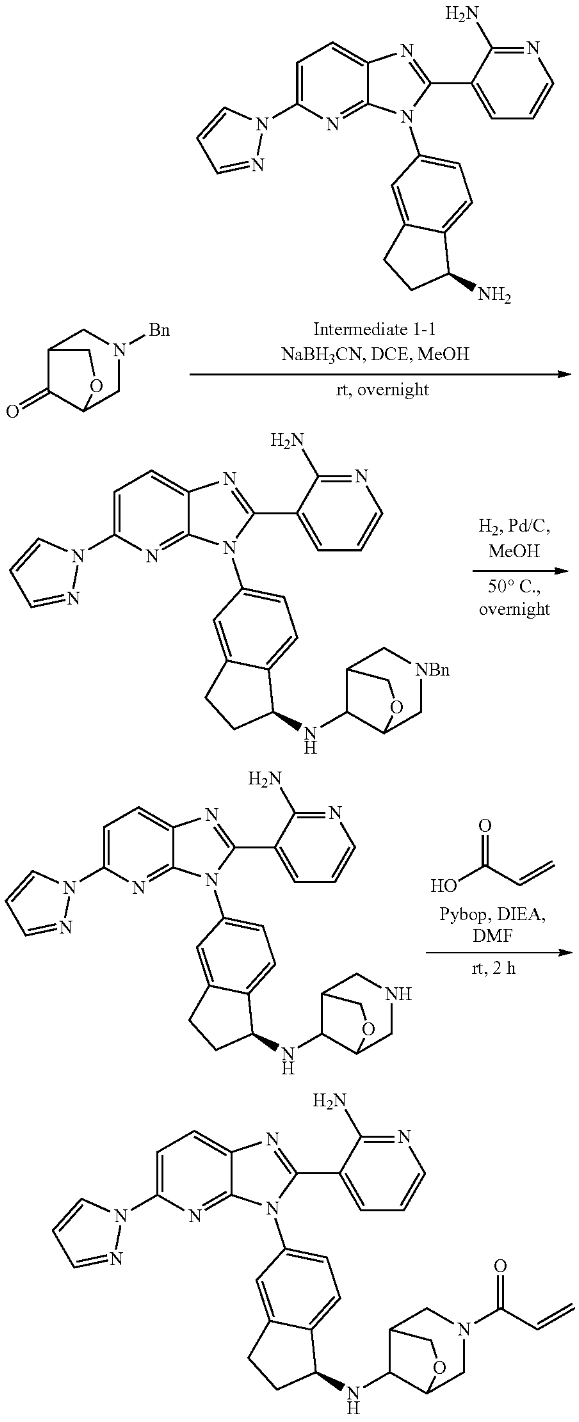

Example 224

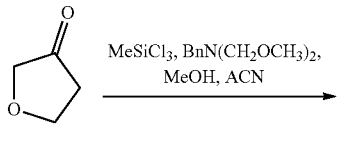

-continued

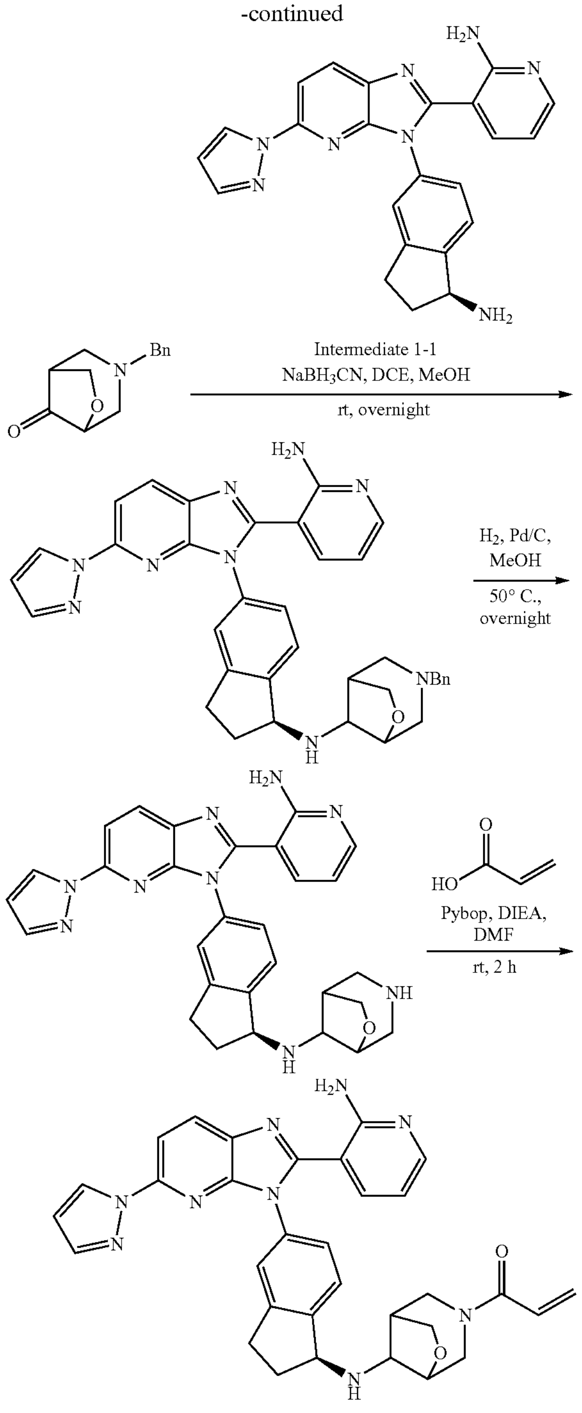

Example 224

Step 1: Synthesis of 3-benzyl-6-oxa-3-azabicyclo [3.2.1]octan-8-one

To a solution of dihydrofuran-3-one (4.4 g, 51.1 mmol, 1 equiv) in ACN (380 mL) was added benzylbis(methoxymethyl)amine (18 g, 92 mmol, 1.8 equiv), methyltrichlorosilane (12.99 g, 86.89 mmol, 1.7 equiv) and MeOH (20 mL). After stirring overnight at rt, the reaction was quenched by the addition of water (200 mL) at 0° C. The mixture was basified to pH=9 with NaOH (1N in water). The resulting mixture was extracted with ethyl acetate (500 mL×3). The combined organic layers were washed with water (500 mL×3) and dried over anhydrous $Na_2SO_4$. After filtration, the filtrate was concentrated under reduced pressure. The residue was purified by silica gel column chromatography (0-80% ethyl acetate in petroleum ether) giving 3-benzyl-6-oxa-3-azabicyclo[3.2.1]octan-8-one (2 g, 18% yield) as a light yellow oil. MS (ESI) calcd. for $C_{13}H_{15}NO_2$, 217.11 m/z, found 217.10.

Step 2: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-3-benzyl-6-oxa-3-azabicyclo[3.2.1]octan-8-amine To a solution of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (300 mg, 0.734 mmol, 1 equiv) in DCE (4 mL) and MeOH (0.4 mL) was added 3-benzyl-6-oxa-3-azabicyclo[3.2.1]octan-8-one (239.36 mg, 1.101 mmol, 1.5 equiv) and $NaBH_3CN$ (138.5 mg, 2.202 mmol, 3 equiv) at 0° C. After being stirred overnight at room temperature, water (4 mL) was added to the solution and the mixture was concentrated directly. The residue was purified by reverse-phase flash chromatography on C18 silica gel using a gradient of acetonitrile in water (+0.05% ammonium bicarbonate) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-3-benzyl-6-oxa-3-azabicyclo[3.2.1]octan-8-amine (300 mg, 67% yield) as a light yellow solid. MS (ESI) calcd. for $C_{36}H_{35}N_9O$, 609.30 m/z, found 610.35 $[M+H]^+$.

Step 3: Synthesis of N-[(1S)-5-[2-(2-aminopyridin-3-yl)-5-(pyrazol-1-yl)imidazo[4,5-b]pyridin-3-yl]-2,3-dihydro-1H-inden-1-yl]-6-oxa-3-azabicyclo[3.2.1]octan-8-amine To a solution of N-[(1S)-5-[2-(2-aminopyridin-3-yl)-5-(pyrazol-1-yl)imidazo[4,5-b]pyridin-3-yl]-2,3-dihydro-1H-inden-1-yl]-3-benzyl-6-oxa-3-azabicyclo[3.2.1]octan-8-amine (300 mg, 0.492 mmol, 1 equiv) in MeOH (30 mL) was added Pd/C (10%, 149.75 mg). The mixture was stirred at room temperature under hydrogen atmosphere for 18 h. The mixture was filtered through a Celite pad and concentrated under reduced pressure giving N-[(1S)-5-[2-(2-aminopyridin-3-yl)-5-(pyrazol-1-yl)imidazo[4,5-b]pyridin-3-yl]-2,3-dihydro-1H-inden-1-yl]-6-oxa-3-azabicyclo[3.2.1]octan-8-amine (140 mg, 55% yield) as a light yellow solid. MS (ESI) calcd. for $C_{29}H_{29}N_9O$, 519.25 m/z, found 520.30 $[M+H]^+$.

Step 4: Synthesis of 1-(8-{[(1S)-5-[2-(2-aminopyridin-3-yl)-5-(pyrazol-1-yl)imidazo[4,5-b]pyridin-3-yl]-2,3-dihydro-1H-inden-1-yl]amino}-6-oxa-3-azabicyclo[3.2.1]octan-3-yl)prop-2-en-1-one To a solution of N-[(1S)-5-[2-(2-aminopyridin-3-yl)-5-(pyrazol-1-yl)imidazo[4,5-b]pyridin-3-yl]-2,3-dihydro-1H-inden-1-yl]-6-oxa-3-azabicyclo[3.2.1]octan-8-amine (50 mg, 0.096 mmol, 1 equiv) in DMF (3 mL) was added DIEA (24.87 mg, 0.192 mmol, 2 equiv) Pybop (50.08 mg, 0.096 mmol, 1 equiv) and acrylic acid (6.93 mg, 0.096 mmol, 1 equiv) The reaction mixture was stirred at room temperature for 2 h. The residue was purified directly by Prep-HPLC on a XSelect CSH F-phenyl OBD Column using a gradient of acetonitrile in water (+0.1% formic acid) to afford 1-(8-{

[(1S)-5-[2-(2-aminopyridin-3-yl)-5-(pyrazol-1-yl)imidazo[4,5-b]pyridin-3-yl]-2,3-dihydro-1H-inden-1-yl]amino}-6-oxa-3-azabicyclo[3.2.1]octan-3-yl)prop-2-en-1-one (Example 224, formic acid salt) (3.5 mg, 6% yield) as a light yellow solid. MS (ESI) calcd. for $C_{32}H_{31}N_9O_2$, 573.26 m/z, found 574.35 $[M+H]^+$. $^1H$ NMR (400 MHz, DMSO-$d_6$) δ (ppm): 8.31-8.33 (m, 2H), 7.91-7.98 (m, 2H), 7.77-7.78 (m, 1H), 7.47-7.51 (m, 1H), 7.30-7.31 (m, 1H), 7.22-7.24 (m, 2H), 6.69-6.76 (m, 1H), 6.50-6.54 (m, 1H), 6.40-6.44 (m, 1H), 6.06-6.10 (m, 1H), 5.65-5.69 (m, 1H), 4.21-4.29 (m, 1H), 3.71-4.15 (m, 4H), 3.54-3.67 (m, 3H), 3.27-3.34 (m, 2H), 2.74-3.12 (m, 2H), 2.31-2.33 (m, 1H), 1.79-1.84 (m, 1H).

Example 225: 1-(4-{[(1S)-5-[2-(2-aminopyridin-3-yl)-5-[1-(trifluoromethyl)pyrazol-4-yl]imidazo[4,5-b]pyridin-3-yl]-2,3-dihydro-1H-inden-1-yl]amino}piperidin-1-yl)prop-2-en-1-one Example 225

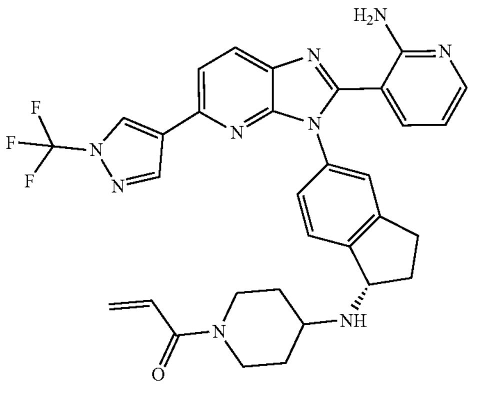

Example 225 was prepared in a manner analogous to Example 190 using Intermediate 85-1 in place of Intermediate 190-1, 4-(4,4,5,5-tetramethyl-1,3,2-dioxaborolan-2-yl)-1-(trifluoromethyl)pyrazole in place of pyridine-3-boronic acid and 4N HCl in dioxane at room temperature for 1 h for the deprotection. MS (ESI) calcd. for $C_{32}H_{30}F_3N_9O$, 613.25 m/z, found 614.15 $[M+H]^+$. $^1H$ NMR (300 MHz, DMSO-$d_6$) δ(ppm) 8.98-8.99 (m, 1H), 8.33-8.34 (m, 1H), 8.31-8.32 (m, 1H), 8.06-8.08 (m, 1H), 7.92-7.94 (m, 1H), 7.70-7.82 (m, 2H), 7.57-7.60 (m, 1H), 7.42-7.44 (m, 1H), 6.74-6.87 (m, 2H), 6.10-6.15 (m, 1H), 5.71-5.72 (m, 1H), 4.99-5.00 (m, 1H), 4.53-4.54 (m, 1H), 4.18-4.20 (m, 1H), 3.12-3.18 (m, 2H), 2.93-3.00 (m, 1H), 2.70-2.76 (m, 1H), 2.55-2.67 (m, 2H), 2.33-2.35 (m, 2H), 2.10-2.13 (m, 1H), 1.51-1.52 (m, 2H). $^{19}F$ NMR (376 MHz, DMSO-$d_6$) δ (ppm): −59.34. (TFA salt)

Example 226: 1-(4-{[(1S)-5-[2-(2-aminopyridin-3-yl)-5-[(3S)-3-fluoropyrrolidin-1-yl]imidazo[4,5-b]pyridin-3-yl]-2,3-dihydro-1H-inden-1-yl]amino}piperidin-1-yl)prop-2-en-1-one Example 226

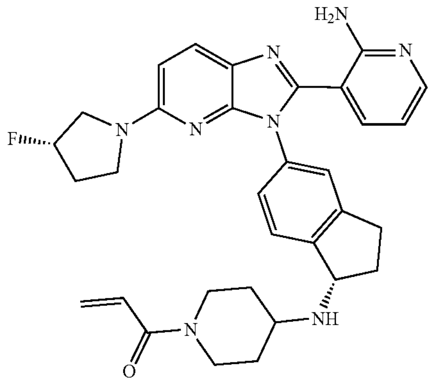

Example 226 was prepared in a manner analogous to Example 86 (via Intermediate 86-2) using (3S)-3-fluoropyrrolidine hydrochloride (+2 eq triethylamine) in place of morpholine, Intermediate 85-1 in place of Intermediate 86-1 and 4N HCl in dioxane in place of TFA in DCM. MS (ESI) calcd. For $C_{32}H_{35}FN_8O$, 566.69 m/z, found 567.15 $[M+H]^+$. $^1HNMR$ (300 MHz, DMSO-$d_6$) δ (ppm): 7.96-7.87 (m, 2H), 7.47-7.38 (m, 1H), 7.22-7.09 (m, 2H), 7.06-6.97 (m, 3H), 6.89-6.74 (m, 1H), 6.58-6.49 (m, 1H), 6.38-6.28 (m, 1H), 6.13-6.01 (m, 1H), 5.70-5.59 (m, 1H), 5.52-5.25 (m, 1H), 4.40-4.15 (m, 2H), 4.08-3.86 (m, 2H), 3.79-3.52 (m, 4H), 3.04-3.26 (m, 1H), 3.00-2.79 (m, 2H), 2.80-2.62 (m, 1H), 2.46-2.35 (m, 1H), 2.31-2.13 (m, 2H), 2.03-1.60 (m, 3H), 1.38-0.99 (m, 3H).

Example 227: 1-(4-{[(1S)-5-[2-(2-aminopyridin-3-yl)-5-(3,3-difluorocyclobutyl)imidazo[4,5-b]pyridin-3-yl]-2,3-dihydro-1H-inden-1-yl]amino}piperidin-1-yl)prop-2-en-1-one Example 227

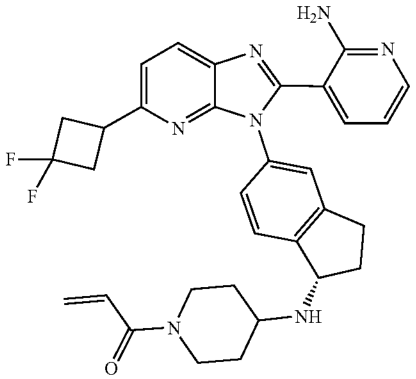

Example 227 was prepared in a manner analogous to Example 195 using 3,3-difluorocyclobutane-1-carboxylic acid in place of cyclobutenecarboxylic acid. MS (ESI) calcd. for $C_{32}H_{33}F_2N_7O$, 569.27 m/z, found 570.30 $[M+H]^+$. $^1H$ NMR (400 MHz, DMSO-$d_6$) δ (ppm): 8.08-8.11 (m, 1H), 7.95-7.97 (m, 1H), 7.45-7.47 (m, 1H), 7.34-7.36 (m, 1H), 7.25-7.26 (m, 1H), 7.14-7.18 (m, 2H), 6.73-6.80 (m, 1H), 6.40-6.44 (m, 1H), 6.04-6.09 (m, 1H), 5.66-5.69 (m, 1H), 4.26-4.37 (m, 2H), 3.93-4.04 (m, 1H), 3.55-3.57 (m, 1H), 3.05-3.10 (m, 1H), 2.90-2.95 (m, 4H), 2.71-2.81 (m, 4H), 2.40-2.42 (m, 1H), 1.97-2.03 (m, 1H), 1.78-1.87 (m, 2H), 1.15-1.28 (m, 2H). $^{19}$F NMR (376 MHz, DMSO-$d_6$) δ (ppm): −80.17, −95.74.

Example 228: 1-(4-{[(1R)-5-[2-(2-aminopyridin-3-yl)-5-[3-(difluoromethyl)pyrazol-1-yl]imidazo[4,5-b]pyridin-3-yl]-2,3-dihydro-1H-inden-1-yl]amino}piperidin-1-yl)prop-2-en-1-one Example 228

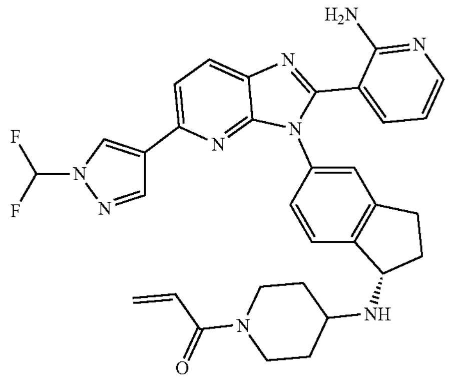

Example 228 was prepared in a manner analogous to Example 13 (via Intermediate 1-1) using 3-(difluoromethyl)-1H-pyrazole in place of pyrazole, Intermediate 85-1 in place of Intermediate 1-2, EPhos/EPhos Pd G4/cesium carbonate in place of tBuBrettPhos/tBuBrettPhos Pd G3/tribasic potassium phosphate, 4N HCl in dioxane at room temperature for 2 h for the deprotection and MeOH instead of DCE for the final step. MS (ESI) calcd. for $C_{32}H_{31}F_2N_9O$: 595.26 m/z, found: 596.30 [M+H]$^+$. $^1$H-NMR (400 MHz, DMSO-$d_6$) δ (ppm): 8.40-8.43 (m, 1H), 8.37-8.39 (m, 1H), 7.99-8.01 (m, 1H), 7.92-7.95 (m, 1H), 7.47-7.49 (m, 1H), 7.30-7.32 (m, 1H), 6.99-7.31 (m, 3H), 6.76-6.83 (m, 2H), 6.41-6.45 (m, 1H), 6.05-6.10 (m, 1H), 5.65-5.68 (m, 1H), 4.30-4.33 (m, 2H), 3.95-4.15 (m, 1H), 3.11-3.18 (m, 1H), 2.70-2.98 (m, 4H), 2.39-2.46 (m, 1H), 1.71-2.01 (m, 3H), 1.18-2.27 (m, 2H).

Example 229: 1-((3*,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-3-methylpiperidin-1-yl)prop-2-en-1-one Example 230: 1-((3*,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-3-methylpiperidin-1-yl)prop-2-en-1-one Example 231: 1-((3*,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-3-methylpiperidin-1-yl)prop-2-en-1-one and Example 232: 1-((3*,4*)-4-(((S)-5-(2-(2-aminopyridin-3-yl)-5-cyclopropyl-3H-imidazo[4,5-b]pyridin-3-yl)-2,3-dihydro-1H-inden-1-yl)amino)-3-methylpiperidin-1-yl)prop-2-en-1-one Example 229

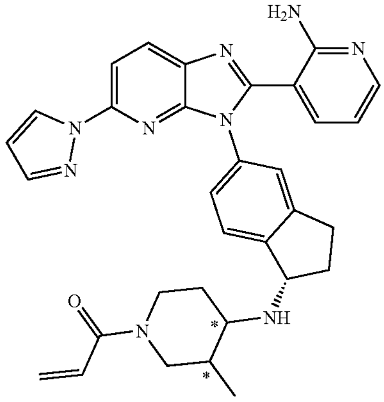

Example 230

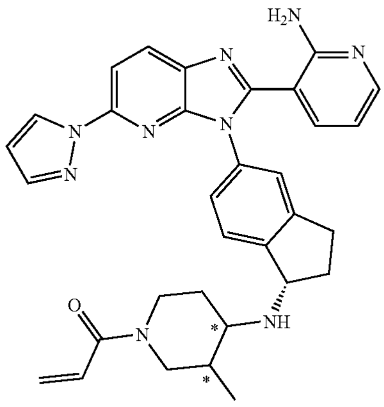

-continued

Example 231

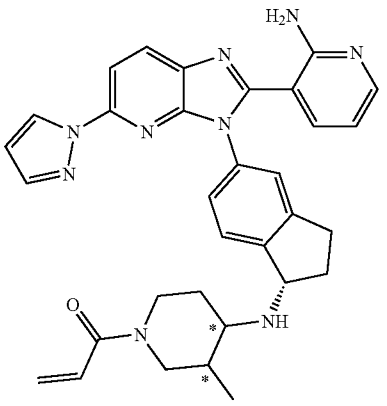

Example 232

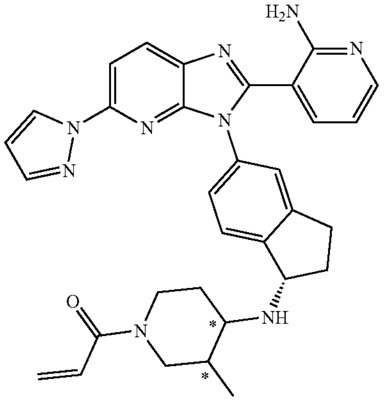

Examples 229, 230, 231 and 232 were prepared in a manner analogous to Example 14 (via Intermediate 14-1) using (3S)-3-methyl-4-oxopiperidine-1-carboxylate in place of tert-butyl 8-oxo-3-azabicyclo[3.2.1]octane-3-carboxylate, Intermediate 85-2 in place of Intermediate 1-1 and 4N HCl in dioxane in place of TFA in DCM. Example 229 was separated from Examples 230, 231 and 232 by chiral Prep-HPLC on a CHIRALPAK IK2 column using a mixture of [Hex/DCM (3:1) (+0.5% 2M $NH_3$-MeOH)] and isopropanol. Examples 230, 231 and 232 were separated by chiral Prep-HPLC on a CHIRALPAK IA column using a mixture of [MtBE (+0.5% 2M $NH_3$-MeOH)] and [EtOH/DCM (1:1)]. * Denotes a stereocenter with undetermined absolute stereocenter of a single diastereomer.

Example 229: MS (ESI) calcd. for $C_{32}H_{35}N_7O$: 533.29 m/z, found: 534.35 $[M+H]^+$. $^1$H-NMR (400 MHz, DMSO-$d_6$) δ (ppm): 7.95-8.02 (m, 2H), 7.42-7.44 (m, 1H), 7.19-7.22 (m, 2H), 7.12-7.14 (m, 2H), 6.77-6.84 (m, 1H), 6.37-7.39 (m, 1H), 6.01-6.11 (m, 1H), 5.65-5.68 (m, 1H), 3.81-4.25 (m, 3H), 3.21-3.28 (m, 1H), 2.67-3.06 (m, 4H), 2.39-2.48 (m, 1H), 2.03-2.16 (m, 2H), 1.73-1.79 (m, 1H), 1.41-1.56 (m, 2H), 0.88-0.94 (m, 2H), 0.78-0.86 (m, 5H).

Example 230: MS (ESI) calcd. for $C_{32}H_{35}N_7O$: 533.29 m/z, found: 534.35 $[M+H]^+$. $^1$H-NMR (400 MHz, DMSO-$d_6$) δ (ppm): 8.00-8.02 (m, 1H), 7.95-7.97 (m, 1H), 7.41-7.43 (m, 1H), 7.20-7.22 (m, 2H), 7.12-7.15 (m, 2H), 6.79-6.85 (m, 1H), 6.54-6.56 (m, 1H), 6.05-6.12 (m, 1H), 5.65-5.68 (m, 1H), 4.30-4.32 (m, 1H), 4.18-4.28 (m, 1H), 3.91-4.08 (m, 1H), 2.83-2.94 (m, 2H), 2.71-2.79 (m, 1H), 2.35-2.42 (m, 2H), 2.05-2.16 (m, 2H), 1.68-1.76 (m, 1H), 1.21-1.42 (m, 3H), 0.88-0.96 (m, 5H), 0.75-0.83 (m, 2H).

Example 231: MS (ESI) calcd. for $C_{32}H_{35}N_7O$: 533.29 m/z, found: 534.35 $[M+H]^+$. $^1$H-NMR (400 MHz, DMSO- $d_6$) δ (ppm): 8.00-8.02 (m, 1H), 7.95-7.97 (m, 1H), 7.44-7.46 (m, 1H), 7.18-7.22 (m, 2H), 7.11-7.15 (m, 2H), 6.78-6.85 (m, 1H), 6.35-6.38 (m, 1H), 6.06-6.10 (m, 1H), 5.64-5.68 (m, 1H), 4.20-4.24 (m, 2H), 3.88-3.99 (m, 1H), 2.85-2.94 (m, 2H), 2.66-2.76 (m, 1H), 2.38-2.47 (m, 2H), 2.13-2.18 (m, 1H), 1.95-2.07 (m, 1H), 1.71-1.78 (m, 1H), 1.15-1.42 (m, 3H), 0.89-0.96 (m, 5H), 0.76-0.81 (m, 2H).

Example 232: MS (ESI) calcd. for $C_{32}H_{35}N_7O$: 533.29 m/z, found: 534.35 $[M+H]^+$. $^1$H-NMR (400 MHz, DMSO-$d_6$) δ (ppm): 8.00-8.02 (m, 1H), 7.95-7.97 (m, 1H), 7.42-7.46 (m, 1H), 7.19-7.20 (m, 2H), 7.12-7.15 (m, 2H), 6.80-6.89 (m, 1H), 6.37-6.40 (m, 1H), 6.07-6.12 (m, 1H), 5.64-5.68 (m, 1H), 4.25-4.27 (m, 1H), 3.72-4.18 (m, 2H), 3.26-3.32 (m, 1H), 2.86-3.18 (m, 3H), 2.69-2.77 (m, 1H), 2.41-2.47 (m, 1H), 2.13-2.19 (m, 1H), 1.93-2.02 (m, 1H), 1.71-1.78 (m, 1H), 1.54-1.67 (m, 2H), 0.90-0.95 (m, 2H), 0.78-0.83 (m, 5H).

Example 233: 1-(4-(((1S,3*)-5-(2-(2-aminopyridin-3-yl)-5-(1H-pyrazol-1-yl)-3H-imidazo[4,5-b]pyridin-3-yl)-3-fluoro-2,3-dihydro-1H-inden-1-yl)amino)piperidin-1-yl)prop-2-en-1-one and Example 234: 1-(4-(((1S,3*)-5-(2-(2-aminopyridin-3-yl)-5-(1H-pyrazol-1-yl)-3H-imidazo[4,5-b]pyridin-3-yl)-3-fluoro-2,3-dihydro-1H-inden-1-yl)amino)piperidin-1-yl)prop-2-en-1-one Example 233

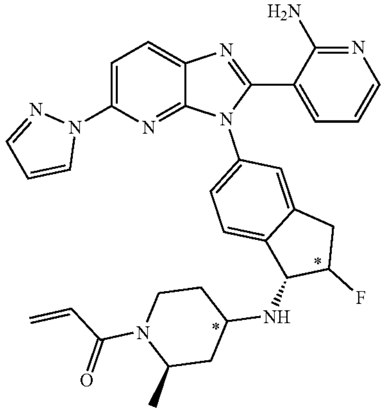

Example 234

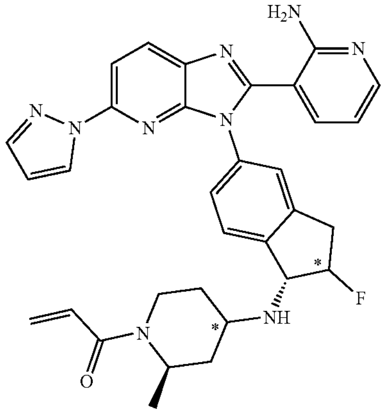

Examples 233 and 234 were prepared in a manner analogous to Example 13 using Intermediates 233-1 and 234-1 in place of Intermediate 1-1 and TFA in place of DCE. *

Denotes a stereocenter with undetermined absolute stereocenter of a single diastereomer.

Example 233: MS (ESI) calcd. for $C_{31}H_{30}FN_9O$: 563.26 m/z, found: 564.15 $[M+H]^+$. $^1H$ NMR (300 MHz, DMSO-d6) δ (ppm): 8.44-8.29 (m, 2H), 8.00-7.92 (m, 1H), 7.86-7.77 (m, 1H), 7.69-7.59 (m, 2H), 7.59-7.48 (m, 1H), 7.32-7.18 (m, 1H), 6.88 (s, 2H), 6.86-6.75 (m, 1H), 6.61-6.51 (m, 1H), 6.51-6.38 (m, 1H), 6.26-5.95 (m, 2H), 5.72-5.59 (m, 1H), 4.61 (s, 1H), 4.26 (s, 1H), 4.00 (s, 1H), 3.56-3.04 (m, 3H), 3.01-2.79 (m, 2H), 2.79-2.57 (m, 1H), 2.33-1.77 (m, 3H), 1.25 (s, 2H).

Example 234: MS (ESI) calcd. for $C_{31}H_{30}FN_9O$: 563.26 m/z, found: 564.15 $[M+H]^+$. $^1H$ NMR (300 MHz, DMSO-$d_6$) δ 8.41-8.37 (m, 1H), 8.36-8.32 (m, 1H), 8.03-7.99 (m, 1H), 7.98-7.94 (m, 1H), 7.83-7.80 (m, 1H), 7.63-7.57 (m, 2H), 7.51-7.45 (m, 1H), 7.31-7.25 (m, 1H), 6.89-6.73 (m, 3H), 6.58-6.54 (m, 1H), 6.47-6.41 (m, 1H), 6.14-5.85 (m, 2H), 5.70-5.63 (m, 1H), 4.30-4.16 (m, 2H), 4.05-3.91 (m, 1H), 3.27-3.11 (m, 1H), 3.06-2.82 (m, 3H), 2.39-2.25 (m, 1H), 2.05-1.91 (m, 2H), 1.89-1.78 (m, 1H), 1.34-1.15 (m, 2H).

Intermediate 233-1: 3-(3-((1S,3*)-1-amino-3-fluoro-2,3-dihydro-1H-inden-5-yl)-5-(1H-pyrazol-1-yl)-3H-imidazo[4,5-b]pyridin-2-yl)pyridin-2-amine and Intermediate 234-1: 3-(3-((1S,3*)-1-amino-3-fluoro-2,3-dihydro-1H-inden-5-yl)-5-(1H-pyrazol-1-yl)-3H-imidazo[4,5-b]pyridin-2-yl)pyridin-2-amine Intermediate 233-1

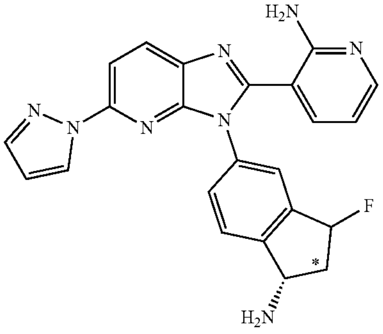

Intermediate 234-1

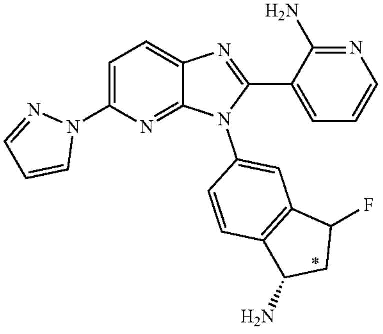

Synthetic Route:

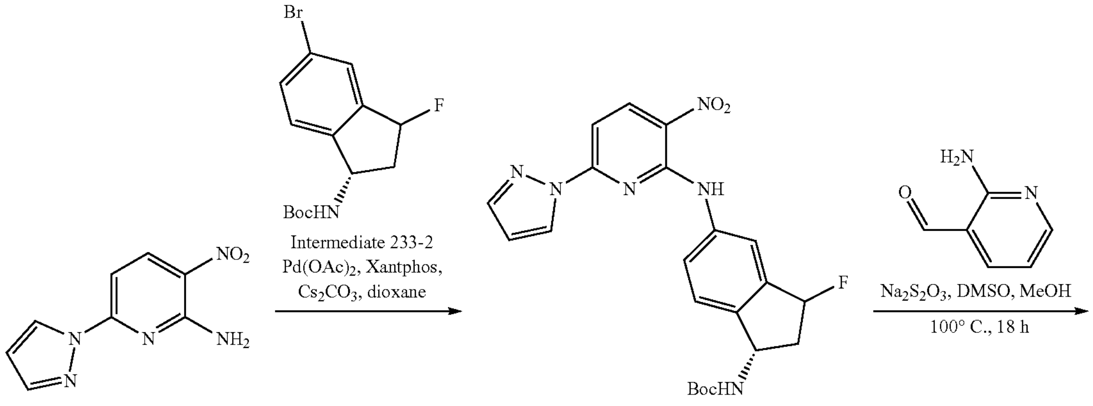

-continued

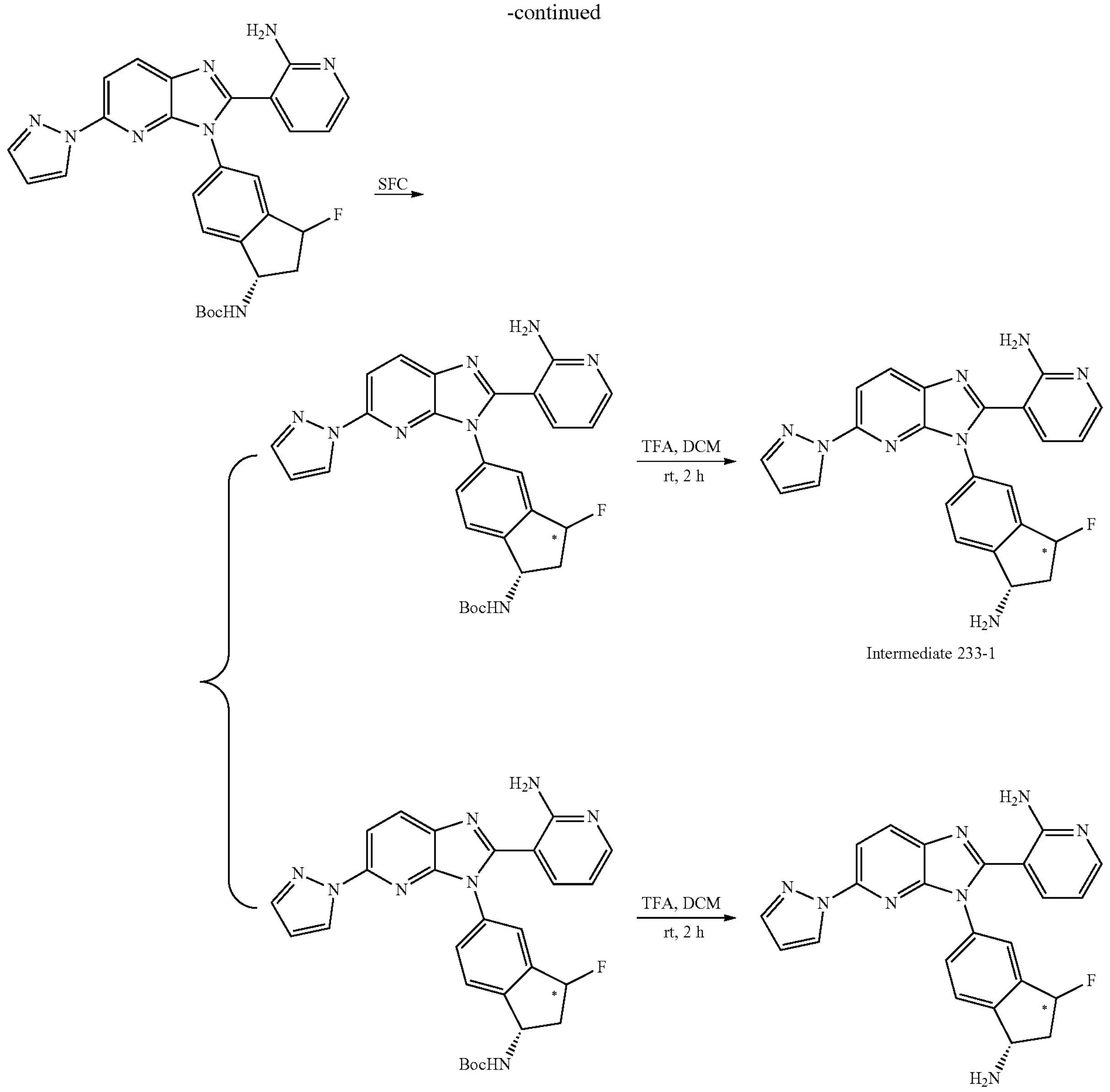

Intermediate 233-1

Intermediate 234-1

Step 1: Synthesis of tert-butyl ((1S)-3-fluoro-5-((3-nitro-6-(1H-pyrazol-1-yl)pyridin-2-yl)amino)-2,3-dihydro-1H-inden-1-yl)carbamate To a solution of tert-butyl ((1S)-5-bromo-3-fluoro-2,3-dihydro-1H-inden-1-yl)carbamate (Intermediate 233-2) (4 g, 12 mmol, 1 equiv) and 3-nitro-6-(1H-pyrazol-1-yl)pyridin-2-amine (2.73 g, 13.3 mmol, 1.1 equiv) in 1,4-dioxane (60 mL) were added $Pd(OAc)_2$ (0.27 g, 1.2 mmol, 0.1 equiv), XantPhos (1.40 g, 2.42 mmol, 0.2 equiv) and $Cs_2CO_3$ (7.89 g, 24.2 mmol, 2 equiv). After stirring for 2 h at 100° C. under a nitrogen atmosphere, the resulting mixture was concentrated under reduced pressure. The residue was purified by reverse-phase flash chromatography on C18 silica gel using a gradient of acetonitrile in water (+0.05% ammonium bicarbonate) to afford tert-butyl ((1S)-3-fluoro-5-((3-nitro-6-(1H-pyrazol-1-yl)pyridin-2-yl)amino)-2,3-dihydro-1H-inden-1-yl)carbamate (4 g, 73% yield) as a brown solid. MS (ESI) calcd. for $C_{22}H_{23}FN_6O4$, 454.18 m/z, found 455.15 $[M+H]^+$.

Step 2: Synthesis of tert-butyl ((1S)-5-(2-(2-aminopyridin-3-yl)-5-(1H-pyrazol-1-yl)-3H-imidazo[4,5-b]pyridin-3-yl)-3-fluoro-2,3-dihydro-1H-inden-1-yl) carbamate To a stirred solution of tert-butyl ((1S)-3-fluoro-5-((3-nitro-6-(1H-pyrazol-1-yl)pyridin-2-yl)amino)-2,3-dihydro-1H-inden-1-yl)carbamate (2 g, 4.4 mmol, 1 equiv) and 2-aminonicotinaldehyde (0.59 g, 4.8 mmol, 1.1 equiv) in DMSO (60 mL) and MeOH (10 mL) was added $Na_2S_2O_4$ (1.69 g, 9.68 mmol, 2.2 equiv) at room temperature. The resulting mixture was stirred for 18 h at 100° C. The mixture was allowed to cool to room temperature. The mixture was basified to pH 7 with saturated aqueous sodium bicarbonate.

The resulting mixture was extracted with ethyl acetate (3×200 mL). The combined organic layers were washed with brine (300 mL) and dried over anhydrous $Na_2SO_4$. After filtration, the filtrate was concentrated under reduced pressure. The residue was purified by reverse-phase flash chromatography on C18 silica gel using a gradient of acetonitrile in water (+0.05% ammonium bicarbonate). The diastereomers were separated by chiral Prep-HPLC on CHIRALPAK IG column using a mixture of [Hex (+0.5% 2M $NH_3$-MeOH)] and [IPA/DCM (1:1)] to afford tert-butyl ((1S,3*)-5-(2-(2-aminopyridin-3-yl)-5-(1H-pyrazol-1-yl)-3H-imidazo[4,5-b]pyridin-3-yl)-3-fluoro-2,3-dihydro-1H-inden-1-yl)carbamate (250 mg, 11% yield) as a yellow solid and first eluting peak (MS (ESI) calcd. for $C_{28}H_{27}FN_8O_2$, 526.22 m/z, found 527.15 $[M+H]^+$) and tert-butyl ((1S,3*)-5-(2-(2-aminopyridin-3-yl)-5-(1H-pyrazol-1-yl)-3H-imidazo[4,5-b]pyridin-3-yl)-3-fluoro-2,3-dihydro-1H-inden-1-yl)carbamate (230 mg, 9.9% yield) as a yellow solid (MS (ESI) calcd. for $C_{28}H_{27}FN_8O_2$, 526.22 m/z, found 527.15 [M+H]). * Denotes a stereocenter with undetermined absolute stereocenter of a single diastereomer.

Step 3: Synthesis of 3-(3-((1S,3R*)-1-amino-3-fluoro-2,3-dihydro-1H-inden-5-yl)-5-(1H-pyrazol-1-yl)-3H-imidazo[4,5-b]pyridin-2-yl)pyridin-2-amine (Intermediate 233-1) and 3-(3-((1S,3S*)-1-amino-3-fluoro-2,3-dihydro-1H-inden-5-yl)-5-(1H-pyrazol-1-yl)-3H-imidazo[4,5-b]pyridin-2-yl)pyridin-2-amine (Intermediate 234-1)

The products of Step 2 vide supra were deprotected separately by dissolving the starting material (100 mg, 0.190 mmol, 1 equiv) in DCM (0.8 mL) and adding TFA (0.2 mL). The resulting mixture was stirred for 2 h at room temperature. The residue was purified by reverse-phase flash chromatography on C18 silica gel using a gradient of acetonitrile in water (+0.05% ammonium bicarbonate) to afford 3-(3-((1S,3*)-1-amino-3-fluoro-2,3-dihydro-1H-inden-5-yl)-5-(1H-pyrazol-1-yl)-3H-imidazo[4,5-b]pyridin-2-yl)pyridin-2-amine (Intermediate 233-1) (MS (ESI) calcd. for $C_{23}H_{19}FN_8$, 426.17 m/z, found: 427.15 $[M+H]^+$) and 3-(3-((1S,3*)-1-amino-3-fluoro-2,3-dihydro-1H-inden-5-yl)-5-(1H-pyrazol-1-yl)-3H-imidazo[4,5-b]pyridin-2-yl)pyridin-2-amine (Intermediate 234-1) (25.4 mg, 30.49% yield) as yellow solid (MS (ESI) calcd. for $C_{23}H_{19}FN_8$, 426.17 m/z, found: 427.15 $[M+H]^+$). * Denotes a stereocenter with undetermined absolute stereocenter of a single diastereomer.

Intermediate 233-2: tert-butyl ((1S)-5-bromo-3-fluoro-2,3-dihydro-1H-inden-1-yl)carbamate Intermediate 233-2

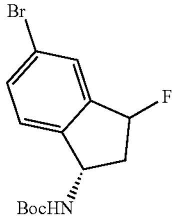

Synthetic Route:

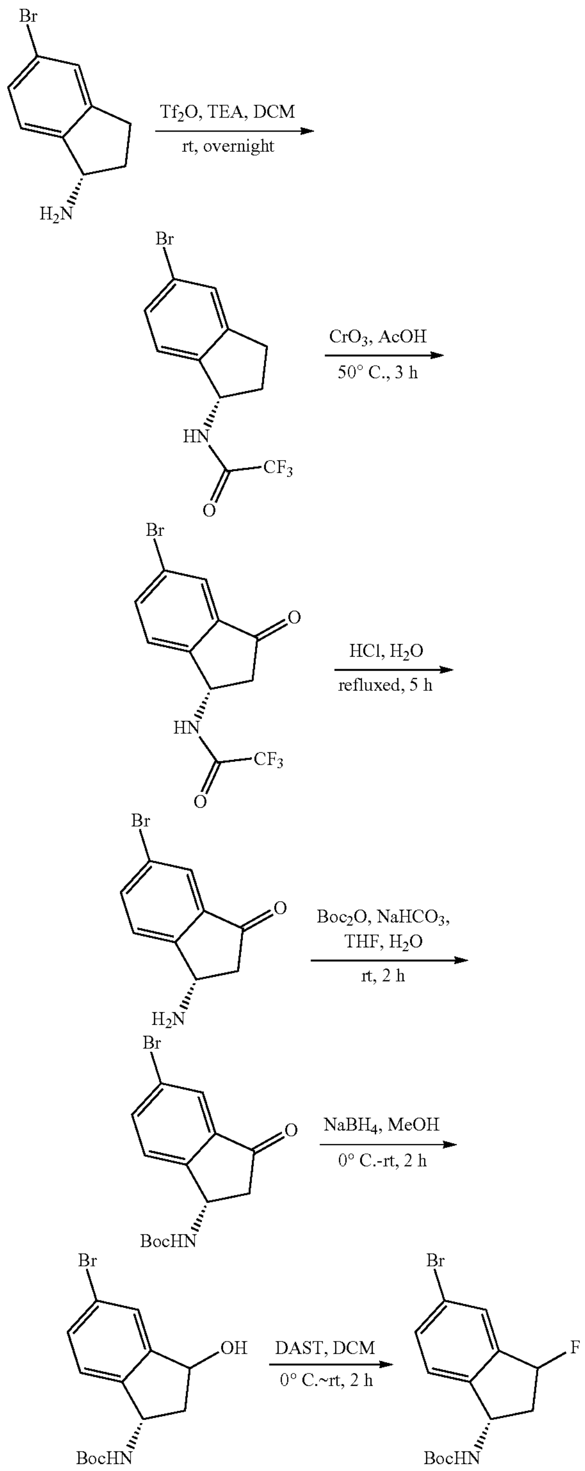

Intermediate 233-2

Step 1: Synthesis of (S)-N-(5-bromo-2,3-dihydro-1H-inden-1-yl)-2,2,2-trifluoroacetamide A solution of (1S)-5-bromo-2,3-dihydro-1H-inden-1-amine (50 g, 236 mmol, 1 equiv) and TEA (55.7 g, 550 mmol, 2 equiv) in DCM (750 mL) was added TFAA (63.25 g, 301.1 mmol, 1.3 equiv) at 0° C. The resulting mixture was stirred overnight at room temperature. The reaction was quenched with $H_2O$ (500 mL) at room temperature. The aqueous layer was extracted with DCM (2×500 mL). The combined organic layers were dried over anhydrous $Na_2SO_4$. After filtration, the filtrate was concentrated under reduced pressure to afford crude product (S)-N-(5-bromo-2,3-dihydro-1H-inden-1-yl)-2,2,2-trifluoroacetamide (86 g) as a white solid. MS (ESI) calcd. for $C_{11}H_9BrF_3NO$, 306.98 m/z, found: 306.10 $[M-H]^-$.

Step 2: Synthesis of (S)-N-(5-bromo-3-oxo-2,3-dihydro-1H-inden-1-yl)-2,2,2-trifluoroacetamide A solution of (S)-N-(5-bromo-2,3-dihydro-1H-inden-1-yl)-2,2,2-trifluoroacetamide (50 g, 162 mmol, 1.00 equiv) and $CrO_3$ (48.8 g, 488 mmol, 3.00 equiv) in AcOH (600 mL) was stirred for 2 h at 50° C. under air atmosphere. The mixture was allowed to cool to room temperature. The resulting mixture was concentrated under reduced pressure. The residue was purified by silica gel column chromatography, eluting with ethyl acetate in petroleum ether (0~20%) to afford (S)-N-(5-bromo-3-oxo-2,3-dihydro-1H-inden-1-yl)-2,2,2-trifluoroacetamide (11.5 g, 22%) as a white solid. MS (ESI) calcd. for $C_{11}H_7BrF_3NO_2$, 320.96 m/z, found: 319.90 $[M-H]^-$.

Step 3: Synthesis of (S)-3-amino-6-bromo-2,3-dihydro-1H-inden-1-one

A solution of (S)-N-(5-bromo-3-oxo-2,3-dihydro-1H-inden-1-yl)-2,2,2-trifluoroacetamide (10 g, 31 mmol, 1 equiv) in 6M aqueous HCl (200 mL) was refluxed 5 h. The resulting mixture was concentrated under reduced pressure and the residue was triturated with $Et_2O$ (200 mL). The residue was filtered and dried to afford (S)-3-amino-6-bromo-2,3-dihydro-1H-inden-1-one (7 g, crude quant.) as a white solid. MS (ESI) calcd. for $C_9H_8BrNO$, 224.98 m/z, found 224.05 $[M-H]^-$.

Step 4: Synthesis of tert-butyl (S)-(5-bromo-3-oxo-2,3-dihydro-1H-inden-1-yl)carbamate To a stirred solution of (S)-3-amino-6-bromo-2,3-dihydro-1H-inden-1-one (7 g, 31 mmol, 1 equiv) in THE (60 mL) and $H_2O$ (15 mL) were added $NaHCO_3$ (5.20 g, 61.9 mmol, 2 equiv) and $Boc_2O$ (8.11 g, 37.2 mmol, 1.2 equiv) in portions at 0° C. The resulting mixture was stirred for 2 h at room temperature. The reaction was quenched with water (100 mL). The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0~50%) to afford tert-butyl (S)-(5-bromo-3-oxo-2,3-dihydro-1H-inden-1-yl)carbamate (7 g, 69% yield) as an off-white solid. MS (ESI) calcd. for $C_{14}H_{16}BrNO_3$, 325.03 m/z, found 324.10 $[M-H]^-$.

Step 5: Synthesis of tert-butyl ((1S)-5-bromo-3-hydroxy-2,3-dihydro-1H-inden-1-yl)carbamate To a stirred solution of tert-butyl (S)-(5-bromo-3-oxo-2,3-dihydro-1H-inden-1-yl)carbamate (7 g, 21 mmol, 1 equiv) in MeOH (100 mL) was added $NaBH_4$ (1.62 g, 42.9 mmol, 2 equiv) in portions at 0° C. The resulting mixture was stirred for 2 h at room temperature. The reaction was quenched by the addition of water (200 mL) at room temperature. The resulting mixture was extracted with ethyl acetate (3×300 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0~50%) to afford tert-butyl ((1S)-5-bromo-3-hydroxy-2,3-dihydro-1H-inden-1-yl)carbamate (5 g, 71%) as a white solid. MS (ESI) calcd. for $C_{14}H_{18}BrNO_3$, 327.05 m/z, found 326.10 $[M-H]^-$.

Step 6: Synthesis of tert-butyl ((1S)-5-bromo-3-fluoro-2,3-dihydro-1H-inden-1-yl)carbamate (Intermediate 233-2

To a stirred solution of tert-butyl ((1S)-5-bromo-3-hydroxy-2,3-dihydro-1H-inden-1-yl)carbamate (5 g, 15 mmol, 1 equiv) in DCM (100 mL) was added DAST (4.91 g, 30.5 mmol, 2 equiv) in portions at 0° C. The resulting mixture was stirred for 2 h at room temperature. The reaction was quenched by the addition of saturated aqueous sodium bicarbonate (200 mL) at room temperature. The resulting mixture was extracted with ethyl acetate (3×300 mL). The combined organic layers were washed with brine (300 mL) and dried over anhydrous $Na_2SO_4$. After filtration, the filtrate was concentrated under reduced pressure. The residue was purified by silica gel column chromatography, eluting with ethyl acetate in petroleum ether (0~30%) to afford tert-butyl ((1S)-5-bromo-3-fluoro-2,3-dihydro-1H-inden-1-yl)carbamate (Intermediate 233-2) (4 g, 80% yield) as a white solid. MS (ESI) calcd. for $C_{14}H_{17}BrFNO_2$, 329.04 m/z, found 310.15 [M-F]*.

Example 235: (S)-2-acryloyl-N-(5-(2-(2-aminopyridin-3-yl)-5-(1H-pyrazol-1-yl)-3H-imidazo[4,5-b]pyridin-3-yl)-2,3-dihydro-1H-inden-1-yl)-1,2,3,4-tetrahydroisoquinoline-8-carboxamide Example 235

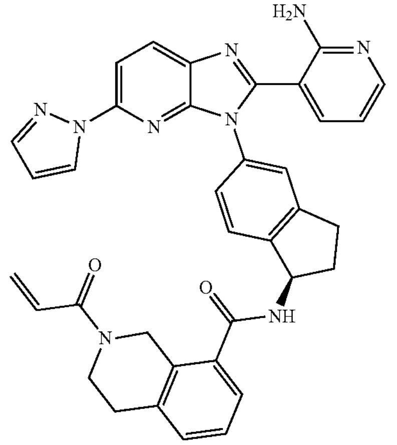

Example 235 was prepared in a manner analogous to Example 2 (via Intermediate 2-1) using 2-(tert-butoxycarbonyl)-3,4-dihydro-1H-isoquinoline-8-carboxylic acid in place of 3-((tert-butoxycarbonyl)amino)benzoic acid, 4N HCl in dioxane in place of TFA in DCM, sodium bicarbonate in place of triethylamine and tetrahydrofuran/water (4:1) in place of DCM. For the final step, the reagents were added at 0° C. followed by stirring at room temperature for 30 min. MS (ESI) calcd. for $C_{36}H_{31}N_9O_2$, 621.26 m/z, found 622.25 $[M+H]^+$. $^1H$ NMR (400 MHz, DMSO-$d_6$) δ (ppm): 8.87-8.93 (m, 1H), 8.30-8.40 (m, 2H), 7.98-8.05 (m, 1H), 7.92-7.97 (m, 1H), 7.81 (s, 1H), 7.45-7.51 (m, 1H), 7.21-7.45 (m, 6H), 6.83-6.99 (m, 3H), 6.54 (s, 1H), 6.40-6.48 (m, 1H), 5.98-6.20 (m, 1H), 5.57-5.75 (m, 2H), 4.85-4.98 (m, 2H), 3.78-3.88 (m, 1H), 3.71-3.76 (m, 1H), 2.98-3.07 (m, 1H), 2.85-2.96 (m, 3H), 2.52-2.60 (m, 1H), 2.00-2.10 (m, 1H).

Example 236: 1-(4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one and

Example 237: 1-(4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one Example 236

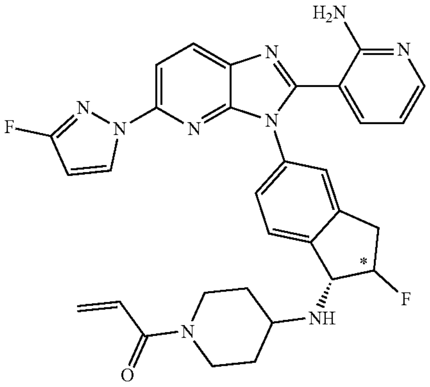

Example 237

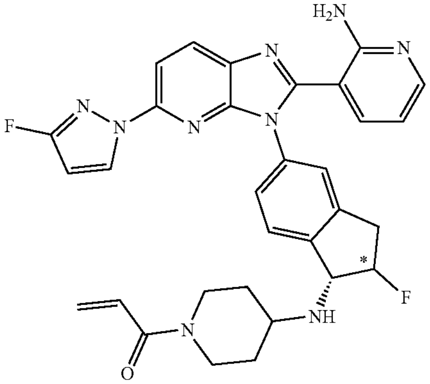

Example 236 and 237 were prepared in a manner analogous to Example 13 using Intermediate 236-1 and 237-1, respectively, in place of Intermediate 1-1. * Denotes a stereocenter with undetermined absolute stereocenter of a single diastereomer.

Example 236: MS (ESI) calcd. for $C_{31}H_{29}F_2N_9O$: 581.24 m/z, found: 582.15 $[M+H]^+$. $^1H$ NMR (300 MHz, DMSO-$d_6$) δ (ppm): 8.35-8.39 (m, 1H), 8.26-8.30 (m, 1H), 7.99-8.02 (m, 1H), 7.73-7.80 (m, 1H), 7.43-7.50 (m, 1H), 7.31-7.38 (m, 2H), 7.20-7.28 (m, 1H), 6.79-6.89 (m, 1H), 6.31-6.46 (m, 2H), 6.05-6.13 (m, 1H), 5.62-5.68 (m, 1H), 5.38-5.44 (m, 1H), 4.38-4.47 (m, 1H), 4.18-4.30 (m, 1H), 3.91-4.05 (m, 1H), 3.11-3.28 (m, 2H), 2.91-3.12 (m, 3H), 1.98-2.07 (m, 1H), 1.82-1.92 (m, 1H), 1.22-1.40 (m, 2H). $^{19}F$-NMR (400 MHz, DMSO) δ (ppm): −127.30, −196.72.

Example 237: MS (ESI) calcd. for $C_{31}H_{29}F_2N_9O$: 581.24 m/z, found: 582.20 $[M+H]^+$. $^1H$ NMR (300 MHz, DMSO-$d_6$) δ (ppm): 8.29-8.39 (m, 2H), 7.99-8.02 (m, 1H), 7.73-7.80 (m, 1H), 7.47-7.52 (m, 1H), 7.38-7.41 (m, 1H), 7.20-7.37 (m, 2H), 6.79-6.89 (m, 1H), 6.31-6.46 (m, 2H), 6.05-6.13 (m, 1H), 5.62-5.70 (m, 1H), 5.17-5.32 (m, 1H), 4.36-4.44 (m, 1H), 4.21-4.31 (m, 1H), 3.91-4.05 (m, 1H), 3.49-3.52 (m, 1H), 3.09-3.20 (m, 1H), 2.93-3.06 (m, 2H), 2.79-2.90 (m, 1H), 1.82-1.98 (m, 2H), 1.18-1.29 (m, 2H). $^{19}F$-NMR (400 MHz, DMSO) δ (ppm): −127.28, −175.93.

Intermediate 236-1: 3-(3-((1R,S*)-1-amino-2-fluoro-2,3-dihydro-1H-inden-5-yl)-5-(3-fluoro-1H-pyrazol-1-yl)-3H-imidazo[4,5-b]pyridin-2-yl)pyridin-2-amine and

Intermediate 237-1: 3-(3-((1R,2*)-1-amino-2-fluoro-2,3-dihydro-1H-inden-5-yl)-5-(3-fluoro-1H-pyrazol-1-yl)-3H-imidazo[4,5-b]pyridin-2-yl)pyridin-2-amine Intermediate 236-1

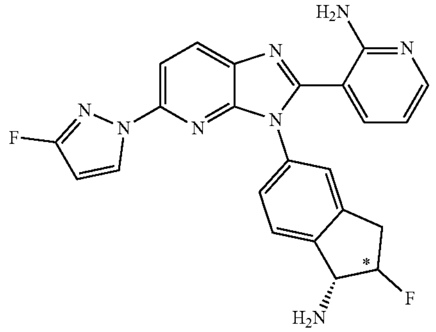

Intermediate 237-1

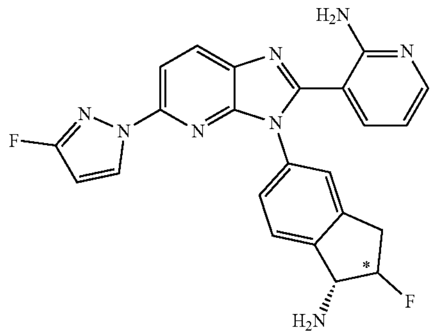

Intermediates 236-1 and 237-1 were prepared in a manner analogous to Intermediate 75-1 and 76-1 (last 3 steps only) using Intermediate 236-2 in place of (S)-N-((1R)-5-((3-amino-6-(1H-pyrazol-1-yl)pyridin-2-yl)amino)-2-fluoro-2,3-dihydro-1H-inden-1-yl)-2-methylpropane-2-sulfinamide. * Denotes a stereocenter with undetermined absolute stereocenter of a single diastereomer.

Intermediate 236-1: MS (ESI) calcd. for $C_{23}H_{18}F_2N_8$, 444.16 m/z, found 445.15 $[M+H]^+$.

Intermediate 237-1: MS (ESI) calcd. for $C_{23}H_{18}F_2N_8$, 444.16 m/z, found 445.15 $[M+H]^+$.

Intermediate 236-2: (S)-N-[(1R)-5-{[3-amino-6-(3-fluoropyrazol-1-yl)pyridin-2-yl]amino}-2-fluoro-2,3-dihydro-1H-inden-1-yl]-2-methylpropane-2-sulfinamide Intermediate 236-2

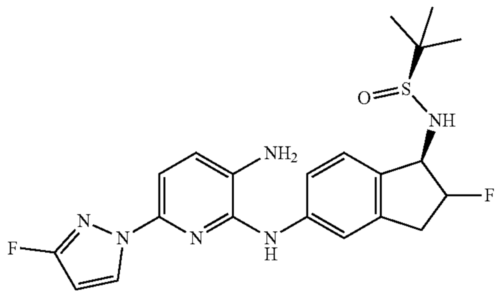

Intermediate 236-2 was prepared in a manner analogous to Intermediate 75-1 (using the first 5 steps only) and using Intermediate 236-3 in place of 3-nitro-6-(pyrazol-1-yl)pyridin-2-amine. MS (ESI) calcd. for $C_{21}H_{24}F_2N_6OS$, 446.17 m/z, found 447.25 $[M+H]^+$.

Intermediate 236-3: 6-(3-fluoropyrazol-1-yl)-3-nitropyridin-2-amine

Intermediate 236-3

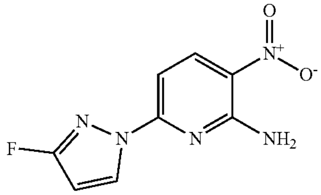

Step 1: Synthesis of 6-(3-fluoropyrazol-1-yl)-3-nitropyridin-2-amine

To a solution of 6-bromo-3-nitropyridin-2-amine (5 g, 22.935 mmol, 1 equiv) in DMF (80 mL) was added $K_2CO_3$ (9.51 g, 68.805 mmol, 3 equiv) and then 3-fluoro-1H-pyrazole (2.17 g, 25.229 mmol, 1.1 equiv) at 0° C. The resulting suspension was stirred overnight at 60° C. The mixture was poured into water (250 mL). The precipitated solids were collected by filtration and washed with water (3×150 mL) to afford 6-(3-fluoropyrazol-1-yl)-3-nitropyridin-2-amine (4.9 g, 95.74% yield) as a yellow solid. MS (ESI) calcd. for $C_8H_6FN_5O_2$, 223.05 m/z, found 224.15 $[M+H]^+$.

Example 238: 1-(4-{[(1S)-5-[2-(2-aminopyridin-3-yl)-5-(4-fluoropiperidin-1-yl)imidazo[4,5-b]pyridin-3-yl]-2,3-dihydro-1H-inden-1-yl]amino}piperidin-1-yl)prop-2-en-1-one Example 238

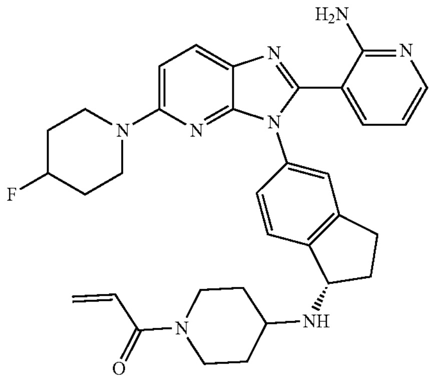

Example 238 was prepared in a manner analogous to Example 170 (via Intermediate 170-1) using 4-fluoropiperidine in place of pyrrolidine, NMP in place of DMSO and the first step was run in the microwave at 120° C. overnight. MS (ESI) calcd. for $C_{33}H_{37}FN_8O$: 580.31 m/z, found: 581.40 $[M+H]^+$. $^1H$ NMR (400 MHz, DMSO-$d_6$) δ 9.27-9.23 (m, 1H), 9.20-9.16 (m, 1H), 8.06-7.97 (m, 2H), 7.80-7.73 (m, 1H), 7.47-7.41 (m, 2H), 7.41-7.34 (m, 1H), 7.05-6.98 (m, 1H), 6.94-6.78 (m, 1H), 6.67-6.60 (m, 1H), 6.18-6.09 (m, 1H), 5.75-5.67 (m, 1H), 5.06-4.77 (m, 2H), 4.56-4.51 (m, 1H), 4.23-4.18 (m, 1H), 3.83-3.64 (m, 3H), 3.59-3.54 (m, 1H), 3.50-3.41 (m, 2H), 3.17-3.09 (m, 2H), 2.97-2.85 (m, 1H), 2.77-2.66 (m, 1H), 2.60-2.52 (m, 1H), 2.26-2.19 (m, 2H), 2.15-2.08 (m, 1H), 1.96-1.84 (m, 2H), 1.71-1.67 (m, 2H), 1.58-1.53 (m, 2H). $^{19}F$ NMR (376 MHz, DMSO-$d_6$) δ −73.90, −176.58. (TFA salt)

Example 239: 1-(4-{[(1S)-5-[5-(pyrazol-1-yl)-2-(thiophen-2-yl)imidazo[4,5-b]pyridin-3-yl]-2,3-dihydro-1H-inden-1-yl]amino}piperidin-1-yl)prop-2-en-1-one Example 239

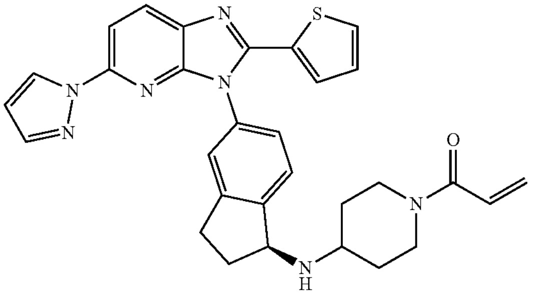

Synthetic Route:

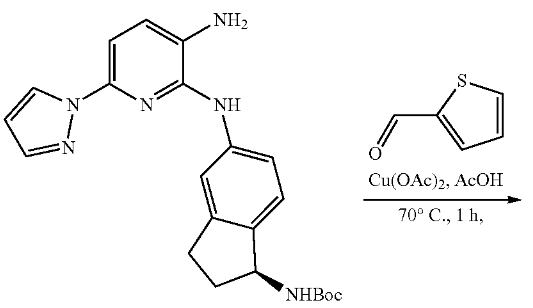

Intermediate 239-1

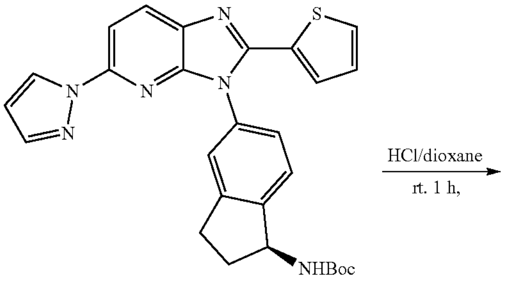

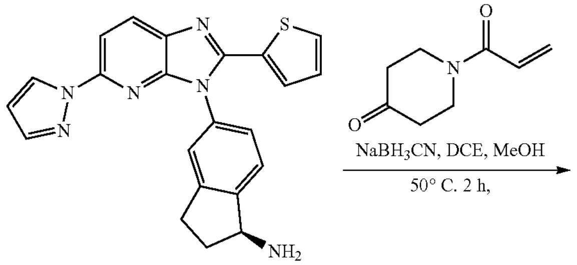

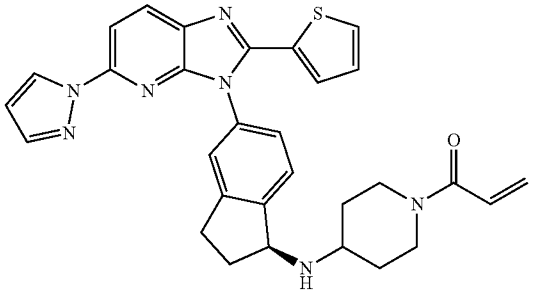

Example 239

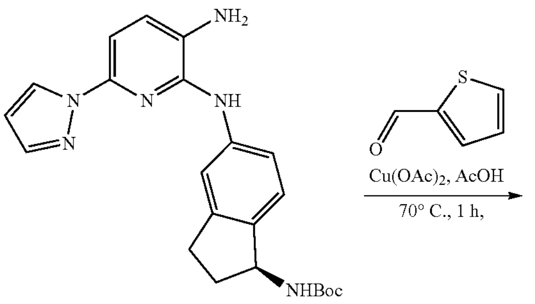

Intermediate 239-1

-continued

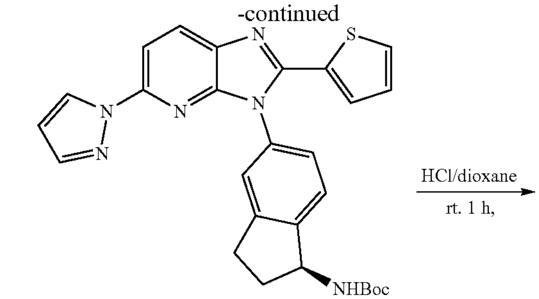

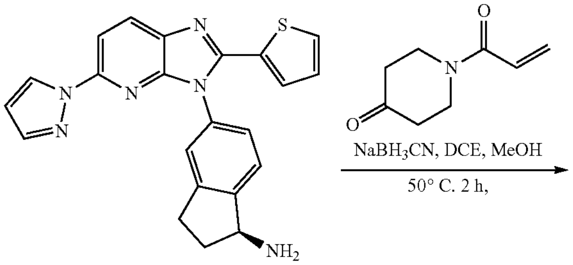

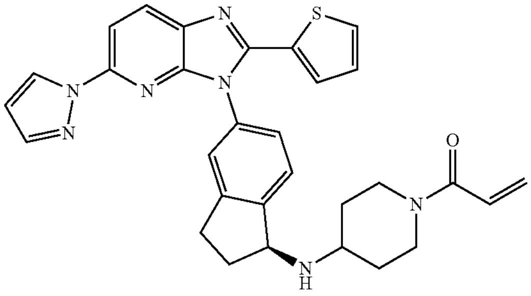

Example 239

Step 1: Synthesis of tert-butyl N-[(1S)-5-[5-(pyrazol-1-yl)-2-(thiophen-2-yl)imidazo[4,5-b]pyridin-3-yl]-2,3-dihydro-1H-inden-1-yl]carbamate To a solution of tert-butyl N-[(1S)-5-{[3-amino-6-(pyrazol-1-yl)pyridin-2-yl]amino}-2,3-dihydro-1H-inden-1-yl] carbamate (Intermediate 239-1) (500 mg, 1.230 mmol, 1 equiv) in AcOH (8 mL) was added $Cu(OAc)_2$ (44.68 mg, 0.246 mmol, 0.2 equiv) and thiophene-2-carbaldehyde (165.54 mg, 1.476 mmol, 1.2 equiv) and the resulting mixture was stirred at 70° C. for 1 h. The reaction was quenched with $H_2O$ (2 mL) and the resulting mixture was concentrated. The residue was purified by Prep-HPLC on a XSelect CSH OBD Column using a gradient of acetonitrile in water (+0.05% $NH_4HCO_3$) to afford tert-butyl N-[(1S)-5-[5-(pyrazol-1-yl)-2-(thiophen-2-yl)imidazo[4,5-b]pyridin-3-yl]-2,3-dihydro-1H-inden-1-yl]carbamate (300 mg, 48.91% yield) as a yellow solid. MS (ESI) calcd. for $C_{27}H_{26}N_6O_2S$: 498.18 m/z, found: 499.20 $[M+H]^+$.

Step 2: Synthesis of (1S)-5-[5-(pyrazol-1-yl)-2-(thiophen-2-yl)imidazo[4,5-b]pyridin-3-yl]-2,3-dihydro-1H-inden-1-amine A solution of tert-butyl N-[(1S)-5-[5-(pyrazol-1-yl)-2-(thiophen-2-yl)imidazo[4,5-b]pyridin-3-yl]-2,3-dihydro-1H-inden-1-yl]carbamate (200 mg, 0.401 mmol, 1 equiv) in 4N HCl in dioxane (6 mL) was stirred at r.t for 1 h. The resulting mixture was concentrated to afford (1S)-5-[5-(pyrazol-1-yl)-2-(thiophen-2-yl)imidazo[4,5-b]pyridin-3- yl]-2,3-dihydro-1H-inden-1-amine (159 mg, crude) as a yellow solid. MS (ESI) calcd. for $C_{22}H_{18}N_6S$: 398.13 m/z, found: 399.25 $[M+H]^+$.

Step 3: Synthesis of 1-(4-{[(1S)-5-[5-(pyrazol-1-yl)-2-(thiophen-2-yl)imidazo[4,5-b]pyridin-3-yl]-2,3-dihydro-1H-inden-1-yl]amino}piperidin-1-yl)prop-2-en-1-one (Example 239)

A solution of (1S)-5-[5-(pyrazol-1-yl)-2-(thiophen-2-yl)imidazo[4,5-b]pyridin-3-yl]-2,3-dihydro-1H-inden-1-amine (160 mg, 0.402 mmol, 1 equiv) and 1-(prop-2-enoyl)piperidin-4-one (92.26 mg, 0.603 mmol, 1.5 equiv) in DCE (8 mL) and MeOH (0.8 mL) stirred at 50° C. for 1 h. $NaBH_3CN$ (126.16 mg, 2.010 mmol, 5 equiv) was added and the mixture was stirred at 50° C. for 1 h. The reaction was quenched with $H_2O$ (2 mL) and the mixture was concentrated. The residue was purified by Prep HPLC on XBridge Prep Phenyl Hexy OBD C18 Column using a gradient of acetonitrile in water (+10 mmol/L $NH_4HCO_3$) to afford 1-(4-{[(1S)-5-[5-(pyrazol-1-yl)-2-(thiophen-2-yl)imidazo[4,5-b]pyridin-3-yl]-2,3-dihydro-1H-inden-1-yl]amino}piperidin-1-yl)prop-2-en-1-one (Example 239) (81.7 mg, 36.43% yield) as an off-white solid. MS (ESI) calcd. for $C_{30}H_{29}N_7OS$: 535.21 m/z, found: 536.15$[M+H]^+$. $^1H$ NMR (300 MHz, DMSO-$d_6$) δ (ppm): 8.23-8.29 (m, 2H), 7.88-7.92 (m, 1H), 7.72-7.82 (m, 2H), 7.59-7.65 (m, 1H), 7.39-7.48 (m, 2H), 7.00-7.08 (m, 1H), 6.79-6.89 (m, 2H), 6.47-6.52 (m, 1H), 6.07-6.13 (m, 1H), 5.63-5.70 (m, 1H), 4.38-4.45 (m, 1H), 4.23-4.33 (m, 1H), 3.96-4.08 (m, 1H), 3.11-3.22 (m, 1H), 2.79-3.04 (m, 4H), 2.48-2.52 (m, 1H), 1.92-2.01 (m, 1H), 1.79-1.97 (m, 2H), 1.19-1.37 (m, 2H).

Intermediate 239-1: tert-butyl (S)-(5-((3-amino-6-(1H-pyrazol-1-yl)pyridin-2-yl)amino)-2,3-dihydro-1H-inden-1-yl)carbamate and

Intermediate 239-0: tert-butyl (S)-(5-((3-nitro-6-(1H-pyrazol-1-yl)pyridin-2-yl)amino)-2,3-dihydro-1H-inden-1-yl)carbamate Intermediate 239-0

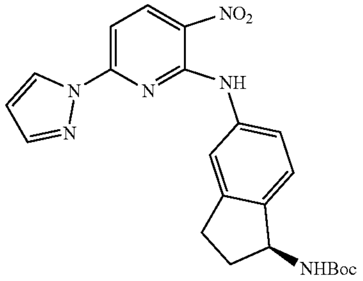

Intermediate 239-1

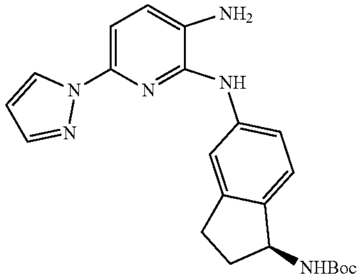

Synthetic Route:

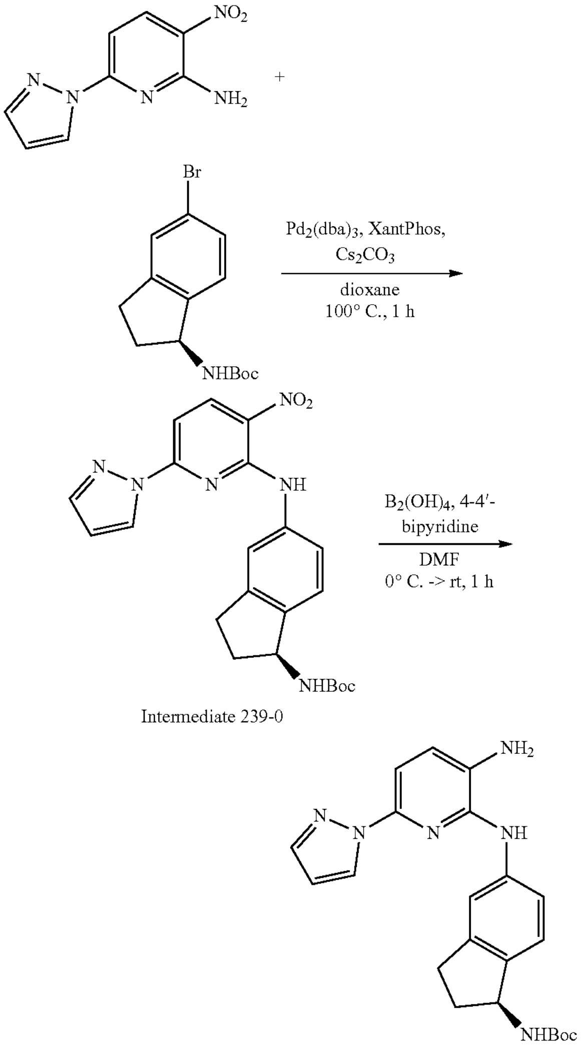

Step 1: Synthesis of tert-butyl N-[(1S)-5-{[3-nitro-6-(pyrazol-1-yl)pyridin-2-yl]amino}-2,3-dihydro-1H-inden-1-yl]carbamate (Intermediate 239-0

A mixture of tert-butyl N-[(1S)-5-bromo-2,3-dihydro-1H-inden-1-yl]carbamate (500 mg, 1.602 mmol, 1 equiv), 3-nitro-6-(pyrazol-1-yl)pyridin-2-amine (328.59 mg, 1.602 mmol, 1 equiv), $Pd_2(dba)_3$ (146.65 mg, 0.160 mmol, 0.1 equiv), xantphos (185.34 mg, 0.320 mmol, 0.2 equiv) and $Cs_2CO_3$ (1565.40 mg, 4.806 mmol, 3 equiv) in dioxane (10 mL) was stirred under $N_2$ at 100° C. for 1 h. After concentration the crude material was washed with $H_2O$ (80 mL). After drying, the residue was purified by silica gel column chromatography using a gradient of ethyl acetate in petroleum ether to afford tert-butyl N-[(1S)-5-{[3-nitro-6-(pyrazol-1-yl)pyridin-2-yl]amino}-2,3-dihydro-1H-inden-1-yl]carbamate (Intermediate 239-0) (500 mg, 71.53% yield) as a yellow solid. MS (ESI) calcd. for $C_{22}H_{24}N_6O_4$: 436.18 m/z, found: 437.20$[M+H]^+$.

Step 2: Synthesis of tert-butyl N-[(1S)-5-{[3-amino-6-(pyrazol-1-yl)pyridin-2-yl]amino}-2,3-dihydro-1H-inden-1-yl]carbamate (Intermediate 239-1

To a solution of tert-butyl N-[(1S)-5-{[3-nitro-6-(pyrazol-1-yl)pyridin-2-yl]amino}-2,3-dihydro-1H-inden-1-yl]carbamate (Intermediate 239-0) (500 mg, 1.146 mmol, 1 equiv) in DMF (4 mL) was added 4-(pyridin-4-yl)pyridine (8.95 mg, 0.057 mmol, 0.05 equiv) and $B_2(OH)_4$ (308.10 mg, 3.438 mmol, 3 equiv) at 0° C. The resulting mixture was stirred at r.t for 1 h. Water was added and the precipitate was collected by filtration to afford tert-butyl N-[(1S)-5-{[3-amino-6-(pyrazol-1-yl)pyridin-2-yl]amino}-2,3-dihydro-1H-inden-1-yl]carbamate (Intermediate 239-1) (450 mg, 86.97% yield) as a black solid. MS (ESI) calcd. for $C_{22}H_{26}N_6O_2$: 406.21 m/z, found: 407.20 $[M+H]^+$.

Example 240: 1-(4-{[(1S)-5-[2-(3-fluorophenyl)-5-(pyrazol-1-yl)imidazo[4,5-b]pyridin-3-yl]-2,3-dihydro-1H-inden-1-yl]amino}piperidin-1-yl)prop-2-en-1-one Example 240

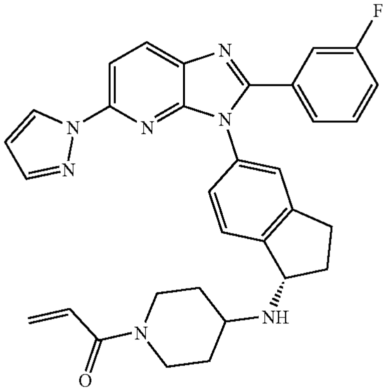

Example 240 was prepared in a manner analogous to Example 239 using 3-fluorobenzaldehyde in place of thiophene-2-carbaldehyde. MS (ESI) calcd. for $C_{32}H_{30}FN_7O$: 547.25 m/z, found: 548.15$[M+H]^+$. $^1H$ NMR (300 MHz, DMSO-$d_6$) δ (ppm): 8.29-8.40 (m, 2H), 7.92-8.01 (m, 1H), 7.72-7.82 (m, 1H), 7.22-7.68 (m, 7H), 6.79-6.89 (m, 1H), 6.49-6.58 (m, 1H), 6.08-6.16 (m, 1H), 5.63-5.71 (m, 1H), 4.25-4.39 (m, 2H), 3.92-4.03 (m, 1H), 3.05-3.20 (m, 1H), 2.71-2.99 (m, 4H), 2.40-2.52 (m, 1H), 1.73-2.01 (m, 3H), 1.16-1.34 (m, 2H).

Example 241: 1-(4-{[(1S)-5-[2-(2-fluorophenyl)-5-(pyrazol-1-yl)imidazo[4,5-b]pyridin-3-yl]-2,3-dihydro-1H-inden-1-yl]amino}piperidin-1-yl)prop-2-en-1-one Example 241

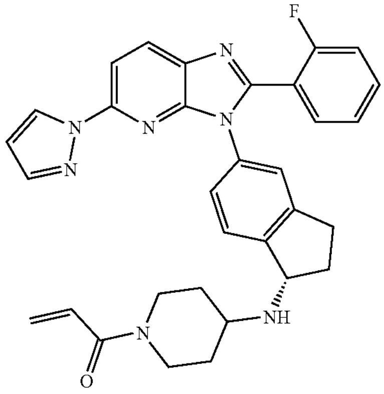

Example 241 was prepared in a manner analogous to Example 239 using 2-fluorobenzaldehyde in place of thiophene-2-carbaldehyde. MS (ESI) calcd for $C_{32}H_{30}FN_7O$: 547.25, found: 548.30 $[M+H]^+$. $^1H$ NMR (300 MHz, DMSO-$d_6$) δ(ppm) 8.39-8.45 (m, 2H), 7.99-8.01 (m, 1H), 7.83-7.84 (m, 1H), 7.74-7.78 (m, 1H), 7.61-7.66 (m, 1H), 7.51-7.59 (m, 1H), 7.37-7.39 (m, 1H), 7.32-7.35 (m, 2H), 7.21-7.26 (m, 1H), 6.80-6.86 (m, 1H), 6.58-6.60 (m, 1H), 6.10-6.15 (m, 1H), 5.70-5.73 (m, 1H), 4.96-4.99 (m, 1H), 4.52-4.55 (m, 1H), 4.18-4.20 (m, 1H), 3.12-3.18 (m, 2H), 2.89-2.96 (m, 1H), 2.68-2.74 (m, 1H), 2.54-2.60 (m, 2H), 2.08-2.23 (m, 3H), 1.46-1.51 (m, 2H). $^{19}F$ NMR (376 MHz, DMSO-$d_6$) δ (ppm): −74.08, −112.64. (TFA salt)

Example 242: 1-(4-{[(1S)-5-[2-(2-aminopyridin-3-yl)-5-isopropylimidazo[4,5-b]pyridin-3-yl]-2,3-dihydro-1H-inden-1-yl]amino}piperidin-1-yl)prop-2-en-1-one Example 242

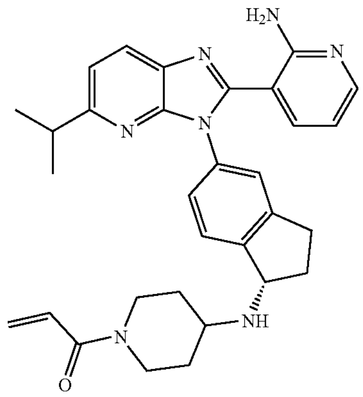

Synthetic Route:

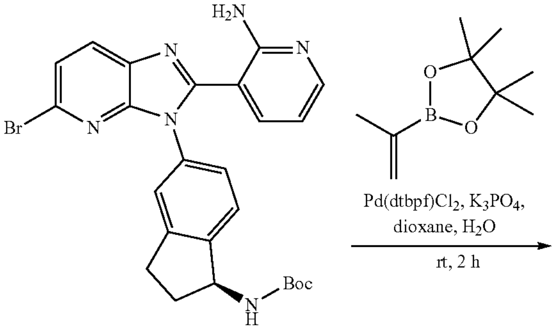

Intermediate 85-1

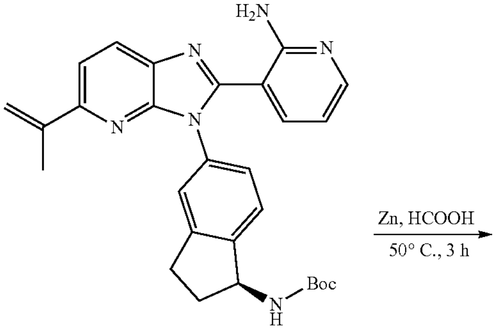

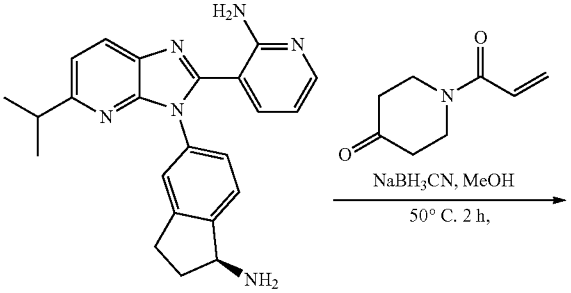

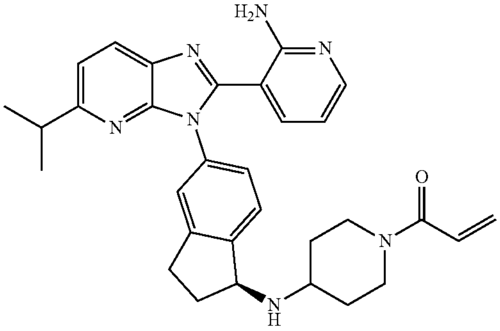

Example 242

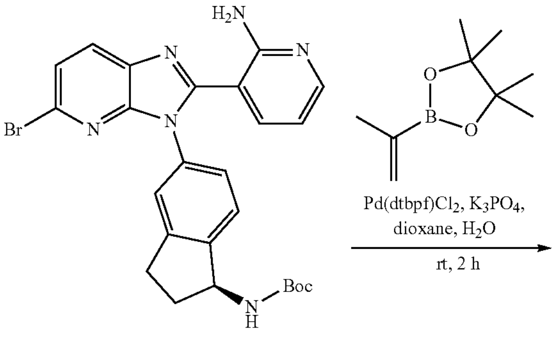

Intermediate 85-1

-continued

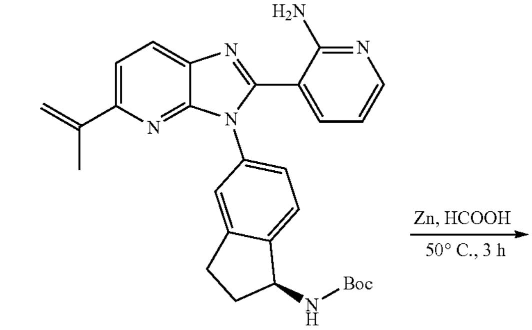

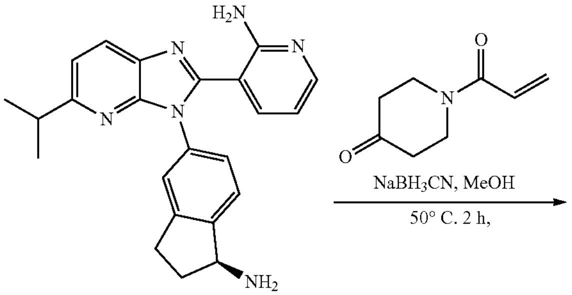

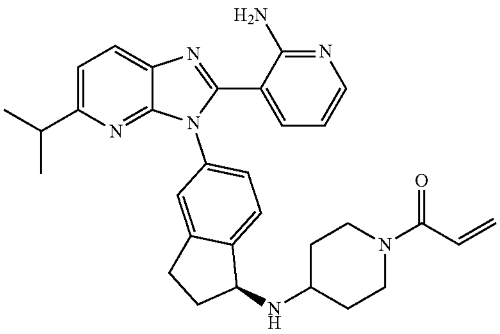

Example 242

Step 1: Synthesis of tert-butyl N-[(1S)-5-[2-(2-aminopyridin-3-yl)-5-(prop-1-en-2-yl)imidazo[4,5-b]pyridin-3-yl]-2,3-dihydro-1H-inden-1-yl]carbamate To a solution of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 85-1) (600 mg, 1.151 mmol, 1 equiv) in dioxane (6 mL) and $H_2O$ (1.5 mL) was added 4,4,5,5-tetramethyl-2-(prop-1-en-2-yl)-1,3,2-dioxaborolane (290.05 mg, 1.727 mmol, 1.5 equiv), $Pd(dtbpf)Cl_2$ (75.00 mg, 0.115 mmol, 0.1 equiv) and $K_3PO_4$ (732.76 mg, 3.453 mmol, 3 equiv). After stirring for 2 h at r.t under a nitrogen atmosphere, the reaction was quenched by the addition of saturated aqueous ammonium chloride at 0° C. The resulting mixture was extracted with ethyl acetate (20 mL×3). The combined organic layers were washed with water (10 mL×3) and dried over anhydrous $Na_2SO_4$. After filtration, the filtrate was concentrated under reduced pressure. The residue was purified by silica gel column chromatography (0-5% MeOH/DCM) giving tert-butyl N-[(1S)-5-[2-(2-aminopyridin-3-yl)-5-(prop-1-en-2-yl)imidazo[4,5-b]pyridin-3-yl]-2,3-dihydro-1H-inden-1-yl]carbamate (300 mg, 54.02% yield) as a light yellow solid. MS (ESI) calcd. for $C_{28}H_{30}N_6O_2$: 482.24 m/z, found: 483.20 $[M+H]^+$.

Step 2: Synthesis of 3-{3-[(1S)-1-amino-2,3-dihydro-1H-inden-5-yl]-5-isopropylimidazo[4,5-b]pyridin-2-yl}pyridin-2-amine To a solution of tert-butyl N-[(1S)-5-[2-(2-aminopyridin-3-yl)-5-(prop-1-en-2-yl)imidazo[4,5-b]pyridin-3-yl]-2,3-dihydro-1H-inden-1-yl]carbamate (200 mg, 0.414 mmol, 1 equiv) in formic acid (6 mL) was added Zn (200 mg, 3.059 mmol, 7.38 equiv) and the resulting mixture was stirred at 50° C. for 3 h. The reaction was quenched with $H_2O$ (2 mL) and concentrated. The residue was purified by Prep-HPLC on a XSelect CSH OBD Column using a gradient of acetonitrile in water (+0.05% $NH_4HCO_3$) to afford 3-{3-[(1S)-1-amino-2,3-dihydro-1H-inden-5-yl]-5-isopropylimidazo[4,5-b]pyridin-2-yl}pyridin-2-amine (90 mg, 56.48% yield) as a yellow solid. MS (ESI) calcd. for $C_{23}H_{34}N_6$: 384.20 m/z, found: 385.25 $[M+H]^+$.

Step 3: Synthesis of 1-(4-{[(1S)-5-[2-(2-aminopyridin-3-yl)-5-isopropylimidazo[4,5-b]pyridin-3-yl]-2,3-dihydro-1H-inden-1-yl]amino}piperidin-1-yl)prop-2-en-1-one (Example 242)

A solution of 3-{3-[(1S)-1-amino-2,3-dihydro-1H-inden-5-yl]-5-isopropylimidazo[4,5-b]pyridin-2-yl}pyridin-2-amine (80 mg, 0.208 mmol, 1 equiv) and 1-(prop-2-enoyl)piperidin-4-one (47.81 mg, 0.312 mmol, 1.5 equiv) in DCE (4 mL) and MeOH (0.4 mL) was stirred at 50° C. for 2 h. $NaBH_3CN$ (65.38 mg, 1.040 mmol, 5 equiv) was added and the mixture was stirred at 50° C. for 1 h. The reaction was quenched with $H_2O$ (2 mL) and concentrated. The residue was purified by Prep-HPLC on a XSelect CSH OBD Column using a gradient of acetonitrile in water (+0.1% FA) to afford 1-(4-{[(1S)-5-[2-(2-aminopyridin-3-yl)-5-isopropylimidazo[4,5-b]pyridin-3-yl]-2,3-dihydro-1H-inden-1-yl]amino}piperidin-1-yl)prop-2-en-1-one (Example 242) (16.0 mg, 14.52% yield) as an off-white solid. MS (ESI) calcd. for $C_{31}H_{35}N_7O$: 521.29 m/z, found: 522.25$[M+H]^+$. $^1H$ NMR (300 MHz, DMSO-$d_6$) δ (ppm): 8.20-8.27 (m, 1H), 8.09-8.15 (m, 1H), 7.96-8.02 (m, 1H), 7.45-7.50 (m, 1H), 7.27-7.32 (m, 2H), 7.16-7.23 (m, 2H), 6.78-6.92 (m, 1H), 6.37-6.39 (m, 1H), 6.06-6.15 (m, 1H), 5.63-5.69 (m, 1H), 4.38-4.45 (m, 1H), 4.25-4.31 (m, 1H), 3.96-4.06 (m, 1H), 3.46-3.50 (m, 1H), 3.10-3.21 (m, 1H), 2.90-3.09 (m, 3H), 2.72-2.89 (m, 2H), 2.50-2.52 (m, 1H), 1.95-2.04 (m, 1H), 1.78-1.92 (m, 2H), 1.25-1.36 (m, 1H), 1.20-1.24 (m, 6H). (formic acid salt)

Example 243: 1-(4-{[(1S)-5-[2-(2-aminopyridin-3-yl)-5-(3-methylpyrazol-1-yl)imidazo[4,5-b]pyridin-3-yl]-2,3-dihydro-1H-inden-1-yl]amino}piperidin-1-yl)prop-2-en-1-one Example 243

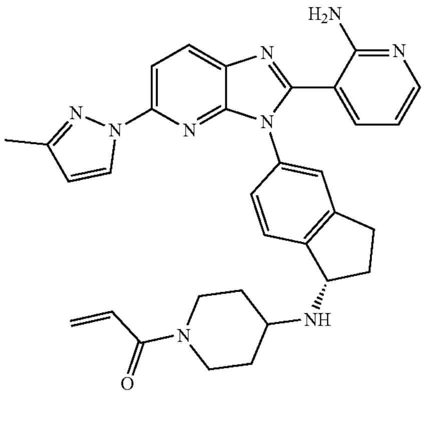

Example 243 was prepared in a manner analogous to Example 13 (via Intermediate 1-1) using Intermediate 85-1 in place of Intermediate 1-2, 3-methyl-1H-pyrazole in place of pyrazole, EPhos/EPhos Pd G4/cesium carbonate in place of tBuBrettPhos/tBuBrettPhos Pd G3/tribasic potassium phosphate, a reaction time of 4 h for step 1, 4N HCl in dioxane at room temperature overnight for the deprotection and tetrahydrofuran instead of DCE for the final step. MS (ESI) calcd. For $C_{32}H_{33}N_9O$, 559.28 m/z, found 560.35 $[M+H]^+$. $^1H$ NMR (300 MHz, DMSO-$d_6$) δ(ppm): 8.51-8.29 (m, 2H), 8.25-8.19 (m, 1H), 8.05-7.95 (m, 1H), 7.92-7.82 (m, 1H), 7.58-7.42 (m, 1H), 7.33 (s, 1H), 7.27-7.17 (m, 2H), 6.93 (s, 2H), 6.90-6.73 (m, 1H), 6.51-6.30 (m, 2H), 6.15-6.04 (m, 1H), 5.74-5.61 (m, 1H), 4.44-4.32 (m, 1H), 4.26 (s, 1H), 4.00 (s, 1H), 3.18 (s, 1H), 2.93 (s, 3H), 2.85-2.68 (m, 1H), 2.51 (s, 1H), 2.29 (s, 3H), 1.96 (s, 1H), 1.90-1.66 (m, 2H), 1.25 (s, 2H). (formic acid salt)

Example 244: 1-(4-(((*)-5-(2-(2-aminopyridin-3-yl)-5-((*)-2,2-difluorocyclopropyl)-3H-imidazo[4,5-b]pyridin-3-yl)-2,3-dihydro-1H-inden-1-yl)amino)piperidin-1-yl)prop-2-en-1-one and Example 245: 1-(4-(((*)-5-(2-(2-aminopyridin-3-yl)-5-((*)-2,2-difluorocyclopropyl)-3H-imidazo[4,5-b]pyridin-3-yl)-2,3-dihydro-1H-inden-1-yl)amino)piperidin-1-yl)prop-2-en-1-one Example 244

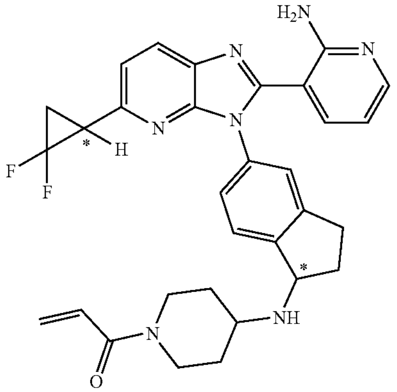

Example 245

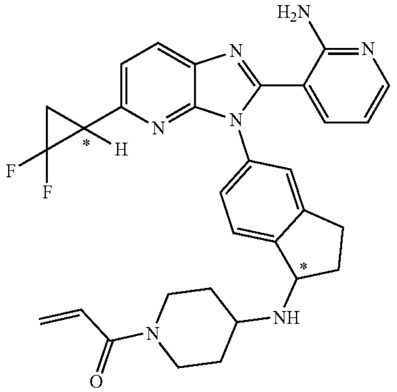

Examples 244 and 245 were prepared in a manner analogous to Example 190 using Intermediate 85-1 in place of Intermediate 190-1, potassium (2,2-difluorocyclopropyl)trifluoroborate in place of potassium cyclopropyltrifluoroborate, a reaction time of 2 h for the first step and 4N HCl in dioxane at room temperature for 1 h for the deprotection. The diastereomers were separated by chiral Prep-HPLC on a CelluloseSB column using a mixture of [MtBE/Hex (1:1) (+0.1% DEA)] and [IPA/tetrahydrofuran (1:1)]. * Denotes a stereocenter with undetermined absolute stereocenter of a single enantiomer.

Example 244: MS (ESI) calcd. For $C_{31}H_{31}F_2N_7O$: 555.26 m/z, found: 556.35 $[M+H]^+$. $^1H$ NMR (300 MHz, DMSO-$d_6$) δ 8.17-8.17 (m, 1H), 7.97-7.99 (m, 1H), 7.41-7.45 (m, 2H), 7.20-7.38 (m, 1H), 7.16-7.19 (m, 2H), 6.81-6.90 (s, 2H), 6.77 (s, 1H), 6.37-6.42 (m, 1H), 6.05-6.11 (m, 1H), 5.63-5.67 (m, 1H), 4.30-4.35 (m, 1H), 4.21-4.30 (m, 1H), 3.90-4.02 (m, 1H), 3.18-3.32 (m, 2H), 2.88-2.91 (m, 3H), 2.72-2.77 (m, 1H), 2.42-2.50 (m, 1H), 2.13-2.16 (m, 1H), 1.90-1.99 (m, 3H), 1.84-1.88 (m, 1H).

Example 244: MS (ESI) calcd. For $C_{31}H_{31}F_2N_7O$: 555.26 m/z, found: 556.30$[M+H]^+$. $^1H$ NMR (300 MHz, DMSO-$d_6$) δ 8.14-8.17 (s, 1H), 7.97-8.00 (m, 1H), 7.20-7.48 (m, 2H), 7.18 (m, 3H), 6.89 (m, 3H), 6.38-6.42 (m, 1H), 6.05-6.06 (m, 1H), 5.63-5.68 (m, 1H), 4.39 (m, 1H), 4.26 (m, 1H), 4.00-4.02 (m, 1H), 3.12-3.33 (m, 2H), 2.50-2.98 (m, 4H), 2.42-2.49 (m, 1H), 2.11-2.17 (m, 1H), 1.23-1.99 (m, 4H).

Example 246: 1-(4-{[(1S)-5-{5-cyclopropyl-2-phenylimidazo[4,5-b]pyridin-3-yl}-2,3-dihydro-1H-inden-1-yl]amino}piperidin-1-yl)prop-2-en-1-one Example 246

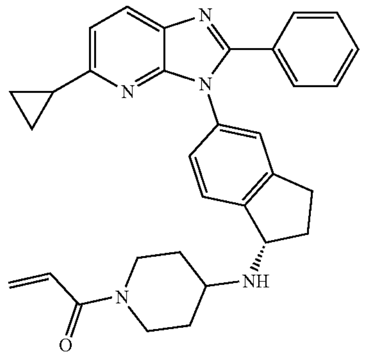

Example 246 was prepared in a manner analogous to Example 199 using Intermediate 246-1 in place of Intermediate 190-1 and tetrahydrofuran as the solvent for the final step. MS (ESI) calcd. For $C_{32}H_{33}N_5O$: 503.27 m/z, found: 504.15 $[M+H]^+$. $^1H$ NMR (300 MHz, DMSO-d6) δ (ppm): 8.11-7.90 (m, 111), 7.57-7.44 (m, 3H), 7.44-7.27 (m, 3H), 7.27-7.07 (m, 3H), 6.90-6.66 (m, 1H), 6.18-5.92 (m, 1H), 5.72-5.55 (m, 1H), 4.50-4.36 (m, 1H), 4.28 (s, 1H), 4.15-3.89 (m, 1H), 3.25-3.06 (m, 1H), 3.06-2.56 (m, 5H), 2.47-2.29 (m, 1H), 2.23-2.05 (m, 1H), 2.05-1.68 (m, 3H), 1.40-1.08 (m, 2H), 1.08-0.52 (m, 4H). (formic acid salt)

Intermediate 246-1: N-[(1S)-5-{5-bromo-2-phenylimidazo[4,5-b]pyridin-3-yl}-2,3-dihydro-1H-inden-1-yl]acetamide Intermediate 246-1

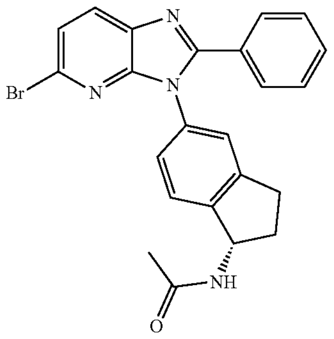

Synthetic Route:

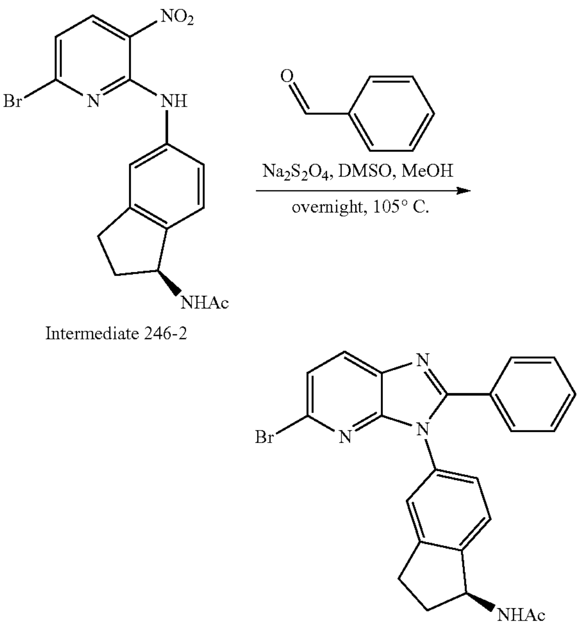

Intermediate 246-2

Intermediate 246-1

Step 1: Synthesis N-[(1S)-5-{5-bromo-2-phenylimidazo[4,5-b]pyridin-3-yl}-2,3-dihydro-1H-inden-1-yl]acetamide (Intermediate 246-1

A solution of N-[(1S)-5-[(6-bromo-3-nitropyridin-2-yl)amino]-2,3-dihydro-1H-inden-1-yl]acetamide (Intermediate 246-2) (3 g, 7.668 mmol, 1 equiv) and $Na_2S_2O_4$ (2.94 g, 16.870 mmol, 2.2 equiv) in DMSO/MeOH (30 mL: 5 mL) was treated with benzaldehyde (0.85 g, 8.051 mmol, 1.05 equiv) at room temperature. The resulting mixture was stirred overnight at 105° C. under air atmosphere. The mixture was allowed to cool to room temperature. The reaction was quenched with water at room temperature. The resulting mixture was extracted with ethyl acetate (3×40 mL). The combined organic layers were washed with water (3×40 mL) and dried over anhydrous $Na_2SO_4$. After filtration, the filtrate was concentrated under reduced pressure. The residue was purified by trituration with $Et_2O$ (500 mL) to afford N-[(1S)-5-{5-bromo-2-phenylimidazo[4,5-b]pyridin-3-yl}-2,3-dihydro-1H-inden-1-yl]acetamide (Intermediate 246-1) (1.26 g, 23.88%) as a brown yellow solid. The crude product was used in subsequent steps without further purification. MS (ESI) calcd. For $C_{23}H_{19}BrN_4O$: 446.07 m/z, found: 447.10 $[M+H]^+$.

Intermediate 246-2: (S)-N-(5-((6-bromo-3-nitropyridin-2-yl)amino)-2,3-dihydro-1H-inden-1-yl)acetamide Intermediate 246-2

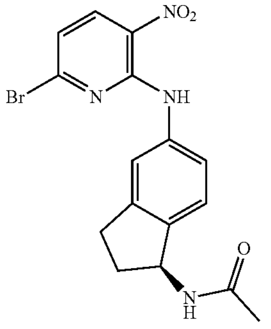

Synthetic Route:

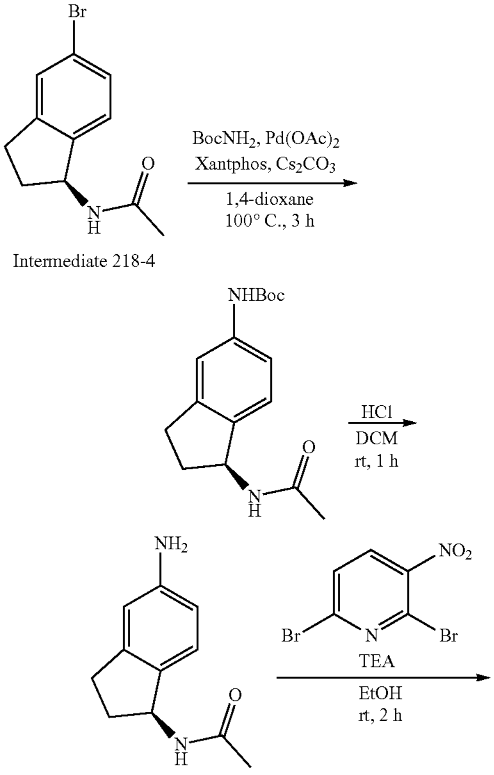

Intermediate 218-4

-continued

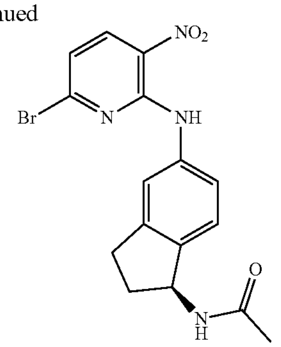

Intermediate 246-2

Step 1: Synthesis of tert-butyl (S)-(1-acetamido-2,3-dihydro-1H-inden-5-yl)carbamate To a mixture of N-[(1S)-5-bromo-2,3-dihydro-1H-inden-1-yl]acetamide (Intermediate 218-4) (40 g, 157 mmol, 1 equiv), tert-butyl carbamate (27.66 g, 236 mmol, 1.5 equiv), XantPhos (CAS: 161265-03-8) (9.11 g, 15.7 mmol, 10 mol %), $Pd(Oac)_2$ (3.54 g, 15.7 mmol, 10 mol %), and cesium carbonate (154 g, 472 mmol, 10 mol %) was added 1,4-dioxane (300 mL) under nitrogen atmosphere. The resulting mixture was stirred for 3 h at 100° C. The reaction mixture was quenched by addition of water (50 mL) and extracted with ethyl acetate (3×50 mL). The combined organic layers were dried over anhydrous sodium sulfate and concentrated under reduced pressure. The residue was purified by silica gel column chromatography using an eluent of petroleum ether/dichloromethane/methanol (70:27:3) to afford tert-butyl N-[(1S)-1-acetamido-2,3-dihydro-1H-inden-5-yl]carbamate (43.1 g, 48% yield). MS (ESI) calculated for $C_{16}H_{22}N_2O_3$: 290.16, found 289.05 $[M-H]^-$.

Step 2: Synthesis of (S)-N-(5-amino-2,3-dihydro-1H-inden-1-yl)acetamide

To a stirred solution of tert-butyl N-[(1S)-1-acetamido-2,3-dihydro-1H-inden-5-yl]carbamate (43.1 g, 148 mmol, 1 equiv) in dichloromethane (180 mL) was added 4N HCl in 1,4-dioxane (185 mL, 742 mmol, 5 equiv). The reaction mixture was stirred for 1 h at room temperature. The reaction mixture was concentrated in vacuo and re-crystallized from ethyl acetate to afford N-[(1S)-5-amino-2,3-dihydro-1H-inden-1-yl]acetamide (hydrochloride salt) (23 g, 81% yield) as a white solid. MS (ESI) calculated for $C_{11}H_{14}N_2O$: 190.11, found 191.15 $[M+H]^+$.

Step 3: (S)-N-(5-((6-bromo-3-nitropyridin-2-yl)amino)-2,3-dihydro-1H-inden-1-yl)acetamide (Intermediate 246-2

N-[(1S)-5-amino-2,3-dihydro-1H-inden-1-yl]acetamide (17 g, 89 mmol) and 2,6-dibromo-3-nitropyridine (25.19 g, 89.36 mmol) were dissolved in triethylamine (45.21 g, 446.8 mmol, 5 equiv) and ethanol (200 mL). The reaction mixture was stirred at room temperature for 2 h. The reaction mixture was quenched with 400 mL water and the precipitate was rinsed with 1:1 ethanol/water (800 mL:800 mL) to afford N-[(1S)-5-[(6-bromo-3-nitropyridin-2-yl)amino]-2,3-dihydro-1H-inden-1-yl]acetamide (Intermediate 246-2) (26 g, 74% yield) as an orange solid. MS (ESI) calculated for $C_{16}H_{15}BrN_4O_3$: 390.03, found 413.00 $[M+Na]^+$, 415.00 $[M+Na+2]^+$.

Example 247: 1-(4-{[(1S)-5-[2-(4-fluorophenyl)-5-(pyrazol-1-yl)imidazo[4,5-b]pyridin-3-yl]-2,3-dihydro-1H-inden-1-yl]amino}piperidin-1-yl)prop-2-en-1-one Example 247

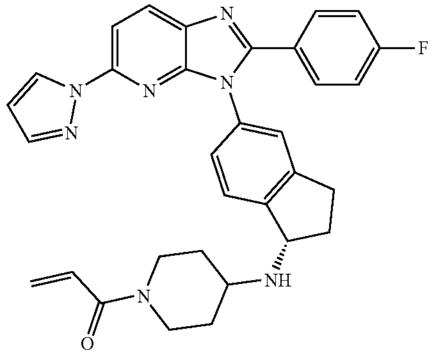

Example 247 was prepared in a manner analogous to Example 239 using 4-fluorobenzaldehyde in place of thiophene-2-carbaldehyde. MS (ESI) calcd. For $C_{32}H_{30}FN_7O$: 547.25 m/z, found: 548.30 $[M+H]^+$. $^1$H-NMR (400 MHz, DMSO) S (ppm): 8.32-8.40 (m, 2H), 7.95-8.00 (m, 1H), 7.78-7.85 (m, 1H), 7.66-7.75 (m, 1H), 7.56-7.65 (m, 2H), 7.52-7.55 (m, 1H), 7.72-7.40 (m, 1H), 7.20-7.31 (m, 2H), 6.75-6.90 (m, 1H), 6.54-6.60 (m, 1H), 6.09-6.20 (m, 1H), 5.70-5.79 (m, 1H), 4.96-5.05 (m, 1H), 4.48-4.60 (m, 1H), 4.12-4.25 (m, 1H), 3.51-3.63 (m, 1H), 3.10-3.22 (m, 2H), 2.91-3.05 (m, 1H), 2.65-2.80 (m, 1H), 2.55-2.64 (m, 1H), 2.18-2.30 (m, 2H), 2.08-2.15 (m, 1H), 1.40-1.60 (m, 2H). $^{19}$F NMR (376 MHz, DMSO-$d_6$) δ (ppm): −109.90, −73.89. (TFA salt)

Example 248: (S)-1-(4-((5-(2-cyclopropyl-5-(1H-pyrazol-1-yl)-3H-imidazo[4,5-b]-430-pyridine-3-yl)-2,3-dihydro-1H-inden-1-yl)amino)piperidin-1-yl) prop-2-en-1-one Example 248

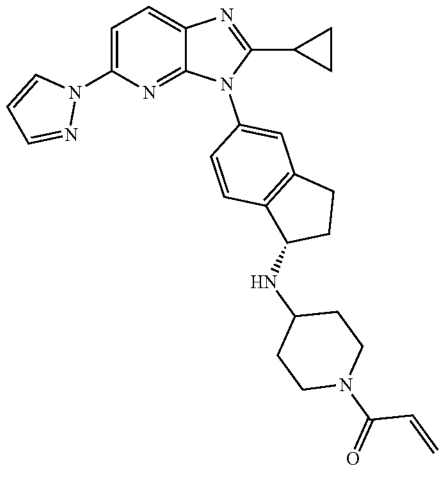

Example 248 was prepared in a manner analogous to Example 239 using cyclopropanecarbaldehyde in place of thiophene-2-carbaldehyde. MS (ESI) calcd. For $C_{29}H_{31}N_7O$: 493.26 m/z, found: 494.15 $[M+H]^+$. $^1$H-NMR (400 MHz, DMSO) S (ppm): 8.25-8.33 (m, 1H), 8.11-8.20 (m, 1H), 7.81-7.90 (m, 2H), 7.75-7.80 (m, 1H), 7.65-7.74 (m, 1H), 7.60-7.64 (m, 1H), 6.75-6.90 (m, 1H), 6.50-6.55 (m, 1H), 6.10-6.20 (m, 1H), 5.70-5.79 (m, 1H), 4.99-5.10 (m, 1H), 4.48-4.60 (m, 1H), 4.13-4.25 (m, 1H), 3.55-3.65 (m, 1H), 3.12-3.30 (m, 2H), 3.00-3.11 (m, 1H), 2.68-2.81 (m, 1H), 2.55-2.67 (m, 1H), 2.20-2.30 (m, 2H), 2.10-2.19 (m, 1H), 1.88-1.99 (m, 1H), 1.44-1.62 (m, 2H), 1.18-1.25 (m, 2H), 1.05-1.17 (m, 2H). (TFA salt)

Example 249: 1-(4-(((1R,2*)-2-fluoro-5-(2-phenyl-5-(1H-pyrazol-1-yl)-3H-imidazo[4,5-b]pyridin-3-yl)-2,3-dihydro-1H-inden-1-yl)amino)piperidin-1-yl) prop-2-en-1-one and Example 250: 1-(4-(((1R,2*)-2-fluoro-5-(2-phenyl-5-(1H-pyrazol-1-yl)-3H-imidazo[4,5-b]pyridin-3-yl)-2,3-dihydro-1H-inden-1-yl)amino)piperidin-1-yl) prop-2-en-1-one Example 249

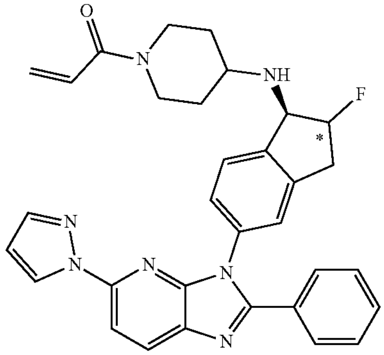

Example 250

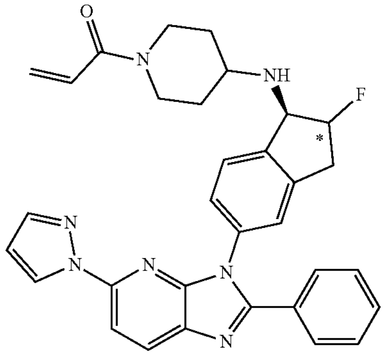

Examples 249 and 250 were prepared in a manner analogous to Example 13 using Intermediates 249-1 and 250-1, respectively, in place of Intermediate 1-1 and MeOH/room temperature/2 h instead of DCE/40° C. overnight. * Denotes a stereocenter with undetermined absolute stereocenter of a single diastereomer.

Example 249: MS (ESI) calcd. For $C_{32}H_{30}FN_7O$: 547.25 m/z, found: 548.30 $[M+H]^+$. $^1$H-NMR (400 MHz, DMSO-$d_6$) δ (ppm): 8.35-8.37 (m, 2H), 7.94-7.96 (m, 1H), 7.80-7.81 (m, 1H), 7.38-7.57 (m, 7H), 7.28-7.30 (m, 1H), 6.77-6.84 (m, 1H), 6.54-6.55 (m, 1H), 6.06-6.11 (m, 1H), 5.65-

5.69 (m, 1H), 5.15-5.35 (m, 1H), 4.37-4.42 (m, 1H), 4.25-4.30 (m, 1H), 3.95-4.05 (m, 1H), 3.41-3.47 (m, 1H), 3.12-3.19 (m, 1H), 2.92-3.02 (m, 2H), 2.81-2.86 (m, 1H), 1.84-2.02 (m, 2H), 1.18-1.28 (m, 2H).

Example 250: MS (ESI) calcd. For $C_{32}H_{30}FN_7O$: 547.25 m/z, found: 548.30 $[M+H]^+$. $^1H$-NMR (400 MHz, DMSO-$d_6$) δ (ppm): 8.34-8.37 (m, 2H), 7.94-7.96 (m, 1H), 7.79-7.81 (m, 1H), 7.51-7.59 (m, 2H), 7.42-7.50 (m, 1H), 7.31-7.41 (m, 5H), 6.75-6.85 (m, 1H), 6.54-6.55 (m, 1H), 6.05-6.11 (m, 1H), 5.65-5.69 (m, 1H), 5.40-5.55 (m, 1H), 4.39-4.48 (m, 1H), 3.95-4.28 (m, 2H), 3.19-3.25 (m, 2H), 3.01-3.28 (m, 2H), 2.91-2.99 (m, 1H), 1.81-2.06 (m, 2H), 1.22-1.38 (m, 2H).

Intermediate 249-1: (1R,2*)-2-fluoro-5-(2-phenyl-5-(1H-pyrazol-1-yl)-3H-imidazo[4,5-b]pyridin-3-yl)-2,3-dihydro-1H-inden-1-amine and Intermediate 250-1: (1R,2*)-2-fluoro-5-(2-phenyl-5-(1H-pyrazol-1-yl)-3H-imidazo[4,5-b]pyridin-3-yl)-2,3-dihydro-1H-inden-1-amine Intermediate 249-1

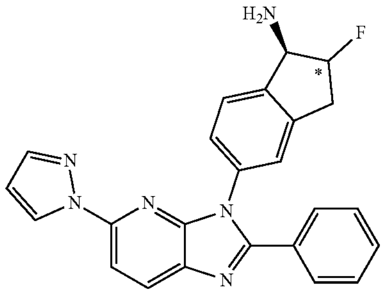

Intermediate 250-1

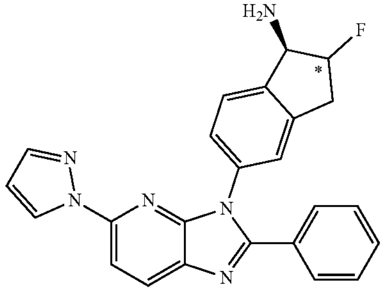

Intermediates 249-1 and 250-1 were prepared in a manner analogous to Intermediates 75-1 and 76-1 using benzaldehyde in place of 2-aminopyridine-3-carbaldehyde. * Denotes a stereocenter with undetermined absolute stereocenter of a single diastereomer.

Intermediate 249-1: MS (ESI) calcd. For $C_{24}H_{19}FN_6$: 410.16 m/z, found: 411.15 $[M+H]^+$.

Intermediate 250-1: MS (ESI) calcd. For $C_{24}H_{19}FN_6$: 410.16 m/z, found: 411.15 $[M+H]^+$.

Example 251: 1-(4-{[(1S)-5-[2-(2-fluoropyridin-3-yl)-5-(pyrazol-1-yl)imidazo[4,5-b]pyridin-3-yl]-2,3-dihydro-1H-inden-1-yl]amino}piperidin-1-yl)prop-2-en-1-one Example 251

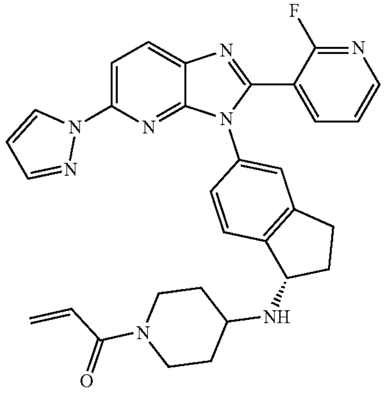

Example 251 was prepared in a manner analogous to Example 239 using 2-fluoropyridine-3-carbaldehyde in place of thiophene-2-carbaldehyde. MS (ESI) calcd. For $C_{31}H_{29}FN_8O$: 548.24 m/z, found: 549.30 $[M+H]^+$. $^1H$ NMR (400 MHz, DMSO-$d_6$) δ (ppm): 8.37-8.45 (m, 4H), 8.03-8.05 (m, 1H), 7.85-7.86 (m, 1H), 7.68-7.70 (m, 1H), 7.55-7.61 (m, 2H), 7.38-7.40 (m, 1H), 6.80-6.87 (m, 1H), 6.59-6.61 (m, 1H), 6.14-6.18 (m, 1H), 5.76-5.79 (m, 1H), 4.99-5.04 (m, 1H), 4.55-4.56 (m, 1H), 4.19-4.20 (m, 1H), 3.62-3.93 (m, 1H), 3.15-3.21 (m, 2H), 2.96-3.00 (m, 1H), 2.73-2.79 (m, 1H), 2.58-2.63 (m, 1H), 2.20-2.27 (m, 2H), 2.11-2.14 (m, 1H), 1.51-1.56 (m, 2H). $^{19}F$ NMR (376 MHz, DMSO-$d_6$) δ (ppm): −66.94, −73.93. (TFA salt)

Example 252: 1-(4-{[(1S)-5-[2-(2-aminopyridin-3-yl)-5-(3-chloropyrazol-1-yl)imidazo[4,5-b]pyridin-3-yl]-2,3-dihydro-1H-inden-1-yl]amino}piperidin-1-yl)prop-2-en-1-one Example 252

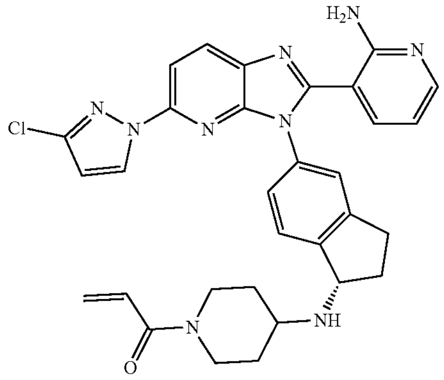

Example 252 was prepared in a manner analogous to Example 13 (via Intermediate 1-1) using Intermediate 85-1 in place of Intermediate 1-2, 3-chloro-1H-pyrazole in place of pyrazole, Ephos/Ephos Pd G4/cesium carbonate in place of tBuBrettPhos/tBuBrettPhos Pd G3/tribasic potassium phosphate, 4N HCl in dioxane at room temperature overnight for the deprotection and MeOH instead of DCE for the final step. MS (ESI) calcd. For $C_{31}H_{30}ClN_9O$, 579.23 m/z, found 580.15 $[M+H]^+$. $^1H$ NMR (300 MHz, DMSO-$d_6$) δ (ppm): 8.34-8.37 (m, 2H), 7.98-8.00 (m, 1H), 7.84 (d, J=8.7 MHz, 1H), 7.46-7.49 (m, 2H), 7.21-7.33 (m, 2H), 6.91 (s, 2H), 6.64-6.86 (m, 2H), 6.39-6.43 (m, 1H), 6.04-6.11 (m, 1H), 5.63-5.67 (m, 1H), 4.25-4.35 (m, 2H), 3.96-4.02 (m, 1H), 3.16-3.20 (m, 1H), 2.77-2.93 (m, 4H), 2.41-2.45 (m, 1H), 1.85-1.98 (m, 3H), 1.22-1.25 (m, 2H).

Example 253: 1-(4-{[(1S)-5-[2-(2-aminopyridin-3-yl)-5-(4-methyl-1,3-oxazol-2-yl)imidazo[4,5-b]pyridin-3-yl]-2,3-dihydro-1H-inden-1-yl]amino}piperidin-1-yl)prop-2-en-1-one Example 253

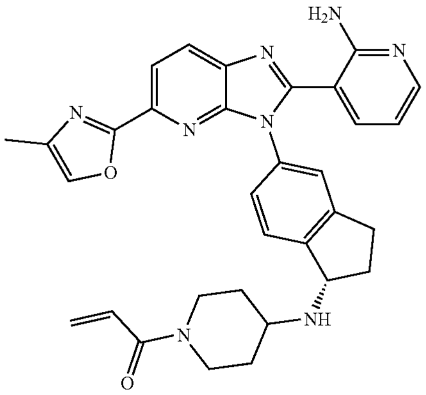

Example 253 was prepared in a manner analogous to Example 109 (via Intermediate 109-2) using 2-bromo-4-methyl-1,3-oxazole in place of 2-bromo-1,3-oxazole, 4N HCl in dioxane in place of TFA in DCM and MeOH in place of DCE. MS (ESI) calcd. For $C_{32}H_{32}N_8O_2$, 560.20 m/z, found 561.20 $[M+H]^+$. $^1H$ NMR (400 MHz, DMSO-$d_6$) δ 8.31 (d, J=8.4 Hz, 1H), 8.10 (d, J=8.4 Hz, 1H), 7.99-8.00 (m, 1H), 7.92-7.93 (m, 1H), 7.49 (d, J=8.0 Hz, 1H), 7.32-7.33 (m, 1H), 7.23-7.28 (m, 2H), 6.99 (s, 2H), 6.80-6.87 (m, 1H), 6.39-6.43 (m, 1H), 6.07-6.11 (m, 1H), 5.64-5.67 (m, 1H), 4.34-4.36 (m, 1H), 4.22-4.26 (m, 1H), 3.97-4.02 (m, 1H), 3.16-3.20 (m, 1H), 2.89-2.95 (m, 3H), 2.75-2.79 (m, 1H), 2.44-2.46 (m, 1H), 2.12-2.17 (m, 4H), 1.88-1.97 (m, 2H), 1.78-1.81 (m, 1H), 1.23-1.27 (m, 2H).

Example 254: (S)-1-(4-((5-(2-(2-aminopyridin-3-yl)-5-(4-fluoro-1H-pyrazol-1-yl)-3H-imidazo[4,5-b]pyridin-3-yl)-2,3-dihydro-1H-inden-1-yl)amino)piperidin-1-yl)prop-2-en-1-one Example 254

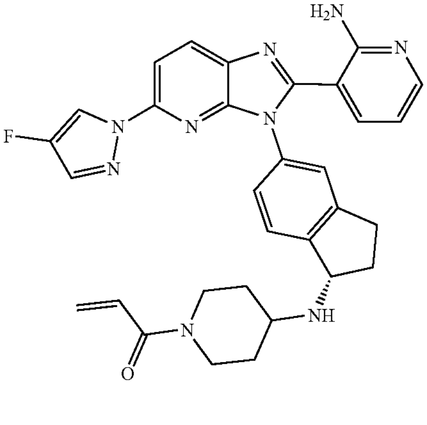

Example 254 was prepared in a manner analogous to Example 13 (via Intermediate 1-1) using Intermediate 85-1 in place of Intermediate 1-2, 4-fluoro-1H-pyrazole in place of pyrazole, Ephos/Ephos Pd G4/cesium carbonate in place of tBuBrettPhos/tBuBrettPhos Pd G3/tribasic potassium phosphate, a reaction time of overnight for step 1, 4N HCl in dioxane at room temperature for 1 h for the deprotection and MeOH instead of DCE for the final step. MS (ESI) calcd. For $C_{31}H_{30}FN_9O$, 563.26 m/z, found 564.20 $[M+H]^+$. $^1H$ NMR (400 MHz, DMSO-$d_6$) δ (ppm): 8.36-8.40 (m, 2H), 8.24 (s, 1H), 7.91-8.02 (m, 3H), 7.49 (d, J=8.0 MHz, 1H), 7.33-7.34 (m, 1H), 7.22-7.26 (m, 2H), 6.93 (s, 2H), 6.80-6.87 (m, 1H), 6.41-6.44 (m, 1H), 6.07-6.11 (m, 1H), 5.64-5.68 (m, 1H), 4.35-4.39 (m, 1H), 4.25-4.29 (m, 1H), 4.00-4.01 (m, 1H), 3.14-3.19 (m, 1H), 2.80-2.99 (m, 4H), 2.44-2.46 (m, 1H), 1.97-1.98 (m, 1H), 1.85-1.87 (m, 1H), 1.79-1.80 (m, 1H), 1.23-1.26 (m, 2H). $^{19}F$ NMR (376 MHz, DMSO-$d_6$) δ (ppm): −174.36. (formic acid salt)

Example 255: 1-(4-{[(1S)-5-[2-(2-aminopyridin-3-yl)-5-(5-methyl-1,3-oxazol-2-yl)imidazo[4,5-b]pyridin-3-yl]-2,3-dihydro-1H-inden-1-yl]amino}piperidin-1-yl)prop-2-en-1-one Example 255

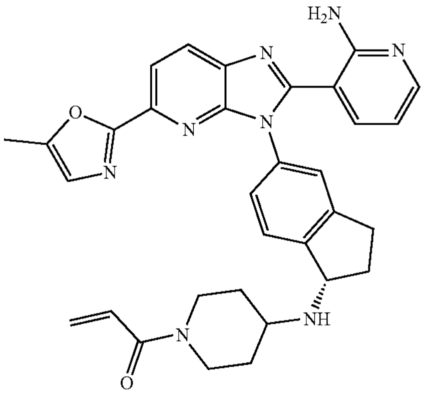

Example 255 was prepared in a manner analogous to Example 159 (via Intermediate 159-1) using 5-methyl-2-(tributylstannyl)-1,3-oxazole in place of 2-(tributylstannyl)-1,3-thiazole, Intermediate 85-1 in place of Intermediate 1-2 and 4N HCl in dioxane at room temperature for 2 h for the deprotection. MS (ESI) calcd. For $C_{32}H_{32}N_8O_2$, 560.66 m/z, found 561.15$[M+H]^+$. $^1H$ NMR (500 MHz, DMSO-d6) δ 8.31 (d, J=8.4 Hz, 1H), 8.10 (d, J=8.3 Hz, 1H), 8.00 (dd, J=4.8, 1.8 Hz, 1H), 7.50 (d, J=7.9 Hz, 1H), 7.34 (s, 1H), 7.27 (dd, J=7.9, 2.0 Hz, 1H), 7.23 (dd, J=7.7, 1.9 Hz, 1H), 7.04 (d, J=1.3 Hz, 1H), 6.97 (s, 2H), 6.86-6.81 (m, 1H), 6.42-6.40 (m, 1H), 6.09 (dd, J=16.7, 2.5 Hz, 1H), 5.66 (dd, J=10.5, 2.5 Hz, 1H), 4.39-4.33 (m, 1H), 4.28-4.22 (m, 1H), 4.00-3.96 (m, 1H), 3.21-3.15 (m, 1H), 2.98-2.90 (m, 3H), 2.82-2.75 (m, 1H), 2.41-2.36 (m, 3H), 2.14-2.09 (m, 1H), 2.01-1.94 (m, 1H), 1.91-1.86 (m, 1H), 1.85-1.74 (m, 1H), 1.24 (s, 3H).

Example 256: (S)-1-(4-((5-(2-(2-aminopyridin-3-yl)-5-(5-methyl-1,3,4-oxadiazol-2-yl)-3H-imidazo[4,5-b]pyridin-3-yl)-2,3-dihydro-1H-inden-1-yl)amino)piperidin-1-yl)prop-2-en-1-one Example 256

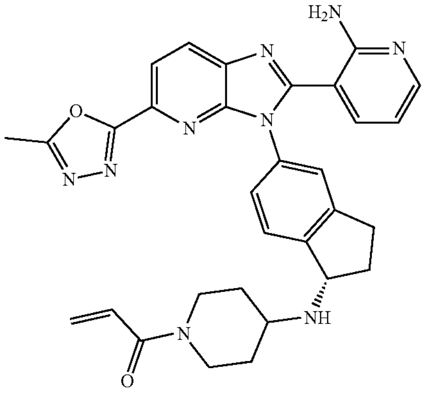

Example 256 was prepared in a manner analogous to Example 109 (via Intermediate 109-2) using 2-bromo-5-methyl-1,3,4-oxadiazole instead of 2-bromo-1,3-oxazole, $Pd(dppf)Cl_2$ and tribasic potassium phosphate instead of $Pd(dtbpf)Cl_2$ and potassium carbonate and HCl in dioxane instead of TFA/DCM. MS (ESI) mass calcd. For $C_{31}H_{31}N_9O_2$, 561.00 m/z, found 562.20[M+H]$^+$. $^1$H NMR (400 MHz, DMSO-$d_6$) δ 8.40 (d, J=8.3 Hz, 1H), 8.17 (d, J=8.2 Hz, 1H), 8.02 (d, J=4.8 Hz, 1H), 7.50 (d, J=8.0 Hz, 1H), 7.35 (s, 1H), 7.27 (t, J=8.1 Hz, 2H), 6.98 (s, 2H), 6.84 (dd, J=16.7, 10.4 Hz, 1H), 6.46-6.39 (m, 1H), 6.14-6.04 (m, 1H), 5.70-5.62 (m, 1H), 4.36 (t, J=7.3 Hz, 1H), 4.27-4.23 (m, 1H), 4.02-3.98 (m, 1H), 3.20-3.16 (m, 2H), 2.95-2.90 (m, 3H), 2.89-2.72 (m, 2H), 2.58 (s, 3H), 1.99-1.95 (m, 1H), 1.90-1.86 (m, 1H), 1.81-1.77 (m, 1H), 1.27-1.23 (m, 2H).

Example 257: (S)-1-(4-((5-(2-(2-aminopyridin-3-yl)-5-(5-methyl-1,3,4-thiadiazol-2-yl)-3H-imidazo[4,5-b]pyridin-3-yl)-2,3-dihydro-1H-inden-1-yl)amino)piperidin-1-yl)prop-2-en-1-one Example 257

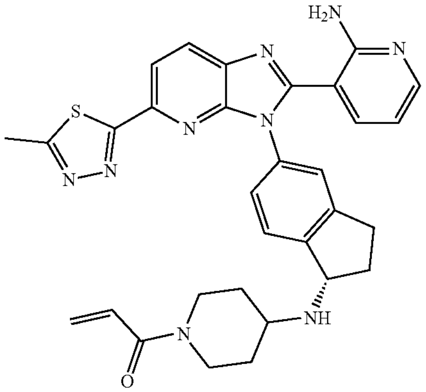

Example 257 was prepared in a manner analogous to Example 109 (via Intermediate 109-2) using 2-bromo-5-methyl-1,3,4-thiadiazole, $Pd(dppf)Cl_2$ and tribasic potassium phosphate instead of 2-bromo-1,3-oxazole, $Pd(dtbpf)Cl_2$ and potassium carbonate, HCl in dioxane instead of TFA/DCM. MS (ESI) mass calcd. For $C_{31}H_{31}N_9OS$, 577.24 m/z, found 578.35[M+H]$^+$. $^1$H NMR (400 MHz, DMSO-$d_6$) δ 8.37 (d, J=8.3 Hz, 1H), 8.26 (d, J=8.3 Hz, 1H), 8.03 (dd, J=4.8, 1.8 Hz, 1H), 7.49 (d, J=7.9 Hz, 1H), 7.33 (s, 1H), 7.31-7.23 (m, 2H), 6.94 (s, 2H), 6.84 (dd, J=16.7, 10.4 Hz, 1H), 6.44 (dd, J=7.7, 4.8 Hz, 1H), 6.10 (dd, J=16.7, 2.5 Hz, 1H), 5.67 (dd, J=10.4, 2.5 Hz, 1H), 4.37 (t, J=7.2 Hz, 1H), 4.29-4.25 (m, 1H), 4.03-3.99 (m, 1H), 3.20-3.16 (m, 1H), 2.99-2.78 (m, 5H), 2.74 (s, 3H), 2.50-2.43 (m, 1H), 2.01-1.97 (m, 1H), 1.90-1.72 (m, 2H), 1.29-1.22 (m, 2H).

Example 258: 1-(4-{[(1S)-5-[2-(2-aminopyridin-3-yl)-5-{8-oxa-3-azabicyclo[3.2.1]octan-3-yl}imidazo[4,5-b]pyridin-3-yl]-2,3-dihydro-1H-inden-1-yl]amino}piperidin-1-yl)prop-2-en-1-one Example 258

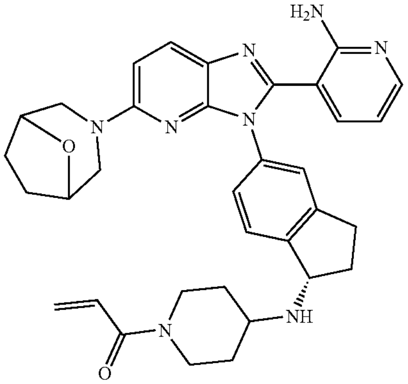

Example 258 was prepared in a manner analogous to Example 75 (via Intermediate 75-1) omitting steps 1-3 and the chiral separation (of Intermediate 75-1) and using tert-butyl (S)-(5-bromo-2,3-dihydro-1H-inden-1-yl)carbamate in place of (S)-N-((1R)-5-bromo-2-fluoro-2,3-dihydro-1H-inden-1-yl)-2-methylpropane-2-sulfinamide and Intermediate 258-1 in place of 3-nitro-6-(pyrazol-1-yl)pyridin-2-amine. MS (ESI) calcd. For $C_{34}H_{38}N_8O_2$: 590.31 m/z, found: 591.20 [M+H]$^+$. $^1$H-NMR (400 MHz, DMSO) S (ppm): 7.98-8.10 (m, 2H), 7.65-7.75 (m, 1H), 7.43-7.60 (m, 2H), 7.35-7.42 (m, 1H), 6.78-6.90 (m, 2H), 6.69-6.76 (m, 1H), 6.11-6.20 (m, 1H), 5.70-5.80 (m, 1H), 4.95-5.05 (m, 1H), 4.50-4.61 (m, 1H), 4.40-4.49 (m, 2H), 4.15-4.25 (m, 1H), 3.75-3.85 (m, 2H), 3.51-3.65 (m, 1H), 3.10-3.25 (m, 2H), 2.85-3.05 (m, 3H), 2.65-2.80 (m, 1H), 2.55-2.64 (m, 1H), 2.08-2.30 (m, 3H), 1.80-1.90 (m, 2H), 1.63-1.75 (m, 2H), 1.45-1.62 (m, 2H). (TFA salt).

Intermediate 258-1: 6-(8-oxa-3-azabicyclo[3.2.1]octan-3-yl)-3-nitropyridin-2-amine Intermediate 258-1

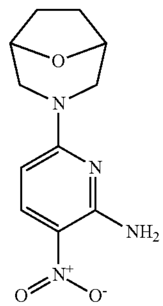

Synthetic Route:

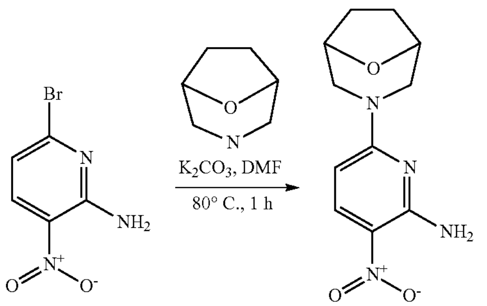

Intermediate 258-1

Step 1: Synthesis of 6-(8-oxa-3-azabicyclo[3.2.1]octan-3-yl)-3-nitropyridin-2-amine A mixture of 6-bromo-3-nitropyridin-2-amine (1.2 g, 5.504 mmol, 1 equiv), 8-oxa-3-azabicyclo[3.2.1]octane (0.62 g, 5.504 mmol, 1 equiv) and $K_2CO_3$ (2.28 g, 16.512 mmol, 3 equiv) in DMF (15 mL) was stirred for 1 h at room temperature. The product was precipitated by the addition of $H_2O$ (50 mL). The precipitated solids were collected by filtration and washed with $H_2O$ (3x10 mL) to afford tert-butyl N-[(1S)-5-[(3-nitro-6-{8-oxa-3-azabicyclo[3.2.1]octan-3-yl}pyridin-2-yl)amino]-2,3-dihydro-1H-inden-1-yl]carbamate (1.35 g, crude) as a yellow solid. MS (ESI) calcd. For $C_{11}H_{14}N_4O_3$: 250.11 m/z, found: 251.05 $[M+H]^-$.

Example 259: 1-(4-{[(1S)-5-[2-(2-aminopyridin-3-yl)-5-(4-methylpiperazin-1-yl)imidazo[4,5-b]pyridin-3-yl]-2,3-dihydro-1H-inden-1-yl]amino}piperidin-1-yl)prop-2-en-1-one Example 259

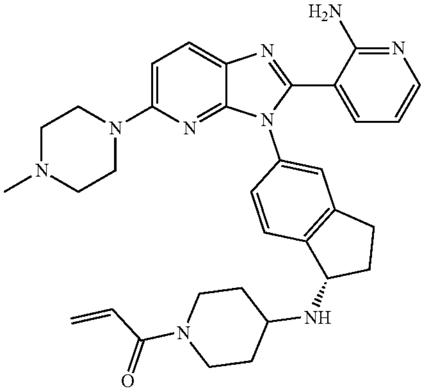

Example 259 was prepared in a manner analogous to Example 170 (via Intermediate 170-1) using 1-methylpiperazine in place of pyrrolidine and TFA in DCM in place of HCl in dioxane. MS (ESI) calcd. For $C_{33}H_{39}N_9O$, 577.33 m/z, found 578.20 $[M+H]^+$. $^1H$ NMR (400 MHz, DMSO-d6) δ (ppm): 7.81-8.08 (m, 2H), 7.32-7.61 (m, 1H), 6.98-7.29 (m, 3H), 6.65-6.98 (m, 2H), 6.28-6.52 (m, 1H), 5.95-6.25 (m, 1H), 5.56-5.82 (m, 1H), 4.18-4.48 (m, 2H), 3.92-4.18 (m, 1H), 3.79-3.92 (m, 5H), 3.02-3.28 (m, 1H), 2.62-3.02 (m, 4H), 2.32-2.47 (m, 4H), 2.08-2.29 (m, 3H), 1.92-2.08 (m, 1H), 1.84-1.92 (m, 1H), 1.61-1.92 (m, 1H), 1.04-1.42 (m, 2H).

Example 260: 1-(4-{[(1S)-5-[2-(2-aminopyridin-3-yl)-5-(morpholin-4-ylmethyl)imidazo[4,5-b]pyridin-3-yl]-2,3-dihydro-1H-inden-1-yl]amino}piperidin-1-yl)prop-2-en-1-one Example 260

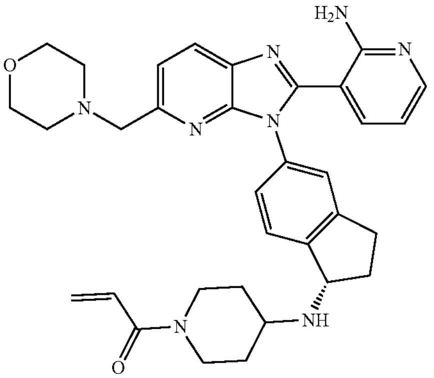

Example 260 was prepared in a manner analogous to Example 199 using Intermediate 85-1 in place of Intermediate 190-1, potassium trifluoro(morpholin-4-ylmethyl)borate in place of potassium cyclopropyltrifluoroborate and 4N HCl in dioxane at room temperature for 1 h for the deprotection. MS (ESI) calcd. For $C_{33}H_{38}N_8O_2$: 578.31. found 579.40 $[M+H]^+$. $^1H$ NMR (400 MHz, DMSO-$d_6$) δ 8.32-

8.35 (m, 1H), 8.00-8.01 (m, 1H), 7.60-7.65 (m, 3H), 7.52-7.58 (m, 1H), 7.31-7.34 (m, 1H), 6.70-6.79 (m, 2H), 6.09-6.14 (m, 1H), 5.73-5.76 (m, 1H), 4.92 (m, 1H), 4.48-4.50 (m, 3H), 3.53-3.93 (m, 4H), 3.10-3.49 (m, 6H), 2.90-2.95 (m, 1H), 2.69-2.72 (m, 1H), 2.61-2.68 (m, 1H), 2.01-2.29 (m, 4H), 1.42-1.59 (m, 3H). (formic acid salt)

Example 261: 1-[(2R,4*)-4-{[(1S)-5-[2-(2-amino-pyridin-3-yl)-5-(1,2,3-triazol-2-yl)imidazo[4,5-b]pyridin-3-yl]-2,3-dihydro-1H-inden-1-yl]amino}-2-methylpiperidin-1-yl]prop-2-en-1-one and Example 262: 1-[(2R,4*)-4-{[(1S)-5-[2-(2-amino-pyridin-3-yl)-5-(1,2,3-triazol-2-yl)imidazo[4,5-b]pyridin-3-yl]-2,3-dihydro-1H-inden-1-yl]amino}-2-methylpiperidin-1-yl]prop-2-en-1-one Example 261

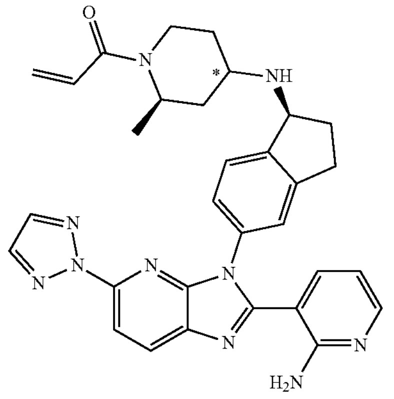

Example 262

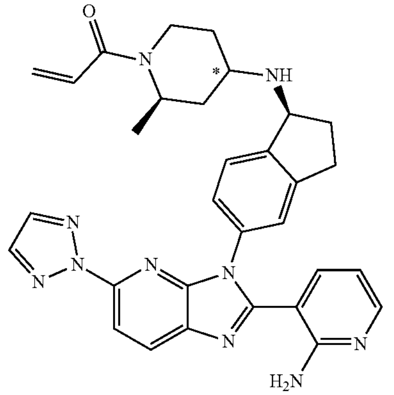

Example 261 and 262 were prepared in a manner analogous to Example 14 (via Intermediate 14-1) using tert-butyl (2R)-2-methyl-4-oxopiperidine-1-carboxylate in place of tert-butyl 8-oxo-3-azabicyclo[3.2.1]octane-3-carboxylate and 4N HCl in dioxane in place of TFA in DCM. The diastereomers were separated by Prep HPLC on a Xselect CSH OBD Column using a gradient of acetonitrile in water (+0.05% formic acid). * Denotes a stereocenter with undetermined absolute stereocenter of a single diastereomer.

Example 261: MS (ESI) calcd. For $C_{31}H_{32}N_{10}O$: 560.27 m/z, found: 561.20[M+H]$^+$. $^1$H NMR (300 MHz, DMSO-d$_6$) δ (ppm): 8.35-8.45 (m, 1H), 7.96-8.32 (m, 4H), 7.49-7.56 (m, 1H), 7.22-7.48 (m, 3H), 6.89-7.01 (m, 2H), 6.78-6.89 (m, 1H), 6.39-6.46 (m, 1H), 6.02-6.12 (m, 1H), 5.61-5.70 (m, 1H), 4.78-4.89 (m, 1H), 4.33-4.52 (m, 2H), 3.09-3.24 (m, 2H), 2.90-3.03 (m, 1H), 2.72-2.86 (m, 2H), 2.40-2.45 (m, 1H), 2.02-2.10 (m, 1H), 1.72-1.96 (m, 2H), 1.31-1.49 (m, 1H), 1.06-1.26 (m, 4H). (formic acid salt)

Example 262: MS (ESI) calcd. For $C_{31}H_{32}N_{10}O$: 560.27 m/z, found: 561.20[M+H]$^+$. $^1$H NMR (300 MHz, DMSO-d$_6$) δ (ppm): 8.38-8.45 (m, 1H), 8.10-8.17 (m, 2H), 7.97-8.05 (m, 2H), 7.45-7.52 (m, 1H), 7.23-7.39 (m, 3H), 6.90-6.99 (m, 2H), 6.72-6.82 (m, 1H), 6.39-6.43 (m, 1H), 6.04-6.11 (m, 1H), 5.60-5.66 (m, 1H), 4.30-4.40 (m, 2H), 3.90-4.02 (m, 1H), 3.09-3.15 (m, 1H), 2.90-2.98 (m, 1H), 2.72-2.81 (m, 1H), 2.45-2.50 (m, 1H), 2.00-2.10 (m, 1H), 1.60-1.90 (m, 5H), 1.38-1.45 (m, 3H), 1.02-1.19 (m, 1H). (formic acid salt)

Example 263: (S)-N-[(1S)-5-[2-(2-aminopyridin-3-yl)-5-(1,2,3-triazol-2-yl)imidazo[4,5-b]pyridin-3-yl]-2,3-dihydro-1H-inden-1-yl]-2-(prop-2-enamidomethyl)benzamide Example 263

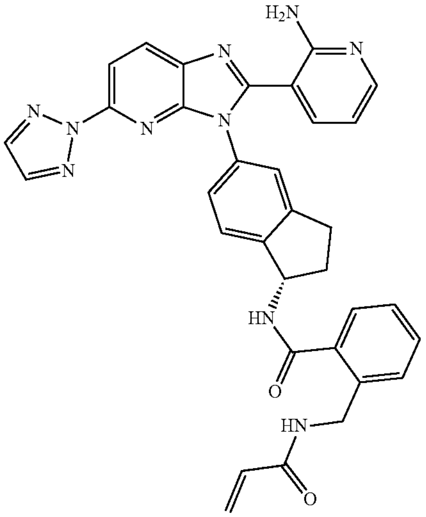

Example 263 was prepared in a manner analogous to Example 2 (via Intermediate 2-1) using 2-{[(tert-butoxycarbonyl)amino]methyl}benzoic acid in place of 3-((tert-butoxycarbonyl)amino)benzoic acid, Intermediate 19-1 in place of Intermediate 1-1, 4N HCl in dioxane in place of TFA in DCM, sodium bicarbonate in place of triethylamine and THF/water (4:1) in place of DCM. In the final step, the reagents were added 0° C. MS (ESI) calcd. For $C_{33}H_{28}N_{10}O_2$, 596.24 m/z, found 597.20 [M+H]$^+$. $^1$H NMR (400 MHz, DMSO-d$_6$) δ (ppm): 8.95 (d, J=8.3 Hz, 1H), 8.52 (t, J=6.0 Hz, 1H), 8.43 (d, J=8.6 Hz, 1H), 8.13 (s, 2H), 7.99-8.04 (m, 2H), 7.47-7.50 (m, 2H), 7.39-7.45 (m, 2H), 7.29-7.36 (m, 3H), 7.26-7.28 (m, 1H), 6.95 (s, 2H), 6.41-6.44 (m, 1H), 6.29-6.36 (m, 1H), 6.09-6.14 (m, 1H), 5.58-5.65 (m, 2H), 4.49-4.60 (m, 2H), 2.97-3.03 (m, 1H), 2.85-2.94 (m, 1H), 2.53-2.58 (m, 1H), 2.01-2.10 (m, 1H).

Example 264: N-[(1S)-5-[2-(2-aminopyridin-3-yl)-5-(pyrazol-1-yl)imidazo[4,5-b]pyridin-3-yl]-2,3-dihydro-1H-inden-1-yl]-2-[(2-fluoroprop-2-enamido)methyl]benzamide Example 264

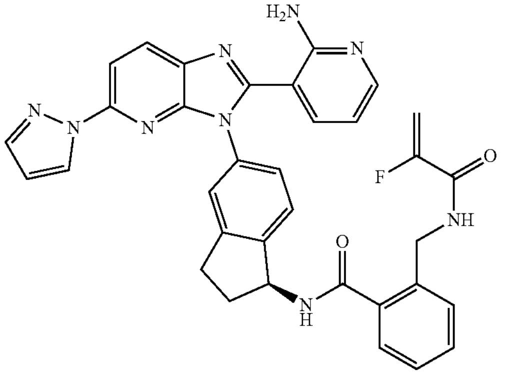

Synthetic Route:

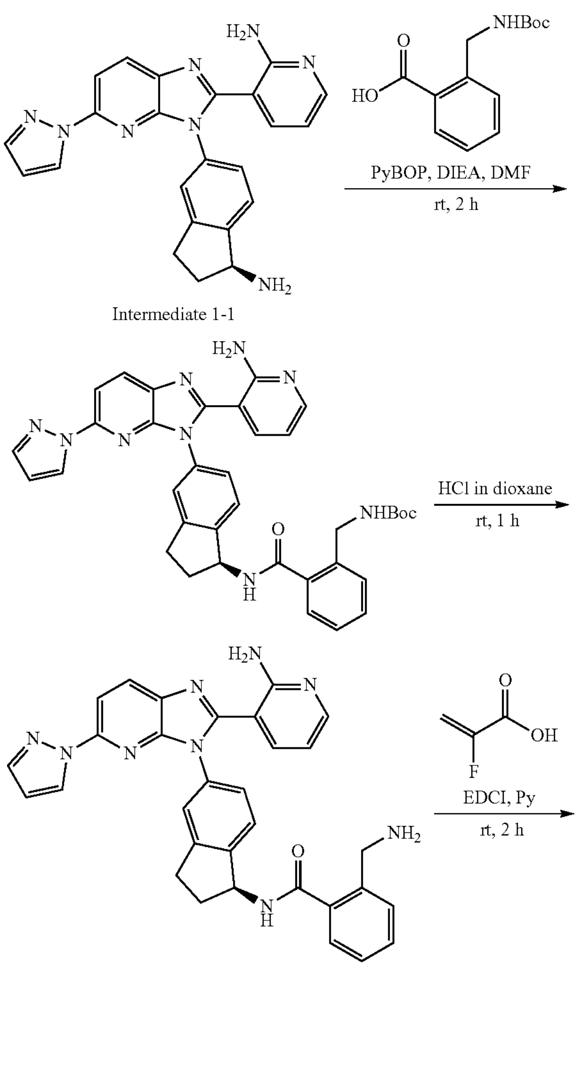

-continued

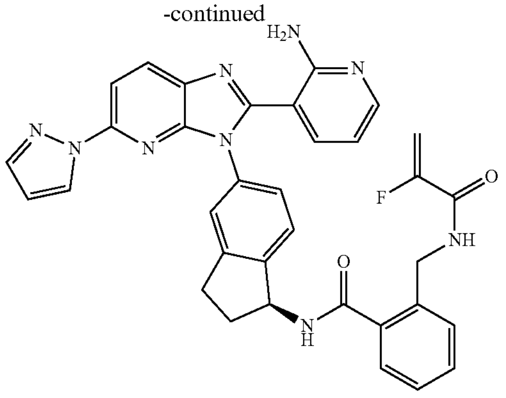

Example 264

Step 1: tert-butyl N-[(2-{[(1S)-5-[2-(2-aminopyridin-3-yl)-5-(pyrazol-1-yl)imidazo[4,5-b]pyridin-3-yl]-2,3-dihydro-1H-inden-1-yl]carbamoyl}phenyl)methyl]carbamate A mixture of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (500 mg, 1.224 mmol, 1.00 equiv), 2-{[(tert-butoxycarbonyl)amino]methyl}benzoic acid (301 mg, 1.198 mmol, 0.98 equiv) and PyBOP (640 mg, 1.230 mmol, 1.00 equiv) in DMF (10 mL) was added DIEA (0.64 mL, 3.674 mmol, 3.00 equiv) in portions at room temperature. The resulting mixture was stirred for 30 min at room temperature then quenched with water (50 mL) at 0° C. The precipitated solids were collected by filtration, washed with water (3×10 mL) and purified by silica gel column chromatography, eluting with 7% MeOH in DCM to afford tert-butyl N-[(2-{[(1S)-5-[2-(2-aminopyridin-3-yl)-5-(pyrazol-1-yl)imidazo[4,5-b]pyridin-3-yl]-2,3-dihydro-1H-inden-1-yl]carbamoyl}phenyl)methyl]carbamate (490 mg, 59.26% yield) as a yellow solid. MS (ESI) calcd. For $C_{36}H_{35}N_9O_3$: 641.29 m/z, found: 642.35 $[M+H]^+$.

Step 2: 2-(aminomethyl)-N-[(1S)-5-[2-(2-aminopyridin-3-yl)-5-(pyrazol-1-yl)imidazo[4,5-b]pyridin-3-yl]-2,3-dihydro-1H-inden-1-yl]benzamide (HCl salt To a stirred solution of tert-butyl N-[(2-{[(1S)-5-[2-(2-aminopyridin-3-yl)-5-(pyrazol-1-yl)imidazo[4,5-b]pyridin-3-yl]-2,3-dihydro-1H-inden-1-yl]carbamoyl}phenyl)methyl]carbamate (450 mg, 0.701 mmol, 1.00 equiv) in 1,4-dioxane (5 mL) was added HCl (2.5 mL, 4M in 1,4-dioxane) dropwise at 0° C. under nitrogen atmosphere. After stirring for 2 h at room temperature, the resulting mixture was concentrated under reduced pressure to afford 2-(aminomethyl)-N-[(1S)-5-[2-(2-aminopyridin-3-yl)-5-(pyrazol-1-yl)imidazo[4,5-b]pyridin-3-yl]-2,3-dihydro-1H-inden-1-yl]benzamide (400 mg, 74.78% yield) (HCl salt) as a light yellow solid. MS (ESI) calcd. For $C_{31}H_{27}N_9O$: 541.23 m/z, found: 542.30 $[M+H]^+$.

Step 3: N-[(1S)-5-[2-(2-aminopyridin-3-yl)-5-(pyrazol-1-yl)imidazo[4,5-b]pyridin-3-yl]-2,3-dihydro-1H-inden-1-yl]-2-[(2-fluoroprop-2-enamido)methyl]benzamide (Example 264)

To a mixture of 2-(aminomethyl)-N-[(1S)-5-[2-(2-amino-pyridin-3-yl)-5-(pyrazol-1-yl)imidazo[4,5-b]pyridin-3-yl]-

2,3-dihydro-1H-inden-1-yl]benzamide (150 mg, 0.277 mmol, 1.00 equiv, HCl salt) and 2-fluoroprop-2-enoic acid (25 mg, 0.278 mmol, 1.00 equiv) DMF (4 mL) was added EDCI (80 mg, 0.417 mmol, 1.51 equiv) in in portions at room temperature. After stirring for 30 min at room temperature, the resulting mixture was quenched with water (20 mL). The precipitated solids were collected by filtration, washed with water (3×10 mL) and purified by silica gel column chromatography, eluting with 5% MeOH in DCM. The material was further purified Prep-HPLC on a Xbridge Prep Shield RP18 OBD C18 Column using a gradient of acetonitrile in water (+0.1% formic acid) to afford N-[(1S)-5-[2-(2-aminopyridin-3-yl)-5-(pyrazol-1-yl)imidazo[4,5-b]pyridin-3-yl]-2,3-dihydro-1H-inden-1-yl]-2-[(2-fluoroprop-2-enamido)methyl]benzamide (Example 264) (42.0 mg, 24.34% yield) as an off-white solid. MS (ESI) calcd. For $C_{34}H_{28}FN_9O_2$: 613.23 m/z, found: 614.40 $[M+H]^+$. $^1$H-NMR (400 MHz, DMSO-$d_6$) δ (ppm): 8.81-9.07 (m, 2H), 8.28-8.41 (m, 2H), 7.99-8.05 (m, 1H), 7.96 (d, J=8.5 Hz, 1H), 7.81 (s, 1H), 7.42-7.56 (m, 3H), 7.40 (s, 1H), 7.29-7.38 (m, 3H), 7.25 (d, J=7.6 Hz, 1H), 6.94 (s, 2H), 6.54-6.56 (m, 1H), 6.40-6.47 (m, 1H), 5.47-5.68 (m, 2H), 5.30 (dd, J=16.0, 4.0 Hz, 1H), 4.54-4.66 (m, 2H), 3.00-3.06 (m, 1H), 2.87-2.95 (m, 1H), 2.53-2.61 (m, 1H), 2.00-2.14 (m, 1H). $^{19}$F-NMR (376 MHz, DMSO-$d_6$) δ (ppm): −117.97.

Example 265: (S)-N-(5-(2-(2-aminopyridin-3-yl)-5-(1H-pyrazol-1-yl)-3H-imidazo[4,5-b]pyridin-3-yl)-2,3-dihydro-1H-inden-1-yl)-2-((N-methylacrylamido)methyl)benzamide Example 265

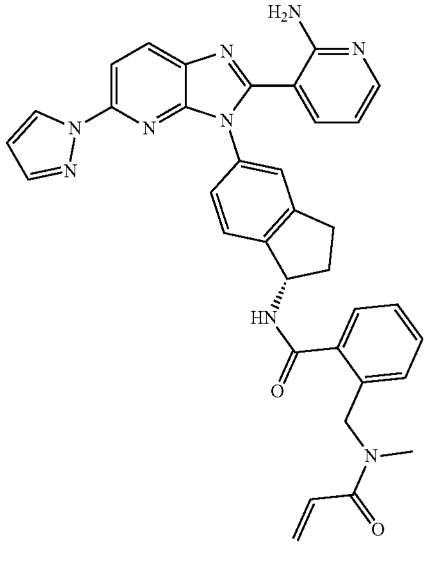

Example 265 was prepared in a manner analogous to Example 2 using Intermediate 265-1 in place of Intermediate 2-1, sodium bicarbonate in place of triethylamine and THF/water (4:1) in place of DCM. In the final step, the reagents were added at 0° C. MS (ESI) calcd. For $C_{35}H_{31}N_9O_2$, 609.26 m/z, found 610.25 $[M+H]^+$. $^1$H NMR (400 MHz, DMSO-$d_6$) δ (ppm): 8.95 (d, J=8.2 Hz, 1H), 8.35-8.39 (m, 2H), 8.00-8.03 (m, 1H), 7.96 (d, J=8.6 Hz, 1H), 7.81 (s, 1H), 7.29-7.56 (m, 6H), 7.26 (d, J=7.7 Hz, 1H), 7.17 (dd, J=19.8, 7.8 Hz, 1H), 6.90-6.98 (m, 2H), 6.67-6.89 (m, 1H), 6.53-6.57 (m, 1H), 6.44 (dd, J=7.6, 4.8 Hz, 1H), 6.14-6.23 (m, 1H), 5.55-5.77 (m, 2H), 4.81-4.94 (m, 1H), 4.78 (s, 1H), 2.84-3.09 (m, 5H), 2.53-2.60 (m, 1H), 1.98-2.11 (m, 1H).

Intermediate 265-1: 2-(aminomethyl)-N-[(1S)-5-[2-(2-aminopyridin-3-yl)-5-(pyrazol-1-yl)imidazo[4,5-b]pyridin-3-yl]-2,3-dihydro-1H-inden-1-yl]benzamide Intermediate 265-1

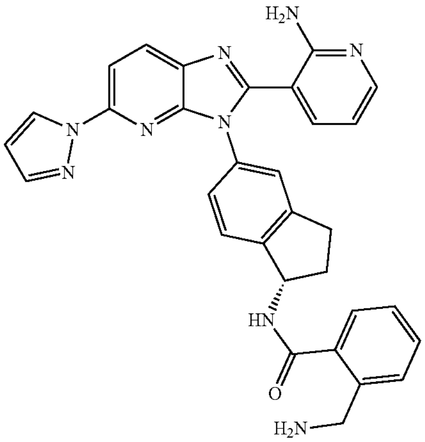

Intermediate 265-1 was prepared in a manner analogous to Intermediate 2-2 using 2-{[(tert-butoxycarbonyl)(methyl)amino]methyl}benzoic acid in place of 3-((tert-butoxycarbonyl)amino)benzoic acid, 4N HCl in dioxane in place of TFA in DCM. MS (ESI) calcd. For $C_{31}H_{27}N_9O$: 541.23 m/z, found: 542.30 $[M+H]^+$.

Example 266: (S)-2-acryloyl-N-(5-(2-(2-aminopyridin-3-yl)-5-(1H-pyrazol-1-yl)-3H-imidazo[4,5-b]pyridin-3-yl)-2,3-dihydro-1H-inden-1-yl)isoindoline-4-carboxamide Example 266

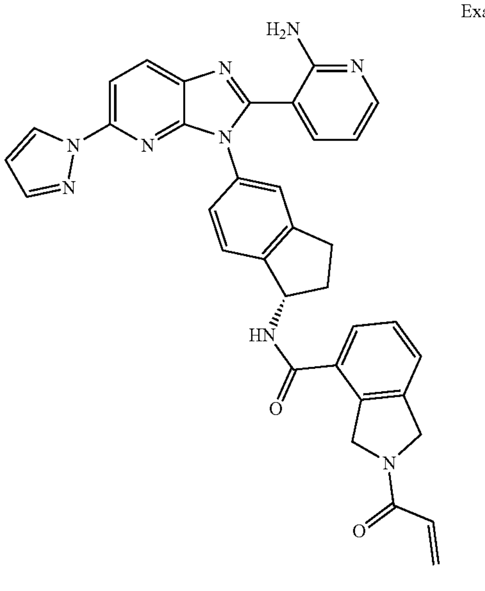

Example 266 was prepared in a manner analogous to Example 2 (via Intermediate 2-1) using 2-(tert-butoxycarbonyl)-1,3-dihydroisoindole-4-carboxylic acid in place of 3-((tert-butoxycarbonyl)amino)benzoic acid, 4N HCl in dioxane in place of TFA in DCM, sodium bicarbonate in place of triethylamine and THF/water (4:1) in place of DCM. In the final step, the reagents were added at 0° C. MS (ESI) calcd. For $C_{35}H_{29}N_9O_2$: 607.24 m/z, found: 608.20 $[M+H]^+$. $^1$H NMR (400 MHz, DMSO-$d_6$) δ (ppm): 8.94 (t, J=7.6 Hz, 1H), 8.33-8.38 (m, 2H), 8.00-8.03 (m, 1H), 7.95 (d, J=4.0 Hz, 1H), 7.77-7.82 (m, 2H), 7.48-7.57 (m, 1H), 7.38-7.46 (m, 3H), 7.25-7.34 (m, 2H), 6.91 (s, 2H), 6.66-6.76 (m, 1H), 6.53-6.56 (m, 1H), 6.42-6.47 (m, 1H), 6.18-6.28 (m, 1H), 5.72-5.79 (m, 1H), 5.65 (q, J=8.4 Hz, 1H), 5.24 (s, 1H), 5.00 (d, J=9.6 Hz, 2H), 4.75 (s, 1H), 2.99-3.09 (m, 1H), 2.85-2.99 (m, 1H), 2.51-2.58 (m, 1H), 2.05-2.18 (m, 1H).

Example 267: N-[(1S)-5-[2-(2-aminopyridin-3-yl)-5-(pyrazol-1-yl)imidazo[4,5-b]pyridin-3-yl]-2,3-dihydro-1H-inden-1-yl]-2-(but-2-ynamidomethyl) benzamide Example 267

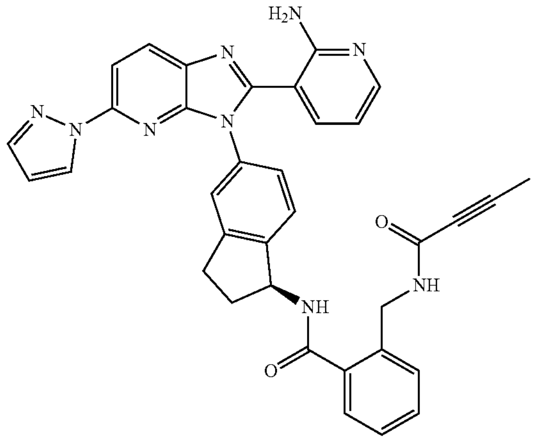

Intermediate 267 was prepared in a manner analogous to Example 4 (last step only) using Intermediate 265-1 in place of Intermediate 1-1 and 2-butynoic acid in place of 2-(N-methylprop-2-enamido)benzoic acid. MS (ESI) calcd. For $C_{35}H_{29}N_9O_2$: 607.24 m/z, found: 608.45 $[M+H]^+$. $^1$H-NMR (400 MHz, DMSO-$d_6$) δ (ppm): 8.84-8.95 (m, 2H), 8.34-8.40 (m, 2H), 7.99-8.06 (m, 1H), 7.96 (d, J=8.6 Hz, 1H), 7.81 (s, 1H), 7.42-7.53 (m, 3H), 7.39 (s, 1H), 7.28-7.37 (m, 3H), 7.22-7.28 (m, 1H), 6.95 (s, 2H), 6.52-6.58 (m, 1H), 6.40-6.48 (m, 1H), 5.60 (q, J=8.2 Hz, 1H), 4.41-4.57 (m, 2H), 2.97-3.08 (m, 1H), 2.84-2.96 (m, 1H), 2.53-2.60 (m, 1H), 2.01-2.14 (m, 1H), 1.96 (s, 3H).

Example 268: (S)-2-(2-acrylamidoethyl)-N-(5-(2-(2-aminopyridin-3-yl)-5-(1H-pyrazol-1-yl)-3H-imidazo[4,5-b]pyridin-3-yl)-2,3-dihydro-1H-inden-1-yl)benzamide Example 268

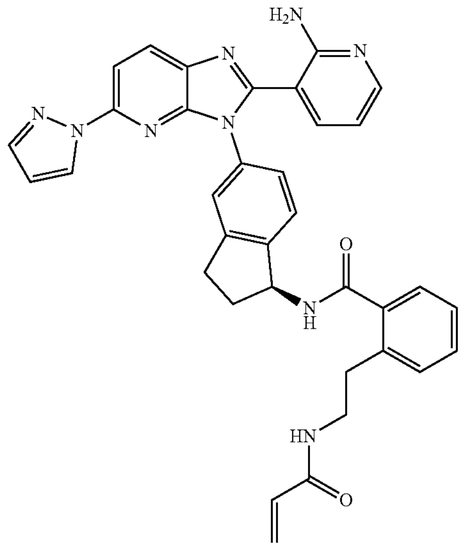

Example 268 was prepared in a manner analogous to Example 4 (omitting step 2) using 2-(2-aminoethyl)benzoic acid hydrochloride in place of methyl 2-(methylamino) benzoate and THF/water (4:1) in place of DCM. MS (ESI) calcd. For $C_{35}H_{31}N_9O_2$, 609.26 m/z, found 610.45 $[M+H]^+$. $^1$H NMR (400 MHz, DMSO-$d_6$) δ (ppm): 8.87 (d, J=8.0 Hz, 1H), 8.34-8.40 (m, 2H), 8.32 (t, J=13.2 Hz, 1H), 7.99-8.03 (m, 1H), 7.95 (d, J=8.4 Hz, 1H), 7.81 (s, 1H), 7.48 (d, J=8.0 Hz, 1H), 7.36-7.45 (m, 3H), 7.9-7.34 (m, 3H), 7.23-7.27 (m, 1H), 6.93 (s, 2H), 6.52-6.56 (m, 1H), 6.40-6.46 (m, 1H), 6.13-6.23 (m, 1H), 6.01-6.08 (m, 1H), 5.61 (q, J=8.2 Hz, 1H), 5.50-5.56 (m, 1H), 3.41 (q, J=5.6 Hz, 2H), 2.98-3.08 (m, 1H), 2.83-2.97 (m, 3H), 2.52-2.60 (m, 1H), 1.99-2.11 (m, 1H).

Example 269: 1-(4-{[(1S)-5-[2-(2-aminopyridin-3-yl)-6-(pyridin-2-yl)imidazo[4,5-b]pyridin-3-yl]-2,3-dihydro-1H-inden-1-yl]amino}piperidin-1-yl)prop-2-en-1-one Example 269

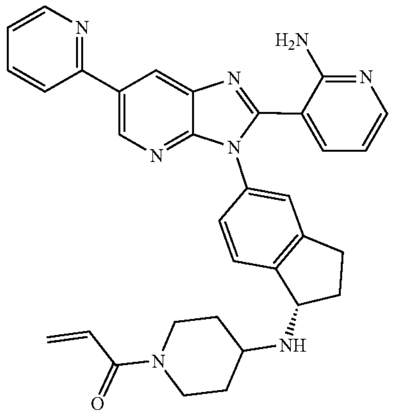

Example 269 was prepared in a manner analogous to Example 159 (via Intermediate 159-1) using 2-(tributylstannyl)pyridine in place of 2-(tributylstannyl)-1,3-thiazole and Intermediate 190-1 in place of Intermediate 1-2. MS (ESI) calcd. For $C_{33}H_{32}N_8O$: 556.27 m/z, found: 557.00 $[M+H]^+$. $^1H$ NMR (400 MHz, DMSO-$d_6$) δ (ppm): 9.10-911 (m, 1H), 8.88-8.89 (m, 1H), 8.75-8.76 (m, 1H), 8.16-8.19 (m, 1H), 8.05-8.09 (m, 2H), 7.91-7.93 (m, 1H), 7.72-7.75 (m, 1H), 7.60-7.61 (m, 1H), 7.52-7.55 (m, 1H), 7.43-7.45 (m, 1H), 6.81-6.88 (m, 2H), 6.14-6.18 (m, 1H), 5.76-5.79 (m, 1H), 5.00-5.02 (m, 1H), 4.56-4.58 (m, 1H), 4.20-4.22 (m, 1H), 3.59-3.60 (m, 1H), 3.16-3.22 (m, 2H), 3.00-3.02 (m, 1H), 2.76-2.79 (m, 1H), 2.59-2.62 (m, 1H), 2.24-2.27 (m, 2H), 2.14-2.17 (m, 1H), 1.51-1.57 (m, 2H). (TFA salt)

Example 270: 1-((2S,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one and Example 271: 1-((2S,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one Example 270

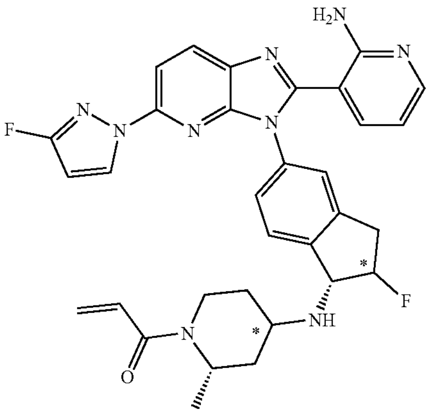

Example 271

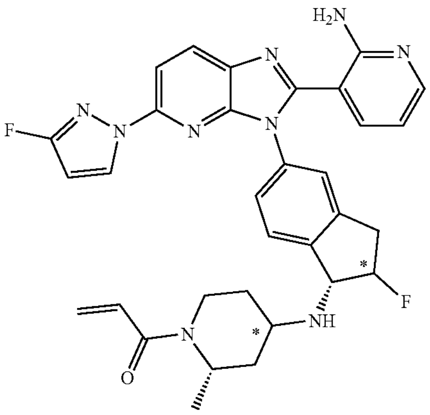

Examples 270 and 271 were prepared in a manner analogous to Example 14 (via Intermediate 14-1) using Intermediate 236-1 in place of Intermediate 1-1 and tert-butyl (S)-2-methyl-4-oxopiperidine-1-carboxylate in place of tert-butyl 8-oxo-3-azabicyclo[3.2.1]octane-3-carboxylate. The diastereomers were separated by chiral Prep-HPLC on a CHIRALPAK IK column using a mixture of [MtBE (+0.5% 2M $NH_3$-MeOH)] and [IPA/DCM (1:1)]. * Denotes a stereocenter with undetermined absolute stereocenter of a single diastereomer.

Example 270: MS (ESI) calcd. For $C_{32}H_{31}F_2N_9O$, 595.26 m/z, found 596.20 $[M+H]^+$. $^1H$ NMR (400 MHz, DMSO-$d_6$) δ (ppm): 8.30-8.32 (m, 1H), 8.23-8.25 (m, 1H), 7.96-7.98 (m, 1H), 7.72-7.74 (m, 1H), 7.47-7.49 (m, 1H), 7.22-7.33 (m, 3H), 6.73-6.77 (m, 1H), 6.41-6.45 (m, 1H), 6.27-6.30 (m, 1H), 6.04-6.09 (m, 1H), 5.66-5.69 (m, 1H), 5.36-5.51 (m, 1H), 4.33-4.47 (m, 2H), 3.06-3.28 (m, 3H), 2.77-2.83 (m, 1H), 1.91-2.07 (m, 2H), 1.13-1.41 (m, 6H). $^{19}F$ NMR (376 MHz, DMSO-d6) δ (ppm): −126.98, −196.72.

Example 271: MS (ESI) calcd. For $C_{32}H_{31}F_2N_9O$, 595.26 m/z, found 596.20 $[M+H]^+$. $^1H$ NMR (400 MHz, DMSO-$d_6$) δ (ppm): 8.29-8.31 (m, 1H), 8.21-8.22 (m, 1H), 7.96-7.97 (m, 1H), 7.70-7.72 (m, 1H), 7.46-7.48 (m, 1H), 7.21-7.30 (m, 3H), 6.72-6.76 (m, 1H), 6.40-6.44 (m, 1H), 6.26-6.28 (m, 1H), 6.04-6.09 (m, 1H), 5.65-5.68 (m, 1H), 5.36-5.51 (m, 1H), 4.31-4.46 (m, 2H), 3.32-3.47 (m, 1H), 3.06-3.28 (m, 3H), 1.56-1.90 (m, 5H), 1.24-1.35 (m, 3H). $^{19}F$ NMR (376 MHz, DMSO-d6) δ (ppm): −127.01, −197.59.

Example 272: 1-((2S,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one and Example 273: 1-((2S,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one Example 272

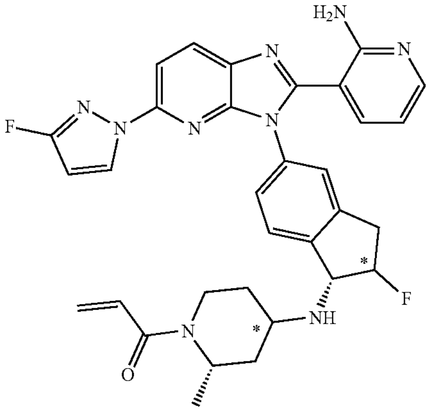

-continued

Example 273

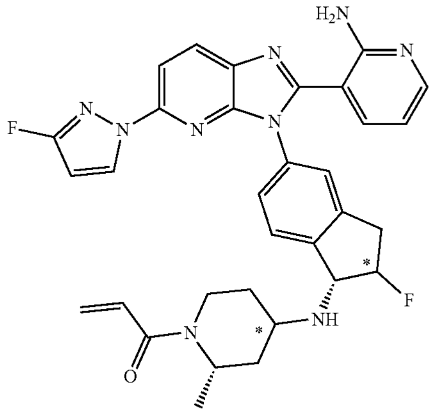

Examples 272 and 273 were prepared in a manner analogous to Example 14 (via Intermediate 14-1) using Intermediate 237-1 in place of Intermediate 1-1 and tert-butyl (S)-2-methyl-4-oxopiperidine-1-carboxylate in place of tert-butyl 8-oxo-3-azabicyclo[3.2.1]octane-3-carboxylate. The diastereomers were separated by chiral Prep-HPLC on a CHIRAL ART Cellulose-SB column using a mixture of [MtBE (+0.5% 2M $NH_3$-MeOH)] and MeOH. * Denotes a stereocenter with undetermined absolute stereocenter of a single diastereomer.

Example 272: MS (ESI) calcd. For $C_{32}H_{31}F_2N_9O$, 595.26 m/z, found 596.20 $[M+H]^+$. $^1H$ NMR (400 MHz, DMSO-$d_6$) δ (ppm): 8.29-8.31 (m, 1H), 8.24-8.25 (m, 1H), 7.96-7.98 (m, 1H), 7.71-7.74 (m, 1H), 7.46-7.48 (m, 1H), 7.25-7.26 (m, 1H), 7.20-7.23 (m, 2H), 6.68-6.74 (m, 1H), 6.40-6.44 (m, 1H), 6.26-6.28 (m, 1H), 6.04-6.09 (m, 1H), 5.65-5.68 (m, 1H), 5.23-5.36 (m, 1H), 4.28-4.37 (m, 2H), 3.40-3.50 (m, 1H), 3.24-3.35 (m, 1H), 3.14-3.20 (m, 1H), 2.94-3.05 (m, 1H), 1.53-1.90 (m, 5H), 1.24-1.35 (m, 3H). $^{19}F$ NMR (376 MHz, DMSO-d6) δ (ppm): −126.98, −175.13.

Example 273: MS (ESI) calcd. For $C_{32}H_{31}F_2N_9O$, 595.26 m/z, found 596.20 $[M+H]^+$. $^1H$ NMR (400 MHz, DMSO-$d_6$) δ (ppm): 8.31-8.33 (m, 1H), 8.26-8.28 (m, 1H), 7.96-7.98 (m, 1H), 7.73-7.76 (m, 1H), 7.51-7.53 (m, 1H), 7.37-7.39 (m, 1H), 7.22-7.27 (m, 2H), 6.68-6.74 (m, 1H), 6.41-6.44 (m, 1H), 6.28-6.30 (m, 1H), 6.04-6.09 (m, 1H), 5.65-5.68 (m, 1H), 5.23-5.36 (m, 1H), 4.31-4.47 (m, 2H), 3.40-3.50 (m, 1H), 3.13-3.25 (m, 1H), 2.80-3.08 (m, 2H), 1.90-1.99 (m, 2H), 1.16-1.38 (m, 6H). $^{19}F$ NMR (376 MHz, DMSO-d6) δ (ppm): −126.96, −176.06.

Example 274: 1-((2R,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one and Example 275: 1-((2R,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one Example 274

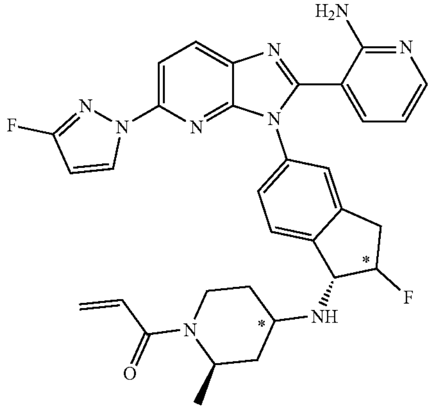

Example 275

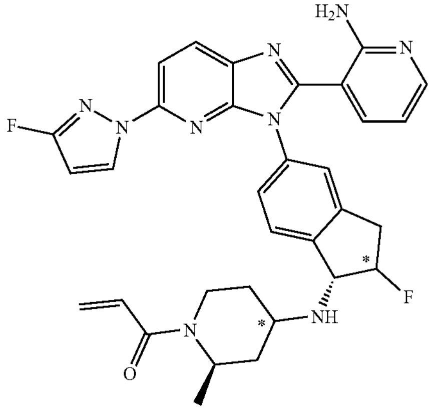

Examples 274 and 275 were prepared in a manner analogous to Example 14 (via Intermediate 14-1) using Intermediate 236-1 in place of Intermediate 1-1 and tert-butyl (R)-2-methyl-4-oxopiperidine-1-carboxylate in place of tert-butyl 8-oxo-3-azabicyclo[3.2.1]octane-3-carboxylate. The diastereomers separated during Prep HPLC on a Xselect CSH F-Phenyl OBD column using a gradient of acetonitrile in water (+0.1% formic acid). * Denotes a stereocenter with undetermined absolute stereocenter of a single diastereomer.

Example 274: MS (ESI) calcd. for $C_{32}H_{31}F_2N_9O$, 595.26 m/z, found 596.20 $[M+H]^+$. $^1H$ NMR (400 MHz, DMSO-$d_6$) δ (ppm): 8.29-8.32 (m, 1H), 8.22-8.24 (m, 1H), 7.96-7.98 (m, 1H), 7.73-7.76 (m, 1H), 7.47-7.49 (m, 1H), 7.21-7.38 (m, 3H), 6.72-6.79 (m, 1H), 6.41-6.44 (m, 1H), 6.27-6.30 (m, 1H), 6.04-6.09 (m, 1H), 5.65-5.68 (m, 1H), 5.41-5.55 (m, 1H), 4.31-4.47 (m, 2H), 3.12-3.20 (m, 2H), 3.05-3.07 (m, 1H), 2.79-2.80 (m, 1H), 2.11-2.13 (m, 1H), 1.77-1.79 (m, 1H), 1.12-1.51 (m, 6H). $^{19}F$ NMR (376 MHz, DMSO-d6) δ (ppm): −127.01, −197.01. (formic acid salt)

Example 275: MS (ESI) calcd. for $C_{32}H_{31}F_2N_9O$, 595.26 m/z, found 596.20 $[M+H]^+$. $^1H$ NMR (400 MHz, DMSO-$d_6$) δ (ppm): 8.29-8.32 (m, 1H), 8.22-8.24 (m, 1H), 7.96-7.98 (m, 1H), 7.73-7.76 (m, 1H), 7.47-7.49 (m, 1H), 7.24-7.33 (m, 3H), 6.70-6.77 (m, 1H), 6.41-6.44 (m, 1H), 6.27-6.30 (m, 1H), 6.04-6.09 (m, 1H), 5.65-5.68 (m, 1H), 5.40-5.55 (m, 1H), 4.31-4.47 (m, 2H), 3.31-3.50 (m, 1H), 3.03-3.27 (m, 3H), 1.59-1.92 (m, 5H), 1.44-1.51 (m, 3H). $^{19}F$ NMR (376 MHz, DMSO-d6) δ (ppm): −127.02, −198.02. (formic acid salt)

Example 276: 1-((2R,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one and Example 277: 1-((2R,4*)-4-(((1R,2*)-5-(2-(2-aminopyridin-3-yl)-5-(3-fluoro-1H-pyrazol-1-yl)-3H-imidazo[4,5-b]pyridin-3-yl)-2-fluoro-2,3-dihydro-1H-inden-1-yl)amino)-2-methylpiperidin-1-yl)prop-2-en-1-one Example 276

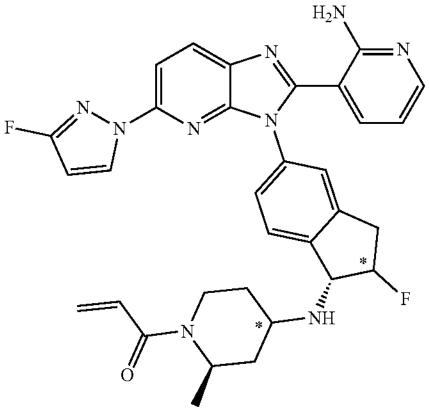

Example 277

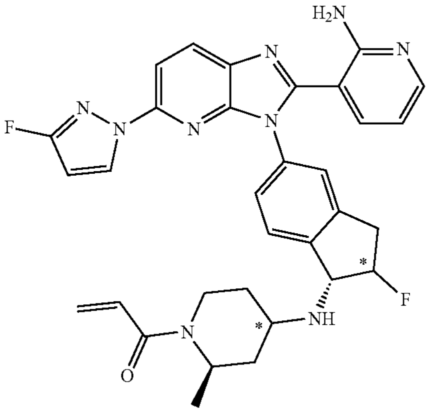

Examples 276 and 277 were prepared in a manner analogous to Example 14 (via Intermediate 14-1) using Intermediate 237-1 in place of Intermediate 1-1 and tert-butyl (R)-2-methyl-4-oxopiperidine-1-carboxylate in place of tert-butyl 8-oxo-3-azabicyclo[3.2.1]octane-3-carboxylate. The diastereomers were separated by chiral Prep-HPLC on a CHIRALPAK-IK, column using a mixture of [MtBE (+0.5% 2M $NH_3$-MeOH)] and [MeOH/DCM (1:1)]. * Denotes a stereocenter with undetermined absolute stereocenter of a single diastereomer.

Example 276: MS (ESI) calcd. for $C_{32}H_{31}F_2N_9O$, 595.26 m/z, found 596.20 $[M+H]^+$. $^1H$ NMR (400 MHz, DMSO-$d_6$) δ (ppm): 8.29-8.32 (m, 1H), 8.22-8.24 (m, 1H), 7.96-7.98 (m, 1H), 7.72-7.75 (m, 1H), 7.45-7.48 (m, 1H), 7.31-7.33 (m, 1H), 7.21-7.26 (m, 2H), 6.70-6.75 (m, 1H), 6.42-6.45 (m, 1H), 6.27-6.30 (m, 1H), 6.04-6.09 (m, 1H), 5.65-5.68 (m, 1H), 5.18-5.32 (m, 1H), 4.23-4.38 (m, 2H), 3.39-3.47 (m, 1H), 3.21-3.27 (m, 1H), 3.11-3.15 (m, 1H), 2.97-3.04 (m, 1H), 1.56-1.82 (m, 5H), 1.29-1.38 (m, 3H). $^{19}F$ NMR (376 MHz, DMSO-d6) δ (ppm): −127.00, −175.17.

Example 277: MS (ESI) calcd. for $C_{32}H_{31}F_2N_9O$, 595.26 m/z, found 596.20 $[M+H]^+$. $^1H$ NMR (400 MHz, DMSO-$d_6$) δ (ppm): 8.30-8.33 (m, 1H), 8.24-8.26 (m, 1H), 7.96-7.99 (m, 1H), 7.72-7.75 (m, 1H), 7.45-7.49 (m, 1H), 7.33-7.36 (m, 1H), 7.21-7.26 (m, 2H), 6.71-6.77 (m, 1H), 6.42-6.45 (m, 1H), 6.27-6.30 (m, 1H), 6.04-6.09 (m, 1H), 5.65-5.68 (m, 1H), 5.18-5.33 (m, 1H), 4.32-4.43 (m, 2H), 3.38-3.50 (m, 1H), 2.77-3.16 (m, 3H), 2.04-2.07 (m, 1H), 1.80-1.87 (m, 1H), 1.14-1.21 (m, 6H). $^{19}F$ NMR (376 MHz, DMSO-d6) δ (ppm): −126.99, −175.64.

Example 278: 1-(4-{[(1S)-5-[2-(2-aminopyridin-3-yl)-5-{3-oxa-8-azabicyclo[3.2.1]octan-8-yl}imidazo[4,5-b]pyridin-3-yl]-2,3-dihydro-1H-inden-1-yl]amino}piperidin-1-yl)prop-2-en-1-one Example 278

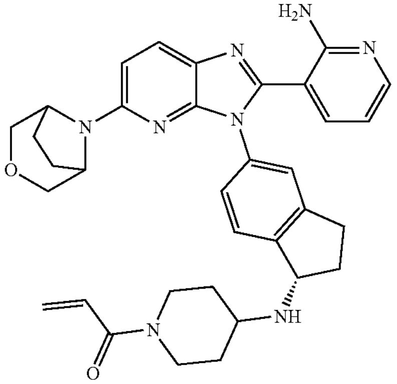

Example 278 was prepared in a manner analogous to Example 75 (via Intermediate 75-1) omitting steps 1-3 and the chiral separation (of Intermediate 75-1) and using tert-butyl (S)-(5-bromo-2,3-dihydro-1H-inden-1-yl)carbamate in place of (S)-N-((1R)-5-bromo-2-fluoro-2,3-dihydro-1H-inden-1-yl)-2-methylpropane-2-sulfinamide and Intermediate 278-1 in place of 3-nitro-6-(pyrazol-1-yl)pyridin-2-amine. MS (ESI) calcd. for $C_{34}H_{38}N_8O_2$: 590.31 m/z, found: 591.40 $[M+H]^+$. $^1H$ NMR (400 MHz, DMSO-$d_6$) δ (ppm): 8.02-8.06 (m, 2H), 7.68-7.70 (m, 1H), 7.57-7.59 (m, 1H), 7.47 (s, 1H), 7.36-7.39 (m, 1H), 6.93-6.96 (m, 1H), 6.82-6.85 (m, 1H), 6.72-6.75 (m, 1H), 6.12-6.17 (m, 1H), 5.72-5.76 (m, 1H), 4.97-5.00 (m, 1H), 4.54-4.56 (m, 1H), 4.41-4.42 (m, 2H), 4.20-4.22 (m, 1H), 3.60-3.68 (m, 2H), 3.51-3.58 (m, 3H), 3.10-3.16 (m, 2H), 2.93-2.95 (m, 1H), 2.73-2.74 (m, 1H), 2.52-2.58 (m, 1H), 2.21-2.25 (m, 2H), 2.08-2.14 (m, 1H), 1.94-2.04 (m, 4H), 1.50-1.55 (m, 2H). (TFA salt)

Example 279: 1-(4-{[(1S)-5-[2-(2-aminopyridin-3-yl)-5-(oxetan-3-yl)imidazo[4,5-b]pyridin-3-yl]-2,3-dihydro-1H-inden-1-yl]amino}piperidin-1-yl)prop-2-en-1-one Example 279

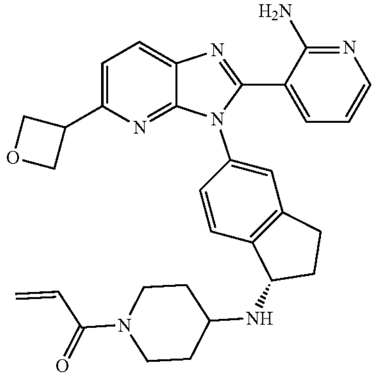

Synthetic Route:

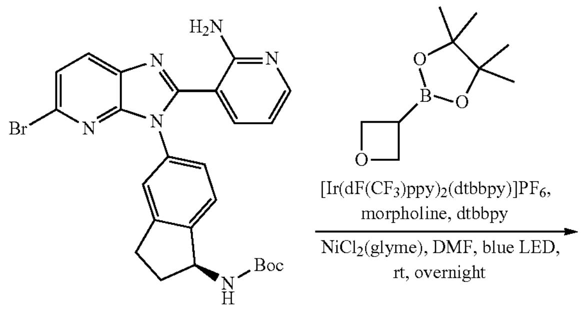

Intermediate 85-1

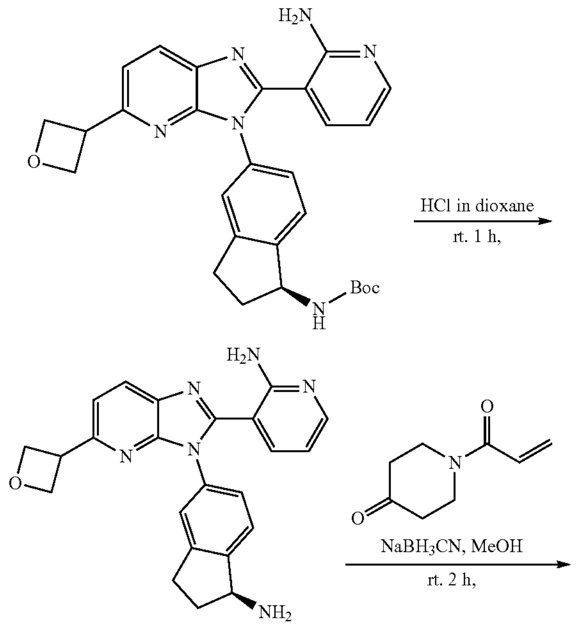

-continued

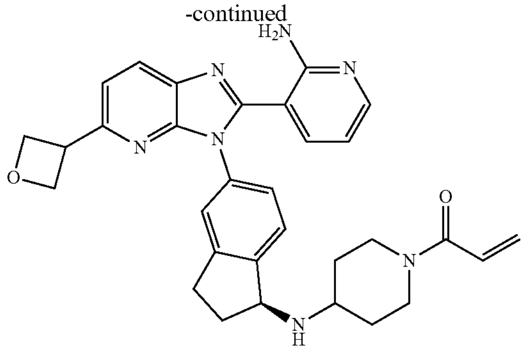

Example 279

Step 1: Synthesis of tert-butyl N-[(1S)-5-[2-(2-aminopyridin-3-yl)-5-(oxetan-3-yl)imidazo[4,5-b]pyridin-3-yl]-2,3-dihydro-1H-inden-1-yl]carbamate To a solution of tert-butyl N-[(1S)-5-[2-(2-aminopyridin-3-yl)-5-bromoimidazo[4,5-b]pyridin-3-yl]-2,3-dihydro-1H-inden-1-yl]carbamate (Intermediate 85-1) (100 mg, 0.192 mmol, 1 equiv) in DMF (5 mL) was added 4,4,5,5-tetramethyl-2-(oxetan-3-yl)-1,3,2-dioxaborolane (70.59 mg, 0.384 mmol, 2 equiv), morpholine (25.06 mg, 0.288 mmol, 1.5 equiv), dtbbpy (2.57 mg, 0.010 mmol, 0.05 equiv), iridium (1+) bis(2-(2,4-difluorophenyl)-5-(trifluoromethyl)pyridine) 4,4'-di-tert-butyl-2,2'-bipyridine hexafluoro-lambda5-phosphanuide (2.16 mg, 0.002 mmol, 0.01 equiv) and $NiCl_2$ (glyme) (2.11 mg, 0.010 mmol, 0.05 equiv). The resulting mixture was stirred at rt overnight under $N_2$ atmosphere and blue LED. After cooling to room temperature, the mixture was poured into water. The resulting precipitate was isolated by filtration to afford crude tert-butyl N-[(1S)-5-[2-(2-aminopyridin-3-yl)-5-(oxetan-3-yl)imidazo[4,5-b]pyridin-3-yl]-2,3-dihydro-1H-inden-1-yl]carbamate (70 mg, crude) MS (ESI) calcd. for $C_{28}H_{30}N_6O_3$: 498.24 m/z, found: 499.20 $[M+H]^+$.

Step 2: Synthesis of 3-{3-[(1S)-1-amino-2,3-dihydro-1H-inden-5-yl]-5-(oxetan-3-yl)imidazo[4,5-b]pyridine-2-yl}pyridin-2-amine A solution of tert-butyl N-[(1S)-5-[2-(2-aminopyridin-3-yl)-5-(oxetan-3-yl)imidazo[4,5-b]pyridin-3-yl]-2,3-dihydro-1H-inden-1-yl]carbamate (60 mg, 0.120 mmol, 1 equiv) in HCl (10 mL, 4 M in 1,4-dioxane) was stirred at room temperature for 1 h. The solvent was removed by distillation under vacuum to afford 3-{3-[(1S)-1-amino-2,3-dihydro-1H-inden-5-yl]-5-(oxetan-3-yl)imidazo[4,5-b]pyridin-2-yl}pyridin-2-amine (60 mg, crude) as a light yellow solid. MS (ESI) calcd. for $C_{23}H_{22}N_6O$: 398.19 m/z, found: 399.15 $[M+H]^+$.

Step 3: Synthesis of 1-(4-{[(1S)-5-[2-(2-aminopyridin-3-yl)-5-(oxetan-3-yl)imidazo[4,5-b]pyridin-3-yl]-2,3-dihydro-1H-inden-1-yl]amino}piperidin-1-yl)prop-2-en-1-one (Example 279)

A solution of 3-{3-[(1S)-1-amino-2,3-dihydro-1H-inden-5-yl]-5-(oxetan-3-yl)imidazo[4,5-b]pyridin-2-yl}pyridin-2-amine (50 mg, 0.125 mmol, 1 equiv) and 1-(prop-2-enoyl)piperidin-4-one (76.88 mg, 0.500 mmol, 4 equiv) in MeOH (4 mL) was stirred at 40° C. for 1 h. $NaBH_3CN$ (31.54 mg, 0.500 mmol, 4 equiv) was added and the mixture was stirred at 40° C. for 1 h. The solvent was removed under vacuum and the crude material was purified by Prep-HPLC on a XBridge Prep Shield RP OBD C18 Column using a gradient of acetonitrile in water (+0.1% formic acid) to afford 1-(4-{[(1S)-5-[2-(2-aminopyridin-3-yl)-5-(oxetan-3-yl)imidazo[4,5-b]pyridin-3-yl]-2,3-dihydro-1H-inden-1-yl]amino}piperidin-1-yl)prop-2-en-1-one (Example 279) (8.5 mg, 12.14%) as light yellow solid. MS (ESI) calcd. for $C_{31}H_{33}N_7O_2$, 535.27 m/z, found 536.15 $[M+H]^+$. $^1H$ NMR (400 MHz, DMSO-d6) δ (ppm): 8.09-8.52 (m, 2H), 7.82-8.09 (m, 1H), 7.51-7.75 (m, 1H), 7.32-7.51 (m, 2H), 7.08-7.32 (m, 2H), 6.65-6.95 (m, 1H), 6.32-6.65 (m, 1H), 5.95-6.26 (m, 1H), 5.56-5.86 (m, 1H), 4.84-4.96 (m, 2H), 4.67-4.84 (m, 3H), 4.34-4.53 (m, 2H), 4.08-4.19 (m, 1H), 3.98-4.02 (m, 1H), 3.25-3.51 (m, 1H), 2.95-3.25 (m, 2H), 2.82-2.95 (m, 1H), 2.65-2.82 (m, 1H) 1.85-2.28 (m, 3H), 1.22-1.61 (m, 2H). (formic acid salt)

Example 280: 1-(4-{[(1S)-5-[2-(2-aminopyridin-3-yl)-5-[3-(methoxymethyl)pyrazol-1-yl]imidazo[4,5-b]pyridin-3-yl]-2,3-dihydro-1H-inden-1-yl]amino}piperidin-1-yl)prop-2-en-1-one Example 280

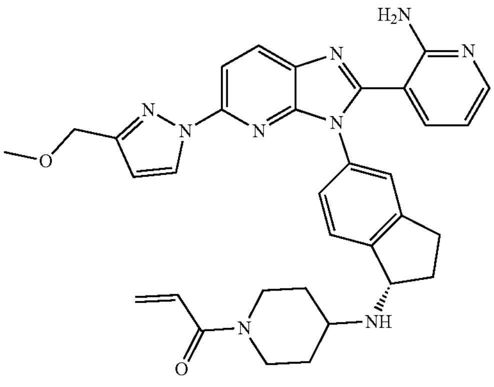

Example 280 was prepared in a manner analogous to Example 13 (via Intermediate 1-1) using Intermediate 85-1 in place of Intermediate 1-2, 3-(methoxymethyl)-1H-pyrazole in place of pyrazole, Ephos/EPhos Pd G4/cesium carbonate in place of tBuBrettPhos/tBuBrettPhos Pd G3/tribasic potassium phosphate and 4N HCl in dioxane at room temperature for 2 h for the deprotection. MS (ESI) calcd. for $C_{33}H_{35}N_9O_2$: 589.29 m/z, found: 590.35 $[M+H]^+$. $^1H$ NMR (400 MHz, DMSO-$d_6$) δ (ppm): 8.43-8.44 (m, 1H), 8.33-8.34 (m, 111), 8.08-8.10 (m, 1H), 7.98-7.99 (m, 1H), 7.73-7.77 (m, 2H), 7.58-7.59 (m, 1H), 7.45-7.47 (m, 1H), 6.80-6.86 (m, 1H), 6.76-6.78 (m, 1H), 6.57-6.58 (m, 1H), 6.13-6.18 (m, 1H), 5.74-5.77 (m, 1H), 5.00-5.03 (m, 1H), 4.55-4.57 (m, 1H), 4.48 (s, 2H), 4.20-4.21 (m, 1H), 3.60-3.74 (m, 1H), 3.16-3.23 (m, 3H), 2.97-2.99 (m, 2H), 2.75-2.76 (m, 1H), 2.58-2.61 (m, 1H), 2.52-2.53 (m, 1H), 2.24-2.27 (m, 2H), 2.12-2.15 (m, 1H), 1.51-1.57 (m, 2H). (TFA salt)

Example 281: 1-(4-{[(1S)-5-[2-(2-aminopyridin-3-yl)-5-(3-isopropylpyrazol-1-yl)imidazo[4,5-b]pyridin-3-yl]-2,3-dihydro-1H-inden-1-yl]amino}piperidin-1-yl)prop-2-en-1-one Example 281

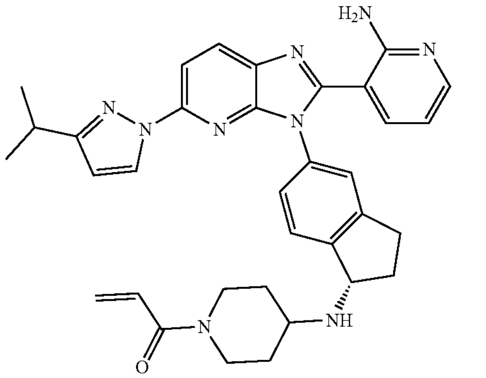

Example 281 was prepared in a manner analogous to Example 13 (via Intermediate 1-1) using 3-isopropyl-1H-pyrazole in place of pyrazole. MS (ESI) calcd for $C_{34}H_{37}N_9O$: 587.31, found 588.25 $[M+H]^+$. $^1H$ NMR (400 MHz, DMSO-d6) δ (ppm): 8.31 (d, J=8.4 Hz, 1H), 8.22 (s, 1H), 8.01 (d, J=1.8 Hz, 1H), 7.90 (d, J=8.4 Hz, 1H), 7.48 (d, J=7.8 Hz, 1H), 7.31 (s, 1H), 7.20-7.25 (m, 2H), 6.87-6.90 (m, 1H), 6.81-6.86 (m, 1H), 6.40-6.45 (m, 2H), 6.07 (d, J=16.8 Hz, 1H), 6.66 (d, J=10.5 Hz, 1H), 4.31-4.33 (m, 1H), 4.20-4.25 (m, 1H), 3.99-4.02 (m, 1H), 3.42-3.46 (m, 1H), 3.15-3.20 (m, 1H), 2.80-3.02 (m, 5H), 2.42-2.45 (m, 1H), 1.70-2.00 (m, 3H), 1.26 (d, J=6.9 Hz, 6H), 1.21-1.23 (m, 1H).

Example 282: 1-(4-{[(1S)-5-[5-(3-fluoropyrazol-1-yl)-2-phenylimidazo[4,5-b]pyridin-3-yl]-2,3-dihydro-1H-inden-1-yl]amino}piperidin-1-yl)prop-2-en-1-one Example 282

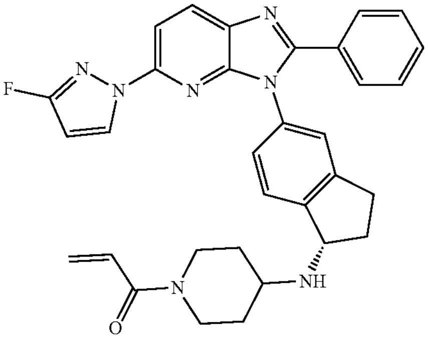

Example 282 was prepared in a manner analogous to Example 13 using Intermediate 282-1 in place of Intermediate 1-1 and using 5 eq of TEA. MS (ESI) calcd. for $C_{32}H_{30}FN_7O$: 547.25. found: 548.20 $[M+H]^+$. $^1H$ NMR (300 MHz, DMSO-$d_6$) δ(ppm): 8.34 (d, J=8.7 Hz, 1H), 8.29 (s, 1H), 7.77 (m, 1H), 7.53-7.58 (m, 2H), 7.39-7.45 (m, 4H), 7.32 (s, 1H), 7.19-7.25 (m, 1H), 6.75-6.84 (m, 1H), 6.31-

6.34 (m, 1H), 6.06 (d, J=2.4 Hz, 1H), 6.06 (d, J=3.0 Hz, 1H), 4.21-4.38 (m, 2H), 3.95-4.05 (m, 1H), 3.11-3.20 (m, 1H), 2.71-2.92 (m, 4H), 2.31-2.49 (m, 1H), 1.69-1.82 (m, 3H), 1.23 (m, 2H). $^{19}F$ NMR (282 MHz, DMSO-$d_6$) δ (ppm): −127.31.

Intermediate 282-1: (S)-5-(5-(3-fluoro-1H-pyrazol-1-yl)-2-phenyl-3H-imidazo[4,5-b]pyridin-3-yl)-2,3-dihydro-1H-inden-1-amine Intermediate 282-1

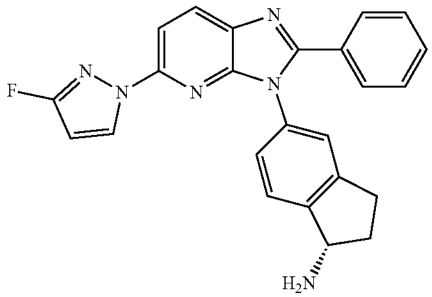

Intermediate 282-1 was prepared in a manner analogous to Intermediate 50-1 using Intermediate 236-3 in place of 6-methyl-3-nitropyridin-2-amine, tert-butyl N-[(1S)-5-bromo-2,3-dihydro-1H-inden-1-yl]carbamate in place of Intermediate 218-4, benzaldehyde in place of 2-aminopyridine-3-carbaldehyde and 4N HCl in dioxane/DCM (1:1) at room temperature for 2 h for the deprotection. MS (ESI) calcd. for $C_{24}H_{19}FN_6$: 410.17. found: 411.20 $[M+H]^+$.

Example 283: 1-(4-{[(1S)-5-[2-(2-aminopyridin-3-yl)-5-(3-cyclobutylpyrazol-1-yl)imidazo[4,5-b]pyridin-3-yl]-2,3-dihydro-1H-inden-1-yl]amino}piperidin-1-yl)prop-2-en-1-one Example 283

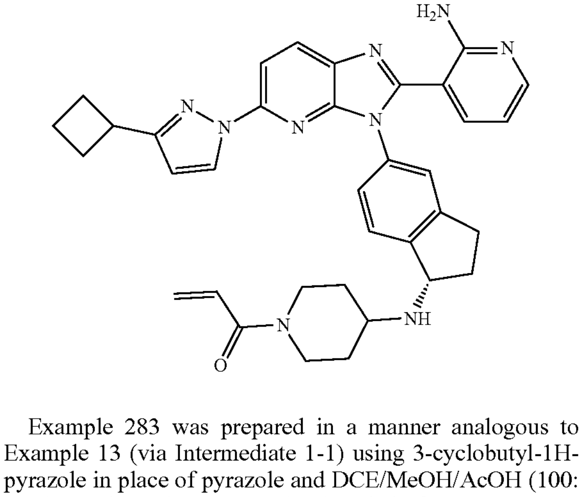

Example 283 was prepared in a manner analogous to Example 13 (via Intermediate 1-1) using 3-cyclobutyl-1H-pyrazole in place of pyrazole and DCE/MeOH/AcOH (100:10:1) as the solvent. MS (ESI) calcd. for $C_{35}H_{37}N_9O$: 599.31. found: 600.23$[M+H]^+$. $^1H$ NMR (300 MHz, DMSO-d6) δ (ppm): 8.31 (d, J=8.4 Hz, 1H), 8.24 (s, 1H), 8.01 (s, 1H), 7.89 (d, J=8.4 Hz, 1H), 7.48 (d, J=7.84 Hz, 1H), 7.31 (s, 1H), 7.22-7.25 (m, 2H), 6.81-6.91 (m, 1H), 6.47 (s, 1H), 6.40-6.45 (m, 1H), 6.08 (d, J=16.5 Hz, 1H), 5.67 (d, J=10.5 Hz, 1H), 4.22-4.33 (m, 2H), 3.95-4.02 (m, 1H), 3.56-3.60 (m, 1H), 3.12-3.18 (m, 1H), 2.65-2.90 (m, 4H), 2.40-2.42 (m, 1H), 2.25-2.30 (m, 2H), 2.15-2.22 (m, 2H), 1.75-2.08 (m, 5H), 1.20-1.30 (m, 2H).

Example 284: 2-{3-[(1S)-1-{[1-(prop-2-enoyl)piperidin-4-yl]amino}-2,3-dihydro-1H-inden-5-yl]-5-(pyrazol-1-yl)imidazo[4,5-b]pyridin-2-yl}benzonitrile Example 284

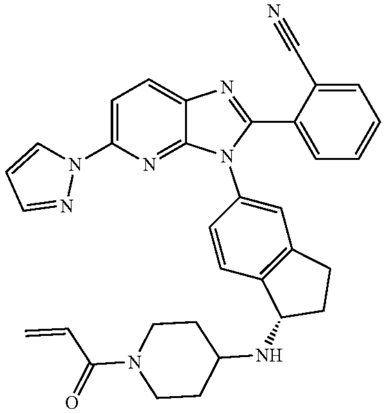

Synthetic Route:

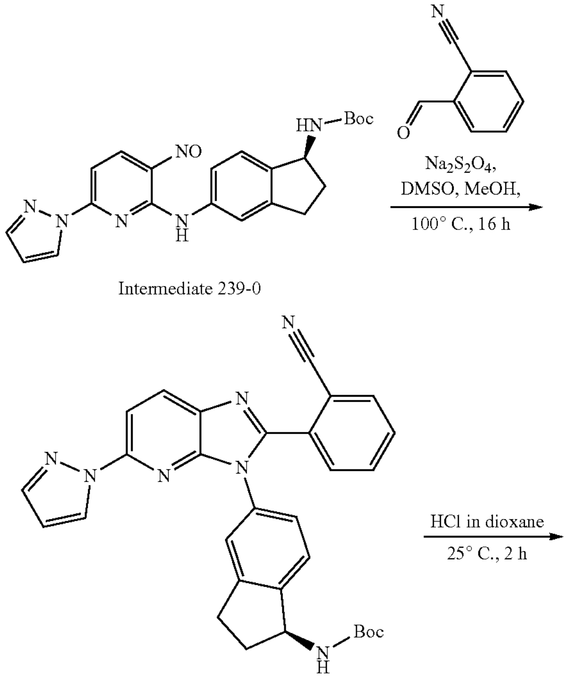

-continued

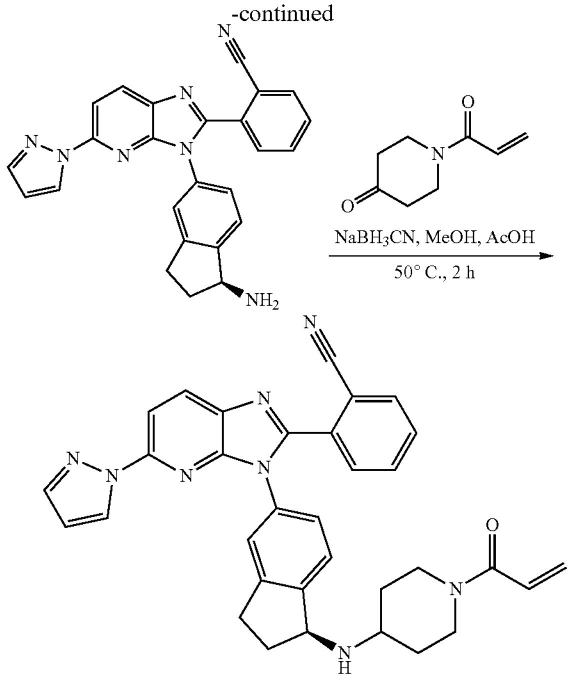

Example 284

Step 1: Synthesis of tert-butyl N-[(1S)-5-[2-(2-cyanophenyl)-5-(pyrazol-1-yl)imidazo[4,5-b]pyridin-3-yl]-2,3-dihydro-1H-inden-1-yl]carbamate To a stirred solution of tert-butyl N-[(1S)-5-{[3-nitro-6-(pyrazol-1-yl)pyridin-2-yl]amino}-2,3-dihydro-1H-inden-1-yl]carbamate (Intermediate 239-0) (500 mg, 1.146 mmol, 1 equiv) and 2-formylbenzonitrile (180.26 mg, 1.375 mmol, 1.2 equiv) in DMSO (24 mL) and MeOH (4 mL) was added $Na_2S_2O_4$ (498.60 mg, 2.865 mmol, 2.5 equiv) in portions at 25° C. The resulting mixture was stirred at 100° C. for 16 h. The mixture was allowed to cool to room temperature. The reaction was quenched with water at 0° C. The precipitated solids were collected by filtration and washed with water (3 mL×5). The residue was dissolved in MeOH (4 mL) and purified by silica gel column chromatography, eluting with 0-50%, ethyl acetate in petroleum ether to afford tert-butyl N-[(1S)-5-[2-(2-cyanophenyl)-5-(pyrazol-1-yl)imidazo[4,5-b]pyridin-3-yl]-2,3-dihydro-1H-inden-1-yl]carbamate (170 mg, 25.80%) as a yellow oil. MS (ESI) calcd. for $C_{30}H_{27}N_7O_2$: 517.22 m/z, found: 518.20 $[M+H]^+$.

Step 2: Synthesis of 2-{3-[(1S)-1-amino-2,3-dihydro-1H-inden-5-yl]-5-(pyrazol-1-yl)imidazo[4,5-b]pyridin-2-yl}benzonitrile To a stirred solution of tert-butyl N-[(1S)-5-[2-(2-cyanophenyl)-5-(pyrazol-1-yl)imidazo[4,5-b]pyridin-3-yl]-2,3-dihydro-1H-inden-1-yl]carbamate (170 mg, 0.328 mmol, 1 equiv) in DCM (3 mL) was added 4N HCl in 1,4-dioxane (10 mL) dropwise at 25° C. The resulting mixture was stirred at 25° C. for 2 h. The resulting mixture was concentrated under reduced pressure to afford 2-{3-[(1S)-1-amino-2,3-dihydro-1H-inden-5-yl]-5-(pyrazol-1-yl)imidazo[4,5-b]pyridin-2-yl}benzonitrile (80 mg, 58.34%) as a yellow oil. MS (ESI) calcd. for $C_{25}H_{19}N_7$: 417.17 m/z, found: 418.10 $[M+H]^+$.

Step 3: Synthesis of 2-{3-[(1S)-1-{[1-(prop-2-enoyl)piperidin-4-yl]amino}-2,3-dihydro-1H-inden-5-yl]-5-(pyrazol-1-yl)imidazo[4,5-b]pyridin-2-yl}benzonitrile (Example 284)

To a stirred solution of 2-{3-[(1S)-1-amino-2,3-dihydro-1H-inden-5-yl]-5-(pyrazol-1-yl)imidazo[4,5-b]pyridin-2-yl}benzonitrile (80 mg, 0.192 mmol, 1 equiv) in MeOH (2 mL) and DCE (20 mL) were added TEA (96.96 mg, 0.960 mmol, 5 equiv) dropwise at 25° C. The resulting mixture was stirred at 25° C. for 0.5 h. To the above mixture was added 1-(prop-2-enoyl)piperidin-4-one (58.71 mg, 0.384 mmol, 2 equiv) and AcOH (0.1 mL, 1.745 mmol, 9.11 equiv) in portions at 25° C. The resulting mixture was stirred at 50° C. for 1 h. To the above mixture was added $NaBH_3CN$ (36.13 mg, 0.576 mmol, 3 equiv) in portions at 0° C. The resulting mixture was stirred at 50° C. for 0.5 h. The residue was purified by silica gel column chromatography, eluting with 0-10% MeOH in DCM. The product was further purified by Prep-HPLC on a XSelect CSH OBD Column using a gradient of acetonitrile in water (+0.05% TFA) to afford 2-{3-[(1S)-1-{[1-(prop-2-enoyl)piperidin-4-yl]amino}-2,3-dihydro-1H-inden-5-yl]-5-(pyrazol-1-yl)imidazo[4,5-b]pyridin-2-yl}benzonitrile (Example 284, TFA salt) (14.2 mg, 10.66%) as a white solid. MS (ESI) calcd. for $C_{33}H_{30}N_8O$: 554.25 m/z, found: 555.25 $[M+H]^+$. H NMR (400 MHz, DMSO-$d_6$) δ ppm: 8.52-8.54 (m, 1H), 8.42 (s, 1H), 8.01-8.06 (m, 2H), 7.86 (s, 1H), 7.74-7.77 (m, 2H), 7.67-7.72 (m, 2H), 7.54 (s, 1H), 7.37 (d, J=8.0 Hz, 1H), 6.82-6.91 (m, 1H), 6.60-6.62 (m, 1H), 6.12-6.17 (m, 1H), 5.72-5.76 (m, 1H), 4.99-5.02 (m, 1H), 4.52-4.56 (m, 1H), 4.14-4.22 (m, 1H), 3.53-3.55 (m, 1H), 3.13-3.18 (m, 2H), 2.91-2.98 (m, 1H), 2.72-2.77 (m, 1H), 2.56-2.58 (m, 1H), 2.14-2.21 (m, 2H), 2.06-2.12 (m, 1H), 1.43-1.52 (m, 2H).

Example 285: (S)-1-(4-((5-(2-(2-(difluoromethyl)phenyl)-5-(1H-pyrazol-1-yl)-3H-imidazo[4,5-b]pyridin-3-yl)-2,3-dihydro-1H-inden-1-yl)amino)piperidin-1-yl)prop-2-en-1-one Example 285

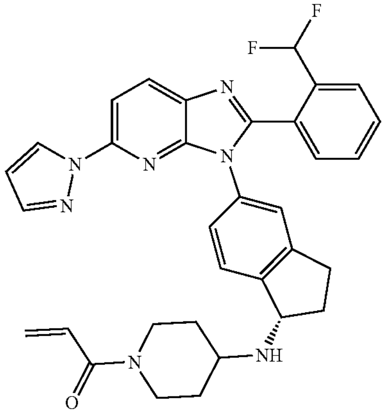

Example 285 was prepared in a manner analogous to Example 284 using 2-(difluoromethyl)benzaldehyde in place of 2-formylbenzonitrile. MS (ESI) calcd. for $C_{33}H_{31}F_2N_7O$: 579.26. found: 580.20 $[M+H]^+$, $^1H$ NMR (300 MHz, DMSO-d6) δ (ppm): 8.38-8.42 (m, 2H), 8.00 (d, J=8.4 Hz, 1H), 7.80-7.83 (m, 2H), 6.65 (t, J=7.5 Hz, 1H), 7.50-7.53 (m, 1H), 7.13-7.48 (m, 5H), 6.75-6.85 (m, 1H), 6.57 (s, 1H), 6.09 (d, J=16.8 Hz, 1H), 5.69 (d, J=10.5 Hz, 1H), 4.26-4.31 (m, 2H), 3.98-4.02 (m, 1H), 3.11-3.20 (m, 1H), 2.70-3.00 (m, 4H), 2.41-2.45 (m, 1H), 1.85-2.00 (m, 2H), 1.70-1.75 (m, 1H), 1.12-1.30 (m, 2H).

Example 286: 1-(4-(((1R,2*)-5-(2-(2-aminopyridin-3-yl)-5-(3-methoxy-1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one and Example 287: 1-(4-(((1R,2*)-5-(2-(2-aminopyridin-3-yl)-5-(3-methoxy-1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one Example 286

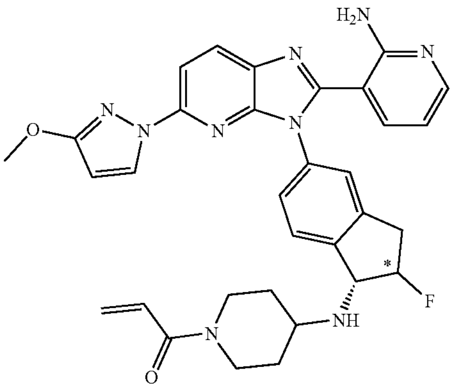

Example 287

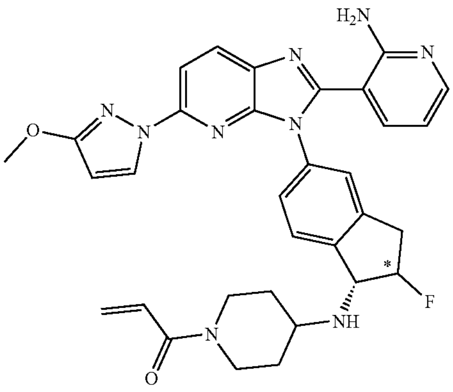

Examples 286 and 287 were prepared in a manner analogous to Example 13 using Intermediate 286-1 in place of Intermediate 1-1. The diastereomers were separated by chiral Prep-HPLC on a CHIRALPAK IK3 column using a mixture of [MtBE (+0.1% DEA)] and [EtOH/DCM (1:1)]. * Denotes a stereocenter with undetermined absolute stereocenter of a single diastereomer.

Example 286: MS (ESI) calcd. for $C_{32}H_{32}FN_9O_2$, 593.26 m/z, found 594.20 $[M+H]^+$. $^1H$ NMR (400 MHz, DMSO-d6) δ 8.31 (d, J=8.6 Hz, 1H), 8.19 (d, J=2.7 Hz, 1H), 8.00 (dd, J=4.9, 1.8 Hz, 1H), 7.78 (d, J=8.6 Hz, 1H), 7.49 (d, J=8.0 Hz, 1H), 7.39 (s, 1H), 7.29 (d, J=8.1 Hz, 1H), 7.21 (dd, J=7.6, 1.9 Hz, 1H), 6.91 (s, 2H), 6.86-6.72 (m, 1H), 6.42 (dd, J=7.6, 4.8 Hz, 1H), 6.12-6.04 (m, 2H), 5.66 (dd, J=10.4, 2.5 Hz, 1H), 5.34-5.08 (m, 1H), 4.48-4.12 (m, 1H), 4.24 (s, 1H), 4.00 (s, 1H), 3.92 (s, 3H), 3.57-3.39 (m, 1H), 3.17-3.02 (m, 1H), 3.08-2.99 (m, 2H), 2.87 (s, 1H), 2.32 (s, 2H), 2.00 (s, 1H), 1.89 (s, 1H). $^{19}F$ NMR (377 MHz, DMSO-d6) δ −176.017.

Example 287: MS (ESI) calcd. for $C_{32}H_{32}FN_9O_2$, 593.26 m/z, found 594.20 $[M+H]^+$. $^1H$ NMR (400 MHz, DMSO-d6) δ 8.31 (d, J=8.6 Hz, 1H), 8.17 (d, J=2.7 Hz, 1H), 8.00 (dd, J=4.9, 1.9 Hz, 1H), 7.77 (d, J=8.6 Hz, 1H), 7.48 (d, J=7.9 Hz, 1H), 7.38-7.29 (m, 2H), 7.22 (dd, J=7.7, 1.9 Hz, 1H), 6.92 (s, 2H), 6.90-6.78 (m, 1H), 6.41 (dd, J=7.7, 4.8 Hz, 1H), 6.15-6.01 (m, 2H), 5.66 (m, 1H), 5.60-5.35 (m, 1H), 4.54-4.44 (m, 1H), 4.23 (s, 1H), 4.01 (s, 1H), 3.91 (s, 3H), 2.5 (s, 1H), 3.27-2.88 (m, 5H), 2.23 (s, 1H), 2.00 (s, 1H), 1.88 (s, 1H). $^{19}F$ NMR (377 MHz, DMSO-d6) δ −196.70.

Intermediate 286-1: 3-(3-((1R)-1-amino-2-fluoro-2,3-dihydro-1H-inden-5-yl)-5-(3-methoxy-1H-pyrazol-1-yl)-3H-imidazo[4,5-b]pyridin-2-yl)pyridin-2-amine Intermediate 286-1

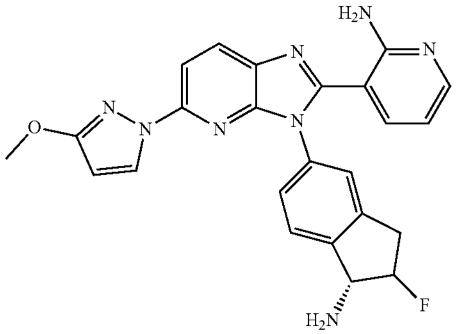

Synthetic Route:

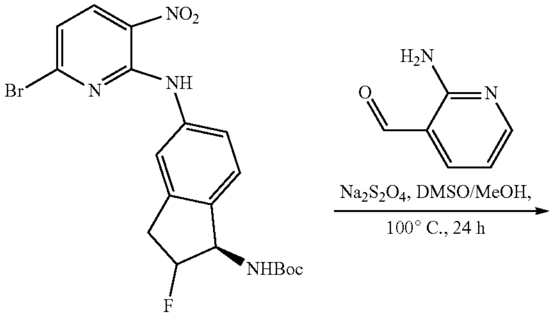

Intermediate 286-2

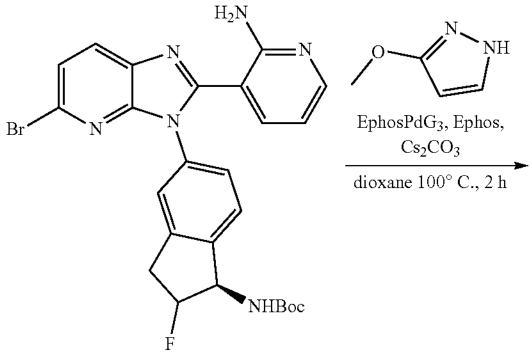

-continued

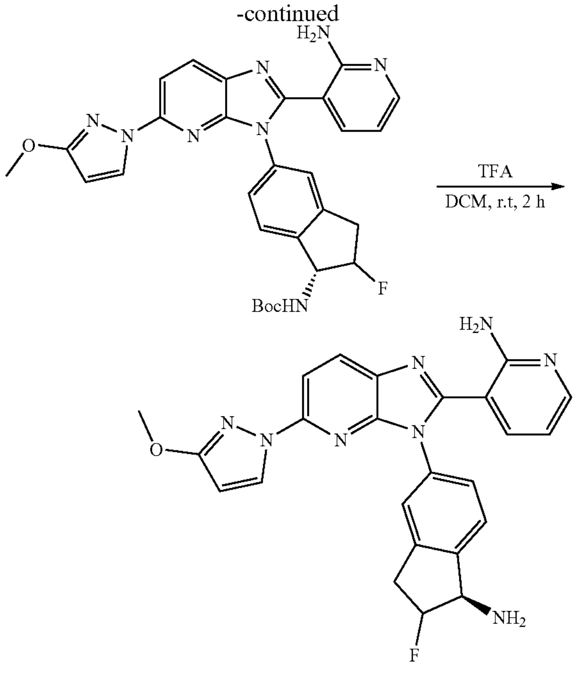

Intermediate 286-1

Step 1: Synthesis of tert-butyl ((1R)-5-(2-(2-amino-pyridin-3-yl)-5-bromo-3H-imidazo[4,5-b]pyridin-3-yl)-2-fluoro-2,3-dihydro-1H-inden-1-yl)carbamate A solution of tert-butyl ((1R)-5-((6-bromo-3-nitropyridin-2-yl)amino)-2-fluoro-2,3-dihydro-1H-inden-1-yl)carbamate (Intermediate 286-2) (1 g, 2.140 mmol, 1 equiv) in DMSO (10 mL) and MeOH (1.5 mL) was treated with 2-aminonicotinaldehyde (287.48 mg, 2.354 mmol, 1.1 equiv) and $Na_2S_2O_4$ (819.65 mg, 4.708 mmol, 2.2 equiv) for 24 h at 100° C. under nitrogen atmosphere. The reaction was quenched with $H_2O$ at r.t. The resulting mixture was extracted with ethyl acetate (100 mL×3). The combined organic layers were washed with brine (100 mL) and dried over anhydrous $Na_2SO_4$. After filtration, the filtrate was concentrated under reduced pressure. The residue was purified by silica gel column chromatography, eluting with ethyl acetate in petroleum ether (60~80%) to afford tert-butyl ((1R)-5-(2-(2-aminopyridin-3-yl)-5-bromo-3H-imidazo[4,5-b]pyridin-3-yl)-2-fluoro-2,3-dihydro-1H-inden-1-yl)carbamate (380 mg, 28%) as a yellow solid. MS (ESI) calcd. for $C_{25}H_{24}BrFN_6O2$, 538.11 m/z, found 539.20 $[M+H]^+$.

Step 2: Synthesis of tert-butyl ((1R)-5-(2-(2-amino-pyridin-3-yl)-5-(3-methoxy-1H-pyrazol-1-yl)-3H-imidazo[4,5-b]pyridin-3-yl)-2-fluoro-2,3-dihydro-1H-inden-1-yl)carbamate A solution of tert-butyl ((1R)-5-(2-(2-aminopyridin-3-yl)-5-bromo-3H-imidazo[4,5-b]pyridin-3-yl)-2-fluoro-2,3-dihydro-1H-inden-1-yl)carbamate (150 mg, 0.278 mmol, 1 equiv) in dioxane (5 mL) was treated with 3-methoxy-1H-pyrazole (54.56 mg, 0.556 mmol, 2 equiv), $Cs_2CO_3$ (181.21 mg, 0.556 mmol, 2 equiv), Ephos (29.74 mg, 0.056 mmol, 0.2 equiv) and EPhos Pd G4 (25.54 mg, 0.028 mmol, 0.1 equiv) at 100° C. for 2 h under nitrogen atmosphere. The mixture was allowed to cool to r.t and was quenched with $H_2O$. The resulting mixture was extracted with ethyl acetate (100 mL). The combined organic layers were washed with brine (30 mL) and dried over anhydrous $Na_2SO_4$. After filtration, the filtrate was concentrated under reduced pressure. The residue was purified by silica gel column chromatography, eluting with ethyl acetate in petroleum ether (60~70%) to afford tert-butyl ((1R)-5-(2-(2-aminopyridin-3-yl)-5-(3-methoxy-1H-pyrazol-1-yl)-3H-imidazo[4,5-b]pyridin-3-yl)-2-fluoro-2,3-dihydro-1H-inden-1-yl)carbamate (120 mg, 62.02%) as a yellow oil. MS (ESI) calcd. for $C_{29}H_{29}FN_8O_3$, 556.23 m/z, found 557.30 $[M+H]^+$.

Step 3: Synthesis of 3-(3-((1R)-1-amino-2-fluoro-2,3-dihydro-1H-inden-5-yl)-5-(3-methoxy-1H-pyrazol-1-yl)-3H-imidazo[4,5-b]pyridin-2-yl)pyridin-2-amine (Intermediate 286-1

A solution of tert-butyl ((1R)-5-(2-(2-aminopyridin-3-yl)-5-(3-methoxy-1H-pyrazol-1-yl)-3H-imidazo[4,5-b]pyridin-3-yl)-2-fluoro-2,3-dihydro-1H-inden-1-yl)carbamate (110 mg, 0.198 mmol, 1 equiv) in DCM (5 mL) was treated with TFA (1 mL) at r.t for 1 h. The resulting mixture was concentrated under reduced pressure to afford 3-(3-((1R)-1-amino-2-fluoro-2,3-dihydro-1H-inden-5-yl)-5-(3-methoxy-1H-pyrazol-1-yl)-3H-imidazo[4,5-b]pyridin-2-yl)pyridin-2-amine (Intermediate 286-1) (90 mg, 99.76%) as a crude yellow solid which was used in subsequent transformations directly. MS (ESI) calcd. for $C_{24}H_{21}FN_8O$, 456.18 m/z, found 457.20 $[M+H]^+$.

Intermediate 286-2: tert-butyl ((1R)-5-((6-bromo-3-nitropyridin-2-yl)amino)-2-fluoro-2,3-dihydro-1H-inden-1-yl)carbamate Intermediate 286-2

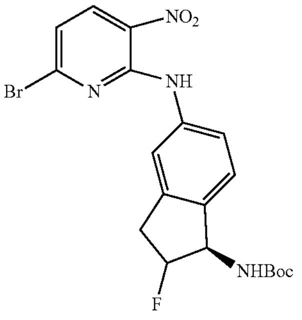

Intermediate 286-2 was prepared using procedure analogous to the first 3 steps in the route for Intermediate 85-1 using Intermediate 286-3 in place of tert-butyl N-[(1S)-5-bromo-2,3-dihydro-1H-inden-1-yl]carbamate. MS (ESI) calcd. for $C_{19}H_{20}BrFN_4O_4$, 466.07 m/z, found 467.10 $[M+H]^+$.

Intermediate 286-3: tert-butyl ((1R)-5-bromo-2-fluoro-2,3-dihydro-1H-inden-1-yl)carbamate

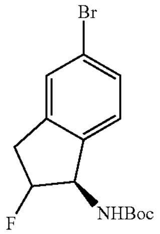

Intermediate 286-3

Synthetic Route:

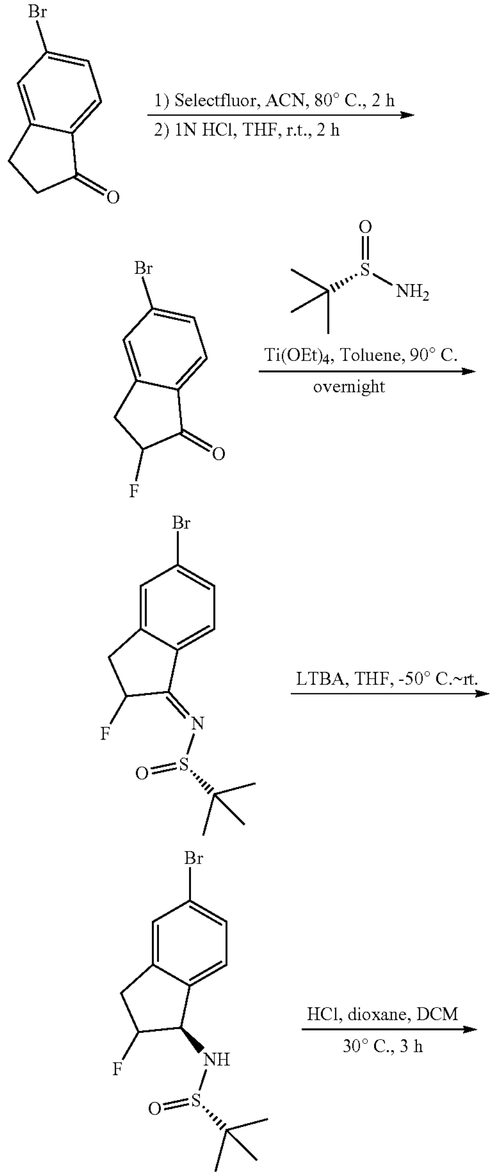

-continued

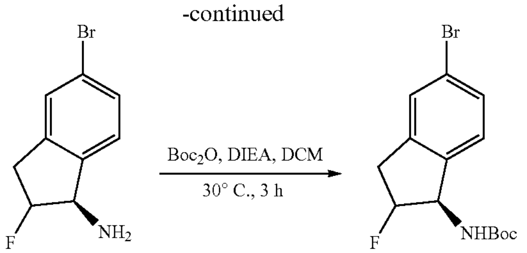

Intermediate 286-3

Step 1: Synthesis of 5-bromo-2-fluoro-2,3-dihydro-1H-inden-1-one

To a solution of 5-bromo-1-indanone (5.00 g, 23.8 mmol) in methanol (50 mL) was added SelectFluor (10.0 g, 28.2 mmol) and the resulting mixture was stirred under reflux for 2 hours. The reaction mixture was filtered through Celite, and the filtrate was concentrated under reduced pressure. The resulting residue was dissolved in tetrahydrofuran (50 mL), and 1 N hydrochloric acid (50 mL) was added followed by stirring at room temperature for 3 hours. To the reaction mixture, a 2 N aqueous sodium hydroxide solution (50 mL) was added, and the mixture was diluted with a saturated aqueous sodium bicarbonate solution. The mixture was extracted with ethyl acetate. The organic layer was washed with brine, dried over anhydrous magnesium sulfate, and then concentrated under reduced pressure to afford 5-bromo-2-fluoro-2,3-dihydroinden-1-one (4.0 g, 74% yield) as a white solid. MS (ESI) calcd. for $C_9H_6BrFO$, 227.96 m/z, found: 229.00 $[M+H]^+$.

Step 2: Synthesis of (S)-N-((Z)-5-bromo-2-fluoro-2,3-dihydro-1H-inden-1-ylidene)-2-methylpropane-2-sulfinamide To a solution of 5-bromo-2-fluoro-2,3-dihydroinden-1-one (3.0 g, 13 mmol) in toluene (5 mL) was added (S)-2-methylpropane-2-sulfinamide (1.90 g, 15.7 mmol) and $Ti(OEt)_4$ (5.08 g, 22.2 mmol). The mixture was stirred at 90° C. for 2 h. After cooling to room temperature, the reaction was quenched by the addition of 2M Rochelle's salt (30 mL). The resulting mixture was diluted with brine (50 mL) and extracted with ethyl acetate (3×50 mL). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)-N-(5-bromo-2-fluoro-2,3-dihydro-1H-inden-1-ylidene)-2-methylpropane-2-sulfinamide (3.0 g, 69% yield) as a yellow solid. MS (ESI) calcd. for $C_{13}H_{15}BrFNOS$: 331.00 m/z, found: 332.10 $[M+H]^+$. Note that the (S)- applies to the sulfur stereocenter and not the C—F bond for this and all instances vide infra.

Step 3: Synthesis of (S)-N-((1R)-5-bromo-2-fluoro-2,3-dihydro-1H-inden-1-yl)-2-methylpropane-2-sulfinamide To a cooled (−50° C.) solution of (S)-N-((Z)-5-bromo-2-fluoro-2,3-dihydro-1H-inden-1-ylidene)-2-methylpropane-2-sulfinamide (3.0 g, 9.0 mmol) was added LTBA (3.90 g, 15.4 mmol) and the resulting mixture was stirred at room temperature for 2 h. The reaction was quenched by the addition of 2M Rochelle's salt (30 mL). The mixture was diluted with brine (50 mL) and extracted with ethyl acetate (3×50 mL). The combined organic layers were dried over anhydrous $Na_2SO_4$. After filtration, the filtrate was concentrated under reduced pressure. The residue was purified by silica gel column chromatography using a gradient of ethyl acetate in petroleum ether to afford (S)-N-((1R)-5-bromo-2-fluoro-2,3-dihydro-1H-inden-1-yl)-2-methylpropane-2-sulfinamide (2.0 g, 66% yield) as a yellow solid. MS (ESI) calcd. for $C_{13}H_{17}BrFNOS$: 333.02 m/z, found: 334.10 $[M+H]^+$.

Step 4: (S)-N-((1R)-5-bromo-2-fluoro-2,3-dihydro-1H-inden-1-yl)-2-methylpropane-2-sulfinamide To a solution of N-[(1R)-5-bromo-2-fluoro-2,3-dihydro-1H-inden-1-yl]-2-methylpropane-2-sulfinamide (20 g, 59.835 mmol, 1 equiv) in DCM (200 mL) was added 4N HCl in 1,4-dioxane (40 mL). The resulting mixture was maintained under nitrogen and stirred at 30° C. for 3 h. After cooling to rt, the mixture was concentrated under vacuum and purified by recrystallization with DCM (100 mL). The material was diluted with water, then adjusted to pH 9-10 with sodium bicarbonate. The resulting solution was extracted with DCM (3×500 mL). The organic layers were combined, washed with brine (500 mL), dried and concentrated under vacuum to afford (1R)-5-bromo-2-fluoro-2,3-dihydro-1H-inden-1-amine (12 g, 81.06% yield) as a yellow solid. MS (ESI) calcd. for $C_9H_9BrFN$: 228.99 m/z, found: 230.00 $[M+H]^+$.

Step 5: tert-butyl ((1R)-5-bromo-2-fluoro-2,3-dihydro-1H-inden-1-yl)carbamate (Intermediate 286-3

To a solution of (1R)-5-bromo-2-fluoro-2,3-dihydro-1H-inden-1-amine (12 g, 52.156 mmol, 1 equiv) in DCM (200 mL) was added DIEA (20.22 g, 156.468 mmol, 3.0 equiv) and $Boc_2O$ (12.52 g, 57.372 mmol, 1.1 equiv). The resulting mixture was maintained under nitrogen and stirred at 30° C. for 3 h. After cooling to rt, the reaction was quenched with water (50 mL). The resulting mixture was extracted with ethyl acetate (3×50 mL). The organic layers were combined, dried over anhydrous sodium sulfate, filtered and concentrated. The residue obtained was purified by silica gel chromatography (0-20% ethyl acetate/petroleum ether) to afford tert-butyl N-[(1R)-5-bromo-2-fluoro-2,3-dihydro-1H-inden-1-yl]carbamate (Intermediate 286-3) (14 g, 75.60% yield) as a yellow solid. MS (ESI) calcd. for $C_{14}H_{17}BrFNO_2$: 329.04 m/z, found: 273.95 $[M-56]^+$.

Example 288: 1-[(3*,4*)-4-{[(1R,2*)-5-[2-(2-aminopyridin-3-yl)-5-(pyrazol-1-yl)imidazo[4,5-b]pyridin-3-yl]-2-fluoro-2,3-dihydro-1H-inden-1-yl]amino}-3-methylpiperidin-1-yl]prop-2-en-1-one Example 289: 1-[(3*,4*)-4-{[(1R,2*)-5-[2-(2-aminopyridin-3-yl)-5-(pyrazol-1-yl)imidazo[4,5-b]pyridin-3-yl]-2-fluoro-2,3-dihydro-1H-inden-1-yl]amino}-3-methylpiperidin-1-yl]prop-2-en-1-one Example 290: 1-[(3*,4*)-4-{[(1R,2*)-5-[2-(2-aminopyridin-3-yl)-5-(pyrazol-1-yl)imidazo[4,5-b]pyridin-3-yl]-2-fluoro-2,3-dihydro-1H-inden-1-yl]amino}-3-methylpiperidin-1-yl]prop-2-en-1-one and Example 291: 1-[(3*,4*)-4-{[(1R,2*)-5-[2-(2-aminopyridin-3-yl)-5-(pyrazol-1-yl)imidazo[4,5-b]pyridin-3-yl]-2-fluoro-2,3-dihydro-1H-inden-1-yl]amino}-3-methylpiperidin-1-yl]prop-2-en-1-one Example 288

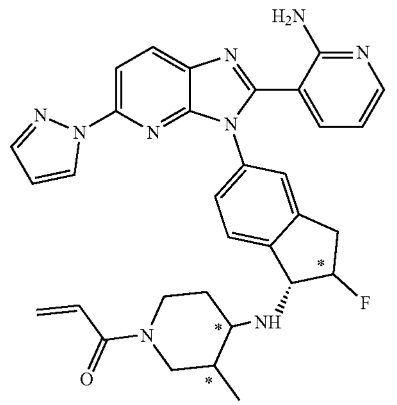

Example 289

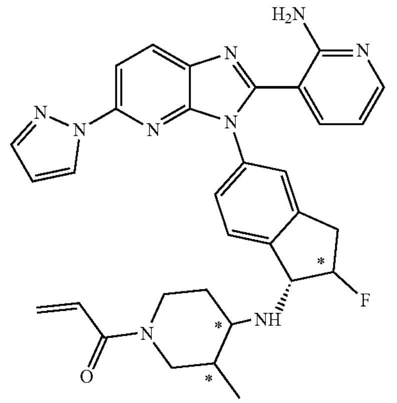

-continued

Example 290

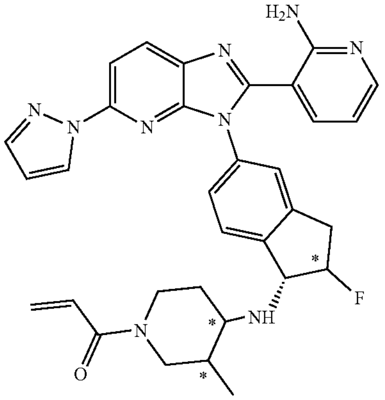

Example 291

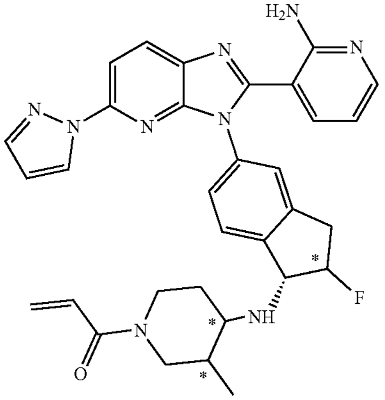

Examples 288, 289, 290 and 291 were prepared in a manner analogous to Example 14 (via Intermediate 14-1) using tert-butyl (S)-3-methyl-4-oxopiperidine-1-carboxylate in place of tert-butyl 8-oxo-3-azabicyclo[3.2.1]octane-3-carboxylate, MeOH in place of DCE for the final step, room temperature as the reaction temp for the final step and Intermediate 76-1 in place of Intermediate 1-1. Example 288 was separated from the other 3 isomers by chiral Prep HPLC on a CHIRALPAK Ik column using a mixture of [MtBE (+0.5% 2M $NH_3$-MeOH)] and [EtOH/DCM (1:1)]. Example 289 was separated from Examples 290 and 291 by chiral Prep-HPLC on a CHIRALPAK IG column using a mixture of [Hex/DCM (3:1) (+0.5% 2M $NH_3$-MeOH)] and isopropanol. Examples 290 and 291 were separated by chiral Prep-HPLC on a CHIRAL ART Cellulose-SB column using a mixture of [MtBE (+0.5% 2M $NH_3$-MeOH)] and [EtOH/DCM (1:1)]. Note that the methyl group epimerized during the synthesis. * Denotes a stereocenter with undetermined absolute stereocenter of a single diastereomer.

Example 288: MS (ESI) calcd. for $C_{32}H_{32}FN_9O$: 577.27 m/z, found: 578.35 $[M+H]^+$. $^1$H-NMR (400 MHz, DMSO-$d_6$) δ (ppm): 8.32-8.39 (m, 2H), 7.98-8.02 (m, 1H), 7.92-7.97 (m, 1H), 7.78-7.82 (m, 1H), 7.48-7.53 (m, 1H), 7.39-7.42 (m, 1H), 7.30-7.35 (m, 1H), 7.21-7.28 (m, 1H), 6.78-6.85 (m, 1H), 6.54-6.56 (m, 1H), 6.42-6.46 (m, 1H), 6.05-6.13 (m, 1H), 5.63-5.69 (m, 1H), 5.12-5.25 (m, 1H), 4.35-4.43 (m, 1H), 4.21-4.31 (m, 1H), 3.91-4.17 (m, 1H), 2.81-3.22 (m, 2H), 2.81-2.89 (m, 1H), 2.12-2.24 (m, 1H), 1.22-1.42 (m, 3H), 0.92-0.99 (m, 3H). $^{19}$F-NMR (300 MHz, DMSO-d6) δ (ppm): −176.03.

Example 289: MS (ESI) calcd. for $C_{32}H_{32}FN_9O$: 577.27 m/z, found: 578.35 $[M+H]^+$. $^1$H-NMR (400 MHz, DMSO- $d_6$) δ (ppm): 8.31-8.39 (m, 2H), 7.92-8.03 (m, 2H), 7.78-7.83 (m, 1H), 7.51-7.56 (m, 1H), 7.38-7.42 (m, 1H), 7.21-7.32 (m, 2H), 6.76-6.84 (m, 1H), 6.55-6.56 (m, 1H), 6.39-6.43 (m, 1H), 6.05-6.12 (m, 1H), 5.64-5.69 (m, 1H), 5.12-5.35 (m, 1H), 4.30-4.41 (m, 1H), 4.11-4.22 (m, 1H), 3.78-3.88 (m, 1H), 3.40-3.52 (m, 1H), 3.22-3.32 (m, 1H), 2.94-3.08 (m, 2H), 1.94-2.05 (m, 1H), 1.18-1.25 (m, 3H), 0.80-0.91 (m, 3H). $^{19}$F-NMR (300 MHz, DMSO-d6) δ (ppm): −176.0.

Example 290: MS (ESI) calcd. for $C_{32}H_{32}FN_9O$: 577.27 m/z, found: 578.40 $[M+H]^+$. $^1$H-NMR (400 MHz, DMSO-$d_6$) δ (ppm): 8.33-8.38 (m, 2H), 8.01-8.04 (m, 1H), 7.96-7.99 (m, 1H), 7.81-7.82 (m, 1H), 7.51-7.53 (m, 1H), 7.41-7.43 (m, 1H), 7.32-7.37 (m, 1H), 7.21-7.27 (m, 1H), 6.78-6.84 (m, 1H), 6.57-6.58 (m, 1H), 6.41-6.45 (m, 1H), 6.04-6.15 (m, 1H), 5.64-5.69 (m, 1H), 5.22-5.45 (m, 1H), 4.30-4.38 (m, 1H), 4.20-4.29 (m, 1H), 3.81-3.95 (m, 1H), 3.41-3.46 (m, 1H), 3.21-3.28 (m, 1H), 3.01-3.13 (m, 2H), 2.06-2.14 (m, 1H), 1.20-1.62 (m, 3H), 0.82-0.88 (m, 3H). $^{19}$F-NMR (300 MHz, DMSO-d6) δ (ppm): −175.601.

Example 291: MS (ESI) calcd. for $C_{32}H_{32}FN_9O$: 577.27 m/z, found: 578.40 $[M+H]^+$. $^1$H-NMR (400 MHz, DMSO-$d_6$) δ (ppm): 8.32-8.38 (m, 2H), 7.98-8.02 (m, 1H), 7.92-7.98 (m, 1H), 7.79-7.81 (m, 1H), 7.52-7.57 (m, 1H), 7.39-7.42 (m, 1H), 7.31-7.35 (m, 1H), 7.22-7.25 (m, 1H), 6.76-6.84 (m, 1H), 6.55-6.56 (m, 1H), 6.38-6.43 (m, 1H), 6.06-6.11 (m, 1H), 5.65-5.69 (m, 1H), 5.13-5.27 (m, 1H), 4.31-4.39 (m, 1H), 4.18-4.26 (m, 1H), 3.82-4.15 (m, 1H), 3.39-3.48 (m, 1H), 2.85-3.21 (m, 3H), 2.02-2.15 (m, 1H), 1.20-1.42 (m, 3H), 0.89-0.93 (m, 3H). $^{19}$F-NMR (300 MHz, DMSO-d6) δ (ppm): −176.832.

Example 292: 1-((R)-4-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)methyl)-2-methylpiperazin-1-yl)prop-2-en-1-one and Example 293: 1-((R)-4-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)methyl)-2-methylpiperazin-1-yl)prop-2-en-1-one Example 292

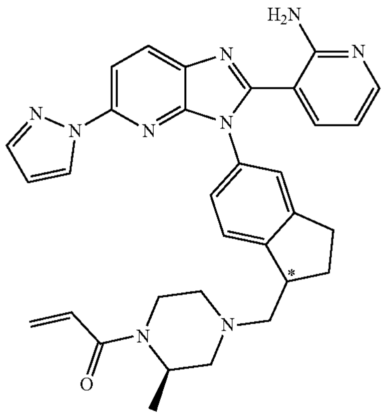

-continued

Example 293

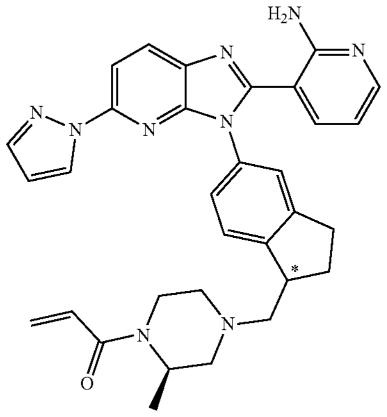

Examples 292 and 293 were prepared in a manner analogous to Example 174 using tert-butyl (2R)-2-methylpiperazine-1-carboxylate in place of tert-butyl piperazine-1-carboxylate. The diastereomers were separated by chiral Prep-HPLC on a CHIRALPAK IG column using a mixture of [Hex/DCM (3:1) (+0.5% 2M $NH_3$-MeOH)] and EtOH. * Denotes a stereocenter with undetermined absolute stereocenter of a single diastereomer.

Example 292: MS (ESI) calcd. for $C_{32}H_{33}N_9O$: 559.28 m/z, found: 560.40. $[M+H]^+$. $^1H$ NMR (300 MHz, DMSO-d6) δ (ppm): 8.42-8.30 (m, 2H), 8.06-7.98 (m, 1H), 7.98-7.90 (m, 1H), 7.86-7.78 (m, 1H), 7.55-7.44 (m, 1H), 7.34 (s, 1H), 7.28-7.15 (m, 2H), 6.95 (s, 2H), 6.87-6.72 (m, 1H), 6.58-6.51 (m, 1H), 6.47-6.37 (m, 1H), 6.17-6.05 (m, 1H), 5.74-5.61 (m, 1H), 4.73-3.77 (m, 2H), 3.53-3.40 (m, 1H), 3.05-2.89 (m, 2H), 2.89-2.76 (m, 2H), 2.64-2.54 (m, 1H), 2.46-2.35 (m, 1H), 2.35-2.19 (m, 1H), 2.11 (s, 1H), 2.04-1.74 (m, 2H), 1.25 (s, 4H).

Example 293: MS (ESI) calcd. for $C_{32}H_{33}N_9O$: 559.28 m/z, found: 560.40 $[M+H]^+$. $^1H$ NMR (300 MHz, DMSO-$d_6$) δ(ppm): 8.40-8.28 (m, 2H), 8.05-7.98 (m, 1H), 7.98-7.91 (m, 1H), 7.84-7.75 (m, 1H), 7.58-7.47 (m, 1H), 7.34 (s, 1H), 7.27-7.16 (m, 2H), 6.94 (s, 2H), 6.86-6.67 (m, 1H), 6.58-6.49 (m, 1H), 6.46-6.36 (m, 1H), 6.17-6.03 (m, 1H), 5.73-5.61 (m, 1H), 4.74-3.77 (m, 2H), 3.56-3.38 (m, 1H), 3.03-2.89 (m, 2H), 2.89-2.78 (m, 2H), 2.73-2.57 (m, 1H), 2.44-2.18 (m, 2H), 2.12 (s, 1H), 2.04-1.72 (m, 2H), 1.38-1.12 (m, 4H).

Example 294: 1-(2-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-6-azabicyclo[3.2.1]octan-6-yl)prop-2-en-1-one Example 294

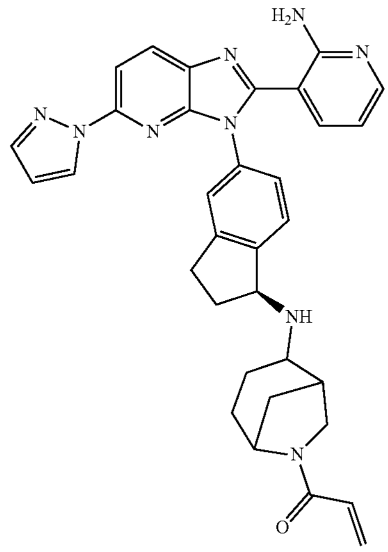

Example 294 was prepared in a manner analogous to Example 14 (via Intermediate 14-1) using tert-butyl 2-oxo-6-azabicyclo[3.2.1]octane-6-carboxylate in place of tert-butyl 8-oxo-3-azabicyclo[3.2.1]octane-3-carboxylate, sodium bicarbonate in place of triethylamine, THF/water (4:1) in place of DCM (for step 2) and DCE/MeOH (10:1) for the final step. MS (ESI) calcd. for $C_{33}H_{33}N_9O$, 571.28 m/z, found 572.25 $[M+H]^+$. $^1H$ NMR (400 MHz, DMSO-$d_6$) δ (ppm): 8.34-8.38 (m, 2H), 7.99-8.03 (m, 1H), 7.95 (d, J=8.6 Hz, 1H), 7.80-7.82 (m, 1H), 7.49-7.56 (m, 1H), 7.33-7.37 (m, 1H), 7.22-7.31 (m, 2H), 6.95 (s, 2H), 6.53-6.70 (m, 2H), 6.40-6.45 (m, 1H), 6.12-6.20 (m, 1H), 5.61-5.71 (m, 1H), 4.23-4.41 (m, 2H), 3.61-3.85 (m, 1H), 3.20-3.49 (m, 2H), 2.92-3.05 (m, 2H), 2.72-2.84 (m, 1H), 2.52-2.58 (m, 0.5H), 2.25-2.48 (m, 1.5H), 1.72-1.99 (m, 3H), 1.36-1.70 (m, 3H), 1.04-1.17 (m, 1H). (formic acid salt)

Example 295: 1-(4-{[(2R)-6-[2-(2-aminopyridin-3-yl)-5-(pyrazol-1-yl)imidazo[4,5-b]pyridin-3-yl]-1,2,3,4-tetrahydronaphthalen-2-yl]amino}piperidin-1-yl)prop-2-en-1-one Example 295

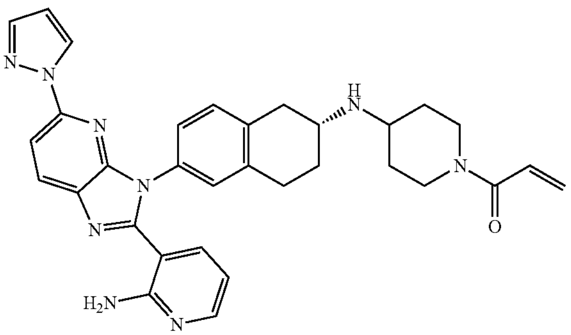

Example 295 was prepared in a manner analogous to Example 13 using Intermediate 295-1 in place of Intermediate 1-1 and DCE/MeOH (10:1) as the solvent. MS (ESI) calcd. for $C_{32}H_{33}N_9O$: 559.68. found: 560.35 $[M+H]^+$. $^1H$ NMR (400 MHz, DMSO-$d_6$) 8.28-8.32 (m, 2H), 7.95-7.97 (m, 1H), 7.84-7.90 (m, 1H), 7.76 (s, 1H), 7.30-7.35 (m, 1H), 7.23-7.25 (m, 2H), 7.12-7.19 (m, 1H), 6.68-6.75 (m, 1H), 6.48-6.53 (m, 2H), 6.05-6.09 (m, 1H), 5.70-5.72 (m, 1H), 4.40-4.43 (m, 1H), 4.05-4.08 (m, 1H), 3.21-3.34 (m, 2H), 3.10-3.19 (m, 2H), 2.83-2.94 (m, 1H), 2.65-2.70 (m, 2H), 2.11-2.13 (m, 1H), 2.00-2.03 (m, 2H), 1.59-1.62 (m, 1H), 1.33 (m, 2H).

Intermediate 295-1: (R)-3-(3-(6-amino-5,6,7,8-tetrahydronaphthalen-2-yl)-5-(1H-pyrazol-1-yl)-3H-imidazo[4,5-b]pyridin-2-yl)pyridin-2-amine Intermediate 295-1

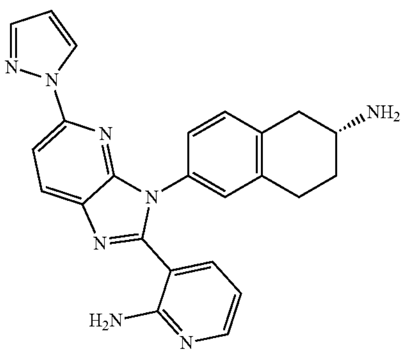

Intermediate 295-1 was prepared in a manner analogous to Intermediate 75-1 (starting from Step 2) using 6-bromo-3,4-dihydro-1H-naphthalen-2-one in place of 5-bromo-2-fluoro-2,3-dihydroinden-1-one and omitting the chiral separation. MS (ESI) calcd. for $C_{24}H_{22}N_8$: 422.20. found: 423.25 $[M+H]^+$.

Example 296: 1-(4-{[(2S)-6-[2-(2-aminopyridin-3-yl)-5-(pyrazol-1-yl)imidazo[4,5-b]pyridin-3-yl]-1,2,3,4-tetrahydronaphthalen-2-yl]amino}piperidin-1-yl)prop-2-en-1-one Example 296

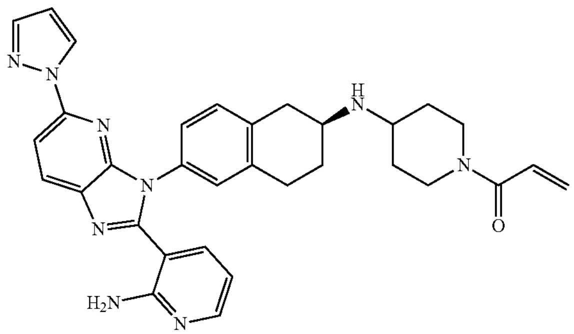

Example 296 was prepared in a manner analogous to Example 13 using Intermediate 296-1 in place of Intermediate 1-1 and DCE/MeOH (10:1) as the solvent. MS (ESI) calcd. for $C_{32}H_{33}N_9O$: 559.28 m/z, found: 560.40$[M+H]^+$. $^1H$ NMR (300 MHz, DMSO-$d_6$) δ (ppm): 8.35-8.39 (m, 2H), 7.93-8.05 (m, 2H), 7.79-7.82 (m, 1H), 7.18-7.28 (m, 4H), 6.90-6.98 (m, 2H), 6.79-6.88 (m, 1H), 6.42-6.56 (m, 2H), 6.07-6.13 (m, 1H), 5.65-5.71 (m, 1H), 4.33-4.42 (m, 1H), 4.02-4.12 (m, 1H), 3.30-3.35 (m, 1H), 3.08-3.21 (m, 2H), 2.65-2.96 (m, 4H), 1.56-2.21 (m, 5H), 1.20-1.39 (m, 3H).

Intermediate 296-1: (S)-3-(3-(6-amino-5,6,7,8-tetrahydronaphthalen-2-yl)-5-(1H-pyrazol-1-yl)-3H-imidazo[4,5-b]pyridin-2-yl)pyridin-2-amine Intermediate 296-1

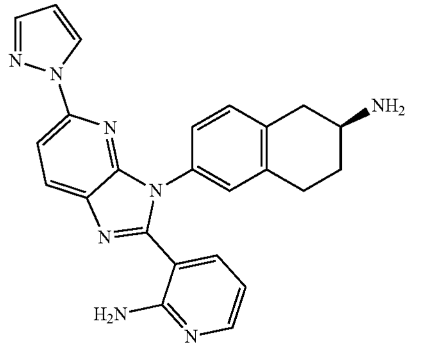

Intermediate 296-1 was prepared in a manner analogous to Intermediate 75-1 (starting from Step 2) using 6-bromo-3,4-dihydro-1H-naphthalen-2-one in place of 5-bromo-2-fluoro-2,3-dihydroinden-1-one, (R)-2-methylpropane-2-sulfinamide in place of (S)-2-methylpropane-2-sulfinamide and omitting the chiral separation. MS (ESI) calcd. for $C_{24}H_{22}N_8$: 422.20. found: 423.10 $[M+H]^+$.

Example 297: 1-(4-(((1R,2*)-5-(2-(2-aminopyridin-3-yl)-5-(3-cyclopropyl-1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one and Example 298: 1-(4-(((1R,2*)-5-(2-(2-aminopyridin-3-yl)-5-(3-cyclopropyl-1H-pyrazol-1-yl)-3H-imidazo[4,5-b]pyridin-3-yl)-2-fluoro-2,3-dihydro-1H-inden-1-yl)amino)piperidin-1-yl)prop-2-en-1-one Example 297

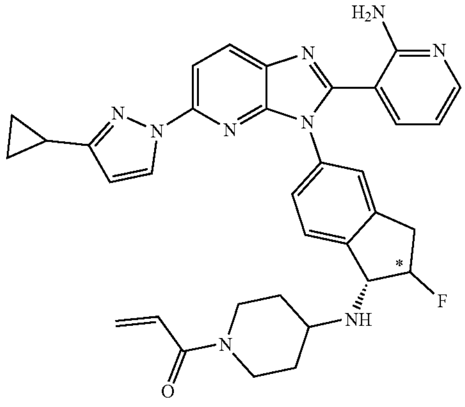

-continued

Example 298

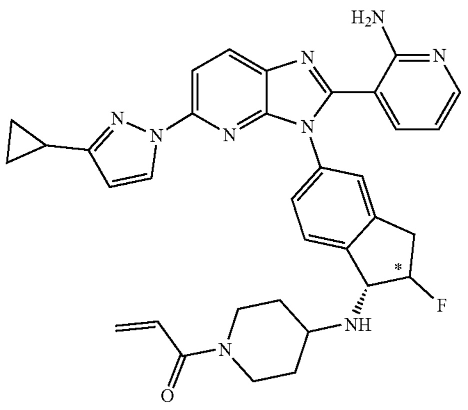

Examples 297 and 298 were prepared in a manner analogous to Examples 286 and 287 (via Intermediate 286-1) using 3-cyclopropyl-1H-pyrazole in place of 3-methoxy-1H-pyrazole. The diastereomers separated after the final step by Prep-HPlC on a XSelect CSH OBD Column using a gradient of acetonitrile in water (+0.1% FA). * Denotes a stereocenter with undetermined absolute stereocenter of a single diastereomer.

Example 297: MS (ESI) calcd. for $C_{34}H_{34}FN_9O$, 603.29 m/z, found 604.30 $[M+H]^+$. $^1$H NMR (300 MHz, DMSO-$d_6$) δ 9.55 (s, 2H), 8.36 (d, J=8.6 Hz, 1H), 8.19 (d, J=2.5 Hz, 1H), 8.05 (dd, J=5.1, 1.7 Hz, 1H), 7.90 (d, J=8.6 Hz, 1H), 7.77 (d, J=8.2 Hz, 1H), 7.59 (s, 1H), 7.54-7.38 (m, 2H), 7.16 (s, 1H), 6.88 (s, 1H), 6.54 (t, J=6.4 Hz, 1H), 6.29 (d, J=2.6 Hz, 1H), 6.19-6.09 (m, 1H), 5.96 (s, 1H), 5.78-5.68 (m, 1H), 5.33 (s, 1H), 4.65-4.46 (m, 1H), 4.24 (s, 1H), 3.41 (s, 1H), 3.30 (s, 1H), 3.28-3.12 (m, 1H), 2.78-2.69 (m, 1H), 2.41-2.29 (m, 1H), 2.16 (s, 1H), 2.02 (d, J=4.9 Hz, 1H), 1.71-1.45 (m, 2H), 1.56 (s, 1H), 0.98 (dq, J=8.5, 4.5, 2.5 Hz, 2H), 0.88-0.72 (m, 2H). $^{19}$F NMR (282 MHz, DMSO-$d_6$) δ −195.54.

Example 298: MS (ESI) calcd. for $C_{34}H_{34}FN_9O$, 603.29 m/z, found 604.25 $[M+H]^+$. $^1$H HMR (300 MHz, DMSO-$d_6$) δ 8.33 (d, J=8.6 Hz, 1H), 8.21 (d, J=2.5 Hz, 1H), 8.02 (dd, J=4.8, 1.8 Hz, 1H), 7.88 (d, J=8.6 Hz, 1H), 7.50 (s, 2H), 7.38 (s, 1H), 6.98-6.75 (m, 2H), 6.44 (dd, J=7.6, 4.8 Hz, 1H), 6.27 (d, J=2.6 Hz, 1H), 6.18-6.03 (m, 1H), 5.76-5.67 (m, 1H), 4.11 (s, 2H), 3.79-3.47 (m, 2H), 3.15 (s, 3H), 2.82 (s, 1H), 2.12 (s, 1H), 2.05-1.96 (m, 2H), 1.76-1.23 (m, 4H), 1.24 (s, 1H), 1.02-0.90 (m, 3H), 0.89-0.71 (m, 2H). $^{19}$F NMR (282 MHz, DMSO-$d_6$) δ −176.10.

Example 299: 1-(4-(((1R,2*)-2-fluoro-5-(2-(2-fluorophenyl)-5-(1H-pyrazol-1-yl)-3H-imidazo[4,5-b]pyridin-3-yl)-2,3-dihydro-1H-inden-1-yl)amino)piperidin-1-yl)prop-2-en-1-one and Example 300: 1-(4-(((1R,2*)-2-fluoro-5-(2-(2-fluorophenyl)-5-(1H-pyrazol-1-yl)-3H-imidazo[4,5-b]pyridin-3-yl)-2,3-dihydro-1H-inden-1-yl)amino)piperidin-1-yl)prop-2-en-1-one Example 299

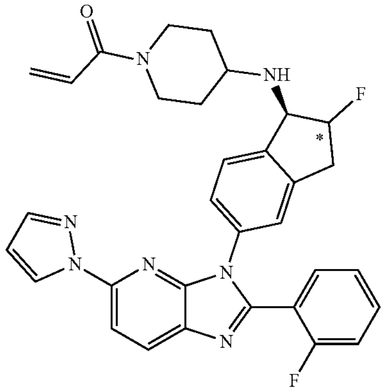

Example 300

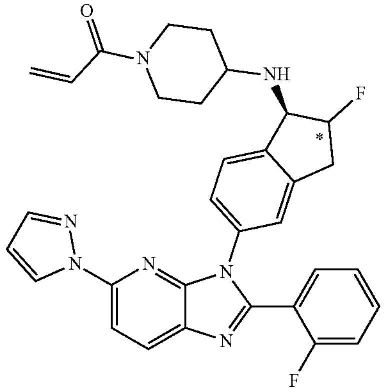

Examples 299 and 300 were prepared in a manner analogous to Example 13 using Intermediate 299-1 in place of Intermediate 1-1, and DCE/MeOH (1:1) instead of DCE. The diastereomers were separated by silica gel column chromatography using 0-30% MeOH in DCM. * Denotes a stereocenter with undetermined absolute stereocenter of a single diastereomer.

Example 299: MS (ESI) calcd for $C_{32}H_{29}F_2N_7O$ 565.24 m/z, found 566.15 $[M+H]^+$. $^1$H NMR (500 MHz, DMSO-d6) δ 8.45-8.39 (m, 2H), 8.00 (d, J=8.6 Hz, 1H), 7.83 (d, J=1.6 Hz, 1H), 7.75-7.72 (m, 1H), 7.60-7.56 (m, 1H), 7.44 (d, J=8.0 Hz, 1H), 7.39-7.32 (m, 2H), 7.30-7.22 (m, 2H), 6.87-6.81 (m, 1H), 6.57 (t, J=2.1 Hz, 1H), 6.10 (dd, J=16.7, 2.5 Hz, 1H), 5.67 (dd, J=10.2, 2.5 Hz, 1H), 5.44 (d, J=54.5 Hz, 1H), 4.42 (d, J=26.1 Hz, 1H), 4.24-4.20 (m, 1H), 4.04-3.97 (m, 1H), 3.27-3.15 (m, 2H), 3.13-2.91 (m, 3H), 2.21 (s, 1H), 2.02-1.95 (m, 1H), 1.92-1.84 (m, 1H), 1.39-1.24 (m, 2H).

Example 300: MS (ESI) calcd for $C_{32}H_{29}F_2N_7O$ 565.24 m/z, found 566.15 $[M+H]^+$. $^1$H NMR (500 MHz, DMSO-$d_6$) δ 8.46-8.38 (m, 2H), 8.00 (d, J=8.6 Hz, 1H), 7.84 (d, J=1.6 Hz, 1H), 7.74 (s, 1H), 7.61-7.57 (m, 1H), 7.46-7.34 (m, 3H), 7.26 (t, J=9.3 Hz, 2H), 6.86-6.81 (m, 1H), 6.58-6.57 (m, 1H), 6.10 (d, J=16.6 Hz, 1H), 5.67 (d, J=10.3 Hz, 1H), 5.23

(d, J=53.9 Hz, 1H), 4.43-4.33 (m, 2H), 4.01 (s, 1H), 3.20-3.12 (m, 1H), 2.99 (s, 2H), 1.99 (s, 2H), 1.69-1.03 (m, 4H), 0.97-0.78 (m, 1H).

Intermediate 299-1: (1R)-2-fluoro-5-(2-(2-fluorophenyl)-5-(1H-pyrazol-1-yl)-3H-imidazo[4,5-b]pyridin-3-yl)-2,3-dihydro-1H-inden-1-amine Intermediate 299-1

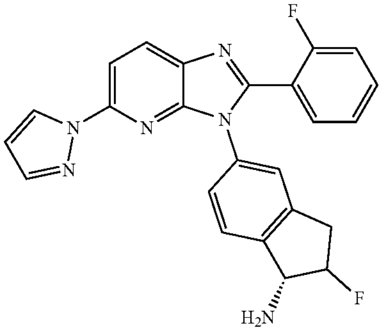

Intermediate 299-1 was prepared in a manner analogous to Intermediate 75-1 using 2-fluorobenzaldehyde in place of 2-aminopyridine-3-carbaldehyde and omitting the chiral separation. MS (ESI) calcd for $C_{24}H_{18}F_2N_6$ 428.16 m/z, found 429.50 $[M+H]^+$.

Example 301: 1-((2*,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one Example 302: 1-((2*,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one Example 303: 1-((2*,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one and Example 304: 1-((2*,4*)-4-(((1R,2*)-5-(2-(2-aminopyridin-3-yl)-5-(1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one Example 301

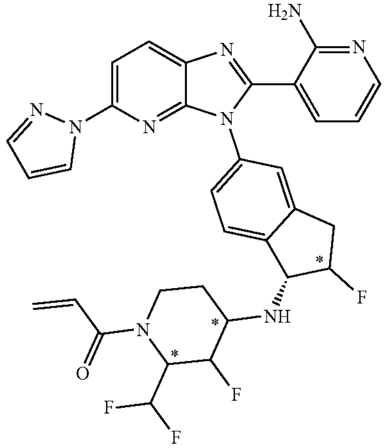

-continued

Example 302

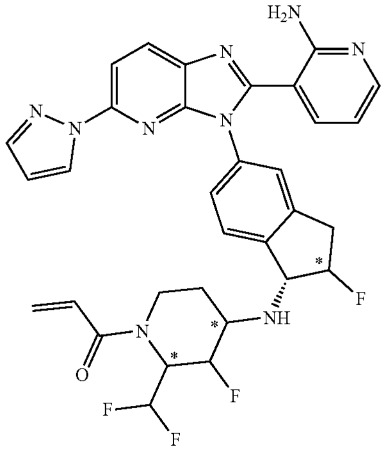

Example 303

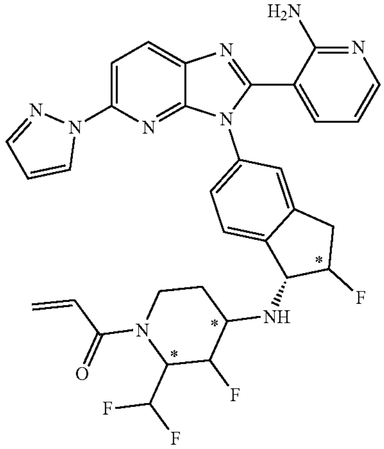

Example 304

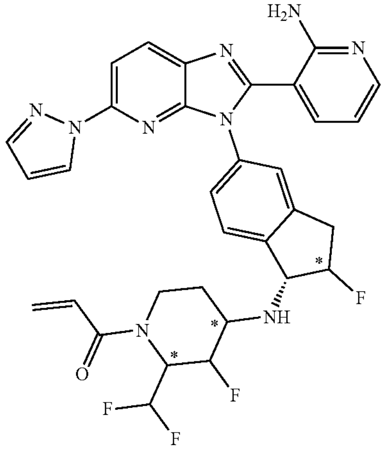

Examples 301-304 were prepared in a manner analogous to Example 14 (via Intermediate 14-1) using tert-butyl 2-(difluoromethyl)-4-oxopiperidine-1-carboxylate in place of tert-butyl 8-oxo-3-azabicyclo[3.2.1]octane-3-carboxylate, Intermediate 75-1 in place of Intermediate 1-1 and MeOH at 60° C. for the final step. * Denotes a stereocenter with undetermined absolute stereocenter of a single diastereomer. The four stereoisomers partially separated by Prep HPlC on a XSelect CSH OBD column using a gradient of acetonitrile in water (+0.05% TFA). The following groups were obtained:

Group 1: Examples 302 and 303

Group 2: Examples 301 and an undetermined mix of isomers

Group 3: Examples 304 and an undetermined mix of isomers

Examples 302 and 303 were separated by chiral Prep-HPLC on a CHIRALPAK AD-H column using a mixture of [HEX (+0.5% 2M $NH_3$-MeOH)] and isopropanol.

Examples 301 was separated from an undetermined mix of isomers by chiral Prep-HPLC on a CHIRALPAK IF column using a mixture of [MtBE (+0.5% 2M NH3-MeOH)] and [ethanol/DCM (1:1)].

Examples 304 was separated from an undetermined mix of isomers by chiral Prep-HPLC on a CHIRALPAK IG column using a mixture of [Hex/DCM (3:1) (+0.5% 2M NH3-MeOH)] and ethanol.

Example 301: MS (ESI) calcd. for $C_{32}H_{30}F_3N_9O$, 613.25 m/z, found: 614.20 $[M+H]^+$. $^1H$ NMR (400 MHz, DMSO-d6) δ (ppm): 8.21-8.48 (m, 2H), 7.86-8.14 (m, 2H), 7.71-7.86 (m, 1H), 7.45-7.71 (m, 1H), 7.16-7.45 (m, 3H), 6.65-6.96 (m, 2H), 6.52-6.65 (m, 1H), 6.36-6.52 (m, 1H), 6.02-6.31 (m, 1H), 5.68-5.91 (m, 1H), 5.37-5.68 (m, 1H), 4.18-4.62 (m, 2H), 3.53-3.91 (m, 1H), 3.31-3.45 (m, 1H), 3.16-3.31 (m, 1H), 2.98-3.16 (m, 1H), 2.44-2.54 (m, 1H), 1.81-2.18 (m, 3H), 1.48-1.81 (m, 1H).

Example 302: MS (ESI) calcd. for $C_{32}H_{30}F_3N_9O$, 613.25 m/z, found: 614.20 $[M+H]^+$. $^1H$ NMR (400 MHz, DMSO-d6) δ (ppm): 8.18-8.52 (m, 2H), 7.89-8.18 (m, 2H), 7.64-7.89 (m, 1H), 7.45-7.64 (m, 1H), 7.12-7.45 (m, 3H), 6.71-7.04 (m, 1H), 6.01-6.71 (m, 4H), 5.68-5.96 (m, 1H), 5.24-5.68 (m, 1H), 4.32-4.78 (m, 2H), 2.82-3.35 (m, 4H), 2.05-2.41 (m, 2H), 1.32-1.71 (m, 2H), 1.24-1.31 (m, 1H).

Example 303: MS (ESI) calcd. for $C_{32}H_{30}F_3N_9O$, 613.25 m/z, found: 614.15 $[M+H]^+$. $^1H$ NMR (400 MHz, DMSO-d6) δ (ppm): 8.21-8.52 (m, 2H), 7.86-8.14 (m, 2H), 7.65-7.86 (m, 1H), 7.42-7.65 (m, 1H), 7.16-7.42 (m, 3H), 6.69-6.96 (m, 1H), 6.55-6.69 (m, 1H), 6.44-6.55 (m, 1H), 6.22-6.44 (m, 1H), 6.11-6.22 (m, 1H), 5.68-5.95 (m, 1H), 5.32-5.68 (m, 1H), 4.26-4.76 (m, 2H), 2.82-2.41 (m, 4H), 2.32-2.41 (m, 1H), 2.09-2.28 (m, 1H), 1.96-2.09 (m, 1H), 1.25-1.72 (m, 2H).

Example 304: MS (ESI) calcd. for $C_{32}H_{30}F_3N_9O$, 613.25 m/z, found: 614.20 $[M+H]^+$. $^1H$ NMR (400 MHz, DMSO-d6) δ (ppm): 8.18-8.48 (m, 2H), 7.96-8.18 (m, 1H), 7.86-7.96 (m, 1H), 7.76-7.86 (m, 1H), 7.42-7.62 (m, 1H), 7.24-7.42 (m, 3H), 6.66-7.24 (m, 2H), 6.38-6.66 (m, 2H), 6.01-6.33 (m, 1H), 5.72-5.95 (m, 1H), 5.37-5.72 (m, 1H), 4.21-4.68 (m, 2H), 3.61-4.08 (m, 1H), 3.36-3.61 (m, 1H), 2.92-3.34 (m, 4H), 2.14-2.34 (m, 1H), 1.56-1.92 (m, 3H).

Example 305: (S)-1-(4-((5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)amino)piperidin-1-yl)prop-2-en-1-one Example 305

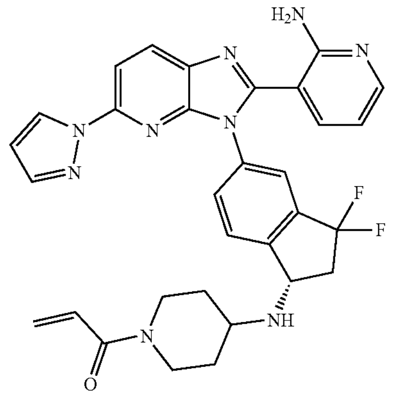

Example 305 was prepared in a manner analogous to Example 13 using Intermediate 305-2 in place of Intermediate 1-1 and DCE/MeOH (10:1) as the solvent. MS (ESI) calcd. for $C_{31}H_{29}F_2N_9O$, 581.25 m/z, found 582.30 $[M+H]^+$. $^1H$ NMR (300 MHz, DMSO-$d_6$) δ (ppm): 8.32-8.40 (m, 1H), 8.27-8.32 (m, 1H), 7.98-8.04 (m, 1H), 7.91-7.98 (m, 1H), 7.76-7.83 (m, 1H), 7.60-7.75 (m, 3H), 7.26-7.35 (m, 1H), 6.69-6.86 (m, 1H), 6.52-6.58 (m, 1H), 6.41-6.52 (m, 1H), 6.01-6.13 (m, 1H), 5.62-5.72 (m, 1H), 4.42-4.55 (m, 1H), 4.15-4.33 (m, 1H), 3.88-4.06 (m, 1H), 2.98-3.22 (m, 2H), 2.75-2.95 (m, 2H), 2.28-2.46 (m, 1H), 1.92-2.05 (m, 1H), 1.73-1.89 (m, 1H), 1.10-1.34 (m, 2H). $^{19}F$ NMR (282 MHz, DMSO-$d_6$) δ (ppm): −82.56, −85.53.

Intermediate 305-2: (S)-3-(3-(1-amino-3,3-difluoro-2,3-dihydro-1H-inden-5-yl)-5-(1H-pyrazol-1-yl)-3H-imidazo[4,5-b]pyridin-2-yl)pyridin-2-amine Intermediate 305-2

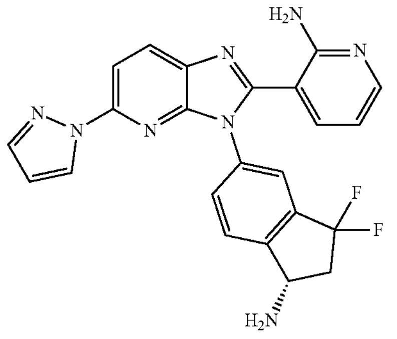

Synthetic Route:

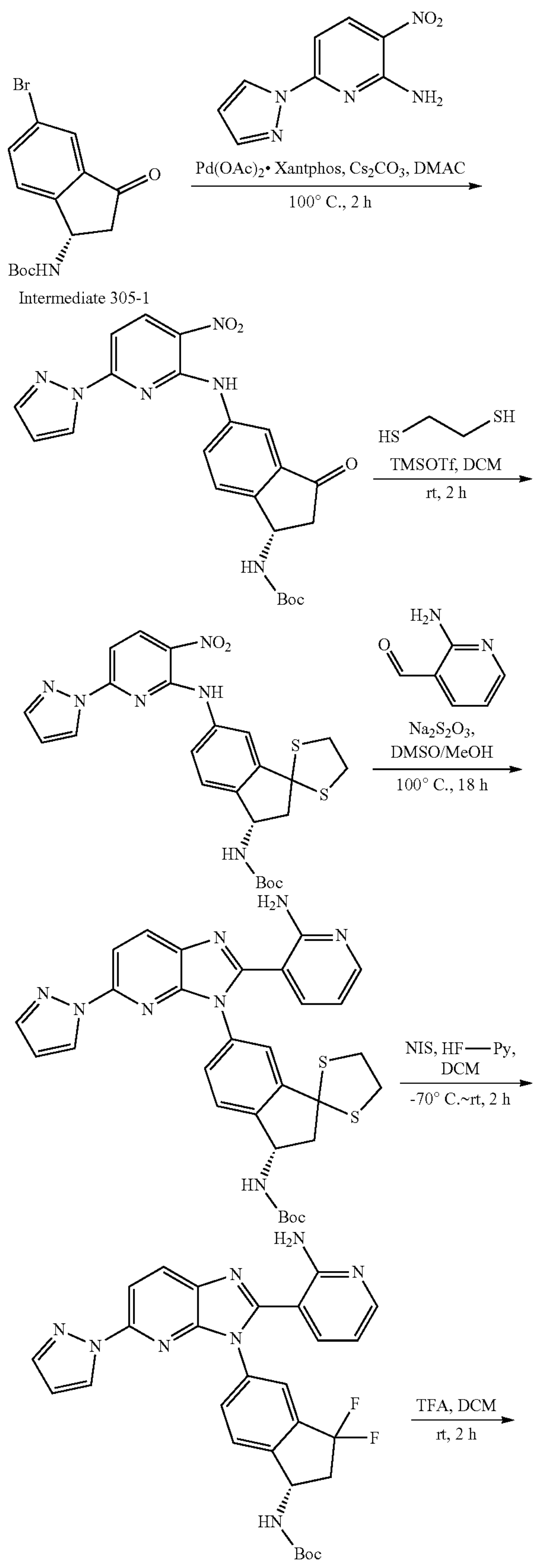

Intermediate 305-1

-continued

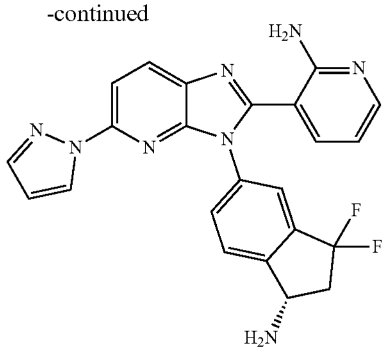

Intermediate 305-2

Step 1: Synthesis of tert-butyl (S)-(5-((3-nitro-6-(1H-pyrazol-1-yl)pyridin-2-yl)amino)-3-oxo-2,3-dihydro-1H-inden-1-yl)carbamate To a solution of tert-butyl (S)-(5-bromo-3-oxo-2,3-dihydro-1H-inden-1-yl)carbamate (Intermediate 305-1) (1 g, 3.066 mmol, 1 equiv) and 3-nitro-6-(1H-pyrazol-1-yl)pyridin-2-amine (0.69 g, 3.4 mmol, 1.1 equiv) in 1,4-dioxane (15 mL) were added $Cs_2CO_3$ (2.00 g, 6.13 mmol, 2 equiv), $Pd(OAc)_2$ (0.07 g, 0.3 mmol, 0.1 equiv) and XantPhos (0.35 g, 0.61 mmol, 0.2 equiv) at room temperature under $N_2$ atmosphere. After stirring for 2 h at 100° C. under a nitrogen atmosphere, the mixture was allowed to cool to room temperature. The resulting mixture was filtered, the filter cake was washed with ethyl acetate (3×50 mL). The filtrate was concentrated under reduced pressure. The residue was purified by reverse-phase flash chromatography on C18 silica gel using a gradient of acetonitrile in water (+0.05% ammonium bicarbonate) to afford tert-butyl (S)-(5-((3-nitro-6-(1H-pyrazol-1-yl)pyridin-2-yl)amino)-3-oxo-2,3-dihydro-1H-inden-1-yl)carbamate (1 g, 72%) as a brown solid. MS (ESI) calcd. for $C_{22}H_{22}N_6O_5$, 450.17 m/z, found 451.15 $[M+H]^+$.

Step 2: Synthesis of tert-butyl (S)-(6-((3-nitro-6-(1H-pyrazol-1-yl)pyridin-2-yl)amino)-2,3-dihydrospiro[indene-1,2'-[1,3]dithiolan]-3-yl)carbamate To a stirred solution of tert-butyl (S)-(5-((3-nitro-6-(1H-pyrazol-1-yl)pyridin-2-yl)amino)-3-oxo-2,3-dihydro-1H-inden-1-yl)carbamate (1 g, 2.2 mmol, 1 equiv) and ethane-1,2-dithiol (0.42 g, 4.4 mmol, 2 equiv) in DCM (30 mL) was added TMSOTf (0.10 g, 0.44 mmol, 0.2 equiv) dropwise at 0° C. The resulting mixture was stirred for 2 h at room temperature. The reaction was quenched with water (100 mL). The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0-50%) to afford tert-butyl (S)-(6-((3-nitro-6-(1H-pyrazol-1-yl)pyridin-2-yl)amino)-2,3-dihydrospiro[indene-1,2'-[1,3]dithiolan]-3-yl)carbamate (900 mg, 77% yield) as a brown solid. MS (ESI) calcd. for $C_{24}H_{26}N_6O_4S_2$, 526.15 m/z, found 527.10 $[M+H]^+$.

Step 3: Synthesis of tert-butyl (S)-(6-(2-(2-amino-pyridin-3-yl)-5-(1H-pyrazol-1-yl)-3H-imidazo[4,5-b]pyridin-3-yl)-2,3-dihydrospiro[indene-1,2'-[1,3]dithiolan]-3-yl)carbamate To a stirred solution of tert-butyl (S)-(6-((3-nitro-6-(1H-pyrazol-1-yl)pyridin-2-yl)amino)-2,3-dihydrospiro[indene- 1,2'-[1,3]dithiolan]-3-yl)carbamate (900 mg, 1.709 mmol, 1 equiv) and 2-aminonicotinaldehyde (229.58 mg, 1.880 mmol, 1.1 equiv) in DMSO (24 mL) and MeOH (4 mL) was added $Na_2S_2O_4$ (654.57 mg, 3.760 mmol, 2.2 equiv) at room temperature. The resulting mixture was stirred for 18 h at 100° C. The mixture was allowed to cool to room temperature. The mixture was basified to pH 7 with sat. $NaHCO_3$. The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by reverse-phase flash chromatography on C18 silica gel using a gradient of acetonitrile in water (+0.05% ammonium bicarbonate) to afford tert-butyl (S)-(6-(2-(2-aminopyridin-3-yl)-5-(1H-pyrazol-1-yl)-3H-imidazo[4,5-b]pyridin-3-yl)-2,3-dihydrospiro[indene-1,2'-[1,3]dithiolan]-3-yl)carbamate (500 mg, 48.86% yield) as a yellow solid. MS (ESI) calcd. for $C_{30}H_{30}N_8O_2S_2$, 598.19 m/z, found 599.20 $[M+H]^+$.

Step 4: Synthesis of tert-butyl (S)-(5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)carbamate To a solution of NIS (338.19 mg, 1.503 mmol, 3 equiv) in DCM (5 mL) was added dropwise pyridine hydrofluoride (993.15 mg, 10.020 mmol, 20 equiv) (70% in Pyridine) at −78° C. under $N_2$ atmosphere. The reaction mixture was stirred at −78° C. for 30 mins. Then a solution of tert-butyl (S)-(6-(2-(2-aminopyridin-3-yl)-5-(1H-pyrazol-1-yl)-3H-imidazo[4,5-b]pyridin-3-yl)-2,3-dihydrospiro[indene-1,2'-[1,3]dithiolan]-3-yl)carbamate (300 mg, 0.501 mmol, 1 equiv) in 2 mL DCM was added dropwise and the mixture was stirred for another 10 mins at −78° C. The resulting mixture was stirred for 2 h at room temperature. The reaction was quenched with sat. $NaHCO_3$ (50 mL), and the mixture was extracted with ethyl acetate (2*50 mL). The combined organic extracts were washed with brine (50 mL), dried over anhydrous $Na_2SO_4$, and concentrated under vacuum. The residue was purified by reverse-phase flash chromatography on C18 silica gel using a gradient of acetonitrile in water (+0.05% ammonium bicarbonate) to afford tert-butyl (S)-(5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)carbamate (110 mg, 40.31% yield) as a yellow solid. MS (ESI) calcd. for $C_{28}H_{26}F_2N_8O_2$, 544.21 m/z, found 545.20 $[M+H]^+$.

Step 5: Synthesis of (S)-3-(3-(1-amino-3,3-difluoro-2,3-dihydro-1H-inden-5-yl)-5-(1H-pyrazol-1-yl)-3H-imidazo[4,5-b]pyridin-2-yl)pyridin-2-amine (Intermediate 305-1

A solution of tert-butyl (S)-(5-(2-(2-aminopyridin-3-yl)-5-(1H-pyrazol-1-yl)-3H-imidazo[4,5-b]pyridin-3-yl)-3,3-difluoro-2,3-dihydro-1H-inden-1-yl)carbamate (50 mg, 0.092 mmol, 1 equiv) in DCM (1.5 mL) was treated with TFA (0.5 mL) at room temperature. The resulting mixture was stirred for 2 h at room temperature. The mixture was concentrated under vacuum and the residue was purified by reverse-phase flash chromatography on C18 silica gel using a gradient of acetonitrile in water (+0.05% ammonium bicarbonate) to afford (S)-3-(3-(1-amino-3,3-difluoro-2,3-dihydro-1H-inden-5-yl)-5-(1H-pyrazol-1-yl)-3H-imidazo[4,5-b]pyridin-2-yl)pyridin-2-amine (Intermediate 305-1) (9.5 mg, 22% yield) as a white solid. MS (ESI) calcd. for $C_{23}H_{18}F_2N_8$, 444.16 m/z, found 445.10 $[M+H]^+$.

Intermediate 305-1: tert-butyl (S)-(5-bromo-3-oxo-2,3-dihydro-1H-inden-1-yl)carbamate Intermediate 305-1

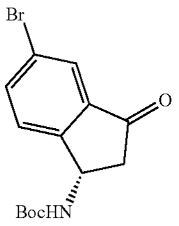

Synthetic Route:

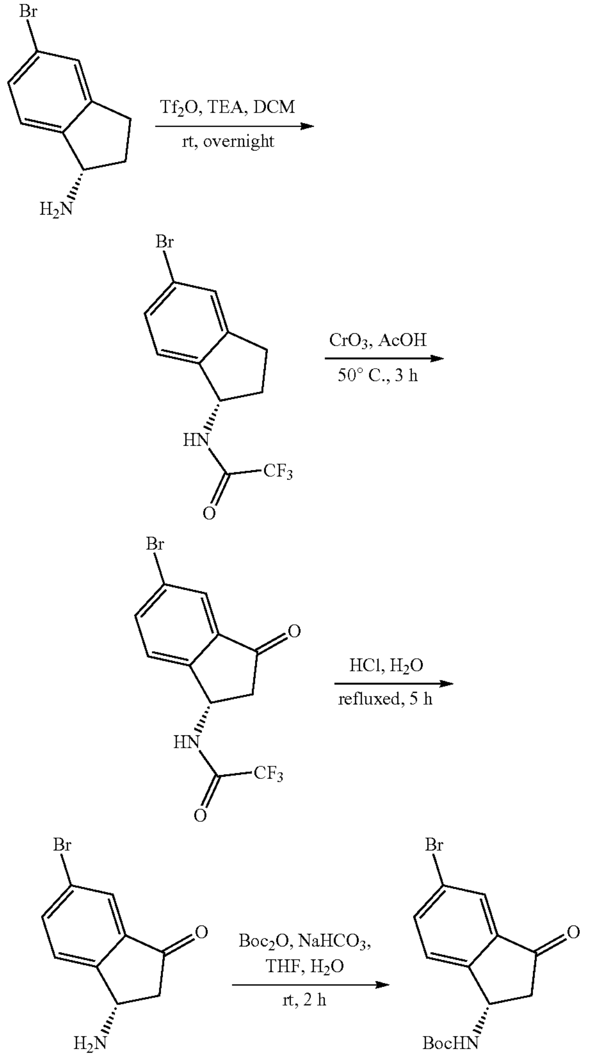

Intermediate 305-1

Step 1: Synthesis of (S)-N-(5-bromo-2,3-dihydro-1H-inden-1-yl)-2,2,2-trifluoroacetamide A solution of (1S)-5-bromo-2,3-dihydro-1H-inden-1-amine (50 g, 236 mmol, 1 equiv) and TEA (55.7 g, 550 mmol, 2 equiv) in DCM (750 mL) was added TFAA (63.25 g, 301.1 mmol, 1.3 equiv) at 0° C. The resulting mixture was stirred overnight at room temperature. The reaction was quenched with $H_2O$ (500 mL) at room temperature. The aqueous layer was extracted with DCM (2×500 mL). The combined organic layers were dried over anhydrous $Na_2SO_4$. After filtration, the filtrate was concentrated under reduced pressure to afford crude product (S)-N-(5-bromo-2,3-dihydro-1H-inden-1-yl)-2,2,2-trifluoroacetamide (86 g) as a white solid. MS (ESI) calcd. for $C_{11}H_9BrF_3NO$, 306.98 m/z, found: 306.10 $[M-H]^-$.

Step 2: Synthesis of (S)-N-(5-bromo-3-oxo-2,3-dihydro-1H-inden-1-yl)-2,2,2-trifluoroacetamide A solution of (S)-N-(5-bromo-2,3-dihydro-1H-inden-1-yl)-2,2,2-trifluoroacetamide (50 g, 162 mmol, 1.00 equiv) and $CrO_3$ (48.8 g, 488 mmol, 3.00 equiv) in AcOH (600 mL) was stirred for 2 h at 50° C. under air atmosphere. The mixture was allowed to cool to room temperature. The resulting mixture was concentrated under reduced pressure. The residue was purified by silica gel column chromatography, eluting with ethyl acetate in petroleum ether (0~20%) to afford (S)-N-(5-bromo-3-oxo-2,3-dihydro-1H-inden-1-yl)-2,2,2-trifluoroacetamide (11.5 g, 22%) as a white solid. MS (ESI) calcd. for $C_{11}H_7BrF_3NO_2$, 320.96 m/z, found: 319.90 $[M-H]^-$.

Step 3: Synthesis of (S)-3-amino-6-bromo-2,3-dihydro-1H-inden-1-one

A solution of (S)-N-(5-bromo-3-oxo-2,3-dihydro-1H-inden-1-yl)-2,2,2-trifluoroacetamide (10 g, 31 mmol, 1 equiv) in 6M aqueous HCl (200 mL) was refluxed 5 h. The resulting mixture was concentrated under reduced pressure and the residue was triturated with $Et_2O$ (200 mL). The residue was filtered and dried to afford (S)-3-amino-6-bromo-2,3-dihydro-1H-inden-1-one (7 g, crude quant.) as a white solid. MS (ESI) calcd. for $C_9H_8BrNO$, 224.98 m/z, found 224.05 $[M-H]^-$.

Step 4: Synthesis of tert-butyl (S)-(5-bromo-3-oxo-2,3-dihydro-1H-inden-1-yl)carbamate (Intermediate 305-1

To a stirred solution of (S)-3-amino-6-bromo-2,3-dihydro-1H-inden-1-one (7 g, 31 mmol, 1 equiv) in THF (60 mL) and $H_2O$ (15 mL) were added $NaHCO_3$ (5.20 g, 61.9 mmol, 2 equiv) and $Boc_2O$ (8.11 g, 37.2 mmol, 1.2 equiv) in portions at 0° C. The resulting mixture was stirred for 2 h at room temperature. The reaction was quenched with water (100 mL). The resulting mixture was extracted with ethyl acetate (3×200 mL). The combined organic layers were washed with brine (200 mL) and dried over anhydrous $Na_2SO_4$. After filtration, the filtrate was concentrated under reduced pressure. The residue was purified by silica gel column chromatography, eluting with ethyl acetate in petroleum ether (0~50%) to afford tert-butyl (S)-(5-bromo-3-oxo-2,3-dihydro-1H-inden-1-yl)carbamate (Intermediate 305-1) (7 g, 69% yield) as an off-white solid. MS (ESI) calcd. for $C_{14}H_{16}BrNO_3$, 325.03 m/z, found 324.10 $[M-H]^-$.

Example 306: 1-(4-{[(1S)-5-[2-(2-aminopyridin-3-yl)-5-(3-cyclopentylpyrazol-1-yl)imidazo[4,5-b]pyridin-3-yl]-2,3-dihydro-1H-inden-1-yl]amino}piperidin-1-yl)prop-2-en-1-one Example 306

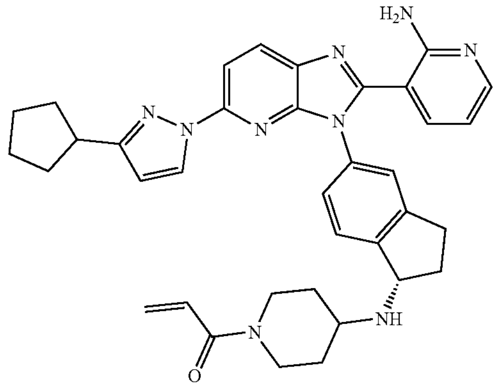

Example 306 was prepared in a manner analogous to Example 13 (via Intermediate 1-1) using 3-cyclopentyl-1H-pyrazole in place of pyrazole and DCE/MeOH (10:1) as the solvent for the final step. MS (ESI) calcd. for $C_{36}H_{39}N_9O$: 613.33. found: 614.35 $[M+H]^+$. $^1H$ NMR (400 MHz, DMSO-$d_6$) δ(ppm): 8.31 (d, J=8.4 Hz, 1H), 8.22 (s, 1H), 7.99 (d, J=1.6 Hz, 1H), 7.89-7.90 (m, 1H), 7.41-7.45 (m, 1H), 7.30 (s, 1H), 7.26-7.29 (m, 2H), 6.88-6.91 (m, 1H), 6.81-6.89 (m, 1H), 6.50-6.55 (m, 2H), 6.11 (d, J=2.4 Hz, 1H), 5.66 (d, J=2.4 Hz, 1H), 4.21-4.32 (m, 2H), 3.91-4.05 (m, 1H), 3.11-3.20 (m, 2H), 2.81-2.92 (m, 4H), 2.35-2.41 (m, 1H), 1.91-1.99 (m, 3H), 1.72-7.75 (m, 1H), 1.51-1.69 (m, 7H), 1.11-1.21 (m, 2H).

Example 307: 1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidin-1-yl)prop-2-en-1-one Example 308: 1-((3*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidin-1-yl)prop-2-en-1-one and Example 309:1-((3*,4*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidin-1-yl)prop-2-en-1-one Example 307

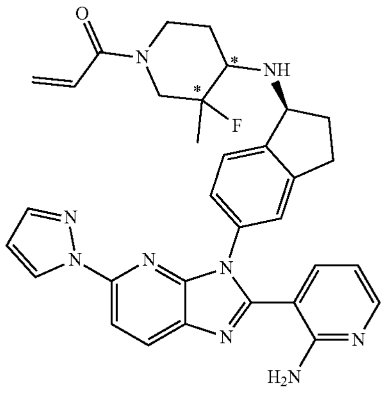

-continued
Example 308
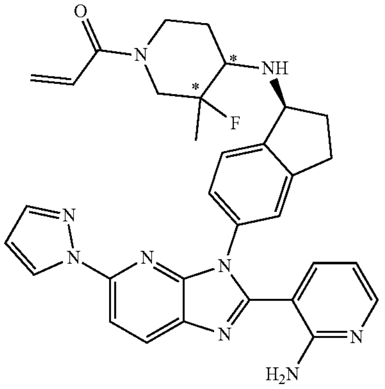
Example 309
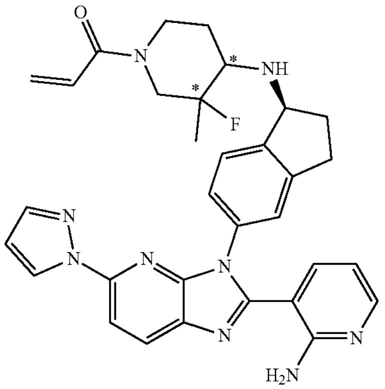
Synthetic Route:
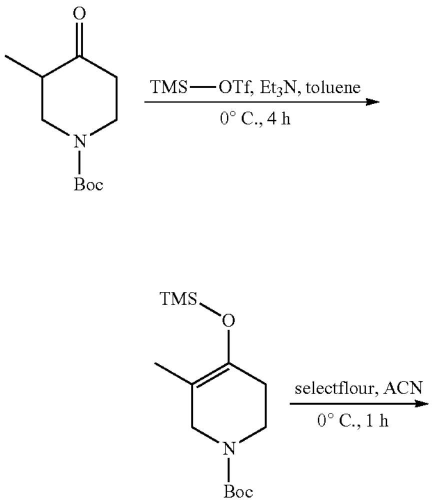
-continued
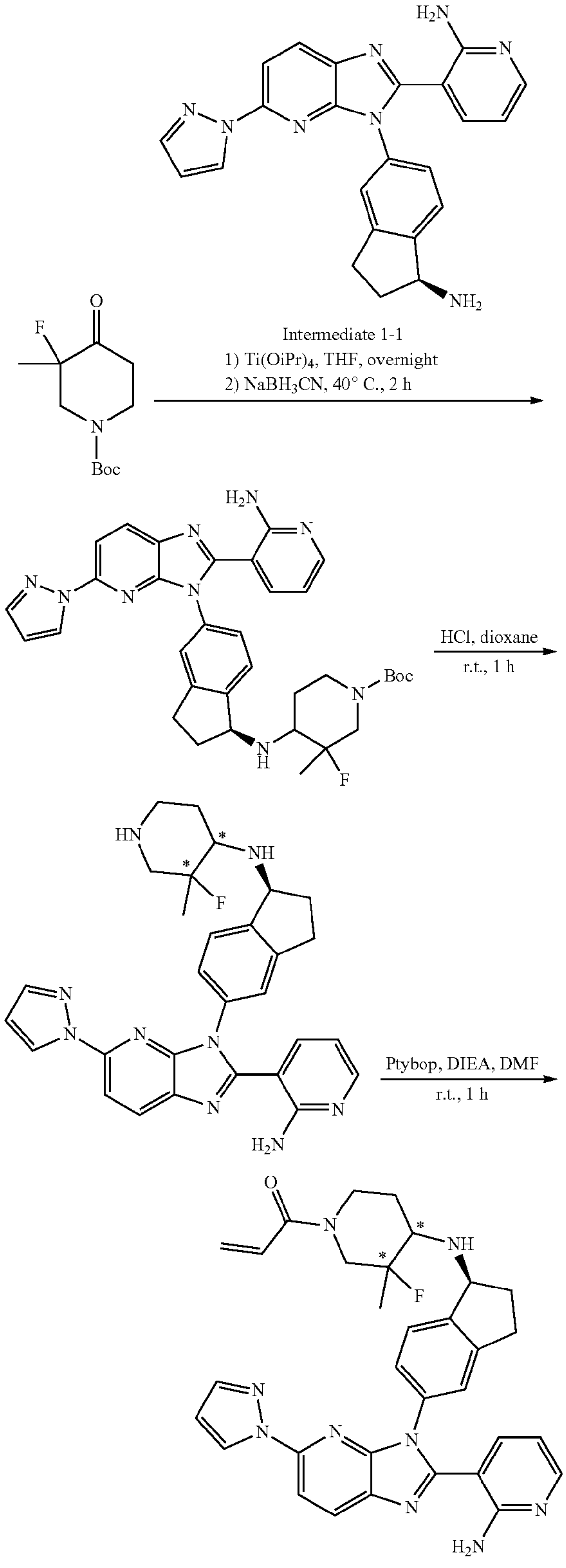
Example 307

-continued

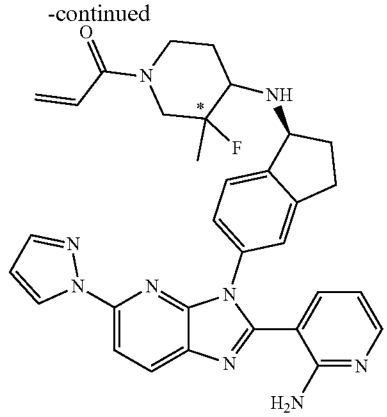

Example 308

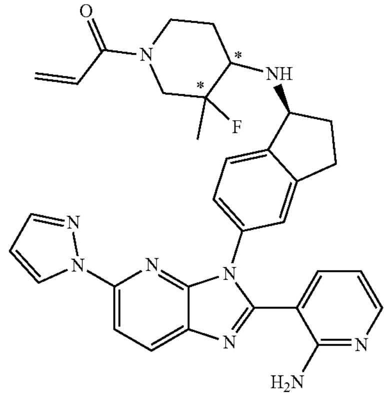

Example 309

Step 1: Synthesis of tert-butyl 3-methyl-4-[(trimethylsilyl)oxy]-5,6-dihydro-2H-pyridine-1-carboxylate To a solution of TMSOTf (6.25 g, 28.133 mmol, 1.2 equiv) in toluene (50 mL) was added tert-butyl 3-methyl-4-oxopiperidine-1-carboxylate (5 g, 23.444 mmol, 1 equiv) and $Et_3N$ (5.69 g, 56.266 mmol, 2.4 equiv) at 0° C. and the resulting mixture was stirred for 4 h at 0° C. The solution was quenched with water (40 ml) and extracted twice with ethyl acetate. The organic layers were combined, washed with brine, dried over anhydrous sodium sulfate and concentrated in vacuum to afford tert-butyl 3-methyl-4-[(trimethylsilyl)oxy]-5,6-dihydro-2H-pyridine-1-carboxylate (4 g, 59.77%) as yellow oil. MS (ESI) calcd. for $C_{14}H_{27}NO_3Si$: 285.18. found: 286.45 $[M+H]^+$.

Step 2: Synthesis of tert-butyl 3-fluoro-3-methyl-4-oxopiperidine-1-carboxylate

To a solution of tert-butyl 3-methyl-4-[(trimethylsilyl)oxy]-5,6-dihydro-2H-pyridine-1-carboxylate (4 g, 14.013 mmol, 1 equiv) in ACN (35 mL) was added SelectFluor (5.46 g, 15.414 mmol, 1.10 equiv) at 0° C. and the resulting mixture was stirred for 1 h. The solution was diluted with water (50 ml) and extracted with ethyl acetate. The organic layers washed with brine, dried over anhydrous sodium sulfate, filtered and concentrate in vacuum to afford tert-butyl 3-fluoro-3-methyl-4-oxopiperidine-1-carboxylate (2 g, 61.72%) as a light yellow oil. MS (ESI) calcd. for $C_{11}H_{18}FNO_3$: 231.13. found: 232.26 $[M+H]^+$.

Step 3: Synthesis of tert-butyl 4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidine-1-carboxylate To a mixture of 3-{3-[(1S)-1-amino-2,3-dihydro-1H-inden-5-yl]-5-(pyrazol-1-yl)imidazo[4,5-b]pyridin-2-yl}pyridin-2-amine (Intermediate 1-1) (3.55 g, 8.685 mmol, 1 equiv) in THF (20 mL) were added tert-butyl (3S)-3-fluoro-3-methyl-4-oxocyclohexane-1-carboxylate (2 g, 8.685 mmol, 1.00 equiv) and tetrakis(propan-2-yloxy)titanium (2.47 g, 8.685 mmol, 1 equiv). The reaction was stirred at 40° C. for 1 h, then $NaBH_3CN$ (2.18 g, 34.740 mmol, 4 equiv) was added and the mixture was stirred at 40° C. for 1 h. The reaction was quenched with $H_2O$ (15 mL) at 25° C. The resulting mixture was extracted with ethyl acetate (3×30 ml). The combined organic layers were washed with $H_2O$ (3×10 ml) and dried over anhydrous $Na_2SO_4$. After filtration, the filtrate was concentrated under reduced pressure. The crude product was purified by reverse-phase flash chromatography on C18 silica gel using a gradient of acetonitrile in water (+0.05% ammonium bicarbonate) to afford tert-butyl 4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidine-1-carboxylate (700 mg, 10.32%) as a light yellow oil. MS (ESI) calcd. for $C_{34}H_{38}FN_9O_2$: 623.31. found: 624.35 $[M+H]^+$.

Step 4: Synthesis of 3-(3-((1S)-1-((3-fluoro-3-methylpiperidin-4-yl)amino)-2,3-dihydro-1H-inden-5-yl)-5-(1H-pyrazol-1-yl)-3H-imidazo[4,5-b]pyridin-2-yl)pyridin-2-amine A solution of tert-butyl 4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidine-1-carboxylate (500 mg, 0.802 mmol, 1 equiv) in TFA (3 mL) and DCM (1 mL) was stirred at r.t. for 1 h. The solvent was removed by distillation under vacuum to afford 3-(3-((1S)-1-((3-fluoro-3-methylpiperidin-4-yl)amino)-2,3-dihydro-1H-inden-5-yl)-5-(1H-pyrazol-1-yl)-3H-imidazo[4,5-b]pyridin-2-yl)pyridin-2-amine (620 mg, 62.04%) as a brown oil. MS (ESI) calcd. for $C_{29}H_{30}FN_9$: 523.26. found: 524.45 $[M+H]^+$.

Step 5: Synthesis of 1-(4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidin-1-yl)prop-2-en-1-one (Examples 307-308)

To a solution of 3-{3-[(1S)-1-[(3-fluoro-3-methylpiperidin-4-yl)amino]-2,3-dihydro-1H-inden-5-yl]-5-(pyrazol-1-yl)imidazo[4,5-b]pyridin-2-yl}pyridin-2-amine (331 mg, 0.632 mmol, 1 equiv) in DCM (20 mL) was added TEA (191.90 mg, 1.896 mmol, 3 equiv). After cooled to 0° C., acryloyl chloride (28.61 mg, 0.316 mmol, 0.5 equiv) was added and the mixture was stirred at r.t for 30 min. The residue was purified by reverse-phase flash chromatography on C18 silica gel using a gradient of acetonitrile in water (+0.05% ammonium bicarbonate) to afford 1-(4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidin-1-yl)prop-2-en-1-one (Examples 307-309). The isomers were partially separated by chiral Prep-HPLC on a CHIRAL CelluloseSB column using a mixture of [Hex/DCM (3:1) (+0.1% diethylamine)] and ethanol to afford:

Example 307: 1-[(3*,4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3-fluoro-3-methylpiperidin-1-yl]prop-2-en-1-one (14.6 mg, 3.90%) as a light yellow solid. MS (ESI) calcd. for $C_{32}H_{32}FN_9O$: 577.27. found: 578.25 $[M+H]^+$. $^1H$ NMR (400 MHz, DMSO-$d_6$) 8.28-8.31 (m, 2H), 7.87-7.95 (m, 2H), 7.76 (s, 1H), 7.49 (m, 1H), 7.18-7.32 (m, 3H), 6.65-6.91 (m, 1H), 6.39-6.50 (m, 2H), 6.01-6.11 (m, 1H), 5.59-5.81 (m, 1H), 3.07-3.34 (m, 1H), 2.79-2.96 (m, 5H), 2.33-2.40 (m, 2H), 2.03-2.13 (m, 1H), 1.78-1.91 (m, 2H), 1.31-1.46 (m, 4H), 0.95-0.96 (m, 1H).

Example 308: 1-((3*)-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-fluoro-3-methylpiperidin-1-yl)prop-2-en-1-one (9 mg, 2.45%) as a white solid. MS (ESI) calcd. for $C_{32}H_{32}FN_9O$: 577.27. found: 578.25 $[M+H]^+$. $^1H$ NMR (400 MHz, DMSO-$d_6$) 8.28-8.31 (m, 3H), 7.87-7.95 (m, 2H), 7.76 (s, 1H), 7.49 (m, 1H), 7.18-7.29 (m, 3H), 6.70-6.75 (m, 1H), 6.43-6.52 (m, 2H), 6.05-6.11 (m, 1H), 5.69-5.72 (m, 1H), 3.77 (m, 1H), 3.03-3.46 (m, 2H), 2.69-3.01 (m, 4H), 178-1.94 (m, 3H), 1.22-1.54 (m, 5H), 0.95-0.96 (m, 1H). (mix of diastereomers)

Example 309: 1-[(3*,4*)-4-{[(1S)-5-[2-(2-aminopyridin-3-yl)-5-(pyrazol-1-yl)imidazo[4,5-b]pyridin-3-yl]-2,3-dihydro-1H-inden-1-yl]amino}-3-fluoro-3-methylpiperidin-1-yl]prop-2-en-1-one (6.1 mg, 1.66%) as a white solid. MS (ESI) calcd. for $C_{32}H_{32}FN_9O$: 577.27. found: 578.25 $[M+H]^+$. $^1H$ NMR (400 MHz, DMSO-$d_6$) 8.28-8.31 (m, 3H), 7.87-7.95 (m, 2H), 7.76 (s, 1H), 7.49 (m, 1H), 7.18-7.29 (m, 3H), 6.70-6.75 (m, 1H), 6.43-6.52 (m, 2H), 6.05-6.11 (m, 1H), 5.69-5.72 (m, 1H), 3.71-3.74 (m, 2H), 3.37-3.47 (m, 2H), 2.90-3.03 (m, 2H), 2.67-2.74 (m, 2H), 178-1.84 (m, 3H), 1.56-1.60 (m, 4H), 0.95-0.96 (m, 1H).

* Denotes a stereocenter with undetermined absolute stereocenter of a single diastereomer.

Example 310: 1-(4-(((1R,2*)-5-(2-(2-aminopyridin-3-yl)-5-(1-(difluoromethyl)-1H-pyrazol-3-yl)-3H-imidazo[4,5-b]pyridin-3-yl)-2-fluoro-2,3-dihydro-1H-inden-1-yl)amino)piperidin-1-yl)prop-2-en-1-one Example 310

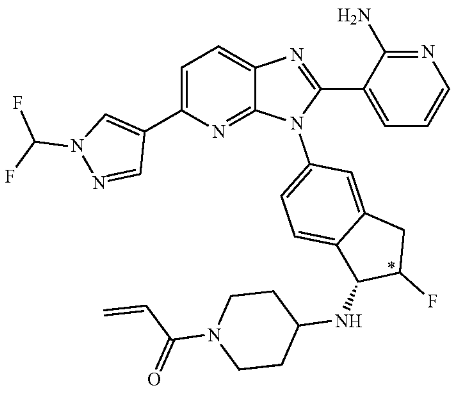

Example 310 was prepared in a manner analogous to Example 190 using Intermediate 310-1 in place of Intermediate 190-1, Pd(dppf)$Cl_2$/sodium carbonate/dioxane/100° C./1 h instead of Pd(dtbpf)$Cl_2$/$K_3PO_4$/THF/50° C./3 h, 1-(difluoromethyl)-3-(4,4,5,5-tetramethyl-1,3,2-dioxaborolan-2-yl)-1H-pyrazole in place of the boronic acid, 4N HCl in dioxane at room temperature for 30 min for the deprotection and DCE/MeOH (10:1) at 40° C. for 2 h for the final step. MS (ESI) calcd. for $C_{32}H_{30}F_3N_9O$: 613.25 m/z, found: 614.15 [M+H]. $^1H$-NMR (400 MHz, DMSO) S (ppm): 8.25-8.40 (m, 2H), 7.98-8.15 (m, 2H), 7.65-7.90 (m, 2H), 7.50-7.68 (m, 2H), 6.80-6.95 (m, 2H), 6.70-6.79 (m, 1H), 6.10-6.20 (m, 1H), 5.78-6.00 (m, 1H), 5.70-5.77 (m, 1H), 5.18-5.32 (m, 1H), 4.50-4.62 (m, 1H), 4.15-4.30 (m, 1H), 3.60-3.65 (m, 2H), 3.29-3.45 (m, 2H), 3.11-3.28 (m, 1H), 2.65-2.82 (m, 1H), 2.30-2.40 (m, 1H), 2.11-2.25 (m, 1H), 1.48-1.65 (m, 2H). $^{19}F$ NMR (376 MHz, DMSO-$d_6$) δ (ppm): −195.60, −73.91, −94.25. * Denotes a stereocenter with undetermined absolute stereocenter of a single diastereomer.

Intermediate 310-0: tert-butyl ((1R)-5-(2-(2-aminopyridin-3-yl)-5-bromo-3H-imidazo[4,5-b]pyridin-3-yl)-2-fluoro-2,3-dihydro-1H-inden-1-yl)carbamate and Intermediate 310-1: tert-butyl ((1R,2*)-5-(2-(2-aminopyridin-3-yl)-5-bromo-3H-imidazo[4,5-b]pyridin-3-yl)-2-fluoro-2,3-dihydro-1H-inden-1-yl)carbamate Intermediate 310-0

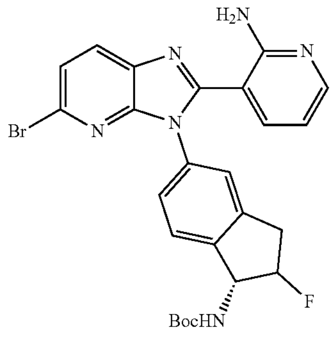

Intermediate 310-1

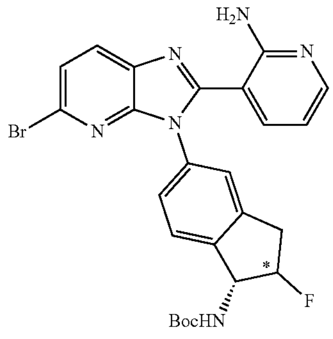

Synthetic Route:

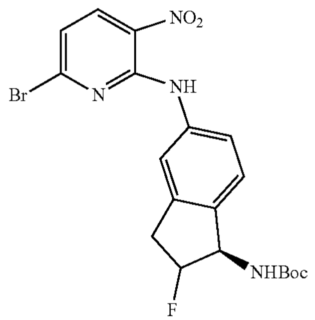

Intermediate 286-2

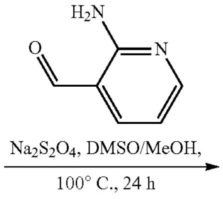

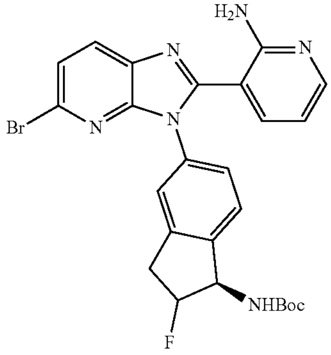

Intermediate 310-0

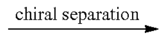

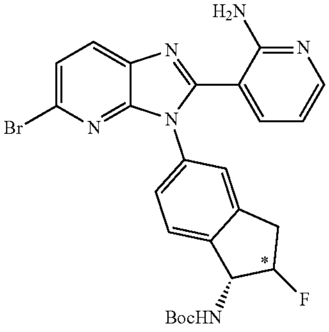

Intermediate 310-1

Step 1: Synthesis of tert-butyl ((1R)-5-(2-(2-aminopyridin-3-yl)-5-bromo-3H-imidazo[4,5-b]pyridin-3-yl)-2-fluoro-2,3-dihydro-1H-inden-1-yl)carbamate (Intermediate 310-0

A solution of tert-butyl ((1R)-5-((6-bromo-3-nitropyridin-2-yl)amino)-2-fluoro-2,3-dihydro-1H-inden-1-yl)carbamate (Intermediate 286-2) (1 g, 2.140 mmol, 1 equiv) in DMSO (10 mL) and MeOH (1.5 mL) was treated with 2-aminonicotinaldehyde (287.48 mg, 2.354 mmol, 1.1 equiv) and $Na_2S_2O_4$ (819.65 mg, 4.708 mmol, 2.2 equiv) for 24 h at 100° C. under nitrogen atmosphere. The reaction was quenched with $H_2O$ at r.t. The resulting mixture was extracted with ethyl acetate (100 mL×3). The combined organic layers were washed with brine (100 mL) and dried over anhydrous $Na_2SO_4$. After filtration, the filtrate was concentrated under reduced pressure. The residue was purified by silica gel column chromatography, eluting with ethyl acetate in petroleum ether (60~80%) to afford tert-butyl ((1R)-5-(2-(2-aminopyridin-3-yl)-5-bromo-3H-imidazo[4,5-b]pyridin-3-yl)-2-fluoro-2,3-dihydro-1H-inden-1-yl)carbamate (Intermediate 310-0) (380 mg, 28%) as a yellow solid. MS (ESI) calcd. for $C_{25}H_{24}BrFN_6O2$, 538.11 m/z, found 539.20 $[M+H]^+$.

Step 2: Synthesis of tert-butyl ((1R,2*)-5-(2-(2-aminopyridin-3-yl)-5-bromo-3H-imidazo[4,5-b]pyridin-3-yl)-2-fluoro-2,3-dihydro-1H-inden-1-yl)carbamate (Intermediate 310-1

The stereoisomers of Intermediate 310-0 were separated by chiral SFC on a CHIRAL ART Amylose-SA column using a mix of $CO_2$ and isopropanol. * Denotes a stereocenter with undetermined absolute stereocenter of a single diastereomer.

Intermediate 310-1: MS (ESI) calcd. for $C_{25}H_{24}BrFN_6O_2$: 538.11 m/z, found: 539.05 $[M+H]^+$. $^1H$ NMR (400 MHz, DMSO-$d_6$) δ (ppm): 8.14-8.17 (m, 1H), 7.99-8.01 (m, 1H), 7.58-7.60 (m, 1H), 7.29-7.38 (m, 4H), 6.45-6.49 (m, 1H), 5.17-5.66 (m, 2H), 3.12-3.18 (m, 2H), 1.46 (s, 9H). $^{19}F$ NMR (376 MHz, DMSO-$d_6$) δ (ppm): −193.67.

Example 311: 1-(3-((1R,2*)-1-((1-acryloylpiperidin-4-yl)amino)-2-fluoro-2,3-dihydro-1H-inden-5-yl)-2-(2-aminopyridin-3-yl)-3H-imidazo[4,5-b]pyridin-5-yl)-1H-pyrazole-3-carbonitrile and Example 312: 1-(3-((1R,2*)-1-((1-acryloylpiperidin-4-yl)amino)-2-fluoro-2,3-dihydro-1H-inden-5-yl)-2-(2-aminopyridin-3-yl)-3H-imidazo[4,5-b]pyridin-5-yl)-1H-pyrazole-3-carbonitrile Example 311

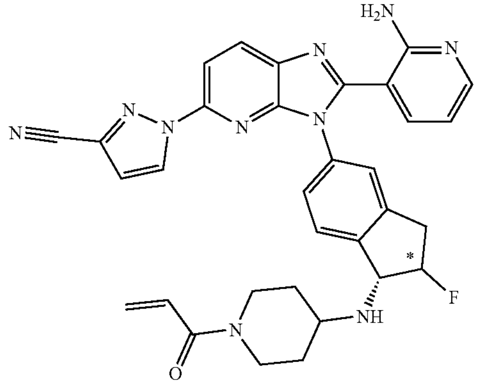

Example 312

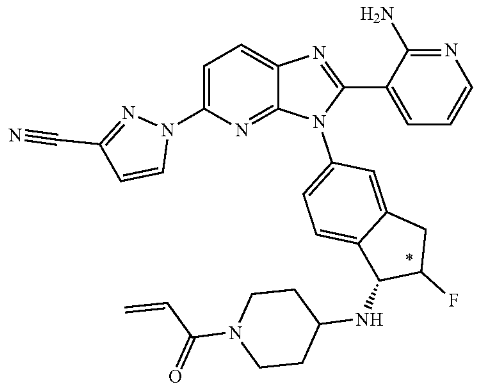

Examples 311 and 312 were prepared in a manner analogous to Examples 286 and 287 (via Intermediate 286-1) using 1H-pyrazole-3-carbonitrile in place of 3-methoxy-1H-pyrazole and a reaction time of overnight for the pyrazole coupling. The diastereomers separated during Prep-HPLC on a XSelect CSH OBD Column using a gradient of acetonitrile in water (+0.1% formic acid). * Denotes a stereocenter with undetermined absolute stereocenter of a single diastereomer.

Example 311: MS (ESI) calcd. for $C_{32}H_{29}FN_{10}O$, 588.25 m/z, found 589.20 $[M+H]^+$. $^1H$ NMR (400 MHz, DMSO-d6) δ 8.57 (d, J=2.7 Hz, 1H), 8.45 (d, J=8.5 Hz, 1H), 8.08-7.96 (m, 2H), 7.49 (m, 3H), 7.28 (m, 2H), 6.84 (m, 3H), 6.44 (m, 1H), 6.11 (m, 1H), 5.84-5.24 (m, 2H), 4.19 (m, 4H), 3.34 (m, 7H), 2.16 (m, 2H). $^{19}F$ NMR (377 MHz, DMSO-d6) δ −196.66. (TFA salt)

Example 312: MS (ESI) calcd. for $C_{32}H_{29}FN_{10}O$, 588.25 m/z, found 589.20 $[M+H]^+$. $^1H$ NMR (400 MHz, DMSO-d6) δ 8.60 (d, J=2.7 Hz, 1H), 8.44 (d, J=8.5 Hz, 1H), 8.02 (dd, J=4.8, 1.9 Hz, 1H), 7.99 (d, J=8.6 Hz, 1H), 7.50 (d, J=8.1 Hz, 1H), 7.42 (s, 1H), 7.32 (dd, J=8.4, 1.9 Hz, 1H), 7.26 (q, J=3.3, 2.6 Hz, 2H), 6.90 (s, 2H), 6.83 (m, 1H), 6.44 (dd, J=7.7, 4.8 Hz, 1H), 6.09 (m, 1H), 5.66 (m, 1H), 5.24 (m, 1H), 4.40 (s, 1H), 4.26 (s, 1H), 4.00 (s, 1H), 3.56-3.40 (m, 2H), 3.23-3.06 (m, 2H), 3.04-2.93 (m, 2H), 2.87 (s, 1H), 2.00 (s, 1H), 1.89 (s, 1H). $^{19}F$ NMR (377 MHz, DMSO-d6) δ −176.04. (TFA salt)

Example 313: 1-(4-{[(1S)-5-[2-(2-aminopyridin-3-yl)-6-fluoro-5-(pyrazol-1-yl)imidazo[4,5-b]pyridin-3-yl]-2,3-dihydro-1H-inden-1-yl]amino}piperidin-1-yl)prop-2-en-1-one Example 313

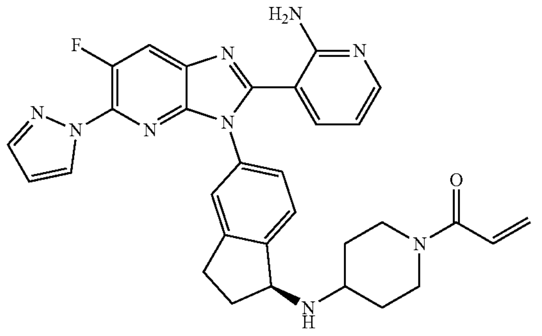

Example 313 was prepared in a manner analogous to Example 13 using Intermediate 313-1 in place of Intermediate 1-1 and DCE/MeOH/AcOH (50:5:1) as the solvent. MS (ESI) calcd. for $C_{31}H_{30}FN_9O$: 563.26. found: 564.20 $[M+H]^+$. $^1H$ NMR (300 MHz, DMSO-d6) δ (ppm): 8.46 (d, J=10.5 Hz, 1H), 8.19-8.21 (m, 1H), 7.99-8.05 (m, 1H), 7.80 (d, J=1.5 Hz, 1H), 7.46 (d, J=8.1 Hz, 1H), 7.30-7.36 (m, 1H), 7.19-7.29 (m, 2H), 6.75-6.90 (m, 1H), 6.55-6.61 (m, 1H), 6.39-6.48 (m, 1H), 6.03-6.15 (m, 1H), 5.62-5.72 (m, 1H), 4.31 (t, J=6.9 Hz, 1H), 3.93-4.25 (m, 2H), 3.09-3.22 (m, 1H), 2.82-2.99 (m, 3H), 2.71-2.81 (m, 1H), 2.36-2.46 (m, 1H), 1.69-2.01 (m, 3H), 1.12-1.34 (m, 2H). $^{19}F$ NMR (282 MHz, DMSO-d6) δ (ppm): −134.50.

Intermediate 313-1: (S)-3-(3-(1-amino-2,3-dihydro-1H-inden-5-yl)-6-fluoro-5-(1H-pyrazol-1-yl)-3H-imidazo[4,5-b]pyridin-2-yl)pyridin-2-amine Intermediate 313-1

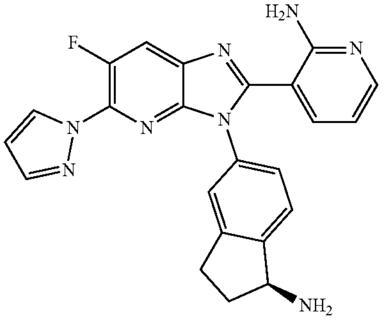

Synthetic Route:

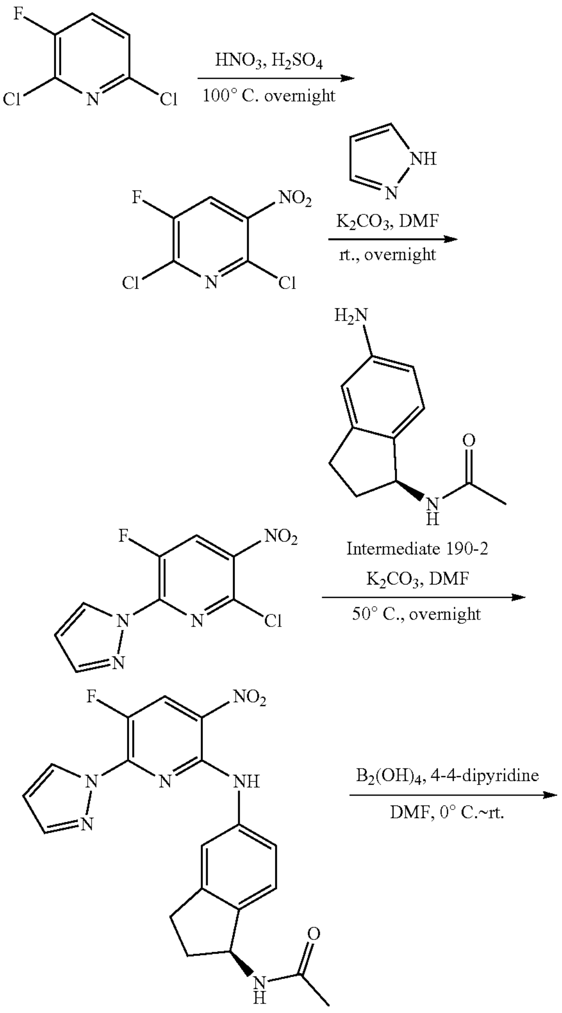

-continued

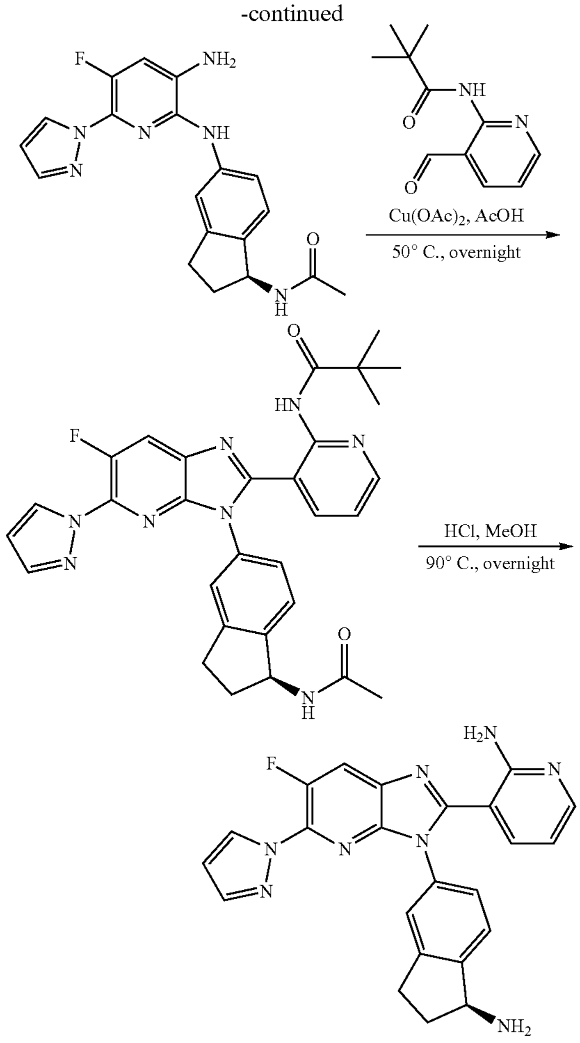

Intermediate 313-1

Step 1: Synthesis of 2,6-dichloro-3-fluoro-5-nitropyridine

To a stirred solution of 2,6-dichloro-3-fluoropyridine (10 g, 60.248 mmol, 1 equiv) in $H_2SO_4$ (23.69 g, 241.594 mmol, 4.01 equiv) were added $HNO_3$ (29.19 g, 463.307 mmol, 7.69 equiv) in portions at 0° C. The resulting mixture was stirred at 0° C. for 1 h. Then the resulting mixture was stirred at 100° C. for 16 h. The mixture was allowed to cool to 25° C. To 200 ml ice water was added to the resulting mixture. The aqueous layer was extracted with DCM (3×200 mL). The resulting mixture was concentrated under reduced pressure to afford 2,6-dichloro-3-fluoro-5-nitropyridine (5 g, 33.90%) as a yellow oil. MS (ESI) calcd. for $C_5HCl_2FN_2O_2$: 209.94. found: 208.80 [M−H]$^+$ Step 2: Synthesis of 2-chloro-5-fluoro-3-nitro-6-(pyrazol-1-yl)pyridine To a stirred solution of 2,6-dichloro-3-fluoro-5-nitropyridine (4.8 g, 22.752 mmol, 1 equiv) and pyrazole (929.36 mg, 13.651 mmol, 0.6 equiv) in DMF (30 mL) was added $K_2CO_3$ (6.29 g, 45.504 mmol, 2 equiv) in portions at 25° C. The resulting mixture was stirred at 25° C. for 16 h. The reaction was quenched by the addition of water (50 mL) at 25° C. The aqueous layer was extracted with ethyl acetate (3×50 mL). The resulting mixture was washed with brine (3×50 mL) and concentrated under reduced pressure. The residue was purified by silica gel column chromatography, eluting with petroleum ether/ethyl acetate (1:1) to afford 2-chloro-5-fluoro-3-nitro-6-(pyrazol-1-yl)pyridine (2.4 g, 41.16%) as a yellow solid. MS (ESI) calcd. for $C_8H_4ClFN_4O_2$: 242.00. found: 243.10 [M+H]$^+$.

Step 3: Synthesis of N-[(1S)-5-{[5-fluoro-3-nitro-6-(pyrazol-1-yl)pyridin-2-yl]amino}-2,3-dihydro-1H-inden-1-yl]acetamide To a stirred solution of 2-chloro-5-fluoro-3-nitro-6-(pyrazol-1-yl)pyridine (1.4 g, 5.771 mmol, 1 equiv) and N-[(1S)-5-amino-2,3-dihydro-1H-inden-1-yl]acetamide (Intermediate 190-2) (1.44 g, 6.348 mmol, 1.1 equiv) in DMF (20 mL) were added $K_2CO_3$ (3.99 g, 28.855 mmol, 5 equiv) in portions at 25° C. The resulting mixture was stirred at 50° C. for 16 h. The reaction was quenched by the addition of water (50 mL) at 25° C. The aqueous layer was extracted with ethyl acetate (3×50 mL). The resulting mixture was washed with brine (3×50 mL). The resulting mixture was concentrated under reduced pressure. The residue was purified by silica gel column chromatography, eluting with DCM/MeOH (10:1) to afford N-[(1S)-5-{[5-fluoro-3-nitro-6-(pyrazol-1-yl)pyridin-2-yl]amino}-2,3-dihydro-1H-inden-1-yl]acetamide (800 mg, 34.97%) as a yellow solid. MS (ESI) calcd. for $C_{19}H_{17}FN_6O_3$: 396.13. found: 397.10 [M+H]$^+$.

Step 4: Synthesis of N-[(1S)-5-{[3-amino-5-fluoro-6-(pyrazol-1-yl)pyridin-2-yl]amino}-2,3-dihydro-1H-inden-1-yl]acetamide To a stirred solution of N-[(1S)-5-{[5-fluoro-3-nitro-6-(pyrazol-1-yl)pyridin-2-yl]amino}-2,3-dihydro-1H-inden-1-yl]acetamide (750 mg, 1.892 mmol, 1 equiv) and 4-(pyridin-4-yl)pyridine (29.55 mg, 0.189 mmol, 0.1 equiv) in DMF (15 mL) was added $B_2(OH)_4$ (508.88 mg, 5.676 mmol, 3 equiv) in portions at 0° C. The resulting mixture was stirred at 0° C. for 2 h. The reaction was purified by reverse-phase flash chromatography on C18 silica gel using a gradient of acetonitrile in water (+0.05% ammonium bicarbonate) to afford N-[(1S)-5-{[3-amino-5-fluoro-6-(pyrazol-1-yl)pyridin-2-yl]amino}-2,3-dihydro-1H-inden-1-yl]acetamide (400 mg, 57.70%) as a yellow solid. MS (ESI) calcd. for $C_{19}H_{19}FN_6O$: 366.16. found: 367.10 [M+H]$^+$.

Step 5: Synthesis of N-(3-{3-[(1S)-1-acetamido-2,3-dihydro-1H-inden-5-yl]-6-fluoro-5-(pyrazol-1-yl)imidazo[4,5-b]pyridin-2-yl}pyridin-2-yl)-2,2-dimethylpropanamide To a stirred solution of N-[(1S)-5-{[3-amino-5-fluoro-6-(pyrazol-1-yl)pyridin-2-yl]amino}-2,3-dihydro-1H-inden-1-yl]acetamide (370 mg, 1.010 mmol, 1 equiv) and N-(3-formylpyridin-2-yl)-2,2-dimethylpropanamide (249.93 mg, 1.212 mmol, 1.2 equiv) in AcOH (15 mL) was added $Cu(OAc)_2$ (36.68 mg, 0.202 mmol, 0.2 equiv) in portions at 25° C. The resulting mixture was stirred at 60° C. for 16 h. The resulting mixture was concentrated under reduced pressure. The residue was dissolved in DMF (10 mL). The resulting mixture was purified by reverse-phase flash chromatography on C18 silica gel using a gradient of acetonitrile in water (+0.05% TFA) to afford N-(3-{3-[(1S)-1-acetamido-2,3-dihydro-1H-inden-5-yl]-6-fluoro-5-(pyrazol-1-yl)imidazo[4,5-b]pyridin-2-yl}pyridin-2-yl)-2,2-dimethylpropanamide (400 mg, 71.68%) as a yellow solid. MS (ESI) calcd. for $C_{30}H_{29}FN_8O_2$: 552.24. found: 553.35 [M+H]$^+$.

Step 6: Synthesis of 3-{3-[(1S)-1-amino-2,3-dihydro-1H-inden-5-yl]-6-fluoro-5-(pyrazol-1-yl)imidazo[4,5-b]pyridin-2-yl}pyridin-2-amine (Intermediate 313-1

N-(3-{3-[(1S)-1-acetamido-2,3-dihydro-1H-inden-5-yl]-6-fluoro-5-(pyrazol-1-yl)imidazo[4,5-b]pyridin-2-yl}pyridin-2-yl)-2,2-dimethylpropanamide (370 mg, 0.670 mmol, 1 equiv) was dissolved in MeOH (10 mL) and HCl (10 mL) at 25° C. The resulting mixture was stirred at 90° C. for 16 h. The resulting mixture was concentrated under reduced pressure. The residue was dissolved in DMF (10 mL). The resulting mixture was purified by reverse-phase flash chromatography on C18 silica gel using a gradient of acetonitrile in water (+0.05% ammonium bicarbonate) to afford 3-{3-[(1S)-1-amino-2,3-dihydro-1H-inden-5-yl]-6-fluoro-5-(pyrazol-1-yl)imidazo[4,5-b]pyridin-2-yl}pyridin-2-amine (Intermediate 313-1) (180 mg, 63.04%) as a yellow solid. MS (ESI) calcd. for $C_{23}H_{19}FN_8$: 426.17. found: 427.05 [M+H]$^+$.

Example 314: 1-(4-{[(1S)-5-[2-(2-aminopyridin-3-yl)-5-(3-cyclopropoxypyrazol-1-yl)imidazo[4,5-b]pyridin-3-yl]-2,3-dihydro-1H-inden-1-yl]amino}piperidin-1-yl)prop-2-en-1-one Example 314

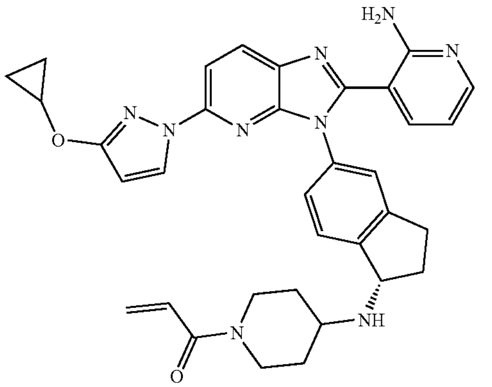

Example 314 was prepared in a manner analogous to Example 13 (via Intermediate 1-1) using DCE/MeOH (10:1)+0.1 eq AcOH as the solvent for the final step and 3-cyclopropoxy-1H-pyrazole in place of pyrazole. MS (ESI) calcd. for $C_{34}H_{35}N_9O_2$: 601.29. found: 602.35 [M+H]$^+$. $^1$H NMR (300 MHz, DMSO-d$_6$) δ(ppm): 8.29 (d, J=8.4 Hz, 1H), 8.12 (s, 1H), 7.99 (d, J=1.8 Hz, 1H), 7.76 (d, J=8.7 Hz, 1H), 7.41-7.45 (m, 1H), 7.25 (s, 1H), 7.12-7.21 (m, 2H), 6.91-6.95 (m, 2H), 6.78-6.88 (m, 1H), 6.32-6.42 (m, 1H), 6.17-6.19 (m, 1H), 6.08-6.11 (m, 1H), 5.65 (d, J=8.1 Hz, 1H), 4.27-4.31 (m, 1H), 4.21-4.23 (m, 1H), 4.02-4.07 (m, 1H), 3.92-3.98 (m, 1H), 3.27 (s, 1H), 3.01-3.11 (m, 3H), 2.79-2.85 (m, 1H), 2.49 (s, 1H), 2.19-2.20 (m, 1H), 2.01-2.05 (m, 1H), 1.91-1.97 (m, 1H), 1.79-1.85 (m, 1H), 1.11-1.25 (m, 2H), 0.72-0.77 (m, 4H).

Example 315: 2-(2-aminopyridin-3-yl)-3-[(1S)-1-{[1-(prop-2-enoyl)piperidin-4-yl]amino}-2,3-dihydro-1H-inden-5-yl]-5-(pyrazol-1-yl)imidazo[4,5-b]pyridine-7-carbonitrile Example 315

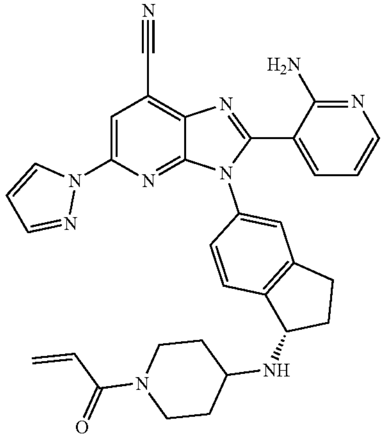

Example 315 was prepared in a manner analogous to Example 13 using Intermediate 315-2 in place of Intermediate 1-1 and MeOH/room temperature instead of DCE/40° C. MS (ESI) calcd. for $C_{32}H_{30}N_{10}O$, 570.26 m/z, found 571.35 [M+H]$^+$. $^1$H NMR (400 MHz, DMSO-d$_6$) δ (ppm): 8.28-8.29 (m, 1H), 8.18-8.19 (m, 1H), 7.95-8.00 (m, 1H), 7.80-7.81 (m, 1H), 7.46-7.48 (m, 1H), 7.26-7.28 (m, 2H), 7.19-7.22 (m, 1H), 6.72-6.79 (m, 1H), 6.54-6.56 (m, 1H), 6.43-6.47 (m, 1H), 6.04-6.08 (m, 1H), 5.66-5.69 (m, 1H), 4.27-4.31 (m, 2H), 3.99-4.10 (m, 1H), 3.05-3.11 (m, 1H), 2.84-2.91 (m, 2H), 2.71-2.78 (m, 2H), 2.39-2.41 (m, 1H), 1.84-1.96 (m, 1H), 1.72-1.80 (m, 2H), 1.12-1.27 (m, 2H).

Intermediate 315-2: (S)-3-(1-amino-2,3-dihydro-1H-inden-5-yl)-2-(2-aminopyridin-3-yl)-5-(1H-pyrazol-1-yl)-3H-imidazo[4,5-b]pyridine-7-carbonitrile Intermediate 315-2

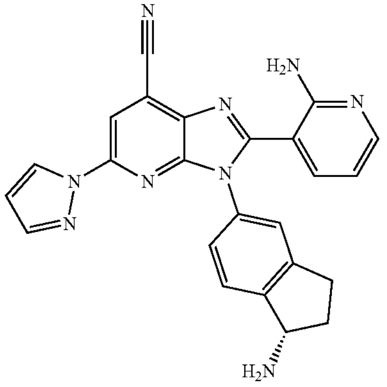

Synthetic Route:

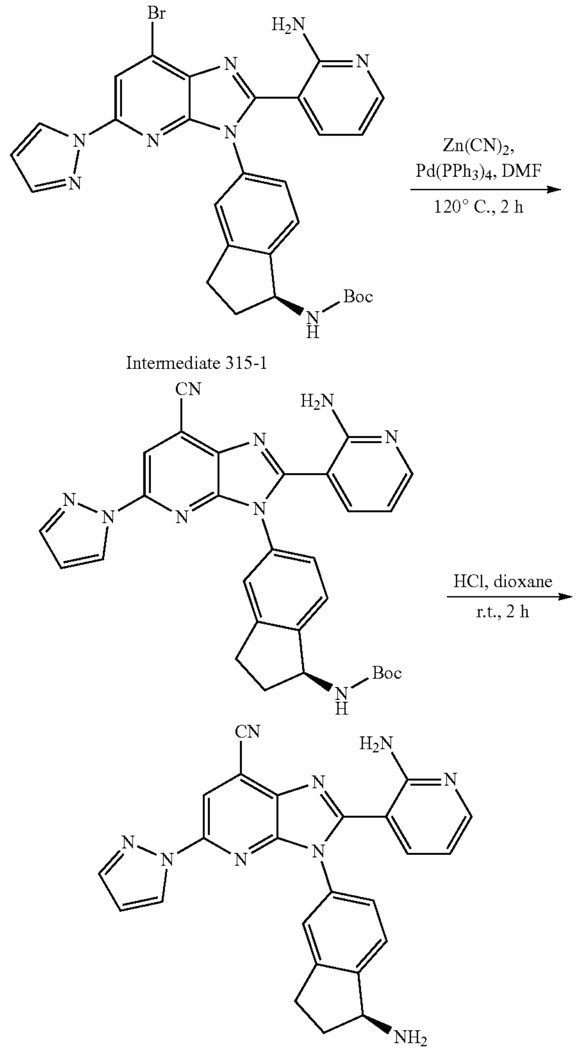

Intermediate 315-2

Step 1: Synthesis of tert-butyl N-[(1S)-5-[2-(2-aminopyridin-3-yl)-7-cyano-5-(pyrazol-1-yl)imidazo[4,5-b]pyridin-3-yl]-2,3-dihydro-1H-inden-1-yl]carbamate To a solution of tert-butyl N-[(1S)-5-[2-(2-aminopyridin-3-yl)-7-bromo-5-(pyrazol-1-yl)imidazo[4,5-b]pyridin-3-yl]-2,3-dihydro-1H-inden-1-yl]carbamate (Intermediate 315-1) (100 mg, 0.170 mmol, 1 equiv) in DMF (2 mL) was added $Zn(CN)_2$ (29.98 mg, 0.255 mmol, 1.5 equiv) and $Pd(PPh_3)_4$ (9.84 mg, 0.009 mmol, 0.05 equiv). The mixture was stirred for 2 h at 120° C. under nitrogen atmosphere. The residue was purified by reverse-phase flash chromatography on C18 silica gel using a gradient of acetonitrile in water (+0.05% ammonium bicarbonate) to afford tert-butyl N-[(1S)-5-[2-(2-aminopyridin-3-yl)-7-cyano-5-(pyrazol-1-yl)imidazo[4,5-b]pyridin-3-yl]-2,3-dihydro-1H-inden-1-yl]carbamate (80 mg, 88.08% yield) as a yellow green solid. MS (ESI) calcd. for $C_{29}H_{27}N_9O_2$, 533.22 m/z, found 534.25 $[M+H]^+$.

Step 2: Synthesis of 3-[(1S)-1-amino-2,3-dihydro-1H-inden-5-yl]-2-(2-aminopyridin-3-yl)-5-(pyrazol-1-yl)imidazo[4,5-b]pyridine-7-carbonitrile (Intermediate 315-2

To a suspension of tert-butyl N-[(1S)-5-[2-(2-aminopyridin-3-yl)-7-cyano-5-(pyrazol-1-yl)imidazo[4,5-b]pyridin-3-yl]-2,3-dihydro-1H-inden-1-yl]carbamate (70 mg, 0.131 mmol, 1 equiv) in dioxane (3 mL) was added HCl (3 mL, 4 M in dioxane). The mixture was stirred for 2 h at rt. The residue was concentrated and purified by reverse-phase flash chromatography on C18 silica gel using a gradient of acetonitrile in water (+0.05% ammonium bicarbonate) to afford 3-[(1S)-1-amino-2,3-dihydro-1H-inden-5-yl]-2-(2-aminopyridin-3-yl)-5-(pyrazol-1-yl)imidazo[4,5-b]pyridine-7-carbonitrile (Intermediate 315-2) (50 mg, 87.93% yield) as a yellow green solid. MS (ESI) calcd. for $C_{24}H_{19}N_9$, 433.17 m/z, found 434.20 $[M+H]^+$.

Intermediate 315-1: tert-butyl (S)-(5-(2-(2-aminopyridin-3-yl)-7-bromo-5-(1H-pyrazol-1-yl)-3H-imidazo[4,5-b]pyridin-3-yl)-2,3-dihydro-1H-inden-1-yl) carbamate Intermediate 315-1

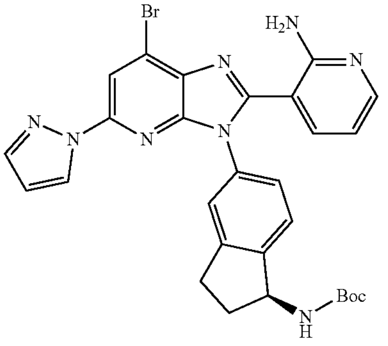

Synthetic Route:

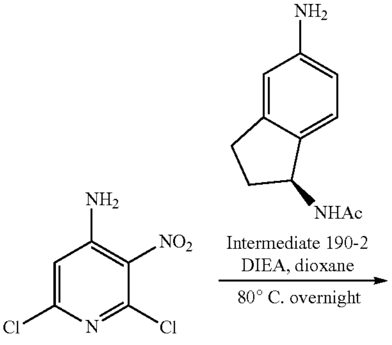

-continued

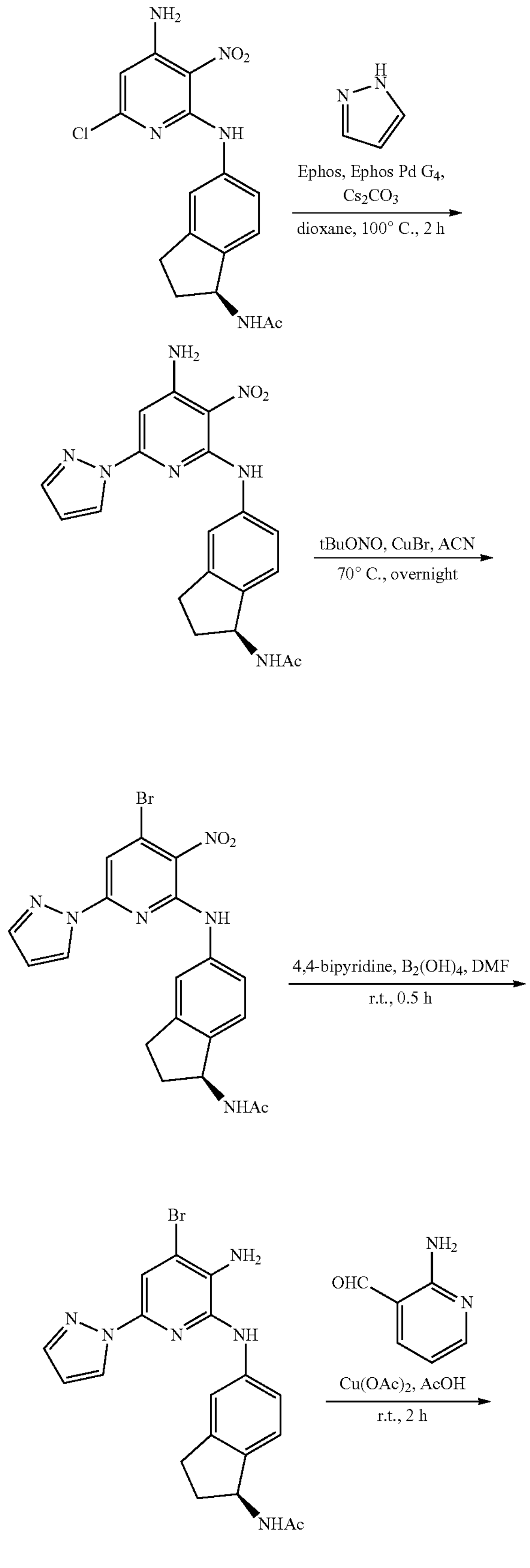

-continued

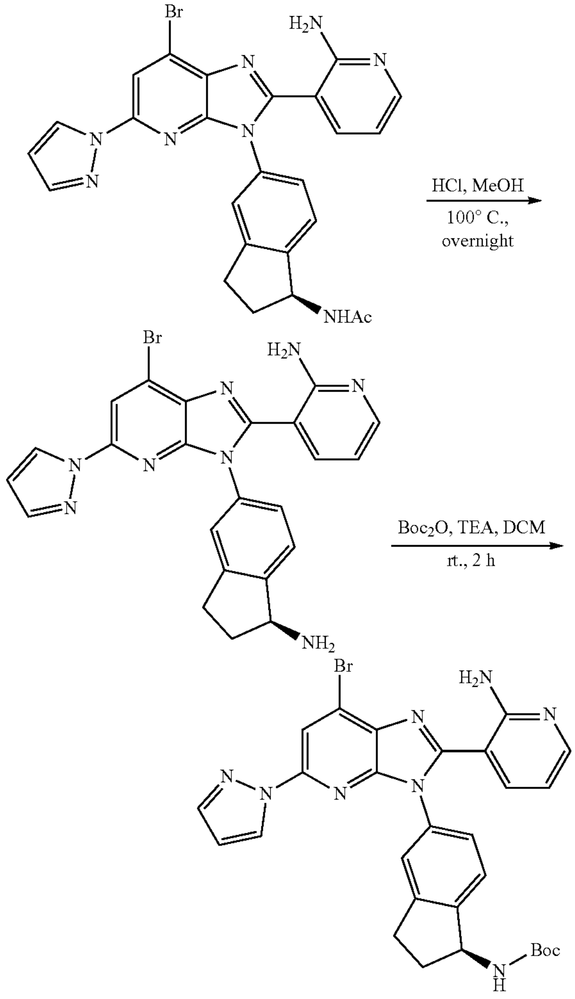

Intermediate 315-1

Step 1: Synthesis of N-[(1S)-5-[(4-amino-6-chloro-3-nitropyridin-2-yl)amino]-2,3-dihydro-1H-inden-1-yl]acetamide To a solution of 2,6-dichloro-3-nitropyridin-4-amine (15 g, 72.115 mmol, 1 equiv) and N-[(1S)-5-amino-2,3-dihydro-1H-inden-1-yl]acetamide (Intermediate 190-2) (13.72 g, 72.115 mmol, 1 equiv) in dioxane (150 mL) was added DIEA (27.96 g, 216.345 mmol, 3 equiv). The mixture was stirred for 4 h at 80° C. After being cooled to rt, the resulting mixture was poured into water (1000 mL). The precipitated solids were collected by filtration and washed with water (2×500 mL). The resulting solid was triturated in ethyl acetate/petroleum ether (200 mL/600 mL) for 1 h. The solids were collected by filtration to afford N-[(1S)-5-[(4-amino-6-chloro-3-nitropyridin-2-yl)amino]-2,3-dihydro-1H-inden-1-yl]acetamide (18 g, 68.99% yield) as a red solid. MS (ESI) calcd. for $C_{16}H_{16}ClN_5O_3$, 361.09 m/z, found 362.15 $[M+H]^+$.

Step 2: Synthesis of N-[(1S)-5-{[4-amino-3-nitro-6-(pyrazol-1-yl)pyridin-2-yl]amino}-2,3-dihydro-1H-inden-1-yl]acetamide To a solution of N-[(1S)-5-[(4-amino-6-chloro-3-nitropyridin-2-yl)amino]-2,3-dihydro-1H-inden-1-yl]acetamide (18 g, 49.753 mmol, 1 equiv) and pyrazole (5.08 g, 74.630 mmol, 1.5 equiv) in dioxane (270 mL) were added EPhos (5.32 g, 9.951 mmol, 0.2 equiv) EPhos Pd G4 (9.14 g, 9.951 mmol, 0.2 equiv) and $Cs_2CO_3$ (32.42 g, 99.506 mmol, 2 equiv). The mixture was stirred for 4 h at 100° C. under nitrogen atmosphere. After being cooled to rt, the resulting mixture was poured into water (1500 mL). The precipitated solids were collected by filtration and washed with water (3×500 mL). The resulting solid was triturated with ethyl acetate/petroleum ether (500 mL/500 mL) for 1 h. The solids were collected by filtration to afford N-[(1S)-5-{[4-amino-3-nitro-6-(pyrazol-1-yl)pyridin-2-yl]amino}-2,3-dihydro-1H-inden-1-yl]acetamide (17 g, 86.85% yield) as a light brown solid. MS (ESI) calcd. for $C_{19}H_{19}N_7O_3$, 393.15 m/z, found 394.25 $[M+H]^+$.

Step 3: Synthesis of N-[(1S)-5-{[4-bromo-3-nitro-6-(pyrazol-1-yl)pyridin-2-yl]amino}-2,3-dihydro-1H-inden-1-yl]acetamide To a solution of N-[(1S)-5-{[4-amino-3-nitro-6-(pyrazol-1-yl)pyridin-2-yl]amino}-2,3-dihydro-1H-inden-1-yl]acetamide (9 g, 22.877 mmol, 1 equiv), CuBr (9.85 g, 68.631 mmol, 3 equiv) in ACN (150 mL) was added tBuONO (10.72 g, 91.508 mmol, 4 equiv) at room temperature and the mixture was stirred for 3 h at 70° C. under $N_2$ atmosphere. The mixture was allowed to cool to room temperature. The reaction was quenched by the addition of saturated aqueous ammonium chloride (500 mL) at room temperature. The resulting mixture was extracted with ethyl acetate (3×800 mL). The combined organic layers were washed with NaCl/$H_2O$ (3×200 mL) and dried over anhydrous $Na_2SO_4$. After filtration, the filtrate was concentrated under reduced pressure. The residue was purified by trituration with ethyl acetate/petroleum ether (1:5, 200 mL) to afford N-[(1S)-5-{[4-bromo-3-nitro-6-(pyrazol-1-yl)pyridin-2-yl]amino}-2,3-dihydro-1H-inden-1-yl]acetamide (9 g, 86.03% yield) as a red solid. Ms (ESI) calcd. for $C_{19}H_{17}BrN_6O3$, 456.05 m/z, found 457.10 $[M+H]^+$.

Step 4: Synthesis of N-[(1S)-5-{[3-amino-4-bromo-6-(pyrazol-1-yl)pyridin-2-yl]amino}-2,3-dihydro-1H-inden-1-yl]acetamide To a solution of N-[(1S)-5-{[4-bromo-3-nitro-6-(pyrazol-1-yl)pyridin-2-yl]amino}-2,3-dihydro-1H-inden-1-yl]acetamide (8 g, 17.494 mmol, 1 equiv) in DMF (80 mL) was added bipyridine (0.14 g, 0.875 mmol, 0.05 equiv) and $B_2(OH)_4$ (4.71 g, 52.482 mmol, 3 equiv) at 0° C. and the mixture was stirred 0.5 h at 0° C. The resulting mixture was poured into ice water (300 mL). The precipitated solids were collected by filtration and washed with water (3×100 mL) to afford N-[(1S)-5-{[3-amino-4-bromo-6-(pyrazol-1-yl)pyridin-2-yl]amino}-2,3-dihydro-1H-inden-1-yl]acetamide (7 g, 93.64% yield) as a black solid. Ms (ESI) calcd. for $C_{19}H_{19}BrN_6O$, 426.08 m/z, found 427.10 $[M+H]^+$.

Step 5: Synthesis of N-[(1S)-5-[2-(2-aminopyridin-3-yl)-7-bromo-5-(pyrazol-1-yl)imidazo[4,5-b]pyridin-3-yl]-2,3-dihydro-1H-inden-1-yl]acetamide To a solution of N-[(1S)-5-{[3-amino-4-bromo-6-(pyrazol-1-yl)pyridin-2-yl]amino}-2,3-dihydro-1H-inden-1-yl]acetamide (3.4 g, 7.957 mmol, 1 equiv) and 2-aminopyridine-3-carbaldehyde (1.17 g, 9.548 mmol, 1.2 equiv) in AcOH (34 mL) was stirred for 2 h at 70° C. The mixture was allowed to cool to room temperature. The mixture was concentrated directly and the residue was purified by reverse-phase flash chromatography on C18 silica gel using a gradient of acetonitrile in water (+0.05% ammonium bicarbonate) to afford N-[(1S)-5-[2-(2-aminopyridin-3-yl)-7-bromo-5-(pyrazol-1-yl)imidazo[4,5-b]pyridin-3-yl]-2,3-dihydro-1H-inden-1-yl]acetamide (400 mg, 9.50% yield) as a brown solid. Ms (ESI) calcd. for $C_{25}H_{21}BrN_8O$, 528.10 m/z, found 529.15 $[M+H]^+$.

Step 6: Synthesis of 3-{3-[(1S)-1-amino-2,3-dihydro-1H-inden-5-yl]-7-bromo-5-(pyrazol-1-yl)imidazo[4,5-b]pyridin-2-yl}pyridin-2-amine To a solution of N-[(1S)-5-[2-(2-aminopyridin-3-yl)-7-bromo-5-(pyrazol-1-yl)imidazo[4,5-b]pyridin-3-yl]-2,3-dihydro-1H-inden-1-yl]acetamide (390 mg, 0.737 mmol, 1 equiv) in MeOH (15 mL) was added HCl (15 mL, conc.) dropwise. The obtained solution was stirred overnight at 100° C. The mixture was allowed to cool to room temperature. The mixture was concentrated directly. The residue was purified by reverse-phase flash chromatography on C18 silica gel using a gradient of acetonitrile in water (+0.05% ammonium bicarbonate) to afford 3-{3-[(1S)-1-amino-2,3-dihydro-1H-inden-5-yl]-7-bromo-5-(pyrazol-1-yl)imidazo[4,5-b]pyridin-2-yl}pyridin-2-amine (350 mg, 97.48%) as a brown solid. Ms (ESI) calcd. for $C_{23}H_{19}BrN_8$, 486.09 m/z, found 487.15 $[M+H]^+$.

Step 7: Synthesis of tert-butyl N-[(1S)-5-[2-(2-aminopyridin-3-yl)-7-bromo-5-(pyrazol-1-yl)imidazo[4,5-b]pyridin-3-yl]-2,3-dihydro-1H-inden-1-yl]carbamate (Intermediate 315-1

To a solution of 3-{3-[(1S)-1-amino-2,3-dihydro-1H-inden-5-yl]-7-bromo-5-(pyrazol-1-yl)imidazo[4,5-b]pyridin-2-yl}pyridin-2-amine (160 mg, 0.328 mmol, 1 equiv) in DCM (6 mL) was added TEA (99.66 mg, 0.984 mmol, 3 equiv) and $Boc_2O$ (107.48 mg, 0.492 mmol, 1.5 equiv) dropwise. The obtained solution was stirred for 1 h at rt. The reaction was quenched by the addition of water (15 mL) at rt. The resulting mixture was extracted with DCM (3×20 mL). The combined organic layers were washed with water (3×20 mL) and dried over anhydrous sodium sulfate. After filtration, the filtrate was concentrated under reduced pressure. The residue was purified by silica gel column chromatography, eluting with MeOH/DCM (7:100) to afford tert-butyl N-[(1S)-5-[2-(2-aminopyridin-3-yl)-7-bromo-5-(pyrazol-1-yl)imidazo[4,5-b]pyridin-3-yl]-2,3-dihydro-1H-inden-1-yl]carbamate (Intermediate 315-1) (100 mg, 51.85%) as a light yellow solid. Ms (ESI) calcd. for $C_{28}H_{27}BrN_8O2$, 586.14 m/z, found 587.15 $[M+H]^+$.

Example 316: 1-((2R,4*)-4-(((1R,2*)-2-fluoro-5-(2-(2-fluorophenyl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one Example 317: 1-((2R,4*)-4-(((1R,2*)-2-fluoro-5-(2-(2-fluorophenyl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one Example 318: 1-((2R,4*)-4-(((1R,2*)-2-fluoro-5-(2-(2-fluorophenyl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one and Example 319: 1-((2R,4*)-4-(((1R,2*)-2-fluoro-5-(2-(2-fluorophenyl)-5-(1H-pyrazol-1-yl)-3H-imidazo[4,5-b]pyridin-3-yl)-2,3-dihydro-1H-inden-1-yl)amino)-2-methylpiperidin-1-yl)prop-2-en-1-one Example 316

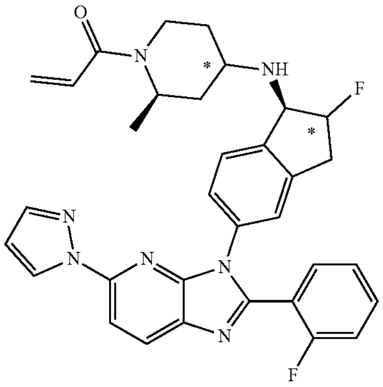

Example 317

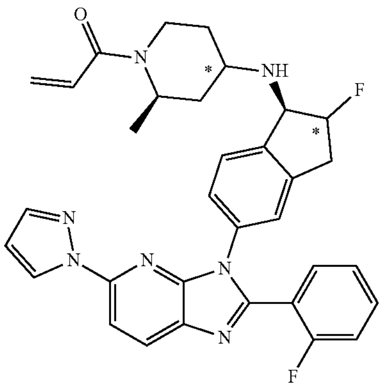

-continued

Example 318

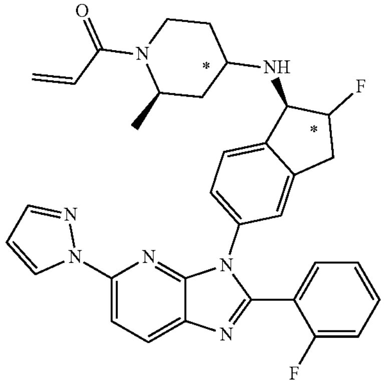

Example 319

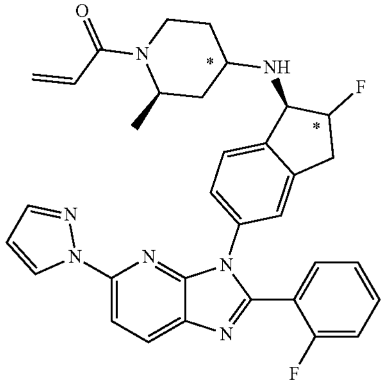

Examples 316, 317, 318 and 319 were prepared in a manner analogous to Example 14 (via Intermediate 14-1) using Intermediates 316-1 in place of Intermediate 1-1, DCE/MeOH (1:1) instead of DCE and tert-butyl (R)-2-methyl-4-oxopiperidine-1-carboxylate in place of tert-butyl 8-oxo-3-azabicyclo[3.2.1]octane-3-carboxylate. Examples 316 and 317 were separated from Example 318 and 319 by reverse-phase flash chromatography on C18 silica gel using a gradient of acetonitrile in water (+0.05% ammonium bicarbonate). Examples 316 and 317 were separated by chiral Prep-HPLC on a CHIRAL ART Cellulose-SB column using a mixture of [MtBE (+0.5% 2M NH3-MeOH)] and [ethanol/DCM (1:1)]. Example 318 and 319 were separated by chiral Prep-HPLC on a CHIRAL ART Cellulose-SB column using a mixture of [Hex (+0.5% 2M NH3-MeOH)] and ethanol. * Denotes a stereocenter with undetermined absolute stereocenter of a single diastereomer.

Example 316: MS (ESI) calcd for $C_{33}H_{31}F_2N_7O$ 579.26 m/z, found 580.40[M+H]$^+$. $^1$H NMR (500 MHz, DMSO-d6) δ 8.45-8.39 (m, 2H), 8.00 (d, J=8.6 Hz, 1H), 7.83-7.82 (m, 1H), 7.75-7.72 (m, 1H), 7.62-7.54 (m, 1H), 7.41 (d, J=8.0 Hz, 1H), 7.39-7.32 (m, 2H), 7.27-7.23 (m, 2H), 6.84-6.79 (m, 1H), 6.57 (dd, J=2.6, 1.7 Hz, 1H), 6.08 (dd, J=16.6, 2.4 Hz, 1H), 5.65 (dd, J=10.5, 2.5 Hz, 1H), 5.54-5.36 (m, 1H), 4.42 (d, J=24.9 Hz, 2H), 3.21-3.14 (m, 2H), 3.13-3.01 (m, 2H), 2.80 (s, 1H), 2.13-2.10 (m, 2H), 1.98-1.78 (m, 1H), 1.49-1.41 (m, 1H), 1.24-1.14 (m, 4H).

Example 317: MS (ESI) calcd for $C_{33}H_{31}F_2N_7O$ 579.26 m/z, found 580.40[M+H]$^+$. $^1$H NMR (500 MHz, DMSO-d6) δ 8.45-8.39 (m, 2H), 8.00 (d, J=8.6 Hz, 1H), 7.84 (d, J=1.6 Hz, 1H), 7.75-7.72 (m, 1H), 7.60-7.56 (m, 1H), 7.46-7.32 (m, 3H), 7.29-7.21 (m, 2H), 6.83-6.78 (m, 1H), 6.58-6.57 (m, 1H), 6.07 (d, J=16.8 Hz, 1H), 5.65 (dd, J=10.4, 2.5 Hz, 1H), 5.28-5.15 (m, 1H), 4.41-4.36 (m, 2H), 3.52-3.39 (m, 1H), 3.24-2.70 (m, 3H), 2.13-2.02 (m, 1H), 1.88-1.76 (m, 1H), 1.67-0.78 (m, 6H).

Example 318: MS (ESI) calcd for $C_{33}H_{31}F_2N_7O$ 579.26 m/z, found 580.35[M+H]$^+$. $^1$H NMR (500 MHz, DMSO-d6) δ 8.45-8.39 (m, 2H), 8.00 (d, J=8.6 Hz, 1H), 7.84-7.83 (m, 1H), 7.76-7.72 (m, 1H), 7.60-7.56 (m, 1H), 7.46 (d, J=8.0 Hz, 1H), 7.38-7.34 (m, 2H), 7.31 (d, J=2.0 Hz, 1H), 7.30-7.23 (m, 1H), 6.82-6.77 (m, 1H), 6.60-6.55 (m, 1H), 6.09 (dd, J=16.6, 2.6 Hz, 1H), 5.65 (dd, J=10.5, 2.5 Hz, 1H), 5.54-5.41 (m, 1H), 4.49 (d, J=26.5 Hz, 2H), 3.25-3.08 (m, 3H), 2.21 (s, 1H), 1.96-1.93 (m, 1H), 1.76-1.62 (m, 3H), 1.45 (d, J=6.9 Hz, 3H), 1.24 (s, 1H), 0.95-0.80 (m, 1H).

Example 319: MS (ESI) calcd for $C_{33}H_{31}F_2N_7O$ 579.26 m/z, found 580.40 [M+H]$^+$. $^1$H NMR (500 MHz, DMSO-d6) δ 8.44-8.42 (m, 2H), 8.00 (d, J=8.6 Hz, 1H), 7.84 (d, J=1.6 Hz, 1H), 7.76-7.72 (m, 1H), 7.61-7.56 (m, 1H), 7.44 (d, J=8.0 Hz, 1H), 7.40-7.33 (m, 2H), 7.30-7.23 (m, 2H), 6.80-6.75 (m, 1H), 6.58-6.53 (m, 1H), 6.08 (dd, J=16.6, 2.6 Hz, 1H), 5.64 (dd, J=10.4, 2.6 Hz, 1H), 5.35-5.19 (m, 1H), 4.40 (d, J=19.3 Hz, 2H), 3.53-3.39 (m, 1H), 3.23-3.21 (m, 1H), 3.04-2.95 (m, 1H), 2.27 (s, 1H), 2.03-1.48 (m, 3H), 1.40 (d, J=6.9 Hz, 3H), 1.24 (s, 1H), 1.03-0.78 (m, 1H).

Intermediate 316-1: (1R)-2-fluoro-5-(2-(2-fluorophenyl)-5-(1H-pyrazol-1-yl)-3H-imidazo[4,5-b]pyridin-3-yl)-2,3-dihydro-1H-inden-1-amine Intermediate 316-1

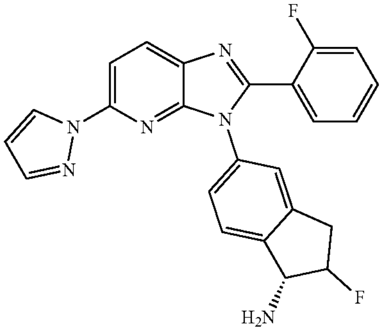

Intermediate 316-1 was prepared in a manner analogous to Intermediate 75-1 using 2-fluorobenzaldehyde in place of 2-aminopyridine-3-carbaldehyde and omitting the chiral separation. MS (ESI) calcd for $C_{24}H_{18}F_2N_6$428.16 m/z, found 429.50 [M+H]$^+$.

Example 320: (S)-1-(4-((5-(2-(2-aminopyridin-3-yl)-5-(5-cyclopropyl-1,3,4-thiadiazol-2-yl)-3H-imidazo[4,5-b]pyridin-3-yl)-2,3-dihydro-1H-inden-1-yl)amino)piperidin-1-yl)prop-2-en-1-one Example 320

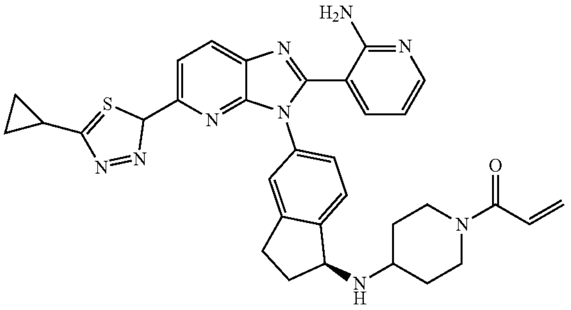

Example 320 was prepared in a manner analogous to Example 13 using Intermediate 320-2 in place of Intermediate 1-1 and DCE/MeOH (10:1) as the solvent. MS (ESI) calcd. for $C_{33}H_{33}N_9OS$, 603.25 m/z, found 604.35[M+H]$^+$. $^1$H NMR (400 MHz, DMSO-d6) δ 8.36 (d, J=8.3 Hz, 1H), 8.24 (d, J=8.3 Hz, 1H), 8.02 (dd, J=4.8, 1.9 Hz, 1H), 7.48 (d, J=8.0 Hz, 1H), 7.36-7.18 (m, 3H), 6.97-6.78 (m, 3H), 6.43 (dd, J=7.7, 4.8 Hz, 1H), 6.09 (dd, J=16.7, 2.5 Hz, 1H), 5.66 (dd, J=10.4, 2.5 Hz, 1H), 4.39-4.22 (m, 2H), 4.09-3.94 (m, 1H), 3.24-3.11 (m, 1H), 3.00-2.87 (m, 3H), 2.87-2.71 (m, 1H), 2.65-2.52 (m, 2H), 2.21-2.05 (m, 1H), 2.03-1.92 (m, 1H), 1.92-1.82 (m, 1H), 1.82-1.72 (m, 1H), 1.36-1.14 (m, 4H), 1.14-1.03 (m, 2H).

Intermediate 320-2: (S)-3-(3-(1-amino-2,3-dihydro-1H-inden-5-yl)-5-(5-cyclopropyl-1,3,4-thiadiazol-2-yl)-3H-imidazo[4,5-b]pyridin-2-yl)pyridin-2-amine Intermediate 320-2

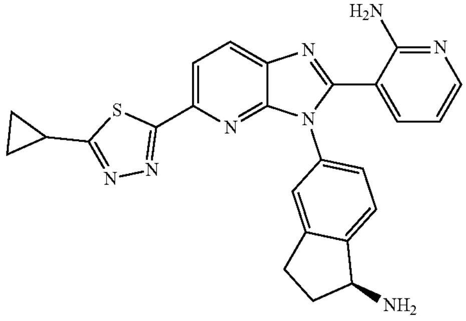

Intermediate 320-2 was prepared in a manner analogous to Intermediate 109-2 using 2-bromo-5-cyclopropyl-1,3,4-thiadiazole instead of 2-bromo-1,3-oxazole, Pd(dppf)$Cl_2$/tribasic potassium phosphate/THF instead of Pd(dtbpf)$Cl_2$/potassium carbonate/dioxane, Intermediate 320-1 in place of Intermediate 109-1 and conc HCl/MeOH (1:1) at 100° C. overnight for the deprotection. MS (ESI) calcd. for $C_{25}H_{22}N_8S$, 466.16 m/z, found 467.30 [M+H]$^+$.

Intermediate 320-1: (S)-N-(5-(2-(2-aminopyridin-3-yl)-5-(4,4,5,5-tetramethyl-1,3,2-dioxaborolan-2-yl)-3H-imidazo[4,5-b]pyridin-3-yl)-2,3-dihydro-1H-inden-1-yl)acetamide Intermediate 320-1

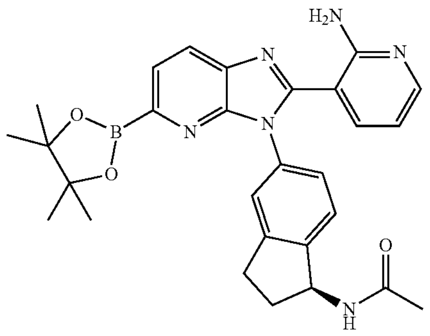

Intermediate 320-1 was prepared in a manner analogous to Intermediate 109-1 using Intermediate 320-0 in place of Intermediate 85-1, $Pd(dppf)Cl_2$ in place of $Pd(OAc)_2/PCy_3$ and a reaction time of overnight. MS (ESI) calcd. for $C_{28}H_{31}BN_6O_3$, 510.26 m/z, found 429.20[M+H]$^+$.

Intermediate 320-0: (S)-N-(5-(2-(2-aminopyridin-3-yl)-5-bromo-3H-imidazo[4,5-b]pyridin-3-yl)-2,3-dihydro-1H-inden-1-yl)acetamide Intermediate 320-0

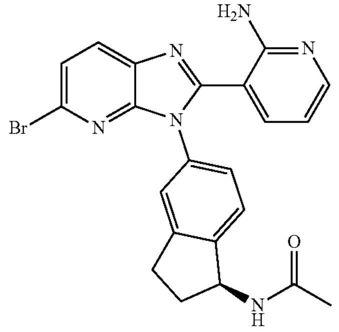

Synthetic Route:

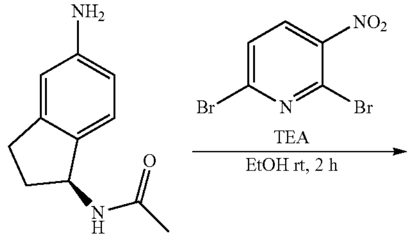

Intermediate 190-2

-continued

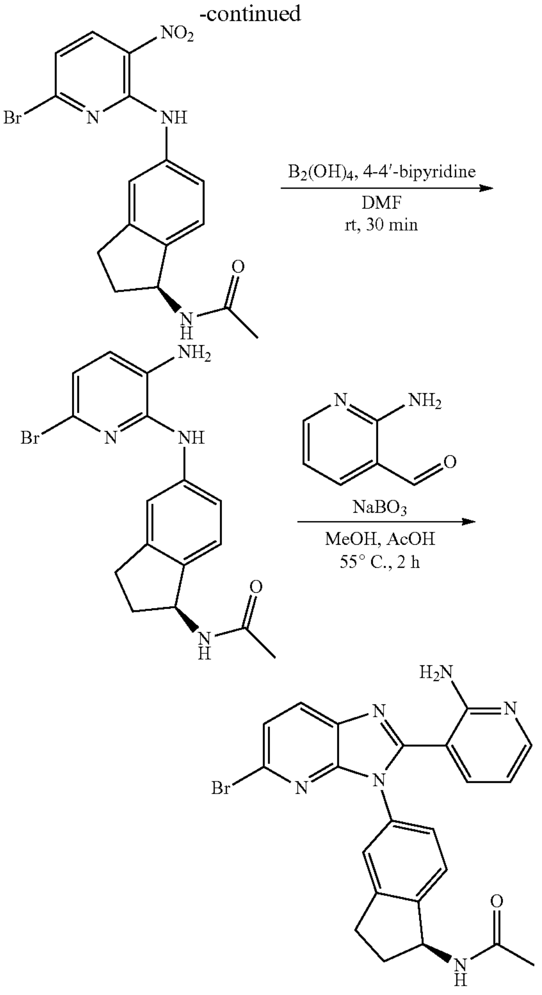

Intermediate 320-0

Step 1: (S)-N-(5-((6-bromo-3-nitropyridin-2-yl)amino)-2,3-dihydro-1H-inden-1-yl)acetamide N-[(1S)-5-amino-2,3-dihydro-1H-inden-1-yl]acetamide (17 g, 89 mmol), 2,6-dibromo-3-nitropyridine (Intermediate 190-2) (25.19 g, 89.36 mmol) was dissolved in triethylamine (45.21 g, 446.8 mmol, 5 equiv) and ethanol (200 mL). The reaction mixture was stirred at room temperature for 2 h. The reaction mixture was quenched with 400 mL water and the precipitate was rinsed with 1:1 ethanol/water (800 mL:800 mL) to afford N-[(1S)-5-[(6-bromo-3-nitropyridin-2-yl)amino]-2,3-dihydro-1H-inden-1-yl]acetamide (26 g, 74% yield) as an orange solid. MS (ESI) calculated for $C_{16}H_{15}BrN_4O_3$: 390.03, found 413.00 [M+Na]$^+$, 415.00 [M+Na+2]$^+$.

Step 2: Synthesis of (S)-N-(5-((3-amino-6-bromopyridin-2-yl)amino)-2,3-dihydro-1H-inden-1-yl)acetamide To a cooled (0° C.) solution of N-[(1S)-5-[(6-bromo-3-nitropyridin-2-yl)amino]-2,3-dihydro-1H-inden-1-yl]acetamide (25 g, 64 mmol, 1 equiv) in N,N-dimethylformamide (250 mL) was added 4,4'-bipyridine (0.5 g, 2 mmol, 3 mol %), followed by hypodiboric acid (17.3 g, 0.192 mol, 3 equiv). The resulting mixture was stirred at 0° C. for 0.5 h.

The reaction mixture was quenched by addition of 500 mL saturated aqueous ammonium chloride. The aqueous layer was extracted with ethyl acetate (3×250 mL). The combined organic layers were dried over anhydrous sodium sulfate, filtered and concentrated in vacuo. The resulting residue was purified by silica gel column chromatography, eluting with petroleum ether/dichloromethane/methanol (70:27:3) to afford N-[(1S)-5-[(3-amino-6-bromopyridin-2-yl)amino]-2,3-dihydro-1H-inden-1-yl]acetamide (16 g, 69%). MS (ESI) calculated for $C_{16}H_{17}BrN_4O$: 360.06, found 361.00 $[M+H]^+$, 363.00 $[M+2+H]^+$.

Step 3: Synthesis of (S)-N-(5-(2-(2-aminopyridin-3-yl)-5-bromo-3H-imidazo[4,5-b]pyridin-3-yl)-2,3-dihydro-1H-inden-1-yl)acetamide (Intermediate 320-0

A solution of N-[(1S)-5-[(3-amino-6-bromopyridin-2-yl)amino]-2,3-dihydro-1H-inden-1-yl]acetamide (15.5 g, 42.9 mmol, 1 equiv) in methanol (72 mL) and acetic acid (14 mL) was treated with 2-aminopyridine-3-carbaldehyde (6.29 g, 51.5 mmol, 1.2 equiv) followed by the addition of sodium perborate tetrahydrate (26.41 g, 172 mmol, 4 equiv) portion wise. The resulting mixture was stirred at 55° C. for 2 h. The reaction mixture was concentrated under reduced pressure and then brought to pH 8-9 with saturated aqueous sodium bicarbonate. The resulting precipitate was filtered. The filter cake was then washed with ethyl acetate (3×100 mL). The resulting filtrate was concentrated under reduced pressure and the residue was purified by silica gel column chromatography using a 0 to 20% gradient of ethyl acetate in petroleum ether followed by a 0 to 10% gradient of dichloromethane in methanol to provide (S)-N-(5-(2-(2-amino-pyridin-3-yl)-5-bromo-3H-imidazo[4,5-b]pyridin-3-yl)-2,3-dihydro-1H-inden-1-yl)acetamide (Intermediate 320-0) (4 g, 18% yield). MS (ESI) calculated for $C_{22}H_{19}BrN_6O$: 462.08, found 463.00 $[M+H]^+$, 465.00 $[M+H+2]^+$.

Example 321: 1-(4-{[(1S)-5-[2-(2-aminopyridin-3-yl)-5-[3-(oxan-4-yl)pyrazol-1-yl]imidazo[4,5-b]pyridin-3-yl]-2,3-dihydro-1H-inden-1-yl]amino}piperidin-1-yl)prop-2-en-1-one Example 321

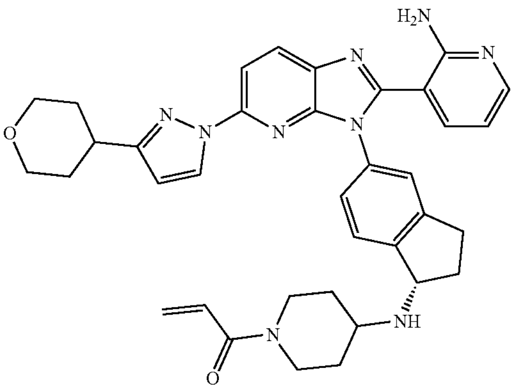

Example 321 was prepared in a manner analogous to Example 13 (via Intermediate 1-1) using DCE/MeOH (10:1) in place of DCE and 3-(oxan-4-yl)-1H-pyrazole in place of pyrazole. MS (ESI) calcd. for $C_{36}H_{39}N_9O_2$: 629.32 m/z, found: 630.40 $[M+H]^+$/$^1H$ NMR (300 MHz, DMSO-d6) δ (ppm): 8.23-8.30 (m, 1H), 7.87-8.00 (m, 2H), 7.47 (d, J=7.8, 1H), 7.19-7.31 (m, 3H), 6.78-6.93 (m, 3H), 6.41-6.43 (m, 2H), 6.05-6.11 (m, 1H), 5.65 (dd, J=2.4, 2.4 Hz, 1H), 4.11-4.39 (m, 2H), 3.90-3.94 (m, 3H), 3.42-3.49 (m, 2H), 3.05-3.32 (m, 1H), 2.65-2.95 (m, 5H), 2.33-2.45 (m, 1H), 1.90-2.02 (m, 2H), 1.76-1.88 (m, 3H), 1.67-1.75 (m, 3H), 1.11-1.40 (m, 2H).

Example 322: (S)-1-(1-(3-(1-((1-acryloylpiperidin-4-yl)amino)-2,3-dihydro-1H-inden-5-yl)-2-(2-aminopyridin-3-yl)-3H-imidazo[4,5-b]pyridin-5-yl)-1H-pyrazol-3-yl)cyclopropane-1-carbonitrile Example 322

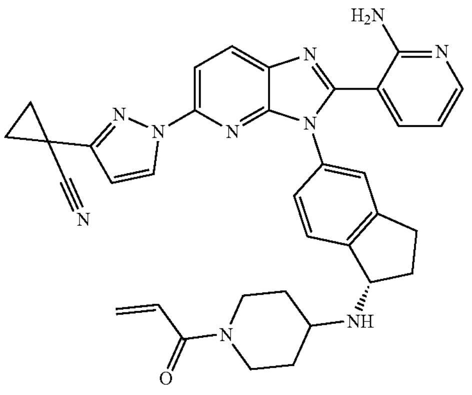

Example 322 was prepared in a manner analogous to Example 13 (via Intermediate 1-1) using Intermediate 85-1 in place of Intermediate 1-2, 1-(1H-pyrazol-3-yl)cyclopropane-1-carbonitrile in place of pyrazole, DCM/4N HCl in dioxane (5:2) at room temperature for 30 min for the deprotection and DCE+3 equiv triethylamine for the final step (imine formation) and DCE/AcOH (25:1) for the reduction. MS (ESI) calcd. for $C_{35}H_{34}N_{10}O$: 610.29 m/z, found: 611.20$[M+H]^+$. $^1H$ NMR (400 MHz, DMSO-$d_6$) δ (ppm): 8.36 (d, J=8.5 Hz, 1H), 8.30 (d, J=2.6 Hz, 1H), 8.00 (dd, J=4.8, 1.9 Hz, 1H), 7.89 (d, J=8.6 Hz, 1H), 7.47 (d, J=8.0 Hz, 1H), 7.32 (s, 1H), 7.28-7.19 (m, 2H), 6.93 (s, 2H), 6.83 (dd, J=16.7, 10.5 Hz, 1H), 6.50 (d, J=2.6 Hz, 1H), 6.42 (dd, J=7.6, 4.8 Hz, 1H), 6.09 (dd, J=16.7, 2.5 Hz, 1H), 5.66 (dd, J=10.4, 2.5 Hz, 1H), 4.33 (t, J=7.2 Hz, 1H), 4.27-4.23 (m, 1H), 4.01-3.97 (m, 1H), 3.19-3.15 (m, 1H), 3.00-2.83 (m, 3H), 2.83-2.71 (m, 1H), 2.48-2.38 (m, 2H), 1.98-1.94 (m, 1H), 1.91-1.70 (m, 4H), 1.59 (q, J=4.8 Hz, 2H), 1.26-1.22 (m, 2H).

Example 323: 1-(4-{[(1S)-5-[2-(2-aminopyridin-3-yl)-5-[3-(1-fluorocyclopropyl)pyrazol-1-yl]imidazo[4,5-b]pyridin-3-yl]-2,3-dihydro-1H-inden-1-yl]amino}piperidin-1-yl)prop-2-en-1-one Example 323

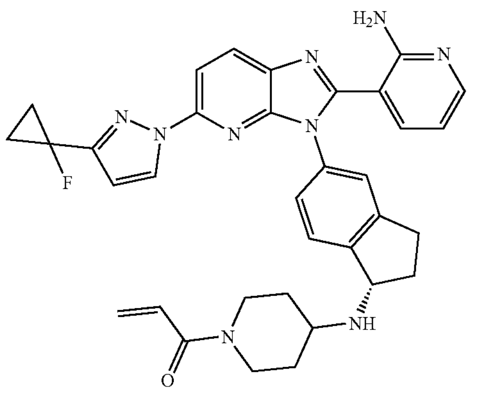

Example 323 was prepared in a manner analogous to Example 13 (via Intermediate 1-1) using Intermediate 320-1 in place of Intermediate 1-2, 3-(1-fluorocyclopropyl)-1H-pyrazole in place of pyrazole, and DCE/MeOH (10:1)+0.5 equiv AcOH instead of DCE. MS (ESI) calcd. for $C_{34}H_{34}FN_9O$: 603.29 m/z, found: 604.40 $[M+H]^+$/$^1$H NMR (300 MHz, DMSO-d6) δ (ppm): 8.32-8.35 (m, 2H), 7.99-8.01 (m, 1H), 7.87 (d, J=8.4 Hz, 1H), 7.47 (d, J=7.8 Hz, 1H), 7.20-7.32 (m, 3H), 6.77-7.21 (m, 3H), 6.61 (d, J=2.7 Hz, 1H), 6.39-6.43 (m, 1H), 6.05-6.11 (m, 1H), 5.65 (d, J=10.5, 1H), 4.33-4.40 (m, 1H), 4.20-4.22 (m, 1H), 3.90-4.10 (m, 1H), 3.18 (t, J=12.4 Hz, 1H), 2.75-2.93 (m, 4H), 2.35-2.49 (m, 1H), 2.02-2.21 (m, 1H), 1.95-2.00 (m, 1H), 1.71-1.90 (m, 2H), 2.45-2.52 (m, 2H), 1.15-1.25 (m, 4H).

Example 324: 1-(4-{[(1R,2*)-5-{2,5-diphenylimidazo[4,5-b]pyridin-3-yl}-2-fluoro-2,3-dihydro-1H-inden-1-yl]amino}piperidin-1-yl)prop-2-en-1-one and Example 325: 1-(4-{[(1R,2*)-5-{2,5-diphenylimidazo[4,5-b]pyridin-3-yl}-2-fluoro-2,3-dihydro-1H-inden-1-yl]amino}piperidin-1-yl)prop-2-en-1-one Example 324

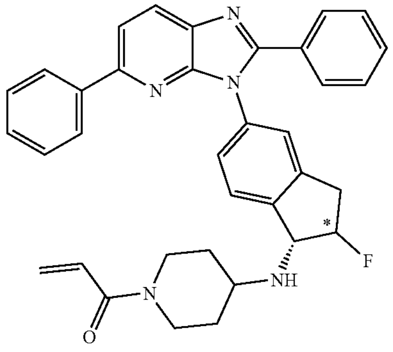

-continued

Example 325

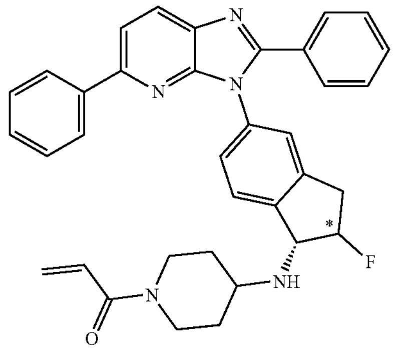

Examples 324 and 325 were prepared in a manner analogous to Example 13 using Intermediates 324-1 and 325-1, respectively, in place of Intermediate 1-1 and MeOH in place of DCE. * Denotes a stereocenter with undetermined absolute stereocenter of a single diastereomer.

Example 324: MS (ESI) calcd. for $C_{35}H_{32}FN_5O$: 557.25 m/z, found: 558.40 $[M+H]^+$. $^1$H-NMR (400 MHz, DMSO-$d_6$) δ (ppm): 8.24-8.26 (m, 1H), 7.95-8.01 (m, 3H), 7.57-7.62 (m, 3H), 7.34-7.56 (m, 8H), 6.77-6.84 (m, 1H), 6.05-6.12 (m, 1H), 5.65-5.69 (m, 1H), 5.37-5.55 (m, 1H), 4.39-4.48 (m, 1H), 4.18-4.28 (m, 1H), 3.95-4.15 (m, 1H), 2.89-3.26 (m, 5H), 1.83-2.07 (m, 2H), 1.25-1.34 (m, 2H). $^{19}$F-NMR (300 MHz, DMSO-d6) δ (ppm): −196.86.

Example 325: MS (ESI) calcd. for $C_{35}H_{32}FN_5O$: 557.25 m/z, found: 558.20 $[M+H]^+$. $^1$H-NMR (400 MHz, DMSO-$d_6$) δ (ppm): 8.24-8.26 (m, 1H), 7.95-8.03 (m, 3H), 7.39-7.62 (m, 10H), 7.31-7.35 (m, 1H), 6.78-6.84 (m, 1H), 6.05-6.12 (m, 1H), 5.65-5.69 (m, 1H), 5.17-5.35 (m, 1H), 4.39-4.45 (m, 1H), 3.95-4.28 (m, 2H), 3.38-3.50 (m, 1H), 3.12-3.19 (m, 1H), 2.93-3.02 (m, 2H), 2.81-2.89 (m, 1H), 1.86-2.03 (m, 2H), 1.18-1.29 (m, 2H). $^{19}$F-NMR (300 MHz, DMSO-d6) δ (ppm): −175.79.

Intermediate 324-1: (1R,2*)-5-(2,5-diphenyl-3H-imidazo[4,5-b]pyridin-3-yl)-2-fluoro-2,3-dihydro-1H-inden-1-amine and Intermediate 325-1: (1R,2*)-5-(2,5-diphenyl-3H-imidazo[4,5-b]pyridin-3-yl)-2-fluoro-2,3-dihydro-1H-inden-1-amine Intermediate 324-1

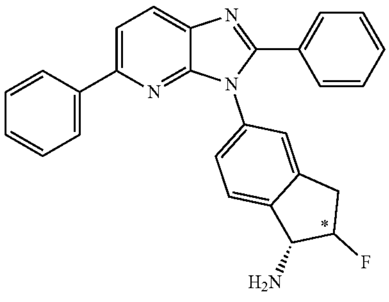

-continued

Intermediate 325-1

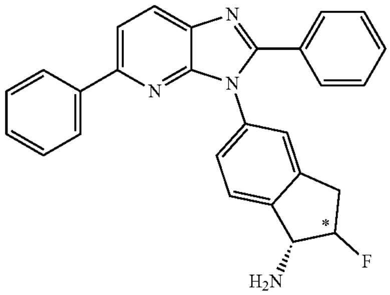

Intermediates 324-1 and 325-1 were prepared in a manner analogous to Intermediates 75-1 and 76-1 using 3-nitro-6-phenylpyridin-2-amine in place of 3-nitro-6-(pyrazol-1-yl) pyridin-2-amine and benzaldehyde in place of 2-aminopyridine-3-carbaldehyde. The diastereomers were separated prior to the final step by chiral prep-HPLC on a CHIRALPAK SS column using a mixture of [Hex/DCM (3:1) (+0.5% 2M NH3-MeOH)] and EtOH. * Denotes a stereocenter with undetermined absolute stereocenter of a single diastereomer.

Intermediate 324-1: MS (ESI) calcd. for $C_{27}H_{21}FN_4$: 420.17 m/z, found: 421.15 $[M+H]^+$.

Intermediate 325-1: MS (ESI) calcd. for $C_{27}H_{21}FN_4$: 420.17 m/z, found: 421.15 $[M+H]^+$.

Example 326: 2-((2*,4*)-1-acryloyl-4-(((S)-5-(2-(2-aminopyridin-3-yl)-5-(1H-pyrazol-1-yl)-3H-imidazo [4,5-b]pyridin-3-yl)-2,3-dihydro-1H-inden-1-yl) amino)piperidin-2-yl)acetonitrile and Example 327: 2-((2*,4*)-1-acryloyl-4-(((S)-5-(2-(2-aminopyridin-3-yl)-5-(1H-pyrazol-1-yl)-3H-imidazo [4,5-b]pyridin-3-yl)-2,3-dihydro-1H-inden-1-yl) amino)piperidin-2-yl)acetonitrile Example 326

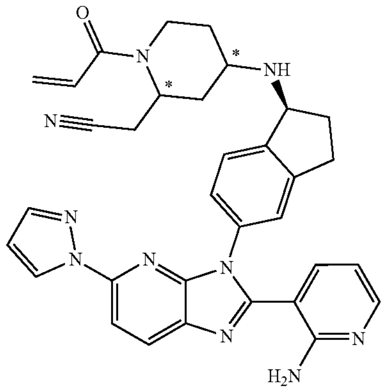

-continued

Example 327

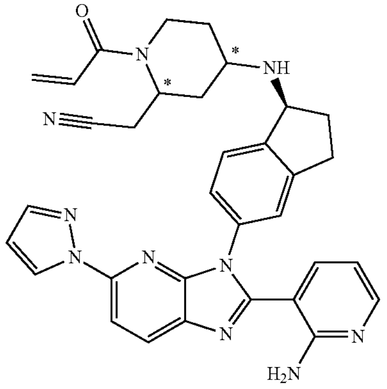

Examples 326 and 327 were prepared in a manner analogous to Example 13 using Intermediate 326-1 in place of the ketone and DCE/MeOH (1:1) as the solvent. The diastereomers were separated by Prep-HPLC on a XBridge Prep Shield RP OBD C18 column using a gradient of acetonitrile in water (+10 mM ammonium bicarbonate). * Denotes a stereocenter with undetermined absolute stereocenter of a single diastereomer.

Example 326: MS (ESI) calcd. for $C_{33}H_{32}N_{10}O$, 584.28 m/z, found, 585.20 $[M+H]^+$. $^1H$ NMR (500 MHz, Methanol-$d_4$) δ 8.41-8.35 (m, 1H), 8.31-8.23 (m, 1H), 8.08-7.88 (m, 2H), 7.75 (dd, J=3.3, 1.6 Hz, 1H), 7.61-7.54 (m, 1H), 7.43-7.20 (m, 3H), 6.84 (dd, J=17.0, 11.0 Hz, 1H), 6.48 (ddq, J=10.2, 5.0, 2.2 Hz, 2H), 6.25 (dd, J=16.7, 1.9 Hz, 1H), 5.80 (dd, J=10.8, 1.9 Hz, 1H), 4.77 (s, 1H), 4.46-4.40 (m, 1H), 4.03 (s, 1H), 3.59 (s, 1H), 3.46-3.33 (m, 2H), 3.15 (dd, J=16.4, 6.3 Hz, 1H), 3.06 (d, J=5.7 Hz, 1H), 2.93-2.86 (m, 1H), 2.58 (s, 1H), 2.06-2.02 (m, 1H), 1.92 (s, 4H).

Example 327: MS (ESI) calcd. for $C_{33}H_{32}N_{10}O$, 584.28 m/z, found, 585.20 $[M+H]^+$. $^1H$ NMR (500 MHz, Methanol-$d_4$) δ 8.38 (d, J=2.6 Hz, 1H), 8.28 (dd, J=8.6, 1.3 Hz, 1H), 8.03 (dd, J=8.6, 1.0 Hz, 1H), 7.99 (dd, J=5.0, 1.8 Hz, 1H), 7.76 (d, J=1.7 Hz, 1H), 7.60 (d, J=8.0 Hz, 1H), 7.40-7.34 (m, 2H), 7.29 (d, J=7.9 Hz, 1H), 6.94-6.77 (m, 1H), 6.52-6.45 (m, 2H), 6.24 (dd, J=16.9, 8.2 Hz, 1H), 5.81 (t, J=9.2 Hz, 1H), 5.26 (d, J=7.4 Hz, 1H), 4.72-4.06 (m, 2H), 3.50-3.34 (m, 1H), 3.30-3.22 (m, 1H), 3.16-3.10 (m, 1H), 2.97-2.88 (m, 3H), 2.59-2.52 (m, 1H), 2.32 (d, J=15.8 Hz, 1H), 2.10 (d, J=13.0 Hz, 1H), 2.03-1.92 (m, 1H), 1.61-1.51 (m, 1H), 1.41 (s, 1H).

Intermediate 326-1: (*)-2-(1-acryloyl-4-oxopiperidin-2-yl)acetonitrile and

Intermediate 327-2: (*)-2-(1-acryloyl-4-oxopiperidin-2-yl)acetonitrile

Intermediate 326-1

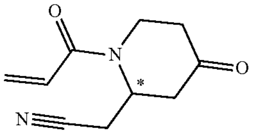

-continued
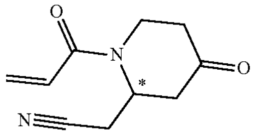
Intermediate 327-1
Synthetic Procedure:

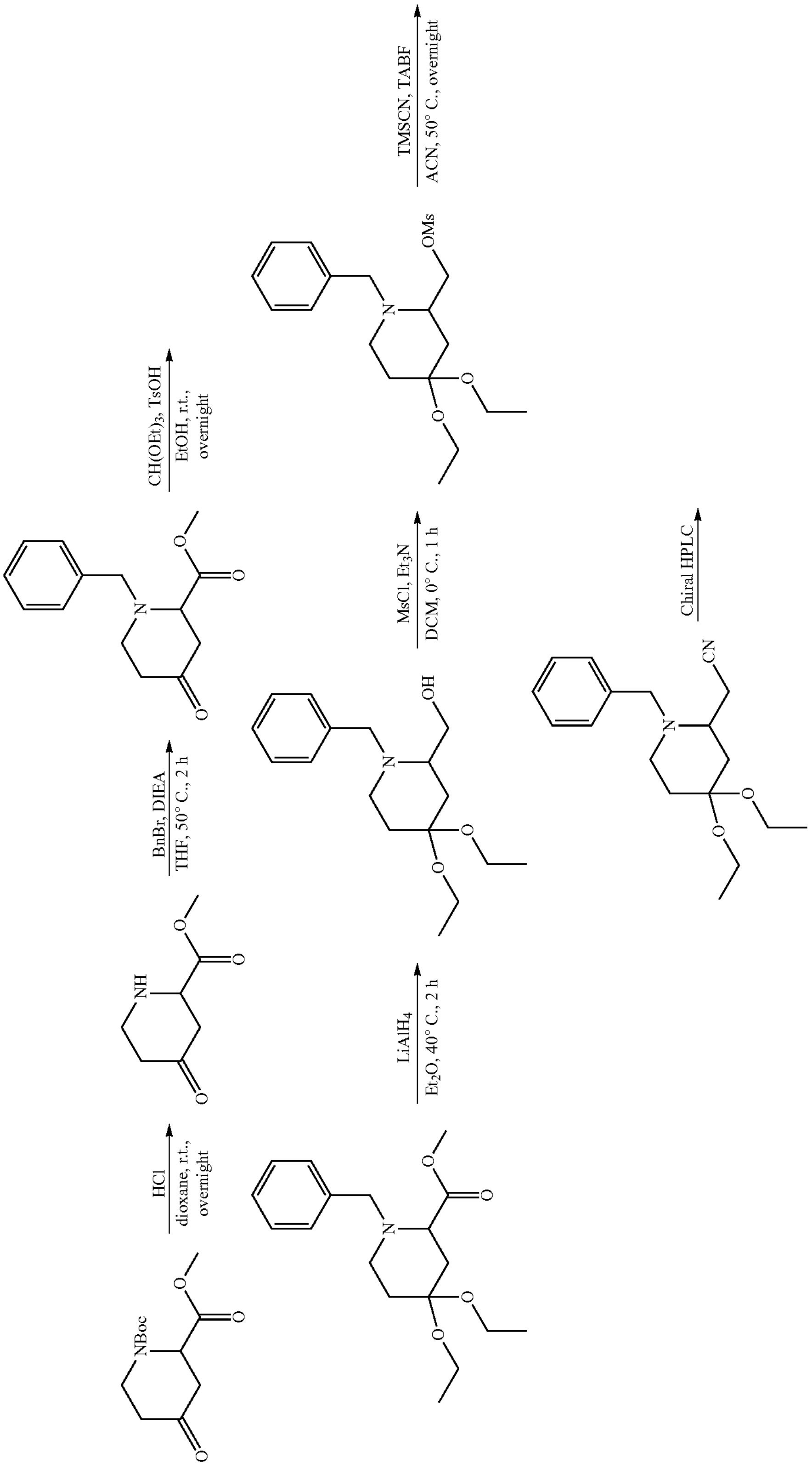
HCl
dioxane, r.t.,
overnight
BnBr, DIEA
THF, 50° C., 2 h
CH(OEt)3, TsOH
EtOH, r.t.,
overnight
LiAlH4
Et2O, 40° C., 2 h
MsCl, Et3N
DCM, 0° C., 1 h
TMSCN, TABF
ACN, 50° C., overnight
Chiral HPLC -continued
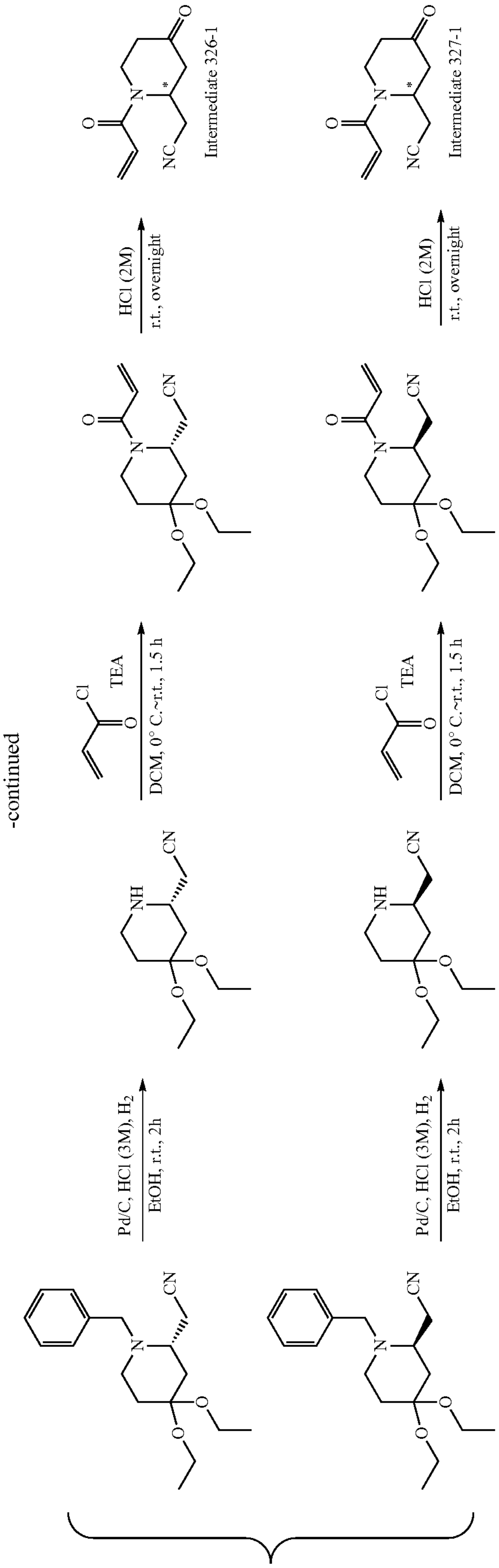
Intermediate 326-1
Intermediate 327-1

Step 1: Synthesis of methyl-4-oxopiperidine-2-carboxylate 1-tert-butyl 2-methyl 4-oxopiperidine-1,2-dicarboxylate (25 g, 97.17 mmol) was dissolved in 4M HCl in dioxane (100 mL) and the resulting mixture was stirred overnight then concentrated under vacuum to afford methyl 4-oxopiperidine-2-carboxylate hydrochloride (50 g, crude) as a light yellow solid, which was used in the next step without further purification. MS (ESI) calcd. for $C_7H_{11}NO_3$: 157.07 m/z, found: 158.10 $[M+H]^+$.

Step 2: Synthesis of methyl 1-benzyl-4-oxopiperidine-2-carboxylate

A mixture of methyl 4-oxopiperidine-2-carboxylate hydrochloride (50 g, 258.22 mmol) and THF (500 mL) was treated with DIEA (134 g, 1036.78 mmol) and BnBr (53 g, 309.87 mmol) at rt. The resulting mixture was stirred at 50° C. for 2 h. The reaction was diluted with water and extracted with DCM (3×800 mL). The organic layers were washed with brine, dried over $Na_2SO_4$ and concentrated under vacuum pressure. The obtained residue was purified by silica gel column (0-80% petroleum ether/ethyl acetate) to afford methyl 1-benzyl-4-oxopiperidine-2-carboxylate (25 g, 39.15% yield) as a white solid. MS (ESI) calcd. for $C_{14}H_{17}NO_3$: 247.12 m/z, found: 248.15 $[M+H]^+$.

Step 3: Synthesis of methyl 1-benzyl-4,4-diethoxypiperidine-2-carboxylate

To a solution of methyl-1-benzyl-4-oxopiperidine-2-carboxylate (20 g, 80.875 mmol, 1 equiv) in EtOH (190 ml) were added $CH(OEt)_3$ (113 g, 762.473 mmol, 9.43 equiv) dropwise, and TsOH (22 g, 127.758 mmol, 1.58 equiv) in batches at r.t. The resulting mixture was stirred overnight at r.t., then washed with a solution of $NaHCO_3$ (200 mL×3). The combined $NaHCO_3$ aqueous washes were washed with DCM (500 mL×3). Then the combined organic layer was washed with brine, dried over anhydrous sodium sulfate, filtered, and concentrated under vacuum. The residue was purified by silica gel column chromatography, eluting with (0-29% petroleum ether/ethyl acetate) to afford methyl-1-benzyl-4,4-diethoxypiperidine-2-carboxylate (25 g, 96.17%) as colorless oil. MS (ESI) calcd. for $C18H_{27}NO_4$, 321.19 m/z, found, 322.10 $[M+H]^+$.

Step 4: Synthesis of (1-benzyl-4,4-diethoxypiperidin-2-yl)methanol

To a solution of methyl-1-benzyl-4,4-diethoxypiperidine-2-carboxylate (24 g, 74.669 mmol, 1 equiv) in $Et_2O$ (240 mL) was added $LiAlH_4$ (95 mL, 95.000 mmol, 1.27 equiv, 1M/L) dropwise at r.t. under $N_2$. The resulting mixture was stirred for 2 h at 40° C. then quenched with water (7 mL), filtered, and washed with DCM (3×200 mL). The filtrate was dried over anhydrous sodium sulfate and concentrated under vacuum. The residue was purified by silica gel column chromatography, eluting with (0-78% ethyl acetate in petroleum ether) to afford (1-benzyl-4,4-diethoxypiperidin-2-yl) methanol (19.3 g, 88.09%) as a colorless oil. MS (ESI) calcd. for $C_{17}H_{27}NO_3$, 293.20 m/z, found, 294.15 $[M+H]^+$.

Step 5: Synthesis of (1-benzyl-4,4-diethoxypiperidin-2-yl)methyl methanesulfonate A solution of (1-benzyl-4,4-diethoxypiperidin-2-yl) methanol (5 g, 17.041 mmol, 1 equiv) and $Et_3N$ (2.6 g, 25.693 mmol, 1.51 equiv) in DCM (50 mL) was treated with MsCl (3.1 g, 27.065 mmol, 1.59 equiv) dropwise at 0° C. The resulting mixture was stirred for 1 h at 0° C. then diluted with water and extracted with DCM (3×100 mL). The combined organic layers were washed with brine, dried over anhydrous sodium sulfate, filtered, and concentrated under vacuum to afford (1-benzyl-4,4-diethoxypiperidin-2-yl) methyl methanesulfonate (6.33 g, 99.99%). MS (ESI) calcd. for $C18H_{29}NO_5S$, 371.18 m/z, found, 372.10 $[M+H]^+$.

Step 6: Synthesis of 2-(1-benzyl-4,4-diethoxypiperidin-2-yl)acetonitrile

A solution of (1-benzyl-4,4-diethoxypiperidin-2-yl) methyl methanesulfonate (6.33 g, 17.039 mmol, 1 equiv) in DCM (60 mL) was treated with TMSCN (2.7 g, 27.216 mmol, 1.60 equiv) and TBAF (22 mL, 22.000 mmol, 1.29 equiv, 1M/L) dropwise at r.t. The resulting mixture was stirred overnight at 50° C. then diluted with water and extracted with DCM (3×100 mL). The combined organic layers were washed with brine, dried over anhydrous sodium sulfate, filtered, and concentrated under vacuum. The residue was purified by silica gel column chromatography, eluting with (0-27% ethyl acetate in petroleum ether) to afford 2-(1-benzyl-4,4-diethoxypiperidin-2-yl)acetonitrile (4.18 g, 81.12%) as white solid. MS (ESI) calcd. for $C18H_{26}N_2O_2$, 302.20 m/z, found, 303.15 $[M+H]^+$. The two enantiomeric products were separated by chiral Prep HPLC on a CHIRALPAK IG column using a mixture of $CO_2$ and MeOH (+0.1% 2M $NH_3$-MeOH). The second eluting peak was carried through steps 7-9 vide infra to provide Intermediate 326-1. The first eluting peak was carried through the same procedure to provide Intermediate 327-2. * Denotes a stereocenter with undetermined absolute stereocenter of a single enantiomer.

Step 7: Synthesis of (*)-2-(4,4-diethoxypiperidin-2-yl)acetonitrile

A solution of (*)-2-(1-benzyl-4,4-diethoxypiperidin-2-yl) acetonitrile (400 mg, 1.323 mmol, 1 equiv) in EtOH (8 mL) was treated with Pd/C (40 mg, 0.376 mmol, 0.28 equiv) in batches and HCl (0.66 mL, 1.980 mmol, 1.50 equiv, 3M/L) dropwise at r.t. The resulting mixture was stirred for 2 h at r.t., under $H_2$ then filtered and concentrated under vacuum to afford (S*)-2-(4,4-diethoxypiperidin-2-yl)acetonitrile (383 mg, crude) as an off-white solid. MS (ESI) calcd. for $C_{11}H_{20}N_2O_2$, 212.15 m/z, found, 167.15 $[M-C_2H_5O]1$.

Step 8: Synthesis of (*)-2-(1-acryloyl-4,4-diethoxypiperidin-2-yl)acetonitrile

A solution of (*)-2-(4,4-diethoxypiperidin-2-yl)acetonitrile (281 mg, 1.324 mmol, 1 equiv) and triethylamine (437 mg, 4.318 mmol, 3.26 equiv) in DCM (5 mL) was treated with acryloyl chloride (146 mg, 1.613 mmol, 1.22 equiv) dropwise at 0° C. The resulting mixture was stirred for 1.5 h at r.t. then diluted with water and extracted with DCM (3×20 mL). The combined organic layers were washed with brine, dried over anhydrous sodium sulfate, filtered, and concentrated under vacuum to afford (*)-2-(1-acryloyl-4,4-diethoxypiperidin-2-yl)acetonitrile (396 mg, crude) as colorless oil. MS (ESI) calcd. for $C_{14}H_{22}N_2O_3$, 266.16 m/z, found, 221.10 $[M-C_2H_5O]1$.

Step 9: Synthesis of (*)-2-(1-acryloyl-4-oxopiperidin-2-yl)acetonitrile (Intermediate 326-1

A mixture of (*)-2-(1-acryloyl-4,4-diethoxypiperidin-2-yl)acetonitrile (396 mg, 1.487 mmol, 1 equiv) in HCl (4 mL, 2M/L) aq was stirred overnight at r.t. then diluted with water and extracted with DCM (3×20 mL). The combined organic layer was washed with brine, dried over anhydrous sodium sulfate, filtered, and concentrated under vacuum. The residue was purified by silica gel column chromatography, eluting with (0-7% MeOH in DCM) to afford (*)-2-(1-acryloyl-4-oxopiperidin-2-yl)acetonitrile (Intermediate 326-1) (104 mg, three-step yield: 40.94%) as colorless oil. MS (ESI) calcd. for $C_{10}H_{12}N_2O_2$, 192.09 m/z, found, 193.10 $[M+H]^+$. * Denotes a stereocenter with undetermined absolute stereocenter of a single enantiomer.

Example 328: 1-((2*,4*)-2-(difluoromethyl)-4-(((1R,2*)-2-fluoro-5-(2-phenyl-5-(1H-pyrazol-1-yl)-3H-imidazo[4,5-b]pyridin-3-yl)-2,3-dihydro-1H-inden-1-yl)amino)piperidin-1-yl)prop-2-en-1-one Example 329: 1-((2*,4*)-2-(difluoromethyl)-4-(((1R,2*)-2-fluoro-5-(2-phenyl-5-(1H-pyrazol-1-yl)-3H-imidazo[4,5-b]pyridin-3-yl)-2,3-dihydro-1H-inden-1-yl)amino)piperidin-1-yl)prop-2-en-1-one Example 330: 1-((2*,4*)-2-(difluoromethyl)-4-(((1R,2*)-2-fluoro-5-(2-phenyl-5-(1H-pyrazol-1-yl)-3H-imidazo[4,5-b]pyridin-3-yl)-2,3-dihydro-1H-inden-1-yl)amino)piperidin-1-yl)prop-2-en-1-one and Example 331: 1-((2*,4*)-2-(difluoromethyl)-4-(((1R,2*)-2-fluoro-5-(2-phenyl-5-(1H-pyrazol-1-yl)-3H-imidazo[4,5-b]pyridin-3-yl)-2,3-dihydro-1H-inden-1-yl)amino)piperidin-1-yl)prop-2-en-1-one Example 328

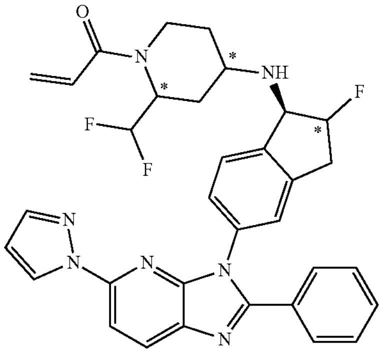

Example 329

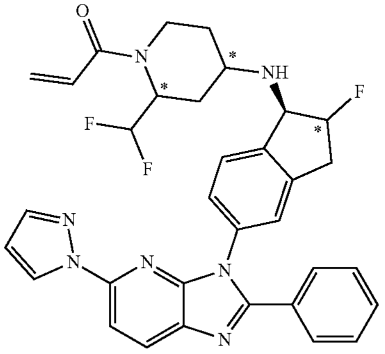

-continued

Example 330

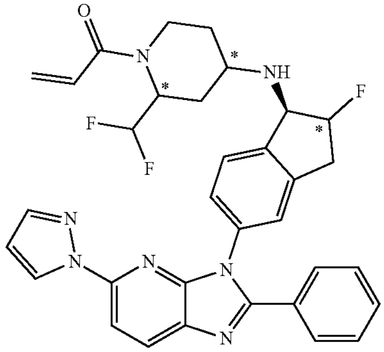

Example 331

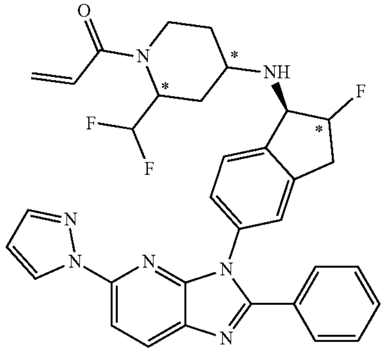

Examples 328, 329, 330 and 331 were prepared in a manner analogous to Example 14 (via Intermediate 14-1) using tert-butyl 2-(difluoromethyl)-4-oxopiperidine-1-carboxylate in place of tert-butyl 8-oxo-3-azabicyclo[3.2.1]octane-3-carboxylate and Intermediate 324-1 in place of Intermediate 1-1. Examples 328 and 329 were separated from 330 and 331 by Prep HPLC on XBridge Prep Shield RP OBD C18 column using a gradient of acetonitrile in water (+0.05% ammonium bicarbonate). Examples 328 and 329 were separated by chiral Prep-HPLC on a CHIRALPAK IG column using a mixture of [Hex/DCM (3:1) (+0.5% 2M $NH_3$-MeOH)] and ethanol. Examples 330 and 331 were separated by chiral Prep-HPLC on a CHIRAL ART Cellulose-SB column using a mixture of [hexanes (+0.5% 2M $NH_3$-MeOH)] and ethanol. * Denotes a stereocenter with undetermined absolute stereocenter of a single diastereomer.

Example 328: MS (ESI) calcd. for $C_{33}H_{30}F_3N_7O$: 597.25 m/z, found: 598.20 $[M+H]^+$. $^1H$ NMR (300 MHz, DMSO-$d_6$) δ(ppm): 8.41-8.29 (m, 2H), 7.98-7.90 (m, 1H), 7.82-7.77 (m, 1H), 7.60-7.53 (m, 2H), 7.53-7.29 (m, 6H), 6.94-6.78 (m, 1H), 6.62-6.20 (m, 2H), 6.20-6.08 (m, 1H), 5.78-5.64 (m, 1H), 5.55-5.26 (m, 1H), 4.73-4.34 (m, 2H), 3.26-3.02 (m, 4H), 2.23-2.06 (m, 2H), 1.45 (s, 2H), 1.22 (s, 2H). $^{19}F$ NMR (282 MHz, DMSO-d6) δ −119.45-126.62 (m), −196.47.

Example 329: MS (ESI) calcd. for $C_{33}H_{30}F_3N_7O$: 597.25 m/z, found: 598.20 $[M+H]^+$. $^1H$ NMR (300 MHz, DMSO-$d_6$) δ(ppm): 8.43-8.28 (m, 2H), 7.99-7.89 (m, 1H), 7.80 (s, 1H), 7.61-7.52 (m, 2H), 7.52-7.23 (m, 6H), 6.94-6.76 (m, 1H), 6.64-6.20 (m, 2H), 6.19-6.07 (m, 1H), 5.71 (s, 1H), 5.53-5.25 (m, 1H), 5.12-3.96 (m, 2H), 3.26-2.65 (m, 5H), 2.37-2.11 (m, 2H), 2.10-1.90 (m, 1H), 1.67-1.36 (m, 1H), 1.35-1.07 (m, 1H). $^{19}F$ NMR (282 MHz, DMSO-d6) δ −119.22-125.65 (m), −196.20.

Example 330: MS (ESI) calcd. for $C_{33}H_{30}F_3N_7O$: 597.25 m/z, found: 598.20 $[M+H]^+$. $^1H$ NMR (300 MHz, DMSO-d6) δ(ppm): 8.43-8.27 (m, 2H), 8.03-7.89 (m, 1H), 7.87-7.74 (m, 1H), 7.66-7.52 (m, 3H), 7.52-7.31 (m, 5H), 7.31-6.97 (m, 1H), 6.97-6.79 (m, 1H), 6.59-6.47 (m, 1H), 6.22-6.08 (m, 1H), 5.79-5.38 (m, 2H), 5.04-3.42 (m, 3H), 3.32-2.96 (m, 4H), 2.45 (s, 1H), 2.32-2.08 (m, 1H), 1.78 (s, 3H). $^{19}$F NMR (282 MHz, DMSO-$d_6$) δ −117.89 (dd, J=279.2, 194.5 Hz), −127.34 (dd, J=278.4, 84.4 Hz), −198.29 (d, J=44.8 Hz).

Example 331: MS (ESI) calcd. for $C_{33}H_{30}F_3N_7O$: 597.25 m/z, found: 598.20 $[M+H]^+$. $^1$H NMR (300 MHz, DMSO-$d_6$) δ(ppm): 8.40-8.31 (m, 2H), 8.01-7.89 (m, 1H), 7.83-7.77 (m, 1H), 7.67-7.55 (m, 3H), 7.52-7.31 (m, 5H), 7.07-6.76 (m, 2H), 6.69-6.49 (m, 1H), 6.21-6.09 (m, 1H), 5.77-5.33 (m, 2H), 4.95-4.15 (m, 3H), 3.51 (s, 1H), 3.25-2.99 (m, 3H), 2.21-1.79 (m, 4H), 1.65 (s, 1H). $^{19}$F NMR (282 MHz, DMSO-$d_6$) δ −119.19 (t, J=260.3 Hz), −126.55 (d, J=280.4 Hz), −197.88.

Example 332: 1-(4-(((1R,2*)-2-fluoro-5-(5-(3-fluoro-1H-pyrazol-1-yl)-2-phenyl-3H-imidazo[4,5-b]pyridin-3-yl)-2,3-dihydro-1H-inden-1-yl)amino) piperidin-1-yl)prop-2-en-1-one Example 332

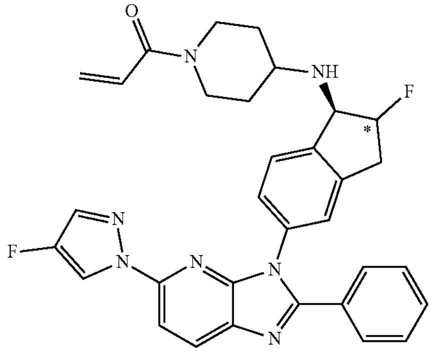

Example 332 was prepared in a manner analogous to Example 13 using Intermediate 332-1 in place of Intermediate 1-1. The diastereomers were separated by chiral Prep HPLC on a CHIRALPAK IA column using a mixture of [Hex (+0.5% 2M $NH_3$-MeOH)] and IPA. * Denotes a stereocenter with undetermined absolute stereocenter of a single diastereomer. MS (ESI) calcd. for $C_{32}H_{29}F_2N_7O$: 565.24 m/z, found: 566.15 $[M+H]^+$. 1H NMR (400 MHz, DMSO-d6) δ (ppm): 8.34-8.41 (m, 1H), 8.26-8.31 (m, 1H), 7.73-7.81 (m, 1H), 7.55-7.61 (m, 2H), 7.44-7.54 (m, 2H), 7.30-7.43 (m, 4H), 6.76-6.89 (m, 1H), 6.32-6.39 (m, 1H), 6.05-6.16 (m, 1H), 5.64-5.73 (m, 1H), 5.38-5.58 (m, 1H), 4.36-4.51 (m, 1H), 4.17-4.34 (m, 1H), 3.92-4.11 (m, 1H), 3.18-3.31 (m, 2H), 3.14-3.17 (m, 1H), 3.01-3.13 (m, 1H), 2.87-3.00 (m, 1H), 1.97-2.11 (m, 1H), 1.82-1.96 (m, 1H), 1.19-1.46 (m, 2H). $^{19}$F-NMR (376 MHz, DMSO-d6) δ (ppm): −127.25, −196.93.

Intermediate 332-1: (1R)-2-fluoro-5-(5-(3-fluoro-1H-pyrazol-1-yl)-2-phenyl-3H-imidazo[4,5-b]pyridin-3-yl)-2,3-dihydro-1H-inden-1-amine Intermediate 332-1

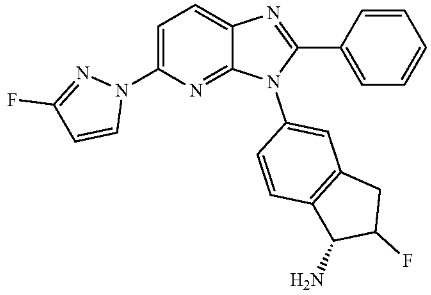

Intermediate 332-1 was prepared in a manner analogous to Intermediate 75-1 (starting from Step 4) using Intermediate 286-3 in place of the bromide, Intermediate 236-3 in place of the aniline, a reaction time of overnight for the Buchwald coupling, benzaldehyde in place of 2-aminopyridine-3-carbaldehyde, AcOH/MeOH under air at 60° C. for 3 h instead of AcOH/Cu(OAc)$_2$, DCM/TFA (3:1) at room temperature overnight for the deprotection and omitting the chiral separation. MS (ESI) calcd. for $C_{24}H_{18}F_2N_6$: 428.16 m/z, found: 429.15 $[M+H]^+$.

Example 333: 1-((2*,4*)-4-(((1*,2*)-5-(2-(2-aminopyridin-3-yl)-5-(3-cyclopropyl-H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one Example 334: 1-((2*,4*)-4-(((1*,2*)-5-(2-(2-aminopyridin-3-yl)-5-(3-cyclopropyl-1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one Example 335: 1-((2*,4*)-4-(((1*,2*)-5-(2-(2-aminopyridin-3-yl)-5-(3-cyclopropyl-1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one and Example 336: 1-((2*,4*)-4-(((1*,2*)-5-(2-(2-aminopyridin-3-yl)-5-(3-cyclopropyl-1H-pyrazol-1-yl)-3H-imidazo[4,5-b]pyridin-3-yl)-2-fluoro-2,3-dihydro-1H-inden-1-yl)amino)-2-(difluoromethyl)piperidin-1-yl)prop-2-en-1-one Example 333

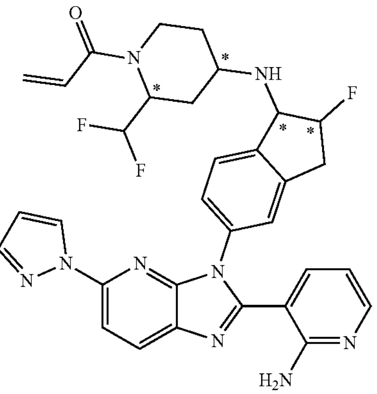

-continued

Example 334

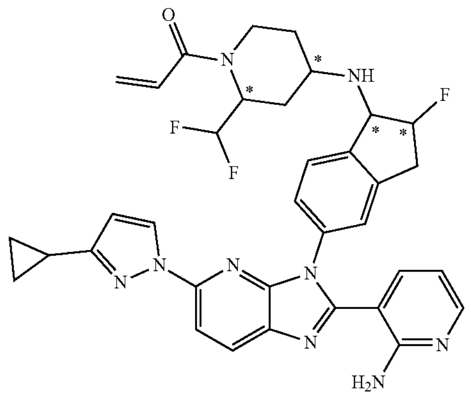

Example 335

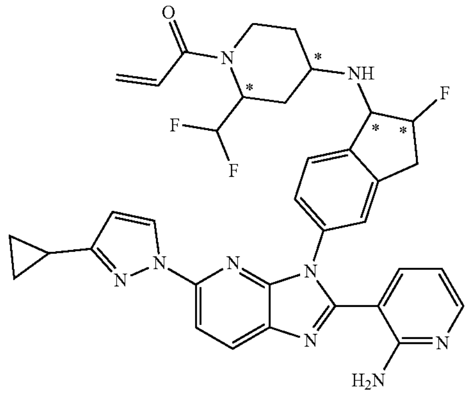

Example 336

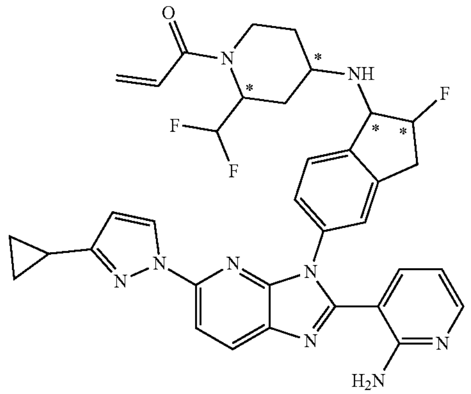

Examples 333, 334, 335 and 336 were prepared in a manner analogous to Example 14 (via Intermediate 14-1) using tert-butyl 2-(difluoromethyl)-4-oxopiperidine-1-carboxylate in place of tert-butyl 8-oxo-3-azabicyclo[3.2.1] octane-3-carboxylate and Intermediate 333-1 in place of Intermediate 1-1. Examples 333 and 334 were separated from 335 and 336 by Prep HPLC on XSelect CSH OBD Column using a gradient of acetonitrile in water (+0.05% formic acid). Examples 333 and 334 were separated by chiral Prep-HPLC on a CHIRAL ART Cellulose-SB column using a mixture of [MtBE (+2 mM NH3-MEOH)] and EtOH. Examples 335 and 336 were separated by Prep-HPLC on a XSelect CSH OBD column using a gradient of acetonitrile in water (+0.1% formic acid). * Denotes a stereocenter with undetermined absolute stereocenter of a single diastereomer.

Example 333: MS (ESI) calcd. for $C_{35}H_{34}F_3N_9O$, 653.28 m/z, found: 654.20 $[M+H]^+$. $^1H$ NMR (400 MHz, DMSO-d6) δ (ppm): 8.25-8.42 (m, 1H), 8.08-8.25 (m, 1H), 7.95-8.08 (m, 1H), 7.79-7.95 (m, 1H), 7.39-7.65 (m, 1H), 7.18-7.39 (m, 3H), 6.68-6.93 (m, 1H), 6.43-6.59 (m, 1H), 6.06-6.42 (m, 3H), 5.71-5.92 (m, 1H), 5.28-5.62 (m, 1H), 4.92-5.11 (m, 1H), 4.31-4.72 (m, 2H), 2.82-3.34 (m, 4H), 2.26-2.42 (m, 1H), 1.92-2.14 (m, 2H), 1.43-1.69 (m, 1H), 1.22-1.41 (m, 1H), 0.91-1.10 (m, 2H), 0.61-0.87 (m, 2H).

Example 334: MS (ESI) calcd. for $C_{35}H_{34}F_3N_9O$, 653.28 m/z, found: 654.25 $[M+H]^+$. $^1H$ NMR (400 MHz, DMSO-d6) δ (ppm): 8.25-8.42 (m, 1H), 8.11-8.25 (m, 1H), 7.95-8.11 (m, 1H), 7.73-7.95 (m, 1H), 7.42-7.64 (m, 1H), 7.15-7.42 (m, 3H), 6.68-6.96 (m, 1H), 6.42-6.59 (m, 1H), 6.06-6.42 (m, 3H), 5.68-5.92 (m, 1H), 5.28-5.62 (m, 1H), 4.84-5.14 (m, 1H), 4.51-4.75 (m, 1H), 4.34-4.51 (m, 1H), 2.82-3.36 (m, 4H), 2.08-2.38 (m, 2H), 1.98-2.07 (m, 1H), 1.47-1.68 (m, 1H), 1.21-1.39 (m, 1H), 0.93-1.06 (m, 2H), 0.69-0.87 (m, 2H).

Example 335: MS (ESI) calcd. for $C_{35}H_{34}F_3N_9O$, 653.28 m/z, found: 654.25 $[M+H]^+$. $^1H$ NMR (400 MHz, DMSO-d6) δ (ppm): 8.25-8.42 (m, 1H), 8.06-8.25 (m, 1H), 7.95-8.09 (m, 1H), 7.72-7.95 (m, 1H), 7.42-7.62 (m, 1H), 7.21-7.42 (m, 3H), 6.59-7.01 (m, 2H), 6.39-6.59 (m, 1H), 6.06-6.32 (m, 2H), 5.71-5.86 (m, 1H), 5.28-5.65 (m, 1H), 4.08-4.98 (m, 3H), 4.02-4.04 (m, 1H), 3.52-3.93 (m, 1H), 3.14-3.24 (m, 1H), 3.05-3.14 (m, 1H), 1.79-2.11 (m, 4H), 1.55-1.79 (m, 1H), 0.89-1.06 (m, 2H), 0.65-0.81 (m, 2H).

Example 336: MS (ESI) calcd. for $C_{35}H_{34}F_3N_9O$, 653.28 m/z, found: 654.25 $[M+H]^+$. $^1H$ NMR (400 MHz, DMSO-d6) δ (ppm): 8.25-8.38 (m, 1H), 8.10-8.25 (m, 1H), 7.95-8.09 (m, 1H), 7.75-7.94 (m, 1H), 7.42-7.62 (m, 1H), 7.25-7.41 (m, 3H), 6.88-7.25 (m, 1H), 6.66-6.88 (m, 1H), 6.31-6.56 (m, 1H), 6.03-6.31 (m, 2H), 5.68-5.96 (m, 1H), 5.34-5.68 (m, 1H), 4.01-5.09 (m, 3H), 3.60-3.91 (m, 1H), 3.18-3.34 (m, 2H), 3.05-3.18 (m, 1H), 2.13-2.32 (m, 1H), 1.97-2.09 (m, 1H), 1.64-1.81 (m, 3H), 0.89-1.08 (m, 2H), 0.68-0.85 (m, 2H).

Intermediate 333-1: 3-(3-((1R,2S)-1-amino-2-fluoro-2,3-dihydro-1H-inden-5-yl)-5-(3-cyclopropyl-1H-pyrazol-1-yl)-3H-imidazo[4,5-b]pyridin-2-yl)pyridin-2-amine Intermediate 333-1

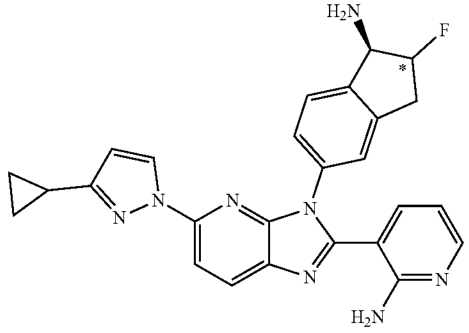

Intermediate 333-1 was prepared in a manner analogous to Intermediate 75-1 using Intermediate 333-0 in place of 3-nitro-6-(pyrazol-1-yl)pyridin-2-amine. MS (ESI) calcd. for $C_{26}H_{23}FN_8$: 466.20 m/z, found: 467.15 $[M+H]^+$. *

Denotes a stereocenter with undetermined absolute stereocenter of a single diastereomer.

Intermediate 333-0: 6-(3-cyclopropyl-1H-pyrazol-1-yl)-3-nitropyridin-2-amine

Intermediate 333-0

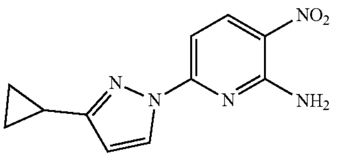

Synthetic Route:

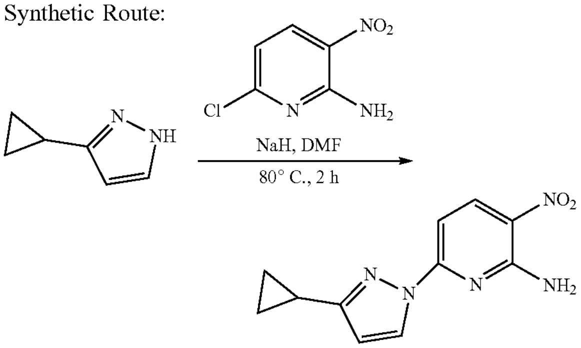

Intermediate 333-0

Step 10: Synthesis of 6-(3-cyclopropylpyrazol-1-yl)-3-nitropyridin-2-amine

To a stirred solution of 3-cyclopropyl-1H-pyrazole (1.37 g, 12.675 mmol, 1.1 equiv) in DMF (50 mL) was added NaH (0.83 g, 34.569 mmol, 3 equiv) and 6-chloro-3-nitropyridin-2-amine (2 g, 11.523 mmol, 1 equiv) at rt. The resulting mixture was stirred for 2 h at 80° C. After cooling to room temperature, the mixture was dropped into water. The mixture was filtered and dried to afford 6-(3-cyclopropylpyrazol-1-yl)-3-nitropyridin-2-amine (Intermediate 333-0) (2.2 g, crude) MS (ESI) calcd. for $C_{11}H_{11}N_5O_2$: 245.09 m/z, found: 246.15 $[M+H]^+$.

Example 337: 1-(4-{[(1S)-5-[2-(2-aminopyridin-3-yl)-7-methoxy-5-(pyrazol-1-yl)imidazo[4,5-b]pyridin-3-yl]-2,3-dihydro-1H-inden-1-yl]amino}piperidin-1-yl)prop-2-en-1-one Example 337

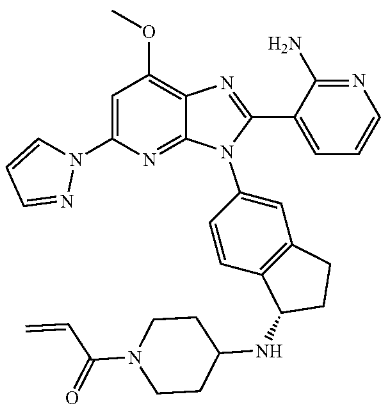

Example 337 was prepared in a manner analogous to Example 13 using MeOH as the solvent and Intermediate 337-2 in place of Intermediate 1-1. MS (ESI) calcd. For $C_{32}H_{33}N_9O_2$, 575.28 m/z, found 576.40 $[M+H]^+$. $^1H$ NMR (300 MHz, DMSO-$d_6$) δ 8.30-8.31 (m, 1H), 7.96-7.98 (m, 1H), 7.78-7.79 (m, 1H), 7.44-7.49 (m, 2H), 7.28-7.29 (m, 1H), 7.15-7.22 (m, 2H), 6.94 (s, 2H), 6.77-6.86 (m, 1H), 6.51-6.52 (m, 1H), 6.37-6.41 (m, 1H), 6.04-6.10 (m, 1H), 5.62-5.66 (m, 1H), 4.23-4.35 (m, 2H), 4.19 (s, 3H), 3.94-4.00 (m, 1H), 3.11-3.20 (m, 1H), 2.87-2.92 (m, 3H), 2.71-2.79 (m, 1H), 2.42-2.44 (m, 1H), 2.14-2.20 (m, 1H), 1.93-1.97 (m, 1H), 1.70-1.83 (m, 2H), 1.22-1.27 (m, 2H).

Intermediate 337-2: (S)-3-(3-(1-amino-2,3-dihydro-1H-inden-5-yl)-7-methoxy-5-(1H-pyrazol-1-yl)-3H-imidazo[4,5-b]pyridin-2-yl)pyridin-2-amine Intermediate 337-2

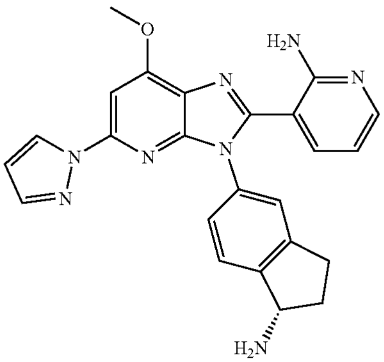

Intermediate 337-2 was prepared in a manner analogous to Intermediate 1-1 using EPhos/EPhos Pd G4/$Cs_2CO_3$ for step 1 and Intermediate 337-1 in place of Intermediate 1-2. MS (ESI) calcd. For $C_{24}H_{22}N_8O$, 438.19 m/z, found 439.25 $[M+H]^+$.

Intermediate 337-1: (S)-N-(5-(2-(2-aminopyridin-3-yl)-5-chloro-7-methoxy-3H-imidazo[4,5-b]pyridin-3-yl)-2,3-dihydro-1H-inden-1-yl)acetamide Intermediate 337-1

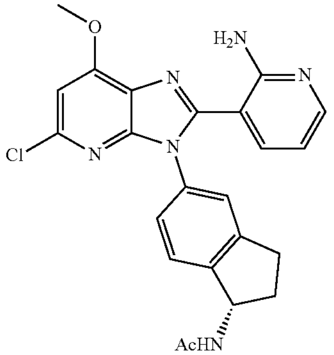

Intermediate 337-1 was prepared in a manner analogous to Intermediate 77-1 using 2,6-dichloro-4-methoxy-3-nitropyridine in place of 5-bromo-2,3-dihydroinden-1-one, Intermediate 218-4 in place of 3-nitro-6-(pyrazol-1-yl)pyridin-2-amine and $Pd_2(dba)_3$/RuPhos/sodium carbonate/overnight instead of $Pd(OAc)_2$/XantPhos/$Cs_2CO_3$/2 h. MS (ESI) calcd. For $C_{23}H_{21}ClN_6O_2$, 448.14 m/z, found 449.20 $[M+H]^+$.

Example 338: 2-((2*,4*)-1-acryloyl-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidin-2-yl)acetonitrile and Example 339: 2-((2*,4*)-1-acryloyl-4-(((S)-5-(2-(2-aminopyridin-3-yl)-5-(1H-pyrazol-1-yl)-3H-imidazo[4,5-b]pyridin-3-yl)-2,3-dihydro-1H-inden-1-yl)amino)piperidin-2-yl)acetonitrile Example 338

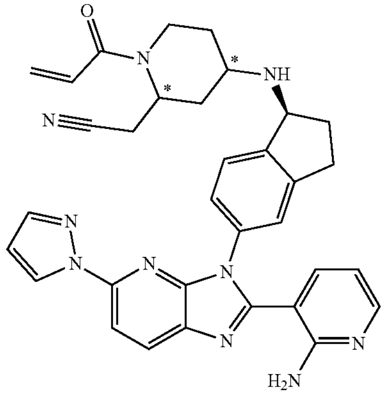

Example 339

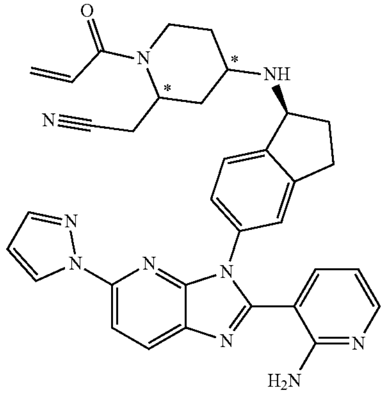

Examples 338 and 339 were prepared in a manner analogous to Example 13 using Intermediate 326-2 in place of the ketone and DCE/MeOH (1:1) as the solvent. The diastereomers were separated by SFC on a DAICEL DCpak P4VP column using a mixture of $CO_2$ and MeOH (+20 mM $NH_3$). * Denotes a stereocenter with undetermined absolute stereocenter of a single diastereomer.

Example 338: MS (ESI) calcd for $C_{33}H_{32}N_{10}O$ 584.68 m/z, found 585.25$[M+H]^+$. $^1$H NMR (500 MHz, Methanol-d4) δ 8.40 (dd, J=2.6, 0.7 Hz, 1H), 8.28 (d, J=8.6 Hz, 1H), 8.02 (d, J=8.6 Hz, 1H), 7.99 (dd, J=5.0, 1.8 Hz, 1H), 7.76 (dd, J=1.7, 0.7 Hz, 1H), 7.59 (d, J=7.9 Hz, 1H), 7.37 (dd, J=7.6, 1.8 Hz, 1H), 7.33 (d, J=1.9 Hz, 1H), 7.30 (dd, J=8.0, 2.0 Hz, 1H), 6.84 (dd, J=16.8, 10.7 Hz, 1H), 6.53-6.45 (m, 2H), 6.24 (dd, J=16.8, 2.0 Hz, 1H), 5.79 (dd, J=10.7, 2.0 Hz, 1H), 4.78 (s, 1H), 4.52-4.49 (m, 1H), 4.04 (s, 1H), 3.57 (s, 1H), 3.35-3.31 (m, 3H), 3.10-3.05 (m, 1H), 2.94-2.88 (m, 1H), 2.66-2.56 (m, 1H), 2.17-2.08 (m, 1H), 2.00-1.82 (m, 3H), 1.77 (d, J=13.9 Hz, 1H).

Example 339: MS (ESI) calcd for $C_{33}H_{32}N_{10}O$ 584.68 m/z, found 585.20$[M+H]^+$. $^1$H NMR (500 MHz, Methanol-d4) δ 8.39 (d, J=2.6 Hz, 1H), 8.29 (d, J=8.6 Hz, 1H), 8.03 (d, J=8.7 Hz, 1H), 7.99 (dd, J=5.0, 1.8 Hz, 1H), 7.76 (dd, J=1.7, 0.8 Hz, 1H), 7.59 (d, J=8.0 Hz, 1H), 7.40-7.34 (m, 2H), 7.29 (dd, J=8.1, 2.0 Hz, 1H), 6.92-6.79 (m, 1H), 6.52-6.45 (m, 2H), 6.27-6.22 (m, 1H), 5.81-5.79 (m, 1H), 5.25 (s, 1H), 4.54-4.51 (m, 1H), 4.15 (d, J=14.5 Hz, 1H), 3.30-3.18 (m, 1H), 3.14-3.11 (m, 1H), 3.01-2.88 (m, 3H), 2.57-2.54 (m, 1H), 2.26-2.21 (m, 1H), 2.17-2.10 (m, 1H), 2.02-1.93 (m, 1H), 1.63-1.61 (m, 1H), 1.50-1.31 (m, 3H).

Example 340: 1-[4-({5-[2-(2-aminopyridin-3-yl)-5-(3-fluoropyrazol-1-yl)imidazo[4,5-b]pyridin-3-yl]-2,3-dihydro-1H-inden-1-yl}methyl)piperazin-1-yl]prop-2-en-1-one Example 340

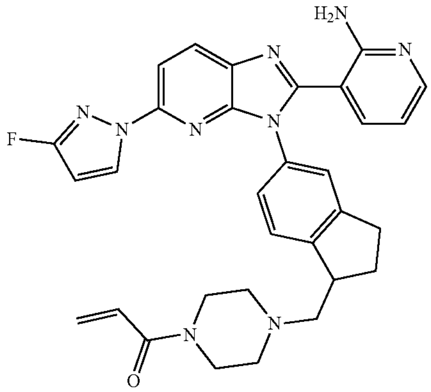

Example 340 was prepared in a manner analogous to Example 174 using Intermediate 236-3 as the starting material. MS (ESI) calcd. for $C_{31}H_{30}FN_9O$: 563.26 m/z, found: 564.20 [M+H]. $^1$H NMR (400 MHz, DMSO-d6) δ 8.40-8.26 (m, 2H), 8.15 (s, 1H), 8.04-7.93 (m, 1H), 7.81-7.71 (m, 1H), 7.59-7.43 (m, 1H), 7.34 (s, 1H), 7.26-7.13 (m, 2H), 6.98-6.87 (m, 2H), 6.86-6.74 (m, 1H), 6.49-6.27 (m, 2H), 6.18-6.04 (m, 1H), 5.81-5.59 (m, 1H), 3.62-3.57 (m, 6H), 3.11-2.73 (m, 4H), 2.71-2.57 (m, 2H), 2.43-2.32 (m, 1H), 2.29-2.18 (m, 1H), 1.91-1.71 (m, 1H). $^{19}$F NMR (376 MHz, DMSO-$d_6$) δ −73.429, −127.376. (TFA salt)

Example 341: 1-(4-(((1R,2*)-5-(2-(2-aminopyridin-3-yl)-5-(1H-pyrazol-1-yl)-3H-imidazo[4,5-b]pyridin-3-yl)-2,7-difluoro-2,3-dihydro-1H-inden-1-yl)amino)piperidin-1-yl)prop-2-en-1-one and Example 342: 1-(4-(((1R,2*)-5-(2-(2-aminopyridin-3-yl)-5-(1H-pyrazol-1-yl)-3H-imidazo[4,5-b]pyridin-3-yl)-2,7-difluoro-2,3-dihydro-1H-inden-1-yl)amino)piperidin-1-yl)prop-2-en-1-one Example 341

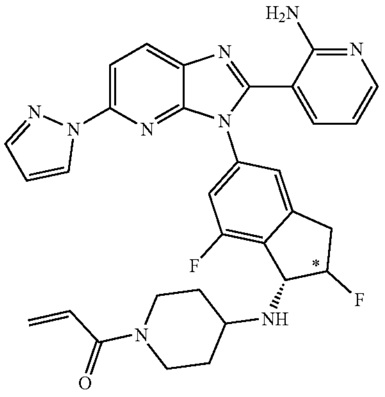

Example 342

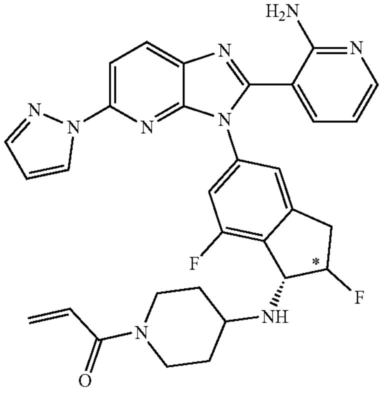

Examples 341 and 342 were prepared in a manner analogous to Examples 75 and 76 using 5-bromo-7-fluoro-2,3-dihydro-1H-inden-1-one as the starting material. The chiral separation was performed after the final step on a CHIRALPAKIF-3 column using a mixture of [Hex/DCM (3:1) (+0.1% DEA)] and ethanol. * Denotes a stereocenter with undetermined absolute stereocenter of a single diastereomer.

Example 341: MS (ESI) calcd. for $C_{31}H_{29}F_2N_9O$, 581.24 m/z, found 582.25 $[M+H]^+$. $^1$H NMR (400 MHz, DMSO-$d_6$) δ 8.38 (dd, J=5.6, 3.1 Hz, 2H), 8.07-8.01 (m, 1H), 7.97 (d, J=8.5 Hz, 1H), 7.82 (s, 1H), 7.33 (s, 3H), 6.81 (s, 3H), 6.57 (s, 1H), 6.49 (dd, J=7.6, 4.9 Hz, 1H), 6.10 (m, 1H), 5.67 (m, 1H), 5.46 (s, 1H), 4.71-4.01 (s, 2H), 3.00 (s, 4H), 2.90 (m, 2H), 2.21 (m, 1H), 1.93 (s, 2H), 1.23 (s, 2H).

Example 342: MS (ESI) calcd. for $C_{31}H_{29}F_2N_9O$, 581.24 m/z, found 582.25 $[M+H]^+$. $^1$H NMR (400 MHz, DMSO-$d_6$) δ 8.40-8.34 (m, 2H), 8.03 (dd, J=4.8, 1.9 Hz, 1H), 7.96 (d, J=8.6 Hz, 1H), 7.82 (d, J=1.6 Hz, 1H), 7.35-7.20 (m, 2H), 6.87 (s, 1H), 6.83 (s, 3H), 6.56 (t, J=2.1 Hz, 1H), 6.48 (dd, J=7.6, 4.8 Hz, 1H), 6.09 (m, 1H), 5.66 (m, 1H), 5.46 (s, 1H), 4.78 (s, 1H), 4.32 (s, 2H), 3.27 (s, 2H), 3.21 (s, 1H), 3.14 (s, 2H), 2.27 (s, 1H), 1.91 (s, 2H), 1.32 (s, 2H).

Example 343: (*)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidin-1-yl)prop-2-en-1-one and Example 344: (*)-1-(4-((5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidin-1-yl)prop-2-en-1-one Example 343

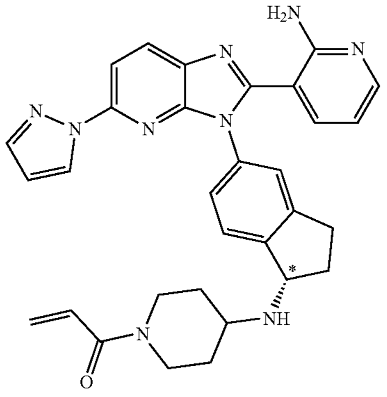

Example 344

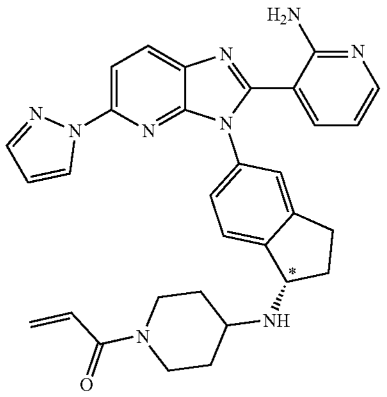

Synthetic Route:

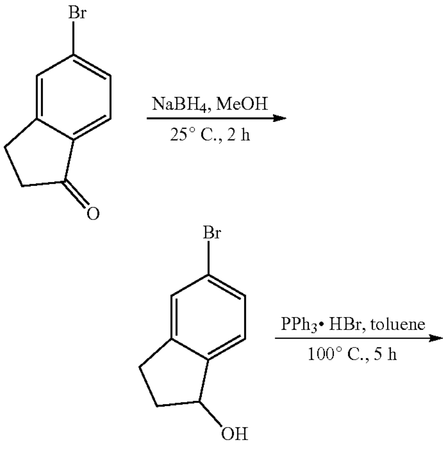

-continued

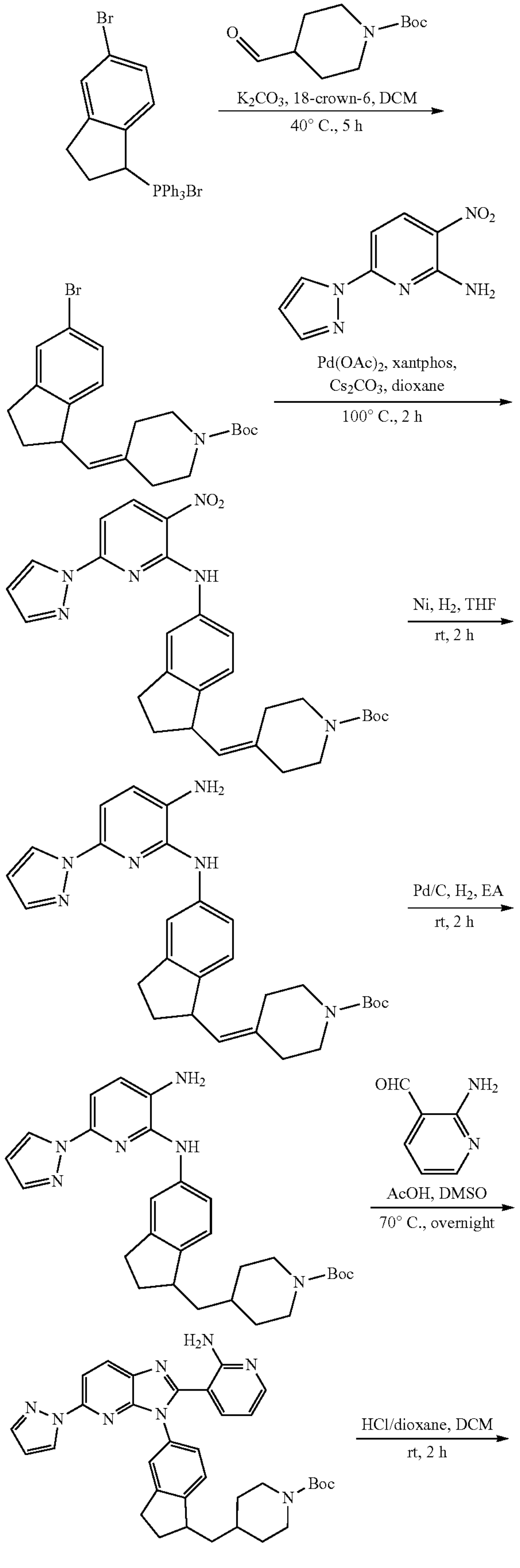

-continued

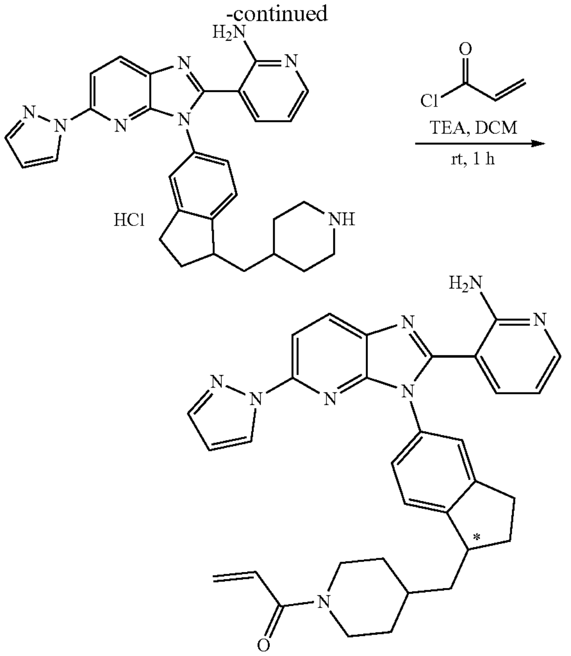

Example 343

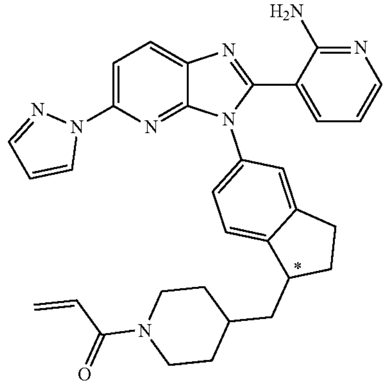

Example 344

Step 1: Synthesis of 5-bromo-2,3-dihydro-1H-inden-1-ol

To a stirred solution of 5-bromo-2,3-dihydroinden-1-one (5 g, 23.690 mmol, 1 equivalents) in MeOH (100 mL) was added $NaBH_4$ (1.79 g, 47.380 mmol, 2 equivalents) at 25° C. The reaction mixture was stirred at 25° C. for 2 h. To this mixture, $Et_2O$ (100 mL) and water (50 mL) were added. After separation of phases, the aqueous phase was extracted with ethyl acetate (100 mL×2). The combined organic layers were washed with brine (30 mL×3), dried over anhydrous $Na_2SO_4$, filtered and concentrated to afford 5-bromo-2,3-dihydro-1H-inden-1-ol (5 g, 99.05% yield) as a white solid. MS (ESI) calculated for $C_9H_9BrO$, 211.98 m/z, found 194.98 $[M+H-OH]^+$.

Step 2: Synthesis of bromo(5-bromo-2,3-dihydro-1H-inden-1-yl)triphenyl-15-phosphane To a stirred solution of 5-bromo-2,3-dihydro-1H-inden-1-ol (2.5 g, 11.733 mmol, 1 equivalents) in toluene (20 mL) was added triphenylphosphine hydrobromide (4.43 g, 12.906 mmol, 1.1 equiv). The reaction mixture was stirred at 100° C. for 5 h under $N_2$. The precipitate was filtered off and dried. The solid was suspended in dry diethyl ether and stirred for 10 min. The phosphonium salt was filtered and washed with diethyl ether to afford bromo(5-bromo-2,3-dihydro-1H-inden-1-yl)triphenyl-15-phosphane (5 g, 79.17% yield) as a yellow solid. MS (ESI) calcd. for $C_{27}H_{23}Br_2P$, 537.99 m/z, found 457.07 [M+H-Br]$^+$.

Step 3: Synthesis of tert-butyl 4-((5-bromo-2,3-dihydro-1H-inden-1-yl)methylene)piperidine-1-carboxylate To a stirred solution of bromo(5-bromo-2,3-dihydro-1H-inden-1-yl)triphenyl-15-phosphane (3.3 g, 6.131 mmol, 1 equiv), tert-butyl 4-formylpiperidine-1-carboxylate (2.62 g, 12.262 mmol, 2 equiv) and 18-crown-6 (243.07 mg, 0.920 mmol, 0.15 equiv) in DCM (27 mL) was added $K_2CO_3$ (8.64 g, 62.536 mmol, 10.2 equiv). The reaction mixture was stirred at 40° C. for 5 h under $N_2$. To this mixture, DCM (50 mL) and water (50 mL) were added. After separation of phases, the aqueous phase was extracted with DCM (50 mL×2). The combined organic layers were washed with brine (30 mL×3), dried over anhydrous $Na_2SO_4$, filtered and concentrated. The residue was then purified by silica gel chromatography (0-100% ethyl acetate/petroleum ether) to afford tert-butyl 4-((5-bromo-2,3-dihydro-1H-inden-1-yl)methylene)piperidine-1-carboxylate (1.2 g, 49.89% yield) as a white solid. MS (ESI) calcd. for $C_{20}H_{26}BrNO_2$, 391.11 m/z, found 336.15 [M+H-tBu]$^+$.

Step 4: Synthesis of tert-butyl 4-((5-(3-nitro-6-(1H-pyrazol-1-yl)pyridin-2-ylamino)-2,3-dihydro-1H-inden-1-yl)methylene)piperidine-1-carboxylate To a stirred solution of tert-butyl 4-((5-bromo-2,3-dihydro-1H-inden-1-yl)methylene)piperidine-1-carboxylate (1 g, 2.549 mmol, 1 equiv), 3-nitro-6-(1H-pyrazol-1-yl)pyridin-2-amine (575.26 mg, 2.804 mmol, 1.1 equiv), Xant-Phos (294.97 mg, 0.510 mmol, 0.2 equiv) and $Pd(OAc)_2$ (114.45 mg, 0.510 mmol, 0.2 equiv) in dioxane (15 mL) was added $Cs_2CO_3$ (2.49 g, 7.647 mmol, 3 equiv). The reaction mixture was stirred at 100° C. for 2 h under $N_2$. To this mixture, ethyl acetate (50 mL) and water (50 mL) were added. After separation of phases, the aqueous phase was extracted with ethyl acetate (50 mL×2). The combined organic layers were washed with brine (30 mL×3), dried over anhydrous $Na_2SO_4$, filtered and concentrated. The residue was then purified by silica gel chromatography (0-100% ethyl acetate/petroleum ether) to afford tert-butyl 4-((5-(3-nitro-6-(1H-pyrazol-1-yl)pyridin-2-ylamino)-2,3-dihydro-1H-inden-1-yl)methylene)piperidine-1-carboxylate (980 mg, 74.43% yield) as a yellow solid. MS (ESI) calcd. for $C_{28}H_{34}N_6O_4$, 516.26 m/z, found 417.15 [M+H-Boc]$^+$.

Step 5: Synthesis of tert-butyl 4-((5-(3-amino-6-(1H-pyrazol-1-yl)pyridin-2-ylamino)-2,3-dihydro-1H-inden-1-yl)methylene)piperidine-1-carboxylate To a stirred solution of tert-butyl 4-((5-(3-nitro-6-(1H-pyrazol-1-yl)pyridin-2-ylamino)-2,3-dihydro-1H-inden-1-yl)methylene)piperidine-1-carboxylate (1.1 g, 2.129 mmol, 1 equiv) in THF (15 mL) was added Raney Nickel (500 mg, 8.519 mmol, 4.00 equiv). The reaction mixture was stirred at room temperature for 2 h under $H_2$. The reaction mixture was filtered and concentrated to afford tert-butyl 4-((5-(3-amino-6-(1H-pyrazol-1-yl)pyridin-2-ylamino)-2,3-dihydro-1H-inden-1-yl)methylene)piperidine-1-carboxylate (930 mg, 89.75% yield) as a yellow solid. MS (ESI) calcd. for $C_{28}H_{34}N_6O_2$, 486.27 m/z, found 487.10 [M+H]$^+$.

Step 6: Synthesis of tert-butyl 4-((5-(3-amino-6-(1H-pyrazol-1-yl)pyridin-2-ylamino)-2,3-dihydro-1H-inden-1-yl)methyl)piperidine-1-carboxylate To a stirred solution of tert-butyl 4-((5-(3-amino-6-(1H-pyrazol-1-yl)pyridin-2-ylamino)-2,3-dihydro-1H-inden-1-yl)methylene)piperidine-1-carboxylate (930 mg, 1.911 mmol, 1 equiv) in ethyl acetate (13 mL) was added Pd/C (500 mg, 4.698 mmol, 2.46 equiv). The reaction mixture was stirred at room temperature for 2 h under $H_2$. The reaction mixture was filtered and concentrated to afford tert-butyl 4-((5-(3-amino-6-(1H-pyrazol-1-yl)pyridin-2-ylamino)-2,3-dihydro-1H-inden-1-yl)methyl)piperidine-1-carboxylate (930 mg, 99.59% yield) as a yellow solid. MS (ESI) calcd. for $C_{28}H_{36}N_6O_2$, 488.29 m/z, found 489.20 [M+H]$^+$.

Step 7: Synthesis of tert-butyl 4-((5-(2-(2-amino-pyridin-3-yl)-5-(1H-pyrazol-1-yl)-3H-imidazo[4,5-b]pyridin-3-yl)-2,3-dihydro-1H-inden-1-yl)methyl) piperidine-1-carboxylate To a stirred solution of tert-butyl 4-((5-(3-amino-6-(1H-pyrazol-1-yl)pyridin-2-ylamino)-2,3-dihydro-1H-inden-1-yl)methyl)piperidine-1-carboxylate (930 mg, 1.903 mmol, 1 equiv) and 2-aminonicotinaldehyde (278.93 mg, 2.284 mmol, 1.2 equiv) in DMSO (16 mL) was added AcOH (4 mL). The reaction mixture was stirred at 70° C. overnight. To this mixture, ethyl acetate (100 mL) and sat. $NH_4HCO_3$ (100 mL) were added. After separation of phases, the aqueous phase was extracted with ethyl acetate (50 mL×2). The combined organic layers were washed with brine (30 mL×3), dried over anhydrous $Na_2SO_4$, filtered and concentrated. The residue was then purified by silica gel chromatography (0-100% ethyl acetate/petroleum ether) to afford tert-butyl 4-((5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidine-1-carboxylate (900 mg, 80.05% yield) as a yellow solid. MS (ESI) calcd. for $C_{34}H_{38}N_8O_2$, 590.31 m/z, found 591.12 [M+H]$^+$.

Step 8: Synthesis of 3-(3-(1-(piperidin-4-ylmethyl)-2,3-dihydro-1H-inden-5-yl)-5-(1H-pyrazol-1-yl)-3H-imidazo[4,5-b]pyridin-2-yl)pyridin-2-amine hydrochloride To a stirred solution of tert-butyl 4-((5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidine-1-carboxylate (900 mg, 1.524 mmol, 1 equiv) in DCM (15 mL) was added HCl (15.00 mL, 60.015 mmol, 39.38 equiv, 4M in dioxane) at room temperature. The mixture was stirred for 2 h at room temperature. The resulting mixture was concentrated to afford 3-(3-(1-(piperidin-4-ylmethyl)-2,3-dihydro-1H-inden-5-yl)-5-(1H-pyrazol-1-yl)-3H-imidazo[4,5-b]pyridin-2-yl)pyridin-2-amine hydrochloride (1.2 g, crude) as a green solid. MS (ESI) calcd. for $C_{29}H_{30}N_8$, 490.26 m/z, found 491.25 [M+H]$^+$.

Step 9: Synthesis of 1-(4-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidin-1-yl)prop-2-en-1-one (Example 343) and 1-(4-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidin-1-yl)prop-2-en-1-one (Example 344)

To a solution of 3-(3-(1-(piperidin-4-ylmethyl)-2,3-dihydro-1H-inden-5-yl)-5-(1H-pyrazol-1-yl)-3H-imidazo[4,5-b]pyridin-2-yl)pyridin-2-amine hydrochloride (750 mg, 1.423 mmol, 1 equiv) and TEA (719.97 mg, 7.115 mmol, 5 equiv) in DCM (10 mL) was added acryloyl chloride (64.40 mg, 0.712 mmol, 0.5 equiv) in DCM (10 mL) at 0° C. The resulting mixture was stirred at room temperature for 1 h. The reaction was quenched by the addition of $H_2O$ (50 mL) at room temperature. The resulting mixture was extracted with DCM (3×50 mL) and the organic layers were combined, then it was concentrated under vacuum. The resulting mixture was purified by reverse-phase flash chromatography on C18 silica gel using a gradient of acetonitrile in water (+0.1% formic acid). The enantiomers were separated by chiral SFC on a CHIRALPAK IH column using a mixture of $CO_2$ and [IPA/DCM (1:1) (+0.1% 7M $NH_3$-MeOH)] to afford 1-(4-{[(*)-5-[2-(2-aminopyridin-3-yl)-5-(pyrazol-1-yl)imidazo[4,5-b]pyridin-3-yl]-2,3-dihydro-1H-inden-1-yl]methyl}piperidin-1-yl)prop-2-en-1-one (Example 343) (99.1 mg, 12.56% yield) as a pink solid. MS (ESI) calcd. for $C_{32}H_{32}N_8O$: 544.27 m/z, found: 545.35 $[M+H]^+$. $^1$H NMR (300 MHz, DMSO-$d_6$) δ (ppm): 8.23-8.49 (m, 2H), 7.88-8.10 (m, 2H), 7.81 (s, 1H), 7.09-7.49 (m, 4H), 6.73-6.87 (m, 1H), 6.47-6.59 (m, 1H), 6.36-6.48 (m, 1H), 6.02-6.16 (m, 1H), 5.60-5.71 (m, 1H), 4.37-4.50 (m, 1H), 4.00-4.11 (m, 1H), 3.19-3.32 (m, 1H), 3.01-3.16 (m, 1H), 2.78-2.82 (m, 2H), 2.60-2.71 (m, 1H), 2.29-2.38 (m, 1H), 1.77-1.89 (m, 5H), 1.31-1.46 (m, 1H), 1.02-1.14 (m, 2H); and 1-(4-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)methyl)piperidin-1-yl)prop-2-en-1-one (Example 343) (103.4 mg, 13.10% purity) as a pink solid. * Denotes a stereocenter with undetermined absolute stereocenter of a single enantiomer. MS (ESI) calcd. for $C_{32}H_{32}N_8O$: 544.27 m/z, found: 545.35 $[M+H]^+$. 1H NMR (300 MHz, DMSO-$d_6$) δ (ppm): 8.22-8.49 (m, 2H), 7.87-8.13 (m, 2H), 7.75-7.87 (m, 1H), 7.15-7.44 (m, 4H), 6.74-6.88 (m, 1H), 6.38-6.61 (m, 2H), 6.01-6.17 (m, 1H), 5.60-6.79 (m, 1H), 4.37-4.50 (m, 1H), 4.00-4.11 (m, 1H), 3.20-3.31 (m, 1H), 3.02-3.14 (m, 1H), 2.79-2.91 (m, 2H), 2.61-2.72 (m, 1H), 2.30-2.42 (m, 1H), 1.84-2.02 (m, 1H), 1.64-1.77 (m, 4H), 1.32-1.45 (m, 1H), 0.94-1.18 (m, 2H).

Example 345: 1-[(1R,5S,6R)-6-({5-[2-(2-aminopyridin-3-yl)-5-(pyrazol-1-yl)imidazo[4,5-b]pyridin-3-yl]-2,3-dihydro-1H-inden-1-yl}amino)-3-azabicyclo[3.1.0]hexan-3-yl]prop-2-en-1-one Example 345

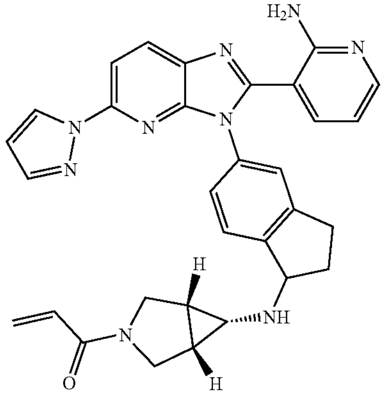

Example 345 was prepared in a manner analogous to Example 34 using Intermediate 77-1 and tert-butyl (1R,5S,6R)-6-amino-3-azabicyclo[3.1.0]hexane-3-carboxylate in MeOH for the reductive amination and prop-2-enoic acid for the final step. MS (ESI) calcd. for $C_{31}H_{29}N_9O$, 543.25 m/z, found 544.20 $[M+H]^+$. $^1$H NMR (300 MHz, DMSO-$d_6$) δ (ppm): 8.33-8.35 (m, 2H), 8.17-8.18 (m, 1H), 7.95-7.98 (m, 1H), 7.93-7.94 (m, 1H), 7.79-7.80 (m, 1H), 7.45-7.47 (m, 1H), 7.33-7.34 (m, 1H), 7.20-7.22 (m, 2H), 6.53-6.54 (m, 1H), 6.45-6.50 (m, 1H), 6.36-6.39 (m, 1H), 6.07-6.11 (m, 1H), 5.63-5.65 (m, 1H), 4.25-4.28 (m, 1H), 3.69-3.72 (m, 1H), 3.35-3.38 (m, 1H), 2.94-2.96 (m, 1H), 2.75-2.79 (m, 1H), 2.33-2.39 (m, 2H), 1.90-1.95 (m, 1H), 1.85-1.90 (m, 1H), 1.54-1.56 (m, 3H).

Example 346: 1-((1R,5S,6s)-6-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-azabicyclo[3.1.0]hexan-3-yl)prop-2-en-1-one and Example 347: 1-((1R,5S,6s)-6-(((*)-5-(2-(2-aminopyridin-3-yl)-5-(1H-pyrazol-1-yl)-3H-imidazo[4,5-b]pyridin-3-yl)-2,3-dihydro-1H-inden-1-yl)amino)-3-azabicyclo[3.1.0]hexan-3-yl)prop-2-en-1-one Example 346

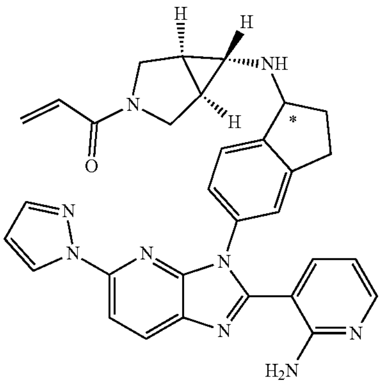

-continued

Example 347

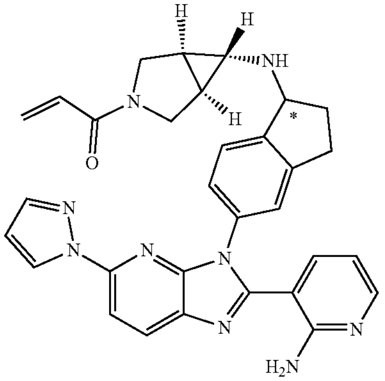

Examples 346 and 347 were prepared in a manner analogous to Example 34 using Intermediate 77-1 and tert-butyl (1R,5S,6S)-6-amino-3-azabicyclo[3.1.0]hexane-3-carboxylate for step 1 and acrylic acid for step 3. The diastereomers were separated by chiral Prep HPLC on a CHIRALPAK AD column using a mixture of [Hexanes (+0.5% 2M $NH_3$-MeOH)] and ethanol. * Denotes a stereocenter with undetermined absolute stereocenter of a single diastereomer.

Example 346: MS (ESI) calcd. for $C_{31}H_{29}N_9O$, 543.25 m/z, found 544.40 $[M+H]^+$. $^1H$ NMR (400 MHz, DMSO-$d_6$) δ (ppm): 8.31-8.35 (m, 2H), 7.92-8.00 (m, 2H), 7.79 (s, 1H), 7.17-7.35 (m, 4H), 6.39-6.54 (m, 1H), 6.05-6.10 (m, 1H), 5.57-5.62 (m, 1H), 4.14-4.19 (m, 1H), 3.73-3.76 (m, 1H), 3.55-3.58 (m, 1H), 3.28-3.48 (m, 2H), 2.88-2.92 (m, 1H), 2.74-2.79 (m, 1H), 2.33-2.42 (m, 2H), 1.66-1.84 (m, 3H).

Example 347: MS (ESI) calcd. for $C_{31}H_{29}N_9O$, 543.25 m/z, found 544.35 $[M+H]^+$. $^1H$ NMR (400 MHz, DMSO-$d_6$) δ (ppm): 8.31-8.35 (m, 2H), 7.98-8.00 (m, 1H), 7.92-7.95 (m, 1H), 7.79 (s, 1H), 7.16-7.35 (m, 4H), 6.53-6.54 (m, 1H), 6.42-6.49 (m, 2H), 6.04-6.10 (m, 1H), 5.55-5.62 (m, 1H), 4.13-4.21 (m, 1H), 3.74-3.78 (m, 1H), 3.55-3.58 (m, 1H), 3.28-3.49 (m, 2H), 2.88-2.93 (m, 1H), 2.73-2.78 (m, 1H), 2.33-2.43 (m, 2H), 1.65-1.84 (m, 3H).

Example 348: AKT1 Inhibition Data

Antiproliferative Effects in LAPC4 Cells.

LAPC4 prostate cancer cells (Klein, K. A. et al. Nat Med 1997, 3, 402-408), which express the AKT1 E17K allele, were grown in IMDM media (Hyclone) supplemented with 12% FBS+1% P/S. To assess compound effects on growth, 1,000 cells/well were seeded in 384 well assay plates, incubated with compound dilutions dissolved in DMSO. After 72 h, intracellular ATP content was assessed with CellTiter Glo reagent (Promega) according to the manufacturer's instructions. $IC_{50}$ values were calculated by fitting luminescence values to a log(inhibitor) vs. response Hill equation.

Determining Live Cell AKT1 E17K, AKT1 WT, and AKT2 Target Engagement by NanoBRET Competitive Probe Displacement.

Live cell target engagement assays were performed as described (Vasta, J. D. et al. Cell Chem Biol 2018, 25(11), 206-214). Briefly, HEK293 cells were transfected with plasmids encoding kinase-NanoLuciferase fusion proteins overnight. Cells were then treated with serial dilutions of compound and an ~$EC_{50}$ concentration of fluorescently-tagged ATP-competitive tracer (Promega). After incubation for 2 h at 37° C., luciferase substrate and extracellular luciferase inhibitor were added to all wells, and luminescent intensity at 460 nm and 600 nm were measured on a multimode plate-reader. The ratio of $E_{600}/E_{460}$ was calculated to give the tracer engagement signal (BRET). $IC_{50}$ values were calculated by fitting BRET values to a log(inhibitor) vs. response Hill equation.

The results of these assay studies are provided in Table 2.

TABLE 2

$IC_{50}$ values for selected compounds of the present disclosure.

| Compound No. | AKT1 E17K $IC_{50}$ (nM) | AKT2 $IC_{50}$ (nM) | AKT1 WT $IC_{50}$ (nM) | LAPC4 proliferation $IC_{50}$ (nM) |
|---|---|---|---|---|
| 1 | 12.2 | 35 | 11.7 | 25.4 |
| 2 | 22.7 | 117 | 18.7 | 189 |
| 3 | 32.8 | 70 | 15.1 | 833 |
| 4 | 823 | 3750 | 212 | 4210 |
| 5 | 46.2 | 271 | 19.4 | 310 |
| 6 | 20.1 | 22 | 11.9 | 144 |
| 7 | 42.8 | 69.4 | 20.7 | 2060 |
| 8 | 112 | 71.5 | 7.07 | 1120 |
| 9 | 96.9 | 440 | 21.9 | 528 |
| 10 | >1.00E+03 | 1470 | 121 | 1860 |
| 11 | 7.03 | 25.9 | 4.29 | 650 |
| 12 | 12.9 | 129 | 11.2 | 343 |
| 13 | 56.1 | 224 | 17 | 144 |
| 14 | 436 | 1420 | 85.3 | 1160 |
| 15 | 78.7 | 377 | 34.3 | 366 |
| 16 | 52.7 | 67.8 | 11.3 | 183 |
| 17 | 146 | 1020 | 43 | 2330 |
| 18 | 243 | 208 | 61.5 | 1570 |
| 19 | 27 | 326 | 15.8 | 88 |
| 20 | 9.64 | 20.2 | 7.5 | 18.3 |
| 21 | 32.8 | 74.8 | 22.6 | 88.5 |
| 23 | 135 | 2250 | 50.1 | 426 |
| 24 | 14.1 | 37.9 | 12 | 238 |
| 25 | >1.00E+03 | >10.0E+03 | >1.00E+03 | >10.0E+03 |
| 26 | >1.00E+03 | >10.0E+03 | >1.00E+03 | 2050 |
| 27 | 107 | 192 | 39.4 | 425 |
| 28 | 81.6 | 250 | 50.1 | 216 |
| 29 | 81.6 | 250 | 50.1 | 216 |
| 30 | >1.00E+03 | 4830 | 296 | 2600 |
| 31 | 12.6 | 57.9 | 12.9 | 30.8 |
| 32 | 10.1 | 41.6 | 13.1 | 14.1 |
| 33 | 20.7 | 152 | 21.2 | 52 |
| 34 | 194 | 1200 | 55.1 | 398 |
| 35 | >1.00E+03 | 2940 | 243 | 5660 |
| 36 | 179 | 982 | 64.5 | 533 |
| 37 | 246 | 738 | 93 | 581 |
| 38 | 881 | 2090 | 204 | >10.0E+03 |
| 39 | 94.9 | 94.8 | 64.2 | 1600 |
| 40 | 94 | 265 | 48.1 | 948 |
| 41 | >1.00E+03 | 5060 | 305 | 9840 |
| 42 | 897 | 252 | 289 | 3650 |
| 43 | >1.00E+03 | >10.0E+03 | 317 | >10.0E+03 |
| 44 | 49 | 103 | 34.5 | 122 |
| 45 | 68.4 | 717 | 43 | 296 |
| 46 | | >10.0E+03 | 726 | |
| 47 | 548 | 2570 | 200 | 4270 |
| 48 | 799 | 1280 | 111 | 1400 |
| 49 | 146 | 980 | 50.9 | 406 |
| 50 | 95.1 | 348 | 17.6 | 161 |
| 51 | 727 | 5560 | 115 | 1460 |
| 52 | 949 | 3480 | 174 | 911 |
| 53 | >1.00E+03 | 3940 | 407 | 2850 |
| 54 | 58.5 | 292 | 27.1 | 107 |
| 55 | 215 | 1120 | 93.7 | 617 |
| 56 | 23.9 | 104 | 6.71 | 144 |
| 57 | 21.9 | 84.6 | 10.4 | 104 |
| 58 | 189 | 1030 | 50.2 | 438 |
| 59 | 242 | 648 | 44.8 | 377 |
| 60 | 406 | 1680 | >1.00E+03 | 1380 |
| 61 | 28.6 | 52.4 | 19 | 72.4 |
| 62 | 8.39 | 31.7 | 9.35 | 17.1 |
| 63 | 47.5 | 248 | 24.1 | 124 |
| 64 | 53.3 | 158 | 20 | 145 |
| 65 | 58.3 | 397 | 29.6 | 203 |

TABLE 2-continued

IC$_{50}$ values for selected compounds of the present disclosure.

| Compound No. | AKT1 E17K IC$_{50}$ (nM) | AKT2 IC$_{50}$ (nM) | AKT1 WT IC$_{50}$ (nM) | LAPC4 proliferation IC$_{50}$ (nM) |
|---|---|---|---|---|
| 66 | 29.6 | 51.5 | 12.1 | 68 |
| 67 | 87.9 | 107 | 21.8 | 287 |
| 68 | 21.9 | 74.2 | 9.84 | 75.6 |
| 69 | 57.7 | 226 | 25.3 | 358 |
| 70 | 288 | 1340 | 83.7 | 1040 |
| 71 | 9.43 | 31.8 | 11.5 | 29.8 |
| 72 | 75.2 | 289 | 15.8 | 493 |
| 73 | 19 | 86.3 | 16 | 74.4 |
| 74 | >1.00E+03 | 2940 | 179 | 1630 |
| 75 | 35.9 | 511 | 20 | 287 |
| 76 | 60.1 | 232 | 23.3 | 369 |
| 77 | 86.3 | 346 | 17.9 | 247 |
| 78 | 63 | 136 | 22 | 212 |
| 79 | 14.2 | 27.1 | 11.9 | 16.8 |
| 80 | 41.7 | 166 | 15.7 | 120 |
| 81 | >1.00E+03 | 1200 | 93.2 | 7600 |
| 82 | 247 | 640 | 78.1 | 568 |
| 83 | 192 | 583 | 56.2 | 506 |
| 84 | 264 | 278 | 34.1 | 327 |
| 85 | 546 | 865 | 46 | 1390 |
| 86 | 153 | 584 | 13.7 | 180 |
| 87 | 165 | 577 | 25.5 | 364 |
| 88 | 48.7 | 180 | 21.5 | 87.7 |
| 89 | 22.9 | 75.2 | 8.15 | 74.9 |
| 90 | 156 | 109 | 41.2 | 351 |
| 91 | 116 | 558 | 36.6 | 351 |
| 92 | 18.9 | 58.8 | 6.94 | 30.7 |
| 93 | 6.16 | 11.4 | 5.63 | 5.02 |
| 94 | 652 | 2640 | 147 | 1170 |
| 95 | 312 | 1190 | 110 | 677 |
| 96 | >1.00E+03 | 3910 | 58 | 3650 |
| 97 | 419 | 1300 | 39.6 | 2600 |
| 98 | 549 | 862 | 39.3 | 1650 |
| 99 | 89.4 | 560 | 33.4 | 716 |
| 100 | 53.6 | 135 | 9.09 | 187 |
| 101 | 82.3 | 290 | 18.3 | 270 |
| 102 | 35.4 | 101 | 8.09 | 147 |
| 103 | 80.1 | 547 | 19.3 | 317 |
| 104 | 20.6 | 92.7 | 4.52 | 120 |
| 105 | 14.8 | 50.1 | 4.51 | 53 |
| 106 | 20.3 | 120 | 3.85 | 93 |
| 107 | 18.1 | 192 | 6.19 | 164 |
| 108 | 42.4 | 165 | 10.2 | 94.3 |
| 109 | 124 | 454 | 24.9 | 3160 |
| 110 | 141 | 628 | 21.8 | 298 |
| 111 | 127 | 143 | 21.6 | 343 |
| 112 | 8.06 | 17.6 | 9.52 | 11.8 |
| 113 | 8.87 | 50.9 | 7.33 | 25.3 |
| 114 | 8.34 | 21.9 | 8.56 | 12.5 |
| 115 | 9.26 | 40.4 | 8.19 | 40.7 |
| 116 | 339 | 942 | 32.1 | 422 |
| 117 | 482 | 780 | 41.6 | 557 |
| 118 | 42 | 320 | 21.3 | 167 |
| 119 | 582 | 3590 | 85.6 | 595 |
| 120 | 185 | 885 | 23.6 | 814 |
| 121 | 174 | 358 | 43.3 | 248 |
| 122 | 112 | 305 | 41.3 | 116 |
| 123 | 42.4 | 393 | 30.9 | 736 |
| 124 | 99.2 | 1120 | 54.1 | 4860 |
| 125 | 914 | 3280 | 292 | 2110 |
| 126 | 671 | 8570 | >1.00E+03 | 5050 |
| 127 | 8.17 | 36.9 | 9.06 | 37.1 |
| 128 | 8.62 | 43 | 10.6 | 44.8 |
| 129 | >1.00E+03 | 2720 | 115 | >10.0E+03 |
| 130 | 76.4 | 672 | 26.5 | 174 |
| 131 | >1.00E+03 | 9530 | >1.00E+03 | 1840 |
| 132 | 326 | 2250 | 97.5 | 1510 |
| 133 | 13.4 | 47 | 9.71 | 16.3 |
| 134 | 232 | 2710 | 72.4 | 1150 |
| 135 | 152 | 478 | 22.2 | 302 |
| 136 | 211 | 1950 | 95.8 | 520 |
| 137 | 71.6 | 244 | 14.2 | 161 |
| 138 | 744 | 1810 | 289 | 963 |
| 139 | 29.7 | 114 | 13.5 | 41.9 |
| 140 | >1.00E+03 | 3580 | 370 | 1490 |
| 141 | 554 | 872 | 148 | 1700 |
| 142 | >1.00E+03 | >10.0E+03 | >1.00E+03 | 3460 |
| 143 | 353 | 1260 | 60.2 | 499 |
| 144 | 74.1 | 1180 | 26 | 293 |
| 145 | 187 | 1030 | 29.7 | 436 |
| 146 | 78.4 | 1580 | 22.9 | 448 |
| 147 | 151 | 903 | 32 | 398 |
| 148 | 38 | 61 | 12.5 | 93.3 |
| 149 | 60.8 | 189 | 23.5 | 109 |
| 150 | 213 | 781 | 31.1 | 478 |
| 151 | >1.00E+03 | >10.0E+03 | >1.00E+03 | >10.0E+03 |
| 152 | >1.00E+03 | >10.0E+03 | >1.00E+03 | >10.0E+03 |
| 153 | 168 | 1080 | 26.9 | 362 |
| 154 | >1.00E+03 | >10.0E+03 | 301 | >10.0E+03 |
| 155 | >1.00E+03 | 1230 | 83.6 | 490 |
| 156 | 11.3 | 64.7 | 9.8 | 30.2 |
| 157 | 54.5 | 216 | 17.2 | 110 |
| 158 | 358 | 1870 | 72.6 | 1090 |
| 159 | 56.2 | 146 | 20 | 71.2 |
| 160 | 26.9 | 29.6 | 9.31 | 27.4 |
| 161 | 110 | 198 | 18.3 | 100 |
| 162 | 645 | 5880 | 102 | 1600 |
| 163 | 642 | 1910 | 71.7 | 879 |
| 164 | 475 | 4100 | 58 | 489 |
| 165 | 143 | 163 | 39.3 | 187 |
| 166 | 74 | 257 | 21.9 | 116 |
| 167 | 37.1 | 151 | 823 | 479 |
| 168 | 32.6 | 369 | 571 | 858 |
| 169 | 53.7 | 115 | 593 | 565 |
| 170 | 12.5 | 61 | 114 | 160 |
| 171 | >1.00E+03 | >1.00E+03 | >10.0E+03 | 6610 |
| 172 | 50.9 | 211 | 5000 | 510 |
| 173 | 56.5 | 324 | 1340 | 748 |
| 174 | 8.46 | 12.7 | 65.5 | 89 |
| 175 | 17.9 | 123 | 820 | 271 |
| 176 | 37.8 | 484 | 967 | 433 |
| 177 | 36.9 | 114 | 1520 | 416 |
| 178 | 18.1 | 26.7 | 33.2 | 71 |
| 179 | 203 | >1.00E+03 | 2890 | 3520 |
| 180 | 18.6 | 160 | 244 | 625 |
| 181 | 58.7 | 513 | 1140 | 941 |
| 182 | 152 | >1.00E+03 | >10.0E+03 | 3160 |
| 183 | 99.4 | 633 | 1260 | 1600 |
| 184 | 17.8 | 27.2 | 104 | 184 |
| 185 | 53.2 | 912 | 2170 | 4130 |
| 186 | 30.6 | 954 | 877 | 801 |
| 187 | 7.3 | 28.7 | 46.4 | 64.4 |
| 188 | 5.65 | 8.14 | 35 | 56.3 |
| 189 | 60.9 | 740 | 1470 | 1370 |
| 190 | 99.4 | >1.00E+03 | 735 | 1320 |
| 191 | 221 | >1.00E+03 | 1250 | 3370 |
| 192 | >1.00E+03 | >1.00E+03 | >10.0E+03 | >10.0E+03 |
| 193 | 10.2 | 12.9 | 71.5 | 58.4 |
| 194 | 13.8 | 142 | 446 | 310 |
| 195 | 7.45 | 80.8 | 415 | 319 |
| 196 | 96.6 | >1.00E+03 | 1990 | 1210 |
| 197 | 18.9 | 28.6 | 121 | 469 |
| 198 | 16 | 27 | 835 | 461 |
| 199 | 67.4 | 802 | 603 | 2380 |
| 200 | 15.9 | 80.1 | 281 | 317 |
| 201 | 10.2 | 41 | 96.8 | 127 |
| 202 | 111 | >1.00E+03 | 5950 | 3090 |
| 203 | 32.2 | 874 | 6630 | 1760 |
| 204 | 287 | >1.00E+03 | 5790 | 3820 |
| 205 | 112 | 835 | 1740 | 1190 |
| 206 | 7.65 | 24.8 | 80.5 | 62.7 |
| 207 | 7.07 | 35.2 | 48.8 | 114 |
| 208 | 5.74 | 26.1 | 77.8 | 69.8 |
| 209 | 2.29 | 7.12 | 3.78 | 17 |
| 210 | 16.8 | 272 | 919 | 380 |
| 211 | 23.7 | 79.8 | 1100 | 319 |
| 212 | 6.9 | 12.7 | 36.1 | 36.6 |
| 213 | 4.87 | 11.8 | 13.8 | 9.69 |

TABLE 2-continued

IC$_{50}$ values for selected compounds of the present disclosure.

| Compound No. | AKT1 E17K IC$_{50}$ (nM) | AKT2 IC$_{50}$ (nM) | AKT1 WT IC$_{50}$ (nM) | LAPC4 proliferation IC$_{50}$ (nM) |
|---|---|---|---|---|
| 214 | 4.72 | 7.48 | 36.5 | 26.7 |
| 215 | 4.56 | 11.4 | 17 | 42.3 |
| 216 | 140 | 352 | 2350 | 3960 |
| 217 | 321 | >1.00E+03 | 1870 | 3470 |
| 218 | 52.3 | 140 | 365 | 226 |
| 219 | 45.8 | 95.7 | 279 | 77.1 |
| 220 | 380 | >1.00E+03 | >10.0E+03 | >10.0E+03 |
| 221 | 567 | >1.00E+03 | >10.0E+03 | >10.0E+03 |
| 222 | >1.00E+03 | >1.00E+03 | >10.0E+03 | >10.0E+03 |
| 223 | >1.00E+03 | >1.00E+03 | >10.0E+03 | >10.0E+03 |
| 224 | 70.6 | 256 | 1240 | 719 |
| 225 | 31.8 | 239 | 308 | 394 |
| 226 | 22.5 | 68.9 | 105 | 276 |
| 227 | 39 | 283 | 703 | 540 |
| 228 | 16.7 | 69.9 | 215 | 161 |
| 229 | 21.9 | 97.7 | 756 | 334 |
| 230 | 41.9 | 346 | 890 | 600 |
| 231 | 74.8 | 174 | 1220 | 398 |
| 232 | 20.8 | 168 | 1080 | 651 |
| 233 | 14.6 | 28 | 59.7 | 70 |
| 234 | 12.1 | 70.4 | 317 | 330 |
| 235 | 12.6 | 14.3 | 51.5 | 65.8 |
| 236 | 12.4 | 87.2 | 778 | 300 |
| 237 | 17.7 | 89.5 | 542 | 362 |
| 238 | 37.2 | 666 | 679 | 667 |
| 239 | 43.2 | 334 | 1450 | 1030 |
| 240 | 42.6 | 309 | 2540 | 1040 |
| 241 | 5.56 | 18.8 | 205 | 77.3 |
| 242 | 30.4 | >1.00E+03 | 1430 | 756 |
| 243 | 17.3 | 98.5 | 217 | 150 |
| 244 | 20.1 | 199 | 984 | 371 |
| 245 | 37.6 | 354 | 715 | 526 |
| 246 | 65.6 | 711 | 2510 | 1600 |
| 247 | 113 | 469 | 3120 | 1680 |
| 248 | >1.00E+03 | >1.00E+03 | >10.0E+03 | >10.0E+03 |
| 249 | 12.6 | 143 | 3890 | 614 |
| 250 | 14.7 | 134 | 5850 | 559 |
| 251 | 113 | 280 | 2160 | 2230 |
| 252 | 10.4 | 38.5 | 127 | 90 |
| 253 | 14.5 | 58.8 | 318 | 127 |
| 254 | 10.9 | 36.8 | 89.7 | 93.3 |
| 255 | 33.2 | 177 | 547 | 214 |
| 256 | 186 | 394 | 1690 | 809 |
| 257 | 13.8 | 73 | 432 | 103 |
| 258 | 94.7 | 915 | 1320 | 526 |
| 259 | 150 | 968 | 3290 | 1520 |
| 260 | >1.00E+03 | >1.00E+03 | >10.0E+03 | >10.0E+03 |
| 261 | 43.3 | 136 | 555 | 227 |
| 262 | 29.6 | 45.9 | 650 | 83.7 |
| 263 | 39.8 | 153 | 2940 | 680 |
| 264 | 27.8 | 171 | 937 | 1330 |
| 265 | 10.2 | 24.6 | 89.6 | 101 |
| 266 | 3.34 | 4.07 | 5.31 | 4.4 |
| 267 | 5.9 | 53.6 | 86.4 | 335 |
| 268 | 14.8 | 55.9 | 297 | 358 |
| 269 | 247 | >1.00E+03 | 2120 | 5390 |
| 270 | 7.21 | 21 | 162 | 76.3 |
| 271 | 21.7 | 248 | 928 | 674 |
| 272 | 23.6 | 92.1 | 1240 | 351 |
| 273 | 11.5 | 27.9 | 157 | 134 |
| 274 | 18.8 | 94.4 | 696 | 323 |
| 275 | 84 | 81.9 | 2620 | 326 |
| 276 | 30.7 | 106 | 1350 | 378 |
| 277 | 23.3 | 54.6 | 821 | 138 |
| 278 | 164 | >1.00E+03 | >10.0E+03 | 1850 |
| 279 | 168 | >1.00E+03 | 5280 | 1570 |
| 280 | 20.3 | 82.1 | 127 | 104 |
| 281 | 15.4 | 80.8 | 254 | 253 |
| 282 | 15.2 | 86 | 1590 | 464 |
| 283 | 9.03 | 42 | 133 | 835 |
| 284 | 273 | >1.00E+03 | 6430 | 7210 |
| 285 | 604 | >1.00E+03 | >10.0E+03 | 1550 |
| 286 | 10.7 | 36.3 | 273 | 124 |
| 287 | 7.68 | 41.8 | 227 | 110 |

TABLE 2-continued

IC$_{50}$ values for selected compounds of the present disclosure.

| Compound No. | AKT1 E17K IC$_{50}$ (nM) | AKT2 IC$_{50}$ (nM) | AKT1 WT IC$_{50}$ (nM) | LAPC4 proliferation IC$_{50}$ (nM) |
|---|---|---|---|---|
| 288 | 38 | 212 | 2090 | 1530 |
| 289 | 19.6 | 145 | 799 | 682 |
| 290 | 19.4 | 122 | 666 | 455 |
| 291 | 68.3 | 358 | 1580 | 1110 |
| 292 | 6.85 | 9.7 | 44.9 | 134 |
| 293 | 29.1 | 86.4 | 282 | 440 |
| 294 | 28.6 | 56.7 | 301 | 217 |
| 295 | 9.37 | 10.9 | 23.5 | 17.9 |
| 296 | 33.2 | 36.6 | 93.4 | 59.1 |
| 297 | 23.8 | 108 | 588 | 509 |
| 298 | 14.2 | 57.3 | 294 | 314 |
| 299 | 9.32 | 61 | 1180 | 603 |
| 300 | 9.07 | 34.9 | 2330 | 389 |
| 301 | 8.86 | 15.1 | 105 | 172 |
| 302 | 16.9 | 33.3 | 82.1 | 129 |
| 303 | 10.9 | 14.5 | 22.1 | 15.1 |
| 304 | 11.6 | 36.2 | 264 | 641 |
| 305 | 63.4 | >1.00E+03 | >10.0E+03 | 2740 |
| 306 | 15.7 | 72.3 | 186 | 203 |
| 307 | 12.3 | 106 | 294 | 345 |
| 308 | 11.8 | 62.3 | 307 | 300 |
| 309 | 8.12 | 22.4 | 146 | 110 |
| 310 | 34.5 | 277 | 1480 | 553 |
| 311 | 34.9 | 246 | 1190 | 496 |
| 312 | 11.6 | 102 | 652 | 440 |
| 313 | 21.8 | 113 | 518 | 347 |
| 314 | 7.44 | 23.8 | 95.1 | 54.9 |
| 315 | 14.3 | 70.3 | 183 | 120 |
| 316 | 19.2 | 112 | 8920 | 540 |
| 317 | 20.3 | 68.4 | 2590 | 464 |
| 318 | 29.7 | 111 | 6880 | 626 |
| 319 | 49.6 | 301 | 7040 | 1600 |
| 320 | 11.8 | 45.5 | 290 | 78.2 |
| 321 | 7.19 | 24.2 | 158 | 80.7 |
| 322 | 5.51 | 41.4 | 247 | 137 |
| 323 | 6.22 | 45.3 | 263 | |
| 324 | 16.3 | 88.1 | 396 | |
| 325 | 7.92 | 101 | 298 | |
| 326 | 7.25 | 29.3 | 98.8 | |
| 327 | 25.2 | 99.4 | 204 | |
| 328 | 17.7 | 90.3 | 4720 | |
| 329 | 5.37 | 17.9 | 156 | |
| 330 | 31 | 69.3 | 1480 | |
| 331 | 18.1 | 128 | 807 | |
| 332 | 27.9 | 481 | 8080 | |
| 333 | 4.33 | 9.57 | 28.5 | |
| 334 | 6.75 | 23.5 | 137 | |
| 335 | 9.48 | 28.3 | 288 | |
| 336 | 16.4 | 25.4 | 523 | |
| 337 | 6.33 | 29.4 | 30.3 | 99.5 |
| 338 | 12.3 | 13.7 | 108 | |
| 339 | 32.7 | 78.8 | 331 | |
| 340 | | | | |
| 341 | 80.3 | >1.00E+03 | >10.0E+03 | |
| 342 | 23.9 | 194 | 3800 | |
| 343 | 6.65 | 15.9 | 86.1 | |
| 344 | 21.4 | 549 | 418 | |
| 345 | 34 | 63.5 | 268 | |
| 346 | 444 | >1.00E+03 | 2770 | |
| 347 | 234 | >1.00E+03 | 2210 | |
| 349 | 32 | 432 | 1640 | 1160 |
| 350 | 72.7 | 416 | 2510 | 1090 |
| 348 | 32 | 362 | 2670 | 872 |

Example 349: Crystallography Studies Showing Covalent Complex Formation

Protein Expression and Purification

Akt1(DrLink)-WT Sequence No. 1:
(SEQ ID NO: 1)

MSHHHHHHHHGSENLYFQSDVAIVKEGWLHKRGEYIKTWRPRYFLLKND

GTFIGYKERPQDVDQREAPLNNFSVAQCQLMKTERPRPNTFIIRCLQWT

TVIERTFHVETPEEREEWTTAIQTVADGLKKQEEEEMDASAEHTDMEVS

LAKPKHRVTMNEFEYLKLLGKGTFGKVILVKEKATGRYYAMKILKKEVI

VAKDEVAHTLTENRVLQNSRHPFLTALKYSFQTHDRLCFVMEYANGGEL

FFHLSRERVFSEDRARFYGAEIVSALDYLHSEKNVVYRDLKLENLMLDK

DGHIKITDFGLCKEGIKDGATMKTFCGTPEYLAPEVLEDNDYGRAVDWW

GLGVVMYEMMCGRLPFYNQDHEKLFELILMEEIRFPRTLGPEAKSLLSG

LLKKDPKQRLGGGSEDAKEIMQHRFFAGIVWQHVYEKKLSPPFKPQVTS

ETDTRYFDEEFTAQM

Akt1(DrLink)-E17K Sequence No. 2:
(SEQ ID NO: 2)

MSHHHHHHHHGSENLYFQSDVAIVKEGWLHKRGKYIKTWRPRYFLLKND

GTFIGYKERPQDVDQREAPLNNFSVAQCQLMKTERPRPNTFIIRCLQWT

TVIERTFHVETPEEREEWTTAIQTVADGLKKQEEEEMDASAEHTDMEVS

LAKPKHRVTMNEFEYLKLLGKGTFGKVILVKEKATGRYYAMKILKKEVI

VAKDEVAHTLTENRVLQNSRHPFLTALKYSFQTHDRLCFVMEYANGGEL

FFHLSRERVFSEDRARFYGAEIVSALDYLHSEKNVVYRDLKLENLMLDK

DGHIKITDFGLCKEGIKDGATMKTFCGTPEYLAPEVLEDNDYGRAVDWW

GLGVVMYEMMCGRLPFYNQDHEKLFELILMEEIRFPRTLGPEAKSLLSG

LLKKDPKQRLGGGSEDAKEIMQHRFFAGIVWQHVYEKKLSPPFKPQVTS

ETDTRYFDEEFTAQM

Akt1(DrLink)-WT/E17K Baculovirus Preparation

Akt1(DrLink)-WT/E17K were gene synthesized and cloned by Gibson assembly into the pFastBac vector. The plasmid was transformed into DH10Bac cells and the recombinant bacmid was isolated and used to generate baculovirus in Sf9 cells.

Expression and Purification of Akt1(DrLink)-WT/E17K

Expression of Akt1(DrLink)-WT/E17K was induced in Sf9 cells by infection of 3.0 L of cultured cells (1.5 M/mL) with 30 mL of baculovirus solution and incubated for 72 h. The cells were harvested (4000 rpm, 10 min) and the pellets were frozen down into 1.5 L cell pellets. One 1.5 L cell pellet was thawed and resuspended in 100 mL lysis buffer (25 mM Hepes, pH 8.0, 150 mM NaCl, 1.0 mM DTT) supplemented with protease inhibitor cocktail (Roche). The cells were lysed by sonication and the cell debris pelleted by centrifugation (12000 rpm, 30 min). The clarified lysate was incubated with Ni-NTA (2.0 mL) for at least one hour at 4° C. and the resin was washed with 5 mL wash buffer (10 mM imidazole, 25 mM Hepes, pH 8.0, 150 mM NaCl, 1.0 mM DTT). Akt1 was eluted in 6 mL of elution buffer (300 mM imidazole, 25 mM Hepes, pH 8.0, 150 mM NaCl, 1.0 mM DTT). The eluted protein was diluted 50 mL in lysis buffer (25 mM Hepes, pH 8.0, 150 mM NaCl, 1.0 mM DTT) and 1.29 mg TEV protease was added and then rotated overnight at 4° C. After overnight, LCMS showed complete TEV cleavage. The resulting protein was purified further by gel filtration on a Superdex 200 (10/300 GL) column (gel filtration buffer: 25 mM HEPES pH 8.0, 150 mM NaCl, 1 mM DTT) through two injections. The protein was then concentrated to 7.67 mg/mL, flash-frozen in liquid nitrogen and stored at −80° C. The final yield was ~1.3 mg Akt1 (DrLink)-WT.

NB41 Sequence No. 3:
(SEQ ID NO: 3)

QVQLQESGGGLVQAGGSLRLSCAASGIDVRIKTMAWYRQAPGKQRELLA

SVLVSGSTNYADPVKGRFTISRDNAKNTVYLQMNKLIPDDTAVYYCNTY

GRLRRDVWGPGTQVTVSSHHHHHHEPEA

NB41 Construct

NB41 was gene synthesized and cloned by Gibson assembly into a PET26b vector containing an N-terminal PelB signal sequence.

NB41 Expression and Purification

Rosetta 2(DE3)pLysS cells were transformed with the NB41 PET26b plasmid. The transformed bacteria were grown in 3 L LB+kanamycin+chloramphenicol at 37° C. until it reached OD600=0.6-0.8. The culture was cooled to 18° C., induced with 0.25 mM IPTG and expressed overnight at 18° C. The bacteria were harvested (5000 rpm, 10 min) and the resulting pellets were frozen into 3 tubes (1 L pellet each).

The 1 L pellet was warmed to 4° C. and lysed in 15 mL TS buffer (TS buffer=200 mM Tris pH 8.0, 500 mM sucrose) supplemented with protease inhibitor cocktail (Roche) with rotation. After 1 h, 30 mL of TS/4 buffer was added (TS/4 buffer=50 mM Tris, 125 mM Sucrose). After a further 45 min rotation at 4° C., the sample was centrifuged for 30 min at 7500 g at 4° C. The supernatant was collected and incubated with 2 mL Ni-NTA resin. The resin was washed with 5 mL wash buffer (10 mM imidazole, 50 mM Tris, pH 8.0, 500 mM NaCl). NB41 was eluted in 5 mL of elution buffer (400 mM imidazole, 50 mM Tris, pH 8.0, 500 mM NaCl). Final concentration of 10 mM EDTA was added to the eluted protein. The resulting protein was purified further by gel filtration on a Superdex 75 (10/300) column (gel filtration buffer: 20 mM Tris pH 8.0, 100 mM NaCl). The protein was then concentrated to 4.8 mg/mL and flash-frozen in liquid nitrogen and stored at −80° C.

Akt1(DrLink)-NB41 Complex Formation

NB41 was added to AKT(DrLink)-WT/E17K using a 1.2:1 molar ratio and incubated for 10 minutes at 4° C. Final concentration of 10 mM EDTA was then added to this complex. The complex was purified by gel filtration on Superdex 200 (10/300 GL) column (gel filtration buffer: 20 mM HEPES pH 8.0, 20 mM NaCl, 5 mM DTT). The resulting complex was then concentrated to ~6 mg/mL and flash-frozen in liquid nitrogen and stored at −80° C. This complex was then used for crystal formation.

Crystallization, Data Collection and Structure Determination 6 mg/mL AKT1 WT or E17K DrLink-NB41 complex is incubated with 1 mM TMB Compound 13 on ice for 2 hours prior to crystallization trials. Crystals were obtained by the vapor diffusion technique at 20'C after mixing an equal volume of the complex with the well solution containing 17-23% PEG3350, 200 mM Li2SO4, 100 mM Bis Tris Propane pH 6.5-9.0, 10% ethylene glycol. Crystals grew within 3 days. Crystals were cryo protected in mother liquor supplemented with 150 ethylene glycol and flash cooled in liquid nitrogen for storage and data collection. All diffraction datasets were collected and processed by Helix Biostructures at ESRF beamline TD30B on Sep. 1, 2023. These datasets were further processed with xia2 (CCP4). The initial structures were determined through molecular replacement with Phaser in CCP4 suite with the structure ofPDB TiD 7APJ as a search model. A chemical restraint dictionary was generated using ACEDRG and CCP4i2. The models were manually adjusted using Coot, refined with REFMAC5 to a final resolution of 2.57 Å and 2.49 Å for the AKT1-WT/Compound 13 and AKT1-E17K/Compound 13 complex.

TABLE 3

Data collection and refinement statistics

| | AKT1(DrLink)-WT-NB41-Compound 13 | AKT1(DrLink)-E17K-NB41-Compound 13 |
|---|---|---|
| Wavelength | 0.8731 | 0.8731 |
| Resolution range | 57.69-2.57 (2.662-2.57) | 43.88-2.49 (2.579-2.49) |
| Space group | C 2 2 2 1 | C 2 2 2 1 |
| Unit cell | 76.74 87.48 202.34 90 90 90 | 77.06 87.75 200.8 90 90 90 |
| Total reflections | 162076 (16955) | 181713 (18987) |
| Unique reflections | 22090 (2166) | 24277 (2400) |
| Multiplicity | 7.3 (7.8) | 7.5 (7.9) |
| Completeness (%) | 99.83 (99.49) | 99.91 (99.79) |
| Mean I/sigma(II) | 11.81 (0.74) | 13.57 (0.78) |
| Wilson B-factor | 80.04 | 79.84 |
| R-merge | 0.116 (3.31) | 0.07873 (2.502) |
| R-meas | 0.1248 (3.542) | 0.08466 (2.678) |
| R-pim | 0.04546 (1.253) | 0.03078 (0.9467) |
| CC½ | 0.998 (0.316) | 0.999 (0.349) |
| CC* | 1 (0.693) | 1 (0.719) |
| Reflections used in refinement | 22072 (2157) | 24266 (2398) |
| Reflections used for R-free | 1103 (95) | 1182 (117) |
| R-work | 0.2228 (0.4333) | 0.2347 (0.4299) |
| R-free | 0.2263 (0.4422) | 0.2406 (0.4402) |
| CC(work) | 0.952 (0.598) | 0.951 (0.579) |
| CC(free) | 0.931 (0.616) | 0.934 (0.634) |
| Number of non-hydrogen atoms | 4292 | 4293 |
| macromolecules | 4243 | 4243 |
| ligands | 46 | 46 |
| solvent | 3 | 4 |
| Protein residues | 523 | 523 |
| RMS(bonds) | 0.008 | 0.007 |
| RMS(angles) | 1.43 | 1.41 |
| Ramachandran favored (%) | 92.04 | 89.90 |
| Ramachandran allowed (%) | 7.18 | 8.35 |
| Ramachandran outliers (%) | 0.78 | 1.75 |
| Rotamer outliers (%) | 4.39 | 3.07 |
| Clashscore | 9.31 | 7.30 |
| Average B-factor | 95.43 | 94.27 |
| macromolecules | 95.61 | 94.44 |

TABLE 3-continued

Data collection and refinement statistics

| | AKT1(DrLink)-WT-NB41-Compound 13 | AKT1(DrLink)-E17K-NB41-Compound 13 |
|---|---|---|
| ligands | 80.89 | 81.52 |
| solvent | 68.54 | 63.64 |

Statistics for the highest-resolution shell are shown in parentheses.

Figure 1B:
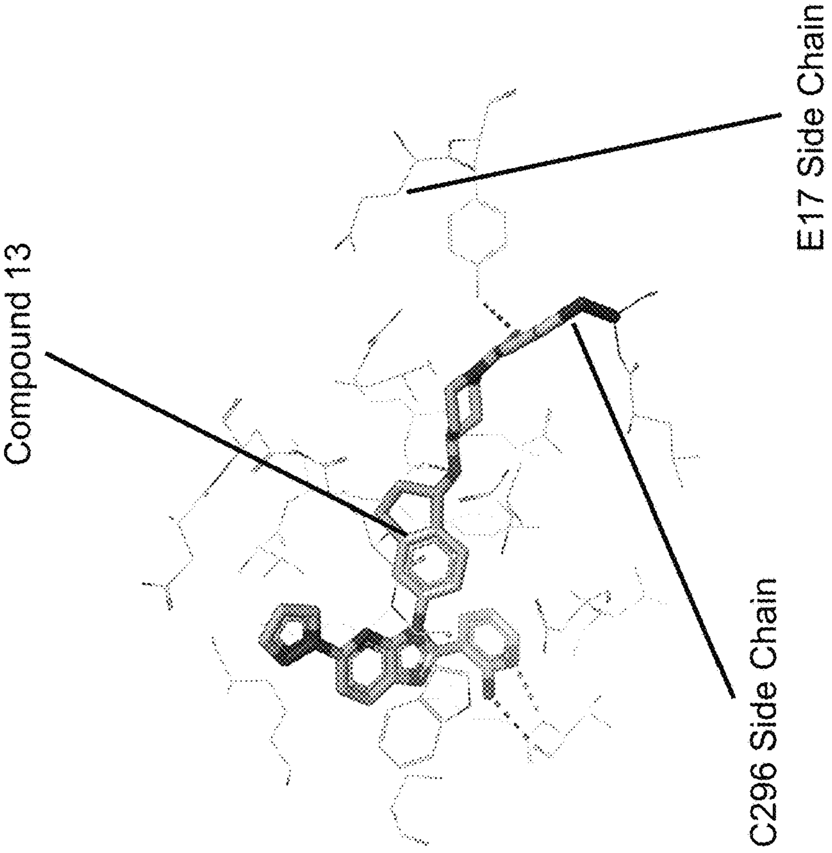
Figure 1C:
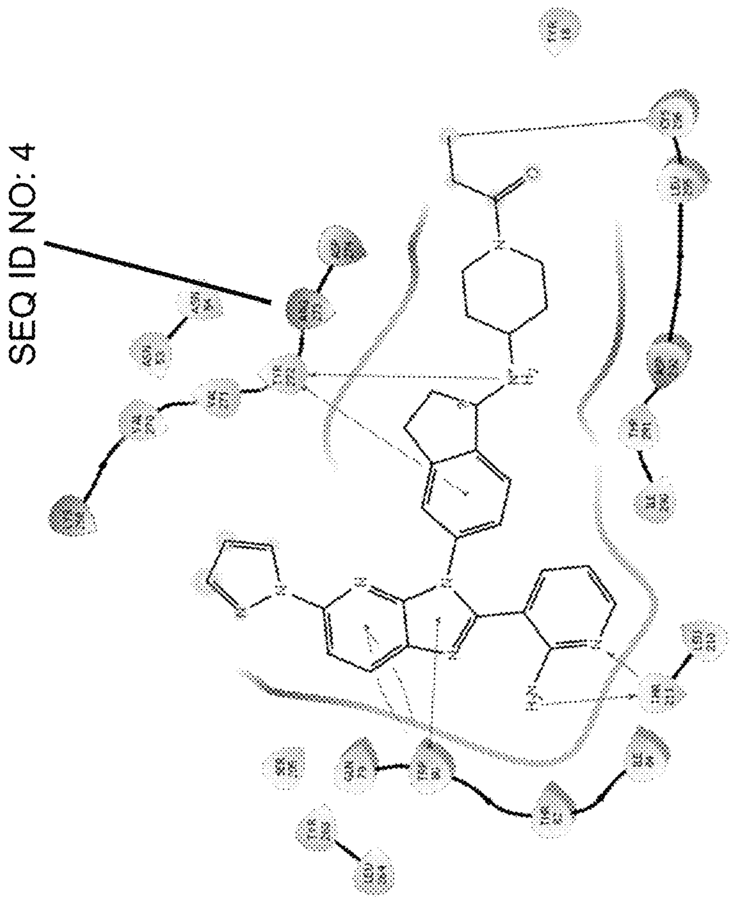

FIGS. 1A to 1C provide crystal structure representations for the co-crystallization of Compound 13 and to AKT1 WT. In FIG. 1A, the AKT1 WT/Compound 13 co-crystallization complex is shown. For the 2Fo-Fc maps contoured at 1.0a, the AKT1 WT complex is shown in cartoon rending and Compound 13 with the side chain of C296 of AKT1 WT are represented by a stick model. The electron density indicates covalent bond formation with C296 and AKT1 WT. FIG. 1B provides a close-up from the crystal structure of the co-crystallization of Compound 13 and AKT1 WT. In FIG. 1B, Compound 13 and the side chain of residue C296 are represented by a thicker stick model and the adjacent residues of AKT1 WT, including the side chain of E17, are represented by a thinner stick model. Hydrogen bonds are depicted by dashed lines. FIG. 1B shows the covalent bond formed between the sulfur of C296 and the acrylamide of Compound 13. FIG. 1C provides a 2-D diagram detailing the interactions between Compound 13 and residues of the AKT1 WT protein. In FIG. 1C, the covalent bond is depicted by the line between C296 and the methylene of Compound 13. Additionally, hydrogen bonds are depicted as arrows between Compound 13 and the residues of the AKT1 WT protein (contains SEQ ID NO: 4).

Figure 2A:
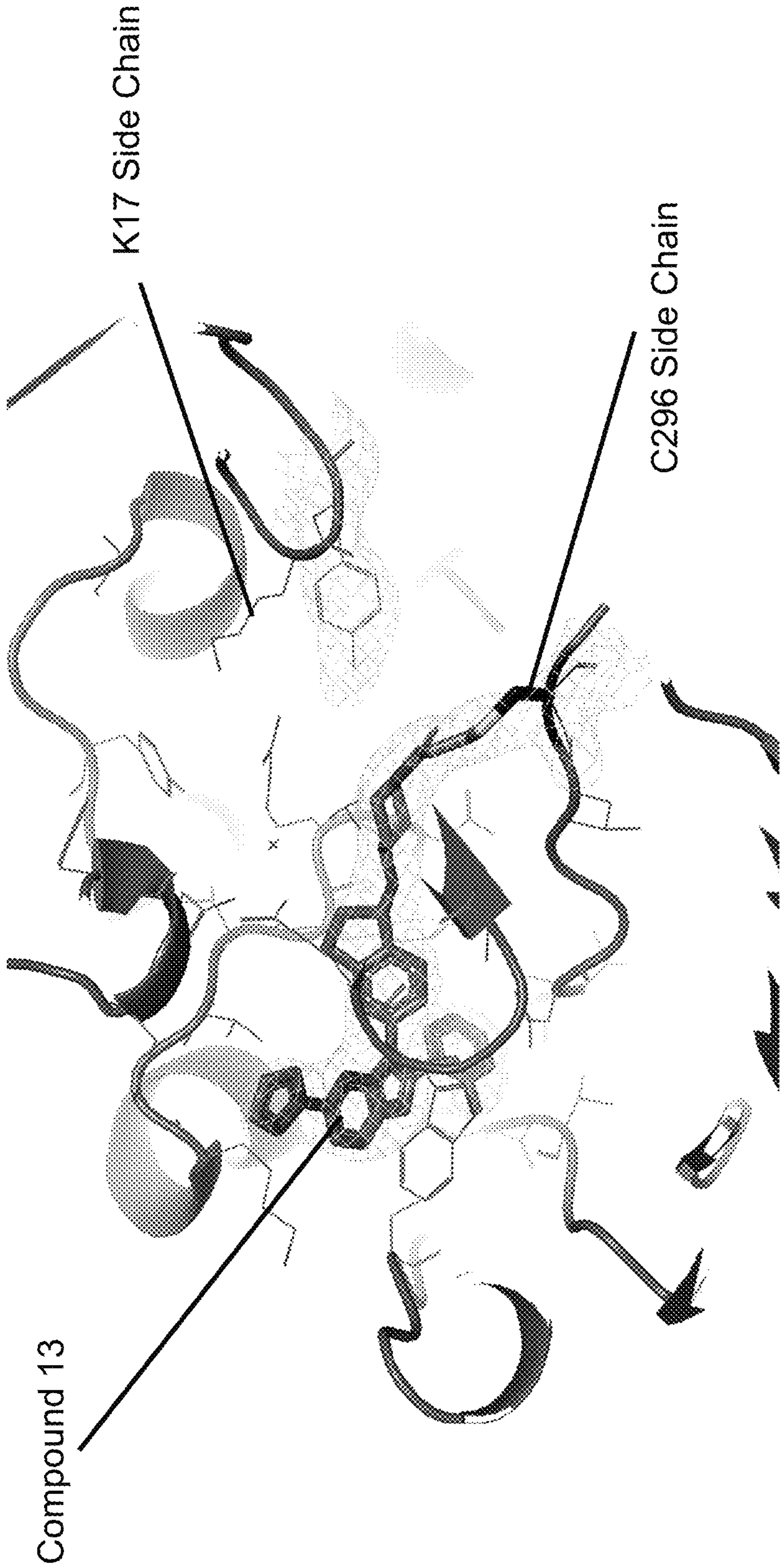
FIGS. 2A-2C provide diagrams of the crystal structure for the Compound 13/AKT E17K co-crystallization complex.
Figure 2C:
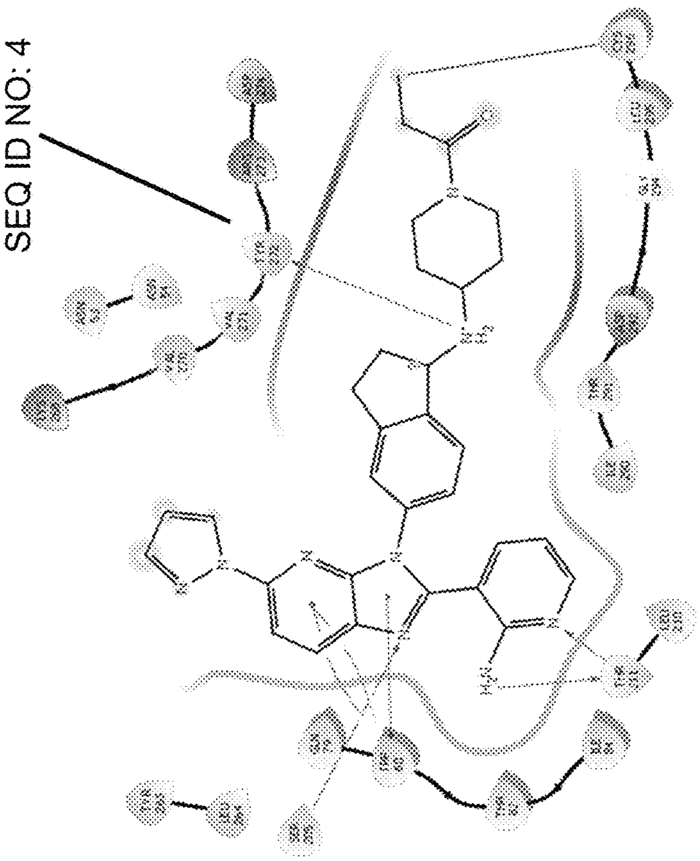
Figure 2B:
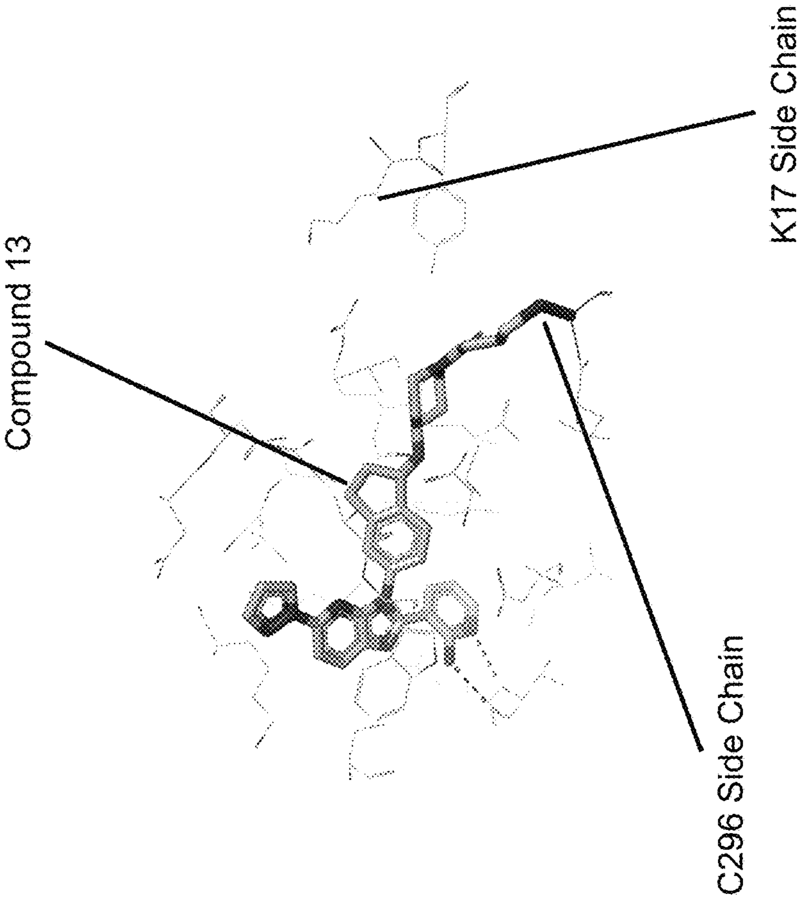

FIGS. 2A to 2C provide crystal structure representations for the co-crystallization of Compound 13 and to AKT1 E17K. In FIG. 2A, the AKT1 E17K/Compound 13 co-crystallization complex is shown. For the 2Fo-Fc maps contoured at 1.0N, the AKT1 E17K complex is shown in cartoon rending and Compound 13 with the side chain of C296 of AKT1 E17K are represented by a stick model. The electron density indicates covalent bond formation with C296 and AKT1 E17K. FIG. 2B provides a close-up from the crystal structure of the co-crystallization of Compound 13 and AKT1 E17K. In FIG. 2B, Compound 13 and the side chain of residue C296 are represented by a thicker stick model and the adjacent residues of AKT1 E17K, including the side chain of E17, are represented by a thinner stick model. Hydrogen bonds are depicted by dashed lines. FIG. 2B shows the covalent bond formed between the sulfur of C296 and the acrylamide of Compound 13. FIG. 2C provides a 2-D diagram detailing the interactions between Compound 13 and residues of the AKT1 E17K protein. In FIG. 2C, the covalent bond is depicted by the line between C296 and the methylene of Compound 13. Additionally, hydrogen bonds are depicted as arrows between Compound 13 and the residues of the AKT1 E17K protein (contains SEQ ID NO: 4).

Sequences

TABLE 4

Protein Amino Acid Sequences

| Sequence No. | Protein Amino Acid Sequence(s) | Annotation(s) |
|---|---|---|
| 1 | MSHHHHHHHHGSENLYFQSDVAIVKEGWLHKRGEYIKTWRPR YFLLKNDGTFIGYKERPQDVDQREAPLNNFSVAQCQLMKTERP RPNTFIIRCLQWTTVIERTFHVETPEEREEWTTAIQTVADGLKKQ | Akt1(DrLink)-WT Sequence |

TABLE 4-continued

Protein Amino Acid Sequences

| Sequence No. | Protein Amino Acid Sequence(s) | Annotation(s) |
|---|---|---|
| | EEEEMDASAEHTDMEVSLAKPKHRVTMNEFEYLKLLGKGTFGK VILVKEKATGRYYAMKILKKEVIVAKDEVAHTLTENRVLQNSR HPFLTALKYSFQTHDRLCFVMEYANGGELFFHLSRERVFSEDRA RFYGAEIVSALDYLHSEKNVVYRDLKLENLMLDKDGHIKITDFG LCKEGIKDGATMKTFCGTPEYLAPEVLEDNDYGRAVDWWGLG VVMYEMMCGRLPFYNQDHEKLFELILMEEIRFPRTLGPEAKSLL SGLLKKDPKQRLGGGSEDAKEIMQHRFFAGIVWQHVYEKKLSP PFKPQVTSETDTRYFDEEFTAQM (SEQ ID NO: 1) | |
| 2 | MSHHHHHHHHGSENLYFQSDVAIVKEGWLHKRGKYIKTWRPR YFLLKNDGTFIGYKERPQDVDQREAPLNNFSVAQCQLMKTERP RPNTFIIRCLQWTTVIERTFHVETPEEREEWTTAIQTVADGLKKQ EEEEMDASAEHTDMEVSLAKPKHRVTMNEFEYLKLLGKGTFGK VILVKEKATGRYYAMKILKKEVIVAKDEVAHTLTENRVLQNSR HPFLTALKYSFQTHDRLCFVMEYANGGELFFHLSRERVFSEDRA RFYGAEIVSALDYLHSEKNVVYRDLKLENLMLDKDGHIKITDFG LCKEGIKDGATMKTFCGTPEYLAPEVLEDNDYGRAVDWWGLG VVMYEMMCGRLPFYNQDHEKLFELILMEEIRFPRTLGPEAKSLL SGLLKKDPKQRLGGGSEDAKEIMQHRFFAGIVWQHVYEKKLSP PFKPQVTSETDTRYFDEEFTAQM (SEQ ID NO: 2) | Akt1(DrLink)-E17K Sequence |
| 3 | QVQLQESGGGLVQAGGSLRLSCAASGIDVRIKTMAWYRQAPGK QRELLASVLVSGSTNYADPVKGRFTISRDNAKNTVYLQMNKLIP DDTAVYYCNTYGRLRRDVWGPGTQVTVSSHHHHHHEPEA (SEQ ID NO: 3) | NB41 Sequence |
| 4 | VVYRD (SEQ ID NO: 4) | Fragment of SEQ ID NO: 1 and SEQ ID NO:2 |

SEQUENCE LISTING

```
Sequence total quantity: 4
SEQ ID NO: 1           moltype = AA  length = 456
FEATURE                Location/Qualifiers
source                 1..456
                       mol_type = protein
                       organism = synthetic construct
SEQUENCE: 1
MSHHHHHHHH GSENLYFQSD VAIVKEGWLH KRGEYIKTWR PRYFLLKNDG TFIGYKERPQ  60
DVDQREAPLN NFSVAQCQLM KTERPRPNTF IIRCLQWTTV IERTFHVETP EEREEWTTAI  120
QTVADGLKKQ EEEEMDASAE HTDMEVSLAK PKHRVTMNEF EYLKLLGKGT FGKVILVKEK  180
ATGRYYAMKI LKKEVIVAKD EVAHTLTENR VLQNSRHPFL TALKYSFQTH DRLCFVMEYA  240
NGGELFFHLS RERVFSEDRA RFYGAEIVSA LDYLHSEKNV VYRDLKLENL MLDKDGHIKI  300
TDFGLCKEGI KDGATMKTFC GTPEYLAPEV LEDNDYGRAV DWWGLGVVMY EMMCGRLPFY  360
NQDHEKLFEL ILMEEIRFPR TLGPEAKSLL SGLLKKDPKQ RLGGGSEDAK EIMQHRFFAG  420
IVWQHVYEKK LSPPFKPQVT SETDTRYFDE EFTAQM                            456

SEQ ID NO: 2           moltype = AA  length = 456
FEATURE                Location/Qualifiers
source                 1..456
                       mol_type = protein
                       organism = synthetic construct
SEQUENCE: 2
MSHHHHHHHH GSENLYFQSD VAIVKEGWLH KRGKYIKTWR PRYFLLKNDG TFIGYKERPQ  60
DVDQREAPLN NFSVAQCQLM KTERPRPNTF IIRCLQWTTV IERTFHVETP EEREEWTTAI  120
QTVADGLKKQ EEEEMDASAE HTDMEVSLAK PKHRVTMNEF EYLKLLGKGT FGKVILVKEK  180
ATGRYYAMKI LKKEVIVAKD EVAHTLTENR VLQNSRHPFL TALKYSFQTH DRLCFVMEYA  240
NGGELFFHLS RERVFSEDRA RFYGAEIVSA LDYLHSEKNV VYRDLKLENL MLDKDGHIKI  300
TDFGLCKEGI KDGATMKTFC GTPEYLAPEV LEDNDYGRAV DWWGLGVVMY EMMCGRLPFY  360
NQDHEKLFEL ILMEEIRFPR TLGPEAKSLL SGLLKKDPKQ RLGGGSEDAK EIMQHRFFAG  420
IVWQHVYEKK LSPPFKPQVT SETDTRYFDE EFTAQM                            456

SEQ ID NO: 3           moltype = AA  length = 126
FEATURE                Location/Qualifiers
source                 1..126
                       mol_type = protein
                       organism = synthetic construct
SEQUENCE: 3
```

-continued

| | | |
|---|---|---|
| QVQLQESGGG LVQAGGSLRL SCAASGIDVR IKTMAWYRQA PGKQRELLAS VLVSGSTNYA | | 60 |
| DPVKGRFTIS RDNAKNTVYL QMNKLIPDDT AVYYCNTYGR LRRDVWGPGT QVTVSSHHHH | | 120 |
| HHEPEA | | 126 |
| | | |
| SEQ ID NO: 4 | moltype = AA length = 5 | |
| FEATURE | Location/Qualifiers | |
| source | 1..5 | |
| | mol_type = protein | |
| | organism = synthetic construct | |
| SEQUENCE: 4 | | |
| VVYRD | | 5 |

What is claimed is:

1. A compound represented by the structure of Formula (I):

(I)

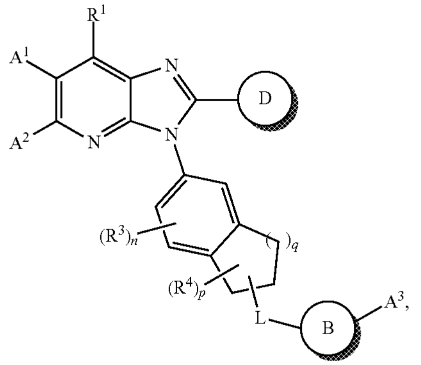

or a pharmaceutically acceptable salt thereof, wherein:

$R^1$ is selected from:

hydrogen, halogen, $—OR^{10}$, $—SR^{10}$, $—N(R^{10})_2$, $—NO_2$, and —CN;

$C_{1-6}$ alkyl optionally substituted with one or more substituents independently selected from: halogen, $—OR^{10}$, $—SR^{10}$, $—N(R^{10})_2$, $—NO_2$, and —CN; and $C_{3-8}$ carbocycle and 4- to 8-membered heterocycle, any of which is optionally substituted with one or more substituents independently selected from halogen, $—OR^{10}$, $—SR^{10}$, $—N(R^{10})_2$, $—NO_2$, —CN, $C_{1-6}$ alkyl, and $C_{1-6}$ haloalkyl;

$A^1$ and $A^2$ are each independently selected from (i), (ii), and (iii):

(i) hydrogen, halogen, $—OR^{11}$, $—SR^{11}$, $—N(R^{11})_2$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, and —CN;

(ii) $C_{1-6}$ alkyl, $C_{2-6}$ alkenyl, and $C_{2-6}$ alkynyl, any of which is optionally substituted with one or more substituents independently selected from:

halogen, $—OR^{11}$, $—SR^{11}$, $—N(R^{11})_2$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2R^{11}$, $—S(O)_2N(R^{11})_2$, $—NO_2$, =O, =S, $=N(R^{11})$, and —CN; and 4- to 10-membered heterocycle and $C_{3-10}$ carbocycle, any of which is optionally substituted with one or more substituents independently selected from:

halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—S(O)_2N(R^{11})_2$, $—NO_2$, =O, =S, $=N(R^{11})$, and —CN; and (iii) 4- to 10-membered heterocycle and $C_{3-10}$ carbocycle, any of which is optionally substituted with one or more substituents independently selected from:

halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—S(O)_2N(R^{11})_2$, $—NO_2$, =O, =S, $=N(R^{11})$, and —CN;

$C_{1-6}$ alkyl, $C_{2-6}$ alkenyl, and $C_{2-6}$ alkynyl, any one of which is optionally substituted with one or more substituents independently selected from:

halogen, $—OR^{11}$, $—SR^{11}$, $—N(R^{11})_2$, $—C(O)R^{11}$, $—C(O)N(R^{11})_2$, $—N(R^{11})C(O)R^{11}$, $—C(O)OR^{11}$, $—OC(O)R^{11}$, $—N(R^{11})C(O)OR^{11}$, $—OC(O)N(R^{11})_2$, $—N(R^{11})C(O)N(R^{11})_2$, $—S(O)R^{11}$, $—S(O)_2R^{11}$, $—N(R^{11})S(O)_2(R^{11})_2$, $—S(O)_2N(R^{11})_2$, $—NO_2$, =O, =S, $=N(R^{11})$, and —CN; and $C_{3-10}$ carbocycle and 3- to 10-membered heterocycle, any of which is optionally substituted with one or more substituents independently selected from:

halogen, $—OR^{11}$, $—N(R^{11})_2$, $—C(O)R^{11}$, $—C(O)N(R^{11})_2$, $—N(R^{11})C(O)R^{11}$, $—C(O)OR^{11}$, $—OC(O)R^{11}$, $—NO_2$, =O, =S, $=N(R^{11})$, —CN;

$C_{1-6}$ alkyl $C_{2-6}$ alkenyl, and $C_{3-6}$ alkynyl, any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—NO_2$, =O, =S, $=N(R^{11})$, and —CN; and $C_{3-10}$ carbocycle and 4- to 10-membered heterocycle any one of which is optionally substituted with one or more substituents independently selected from: halogen, $—OR^{11}$, $—SR^{11}$, $—N(R^{11})_2$, $—C(O)R^{11}$, $—C(O)N(R^{11})_2$, $—N(R^{11})C(O)R^{11}$, $—N(R^{11})S(O)_2R^{11}$, $—C(O)OR^{11}$, $—OC(O)R^{11}$, $—NO_2$, =O, =S, $—N(R^{11})$, and —CN;

$R^3$ is independently selected at each instance from:

halogen, $—OR^{13}$, $—SR^{13}$, $—N(R^{13})_2$, $—C(O)R^{13}$, $—C(O)N(R^{13})_2$, $—N(R^{13})C(O)R^{13}$, $—C(O)OR^{13}$, $—OC(O)R^{13}$, $—NO_2$, and —CN; and $C_{1-6}$ alkyl, $C_{2-6}$ alkenyl, and $C_{2-6}$ alkynyl, any one of which is optionally substituted with one or more substituents independently selected from: halogen, —$OR^{13}$, —$SR^{13}$, —$N(R^{13})_2$, —$C(O)R^{13}$, —$C(O)N(R^{13})_2$, —$N(R^{13})C(O)R^{13}$, —$C(O)OR^{13}$, —$OC(O)R^{13}$, —$NO_2$, —O, =S, =$N(R^{13})$, and —CN;

$R^4$ is independently selected at each instance from:

halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, —O, —S, =$N(R^{14})$, and —CN; and $C_{1-6}$ alkyl, $C_{2-6}$ alkenyl, and $C_{2-6}$ alkynyl, any one of which is optionally substituted with one or more substituents independently selected from halogen, —$OR^{14}$, —$SR^{14}$, —$N(R^{14})_2$, —$C(O)R^{14}$, —$C(O)N(R^{14})_2$, —$N(R^{14})C(O)R^{14}$, —$C(O)OR^{14}$, —$OC(O)R^{14}$, —$NO_2$, =O, =S, —$N(R^{14})$, and —CN;

L is represented by -$L^1$-$L^2$-$L^3$-$L^4$-, wherein $L^1$, $L^2$, $L^3$, and $L^4$ are each independently selected from (a) and (b):

(a) —O—, —$N(R^{15})$—, —S—, —S(O)—, —$S(O)_2$—, —$S(O)(N^{15})$—, $N(R^{15})C(O)$—, —$N(R^{15})C(O)O$—, —$N(R^{15})S(O)_2$—, $N(R^{15})S(O)_2N(R^{15})$—, —$S(O)(N(R^{15})N(R^{15})$—, $N(R^{15})$ $N(R^{15})$—, —$(R^{15})NC(O)N(R^{15})$—, and —$(R^{15})NC(O)N(R^{15})N(R^{15})$—; and (b) $C_{1-6}$ alkylene, $C_{2-6}$ alkenylene, $C_{2-6}$ alkynylene, $C_{3-8}$ carbocyclene, and 3- to 8-membered heterocyclene, any of which is optionally substituted with one or more substituents independently selected from halogen, —$OR^{15}$, —$SR^{15}$, —O, =S, and —CN;

wherein $L^1$, $L^2$, $L^3$, and $L^4$ are each optionally absent;

wherein no more than two of $L^1$, $L^2$, $L^3$, and $L^4$ are selected from (a) and the two selected are not adjacent;

Ring B selected from 3- to 10-membered heterocyclene and $C_{3-10}$ carbocyclene, any of which is optionally substituted with one or more substituents independently selected from:

halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN;

$C_{1-6}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, =S, =$N(R^{16})$, and —CN; and 3- to 6-membered heterocycle and $C_{3-6}$ carbocycle, each of which is optionally substituted with one or more substituents independently selected from: halogen, $C_{1-6}$ alkyl, $C_{1-6}$ haloalkyl, —$OR^{16}$, —$SR^{16}$, —$N(R^{16})_2$, —$C(O)N(R^{16})_2$, —$C(O)OR^{16}$, —$OC(O)R^{16}$, —$N(R^{16})C(O)R^{16}$, —$N(R^{16})S(O)_2R^{16}$, —$S(O)_2N(R^{16})_2$, —$N(R^{16})C(O)N(R^{16})_2$, —$N(R^{16})C(O)OR^{16}$, —$OC(O)N(R^{16})_2$, —$S(O)R^{16}$, —$S(O)_2R^{16}$, —$NO_2$, =O, —S, =$N(R^{16})$, and —CN;

Ring D is selected from:

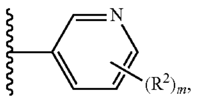,
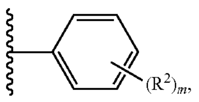,

-continued

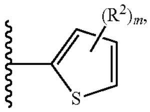 and 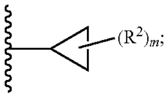;

$R^2$ is independently selected at each instance from halogen, $C_{1-6}$ alkyl, $C_{1-6}$ haloalkyl, —$OR^{12}$, —$SR^{12}$, —$N(R^{12})_2$, —$NO_2$, and —CN;

$A^3$ is cysteine susceptible electrophile;

$R^{10}$, $R^{11}$, $R^{12}$, $R^{13}$, $R^{14}$, $R^{15}$, and $R^{16}$ are each independently selected at each occurrence from:

hydrogen, $C_{1-6}$ alkyl, optionally substituted with one or more substituents independently selected from halogen, —OH, —O—$C_{1-6}$ alkyl, —O—$C_{1-6}$ haloalkyl, $C_{3-6}$ carbocycle, and 3- to 6-membered heterocycle; and $C_{3-6}$ carbocycle and 3- to 6-membered heterocycle, each of which is optionally substituted with one or more substituents independently selected from halogen, —OH, —O—$C_{1-6}$ alkyl, —O—$C_{1-6}$ haloalkyl, $C_{1-6}$ alkyl, and $C_{1-6}$ haloalkyl;

m is selected from 0, 1, 2, and 3;

n is selected from 0, 1, 2, and 3;

q is selected from 1, 2, and 3; and p is selected from 0, 1, 2, 3, 4, and 5.

2. The compound or salt of claim 1, wherein the cysteine susceptible electrophile is selected from a haloacetamide, a haloalkyl ketone, a halo amidine, a halo benzylphosphonate, an acyloxyalkyl ketone, a sulfonyl oxirane, an epoxide, a diazoalkyl ketone, a halotriazine, an acrylamide, a cyano acrylamide, a vinyl sulfone, a vinyl sulfonamide, an acrylate, a fumarate, a carbonyl acrylate, a maleimide, a ketoamide, a nitrile, an alkene, an alkyne, a keto heterocycle, and an ynamide.

3. The compound or salt of claim 1, wherein Ring D is selected from

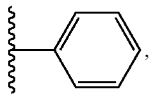,
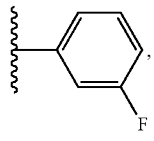,
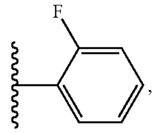,
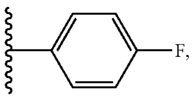,
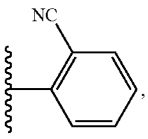,
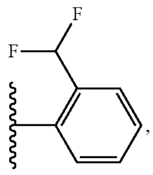,
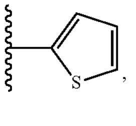,
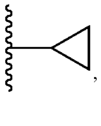, and
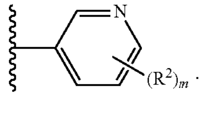.

4. The compound or salt of claim 1, wherein Ring D is

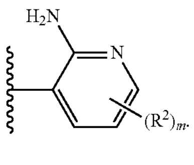.

5. The compound or salt of claim 1, wherein the cysteine susceptible electrophile is an alpha-beta unsaturated carbonyl, an alpha-beta unsaturated sulfone, an alpha-beta unsaturated amide, and an alpha-beta unsaturated sulfonamide.

6. The compound or salt of claim 1, wherein the structure of Formula (I) is represented by the structure of Formula (II-A):

(II-A)

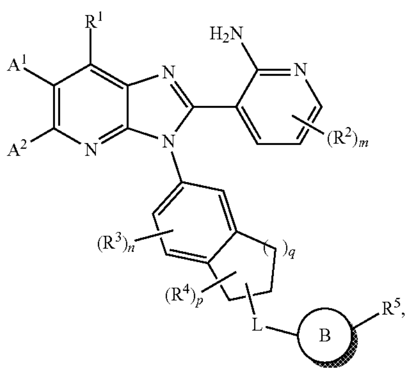

or a pharmaceutically acceptable salt thereof, wherein:

the cysteine susceptible electrophile is $R^5$;

$R^5$ is selected from:

—C(O)$R^{17}$, —S(O)$_2R^{17}$, —N($R^{19}$)C(O)($R^{17}$), —C(O)N($R^{17}$)($R^{19}$), —N($R^{19}$)S(O)$_2R^{17}$, —S(O)$_2$N($R^{17}$)($R^{19}$), and —CN;

$C_{1-6}$ alkyl substituted with one or more substituents independently selected from —C(O)$R^{17}$, —S(O)$_2R^{17}$, —N($R^{19}$)C(O)($R^{17}$), —C(O)N($R^{17}$)($R^{19}$), —N($R^{19}$)S(O)$_2R^{17}$, —S(O)$_2$N($R^{17}$)($R^{19}$), and —CN;

$C_{2-6}$ alkenyl and $C_{2-6}$ alkynyl, each of which is optionally substituted with one or more substituents independently selected from —C(O)$R^{19}$, —S(O)$_2R^{19}$, —N($R^{19}$)C(O)($R^{19}$), —C(O)N($R^{19}$)$_2$, —N($R^{19}$)S(O)$_2R^{19}$, —S(O)$_2$N($R^{19}$)($R^{19}$), and —CN; and $C_{3-6}$ carbocycle and 3- to 6-membered heterocycle, each of which is substituted with one or more substituents independently selected from =O, $C_{2-6}$ alkenyl, $C_{2-6}$ alkynyl, —C(O)$R^{17}$, —S(O)$_2R^{17}$, —N($R^{19}$)C(O)($R^{17}$), —C(O)N($R^{17}$)($R^{19}$), —N($R^{19}$)S(O)$_2R^{17}$, —S(O)$_2$N($R^{17}$)($R^{19}$), and —CN;

$R^{17}$ is independently selected at each occurrence from:

$C_{2-6}$ alkenyl and $C_{2-6}$ alkynyl each of which is optionally substituted with one or more substituents independently selected from halogen, —O$R^{18}$, —S$R^{18}$, —N($R^{18}$)$_2$, —C(O)N($R^{18}$)$_2$, —C(O)O$R^{18}$, —OC(O)$R^{18}$, —N($R^{18}$)C(O)$R^{18}$, —N($R^{18}$)S(O)$_2R^{18}$, —S(O)$_2$N($R^{18}$)$_2$, —N($R^{18}$)C(O)N($R^{18}$)$_2$, —N($R^{18}$)C(O)O$R^{18}$, —OC(O)N($R^{18}$)$_2$, —S(O)$R^{18}$, —S(O)$_2R^{18}$, —$NO_2$, and —CN; and $R^{18}$ and $R^{19}$ are each independently selected at each occurrence from: hydrogen, $C_{1-6}$ alkyl, $C_{1-6}$ haloalkyl, $C_{3-6}$ carbocycle, and 3- to 6-membered heterocycle.

7. The compound or salt of claim 1, wherein the cysteine susceptible electrophile is selected from:

—CN,

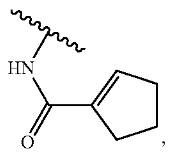, 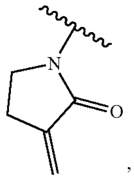, 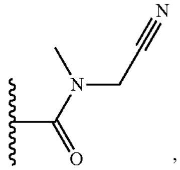,

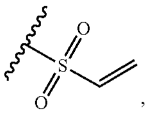, 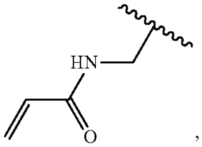, 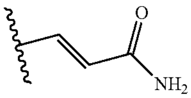,

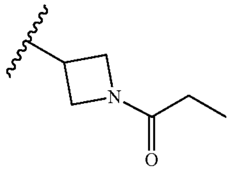, 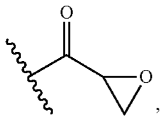, 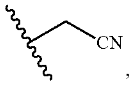,

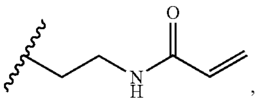, 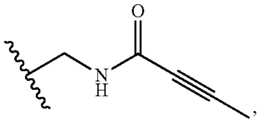,

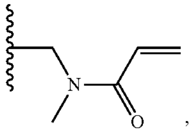, 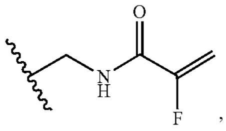,

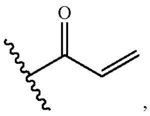, 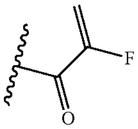, 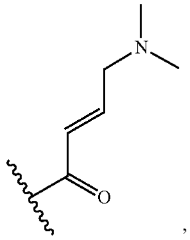,

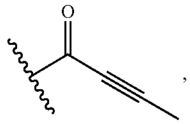, 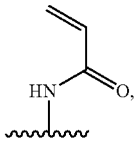, 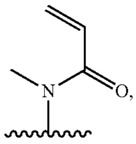,

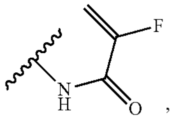, 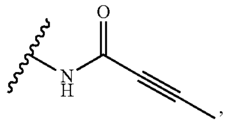,

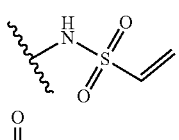, 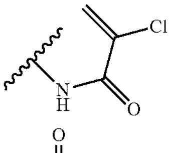,

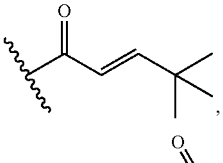, 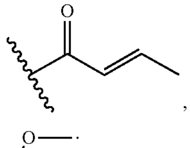, and

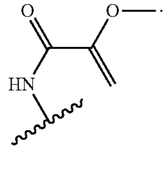.

8. The compound or salt of claim 1, wherein $A^1$ and $A^2$ are each independently selected from (i) and (ii):

(i) hydrogen, halogen, —$OR^{11}$, —$SR^{11}$, —$N(R^{11})_2$, —$C(O)O(R^{11})_2$, —$N(R^{11})C(O)R^{11}$, —$C(O)R^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN; and (ii) $C_{1-6}$ alkyl, $C_{2-6}$ alkenyl, and $C_{2-6}$ alkynyl, any of which is optionally substituted with one or more substituents independently selected from:

halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)C(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and 3- to 10-membered heterocycle and $C_{3-10}$ carbocycle, any of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN.

9. The compound or salt of claim 1, wherein $A^1$ and $A^2$ are each independently selected from (i) and (iii):

(i) hydrogen, halogen, —$OR^{11}$, —$SR^{11}$, —$N(R^{11})_2$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, and —CN; and (iii) 3- to 10-membered heterocycle and $C_{3-10}$ carbocycle, any of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$S(O)_2N(R^{11})_2$, —$NO_2$, =O, =S, =$N(R^{11})$, and —CN;

$C_{1-6}$ alkyl, $C_{2-6}$ alkenyl, and $C_{2-6}$ alkynyl, any one of which is optionally substituted with one or more substituents independently selected from:

halogen, —$OR^{11}$, —$SR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$N(R^{11})C(O)OR^{11}$, —$OC(O)N(R^{11})_2$, —$N(R^{11})C(O)N(R^{11})_2$, —$S(O)R^{11}$, —$S(O)_2R^{11}$, —$N(R^{11})S(O)_2R^{11}$, —$S(O)_2N(R^{11})_2$, —$NO_2$, =O, =S, =$N(R^{11})$, and —CN; and $C_{3-10}$ carbocycle and 3- to 10-membered heterocycle, any of which is optionally substituted with one or more substituents independently selected from:

halogen, —$OR^{11}$, —$N(R^{11})_2$, —$C(O)R^{11}$, —$C(O)N(R^{11})_2$, —$N(R^{11})C(O)R^{11}$, —$C(O)OR^{11}$, —$OC(O)R^{11}$, —$NO_2$, =O, =S, $N(R^{11})$, —CN; and $C_{1-6}$ alkyl $C_{2-6}$ alkenyl, and $C_{2-6}$ alkynyl, any one of which is optionally substituted with one or more substituents independently selected from: halogen, —$OR^{11}$, —$SR^{11}$, —$N(R^{11})_2$, —$C(O)R^{11}$, —$C(O)N(R^{11})_2$, —$N(R^{11})C(O)R^{11}$, —$N(R^{11})S(O)_2R^{11}$, —$C(O)OR^{11}$, —$OC(O)R^{11}$, —$NO_2$, =O, =S, =$N(R^{11})$, and —CN.

10. The compound or salt of claim 1, wherein $A^1$ is selected from hydrogen, fluoro, methyl,

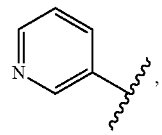,
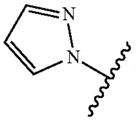, and
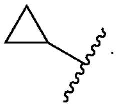.

11. The compound or salt of claim 1, wherein $A^2$ is selected from methyl,

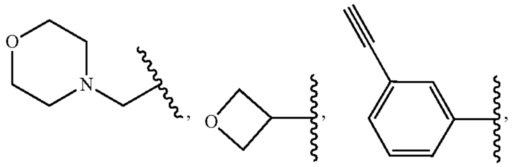

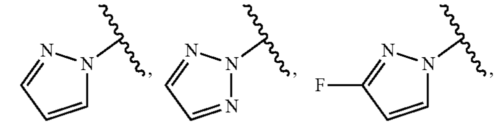

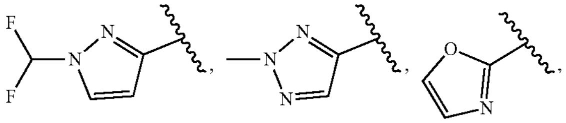

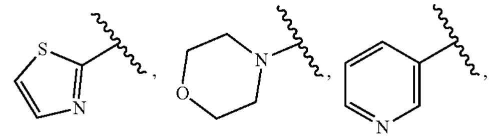

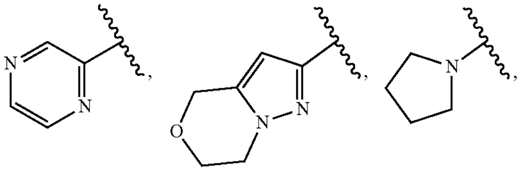

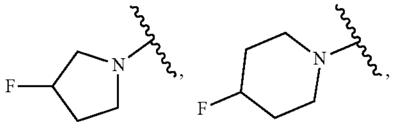

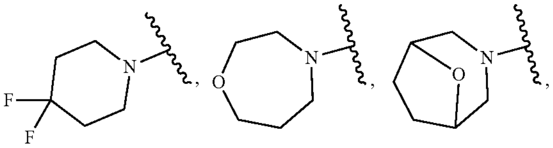

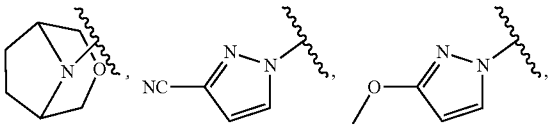

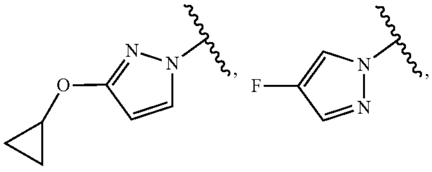

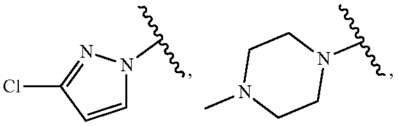

-continued

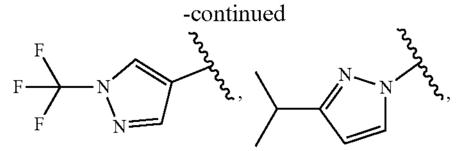

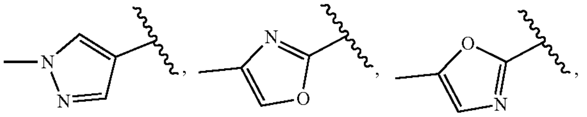

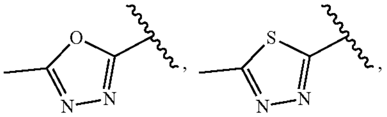

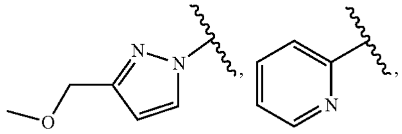

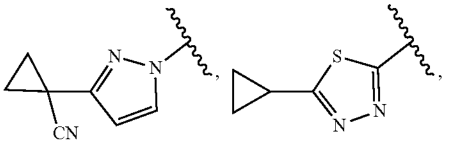

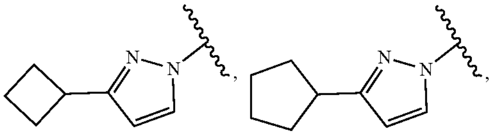

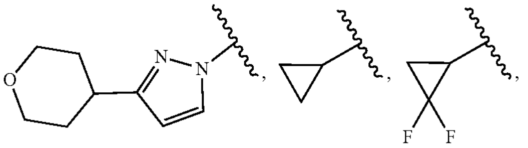

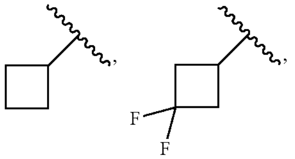

and

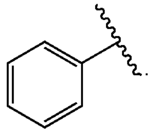

12. The compound or salt of claim 1, wherein Ring B is selected from 3- to 10-membered heterocyclene and $C_{3-10}$ carbocyclene, any of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, =O, and —CN;

$C_{1-4}$ alkyl, $C_{2-6}$ alkenyl, and $C_{2-6}$ alkynyl, each of which is optionally substituted with one or more substituents independently selected from: halogen, —$OR^{16}$, —$SR^{16}$, —$N(R^{16})_2$, —$NO_2$, and —CN; and 4- to 6-membered heterocycle and $C_{3-6}$ carbocycle, each of which is optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

13. The compound or salt of claim 1, wherein Ring B is selected from azetidinylene, pyrrolidinylene, piperidinylene, phenylene, pyridinylene, indolinylene, 3-azabicyclo[3.2.1]octanylene, cyclobutylene, cyclohexylene, pyrazolylene, 1,2,3,4-tetrahydroquinolinylene, azaspiro[3.5]nonanylene, azaspiro[3.3]heptanylene, azaspiro[3.4]octanylene, 1,4-oxazepanylene, 3-azabicyclo[3.1.1]heptanylene, 3-oxa-6-azabicyclo[3.2.2]nonanylene, piperazinylene, azepanylene, 2-azabicyclo[2.2.2]octanylene, 2-abicyclo[2.2.1]heptanylene each of which is optionally substituted with one or more substituents independently selected from:

halogen, —$OR^{16}$, —$N(R^{16})_2$, —$C(O)N(R^{16})_2$, —$C(O)OR^{16}$, —$OC(O)R^{16}$, —$N(R^{16})C(O)R^{16}$, —$NO_2$, —O, and —CN;

$C_{1-4}$ alkyl, $C_{2-6}$ alkenyl, and $C_{2-6}$ alkynyl, any of which is optionally substituted with one or more substituents independently selected from: halogen, —$OR^{16}$, —$SR^{16}$, —$N(R^{16})_2$, —$NO_2$, and —CN; and $C_{3-6}$ carbocycle optionally substituted with one or more substituents independently selected from: halogen, $C_{1-4}$ alkyl, $C_{1-4}$ haloalkyl, —$OR^{16}$, —$N(R^{16})_2$, —$NO_2$, and —CN.

14. The compound or salt of claim 6, wherein

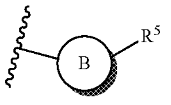

is selected from:

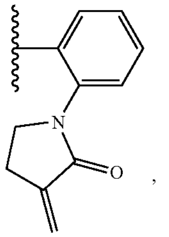

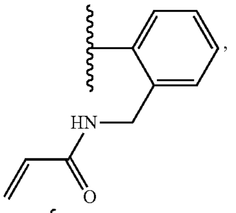

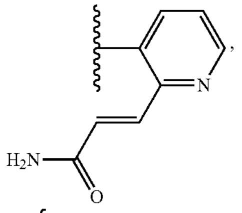

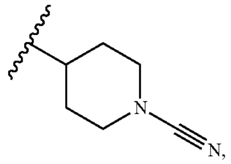

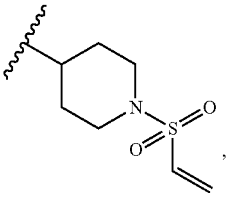

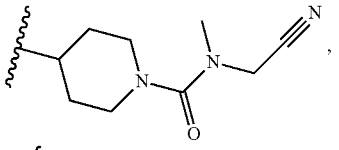

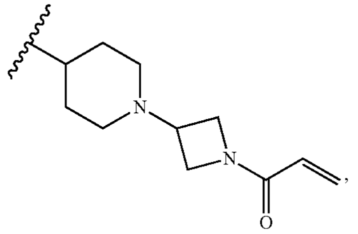

-continued
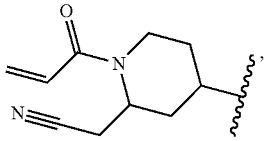,
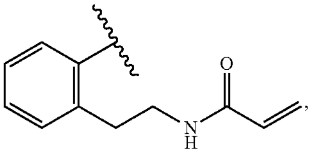,
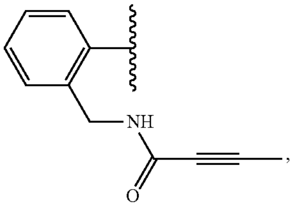,
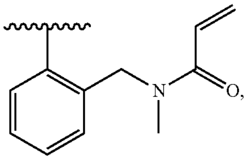, 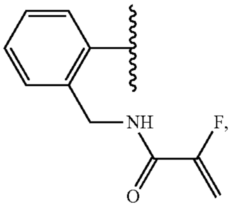,
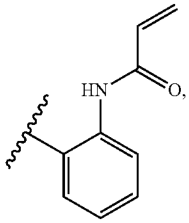, 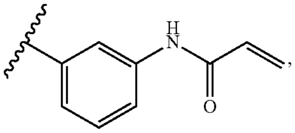,
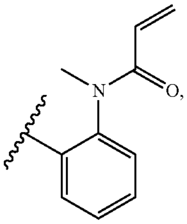, 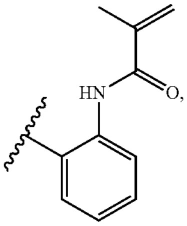, 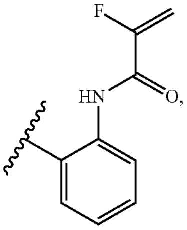,
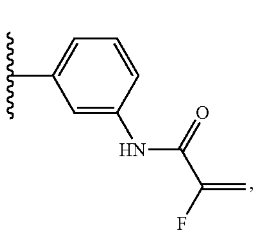, 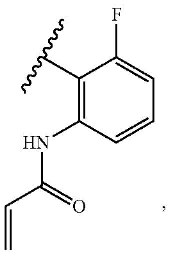,
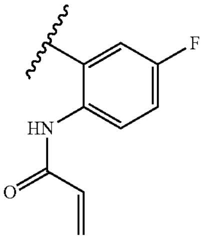, 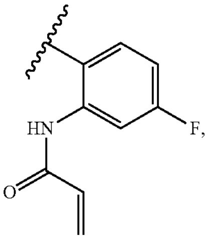,
-continued
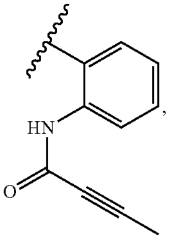, 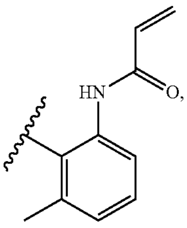,
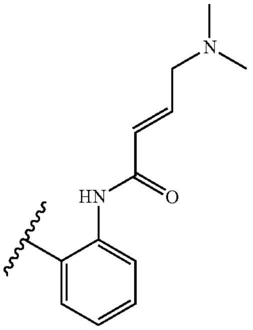, 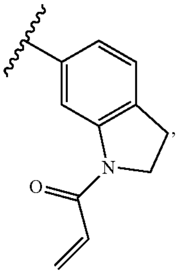,
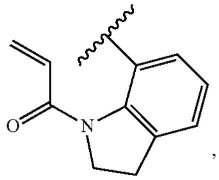, 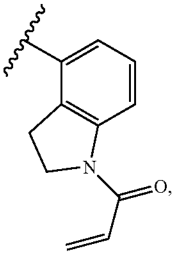,
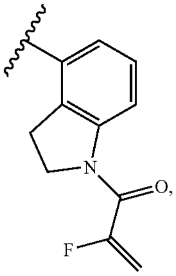, 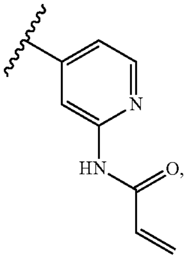, 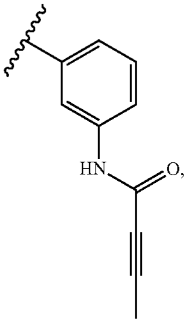,
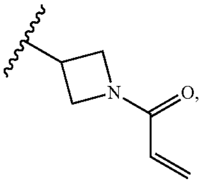, 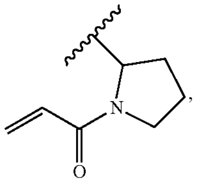,
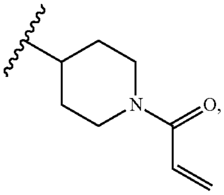, 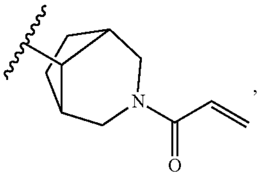, -continued
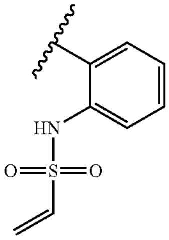
,
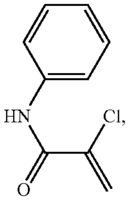
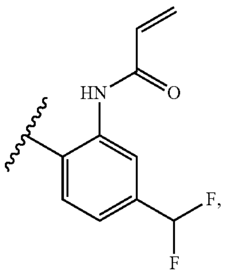
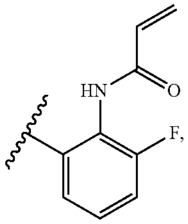
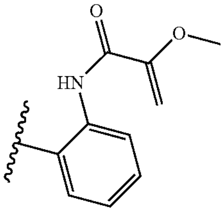
,
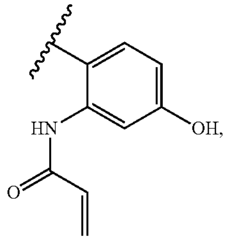
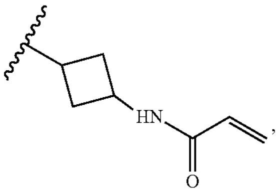
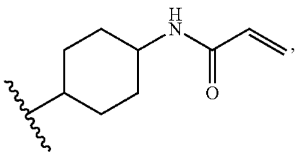
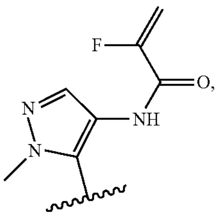
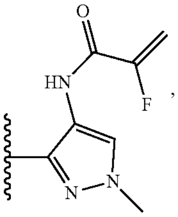
,
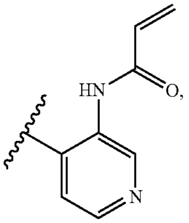
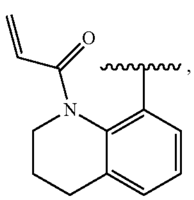
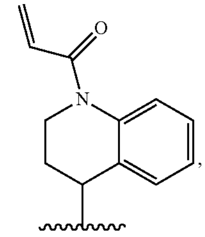
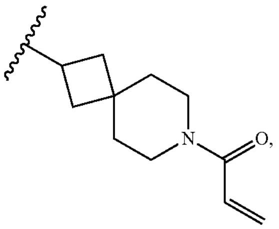
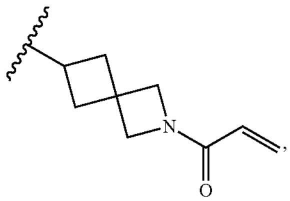
-continued
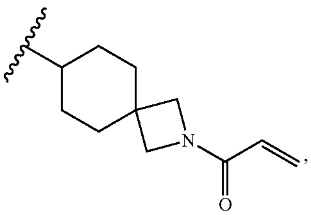
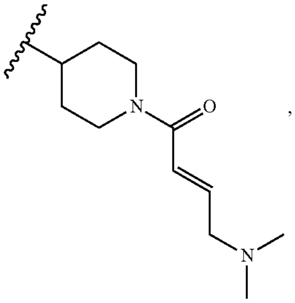
,
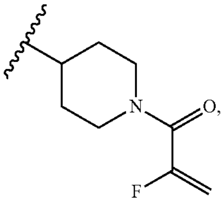
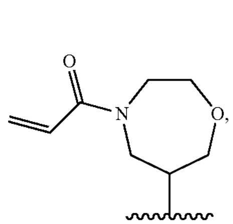
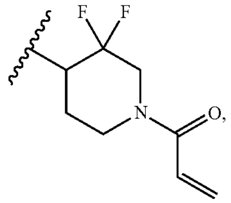
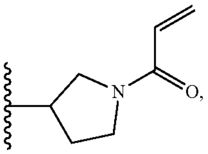
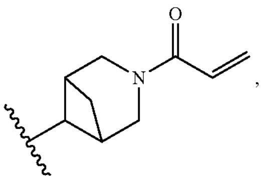
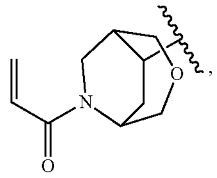
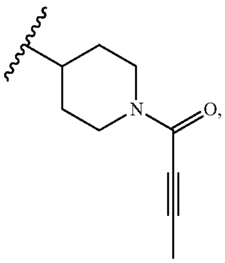
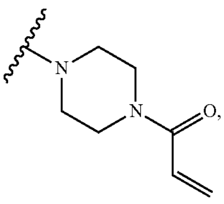
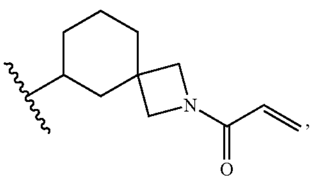
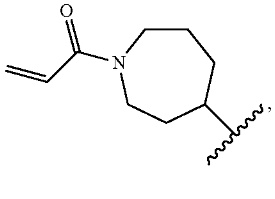
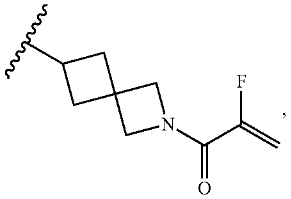

-continued
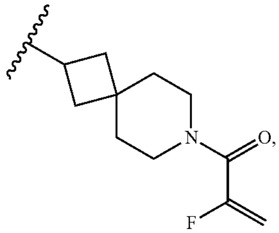 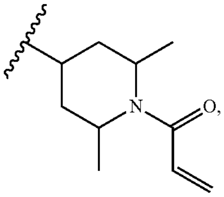
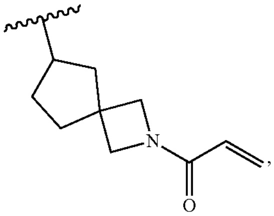, 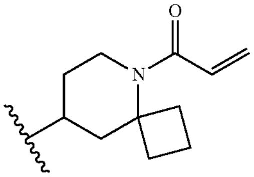,
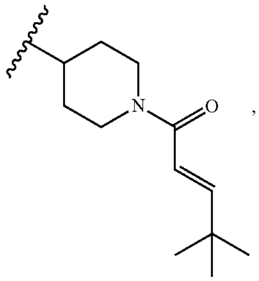, 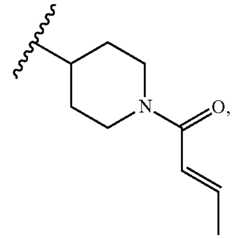
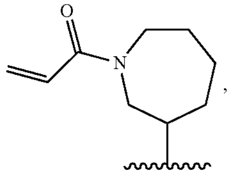, 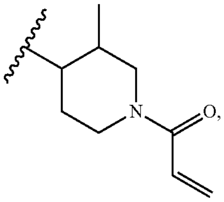
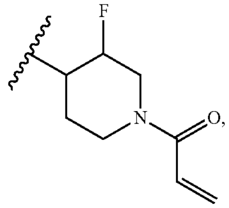 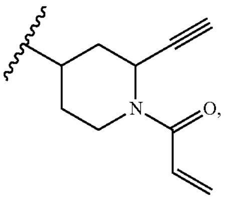
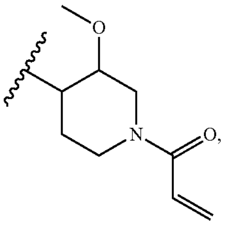 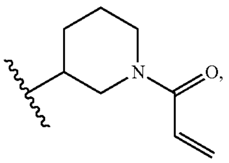
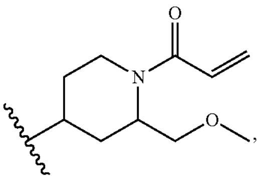, 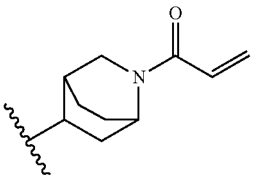,
-continued
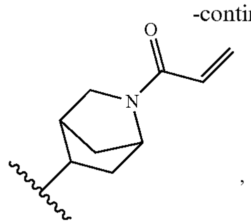, 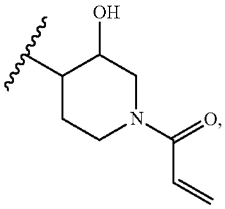
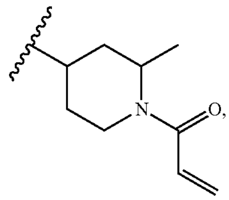 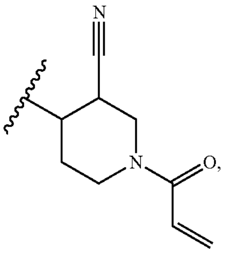
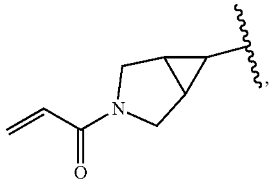, 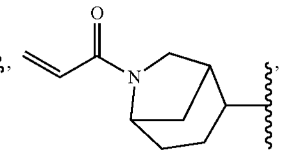
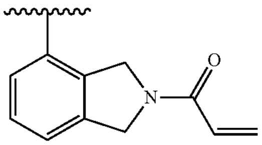, 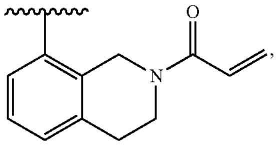
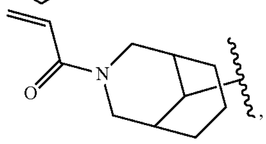 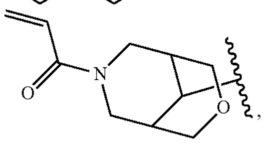
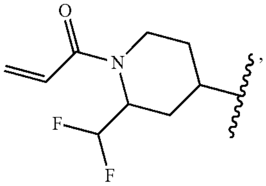 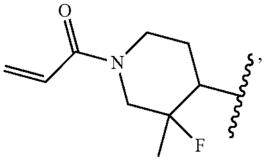
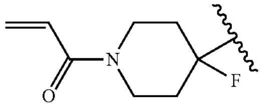
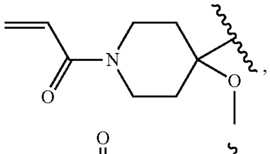, and
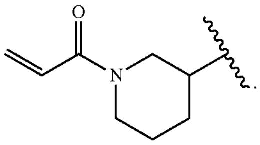
15. The compound or salt of claim 1, wherein $L^1$, $L^2$, $L^3$, and $L^4$ are each independently selected from (a) and (b):
(a) —O—, —N($R^{15}$)—, —S—, —N($R^{15}$)C(O)—, —N($R^{15}$)C(O)O—, —N($R^{15}$)S(0)$_2$, —N($R^{15}$)N($R^{15}$)—, and —($R^{15}$)NC(O)N($R^{15}$)—; and
(b) $C_{1-6}$ alkylene, $C_{2-6}$ alkenylene, $C_{2-6}$ alkynylene, $C_{3-6}$ carbocyclene, and 3- to 6-membered heterocyclene, any of which is optionally substituted with one or more substituents independently selected from halogen, —$OR^{15}$, and —CN;

wherein $L^2$, $L^3$, and $L^4$ are each optionally absent; and wherein no more than two of $L^1$, $L^2$, $L^3$, and $L^4$ are selected from (a) and the two selected are not adjacent.

16. The compound or salt of claim 1, wherein $L^4$ is absent.

17. The compound or salt of claim 1, wherein $L^3$ is absent.

18. The compound or salt of claim 1, wherein $L^2$ is absent or methylene.

19. The compound or salt of claim 1, wherein $L^1$ is selected from —O—, —$N(R^{15})$—, —$N(R^{15})C(O)$—, $C_{1-6}$ alkylene, and 3- to 6-membered heterocyclene.

20. The compound or salt of claim 1, wherein L is selected from: —O—, —NH—, —$CH_2$—, —$N(CH_3)$—,

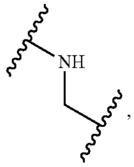,
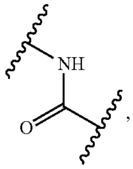,
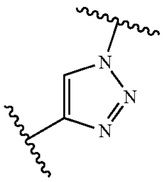,
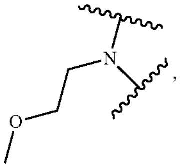, and
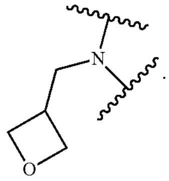.

21. The compound or salt of claim 1, wherein $R^1$ is selected from hydrogen, methoxy, —CN, methyl, ethyl, and (methoxy) methyl.

22. The compound or salt of claim 1, wherein q is 1.

23. The compound or salt of claim 1, wherein m is 0.

24. The compound or salt of claim 1, wherein n is 0.

25. The compound or salt of claim 1, wherein p is selected from 0, 1, and 2.

26. The compound or salt of claim 1, wherein $R^4$ is selected from fluoro, —OH, and —$OCH_3$.

27. The compound or salt of claim 1, wherein the compound or salt of Formula (I) is selected from:

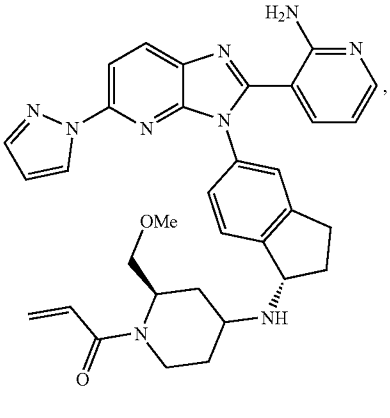,

-continued

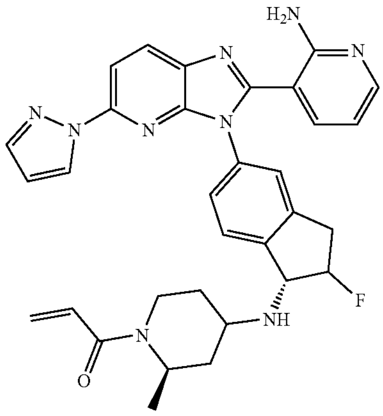,

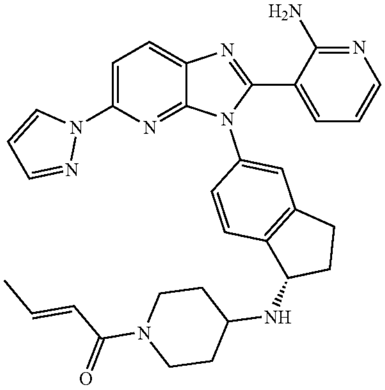,

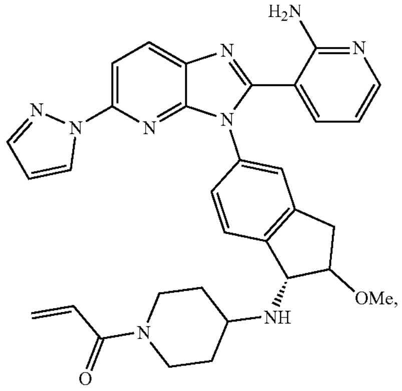

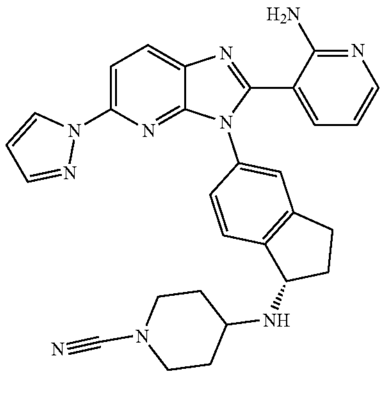,

-continued
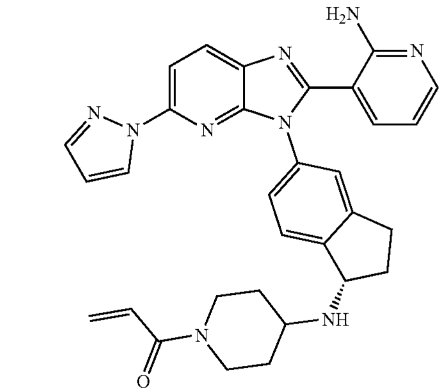
,
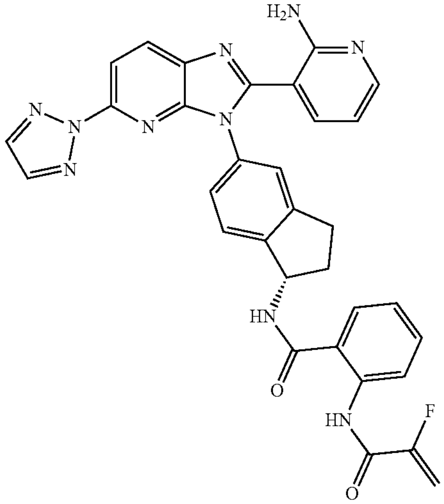
,
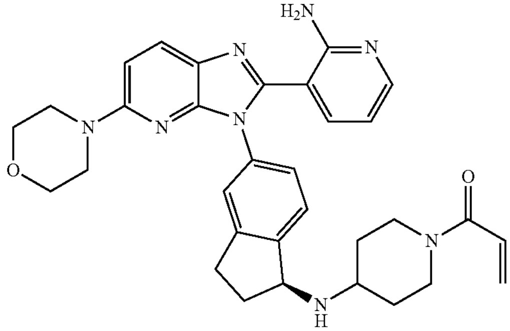
,
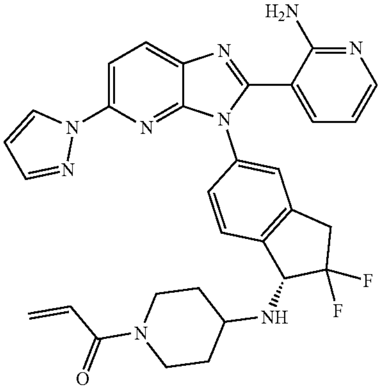
,
-continued
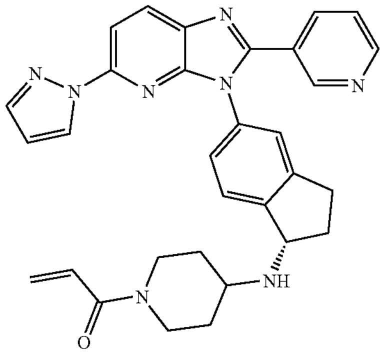
,
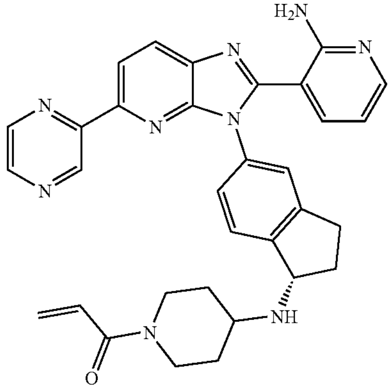
,
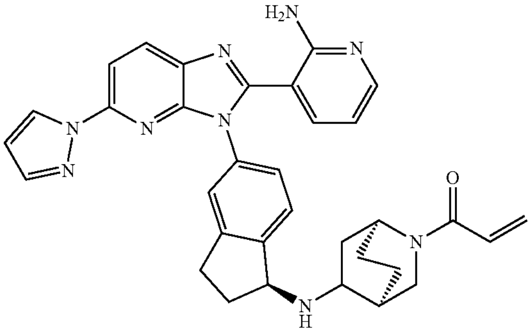
,
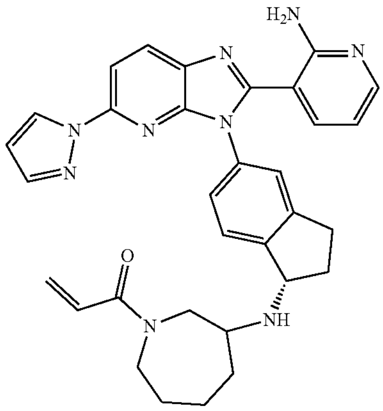
, -continued
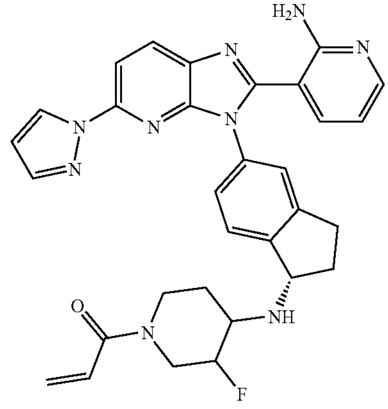,
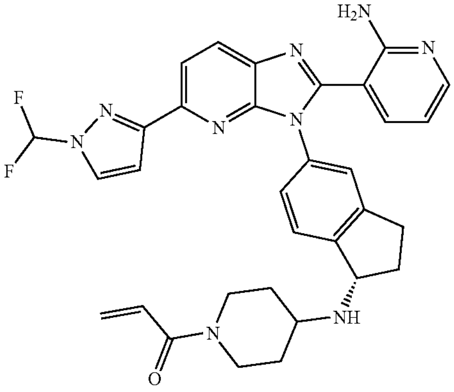,
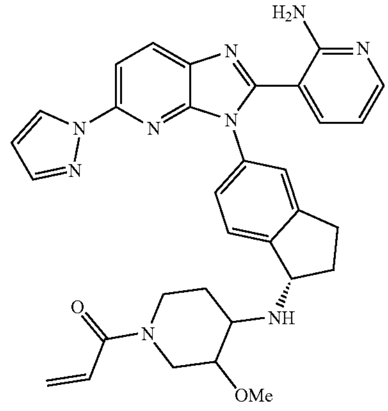,
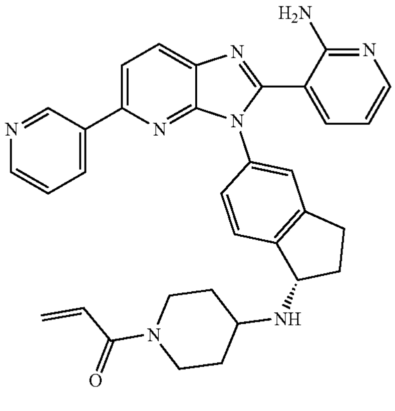,
-continued
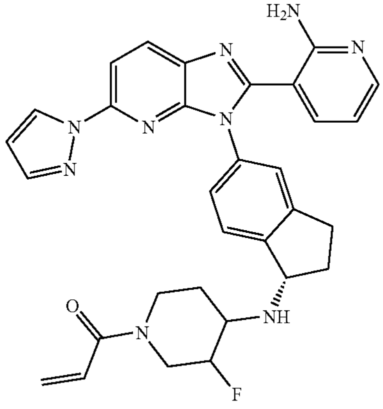,
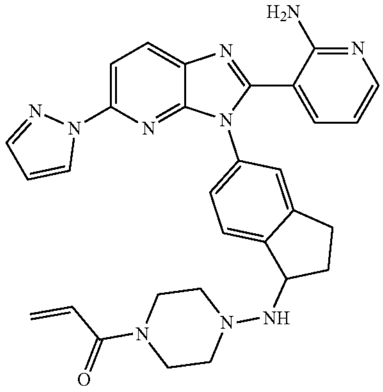,
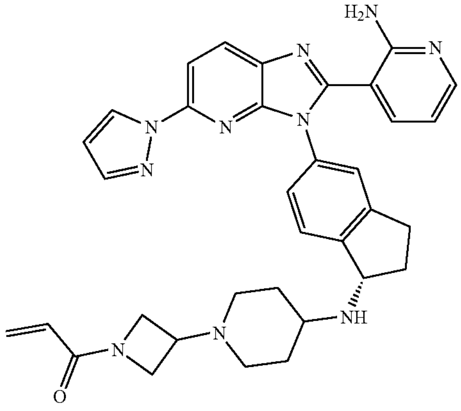,
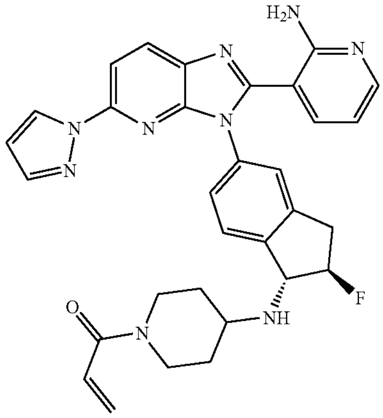, -continued
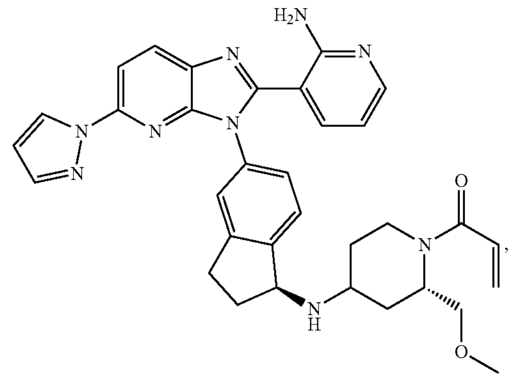
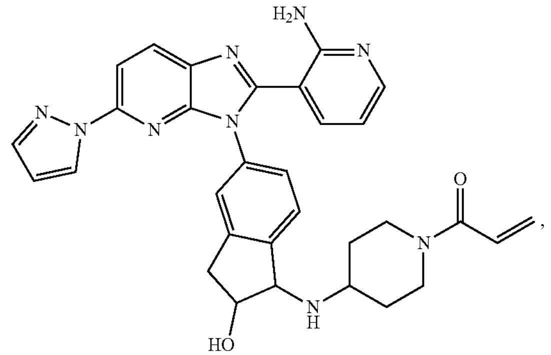
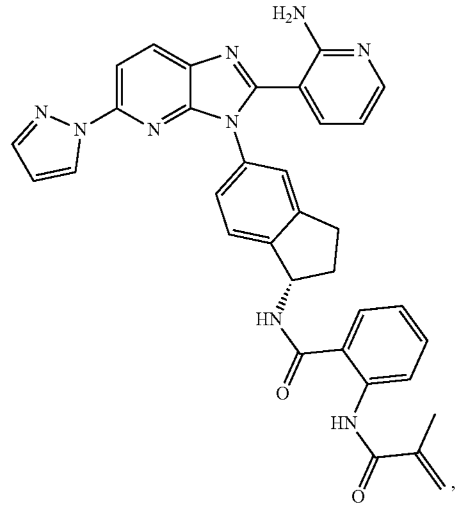
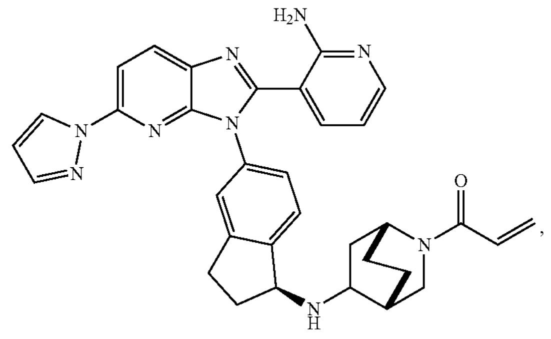
-continued
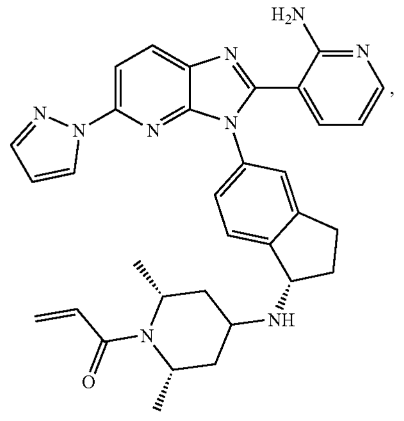
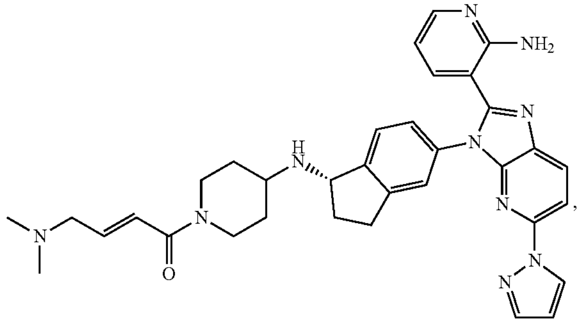
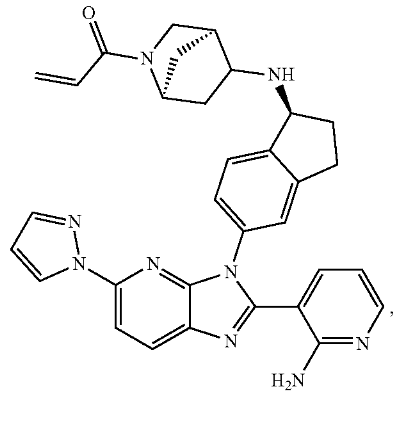
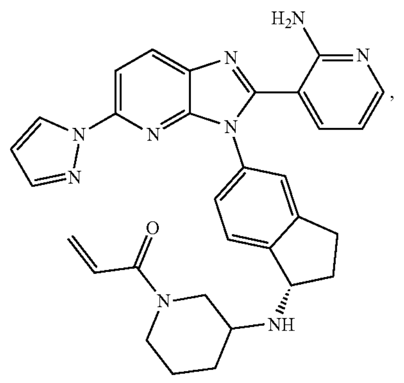

-continued
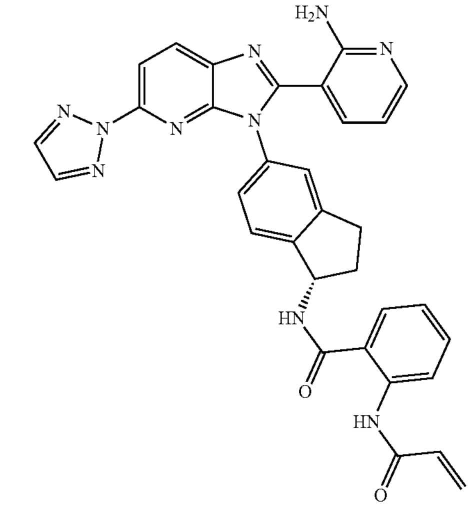
,
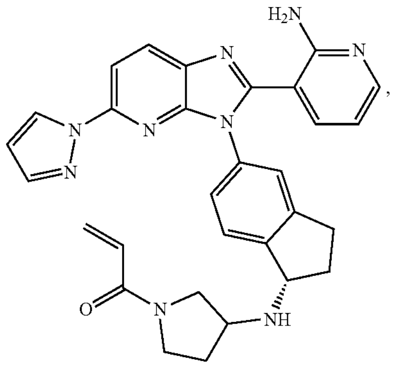
,
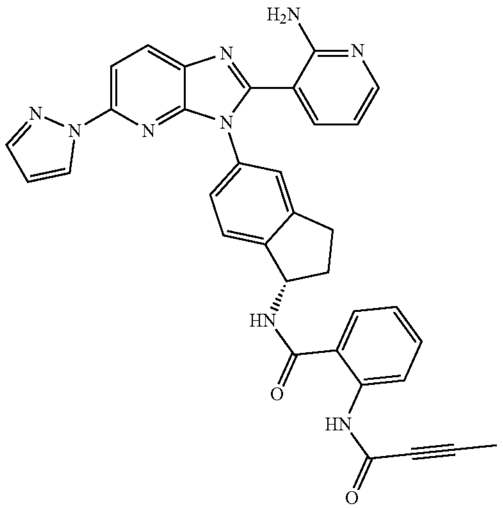
,
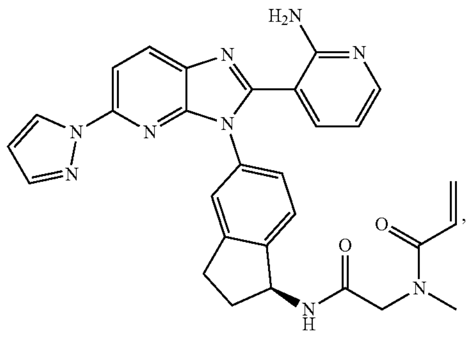
,
-continued
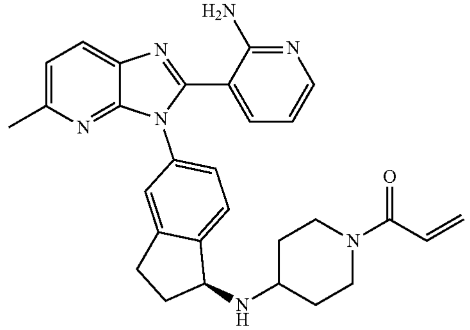
,
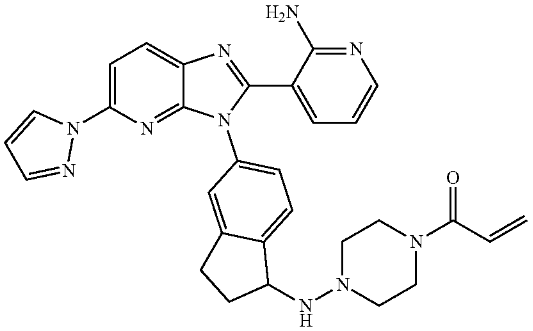
,
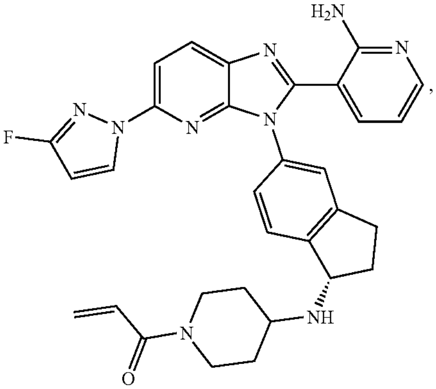
,
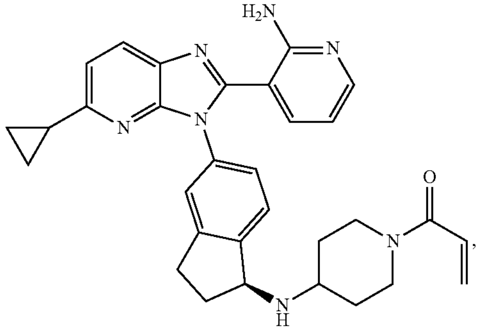
,
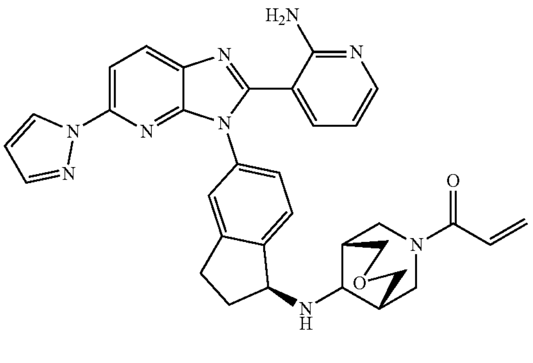
, -continued

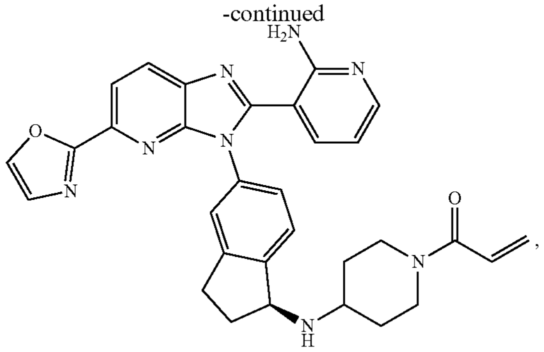

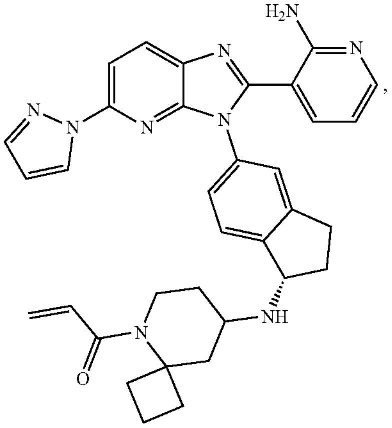

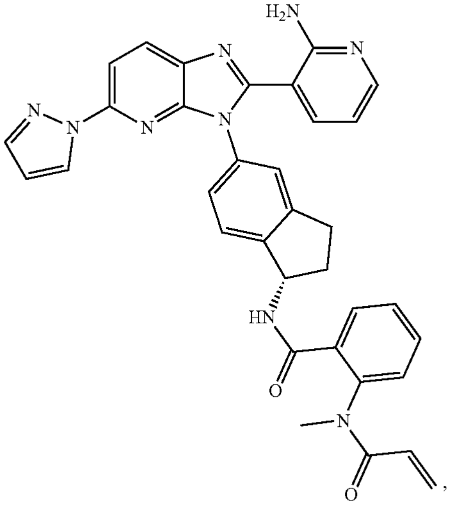

, and

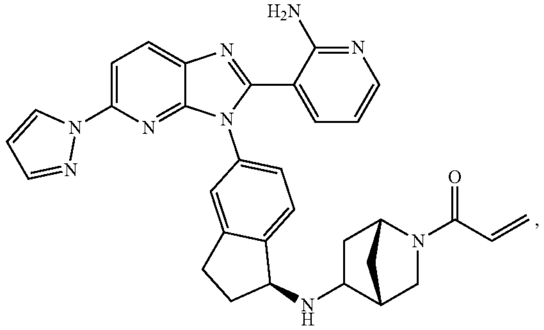

or a pharmaceutically acceptable salt of any one thereof.

28. A pharmaceutical composition comprising a compound or salt of claim 1 and a pharmaceutically acceptable excipient.

29. A method of treating cancer in a subject in need thereof, the method comprising administering to the subject a compound or salt of claim 1, or a pharmaceutical composition comprising a compound or salt of claim 1 and a pharmaceutically acceptable excipient; wherein the administration modulates the activity of wild-type AKT1 or the activity of a mutant AKT1; and wherein the cancer is selected from prostate cancer, breast cancer, colorectal cancer, and meningioma.

30. An AKT1 protein covalently bound to a compound, wherein the compound is covalently bound to a cysteine residue of the AKT1 protein, and wherein the compound is a compound or salt of claim 1.

31. The compound or salt of claim 1, wherein the compound or salt of Formula (I) is

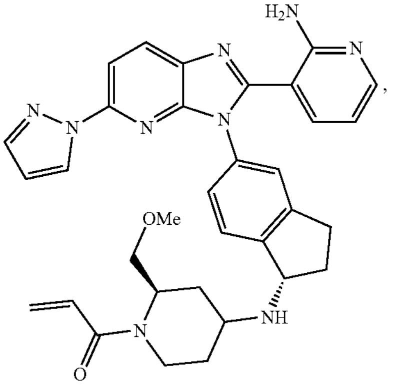 [SMILES: C=CC(=O)N1CCC(N[C@H]2CCc3cc(-n4c(-c5cccnc5N)nc5ccc(-n6cccn6)nc54)ccc32)C[C@@H]1COC]

or a pharmaceutically acceptable salt thereof.

32. The compound or salt of claim 1, wherein the compound or salt of Formula (I) is

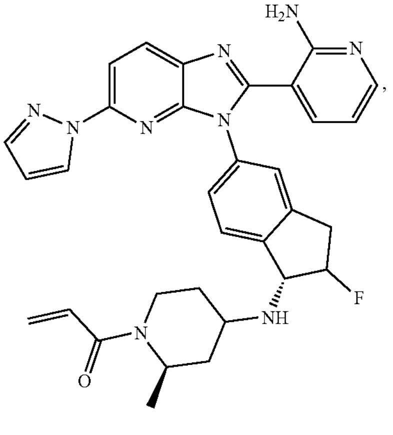 [SMILES: C=CC(=O)N1CCC(N[C@@H]2c3ccc(-n4c(-c5cccnc5N)nc5ccc(-n6cccn6)nc54)cc3CC2F)C[C@H]1C]

or a pharmaceutically acceptable salt thereof.

33. The compound or salt of claim 1, wherein the compound or salt of Formula (I) is

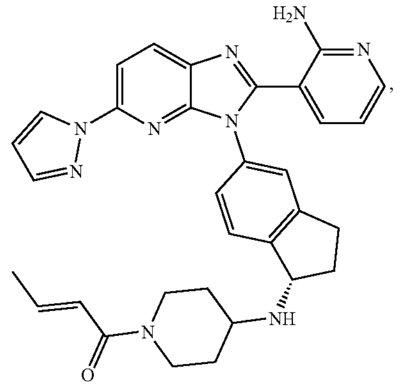 [SMILES: C/C=C/C(=O)N1CCC(N[C@H]2CCc3cc(-n4c(-c5cccnc5N)nc5ccc(-n6cccn6)nc54)ccc32)CC1]

or a pharmaceutically acceptable salt thereof.

34. The compound or salt of claim 1, wherein the compound or salt of Formula (I) is

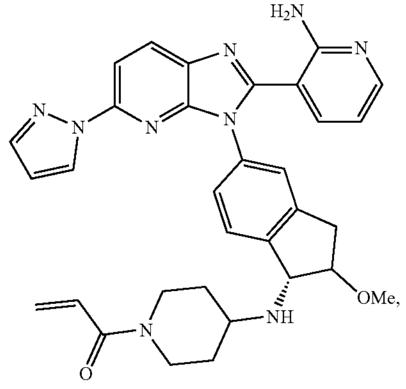 [SMILES: C=CC(=O)N1CCC(N[C@@H]2c3ccc(-n4c(-c5cccnc5N)nc5ccc(-n6cccn6)nc54)cc3CC2OC)CC1]

or a pharmaceutically acceptable salt thereof.

35. The compound or salt of claim 1, wherein the compound or salt of Formula (I) is

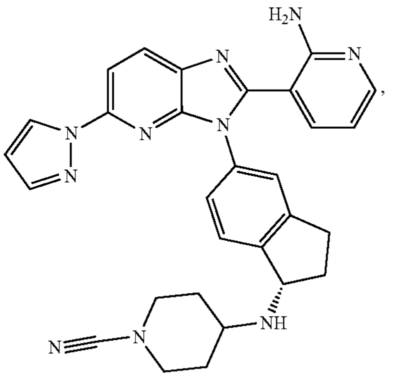 [SMILES: N#CN1CCC(N[C@H]2CCc3cc(-n4c(-c5cccnc5N)nc5ccc(-n6cccn6)nc54)ccc32)CC1]

or a pharmaceutically acceptable salt thereof.

36. The compound or salt of claim 1, wherein the compound or salt of Formula (I) is

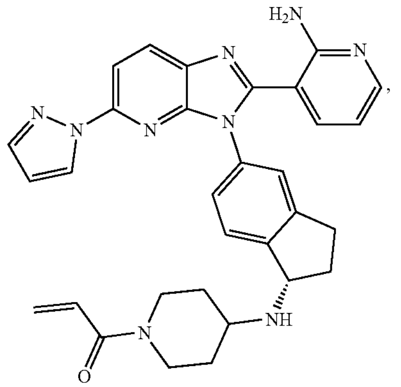 [SMILES: C=CC(=O)N1CCC(N[C@H]2CCc3cc(-n4c(-c5cccnc5N)nc5ccc(-n6cccn6)nc54)ccc32)CC1]

or a pharmaceutically acceptable salt thereof.

37. The compound or salt of claim 1, wherein the compound or salt of Formula (I) is

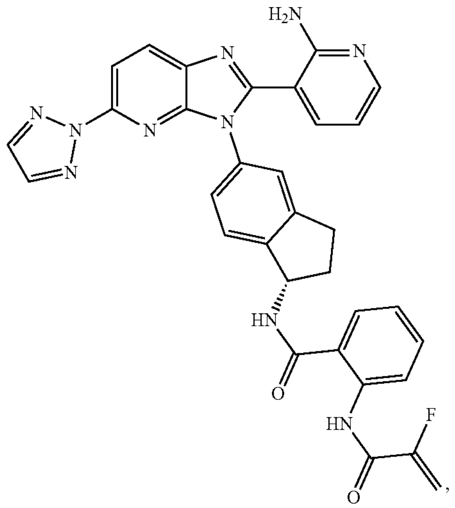 [SMILES: C=C(F)C(=O)Nc1ccccc1C(=O)N[C@H]1CCc2cc(-n3c(-c4cccnc4N)nc4ccc(-n5nccn5)nc43)ccc21]

or a pharmaceutically acceptable salt thereof.

38. The compound or salt of claim 1, wherein the compound or salt of Formula (I) is

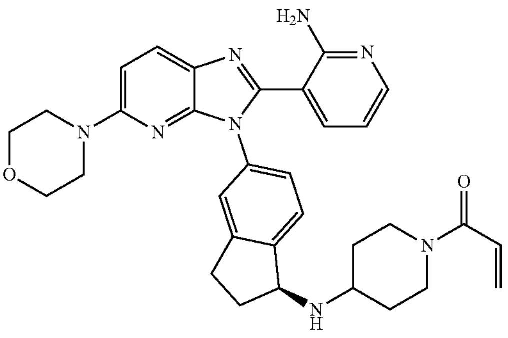 [SMILES: C=CC(=O)N1CCC(N[C@H]2CCc3cc(-n4c(-c5cccnc5N)nc5ccc(N6CCOCC6)nc54)ccc32)CC1]

or a pharmaceutically acceptable salt thereof.

39. The compound or salt of claim 1, wherein the compound or salt of Formula (I) is

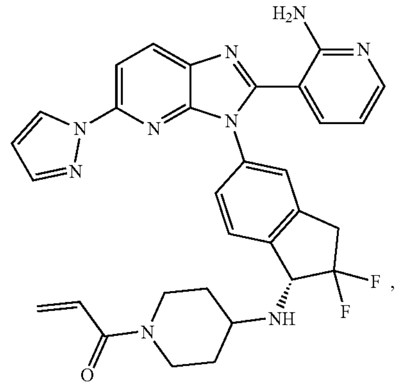 [SMILES: C=CC(=O)N1CCC(N[C@@H]2c3ccc(-n4c(-c5cccnc5N)nc5ccc(-n6cccn6)nc54)cc3CC2(F)F)CC1]

or a pharmaceutically acceptable salt thereof.

40. The compound or salt of claim 1, wherein the compound or salt of Formula (I) is

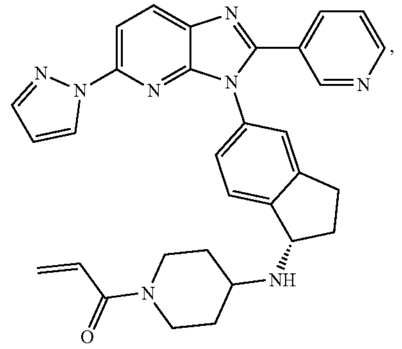 [SMILES: C=CC(=O)N1CCC(N[C@H]2CCc3cc(-n4c(-c5cccnc5)nc5ccc(-n6cccn6)nc54)ccc32)CC1]

or a pharmaceutically acceptable salt thereof.

41. The compound or salt of claim 1, wherein the compound or salt of Formula (I) is

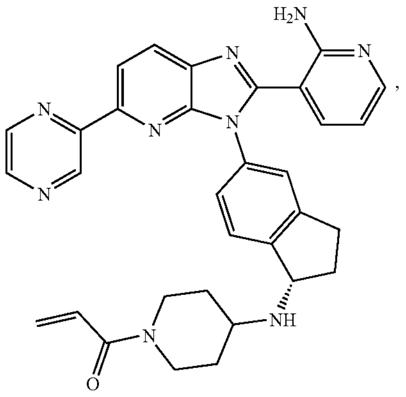 [SMILES: C=CC(=O)N1CCC(N[C@H]2CCc3cc(-n4c(-c5cccnc5N)nc5ccc(-c6cnccn6)nc54)ccc32)CC1]

or a pharmaceutically acceptable salt thereof.

42. The compound or salt of claim 1, wherein the compound or salt of Formula (I) is

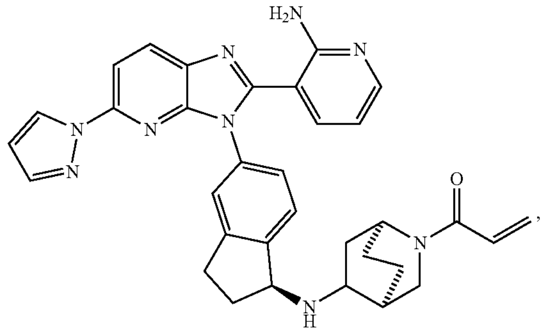

or a pharmaceutically acceptable salt thereof.

43. The compound or salt of claim 1, wherein the compound or salt of Formula (I) is

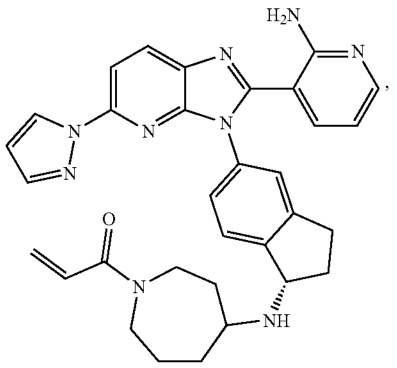 [SMILES: C=CC(=O)N1CCCC(N[C@H]2CCc3cc(-n4c(-c5cccnc5N)nc5ccc(-n6cccn6)nc54)ccc32)CC1]

or a pharmaceutically acceptable salt thereof.

44. The compound or salt of claim 1, wherein the compound or salt of Formula (I) is

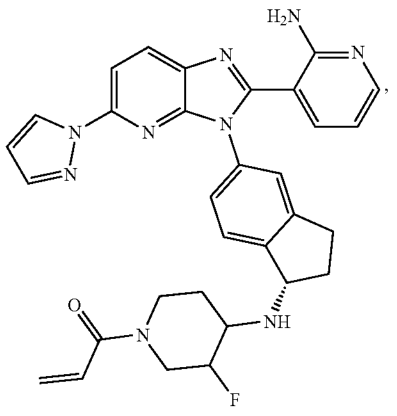 [SMILES: C=CC(=O)N1CCC(N[C@H]2CCc3cc(-n4c(-c5cccnc5N)nc5ccc(-n6cccn6)nc54)ccc32)C(F)C1]

or a pharmaceutically acceptable salt thereof.

45. The compound or salt of claim 1, wherein the compound or salt of Formula (I) is

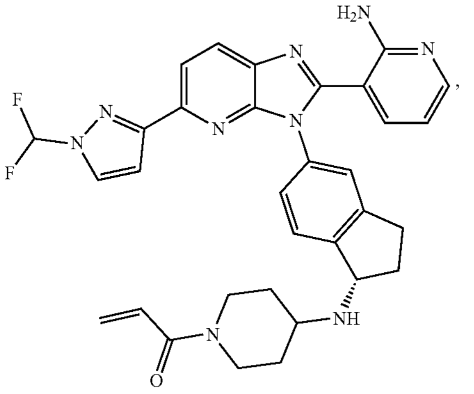 [SMILES: C=CC(=O)N1CCC(N[C@H]2CCc3cc(-n4c(-c5cccnc5N)nc5ccc(-c6ccn(C(F)F)n6)nc54)ccc32)CC1]

or a pharmaceutically acceptable salt thereof.

46. The compound or salt of claim 1, wherein the compound or salt of Formula (I) is

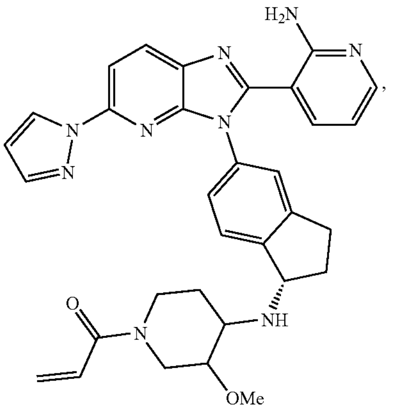 [SMILES: C=CC(=O)N1CCC(N[C@H]2CCc3cc(-n4c(-c5cccnc5N)nc5ccc(-n6cccn6)nc54)ccc32)C(OC)C1]

or a pharmaceutically acceptable salt thereof.

47. The compound or salt of claim 1, wherein the compound or salt of Formula (I) is

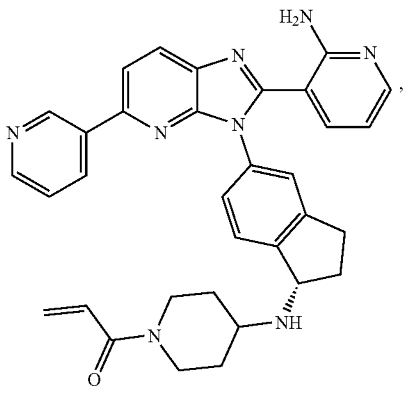 [SMILES: C=CC(=O)N1CCC(N[C@H]2CCc3cc(-n4c(-c5cccnc5N)nc5ccc(-c6cccnc6)nc54)ccc32)CC1]

or a pharmaceutically acceptable salt thereof.

48. The compound or salt of claim 1, wherein the compound or salt of Formula (I) is

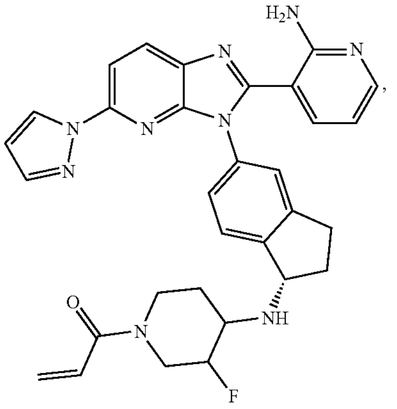 [SMILES: C=CC(=O)N1CCC(N[C@H]2CCc3cc(-n4c(-c5cccnc5N)nc5ccc(-n6cccn6)nc54)ccc32)C(F)C1]

or a pharmaceutically acceptable salt thereof.

49. The compound or salt of claim 1, wherein the compound or salt of Formula (I) is

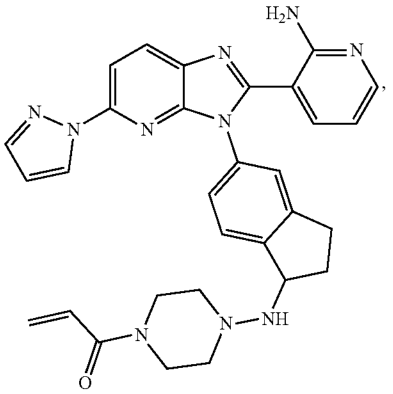 [SMILES: C=CC(=O)N1CCN(NC2CCc3cc(-n4c(-c5cccnc5N)nc5ccc(-n6cccn6)nc54)ccc32)CC1]

or a pharmaceutically acceptable salt thereof.

50. The compound or salt of claim 1, wherein the compound or salt of Formula (I) is

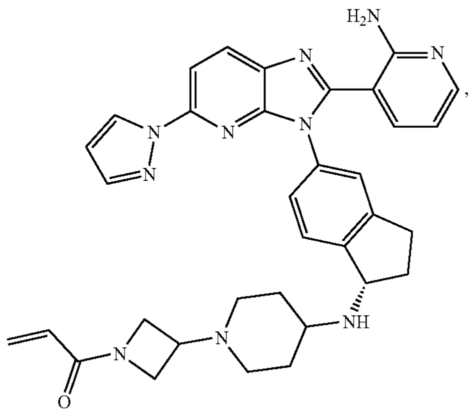 [SMILES: C=CC(=O)N1CC(N2CCC(N[C@H]3CCc4cc(-n5c(-c6cccnc6N)nc6ccc(-n7cccn7)nc65)ccc43)CC2)C1]

or a pharmaceutically acceptable salt thereof.

51. The compound or salt of claim 1, wherein the compound or salt of Formula (I) is

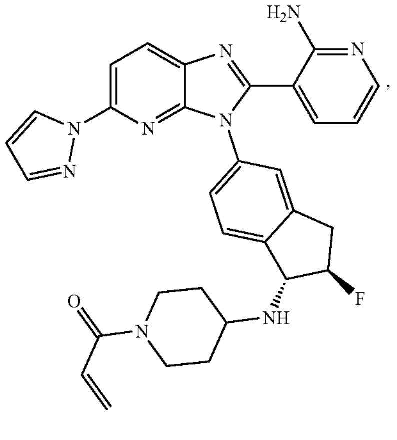 [SMILES: C=CC(=O)N1CCC(N[C@@H]2c3ccc(-n4c(-c5cccnc5N)nc5ccc(-n6cccn6)nc54)cc3C[C@H]2F)CC1]

or a pharmaceutically acceptable salt thereof.

52. The compound or salt of claim 1, wherein the compound or salt of Formula (I) is

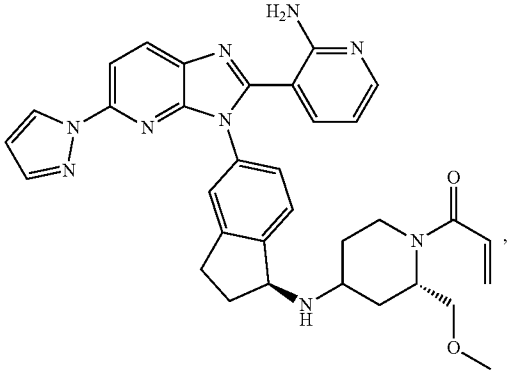 [SMILES: C=CC(=O)N1CCC(N[C@H]2CCc3cc(-n4c(-c5cccnc5N)nc5ccc(-n6cccn6)nc54)ccc32)C[C@H]1COC]

or a pharmaceutically acceptable salt thereof.

53. The compound or salt of claim 1, wherein the compound or salt of Formula (I) is

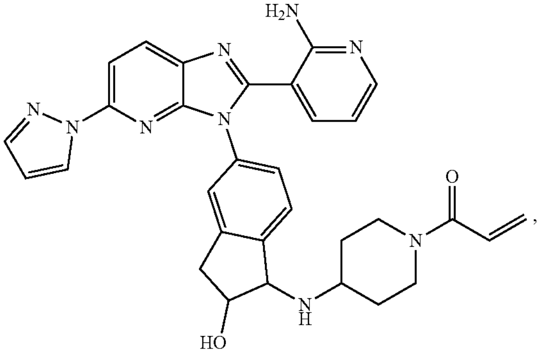 [SMILES: C=CC(=O)N1CCC(NC2c3ccc(-n4c(-c5cccnc5N)nc5ccc(-n6cccn6)nc54)cc3CC2O)CC1]

or a pharmaceutically acceptable salt thereof.

54. The compound or salt of claim 1, wherein the compound or salt of Formula (I) is

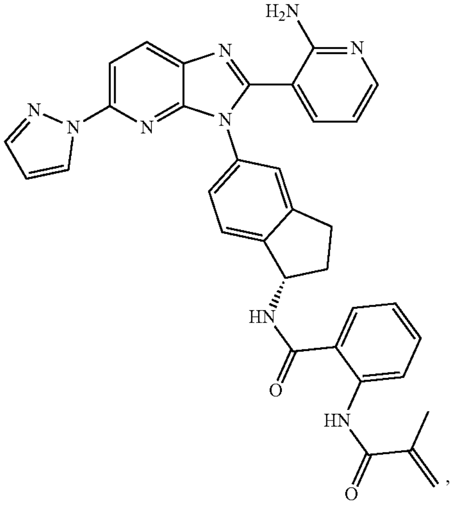 [SMILES: C=C(C)C(=O)Nc1ccccc1C(=O)N[C@H]1CCc2cc(-n3c(-c4cccnc4N)nc4ccc(-n5cccn5)nc43)ccc21]

or a pharmaceutically acceptable salt thereof.

55. The compound or salt of claim 1, wherein the compound or salt of Formula (I) is

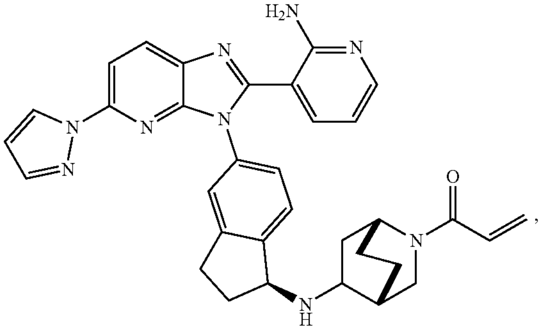

or a pharmaceutically acceptable salt thereof.

* * * * *